US007786161B2

(12) United States Patent
Tani et al.

(10) Patent No.: US 7,786,161 B2
(45) Date of Patent: Aug. 31, 2010

(54) CARBOXYLIC ACID DERIVATIVES AND PHARMACEUTICAL AGENT COMPRISING THE SAME AS ACTIVE INGREDIENT

(75) Inventors: Kousuke Tani, Mishima-gun (JP); Masaki Asada, Mishima-gun (JP); Kaoru Kobayashi, Mishima-gun (JP); Masami Narita, Mishima-gun (JP); Mikio Ogawa, Mishima-gun (JP)

(73) Assignee: ONO Pharmaceutical Co., Ltd., Osaka-shi (JP)

( * ) Notice: Subject to any disclaimer, the term of this patent is extended or adjusted under 35 U.S.C. 154(b) by 106 days.

(21) Appl. No.: 12/259,012

(22) Filed: Oct. 27, 2008

(65) Prior Publication Data

US 2009/0318703 A1 Dec. 24, 2009

Related U.S. Application Data

(62) Division of application No. 10/486,220, filed as application No. PCT/JP02/08120 on Aug. 8, 2002, now Pat. No. 7,491,748.

(30) Foreign Application Priority Data

Aug. 9, 2001 (JP) ............................ 2001-241867

(51) Int. Cl.
*A61K 31/415* (2006.01)
*C07D 231/12* (2006.01)

(52) U.S. Cl. ................. 514/406; 548/375.1; 548/267.2; 548/152; 560/155; 562/400; 514/367; 514/383; 514/546; 514/557

(58) Field of Classification Search ................. 514/406, 514/383, 367, 546, 557; 548/375.1, 267.2, 548/152; 560/155; 562/400

See application file for complete search history.

(56) References Cited

U.S. PATENT DOCUMENTS

| | | | |
|---|---|---|---|
| 3,950,393 | A | 4/1976 | Keck et al. |
| 4,006,246 | A | 2/1977 | Keck et al. |
| RE29,628 | E | 5/1978 | Keck et al. |
| 4,101,671 | A | 7/1978 | Keck et al. |
| 4,113,871 | A | 9/1978 | Stach et al. |
| 4,238,506 | A | 12/1980 | Stach et al. |
| 5,268,389 | A | 12/1993 | Harrison et al. |
| 5,412,101 | A | 5/1995 | Caille et al. |
| 5,599,830 | A | 2/1997 | Caille et al. |
| 5,684,028 | A | 11/1997 | Caille et al. |
| 5,693,827 | A | 12/1997 | Harrison et al. |
| 5,712,298 | A | 1/1998 | Amschler |
| 5,716,993 | A | 2/1998 | Ozaki et al. |
| 5,811,445 | A | 9/1998 | Corbier et al. |
| 5,849,796 | A | 12/1998 | Gericke et al. |
| 5,977,155 | A | 11/1999 | Corbier et al. |
| 6,005,116 | A | 12/1999 | Kojima et al. |
| 6,018,068 | A | 1/2000 | Nagao et al. |
| 6,043,275 | A | 3/2000 | Maruyama et al. |
| 6,462,081 | B1 | 10/2002 | Maruyama et al. |
| 6,835,752 | B2 * | 12/2004 | Tani et al. .................. 514/563 |

FOREIGN PATENT DOCUMENTS

| | | | |
|---|---|---|---|
| EP | 0 073 663 | A2 | 3/1983 |
| EP | 0 081 993 | A2 | 6/1983 |
| EP | 985663 | A1 | 3/2000 |
| EP | 1114816 | A1 | 7/2001 |
| EP | 02/16311 | A1 | 2/2002 |
| WO | 96/10569 | A1 | 4/1996 |
| WO | 99/47497 | A2 | 9/1999 |
| WO | 00/03980 | A1 | 1/2000 |
| WO | 00/20371 | A1 | 1/2000 |
| WO | 00/15608 | A1 | 3/2000 |
| WO | 01/49661 | A1 | 7/2001 |
| WO | 02/016311 | A1 | 2/2002 |
| WO | 97/05091 | A1 | 2/2007 |

OTHER PUBLICATIONS

International Search Report dated Dec. 17, 2002.
Russian Office Action dated Mar. 5, 2004.
Polish Office Action issued in Application No. P-368129, dated Feb. 23, 2010.

* cited by examiner

*Primary Examiner*—Charanjit S Aulakh
(74) *Attorney, Agent, or Firm*—Sughrue Mion, PLLC

(57) ABSTRACT

A carboxylic acid derivative of formula (I):

(I)

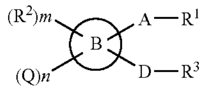

wherein $R^1$ is —COOH, —$COOR^6$, etc.; A is a single bond, alkylene, etc.; $R^2$ is alkyl, alkoxy, etc.; B is a carbocyclic ring or a heterocyclic ring; Q is alkylnene-Cyc2, etc.; D is a linking chain; and $R^3$ is alkyl, a carbocyclic ring or a heterocyclic ring, or a non-toxic salt thereof. The compound of formula (I) binds to $PGE_2$ receptor, especially subtypes $EP_3$ and/or $EP_4$ and show the antagonizing activity, are useful for the prevention and/or treatment of diseases induced pain, itch, urticaria, allergy, urinary frequency, urinary disturbance, Alzheimer's disease, cancer, dysmenorrhea, endometriosis, etc.

4 Claims, No Drawings

CARBOXYLIC ACID DERIVATIVES AND PHARMACEUTICAL AGENT COMPRISING THE SAME AS ACTIVE INGREDIENT

This is a divisional of application Ser. No. 10/486,220 filed Sep. 9, 2004, which is a National Stage Application filed under § 371 of PCT Application No. PCT/JP02/08120 filed Aug. 8, 2002. The entire disclosure of the prior applications is considered part of the disclosure of the accompanying divisional application and is hereby incorporated by reference.

TECHNICAL FIELD

The present invention relates to carboxylic acid derivatives. More specifically, the present invention relates to a carboxylic acid derivative of formula (I)

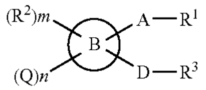

(I)

wherein all symbols have the same meanings as described below;

a non-toxic salt thereof and a pharmaceutical agent comprising the same as an active ingredient.

BACKGROUND ART

Prostaglandin $E_2$ ($PGE_2$) has been known as a metabolite in the arachidonic acid cascade. It has been known that $PGE_2$ possesses cyto-protective activity, uterine contractile activity, a pain-inducing effect, a promoting effect on digestive peristalsis, an awaking effect, a suppressive effect on gastric acid secretion, hypotensive activity, and diuretic activity.

In the recent study, it was found that $PGE_2$ receptor was divided into some subtypes, which possesses different physical roles from each other. At present, four receptor subtypes are known and they are called $EP_1$, $EP_2$, $EP_3$ and $EP_4$ respectively [*J. Lipid Mediators Cell Signaling,* 12, 379-391 (1995)].

Among these subtypes, $EP_3$ receptor was believed to be involved in signal transduction of peripheral nerve, control of exothermal reaction in central nerve, formation of memory by expressing in cerebral neuron, vascularization, reabsorption of urine by expressing in renal tubular, uterine contraction, production of ACTH, platelet aggregation. Besides, it was expressed in vascular smooth muscle, heart and gastrointestinal tract also. $EP_4$ receptor was believed to be involved in suppression of TNF-α production and induction of IL-10 production.

So the compounds which can bind to $EP_3$ receptor and/or $EP_4$ receptor strongly and show the antagonizing activity, are useful for the prevention and/or treatment of diseases induced by excess activation of $EP_3$ receptor and/or $EP_4$ receptor, for example, pain such as cancerous pain, fractural pain, pain following surgical and dental procedures; allodynia, hyperalgesia, pruritus, urticaria, atopic dermatitis, contact dermatitis, rhus dermatitis, allergic conjunctivitis, various symptoms by treating with dialysis, asthma, rhinitis, sneeze, urinary frequency such as neurogenic bladder, neurogenic bladder, irritant bladder, unstable bladder, urinary frequency that originate with prostate-gland enlargement; urinary disturbance, ejaculatory failure, fever, systemic inflammatory response syndrome, learning disturbance, Alzheimer's disease, angiogenesis, cancer such as formulation of cancer, growth of cancer and metastasis of cancer; retinopathy, patch of red, erythematous patches, achromoderma, pigmented spot, scald, burn, burn by steroid, renal failure, nephropathy, acute nephritis, chronic nephritis, abnormal blood levels of electrolytes, threatened premature delivery, abortion threatened, hypermenorrhea, dysmenorrhea, uterine fibroids, premenstrual syndrome, reproductive disorder, stress, anxiety disorders, depression, psychosomatic disorder, mental disorder, thrombosis, embolism, transient ischemia attack, cerebral infarction, atheroma, organ transplant, myocardial infarction, cardiac failure, hypertension, arteriosclerosis, circulatory failure and circulatory failure induced ulcer, neuropathies, vascular dementia, edema, various arthritis, rheumatism, diarrhea, constipation, disorder of bilious excretion, ulcerative colitis, Crohn's disease, irritable bowel syndrome, alleviation of rebound phenomenon after steroid, dose reduction of steroid and adjunct for steroid withdrawal and/or bone diseases such as osteoporosis, rheumatoid arthritis, osteoarthritis, abnormal bone formation; cancer such as formation of cancer, proliferation of cancer, metastasis of cancer to organs and to bones and hypercalcemia induced metastasis to bones of cancer; systemic granuloma, immunological diseases such as ALS, multiple sclerosis, Sjoegren's syndrome, systemic lupus erythematosus, AIDS; allergy such as allergic conjunctivitis, allergic rhinitis, contact dermatitis, psoriasis; atopy such as atopic dermatitis; asthma, pyorrhea, gingivitis, periodontitis, neuronal cell death, Alzheimer's disease, pulmonary injury, hepatopathy, acute hepatopathy, nephritis, renal failure, myocardial ischemia, Kawasaki disease, scald, ulcerative colitis, Crohn's disease, multiple organ failure, chronic headache such as migraine headache, tension-type headache or mixed headache thereof, cluster headache; pain, angiogenesis, angiitis, venous insufficiency, varicose veins, anal fistula, diabetes insipidus, stress, endometriosis, adenomyosis of the uterus, neonatal patent ductus arteriosus, cholelithiasis etc. Moreover, it relates to sleeping disorder and platelet aggregation, so the compounds are considered to be useful for them.

As a compound useful for a treatment of a disease related prostaglandin E receptor, for example, (A) in a specification of WO 99/47497, a compound of formula (A):

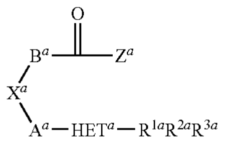

(A)

wherein $HET^a$ is a 5- to 12-membered mono- or bi-aromatic ring; $A^a$ is a group of one or two atoms; $X^a$ is 5- to 10-membered mono- or bi-aryl, heteroaryl, and the rings may be substituted with $R^{14a}$ and $R^{15a}$; $B^a$ is —$(C(R^{18a})_2)_{pa}$—$Y^a$—$(C(R^{18a})_{qa}$—; $R^{1a}$, $R^{2a}$ and $R^{3a}$ are hydrogen, halogen, lower alkyl, lower alkenyl, lower alkynyl, etc.; and (B) in a specification of WO 00/20371, a compound of formula (B)

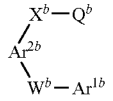

(B)

wherein $Ar^{1b}$ is aryl or heteroaryl; $W^b$ is a 3- to 6-membered linking chain containing 0-2 of a hetero atom(s); $Ar^{2b}$ is aryl or heteroaryl which may be substituted with $R^{3b}$; $R^{3b}$ is hydrogen, lower alkyl, lower alkenyl, lower alkynyl, $CHF_2$, $CF_3$, halogen, halo(C1-6) alkyl, $N(R^{5b})_2$, cyano, nitro, $C(R^{6b})_3$; $X^b$ is a linking chain; $Q^b$ is COOH, tetrazole, $SO_3H$, hydroxamic acid, $CONHSO_2R^{12b}$, $SO_2NHCOR^{12b}$; were described.

DISCLOSURE OF THE INVENTION

The present inventors have energetically studied to find the compound which bind to $PGE_2$ receptor, $EP_3$ and/or $EP_4$ receptor specifically and show an inhibitory activity against it, to find out that the carboxylic acid derivatives of formula (I) achieve the purpose and completed the present invention.

The present invention is relates to (1) a carboxylic acid derivative of formula (I):

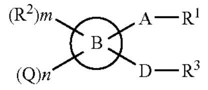

(I)

wherein $R^1$ is —COOH, —$COOR^4$, —$CH_2OH$, —$CONR^5SO_2R^6$, —$CONR^7R^8$, —$CH_2NR^5SO_2R^6$, —$CH_2NR^9COR^{10}$, —$CH_2NR^9CONR^5SO_2R^6$, —$CH_2SO_2NR^9COR^{10}$, —$CH_2OCONR^5SO_2R^6$, tetrazole, 1,2,4-oxadiazol-5-one, 1,2,4-oxadiazol-5-tione, 1,2,4-thiadiazol-5-one, 1,3-thiazolidin-2,4-dione or 1,2,3,5-oxathiadiazol-2-one, $R^4$ is C1-6 alkyl or —(C1-4 alkylene)-$R^{11}$, $R^{11}$ is hydroxy, C1-4 alkoxy, —COOH, C1-4 alkoxycarbonyl or —$CONR^7R^8$, $R^5$ is hydrogen or C1-6 alkyl, $R^6$ is (i) C1-6 alkyl, (ii) a C3-15 mono-, bi- or tri-carbocyclic ring or a 3- to 15-membered mono-, bi- or tri-heterocyclic ring which is substituted with 1-5 of $R^{12}$ or unsubstituted, (iii) C1-6 alkyl, C2-6 alkenyl or C2-6 alkynyl substituted with a C3-15 mono-, bi- or tri-carbocyclic ring or a 3- to 15-membered mono-, bi- or tri-heterocyclic ring which is substituted with 1-5 of $R^{12}$ or unsubstituted, $R^7$ and $R^8$ each independently, is (i) hydrogen, (ii) C1-6 alkyl, (iii) hydroxy, (iv) —$COR^{17}$, (v) a C3-15 mono-, bi- or tri-carbocyclic ring or a 3- to 15-membered mono-, bi- or tri-heterocyclic ring which is substituted with 1-5 of $R^{12}$ or unsubstituted, or (vi) C1-4 alkyl substituted with a C3-15 mono-, bi- or tri-carbocyclic ring or a 3- to 15-membered mono-, bi- or tri-heterocyclic ring which is substituted with 1-5 of $R^{12}$ or unsubstituted, $R^9$ is hydrogen or C1-6 alkyl, $R^{10}$ is (i) hydrogen, (ii) C1-6 alkyl, (iii) a C3-15 mono-, bi- or tri-carbocyclic ring or a 3- to 15-membered mono-, bi- or tri-heterocyclic ring which is substituted with 1-5 of $R^{12}$ or unsubstituted, or (iv) C1-6 alkyl, C2-6 alkenyl or C2-6 alkynyl substituted with a C3-15 mono-, bi- or tri-carbocyclic ring or a 3- to 15-membered mono-, bi- or tri-heterocyclic ring which is substituted with 1-5 of $R^{12}$ or unsubstituted, $R^{12}$ is (a) C1-6 alkyl, (b) C1-6 alkoxy, (c) C1-6 alkylthio, (d) halogen, (e) $CF_3$, (f) cyano, (g) nitro, (h) hydroxy, (i) —$COOR^{13}$, (j) —$NHCOR^{13}$, (k) —$SO_2R^{14}$, (l) —$NR^{15}R^{16}$, (m) a C3-7 mono-carbocyclic ring which is substituted with C1-4 alkyl or oxo or unsubstituted, (n) a 3- to 7-membered mono-heterocyclic ring which is substituted with enhanced C1-4 alkyl or oxo or unsubstituted, or (o) C1-4 alkyl substituted with hydroxy, —$COOR^{13}$, —$NHCOR^{13}$, —$SO_2R^{14}$ or —$NR^{15}R^{16}$, $R^{13}$ is hydrogen, C1-4 alkyl, phenyl, or phenyl-(C1-4) alkyl, $R^{14}$ is C1-4 alkyl, $R^{15}$ and $R^{16}$ each independently, is hydrogen, C1-4 alkyl, phenyl, or phenyl-(C1-4) alkyl, $R^{17}$ is C1-4 alkyl or phenyl, A is (i) a single bond, (ii) C1-6 alkylene, (iii) C2-6 alkenylene, (iv) C2-6 alkynylene, (V) —O—(C1-3 alkylene), (vi) —S—(C1-3 alkylene), (vii) —$NR^{20}$—(C1-3 alkylene), (viii) —$CONR^{21}$—(C1-3 alkylene), (ix) —(C1-3 alkylene)-O—(C1-3 alkylene), (x) —(C1-3 alkylene)-S—(C1-3 alkylene), (xi) —(C1-3 alkylene)-$NR^{20}$—(C1-3 alkylene), (xii) —(C1-3 alkylene)-$CONR^{21}$—(C1-3 alkylene), (xiii) -Cyc1, (xiv) —(C1-4 alkylene)-Cyc1 or (xv) -Cyc1-(C1-4 alkylene), the alkylene, alkenylene and alkynylene in A may be substituted with 1-6 of the following substituents of (a)-(i):

(a) C1-6 alky, (b) C1-6 alkoxy, (c) halogen, (d) $CHF_2$, (e) $CF_3$, (f) $OCHF_2$, (g) $OCF_3$, (h) hydroxy, (i) hydroxy-(C1-4) alkyl, $R^{20}$ is hydrogen, C1-4 alkyl, —$SO_2$—(C1-4) alkyl or C2-5 acyl, $R^{21}$ is hydrogen or C1-4 alkyl, Cyc1 is a C3-7 mono-carbocyclic ring or a 3- to 7-membered mono-heterocyclic ring which is substituted with 1-4 of C1-6 alkyl, C1-6 alkoxy, C1-6 alkylthio, C2-6 alkenyl, C2-6 alkynyl, halogen, $CHF_2$, $CF_3$, nitro or cyano, or unsubstituted, B ring is a C3-12 mono- or bi-carbocyclic ring or a 3- to 12-membered mono- or bi-heterocyclic ring, $R^2$ is C1-6 alkyl, C1-6 alkoxy, C1-6 alkylthio, C2-6 alkenyl, C2-6 alkynyl, halogen, $CHF_2$, $CF_3$, nitro, cyano, phenyl or oxo, m is 0, 1 or 2, n is 1 or 2 when -D-$R^3$ binds to B ring at the ortho position based on -A-$R^1$, n is 0, 1 or 2 when -D-$R^3$ binds to B ring at the non-ortho position based on -A-$R^1$, Q is (1)(i) —(C1-4 alkylene, C2-4 alkenylene or C2-4 alkynylene)-Cyc2, (ii) —(C1-4 alkylene)-Z-Cyc3, (iii) C1-4 alkyl substituted with a substituent(s) selected from —$NR^{24}R^{25}$, —$S(O)_pR^{25}$, cyano, —$NR^{23}COR^{27}$, —$NR^{23}SO_2R^{28}$ and —$NR^{23}CONR^{24}R^{25}$, (iv) C1-4 alkoxy(C1-4) alkoxy, —$NR^{23}COR^{27}$, —$COR^{28}$, —$OSO_2R^{28}$, —$NR^{23}SO_2R^{28}$ or —$NR^{23}CONR^{24}R^{25}$, (v) a C3-7 mono-carbocyclic ring or a 3- to 6-membered mono-heterocyclic ring which is substituted with 1-5 of $R^{20}$, wherein one $R^{20}$ of them always binds to the ring at the non 1-position, (vi) a C8-15 mono-, bi- or tri-carbocyclic ring or a 7- to 15-membered mono-, bi- or tri-heterocyclic ring which is substituted with 1-5 of $R^{30}$ or unsubstituted, (vii) -T-Cyc5, (viii) -L-$Cyc^{6-1}$, -L-(C3-6 cycloalkyl), -L-$CH_2$—(C3-6 cycloalkyl), -L-(C2-4 alkylene)-$Cyc^{6-2}$ or -L-(C1-4 alkylene)$_q$-$Cyc^{6-3}$, wherein the cycloalkyl is substituted with 1-5 of $R^{30}$ or unsubstituted, (2) (i) phenoxy, (ii) benzyloxy, (iii) hydroxy(C1-4) alkyl, (iv) C1-4 alkoxy(C1-4) alkyl, or (v) —(C1-4 alkylene)-O-benzyl, or (3) (i) C2-6 alkenyl, (ii) C2-6 alkynyl, (iii) C1-6 alkyl substituted with 1-3 halogen(s), (iv) cyano, (v) nitro, (vi) —$NR^{33}R^{34}$, (vii) —$CONR^{33}R^{34}$, (viii) —$S(O)_p$—(C1-4) alkynyl, (ix) —$S(O)_p$—$CHF_2$, (x) $S(O)_p$—$NR^{33}R^{34}$, (xi) —O—(C3-6) alkynyl, (xii) —O—$CHF_2$, or (xiii) C3-7 cycloalkyl, $R^{22}$ is hydrogen, C1-4 alkyl, —$SO_2$—(C1-4) alkyl or C2-5 acyl, $R^{23}$ is hydrogen, C1-4 alkyl, phenyl or phenyl(C1-4) alkyl, $R^{24}$ and $R^{25}$ each independently, is hydrogen, C1-4 alkyl, Cyc4 or (C1-4 alkylene)-Cyc4, $R^{26}$ is C1-4 alkyl or Cyc4, $R^{27}$ is hydrogen, C1-4 alkyl, —$OR^{29}$ or Cyc4, $R^{28}$ is C1-4 alkyl, Cyc4 or —(C1-4 alkylene)-Cyc4, $R^{29}$ is hydrogen, C1-4 alkyl, Cyc4 or (C1-4 alkylene)-Cyc4, $R^{30}$ is C1-8 alkyl, C1-8 alkoxy, C1-8 alkylthio, halogen, $CF_3$, $OCF_3$, $SCF_3$, $CHF_2$, $SCHF_2$, hydroxy, cyano, nitro, —$NR^{31}R^{32}$, —$CONR^{31}R^{32}$, formyl, C2-5 acyl, hydroxy(C1-4) alkyl, C1-4 alkoxy(C1-4) alkyl, C1-4 alkylthio(C1-4) alkyl, —(C1-4 alkylene)-$CONR^{31}R^{32}$, —$SO_2$(C1-4) alkyl, —$NR^{23}CO$—(C1-4) alkyl, —$NR^{23}SO_2$—(C1-4) alkyl, benzoyl, oxo, a C3-7 mono-carbocyclic ring, a 3- to 7-membered mono-heterocyclic ring, —(C1-4 alkylene)-$NR^{31}R^{32}$, -M-(C3-7 mono-carbocyclic ring), or -M-(3- to 7-membered mono-heterocyclic ring), the C3-7 mono-carbocyclic ring and 3- to 7-membered mono-heterocyclic ring in $R^{30}$ may be substituted with 1-5 of the following substituents (a)-(l):

(a) C1-6 alkyl, (b) C2-6 alkenyl, (c) C2-6 alkyl, (d) c1-6 alkoxy, (e) C1-6 alkylthio, (f) halogen, (g) $CHF_2$, (h) $CF_3$, (I) nitro, (j) cyano, (k) hydroxy, (l) amino;

M is —O—, —S—, C1-4 alkylene, —O—(C1-4 alkylene)-, —S—(C1-4 alkylene)-, —(C1-4 alkylene)-O— or —(C1-4 alkylene)-S—, $R^{31}$ and $R^{32}$ each independently, is hydrogen or C1-4 alkyl, Cyc2 is a C3-15 mono-, bi- tri-carbocyclic ring or a 3- to 15-membered mono-, bi- tri-heterocyclic ring which is substituted with 1-5 of $R^{30}$ or unsubstituted, Z is —O—, —S(O)P—, —$NR^{22}$—, —$NR^{23}CO$—, —$NR^{23}SO_2$—, —$NR^{22}$—(C1-4 alkylene)-, —$S(O)_p$—(C1-4 alkylene)-, —O—(C2-4 alkylene)-, —$NR^{23}CO$—(C1-4 alkylene) or —$NR^{23}SO_2$—(C1-4 alkylene), p is 0, 1 or 2, Cyc3 is a C3-15 mono-, bi- tri-carbocyclic ring or a 3- to 15-membered mono-, bi- tri-heterocyclic ring which is substituted with 1-5 of $R^{30}$ or unsubstituted, Cyc4 is a C3-12 mono-, bi-carbocyclic ring or a 3- to 12-membered mono-, bi-heterocyclic ring which is substituted with 1-5 of $R^{30}$ or unsubstituted, T is —O—, —$NR^{22}$—, —O—(C1-4 alkylene)-, —$S(O)_p$—(C1-4 alkylene)- or —$NR^{22}$—(C1-4 alkylene)-, Cyc5 is a 3- to 15-membered mono-, bi- tri-heterocyclic ring which is substituted with 1-5 of $R^{30}$ or unsubstituted, q is 0 or 1, L is —O— or —$NR^{23}$—, $Cyc^{6-1}$ is phenyl or benzyl which is substituted with one or more $R^{30}$, $Cyc^{6-2}$ is a C3-6 mono-carbocyclic ring which is substituted with 1-5 of $R^{30}$ or unsubstituted, $Cyc^{6-3}$ is a C7-15 mono-, bi- or tri-carbocyclic ring which is substituted with 1-5 of $R^{30}$ or unsubstituted, $R^{33}$ and $R^{34}$ each independently, is hydrogen, C1-4 alkyl, phenyl or benzyl, or $NR^{33}R^{34}$ is a 3- to 6-membered mono-heterocyclic ring containing one nitrogen and optionally containing one hetero atom selected from nitrogen, oxygen and sulfur, D is (1) a 1- or 2-membered linking chain comprising an atom(s) selected from carbon, nitrogen, oxygen and sulfur, which may contain a double bond or a triple bond in the chain and may be substituted with 1-4 of $R^{40}$, (2) a 3- to 6-membered linking chain comprising atoms selected from carbon, nitrogen, oxygen and sulfur, which may contain a double bond or a triple bond in the chain and may be substituted with 1-12 of $R^{40}$, wherein $R^{40}$ substituted on the atom bound to $R^3$, and $R^{42}$ which is a substituent of $R^3$, taken together may form —$(CH_2)_y$—, in which y is 1-4, or (3) a 7- to 10-membered linking chain comprising atoms selected from carbon, nitrogen, oxygen and sulfur, which may contain a double bond or a triple bond and may be substituted with 1-20 of $R^{40}$, wherein $R^{40}$ substituted on the atom bound to $R^3$, and $R^{42}$ which is a substituent of $R^3$, taken together may form —$(CH_2)_y$—, $R^{40}$ is (a) C1-8 alkyl, (b) C2-8 alkenyl, (c) C2-8 alkynyl, (d) oxo, (e) halogen, (f) $CF_3$, (g) hydroxy, (h) C1-6 alkoxy, (i) C2-6 alkenyloxy, (j) C2-6 alkynyloxy, (k) $OCF_3$, (l) —$S(O)_p$—(C1-6) alkyl, (m) —$S(O)_p$—(C2-6) alkenyl, (n) —$S(O)_p$—(C2-6) alkynyl, (o) C2-5 acyl, (p) Cyc9, (q) C1-4 alkoxy(C1-4) alkoxy, or (r) C1-8 alkyl, C2-8 alkenyl or C2-8 alkynyl substituted with 1 or 2 of substituents selected from halogen, $CF_3$, $OCF_3$, hydroxy, cyano, C1-4 alkoxy, —$S(O)_p$—(C1-6) alkyl, Cyc9 and C1-4 alkoxy(C1-4) alkoxy or two $R^{40}$'s taken together with the atom of a linking chain to which they bind, may form a C3-15 mono-, bi- or tri-carbocyclic ring or a 3- to 15-membered mono-, bi- or tri-heterocyclic ring containing 1-2 hetero atom(s) selected from O, S, $SO_2$ and N, wherein the carbocyclic ring and the heterocyclic ring may be substituted with 1-3 substituent(s) selected from C1-4 alkyl, C1-4 alkoxy, C2-5 acyl, $SO_2$(C1-4 alkyl), phenyl and phenyl(C1-4) alkyl, Cyc9 is a C3-6 mono-carbocyclic ring or a 3- to 6-membered mono-heterocyclic ring, which is substituted with 1-5 of $R^{41}$ or unsubstituted, $R^{41}$ is C1-4 alkyl, C1-4 alkoxy, C1-4 alkylthio, C1-4 alkoxy(C1-4) alkyl, halogen, $CF_3$, $OCF_3$, $SCF_3$, hydroxy, cyano, formyl, C2-5 acyl, —$SO_2$—(C1-4) alkyl, —$NR^{23}$CO—(C1-4) alkyl, benzoyl or oxo, $R^3$ is (1) C1-6 alkyl or (2) a C3-15 mono-, bi- or tri-carbocyclic ring or a 3- to 15-membered mono-, bi- or tri-heterocyclic ring which is substituted with 1-5 of $R^{42}$ or unsubstituted, $R^{42}$ is (a) C1-6 alkyl, (b) C1-6 alkoxy, (c) C1-6 alkylthio, (d) halogen, (e) cyano, (f) $CF_3$, (g) $CHF_2$, (h) $OCF_3$, (i) $OCHF_2$, 0) $SCF_3$, (k) —$NR^{43}R^{44}$, (l) —$SO_2R^{45}$, (m) —$NR^{45}COR^{47}$, (n) hydroxy, (o) oxo, (p) C1-4 alkoxy(C1-4) alkyl, (q) Cyc10, (r) C1-6 alkylene-Cyc10, (s) —CO-Cyc10, (t) —W-Cyc10, (u) —(C1-6 alkylene)-W-Cyc10, (v) —W—(C1-6 alkylene)-Cyc10 or (w) —(C1-6 alkylene)-W—(C1-6 alkylene)-Cyc10, $R^{43}$ and $R^{44}$ each independently, is hydrogen or C1-4 alkyl, $R^{45}$ is C1-4 alkyl, $R^{46}$ is hydrogen or C1-4 alkyl, $R^{47}$ is hydrogen or C1-4 alkyl, Cyc10 is a C3-12 mono- or bi-carbocyclic ring or a 3- to 12-membered mono- or bi-heterocyclic ring which is substituted with 1-5 of substitutes of the following (a)-(j) or unsubstituted, (a) C1-4 alkyl, (b) C2-5 acyl, (c) 1-4 alkoxy, (d) halogen, (e) hydroxy, (f) nitro, (g) cyano, (h) amine, (i) $CF_3$, (j) $OCF_3$, W is —O—, —$S(O)_p$— or —$NR^{48}$—, $R^{48}$ is hydrogen or C1-4 alkyl;

or a non-toxic salt thereof, (2) a process of the preparation thereof, and (3) a pharmaceutical agent comprising the same as an active ingredient.

DETAILED DESCRIPTION OF THE INVENTION

In the present invention, the C1-4 alkyl includes methyl, ethyl, propyl, butyl and isomers thereof.

In the present invention, the C1-6 alkyl includes methyl, ethyl, propyl, butyl, pentyl, hexyl and isomers thereof.

In the present invention, the C1-8 alkyl includes methyl, ethyl, propyl, butyl, pentyl, hexyl, heptyl, octyl and isomers thereof.

In the present invention, the C2-6 alkenyl includes ethenyl, propenyl, butenyl, pentenyl, hexenyl and isomers thereof.

In the present invention, the C2-8 alkenyl includes ethenyl, propenyl, butenyl, pentenyl, hexenyl, heptenyl, octenyl and isomers thereof.

In the present invention, the C2-6 alkynyl includes ethynyl, propynyl, butynyl, pentynyl, hexynyl and isomers thereof.

In the present invention, the C2-8 alkynyl includes ethynyl, propynyl, butynyl, pentynyl, hexynyl, heptynyl, octynyl and isomers thereof.

In the present invention, the C3-6 alkynyl includes propynyl, butynyl, pentynyl, hexynyl and isomers thereof.

In the present invention, the C1-4 alkoxy includes methoxy, ethoxy, propoxy, butoxy and isomers thereof.

In the present invention, the C1-6 alkoxy includes methoxy, ethoxy, propoxy, butoxy, pentyloxy, hexyloxy and isomers thereof.

In the present invention, the C1-8 alkoxy includes methoxy, ethoxy, propoxy, butoxy, pentyloxy, hexyloxy, heptyloxy, octyloxy and isomers thereof.

In the present invention, the C1-4 alkylthio includes methylhio, ethylthio, propylthio, butylthio and isomers thereof.

In the present invention, the C1-6 alkylthio includes methylhio, ethylthio, propylthio, butylthio, pentylthio, hexylthio and isomers thereof.

In the present invention, the C1-6 alkylthio includes methylhio, ethylthio, propylthio, butylthio, pentylthio, hexylthio, hepthylthio, octylthio and isomers thereof.

In the present invention, the phenyl(C1-4) alkyl includes phenylmethyl, phenylethyl, phenylpropyl, phenylbutyl and isomers thereof.

In the present invention, the hydroxy(C1-4) alkyl includes hydroxymethyl, hydroxyethyl, hydroxypropyl, hydroxybutyl and isomers thereof.

In the present invention, the C1-4 alkoxy(C1-4) alkyl includes methoxymethyl, methoxyethyl, methoxypropyl, methoxybutyl, ethoxymethyl, ethoxyethyl, ethoxypropyl, ethoxybutyl, propoxymethyl, butoxymethyl and isomers thereof.

In the present invention, the C1-4 alkylthio(C1-4) alkyl includes methylthiomethyl, methylthiothyl, methylthiopropyl, methylthiobutyl, ethylthiomethyl, ethylthioethyl, ethylthiopropyl, ethylthiobutyl, propylthiomethyl, butylthiomethyl and isomers thereof.

In the present invention, the C1-4 alkoxy(C1-4) alkoxy includes methoxymethoxy, methoxyethoxy, methoxypropoxy, methoxybutoxy, ethoxymethoxy, ethoxyethoxy, ethoxypropoxy, ethoxybutoxy and isomers thereof.

In the present invention, the C1-4 alkoxycarbonyl includes methoxycarbonyl, ethoxycarbonyl, propoxycarbonyl, butoxycarbonyl and isomers thereof.

In the present invention, the C1-3 alkylene includes methylene, ethylene, trimethylene and isomers thereof.

In the present invention, the C1-4 alkylene includes methylene, ethylene, trimethylene, tetramethylene and isomers thereof.

In the present invention, the C1-6 alkylene includes methylene, ethylene, trimethylene, tetramethylene, pentamethylene, hexamethylene and isomers thereof.

In the present invention, the C2-6 alkylenylene includes ethylene, trimethylene, tetramethylene, pentamethylene and hexamethylene having one or two double bond(s) and isomers thereof.

In the present invention, the C2-6 alkynylene is ethylene, trimethylene, tetramethylene, pentamethylene and hexamethylene having one or two triple bond(s) and isomers thereof.

In the present invention, the halogen includes fluoride, chloride, bromide and iodide.

In the present invention, the C2-5 acyl includes acetyl, propionyl, butyryl, valeryl and isomers thereof.

In the present invention, the C3-6 mono-carbocyclic ring includes a C3-6 unsaturated or partially or fully saturated mono-carbocyclic ring, for example, cyclopropane, cyclobutane, cyclopentane, cyclohexane, cyclopentene, cyclohexene, and benzene.

In the present invention, the C3-7 saturated mono-carbocyclic ring includes cyclopropane, cyclobutane, cyclopentane, cyclohexane, cyclopentene, cyclohexene, and cycloheptene.

In the present invention, the 3- to 6-membered mono-heterocyclic ring includes a 3- to 6-membered unsaturated or partially or fully saturated mono-heterocyclic ring containing 1-4 nitrogen(s), one oxygen and/or one sulfur, for example, aziridine, oxirane, thiirane, azetidine, oxetane, thietane, pyrrolidine, pyrroline, imidazoline, imidazolidine, pyrazoline, pyrazolidine, furan, thiophene, pyrrole, oxazole, isoxazole, thiazole, isothiazole, imidazole, pyrazole, triazole, tetrazole, pyridine, pyrimidine, pyrazine, piperidine, piperazine, morpholine, thiomorpholine, pyran, and thiopyran ring.

In the present invention, the 3- to 7-membered saturated mono-heterocyclic ring containing 1 or 2 hetero atom(s) selected from O, S, $SO_2$ and N or benzene fused thereof, for example, aziridine, azetidine, pyrrolidine, imidazolidine, pyrazolidine, piperidine, piperazine, perhydropyridazine, perhydroazepine, perhydrodiazepine, oxirane, oxetane, tetrahydrofuran, tetrahydropyran, perhydrooxepine, thiirane, thiiran-1,1-dione, thietane, thietan-1,1-dione, tetrahydrothiophene, tetrahydrothiophen-1,1-dione, tetrahydrothiopyran, tetrahydrothiopyran-1,1-dione, perhydrothiepine, perhydrothiepin-1,1-dione, oxazolidine, isoxazolidine, thiazolidine, isothiazolidine, tetrahydrooxazine, perhydrooxazepine, tetrahydrothiazine, perhydrothiazepine, morpholine, thiomorpholine, indoline, isoindoline, dihydrobenzofuran, dihydroisobenzofuran, dihydrobenzothiophene, dihydroisobenzothiophene, dihydroindazole, tetrahydroquinoline, tetrahydroisoquinoline, and chroman ring.

In the present invention, the 3- to 6-membered mono-heterocyclic ring containing one nitrogen and optionally containing one hetero atom selected from nitrogen, oxygen and sulfur includes 3- to 6-membered unsaturated or partially or fully saturated mono-heterocyclic ring containing 1-2 nitrogen(s), one nitrogen and one oxygen, or one nitrogen and one sulfur, for example, aziridine, oxirane, thiirane, azetidine, oxetane, thietane, pyrrolidine, pyrroline, imidazoline, imidazolidine, pyrazoline, pyrazolidine, pyrrole, oxazole, isoxazole, thiazole, isothiazole, imidazole, pyrazole, pyridine, pyrimidine, pyrazine, piperidine, piperazine, morpholine, and thiomorpholine ring.

In the present invention, the C3-7 mono-carbocyclic ring includes a C3-7 unsaturated or partially or fully saturated mono-carbocyclic ring, for example, cyclopropane, cyclobutane, cyclopentane, cyclohexane, cycloheptane, cyclopentene, cyclohexene, and benzene.

In the present invention, the 3- to 7-membered mono-heterocyclic ring includes a 3- to 7-membered mono-heterocyclic ring containing 1-4 nitrogen(s), one oxygen and/or one sulfur, for example, aziridine, oxirane, thiirane, azetidine, oxetane, thietane, pyrrolidine, pyrroline, imidazoline, imidazolidine, pyrazoline, pyrazolidine, furan, thiophene, pyrrole, oxazole, isothiazole, thiazole, isothiazole, imidazole, pyrazole, triazole, tetrazole, pyridine, pyrimidine, pyrazine, piperidine, piperazine, morpholine, thiomorpholine, pyran, thiopyran, azepine, and diazepine ring.

In the present invention, the C7-15 mono-, bi- or tri-carbocyclic ring includes an unsaturated or partially or fully saturated C7-15 mono-, bi- or tri-carbocyclic ring, for example, cycloheptane, cycloheptene, indene, naphthalene, indan, tetrahydronaphthaldene, azulene, fluorene, phenanthrene, anthracene, and biphenylene ring.

In the present invention, the 7- to 15-membered mono-, bi- or tri-heterocyclic ring includes an unsaturated or partially or fully saturated 7- to 15-membered mono-, bi- or tri-heterocyclic ring containing 1-4 nitrogen(s), 1-2 oxygen(s), one sulfur, one nitrogen and one oxygen, or one nitrogen and one sulfur, for example, azepine, diazepine, perhydroazepine, benzofuran, benzothiophene, benzothiazole, indole, benzoxazole, benzimidazole, benzopyrazole, benzotriazole, benzodioxane, thienopyridine, indoline, isoindoline, 1,3-dioxaindan, chroman, isochroman, quinoline, isoquinoline, quinazoline, quinoxaline, tetrahydroquinoline, tetrahydroisoquinoline, carbazole, acridine, phenanthridine, xanthene, phenazine, phenothiazine, phenoxathiin, phenoxazine, and thianthrene ring.

In the present invention, the C3-12 mono- or bi-carbocyclic ring is an unsaturated or partially or fully saturated C3-12 mono- or bi-carbocyclic ring, for example, cyclopropane, cyclobutane, cyclopentane, cyclohexane, cycloheptane, cyclopentene, cyclohexene, cycloheptene, benzene, indene, naphthalene, indan, tetrahydronaphthalene, and azulene.

In the present invention, the 3- to 12-membered mono- or bi-heterocyclic ring includes an unsaturated or partially or fully saturated 3- to 12-membered mono- or bi-heterocyclic ring containing 1-4 nitrogen(s), 1-2 oxygen(s) and/or one sulfur, for example, aziridine, oxirane, thiirane, azetidine, oxetane, thietane, pyrrolidine, pyrroline, imidazoline, imidazolidine, pyrazoline, pyrazolidine, furan, thiophene, pyrrole, oxazole, isoxazole, thiazole, isothiazole, imidazole, pyrazole, triazole, tetrazole, pyridine, pyrimidine, pyrazine, piperidine, piperazine, morpholine, thiomorpholine, pyran, thiopyran, azepine, benzofuran, benzothiophene, benzothiazole, indole, isoindole, benzoxazole, benzimidazole, benzopyrazole, benzotriazole, benzodioxane, thienopyridine, indoline, isoindoline, 1,3-dioxaindan, chroman, isochroman, quinoline, isoquinoline, quinazoline, quinoxaline, tetrahydroquinoline, and tetrahydroisoquinoline ring.

In the present invention, the C3-15 mono-, bi- or tri-carbocyclic ring includes an unsaturated or partially or fully saturated C3-15 mono-, bi- or tri-carbocyclic ring, for example, cyclopropane, cyclobutane, cyclopentane, cyclohexane, cycloheptane, cyclopentene, cyclohexene, cycloheptene, benzene, indene, naphthalene, indan, tetrahydronaphthalene, azulene, fluorene, phenanthrene, anthracene, and biphenylene.

In the present invention, the 3- to 15-membered mono-, bi- or tri-heterocyclic ring includes an unsaturated or partially or fully saturated 3- to 15-membered mono-, bi- or tri-heterocyclic ring containing 1-4 nitrogen(s), 1-2 oxygen(s) and/or one sulfur, for example, aziridine, oxirane, thiirane, azetidine, oxetane, thietane, pyrrolidine, pyrroline, imidazoline, imidazolidine, pyrazoline, pyrazolidine, furan, thiophene, pyrrole, oxazole, isoxazole, thiazole, isothiazole, imidazole, pyrazole, triazole, tetrazole, pyridine, pyrimidine, pyrazine, piperidine, piperazine, morpholine, thiomorpholine, pyran, thiopyran, azepine, diazepine, perhydroazepine, benzofuran, benzothiophene, benzothiazole, indole, isoindole, benzoxazole, benzimidazole, benzopyrazole, benzotriazole, benzodioxane, thienopyridine, indoline, isoindoline, 1,3-dioxaindan, chroman, isochroman, quinoline, isoquinoline, quinazoline, quinoxaline, tetrahydroquinoline, tetrahydroisoquinoline, carbazole, acridine, phenanthridine, xanthene, phenazine, phenothiazine, phenoxathiin, phenoxazine, and thianthrene ring.

In the present invention, the 1- or 2-membered linking chain comprising an atom(s) selected from carbon, nitrogen, oxygen and sulfur, which may contain a double bond or a triple bond in the chain and may be substituted with 1-4 of $R^{40}$, includes —C($R^{40}$)u-, -G-, —C($R^{40}$)u-C($R^{40}$)u-, —CH═CH—, —C≡C—, -G-C($R^{40}$)u-, —C($R^{40}$)u-G-, —NHCO—, —$NR^{40-1}$—CO—, —$NHSO_2$—, —$NR^{40-1}$—$SO_2$—, —CONH—, —$CONR^{40-1}$—, —$SO_2$—NH—, or —$SO_2$—$NR^{40-1}$—, wherein u is 0, 1 or 2; G is —O—, —S—, —SO—, —$SO_2$—, —NH—, —$NR^{40-1}$—, or —CO—; $R^{40-1}$ is C1-8 alkyl, C2-8 alkynyl, —S(O)p-C1-6 alkyl, —S(O)p-C2-6 alkenyl, —S(O)p-C2-6 alkynyl, C2-5 acyl, Cyc9, or C1-8 alkyl, C2-8 alkenyl or C2-8 alkynyl substituted with 1-2 substituent(s) selected from halogen, $CF_3$, $OCF_3$, hydroxy, C1-4 alkoxy, —S(O)p-(C1-6) alkyl, Cyc9 and C1-4 alkoxy (C1-4) alkoxy.

In the present invention, the 3- to 6-membered linking chain comprising atoms selected from carbon, nitrogen, oxygen and sulfur, which may contain a double bond or a triple bond in the chain and may be substituted with 1-12 of $R^{40}$, includes —$[C(R^{40})u]_3$-, —$[C(R^{40})u]_4$-, —$[C(R^{40})u]_5$-, —$[C(R^{40})u]_6$-, —CH═CH—$C(R^{40})$u-, —CH═CH—$[C(R^{40})u]_2$-, —$C(R^{40})$u-CH═CH—$C(R^{40})$u-, —$C(R^{40})$u-CH═CH—, —$[C(R^{40})u]_2$-CH═CH—, —C≡C—$C(R^{40})$u-, —C≡C—$[C(R^{40})u]_2$-, —$C(R^{40})$u-C≡C—$C(R^{40})$u-, —$C(R^{40})$u-C≡C—, —$[C(R^{40})u]_2$-C≡C—, —$[C(R^{40})u]_2$-G-, —$[C(R^{40})_u]_3$-G-, —$[C(R^{40})_u]_4$-G-, —$[C(R^{40})_u]_5$-G-, -G-$[C(R^{40})_u]_2$—, -G-$[C(R^{40})_u]_3$—, -G-$[C(R^{40})_u]_4$—, -G-$[C(R^{40})_u]_5$—, -E-$C(R^{40})_u$—, -E-$[C(R^{40})_u]_2$—, -E-$[C(R^{40})_u]_3$—, -E-$[C(R^{40})_u]_4$—, —$C(R^{40})_u$-G-$C(R^{40})_u$-, —$C(R^{40})_u$-E-$C(R^{40})_u$—, -G-$C(R^{40})_u$-G-, -G-$[C(R^{40})_u]_2$-G-, -G-$[C(R^{40})_u]_3$-G-, -G-$[C(R^{40})_u]_4$-G-, -G-$C(R^{40})_u$-E-, -G-$[C(R^{40})_u]_2$-E-, -G-$[C(R^{40})_u]_3$-E-, -G-$C(R^{40})_u$-E-$C(R^{40})$—, -G-$[C(R^{40})_u]_2$-E-$C(R^{40})$—, -G-$C(R^{40})_u$-CH═CH—, -G-$[C(R^{40})_u]_2$-CH═CH—,

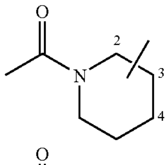, 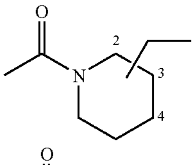,

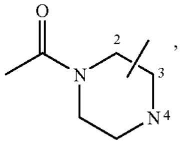, 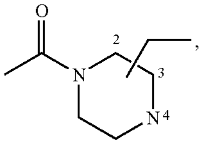,

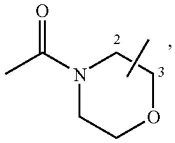, 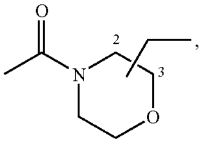,

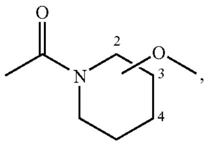, 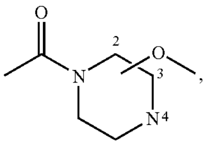,

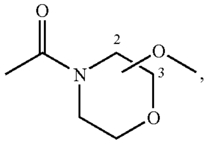, 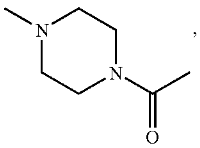,

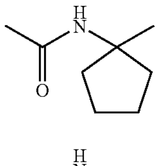, 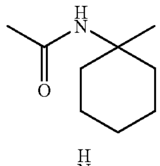, 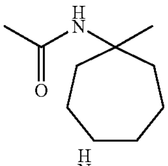,

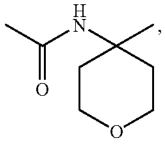, 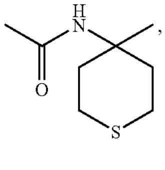, 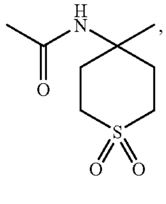,

-continued

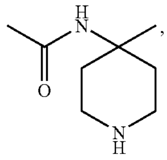, 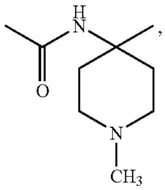,

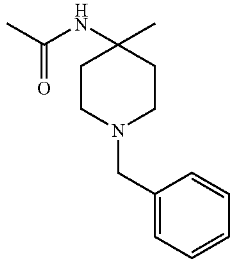

wherein E is —NHCO—, $NR^{40-1}$ CO—, $NHSO_2$—, $NR^{40-1}SO^2$—, —CONH—, —$CONR^{40-1}$—, —$SO_2NH$—, or —$SO_2NR^{40-1}$—, wherein the group containing a ring is bound at the position where the number is described, and the other symbols have the same meanings as described above.

In the present invention, the 7- to 10-membered linking chain comprising atoms selected from carbon, nitrogen, oxygen and sulfur, which may contain a double bond or a triple bond in the chain and may be substituted with 1-20 of $R^{40}$, includes —$[C(R^{40})_u]_7$—, —$[C(R^{40})_u]_8$—, —$[C(R^{40})_u]_9$—, —$[C(R^{40})_u]_{10}$—, —CH═CH—$[C(R^{40})_u]_5$—, —$[C(R^{40})_u]_5$—CH═CH—, —C≡C—$[C(R^{40})_u]_5$—, —$[C(R^{40})_u]_5$—C≡C—, —$[C(R^{40})_u]_6$-G-, —$[C(R^{40})_u]_7$-G-, —$[C(R^{40})_u]_8$-G-, —$[C(R^{40})_u]_9$-G-, -G-$[C(R^{40})_u]_6$—, -G-$[C(R^{40})_u]_7$—, -G-$[C(R^{40})_u]_8$—, -G-$[C(R^{40})_u]_9$—, -E-$[C(R^{40})_u]_5$—, -E-$[C(R^{40})_u]_6$—, -E-$[C(R^{40})_u]_7$—, -E-$[C(R^{40})_u]_8$—, —$C(R^{40})_u$-G-$[C(R^{40})_u]_5$—, —$[C(R^{40})_u]_5$-G-$C(R^{40})_u$—, —$C(R^{40})_u$-E-$[C(R^{40})_u]_4$—, —$[C(R^{40})_u]_4$-E-$C(R^{40})_u$—, -G-$[C(R^{40})_u]_5$-G-, -G-$[C(R^{40})_u]_6$-G-, -G-$[C(R^{40})_u]_7$-G-, -G-$[C(R^{40})_u]_8$-G-, -G-$[C(R^{40})_u]_4$-E-, -G-$[C(R^{40})_u]_5$-E-, -G-$[C(R^{40})_u]_6$-E-, -G-$[C(R^{40})_u]_7$-E-, -G-$[C(R^{40})_u]_3$-E-$C(R^{40})$—, -G-$[C(R^{40})_u]_4$-E-$C(R^{40})$—,

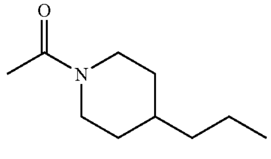,

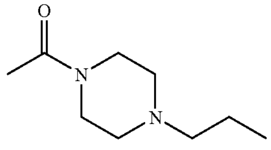,

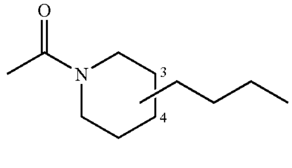,

-continued

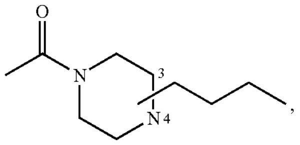

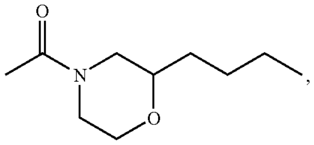

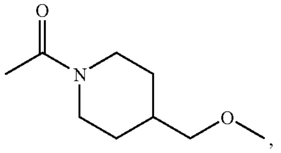

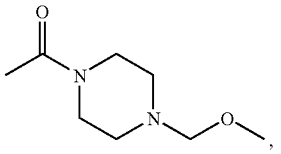

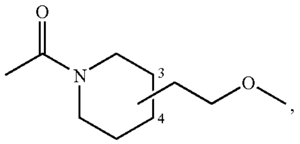

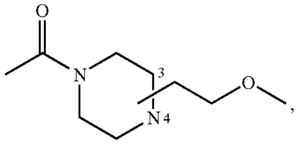

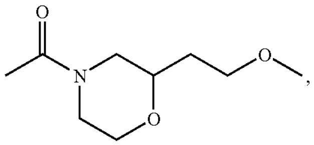

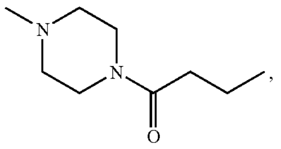

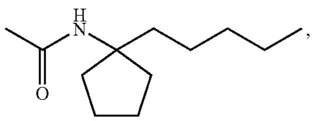

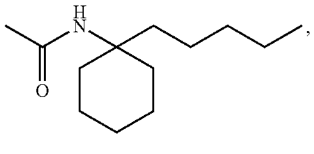

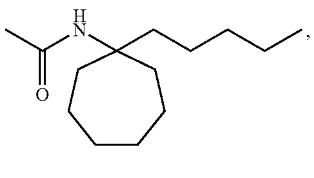

-continued

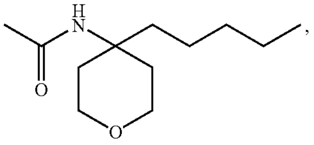

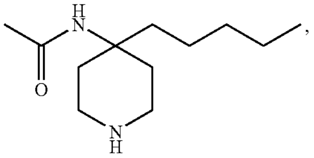

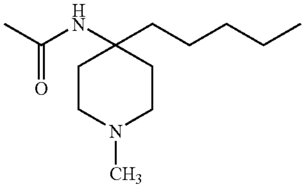

wherein all symbols have the same meanings as described above.

Unless otherwise specified, all isomers are included in the present invention. For example, alkyl, alkenyl, alkynyl and alkylene groups include straight-chain and also branched-chain ones. In addition, isomers in double bond, ring, fused ring (E-, Z—, cis-, trans-isomer), isomers generated from asymmetric carbon atom(s) (R—, S—, α-, β-isomer, enantiomer, diastereomer), optically active isomers having optical rotation (D-, L-, d-, l-isomer), polar compounds separated by chromatography (more polar compound, less polar compound), equilibrium compounds, mixtures thereof at arbitrary ratios and racemic mixtures are included in the present invention.

A preferably compound of formula (I) is the compound which is

[I] n is 1 or 2,

Q is (1) (i) —(C1-4 alkylene, C2-4 alkenylene or C2-4 alkynylene)-Cyc2, (ii) —(C1-4 alkylene)-Z-Cyc3, (iii) C1-4 alkyl substituted with —$NR^{24}R^{25}$, —$S(O)_pR^{25}$, cyano, —$NR^{23}COR^{27}$, —$NR^{23}SO_2R^{28}$ or —$NR^{23}CONR^{24}R^{25}$, (iv) C1-4 alkoxy(C1-4) alkoxy, —$NR^{23}COR^{27}$, —$COR^{28}$, —$OSO_2R^{28}$, —$NR^{23}SO_2R^{28}$ or —$NR^{23}CONR^{24}R^{25}$, (v) a C3-7 mono-carbocyclic ring or 3- to 6-membered mono-heterocyclic ring which is substituted with 1-5 of $R^{30}$, wherein one $R^{30}$ is always substituted on the ring at the non 1-position, (vi) a C8-15 mono-, bi- or tri-carbocyclic ring or 7- to 15-membered mono-, bi- or tri-heterocyclic ring which is substituted with 1-5 of $R^{30}$ or unsubstituted, (vii) -T-Cyc5, (viii) -L-$Cyc^{6-1}$, -L-(C2-4 alkylene)-$Cyc^{6-2}$ or -L-(C1-4 alkylene)$_q$-$Cyc^{6-3}$, D is (1) a 1- or 2-membered linking chain comprising an atom(s) selected from carbon, nitrogen, oxygen and sulfur, which may contain a double bond or a triple bond in the chain and may be substituted with 1-4 of $R^{40}$, (2) a 3- to 6-membered linking chain comprising atoms selected from carbon, nitrogen, oxygen and sulfur, which may contain a double bond or a triple bond in the chain and may be substituted with 1-12 of $R^{40}$, wherein $R^{40}$ substituted on the atom bound to $R^3$, and $R^{42}$ which is a substituent of $R^3$, taken together may form —$(CH_2)_y$—, in which y is 1-4;

[II] n is 1 or 2,

Q is (2) (i) phenoxy, (ii) benzyloxy, (iii) hydroxy(C1-4) alkyl, (iv) C1-4 alkoxy(C1-4) alkyl, or (v) —(C1-4 alkylene)-O—(C1-4 alkylene)-Cyc7, D is (2) a 3- to 6-membered linking chain comprising atoms selected from carbon, nitrogen, oxygen and sulfur, which may contain a double bond or a triple bond in the chain and may be substituted with 1-12 of $R^{40}$, wherein $R^{40}$ substituted on the atom bound to $R^3$, and $R^{42}$ which is a substituent of $R^3$, taken together may form —$(CH_2)_y$—, in which y is 1-4;

[III] n is 1 or 2,

Q is (3) (i) C2-6 alkenyl, (ii) C2-6 alkynyl, (iii) C1-6 alkyl substituted with 1-3 halogen(s), (iv) cyano, (v) nitro, (vi) —$NR^{33}R^{34}$, (vii) —$CONR^{33}R^{34}$, (viii) —$S(O)_p$—(C2-4) alkynyl, (ix) —$S(O)_p$—$CHF_2$, (x) —$S(O)_p$—$NR^{33}R^{34}$, (xi) —O—(C3-6) alkynyl, (xii) —O—$CHF_2$, or (xiii) C3-7 cycloalkyl, D is (1) a 1- or 2-membered linking chain comprising an atom(s) selected from carbon, nitrogen, oxygen and sulfur, which may contain a double bond or a triple bond in the chain and may be substituted with 1-4 of $R^{40}$;

[IV] n is 0,

D is (1) a 1- or 2-membered linking chain comprising an atom(s) selected from carbon, nitrogen, oxygen and sulfur, which may contain a double bond or a triple bond in the chain and may be substituted with 1-4 of $R^{40}$, (2) a 3- to 6-membered linking chain comprising atoms selected from carbon, nitrogen, oxygen and sulfur, which may contain a double bond or a triple bond in the chain and may be substituted with 1-12 of $R^{40}$, wherein $R^{40}$ substituted on the atom bound to $R^3$, and $R^{42}$ which is a substituent of $R^3$, taken together may form —$(CH_2)_y$—, in which y is 1-4;

[V] n is 0, 1 or 2,

Q is (1) (i) —(C1-4 alkylene, C2-4 alkenylene or C2-4 alkynylene)-Cyc2, (ii) —(C1-4 alkylene)-Z-Cyc3, (iii) C1-4 alkyl substituted with —$NR^{24}R^{25}$, —$S(O)_pR^{25}$, cyano, —$NR^{23}COR^{27}$, —$NR^{23}SO_2R^{28}$ or —$NR^{23}CONR^{24}R^{25}$, (iv) C1-4 alkoxy(C1-4) alkoxy, —$NR^{23}COR^{27}$, —$COR^{28}$, —$OSO_2R^{28}$, —$NR^{23}SO_2R^{28}$ or —$NR^{23}CONR^{24}R^{25}$, (v) a C3-7 mono-carbocyclic ring or 3- to 6-membered mono-heterocyclic ring which is substituted with 1-5 of $R^{30}$, wherein one $R^{30}$ is always substituted on the rings at the non 1-position, (vi) a C8-15 mono-, bi- or tri-carbocyclic ring or 7- to 15-membered mono-, bi- or tri-heterocyclic ring which is substituted with 1-5 of $R^{30}$ or unsubstituted, (vii) -T-Cyc5, (viii) -L-$Cyc^{6-1}$, -L-(C2-4 alkylene)-$Cyc^{6-2}$ or -L-(C1-4 alkylene)$_q$-$Cyc^{6-3}$, (2) (i) phenoxy, (ii) benzyloxy, (iii) hydroxy(C1-4) alkyl, (iv) C1-4 alkoxy(C1-4) alkyl, or (v) —(C1-4 alkylene)-O—(C1-4 alkylene)-Cyc7, or (3) (i) C2-6 alkenyl, (ii) C2-6 alkynyl, (iii) C1-6 alkyl substituted with 1-3 halogen(s), (iv) cyano, (v) nitro, (vi) —$NR^{33}R^{34}$, (vii) —$CONR^{33}R^{34}$, (viii) —$S(O)_p$—(C1-4) alkynyl, (ix) —$S(O)_p$—$CHF_2$, (x) —$S(O)_p$—$NR^{33}R^{34}$, (xi) —O—(C3-6) alkynyl, (xii) —O—$CHF_2$, or (xiii) C3-7 cycloalkyl, D is (3) a 7- to 10-membered linking chain comprising atoms selected from carbon, nitrogen, oxygen and sulfur, which may contain a double bond or a triple bond in the chain and may be substituted with 1-20 of $R^{40}$, wherein $R^{40}$ substituted on the atom bound to $R^3$, and $R^{42}$ which is a substituent of $R^3$, taken together may form —$(CH_2)_y$—.

In the compound specified in [III], when D is —$NR^{40-2}$CO— or —$NR^{40-2}$CS—, wherein $R^{40-2}$ is hydrogen or C1-8 alkyl, and Q is C1-6 alkyl substituted with 1-3 halogen(s), cyano or nitro, A is (i) a single bond, (ii) C1-6 alkylene, (iii) C2-6 alkenylene, (iv) C2-6 alkynylene, (v) —O—(C1-3 alkylene), (vi) —S—(C1-3 alkylene), (vii) —$NR^{20}$—(C1-3 alkylene), (viii) —$CONR^{21}$—(C1-3 alkylene), (ix) —(C1-3 alkylene)-O—(C1-3 alkylene), (x) —(C1-3 alkylene)-S—(C1-3 alkylene), (xi) —(C1-3 alkylene)-$NR^{20}$—(C1-3 alkylene), (xii) —(C1-3 alkylene)-$CONR^{21}$—(C1-3 alkylene), (xiii) —Cyc1 or (xv) —Cyc1-(C1-4 alkylene).

In the compound specified in [V], when D is —$NR^{40-2}$CO—(C5-6 alkylene) or —$NR^{40-2}$CS—(C5-6 alkylene), in which the carbon atoms of the C5-6 alkylene are unsubstituted or substituted with C1-6 alkoxy, and Q is C1-6 alkyl substituted with 1-3 halogen(s), cyano or nitro, A is (i) a single bond, (ii) C1-6 alkylene, (iii) C2-6 alkenylene, (iv) C2-6 alkynylene, (v) —O—(C1-3 alkylene), (vi) —S—(C1-3 alkylene), (vii) —$NR^{20}$—(C1-3 alkylene), (viii) —$CONR^{21}$—(C1-3 alkylene), (ix) —(C1-3 alkylene)-O—(C1-3 alkylene), (x) —(C1-3 alkylene)-S—(C1-3 alkylene), (xi) —(C1-3 alkylene)-$NR^{20}$—(C1-3 alkylene), (xii) —(C1-3 alkylene)-$CONR^{21}$—(C1-3 alkylene), (xiii) —Cyc1 or (xv) —Cyc1-(C1-4 alkylene).

Among the compounds specified in [I], preferred is a compound wherein

[I-1] n is 1 or 2,

Q is (1) (i) —(C1-4 alkylene, C2-4 alkenylene or C2-4 alkynylene)-Cyc2, (ii) —(C1-4 alkylene)-Z-Cyc3, (iii) C1-4 alkyl substituted with —$NR^{24}R^{25}$, —$S(O)_pR^{25}$, cyano, —$NR^{23}COR^{27}$, —$NR^{23}SO_2R^{28}$ or —$NR^{23}CONR^{24}R^{25}$, (iv) C1-4 alkoxy(C1-4) alkoxy, —$NR^{23}COR^{27}$, —$COR^{28}$, —$OSO_2R^{28}$, —$NR^{23}SO_2R^{28}$ or —$NR^{23}CONR^{24}R^{25}$, (v) a C3-7 mono-carbocyclic ring or 3- to 6-membered mono-heterocyclic ring which is substituted with 1-5 of $R^{20}$, wherein one $R^{20}$ is always substituted on the ring at the non 1-position,
(vi) a C8-15 mono-, bi- or tri-carbocyclic ring or 7- to 15-membered mono-, bi- or tri-heterocyclic ring which is substituted with 1-5 of $R^{30}$ or unsubstituted,
(vii) -T-Cyc5,
(viii) -L-$Cyc^{6-1}$, -L-(C2-4 alkylene)-$Cyc^{6-2}$ or -L-(C1-4 alkylene)$_q$-$Cyc^{6-3}$,
D is
(1) a 1- or 2-membered linking chain comprising an atom(s) selected from carbon, nitrogen, oxygen and sulfur, which may contain a double bond or a triple bond in the chain and may be substituted with 1-4 of $R^{40}$, and
[I-2] n is 1 or 2,
Q is
(1) (i) —(C1-4 alkylene, C2-4 alkenylene or C2-4 alkynylene)-Cyc2,
(ii) —(C1-4 alkylene)-Z-Cyc3,
(iii) C1-4 alkyl substituted with —$NR^{24}R^{25}$, —$S(O)_pR^{25}$, cyano, —$NR^{23}COR^{27}$, —$NR^{23}SO_2R^{28}$ or —$NR^{23}CONR^{24}R^{25}$,
(iv) C1-4 alkoxy(C1-4) alkoxy, —$NR^{23}COR^{27}$, —$COR^{28}$, —$OSO_2R^{28}$, —$NR^{23}SO_2R^{28}$ or —$NR^{23}CONR^{24}R^{25}$,
(v) a C3-7 mono-carbocyclic ring or 3- to 6-membered mono-heterocyclic ring which is substituted with 1-5 of $R^{20}$, wherein $R^{20}$ is always substituted on the above ring at the non 1-position,
(vi) a C8-15 mono-, bi- or tri-carbocyclic ring or 7- to 15-membered mono-, bi- or tri-heterocyclic ring which is substituted with 1-5 of $R^{30}$ or unsubstituted,
(vii) -T-Cyc5,
(viii) -L-$Cyc^{6-1}$, -L-(C2-4 alkylene)-$Cyc^{6-2}$ or -L-(C1-4 alkylene)$_q$-$Cyc^{6-3}$,
D is
(2) a 3- to 6-membered linking chain comprising atoms selected from carbon, nitrogen, oxygen and sulfur, which may contain a double bond or a triple bond in the chain and may be substituted with 1-12 of $R^{40}$, wherein $R^{40}$ substituted on the atom bound to $R^3$, and $R^{42}$ which is a substituent of $R^3$, taken together may form —$(CH_2)_y$—, in which y is 1-4.

More preferably A in the present compound of formula (I) is
(i) a single bond,
(ii) C1-4 alkylene,
(iii) C2-4 alkenylene,
(iv) C2-4 alkynylene,
(v) —O—(C1-2 alkylene),
(vi) —S—(C1-2 alkylene),
(vii) —$NR^{20}$—(C1-2 alkylene),
(viii) —$CONR^{21}$—(C1-2 alkylene),
(ix) —$CH_2$—O—(C1-2 alkylene),
(x) —$CH_2$—S—(C1-2 alkylene),
(xi) —$CH_2$—$NR^{20}$—(C1-2 alkylene),
(xii) —$CH_2$—$CONR^{21}$—(C1-2 alkylene),
(xiii) —Cyc1,
(xiv) —(C1-2 alkylene)-Cyc1 or
(xv) —Cyc1-(C1-2 alkylene).

Especially preferable A is a single bond, methylene, ethylene, trimethylene, tetramethylene, vinylene, 1-propenylene, ethynylene, 1-propynilene, —O—$CH_2$—, —O—$(CH_2)_2$—, —$CH_2$—O—$CH_2$—, —S—$CH_2$—, —S—$(CH_2)_2$—, —$CH_2$—S—$CH_2$—, —$NR^{20}$—$CH_2$—, —$NR^{20}$—$(CH_2)_2$—, —$CH_2$—$NR^{20}$—$CH_2$—, —$CH_2$-phenyl, or —CONH—$CH_2$.

Preferable B ring in the present compound of formula (I) is a C3-12 mono- or bi-carbocyclic ring or 3- to 12-membered mono- or bi-heterocyclic ring containing 1-4 nitrogen(s), 1-2 oxygen(s) and/or one sulfur.

Concrete B ring includes cyclopropane, cyclobutane, cyclopentane, cyclohexane, cycloheptane, cyclopentene, cyclohexene, cycloheptene, benzene, indene, naphthalene, indan, tetrahydronaphthalene, azulene, aziridine, oxirane, thiirane, azetidine, oxetane, thietane, pyrrolidine, pyrroline, imidazoline, imidazolidine, pyrazoline, pyrazolidine, furan, thiophene, pyrrole, oxazole, isoxazole, thiazole, isothiazole, imidazole, pyrazole, triazole, pyridine, pyrimidine, pyrazine, piperidine, piperazine, morpholine, thiomorpholine, pyran, thiopyran, azepine, diazepine, perhydroazepine, benzofuran, benzothiophene, benzothiazole, indole, isoindole, benzoxazole, benzimidazole, benzopyrazole, benzotriazole, benzodioxane, thienopyridine, indoline, isoindoline, 1,3-dioxaindan, chroman, isochroman, quinoline, isoquinoline, quinazoline, quinoxaline, tetrahydroquinoline, and tetrahydroisoquinoline ring.

Preferable B ring is cyclopentane, cyclohexane, cycloheptane, cyclopentene, cyclohexene, benzene, indene, naphthalene, indan, tetrahydronaphthalene, furan, thiophene, pyrrole, oxazole, isoxazole, thiazole, isothiazole, imidazole, pyrazole, pyridine, pyrimidine, pyrazine, azepine, benzofuran, benzothiophene, benzothiazole, indole, isoindole, benzoxazole, benzimidazole, benzopyrazole, indoline, isoindoline, quinoline, and tetrahydroquinoline ring. Especially preferable B ring is cyclohexane, benzene, indene, naphthalene, indan, tetrahydronaphthalene, furan, thiophene, pyrrole, pyridine, benzofuran, benzothiophene, indole, isoindole, indoline, isoindoline, quinoline, or tetrahydroquinoline ring.

Preferable Q in the present compound of formula (I) is
(1)(i) —(C1-4 alkylene or C2-4 alkenylene)-Cyc2,
(ii) —(C1-4 alkylene)-Z-Cyc3,
(iii) C1-4 alkyl substituted with —$NR^{24}R^{25}$, —$S(O)_pR^{25}$, cyano, —$NR^{23}COR^{27}$, —$NR^{23}SO_2R^{28}$ or —$NR^{23}CONR^{24}R^{25}$,
(iv) C1-4 alkoxy(C1-4) alkoxy, —$NR^{23}COR^{27}$, —$COR^{28}$, —$OSO_2R^{28}$, —$NR^{23}SO_2R^{28}$ or —$NR^{23}CONR^{24}R^{25}$,
(vi) a C7-12 mono- or bi-carbocyclic ring or 7- or 12-membered mono- or bi-heterocyclic ring which is substituted with 1-5 of $R^{30}$ or unsubstituted,
(vii) -T-Cyc5,
(viii) -L-$Cyc^{6-1}$, -L-(C3-6 cycloalkyl), -L-$CH_2$—(C3-6 cycloalkyl), -L-(C2-4 alkylene)-$Cyc^{6-2}$ or -L-(C1-4 alkylene)$_q$-$Cyc^{6-3}$,
(2) (i) phenoxy,
(ii) benzyloxy,
(iii) hydroxy(C1-4) alkyl,
(iv) C1-4 alkoxy(C1-4) alkyl, or
(v) —(C1-4 alkylene)-O-benzyl, or
(3) (i) C2-6 alkenyl,
(ii) C2-6 alkynyl,
(iii) C1-6 alkyl substituted with 1-3 halogen(s),
(iv) cyano,
(v) nitro,
(vi) —$NR^{33}R^{34}$,
(vii) —$CONR^{33}R^{34}$,
(viii) —Cyc8.

In preferable Q, preferable Cyc2 is a C3-12 mono- or bi-carbocyclic ring or 3- to 12-membered mono- or bi-heterocyclic ring containing 1-4 nitrogen(s), 1-2 oxygen(s) and/or one sulfur, which is substituted with 1-5 of $R^{30}$ or unsubstituted. Concrete Cyc2 includes cyclopropane, cyclobutane, cyclopentane, cyclohexane, cycloheptane, cyclopentene, cyclohexene, cycloheptene, benzene, indene, naphthalene, indan, tetrahydronaphthalene, azulene, aziridine, oxirane, thiirane, azetidine, oxetane, thietane, pyrrolidine, pyrroline, imidazoline, imidazolidine, pyrazoline, pyrazolidine, furan, thiophene, pyrrole, oxazole, isoxazole, thiazole, isothiazole, imidazole, pyrazole, triazole, tetrazole, pyridine, pyrimidine, pyrazine, piperidine, piperazine, morpholine, thiomorpholine, pyran, thiopyran, azepine, diazepine, perhydroazepine, benzofuran, benzothiophene, benzothiazole, indole, benzoxazole, benzimidazole, benzopyrazole, benzotriazole, benzodioxane, thienopyridine, indoline, isoindoline, 1,3-dioxaindan, chroman, isochroman, quinoline, isoquinoline, quinazoline, and quinoxaline ring.

More preferable Q is cyclopropane, cyclohexane, benzene, naphthalene, tetrahydronaphthalene, pyrrolidine, imidazoline, furan, thiophene, pyrrole, oxazole, thiazole, imidazole, pyrazole, triazole, pyridine, pyrimidine, pyrazine, piperazine, morpholine, indole, benzimidazole, or benzothiazole.

All groups of Z is preferable.

Preferable Cyc3 is a C3-12 mono- or bi-carbocyclic ring or 3- to 12-membered mono- or bi-heterocyclic ring containing 1-4 nitrogen(s), 1-2 oxygen(s) and/or one sulfur, which is substituted with 1-5 of $R^{30}$ or unsubstituted. Concrete Cyc3 includes cyclopropane, cyclobutane, cyclopentane, cyclohexane, cycloheptane, cyclopentene, cyclohexene, cycloheptene, benzene, indene, naphthalene, indan, tetrahydronaphthalene, azulene, aziridine, oxirane, thiirane, azetidine, oxetane, thietane, pyrrolidine, pyrroline, imidazoline, imidazolidine, pyrazoline, pyrazolidine, furan, thiophene, pyrrole, oxazole, isoxazole, thiazole, isothiazole, imidazole, pyrazole, triazole, tetrazole, pyridine, pyrimidine, pyrazine, piperidine, piperazine, morpholine, thiomorpholine, pyran, thiopyran, azepine, diazepine, perhydroazepine, benzofuran, benzothiophene, benzothiazole, indole, benzoxazole, benzimidazole, benzopyrazole, benzotriazole, benzodioxane, thienopyridine, indoline, isoindoline, 1,3-dioxaindan, chroman, isochroman, quinoline, isoquinoline, quinazoline, and quinoxaline ring.

More preferable Cyc3 is cyclopropane, cyclohexane, benzene, naphthalene, tetrahydronaphthalene, pyrrolidine, furan, thiophene, pyrrole, oxazole, thiazole, imidazole, pyrazole, triazole, pyridine, pyrimidine, pyrazine, piperazine, morpholine, indole, benzimidazole, or benzothiazole.

All groups of T is preferable.

Preferable Cyc5 is 3- to 12-membered mono- or bi-heterocyclic ring containing 1-4 nitrogen(s), 1-2 oxygen(s) and/or one sulfur that they are substituted with 1-5 of $R^{30}$ or unsubstituted. Concrete Cyc5 includes aziridine, oxirane, thiirane, azetidine, oxetane, thietane, pyrrolidine, pyrroline, imidazoline, imidazolidine, pyrazoline, pyrazolidine, furan, thiophene, pyrrole, oxazole, isoxazole, thiazole, isothiazole, imidazole, pyrazole, triazole, tetrazole, pyridine, pyrimidine, pyrazine, piperidine, piperazine, morpholine, thiomorpholine, pyran, thiopyran, azepine, diazepine, perhydroazepine, benzofuran, benzothiophene, benzothiazole, indole, benzoxazole, benzimidazole, benzopyrazole, benzotriazole, benzodioxane, thienopyridine, indoline, isoindoline, 1,3-dioxaindan, chroman, isochroman, quinoline, isoquinoline, quinazoline, or quinoxaline ring.

More preferable Cyc5 is pyrrolidine, furan, thiophene, pyrrole, oxazole, thiazole, imidazole, pyrazole, triazole, pyridine, pyrimidine, pyrazine, piperazine, morpholine, indole, benzimidazole, benzothiazole, benzodioxane, or 1,3-dioxaindan.

In the compound of formula (I) of the present invention, (1) preferable D as the 1- or 2-membered linking chain comprising an atom(s) selected from carbon, nitrogen, oxygen and sulfur is $—CH_2—$, $—(CH_2)_2—$, —CH=CH—, —C≡C—, —O—, —NH—, —CO—, $—O—CH_2—$, $—CH_2—O—$, —CONH—, —NHCO—, $—NHSO_2—$, $—N(CH_3)—SO_2—$, or $—SO_2NH—$, (2) preferable D as the 3- to 6-membered linking chain comprising atoms selected from carbon, nitrogen, oxygen and sulfur is $—(CH_2)_3—$, $—(CH_2)_4—$, $—(CH_2)_5—$, $—(CH_2)_6—$, $—CH=CH—CH_2—$, $—CH=CH—(CH_2)_2—$, $—CH=CH—(CH_2)_3—$, $—C≡C—CH_2—$, $—C≡C—(CH_2)_2—$, $—C≡C—(CH_2)_3—$, $—(CH_2)_2—O—$, $—(CH_2)_3—O—$, $—(CH_2)_4—O—$, $—O—(CH_2)_5—$, $—O—CH_2—CH(R^{40})—$, $—O—CH_2—CH(R^{40})—CH_2—$, $—O—CH_2—CH_2—CH(R^{40})—$, $—O—CH_2—CH=CH—$, $—O—(CH_2)_2—CH=CH—$, $—NR^{40-1}—(CH_2)_2—$, $—NR^{40-1}—(CH_2)_3—$, $—S—(CH_2)_2—$, $—S—(CH_2)_3—$, $—SO_2—(CH_2)_2—$, $—SO_2—(CH_2)_3—$, $—CH_2—NHCO—$, $—NHCO—CH_2—$, $—NR^{40-1}CO—CH_2—$, $—NHCO—CHR^{40}—$, $—NHCO—C(R^{40})_2—$, $—NHCO—(CH_2)_2—$, $—NHCO—CHR^{40}—CH_2—$, $—NHCO—CH_2—CHR^{40}—$, $—NHCO—CHR^{40}—CHR^{40}—$, $—CONH—CH_2—$, $—CONR^{40-1}—CH_2—$, $—CONH—CHR^{40}—$, $—CONH—C(R^{40})_2—$, $—CONH—(CH_2)_2—$, $—CONH—CHR^{40}—CH_2—$, $—CONH—CHR^{40}—(CH_2)_2—$, $—CONH—CH_2—CHR^{40}—$, $—CONH—CH(R^{40})—CH(R^{40})—$, $—NHSO_2—CH_2—$, $—NR^{40-1}SO_2—CH_2—$, $—NHSO_2—CHR^{40}—$, $—NHSO_2—C(R^{40})_2—$, $—NHSO_2—(CH_2)_2—$, $—NHSO_2—CHR^{40}—CH_2—$, $—NHSO_2—CH_2—CHR^{40}—$, $—NHSO_2—CH(R^{40})—CH(R^{40})—$, $—SO_2NH—CH_2—$, $—SO_2NR^{40-1}—CH_2—$, $—SO_2NH—CHR^{40}—$, $—SO_2NH—C(R^{40})_2—$, $—SO_2NH—(CH_2)_2—$, $—SONH_2—CHR^{40}—CH_2—$, $—SO_2NH—CH_2—CHR^{40}—$, $—SO_2NH—CH(R^{40})—CH(R^{40})—$, $—CH_2—O—CH_2—$, $—CH_2—O—(CH_2)_2—$, $—(CH_2)_2—O—CH_2—$, $—(CH_2)_2—O—(CH_2)_2—$, $—O—(CH_2)_2—O—$, $—O—(CH_2)_3—O—$, $—O—(CH_2)_4—O—$, $—O—CH_2—CH(R^{40})—CH_2—O—$, $—O—CH_2—CO—$, $—O—CH_2—NR^{40-1}—$, $—O—(CH_2)_2—NR^{40-1}—$, $—O—(CH_2)_2—NR^{40-1}—CH_2—$, $—O—(CH_2)_3—NR^{40-1}$, $—O—CH_2—CH_2—NHCO—$, $—O—CH_2—CH_2—NR^{40-1}CO—$, $—O—CH_2—CH(R^{40})—NHCO—$, $—O—CH_2—CH(R^{40})—NR^{40-1}—CO—$, $—O—CH_2—CH_2—NHSO_2—$, $—O—CH_2—CH_2—NR^{40-1}SO_2—$, $—O—CH_2—CH(R^{40})—NHSO_2—$, $—O—CH_2—CH(R^{40})—NR^{40-1}SO_2—$, $—O—CH_2—CONH—$, $—O—CH_2—CONR^{40-1}—$, $—O—CH_2—CONH—CH_2—$, $—O—(CH_2)_2—CONH—CH_2—$, $—O—CH_2—CONR^{40-1}—CHR^{40}—$, $—O—CH_2—NHCO—CH_2—$, $—O—(CH_2)_2—NHCO—CH_2—$, $—O—CH_2—NR^{40-1}—CO—CHR^{40}—$,

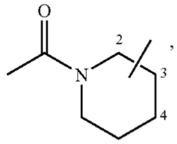
,
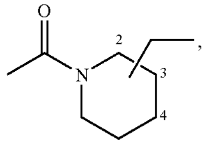
,
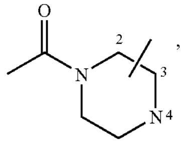
,
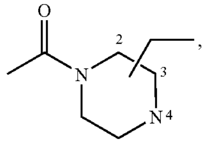
,

-continued

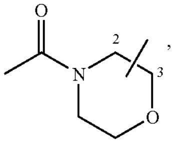, 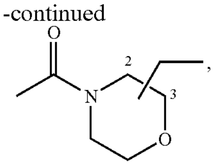,

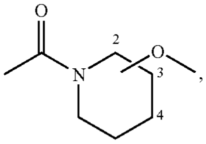, 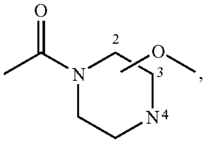,

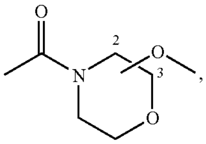, 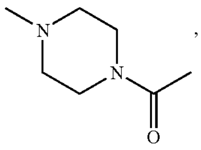,

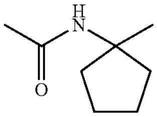, 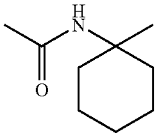, 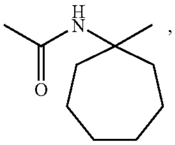,

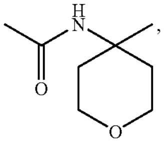, 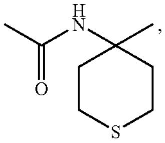, 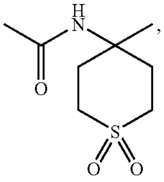,

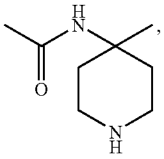, 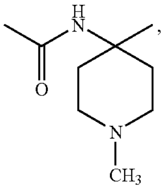,

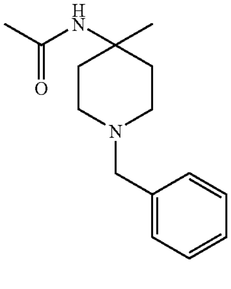

(3) preferable D as, the 7- to 10-membered linking chain comprising atoms selected from carbon, nitrogen, oxygen and sulfur is —$(CH_2)_7$—, —$(CH_2)_8$—, —$(CH_2)_9$—, —$(CH_2)_{10}$—, —O—$(CH_2)_6$—, —O—$(CH_2)_7$—, —O—$(CH_2)_8$—, —O—$(CH_2)_9$—, —$NR^{40-1}$—$(CH_2)_6$—, —$NR^{40-1}$—$(CH_2)_7$—, —S—$(CH_2)_6$—, —S—$(CH_2)_7$—, —$SO_2$—$(CH_2)_6$—, —$SO_2$—$(CH_2)_7$—, —NHCO—$(CH_2)_5$—, —$NR^{40-1}$—CO—$(CH_2)_5$—, —CONH—$(CH_2)_5$—, CO—$NR^{40-1}$—$(CH_2)_5$—, —$NHSO_2$—$(CH_2)_5$—, —$NR^{40-1}$—$SO_2$—$(CH_2)_5$—, —$SO_2NH$—$(CH_2)_5$—, —$SO_2NR^{40-1}$—$(CH_2)_5$—, —O—$(CH_2)_5$—O—, —O—$(CH_2)_6$—O—, —O—$(CH_2)_5$—$NR^{40-1}$—, —O—$(CH_2)_5$—$NR^{40-1}$—, —O—$(CH_2)_4$—NHCO—, —O—$(CH_2)_4$—$NR^{40-1}$—CO—, —O—$(CH_2)_4$—CONH—, —O—$(CH_2)_4$—$CONR^{40-1}$—, —$(CH_2)_6$—O—, —$(CH_2)_7$—O—, —$(CH_2)_8$—O—, —$(CH_2)_9$—O—,

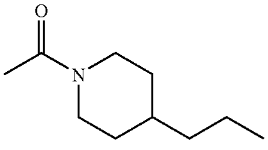,

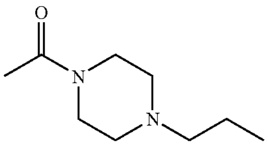,

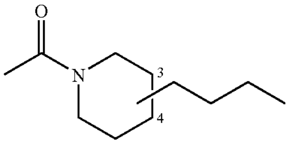,

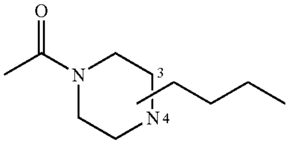,

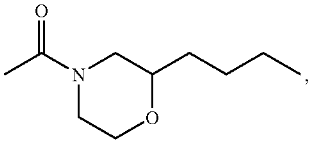,

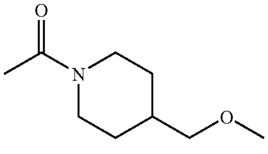,

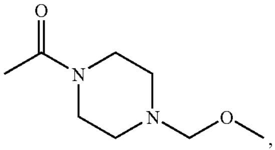,

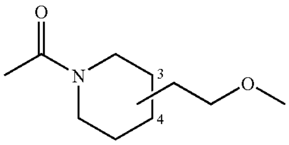,

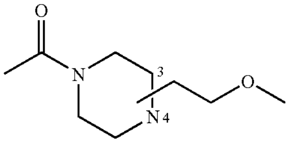,

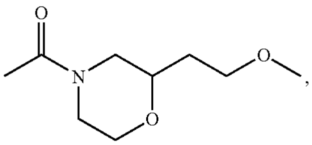,

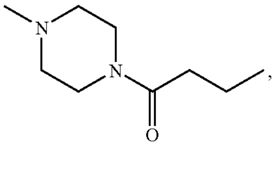,

-continued

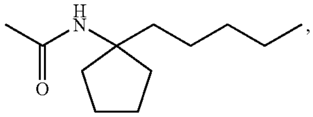
,
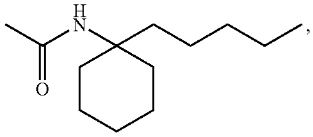
,
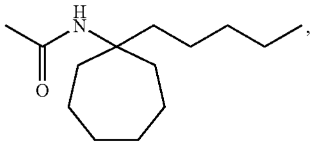
,
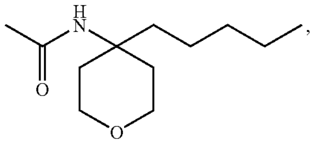
,
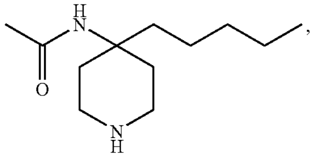
,
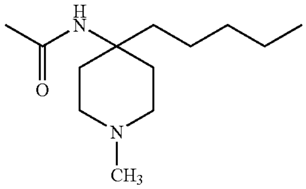

Preferable $R^{40}$ is methyl, ethyl, propyl, isopropyl, butyl, isobutyl, methoxy, ethoxy, propoxy, butoxy, methoxymethyl, methoxyethyl, hydroxy, hydroxymethyl, hydroxyethyl, cyclopropyl, cyclohexyl, benzene, cyclopropylmethyl, cyclohexylmethyl, benzyl, or acetyl.

Preferable $R^{40-1}$ is methyl, ethyl, propyl, isopropyl, butyl, isobutyl, methoxymethyl, methoxyethyl, hydroxymethyl, hydroxyethyl, cyanomethyl, cyanoethyl, methylsulfonyl, cyclopropyl, cyclohexyl, benzene, cyclopropylmethyl, cyclohexylmethyl, benzyl, or acetyl.

In the compound of the present invention, in the linking of D, a structure wherein $R^{40}$ which binds to the atom bound to $R^3$, and $R^{42}$ which is a substituent of $R^3$, taken together forms $-(CH_2)_y-$, is a ring of formula:

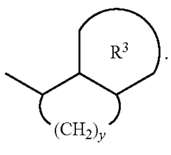
.

Concretely, it is

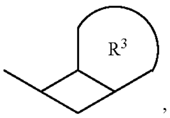
,
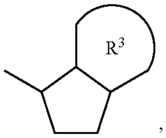
,
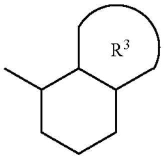
or
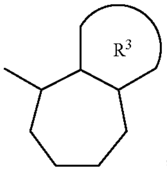
, and especially, it is preferable that $R^3$ is benzene ring.

In the compound of the present invention, preferable $R^3$ is (1) C1-6 alkyl, or (2) a C3-12 mono- or bi-carbocyclic ring or 3- to 12-membered mono-, bi- or tri-heterocyclic ring containing 1-4 nitrogen(s), 1-2 oxygen(s) and/or one sulfur. Concretely, examples include (1) methyl, ethyl, propyl, isopropyl, butyl, isobutyl, t-butyl, pentyl and hexyl, and (2) substituted with 1-5 of $R^{42}$ or unsubstituted, cyclopropane, cyclobutane, cyclopentane, cyclohexane, cycloheptane, cyclopentene, cyclohexene, cycloheptene, benzene, indene, naphthalene, indan, tetrahydronaphthalene, azulene, aziridine, oxirane, thiirane, azetidine, oxetane, thietane, pyrrolidine, pyrroline, imidazoline, imidazolidine, pyrazoline, pyrazolidine, furan, thiophene, pyrrole, oxazole, isoxazole, thiazole, isothiazole, imidazole, pyrazole, triazole, tetrazole, pyridine, pyrimidine, pyrazine, piperidine, piperazine, tetrahydropyridine, morpholine, thiomorpholine, pyran, thiopyran, azepine, diazepine, perhydroazepine, benzofuran, benzothiophene, benzothiazole, indole, benzoxazole, benzimidazole, benzopyrazole, benzotriazole, benzodioxane, thienopyridine, indoline, isoindoline, 1,3-dioxaindan, chroman, isochroman, quinoline, isoquinoline, quinazoline, quinoxaline, tetrahydroquinoline, tetrahydroisoquinoline, carbazole, phenoxazine, acridine, and 9,10-dihydroacridine.

More preferable $R^3$ is (1) propyl, isopropyl, butyl, isobutyl, pentyl or hexyl, or (2) cyclohexane, benzene, naphthalene, tetrahydronaphthalene, furan, thiophene, pyrrole, imidazole, pyrazole, triazole, pyridine, piperidine, piperazine, tetrahydropyridine, morpholine, benzofuran, benzothiophene, indole, benzimidazole, benzopyrazole, benzotriazole, benzodioxane, 1,3-dioxaindan, chroman, quinoline, isoquinoline, tetrahydroquinoline, tetrahydroisoquinoline, carbazole, phenoxazine, or 9,10-dihydroacridine which is substituted with 1-5 of $R^{42}$ or unsubstituted.

In the compounds of the present invention of formula (I), for example, concrete compounds are the compounds described in examples.

Salt:

The compound of the present invention of formula (I) may be converted into a corresponding salt by known methods. Non-toxic and water-soluble salts are preferable. In the present invention, salts are salts of alkali metals, such as potassium, sodium, etc.; salts of alkaline-earth metals, such as calcium, magnesium, etc.; ammonium salts, pharmaceutically acceptable organic amines, such as tetramethylammonium, triethylamine, methylamine, dimethylamine, cyclopentylamine, benzylamine, phenethylamine, piperidine, monoethanolamine, diethanolamine, tris(hydroxymethyl)methylamine, lysine, arginine, N-methyl-D-glucamine, etc.

In the present invention, preferable acid addition salts are non-toxic and water-soluble salts. In the present invention, acid addition salts are salts of inorganic acids such as hydrochloride, hydrobromide, sulfate, phosphate, nitrate; salts of organic acids e.g. acetate, lactate, tartrate, oxalate, fumarate, maleate, citrate, benzoate, methanesulphonate, ethanesulphonate, benzenesulphonate, toluenesulphonate, isethionate, glucuronate, gluconate.

The compound of formulae (I) and a salt thereof may be converted into the corresponding hydrates by conventional means.

Preparation of the Compound of the Present Invention

The present compound of formula (I) may be prepared, for example, by the following method.

(1) In the compound of formula (I), wherein $R^1$ is COOH, that is, the compound of formula (Ia):

(Ia)

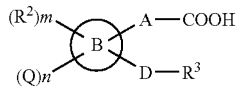

wherein all symbols have the same meanings as described above;

may be prepared by subjecting to deprotection the compound of formula (Ib)

(Ib)

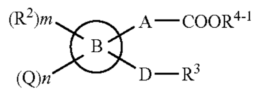

wherein $R^{4-1}$ is C1-6 alkyl and the other symbols have the same meanings as described above.

The method of deprotection is known, for example, it includes the method of (1) deprotection under alkaline conditions, (2) deprotection under acidic conditions, (3) hydrogenolysis.

Deprotection under alkaline conditions is known, for example it may be carried out in water-miscible organic solvent (e.g. methanol, ethanol, tetrahydrofuran, dioxane or a mixture thereof), using an aqueous solution of alkali (e.g. sodium hydroxide, potassium hydroxide or potassium carbonate), or a mixture thereof at −10-90° C.

Deprotection under acidic conditions may be carried out, for example, in a organic solvent (e.g. dichloromethane, chloroform, dioxane, ethyl acetate, anisole), using an organic acid (e.g. acetic acid, trifluoroacetic acid, methanesulfonic acid, p-tosylic acid), or an inorganic acid (e.g. hydrogen chloride or sulfuric acid) or a mixture thereof (e.g. hydrogen bromide/acetic acid) at 0-100° C.

Hydrogenolysis may be carried out, for example, in a solvent (ether, e.g. tetrahydrofuran, dioxane, dimethoxyethane, diethyl ether; alcohol, e.g. methanol, ethanol; benzene, e.g. benzene, toluene; ketone, e.g. acetone, methyl ethyl ketone; nitrile, e.g. acetonitrile; amide, e.g. dimethylformamide; water, ethyl acetate, acetic acid or two more mixture thereof), in the presence of a catalyst (e.g. palladium on carbon, palladium black, palladium hydroxide, platinum dioxide or Raney-nickel), at ordinary or elevated pressure of hydrogen gas or in the presence of ammonium formate at 0-200° C.

(2) The compound of formula (Ib) may be prepared by reacting (i) the compound of formula (II-1)

(II-1)

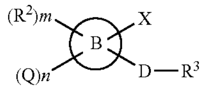

wherein X is halogen and the other symbols have the same meanings as described above; and the compound of formula (III-1)

H-A-$COOR^{4-1}$ (III-1)

wherein all symbols have the same meanings as described above; or (ii) the compound of formula (II-1) and the compound of formula (III-2)

XZn-A-$COOR^{4-1}$ (III-2)

wherein all symbols have the same meanings as described above.

Besides, (iii) the compound of formula (Ib) may be also prepared by reacting the compound of formula (II-2)

(II-2)

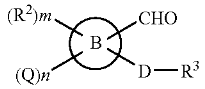

wherein all symbols have the same meanings as described above;

and a Wittig reagent or a malonic acid.

The above reactions (i) and (ii) are known, for example, it may be carried out in an organic solvent (e.g. dimethylsulfoxide, tetrahydrofuran, dimethylformamide), in the presence or absence of a tertiary amine (e.g. dimethylaminopyridine, pyridine, triethylamine), using a ligand (e.g. 1,1'-bis(diphenylphosphino)ferrocene) and a palladium complex (e.g. bisacetoxy palladium) at 60-120° C.

The above reaction (iii) is known, for example, the reaction with a Wittig reagent may be carried out in an organic solvent (e.g. tetrahydrofuran, dimethylsulfoxide), in the presence of an base (sodium hydroxide, potassium t-butoxide), using a Wittig reagent (e.g. triethyl phosphonoacetate, 4-triphenyl phosphinobutyrate), at 0-50° C., and the reaction with a malonic acid may be carried out in an organic solvent (e.g. pyridine), using piperidine at 100-120° C.

Besides, (iv) in the compound of formula (Ib), the compound wherein one of Q is —(C1-4 alkylene, C2-4 alkenylene or C2-4 alkynylene)-Cyc2, —(C1-4 alkylene)-O-Cyc3, —O-$Cyc^{6-1}$, —O—$CH_2$-$Cyc^{6-1}$, —O—(C2-4 alkylene)-$Cyc^{6-2}$ or —O—(C1-4 alkylene)$_q$-$Cyc^{6-3}$, that is, the compound of formula (Ib-1)

(Ib-1)

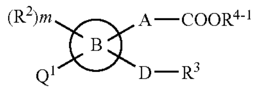

wherein $Q^1$ is —(C1-4 alkylene, C2-4 alkenylene or C2-4 alkynylene)-Cyc2, —(C1-4 alkylene)-O-Cyc3, —O-$Cyc^{6-1}$, —O—$CH_2$-$Cyc^{6-1}$, —O—(C2-4 alkylene)-$Cyc^{6-2}$ or —O—(C1-4 alkylene)$_q$-$Cyc^{6-3}$, and the other symbols have the same meanings as described above;

may be also prepared by reacting the compound of formula (Ib-2)

(Ib-2)

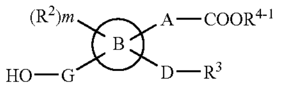

wherein G is a single bond, C1-4 alkylene, C2-4 alkenylene or C2-4 alkynylene and the other symbols have the same meanings as described above; with (a) mesyl chloride, subsequently, by reacting the compound of formula (IV-1)

Cyc2 (IV-1)

wherein all symbols have the same meanings as described above; or (b) the compound of formula (IV-2)

Cyc3-OH (IV-2), the compound of formula (IV-3)

$Cyc^{6-1}$-OH (IV-3), the compound of formula (IV-4)

$Cyc^{6-1}$-$CH_2$—OH (IV-4), the compound of formula (IV-5)

$Cyc^{6-2}$-(C2-4 alkylene)-OH (IV-5)

or the compound of formula (IV-6)

$Cyc^{6-3}$-(C1-4 alkylene)-OH (IV-6)

wherein all symbols have the same meanings as described above.

The above reactions are known, for example, the reaction (a) is carried out in an organic solvent (e.g. tetrahydrofuran, dimethylformamide), in the presence of a tertiary amine (e.g. dimethylaminopyridine, pyridine, triethylamine), with mesyl chloride, and then a obtained compound was added to a mixture of the compound of formula (IV-1) and sodium hydride, in an organic solvent (e.g. tetrahydrofuran, dimethylformamide).

The reaction (b) is carried out in an organic solvent (e.g. tetrahydrofuran), using triphenyl phosphine and diethyl azodicarbonate, at 0-50° C.

Besides, in the compound of formula (Ib), the compound in which A is the group including alkylene may be also prepared by subjecting to reduction the compound in which A is the group including alkenylene.

Reduction reaction is known, for example, it is carried out in organic solvent (e.g. tetrahydrofuran, ethanol or a mixture thereof), using a nickel salt (e.g. nickel dichloride or a hydrate thereof) or a cobalt salt, and sodium borohydride, at 0-50° C. or in organic solvent (e.g. tetrahydrofuran, dimethoxyethane, diethyl ether, methanol, ethanol, benzene, toluene, dimethylformamide, water, ethyl acetate, acetic acid or a mixture of two or more thereof), in the presence of a catalytic agent (palladium-carbon, palladium black, palladium hydroxide, platinum dioxide or Raney-nickel), in the presence or absence of an inorganic acid such as hydrochloric acid, sulfuric acid, hypochlorous acid, boric acid, tetrafluoroboric acid) or an organic acids (e.g. acetic acid, p-toluenesulfonic acid, oxalic acid, trifluoroacetic acid, formic acid), under atmosphere of hydrogen gas, under atmospheric or reduced pressure, at 0-200° C.

(3) The compound of formula (Ib) may be also prepared by methods of (i)-(ix).

(i) In the compound of formula (Ib), wherein D is —$CONR^{40}$-$D^a$-, that is, the compound of formula (Ib-3)

(Ib-3)

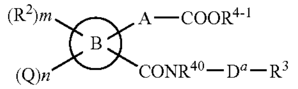

wherein $D^a$ is, as —$CONR^{40}$-$D^a$-, (1) a 2-membered linking chain, (2) a 3- to 6-membered linking chain or (3) a 7- to 10-membered linking chain, and the other symbols have the same meanings as described above;

may be prepared by subjecting to amidation reaction the compound of formula (V-1)

(V-1)

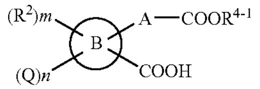

wherein all symbols have the same meanings as described above;

and the compound of formula (VI)

$R^{40}HN$-$D^a$-$R^3$ (VI)

wherein all symbols have the same meanings as described above.

Amidation reaction is known, for example, it is carried out in an organic solvent (e.g. tetrahydrofuran, methylene chloride, chloroform, benzene, toluene, acetone, acetonitrile, diethyl ether, dimethylformamide or a mixture thereof), in the presence or absence of a tertiary amines (e.g. dimethylaminopyridine, pyridine, triethylamine), using a condensing agent (e.g. 1,3-dicyclohexylcarbodiimide (DCC), 1-ethyl-3-[3-(dimethylamino)propyl]carbodiimide (EDC), 2-chloro-1-methylpyridium iodide), or in the presence or absence of a catalytic amount of dimethylformamide, using acyl halide (e.g. oxalyl chloride, thionyl chloride, phosphorus oxychloride) at 0-50° C.

(ii) In the compound of formula (Ib), wherein D is —$NR^{40}CO$-$D^a$-, that is, the compound of formula (Ib-4):

(Ib-4)

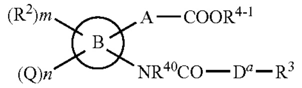

wherein $D^a$ represents, as —$NR^{40}CO$-$D^a$-, (1) a 2-membered linking chain, (2) a 3- to 6-membered linking chain, or (3) a 7- to 10-membered linking chain; and other symbols have the same meanings as described below;

may be prepared by subjecting to amidation reaction the compound of formula (V-2):

(V-2)

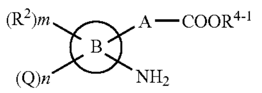

wherein all symbols have the same meanings as described below;

with the compound of formula (VII-1):

$HOOC\text{-}D^{a}\text{-}R^3$ (VII-1)

wherein all symbols have the same meanings as described below.

The amidation reaction is publicly known and carried out by, for example, the method as described above.

(iii) In the compound of formula (Ib), wherein D is —CO-$D^b$-, that is, the compound of formula (Ib-5):

(Ib-5)

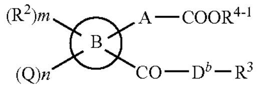

wherein $D^b$ represents, as —CO-$D^b$-, (1) a 1- or 2-membered linking chain, (2) a 3- to 6-membered linking chain, or (3) a 7- to 10-membered linking chain; and other symbols have the same meanings as described below;

may be prepared by reacting the compound of formula (V-3):

(V-3)

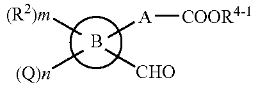

wherein all symbols have the same meanings as described below;

with the compound of formula (VIII):

$XMg\text{-}D^{b}\text{-}R^3$ (VIII)

wherein all symbols have the same meanings as described below;

followed by oxidation reaction.

The reaction is publicly known and carried out in, for example, an organic solvent (tetrahydrofuran, etc.) by using a Grignard reagent (X) (4-methyl-2-phenylpentylmagnesium bromide, etc.) at −78° C.

The oxidation reaction is publicly known and carried out in, for example, an organic solvent (dimethyl sulfoxide, etc.) in the presence of a tertiary amine (dimethylaminopyridine, pyridine, triethylamine, etc.) by using an oxidizing agent (a sulfur trioxide-pyridine complex, etc.) at 0 to 50° C.

(iv) In the compound of formula (Ib), wherein D is —O-$D^b$, that is, the compound of formula (Ib-6):

(Ib-6)

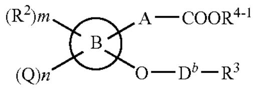

wherein $D^b$ represents, as —O-$D^b$-, (1) a 1- or 2-membered linking chain, (2) a 3- to 6-membered linking chain, or (3) a 7- to 10-membered linking chain; and other symbols have the same meanings as described below;

may be prepared by reacting the compound of formula (V-4):

(V-4)

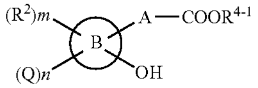

wherein all symbols have the same meanings as described below;

with the compound of formula (IX):

$HO\text{-}D^{b}\text{-}R^3$ (IX)

wherein all symbols have the same meanings as described below.

The reaction is publicly known and carried out in, for example, an organic solvent (tetrahydrofuran, methylene chloride, diethyl ether, acetone, etc.) in the presence of an azo compound (diethyl azodicarboxylate, diisopropyl azodicarboxylate, 1,1'-(azodicarbonyl)dipiperidine, 1,1'-azobis(N,N-dimethylformamide), etc.) and a phosphine compound (triphenylphosphine, tributylphosphine, trimethylmethylphosphine, etc.) at 0 to 60° C.

(v) In the compound of formula (Ib), wherein D is —$SO_2$-$D^b$-, that is, the compound of formula (Ib-7):

(Ib-7)

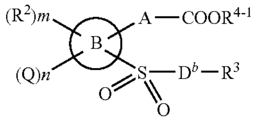

wherein $D^b$ represents, as —$SO_2$-$D^b$-, (1) a 1- or 2-membered linking chain, (2) a 3- to 6-membered linking chain, or (3) a 7- to 10-membered linking chain; and other symbols have the same meanings as described below;

may be prepared by subjecting to oxidation reaction the compound of formula (Ib-8):

(Ib-8)

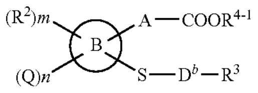

wherein all symbols have the same meanings as described below;

with the compound of formula (VIII).

The oxidation reaction is publicly known and carried out in, for example, an organic solvent (methylene chloride, etc.) in the presence of disodium hydrogen phosphate by using a peracid (3-chloroperbenzoic acid, etc.) at −30 to 50° C.

The compound of formula (Ib-8) may be prepared by reacting the compound of formula (V-5):

(V-5)

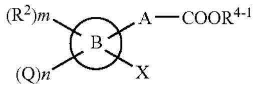

wherein all symbols have the same meanings as described below;

with the compound of formula (X):

$HS\text{-}D^{b}\text{-}R^{3}$ (X)

wherein all symbols have the same meanings as described below.

The reaction is publicly known and carried out in, for example, an organic solvent (dimethylformamide, etc.) by using sodium hydride at 0 to 50° C.

(vi) In the compound of formula (Ib), wherein D is (1) a 2-carbon atom membered linking chain, (2) a 3- to 6-carbon atom membered linking chain, or a 7- to 10-carbon atom membered linking chain, that is, the compound of formula (Ib-9):

(Ib-9)

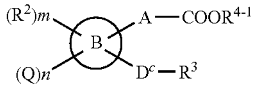

wherein DC represents (1) a 2-carbon atom membered linking chain, (2) a 3- to 6-carbon atom membered linking chain, or a 7- to 10-carbon atom membered linking chain; and other symbols have the same meanings as described below;

may be prepared by reacting the compound of formula (V-6):

(V-6)

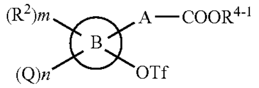

wherein Tf represents trifluoromethylsulfoxy; and other symbols have the same meanings as described below;

with the compound of formula (XI-1):

$\equiv\text{-}D^{c-1}\text{-}R_3$ (XI-1)

wherein $D^{c-1}$ represents (1) a single bond, (2) a 1- to 4-carbon atom membered linking chain, or (3) a 5- to 8-carbon atom membered linking chain; and other symbols have the same meanings as described below;

or the compound of formula (XI-2):

(XI-2)

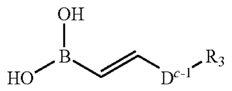

wherein all symbols have the same meanings as described below;

or subjecting the reaction product obtained by the reaction to reduction reaction.

The reaction between the compound of formula (V-6) and the compound of formula (XI-1) is publicly known and carried out in, for example, an organic solvent (dimethylformamide, etc.) by using di(triphenylphosphine)palladium chloride, copper iodide, tetrabutylammonium iodide and a base (triethylamine, etc.) at 0 to 50° C.

The reaction between the compound of formula (V-6) and the compound of formula (XI-1) is publicly known and carried out in, for example, an organic solvent (dimethylformamide, etc.) by using tetrakis(triphenylphosphine)palladium and potassium phosphate at 20 to 100° C.

The reduction reaction is carried out by the same method as described above.

(vii) In the compound of formula (Ib), wherein D is $-CH_2-NR^{40}CO\text{-}D^{d}\text{-}$, that is, the compound of formula (Ib-10):

(Ib-10)

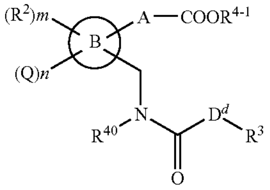

wherein $D^{d}$ represents, as $-CH_2NR^{41}CO\text{-}D^{d}\text{-}$, (1) a 3- to 6-membered linking chain, or (2) a 7- to 10-membered linking chain; and other symbols have the same meanings as described below;

may be prepared by subjecting to amidation reaction the compound of formula (V-7):

(V-7)

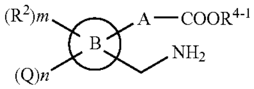

wherein all symbols have the same meanings as described below;

with the compound of formula (VII-2):

$HOOC\text{-}D^{d}\text{-}R^{3}$ (VII-2)

wherein all symbols have the same meanings as described below.

The amidation reaction is carried out by the same method as described above.

(viii) In the compound of formula (Ib), wherein D is:

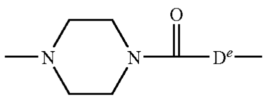

wherein $D^e$ represents, as

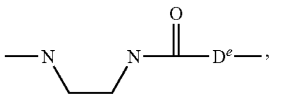

(1) a 5- or 6-membered linking chain, or (2) a 7- to 10-membered linking chain;

that is, the compound of formula (Ib-11):

(Ib-11)

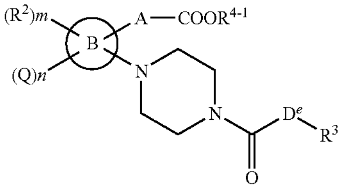

wherein all symbols have the same meanings as described below;

may be prepared by reacting the compound of formula (V-5):

(V-5)

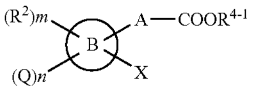

wherein all symbols have the same meanings as described below;

with piperazine and then subjecting to amidation reaction with the compound of formula (VII-3):

$HOOC\text{-}D^e\text{-}R^3$ (VII-3)

wherein all symbols have the same meanings as described below.

The reaction between the compound of formula (V-5) with piperazine is publicly known and carried out in, for example, an organic solvent (dioxane, t-butanol, methylene chloride or a solvent mixture thereof) by using tris(dibenzylideneacetone)dipallarium(0), 2-dicylohexylphosphino-2'-(N,N-dimethylamino)biphenyl and cesium carbonate at 80 to 120° C.

The amidation reaction is carried out by the same method as described above.

(ix) In the compound of formula (Ib), the compound of formula (Ib-12):

(Ib-12)

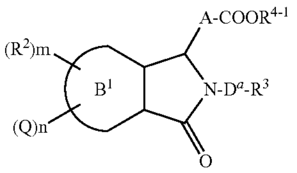

wherein

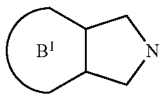

represents a bicyclic heterocycle represented by

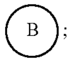;

and other symbols have the same meanings as described below;

may be prepared by subjecting to cyclization reaction the compound of formula (Ib-3) wherein $R^{40}$ is a hydrogen atom, that is, the compound of formula (Ib-3-1):

(Ib-3-1)

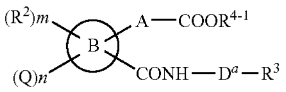

wherein all symbols have the same meanings as described below.

The cyclization reaction is publicly known and carried out in, for example, an organic solvent (methanol, etc.) by using potassium carbonate at 0 to 50° C. and then by using trimethylsilyldiazomethane at 0 to 50° C.

(4) In the compound of formula (I), wherein $R^1$ is $COOR^{4-2}$ (wherein $R^{4-2}$ represents —(C1 to 4 alkylene)-$R^{11}$ group), that is, the compound of formula (Ic):

(Ic)

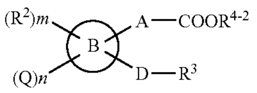

wherein all symbols have the same meanings as described below;

may be prepared by reacting the compound of formula (Ia) with the compound of formula (XII):

X—(C1-4 alkylene)-$R^{11}$ (XII)

wherein all symbols have the same meanings as described below.

The reaction is publicly known and carried out in, for example, an organic solvent (dimethylformamide, tetrahydrofuran, acetone, acetonitrile, etc.) by using potassium carbonate, sodium carbonate, sodium hydride, etc. at 0 to 50° C.

(5) In the compound of formula (I), wherein $R^1$ is $CONR^7R^8$ or $CONR^5SO_2R^6$, that is, the compound of formula (Id-1):

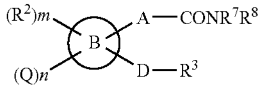

(Id-1)

wherein all symbols have the same meanings as described below;

or the compound of formula (Id-2):

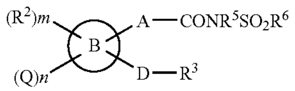

(Id-2)

wherein all symbols have the same meanings as described below;

may be prepared by subjecting the compound of formula (Ia) to amidation reaction with the compound of formula (XIII-1):

$NHR^7R^8$ (XIII-1)

wherein all symbols have the same meanings as described below;

or the compound of formula (XIII-2):

$NHR^5SO_2R^6$ (XIII-2)

wherein all symbols have the same meanings as described below.

The amidation reaction is publicly known and carried out by the above-described method or, alternatively, by reacting in, for example, an organic solvent (tetrahydrofuran, etc.) in the presence/absence of a catalytic amount of dimethylformamide by using an acid halide (ethyl chloroformate, oxalyl chloride, thionyl chloride, phosphorus oxychloride, etc.) and aqueous ammonia at 0 to 50° C.

(6) In the compound of formula (I), wherein $R^1$ is tetrazole, that is, the compound of formula (Ie):

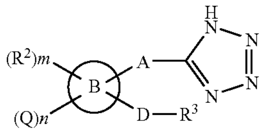

(Ie)

wherein all symbols have the same meanings as described below;

may be prepared by reacting the compound of formula (XIV):

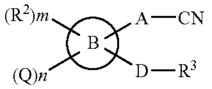

(XIV)

with trimethyltin azide.

The reaction is publicly known and carried out in, for example, an organic solvent (methanol, toluene, etc.) at 100 to 130° C.

(7) In the compound of formula (I), wherein $R^1$ is 1,2,4-oxadiazol-5-one, 1,2,4-oxadiazole-5-thione, 1,2,4-thiadiazol-5-one or 1,2,3,5-oxathiadiazol-2-one, that is, the compound of formula (If):

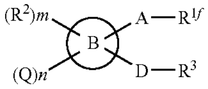

(If)

wherein $R^{1f}$ represents 1,2,4-oxadiazol-5-one, 1,2,4-oxadiazole-5-thione, 1,2,4-thiadiazol-5-one or 1,2,3,5-oxathiadiazol-2-one; and other symbols have the same meanings as described below;

may be prepared by reacting the compound of formula (XV):

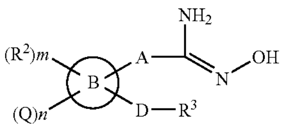

(XV)

with, (i) a compound (XVI-1):

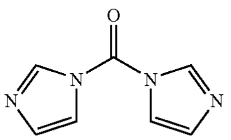

(XVI-1)

or a compound (XVI-2):

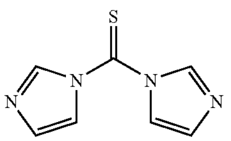

(XVI-2)

or (ii) a compound (XVI-3):

$SOCl_2$ (XVI-3)

or (iii) after reacting with a compound (XV-2), further reacting with a boron trifluoride ether complex salt.

The reaction (i) is publicly known and carried out in, for example, an organic solvent (acetonitrile, tetrahydrofuran, etc.) in the presence of 1,8-diazabicyclo[5.4.0]undec-7-ene at 0 to 50° C.

The reaction (ii) is publicly known and carried out in, for example, an organic solvent (acetonitrile, tetrahydrofuran, etc.) in the presence/absence of a tertiary amine (dimethylaminopyridine, pyridine, triethylamine, etc.) at 0 to 50° C.

The reaction (iii) is publicly known and carried out by, for example, reacting with the compound (XV-2) in an organic solvent (acetonitrile, tetrahydrofuran, etc.) and then using a boron trifluoride ether complex salt at 0 to 50° C.

(8) In the compound of formula (I), wherein $R^1$ is $CH_2$—OH, that is, the compound of formula (Ig):

(Ig)

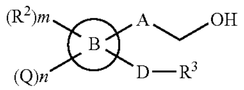

wherein all symbols have the same meanings as described below;

may be prepared by subjecting the compound of formula (Ia) to reduction reaction.

The reduction reaction is publicly known and carried out in, for example, an organic solvent (tetrahydrofuran, diglyme, etc.) by using a borane complex at 0 to 50° C.

(9) In the compound of formula (I), wherein $R^1$ is —$CH_2$—$NR^9SO_2R^6$, —$CH_2$—$NR^9COR^{10}$ or —$CH_2$—$NR^9CO$—$NR^5SO_2R^6$, that is, the compound of formula (Ih-1):

(Ih-1)

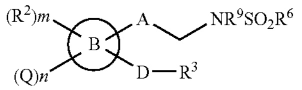

wherein all symbols have the same meanings as described below;

the compound of formula (Ih-2):

(Ih-2)

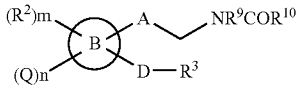

wherein all symbols have the same meanings as described below; or the compound of formula (Ih-3):

(Ih-3)

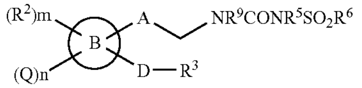

wherein all symbols have the same meanings as described below;

may be prepared by subjecting to amidation reaction the compound of formula (XVII):

(XVII)

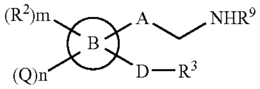

wherein all symbols have the same meanings as described below;

with the compound of formula (XVIII-1):

$R^6SO_2Cl$ (XVIII-1)

wherein all symbols have the same meanings as described below; or the compound of formula (XVIII-2):

$R^{10}COCl$ (XVIII-2)

wherein all symbols have the same meanings as described below; or reacting the compound of formula (XVI) with the compound of formula (XVIII-3):

$R^6SO_2N{=}C{=}O$ (XVIII-3)

wherein all symbols have the same meanings as described below.

The amidation reaction is publicly known and carried out by, for example, the above-described method.

The reaction between the compound of formula (XVI) and the compound of formula (XVII-3) is publicly known and carried out in, for example, an organic solvent (acetonitrile, toluene, benzene, methylene chloride, tetrahydrofuran, dimethylformamide, pyridine, etc.) at 0° C. to 50° C.

(10) In the compound of formula (I), wherein $R^1$ is —$CH_2$—$OCONR^5SO_2R^6$, that is, the compound of formula (II):

(Ii)

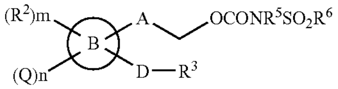

wherein all symbols have the same meanings as described below;

may be prepared by reacting the compound of formula (Ig):

(Ig)

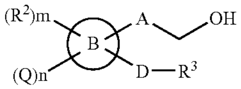

wherein all symbols have the same meanings as described below;

with the compound of formula (XVIII-3):

$R^6SO_2N{=}C{=}O$ (XVIII-3)

wherein all symbols have the same meanings as described below.

The reaction is publicly known and carried out in the same manner as the reaction between the compound of formula (XVI) and the compound of formula (XVII-3) as described above.

(11) In the compound of formula (I), wherein $R^1$ is $—SO_2NR^7COR^{10}$, that is, the compound of formula (Ij):

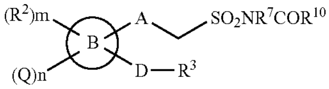

(Ij)

wherein all symbols have the same meanings as described below;

may be prepared by subjecting to amidation reaction a compound wherein $R^8$ is a hydrogen atom in the compounds represented by formula (XIX):

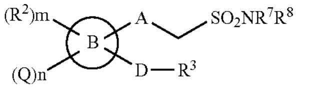

(XIX)

wherein all symbols have the same meanings as described below;

with the compound of formula (XX):

$R^{10}COOH$ (XX)

wherein all symbols have the same meanings as described below.

The amidation reaction is publicly known and carried out by, for example, the above-described method.

In the compound of formula (Ij), wherein $-A-SO_2NR^7COR^{10}$ is $-A^{j-i}-CH_2—SO_2NR^7COR^{10}$, that is, the compound of formula (IJ-1):

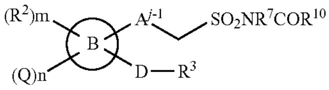

(Ij-1)

wherein $A^{j-i}$ represents a group lacking one carbon atom in an alkylene group A in (ii), (v) to (xii) and (xv), (iii) C2-5 alkenylene or (iv) C2-5 alkynylene, wherein all symbols have the same meanings as described below;

may be prepared by subjecting to amidation reaction the compound of formula (XXI):

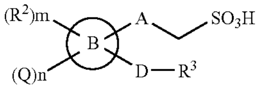

(XXI)

with the compound of formula (XXII):

$NHR^7COR^{10}$ (XXII)

wherein all symbols have the same meanings as described below.

The amidation reaction is publicly known and carried out by, for example, the above-described method.

The compounds represented by formulae (II-1) and (II-2) may be prepared by a method in accordance with the following reaction scheme 1.

Reaction scheme 1

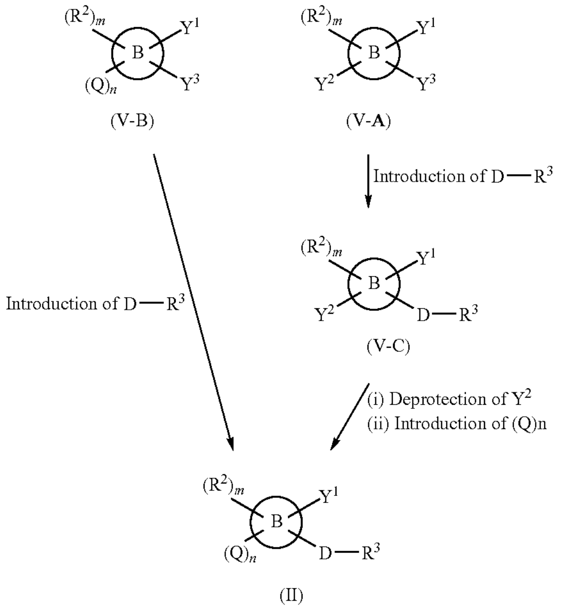

The compounds represented by formulae (V-1), (V-2), (V-3), (V-4), (V-5), (V-6) and (V-7) may be prepared by a method in accordance with the following reaction schemes 2-1 and 2-2.

Reaction scheme 2-1

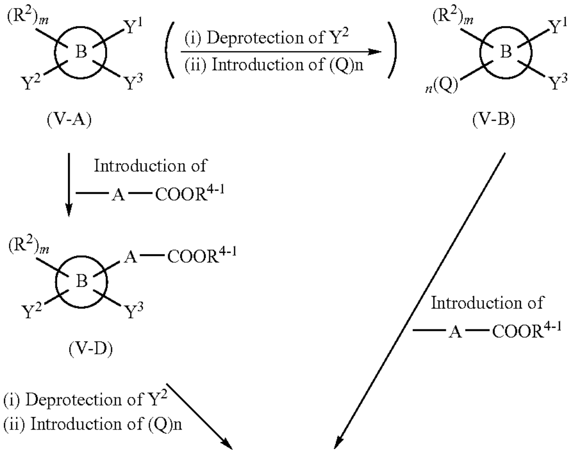

-continued

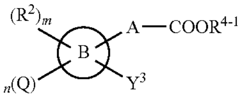

(V)

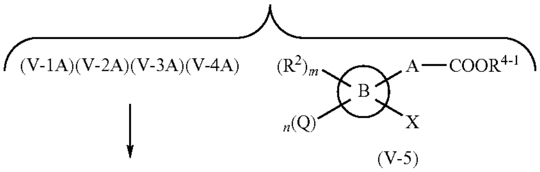

(V-5)

To Reaction scheme 2-2

Reaction scheme 2-2

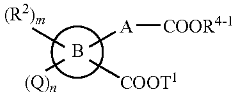

(V-1A)

Deprotection

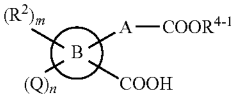

(V-1)

Reduction

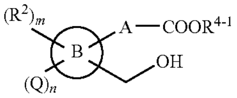

(V-7)

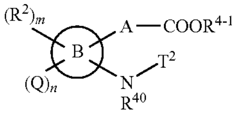

(V-2A)

Deprotection

-continued

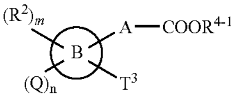

(V-3A)

Deprotection

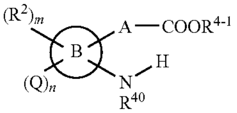

(V-2)

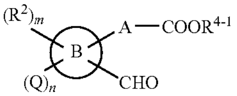

(V-3)

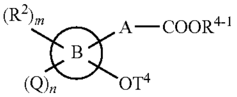

(V-4A)

Deprotection

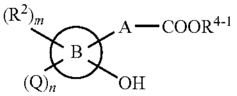

(V-4)

Tf化

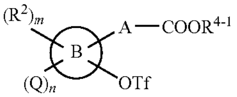

(V-6)

The compound of formula (Ib-2) may be prepared by a method in accordance with the following reaction scheme 3-1 or 3-2.

Reaction scheme 3-1

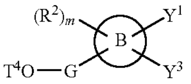

(V-A-1)

Introduction of —A—$COOR^{4-1}$

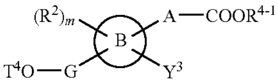

(V-D-1)

Deprotection of $Y^3$

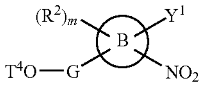

(V-A-2)

Introduction of —A—$COOR^{4-1}$

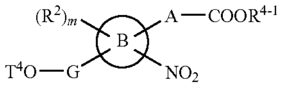

(V-D-3)

Reduction

-continued
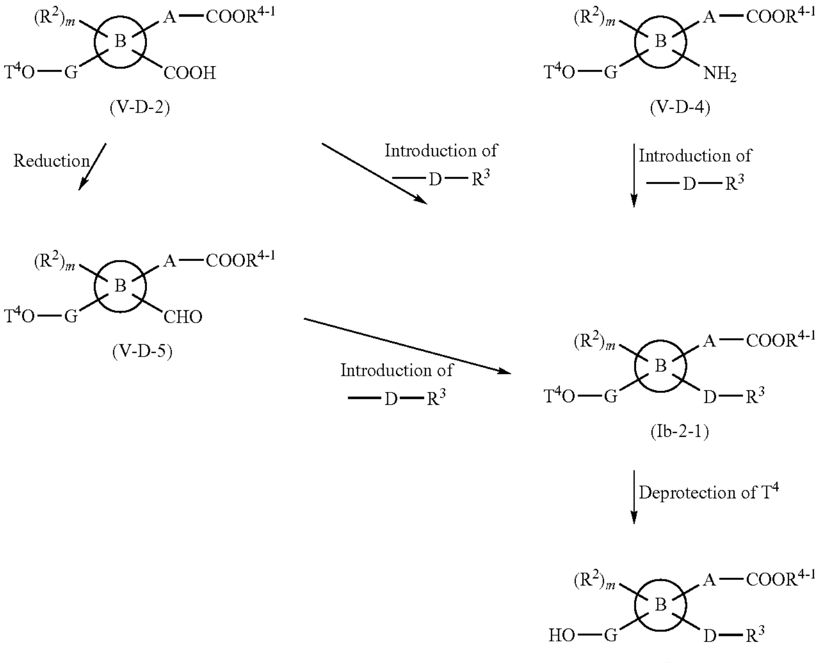
(V-D-2) (V-D-4) (V-D-5) (Ib-2-1) (Ib-2)
Reaction scheme 3-2
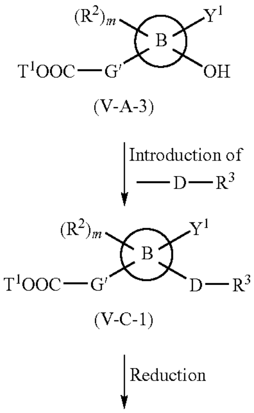
(V-A-3) (V-C-1)
-continued
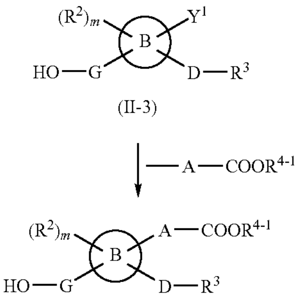
(II-3) (Ib-2)
In the compound of formula (Ib-2), wherein -A- is ethylene may be prepared by a method in accordance with the following reaction scheme 4 too.
Reaction scheme 4
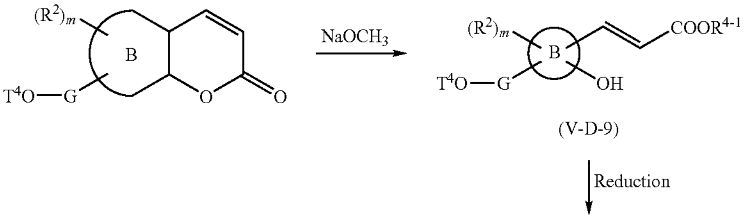
(V-D-9)

-continued

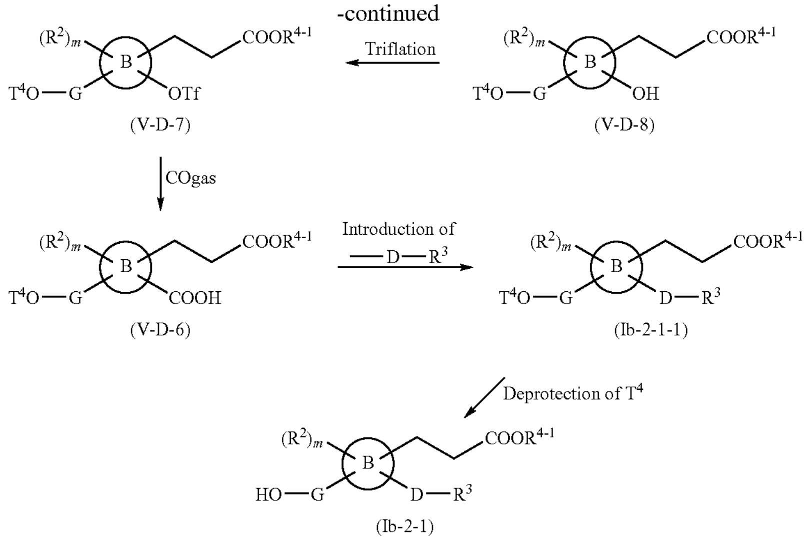

(V-D-7) (V-D-8) (V-D-6) (Ib-2-1-1) (Ib-2-1)

The compounds represented by formulae (XIX) and (XXI) may be prepared by a method in accordance with the following reaction scheme 5.

Reaction scheme 5

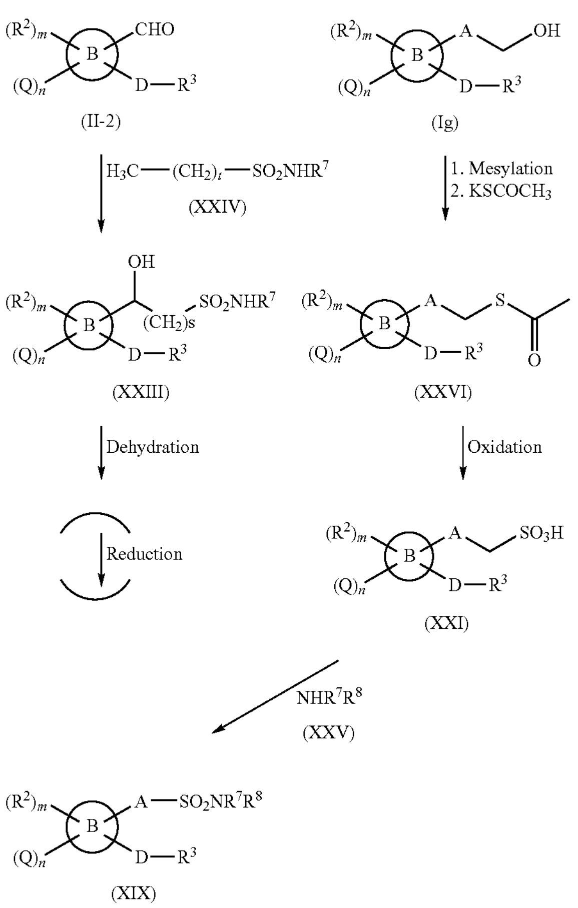

(II-2) (Ig) (XXIII) (XXVI) (XXI) (XIX)

The compounds represented by formulae (XIV), (XV) and (XVII) may be prepared by a method in accordance with the following reaction scheme 6.

Reaction scheme 6

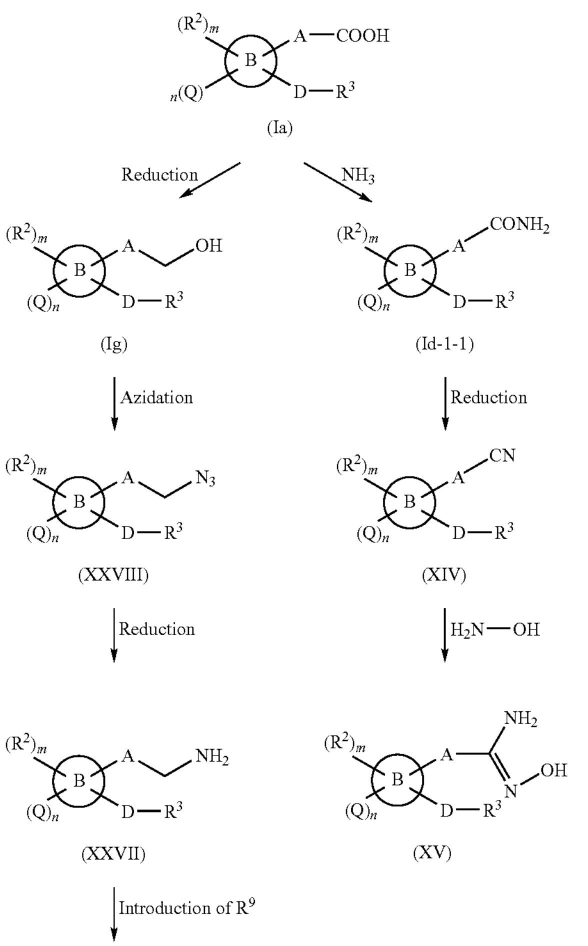

(Ia) (Ig) (Id-1-1) (XXVIII) (XIV) (XXVII) (XV)

-continued

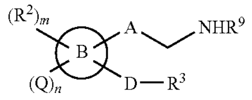

(XVII)

In the Reaction schemes 1 to 4, $Y^1$ represents formyl or X (wherein X has the same meaning as defined above);

$Y^2$ represents a group in the stage before the introduction of $(Q)_n$, i.e., blocked (C1 to 4) alkyl-OH, an ester group, etc.;

$Y^3$ represents:

(i) $COOT^1$ (wherein $T^1$ represents a carboxyl-protective group (for example, methyl, ethyl, t-butyl, benzyl, etc.));

(ii) $NR^{40}T^2$ (wherein $T^2$ represents an amino-protective group (for example, t-butoxycarbonyl, etc.));

(iii) $T^3$ (wherein $T^3$ represents a protected aldehyde group (for example, dimethylacetal, etc.));

(iv) $OT^4$ (wherein $T^4$ represents a hydroxy-protective group (for example, methoxymethyl, tetrahydropyranyl, etc.)); or (v) fluorine;

G' represents a single bond, C1-3 alkylene, a C2-3 alkenylene or C2-3 alkynylene;

s is 1 to 5; and t is 1 to 4.

The compounds of formula (V-A) are either publicly known or may be prepared by a publicly known method.

Among other starting compounds, the compounds represented by formulae (III-1), (III-2), (IV-1), (IV-2), (IV-3), (IV-4), (IV-5), (IV-6), (VI), (VII-1), (VII-2), (VII-3), (VIII), (IX), (X), (XI-1), (XI-2), (XII), (XIII-1), (XIII-2), (XVI-1), (XVI-2), (XVI-3), (XVIII-1), (XVIII-2), (XVIII-3), (XX) and (XXII) are either publicly known or may be prepared by a publicly known method.

The reagents are each either publicly known per se or may be prepared by a publicly known method.

In the case of the compound of the present invention having hydroxyl and amino, the target compound of the present invention can be easily produced by using a compound having respectively adequate protective groups preliminarily introduced thereinto, subjecting the compound to various reactions and then performing deprotection by appropriately selecting deprotection reactions suiting them, i.e., an alkali hydrolysis, a deprotection reaction under acidic conditions or a deprotection reaction by hydrogenolysis.

It can be easily understood by a person skilled in the art that examples of the hydroxy-protective group include methoxymethyl, tetrahydropyranyl, t-butyldimethylsilyl, acetyl and benzyl. However, other protective groups may be used without particular restriction, so long as they can be easily and selectively removed.

Examples of the amino include benzyloxycarbonyl, t-butoxycarbonyl and trifluoroacetyl. However, other protective groups may be used without particular restriction, so long as they can be easily and selectively removed. For example, those reported by T. W. Greene, *Protective Groups in Organic Synthesis*, Wiley, New York (1991) can be used.

In each reaction described herein, a reaction product can be purified by a purification procedure commonly employed, for example, distillation under atmospheric or reduced pressure, high-performance liquid chromatography by using silica gel or magnesium silicate, thin layer chromatography, column chromatography, washing, recrystallization and the like.

Purification may be carried out either after the completion of each reaction or after the completion of several successive reactions.

Pharmacological Activity of the Compound of the Present Invention:

The compound of the present invention of formula (I) strongly binds to $PGE_2$ receptors, in particular, $EP_3$ and/or $EP_4$ receptors which are subtypes thereof and antagonize the same.

The pharmacological activity is confirmed by the following receptor-binding experiment by using cells expressing prostanoid receptor subtypes.

(i) Receptor-binding experiment by using cells expressing prostanoid receptor subtypes In accordance with the method of Sugimoto et al. [*J. Biol. Chem.,* 267, 6463-6466 (1992)], CHO cells respectively expressing prostanoid receptor subtypes (mouse $EP_1$, $EP_2$, $EP_3$, and $EP_4$) were prepared to give membrane preparations.

Each membrane fraction (50 μl) thus prepared and a reaction solution (150 μl) containing $^3H\text{-}PGE_2$ were incubated at room temperature for 1 hour. After ceasing the reaction with an ice-cooled buffer (3 ml), the bound $^3H\text{-}PGE_2$ was trapped in a glass filter (GF/B) by filtering with suction under reduced pressure. Then the bound radioactivity was measured with a liquid scintillator.

Kd value and Bmax value were determined by Scatchard plots [*Ann. N.Y. Acad. Sci.,* 51, 660 (1949)]. Nonspecific bond was determined as bond in the presence of unlabeled $PGE_2$ in excess (2.5 μM). The $^3H\text{-}PGE_2$-binding inhibitory effects of the invention compounds were measured by adding $^3H\text{-}PGE_2$ (2.5 nM) and the invention compounds at various concentrations. In every reaction, the following buffer was employed.

Buffer: potassium phosphate (10 mM, pH 6.0), EDTA (1 mM), $MgCl_2$ (10 mM), NaCl (0.1 M).

The dissociation constant Ki (μM) of each compound was determined in accordance with the following formula. Table 1 shows the results.

$$Ki = IC_{50}/(1+([C]/Kd))$$

TABLE 1

| | Ki (μM) | | | |
|---|---|---|---|---|
| Ex. compound | $EP_1$ receptor | $EP_2$ receptor | $EP_3$ receptor | $EP_4$ receptor |
| 8(13) | >10 | >10 | 0.27 | 0.038 |

(ii) $EP_3$ antagonistic activity measurement experiment by using cells expressing prostanoid receptor subtype In accordance with the method of Sugimoto et al. [*J. Biol. Chem.,* 267, 6463-6466 (1992)], CHO cells expressing a mouse $EP_3$ receptor subtype. These cells were sowed in a 96-well microplate at a density of $10^4$ cells/well and incubated for 2 days before using in the experiment. After washing each well with PBS (100 μl), the cells were allowed to intake Fura-2AM for 60 minutes. After washing with an HEPES solution, a test compound and $PGE_2$ (10 nM) were added at 37° C. and a change in the intracellular calcium concentration was measured. Namely, after exciting at 340/380 nm in wavelength, the fluorescences at 510 nm were measured and thus the fluorescence intensity ratio was determined.

The antagonistic action of the test compound was calculated as the inhibitory ratio to the reaction using $PGE_2$ (10 nM) alone and $IC_{50}$ was determined.

(iii) $EP_4$ antagonistic activity measurement experiment by using cells expressing prostanoid receptor subtype In accordance with the method of Nishigaki et al. [*FEBS Lett.,* 364, 339-341 (1995)], CHO cells respectively expressing mouse $EP_4$ receptor subtypes were prepared. After sowing on a 24-well microplate at a density of $10^5$ cells/well, the cells were incubated for 2 days before use in the experiment. After washing each cell with MEM (minimum essential medium) (500 μl), an assay medium (MEM containing 1 mmol/L IBMX, 1% BSA) (450 μl) was added and the cells were incubated at 37° C. for 10 minutes. Next, $PGE_2$ was added alone or together with a solution (50 μl) containing a test compound and the reaction was initiated. After reacting at 37° C. for 10 min, ice-cooled TCA (10% w/v) (500 μl) was added to thereby cease the reaction. The liquid reaction mixture was once frozen (−80° C.) and thawed. Next, the cells were peeled with a scraper and centrifuged at 13,000 rpm for 3 minutes. Using the supernatant thus obtained, the cAMP concentration was measured with a cAMP assay kit. Namely, a buffer of a [$^{125}$I]cAMP assay kit (manufactured by Amersham) was added to 125 μl of the supernatant to give a total volume of 500 μl. Then this mixture was mixed with a 0.5 mol/L of a solution (1 ml) of tri-n-octylamine in chloroform. After removing TCA in the chloroform layer, the aqueous layer was employed as a sample and the cAMP in the sample was quantified in accordance with the method described in the [$^{125}$I]cAMP assay kit.

The antagonistic effect ($IC_{50}$) of the test compound was calculated as the inhibitory ratio to the reaction at 100 nM, i.e., the concentration at which $PGE_2$ alone shows a submaximal cAMP producing effect, and $IC_{50}$ was determined.

As the results of the above experiments, it was clarified that the invention compounds have a potent $EP_3$ and/or $EP_4$ receptor antagonistic activity.

Toxicity:

It has been confirmed that the compounds of the present invention of formula (I) have sufficiently low toxicity and thus are safe enough in using as drugs.

INDUSTRIAL APPLICABILITY

Application to Drugs

The compounds of the present invention of formula (I) bind to a $PGE_2$ receptor and show an antagonism, which makes them useful. In particular, these compounds bind to the subtypes $EP_3$ and/or $EP_4$ and antagonize the receptors. Therefore, they are expected as useful in preventing and/or treating diseases such as pain (cancerous pain, pain accompanying bone fracture, postoperative pain, post-extraction toothache, etc.), allodynia, hyperalgesia, itch, urticaria, atopic dermatitis, contact dermatitis, poison ivy dermatitis, allergic conjunctivitis, various symptoms in dialysis, asthma, rhinitis, allergic rhinitis, nasal obstruction, sneeze, psoriasis, urinary frequency (neurogenic bladder, nervous bladder, irritative bladder, unstable bladder, urinary frequency accompanying prostate-gland enlargement, etc.), urinary disturbance, dysspermia, fever, systemic inflammatory response syndrome, learning disability, Alzheimer's disease, angiogenesis, cancer (canceration, cancer proliferation, cancer metastasis into organ, cancer metastasis into bone, hypercalcemia accompanying cancer metastasis into bone, etc.), retinosis, red spot, erythema, leukoma, skin spot, burn, ambustion, steroid burn, renal insufficiency, nephropathy, acute nephritis, chronic nephritis, blood electrolyte imbalance, threatened premature delivery, threatened abortion, epimenorrhagia, dysmenorrhea, endometriosis, premenstrual syndrome, adenomyosis uteri, reproductive disturbance, stress, anxiety, depression, psychosomatic disorder, mental diseases, thrombosis, embolism, transient ischemic attack, brain infraction, atheroma, organ transplantation, myocardial infarction, heart failure, hypertension, arteriosclerosis, circulatory disturbance and ulcer accompanying the same, nerve disorder, vascular dementia, edema, diarrhea, constipation, biliary discharge disorder, ulcerative colitis, Crohn's disease, irritable colitis, relieving rebound phenomena after using steroids, accelerating reduction and elimination of steroids, bone diseases (osteoporosis, rheumatoid arthritis, arthritis deformans, osteodysplasty, etc.), systemic granuloma, immune diseases (amyotrophic lateral sclerosis (ALS), multiple sclerosis, Sjoegren's syndrome, systemic lupus erythematosus, AIDS, etc.), pyorrhea alveolaris, gingivitis, periodontal disease, nerve cell death, lung injury, liver injury, acute hepatitis, myocardial ischemia, Kawasaki's disease, multiple organ failure, chronic headache (hemicrania, tension headache, mixed headache thereof or cluster headache), angiitis, venous insufficiency, varicose vein, anal fistula, diabetes insipidus, newborn patent ductus arteriosus, cholelithiasis, sleep disturbance and platelet aggregation.

The compounds of the present invention of formula (I) or nontoxic salts thereof may be combined with other drugs and administered as combination drugs for:

(1) complementing and/or enhancing the preventive and/or therapeutic effects of the compounds;

(2) improving the dynamics and absorption of the compounds and reducing the administration dose thereof, and/or (3) relieving the side effects of the compounds.

A combination drug of the compound of formula (I) with other drug may be administered in the form of a blend containing both of the components in a single preparation. Alternatively, the components may be processed into separate preparations and administered. The separate preparations may be administered either at the same time or at a definite time interval. In the case of administering at a definite time interval, the compound of formula (I) may be administered first followed by the administration of the other drug. Alternatively, the other drug may be administered first followed by the administration of the compound of formula (I). The administration methods may be either the same or different.

Diseases on which the preventive and/or therapeutic effects are exerted by the combination drug are not particularly restricted. That is, they may be any diseases so long as the preventive and/or therapeutic effects of the compounds of formula (I) thereon can be complemented and/or enhanced.

Examples of other drugs for complementing and/or enhancing the preventive and/or therapeutic effect of the compounds of formula (I) on pain include nonsteroid antiinflammatory agents, N-type calcium channel inhibitors, nitrogen monoxide synthase inhibitors, cannabinoid-2 receptor stimulating agents and the like.

Examples of other drugs for complementing and/or enhancing the preventive and/or therapeutic effect of the compounds of formula (I) on itch, urticaria, atopic dermatitis, contact dermatitis, allergic conjunctivitis and various symptoms in dialysis include steroids, nonsteroid antiinflammatory agents, immune suppressants, antiallergic agents, mediator release inhibitors, leukotriene receptor antagonists, antihistamines, forskolin preparations, phosphodiesterase inhibitors, nitrogen monoxide synthase inhibitors, cannabinoide-2 receptor stimulating agents and the like.

Examples of other drugs for complementing and/or enhancing the preventive and/or therapeutic effect of the compounds of formula (I) on cancer (canceration, cancer proliferation, cancer metastasis into organ, cancer metastasis into bone, hypercalcemia accompanying cancer metastasis into bone, etc.) include anticancer agents, analgesics, bisphosphonate preparations, calcitonin preparations, metalloproteinase inhibitors and the like.

Examples of other drugs for complementing and/or enhancing the preventive and/or therapeutic effect of the compounds of formula (I) on chronic headache include nonsteroid antiinflammatory agents, ergotamine preparations, calcium antagonists, serotonin agonists, EDG-5 agonists and the like.

Examples of the nonsteroid antiinflammatory agents include salsalate, sodium salicylate, aspirin, aspirin dialuminate blend, diflunisal, indomethacin, sprofen, ufenamate, dimethylisopropylazulene, bufexamac, felbinac, diclofenac, tolmetin sodium, clinoril, fenbufen, nabumetone, proglumetacin, indometacin farncecil, acemetacin, proglumetacin maleate, amfenac sodium, mofezolac, etodolac, ibuprofen, ibuprofen piconol, naproxen, flurbiprofen, flurbiprofen axetil, ketoprofen, fenoprofen calcium, tiaprofen, oxaprozin, pyranoprofen, loxoprofen sodium, alminoprofen, zaltoprofen, mefenamic acid, aluminum mefenamate, tolfenamic acid, floctafenine, ketophenylbutazone, oxyfenbutazone, piroxicam, tenoxicam, ampiroxicam, napageln ointment, epirizol, tiaramide hydrochloride, tinoridine hydrochloride, emorfazone, sulpirin, migrenin, saridon, sedes G, amipylo N, sorbon, pyrazolone-based remedies for cold, acetoaminophen, fenacetine, dimethothiazine mesylate, meloxicam, celecoxib, rofecoxib, valdecoxib, simetride-containing agents, pyrazolone-free remedies for cold and the like.

Examples of the steroids include, e.g., as drugs for external use, clobetasol propionate, diflorasone acetate, fluocinonide, mometazone furancarboxylate, betametazone dipropionate, betametazone butyrate propionate, betametazone valerate, difluprednate, budesonide, diflucortolone valerate, amicinonide, halcinonide, dexamethasone, dexamethasone propionate, dexamethasone valerate, dexamethasone acetate, hydrocortisone acetate, hydrocortisone butyrate, hydrocortisone butyrate propionate, deprodone propionate, prednisolone valerate acetate, fluocinolone acetonide, beclometasone propionate, triamcinolone acetonide, flumetasone pivalate, alclometasone propionate, clobetasone butyrate, prednisolone, beclomethasone propionate, fludroxycortide and the like.

Examples of drugs for internal use and injections include cortisone acetate, hydrocortisone, hydrocortisone sodium phosphate, hydrocortisone sodium succinate, fludrocortisone acetate, prednisolone, prednisolone acetate, prednisolone sodium succinate, prednisolone butyl acetate, prednisolone sodium phosphate, halopredone acetate, methylprednisolone, methylprednisolone acetate, methylprednisolone sodium succinate, triamcinolone, triamcinolone acetate, triamcinolone acetonide, dexamethasone, dexamethasone acetate, dexamethasone sodium phosphate, dexamethasone palmitate, paramethasone acetate, betamethasone and the like.

Examples of inhalations include beclometasone propionate, fluticasone propionate, budesonide, flunisolide, triamcinolone, ST-126P, ciclesonide, dexamethasone palomithionate, monometasone furancarboxylate, prasterone sulfonate, deflazacort, methylprednisolon sleptanate, methylprednisolon sodium succinate and the like.

Examples of the immune suppressants include protopic (FK-506), methotrexate, cyclosporin, ascomycin, leflunomide, bucillamine, salazosulfapyridine and the like.

Examples of the mediator release inhibitors include tranilast, sodium cromoglycate, amlexanox, repirinast, ibudilast, tazanolast, pemirolast potassium and the like.

Examples of the leukotriene receptor antagonists include pranlukast hydrate, montelukast, zafirlukast, MCC-847, KCA-757, CS-615, YM-158, L-740515, CP-195494, LM-1484, RS-635, A-93178, S-36496, BIIL-284, ONO-4057 and the like.

Examples of the antihistamines include ketotifen fumarate, mequitazine, azelastine hydrochloride, oxatomide, terfenadine, emedastine fumarate, epinastine hydrochloride, astemizole, ebastine, cetirizine hydrochloride, bepotastine, fexofenadine, loratadine, desloratadine, olopatadine hydrochloride, TAK-427, ZCR-2060, NIP-530, mometasone furoate, mizolastine, BP-294, andolast, auranofin, acrivastine, etc.

Examples of the anticancer agents include alkylating agents (nitrogen mustard-N-oxide hydrochloride, cyclophosphamide, ifosfamide, melphalan, thiotepa, carboquaone, busulfan, etc.), nitrosourea derivatives (nimustine hydrochloride, ranimustine, etc.), metabolic antagonists (methotrexate, mercaptopurine, 6-mercaptopurine riboside, fluorouracil, tegafur, UFT, carmofur, doxyfluridine, cytarabine, enocitabine, etc.), anticancer antibiotics (actinomycin D, mitomycin C, daunorubicin hydrochloride, doxorubicin hydrochloride, aclarubicin hydrochloride, neocarzinostatin, pirarubicin, epirubicin, idarubicin, chromomycin A3, bleomycin, heplomycin sulfate, etc.), plant alkaloids (vinblastine sulfate, vincristine sulfate, vindensine sulfate, etc.), hormone drugs (estramustine phosphate sodium, mepitiostane, epitiostanol, tamoxifen citrate, diesthylstilbestrol phosphate, medroxyprogesterone acetate, anastrozole, fadrozole, leuprolide, etc.), immunopotentiators (lentinan, picibanil, krestin, sizofuran, ubenimex, interferon, etc.) and others (L-asparaginase, procarbazine hydrochloride, mitoxantrone hydrochloride, cisplatin, carboplatin, etc.).

Examples of the phosphodiesterase inhibitors include PDE4 inhibitors such as roliplam, cilomilast (trade name: Ariflo), Bay 19-8004, NIK-616, roflumilast (BY-217), cipamfylline (BRL-61063), atizoram (CP-80633), SCH-351591, YM-976, V-11294A, PD-168787, D-4396, IC-485 and the like.

Examples of the ergotamine preparations include dihydroergotamine mesylate, ergotamine tartarate and the like.

Examples of the calcium antagonists include nifedipine, benidipine hydrochloride, diltiazem hydrochloride, verapamil hydrochloride, nisoldipine, nitrendipine, bepridil hydrochloride, amlodipine besylate, lomerizine hydrochloride and the like.

Examples of the serotonin agonists include sumatriptan, zolmitriptan, naratriptan, rizatriptan, eletriptan, almotriptan, frovatriptan and the like.

The ratio by mass of the compounds of formula (I) to other drugs is not particularly limited.

Two or more of other drugs optionally selected can be used in combination.

Other drugs to be used for complementing and/or enhancing the preventive and/or therapeutic effects of the compounds of formula (I) involve not only those which have been found out hitherto based on the above-described mechanism but also those which will found out in future.

To employ the compounds of formula (I) or combination drugs of the compounds of formula (I) with other drugs for the above-described purposes, they are usually administered systemically or topically, and orally or parenterally.

Although the administration dose varies depending on the age, body weight and conditions of a patient, therapeutic effect, administration route, treatment time, etc., the single administration dose to an adult usually ranges from 1 ng to 100 mg and the administration is made once to several times per day in the case of oral administration. Alternatively, the single administration dose ranges from 0.1 ng to 10 mg and the administration is made once to several times per day in the case of parenteral administration. Alternatively, intravenous administration is continuously made for 1 hour to 24 hours per day.

Needless to say, the administration dose varies depending on various factors as discussed above. Thus, an administration dose smaller than the lower limit as defined above is enough in some cases, while an administration dose exceeding the upper limit is needed in other cases.

To administrate the compounds of formula (I) or combination drugs of the compounds of formula (I) with other drugs, use is made of solid preparations for internal use and liquid preparations for internal use for oral administration as well as injections, preparations for external use, suppositories, eye drops, inhalations and the like for parenteral administration.

Examples of the solid preparations for internal use include tablets, pills, capsules, dusts, granules and the like. The capsules include hard capsules and soft capsules.

Such a solid preparation for internal use is prepared by a formulation method commonly employed by using one or more active substances either as such or as a mixture with an excipient (lactose, mannitol, glucose, microcrystalline cellulose, starch, etc.), a binder (hydroxypropylcellulose, polyvinylpyrrolidone, magnesium metasilicate aluminate, etc.) a disintegrating agent (calcium cellulose glycolate, etc.), a lubricant (magnesium stearate, etc.), a stabilizer, and a dissolution aid (glutamic acid, aspartic acid, etc.). If necessary, it may be coated with a coating agent (sucrose, gelatin, hydroxypropylcellulose, hydroxypropylmethylcellulose phthalate, etc.). It may be coated with two or more layers. Moreover, capsules made of an absorbable material such as gelatin are involved in the scope thereof.

The liquid preparations for internal use involve pharmaceutically acceptable solutions, suspensions, emulsions, syrups, elixirs and the like. Such a liquid preparation is prepared by dissolving, suspending or emulsifying one or more active substances in a diluent commonly employed (purified water, ethanol, a mixture thereof, etc.). The liquid preparation may further contain a moistening agent, a suspending agent, an emulsifier, a sweetener, a flavor, a perfume, a preservative, a buffer and the like.

The dosage forms of the parenteral administration preparations for external use involve ointments, gels, creams, fomentations, patches, liniments, atomized agents, inhalations, sprays, aerosols, nasal drops and the like. Such a preparation contains one or more active substances and is prepared by a publicly known method or in accordance with a formulation commonly employed.

Ointments are prepared in accordance with a publicly known formulation or a formulation commonly employed. For example, they are prepared by levigating or melting one or more active substances in a base. The ointment base is selected from among publicly known ones or those commonly employed. For example, use may be made of one base or a mixture of two or more thereof selected from higher fatty acids or higher fatty acid esters (adipic acid, myristic acid, palmitic acid, stearic acid, oleic acid, adipic acid esters, myristic acid esters, palmitic acid esters, stearic acid esters, oleic acid esters, etc.), waxes (beeswax, whale wax, ceresin, etc.), surfactants (polyoxyethylene alkyl ether phosphoric acid esters, etc.), higher alcohols (cetanol, stearyl alcohol, cetostaryl alcohol, etc.), silicone oils (dimethylpolysiloxane, etc.), hydrocarbons (hydrophilic vaseline, white vaseline, refined lanolin, liquid paraffin, etc.), glycols (ethylene glycol, diethylene glycol, propylene glycol, polyethylene glycol, macrogol, etc.), vegetable oils (castor oil, olive oil, sesame oil, turpentine oil, etc.), animal oils (mink oil, yolk oil, squalane, squalene, etc.), water, absorption promoters and skin irritation inhibitors. The ointments may further contain a humectant, a preservative, a stabilizer, an antioxidant, a flavor, etc.

Gels are prepared in accordance with a publicly known formulation or a formulation commonly employed. For example, they are prepared by melting one or more active substances in a base. The gel base is selected from among publicly known ones or those commonly employed. For example, use may be made of one base or a mixture of two or more thereof selected from among lower alcohols (ethanol, isopropyl alcohol, etc.), gelling agents (carboxymethylcellulose, hydroxyethylcellulose, hydroxypropylcellulose, ethylcellulose, etc.), neutralizing agents (triethanolamine, diisopropanolamine, etc.), surfactants (polyethylene glycol monostearate, etc.), gums, water, absorption promoters and skin irritation inhibitors. The gels may further contain a preservative, an antioxidant, a flavor, etc.

Creams are prepared in accordance with a publicly known formulation or a formulation commonly employed. For example, they are prepared by melting or emulsifying one or more active substances in a base. The cream base is selected from among publicly known ones or those commonly employed. For example, use may be made of one base or a mixture of two or more thereof selected from among higher fatty acid esters, lower alcohols, hydrocarbons, polyhydric alcohols (propylene glycol, 1,3-butylene glycol, etc.), higher alcohols (2-hexyldecanol, cetanol, etc.), emulsifiers (polyoxyethylene alkyl ethers, fatty acid esters, etc.), water, absorption promoters and skin irritation inhibitors. The creams may further contain a preservative, an antioxidant, a flavor, etc.

Fomentations are prepared in accordance with a publicly known formulation or a formulation commonly employed. For example, they are prepared by melting one or more active substances in a base, kneading and then applying and spreading the kneaded matter on a substrate. The fomentation base is selected from among publicly known ones or those commonly employed. For example, use may be made of one base or a mixture of two or more thereof selected from among thickeners (polyacrylic acid, polyvinylpyrrolidone, acacia, starch, gelatin, methylcellulose, etc.), moistening agents (urea, glycerol, propylene glycol, etc.), fillers (kaolin, zinc oxide, talc, calcium, magnesium, etc.), water, dissolution aids, tackifiers and skin irritation inhibitors. The fomentations may further contain a preservative, an antioxidant, a flavor, etc.

Patches are prepared in accordance with a publicly known formulation or a formulation commonly employed. For example, they are prepared by melting one or more active substances in a base and then applying and spreading on a substrate. The patch base is selected from among publicly known ones or those commonly employed. For example, use may be made of one base or a mixture of two or more thereof selected from among polymer bases, fats and oils, higher fatty acids, tackifiers and skin irritation inhibitors. The patches may further contain a preservative, an antioxidant, a flavor, etc.

Liniments are prepared in accordance with a publicly known formulation or a formulation commonly employed. For example, they are prepared by dissolving, suspending or emulsifying one or more active substances in one or more media selected from among water, alcohols (ethanol, polyethylene glycol, etc.), higher fatty acids, glycerol, soap, emulsifiers, suspending agents and the like. The liniments may further contain a preservative, an antioxidant, a flavor, etc.

Atomized agents, inhalations and sprays may contain, in addition to a diluent commonly employed, a stabilizer such as sodium hydrogen sulfite, a buffer for imparting isotonicity, for example, an isotonic agent such as sodium chloride, sodium citrate or citric acid. Methods for producing a spray are described in detail in, for example, U.S. Pat. No. 2,868,691 and U.S. Pat. No. 3,095,355.

The injections for parenteral administration involve solutions, suspensions, emulsions and solid injections to be dissolved or suspended before use. Such an injection is used by dissolving, suspending or emulsifying one or more active substances in a solvent. As the solvent, use is made of, for example, distilled water for injection, physiological saline, vegetable oils, alcohols such as propylene glycol, polyethylene glycol or ethanol and mixtures thereof. The injection may further contain a dissolution aid (glutamic acid, aspartic acid, polysorbate 80 (registered trade name), etc.), a suspending agent, an emulsifier, a soothing agent, a buffer, a preservative, etc. Such an injection is produced by sterilizing at the final step or employing aseptic conditions. Alternatively, it is also possible that an aseptic solid product such as a freeze-dried product is produced and sterilized or dissolved in aseptic distilled water for injection or another solvent before use.

The inhalations for parenteral administration involve aerosols, powders to be inhaled and liquids to be inhaled. Such inhalations may be in the form to be dissolved or suspended in water or another adequate medium before use.

The inhalations may be produced in accordance with a publicly known method.

For example, liquid preparations for inhalation are prepared by appropriately selecting a preservative (benzalkonium chloride, paraben, etc.), a colorant, a buffer (sodium phosphate, sodium acetate, etc.), an isotonic agent (sodium chloride, concentrated glycerol, etc.), a thickener (carboxyvinyl polymer, etc.), an absorption promoter and the like.

Powdery preparations for inhalation are prepared by appropriately selecting a lubricant (stearic acid, its salt, etc.), a binder (starch, dextrin, etc.), an excipient (lactose, cellulose, etc.), a coloring agent, a preservative (benzalkonium chloride, paraben, etc.), an absorption promoter, etc.

To administrate liquid preparation for inhalation, a spraying device (atomizer, nebulizer, etc.) are usually employed. To administer powdery preparations for inhalation, a device of administering a powdery drug for inhalation is usually employed.

Examples of other compositions for parenteral administration include suppositories for rectal administration and pessaries for vaginal administration which contain one or more active substances and are prepared in accordance with common formulations.

Best Mode for Carrying Out the Invention

Now, the present invention is described in greater detail by reference to the following Referential Examples and Examples, although the present invention is not construed as being restricted thereto.

Solvents given in parentheses concerning chromatographic separation and TLC indicate each the elution solvent or the developing solvent employed and the ratio is expressed in ratio by volume.

Solvents given in parentheses concerning NMR indicate each the solvent employed in measurement.

BEST MODE FOR CARRYING OUT THE INVENTION

The present invention is explained below in detail based on Reference Examples and Examples, however, the present invention is not limited thereto.

The solvents in the parentheses show the developing or eluting solvents and the ratios of the solvents used are by volume in chromatographic separations or TLC. The solvents in the parentheses in NMR show the solvents for measurement.

Reference Example 1

4-amino-3-hydroxybenzoic acid methyl ester hydrochloride

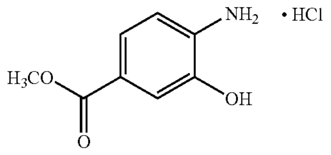

To an anhydrous methanol (100 ml) was added thionyl chloride (14.0 ml) at −10° C. during 20 minutes. After stirring the mixture for 15 minutes, 3-hydroxy-4-aminobenzoic acid (10.0 g) was added at the same temperature. The appeared suspension was stirred at room temperature overnight. The mixture was concentrated and then azeotroped with methanol (50 ml, twice). To the residue was added diethyl ether, and the residue was collected by suction filtration in washing with diethyl ether to give the title compound (12.8 g) having the following physical data.

TLC: Rf 0.49 (n-hexane:ethyl acetate=1:1).

Reference Example 2

3-hydroxy-4-iodobenzoic acid methyl ester

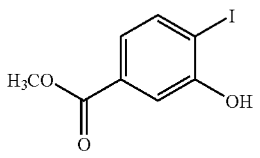

To a solution of the compound prepared in Reference Example 1 (4.90 g) in concentrated hydrochloric acid (20 ml) was added a solution of sodium nitrite (1.83 g) in water (15 ml) during 15 minutes. The mixture was stirred for 20 minutes. To the mixture was added a solution of potassium iodide (8.00 g) in water (30 ml) during 10 minutes. The mixture was stirred at room temperature for 20 minutes and then stirred at 60° C. for 1 hour. The reaction mixture was extracted with ethyl acetate, and then the organic layer was washed with a saturated aqueous solution of sodium thiosulfate, water and a saturated aqueous solution of sodium chloride subsequently, dried over anhydrous magnesium sulfate and then concentrated. The residue was purified by column chromatography (n-hexane:ethyl acetate=4:1~2:1) to give the title compound (4.57 g) having the following physical data.

TLC: Rf 0.33 (hexane:ethyl acetate=4:1).

Reference Example 3

4-iodo-3-[2-(naphthalen-2-yl)ethyloxy]benzoic acid methyl ester

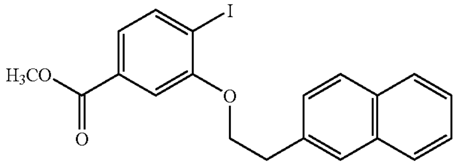

A solution of the compound prepared in Reference Example 2 (3.00 g), 2-(2-naphthyl)ethanol (2.23 g), triphenylphosphine (4.25 g) and 1,1'-(azodicarbonyl)dipiperidine (4.09 g) in anhydrous tetrahydrofuran (50 ml) was stirred at room temperature for 12 hours under an atmosphere of argon. The mixture was diluted with diethyl ether and filtered. The filtrate was concentrated. The residue was purified by column chromatography (n-hexane:ethyl acetate=20:1~10:1~5:1) to give the title compound (4.64 g) having the following physical data.

TLC: Rf 0.54 (n-hexane:ethyl acetate=4:1).

Reference Example 4

4-hydroxymethyl-2-[2-(naphthalen-2-yl)ethyloxy] phenyl iodide

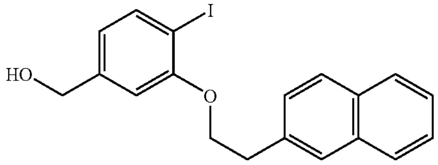

To a solution of the compound prepared in Reference Example 2 (4.61 g) in anhydrous methylene chloride (40 ml) was added Diisobutyl aluminum hydride (0.95M hexane solution, 28 ml) during 10 minutes at −78° C. under an atmosphere of argon. The temperature of the mixture was arised to −40° C. during 1 hour. To the reaction mixture were added methanol and a saturated aqueous solution of sodium sulfate. The appeared solid was filtered off and then the filtrate was concentrated.

The residue was purified by column chromatography on silica gel (n-hexane:ethyl acetate=4:1~3:1) to give the title compound (4.21 g) having the following physical data.

TLC: Rf 0.55 (n-hexane:ethyl acetate=1:1).

Example 1

4-hydroxymethyl-2-[2-(naphthalen-2-yl)ethyloxy] cinnamic acid ethyl ester

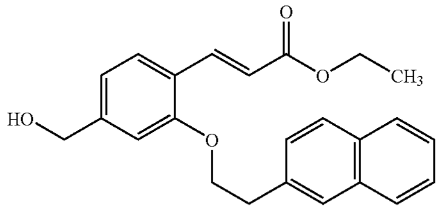

The mixture of the compound prepared in Reference Example 4 (2.54 g), ethyl acrylate (1.36 ml), triethylamine (4.38 ml), 1,1'-bis(diphenylphosphino)ferrocene (348 mg) and palladium(II) acetate (141 mg) in anhydrous dimethylsulfoxide (25 ml) was stirred at 100° C. for 30 minutes under an atmosphere of argon. To the reaction mixture were added water and ethyl acetate and the mixture was filtered. The filtrate was extracted with ethyl acetate and the organic layer was washed with water and a saturated aqueous solution of sodium chloride, subsequently, dried over anhydrous sodium sulfate and then concentrated. The residue was purified by column chromatography on silica gel (n-hexane:ethyl acetate=2:1~1:1) to give the title compound (2.07 g) having the following physical data.

TLC: Rf 0.47 (n-hexane:ethyl acetate=1:1);

NMR (300 MHz, $CDCl_3$): δ 7.99 (d, J=16 Hz, 1H), 7.86-7.76 (m, 4H), 7.50-7.40 (m, 4H), 6.94 (s, 1H), 6.90 (d, J=2.1 Hz, 1H), 6.52 (d, J=16 Hz, 1H), 4.67 (d, J=5.4 Hz, 2H), 4.34 (t, J=6.6 Hz, 2H), 4.27 (q, J=7.2 Hz, 2H), 3.33 (t, J=6.6 Hz, 2H), 1.34 (t, J=7.2 Hz, 3H).

Example 2

2-[2-(naphthalen-2-yl)ethyloxy]-4-(1-pyrazolylmethyl)cinnamic acid ethyl ester

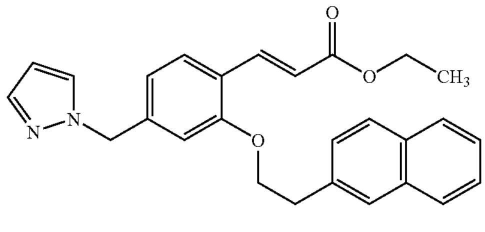

To a solution of the compound prepared in Example 1 (1.74 g) and triethylamine (1.29 ml) in anhydrous tetrahydrofuran (20 ml) was added mesyl chloride (537 μl) under an atmosphere of argon and the mixture was stirred for 15 minutes. The reaction mixture was extracted with ethyl acetate, and the organic layer was washed with water and a saturated aqueous solution of sodium chloride subsequently, dried over anhydrous sodium sulfate and concentrated. To a solution of pyrazole (346 mg) in anhydrous N,N-dimethylformamide (8 ml) was added sodium hydride (63.1% in oil) (193 mg) at 0° C. under an atmosphere of argon and the mixture was stirred for 10 minutes. To the mixture was added the solution of the above-mentioned crude product in anhydrous N,N-dimethylformamide (8 ml) and the mixture was stirred at room temperature for 1 hour. To the reaction mixture was added water at 0° C. and the mixture was extracted with diethyl ether. The organic layer was washed with water and a saturated aqueous solution of sodium chloride subsequently, dried over anhydrous sodium sulfate and concentrated to give the title compound (crude, 1.17 g). The compound was used to the next step without further purification.

TLC: Rf 0.36 (n-hexane:ethyl acetate=2:1).

Example 2(1)~2(12)

Using corresponding compounds, the following compounds were obtained by the same procedure of Example 2.

Example 2(1)

(2E)-3-(2-(2-(chroman-2-yl)ethoxy)-4-(imidazol-1-ylmethyl)phenyl)-2-propenic acid ethyl ester

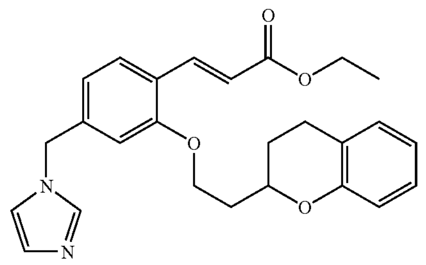

TLC: Rf 0.53 (chloroform:methanol=9:1).

Example 2(2)

(2E)-3-(2-(2-(naphthalen-2-yl)ethoxy)-4-(imidazol-1-ylmethyl)phenyl)-2-propenic acid ethyl ester

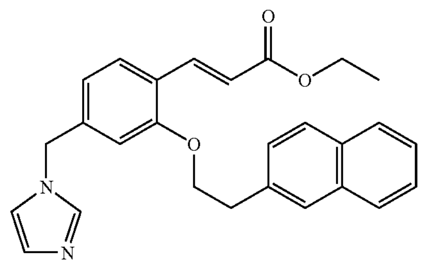

TLC: Rf 0.67 (chloroform:methanol=9:1).

Example 2(3)

3-(2-(2-(naphthalen-2-yl)ethoxy)-4-(pyrazol-1-ylmethyl)phenyl)propanoic acid ethyl ester

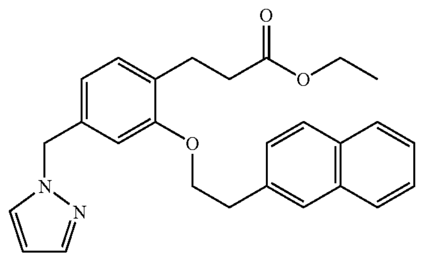

TLC: Rf 0.45 (n-hexane:ethyl acetate=2:1).

Example 2(4)

(2E)-3-(2-(2-(naphthalen-2-yl)ethoxy)-4-(thiophen-2-ylmethyl)phenyl)-2-propenic acid ethyl ester

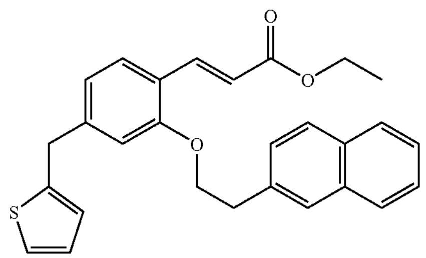

TLC: Rf 0.31 (n-hexane:ethyl acetate=3:1).

Example 2(5)

(2E)-3-(2-(2-(naphthalen-1-yl)ethoxy)-4-(pyrazol-1-ylmethyl)phenyl)-2-propenic acid ethyl ester

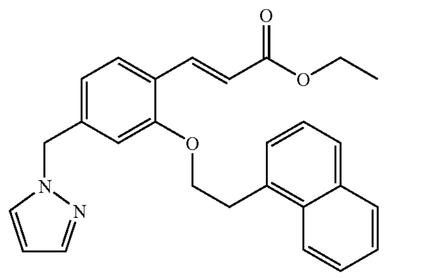

TLC: Rf 0.62 (n-hexane:ethyl acetate=3:1).

Example 2(6)

(2E)-3-(2-(2-(naphthalen-2-yl)ethoxy)-4-phenoxymethylphenyl)-2-propenic acid ethyl ester

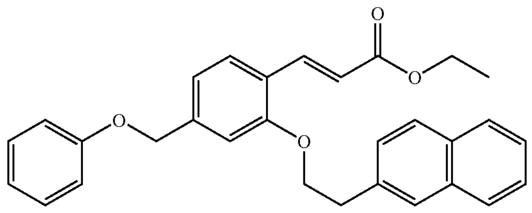

TLC: Rf 0.46 (n-hexane:ethyl acetate=4:1).

Example 2(7)

(2E)-3-(2-(2-(benzoylamino)ethoxy)-4-(pyrazol-1-ylmethyl)phenyl)-2-propenic acid ethyl ester

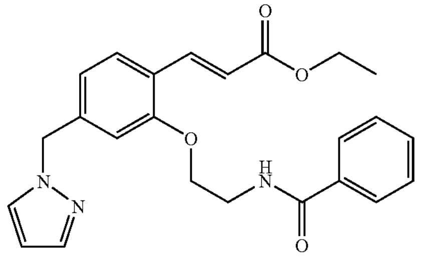

TLC: Rf 0.46 (chloroform:methanol=10:1).

Example 2(8)

(2E)-3-(2-(2-methoxy-2-(naphthalen-2-yl)ethoxy)-4-(pyrazol-1-ylmethyl)phenyl)-2-propenic acid ethyl ester

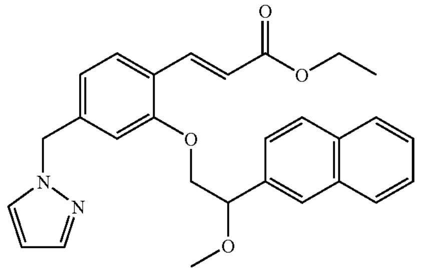

TLC: Rf 0.46 (n-hexane:ethyl acetate=1:1).

Example 2(9)

3-(2-(2-(naphthalen-2-yl)ethoxy)-4-(2-methylpyridin-3-yloxymethyl)phenyl)propanoic acid ethyl ester

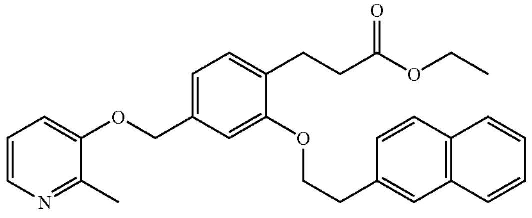

TLC: Rf 0.48 (n-hexane:ethyl acetate=1:1).

Example 2(10)

3-(2-(2-(naphthalen-2-yl)ethoxy)-4-(pyridin-2-yloxy)phenyl)propanoic acid methyl ester

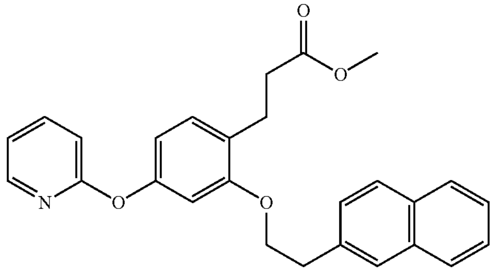

TLC: Rf 0.55 (n-hexane:ethyl acetate=2:1).

Example 2(11)

3-(2-(4-methyl-2-(4-fluoro-3-methylphenyl)pentyloxy)-4-(pyrazol-1-ylmethyl)phenyl)propanoic acid methyl ester

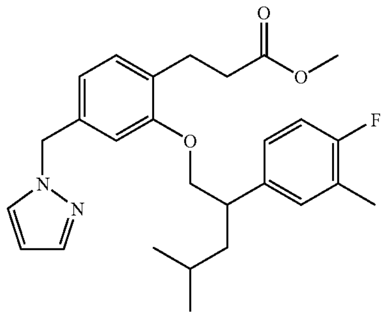

TLC: Rf 0.50 (n-hexane:ethyl acetate=2:1).

Example 2(12)

3-(2-(2-(9,10-dihydroacridin-9-one-10-yl)ethoxy)-4-(pyrazol-1-ylmethyl)phenyl)propanoic acid methyl ester

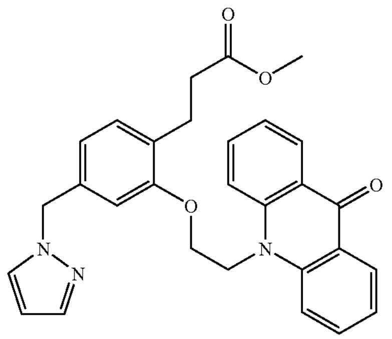

TLC: Rf 0.32 (n-hexane:ethyl acetate=1:2).

Example 3

(2E)-3-(2-(2-(naphthalen-2-yl)ethoxy)-4-(pyrazol-1-ylmethyl)phenyl)-2-propenoic acid

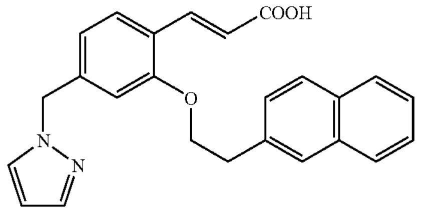

To a mixture of the compound prepared in Example 2 (253 mg) in tetrahydrofuran (2 ml)-methanol (1.5 ml) was added 2N aqueous solution of sodium hydroxide (1.5 ml) and the mixture was stirred at 50° C. for 1 hour. The reaction mixture was neutralized with 1N hydrochloric acid and then extracted with ethyl acetate. The organic layer was washed with water and a saturated aqueous solution of sodium chloride subsequently, dried over anhydrous magnesium sulfate and concentrated. The residue was purified by column chromatography on silica gel (n-hexane:ethyl acetate=3:2~2:3) to give the title compound (186 mg) having the following physical data.

TLC: Rf 0.28 (n-hexane:ethyl acetate=1:1);

NMR (200 MHz, $CDCl_3$): δ 8.07 (d, J=16.0 Hz, 1H), 7.88-7.72 (m, 4H), 7.57 (d, J=2.0 Hz, 1H), 7.51-7.35 (m, 5H), 6.77 (brd, J=7.8 Hz, 1H), 6.72 (brs, 1H), 6.51 (d, J=16.0 Hz, 1H), 6.29 (t, J=2.0 Hz, 1H), 5.30 (s, 2H), 4.25 (t, J=6.6 Hz, 2H), 3.28 (t, J=6.6 Hz, 2H).

Example 3(1)~Example 3(202)

Using the compounds prepared in Example 2(1)~2(12) or corresponding compounds, the following compounds were obtained by the same procedure of Example 3 or continued conversion to known salts.

Example 3(1)

(2E)-3-(2-(2-(2,5,7,8-tetramethyl-6-hydroxychroman-2-yl)ethoxy)-4-hydroxymethylphenyl)-2-propenoic acid

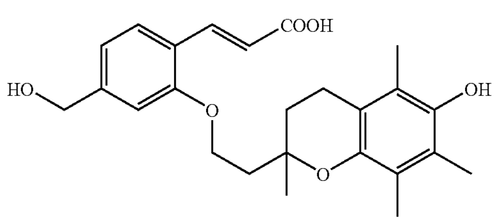

TLC: Rf 0.50 (chloroform:methanol=9:1);

NMR (300 MHz, $CDCl_3$): δ 8.05 (d, J=16 Hz, 1H), 7.50 (d, J=8.1 Hz, 1H), 6.97-6.88 (m, 2H), 6.50 (d, J=16 Hz, 1H), 4.68 (s, 2H), 4.37-4.19 (m, 2H), 2.68 (t, J=6.6 Hz, 2H), 2.37-2.07 (m, 2H), 2.16 (s, 3H), 2.12 (s, 6H), 2.00-1.81 (m, 2H), 1.37 (s, 3H).

Example 3(2)

(2E)-3-(2-(2-(2,5,7,8-tetramethyl-6-methoxychroman-2-yl)ethoxy)-4-(imidazol-1-ylmethyl)phenyl)-2-propenoic acid hydrochloride

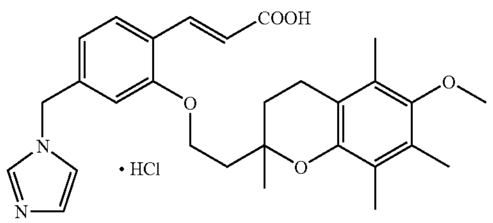

TLC: Rf 0.55 (chloroform:methanol=9:1);

NMR (300 MHz, DMSO-$d_6$): δ 9.29 (s, 1H), 7.90-7.65 (m, 4H), 7.26 (s, 1H), 6.98 (d, J=7.5 Hz, 1H), 6.53 (d, J=16.2 Hz, 1H), 5.42 (s, 2H), 4.40-4.10 (m, 2H), 3.52 (s, 3H), 2.66-2.56 (m, 2H), 2.20-1.76 (m, 4H), 2.09 (s, 3H), 2.07 (s, 3H), 2.00 (s, 3H), 1.32 (s, 3H).

Example 3(3)

(2E)-3-(2-(2-(2,5,7,8-tetramethylchroman-2-yl)ethoxy)-4-(imidazol-1-ylmethyl)phenyl)-2-propenoic acid hydrochloride

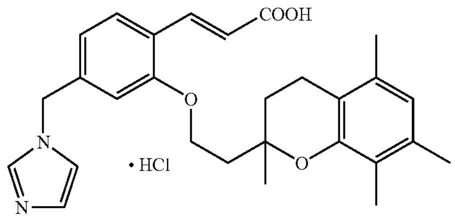

TLC: Rf 0.52 (chloroform:methanol=9:1);

NMR (300 MHz, DMSO-$d_6$): δ 9.28 (s, 1H), 7.85-7.65 (m, 4H), 7.26 (s, 1H), 6.68 (d, J=7.8 Hz, 1H), 6.60-6.46 (m, 2H), 5.42 (s, 2H), 4.40-4.15 (m, 2H), 2.64-2.54 (m, 2H), 2.24-1.76 (m, 4H), 2.12 (s, 3H), 2.11 (s, 3H), 1.98 (s, 3H), 1.33 (s, 3H).

Example 3(4)

(2E)-3-(2-(2-(2,5,7,8-tetramethyl-6-hydroxychroman-2-yl)ethoxy)-4-(pyrazol 1-ylmethyl)phenyl)-2-propenoic acid

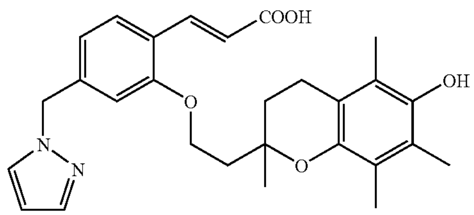

TLC: Rf 0.38 (chloroform:methanol=19:1);

NMR (300 MHz, DMSO-$d_6$): δ 12.28 (bs, 1H), 7.82 (d, J=1.8 Hz, 1H), 7.77 (d, J=16 Hz, 1H), 7.61 (d, J=8.0 Hz, 1H), 7.46 (d, J=1.8 Hz, 1H), 7.41 (bs, 1H), 6.92 (s, 1H), 6.71 (d, J=8.0 Hz, 1H), 6.46 (d, J=16 Hz, 1H), 6.27 (t, J=1.8 Hz, 1H), 5.32 (s, 2H), 4.27-4.03 (m, 2H), 2.56 (m, 2H), 2.17-1.71 (m, 4H), 2.04 (s, 3H), 2.01 (s, 3H), 1.98 (s, 3H), 1.27 (s, 3H).

Example 3(5)

(2E)-3-(2-(3-phenoxypropoxy)-4-(imidazol-1-ylmethyl)phenyl)-2-propenoic acid hydrochloride

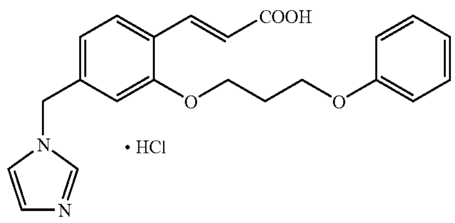

TLC: Rf 0.60 (chloroform:methanol=9:1);

NMR (300 MHz, DMSO-$d_6$): δ 9.29 (m, 1H), 7.80 (d, J=16 Hz, 1H), 7.79 (m, 1H), 7.71 (d, J=7.8 Hz, 1H), 7.67 (m, 1H), 7.32-7.22 (m, 3H), 7.04-6.88 (m, 4H), 6.55 (d, J=16 Hz, 1H), 5.41 (s, 2H), 4.24 (t, J=6.2 Hz, 2H), 4.15 (t, J=6.1 Hz, 2H), 2.24 (m, 2H).

Example 3(6)

(2E)-3-(2-(4-phenoxybutoxy)-4-(imidazol-1-ylmethyl)phenyl)-2-propenoic acid hydrochloride

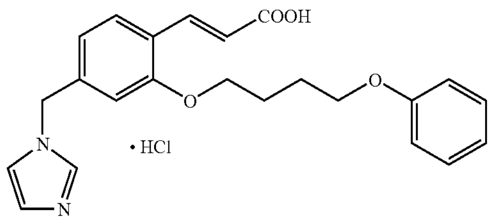

TLC: Rf 0.56 (chloroform:methanol=9:1);

NMR (300 MHz, DMSO-$d_6$): δ 9.29 (m, 1H), 7.81 (m, 1H), 7.80 (d, J=16 Hz, 1H), 7.71 (d, J=7.8 Hz, 1H), 7.67 (m, 1H), 7.32-7.21 (m, 3H), 7.04-6.86 (m, 4H), 6.57 (d, J=16 Hz, 1H), 5.41 (s, 2H), 4.15 (t, J=5.7 Hz, 2H), 4.03 (t, J=6.0 Hz, 2H), 2.02-1.81 (m, 4H).

Example 3(7)

(2E)-3-(2-(2-(chroman-2-yl)ethoxy)-4-(imidazol-1-ylmethyl)phenyl)-2-propenoic acid hydrochloride

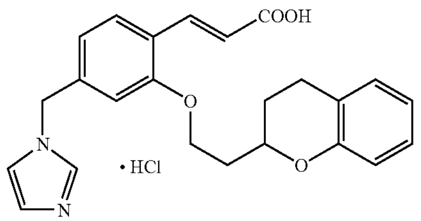

TLC: Rf 0.62 (chloroform:methanol=9:1);

NMR (300 MHz, DMSO-$d_6$): δ 9.26 (s, 1H), 7.81 (m, 1H), 7.79 (d, J=16 Hz, 1H), 7.71 (d, J=8.1 Hz, 1H), 7.67 (m, 1H), 7.30 (s, 1H), 7.08-6.96 (m, 3H), 6.83-6.70 (m, 2H), 6.56 (d, J=16 Hz, 1H), 5.42 (s, 2H), 4.35-4.17 (m, 3H), 2.90-2.66 (m, 2H), 2.29-2.02 (m, 3H), 1.82-1.65 (m, 1H).

Example 3(8)

(2E)-3-(2-(6-phenoxyhexyloxy)-4-(imidazol-1-ylmethyl)phenyl)-2-propenoic acid hydrochloride

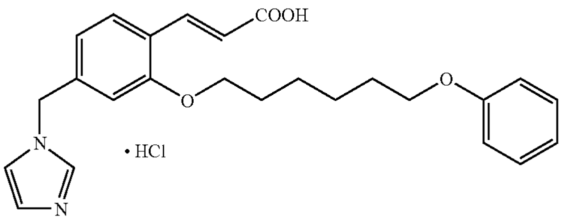

TLC: Rf 0.56 (chloroform:methanol=9:1);

NMR (300 MHz, DMSO-$d_6$): δ 9.22 (s, 1H), 7.78 (s, 1H), 7.77 (d, J=16 Hz, 1H), 7.69 (d, J=8.1 Hz, 1H), 7.64 (s, 1H), 7.31-7.20 (m, 3H), 7.01-6.85 (m, 4H), 6.55 (d, J=16 Hz, 1H), 5.40 (s, 2H), 4.08 (t, J=6.3 Hz, 2H), 3.95 (t, J=6.5 Hz, 2H), 1.89-1.66 (m, 4H), 1.60-1.40 (m, 4H).

Example 3(9)

(2E)-3-(2-(2-(naphthalen-2-yl)ethoxy)-4-(imidazol-1-ylmethyl)phenyl)-2-propenoic acid hydrochloride

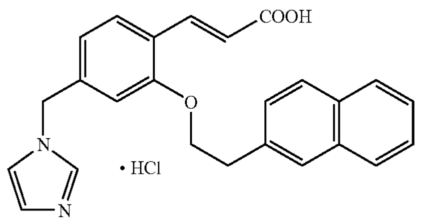

TLC: Rf 0.36 (chloroform:methanol=19:1);

NMR (300 MHz, DMSO-$d_6$): δ 9.28 (m, 1H), 7.92-7.77 (m, 6H), 7.72-7.64 (m, 2H), 7.56-7.42 (m, 3H), 7.27 (s, 1H), 6.98 (d, J=7.8 Hz, 1H), 6.55 (d, J=16 Hz, 1H), 5.39 (s, 2H), 4.35 (t, J=6.6 Hz, 2H), 3.27 (t, J=6.6 Hz, 2H).

Example 3(10)

(2E)-3-(2-(2-(benzofuran-2-yl)ethoxy)-4-(imidazol-1-ylmethyl)phenyl)-2-propenoic acid hydrochloride

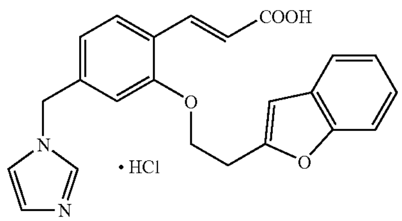

TLC: Rf 0.52 (chloroform:methanol=9:1);

NMR (300 MHz, DMSO-$d_6$): δ 9.28 (s, 1H), 7.84-7.65 (m, 4H), 7.58-7.47 (m, 2H), 7.31 (s, 1H), 7.27-7.15 (m, 2H), 7.00 (d, J=8.1 Hz, 1H), 6.73 (s, 1H), 6.57 (d, J=16 Hz, 1H), 5.41 (s, 2H), 4.41 (t, J=6.3 Hz, 2H), 3.34 (t, J=6.3 Hz, 2H).

Example 3(11)

(2E)-3-(2-(2-(2,5,7,8-tetramethyl-6-hydroxychroman-2-yl)ethoxy)-4-(2-methylimidazol-1-ylmethyl)phenyl)-2-propenoic acid hydrochloride

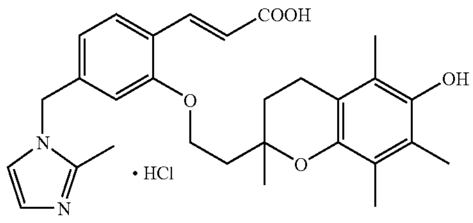

TLC: Rf 0.50 (chloroform:methanol=9:1);

NMR (300 MHz, $CD_3OD$): δ 7.93 (d, J=16 Hz, 1H), 7.61 (d, J=8.1 Hz, 1H), 7.45 (s, 2H), 6.93 (s, 1H), 6.81 (d, J=8.1 Hz, 1H), 6.52 (d, J=16 Hz, 1H), 5.32 (d, J=15 Hz, 1H), 5.28 (d, J=15 Hz, 1H), 4.41-4.21 (m, 2H), 2.65 (t, J=7.1 Hz, 2H), 2.61 (s, 3H), 2.29-1.80 (m, 4H), 2.11 (s, 3H), 2.08 (s, 3H), 2.05 (s, 3H), 1.35 (s, 3H).

Example 3(12)

3-(2-(2-(naphthalen-2-yl)ethoxy)-4-(pyrazol-1-ylmethyl)phenyl)propanoic acid

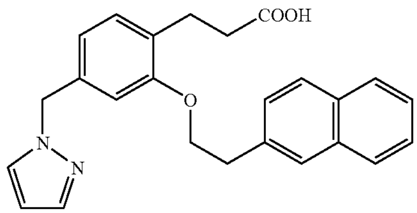

[Salt-free]

TLC: Rf 0.33 (hexane:ethyl acetate=1:1);

NMR (200 MHz, $CDCl_3$): δ 7.84-7.68 (m, 4H), 7.54 (d, J=1.8 Hz, 1H), 7.48-7.35 (m, 3H), 7.33 (d, J=2.2 Hz, 1H), 7.08 (d, J=7.4 Hz, 1H), 6.74-6.65 (m, 2H), 6.28-6.23 (m, 1H), 5.24 (s, 2H), 4.19 (t, J=6.4 Hz, 2H), 3.22 (t, J=6.4 Hz, 2H), 2.93-2.82 (m, 2H), 2.56-2.45 (m, 2H).

Sodium Salt:

TLC: Rf 0.33 (n-hexane:ethyl acetate=1:1);

NMR (300 MHz, DMSO-$d_6$): δ7.94-7.82 (m, 4H), 7.77 (d, J=2.1 Hz, 1H), 7.56-7.40 (m, 4H), 7.07 (d, J=7.8 Hz, 1H), 6.83 (s, 1H), 6.64 (d, J=8.1 Hz, 1H), 6.24 (t, J=2.1 Hz, 1H), 5.23 (s, 2H), 4.17 (t, J=6.6 Hz, 2H), 3.19 (t, J=6.6 Hz, 2H), 2.70 (t, J=7.8 Hz, 2H), 2.18 (t, J=7.8 Hz, 2H).

Example 3(13)

(2E)-3-(2-(naphthalen-2-ylmethoxy)-4-(pyrazol-1-ylmethyl)phenyl)-2-propenoic acid

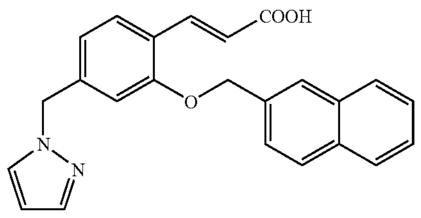

TLC: Rf 0.57 (hexane:ethyl acetate=1:3);

NMR (500 MHz, DMSO-$d_6$): δ 8.01-7.87 (m, 4H), 7.78 (d, J=2.0 Hz, 1H), 7.69 (d, J=16 Hz, 1H), 7.63-7.48 (m, 4H), 7.43 (d, J=2.0 Hz, 1H), 7.08 (s, 1H), 6.73 (d, J=8.0 Hz, 1H), 6.47 (d, J=16 Hz, 1H), 6.23 (t, J=2.0 Hz, 1H), 5.30 (s, 2H), 5.29 (s, 2H).

Example 3(14)

(2E)-3-(2-(2-(2,5,7,8-tetramethyl-6-hydroxychroman-2-yl)ethoxy)-4-(2H-1,2,3-triazol-2-ylmethyl)phenyl)-2-propenoic acid

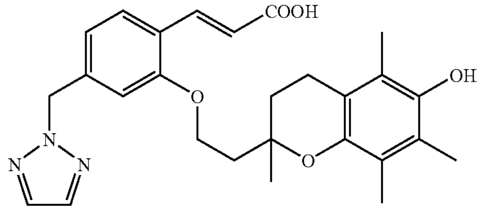

TLC: Rf 0.60 (chloroform:methanol=9:1);

NMR (200 MHz, $CD_3OD$): δ 7.92 (d, J=16.2 Hz, 1H), 7.71 (s, 2H), 7.52 (d, J=7.6 Hz, 1H), 6.85 (s, 1H), 6.80 (d, J=8.4 Hz, 1H), 6.47 (d, J=16.2 Hz, 1H), 5.56 (s, 2H), 4.36-4.08 (m, 2H), 2.64 (t, J=6.6 Hz, 2H), 2.20-2.00 (m, 2H), 2.12 (s, 3H), 2.08 (s, 3H), 2.05 (s, 3H), 1.96-1.80 (m, 2H), 1.33 (s, 3H).

Example 3(15)

(2E)-3-(2-(2-(2,5,7,8-tetramethyl-6-hydroxychroman-2-yl)ethoxy)-4-(1H-1,2,3-triazol-1-ylmethyl)phenyl)-2-propenoic acid hydrochloride

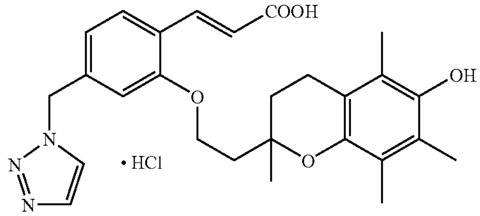

TLC: Rf 0.49 (chloroform:methanol=9:1);

NMR (200 MHz, $CD_3OD$): δ 8.37 (d, J=1.2 Hz, 1H), 8.24 (d, J=1.2 Hz, 1H), 7.93 (d, J=16.4 Hz, 1H), 7.59 (d, J=8.2 Hz, 1H), 7.01 (brs, 1H), 6.93 (brd, J=8.2 Hz, 1H), 6.50 (d, J=16.4 Hz, 1H), 5.70 (s, 2H), 4.90 (s, 2H), 4.45-4.15 (m, 2H), 2.72-2.58 (m, 2H), 2.26-1.80 (m, 4H), 2.11 (s, 3H), 2.08 (s, 3H), 2.05 (s, 3H), 1.34 (s, 3H).

Example 3(16)

(2E)-3-(2-(2-(naphthalen-2-yl)ethoxy)-4-benzylphenyl)-2-propenoic acid

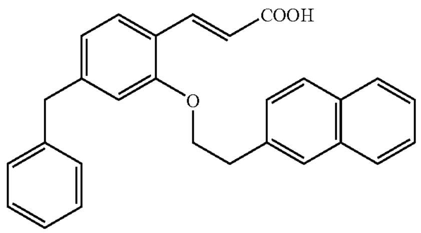

TLC: Rf 0.37 (hexane:ethyl acetate=2:1);

NMR (200 MHz, $CDCl_3$): δ 8.12 (d, J=16.4 Hz, 1H), 7.88-7.74 (m, 4H), 7.52-7.10 (m, 9H), 6.79 (brd, J=8.0 Hz, 1H), 6.72 (brs, 1H), 6.52 (d, J=16.4 Hz, 1H), 4.26 (t, J=6.6 Hz, 2H), 3.95 (s, 2H), 3.29 (t, J=6.6 Hz, 2H).

Example 3(17)

(2E)-3-(2-(2-(naphthalen-2-yl)ethoxy)-4-(thiophen-2-ylmethyl)phenyl)-2-propenoic acid

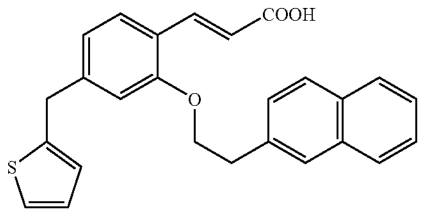

TLC: Rf 0.31 (hexane:ethyl acetate=2:1);

NMR (300 MHz, $CDCl_3$): δ 8.12 (d, J=16.2 Hz, 1H), 7.86-7.74 (m, 4H), 7.50-7.38 (m, 4H), 7.15 (dd, J=5.1, 1.2 Hz, 1H), 6.92 (dd, J=5.1, 3.6 Hz, 1H), 6.84 (d, J=7.5 Hz, 1H), 6.82-6.76 (m, 2H), 6.53 (d, J=16.2 Hz, 1H), 4.29 (t, J=6.8 Hz, 2H), 4.12 (s, 2H), 3.31 (t, J=6.8 Hz, 2H).

Example 3(18)

(2E)-3-(2-(2-(naphthalen-2-yl)ethoxy)-4-(thiophen-3-ylmethyl)phenyl)-2-propenoic acid

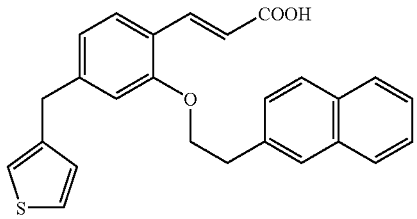

TLC: Rf 0.31 (hexane:ethyl acetate=2:1);

NMR (200 MHz, $CDCl_3$): δ 8.13 (d, J=16.0 Hz, 1H), 7.88-7.74 (m, 4H), 7.52-7.36 (m, 4H), 7.25 (dd, J=4.6, 3.2 Hz,

1H), 6.96-6.85 (m, 2H), 6.80 (brd, J=8.0 Hz, 1H), 6.73 (brs, 1H), 6.53 (d, J=16.0 Hz, 1H), 4.27 (t, J=6.6 Hz, 2H), 3.95 (s, 2H), 3.30 (t, J=6.6 Hz, 2H).

Example 3(19)

4-(2-(2-(naphthalen-2-yl)ethoxy)-4-(pyrazol-1-ylmethyl)phenyl)butanoic acid

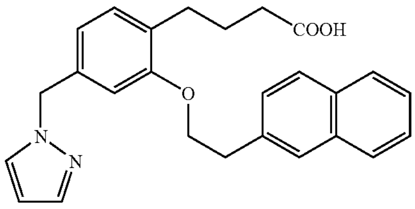

TLC: Rf 0.35 (hexane:ethyl acetate=1:1);

NMR (200 MHz, $CDCl_3$): δ 7.84-7.73 (m, 3H), 7.69 (brs, 1H), 7.54 (d, J=1.6 Hz, 1H), 7.50-7.32 (m, 4H), 7.02 (d, J=7.6 Hz, 1H), 6.74-6.64 (m, 2H), 6.25 (t, J=2.1 Hz, 1H), 5.24 (s, 2H), 4.18 (t, J=6.6 Hz, 2H), 3.21 (t, J=6.6 Hz, 2H), 2.57 (t, J=7.5 Hz, 2H), 2.20 (t, J=7.4 Hz, 2H), 1.88-1.68 (m, 2H).

Example 3(20)

(2E)-3-(2-(2-(naphthalen-1-yl)ethoxy)-4-(pyrazol-1-ylmethyl)phenyl)-2-propenoic acid

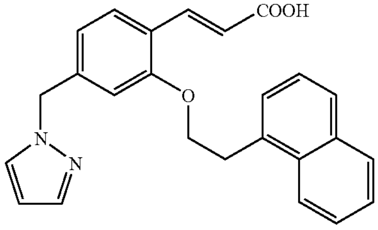

TLC: Rf 0.26 (hexane:ethyl acetate=1:1);

NMR (200 MHz, $CDCl_3$): δ 8.14-8.02 (m, 2H), 7.90-7.72 (m, 2H), 7.60-7.34 (m, 7H), 6.76 (brd, J=8.0 Hz, 1H), 6.70 (brs, 1H), 6.53 (d, J=16.2 Hz, 1H), 6.27 (t, J=2.1 Hz, 1H), 5.26 (s, 2H), 4.32 (t, J=7.0 Hz, 2H), 3.62 (t, J=7.0 Hz, 2H).

Example 3(21)

(2E)-3-(2-(3-(naphthalen-2-yl)propoxy)-4-(pyrazol-1-ylmethyl)phenyl)-2-propenoic acid

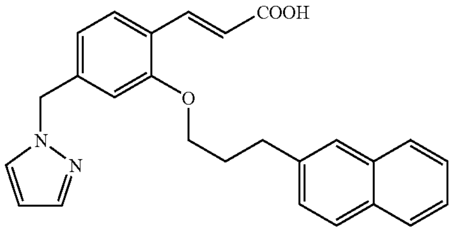

TLC: Rf 0.26 (hexane:ethyl acetate=1:1);

NMR (200 MHz, $CDCl_3$): δ 8.09 (d, J=16.2 Hz, 1H), 7.84-7.72 (m, 3H), 7.66-7.30 (m, 7H), 6.77 (brd, J=8.0 Hz, 1H), 6.66 (brs, 1H), 6.59 (d, J=16.2 Hz, 1H), 6.27 (t, J=2.1 Hz, 1H), 5.28 (s, 2H), 4.00 (t, J=6.3 Hz, 2H), 2.97 (t, J=7.5 Hz, 2H), 2.32-2.14 (m, 2H).

Example 3(22)

(2E)-3-(2-(2-(naphthalen-2-yl)ethoxy)-4-phenoxymethylphenyl)-2-propenoic acid

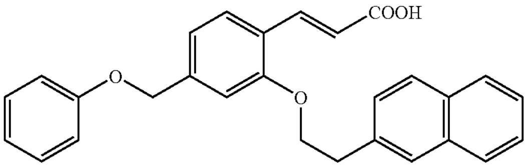

TLC: Rf 0.52 (hexane:ethyl acetate=1:1);

NMR (300 MHz, $CDCl_3$): δ 8.13 (d, J=16 Hz, 1H), 7.87-7.76 (m, 4H), 7.57-7.39 (m, 4H), 7.34-7.24 (m, 2H), 7.06-6.92 (m, 5H), 6.56 (d, J=16 Hz, 1H), 5.05 (s, 2H), 4.35 (t, J=6.8 Hz, 2H), 3.33 (t, J=6.8 Hz, 2H).

Example 3(23)

2-(2-(2-(naphthalen-2-yl)ethoxy)-4-(pyrazol-1-ylmethyl)phenyl)acetic acid

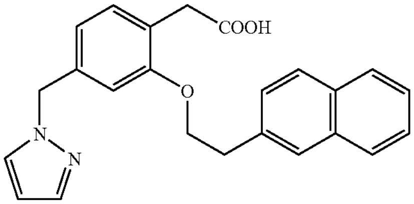

TLC: Rf 0.48 (hexane:ethyl acetate=1:4);

NMR (300 MHz, $CDCl_3$): δ 7.83-7.73 (m, 3H), 7.68 (s, 1H), 7.54 (d, J=1.8 Hz, 1H), 7.49-7.32 (m, 4H), 7.11 (d, J=7.5 Hz, 1H), 6.74 (dd, J=7.8, 1.5 Hz, 1H), 6.69 (d, J=1.5 Hz, 1H), 6.26 (t, J=2.1 Hz, 1H), 5.26 (s, 2H), 4.17 (t, J=6.6 Hz, 2H), 3.58 (s, 2H), 3.17 (t, J=6.6 Hz, 2H).

Example 3(24)

(2E)-3-(2-(2-(naphthalen-2-yl)ethoxy)-4-(2-oxopyrrolidin-1-yl)phenyl)-2-propenoic acid

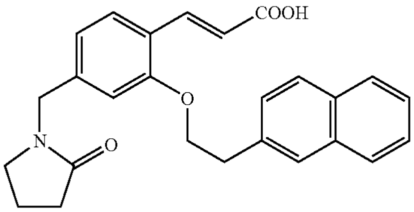

TLC: Rf 0.36 (chloroform:methanol=10:1);

NMR (200 MHz, $CDCl_3$): δ 8.10 (d, J=16.0 Hz, 1H), 7.90-7.76 (m, 4H), 7.52-7.36 (m, 4H), 6.86-6.76 (m, 2H), 6.54 (d, J=16.0 Hz, 1H), 4.41 (s, 2H), 4.31 (t, J=6.5 Hz, 2H), 3.32 (t, J=6.5 Hz, 2H), 3.24 (t, J=7.0 Hz, 2H), 2.45 (t, J=8.0 Hz, 2H), 2.10-1.88 (m, 2H).

Example 3(25)

2-(2-(2-(naphthalen-2-yl)ethoxy)-4-(pyrazol-1-ylmethyl)phenoxy)acetic acid

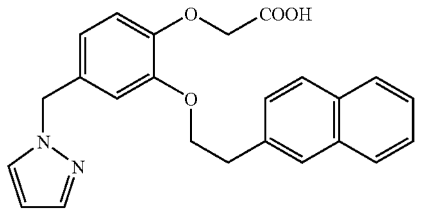

TLC: Rf 0.68 (chloroform:methanol:acetic acid=20:1:1);

NMR (300 MHz, $CDCl_3$): δ 7.83-7.75 (m, 3H), 7.70 (s, 1H), 7.55 (dd, J=1.8, 0.6 Hz, 1H), 7.49-7.32 (m, 4H), 6.84 (d, J=7.8 Hz, 1H), 6.78-6.71 (m, 2H), 6.26 (t, J=2.1 Hz, 1H), 5.22 (s, 2H), 4.59 (s, 2H), 4.25 (t, J=7.1 Hz, 2H), 3.25 (t, J=7.1 Hz, 2H).

Example 3(26)

(2E)-3-(2-(2-(naphthalen-2-yl)ethoxy)-4-benzyloxyphenyl)-2-propenoic acid

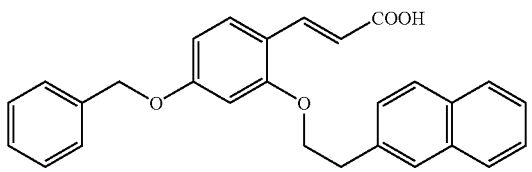

TLC: Rf 0.46 (hexane:ethyl acetate=1:1);

NMR (300 MHz, $CDCl_3$): δ 8.06 (d, J=16 Hz, 1H), 7.87-7.76 (m, 4H), 7.50-7.29 (m, 9H), 6.60-6.51 (m, 2H), 6.46 (d, J=16 Hz, 1H), 5.05 (s, 2H), 4.29 (t, J=6.8 Hz, 2H), 3.33 (t, J=6.8 Hz, 2H).

Example 3(27)

(2E)-3-(2-(2-(naphthalen-2-yl)ethoxy)-4-dimethylaminomethylphenyl)-2-propenoic acid

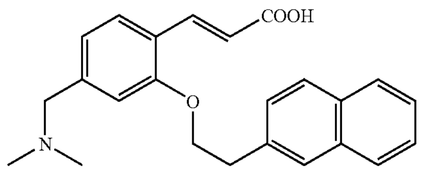

TLC: Rf 0.48 (chloroform:methanol=5:1);

NMR (200 MHz, DMSO-$d_6$): δ 7.92-7.80 (m, 5H), 7.62-7.40 (m, 4H), 7.01 (brs, 1H), 6.88 (d, J=7.6 Hz, 1H), 6.50 (d, J=16.0 Hz, 1H), 4.33 (t, J=6.4 Hz, 2H), 3.37 (s, 2H), 3.26 (t, J=6.4 Hz, 2H), 2.13 (s, 6H).

Example 3(28)

(2E)-3-(2-(2-(naphthalen-2-yl)ethoxy)-4-phenylcarbamoylphenyl)-2-propenoic acid

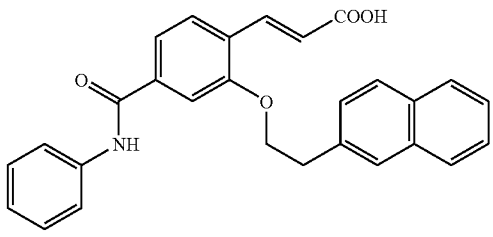

TLC: Rf 0.40 (chloroform:methanol=10:1);

NMR (200 MHz, DMSO-$d_6$): δ 10.26 (s, 1H), 7.98-7.70 (m, 8H), 7.65-7.30 (m, 7H), 7.12 (t, J=7.3 Hz, 1H), 6.67 (d, J=16.2 Hz, 1H), 4.49 (t, J=6.4 Hz, 2H), 3.42-3.24 (m, 2H).

Example 3(29)

(2E)-3-(2-(2-phenylethoxy)-4-(pyrazol-1-ylmethyl)phenyl)-2-propenoic acid

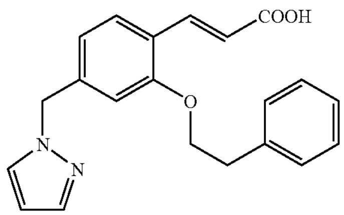

TLC: Rf 0.57 (chloroform:methanol=9:1);

NMR (300 MHz, $CDCl_3$): δ 8.03 (d, J=16 Hz, 1H), 7.57 (d, J=2.1 Hz, 1H), 7.46 (d, J=8.0 Hz, 1H), 7.40 (d, J=2.1 Hz, 1H), 7.37-7.20 (m, 5H), 6.78 (d, J=8.0 Hz, 1H), 6.71 (s, 1H), 6.50 (d, J=16 Hz, 1H), 6.30 (t, J=2.1 Hz, 1H), 5.31 (s, 2H), 4.18 (t, J=6.9 Hz, 2H), 3.13 (t, J=6.9 Hz, 2H).

Example 3(30)

(2E)-3-(2-(naphthalen-2-ylmethoxymethyl)-4-(pyrazol-1-ylmethyl)phenyl)-2-propenoic acid

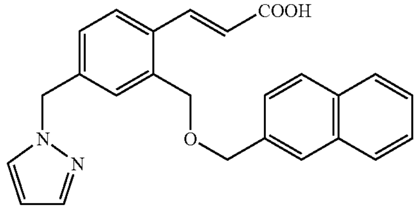

TLC: Rf 0.38 (chloroform:methanol=19:1);

NMR (300 MHz, $CDCl_3$): δ 8.12 (d, J=16 Hz, 1H), 7.88-7.78 (m, 4H), 7.61 (d, J=8.1 Hz, 1H), 7.57 (d, J=2.2 Hz, 1H), 7.53-7.39 (m, 4H), 7.27 (m, 1H), 7.17 (d, J=8.1 Hz, 1H), 6.40 (d, J=16 Hz, 1H), 6.30 (t, J=2.2 Hz, 1H), 5.35 (s, 2H), 4.75 (s, 2H), 4.65 (s, 2H).

Example 3(31)

(2E)-3-(2-((3E)-4-phenyl-3-butenyloxy)-4-(pyrazol-1-ylmethyl)phenyl)-2-propenoic acid

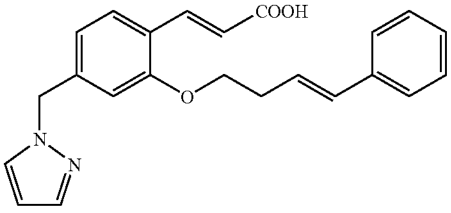

TLC: Rf 0.23 (hexane:ethyl acetate=1:1);

NMR (200 MHz, $CDCl_3$): δ 8.03 (d, J=16.0 Hz, 1H), 7.58-7.18 (m, 8H), 6.81-6.74 (m, 2H), 6.56 (d, J=16.0 Hz, 2H), 6.34-6.19 (m, 2H), 5.33 (s, 2H), 4.10 (t, J=6.5 Hz, 2H), 2.74 (q, J=6.5 Hz, 2H).

Example 3(32)

(2E)-3-(2-(2-hydroxy-3-phenoxypropoxy)-4-(pyrazol-1-ylmethyl)phenyl)-2-propenoic acid

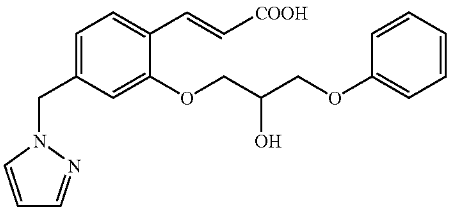

TLC: Rf 0.47 (chloroform:methanol=9:1);

NMR (300 MHz, DMSO-$d_6$): δ 12.28 (bs, 1H), 7.86-7.77 (m, 2H), 7.62 (d, J=8.0 Hz, 1H), 7.46 (dd, J=2.0, 0.8 Hz, 1H), 7.32-7.23 (m, 2H), 7.03-6.88 (m, 4H), 6.73 (d, J=8.0 Hz, 1H), 6.52 (d, J=16 Hz, 1H), 6.27 (t, J=2.0 Hz, 1H), 5.47 (bs, 1H), 5.33 (s, 2H), 4.26-3.99 (m, 5H).

Example 3(33)

(2E)-3-(2-(2-(1,4-benzodioxan-6-yl)ethoxy)-4-(pyrazol-1-ylmethyl)phenyl)-2-propenoic acid

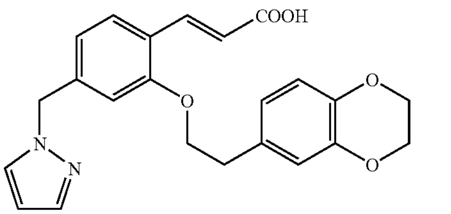

TLC: Rf 0.44 (chloroform:methanol=10:1);

NMR (300 MHz, $CDCl_3$): δ 8.01 (d, J=16.0 Hz, 1H), 7.57 (d, J=2.0 Hz, 1H), 7.46 (d, J=8.0 Hz, 1H), 7.40 (d, J=2.0 Hz, 1H), 6.83-6.73 (m, 4H), 6.70 (s, 1H), 6.48 (d, J=16.0 Hz, 1H), 6.30 (t, J=2.0 Hz, 1H), 5.30 (s, 2H), 4.23 (br, 4H), 4.13 (t, J=7.0 Hz, 2H), 3.01 (t, J=7.0 Hz, 2H).

Example 3(34)

(2E)-3-(2-(2-(1,4-benzodioxan-2-yl)ethoxy)-4-(pyrazol-1-ylmethyl)phenyl)-2-propenoic acid

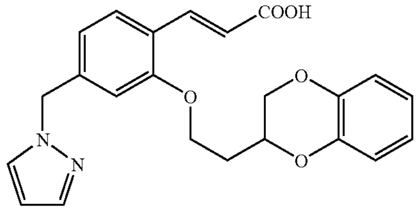

TLC: Rf 0.44 (chloroform:methanol=10:1);

NMR (300 MHz, $CDCl_3$): δ 8.02 (d, J=16.0 Hz, 1H), 7.58 (dd, J=2.0, 0.5 Hz, 1H), 7.50 (d, J=8.0 Hz, 1H), 7.43 (dd, J=2.0, 0.5 Hz, 1H), 6.88-6.76 (m, 6H), 6.48 (d, J=16.0 Hz, 1H), 6.32 (t, J=2.0 Hz, 1H), 5.33 (s, 2H), 4.42 (dq, J=2.0, 7.0 Hz, 1H), 4.32 (dd, J=11.0, 2.0 Hz, 1H), 4.29-4.15 (m, 2H), 4.00 (dd, J=11.0, 7.0 Hz, 1H), 2.18 (q, J=7.0 Hz, 2H).

Example 3(35)

(2E)-3-(2-(2-(naphthalen-2-yl)ethoxy)-4-cyanomethylphenyl)-2-propenoic acid

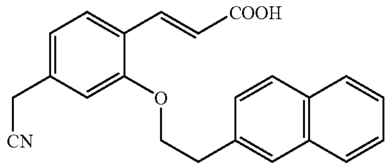

TLC: Rf 0.52 (chloroform:methanol=10:1);

NMR (300 MHz, DMSO-$d_6$): δ 7.94-7.78 (m, 5H), 7.69 (d, J=7.8 Hz, 1H), 7.60-7.42 (m, 3H), 7.12 (s, 1H), 6.96 (d, J=7.8 Hz, 1H), 6.54 (d, J=15.9 Hz, 1H), 4.37 (t, J=6.6 Hz, 2H), 4.04 (s, 2H), 3.40-3.20 (m, 2H).

Example 3(36)

(2E)-3-(2-(2-(naphthalen-2-yloxy)ethyl)-4-(pyrazol-1-ylmethyl)phenyl)-2-propenoic acid

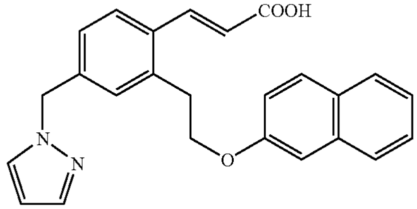

TLC: Rf 0.35 (chloroform:methanol=19:1);

NMR (300 MHz, $CDCl_3$): δ 8.20 (d, J=16 Hz, 1H), 7.75-7.66 (m, 3H), 7.63-7.56 (m, 2H), 7.45-7.37 (m, 2H), 7.35-

7.27 (m, 1H), 7.20-7.04 (m, 4H), 6.41 (d, J=16 Hz, 1H), 6.30 (t, J=2.1 Hz, 1H), 5.35 (s, 2H), 4.23 (t, J=6.7 Hz, 2H), 3.28 (t, J=6.7 Hz, 2H).

Example 3(37)

(2E)-3-(2-(2-(N-benzoyl-N-methylamino)ethoxy)-4-(pyrazol-1-ylmethyl)phenyl)-2-propenoic acid

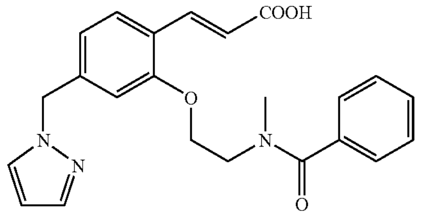

TLC: Rf 0.30 (chloroform:methanol=10:1);

NMR (500 MHz, DMSO-$d_6$ at 100 degrees): δ 7.80 (d, J=16.0 Hz, 1H), 7.73 (d, J=2.0 Hz, 1H), 7.57 (d, J=8.0 Hz, 1H), 7.46 (d, J=2.0 Hz, 1H), 7.41-7.36 (m, 5H), 6.98 (s, 1H), 6.80 (d, J=8.0 Hz, 1H), 6.44 (d, J=16.0 Hz, 1H), 6.26 (t, J=2.0 Hz, 1H), 5.32 (s, 2H), 4.25 (brt, 2H), 3.78 (brt, 2H), 3.02 (s, 3H).

Example 3(38)

(2E)-3-(2-(2-(naphthalen-2-yl)ethoxy)-4-phenylthiomethylphenyl)-2-propenoic acid

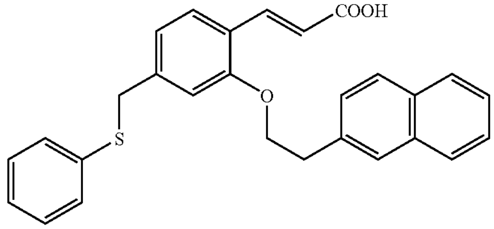

TLC: Rf 0.60 (chloroform:methanol=9:1);

NMR (300 MHz, DMSO-$d_6$): δ 12.30 (brs, 1H), 7.92-7.75 (m, 5H), 7.60-7.42 (m, 4H), 7.37-7.12 (m, 5H), 7.05 (s, 1H), 6.94 (d, J=7.8 Hz, 1H), 6.48 (d, J=16.2 Hz, 1H), 4.26 (t, J=6.6 Hz, 2H), 4.23 (s, 2H), 3.24 (t, J=6.6 Hz, 2H).

Example 3(39)

(2E)-3-(2-(2-(benzoylamino)ethoxy)-4-(pyrazol-1-ylmethyl)phenyl)-2-propenoic acid

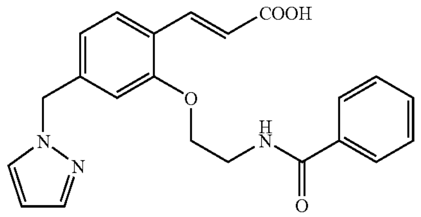

TLC: Rf 0.31 (chloroform:methanol=10:1);

NMR (300 MHz, $CDCl_3$): δ 7.92 (d, J=15.5 Hz, 1H), 7.77 (d, J=7.0 Hz, 2H), 7.56 (s, 1H), 7.50-7.36 (br, 5H), 6.81-6.64 (m, 4H), 6.30 (br, 1H), 5.30 (br, 2H), 4.15 (br, 2H), 3.92 (br, 2H).

Example 3(40)

(2E)-3-(2-(2-methoxy-3-phenoxypropoxy)-4-(pyrazol-1-ylmethyl)phenyl)-2-propenoic acid

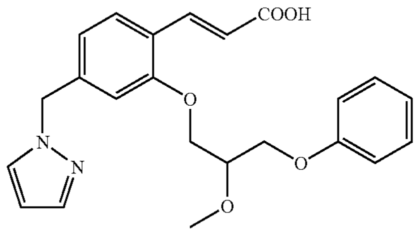

TLC: Rf 0.42 (chloroform:methanol=9:1);

NMR (300 MHz, DMSO-$d_6$): δ 12.29 (brs, 1H), 7.83 (d, J=2.1 Hz, 1H), 7.79 (d, J=16.2 Hz, 1H), 7.62 (d, J=7.8 Hz, 1H), 7.50-7.44 (m, 1H), 7.34-7.23 (m, 2H), 7.06-6.88 (m, 4H), 6.74 (d, J=8.1 Hz, 1H), 6.53 (d, J=16.2 Hz, 1H), 6.28 (t, J=2.1 Hz, 1H), 5.33 (s, 2H), 4.30-4.08 (m, 4H), 4.00-3.88 (m, 1H), 3.44 (s, 3H).

Example 3(41)

(2E)-3-(2-(2-methoxy-2-(naphthalen-2-yl)ethoxy)-4-(pyrazol-1-ylmethyl)phenyl)-2-propenoic acid

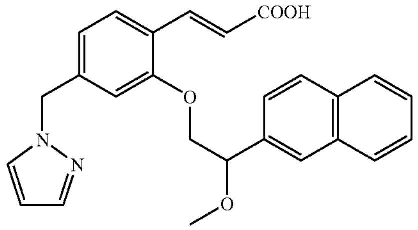

TLC: Rf 0.59 (chloroform:methanol=9:1);

NMR (300 MHz, $CDCl_3$): δ 8.03 (d, J=16 Hz, 1H), 7.92-7.81 (m, 4H), 7.57-7.42 (m, 5H), 7.37 (d, J=2.1 Hz, 1H), 6.78 (dd, J=8.0, 1.2 Hz, 1H), 6.70 (d, J=1.2 Hz, 1H), 6.60 (d, J=16 Hz, 1H), 6.28 (t, J=2.1 Hz, 1H), 5.28 (s, 2H), 4.78 (dd, J=7.2, 4.5 Hz, 1H), 4.27 (dd, J=9.9, 7.2 Hz, 1H), 4.12 (dd, J=9.9, 4.5 Hz, 1H), 3.41 (s, 3H).

Example 3(42)

(2E)-3-(2-(pyrazol-1-ylmethyl)-3-(2-(naphthalen-2-yl)ethoxy)thiophen-4-yl)-2-propenoic acid

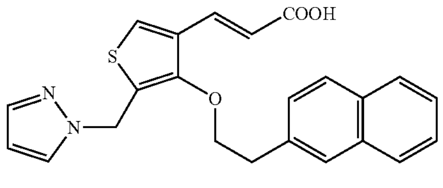

TLC: Rf 0.59 (chloroform:methanol=9:1);

NMR (300 MHz, $CDCl_3$): δ 7.85-7.72 (m, 4H), 7.60 (d, J=16 Hz, 1H), 7.52-7.38 (m, 5H), 7.12 (d, J=2.0 Hz, 1H), 6.45

(d, J=16 Hz, 1H), 6.17 (t, J=2.0 Hz, 1H), 5.16 (s, 2H), 4.21 (t, J=6.8 Hz, 2H), 3.27 (t, J=6.8 Hz, 2H).

Example 3(43)

(2E)-3-(3-(2-(naphthalen-2-yl)ethoxy)-4-(pyrazol-1-ylmethyl)thiophen-2-yl)-2-propenoic acid

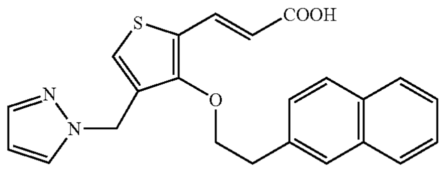

TLC: Rf 0.59 (chloroform:methanol=9:1);

NMR (300 MHz, $CDCl_3$): δ 7.87 (d, J=16 Hz, 1H), 7.84-7.76 (m, 3H), 7.72 (s, 1H), 7.53-7.36 (m, 4H), 7.11 (d, J=2.0 Hz, 1H), 7.08 (s, 1H), 6.17 (t, J=2.0 Hz, 1H), 6.12 (d, J=16 Hz, 1H), 4.97 (s, 2H), 4.26 (t, J=6.8 Hz, 2H), 3.24 (t, J=6.8 Hz, 2H).

Example 3(44)

(2E)-3-(2-(2-(naphthalen-2-yl)ethoxy)-4-(N-mesyl-N-phenylaminomethyl)phenyl)-2-propenoic acid

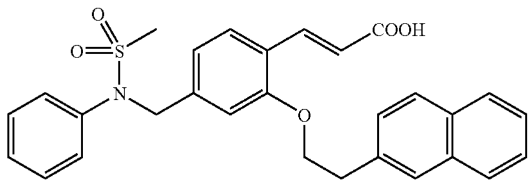

TLC: Rf 0.51 (chloroform:methanol=19:1);

NMR (300 MHz, DMSO-$d_6$): δ 7.89-7.81 (m, 4H), 7.75 (d, J=16 Hz, 1H), 7.56-7.18 (m, 9H), 6.96 (s, 1H), 6.85 (d, J=8.1 Hz, 1H), 6.45 (d, J=16 Hz, 1H), 4.85 (s, 2H), 4.26 (t, J=6.3 Hz, 2H), 3.21 (t, J=6.3 Hz, 2H), 3.08 (s, 3H).

Example 3(45)

(2E)-3-(2-(2-(naphthalen-2-yl)ethoxy)-4-(N-acetyl-N-phenylaminomethyl)phenyl)-2-propenoic acid

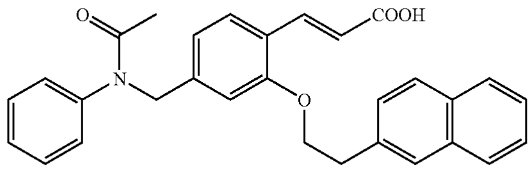

TLC: Rf 0.67 (chloroform:methanol=9:1);

NMR (300 MHz, $CDCl_3$): δ 8.09 (d, J=16 Hz, 1H), 7.88-7.75 (m, 4H), 7.50-7.27 (m, 7H), 7.02-6.94 (m, 2H), 6.82 (s, 1H), 6.73 (d, J=7.8 Hz, 1H), 6.53 (d, J=16 Hz, 1H), 4.85 (s, 2H), 4.25 (t, J=6.6 Hz, 2H), 3.29 (t, J=6.6 Hz, 2H), 1.88 (s, 3H).

Example 3(46)

(2E)-3-(2-(2-(naphthalen-2-yl)ethoxy)-4-(N-benzoyl-N-methylaminomethyl)phenyl)-2-propenoic acid

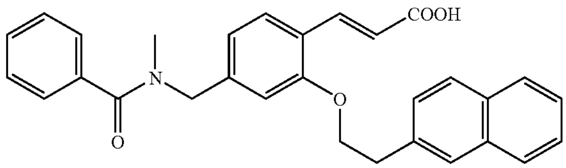

TLC: Rf 0.58 (chloroform:methanol=9:1);

NMR (300 MHz, $CDCl_3$): δ 8.11 (d, J=16 Hz, 1H), 7.89-7.75 (m, 4H), 7.55-7.30 (m, 9H), 7.02-6.61 (m, 2H), 6.55 (d, J=16 Hz, 1H), 4.80-4.22 (m, 4H), 3.34 (t, J=6.6 Hz, 2H), 3.12-2.78 (m, 3H).

Example 3(47)

(2E)-3-(2-(2-(naphthalen-2-yl)propoxy)-4-(pyrazol-1-ylmethyl)phenyl)-2-propenoic acid

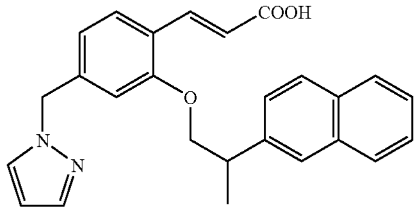

TLC: Rf 0.64 (chloroform:methanol=9:1);

NMR (300 MHz, $CDCl_3$): δ 8.02 (d, J=16 Hz, 1H), 7.88-7.74 (m, 4H), 7.57 (d, J=1.8 Hz, 1H), 7.50-7.36 (m, 5H), 6.76 (d, J=8.1 Hz, 1H), 6.72 (s, 1H), 6.49 (d, J=16 Hz, 1H), 6.29 (t, J=2.3 Hz, 1H), 5.29 (s, 2H), 4.20-4.06 (m, 2H), 3.47 (m, 1H), 1.54 (d, J=6.9 Hz, 3H).

Example 3(48)

3-(2-((naphthalen-2-yl)carbonylmethoxy)-4-(pyrazole-1-methyl)phenyl)propanoic acid

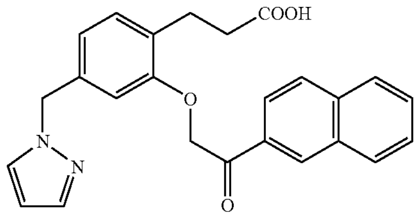

TLC: Rf 0.57 (chloroform:methanol=10:1);

NMR (300 MHz, DMSO-$d_6$): δ 12.08 (brs, 1H), 8.76 (s, 1H), 8.20-7.95 (m, 4H), 7.75-7.60 (m, 3H), 7.36 (d, J=0.9 Hz, 1H), 7.14 (d, J=7.8 Hz, 1H), 6.91 (s, 1H), 6.67 (d, J=7.8 Hz, 1H), 6.18 (t, J=2.0 Hz, 1H), 5.72 (s, 2H), 5.23 (s, 2H), 2.86 (t, J=7.7 Hz, 2H), 2.57 (t, J=7.7 Hz, 2H).

Example 3(49)

3-(2-(2-(naphthalen-2-yl)ethoxy)-4-(pyrrol-1-ylmethyl)phenyl)propanoic acid

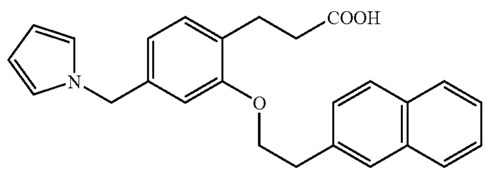

TLC: Rf 0.42 (chloroform:methanol=10:1);

NMR (300 MHz, $CDCl_3$): δ 7.84-7.76 (m, 3H), 7.72 (s, 1H), 7.47-7.37 (m, 3H), 7.07 (d, J=7.5 Hz, 1H), 6.66 (t, J=2.1 Hz, 2H), 6.63 (d, J=7.5 Hz, 1H), 6.55 (d, J=1.5 Hz, 1H), 6.18 (t, J=2.1 Hz, 2H), 4.98 (s, 2H), 4.19 (t, J=6.6 Hz, 2H), 3.23 (t, J=6.6 Hz, 2H), 2.87 (t, J=7.8 Hz, 2H), 2.50 (t, J=7.8 Hz, 2H).

Example 3(50)

3-(2-(2-(naphthalen-2-yl)ethoxy)-4-(4-methylpyrazol-1-ylmethyl)phenyl)propanoic acid

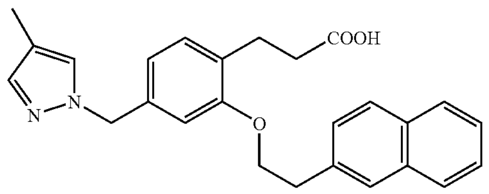

TLC: Rf 0.51 (chloroform:methanol=10:1);

NMR (300 MHz, $CDCl_3$): δ 7.83-7.75 (m, 3H), 7.72 (s, 1H), 7.46-7.37 (m, 3H), 7.32 (s, 1H), 7.12-7.06 (m, 2H), 6.72-6.68 (m, 2H), 5.15 (s, 2H), 4.21 (t, J=6.6 Hz, 2H), 3.23 (t, J=6.6 Hz, 2H), 2.87 (t, J=7.8 Hz, 2H), 2.50 (t, J=7.8 Hz, 2H), 2.03 (s, 3H).

Example 3(51)

3-(2-(2-(naphthalen-2-yl)ethoxy)-4-(3,5-dimethylpyrazol-1-ylmethyl)phenyl)propanoic acid

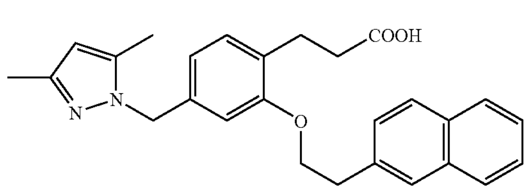

TLC: Rf 0.51 (chloroform:methanol=10:1);

NMR (300 MHz, $CDCl_3$): δ 7.83-7.75 (m, 3H), 7.71 (s, 1H), 7.46-7.37 (m, 3H), 7.04 (d, J=7.8 Hz, 1H), 6.59 (s, 1H), 6.55 (d, J=7.8 Hz, 1H), 5.82 (s, 1H), 5.13 (s, 2H), 4.19 (t, J=6.6 Hz, 2H), 3.21 (t, J=6.6 Hz, 2H), 2.85 (t, J=7.8 Hz, 2H), 2.49 (t, J=7.8 Hz, 2H), 2.23 (s, 3H), 2.12 (s, 3H).

Example 3(52)

3-(2-(2-(naphthalen-2-yl)ethoxy)-4-phenylsulfonylmethylphenyl)propanoic acid

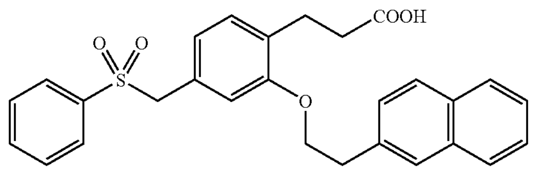

TLC: Rf 0.46 (acetone:toluene=1:1);

NMR (300 MHz, $CDCl_3$): δ 7.85-7.77 (m, 3H), 7.72 (s, 1H), 7.66-7.37 (m, 8H), 6.99 (d, J=7.2 Hz, 1H), 6.58 (d, J=1.8 Hz, 1H), 6.41 (dd, J=7.2, 1.8 Hz, 1H), 4.23 (s, 2H), 4.12 (t, J=6.6 Hz, 2H), 3.22 (t, J=6.6 Hz, 2H), 2.86 (t, J=7.8 Hz, 2H), 2.49 (t, J=7.8 Hz, 2H).

Example 3(53)

3-(2-(2-(1,1'-biphenyl-4-yl)ethoxy)-4-(pyrazol-1-ylmethyl)phenyl)propanoic acid

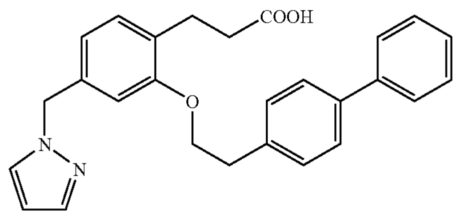

TLC: Rf 0.067 (chloroform);

NMR (300 MHz, $CDCl_3$): δ 7.60-7.50 (m, 5H), 7.45-7.38 (m, 2H), 7.36-7.30 (m, 4H), 7.09 (d, J=7.2 Hz, 1H), 6.70 (d, J=7.2 Hz, 1H), 6.68 (s, 1H), 6.26 (t, J=2.1 Hz, 1H), 5.25 (s, 2H), 4.15 (t, J=6.6 Hz, 2H), 3.10 (t, J=6.6 Hz, 2H), 2.88 (t, J=8.1 Hz, 2H), 2.53 (t, J=8.1 Hz, 2H).

Example 3(54)

3-(2-(2-(naphthalen-2-yl)ethoxy)-4-benzoylaminophenyl)propanoic acid

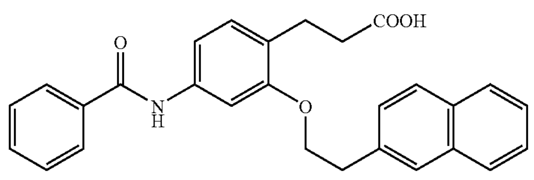

TLC: Rf 0.57 (chloroform:methanol=10:1);

NMR (300 MHz, $CDCl_3$): δ 12.0 (s, 1H), 10.1 (s, 1H), 7.95-7.81 (m, 6H), 7.59-7.41 (m 7H), 7.26 (dd, J=8.1, 1.8 Hz, 1H), 7.05 (d, J=8.1 Hz, 1H), 4.23 (t, J=6.3 Hz, 2H), 3.24 (t, J=6.3 Hz, 2H), 2.70 (t, J=7.5 Hz, 2H), 2.34 (t, J=7.5 Hz, 2H).

Example 3(55)

3-(2-(2-(naphthalen-2-yl)ethoxy)-4-(N-benzoyl-N-methylamino)phenyl)propanoic acid

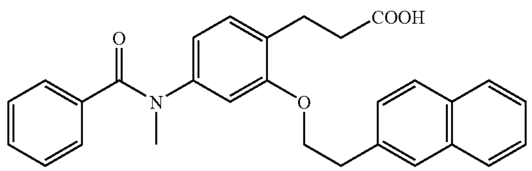

TLC: Rf 0.56 (chloroform:methanol=10:1);

NMR (300 MHz, $CDCl_3$): δ 7.86-7.75 (m, 3H), 7.65 (s, 1H), 7.50-7.40 (m, 2H), 7.37-7.12 (m, 6H), 6.97 (d, J=7.8 Hz, 1H), 6.58 (dd, J=7.8, 1.8 Hz, 1H), 6.43 (d, J=1.8 Hz, 1H), 4.01 (t, J=6.6 Hz, 2H), 3.45 (s, 3H), 3.11 (t, J=6.6 Hz, 2H), 2.79 (t, J=8.1 Hz, 2H), 2.44 (t, J=8.1 Hz, 2H).

Example 3(56)

3-(2-(2-(naphthalen-2-yl)ethoxy)-4-(N-mesyl-N-methylamino)phenyl)propanoic acid

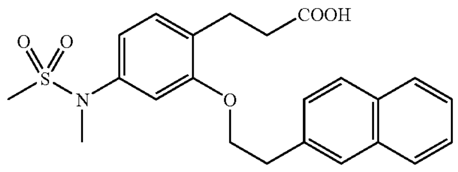

TLC: Rf 0.56 (chloroform:methanol=10:1);

NMR (300 MHz, $CDCl_3$): δ 7.85-7.76 (m, 3H), 7.75 (s, 1H), 7.48-7.39 (m, 3H), 7.12 (d, J=8.1 Hz, 1H), 6.91 (d, J=2.1 Hz, 1H), 6.79 (dd, J=8.1, 2.1 Hz, 1H), 4.28 (t, J=6.6 Hz, 2H), 3.28 (t, J=6.6 Hz, 2H), 3.26 (s, 3H), 2.89 (t, J=8.1 Hz, 2H), 2.89 (s, 3H), 2.52 (t, J=8.1 Hz, 2H).

Example 3(57)

3-(2-(2-(naphthalen-2-yl)ethoxy)-4-mesylaminophenyl)propanoic acid

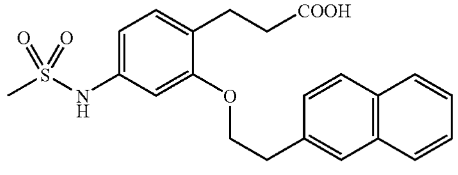

TLC: Rf 0.49 (chloroform:methanol=10:1);

NMR (300 MHz, $CDCl_3$): δ 12.1 (s, 1H), 9.55 (s, 1H), 7.92-7.80 (m, 4H), 7.53-7.42 (m 3H), 7.04 (d, J=8.1 Hz, 1H), 6.81 (d, J=2.4 Hz, 1H), 6.67 (dd, J=8.1, 2.4 Hz, 1H), 4.20 (t,

J=6.3 Hz, 2H), 3.21 (t, J=6.3 Hz, 2H), 2.92 (s, 3H), 2.68 (t, J=7.8 Hz, 2H), 2.35 (t, J=7.8 Hz, 2H).

Example 3(58)

3-(2-(2-(1,1'-biphenyl-2-yl)ethoxy)-4-(pyrazol-1-ylmethyl)phenyl)propanoic acid

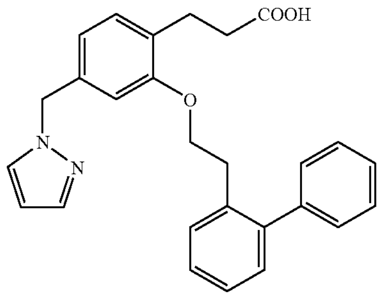

TLC: Rf 0.16 (hexane:ethyl acetate=2:1);

NMR (300 MHz, $CDCl_3$): δ 7.53 (d, J=3.0 Hz, 1H), 7.45-7.21 (m, 10H), 7.07 (d, J=7.8 Hz, 1H), 6.67 (dd, J=7.5, 1.2 Hz, 1H), 6.51 (s, 1H), 6.26 (t, J=2.1 Hz, 1H), 5.21 (s, 2H), 3.94 (t, J=7.2 Hz, 2H), 3.08 (t, J=7.2 Hz, 2H), 2.82 (t, J=7.5 Hz, 2H), 2.47 (t, J=7.5 Hz, 2H).

Example 3(59)

3-(2-(2-(naphthalen-2-yl)ethoxy)-4-(benzimidazol-1-ylmethyl)phenyl)propanoic acid

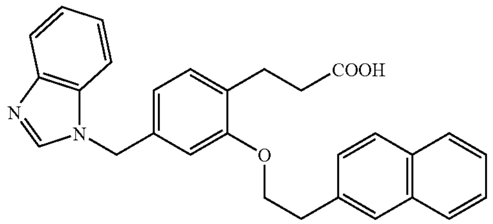

TLC: Rf 0.51 (chloroform:methanol=10:1);

NMR (300 MHz, DMSO-$d_6$): δ 8.72 (s, 1H), 7.89-7.82 (m, 3H), 7.80 (s, 1H), 7.71-7.61 (m, 2H), 7.52-7.42 (m, 3H), 7.30-7.23 (m, 2H), 7.07 (s, 1H), 7.06 (d, J=7.5 Hz, 1H), 6.78 (d, J=7.8 Hz, 1H), 5.46 (s, 2H), 4.22 (t, J=6.6 Hz, 2H), 3.18 (t, J=6.6 Hz, 2H), 2.69 (t, J=8.1 Hz, 2H), 2.34 (t, J=8.1 Hz, 2H).

Example 3(60)

3-(2-(2-(naphthalen-2-yl)ethoxy)-4-(3-methyl-2-oxoimidazolidin-1-ylmethyl)phenyl)propanoic acid

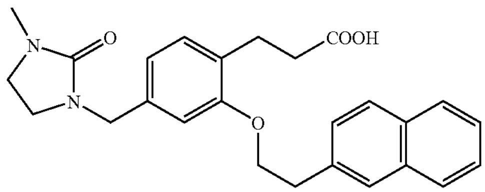

TLC: Rf 0.53 (chloroform:methanol=10:1);

NMR (300 MHz, $CDCl_3$): δ 7.84-7.76 (m, 3H), 7.75 (s, 1H), 7.49-7.38 (m, 3H), 7.06 (d, J=6.9 Hz, 1H), 6.78-6.70 (m, 2H), 4.29 (s, 2H), 4.26 (t, J=6.3 Hz, 2H), 3.36-3.22 (m, 2H), 3.26 (t, J=6.3 Hz, 2H), 3.19-3.09 (m, 2H), 2.88 (t, J=7.8 Hz, 2H), 2.82 (s, 3H), 2.52 (t, J=7.8 Hz, 2H).

Example 3(61)

3-(2-(2-(naphthalen-2-yl)ethoxy)-4-(2-oxopyridin-1-ylmethyl)phenyl)propanoic acid

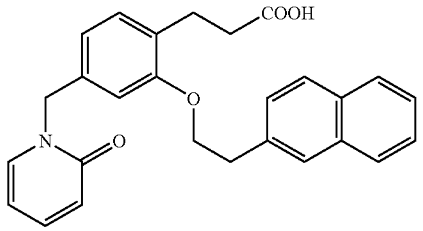

TLC: Rf 0.53 (chloroform:methanol=10:1);

NMR (300 MHz, $CDCl_3$): δ 7.84-7.73 (m, 3H), 7.72 (s, 1H), 7.47-7.35 (m, 3H), 7.29 (m, 1H), 7.21 (dd, J=6.9, 2.1 Hz, 1H), 7.08 (d, J=7.8 Hz, 1H), 6.81 (s, 1H), 6.75 (d, J=7.2 Hz, 1H), 6.63 (d, J=9.0 Hz, 1H), 6.12 (dd, J=6.6, 1.2 Hz, 1H), 5.06 (s, 2H), 4.23 (t, J=6.6 Hz, 2H), 3.23 (t, J=6.6 Hz, 2H), 2.87 (t, J=7.8 Hz, 2H), 2.50 (t, J=7.8 Hz, 2H).

Example 3(62)

3-(2-(2-(1,1'-biphenyl-3-yl)ethoxy)-4-(pyrazol-1-ylmethyl)phenyl)propanoic acid

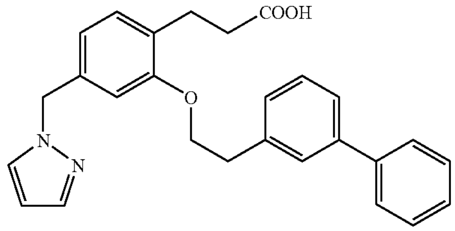

TLC: Rf 0.39 (chloroform:methanol=10:1);

NMR (300 MHz, $CDCl_3$): δ 7.59-7.24 (m, 11H), 7.09 (d, J=7.2 Hz, 1H), 6.72 (d, J=7.5 Hz, 1H), 6.67 (s, 1H), 6.25 (t, J=2.1 Hz, 1H), 5.24 (s, 2H), 4.15 (t, J=6.6 Hz, 2H), 3.14 (t, J=6.6 Hz, 2H), 2.87 (t, J=7.5 Hz, 2H), 2.50 (t, J=7.5 Hz, 2H).

Example 3(63)

3-(2-(2-(naphthalen-2-yl)ethoxy)-4-phenylsulfonylaminophenyl)propanoic acid

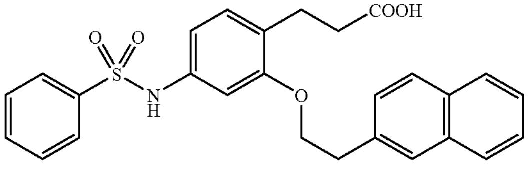

TLC: Rf 0.69 (chloroform:methanol=10:1);

NMR (300 MHz, $CDCl_3$): δ 7.84-7.68 (m, 6H), 7.53-7.36 (m, 6H), 6.93 (d, J=8.1 Hz, 1H), 6.68 (d, J=1.8 Hz, 1H), 6.58 (s, 1H), 6.38 (dd, J=8.1, 1.8 Hz, 1H), 4.16 (t, J=6.6 Hz, 2H), 3.22 (t, J=6.6 Hz, 2H), 2.80 (t, J=7.5 Hz, 2H), 2.46 (t, J=7.5 Hz, 2H).

Example 3(64)

3-(2-(2-(naphthalen-2-yl)ethoxy)-4-acetylaminophenyl)propanoic acid

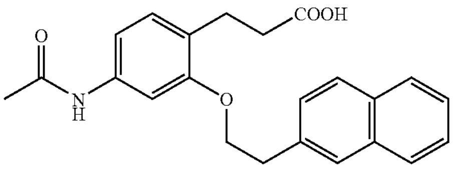

TLC: Rf 0.41 (chloroform:methanol=10:1);

NMR (300 MHz, $CDCl_3$): δ 7.84-7.72 (m, 4H), 7.48-7.38 (m, 4H), 7.10 (d, J=1.8 Hz, 1H), 7.03 (d, J=8.1 Hz, 1H), 6.69 (dd, J=8.1, 1.8 Hz, 1H), 4.29 (t, J=6.6 Hz, 2H), 3.27 (t, J=6.6 Hz, 2H), 2.84 (t, J=7.5 Hz, 2H), 2.48 (t, J=7.5 Hz, 2H), 2.15 (s, 3H).

Example 3(65)

3-(2-(2-(naphthalen-2-yl)ethoxy)-4-(2-methylpyridin-3-yloxymethyl)phenyl)propanoic acid

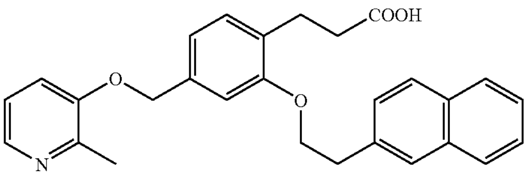

TLC: Rf 0.56 (chloroform:methanol=9:1);

NMR (300 MHz, DMSO-$d_6$): δ 7.98 (dd, J=4.8, 1.2 Hz, 1H), 7.89-7.80 (m, 4H), 7.53-7.41 (m, 3H), 7.35 (dd, J=8.3, 1.1 Hz, 1H), 7.18-7.05 (m, 3H), 6.92 (dd, J=7.7, 1.4 Hz, 1H), 5.07 (s, 2H), 4.28 (t, J=6.4 Hz, 2H), 3.21 (t, J=6.4 Hz, 2H), 2.73 (t, J=7.8 Hz, 2H), 2.38 (t, J=7.8 Hz, 2H), 2.37 (s, 3H).

Example 3(66)

3-(2-(4-methyl-2-(naphthalen-1-yl)pentyloxy)-4-(pyrazol-1-ylmethyl)phenyl)propanoic acid

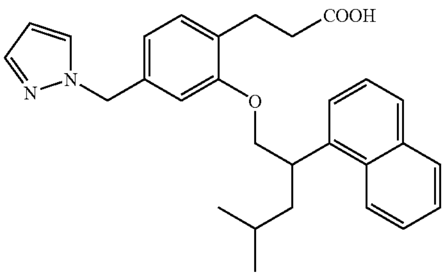

TLC: Rf 0.59 (chloroform:methanol=10:1);

NMR (300 MHz, DMSO-$d_6$): δ 8.23 (d, J=8.4 Hz, 1H), 7.91 (m, 1H), 7.84-7.68 (m, 2H), 7.62-7.34 (m, 5H), 6.98 (d, J=7.2 Hz, 1H), 6.81 (s, 1H), 6.60 (d, J=7.2 Hz, 1H), 6.20 (t, J=2.1 Hz, 1H), 5.18 (s, 2H), 4.18-3.99 (m, 3H), 2.54 (t, J=7.5

Hz, 2H), 2.16 (t, J=7.5 Hz, 2H), 1.99-1.78 (m, 2H), 1.44 (m, 1H), 0.87 (d, J=6.6 Hz, 3H), 0.082 (d, J=6.6 Hz, 3H).

Example 3(67)

3-(2-(2-(benzothiophen-3-yl)ethoxy)-4-(pyrazol-1-ylmethyl)phenyl)propanoic acid

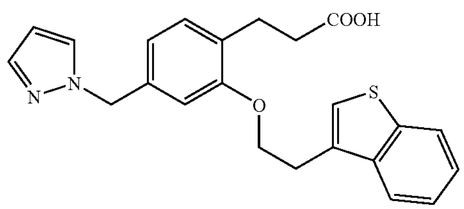

TLC: Rf 0.49 (chloroform:methanol=10:1);

NMR (300 MHz, DMSO-$d_6$): δ 7.97 (dd, J=6.6, 1.2 Hz, 1H), 7.90 (dd, J=6.6, 1.5 Hz, 1H), 7.76 (d, J=1.5 Hz, 1H), 7.54 (s, 1H), 7.45-7.33 (m, 3H), 7.04 (d, J=7.8 Hz, 1H), 6.88 (s, 1H), 6.64 (d, J=7.8 Hz, 1H), 6.23 (t, J=2.1 Hz, 1H), 5.23 (s, 2H), 4.22 (t, J=6.6 Hz, 2H), 3.31 (t, J=6.6 Hz, 2H), 2.68 (t, J=7.5 Hz, 2H), 2.33 (t, J=7.5 Hz, 2H).

Example 3(68)

3-(2-(2-(naphthalen-2-yl)ethoxy)-4-(pyridin-3-yloxymethyl)phenyl)propanoic acid

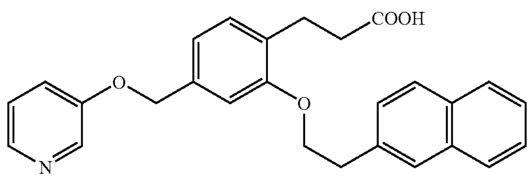

TLC: Rf 0.50 (chloroform:methanol=9:1);

NMR (300 MHz, DMSO-$d_6$): δ 8.32 (d, J=2.7 Hz, 1H), 8.14 (dd, J=4.7, 1.4 Hz, 1H), 7.89-7.80 (m, 4H), 7.54-7.38 (m, 4H), 7.30 (m, 1H), 7.11 (d, J=7.8 Hz, 1H), 7.06 (d, J=1.5 Hz, 1H), 6.92 (dd, J=7.8, 1.5 Hz, 1H), 5.09 (s, 2H), 4.27 (t, J=6.4 Hz, 2H), 3.21 (t, J=6.4 Hz, 2H), 2.73 (t, J=7.6 Hz, 2H), 2.38 (t, J=7.6 Hz, 2H).

Example 3(69)

3-(2-(2-(indol-1-yl)ethoxy)-4-(pyrazol-1-ylmethyl) phenyl)propanoic acid

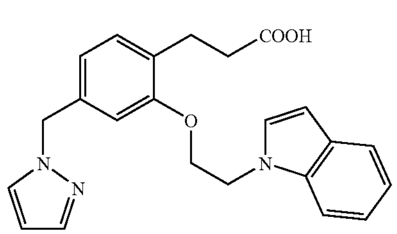

TLC: Rf 0.48 (hexane:ethyl acetate=1:2);

NMR (300 MHz, $CDCl_3$): δ 7.61 (d, J=8.1 Hz, 1H), 7.53 (dd, J=2.1, 0.6 Hz, 1H), 7.37 (dd, J=8.1, 0.8 Hz, 1H), 7.31 (dd, J=2.1, 0.6 Hz, 1H), 7.25-7.17 (m, 2H), 7.13-7.05 (m, 2H), 6.71 (dd, J=7.7, 1.7 Hz, 1H), 6.56 (d, J=1.2 Hz, 1H), 6.50 (dd, J=3.3, 0.9 Hz, 1H), 6.25 (t, J=2.1 Hz, 1H), 5.20 (s, 2H), 4.51 (t, J=5.3 Hz, 2H), 4.20 (t, J=5.3 Hz, 2H), 2.82 (t, J=7.7 Hz, 2H), 2.44 (t, J=7.7 Hz, 2H).

Example 3(70)

3-(2-(2-(1-methylindol-2-yl)ethoxy)-4-(pyrazol-1-ylmethyl)phenyl)propanoic acid

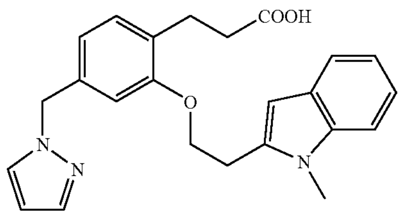

TLC: Rf 0.42 (chloroform:methanol=10:1);

NMR (300 MHz, $CDCl_3$): δ 7.60 (d, J=7.8 Hz, 1H), 7.53 (d, J=1.8 Hz, 1H), 7.33 (d, J=1.8 Hz, 1H), 7.32-7.05 (m, 4H), 6.95 (s, 1H), 6.73-6.65 (m, 2H), 6.25 (t, J=1.8 Hz, 1H), 5.23 (s, 2H), 4.16 (t, J=6.6 Hz, 2H), 3.72 (s, 3H), 3.22 (t, J=6.6 Hz, 2H), 2.90 (t, J=7.8 Hz, 2H), 2.55 (t, J=7.8 Hz, 2H).

Example 3(71)

3-(2-(2-(benzothiophen-2-yl)ethoxy)-4-(pyrazol-1-ylmethyl)phenyl)propanoic acid

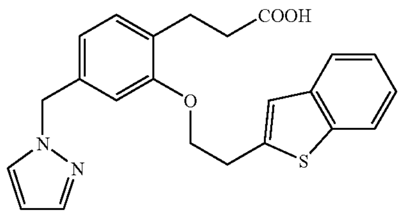

TLC: Rf 0.47 (chloroform:methanol=10:1);

NMR (300 MHz, DMSO-$d_6$): δ 7.86 (m, 1H), 7.78 (d, J=1.8 Hz, 1H), 7.73 (m, 1H), 7.43 (d, J=1.8 Hz, 1H), 7.35-7.23 (m, 3H), 7.07 (d, J=7.5 Hz, 1H), 6.88 (s, 1H), 6.66 (d, J=7.5 Hz, 1H), 6.24 (t, J=1.8 Hz, 1H), 5.25 (s, 2H), 4.20 (t, J=6.0 Hz, 2H), 3.36 (t, J=6.0 Hz, 2H), 2.76 (t, J=7.8 Hz, 2H), 2.39 (t, J=7.8 Hz, 2H).

Example 3(72)

3-(2-(2-(benzofuran-2-yl)ethoxy)-4-(pyrazol-1-ylmethyl)phenyl)propanoic acid

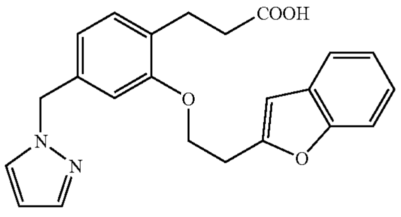

TLC: Rf 0.45 (chloroform:methanol=10:1);

NMR (300 MHz, DMSO-$d_6$): δ 7.78 (d, J=1.8 Hz, 1H), 7.55-7.46 (m, 2H), 7.43 (d, J=1.8 Hz, 1H), 7.26-7.14 (m, 2H), 7.05 (d, J=7.8 Hz, 1H), 6.91 (s, 1H), 6.70-6.62 (m, 2H), 6.24 (t, J=1.8 Hz, 1H), 5.25 (s, 2H), 4.26 (t, J=6.3 Hz, 2H), 3.25 (t, J=6.3 Hz, 2H), 2.68 (t, J=7.8 Hz, 2H), 2.35 (t, J=7.8 Hz, 2H).

Example 3(73)

3-(2-(2-(naphthalen-2-yl)ethoxy)-4-(2-methylpyridin-5-yloxymethyl)phenyl)propanoic acid

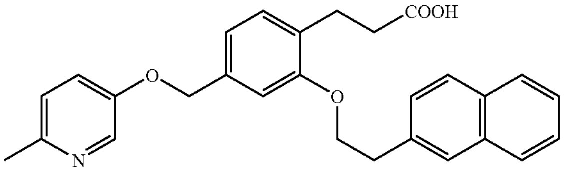

TLC: Rf 0.39 (chloroform:methanol=9:1);

NMR (300 MHz, $CDCl_3$): δ 8.24 (d, J=3.0 Hz, 1H), 7.85-7.72 (m, 4H), 7.50-7.38 (m, 3H), 7.20-7.12 (m, 2H), 7.04 (d, J=8.4 Hz, 1H), 6.95-6.85 (m, 2H), 4.99 (s, 2H), 4.29 (t, J=6.6 Hz, 2H), 3.28 (t, J=6.6 Hz, 2H), 2.91 (t, J=8.1 Hz, 2H), 2.54 (t, J=8.1 Hz, 2H), 2.48 (s, 3H).

Example 3(74)

3-(2-(2-(naphthalen-2-yl)ethoxy)-4-(pyridin-2-yloxy)phenyl)propanoic acid

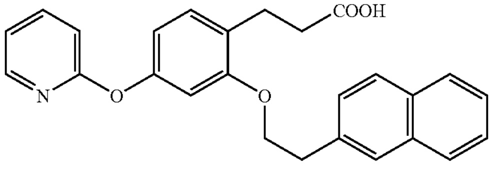

TLC: Rf 0.41 (hexane:ethyl acetate=1:1);

NMR (300 MHz, $CDCl_3$): δ 8.20 (m, 1H), 7.84-7.61 (m, 5H), 7.48-7.37 (m, 3H), 7.13 (d, J=8.1 Hz, 1H), 6.97 (m, 1H), 6.86 (dt, J=8.4, 1.1 Hz, 1H), 6.68-6.59 (m, 2H), 4.22 (t, J=6.7 Hz, 2H), 3.26 (t, J=6.7 Hz, 2H), 2.90 (t, J=7.9 Hz, 2H), 2.55 (t, J=7.9 Hz, 2H).

Example 3(75)

3-(2-(2-(naphthalen-1-yl)ethoxy)-4-(pyrazol-1-ylmethyl)phenyl)propanoic acid

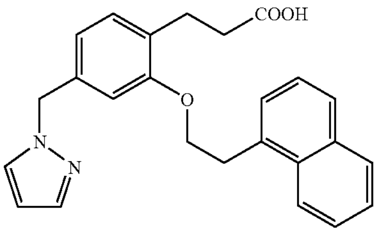

TLC: Rf 0.30 (chloroform:methanol=10:1);

NMR (300 MHz, $CDCl_3$): δ 8.07 (d, J=8.1 Hz, 1H), 7.87 (d, J=7.5 Hz, 1H), 7.76 (dd, J=6.3, 3.3 Hz, 1H), 7.57-7.42 (m, 5H), 7.33 (d, J=2.4 Hz, 1H), 7.08 (d, J=7.5 Hz, 1H), 6.69 (d, J=7.5 Hz, 1H), 6.66 (s, 1H), 6.24 (t, J=2.4 Hz, 1H), 5.21 (s, 2H), 4.27 (t, J=6.6 Hz, 2H), 3.56 (t, J=6.6 Hz, 2H), 2.85 (t, J=7.2 Hz, 2H), 2.49 (t, J=7.2 Hz, 2H).

Example 3(76)

3-(2-(2-(chroman-2-yl)ethoxy)-4-(pyrazol-1-ylmethyl)phenyl)propanoic acid

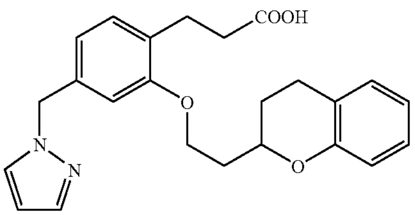

TLC: Rf 0.31 (chloroform:methanol=10:1);

NMR (300 MHz, $CDCl_3$): δ 7.55 (d, J=1.2 Hz, 1H), 7.39 (d, J=1.8 Hz, 1H), 7.13 (d, J=8.4 Hz, 1H), 7.09-7.02 (m, 2H), 6.87-6.70 (m, 4H), 6.28 (t, J=1.8 Hz, 1H), 5.28 (s, 2H), 4.35-4.09 (m, 3H), 2.92 (t, J=7.2 Hz, 2H), 2.90-2.70 (m, 2H), 2.61 (t, J=7.2 Hz, 2H), 2.20-2.00 (m, 3H), 1.88-1.75 (m, 1H).

Example 3(77)

3-(2-(2-(naphthalen-2-yl)ethoxy)-4-phenoxyphenyl)propanoic acid

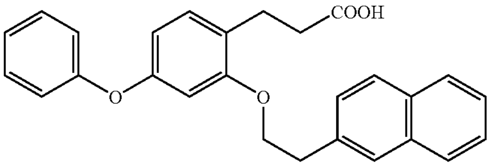

TLC: Rf 0.60 (hexane:ethyl acetate=1:1);

NMR (300 MHz, $CDCl_3$): δ 7.84-7.70 (m, 4H), 7.50-7.25 (m, 5H), 7.14-6.94 (m, 4H), 6.56 (d, J=2.4 Hz, 1H), 6.47 (dd,

J=8.1, 2.4 Hz, 1H), 4.19 (t, J=6.5 Hz, 2H), 3.25 (t, J=6.5 Hz, 2H), 2.88 (t, J=7.8 Hz, 2H), 2.53 (t, J=7.8 Hz, 2H).

Example 3(78)

3-(2-(2-(1-methylindol-3-yl)ethoxy)-4-(pyrazol-1-ylmethyl)phenyl)propanoic acid

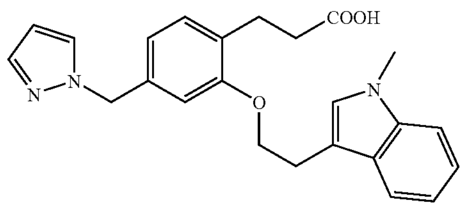

TLC: Rf 0.38 (chloroform:methanol=15:1);

NMR (300 MHz, $CDCl_3$): δ 7.61 (m, 1H), 7.53 (d, J=1.8 Hz, 1H), 7.34 (d, J=1.8 Hz, 1H), 7.33-7.19 (m, 3H), 7.16-7.08 (m, 2H), 6.96 (s, 1H), 6.74-6.66 (m, 2H), 6.25 (t, J=1.8 Hz, 1H), 5.23 (s, 2H), 4.17 (t, J=6.6 Hz, 2H), 3.75 (s, 3H), 3.22 (t, J=6.6 Hz, 2H), 2.91 (t, J=8.1 Hz, 2H), 2.56 (t, J=8.1 Hz, 2H).

Example 3(79)

3-(2-(2-(naphthalen-2-yl)ethoxy)-4-(4-methylimidazol-1-ylmethyl)phenyl)propanoic acid

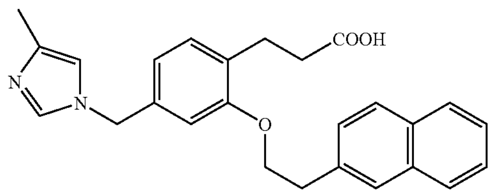

TLC: Rf 0.45 (chloroform:methanol=7:1);

NMR (300 MHz, $CDCl_3$): δ 7.84-7.58 (m, 5H), 7.47-7.36 (m, 3H), 7.14-7.07 (m, 1H), 6.88-6.44 (m, 3H), 4.93 and 4.91 (s, 2H), 4.22-4.08 (m, 2H), 3.27-3.17 (m, 2H), 2.95-2.85 (m, 2H), 2.60-2.49 (m, 2H), 2.20 and 2.08 (s, 3H).

Example 3(80)

3-(2-(4-methyl-2-(naphthalen-2-yl)pentyloxy)-4-(pyrazol-1-ylmethyl)phenyl)propanoic acid

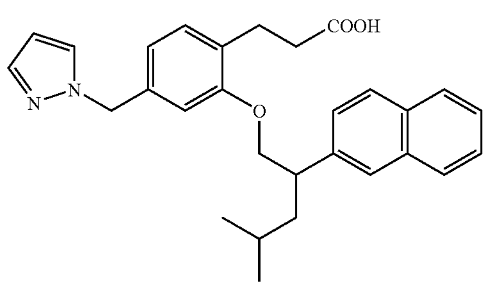

TLC: Rf 0.47 (chloroform:methanol=10:1);

NMR (300 MHz, $CDCl_3$): δ 7.83-7.76 (m, 3H), 7.70 (s, 1H), 7.53 (d, J=1.8 Hz, 1H), 7.47-7.37 (m, 3H), 7.34 (d, J=1.8 Hz, 1H), 7.05 (d, J=7.5 Hz, 1H), 6.71-6.64 (m, 2H), 6.26 (t, J=1.8 Hz, 1H), 5.23 (s, 2H), 4.14-3.99 (m, 2H), 3.33 (m, 1H), 2.89-2.66 (m, 2H), 2.35 (t, J=7.5 Hz, 2H), 1.88-1.42 (m, 3H), 0.91 (d, J=6.3 Hz, 3H), 0.89 (d, J=6.3 Hz, 3H).

Example 3(81)

3-(2-(2-(naphthalen-2-yl)ethoxy)-4-(2-cyanopyridin-3-yloxymethyl)phenyl)propanoic acid

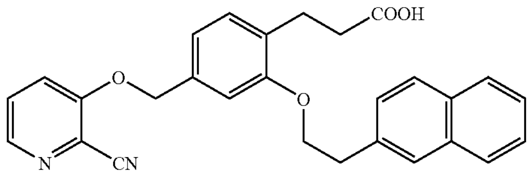

TLC: Rf 0.51 (chloroform:methanol=9:1);

NMR (300 MHz, $CDCl_3$): δ 8.27 (dd, J=4.5, 1.2 Hz, 1H), 7.84-7.70 (m, 4H), 7.50-7.27 (m, 5H), 7.13 (d, J=7.8 Hz, 1H), 6.96 (s, 1H), 6.87 (d, J=7.5 Hz, 1H), 5.17 (s, 2H), 4.31 (t, J=6.3 Hz, 2H), 3.28 (t, J=6.3 Hz, 2H), 2.89 (t, J=8.1 Hz, 2H), 2.52 (t, J=8.1 Hz, 2H).

Example 3(82)

3-(2-(2-methoxy-2-(naphthalen-2-yl)ethoxy)-4-(pyrazol-1-ylmethyl)phenyl)propanoic acid

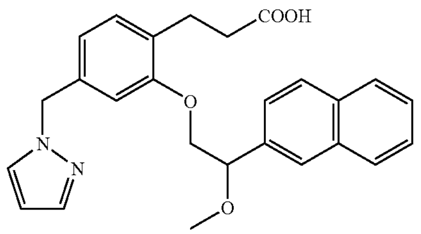

TLC: Rf 0.31 (chloroform:methanol=10:1);

NMR (300 MHz, $CDCl_3$): δ 7.90-7.80 (m, 4H), 7.55-7.45 (m, 4H), 7.33 (d, J=2.1 Hz, 1H), 7.08 (d, J=7.8 Hz, 1H), 6.71 (dd, J=7.8, 1.5 Hz, 1H), 6.64 (s, 1H), 6.25 (t, J=2.1 Hz, 1H), 5.23 (s, 2H), 4.73 (dd, J=6.9, 4.8 Hz, 1H), 4.22 (dd, J=9.9, 6.9 Hz, 1H), 4.07 (dd, J=9.9, 4.8 Hz, 1H), 3.37 (s, 3H), 2.87 (t, J=7.5 Hz, 2H), 2.53 (dt, 7.5, 7.5 Hz, 2H).

Example 3(83)

3-(2-(4-methyl-2-phenylpentyloxy)-4-(pyrazol-1-ylmethyl)phenyl)propanoic acid

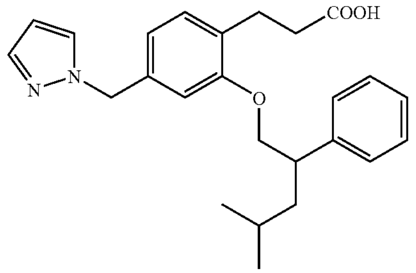

TLC: Rf 0.44 (chloroform:methanol=10:1);

NMR (300 MHz, $CDCl_3$): δ 7.54 (m, 1H), 7.38-7.17 (m, 6H), 7.07 (d, J=7.5 Hz, 1H), 6.69 (dd, J=7.5, 1.5 Hz, 1H), 6.65 (s, 1H), 6.26 (t, J=2.4 Hz, 1H), 5.24 (s, 2H), 4.06-3.91 (m, 2H), 3.15 (m, 1H), 2.90-2.68 (m, 2H), 2.40 (t, J=7.8 Hz, 2H), 1.78-1.40 (m, 3H), 0.89 (d, J=6.6 Hz, 3H), 0.87 (d, J=6.6 Hz, 3H).

Example 3(84)

3-(2-(4-methyl-2-phenylpentyloxy)-4-phenoxymethylphenyl)propanoic acid

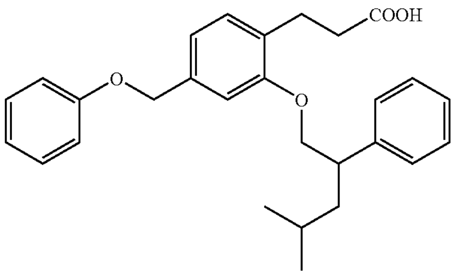

TLC: Rf 0.35 (hexane:ethyl acetate=2:1).

Example 3(85)

3-(2-(2-(naphthalen-2-yl)ethoxy)-4-phenoxymethylphenyl)propanoic acid

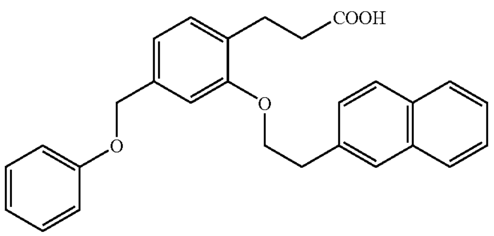

TLC: Rf 0.21 (hexane:ethyl acetate=2:1);

NMR (300 MHz, $CDCl_3$): δ 7.82-7.78 (m, 3H), 7.74 (brs, 1H), 7.48-7.39 (m, 3H), 7.30-7.25 (m, 2H), 7.13 (d, J=7.8 Hz, 1H), 6.97-6.90 (m, 5H), 4.99 (s, 2H), 4.29 (t, J=6.6 Hz, 2H), 3.27 (t, J=6.6 Hz, 2H), 2.93-2.88 (m, 2H), 2.56-2.51 (m, 2H).

Example 3(86)

3-(2-(2-(naphthalen-2-yl)ethoxy)-4-phenylaminomethylphenyl)propanoic acid

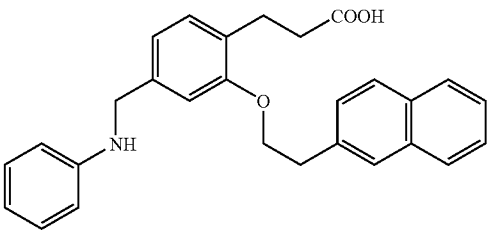

TLC: Rf 0.45 (chloroform:methanol=9:1).

Example 3(87)

3-(2-(2-(naphthalen-2-yl)ethoxy)-4-(N-phenyl-N-methylaminomethyl)phenyl)propanoic acid

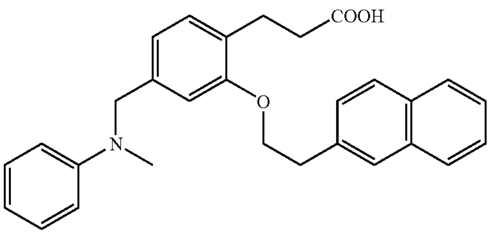

TLC: Rf 0.45 (chloroform:methanol=9:1).

Example 3(88)

3-(2-(2-(naphthalen-2-yl)ethoxy)-4-(N-ethyl-N-phenylaminomethyl)phenyl)propanoic acid

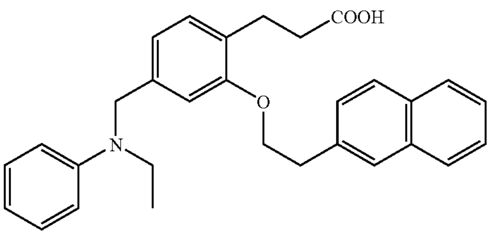

TLC: Rf 0.45 (chloroform:methanol=9:1).

Example 3(89)

3-(2-(2-(naphthalen-2-yl)ethoxy)-4-(3-(pyrazol-1-yl)propyl)phenyl)propanoic acid

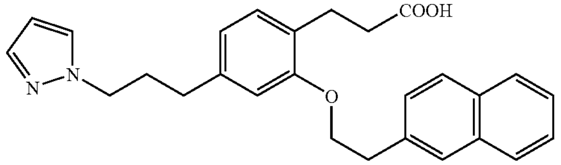

TLC: Rf 0.51 (chloroform:methanol=10:1);

NMR (300 MHz, $CDCl_3$): δ 7.84-7.76 (m, 3H), 7.75 (s, 1H), 7.51 (d, J=2.1 Hz, 1H), 7.49-7.38 (m, 3H), 7.33 (d, J=2.1 Hz, 1H), 7.03 (d, J=7.5 Hz, 1H), 6.69-6.61 (m, 2H), 6.23 (t, J=2.1 Hz, 1H), 4.25 (t, J=6.6 Hz, 2H), 4.11 (t, J=7.2 Hz, 2H), 3.27 (t, J=6.6 Hz, 2H), 2.87 (t, J=7.2 Hz, 2H), 2.58-2.47 (m, 4H), 2.22-2.10 (m, 2H).

Example 3(90)

3-(2-(2-(naphthalen-2-yl)ethoxy)-4-(2-chloro-5-methylphenoxymethyl)phenyl)propanoic acid

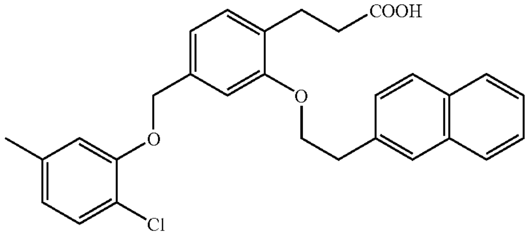

TLC: Rf 0.60 (chloroform:methanol=9:1);

NMR (300 MHz, $CDCl_3$): δ 7.84-7.72 (m, 4H), 7.49-7.38 (m, 3H), 7.24 (d, J=8.1 Hz, 1H), 7.13 (d, J=7.5 Hz, 1H), 7.03 (s, 1H), 6.95-6.89 (m, 1H), 6.77 (s, 1H), 6.74-6.68 (m, 1H), 5.06 (s, 2H), 4.31 (t, J=6.6 Hz, 2H), 3.28 (t, J=6.6 Hz, 2H), 2.90 (t, J=8.1 Hz, 2H), 2.53 (t, J=8.1 Hz, 2H), 2.29 (s, 3H).

Example 3(91)

3-(2-(2-(naphthalen-2-yl)ethoxy)-4-(3-cyanophenoxymethyl)phenyl)propanoic acid

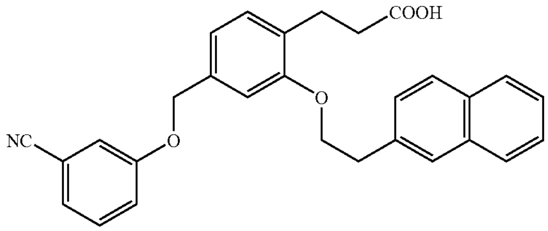

TLC: Rf 0.60 (chloroform:methanol=9:1);

NMR (300 MHz, $CDCl_3$): δ 7.84-7.72 (m, 4H), 7.50-7.31 (m, 4H), 7.28-7.12 (m, 4H), 6.92-6.86 (m, 2H), 4.99 (s, 2H), 4.29 (t, J=6.6 Hz, 2H), 3.28 (t, J=6.6 Hz, 2H), 2.91 (t, J=8.1 Hz, 2H), 2.54 (t, J=8.1 Hz, 2H).

Example 3(92)

3-(2-(2-(naphthalen-2-yl)ethoxy)-4-(2-methoxyphenoxymethyl)phenyl)propanoic acid

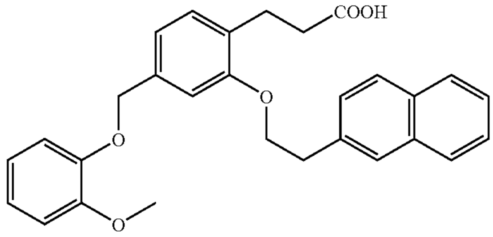

TLC: Rf 0.54 (chloroform:methanol=9:1);

NMR (300 MHz, $CDCl_3$): δ 7.84-7.70 (m, 4H), 7.50-7.38 (m, 3H), 7.11 (d, J=7.5 Hz, 1H), 7.00-6.80 (m, 6H), 5.09 (s, 2H), 4.28 (t, J=6.3 Hz, 2H), 3.86 (s, 3H), 3.26 (t, J=6.3 Hz, 2H), 2.89 (t, J=7.8 Hz, 2H), 2.51 (t, J=7.8 Hz, 2H).

Example 3(93)

3-(2-(2-(naphthalen-2-yl)ethoxy)-4-(2-methylphenoxymethyl)phenyl)propanoic acid

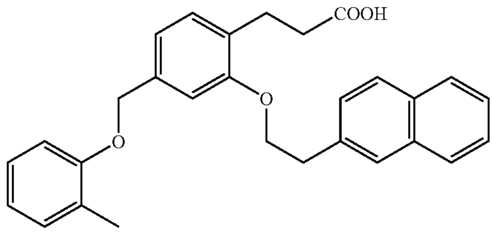

TLC: Rf 0.54 (chloroform:methanol=9:1);

NMR (300 MHz, $CDCl_3$): δ 7.84-7.72 (m, 4H), 7.50-7.38 (m, 3H), 7.20-7.10 (m, 3H), 6.98-6.82 (m, 4H), 5.01 (s, 2H), 4.30 (t, J=6.6 Hz, 2H), 3.28 (t, J=6.6 Hz, 2H), 2.91 (t, J=7.8 Hz, 2H), 2.53 (t, J=7.8 Hz, 2H), 2.27 (s, 3H).

Example 3(94)

3-(2-(2-phenylethoxy)-4-phenoxymethylphenyl)propanoic acid

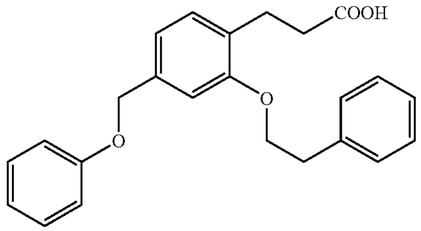

TLC: Rf 0.65 (hexane:ethyl acetate=1:1);

NMR (300 MHz, $CDCl_3$): δ 7.34-7.19 (m, 7H), 7.13 (m, 1H), 6.99-6.90 (m, 5H), 4.99 (s, 2H), 4.20 (t, J=6.6 Hz, 2H), 3.11 (t, J=6.6 Hz, 2H), 2.93-2.87 (m, 2H), 2.57-2.52 (m, 2H).

Example 3(95)

3-(2-(2-phenylethoxy)-4-(pyrazol-1-ylmethyl)phenyl)propanoic acid

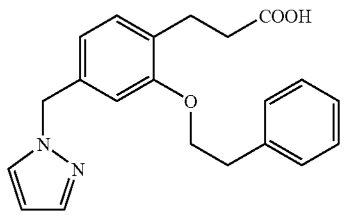

TLC: Rf 0.58 (chloroform:methanol=9:1);

NMR (300 MHz, $CDCl_3$): δ 7.54 (d, J=1.5 Hz, 1H), 7.36-7.20 (m, 6H), 7.09 (d, J=7.2 Hz, 1H), 6.71 (d, J=7.5 Hz, 1H), 6.66 (s, 1H), 6.26 (t, J=1.8 Hz, 1H), 5.22 (s, 2H), 4.12 (t, J=6.6 Hz, 2H), 3.07 (t, J=6.6 Hz, 2H), 2.86 (t, J=7.8 Hz, 2H), 2.51 (t, J=7.8 Hz, 2H).

Example 3(96)

3-(2-(4-methyl-2-(3,5-dimethylphenyl)pentyloxy)-4-(pyrazol-1-ylmethyl)phenyl)propanoic acid

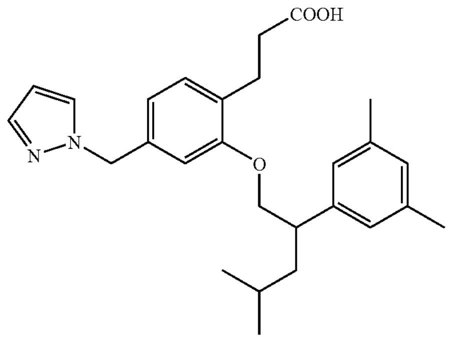

TLC: Rf 0.50 (ethyl acetate);

NMR (300 MHz, $CDCl_3$): δ 7.54 (d, J=2.1 Hz, 1H), 7.35 (d, J=2.1 Hz, 1H), 7.08 (d, J=7.8 Hz, 1H), 6.84 (s, 3H), 6.69 (d, J=7.8 Hz, 1H), 6.65 (s, 1H), 6.26 (d, J=2.1 Hz, 1H), 5.23 (s, 2H), 4.01-3.89 (m, 2H), 3.12-3.02 (m, 1H), 2.90-2.72 (m, 2H), 2.45 (t, J=7.8 Hz, 2H), 2.29 (s, 6H), 1.71-1.42 (m, 3H), 0.90-0.87 (m, 6H).

Example 3(97)

3-(2-(4-methyl-2-(4-fluoro-3-methylphenyl)pentyloxy)-4-(pyrazol-1-ylmethyl)phenyl)propanoic acid

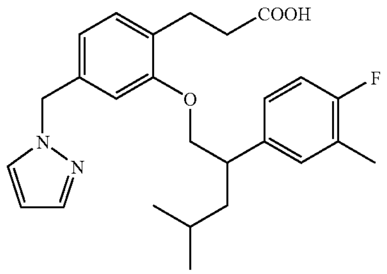

TLC: Rf 0.47 (chloroform:methanol=19:1);

NMR (300 MHz, $CDCl_3$): δ 7.54 (dd, J=2.1, 0.5 Hz, 1H), 7.35 (dd, J=2.1, 0.5 Hz, 1H), 7.10-6.87 (m, 4H), 6.71 (dd, J=7.4, 1.4 Hz, 1H), 6.64 (d, J=1.4 Hz, 1H), 6.27 (t, J=2.1 Hz, 1H), 5.24 (s, 2H), 3.98 (dd, J=8.9, 6.0 Hz, 1H), 3.89 (dd, J=8.9, 7.5 Hz, 1H), 3.09 (m, 1H), 2.89-2.68 (m, 2H), 2.41 (t, J=8.0 Hz, 2H), 2.24 (d, J=1.8 Hz, 3H), 1.71-1.37 (m, 3H), 0.89 (d, J=6.6 Hz, 3H), 0.88 (d, J=6.6 Hz, 3H).

Example 3(98)

2-(2-(2-phenylethoxy)-4-(pyrazol-1-ylmethyl)benzyl)benzoic acid

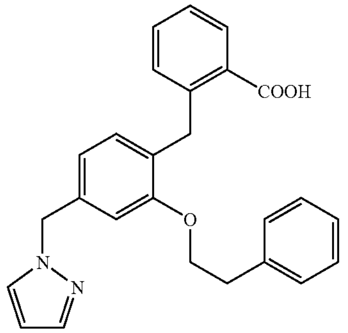

TLC: Rf 0.34 (chloroform:methanol=20:1);

NMR (300 MHz, $CDCl_3$): δ 8.01 (dd, J=7.8, 1.5 Hz, 1H), 7.54 (d, J=1.8 Hz, 1H), 7.40-7.15 (m, 8H), 7.06 (d, J=7.8 Hz, 1H), 6.89 (d, J=7.8 Hz, 1H), 6.70-6.65 (m, 2H), 6.25 (t, J=2.1 Hz, 1H), 5.21 (s, 2H), 4.35 (s, 2H), 4.08 (t, J=6.9 Hz, 2H), 2.97 (t, J=6.9 Hz, 2H).

Example 3(99)

2-(2-(2-(naphthalen-2-yl)ethoxy)-4-(pyrazol-1-ylmethyl)benzyl)benzoic acid

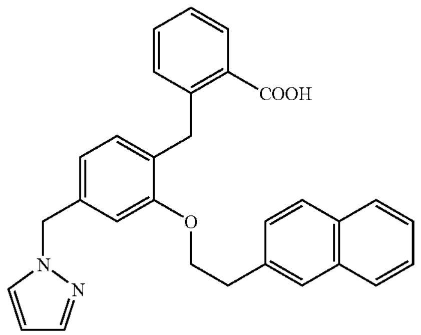

TLC: Rf 0.34 (chloroform:methanol=20:1);

NMR (300 MHz, $CDCl_3$): δ 7.98 (dd, J=7.8, 1.5 Hz, 1H), 7.80-7.67 (m, 3H), 7.60 (s, 1H), 7.53 (d, J=1.8 Hz, 1H), 7.43-7.38 (m, 2H), 7.32-7.18 (m, 4H), 6.99 (d, J=7.8 Hz, 1H), 6.87 (d, J=7.8 Hz, 1H), 6.67-6.60 (m, 2H), 6.23 (s, 1H), 5.18 (s, 2H), 4.35 (s, 2H), 4.14 (t, J=6.3 Hz, 2H), 3.11 (t, J=6.3 Hz, 2H).

Example 3(100)

2-(2-(4-methyl-2-phenylpentyloxy)-4-(pyrazol-1-ylmethyl)benzyl)benzoic acid

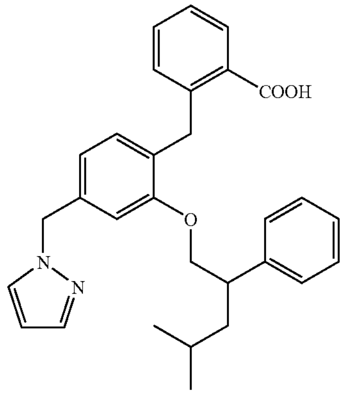

TLC: Rf 0.58 (chloroform:methanol=10:1);

NMR (300 MHz, DMSO-$d_6$): δ 8.04 (d, J=7.5 Hz, 1H), 7.54 (d, J=2.1 Hz, 1H), 7.40-7.10 (m, 8H), 6.97 (d, J=7.8 Hz, 1H), 6.90 (d, J=7.2 Hz, 1H), 6.70-6.60 (m, 2H), 6.25 (t, J=2.1 Hz, 1H), 5.19 (s, 2H), 4.36 (d, J=16.5 Hz, 1H), 4.27 (d, J=16.5 Hz, 1H), 3.94 (d, J=6.3 Hz, 2H), 3.02 (m, 1H), 1.62-1.20 (m, 3H), 0.79 (d, J=6.3 Hz, 6H).

Example 3(101)

2-(2-(4-methyl-2-(3,5-dimethylphenyl)pentyloxy)-4-(pyrazol-1-ylmethyl)benzyl)benzoic acid

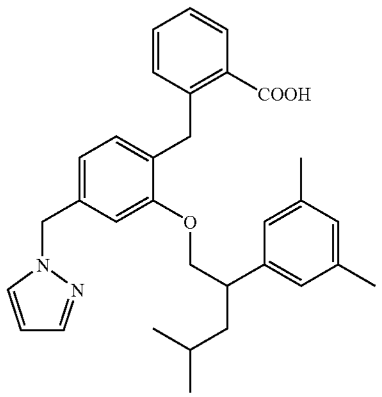

TLC: Rf 0.60 (chloroform:methanol=10:1);

NMR (300 MHz, DMSO-$d_6$): δ 8.03 (dd, J=7.5, 1.2 Hz, 1H), 7.54 (d, J=1.8 Hz, 1H), 7.40-7.23 (m, 3H), 6.99 (d, J=6.9 Hz, 1H), 6.89 (d, J=8.1 Hz, 1H), 6.84-6.76 (m, 3H), 6.68-6.60 (m, 2H), 6.24 (t, J=1.8 Hz, 1H), 5.17 (s, 2H), 4.39 (d, J=16.2 Hz, 1H), 4.31 (d, J=16.2 Hz, 1H), 3.90 (d, J=6.3 Hz, 2H), 2.96 (m, 1H), 2.24 (s, 6H), 1.60-1.26 (m, 3H), 0.79 (d, J=6.3 Hz, 6H).

Example 3(102)

3-(2-(4-methyl-2-(4-methoxy-1,3-dioxaindan-6-yl)pentyloxy)-4-(pyrazol-1-ylmethyl)phenyl)propanoic acid

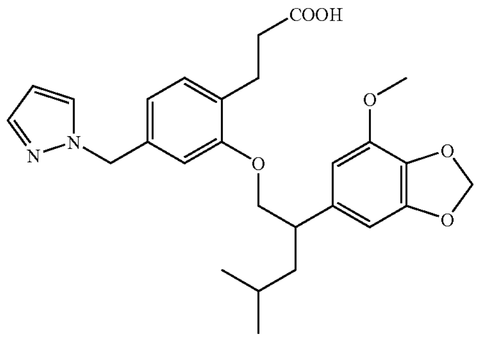

TLC: Rf 0.65 (ethyl acetate);

NMR (300 MHz, $CDCl_3$): δ 7.54 (d, J=2.1 Hz, 1H), 7.36 (d, J=2.1 Hz, 1H), 7.08 (d, J=7.2 Hz, 1H), 6.70 (d, J=7.2 Hz, 1H), 6.65 (s, 1H), 6.44 (d, J=1.5 Hz, 1H), 6.40 (d, J=1.5 Hz, 1H), 6.27 (t, J=2.1 Hz, 1H), 5.93-5.91 (m, 2H), 5.24 (s, 2H), 4.00-3.85 (m, 2H), 3.89 (s, 3H), 3.10-3.00 (m, 1H), 2.91-2.71 (m, 2H), 2.43 (t, J=7.5 Hz, 2H), 1.66-1.43 (m, 3H), 0.90-0.87 (m, 6H).

Example 3(103)

3-(2-(2-(naphthalen-2-yl)ethoxy)-4-(3-cyanopheny-laminomethyl)phenyl)propanoic acid

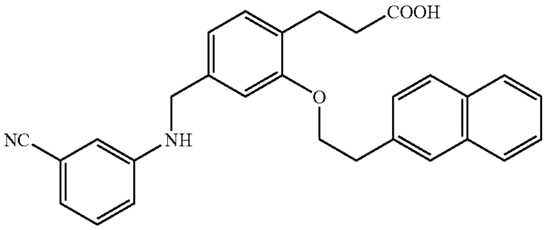

TLC: Rf 0.53 (chloroform:methanol=9:1);

NMR (300 MHz, $CDCl_3$): δ 7.84-7.75 (m, 3H), 7.73 (s, 1H), 7.49-7.38 (m, 3H), 7.22 (t, J=7.8 Hz, 1H), 7.11 (d, J=7.8 Hz, 1H), 6.96 (d, J=7.8 Hz, 1H), 6.86-6.74 (m, 4H), 4.30-4.20 (m, 4H), 3.27 (t, J=6.3 Hz, 2H), 2.90 (t, J=7.8 Hz, 2H), 2.54 (t, J=7.8 Hz, 2H).

Example 3(104)

3-(2-(2-(naphthalen-2-yl)ethoxy)-4-(2-methylpheny-laminomethyl)phenyl)propanoic acid

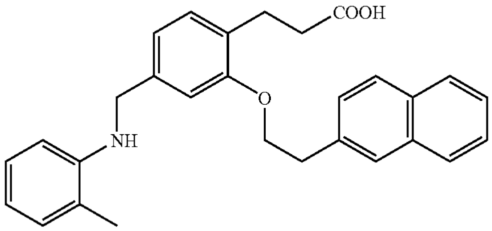

TLC: Rf 0.53 (chloroform:methanol=9:1);

NMR (300 MHz, $CDCl_3$): δ 7.84-7.76 (m, 3H), 7.73 (s, 1H), 7.50-7.38 (m, 3H), 7.14-7.04 (m, 3H), 6.92-6.84 (m, 2H), 6.67 (t, J=7.8 Hz, 1H), 6.60 (d, J=7.8 Hz, 1H), 4.32-4.22 (m, 4H), 3.26 (t, J=6.3 Hz, 2H), 2.90 (t, J=8.1 Hz, 2H), 2.53 (t, J=8.1 Hz, 2H), 2.15 (s, 3H).

Example 3(105)

3-(2-(2-(naphthalen-2-yl)ethoxy)-4-(pyridin-3-ylaminomethyl)phenyl)propanoic acid

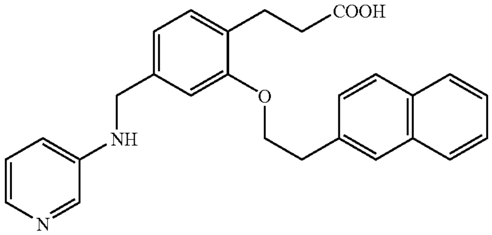

TLC: Rf 0.41 (chloroform:methanol=9:1);

NMR (300 MHz, $CDCl_3$): δ 8.05 (d, J=2.7 Hz, 1H), 7.94 (dd, J=4.5, 1.5 Hz, 1H), 7.84-7.74 (m, 3H), 7.72 (brs, 1H), 7.48-7.36 (m, 3H), 7.14-7.04 (m, 2H), 6.92-6.78 (m, 3H), 4.28-4.18 (m, 4H), 3.25 (t, J=6.6 Hz, 2H), 2.91 (t, J=7.5 Hz, 2H), 2.55 (t, J=7.5 Hz, 2H).

Example 3(106)

3-(2-(2-(benzoylamino)ethoxy)-4-(pyrazol-1-ylm-ethyl)phenyl)propanoic acid

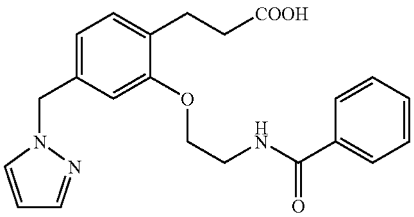

TLC: Rf 0.48 (chloroform:methanol=9:1);

NMR (300 MHz, $CD_3OD$): δ 7.85-7.77 (m, 2H), 7.65 (d, J=2.1 Hz, 1H), 7.55-7.40 (m, 4H), 7.10 (d, J=7.8 Hz, 1H), 6.82 (s, 1H), 6.70 (d, J=7.5 Hz, 1H), 6.30 (dd, J=2.1, 2.1 Hz, 1H), 5.28 (s, 2H), 4.15 (t, J=5.7 Hz, 2H), 3.78 (t, J=5.7 Hz, 2H), 2.89 (t, J=7.5 Hz, 2H), 2.52 (t, J=7.5 Hz, 2H).

Example 3(107)

3-(2-(2-(phenylsulfonylamino)ethoxy)-4-(pyrazol-1-ylmethyl)phenyl)propanoic acid

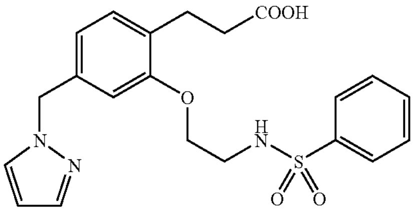

TLC: Rf 0.48 (chloroform:methanol=9:1);

NMR (300 MHz, $CD_3OD$): δ 7.89-7.84 (m, 2H), 7.64 (d, J=2.1 Hz, 1H), 7.58-7.46 (m, 4H), 7.08 (d, J=7.8 Hz, 1H), 6.70 (d, J=7.8 Hz, 1H), 6.66 (s, 1H), 6.31 (t, J=2.1 Hz, 1H), 5.26 (s, 2H), 3.93 (t, J=5.7 Hz, 2H), 3.28 (m, 2H), 2.83 (t, J=7.5 Hz, 2H), 2.49 (t, J=7.5 Hz, 2H).

Example 3(108)

3-(2-(2-(N-methyl-N-phenylsulfonylamino)ethoxy)-4-(pyrazol-1-ylmethyl)phenyl)propanoic acid

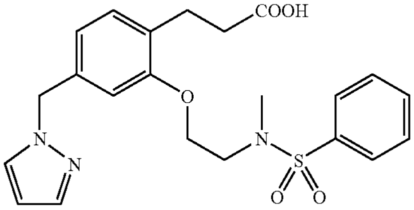

TLC: Rf 0.67 (chloroform:methanol=9:1);

NMR (300 MHz, $CDCl_3$): δ 7.80 (d, J=8.1 Hz, 2H), 7.64-7.49 (m, 4H), 7.40 (d, J=2.1 Hz, 1H), 7.13 (d, J=7.8 Hz, 1H), 6.76 (d, J=7.8 Hz, 1H), 6.65 (d, J=2.1 Hz, 1H), 6.29 (t, J=2.1

Hz, 1H), 5.27 (s, 2H), 4.10 (t, J=5.4 Hz, 2H), 3.44 (t, J=5.4 Hz, 2H), 2.90 (t, J=7.5 Hz, 2H), 2.90 (s, 3H), 2.61 (t, J=7.5 Hz, 2H).

Example 3(109)

3-(2-(2-methoxy-3-phenoxypropoxy)-4-(pyrazol-1-ylmethyl)phenyl)propanoic acid

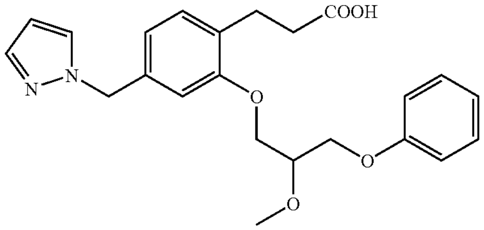

TLC: Rf 0.35 (ethyl acetate);

NMR (300 MHz, $CDCl_3$): δ 7.54 (d, J=2.1 Hz, 1H), 7.37 (d, J=2.1 Hz, 1H), 7.31-7.28 (m, 2H), 7.12 (d, J=7.2 Hz, 1H), 6.98-6.91 (m, 3H), 6.76-6.71 (m, 2H), 6.28 (t, J=2.1 Hz, 1H), 5.26 (s, 2H), 4.20-4.07 (m, 4H), 3.97-3.90 (m, 1H), 3.56 (s, 3H), 2.93 (t, J=7.5 Hz, 2H), 2.64-2.58 (m, 2H).

Example 3(110)

3-(2-(2-ethoxy-3-phenoxypropoxy)-4-(pyrazol-1-ylmethyl)phenyl)propanoic acid

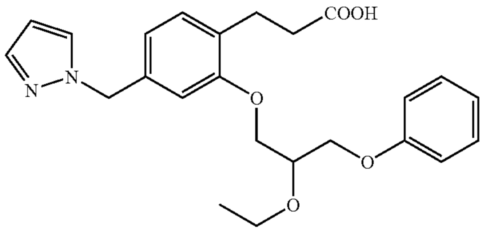

TLC: Rf 0.45 (ethyl acetate);

NMR (300 MHz, $CDCl_3$): δ 7.54 (d, J=1.8 Hz, 1H), 7.36 (d, J=1.8 Hz, 1H), 7.31-7.27 (m, 2H), 7.12 (d, J=7.5 Hz, 1H), 6.98-6.91 (m, 3H), 6.75-6.71 (m, 2H), 6.27 (t, J=1.8 Hz, 1H), 5.26 (s, 2H), 4.16-3.99 (m, 5H), 3.75 (q, J=6.9 Hz, 2H), 2.96-2.90 (m, 2H), 2.65-2.59 (m, 2H), 1.24 (t, J=6.9 Hz, 3H).

Example 3(111)

3-(2-(2-(naphthalen-2-yl)ethoxy)-4-(pyrazol-1-ylmethyl)-5-chlorophenyl)propanoic acid

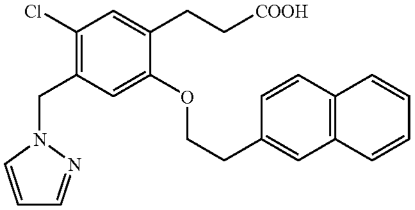

TLC: Rf 0.24 (hexane:ethyl acetate=2:1, 0.5% acetic acid);

NMR (300 MHz, $CDCl_3$): δ 7.82-7.74 (m, 3H), 7.68 (s, 1H), 7.56 (d, J=2.1 Hz, 1H), 7.47-7.38 (m, 3H), 7.36 (dd, J=8.1, 1.8 Hz, 1H), 7.13 (s, 1H), 6.51 (s, 1H), 6.28 (t, J=2.1 Hz, 1H), 5.36 (s, 2H), 4.12 (t, J=6.6 Hz, 2H), 3.18 (t, J=6.6 Hz, 2H), 2.81 (t, J=7.8 Hz, 2H), 2.47 (t, J=7.8 Hz, 2H).

Example 3(112)

3-(2-(2-(naphthalen-2-yl)ethoxy)-4-(pyrazol-1-ylmethyl)-5-methoxyphenyl)propanoic acid

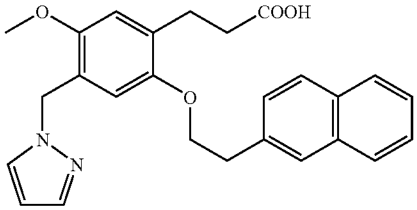

TLC: Rf 0.30 (hexane:ethyl acetate=1:1, 0.5% acetic acid);

NMR (300 MHz, $CDCl_3$): δ 7.82-7.74 (m, 3H), 7.69 (bs, 1H), 7.52 (d, J=2.1 Hz, 1H), 7.47-7.35 (m, 4H), 6.70 (s, 1H), 6.59 (s, 1H), 6.22 (t, J=2.1 Hz, 1H), 5.27 (s, 2H), 4.14 (t, J=6.6 Hz, 2H), 3.76 (s, 3H), 3.18 (t, J=6.6 Hz, 2H), 2.84 (t, J=7.5 Hz, 2H), 2.49 (t, J=7.5 Hz, 2H).

Example 3(113)

3-(2-(2-(benzimidazol-1-yl)ethoxy)-4-(pyrazol-1-ylmethyl)phenyl)propanoic acid

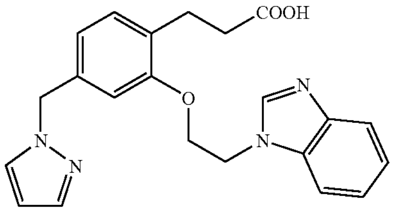

TLC: Rf 0.55 (chloroform:methanol=5:1);

NMR (300 MHz, DMSO-$d_6$): δ 8.24 (s, 1H), 7.74 (m, 1H), 7.68 (d, J=7.8 Hz, 1H), 7.63 (d, J=7.8 Hz, 1H), 7.42 (m, 1H), 7.25 (dd, J=7.8, 7.2 Hz, 1H), 7.18 (dd, J=7.8, 7.2 Hz, 1H), 7.02 (d, J=7.8 Hz, 1H), 6.80 (s, 1H), 6.63 (d, J=7.8 Hz, 1H), 6.22 (m, 1H), 5.20 (s, 2H), 4.69 (t, J=5.1 Hz, 2H), 4.23 (t, J=5.1 Hz, 2H), 2.60 (t, J=7.5 Hz, 2H), 2.26 (t, J=7.5 Hz, 2H).

Example 3(114)

3-(2-(4-methyl-2-(4-fluoro-3-methylphenyl)pentyloxy)-4-(3-cyanophenoxymethyl)phenyl)propanoic acid

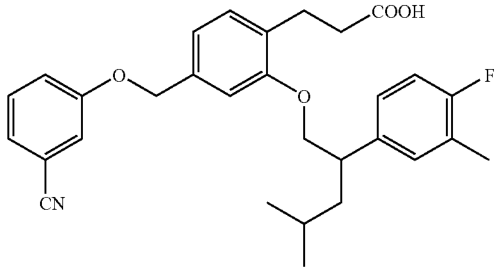

TLC: Rf 0.57 (chloroform:methanol=10:1).

Example 3(115)

3-(2-(4-methyl-2-(4-fluoro-3-methylphenyl)pentyloxy)-4-phenoxymethylphenyl)propanoic acid

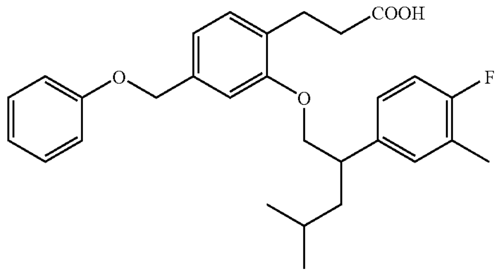

TLC: Rf 0.57 (chloroform:methanol=10:1).

Example 3(116)

3-(2-(2-(2-methylbenzimidazol-1-yl)ethoxy)-4-(pyrazol-1-ylmethyl)phenyl)propanoic acid

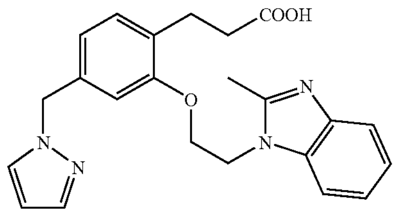

TLC: Rf 0.41 (chloroform:methanol=9:1);

NMR (300 MHz, DMSO-$d_6$): δ 7.73 (dd, J=2.2, 0.6 Hz, 1H), 7.59 (m, 1H), 7.50 (m, 1H), 7.41 (dd, J=2.2, 0.6 Hz, 1H), 7.22-7.10 (m, 2H), 7.01 (d, J=7.7 Hz, 1H), 6.83 (d, J=1.6 Hz, 1H), 6.63 (dd, J=7.7, 1.6 Hz, 1H), 6.22 (t, J=2.2 Hz, 1H), 5.20 (s, 2H), 4.65 (t, J=5.0 Hz, 2H), 4.25 (t, J=5.0 Hz, 2H), 2.60 (s, 3H), 2.57 (t, J=7.7 Hz, 2H), 2.24 (t, J=7.7 Hz, 2H).

Example 3(117)

3-(2-(2-(1H-indazol-1-yl)ethoxy)-4-(pyrazol-1-ylmethyl)phenyl)propanoic acid

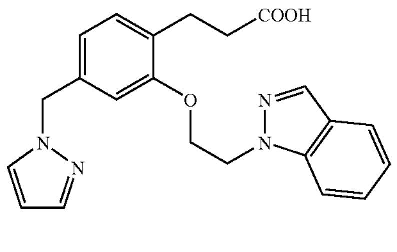

TLC: Rf 0.58 (chloroform:methanol=19:1);

NMR (300 MHz, $CDCl_3$): δ 8.02 (d, J=0.9 Hz, 1H), 7.71 (d, J=7.8 Hz, 1H), 7.55-7.46 (m, 2H), 7.41-7.31 (m, 2H), 7.12 (m, 1H), 7.04 (d, J=7.5 Hz, 1H), 6.70 (d, J=7.5 Hz, 1H), 6.60 (s, 1H), 6.26 (t, J=2.0 Hz, 1H), 5.22 (s, 2H), 4.78 (t, J=5.2 Hz, 2H), 4.35 (t, J=5.2 Hz, 2H), 2.67 (t, J=7.7 Hz, 2H), 2.28 (t, J=7.7 Hz, 2H).

Example 3(118)

3-(2-(2-(2H-benzotriazol-2-yl)ethoxy)-4-(pyrazol-1-ylmethyl)phenyl)propanoic acid

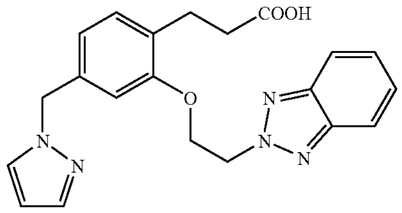

TLC: Rf 0.42 (chloroform:methanol=10:1).

Example 3(119)

3-(2-(2-(1H-benzotriazol-1-yl)ethoxy)-4-(pyrazol-1-ylmethyl)phenyl)propanoic acid

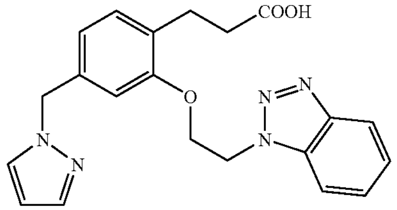

TLC: Rf 0.35 (chloroform:methanol=10:1).

Example 3(120)

3-(2-(2-((3-methylbenzoyl)amino)ethoxy)-4-(pyrazol-1-ylmethyl)phenyl)propanoic acid

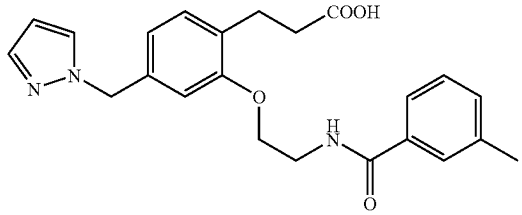

TLC: Rf 0.55 (ethyl acetate:methanol=9:1);

NMR (300 MHz, DMSO-$d_6$): δ 12.03 (s, 1H), 8.60-8.56 (m, 1H), 7.78 (d, J=2.1 Hz, 1H), 7.65-7.60 (m, 2H), 7.43-7.42 (m, 1H), 7.33-7.31 (m, 2H), 7.07 (d, J=7.8 Hz, 1H), 6.88 (s, 1H), 6.67 (d, J=7.8 Hz, 1H), 6.24-6.23 (m, 1H), 5.24 (s, 2H), 4.06 (t, J=5.7 Hz, 2H), 3.65-3.59 (m, 2H), 2.74 (t, J=7.5 Hz, 2H), 2.43 (t, J=7.5 Hz, 2H), 2.33 (s, 3H).

Example 3(121)

3-(2-(2-((3-methoxybenzoyl)amino)ethoxy)-4-(pyrazol-1-ylmethyl)phenyl)propanoic acid

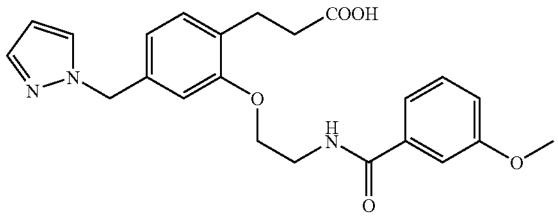

TLC: Rf 0.50 (ethyl acetate:methanol=9:1);

NMR (300 MHz, DMSO-$d_6$): δ 12.01 (s, 1H), 8.65-8.61 (m, 1H), 7.78 (d, J=2.1 Hz, 1H), 7.43-7.32 (m, 4H), 7.08-7.05 (m, 2H), 6.88 (s, 1H), 6.67 (d, J=7.5 Hz, 1H), 6.24 (t, J=2.1 Hz, 1H), 5.24 (s, 2H), 4.06 (t, J=5.7 Hz, 2H), 3.78 (s, 3H), 3.65-3.60 (m, 2H), 2.74 (t, J=7.5 Hz, 2H), 2.42 (t, J=7.5 Hz, 2H).

Example 3(122)

3-(2-(2-((naphthalen-2-ylcarbonyl)amino)ethoxy)-4-(pyrazol-1-ylmethyl)phenyl)propanoic acid

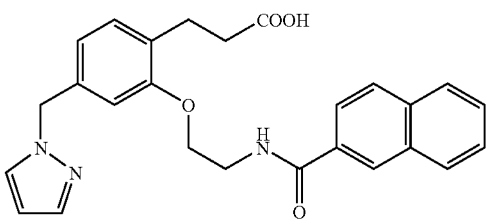

TLC: Rf 0.30 (chloroform:methanol=9:1);

NMR (300 MHz, $CDCl_3$): δ 8.32 (s, 1H), 7.92-7.82 (m, 4H), 7.58-7.48 (m, 3H), 7.36 (d, J=2.1 Hz, 1H), 7.11 (d, J=7.8 Hz, 2H), 6.73 (d, J=7.8 Hz, 1H), 6.65 (s, 1H), 6.26 (dd, J=2.1, 2.1 Hz, 1H), 5.24 (s, 2H), 4.10 (t, J=5.1 Hz, 2H), 3.90 (dt, J=5.1, 5.1 Hz, 2H), 2.96 (t, J=7.2 Hz, 2H), 2.63 (t, J=7.2 Hz, 2H).

Example 3(123)

3-(2-(2-((4-methoxybenzoyl)amino)ethoxy)-4-(pyrazol-1-ylmethyl)phenyl)propanoic acid

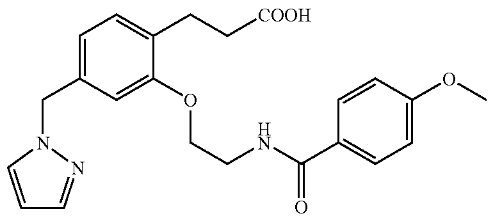

TLC: Rf 0.19 (chloroform:methanol=9:1);

NMR (300 MHz, $CDCl_3$): δ 7.77 (d, J=8.7 Hz, 2H), 7.53 (d, J=1.8 Hz, 1H), 7.37 (d, J=2.1 Hz, 1H), 7.09 (d, J=7.8 Hz, 1H), 6.96 (m, 1H), 6.88 (d, J=9.0 Hz, 1H), 6.72 (d, J=7.8 Hz, 1H), 6.63 (s, 1H), 6.27 (dd, J=2.1, 1.8 Hz, 1H), 5.24 (s, 2H), 4.02 (t, J=4.8 Hz, 2H), 3.81 (s, 3H), 3.80 (m, 2H), 2.93 (t, J=7.5 Hz, 2H), 2.60 (t, J=7.5 Hz, 2H).

Example 3(124)

3-(2-(2-((4-chlorobenzoyl)amino)ethoxy)-4-(pyrazol-1-ylmethyl)phenyl)propanoic acid

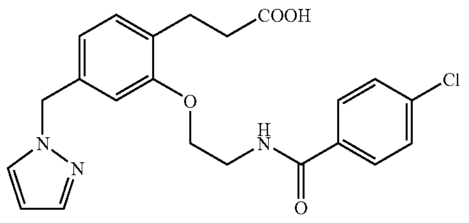

TLC: Rf 0.20 (chloroform:methanol=9:1);

NMR (300 MHz, $CDCl_3$): δ 7.76 (d, J=8.4 Hz, 2H), 7.53 (d, J=2.1 Hz, 1H), 7.38-7.32 (m, 3H), 7.16 (m, 1H), 7.10 (d, J=7.8 Hz, 1H), 6.73 (d, J=7.8 Hz, 1H), 6.63 (s, 1H), 6.27 (dd, J=2.1, 2.1 Hz, 1H), 5.23 (s, 2H), 4.03 (t, J=5.4 Hz, 2H), 3.79 (dt, J=5.4, 5.4 Hz, 2H), 2.94 (t, J=7.2 Hz, 2H), 2.60 (t, J=7.2 Hz, 2H).

Example 3(125)

3-(2-(4-methyl-2-benzoylaminopentyloxy)-4-(pyrazol-1-ylmethyl)phenyl)propanoic acid

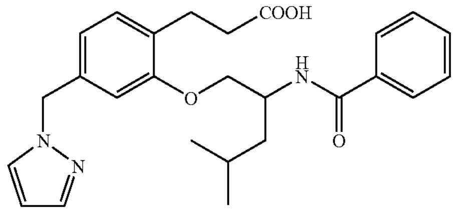

TLC: Rf 0.58 (chloroform:methanol=9:1);

NMR (300 MHz, $CDCl_3$): δ 7.80-7.74 (m, 2H), 7.53 (d, J=2.1 Hz, 1H), 7.51-7.35 (m, 4H), 7.10 (d, J=7.7 Hz, 1H), 6.73 (d, J=7.7 Hz, 1H), 6.64 (s, 1H), 6.48 (d, J=8.7 Hz, 1H), 6.27 (t, J=2.1 Hz, 1H), 5.24 (s, 2H), 4.65 (m, 1H), 4.05 (dd, J=9.3, 3.9 Hz, 1H), 3.92 (dd, J=9.3, 1.8 Hz, 1H), 2.90 (t, J=7.8 Hz, 2H), 2.69-2.46 (m, 2H), 1.81-1.48 (m, 3H), 0.97 (d, J=6.3 Hz, 6H).

Example 3(126)

3-(2-(2-(naphthalen-2-yl)ethoxy)-4-(4-acetylpiperazin-1-ylmethyl)phenyl)propanoic acid

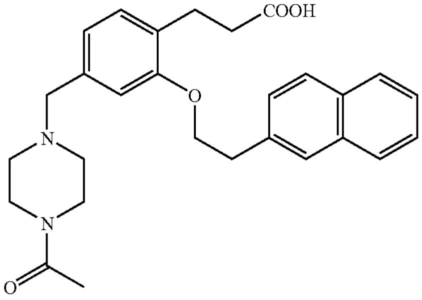

TLC: Rf 0.29 (chloroform:methanol=10:1).

Example 3(127)

3-(2-(2-(naphthalen-2-yl)ethoxy)-4-(morpholin-4-ylmethyl)phenyl)propanoic acid

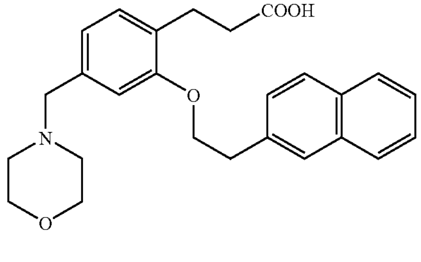

TLC: Rf 0.33 (chloroform:methanol=10:1).

Example 3(128)

3-(2-(2-(4-methylbenzoylamino)ethoxy)-4-(pyrazol-1-ylmethyl)phenyl)propanoic acid

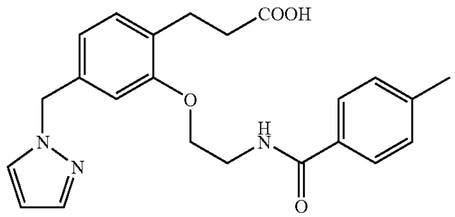

TLC: Rf 0.20 (chloroform:methanol=9:1);

NMR (300 MHz, $CDCl_3$): δ 7.70 (d, J=8.4 Hz, 2H), 7.53 (d, J=2.1 Hz, 1H), 7.37 (d, J=2.1 Hz, 1H), 7.19 (d, J=8.1 Hz, 2H), 7.10 (d, J=7.8 Hz, 1H), 6.98 (brs, 1H), 6.72 (d, J=7.5 Hz, 1H), 6.63 (s, 1H), 6.27 (t, J=2.1 Hz, 1H), 5.24 (s, 2H), 4.03 (t, J=4.8 Hz, 2H), 3.81 (dt, J=5.1, 4.8 Hz, 2H), 2.93 (t, J=7.5 Hz, 2H), 2.60 (t, J=7.5 Hz, 2H), 2.36 (s, 3H).

Example 3(129)

3-(2-(2-(naphthalen-1-ylcarbonylamino)ethoxy)-4-(pyrazol-1-ylmethyl)phenyl)propanoic acid

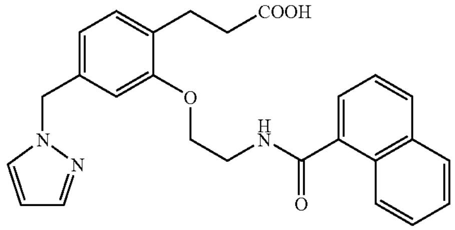

TLC: Rf 0.28 (chloroform:methanol=9:1);

NMR (300 MHz, DMSO-$d_6$): δ 8.74 (m, 1H), 8.20 (m, 1H), 8.02-7.94 (m, 2H), 7.80 (d, J=2.4 Hz, 1H), 7.60-7.50 (m, 4H), 7.43 (d, J=1.8 Hz, 1H), 7.09 (d, J=7.5 Hz, 1H), 6.92 (s, 1H), 6.68 (d, J=7.5 Hz, 1H), 6.24 (dd, J=2.4, 1.8 Hz, 1H), 5.26 (s, 2H), 4.13 (t, J=5.7 Hz, 2H), 3.71 (dt, J=5.1, 5.7 Hz, 2H), 2.80 (t, J=7.2 Hz, 2H), 2.45 (m, 2H).

Example 3(130)

3-(2-(2-(2-benzylcarbonylamino)ethoxy)-4-(pyrazol-1-ylmethyl)phenyl)propanoic acid

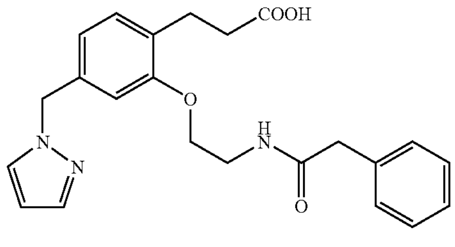

TLC: Rf 0.54 (chloroform:methanol=9:1);

NMR (300 MHz, DMSO-$d_6$): δ 8.22 (m, 1H), 7.78 (d, J=2.4 Hz, 1H), 7.43 (d, J=2.1 Hz, 1H), 7.30-7.15 (m, 5H), 7.07 (d, J=8.1 Hz, 1H), 6.83 (s, 1H), 6.67 (d, J=8.1 Hz, 1H), 6.24 (dd, J=2.4, 1.8 Hz, 1H), 5.24 (s, 2H), 3.94 (t, J=5.4 Hz, 2H), 3.46-3.38 (m, 4H), 2.74 (t, J=7.5 Hz, 2H), 2.45 (t, J=7.5 Hz, 2H).

Example 3(131)

3-(2-(2-(2-methylbenzoylamino)ethoxy)-4-(pyrazol-1-ylmethyl)phenyl)propanoic acid

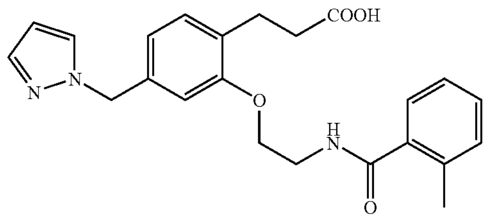

TLC: Rf 0.38 (chloroform:methanol=10:1).

Example 3(132)

3-(2-(2-(2-chlorobenzoylamino)ethoxy)-4-(pyrazol-1-ylmethyl)phenyl)propanoic acid

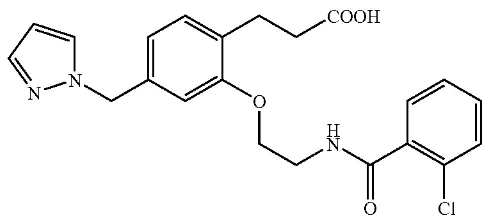

TLC: Rf 0.40 (chloroform:methanol=10:1).

Example 3(133)

3-(2-(2-(2-methoxybenzoylamino)ethoxy)-4-(pyrazol-1-ylmethyl)phenyl)propanoic acid

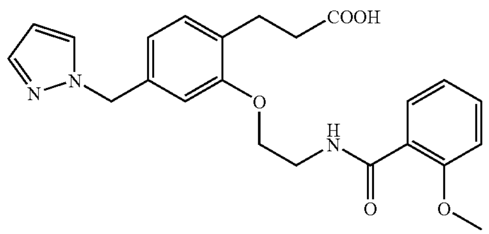

TLC: Rf 0.42 (chloroform:methanol=10:1).

Example 3(134)

3-(2-phenylcarbamoylmethoxy-4-(pyrazol-1-ylmethyl)phenyl)propanoic acid

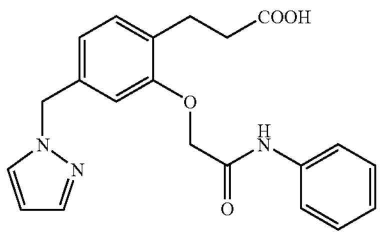

TLC: Rf 0.53 (chloroform:methanol=9:1);

NMR (300 MHz, $CDCl_3$): δ 8.79 (s, 1H), 7.66 (d, J=7.8 Hz, 2H), 7.52 (d, J=2.1 Hz, 1H), 7.38 (d, J=2.1 Hz, 1H), 7.36-7.30 (m, 2H), 7.20-7.10 (m, 2H), 6.78 (d, J=7.8 Hz, 1H), 6.61 (s, 1H), 6.27 (t, J=2.1 Hz, 1H), 5.26 (s, 2H), 4.45 (s, 2H), 3.06 (t, J=7.2 Hz, 2H), 2.72 (t, J=7.2 Hz, 2H).

Example 3(135)

3-(2-(naphthalen-1-ylcarbamoylmethoxy)-4-(pyrazol-1-ylmethyl)phenyl)propanoic acid

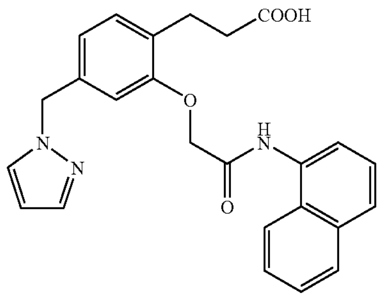

TLC: Rf 0.53 (chloroform:methanol=9:1);

NMR (300 MHz, DMSO-$d_6$): δ 10.04 (s, 1H), 8.04-7.92 (m, 2H), 7.84-7.76 (m, 2H), 7.65 (d, J=7.2 Hz, 1H), 7.58-7.50 (m, 3H), 7.43 (d, J=2.1 Hz, 1H), 7.15 (d, J=7.8 Hz, 1H), 6.94 (s, 1H), 6.75 (d, J=7.8 Hz, 1H), 6.22 (t, J=2.1 Hz, 1H), 5.28 (s, 2H), 4.85 (s, 2H), 2.90 (t, J=7.8 Hz, 2H), 2.55 (t, J=7.8 Hz, 2H).

Example 3(136)

3-(2-(naphthalen-2-ylcarbamoylmethoxy)-4-(pyrazol-1-ylmethyl)phenyl)propanoic acid

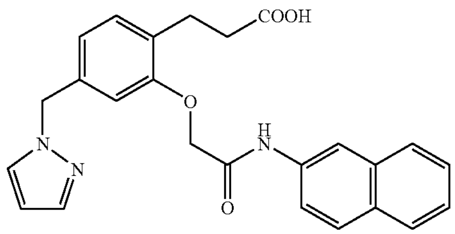

TLC: Rf 0.59 (chloroform:methanol=9:1);

NMR (300 MHz, DMSO-$d_6$): δ 10.21 (s, 1H), 8.29 (s, 1H), 7.90-7.80 (m, 3H), 7.74 (d, J=1.8 Hz, 1H), 7.61 (dd, J=8.7, 1.8 Hz, 1H), 7.50-7.38 (m, 2H), 7.36 (d, J=1.8 Hz, 1H), 7.14 (d, J=7.8 Hz, 1H), 6.85 (s, 1H), 6.72 (d, J=7.8 Hz, 1H), 6.16 (dd, J=1.8, 1.8 Hz, 1H), 5.25 (s, 2H), 4.75 (s, 2H), 2.86 (t, J=7.2 Hz, 2H), 2.55 (t, J=7.2 Hz, 2H).

Example 3(137)

3-(2-(3-phenylpropoxy)-4-phenoxymethylphenyl) propanoic acid

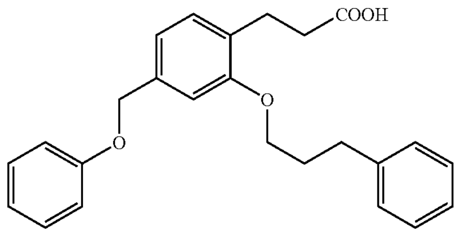

TLC: Rf 0.48 (hexane:ethyl acetate=1:1);

NMR (300 MHz, $CDCl_3$): δ 7.35-7.14 (m, 8H), 7.00-6.80 (m, 5H), 4.99 (s, 2H), 4.00 (t, J=6.3 Hz, 2H), 3.00-2.95 (m, 2H), 2.82 (dd, J=7.8, 7.5 Hz, 2H), 2.72-2.67 (m, 2H), 2.17-2.08 (m, 2H).

Example 3(138)

3-(2-(4-phenylbutoxy)-4-phenoxymethylphenyl) propanoic acid

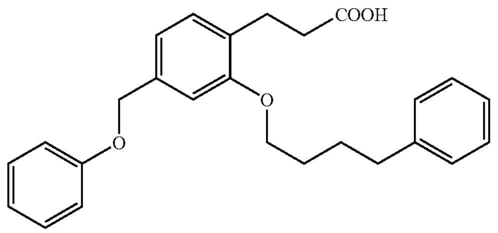

TLC: Rf 0.52 (hexane:ethyl acetate=1:1);

NMR (300 MHz, $CDCl_3$): δ 7.34-7.13 (m, 8H), 7.00-6.90 (m, 5H), 5.00 (s, 2H), 4.01-3.98 (m, 2H), 2.98-2.92 (m, 2H), 2.70-2.64 (m, 4H), 1.85-1.82 (m, 4H).

Example 3(139)

3-(2-(2-(naphthalen-2-yl)ethoxy)-4-(4-methylpiperazin-1-ylmethyl)phenyl)propanoic acid

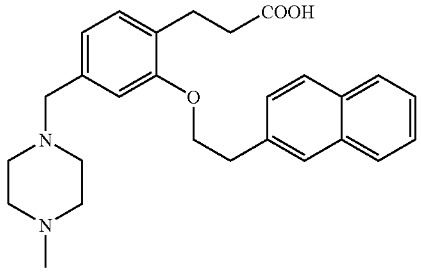

TLC: Rf 0.25 (chloroform:methanol=5:1).

Example 3(140)

2-((2-(2-(naphthalen-2-yl)ethoxy)-4-(pyrazol-1-ylmethyl)benzyl)amino)acetic acid hydrochloride

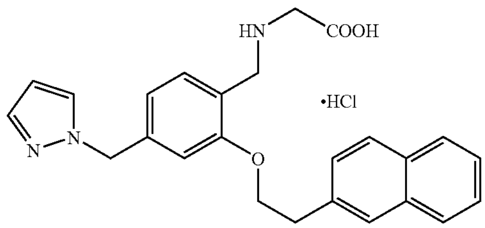

TLC: Rf 0.25 (ethyl acetate:methanol=1:1).

Example 3(141)

2-(N-methyl-N-(2-(2-(naphthalen-2-yl)ethoxy)-4-(pyrazol-1-ylmethyl)benzyl)amino)acetic acid hydrochloride

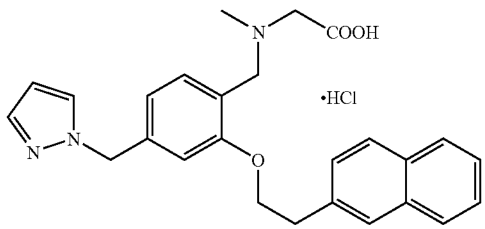

TLC: Rf 0.30 (ethyl acetate:methanol=1:1).

Example 3(142)

2-(N-mesyl-N-(2-(2-(naphthalen-2-yl)ethoxy)-4-(pyrazol-1-ylmethyl)benzyl)amino)acetic acid

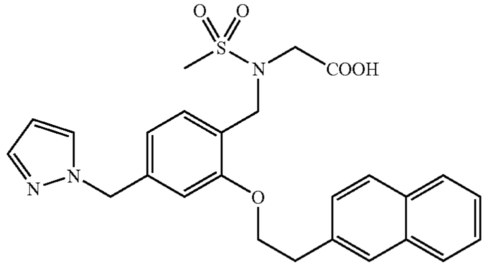

TLC: Rf 0.45 (ethyl acetate:methanol=3:1).

Example 3(143)

2-(2-(naphthalen-2-yl)ethoxy)-4-(pyrazol-1-ylmethyl)benzoic acid

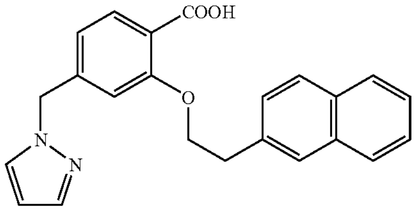

TLC: Rf 0.63 (chloroform:methanol=9:1);

NMR (300 MHz, $CDCl_3$): δ 8.10 (d, J=7.8 Hz, 1H), 7.88-7.77 (m, 3H), 7.71 (s, 1H), 7.59 (d, J=1.5 Hz, 1H), 7.53-7.40 (m, 3H), 7.35 (dd, J=8.4, 1.5 Hz, 1H), 6.91 (d, J=8.4 Hz, 1H), 6.79 (s, 1H), 6.33 (t, J=2.1 Hz, 1H), 5.34 (s, 2H), 4.45 (t, J=6.6 Hz, 2H), 3.32 (t, J=6.6 Hz, 2H).

Example 3(144)

3-(2-(2-(naphthalen-2-yl)ethoxy)-4-(pyridin-2-ylaminomethyl)phenyl)propanoic acid

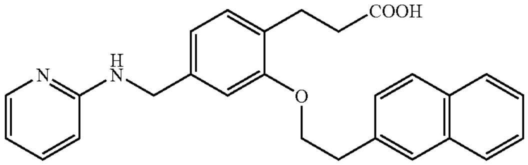

TLC: Rf 0.52 (chloroform:methanol=9:1);

NMR (300 MHz, DMSO-$d_6$): δ 12.04 (s, 1H), 7.92 (dd, J=4.8, 1.5 Hz, 1H), 7.89-7.79 (m, 4H), 7.51-7.41 (m, 3H), 7.33 (m, 1H), 7.01 (d, J=7.5 Hz, 1H), 6.97-6.89 (m, 2H), 6.78 (m, 1H), 6.50-6.42 (m, 2H), 4.38 (d, J=6.0 Hz, 2H), 4.22 (t, J=6.6 Hz, 2H), 3.19 (t, J=6.6 Hz, 2H), 2.70 (t, J=7.5 Hz, 2H), 2.35 (t, J=7.5 Hz, 2H).

Example 3(145)

3-(2-(2-(naphthalen-2-yl)ethoxy)-4-(thiazol-2-ylaminomethyl)phenyl)propanoic acid

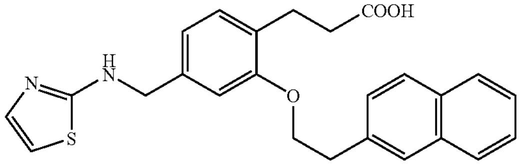

TLC: Rf 0.50 (chloroform:methanol=9:1);

NMR (300 MHz, DMSO-$d_6$): δ 12.04 (s, 1H), 7.94 (t, J=5.7 Hz, 1H), 7.90-7.80 (m, 4H), 7.53-7.41 (m, 3H), 7.04 (d, J=7.5 Hz, 1H), 6.98 (d, J=3.6 Hz, 1H), 6.96 (d, J=1.5 Hz, 1H), 6.79 (m, 1H), 6.58 (d, J=3.6 Hz, 1H), 4.35 (d, J=5.7 Hz, 2H), 4.23 (t, J=6.6 Hz, 2H), 3.20 (t, J=6.6 Hz, 2H), 2.70 (t, J=7.5 Hz, 2H), 2.36 (t, J=7.5 Hz, 2H).

Example 3(146)

3-(2-(2-cyclohexyloxyethoxy)-4-(pyrazol-1-ylmethyl)phenyl)propanoic acid

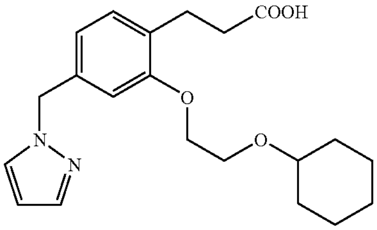

TLC: Rf 0.34 (chloroform:methanol=9:1);

NMR (300 MHz, $CDCl_3$): δ 7.54 (d, J=1.5 Hz, 1H), 7.36 (d, J=1.5 Hz, 1H), 7.12 (d, J=7.8 Hz, 1H), 6.73 (d, J=7.8 Hz, 1H), 6.67 (s, 1H), 6.23 (dd, J=1.5, 1.5 Hz, 1H), 5.26 (s, 2H), 4.05 (t, J=4.8 Hz, 2H), 3.80 (t, J=4.8 Hz, 2H), 3.34 (m, 1H), 2.93 (t, J=7.5 Hz, 2H), 2.65 (t, J=7.5 Hz, 2H), 1.94 (m, 2H), 1.73 (m, 2H), 1.52 (m, 1H), 1.36-1.16 (m, 5H).

Example 3(147)

3-(2-(benzylcarbamoylmethoxy)-4-(pyrazol-1-ylmethyl)phenyl)propanoic acid

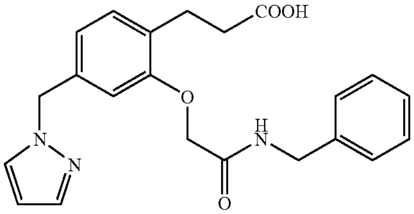

TLC: Rf 0.49 (chloroform:methanol=9:1);

NMR (300 MHz, $CDCl_3$): δ 7.55 (d, J=2.1 Hz, 1H), 7.38 (d, J=2.4 Hz, 1H), 7.34-7.20 (m, 6H), 7.13 (d, J=7.8 Hz, 1H), 6.78 (d, J=7.8 Hz, 1H), 6.59 (s, 1H), 6.29 (dd, J=2.4, 2.1 Hz, 1H), 5.25 (s, 2H), 4.52-4.47 (m, 4H), 2.94 (t, J=7.2 Hz, 2H), 2.58 (t, J=7.2 Hz, 2H).

Example 3(148)

3-(2-((1-phenylethyl)carbamoylmethoxy)-4-(pyrazol-1-ylmethyl)phenyl)propanoic acid

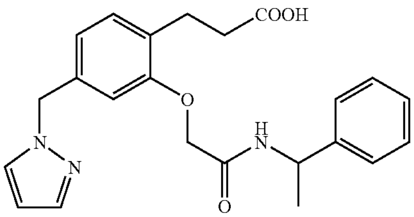

TLC: Rf 0.53 (chloroform:methanol=9:1);

NMR (300 MHz, $CDCl_3$): δ 7.53 (d, J=1.8 Hz, 1H), 7.35 (d, J=2.1 Hz, 1H), 7.32-7.20 (m, 5H), 7.14 (d, J=7.5 Hz, 1H), 7.09 (d, J=8.1 Hz, 1H), 6.77 (d, J=7.5 Hz, 1H), 6.55 (s, 1H), 6.27 (dd, J=2.1, 1.8 Hz, 1H), 5.22 (s, 2H), 5.20 (m, 1H), 4.43 (d, J=15.0 Hz, 1H), 4.37 (d, J=15.0 Hz, 1H), 2.96 (t, J=7.5 Hz, 2H), 2.61 (t, J=7.5 Hz, 2H), 1.49 (d, J=6.9 Hz, 3H).

Example 3(149)

3-(2-(2-(3-chlorobenzoylamino)ethoxy)-4-(pyrazol-1-ylmethyl)phenyl)propanoic acid

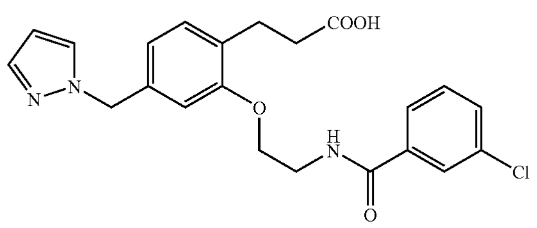

TLC: Rf 0.35 (ethyl acetate);

NMR (300 MHz, DMSO-$d_6$): δ 11.99 (s, 1H), 8.78 (t, J=5.1 Hz, 1H), 7.87-7.78 (m, 3H), 7.60-7.43 (m, 3H), 7.06 (d, J=7.5 Hz, 1H), 6.88 (s, 1H), 6.67 (d, J=7.5 Hz, 1H), 6.24 (t, J=2.1 Hz, 1H), 5.24 (s, 2H), 4.07 (t, J=5.7 Hz, 2H), 3.66-3.61 (m, 2H), 2.73 (t, J=7.5 Hz, 2H), 2.41 (t, J=7.5 Hz, 2H).

Example 3(150)

2-(2-(2-(naphthalen-2-yl)ethoxy)-4-(pyrazol-1-ylmethyl)benzyloxy)acetic acid

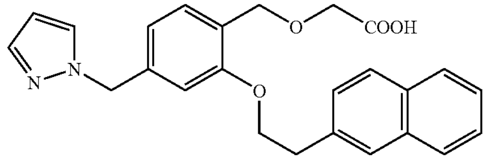

TLC: Rf 0.25 (ethyl acetate);

NMR (300 MHz, $CDCl_3$): δ 7.83 (m, 3H), 7.68 (s, 1H), 7.56-7.23 (m, 6H), 6.80-6.74 (m, 2H), 6.29-6.27 (m, 1H), 5.29 (s, 2H), 4.52 (s, 2H), 4.26 (t, J=6.9 Hz, 2H), 4.01 (s, 2H), 3.23 (t, J=6.9 Hz, 2H).

Example 3(151)

3-(2-(2-(1-oxo-1,2,3,4-tetrahydroisoquinolin-2-yl)ethoxy)-4-(pyrazol 1-ylmethyl)phenyl)propanoic acid

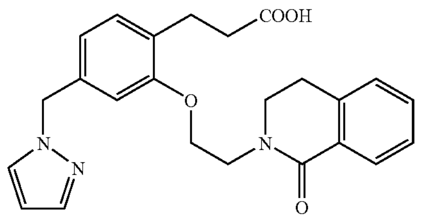

TLC: Rf 0.47 (chloroform:methanol=10:1);

NMR (300 MHz, $CDCl_3$): δ 8.04 (d, J=7.2 Hz, 1H), 7.54 (s, 1H), 7.48-7.04 (m, 5H), 6.74 (d, J=7.2 Hz, 1H), 6.65 (s, 1H), 6.27 (m, 1H), 5.25 (s, 2H), 4.20-4.08 (m, 2H), 4.05-3.94 (m, 2H), 3.18 (t, J=6.6 Hz, 2H), 3.00 (t, J=6.6 Hz, 2H), 2.93-2.80 (m, 2H), 2.66-2.53 (m, 2H).

Example 3(152)

3-(2-(2-(naphthalen-2-yl)ethoxy)-4-(2-(pyrazol-1-yl)ethyl)phenyl)propanoic acid

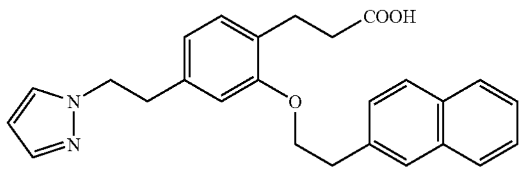

TLC: Rf 0.45 (chloroform:methanol=19:1);

NMR (300 MHz, $CDCl_3$): δ 7.84-7.76 (m, 3H), 7.73 (s, 1H), 7.56-7.37 (m, 4H), 7.13 (d, J=1.9 Hz, 1H), 7.02 (d, J=7.5 Hz, 1H), 6.59 (dd, J=7.5, 1.5 Hz, 1H), 6.43 (d, J=1.5 Hz, 1H), 6.15 (t, J=1.9 Hz, 1H), 4.29 (t, J=7.4 Hz, 2H), 4.16 (t, J=6.7 Hz, 2H), 3.23 (t, J=6.7 Hz, 2H), 3.08 (t, J=7.4 Hz, 2H), 2.86 (t, J=7.8 Hz, 2H), 2.51 (t, J=7.8 Hz, 2H).

Example 3(153)

3-(2-(2-(thiophen-2-yl)ethoxy)-4-(pyrazol-1-ylmethyl)phenyl)propanoic acid

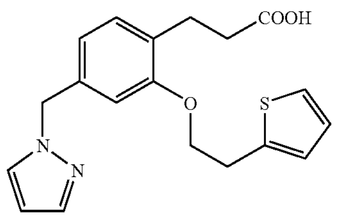

TLC: Rf 0.48 (chloroform:methanol=9:1).

Example 3(154)

3-(2-(2-(thiophen-3-yl)ethoxy)-4-(pyrazol-1-ylmethyl)phenyl)propanoic acid

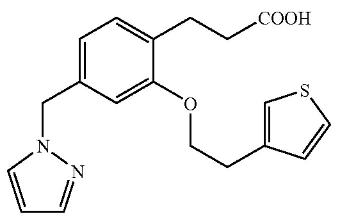

TLC: Rf 0.48 (chloroform:methanol=9:1).

Example 3(155)

3-(2-(3-cyclohexylpropoxy)-4-(pyrazol-1-ylmethyl) phenyl)propanoic acid

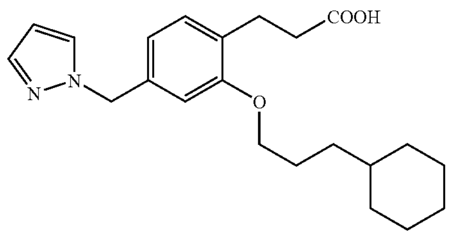

TLC: Rf 0.50 (chloroform:methanol=9:1);

NMR (300 MHz, DMSO-$d_6$): δ 12.03 (s, 1H), 7.78 (d, J=2.1 Hz, 1H), 7.43 (m, 1H), 7.06 (d, J=7.8 Hz, 1H), 6.81 (s, 1H), 6.64 (d, J=7.8 Hz, 1H), 6.24 (t, J=2.1 Hz, 1H), 5.24 (s, 2H), 3.88 (t, J=6.3 Hz, 2H), 2.72 (t, J=7.5 Hz, 2H), 2.42 (t, J=7.5 Hz, 2H), 1.70-1.62 (m, 7H), 1.34-1.14 (m, 6H), 0.92-0.84 (m, 2H).

Example 3(156)

3-(2-(2-phenoxyethoxy)-4-(pyrazol-1-ylmethyl)phenyl)propanoic acid

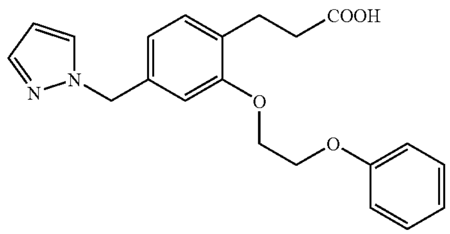

TLC: Rf 0.50 (chloroform:methanol=9:1);

NMR (300 MHz, DMSO-$d_6$): δ 12.01 (s, 1H), 7.79 (d, J=2.1 Hz, 1H), 7.44 (s, 1H), 7.31-7.26 (m, 2H), 7.08 (d, J=7.5 Hz, 1H), 6.98-6.93 (m, 4H), 6.68 (d, J=7.5 Hz, 1H), 6.25-6.24 (m, 1H), 5.26 (s, 2H), 4.32-4.26 (m, 4H), 2.72 (t, J=7.5 Hz, 2H), 2.45-2.43 (m, 2H).

Example 3(157)

3-(2-(2-(N-methyl-N-phenylamino)ethoxy)-4-(pyrazol-1-ylmethyl)phenyl)propanoic acid

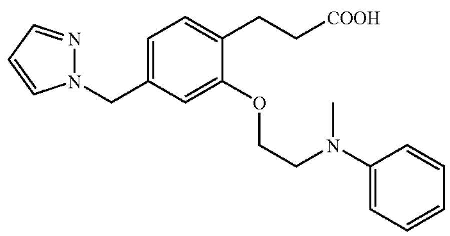

TLC: Rf 0.30 (hexane:ethyl acetate=1:1, 0.5% acetic acid);

NMR (300 MHz, $CDCl_3$): δ 7.53 (d, J=2.1 Hz, 1H), 7.34 (d, J=2.1 Hz, 1H), 7.27-7.19 (m, 2H), 7.11 (d, J=7.8 Hz, 1H), 6.78-6.63 (m, 5H), 6.26 (t, J=2.1 Hz, 1H), 5.23 (s, 2H), 4.09 (t, J=5.4 Hz, 2H), 3.76 (t, J=5.4 Hz, 2H), 3.03 (s, 3H), 2.88 (t, J=7.5 Hz, 2H), 2.58 (t, J=7.5 Hz, 2H).

Example 3(158)

3-(2-(2-phenylethoxy)-4-(3-cyanophenoxymethyl) phenyl)propanoic acid

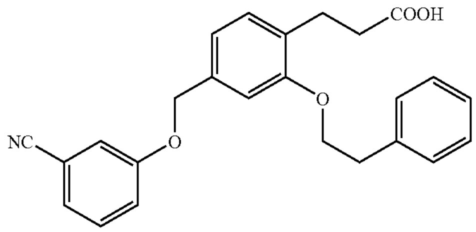

TLC: Rf 0.40 (hexane:ethyl acetate=1:1);

NMR (300 MHz, $CDCl_3$): δ 7.39-7.15 (m, 10H), 6.90-6.87 (m, 2H), 5.00 (s, 2H), 4.20 (t, J=6.6 Hz, 2H), 3.12 (t, J=6.6 Hz, 2H), 2.93-2.88 (m, 2H), 2.58-2.53 (m, 2H).

Example 3(159)

3-(2-(2-phenylethoxy)-4-(2-chloro-4-methylphenoxymethyl)phenyl)propanoic acid

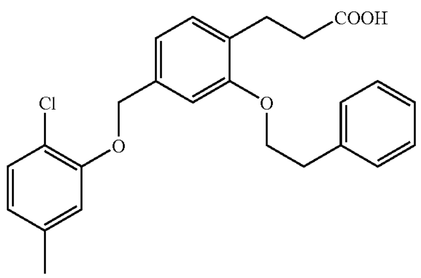

TLC: Rf 0.54 (hexane:ethyl acetate=1:1);

NMR (300 MHz, $CDCl_3$): δ 7.34-7.19 (m, 6H), 7.13 (d, J=7.8 Hz, 1H), 7.00 (brs, 1H), 6.92 (brd, J=7.8 Hz, 1H), 6.78 (brs, 1H), 6.71 (brd, J=7.8 Hz, 1H), 5.06 (s, 2H), 4.22 (t, J=6.6 Hz, 2H), 3.11 (t, J=6.6 Hz, 2H), 2.92-2.87 (m, 2H), 2.57-2.52 (m, 2H), 2.29 (s, 3H).

Example 3(160)

3-(2-(3-phenylpropoxy)-4-(pyrazol-1-ylmethyl)phenyl)propanoic acid

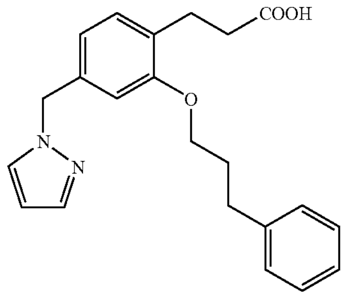

TLC: Rf 0.52 (chloroform:methanol=10:1).

Example 3(161)

3-(2-(4-phenylbutoxy)-4-(pyrazol-1-ylmethyl)phenyl)propanoic acid

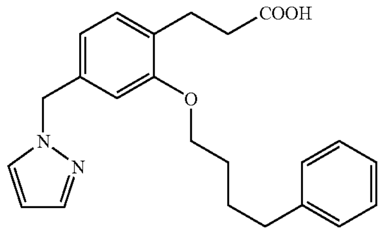

TLC: Rf 0.52 (chloroform:methanol=10:1).

Example 3(162)

(2E)-3-(2-(2-(2,5,7,8-tetramethyl-6-hydroxychroman-2-yl)ethoxy)-4-(imidazol-1-ylmethyl)phenyl)-2-propenoic acid hydrochloride

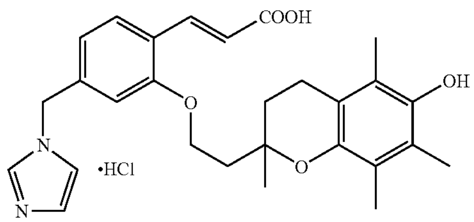

TLC: Rf 0.46 (chloroform:methanol=8:1);

NMR (300 MHz, $CD_3OD$): δ 9.01 (s, 1H), 7.94 (d, J=16.2 Hz, 1H), 7.63 (d, J=8.1 Hz, 1H), 7.60-7.55 (m, 2H), 7.03 (s, 1H), 6.94 (d, J=8.1 Hz, 1H), 6.51 (d, J=16.2 Hz, 1H), 5.45-5.30 (m, 2H), 4.42-4.20 (m, 2H), 2.70-2.60 (m, 2H), 2.26-1.80 (m, 4H), 2.11 (s, 3H), 2.08 (s, 3H), 2.04 (s, 3H), 1.35 (s, 3H).

Example 3(163)

3-(2-(3,3-diphenylpropoxy)-4-(pyrazol-1-ylmethyl)phenyl)propanoic acid

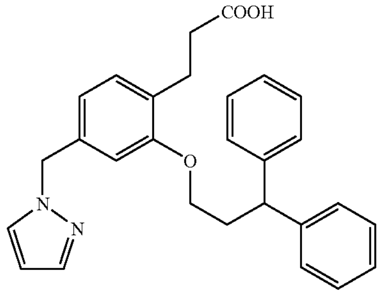

TLC: Rf 0.42 (chloroform:methanol=9:1);

NMR (300 MHz, $CDCl_3$): δ 7.51 (d, J=2.1 Hz, 1H), 7.32 (d, J=2.1 Hz, 1H), 7.30-7.15 (m, 10H), 7.11 (d, J=7.8 Hz, 1H), 6.68 (d, J=7.8 Hz, 1H), 6.54 (s, 1H), 6.24 (t, J=2.1 Hz, 1H), 5.20 (s, 2H), 4.24 (t, J=7.8 Hz, 1H), 3.87 (t, J=6.3 Hz, 2H), 2.94 (t, J=7.8 Hz, 2H), 2.67 (t, J=7.8 Hz, 2H), 2.52 (dt, J=7.8, 6.3 Hz, 2H).

Example 3(164)

3-(2-(2-(N,N-diphenylamino)ethoxy)-4-(pyrazol-1-ylmethyl)phenyl)propanoic acid

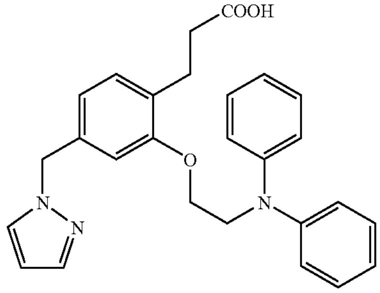

[Salt-free]

TLC: Rf 0.44 (chloroform:methanol=9:1);

NMR (300 MHz, $CDCl_3$): δ 7.52 (d, J=2.1 Hz, 1H), 7.33 (d, J=2.1 Hz, 1H), 7.30-7.20 (m, 4H), 7.12-7.02 (m, 5H), 6.98-6.92 (m, 2H), 6.71 (d, J=7.8 Hz, 1H), 6.63 (s, 1H), 6.25 (t, J=2.1 Hz, 1H), 5.21 (s, 2H), 4.20-4.10 (m, 4H), 2.85 (t, J=7.8 Hz, 2H), 2.54 (t, J=7.8 Hz, 2H).

Sodium Salt:

TLC: Rf 0.50 (chloroform:methanol=10:1).

Example 3(165)

3-(2-(2-(4-phenylpiperazin-1-yl)ethoxy)-4-(pyrazol-1-ylmethyl)phenyl)propanoic acid

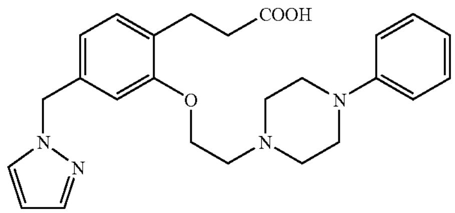

TLC: Rf 0.50 (chloroform:methanol=5:1).

Example 3(166)

3-(2-(2-(4-phenyl-1,2,3,6-tetrahydropyridin-1-yl)ethoxy)-4-(pyrazol-1-ylmethyl)phenyl)propanoic acid

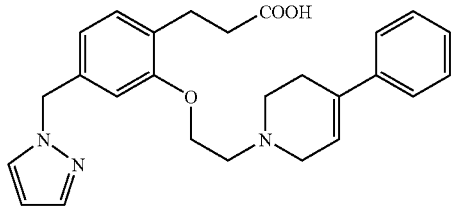

TLC: Rf 0.51 (chloroform:methanol=5:1).

Example 3(167)

3-(2-(2-(4-phenylpiperidin-1-yl)ethoxy)-4-(pyrazol-1-ylmethyl)phenyl)propanoic acid

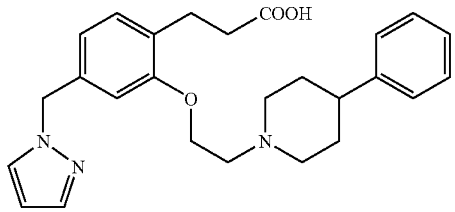

TLC: Rf 0.47 (chloroform:methanol=5:1).

Example 3(168)

3-(2-(2-(phenoxazin-10-yl)ethoxy)-4-(pyrazol-1-ylmethyl)phenyl)propanoic acid

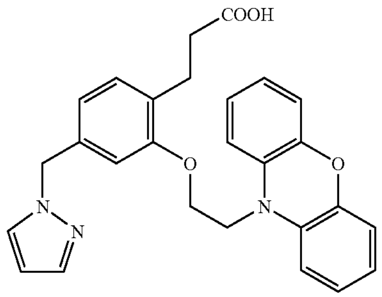

[Salt-free]

TLC: Rf 0.23 (chloroform:methanol=9:1);

NMR (300 MHz, $CDCl_3$): δ 7.53 (d, J=2.1 Hz, 1H), 7.35 (d, J=2.1 Hz, 1H), 7.12 (d, J=7.5 Hz, 1H), 6.83-6.60 (m, 10H), 6.26 (t, J=2.1 Hz, 1H), 5.24 (s, 2H), 4.17 (t, J=5.7 Hz, 2H), 3.98 (t, J=5.7 Hz, 2H), 2.86 (t, J=7.8 Hz, 2H), 2.55 (t, J=7.8 Hz, 2H).

Sodium Salt:

TLC: Rf 0.47 (chloroform:methanol=10:1).

Example 3(169)

4-(2-(2-phenylethoxy)-4-(3-cyanophenoxymethyl)phenyl)butanoic acid

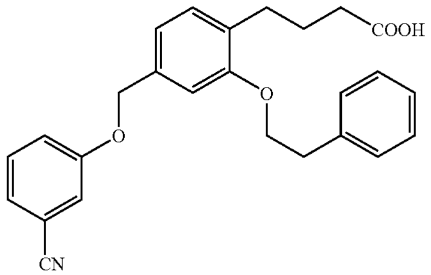

TLC: Rf 0.56 (chloroform:methanol=10:1);

NMR (300 MHz, $CDCl_3$): δ 7.43-7.08 (m, 10H), 6.94-6.84 (m, 2H), 5.00 (s, 2H), 4.18 (t, J=6.8 Hz, 2H), 3.11 (t, J=6.8 Hz, 2H), 2.63 (t, J=7.4 Hz, 2H), 2.31 (t, J=7.4 Hz, 2H), 1.94-1.77 (m, 2H).

Example 3(170)

4-(2-(2-(naphthalen-2-yl)ethoxy)-4-(3-cyanophenoxymethyl)phenyl)butanoic acid

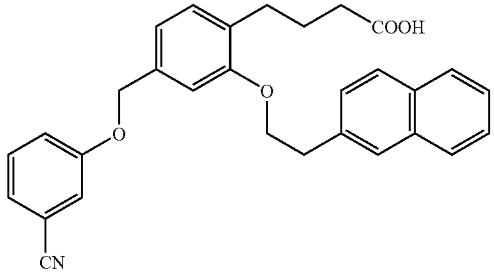

TLC: Rf 0.63 (chloroform:methanol=10:1);

NMR (300 MHz, $CDCl_3$): δ 7.84-7.75 (m, 3H), 7.73 (s, 1H), 7.49-7.31 (m, 4H), 7.28-7.14 (m, 3H), 7.09 (d, J=8.1 Hz, 1H), 6.92-6.84 (m, 2H), 4.99 (s, 2H), 4.27 (t, J=6.6 Hz, 2H), 3.27 (t, J=6.6 Hz, 2H), 2.62 (t, J=7.7 Hz, 2H), 2.25 (t, J=7.7 Hz, 2H), 1.90-1.76 (m, 2H).

Example 3(171)

2-(2-(2-(naphthalen-2-yl)ethoxy)-4-(pyrazol-1-ylmethyl)benzoylamino)acetic acid

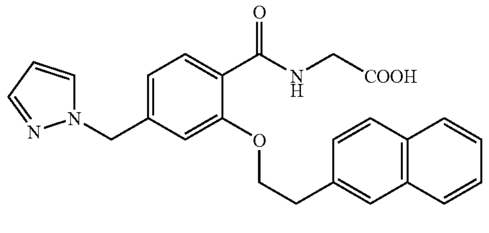

TLC: Rf 0.45 (ethyl acetate:methanol=3:1);

NMR (300 MHz, DMSO-$d_6$): δ 8.25 (t, J=5.4 Hz, 1H), 7.88-7.76 (m, 6H), 7.53-7.45 (m, 4H), 7.10 (s, 1H), 6.79 (dd, J=8.1, 1.5 Hz, 1H), 6.27 (t, J=2.1 Hz, 1H), 5.35 (s, 2H), 4.42 (t, J=6.6 Hz, 2H), 3.84 (d, J=5.4 Hz, 2H), 3.33-3.29 (m, 2H).

Example 3(172)

3-(2-(2-(2-methylimidazol-1-yl)ethoxy)-4-(pyrazol-1-ylmethyl)phenyl)propanoic acid

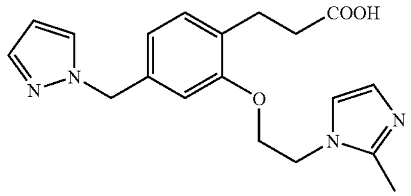

TLC: Rf 0.50 (methanol);

NMR (300 MHz, DMSO-$d_6$): δ 7.77 (d, J=2.1 Hz, 1H), 7.42 (d, J=2.1 Hz, 1H), 7.09-7.05 (m, 2H), 6.83 (s, 1H), 6.71-6.65 (m, 2H), 6.24 (t, J=2.1 Hz, 1H), 5.23 (s, 2H), 4.28 (t, J=4.8 Hz, 2H), 4.14 (t, J=4.8 Hz, 2H), 2.66 (t, J=7.5 Hz, 2H), 2.30-2.26 (m, 5H).

Example 3(173)

3-(2-(5-phenylpentyloxy)-4-(pyrazol-1-ylmethyl)phenyl)propanoic acid

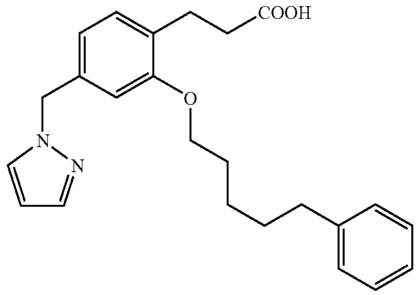

TLC: Rf 0.63 (chloroform:methanol=10:1).

Example 3(174)

3-(2-(6-phenylhexyloxy)-4-(pyrazol-1-ylmethyl)phenyl)propanoic acid

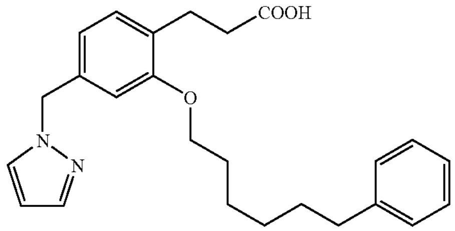

TLC: Rf 0.61 (chloroform:methanol=10:1).

Example 3(175)

3-(2-(2-(naphthalen-2-yl)ethoxy)-4-hydroxymethylphenyl)propanoic acid

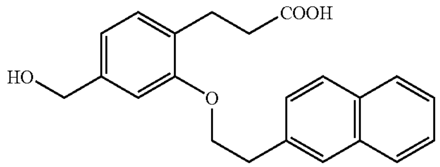

TLC: Rf 0.51 (chloroform:methanol=10:1).

Example 3(176)

3-(2-(3-(N-methyl-N-phenylamino)propoxy)-4-(pyrazol-1-ylmethyl)phenyl)propanoic acid

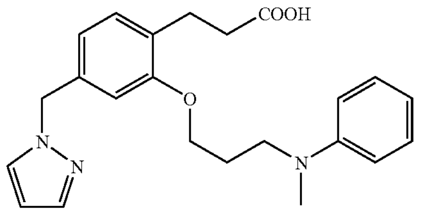

TLC: Rf 0.36 (chloroform:methanol=19:1);

NMR (300 MHz, $CDCl_3$): δ 7.54 (d, J=1.8 Hz, 1H), 7.36 (d, J=2.4 Hz, 1H), 7.28-7.18 (m, 2H), 7.14 (d, J=7.5 Hz, 1H), 6.77-6.62 (m, 5H), 6.27 (dd, J=2.4, 1.8 Hz, 1H), 5.26 (s, 2H), 3.96 (t, J=5.4 Hz, 2H), 3.53 (t, J=7.2 Hz, 2H), 2.98 (t, J=7.8 Hz, 2H), 2.93 (s, 3H), 2.67 (t, J=7.2 Hz, 2H), 2.05 (m, 2H).

Example 3(177)

3-(2-(2-(N-ethyl-N-phenylamino)ethoxy)-4-(pyrazol-1-ylmethyl)phenyl)propanoic acid

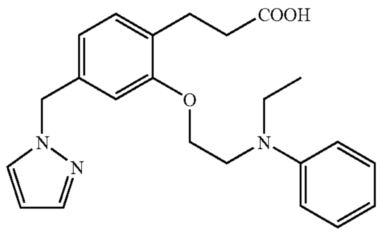

[Salt-free]

TLC: Rf 0.38 (chloroform:methanol=19:1);

NMR (300 MHz, $CDCl_3$): δ 7.53 (d, J=2.1 Hz, 1H), 7.35 (d, J=2.4 Hz, 1H), 7.25-7.18 (m, 2H), 7.12 (d, J=7.5 Hz, 1H), 6.77-6.64 (m, 5H), 6.26 (dd, J=2.4, 2.1 Hz, 1H), 5.23 (s, 2H), 4.07 (t, J=6.0 Hz, 2H), 3.71 (t, J=6.0 Hz, 2H), 3.46 (q, J=6.9 Hz, 2H), 2.91 (t, J=7.2 Hz, 2H), 2.59 (t, J=7.2 Hz, 2H), 1.17 (t, J=6.9 Hz, 2H).

Sodium Salt:

TLC: Rf 0.64 (chloroform:methanol=10:1).

Example 3(178)

3-(2-(2-(N-(2-hydroxyethyl)-N-phenylamino)ethoxy)-4-(pyrazol-1-ylmethyl)phenyl)propanoic acid

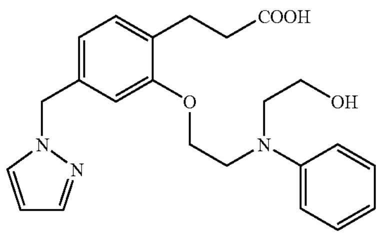

TLC: Rf 0.41 (chloroform:methanol=9:1);

NMR (300 MHz, $CDCl_3$): δ 7.53 (d, J=1.8 Hz, 1H), 7.35 (d, J=2.4 Hz, 1H), 7.27-7.21 (m, 2H), 7.11 (t, J=7.8 Hz, 1H), 6.82-6.69 (m, 5H), 6.26 (dd, J=2.4, 1.8 Hz, 1H), 5.22 (s, 2H), 4.13 (t, J=4.8 Hz, 2H), 3.86-3.78 (m, 4H), 3.61 (t, J=6.0 Hz, 2H), 2.92 (t, J=7.5 Hz, 2H), 2.57 (t, J=7.5 Hz, 2H).

Example 3(179)

3-(2-(2-(3-(piperidin-1-yl)phenyl)ethoxy)-4-(pyrazol-1-ylmethyl)phenyl)propanoic acid

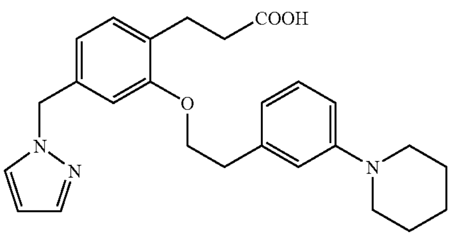

TLC: Rf 0.40 (hexane:ethyl acetate=1:2);

NMR (300 MHz, $CDCl_3$): δ 7.53 (d, J=2.1 Hz, 1H), 7.36 (d, J=2.1 Hz, 1H), 7.20 (t, J=7.8 Hz, 1H), 7.11 (d, J=7.8 Hz, 1H), 6.92 (s, 1H), 6.85-6.70 (m, 3H), 6.66 (s, 1H), 6.26 (t, J=2.1 Hz, 1H), 5.25 (s, 2H), 4.13 (t, J=6.6 Hz, 2H), 3.15-3.11 (m, 4H), 3.02 (t, J=6.6 Hz, 2H), 2.89 (t, J=7.5 Hz, 2H), 2.52 (t, J=7.5 Hz, 2H), 1.76-1.69 (m, 4H), 1.60-1.54 (m, 2H).

Example 3(180)

3-(2-(2-(3-(morpholin-4-yl)phenyl)ethoxy)-4-(pyrazol-1-ylmethyl)phenyl)propanoic acid

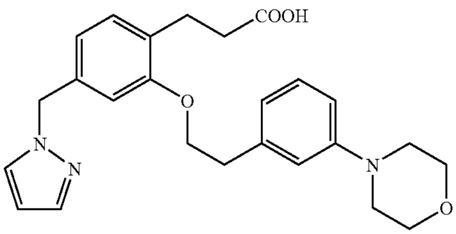

TLC: Rf 0.25 (hexane:ethyl acetate=1:2);

NMR (300 MHz, $CDCl_3$): δ 7.53 (d, J=1.8 Hz, 1H), 7.36 (d, J=1.8 Hz, 1H), 7.22 (t, J=7.8 Hz, 1H), 7.10 (d, J=7.8 Hz, 1H), 6.84-6.66 (m, 5H), 6.27 (t, J=1.8 Hz, 1H), 5.25 (s, 2H), 4.12 (t, J=6.6 Hz, 2H), 3.88-3.85 (m, 4H), 3.17-3.14 (m, 4H), 3.03 (t, J=6.6 Hz, 2H), 2.88 (t, J=7.8 Hz, 2H), 2.53 (t, J=7.8 Hz, 2H).

Example 3(181)

3-(2-(2-(naphthalen-2-yl)ethoxy)-4-(1-hydroxy-1-methylethyl)phenyl)propanoic acid

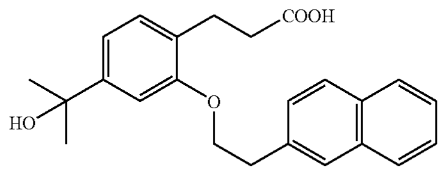

TLC: Rf 0.56 (chloroform:methanol=10:1).

Example 3(182)

3-(2-(2-(naphthalen-2-yl)ethoxy)-4-(pyrazol-1-ylmethyl)phenyl)propynoic acid

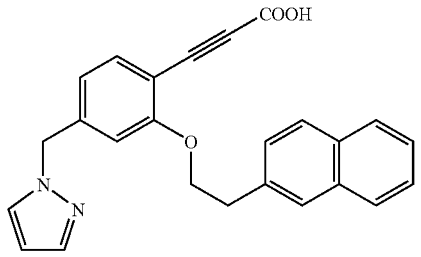

TLC: Rf 0.53 (chloroform:methanol:acetic acid=18:1:1).

Example 3(183)

3-(2-(2-hydroxy-2-(naphthalen-2-yl)ethoxy)-4-(3-cyanophenoxymethyl)phenyl)propanoic acid

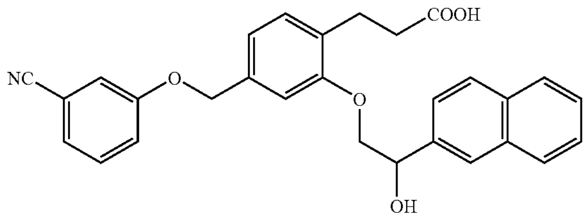

TLC: Rf 0.39 (hexane:ethyl acetate=1:1, 0.5% acetic acid);

NMR (300 MHz, $CDCl_3$): δ 7.92 (s, 1H), 7.88-7.80 (m, 3H), 7.57-7.44 (m, 3H), 7.34 (m, 1H), 7.25-7.12 (m, 4H), 6.93 (d, J=7.8 Hz, 1H), 6.86 (s, 1H), 5.32 (dd, J=7.8, 3.6 Hz, 1H), 4.97 (s, 2H), 4.23 (dd, J=9.3, 3.6 Hz, 1H), 4.14 (dd, J=9.3, 7.8 Hz, 1H), 3.10-2.90 (m, 2H), 2.63 (m, 2H).

Example 3(184)

3-(2-(2-(1,2,3,4-tetrahydroisoquinolin-2-yl)ethoxy)-4-(pyrazol-1-ylmethyl)phenyl)propanoic acid

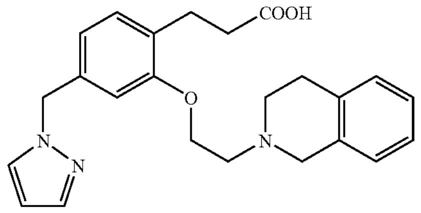

TLC: Rf 0.30 (chloroform:methanol=10:1);

NMR (300 MHz, $CDCl_3$): δ 7.55 (d, J=1.8 Hz, 1H), 7.38 (d, J=2.4 Hz, 1H), 7.18-7.03 (m, 5H), 6.75 (d, J=7.5 Hz, 1H), 6.66 (s, 1H), 6.28 (m, 1H), 5.27 (s, 2H), 4.09 (t, J=4.5 Hz, 2H), 3.88 (s, 2H), 3.11-2.94 (m, 8H), 2.32 (t, J=8.4 Hz, 2H).

Example 3(185)

3-(2-(2-(9-methylcarbazol-2-yl)ethoxy)-4-(pyrazol-1-ylmethyl)phenyl)propanoic acid

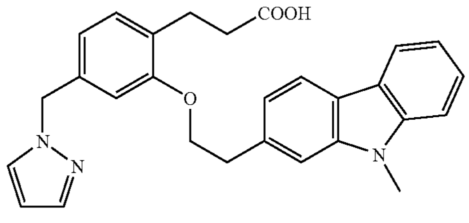

TLC: Rf 0.36 (chloroform:methanol=9:1);

NMR (300 MHz, $CDCl_3$): δ 8.09-7.99 (m, 3H), 7.53 (d, J=1.8 Hz, 1H), 7.49-7.05 (m, 6H), 6.74-6.67 (m, 2H), 6.25 (dd, J=2.1, 1.8 Hz, 1H), 5.24 (s, 2H), 4.23 (t, J=6.6 Hz, 2H), 3.83 (s, 3H), 3.28 (t, J=6.6 Hz, 2H), 2.89 (t, J=7.8 Hz, 2H), 2.52 (t, J=7.8 Hz, 2H).

Example 3(186)

3-(2-(2-(3-(4-methylpiperazin-1-yl)phenyl)ethoxy)-4-(pyrazol 1-ylmethyl)phenyl)propanoic acid

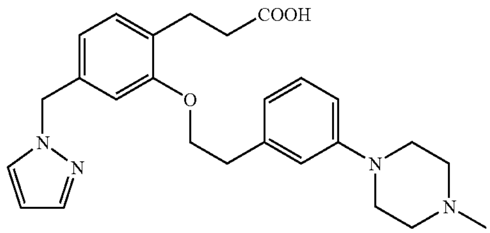

TLC: Rf 0.20 (chloroform:methanol=9:1);

NMR (300 MHz, DMSO-$d_6$): δ 7.77 (d, J=2.1 Hz, 1H), 7.42 (s, 1H), 7.14-7.04 (m, 2H), 6.87-6.63 (m, 5H), 6.23 (t, J=2.1 Hz, 1H), 5.23 (s, 2H), 4.08 (t, J=6.6 Hz, 2H), 3.12-3.08 (m, 4H), 2.94 (t, J=6.6 Hz, 2H), 2.70 (t, J=7.5 Hz, 2H), 2.44-2.41 (m, 4H), 2.35 (t, J=7.5 Hz, 2H), 2.20 (s, 3H).

Example 3(187)

3-(2-(2-(3-(4-acetylpiperazin-1-yl)phenyl)ethoxy)-4-(pyrazol-1-ylmethyl)phenyl)propanoic acid

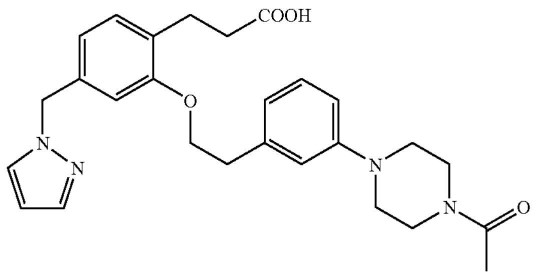

TLC: Rf 0.40 (chloroform:methanol=9:1);

NMR (300 MHz, $CDCl_3$): δ 7.53 (d, J=2.1 Hz, 1H), 7.35 (d, J=2.1 Hz, 1H), 7.21 (t, J=7.8 Hz, 1H), 7.08 (d, J=7.8 Hz, 1H), 6.87-6.65 (m, 5H), 6.26 (t, J=2.1 Hz, 1H), 5.24 (s, 2H), 4.11 (t, J=6.0 Hz, 2H), 3.79-3.75 (m, 2H), 3.64-3.61 (m, 2H), 3.19-3.11 (m, 4H), 3.03 (t, J=6.0 Hz, 2H), 2.86 (t, J=7.8 Hz, 2H), 2.51 (t, J=7.8 Hz, 2H), 2.15 (s, 3H).

Example 3(188)

3-(2-(2-phenylaminoethoxy)-4-(pyrazol-1-ylmethyl)phenyl)propanoic acid

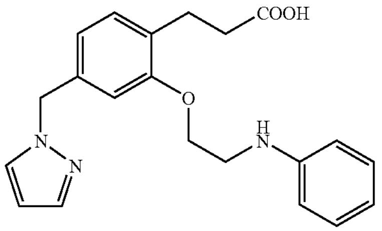

TLC: Rf 0.56 (chloroform:methanol=10:1);

NMR (300 MHz, $CDCl_3$): δ 7.54 (d, J=1.5 Hz, 1H), 7.36 (d, J=2.1 Hz, 1H), 7.22-7.09 (m, 3H), 6.77-6.64 (m, 6H), 6.27 (t, J=2.1 Hz, 1H), 5.25 (s, 2H), 4.10 (t, J=8.1 Hz, 2H), 3.53 (t, J=8.1 Hz, 2H), 2.94 (t, J=7.5 Hz, 2H), 2.61 (t, J=7.5 Hz, 2H).

Example 3(189)

3-(2-(2-(naphthalen-2-yl)ethoxy)-4-(N-acetyl-N-methylaminomethyl)phenyl)propanoic acid

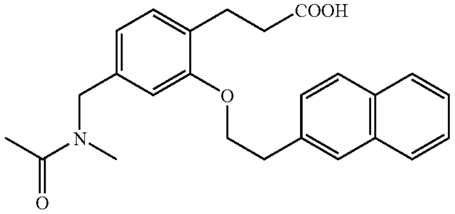

TLC: Rf 0.45 (chloroform:methanol=9:1);

NMR (300 MHz, $CDCl_3$): δ 7.82-7.78 (m, 3H), 7.75 (s, 1H), 7.45-7.41 (m, 3H), 7.11 (d, J=7.5 Hz, 0.4H), 7.06 (d, J=7.5 Hz, 0.6H), 6.75 (brs, 0.6H), 6.71 (brd, J=7.5 Hz, 0.6H), 6.64 (brd, J=7.5 Hz, 0.4H), 6.59 (brs, 0.4H), 4.50 (s, 1.2H), 4.44 (s, 0.8H), 4.27-4.23 (m, 2H), 3.29-3.23 (m, 2H), 2.91 (s, 1.2H), 2.90-2.85 (m, 2H), 2.88 (s, 1.8H), 2.55-2.49 (m, 2H), 2.13 (s, 3H).

Example 3(190)

3-(2-(2-(naphthalen-2-yl)ethoxy)-4-(N-ethoxycarbonyl-N-methylaminomethyl)phenyl)propanoic acid

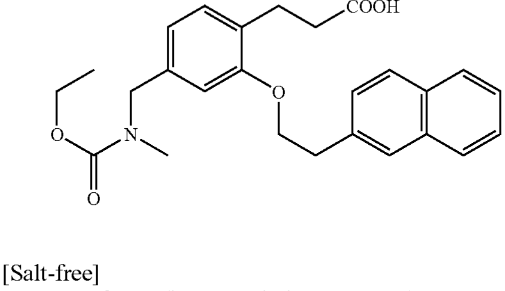

[Salt-free]

TLC: Rf 0.14 (hexane:ethyl acetate=2:1);

NMR (300 MHz, $CDCl_3$): δ 7.81-7.78 (m, 3H), 7.74 (brs, 1H), 7.45-7.41 (m, 3H), 7.07 (d, J=7.5 Hz, 1H), 6.78-6.66 (m, 2H), 4.39 (brs, 2H), 4.25 (t, J=6.6 Hz, 2H), 4.17 (q, J=6.9 Hz, 2H), 3.27 (t, J=6.6 Hz, 2H), 2.91-2.70 (m, 5H), 2.55-2.50 (m, 2H), 1.28-1.23 (m, 3H).

Sodium Salt:

TLC: Rf 0.50 (n-hexane:ethyl acetate=1:2).

Example 3(191)

3-(2-(2-(N-benzyl-N-methylamino)ethoxy)-4-(pyrazol-1-ylmethyl)phenyl)propanoic acid

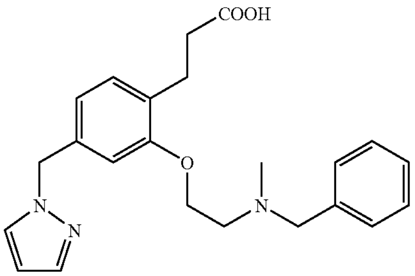

TLC: Rf 0.40 (chloroform:methanol=10:1).

Example 3(192)

3-(2-(2-(N-benzyl-N-ethylamino)ethoxy)-4-(pyrazol-1-ylmethyl)phenyl)propanoic acid

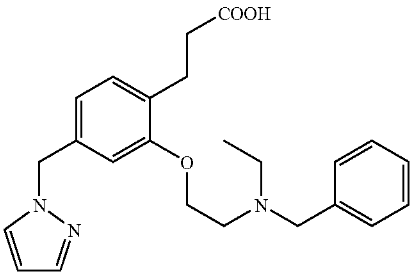

TLC: Rf 0.40 (chloroform:methanol=10:1).

Example 3(193)

3-(2-(2-(N-phenyl-N-propylamino)ethoxy)-4-(pyrazol-1-ylmethyl)phenyl)propanoic acid

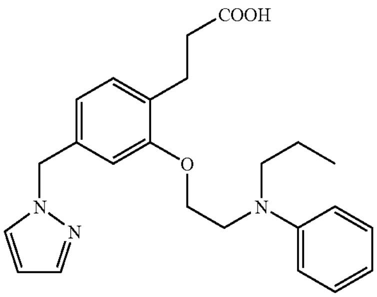

TLC: Rf 0.48 (chloroform:methanol=10:1);

NMR (300 MHz, $CDCl_3$): δ 7.53 (d, J=2.1 Hz, 1H), 7.35 (d, J=2.1 Hz, 1H), 7.26-7.16 (m, 2H), 7.11 (d, J=7.8 Hz, 1H), 6.76-6.61 (m, 5H), 6.26 (t, J=2.1 Hz, 1H), 5.23 (s, 2H), 4.07 (t, J=6.0 Hz, 2H), 3.74 (t, J=6.0 Hz, 2H), 3.33 (t, J=7.8 Hz, 2H), 2.90 (t, J=7.8 Hz, 2H), 2.59 (t, J=7.5 Hz, 2H), 1.72-1.56 (m, 2H), 0.93 (t, J=7.2 Hz, 2H).

Example 3(194)

3-(2-(2-(6-methoxy-naphthalen-2-yl)ethoxy)-4-(pyrazol-1-ylmethyl)phenyl)propanoic acid

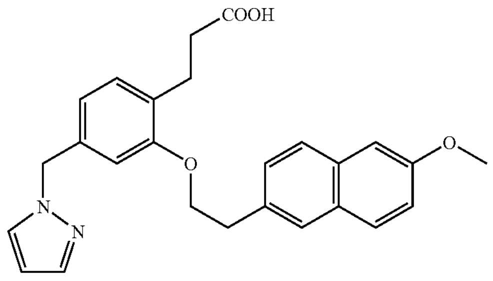

[Salt-free]

TLC: Rf 0.67 (n-hexane:ethyl acetate=1:2);

NMR (300 MHz, $CDCl_3$): δ 7.72-7.62 (m, 3H), 7.53 (d, J=0.9 Hz, 1H), 7.40-7.32 (m, 2H), 7.16-7.05 (m, 3H), 6.74-6.65 (m, 2H), 6.25 (t, J=2.1 Hz, 1H), 5.24 (s, 2H), 4.18 (t, J=6.6 Hz, 2H), 3.89 (s, 3H), 3.19 (t, J=6.6 Hz, 2H), 2.87 (t, J=7.5 Hz, 2H), 2.50 (t, J=7.5 Hz, 2H).

Sodium Salt:

TLC: Rf 0.51 (chloroform:methanol=10:1).

Example 3(195)

3-(2-(2-(carbazol-9-yl)ethoxy)-4-(pyrazol-1-ylmethyl)phenyl)propanoic acid

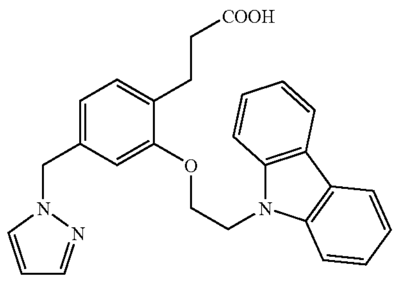

[Salt-free]

TLC: Rf 0.51 (chloroform:methanol=10:1);

NMR (300 MHz, DMSO-$d_6$): δ 8.15 (d, J=8.1 Hz, 2H), 7.77-7.65 (m, 3H), 7.51-7.38 (m, 3H), 7.21 (t, J=7.5 Hz, 2H), 6.96 (d, J=7.8 Hz, 1H), 6.82 (s, 1H), 6.61 (d, J=7.8 Hz, 1H), 6.23 (brs, 1H), 5.19 (s, 2H), 4.92-4.80 (m, 2H), 4.35-4.25 (m, 2H), 2.45 (t, J=7.5 Hz, 2H), 2.12 (t, J=7.5 Hz, 2H).

Sodium Salt:

TLC: Rf 0.51 (chloroform:methanol=10:1);

NMR (300 MHz, DMSO-$d_6$): δ 8.13 (d, J=7.8 Hz, 2H), 7.76-7.68 (m, 3H), 7.45-7.40 (m, 2H), 7.38 (s, 1H), 7.19-7.16 (m, 2H), 7.00 (d, J=7.8 Hz, 1H), 6.74 (s, 1H), 6.58 (d, J=8.4 Hz, 1H), 6.20 (t, J=2.1 Hz, 1H), 5.16 (s, 2H), 4.82-4.76 (m, 2H), 4.26-4.16 (m, 2H), 2.45-2.40 (m, 2H), 2.00-1.92 (m, 2H).

Example 3(196)

3-(2-(2-(9,10-dihydroacridin-9-one-10-yl)ethoxy)-4-(pyrazol-1-ylmethyl)phenyl)propanoic acid

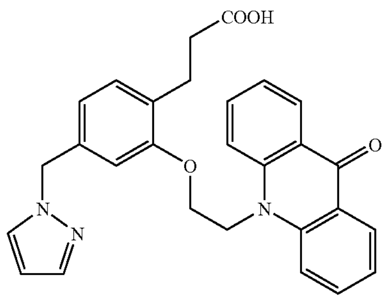

TLC: Rf 0.45 (chloroform:methanol=10:1);

NMR (300 MHz, DMSO-$d_6$): δ 8.37 (dd, J=8.1 Hz, 2H), 8.05 (d, J=8.7 Hz, 2H), 7.90-7.80 (m, 2H), 7.74 (d, J=1.8 Hz, 1H), 7.41 (d, J=1.8 Hz, 1H), 7.36 (t, J=7.2 Hz, 2H), 6.99 (d, J=7.5 Hz, 1H), 6.88 (d, J=1.2 Hz, 1H), 6.63 (dd, J=7.5, 1.2 Hz, 1H), 6.23 (t, J=1.8 Hz, 1H), 5.20 (s, 2H), 5.08 (t, J=5.1 Hz, 2H), 4.43 (t, J=5.1 Hz, 2H), 2.47 (t, J=7.8 Hz, 2H), 2.12 (t, J=7.8 Hz, 2H).

Example 3(197)

3-(2-(2-(N-phenyl-N-methylsulfonylamino)ethoxy)-4-(pyrazol-1-ylmethyl)phenyl)propanoic acid

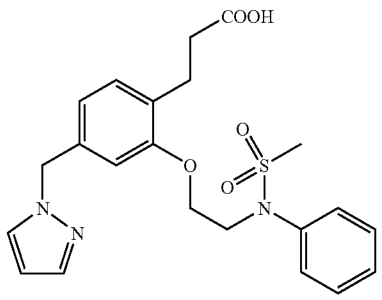

TLC: Rf 0.49 (chloroform:methanol=10:1).

Example 3(198)

3-(2-(2-(N-acetyl-N-phenylamino)ethoxy)-4-(pyrazol-1-ylmethyl)phenyl)propanoic acid

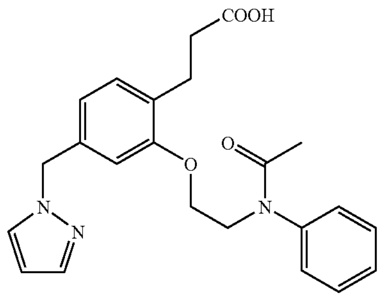

TLC: Rf 0.50 (chloroform:methanol=10:1).

Example 3(199)

3-(2-(2-(N-benzyl-N-phenylamino)ethoxy)-4-(pyrazol-1-ylmethyl)phenyl)propanoic acid

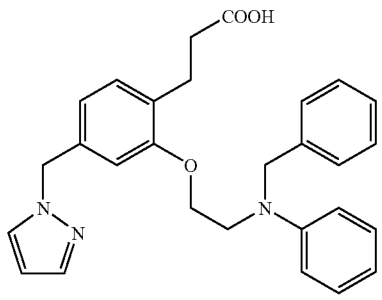

TLC: Rf 0.23 (n-hexane:ethyl acetate=1:1).

Example 3(200)

3-(2-(2-(N-(2-cyanoethyl)-N-phenylamino)ethoxy)-4-(pyrazol 1-ylmethyl)phenyl)propanoic acid

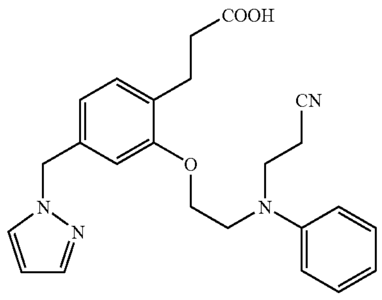

TLC: Rf 0.50 (chloroform:methanol=10:1).

Example 3(201)

3-(2-(3-(phenoxazin-10-yl)propoxy)-4-(pyrazol-1-ylmethyl)phenyl)propanoic acid

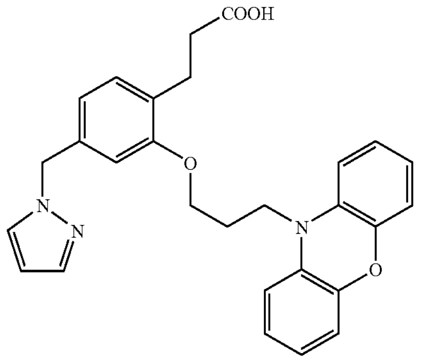

TLC: Rf 0.50 (chloroform:methanol=19:1);

NMR (300 MHz, $CDCl_3$): δ 7.55 (dd, J=2.1, 0.6 Hz, 1H), 7.36 (dd, J=2.1, 0.6 Hz, 1H), 7.15 (d, J=7.5 Hz, 1H), 6.80-6.71 (m, 3H), 6.68-6.59 (m, 5H), 6.56-6.50 (m, 2H), 6.27 (t, J=2.1 Hz, 1H), 5.26 (s, 2H), 4.04 (t, J=5.6 Hz, 2H), 3.78-3.68 (m, 2H), 3.01 (t, J=7.8 Hz, 2H), 2.68 (t, J=7.8 Hz, 2H), 2.20-2.08 (m, 2H).

Example 3(202)

3-(2-(2-(naphthalen-2-yl)ethoxy)-4-(N-phenylcarbamoyl)phenyl)propanoic acid

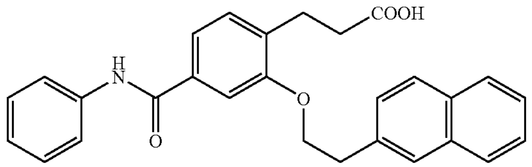

TLC: Rf 0.46 (n-hexane:ethyl acetate=1:2);

NMR (300 MHz, DMSO-$d_6$): δ 10.11 (s, 1H), 7.91-7.82 (m, 4H), 7.76-7.69 (m, 2H), 7.57-7.41 (m, 5H), 7.38-7.29 (m, 2H), 7.26 (d, J=7.8 Hz, 1H), 7.08 (m, 1H), 4.38 (t, J=6.3 Hz, 2H), 3.26 (t, J=6.3 Hz, 2H), 2.80 (t, J=7.6 Hz, 2H), 2.42 (t, J=7.6 Hz, 2H).

Reference Example 5

4-acetoxymethyl-2-(t-butoxycarbonyl)phenyl iodide

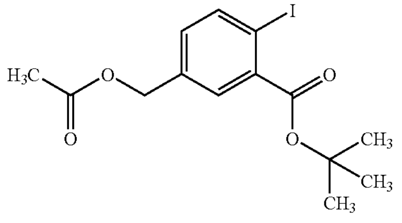

To a solution of 2-t-butoxycarbonyl-4-methylphenyl iodide (1.0 g) in carbon tetrachloride (10.0 ml) was added N-bromosuccinimide (645 mg) and benzoyl peroxide (76 mg), the mixture was refluxed for 16 hours. The reaction mixture was cooled to room temperature and then filtered. The filtrate was poured into water and extracted with methylene chloride. The organic layer was dried over anhydrous magnesium sulfate and concentrated to give the bromide. To a solution of the obtained bromide in N,N-dimethylformamide (3.0 ml) was added potassium acetate (300 mg) and the mixture was stirred at 50° C. for 1 hour. To the reaction mixture was added a saturated aqueous solution of ammonium chloride and the mixture was extracted with diethyl ether. The organic layer was washed with a saturated aqueous solution of sodium chloride, dried over anhydrous magnesium sulfate and concentrated. The residue was purified by column chromatography on silica gel (n-hexane:ethyl acetate=8:1) to give the title compound (285 mg) having the following physical data.

TLC: Rf 0.23 (n-hexane:ethyl acetate=10:1).

Reference Example 6

3-[4-acetoxymethyl-2-(t-butoxycarbonyl)phenyl] propanoic acid ethyl ester

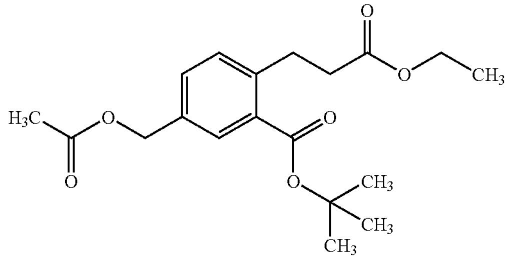

3-[4-Acetoxymethyl-2-(t-butoxycarbonyl)phenyl]propenoic acid ethyl ester (4.5 g) which is prepared by the same procedure of Example 1 using a compound prepared in Reference Example 5 instead of the compound prepared in Reference Example 4 was dissolved in mixture of tetrahydrofuran (50 ml) and methanol (13 ml). To the solution was added nickel(II) chloride hexahydrate (3.4 g) at 0° C. followed by sodium borohydride (2.0 g) portionwise. The mixture was stirred at 0° C. for 20 minutes. To the reaction mixture were added acetone and diethyl ether and the mixture was filtered through Celite (trademark). The filtrate was extracted with diethyl ether, washed with a saturated aqueous solution of sodium chloride, dried over anhydrous magnesium sulfate and concentrated to give the title compound (3.8 g).

TLC: Rf 0.19 (n-hexane:ethyl acetate=5:1).

Reference Example 7

3-(4-acetoxymethyl-2-carboxyphenyl)propanoic acid ethyl ester

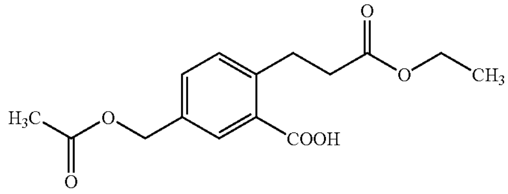

To a solution of the compound prepared in Reference Example 6 (3.8 g) in methylene chloride (4.0 ml) was added anisole (2.0 ml) and trifluoroacetic acid (5.0 ml) at room temperature and the mixture was stirred overnight. The reaction mixture was concentrated and the residue was purified by column chromatography on silica gel (n-hexane:ethyl acetate=5:4→chloroform:methanol=10:1) to give the title compound having the following physical data.

TLC: Rf 0.63 (chloroform:methanol=9:1).

Reference Example 8

3-[2-((naphthalen-1-ylmethyl)carbamoyl)-4-acetoxymethylphenyl]propanoic acid ethyl ester

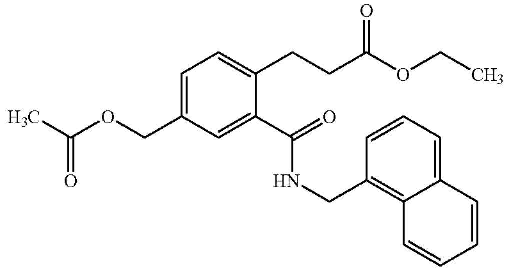

To a solution of the compound prepared in Reference Example 7 (3.2 g) in anhydrous toluene (20 ml) was added oxalyl chloride (1.0 ml) and N,N-dimethylformamide (cat.) at room temperature and the mixture was stirred for 1 hour. The reaction mixture was concentrated and then azeotroped with toluene. To the solution of 1-naphthylmethylamine (2.1 ml) in methylene chloride (30 ml)-pyridine (1.8 ml) was added the solution of the residue in methylene chloride (10 ml) at 0° C. and the mixture was stirred for 1 hour. To the reaction mixture was added 2N hydrochlorid acid (7.0 ml) and the mixture was extracted with methylene chloride. The organic layer was washed with water and a saturated aqueous solution of sodium chloride subsequently and concentrated to give the title compound (4.5 g) having the following physical data.

TLC: Rf 0.25 (n-hexane:ethyl acetate=2:1).

Example 4

3-[2-((naphthalen-1-ylmethyl)carbamoyl)-4-hydroxymethylphenyl]propanoic acid ethyl ester

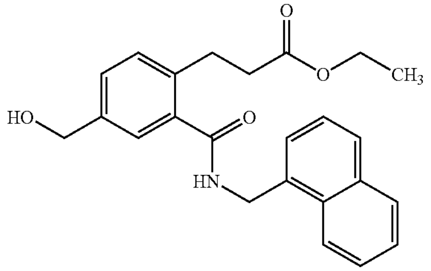

To a solution of the compound prepared in Reference Example 8 (10.9 mmol) in ethanol (40 ml) was added sodium ethoxide (740 mg) and the mixture was stirred for 20 minutes. To the reaction mixture was added acetic acid and the mixture was concentrated.

The residue was extracted with ethyl acetate. The organic layer was washed with water and a saturated aqueous solution of sodium chloride and concentrated. The residue was purified by column chromatography on silica gel (n-hexane:ethyl acetate=1:1) to give the title compound (3.2 g) having the following physical data.

TLC: Rf 0.20 (n-hexane:ethyl acetate=1:1);

NMR (300 MHz, $CDCl_3$): δ 8.14 (d, J=8.7 Hz, 1H), 7.92-7.79 (m, 2H), 7.62-7.40 (m, 3H), 7.36-7.10 (m, 4H), 6.61 (t, J=5.4 Hz, 1H), 5.08 (d, J=5.4 Hz, 2H), 4.59 (s, 2H), 4.03 (q, J=7.2 Hz, 2H), 3.06 (t, J=7.4 Hz, 2H), 2.67 (t, J=7.4 Hz, 2H), 1.19 (t, J=7.2 Hz, 3H).

Example 5

3-[2-((naphthalen-1-ylmethyl)carbamoyl)-4-(2-methylphenyloxymethyl)phenyl]propanoic acid ethyl ester

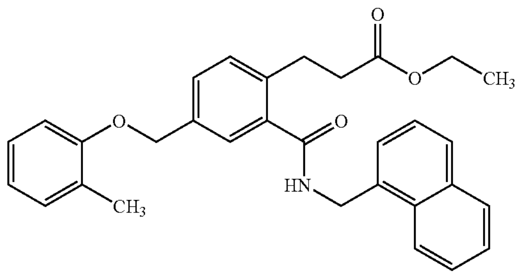

To the solution of the compound prepared in Example 4 (300 mg) and 2-methylphenol (0.12 ml) in tetrahydrofuran (4 ml) were added triphenylphosphine (300 mg) and diethyl azodicarboxylate (0.5 ml, 40% toluene solution) at room temperature and the mixture was stirred overnight. The reaction mixture was concentrated and the residue was purified by column chromatography on silica gel (n-hexane:ethyl acetate=5:1) to give the title compound (330 mg) having the following physical data.

TLC: Rf 0.25 (n-hexane:ethyl acetate=3:1);

NMR (300 MHz, $CDCl_3$): δ 8.15 (d, J=8.1 Hz, 1H), 7.93-7.80 (m, 2H), 7.62-7.36 (m, 7H), 7.16-7.06 (m, 2H), 6.89-6.76 (m, 2H), 6.52 (t, J=5.4 Hz, 1H), 5.10 (d, J=5.4 Hz, 2H), 4.99 (s, 2H), 4.05 (q, J=7.2 Hz, 2H), 3.09 (t, J=7.4 Hz, 2H), 2.69 (t, J=7.4 Hz, 2H), 2.17 (s, 3H), 1.19 (t, J=7.2 Hz, 3H).

Example 5(1)~Example 5(83)

Using corresponding compounds, the following compounds were obtained by the same procedure of Example 5.

Example 5(1)

3-(2-((3-methyl-1-(naphthalen-1-yl)butyl)carbamoyl)-4-phenoxymethylphenyl)propanoic acid ethyl ester

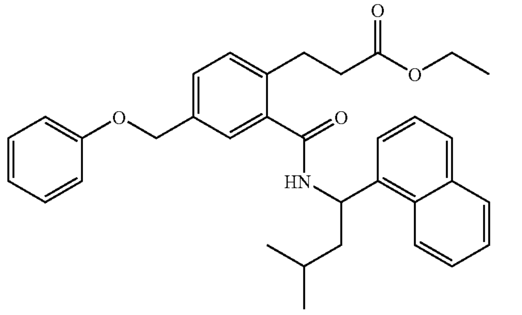

TLC: Rf 0.66 (n-hexane:ethyl acetate=1:1).

Example 5(2)

3-(2-((1-methyl-1-(naphthalen-1-yl)ethyl)carbamoyl)-4-phenoxymethylphenyl)propanoic acid ethyl ester

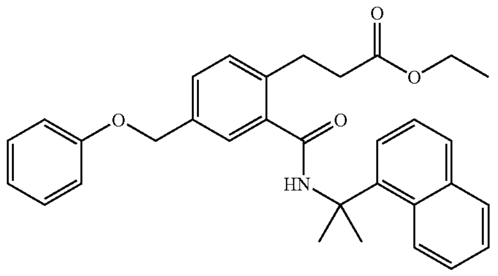

TLC: Rf 0.14 (n-hexane:ethyl acetate=1:1).

Example 5(3)

3-(2-(((1R)-1-(naphthalen-1-yl)ethyl)carbamoyl)-4-phenoxymethylphenyl)propanoic acid ethyl ester

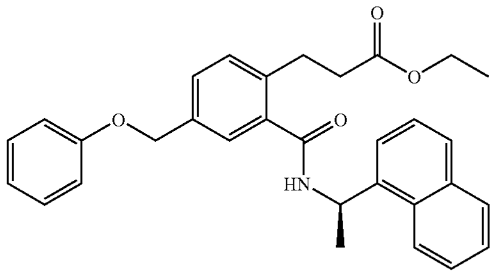

TLC: Rf 0.58 (n-hexane:ethyl acetate=1:1).

Example 5(4)

3-(2-((1-(naphthalen-1-yl)propyl)carbamoyl)-4-phenoxymethylphenyl)propanoic acid ethyl ester

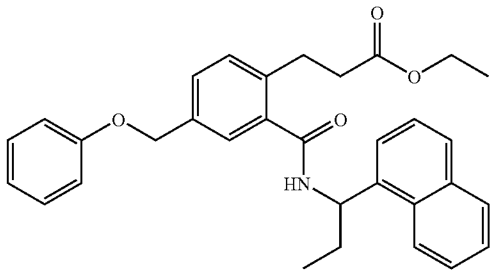

TLC: Rf 0.56 (n-hexane:ethyl acetate=1:1).

Example 5(5)

3-(2-(((1S)-1-(naphthalen-1-yl)ethyl)carbamoyl)-4-phenoxymethylphenyl)propanoic acid ethyl ester

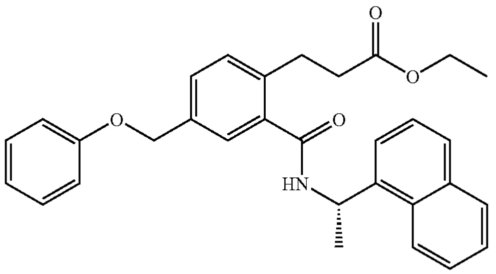

TLC: Rf 0.58 (n-hexane:ethyl acetate=1:1).

Example 5(6)

3-(2-((3-methyl-1-(naphthalen-1-yl)butyl)carbamoyl)-4-(pyridin-3-yloxymethyl)phenyl)propanoic acid ethyl ester

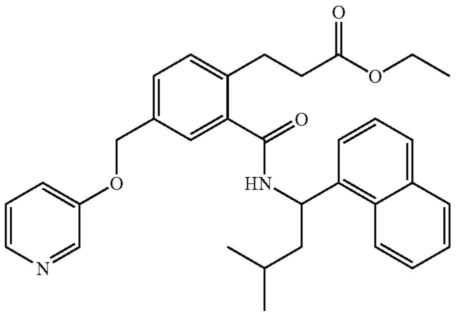

TLC: Rf 0.31 (n-hexane:ethyl acetate=1:1).

Example 5(7)

3-(2-((3-methyl-1-phenylbutyl)carbamoyl)-4-phenoxymethylphenyl)propanoic acid ethyl ester

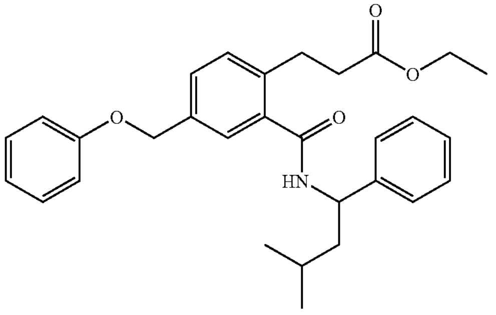

TLC: Rf 0.65 (n-hexane:ethyl acetate=1:1).

Example 5(8)

3-(2-(((1R)-1-(naphthalen-1-yl)ethyl)carbamoyl)-4-phenoxyphenyl)propanoic acid ethyl ester

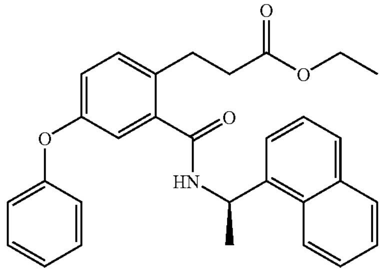

TLC: Rf 0.78 (n-hexane:ethyl acetate=1:1).

Example 5(9)

3-(2-((3-methyl-1-(4-fluorophenyl)butyl)carbamoyl)-4-phenoxymethylphenyl)propanoic acid ethyl ester

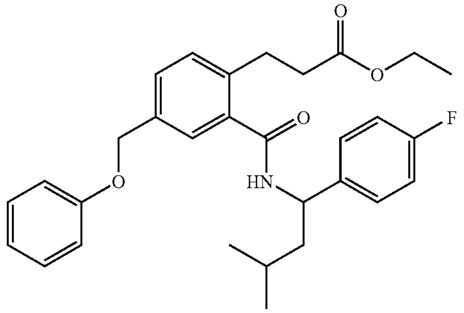

TLC: Rf 0.53 (n-hexane:ethyl acetate=3:1).

Example 5(10)

3-(2-((3-methyl-1-(4-methylphenyl)butyl)carbamoyl)-4-phenoxymethylphenyl)propanoic acid ethyl ester

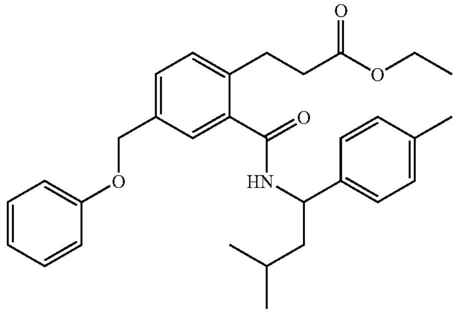

TLC: Rf 0.52 (n-hexane:ethyl acetate=3:1).

Example 5(11)

3-(2-((3-methyl-1-(4-fluorophenyl)butyl)carbamoyl)-4-(3-cyanophenoxymethyl)phenyl)propanoic acid methyl ester

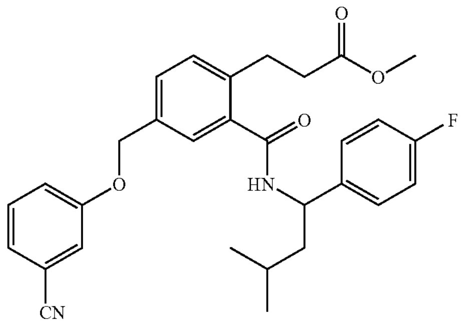

TLC: Rf 0.74 (chloroform:methanol=10:1).

Example 5(12)

3-(2-((3-methyl-1-(4-fluorophenyl)butyl)carbamoyl)-4-(2-chloro-5-methylphenoxymethyl)phenyl)propanoic acid methyl ester

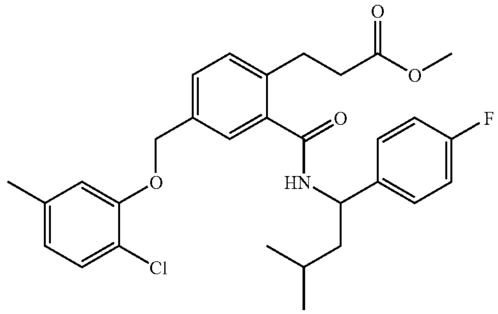

TLC: Rf 0.74 (chloroform:methanol=10:1).

Example 5(13)

3-(2-((3-methyl-1-(3,5-dimethylphenyl)butyl)carbamoyl)-4-phenoxymethylphenyl)propanoic acid methyl ester

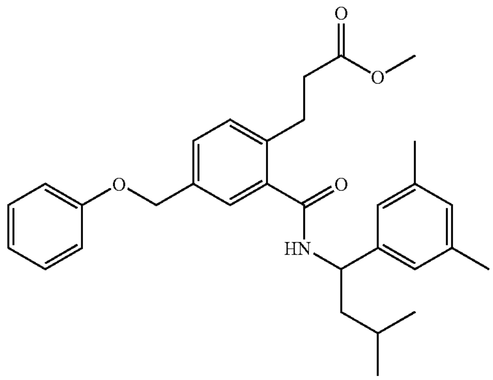

TLC: Rf 0.58 (n-hexane:ethyl acetate=2:1).

Example 5(14)

3-(2-((3-methyl-1-(3,5-dimethylphenyl)butyl)carbamoyl)-4-(3-cyanophenoxymethyl)phenyl)propanoic acid methyl ester

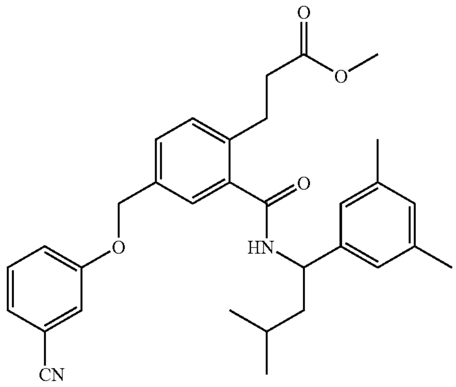

TLC: Rf 0.78 (n-hexane:ethyl acetate=1:1).

Example 5(15)

3-(2-((3-methyl-1-(3,5-dimethylphenyl)butyl)carbamoyl)-4-(2-methylphenoxymethyl)phenyl)propanoic acid methyl ester

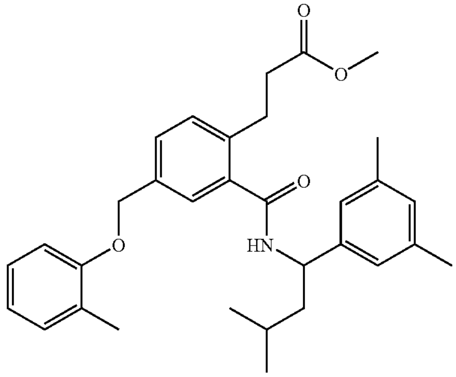

TLC: Rf 0.67 (n-hexane:ethyl acetate=1:1).

Example 5(16)

3-(2-((3-methyl-1-(3,5-dimethylphenyl)butyl)carbamoyl)-4-(2-chloro-5-methylphenoxymethyl)phenyl)propanoic acid methyl ester

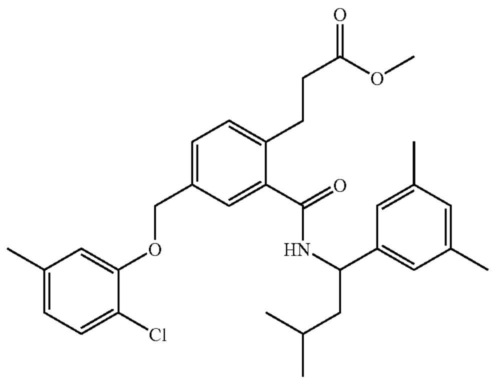

TLC: Rf 0.83 (n-hexane:ethyl acetate=1:1).

Example 5(17)

3-(2-((3-methyl-1-(3,5-dimethylphenyl)butyl)carbamoyl)-4-(pyridin-3-yloxymethyl)phenyl)propanoic acid methyl ester

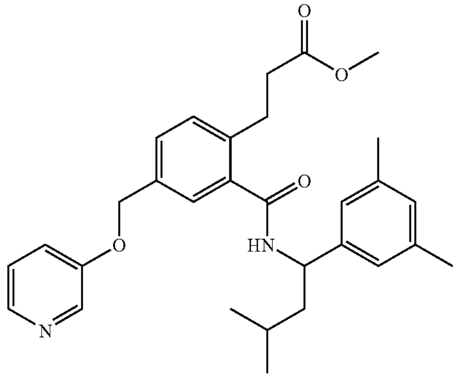

TLC: Rf 0.21 (n-hexane:ethyl acetate=1:1).

Example 5(18)

3-(2-((3-methyl-1-(4-methoxy-1,3-dioxaindan-6-yl)butyl)carbamoyl)-4-(2-chloro-5-methylphenoxymethyl)phenyl)propanoic acid methyl ester

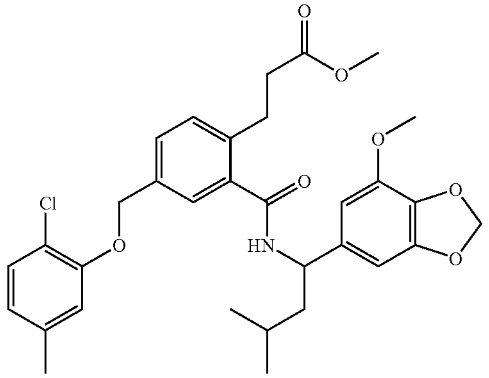

TLC: Rf 0.70 (n-hexane:ethyl acetate=1:2).

Example 5(19)

3-(2-((3-methyl-1-(4-methoxy-1,3-dioxaindan-6-yl)butyl)carbamoyl)-4-(3-cyanophenoxymethyl)phenyl)propanoic acid methyl ester

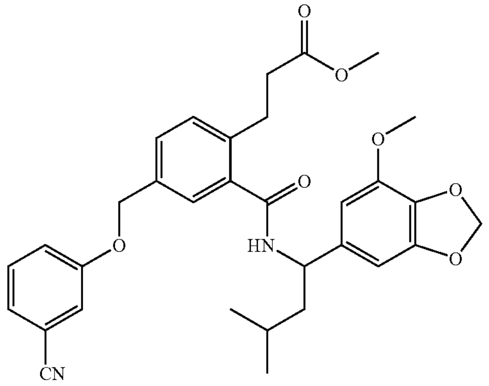

TLC: Rf 0.60 (n-hexane:ethyl acetate=1:2).

Example 5(20)

3-(2-((3-methyl-1-(4-methoxy-1,3-dioxaindan-6-yl)butyl)carbamoyl)-4-(2-methylphenoxymethyl)phenyl)propanoic acid methyl ester

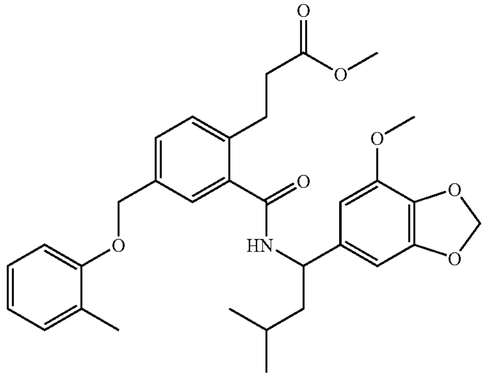

TLC: Rf 0.70 (n-hexane:ethyl acetate=1:2).

Example 5(21)

3-(2-((3-methyl-1-(4-fluoro-3-methylphenyl)butyl)carbamoyl)-4-(2-methylphenoxymethyl)phenyl)propanoic acid methyl ester

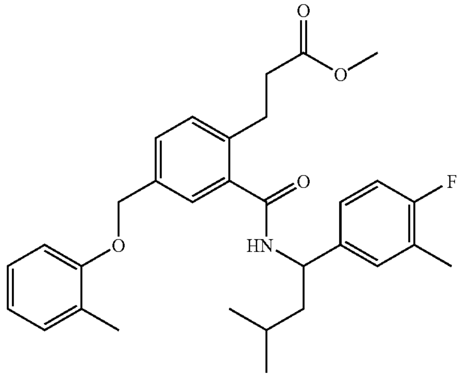

TLC: Rf 0.56 (n-hexane:ethyl acetate=2:1).

Example 5(22)

3-(2-((3-methyl-1-(4-fluoro-3-methylphenyl)butyl)carbamoyl)-4-(2-chloro-5-methylphenoxymethyl)phenyl)propanoic acid methyl ester

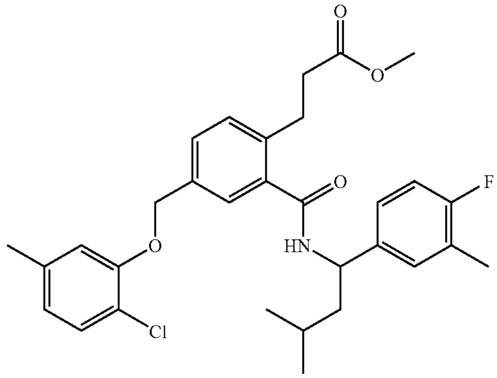

TLC: Rf 0.48 (n-hexane:ethyl acetate=2:1).

Example 5(23)

3-(2-((3-methyl-1-(3-methylphenyl)butyl)carbamoyl)-4-(3-cyanophenoxymethyl)phenyl)propanoic acid methyl ester

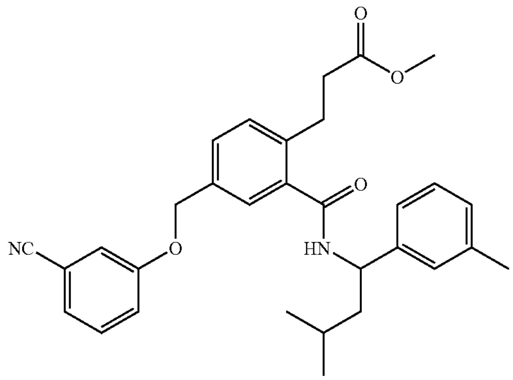

TLC: Rf 0.70 (n-hexane:ethyl acetate=1:1).

Example 5(24)

3-(2-((3-methyl-1-(3-methoxyphenyl)butyl)carbamoyl)-4-(3-cyanophenoxymethyl)phenyl)propanoic acid methyl ester

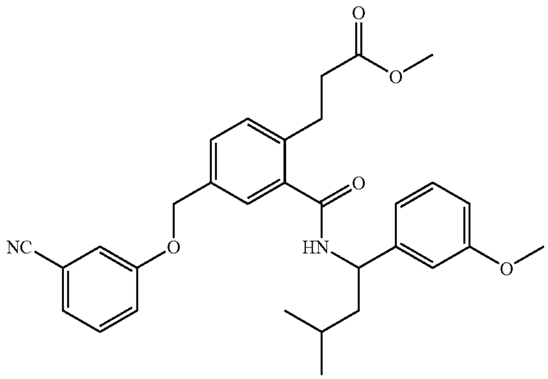

TLC: Rf 0.61 (n-hexane:ethyl acetate=1:1).

Example 5(25)

3-(1-benzyl-3-(3-methyl-1-(3,5-dimethylphenyl)butylcarbamoyl)indol-4-yl)propanoic acid methyl ester

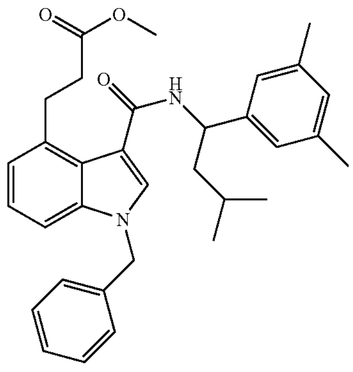

TLC: Rf 0.66 (n-hexane:ethyl acetate=1:1).

Example 5(26)

3-(2-((3-methyl-1-(3,4-dimethoxyphenyl)butyl)carbamoyl)-4-(3-cyanophenoxymethyl)phenyl)propanoic acid methyl ester

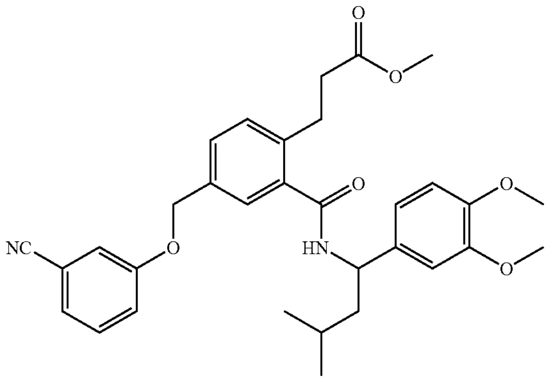

TLC: Rf 0.45 (n-hexane:ethyl acetate=1:1).

Example 5(27)

3-(2-((3-methyl-1-(3-methyl-4-fluorophenyl)butyl)carbamoyl)-4-(3-cyanophenoxymethyl)phenyl)propanoic acid methyl ester

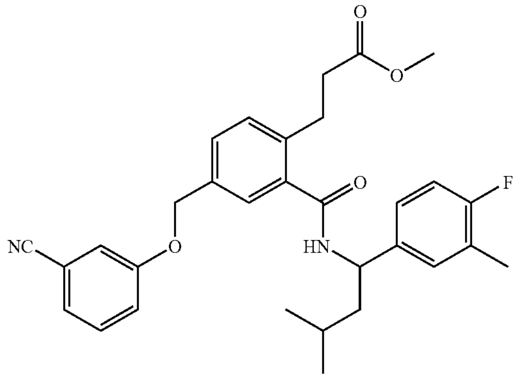

TLC: Rf 0.43 (n-hexane:ethyl acetate=2:1).

Example 5(28)

3-(2-((3-methyl-1-(3,5-dimethoxyphenyl)butyl)carbamoyl)-4-(3-cyanophenoxymethyl)phenyl)propanoic acid methyl ester

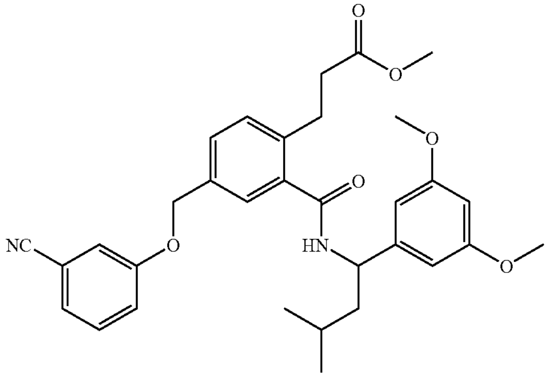

TLC: Rf 0.42 (n-hexane:ethyl acetate=1:1).

Example 5(29)

3-(2-((3-methyl-1-(3,5-dimethylphenyl)butyl)carbamoyl)-4-benzylaminophenyl)propanoic acid ethyl ester

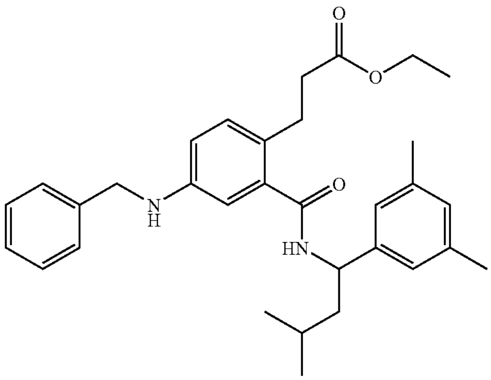

TLC: Rf 0.44 (n-hexane:ethyl acetate=3:1).

Example 5(30)

3-(2-(1-(3,5-dimethylphenyl)butylcarbamoyl)-4-(3-cyanophenoxymethyl)phenyl)propanoic acid methyl ester

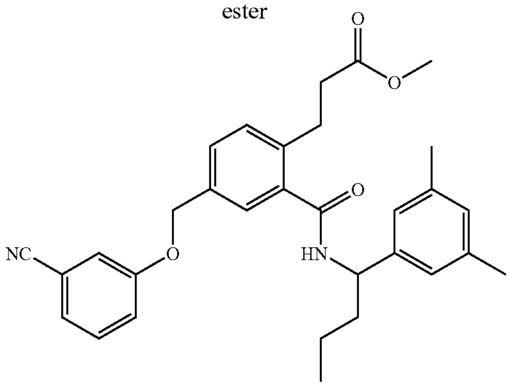

TLC: Rf 0.79 (n-hexane:ethyl acetate=1:1).

Example 5(31)

3-(2-((3-methyl-1-(3,5-dimethylphenyl)butyl)carbamoyl)-4-(2-fluorophenoxymethyl)phenyl)propanoic acid methyl ester

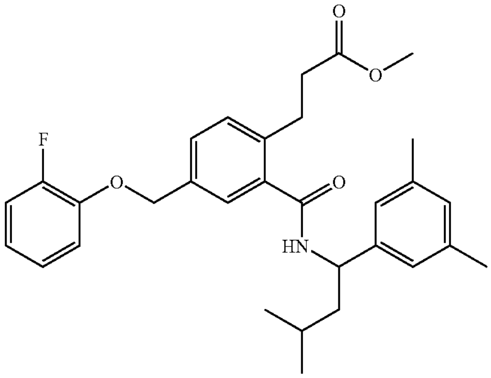

TLC: Rf 0.56 (n-hexane:ethyl acetate=2:1).

Example 5(32)

3-(2-((3-methyl-1-(3,5-dimethylphenyl)butyl)carbamoyl)-4-(2-chlorophenoxymethyl)phenyl)propanoic acid methyl ester

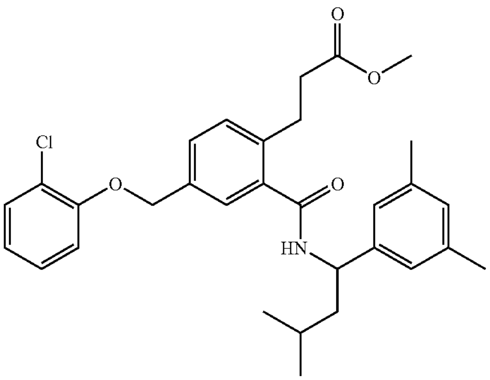

TLC: Rf 0.55 (n-hexane:ethyl acetate=2:1).

Example 5(33)

3-(2-((3-methyl-1-(3,5-dimethylphenyl)butyl)carbamoyl)-4-(2,4-difluorophenoxymethyl)phenyl)propanoic acid methyl ester

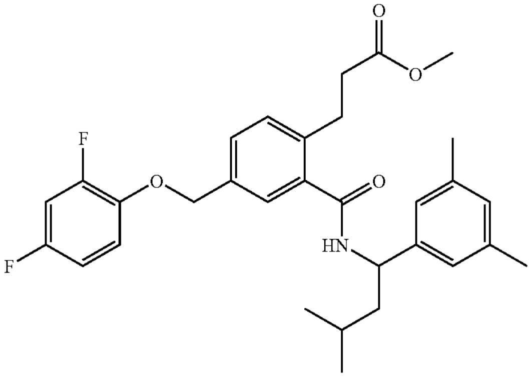

TLC: Rf 0.55 (n-hexane:ethyl acetate=2:1).

Example 5(34)

3-(2-((3-methyl-1-(3,5-dimethylphenyl)butyl)carbamoyl)-4-(3-fluorophenoxymethyl)phenyl)propanoic acid methyl ester

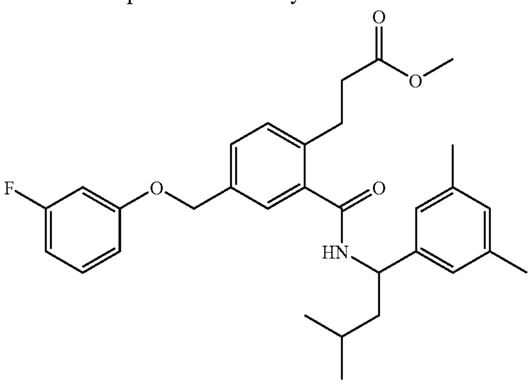

TLC: Rf 0.56 (n-hexane:ethyl acetate=2:1).

Example 5(35)

3-(2-((3-methyl-1-(3,5-dimethylphenyl)butyl)carbamoyl)-4-(2,5-difluorophenoxymethyl)phenyl)propanoic acid methyl ester

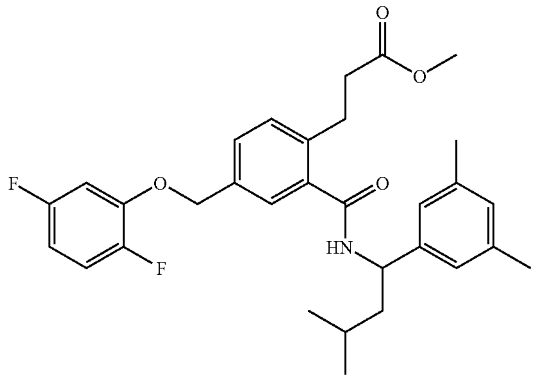

TLC: Rf 0.58 (n-hexane:ethyl acetate=2:1).

Example 5(36)

3-(2-((3-methyl-1-(3,5-dimethylphenyl)butyl)carbamoyl)-4-(2-chloro-5-fluorophenoxymethyl)phenyl)propanoic acid methyl ester

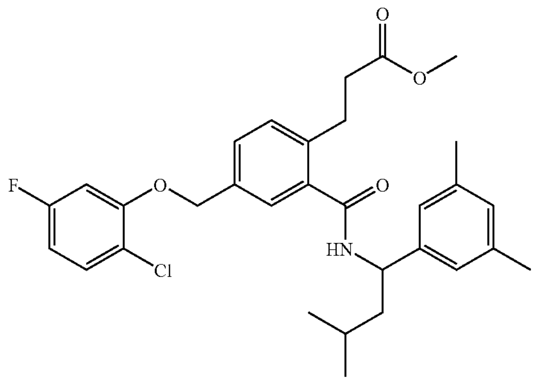

TLC: Rf 0.51 (n-hexane:ethyl acetate=2:1).

Example 5(37)

3-(2-((3-methyl-1-(3,5-dimethylphenyl)butyl)carbamoyl)-4-(4-cyanophenoxymethyl)phenyl)propanoic acid methyl ester

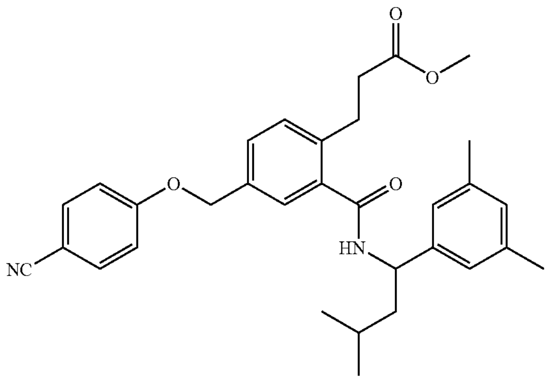

TLC: Rf 0.25 (n-hexane:ethyl acetate=1:1).

Example 5(38)

3-(2-((3-methyl-1-(3,5-dimethylphenyl)butyl)carbamoyl)-4-(3-methoxyphenoxymethyl)phenyl)propanoic acid methyl ester

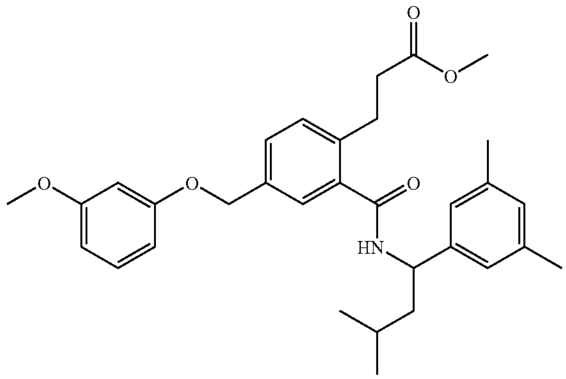

TLC: Rf 0.91 (n-hexane:ethyl acetate=1:1).

Example 5(39)

3-(2-((3-methyl-1-(3,5-dimethylphenyl)butyl)carbamoyl)-4-(3-methylphenoxymethyl)phenyl)propanoic acid methyl ester

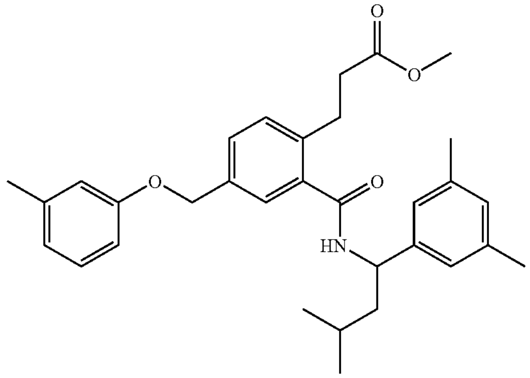

TLC: Rf 0.87 (n-hexane:ethyl acetate=1:1).

Example 5(40)

3-(2-((3-methyl-1-(3,5-dimethylphenyl)butyl)carbamoyl)-4-(2-chloro-4-fluorophenoxymethyl)phenyl)propanoic acid methyl ester

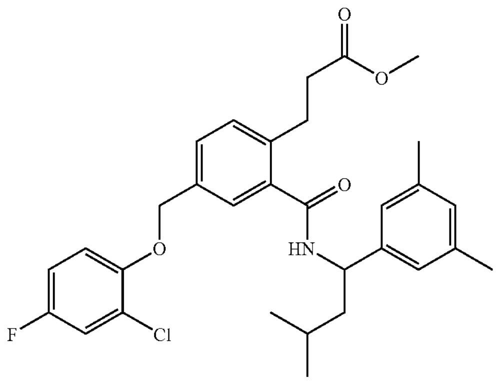

TLC: Rf 0.42 (n-hexane:ethyl acetate=1:1).

Example 5(41)

3-(2-((3-methyl-1-(3,5-dimethylphenyl)butyl)carbamoyl)-4-(2-methyl-4-fluorophenoxymethyl)phenyl)propanoic acid methyl ester

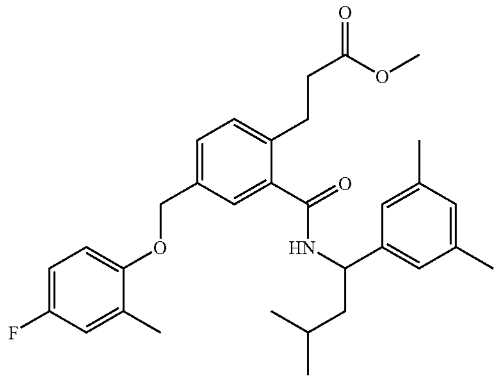

TLC: Rf 0.43 (n-hexane:ethyl acetate=1:1).

Example 5(42)

3-(2-((3-methyl-1-(3,5-dimethylphenyl)butyl)carbamoyl)-4-(2,5-dimethylphenoxymethyl)phenyl) propanoic acid methyl ester

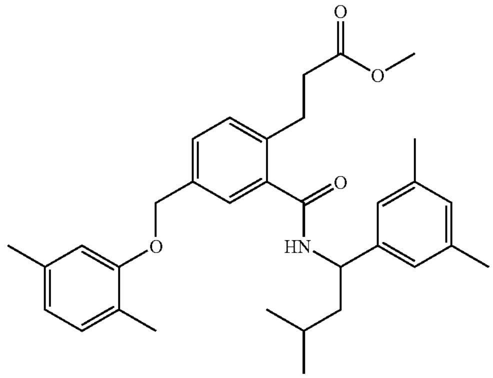

TLC: Rf 0.42 (n-hexane:ethyl acetate=1:1).

Example 5(43)

3-(2-((3-methyl-1-(3,5-dimethylphenyl)butyl)carbamoyl)-4-(2-methoxy-5-methylphenoxymethyl) phenyl)propanoic acid methyl ester

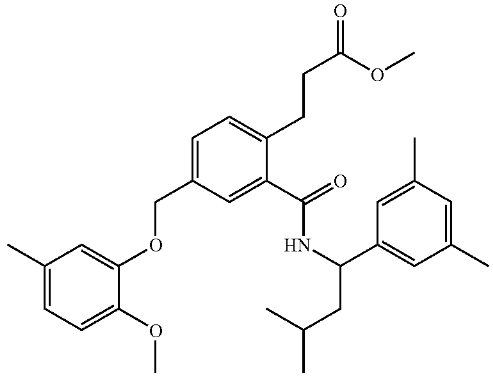

TLC: Rf 0.51 (n-hexane:ethyl acetate=2:1).

Example 5(44)

3-(2-((3-methyl-1-(3,5-dimethylphenyl)butyl)carbamoyl)-4-(4-methylphenoxymethyl)phenyl)propanoic acid methyl ester

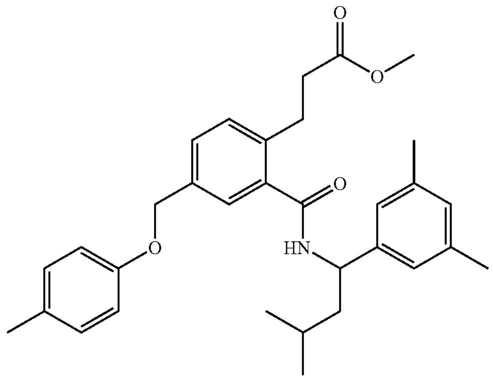

TLC: Rf 0.50 (n-hexane:ethyl acetate=2:1).

Example 5(45)

3-(2-((3-methyl-1-(3,5-dimethylphenyl)butyl)carbamoyl)-4-(4-fluorophenoxymethyl)phenyl)propanoic acid methyl ester

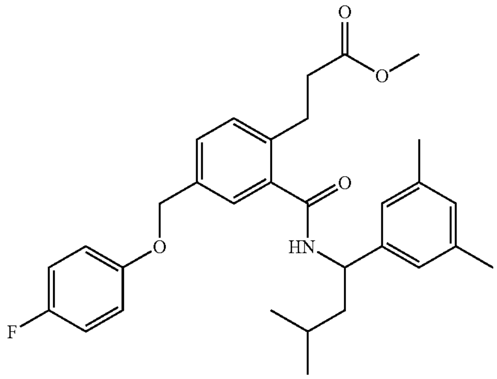

TLC: Rf 0.52 (n-hexane:ethyl acetate=2:1).

Example 5(46)

3-(2-((3-methyl-1-(3,5-dimethylphenyl)butyl)carbamoyl)-4-(3-chlorophenoxymethyl)phenyl)propanoic acid methyl ester

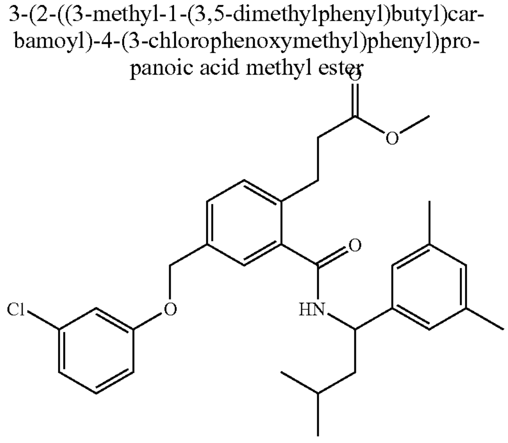

TLC: Rf 0.59 (n-hexane:ethyl acetate=2:1).

Example 5(47)

3-(2-((3-methyl-1-(3,5-dimethylphenyl)butyl)carbamoyl)-4-(2-fluoro-5-methylphenoxymethyl)phenyl)propanoic acid methyl ester

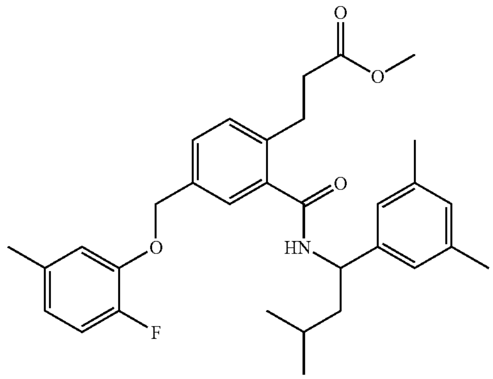

TLC: Rf 0.46 (n-hexane:ethyl acetate=2:1).

Example 5(48)

3-(2-((3-methyl-1-(naphthalen-1-yl)butyl)carbamoyl)-4-(4-fluorophenoxymethyl)phenyl)propanoic acid methyl ester

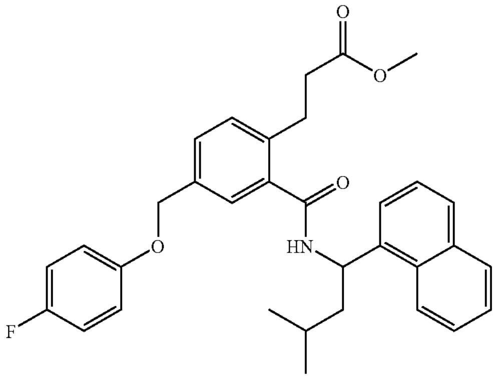

TLC: Rf 0.49 (n-hexane:ethyl acetate=1:1).

Example 5(49)

3-(2-((3-methyl-1-(naphthalen-1-yl)butyl)carbamoyl)-4-(2,5-difluorophenoxymethyl)phenyl)propanoic acid methyl ester

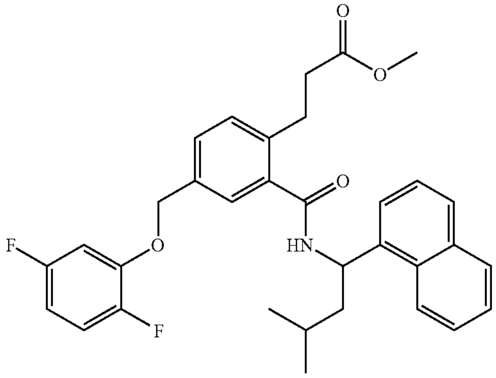

TLC: Rf 0.49 (n-hexane:ethyl acetate=1:1).

Example 5(50)

3-(2-((3-methyl-1-(naphthalen-1-yl)butyl)carbamoyl)-4-(3-cyanophenoxymethyl)phenyl)propanoic acid methyl ester

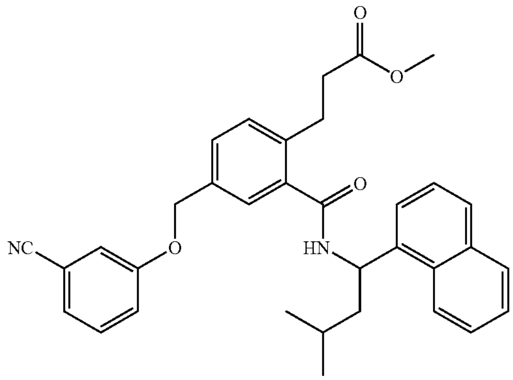

TLC: Rf 0.52 (n-hexane:ethyl acetate=1:1).

Example 5(51)

3-(2-((3-methyl-1-(3,5-dimethylphenyl)butyl)carbamoyl)-4-(3,4-difluorophenoxymethyl)phenyl)propanoic acid methyl ester

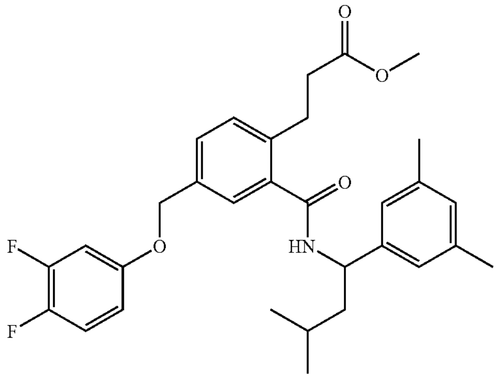

TLC: Rf 0.50 (n-hexane:ethyl acetate=2:1).

Example 5(52)

3-(2-(((1R)-3-methyl-1-(3,5-dimethylphenyl)butyl)carbamoyl)-4-(2,5-difluorophenoxymethyl)phenyl)propanoic acid methyl ester

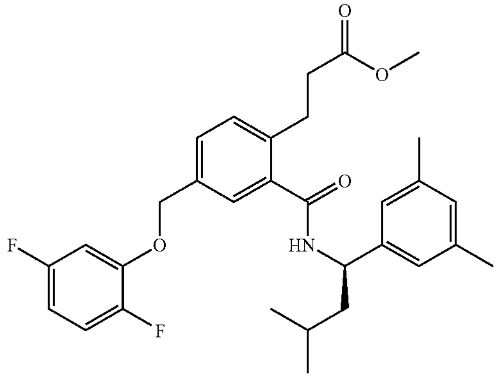

TLC: Rf 0.57 (n-hexane:ethyl acetate=2:1).

Example 5(53)

3-(2-(((1S)-3-methyl-1-(3,5-dimethylphenyl)butyl)carbamoyl)-4-(2,5-difluorophenoxymethyl)phenyl)propanoic acid methyl ester

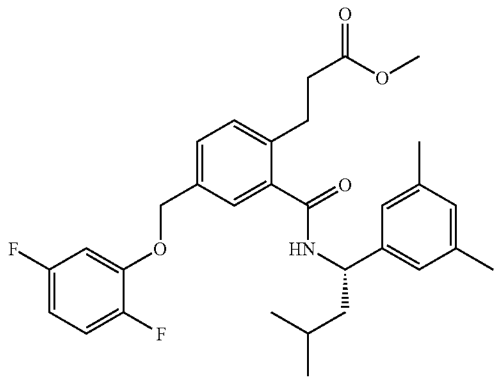

TLC: Rf 0.57 (n-hexane:ethyl acetate=2:1).

Example 5(54)

3-(2-(((1R)-3-methyl-1-(3,5-dimethylphenyl)butyl)carbamoyl)-4-(2-fluorophenoxymethyl)phenyl)propanoic acid methyl ester

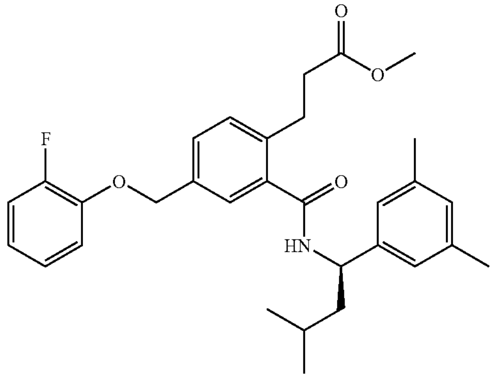

TLC: Rf 0.78 (n-hexane:ethyl acetate=1:1).

Example 5(55)

3-(2-(((1R)-3-methyl-1-(3,5-dimethylphenyl)butyl)carbamoyl)-4-(4-fluorophenoxymethyl)phenyl)propanoic acid methyl ester

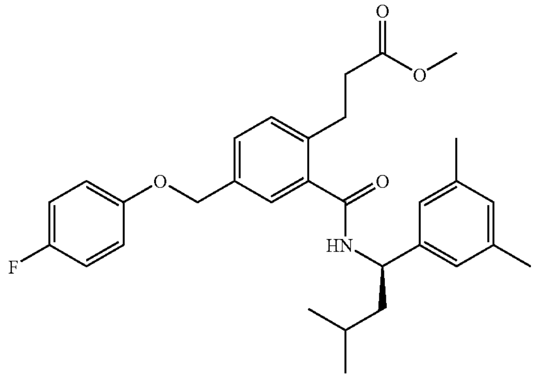

TLC: Rf 0.45 (n-hexane:ethyl acetate=3:1).

Example 5(56)

3-(2-(((1R)-3-methyl-1-(3,5-dimethylphenyl)butyl)carbamoyl)-4-(2-methoxyphenoxymethyl)phenyl)propanoic acid methyl ester

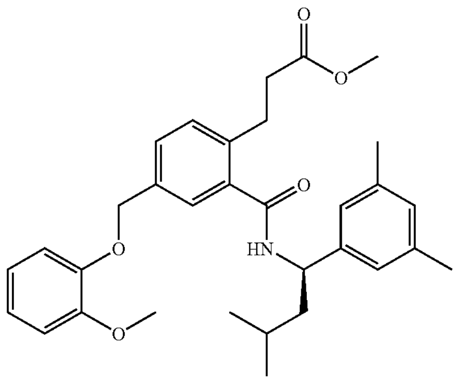

TLC: Rf 0.71 (n-hexane:ethyl acetate=1:1).

Example 5(57)

3-(2-(((1R)-3-methyl-1-(3,5-dimethylphenyl)butyl)carbamoyl)-4-(2-methylphenoxymethyl)phenyl)propanoic acid methyl ester

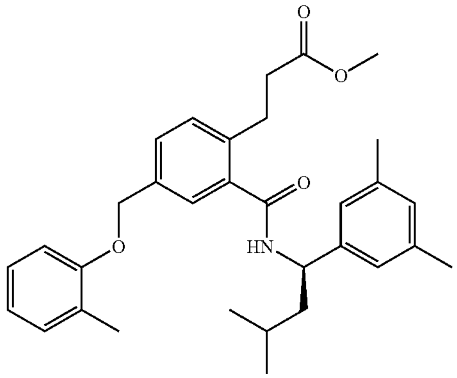

TLC: Rf 0.51 (n-hexane:ethyl acetate=3:1).

Example 5(58)

3-(2-((1-(3,5-dimethylphenyl)cyclohexyl)carbamoyl)-4-(2,5-difluorophenoxymethyl)phenyl)propanoic acid methyl ester

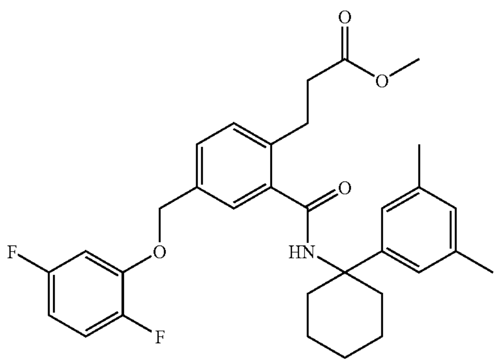

TLC: Rf 0.52 (n-hexane:ethyl acetate=2:1).

Example 5(59)

3-(2-(((1R)-3-methyl-1-(3,5-dimethylphenyl)butyl)carbamoyl)-4-(3-fluorophenoxymethyl)phenyl)propanoic acid methyl ester

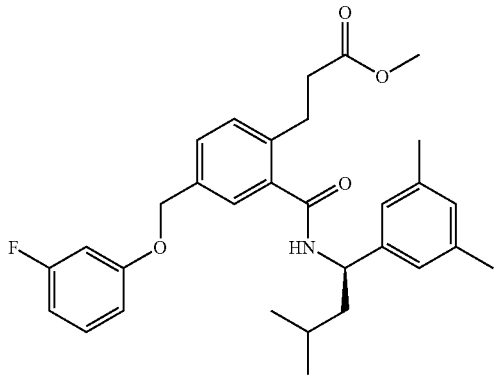

TLC: Rf 0.70 (n-hexane:ethyl acetate=1:1).

Example 5(60)

3-(2-(4-(3,5-dimethylphenyl)perhydropyran-4-yl)carbamoyl)-4-(2,5-difluorophenoxymethyl)phenyl)propanoic acid methyl ester

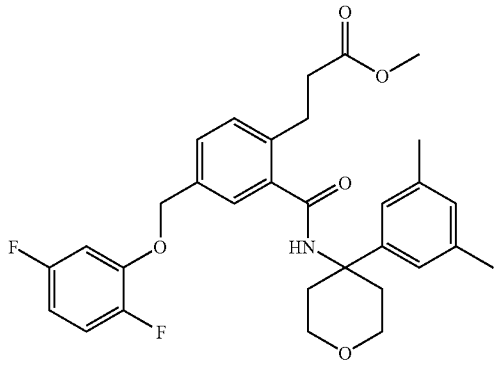

TLC: Rf 0.49 (n-hexane:ethyl acetate=1:1).

Example 5(61)

3-(2-(((1R)-3-methyl-1-(3,5-dimethylphenyl)butyl)carbamoyl)-4-(3-cyanophenoxymethyl)phenyl)propanoic acid methyl ester

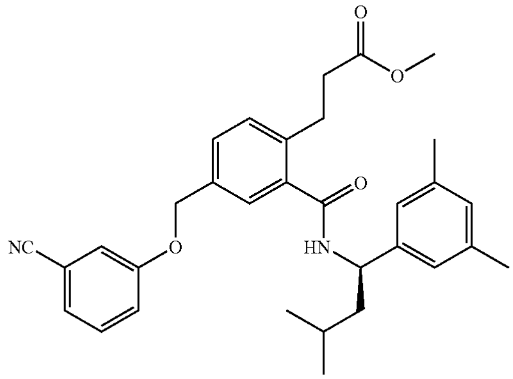

TLC: Rf 0.59 (n-hexane:ethyl acetate=2:1).

Example 5(62)

3-(2-(((1R)-3-methyl-1-(3,5-dimethylphenyl)butyl)carbamoyl)-4-(2,5-dimethylphenoxymethyl)phenyl)propanoic acid methyl ester

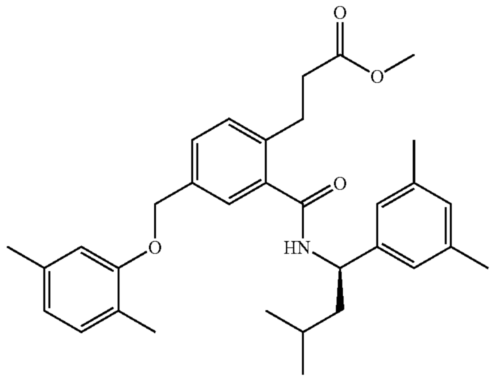

TLC: Rf 0.67 (n-hexane:ethyl acetate=3:1).

Example 5(63)

3-(2-(((1R)-3-methyl-1-(3,5-dimethylphenyl)butyl)carbamoyl)-4-(2-chlorophenoxymethyl)phenyl)propanoic acid methyl ester

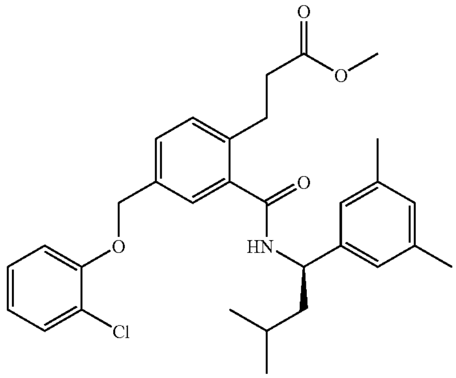

TLC: Rf 0.67 (n-hexane:ethyl acetate=3:1).

Example 5(64)

3-(2-(((1R)-3-methyl-1-(3,5-dimethylphenyl)butyl)carbamoyl)-4-phenoxymethylphenyl)propanoic acid methyl ester

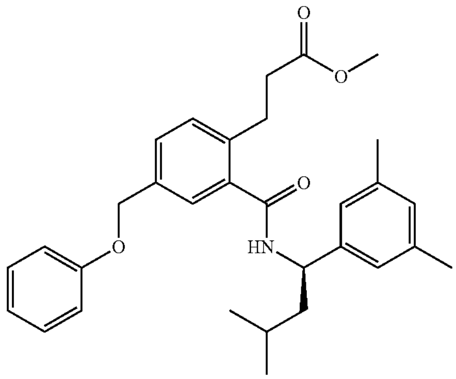

TLC: Rf 0.67 (toluene:ethyl acetate=2:1).

Example 5(65)

3-(2-(((1R)-3-methyl-1-(3,5-dimethylphenyl)butyl)carbamoyl)-4-(3-chlorophenoxymethyl)phenyl)propanoic acid methyl ester

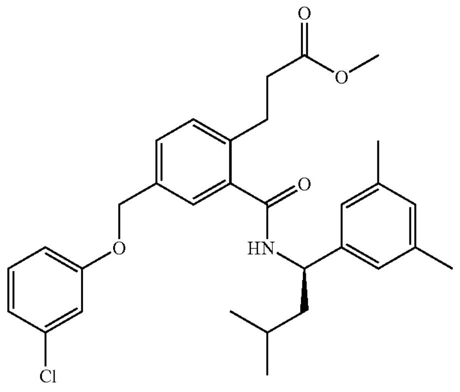

TLC: Rf 0.75 (toluene:ethyl acetate=2:1).

Example 5(66)

3-(2-(4-(3,5-dimethylphenyl)perhydrothiopyran-4-yl)carbamoyl)-4-(2,5-difluorophenoxymethyl)phenyl)propanoic acid methyl ester methyl ester

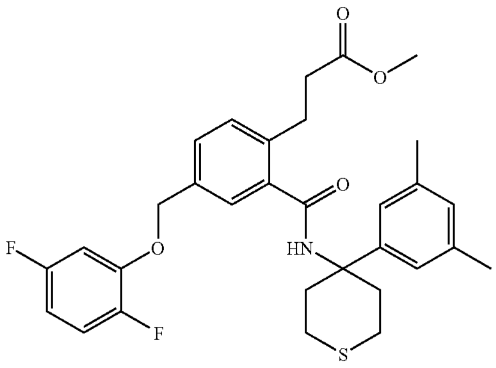

TLC: Rf 0.50 (n-hexane:ethyl acetate=3:1).

Example 5(67)

3-(2-((4-(3,5-dimethylphenyl)perhydropyran-4-yl)carbamoyl)-4-(3-cyanophenoxymethyl)phenyl)propanoic acid methyl ester

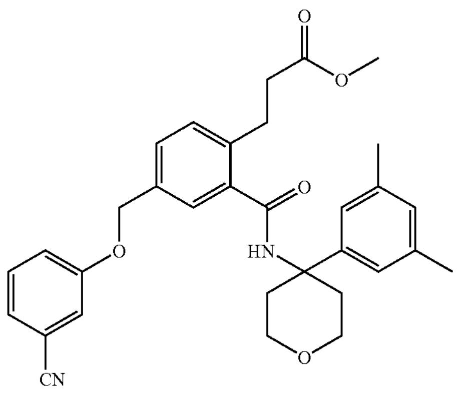

TLC: Rf 0.20 (n-hexane:ethyl acetate=2:1).

Example 5(68)

3-(2-((4-(3,5-dimethylphenyl)perhydropyran-4-yl)carbamoyl)-4-(2-chloro-5-fluorophenoxymethyl)phenyl)propanoic acid methyl ester

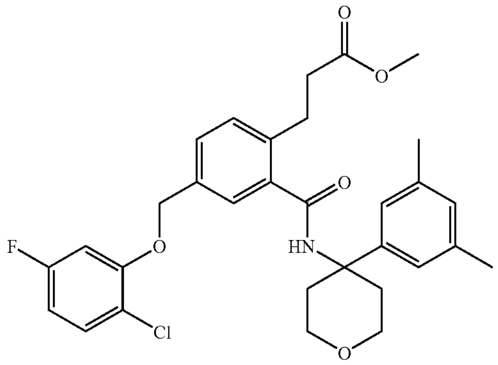

TLC: Rf 0.70 (n-hexane:ethyl acetate=1:1).

Example 5(69)

3-(2-((4-(3,5-dimethylphenyl)perhydropyran-4-yl)carbamoyl)-4-(2-chloro-5-methylphenoxymethyl)phenyl)propanoic acid methyl ester

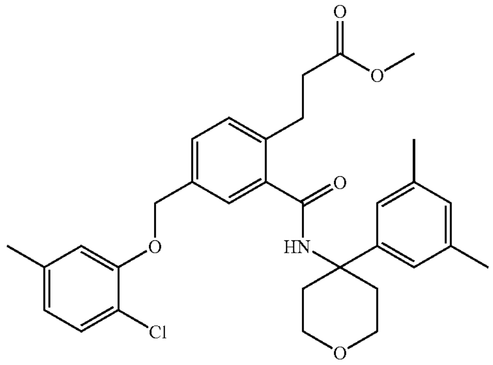

TLC: Rf 0.69 (n-hexane:ethyl acetate=1:1).

Example 5(70)

3-(2-((4-(3,5-dimethylphenyl)perhydropyran-4-yl)carbamoyl)-4-(2,5-dichlorophenoxymethyl)phenyl)propanoic acid methyl ester

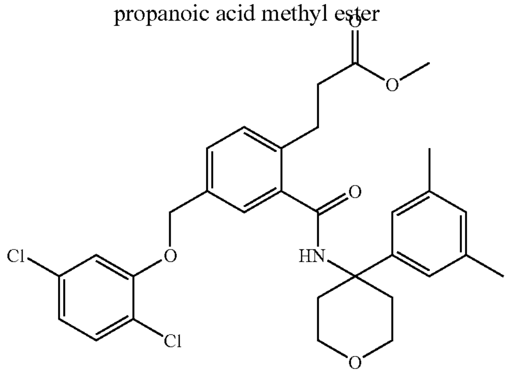

TLC: Rf 0.70 (n-hexane:ethyl acetate=1:1).

Example 5(71)

3-(2-((4-(3,5-dimethylphenyl)perhydropyran-4-yl)carbamoyl)-4-phenoxymethylphenyl)propanoic acid methyl ester

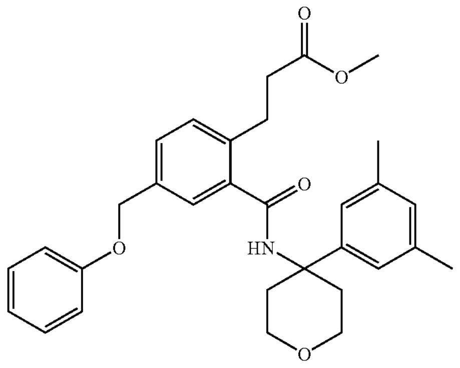

TLC: Rf 0.68 (n-hexane:ethyl acetate=1:1).

Example 5(72)

3-(2-((4-(3,5-dimethylphenyl)perhydropyran-4-yl)carbamoyl)-4-(3-chlorophenoxymethyl)phenyl)propanoic acid methyl ester

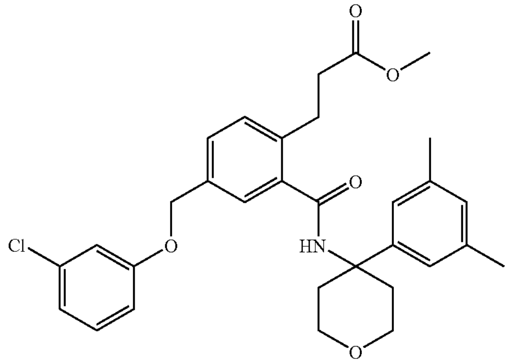

TLC: Rf 0.70 (n-hexane:ethyl acetate=1:1).

Example 5(73)

3-(2-((4-(3,5-dimethylphenyl)perhydropyran-4-yl)carbamoyl)-4-(3-fluorophenoxymethyl)phenyl)propanoic acid methyl ester

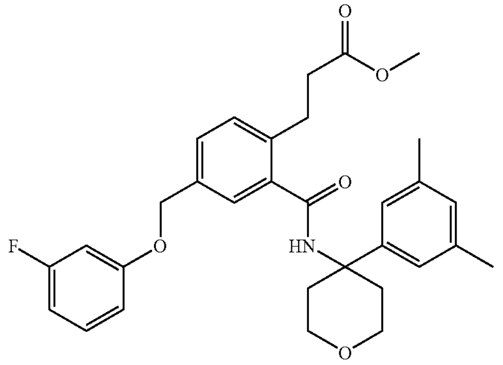

TLC: Rf 0.42 (n-hexane:ethyl acetate=1:1).

Example 5(74)

3-(2-((4-(3,5-dimethylphenyl)perhydropyran-4-yl)carbamoyl)-4-(2,5-dimethylphenoxymethyl)phenyl)propanoic acid methyl ester

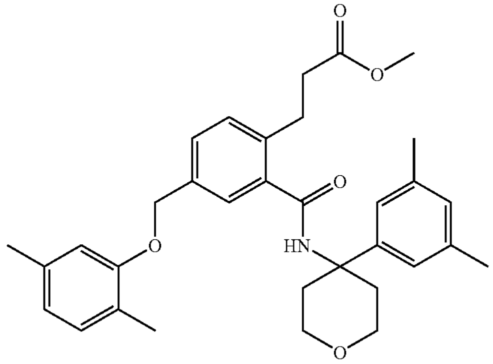

TLC: Rf 0.50 (n-hexane:ethyl acetate=1:1).

Example 5(75)

3-(2-((1-methylsulfonyl-4-(3,5-dimethylphenyl)piperidin-4-yl)carbamoyl)-4-(2,5-difluorophenoxymethyl)phenyl)propanoic acid methyl ester

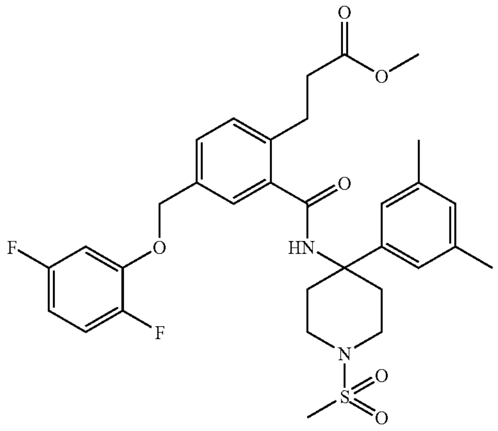

TLC: Rf 0.40 (n-hexane:ethyl acetate=1:1).

Example 5(76)

3-(2-((4-(3,5-dimethylphenyl)perhydropyran-4-yl)carbamoyl)-4-(2-fluorophenoxymethyl)phenyl)propanoic acid methyl ester

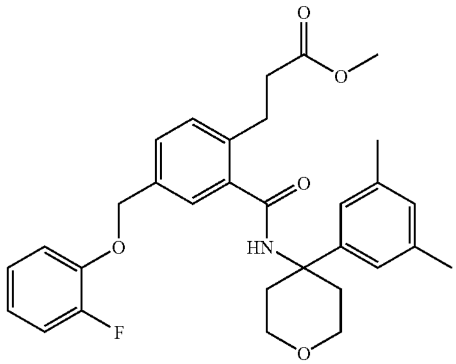

TLC: Rf 0.41 (n-hexane:ethyl acetate=1:1).

Example 5(77)

3-(2-((4-(3,5-dimethylphenyl)perhydropyran-4-yl)carbamoyl)-4-(2-chlorophenoxymethyl)phenyl)propanoic acid methyl ester

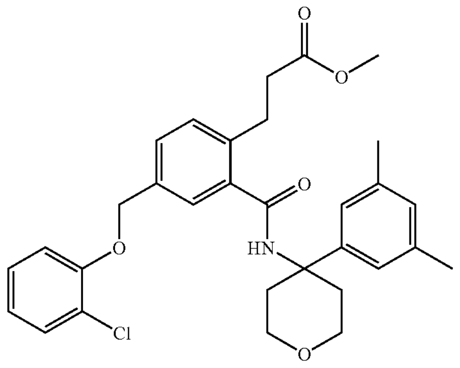

TLC: Rf 0.41 (n-hexane:ethyl acetate=1:1).

Example 5(78)

3-(2-((4-(3-methylphenyl)perhydropyran-4-yl)carbamoyl)-4-(2,5-difluorophenoxymethyl)phenyl)propanoic acid methyl ester

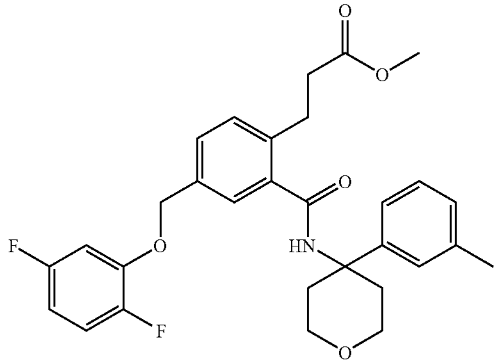

TLC: Rf 0.34 (n-hexane:ethyl acetate=2:1).

Example 5(79)

3-(2-((4-(naphthalen-1-yl)perhydropyran-4-yl)carbamoyl)-4-(2,5-difluorophenoxymethyl)phenyl)propanoic acid methyl ester

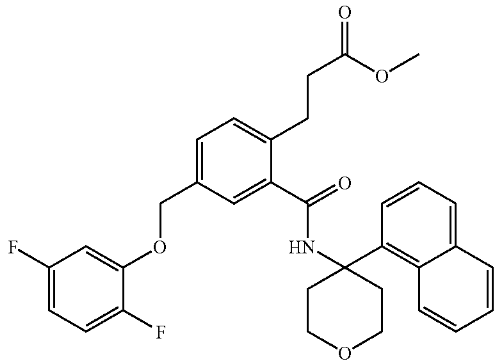

TLC: Rf 0.52 (n-hexane:ethyl acetate=1:1).

Example 5(80)

3-(2-((1-methyl-4-(3,5-dimethylphenyl)piperidin-4-yl)carbamoyl)-4-(2,5-difluorophenoxymethyl)phenyl)propanoic acid methyl ester

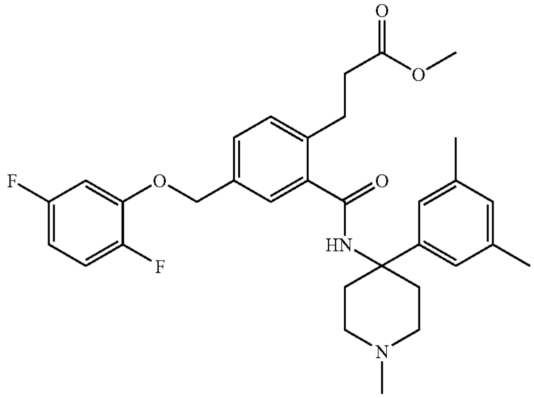

TLC: Rf 0.53 (chloroform:methanol=9:1).

Example 5(81)

3-(2-((1-ethyl-4-(3,5-dimethylphenyl)piperidin-4-yl)carbamoyl)-4-(2,5-difluorophenoxymethyl)phenyl)propanoic acid methyl ester

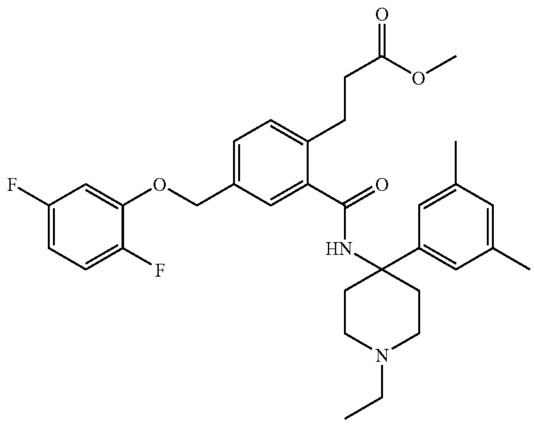

TLC: Rf 0.52 (chloroform:methanol=10:1).

Example 5(82)

2-(2-((3-methyl-1-(3,5-dimethylphenyl)butyl)carbamoyl)-4-benzyloxyphenoxy)acetic acid methyl ester

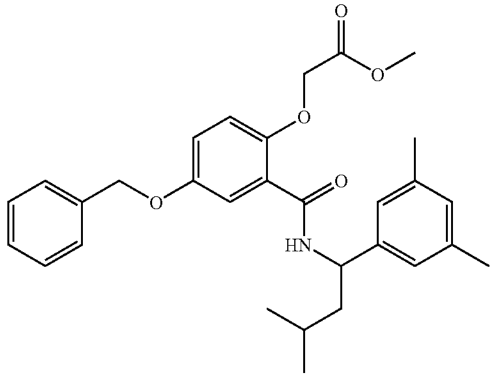

TLC: Rf 0.28 (n-hexane:ethyl acetate=3:1).

Example 5(83)

2-(2-((3-methyl-1-(3,5-dimethylphenyl)butyl)carbamoyl)-4-(2-chloro-6-fluorobenzyloxy)phenoxy) acetic acid methyl ester

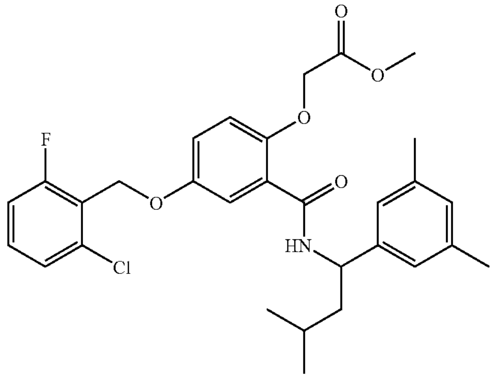

TLC: Rf 0.75 (n-hexane:ethyl acetate=1:1).

Example 6

3-(2-((naphthalen-1-ylmethyl)carbamoyl)-4-(2-methylphenoxymethyl)phenyl)propanoic acid

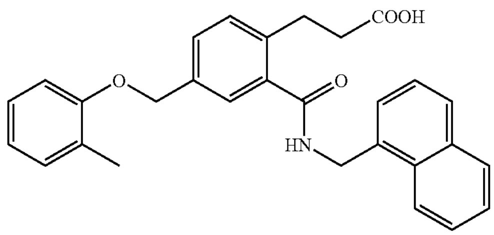

Using the compound prepared in Example 5 (330 mg), the title compound (223 mg) having the following physical data was obtained by the same procedure of Example 3.

TLC: Rf 0.49 (chloroform:methanol=10:1);

NMR (300 MHz, DMSO-$d_6$): δ 9.00 (t, J=5.5 Hz, 1H), 8.24-8.16 (m, 1H), 8.01-7.94 (m, 1H), 7.91-7.84 (m, 1H), 7.63-7.41 (m, 6H), 7.34 (d, J=8.1 Hz, 1H), 7.19-7.10 (m, 2H), 6.99 (d, J=7.8 Hz, 1H), 6.85 (t, J=7.5 Hz, 1H), 5.09 (s, 2H), 4.94 (d, J=5.5 Hz, 2H), 2.96 (t, J=7.8 Hz, 2H), 2.55 (t, J=7.8 Hz, 2H), 2.16 (s, 3H).

Example 6(1)~Example 6(365)

Using the compounds prepared in Example 5(1)~(83) or corresponding compounds, the following compounds were obtained by the same procedure of Example 6 or continued conversion to known salts.

Example 6(1)

(2E)-3-(2-((naphthalen-1-ylmethyl)carbamoyl)-4-(pyrazol-1-ylmethyl)phenyl)-2-propenoic acid

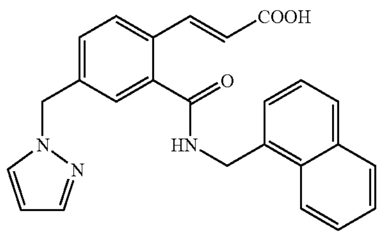

TLC: Rf 0.35 (chloroform:methanol=10:1);

NMR (300 MHz, DMSO-$d_6$): δ 9.10 (t, J=5.7 Hz, 1H), 8.17 (d, J=7.8 Hz, 1H), 8.00-7.82 (m, 5H), 7.65-7.45 (m, 5H), 7.34-7.22 (m, 2H), 6.50 (d, J=15.9 Hz, 1H), 6.29 (t, J=2.1 Hz, 1H), 5.39 (s, 2H), 4.94 (d, J=5.7 Hz, 2H).

Example 6(2)

3-(2-((naphthalen-1-ylmethyl)carbamoyl)-4-(pyrazol-1-ylmethyl)phenyl)propanoic acid

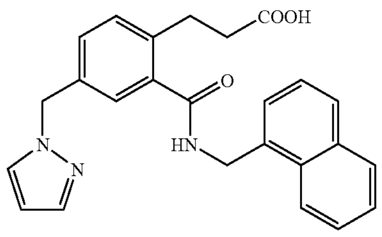

TLC: Rf 0.48 (chloroform:methanol=9:1);

NMR (300 MHz, DMSO-$d_6$): δ 12.11 (s, 1H), 8.93 (t, J=5.7 Hz, 1H), 8.16 (m, 1H), 7.95 (m, 1H), 7.85 (dd, J=7.1, 2.2 Hz, 1H), 7.79 (d, J=2.4 Hz, 1H), 7.61-7.42 (m, 5H), 7.28-7.13 (m, 3H), 6.25 (t, J=2.0 Hz, 1H), 5.29 (s, 2H), 4.89 (d, J=5.7 Hz, 2H), 2.88 (t, J=7.8 Hz, 2H), 2.48 (m, 2H).

Example 6(3)

(2E)-3-(2-((naphthalen-2-ylmethyl)carbamoyl)-4-(pyrazol-1-ylmethyl)phenyl)-2-propenoic acid

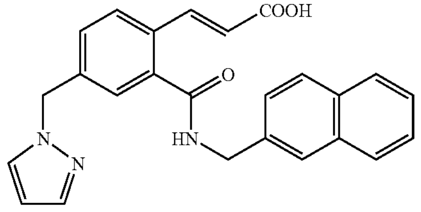

TLC: Rf 0.29 (chloroform:methanol=10:1);

NMR (300 MHz, DMSO-$d_6$): δ 9.13 (t, J=6.0 Hz, 1H), 7.96-7.80 (m, 7H), 7.60-7.44 (m, 4H), 7.39-7.34 (m, 1H), 7.32-7.24 (m, 1H), 6.52 (d, J=15.9 Hz, 1H), 6.31 (t, J=2.0 Hz, 1H), 5.42 (s, 2H), 4.64 (d, J=6.0 Hz, 2H).

Example 6(4)

(2E)-3-(2-(N-(naphthalen-2-ylmethyl)-N-methylcarbamoyl)-4-(pyrazol-1-ylmethyl)phenyl)-2-propenoic acid

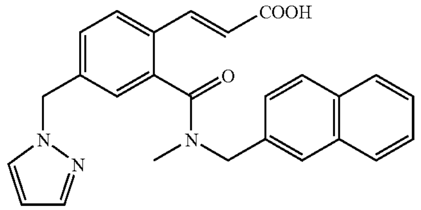

TLC: Rf 0.33 (chloroform:methanol=10:1);

NMR (300 MHz, $CDCl_3$): δ 7.92-7.06 (m, 13H), 6.44 and 6.41 (each d, J=15.9 Hz, 1H), 6.32 and 6.16 (each t, J=2.1 Hz, 1H), 5.38 and 5.28 (each s, 2H), 4.95 and 4.42 (each s, 2H), 3.13 and 2.66 (each s, 3H).

Example 6(5)

(2E)-3-(2-((naphthalen-2-ylmethyl)carbamoyl)-4-phenoxymethylphenyl)-2-propenoic acid

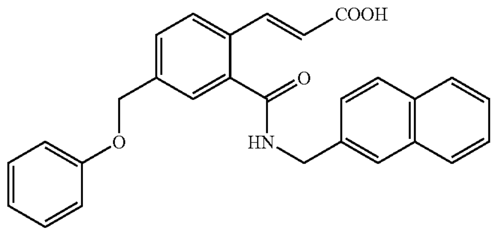

TLC: Rf 0.52 (chloroform:methanol=10:1);

NMR (300 MHz, DMSO-$d_6$): δ 9.19 (t, J=5.8 Hz, 1H), 8.02-7.82 (m, 6H), 7.64-7.44 (m, 5H), 7.38-7.26 (m, 2H), 7.04 (d, J=7.8 Hz, 2H), 6.96 (t, J=7.4 Hz, 1H), 6.55 (d, J=15.9 Hz, 1H), 5.19 (s, 2H), 4.66 (d, J=5.8 Hz, 2H).

Example 6(6)

(2E)-3-(2-((naphthalen-1-ylmethyl)carbamoyl)-4-phenoxymethylphenyl)-2-propenoic acid

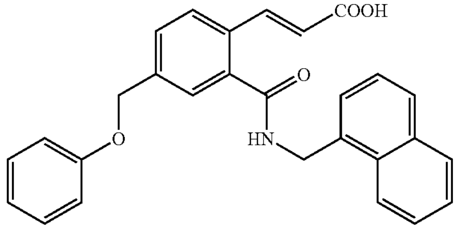

TLC: Rf 0.53 (chloroform:methanol=10:1);

NMR (300 MHz, DMSO-$d_6$): δ 9.14 (t, J=5.4 Hz, 1H), 8.20 (d, J=8.4 Hz, 1H), 8.02-7.84 (m, 4H), 7.66-7.46 (m, 6H), 7.36-7.26 (m, 2H), 7.01 (d, J=7.8 Hz, 2H), 6.96 (t, J=7.5 Hz, 1H), 6.53 (d, J=15.9 Hz, 1H), 5.16 (s, 2H), 4.97 (d, J=5.4 Hz, 2H).

Example 6(7)

3-(2-((naphthalen-1-ylmethyl)carbamoyl)-4-phenoxymethylphenyl)propanoic acid

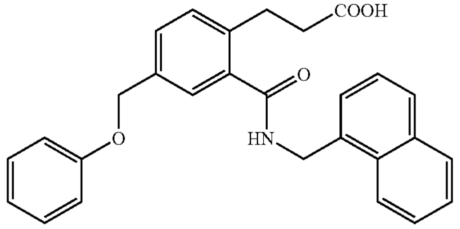

TLC: Rf 0.49 (chloroform:methanol=10:1);

NMR (300 MHz, $CDCl_3$): δ 8.11 (d, J=8.4 Hz, 1H), 7.92-7.79 (m, 2H), 7.62-7.35 (m, 6H), 7.31-7.20 (m, 3H), 6.98-6.84 (m, 3H), 6.37 (t, J=5.1 Hz, 1H), 5.08 (d, J=5.1 Hz, 2H), 4.95 (s, 2H), 3.10 (t, J=7.5 Hz, 2H), 2.76 (t, J=7.5 Hz, 2H).

Example 6(8)

(2E)-3-(2-(1-(naphthalen-1-yl)ethyl)carbamoyl)-4-phenoxymethylphenyl)-2-propenoic acid

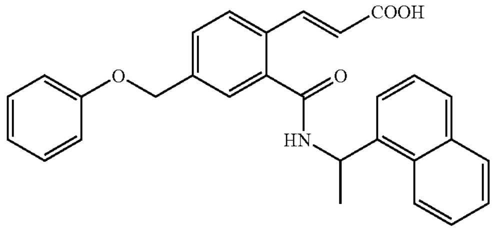

TLC: Rf 0.21 (chloroform:methanol=10:1);

NMR (300 MHz, $CDCl_3$): δ 8.24 (d, J=8.7 Hz, 1H), 8.14 (d, J=15.9 Hz, 1H), 7.88 (d, J=8.4 Hz, 1H), 7.83 (d, J=8.4 Hz, 1H), 7.64-7.42 (m, 6H), 7.30-7.22 (m, 3H), 6.99-6.88 (m,

3H), 6.40 (d, J=15.9 Hz, 1H), 6.18 (m, 1H), 6.03 (brd, J=7.8 Hz, 1H), 5.04 (s, 2H), 1.84 (d, J=6.6 Hz, 3H).

Example 6(9)

3-(2-((naphthalen-1-ylmethyl)carbamoyl)-4-(2,5-dimethylphenoxymethyl)phenyl)propanoic acid

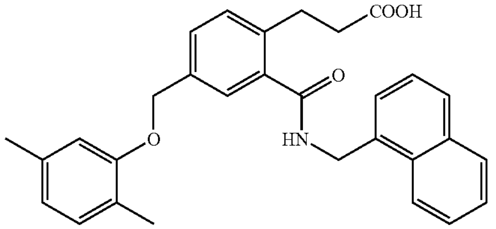

TLC: Rf 0.56 (chloroform:methanol=10:1);

NMR (300 MHz, DMSO-$d_6$): δ 9.00 (t, J=5.5 Hz, 1H), 8.25-8.16 (m, 1H), 8.01-7.93 (m, 1H), 7.88 (d, J=8.1 Hz, 1H), 7.64-7.42 (m, 6H), 7.34 (d, J=8.1 Hz, 1H), 7.02 (d, J=7.5 Hz, 1H), 6.85 (s, 1H), 6.67 (d, J=7.2 Hz, 1H), 5.06 (s, 2H), 4.94 (d, J=5.5 Hz, 2H), 2.96 (t, J=7.8 Hz, 2H), 2.55 (t, J=7.8 Hz, 2H), 2.26 (s, 3H), 2.10 (s, 3H).

Example 6(10)

3-(2-((naphthalen-1-ylmethyl)carbamoyl)-4-(2,5-dichlorophenoxymethyl)phenyl)propanoic acid

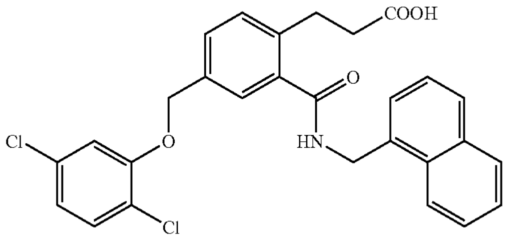

TLC: Rf 0.47 (chloroform:methanol=10:1);

NMR (300 MHz, DMSO-$d_6$): δ 12.1 (s, 1H), 9.00 (t, J=6.0 Hz, 1H), 8.17 (m, 1H), 7.94 (m, 1H), 7.85 (d, J=7.8 Hz, 1H), 7.59-7.40 (m, 7H), 7.35 (d, J=2.1 Hz, 1H), 7.33 (d, J=7.8 Hz, 1H), 7.03 (dd, J=8.4, 2.1 Hz, 1H), 5.19 (s, 2H), 4.91 (d, J=6.0 Hz, 2H), 2.93 (t, J=8.1 Hz, 2H), 2.52 (t, J=8.1 Hz, 2H).

Example 6(11)

3-(2-((naphthalen-1-ylmethyl)carbamoyl)-4-(2-chloro-5-methylphenoxymethyl)phenyl)propanoic acid

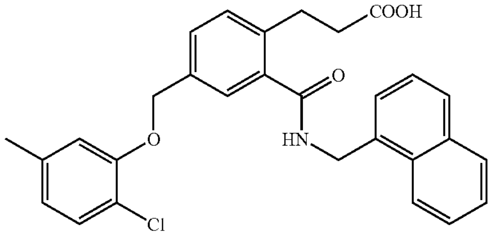

TLC: Rf 0.47 (chloroform:methanol=10:1);

NMR (300 MHz, DMSO-$d_6$): δ 12.1 (s, 1H), 8.98 (t, J=5.4 Hz, 1H), 8.18 (m, 1H), 7.95 (m, 1H), 7.85 (d, J=7.8 Hz, 1H), 7.60-7.41 (m, 6H), 7.37-7.26 (m, 2H), 7.07 (d, J=1.5 Hz, 1H), 6.77 (dd, J=8.1, 1.2 Hz, 1H), 5.13 (s, 2H), 4.91 (d, J=5.4 Hz, 2H), 2.94 (t, J=8.1 Hz, 2H), 2.53 (t, J=8.1 Hz, 2H), 2.27 (s, 3H).

Example 6(12)

3-(2-((3-methyl-1-(naphthalen-1-yl)butyl)carbamoyl)-4-phenoxymethylphenyl)propanoic acid

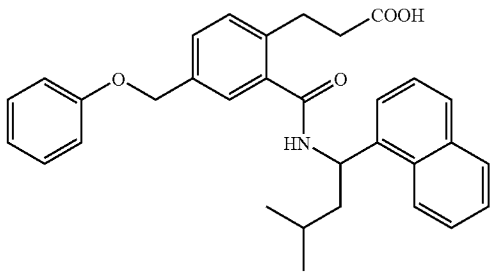

TLC: Rf 0.25 (hexane:ethyl acetate=1:1);

NMR (300 MHz, $CDCl_3$): δ 8.32 (d, J=8.7 Hz, 1H), 7.88 (d, J=7.8 Hz, 1H), 7.80 (d, J=8.4 Hz, 1H), 7.61-7.25 (m, 9H), 7.00-6.90 (m, 3H), 6.38 (d, J=8.7 Hz, 1H), 6.14 (dt, J=8.7, 7.2 Hz, 1H), 4.99 (s, 2H), 3.04 (t, J=7.2 Hz, 2H), 2.74 (t, J=7.2 Hz, 2H), 1.97 (t, J=7.2 Hz, 2H), 1.80 (m, 1H), 1.13 (d, J=6.6 Hz, 3H), 1.01 (d, J=6.6 Hz, 3H).

Example 6(13)

3-(2-((1-methyl-1-(naphthalen-1-yl)ethyl)carbamoyl)-4-phenoxymethylphenyl)propanoic acid

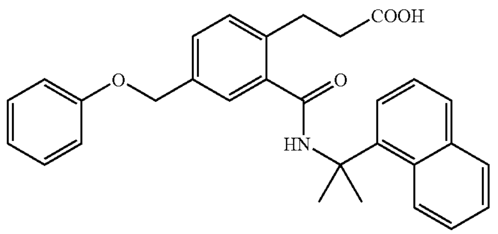

TLC: Rf 0.15 (hexane:ethyl acetate=1:1);

NMR (300 MHz, $CDCl_3$): δ 8.55 (m, 1H), 7.91 (m, 1H), 7.81 (d, J=8.1 Hz, 1H), 7.68 (d, J=7.8 Hz, 1H), 7.50-7.23 (m, 8H), 7.00-6.90 (m, 3H), 6.53 (s, 1H), 4.99 (s, 2H), 2.98 (t, J=7.5 Hz, 2H), 2.69 (t, J=7.5 Hz, 2H), 2.12 (s, 6H).

Example 6(14)

3-(2-((naphthalen-1-ylmethyl)carbamoyl)-4-(2,6-dimethylphenoxymethyl)phenyl)propanoic acid

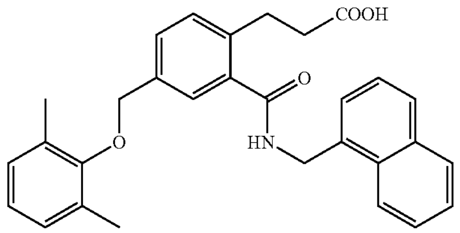

TLC: Rf 0.53 (chloroform:methanol=10:1);

NMR (300 MHz, DMSO-$d_6$): δ 8.98 (t, J=5.4 Hz, 1H), 8.19 (m, 1H), 7.96 (m, 1H), 7.86 (d, J=8.1 Hz, 1H), 7.61-7.44 (m, 6H), 7.33 (d, J=8.7 Hz, 1H), 7.07-7.00 (m, 2H), 6.93 (m, 1H), 4.92 (d, J=5.4 Hz, 1H), 4.74 (s, 2H), 2.95 (t, J=7.8 Hz, 2H), 2.53 (t, J=7.8 Hz, 2H), 2.23 (s, 6H).

Example 6(15)

3-(2-((naphthalen-1-ylmethyl)carbamoyl)-4-(2-chloro-6-methylphenoxymethyl)phenyl)propanoic acid

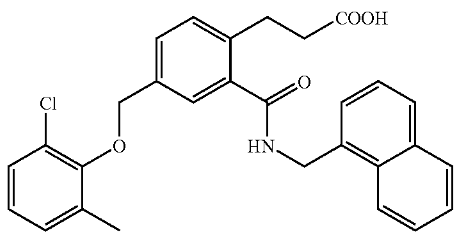

TLC: Rf 0.53 (chloroform:methanol=10:1);

NMR (300 MHz, DMSO-$d_6$): δ 8.98 (t, J=5.4 Hz, 1H), 8.19 (m, 1H), 7.95 (m, 1H), 7.86 (d, J=8.4 Hz, 1H), 7.61-7.44 (m, 6H), 7.37-7.30 (m, 2H), 7.21 (d, J=7.8 Hz, 1H), 7.06 (t, J=8.1 Hz, 1H), 4.92 (d, J=5.4 Hz, 1H), 4.87 (s, 2H), 2.95 (t, J=8.4 Hz, 2H), 2.53 (t, J=8.4 Hz, 2H), 2.25 (s, 3H).

Example 6(16)

3-(2-((naphthalen-1-ylmethyl)carbamoyl)-4-(3-cyanophenoxymethyl)phenyl)propanoic acid

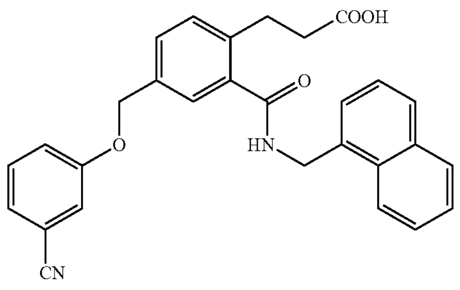

[Salt-free]

TLC: Rf 0.53 (chloroform:methanol=10:1);

NMR (300 MHz, DMSO-$d_6$): δ 8.97 (t, J=5.4 Hz, 1H), 8.18 (m, 1H), 7.95 (m, 1H), 7.85 (d, J=7.2 Hz, 1H), 7.60-7.30 (m, 11H), 5.13 (s, 2H), 4.91 (d, J=5.4 Hz, 2H), 2.94 (t, J=7.8 Hz, 2H), 2.52 (t, J=7.8 Hz, 2H).

Sodium Salt:

TLC: Rf 0.56 (chloroform:methanol=10:1).

Example 6(17)

3-(2-(((1R)-1-(naphthalen-1-yl)ethyl)carbamoyl)-4-phenoxymethylphenyl)propanoic acid

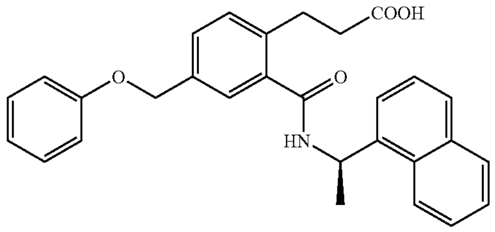

TLC: Rf 0.15 (hexane:ethyl acetate=1:1);

NMR (300 MHz, $CDCl_3$): δ 8.23 (d, J=7.8 Hz, 1H), 7.89 (d, J=7.5 Hz, 1H), 7.83 (d, J=8.4 Hz, 1H), 7.62-7.25 (m, 9H), 6.98-6.88 (m, 3H), 6.36 (d, J=8.4 Hz, 1H), 6.14 (m, 1H), 4.97 (s, 2H), 3.10 (t, J=7.2 Hz, 2H), 2.78 (t, J=7.2 Hz, 2H), 1.80 (d, J=6.6 Hz, 3H).

Example 6(18)

3-(2-((1-(naphthalen-1-yl)propyl)carbamoyl)-4-phenoxymethylphenyl)propanoic acid

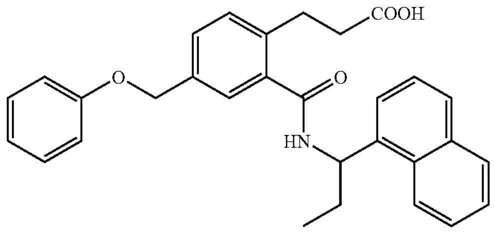

TLC: Rf 0.18 (hexane:ethyl acetate=1:1);

NMR (300 MHz, $CDCl_3$): δ 8.28 (d, J=8.7 Hz, 1H), 7.88 (d, J=8.1 Hz, 1H), 7.81 (d, J=7.8 Hz, 1H), 7.60-7.24 (m, 9H), 7.00-6.89 (m, 3H), 6.37 (d, J=8.7 Hz, 1H), 5.94 (dt, J=8.7, 8.7 Hz, 1H), 4.98 (s, 2H), 3.05 (t, J=7.5 Hz, 2H), 2.75 (t, J=7.5 Hz, 2H), 2.15 (m, 2H), 1.10 (t, J=7.2 Hz, 3H).

Example 6(19)

3-(2-(((1S)-1-(naphthalen-1-yl)ethyl)carbamoyl)-4-phenoxymethylphenyl)propanoic acid

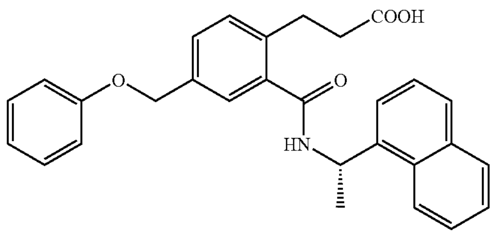

TLC: Rf 0.15 (hexane:ethyl acetate=1:1);

NMR (300 MHz, $CDCl_3$): δ 8.22 (d, J=7.8 Hz, 1H), 7.89 (d, J=7.8 Hz, 1H), 7.83 (d, J=8.1 Hz, 1H), 7.62-7.25 (m, 9H), 6.98-6.88 (m, 3H), 6.36 (d, J=7.8 Hz, 1H), 6.14 (m, 1H), 4.97 (s, 2H), 3.09 (t, J=7.5 Hz, 2H), 2.78 (t, J=7.5 Hz, 2H), 1.80 (d, J=6.9 Hz, 3H).

Example 6(20)

3-(2-((1-(naphthalen-2-yl)ethyl)carbamoyl)-4-phenoxymethylphenyl)propanoic acid

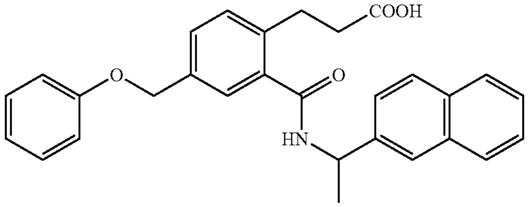

TLC: Rf 0.17 (chloroform:methanol=10:1);

NMR (300 MHz, $CDCl_3$): δ 7.84 (m, 4H), 7.53-7.42 (m, 5H), 7.29 (m, 3H), 6.97 (m, 3H), 6.56 (d, J=8.1 Hz, 1H), 5.50 (m, 1H), 5.02 (s, 2H), 3.07 (t, J=7.5 Hz, 2H), 2.77 (t, J=7.5 Hz, 2H), 1.70 (d, J=6.9 Hz, 3H).

Example 6(21)

3-(2-((4-methoxynaphthalen-1-ylmethyl)carbamoyl)-4-phenoxymethylphenyl)propanoic acid

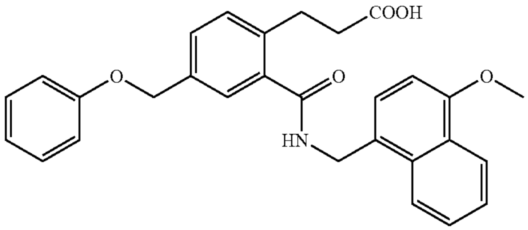

TLC: Rf 0.53 (chloroform:methanol=9:1);

NMR (300 MHz, DMSO-$d_6$): δ 8.87 (t, J=5.6 Hz, 1H), 8.19 (dd, J=8.3, 1.4 Hz, 1H), 8.12 (d, J=7.5 Hz, 1H), 7.62-7.48 (m, 2H), 7.46-7.36 (m, 3H), 7.32-7.23 (m, 3H), 7.00-6.89 (m, 4H), 5.04 (s, 2H), 4.82 (d, J=5.6 Hz, 2H), 3.96 (s, 3H), 2.92 (t, J=7.8 Hz, 2H), 2.50 (m, 2H).

Example 6(22)

3-(2-((naphthalen-1-ylmethyl)carbamoyl)-4-(2-methylthiophenoxymethyl)phenyl)propanoic acid

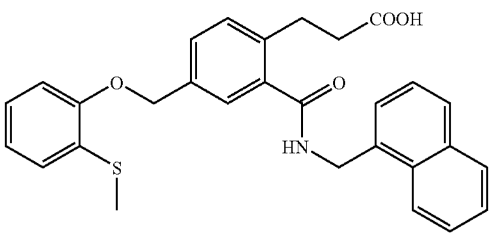

TLC: Rf 0.34 (chloroform:methanol=9:1);

NMR (300 MHz, $CDCl_3$): δ 8.12 (d, J=7.2 Hz, 1H), 7.92 (dd, J=8.1, 1.2 Hz, 1H), 7.84 (d, J=8.1 Hz, 1H), 7.64-7.36 (m, 6H), 7.34-7.25 (m, 1H), 7.14-7.02 (m, 2H), 6.95 (t, J=7.2 Hz, 1H), 6.82 (d, J=7.2 Hz, 1H), 6.45 (brs, 1H), 5.15-5.05 (m, 2H), 5.07 (s, 2H), 3.13 (t, J=7.5 Hz, 2H), 2.80 (t, J=7.5 Hz, 2H), 2.28 (s, 3H).

Example 6(23)

3-(2-((naphthalen-1-ylmethyl)carbamoyl)-4-(2-mesylphenoxymethyl)phenyl)propanoic acid

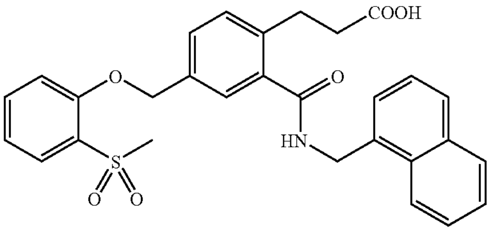

TLC: Rf 0.49 (chloroform:methanol=9:1);

NMR (300 MHz, $CDCl_3$): δ 8.18 (d, J=8.4 Hz, 1H), 7.94 (dd, J=8.4, 1.8 Hz, 1H), 7.93-7.82 (m, 2H), 7.75 (d, J=1.8 Hz, 1H), 7.63-7.37 (m, 6H), 7.32-7.25 (m, 1H), 7.15-6.97 (m, 3H), 5.19 (s, 2H), 5.10 (d, J=5.4 Hz, 2H), 3.16 (t, J=7.5 Hz, 2H), 2.92 (s, 3H), 2.83 (t, J=7.5 Hz, 2H).

Example 6(24)

4-(2-((3-methyl-1-(naphthalen-1-yl)butyl)carbamoyl)-4-phenoxymethylphenyl)butanoic acid

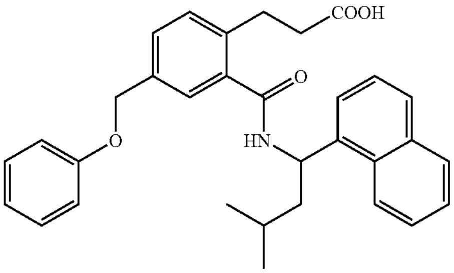

TLC: Rf 0.59 (chloroform:methanol=10:1);

NMR (300 MHz, $CDCl_3$): δ 8.34 (d, J=8.4 Hz, 1H), 7.89 (d, J=7.8 Hz, 1H), 7.80 (d, J=7.8 Hz, 1H), 7.63-7.18 (m, 9H), 7.02-6.88 (m, 3H), 6.20-6.00 (m, 2H), 4.99 (s, 2H), 2.74 (t, J=7.7 Hz, 2H), 2.27-2.17 (m, 2H), 2.00-1.40 (m, 5H), 1.13 (d, J=6.6 Hz, 3H), 1.01 (d, J=6.6 Hz, 3H).

Example 6(25)

3-(2-((4-fluoronaphthalen-1-ylmethyl)carbamoyl)-4-phenoxymethylphenyl)propanoic acid

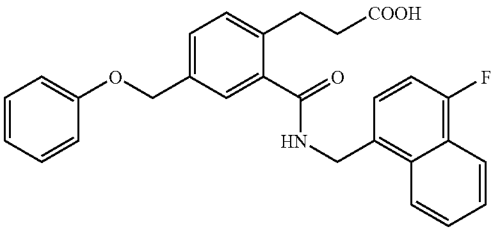

TLC: Rf 0.13 (chloroform:methanol=10:1);

NMR (300 MHz, $CDCl_3$): δ 8.14 (m, 2H), 7.68-7.58 (m, 2H), 7.46-7.38 (m, 3H), 7.31-7.23 (m, 3H), 7.09 (dd, J=9.9, 8.4 Hz, 1H), 6.98-6.87 (m, 3H), 6.39 (t, J=5.1 Hz, 1H), 5.04 (d, J=5.1 Hz, 2H), 4.96 (s, 2H), 3.09 (t, J=6.9 Hz, 2H), 2.77 (t, J=6.9 Hz, 2H).

Example 6(26)

3-(2-((quinolin-4-ylmethyl)carbamoyl)-4-phenoxymethylphenyl)propanoic acid

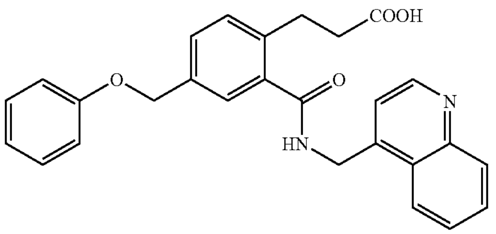

TLC: Rf 0.26 (chloroform:methanol=10:1);

NMR (300 MHz, $CDCl_3$): δ 9.12 (t, J=5.7 Hz, 1H), 8.85 (d, J=4.5 Hz, 1H), 8.24 (d, J=8.1 Hz, 1H), 8.06 (d, J=8.1 Hz, 1H), 7.79 (t, J=7.8 Hz, 1H), 7.66 (t, J=8.1 Hz, 1H), 7.55-7.43 (m, 3H), 7.37-7.25 (m, 3H), 7.01 (m, 2H), 6.94 (t, J=7.2 Hz, 1H), 5.09 (s, 2H), 4.96 (d, J=5.7 Hz, 2H), 2.94 (t, J=7.5 Hz, 2H), 2.52 (t, J=7.5 Hz, 2H).

Example 6(27)

3-(2-((3-methyl-1-(naphthalen-1-yl)butyl)carbamoyl)-4-(pyrazol 1-ylmethyl)phenyl)propanoic acid

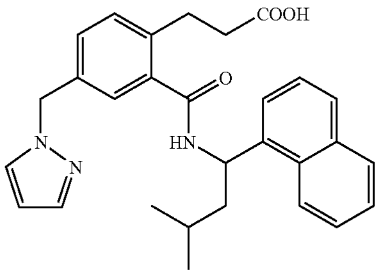

TLC: Rf 0.41 (chloroform:methanol=10:1);

NMR (300 MHz, $CDCl_3$): δ 8.28 (d, J=8.1 Hz, 1H), 7.87 (m, 1H), 7.79 (d, J=7.5 Hz, 1H), 7.62-7.36 (m, 6H), 7.22-7.06 (m, 3H), 6.65 (d, J=8.7 Hz, 1H), 6.27 (t, J=2.1 Hz, 1H), 6.19 (m, 1H), 5.25 (s, 2H), 2.98 (t, J=7.5 Hz, 2H), 2.68 (t, J=7.5 Hz, 2H), 1.92 (t, J=7.1 Hz, 2H), 1.78 (m, 1H), 1.11 (d, J=6.6 Hz, 3H), 0.99 (d, J=6.6 Hz, 3H).

Example 6(28)

3-(2-((naphthalen-1-ylmethyl)carbamoyl)-4-(2-cyanophenoxymethyl)phenyl)propanoic acid

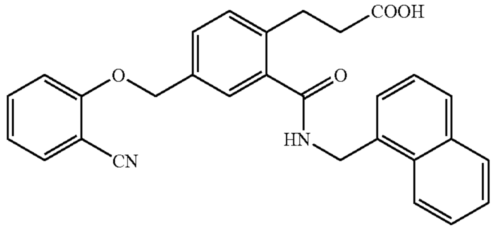

TLC: Rf 0.23 (chloroform:methanol=10:1);

NMR (300 MHz, DMSO-$d_6$): δ 9.01 (t, J=4.8 Hz, 1H), 8.17 (dd, J=7.8, 1.5 Hz, 1H), 7.94 (d, J=6.9 Hz, 1H), 7.85 (d, J=7.2 Hz, 1H), 7.74 (d, J=7.5 Hz, 1H), 7.65 (t, J=7.2 Hz, 1H), 7.60-7.44 (m, 6H), 7.33 (m, 2H), 7.09 (t, J=7.8 Hz, 1H), 5.26 (s, 2H), 4.91 (d, J=4.8 Hz, 2H), 2.93 (t, J=8.1 Hz, 2H), 2.52 (t, J=8.1 Hz, 2H).

Example 6(29)

3-(2-((naphthalen-1-ylmethyl)carbamoyl)-4-(2-chlorophenoxymethyl)phenyl)propanoic acid

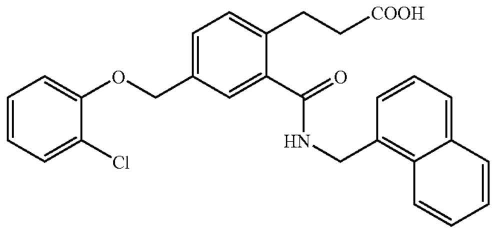

TLC: Rf 0.20 (chloroform:methanol=10:1);

NMR (300 MHz, $CDCl_3$): δ 8.12 (d, J=7.8 Hz, 1H), 7.90 (d, J=7.8 Hz, 1H), 7.84 (d, J=8.4 Hz, 1H), 7.62-7.40 (m, 6H), 7.36-7.26 (m, 2H), 7.15 (ddd, J=8.7, 8.7, 3.0 Hz, 1H), 6.88 (m, 2H), 6.39 (t, J=4.8 Hz, 1H), 5.10 (d, J=4.8 Hz, 2H), 5.05 (s, 2H), 3.12 (t, J=7.5 Hz, 2H), 2.79 (t, J=7.5 Hz, 2H).

Example 6(30)

3-(2-((3-methyl-1-(naphthalen-1-yl)butyl)carbamoyl)-4-(pyridin-3-yloxymethyl)phenyl)propanoic acid

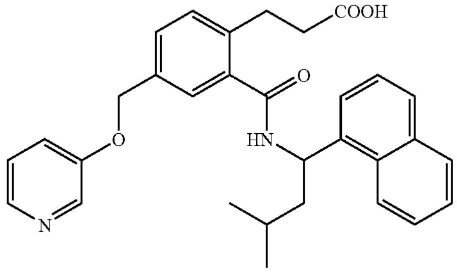

TLC: Rf 0.54 (chloroform:methanol=10:1);

NMR (300 MHz, DMSO-$d_6$): δ 9.09 (d, J=8.1 Hz, 1H), 8.36 (d, J=3.3 Hz, 1H), 8.27-8.16 (m, 2H), 7.97 (d, J=7.8 Hz, 1H), 7.84 (d, J=8.1 Hz, 1H), 7.68-7.43 (m, 6H), 7.41-7.30 (m, 3H), 5.93 (m, 1H), 5.19 (s, 2H), 2.98-2.80 (m, 2H), 2.62-2.38 (m, 2H), 1.97-1.76 (m, 2H), 1.59 (m, 1H), 1.11 (d, J=6.0 Hz, 3H), 0.93 (d, J=6.0 Hz, 3H).

Example 6(31)

3-(2-((naphthalen-1-ylmethyl)carbamoyl)-4-(2-formylphenoxymethyl)phenyl)propanoic acid

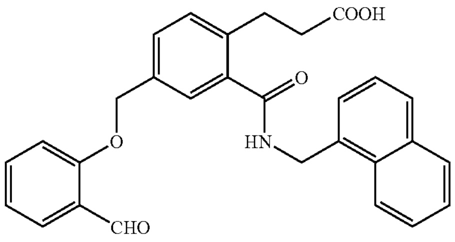

TLC: Rf 0.55 (chloroform:methanol=10:1);

NMR (300 MHz, DMSO-$d_6$): δ 10.44 (s, 1H), 9.02 (t, J=6.0 Hz, 1H), 8.19 (m, 1H), 7.97 (m, 1H), 7.87 (m, 1H), 7.78-7.42 (m, 8H), 7.40-7.28 (m, 2H), 7.11 (t, J=7.5 Hz, 1H), 5.27 (s, 2H), 4.94 (d, J=6.0 Hz, 2H) 2.96 (t, J=7.8 Hz, 2H), 2.55 (t, J=7.8 Hz, 2H).

Example 6(32)

3-(2-((naphthalen-1-ylmethyl)carbamoyl)-4-(2-hydroxymethylphenoxymethyl)phenyl)propanoic acid

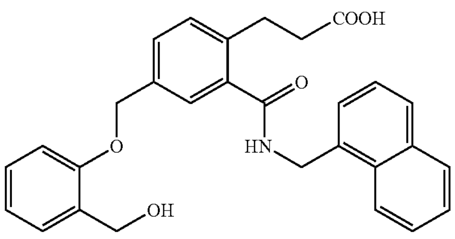

TLC: Rf 0.50 (chloroform:methanol=10:1);

NMR (300 MHz, DMSO-$d_6$): δ 9.00 (t, J=5.7 Hz, 1H), 8.20 (d, J=7.8 Hz, 1H), 7.97 (m, 1H), 7.87 (m, 1H), 7.66-7.30 (m, 8H), 7.20 (m, 1H), 7.02 (d, J=8.1 Hz, 1H), 6.96 (t, J=7.5 Hz 1H), 5.10 (s, 2H), 5.03 (brs, 1H), 4.94 (d, J=5.7 Hz, 2H), 4.57 (s, 2H), 2.96 (t, J=8.0 Hz, 2H), 2.54 (t, J=8.0 Hz, 2H).

Example 6(33)

3-(2-((3-methyl-1-phenylbutyl)carbamoyl)-4-phenoxymethylphenyl)propanoic acid

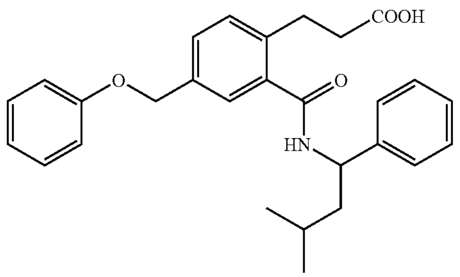

TLC: Rf 0.31 (chloroform:methanol=10:1);

NMR (300 MHz, $CDCl_3$): δ 7.45-7.25 (m, 10H), 7.02-6.93 (m, 3H), 6.40 (d, J=7.2 Hz, 1H), 5.23 (m, 1H), 5.02 (s, 2H), 3.01 (dt, J=2.7, 7.8 Hz, 2H), 2.72 (t, J=7.8 Hz, 2H), 1.85-1.65 (m, 2H), 1.60 (m, 1H), 0.98 (d, J=6.3 Hz, 6H).

Example 6(34)

3-(2-((naphthalen-1-ylmethyl)carbamoyl)-4-(2-acetylaminophenoxymethyl)phenyl)propanoic acid

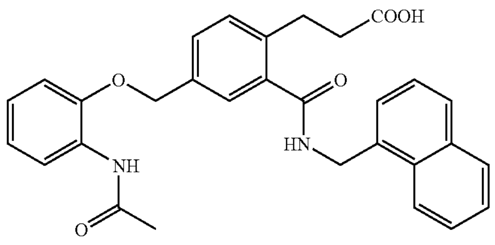

TLC: Rf 0.50 (chloroform:methanol=9:1);

NMR (300 MHz, DMSO-$d_6$): δ 9.07 (s, 1H), 9.00-8.92 (m, 1H), 8.17 (d, J=7.2 Hz, 1H), 7.98-7.91 (m, 1H), 7.88-7.76 (m, 2H), 7.68-7.40 (m, 6H), 7.30 (d, J=8.1 Hz, 1H), 7.10-6.96 (m, 2H), 6.92-6.83 (m, 1H), 5.14 (s, 2H), 4.92 (d, J=5.4 Hz, 2H), 2.94 (t, J=7.5 Hz, 2H), 2.52 (t, J=7.5 Hz, 2H), 2.01 (s, 3H).

Example 6(35)

3-(2-((naphthalen-1-ylmethyl)carbamoyl)-4-(2-methoxyphenoxymethyl)phenyl)propanoic acid

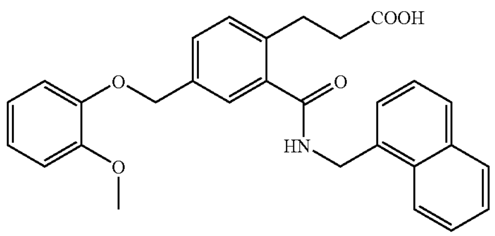

TLC: Rf 0.50 (chloroform:methanol=9:1);

NMR (300 MHz, $CDCl_3$): δ 8.11 (d, J=8.4 Hz, 1H), 7.92-7.80 (m, 2H), 7.61-7.36 (m, 6H), 7.29-7.23 (m, 1H), 6.93-6.78 (m, 4H), 6.42 (m, 1H), 5.08 (d, J=5.4 Hz, 2H), 5.04 (s, 2H), 3.75 (s, 3H), 3.11 (t, J=7.2 Hz, 2H), 2.78 (t, J=7.2 Hz, 2H).

Example 6(36)

3-(2-((naphthalen-1-ylmethyl)carbamoyl)-4-(2-methoxymethylphenoxymethyl)phenyl)propanoic acid

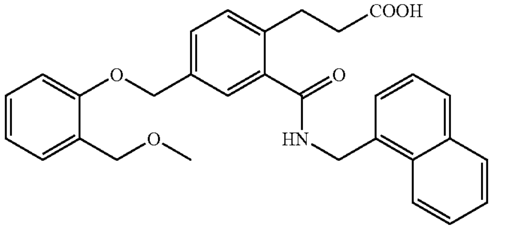

TLC: Rf 0.62 (chloroform:methanol=10:1);

NMR (300 MHz, DMSO-$d_6$): δ 9.03 (brs, 1H), 8.20 (m, 1H), 7.97 (m, 1H), 7.87 (m, 1H), 7.64-7.39 (m, 6H), 7.38-7.20 (m, 3H), 7.06 (d, J=8.1 Hz, 1H), 6.95 (t, J=7.5 Hz, 1H), 5.11 (s, 2H), 4.93 (d, J=5.4 Hz, 2H), 4.43 (s, 2H), 3.26 (s, 3H), 2.95 (t, J=7.8 Hz, 2H), 2.66-2.36 (m, 2H).

Example 6(37)

3-(2-((3-methyl-1-(4-methoxyphenyl)butyl)carbamoyl)-4-phenoxymethylphenyl)propanoic acid

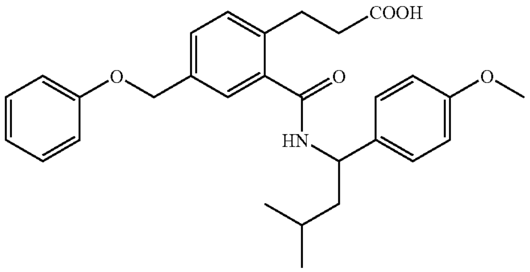

TLC: Rf 0.091 (chloroform:methanol=10:1);

NMR (300 MHz, $CDCl_3$): δ 7.45-7.38 (m, 2H), 7.34-7.23 (m, 5H), 7.03-6.93 (m, 3H), 6.88 (d, J=8.7 Hz, 2H), 6.33 (d, J=8.1 Hz, 1H), 5.19 (dt, J=8.1, 8.1 Hz, 1H), 5.02 (s, 2H), 3.80 (s, 3H), 3.01 (dt, J=3.0, 7.2 Hz, 2H), 2.72 (t, J=7.2 Hz, 2H), 1.85-1.65 (m, 2H), 1.63 (m, 1H), 0.97 (d, J=6.6 Hz, 6H).

Example 6(38)

3-(2-(((1R)-1-(naphthalen-1-yl)ethyl)carbamoyl)-4-phenoxyphenyl)propanoic acid

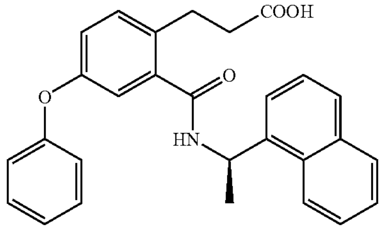

TLC: Rf 0.49 (chloroform:methanol=10:1);

NMR (300 MHz, $CDCl_3$): δ 8.17 (d, J=8.1 Hz, 1H), 7.90-7.76 (m, 2H), 7.60-7.40 (m, 4H), 7.36-7.23 (m, 2H), 7.19 (d, J=8.3 Hz, 1H), 7.10 (m, 1H), 7.00-6.88 (m, 4H), 6.30 (d, J=8.1 Hz, 1H), 6.10 (m, 1H), 3.10-2.98 (m, 2H), 2.80-2.68 (m, 2H), 1.77 (d, J=6.6 Hz, 3H).

Example 6(39)

3-(2-(((1R)-1-(naphthalen-1-yl)ethyl)carbamoyl)-4-(pyridin-2-yloxy)phenyl)propanoic acid

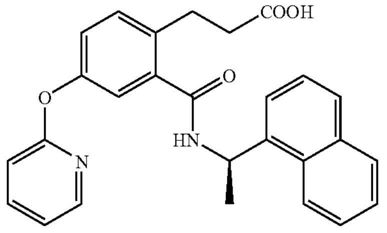

TLC: Rf 0.40 (chloroform:methanol=10:1);

NMR (300 MHz, $CDCl_3$): δ 8.19 (d, J=8.4 Hz, 1H), 8.10 (m, 1H), 7.86 (m, 1H), 7.78 (d, J=7.8 Hz, 1H), 7.68 (m, 1H), 7.59-7.40 (m, 4H), 7.28-7.20 (m, 1H), 7.12-7.04 (m, 2H), 6.99 (m, 1H), 6.89 (d, J=8.4 Hz, 1H), 6.61 (d, J=8.1 Hz, 1H), 6.10 (m, 1H), 3.10-3.00 (m, 2H), 2.76-2.66 (m, 2H), 1.76 (d, J=6.6 Hz, 3H).

Example 6(40)

3-(2-((3-methyl-1-(4-fluorophenyl)butyl)carbamoyl)-4-phenoxymethylphenyl)propanoic acid

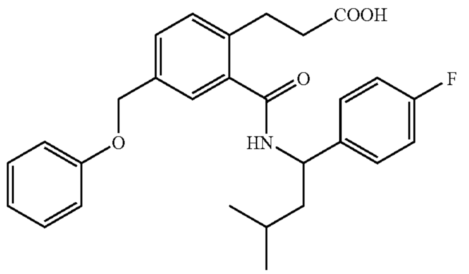

TLC: Rf 0.44 (chloroform:methanol=10:1);

NMR (300 MHz, $CDCl_3$): δ 7.46-7.24 (m, 7H), 7.08-6.93 (m, 5H), 6.40 (d, J=8.4 Hz, 1H), 5.21 (q, J=8.1 Hz, 1H), 5.02 (s, 2H), 3.05-2.95 (m, 2H), 2.76-2.67 (m, 2H), 1.86-1.51 (m, 3H), 0.98 (d, J=6.6 Hz, 6H).

Example 6(41)

3-(2-((3-methyl-1-(4-methylphenyl)butyl)carbamoyl)-4-phenoxymethylphenyl)propanoic acid

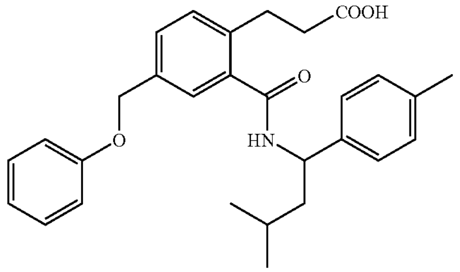

TLC: Rf 0.44 (chloroform:methanol=10:1);

NMR (300 MHz, $CDCl_3$): δ 7.46-7.12 (m, 9H), 7.02-6.92 (m, 3H), 6.33 (d, J=8.4 Hz, 1H), 5.20 (q, J=7.8 Hz, 1H), 5.02 (s, 2H), 3.07-2.95 (m, 2H), 2.78-2.69 (m, 2H), 2.34 (s, 2H), 1.88-1.44 (m, 3H), 0.98 (d, J=6.3 Hz, 6H).

Example 6(42)

3-(2-((3-methyl-1-phenylbutyl)carbamoyl)-4-(pyridin-3-yloxymethyl)phenyl)propanoic acid

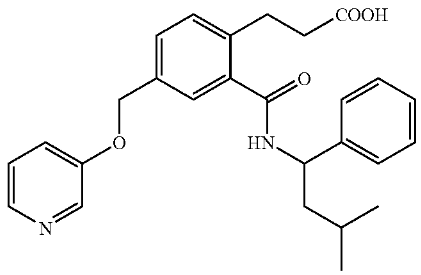

TLC: Rf 0.30 (chloroform:methanol=9:1);

NMR (300 MHz, $CDCl_3$): δ 8.35-8.30 (m, 1H), 8.23 (dd, J=4.2, 1.8 Hz, 1H), 7.44-7.22 (m, 10H), 6.84 (brd, J=9.0 Hz, 1H), 5.24 (q, J=6.9 Hz, 1H), 5.06 (s, 2H), 3.01 (t, J=7.2 Hz, 2H), 2.75 (t, J=7.2 Hz, 2H), 2.30-1.52 (m, 3H), 0.98 (d, J=6.6 Hz, 6H).

Example 6(43)

3-(2-((3-methyl-1-phenylbutyl)carbamoyl)-4-(pyridin-4-yloxymethyl)phenyl)propanoic acid

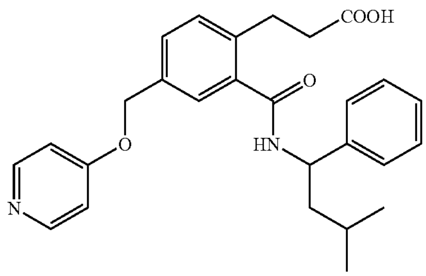

TLC: Rf 0.23 (chloroform:methanol=9:1);

NMR (300 MHz, $CDCl_3$): δ 8.44-8.30 (m, 2H), 7.78 (brd, J=8.1 Hz, 1H), 7.44-7.23 (m, 8H), 6.93-6.82 (m, 2H), 5.24 (q, J=8.1 Hz, 1H), 5.14 (s, 2H), 2.97 (t, J=6.3 Hz, 2H), 2.85-2.74 (m, 2H), 2.30-1.40 (m, 3H), 0.97 (d, J=6.6 Hz, 6H).

Example 6(44)

3-(2-((1-phenylethyl)carbamoyl)-4-phenoxymethylphenyl)propanoic acid

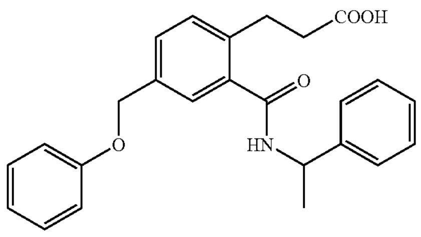

TLC: Rf 0.63 (chloroform:methanol=5:1);

NMR (300 MHz, DMSO-$d_6$): δ 8.92 (d, J=7.8 Hz, 1H), 7.48-7.20 (m, 10H), 7.07-6.91 (m, 3H), 5.13 (m, 1H), 5.09 (s, 2H), 2.87 (t, J=7.9 Hz, 2H), 2.60-2.40 (m, 2H), 1.44 (d, J=7.2 Hz, 3H).

Example 6(45)

3-(2-((3-methyl-1-phenylbutyl)carbamoyl)-4-(pyridin-2-yloxymethyl)phenyl)propanoic acid

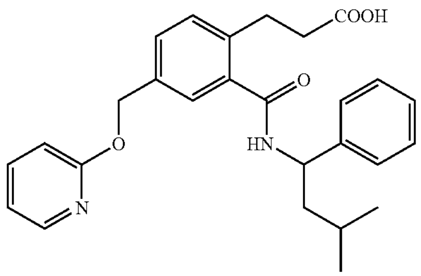

TLC: Rf 0.59 (chloroform:methanol=9:1);

NMR (300 MHz, $CDCl_3$): δ 8.16 (dd, J=5.1, 1.2 Hz, 1H), 7.65-7.55 (m, 1H), 7.50-7.40 (m, 2H), 7.40-7.24 (m, 6H), 6.94-6.86 (m, 1H), 6.79 (d, J=8.4 Hz, 1H), 6.41 (brd, J=8.4 Hz, 1H), 5.34 (s, 2H), 5.24 (q, J=8.4 Hz, 1H), 3.08-2.90 (m, 2H), 2.72 (t, J=7.2 Hz, 2H), 2.00-1.40 (m, 3H), 0.98 (d, J=6.6 Hz, 6H).

Example 6(46)

3-(2-((3-methyl-1-phenylbutyl)carbamoyl)-4-phenylaminomethylphenyl)propanoic acid

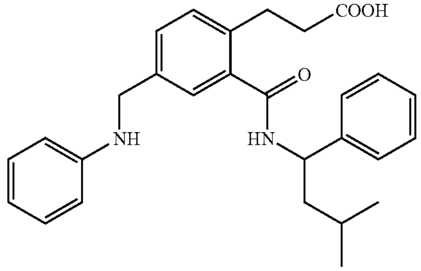

TLC: Rf 0.45 (chloroform:methanol=9:1);

NMR (300 MHz, $CDCl_3$): δ 7.40-7.10 (m, 10H), 6.73 (t, J=7.5 Hz, 1H), 6.61 (d, J=7.5 Hz, 2H), 6.37 (d, J=8.4 Hz, 1H), 5.21 (q, J=7.2 Hz, 1H), 4.29 (s, 2H), 3.05-2.87 (m, 2H), 2.76-2.60 (m, 2H), 1.84-1.47 (m, 3H), 0.96 (d, J=6.6 Hz, 6H).

Example 6(47)

2-(2-((3-methyl-1-phenylbutyl)carbamoyl)-4-phenoxymethylphenoxy)acetic acid

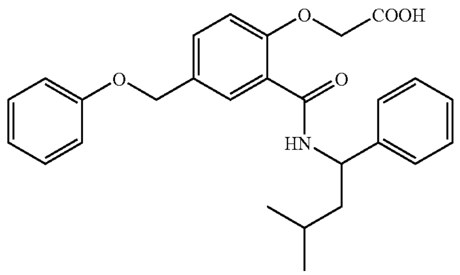

TLC: Rf 0.28 (chloroform:methanol=10:1);

NMR (300 MHz, $CDCl_3$): δ 9.17 (d, J=8.1 Hz, 1H), 7.95 (d, J=2.1 Hz, 1H), 7.54 (dd, J=8.4, 2.1 Hz, 1H), 7.40-7.13 (m, 8H), 7.00-6.87 (m, 3H), 5.12 (m, 1H), 5.05 (s, 2H), 4.92 (s, 2H), 1.84 (m, 1H), 1.68-1.48 (m, 2H), 0.90 (d, J=6.3 Hz, 3H), 0.89 (d, J=6.3 Hz, 3H).

Example 6(48)

3-(2-((1-phenylpropyl)carbamoyl)-4-phenoxymethylphenyl)propanoic acid

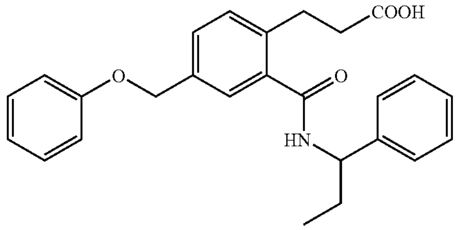

TLC: Rf 0.47 (chloroform:methanol=10:1);

NMR (300 MHz, DMSO-$d_6$): δ 8.83 (d, J=8.4 Hz, 1H), 7.44-7.18 (m, 10H), 7.03-6.90 (m, 3H), 5.08 (s, 2H), 4.86 (m, 1H), 2.84 (t, J=7.8 Hz, 2H), 2.46 (t, J=7.8 Hz, 2H), 1.82-1.64 (m, 2H), 0.90 (t, J=7.5 Hz, 3H).

Example 6(49)

3-(2-((1-phenylbutyl)carbamoyl)-4-phenoxymethylphenyl)propanoic acid

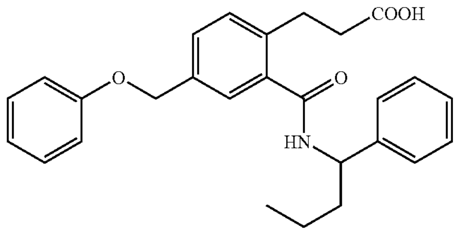

TLC: Rf 0.47 (chloroform:methanol=10:1);

NMR (300 MHz, $CDCl_3$): δ 7.47-7.24 (m, 10H), 7.02-6.91 (m, 3H), 6.41 (d, J=8.1 Hz, 1H), 5.15 (q, J=7.8 Hz, 1H), 5.03 (s, 2H), 3.08-2.97 (m, 2H), 2.78-2.69 (m, 2H), 1.98-1.74 (m, 2H), 1.52-1.23 (m, 2H), 0.96 (t, J=7.2 Hz, 3H).

Example 6(50)

3-(2-((3-methylbutyl)carbamoyl)-4-phenoxymethylphenyl)propanoic acid

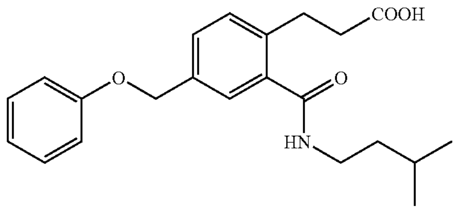

TLC: Rf 0.36 (hexane:ethyl acetate=1:3);

NMR (300 MHz, $CDCl_3$): δ 7.45-7.40 (m, 2H), 7.34-7.26 (m, 3H), 7.02-6.93 (m, 3H), 6.14 (m, 1H), 5.03 (s, 2H), 3.50-3.41 (m, 2H), 3.08 (t, J=7.4 Hz, 2H), 2.79 (t, J=7.4 Hz, 2H), 1.68 (m, 1H), 1.55-1.46 (m, 2H), 0.95 (d, J=6.6 Hz, 6H).

Example 6(51)

3-(2-((3-methyl-1-phenylbutyl)carbamoyl)-4-(pyrimidin-2-yloxymethyl)phenyl)propanoic acid

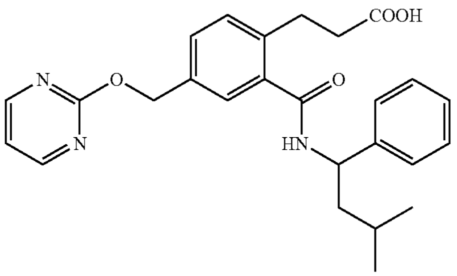

TLC: Rf 0.49 (chloroform:methanol=9:1);

NMR (300 MHz, $CDCl_3$): δ 8.53 (d, J=4.5 Hz, 2H), 7.52-7.46 (m, 2H), 7.40-7.20 (m, 6H), 6.97 (t, J=4.5 Hz, 1H), 6.45 (brd, J=7.8 Hz, 1H), 5.40 (s, 2H), 5.28-5.18 (m, 1H), 3.01 (dt, J=2.7, 7.5 Hz, 2H), 2.72 (t, J=7.5 Hz, 2H), 1.90-1.40 (m, 3H), 0.99 (d, J=6.6 Hz, 6H).

Example 6(52)

3-(2-((3-methyl-1-phenylbutyl)carbamoyl)-4-(pyrazin-2-yloxymethyl)phenyl)propanoic acid

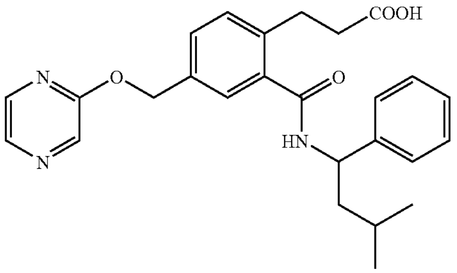

TLC: Rf 0.49 (chloroform:methanol=9:1);

NMR (300 MHz, $CDCl_3$): δ 8.27 (d, J=1.2 Hz, 1H), 8.15 (d, J=2.7 Hz, 1H), 8.09 (dd, J=2.7, 1.2 Hz, 1H), 7.48-7.42 (m, 2H), 7.42-7.24 (m, 6H), 6.44 (brd, J=8.1 Hz, 1H), 5.35 (s, 2H), 5.30-5.20 (m, 1H), 3.06-2.96 (m, 2H), 2.80-2.70 (m, 2H), 1.88-1.40 (m, 3H), 0.99 (d, J=6.6 Hz, 6H).

Example 6(53)

3-(2-((3-methyl-1-phenylbutyl)carbamoyl)-4-(2-methylpyridin-3-yloxymethyl)phenyl)propanoic acid

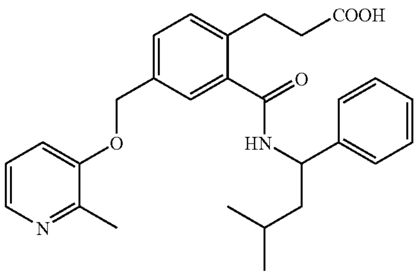

TLC: Rf 0.28 (chloroform:methanol=10:1);

NMR (300 MHz, DMSO-$d_6$): δ 8.00 (dd, J=4.8, 1.2 Hz, 1H), 7.43-7.14 (m, 11H), 5.13 (s, 2H), 5.05 (m, 1H), 2.89-2.76 (m, 2H), 2.48-2.35 (m, 2H), 2.39 (s, 3H), 1.81-1.54 (m, 2H), 1.44 (m, 1H), 0.93 (d, J=6.6 Hz, 3H), 0.90 (d, J=6.6 Hz, 3H).

Example 6(54)

3-(2-((3-methyl-1-phenylbutyl)carbamoyl)-4-phenylthiomethylphenyl)propanoic acid

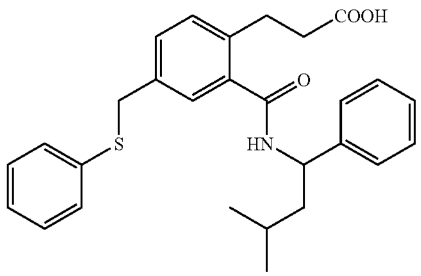

TLC: Rf 0.34 (chloroform:methanol=10:1);

NMR (300 MHz, DMSO-$d_6$): δ 8.75 (d, J=8.7 Hz, 1H), 7.38-7.13 (m, 13H), 5.03 (m, 1H), 4.24 (s, 2H), 2.84-2.73 (m, 2H), 2.47-2.37 (m, 2H), 1.79-1-54 (m, 2H), 1.42 (m, 1H), 0.92 (d, J=6.9 Hz, 3H), 0.90 (d, J=6.9 Hz, 3H).

Example 6(55)

3-(2-((3-methyl-1-phenylbutyl)carbamoyl)-4-(thiazol-2-ylthiomethyl)phenyl)propanoic acid

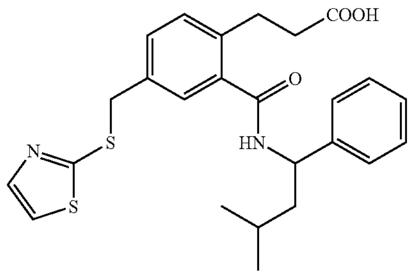

TLC: Rf 0.34 (chloroform:methanol=10:1);

NMR (300 MHz, DMSO-$d_6$): δ 8.77 (d, J=8.7 Hz, 1H), 7.72 (d, J=3.3 Hz, 1H), 7.66 (d, J=3.3 Hz, 1H), 7.39-7.18 (m, 8H), 5.03 (m, 1H), 4.48 (s, 2H), 2.84-2.72 (m, 2H), 2.48-2.38 (m, 2H), 1.79-1-54 (m, 2H), 1.42 (m, 1H), 0.92 (d, J=6.6 Hz, 3H), 0.90 (d, J=6.6 Hz, 3H).

Example 6(56)

3-(2-((3-methyl-1-phenylbutyl)carbamoyl)-4-(1-methylimidazol-2-ylthiomethyl)phenyl)propanoic acid

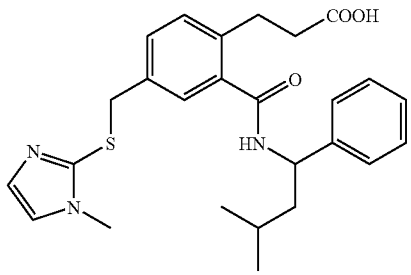

TLC: Rf 0.28 (chloroform:methanol=10:1);

NMR (300 MHz, DMSO-$d_6$): δ 8.70 (d, J=8.1 Hz, 1H), 7.38-7.14 (m, 8H), 7.08 (s, 1H), 6.93 (t, J=1.2 Hz, 1H), 5.02 (m, 1H), 4.18 (s, 2H), 3.37 (s, 3H), 2.85-2.73 (m, 2H), 2.48-

2.37 (m, 2H), 1.80-1-55 (m, 2H), 1.43 (m, 1H), 0.93 (d, J=6.6 Hz, 3H), 0.90 (d, J=6.6 Hz, 3H).

Example 6(57)

3-(2-((2-cyclopropyl-1-phenylethyl)carbamoyl)-4-phenoxymethylphenyl)propanoic acid

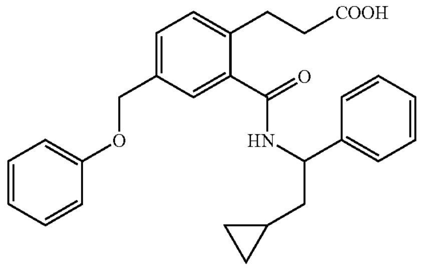

[Salt-free]

TLC: Rf 0.37 (chloroform:methanol=9:1);

NMR (300 MHz, $CDCl_3$): δ 7.74 (m, 1H), 7.48-7.22 (m, 9H), 7.00-6.93 (m, 3H), 6.62 (d, J=7.2 Hz, 1H), 5.25 (dt, J=7.2, 7.5 Hz, 1H), 5.02 (s, 2H), 3.03 (t, J=7.2 Hz, 2H), 2.74 (t, J=7.2 Hz, 2H), 1.88-1.72 (m, 2H), 0.66 (m, 1H), 0.55-0.40 (m, 2H), 0.20-0.01 (m, 2H).

Sodium Salt:

TLC: Rf 0.44 (chloroform:methanol=9:1).

Example 6(58)

3-(2-((3-methyl-1-phenylbutyl)carbamoyl)-4-benzyloxyphenyl)propanoic acid

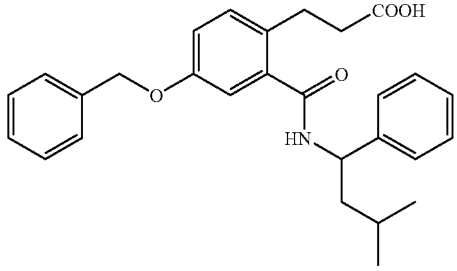

TLC: Rf 0.41 (chloroform:methanol=9:1);

NMR (300 MHz, $CDCl_3$): δ 7.44-7.24 (m, 10H), 7.18 (d, J=9.0 Hz, 1H), 7.00-6.92 (m, 2H), 6.32 (brd, J=8.4 Hz, 1H), 5.26-5.16 (m, 1H), 5.04 (s, 2H), 3.00-2.90 (m, 2H), 2.70 (t, J=6.9 Hz, 2H), 1.84-1.44 (m, 3H), 0.98 (d, J=6.6 Hz, 6H).

Example 6(59)

3-(2-((3-methyl-1-phenylbutyl)carbamoyl)-4-(2-methylphenoxymethyl)phenyl)propanoic acid

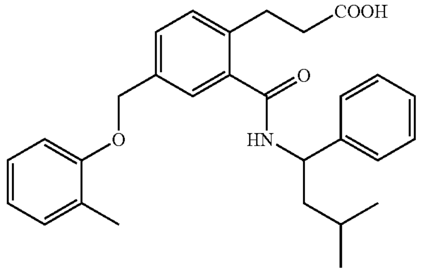

TLC: Rf 0.55 (chloroform:methanol=9:1);

NMR (300 MHz, $CDCl_3$): δ 7.50-7.24 (m, 8H), 7.22-7.10 (m, 2H), 6.95-6.80 (m, 2H), 6.34 (brd, J=8.1 Hz, 1H), 5.30-5.20 (m, 1H), 5.05 (s, 2H), 3.10-2.95 (m, 2H), 2.74 (t, J=7.8 Hz, 2H), 2.27 (s, 3H), 1.90-1.50 (m, 3H), 1.00 (d, J=6.6 Hz, 3H), 0.99 (d, J=6.6 Hz, 3H).

Example 6(60)

3-(2-((3-methyl-1-phenylbutyl)carbamoyl)-4-(2-methoxyphenoxymethyl)phenyl)propanoic acid

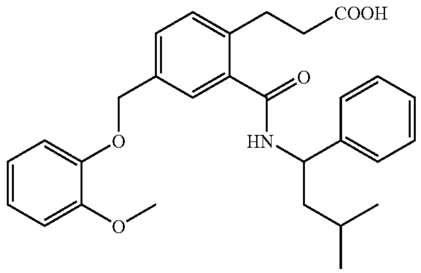

TLC: Rf 0.48 (chloroform:methanol=9:1);

NMR (300 MHz, $CDCl_3$): δ 7.48-7.24 (m, 8H), 7.00-6.84 (m, 4H), 6.44 (brd, J=8.4 Hz, 1H), 5.30-5.15 (m, 1H), 5.09 (s, 2H), 3.86 (s, 3H), 3.08-2.95 (m, 2H), 2.72 (t, J=7.8 Hz, 2H), 1.90-1.50 (m, 3H), 0.98 (d, J=6.6 Hz, 6H).

Example 6(61)

3-(2-((3-methyl-1-phenylbutyl)carbamoyl)-4-(2-hydroxyphenoxymethyl)phenyl)propanoic acid

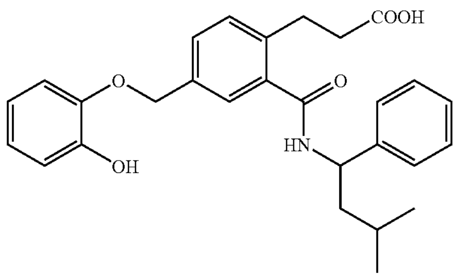

TLC: Rf 0.44 (chloroform:methanol=9:1);

NMR (300 MHz, $CDCl_3$): δ 7.45-7.24 (m, 8H), 7.00-6.80 (m, 4H), 6.43 (brd, J=8.1 Hz, 1H), 5.80-5.50 (brs, 1H), 5.30-5.20 (m, 1H), 5.07 (s, 2H), 3.10-2.97 (m, 2H), 2.74 (t, J=7.2 Hz, 2H), 1.90-1.50 (m, 3H), 0.99 (d, J=6.6 Hz, 6H).

Example 6(62)

3-(2-((2-phenylethyl)carbamoyl)-4-phenoxymethylphenyl)propanoic acid

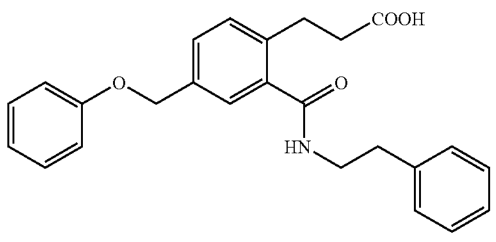

TLC: Rf 0.42 (chloroform:methanol=10:1);

NMR (300 MHz, $CDCl_3$): δ 7.42-7.20 (m, 10H), 7.00-6.90 (m, 3H), 6.25 (m, 1H), 4.98 (s, 2H), 3.72 (dt, J=6.9, 6.0 Hz, 2H), 3.01 (t, J=7.2 Hz, 2H), 2.94 (t, J=6.9 Hz, 2H), 2.74 (t, J=7.2 Hz, 2H).

Example 6(63)

3-(2-benzylcarbamoyl-4-phenoxymethylphenyl)propanoic acid

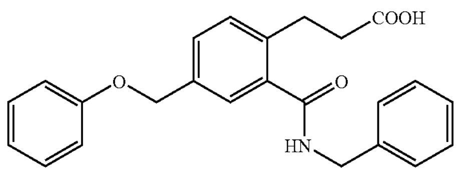

TLC: Rf 0.42 (chloroform:methanol=10:1);

NMR (300 MHz, $CDCl_3$): δ 7.46-7.25 (m, 10H), 6.99-6.92 (m, 3H), 6.48 (m, 1H), 5.00 (s, 2H), 4.61 (d, J=5.7 Hz, 2H), 3.10 (t, J=7.5 Hz, 2H), 2.77 (t, J=7.5 Hz, 2H).

Example 6(64)

3-(2-((3-methyl-1-phenyl-3-butenyl)carbamoyl)-4-phenoxymethylphenyl)propanoic acid

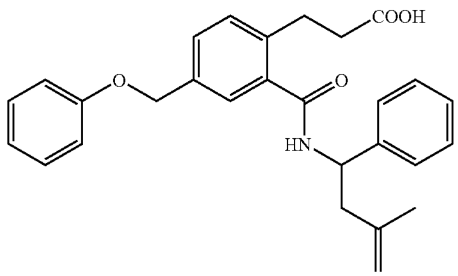

TLC: Rf 0.49 (chloroform:methanol=9:1);

NMR (300 MHz, $CDCl_3$): δ 7.46-7.24 (m, 10H), 7.04-6.92 (m, 3H), 6.43 (brd, J=7.5 Hz, 1H), 5.42-5.32 (m, 1H), 5.04 (s, 2H), 4.86 (brs, 1H), 4.79 (brs, 1H), 3.04 (t, J=7.2 Hz, 2H), 2.74 (t, J=7.2 Hz, 2H), 2.64-2.50 (m, 2H), 1.81 (s, 3H).

Example 6(65)

3-(2-phenylcarbamoyl-4-phenoxymethylphenyl)propanoic acid

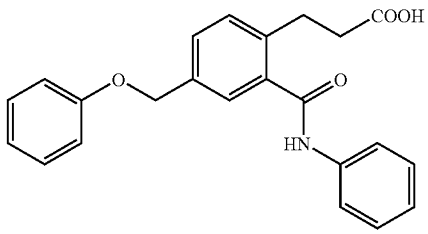

TLC: Rf 0.42 (chloroform:methanol=10:1);

NMR (300 MHz, $CDCl_3$+$CD_3OD$): δ 7.70-7.61 (m, 3H), 7.46 (m, 1H), 7.39-7.27 (m, 5H), 7.14 (m, 1H), 7.00-6.95 (m, 3H), 5.06 (s, 2H), 3.11 (t, J=6.9 Hz, 2H), 2.83 (t, J=6.9 Hz, 2H).

Example 6(66)

3-(2-((3-methyl-1-(4-trifluoromethylphenyl)butyl)carbamoyl)-4-phenoxymethylphenyl)propanoic acid

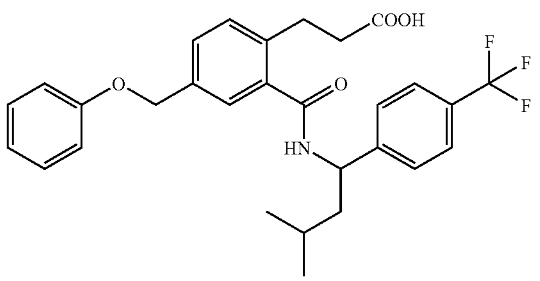

TLC: Rf 0.39 (chloroform:methanol=19:1);

NMR (300 MHz, $CDCl_3$): δ 7.61 (d, J=8.1 Hz, 2H), 7.51-7.40 (m, 4H), 7.35-7.25 (m, 3H), 7.02-6.93 (m, 3H), 6.54 (d, J=8.1 Hz, 1H), 5.26 (m, 1H), 5.03 (s, 2H), 3.01 (t, J=7.2 Hz, 2H), 2.76-2.68 (m, 2H), 1.84-1.55 (m, 3H), 0.99 (d, J=6.3 Hz, 3H), 0.98 (d, J=6.3 Hz, 3H).

Example 6(67)

3-(2-((3-methyl-1-(4-ethoxyphenyl)butyl)carbamoyl)-4-phenoxymethylphenyl)propanoic acid

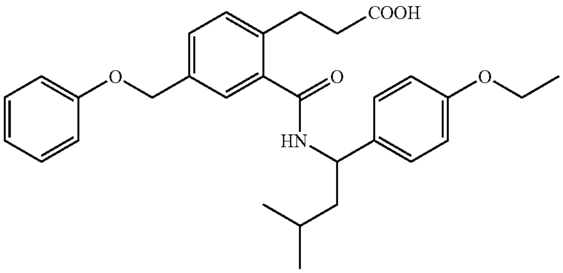

TLC: Rf 0.40 (chloroform:methanol=19:1);

NMR (300 MHz, $CDCl_3$): δ 7.45-7.37 (m, 2H), 7.34-7.24 (m, 5H), 7.02-6.92 (m, 3H), 6.87 (d, J=8.4 Hz, 2H), 6.31 (d, J=8.4 Hz, 1H), 5.18 (m, 1H), 5.01 (s, 2H), 4.02 (q, J=6.9 Hz, 2H), 3.06-2.98 (m, 2H), 2.76-2.68 (m, 2H), 1.85-1.50 (m, 3H), 1.40 (t, J=6.9 Hz, 3H), 0.97 (d, J=6.6 Hz, 6H).

Example 6(68)

3-(2-((3-methyl-1-(3-methylphenyl)butyl)carbamoyl)-4-phenoxymethylphenyl)propanoic acid

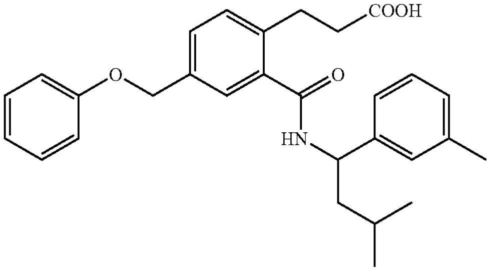

TLC: Rf 0.40 (chloroform:methanol=9:1).

Example 6(69)

3-(2-((3-methyl-1-(3-chlorophenyl)butyl)carbamoyl)-4-phenoxymethylphenyl)propanoic acid

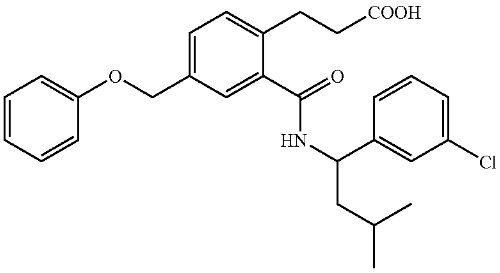

TLC: Rf 0.40 (chloroform:methanol=9:1).

Example 6(70)

3-(2-((3-methyl-1-(4-chlorophenyl)butyl)carbamoyl)-4-phenoxymethylphenyl)propanoic acid

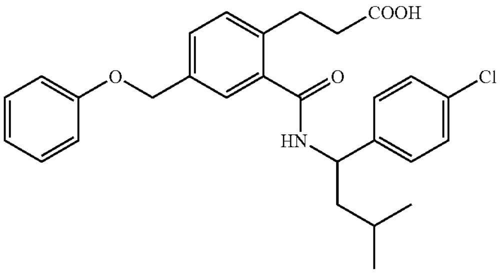

TLC: Rf 0.40 (chloroform:methanol=9:1).

Example 6(71)

3-(2-((3-methyl-1-(3-trifluoromethylphenyl)butyl)carbamoyl)-4-phenoxymethylphenyl)propanoic acid

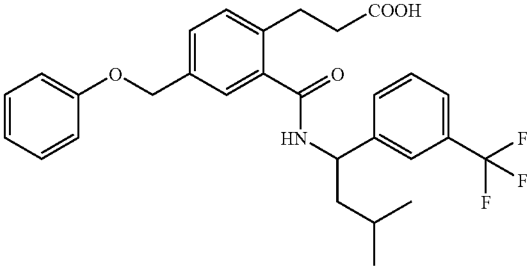

TLC: Rf 0.40 (chloroform:methanol=9:1).

Example 6(72)

3-(2-((3-methyl-1-(3-chloro-4-fluorophenyl)butyl)carbamoyl)-4-phenoxymethylphenyl)propanoic acid

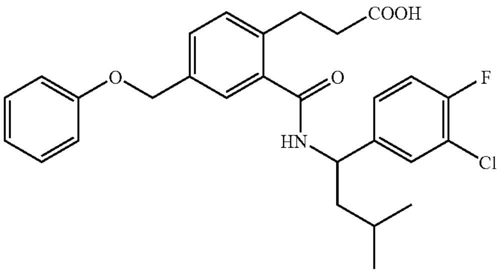

TLC: Rf 0.40 (chloroform:methanol=9:1).

Example 6(73)

3-(2-((3-methyl-1-(3-fluorophenyl)butyl)carbamoyl)-4-phenoxymethylphenyl)propanoic acid

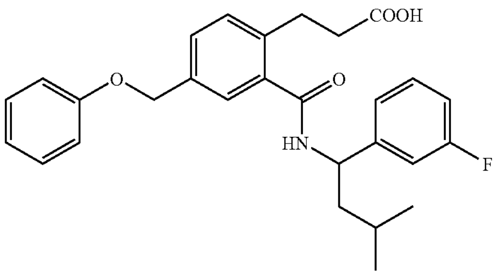

TLC: Rf 0.53 (chloroform:methanol=9:1).

Example 6(74)

3-(2-((3-methyl-1-(3,4,5-trifluorophenyl)butyl)carbamoyl)-4-phenoxymethylphenyl)propanoic acid

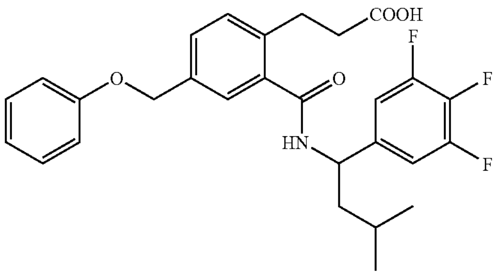

TLC: Rf 0.53 (chloroform:methanol=9:1).

Example 6(75)

3-(2-((3-methyl-1-(3,5-ditrifluoromethylphenyl)butyl)carbamoyl)-4-phenoxymethylphenyl)propanoic acid

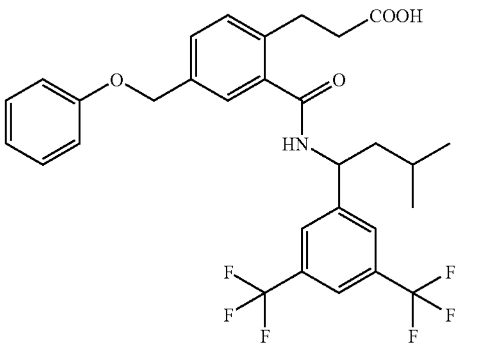

TLC: Rf 0.53 (chloroform:methanol=9:1).

Example 6(76)

3-(2-((3-methyl-1-(3-methoxyphenyl)butyl)carbamoyl)-4-phenoxymethylphenyl)propanoic acid

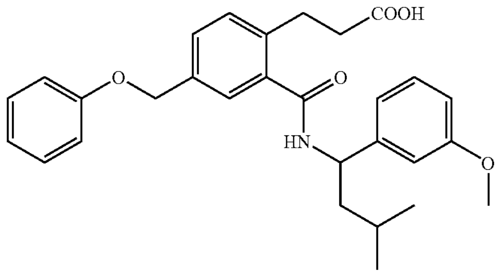

TLC: Rf 0.53 (chloroform:methanol=9:1).

Example 6(77)

3-(2-((3-methyl-1-(4-ethylphenyl)butyl)carbamoyl)-4-phenoxymethylphenyl)propanoic acid

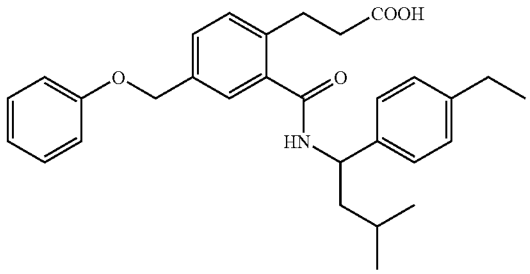

TLC: Rf 0.53 (chloroform:methanol=9:1).

Example 6(78)

3-(2-((3-methyl-1-(4-butylphenyl)butyl)carbamoyl)-4-phenoxymethylphenyl)propanoic acid

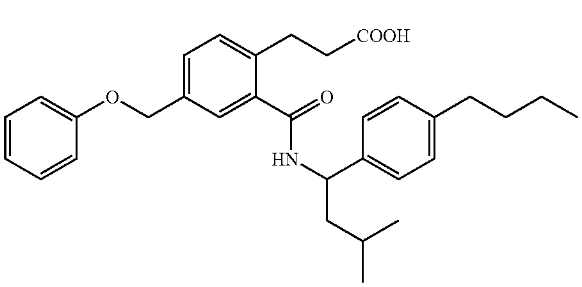

TLC: Rf 0.53 (chloroform:methanol=9:1).

Example 6(79)

3-(2-((3-methyl-1-(4-fluoro-3-methylphenyl)butyl)carbamoyl)-4-phenoxymethylphenyl)propanoic acid

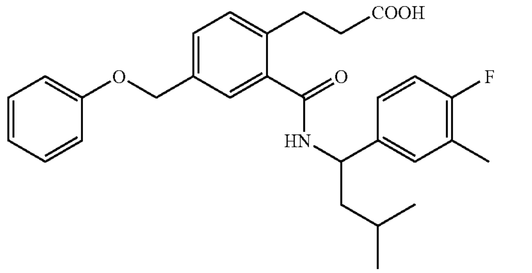

TLC: Rf 0.53 (chloroform:methanol=9:1).

Example 6(80)

3-(2-((3-methyl-1-(3-fluoro-4-methoxyphenyl)butyl)carbamoyl)-4-phenoxymethylphenyl)propanoic acid

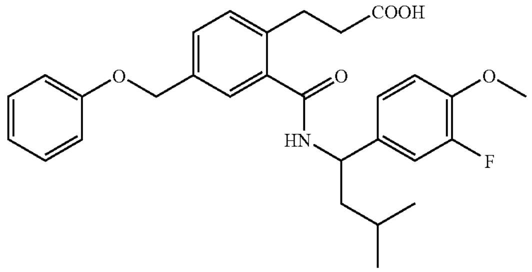

TLC: Rf 0.53 (chloroform:methanol=9:1).

Example 6(81)

3-(2-((3-methyl-1-(3-fluoro-4-methylphenyl)butyl)carbamoyl)-4-phenoxymethylphenyl)propanoic acid

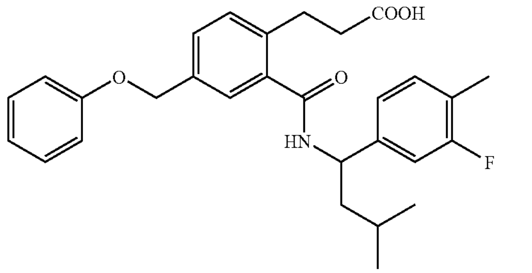

TLC: Rf 0.53 (chloroform:methanol=9:1).

Example 6(82)

3-(2-((3-methyl-1-(4-chloro-3-fluorophenyl)butyl)carbamoyl)-4-phenoxymethylphenyl)propanoic acid

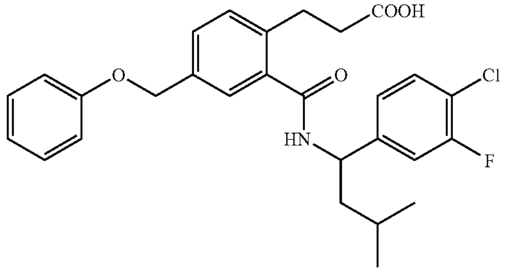

TLC: Rf 0.53 (chloroform:methanol=9:1).

Example 6(83)

3-(2-((3-methyl-1-(4-fluorophenyl)butyl)carbamoyl)-4-(2-methylphenoxymethyl)phenyl)propanoic acid

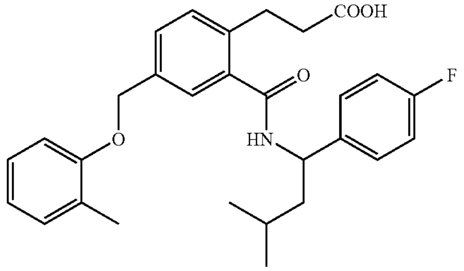

TLC: Rf 0.69 (chloroform:methanol=10:1).

Example 6(84)

3-(2-((3-methyl-1-(4-fluorophenyl)butyl)carbamoyl)-4-(2-chlorophenoxymethyl)phenyl)propanoic acid

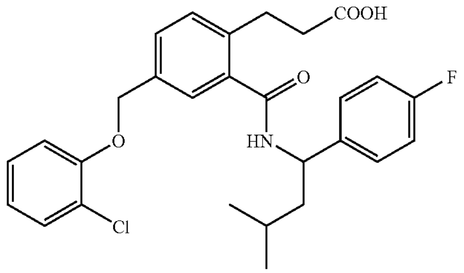

TLC: Rf 0.67 (chloroform:methanol=10:1).

Example 6(85)

3-(2-((3-methyl-1-(4-fluorophenyl)butyl)carbamoyl)-4-(2-methoxyphenoxymethyl)phenyl)propanoic acid

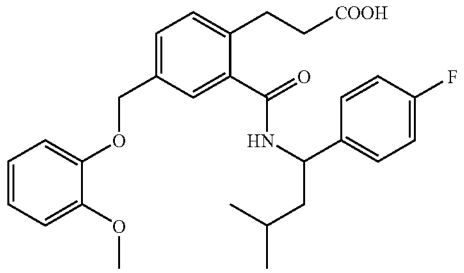

TLC: Rf 0.66 (chloroform:methanol=10:1).

Example 6(86)

3-(2-((3-methyl-1-(4-fluorophenyl)butyl)carbamoyl)-4-(3-cyanophenoxymethyl)phenyl)propanoic acid

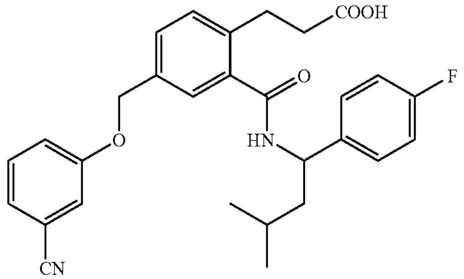

TLC: Rf 0.64 (chloroform:methanol=10:1).

Example 6(87)

3-(2-((3-methyl-1-(4-fluorophenyl)butyl)carbamoyl)-4-(2-chloro-5-methylphenoxymethyl)phenyl)propanoic acid

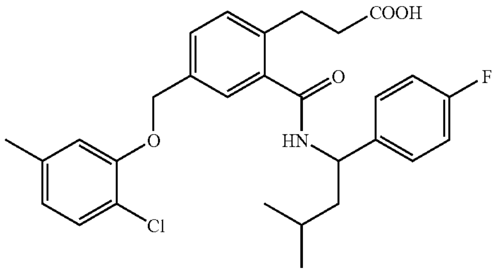

TLC: Rf 0.66 (chloroform:methanol=10:1).

Example 6(88)

3-(2-((3-methyl-1-(4-fluorophenyl)butyl)carbamoyl)-4-(pyridin-3-yloxymethyl)phenyl)propanoic acid

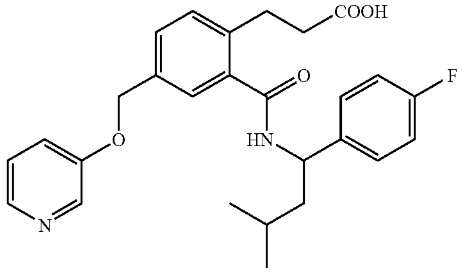

TLC: Rf 0.52 (chloroform:methanol=10:1).

Example 6(89)

3-(2-((3-methyl-1-(4-fluorophenyl)butyl)carbamoyl)-4-(pyrazol-1-ylmethyl)phenyl)propanoic acid

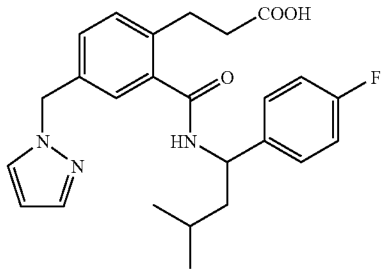

TLC: Rf 0.60 (chloroform:methanol=10:1).

Example 6(90)

3-(2-((3-methyl-1-(4-t-butylphenyl)butyl)carbamoyl)-4-phenoxymethylphenyl)propanoic acid

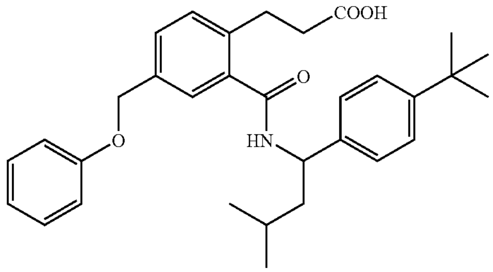

TLC: Rf 0.72 (chloroform:methanol=10:1).

Example 6(91)

3-(2-((3-methyl-1-(2-methoxyphenyl)butyl)carbamoyl)-4-phenoxymethylphenyl)propanoic acid

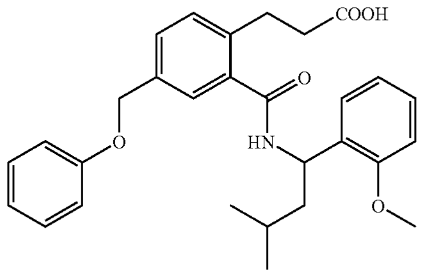

TLC: Rf 0.68 (chloroform:methanol=10:1).

Example 6(92)

3-(2-((3-methyl-1-(4-fluoro-2-methylphenyl)butyl)carbamoyl)-4-phenoxymethylphenyl)propanoic acid

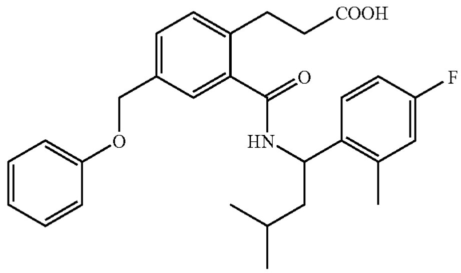

TLC: Rf 0.68 (chloroform:methanol=10:1).

Example 6(93)

3-(2-((3-methyl-1-(3-ethylphenyl)butyl)carbamoyl)-4-phenoxymethylphenyl)propanoic acid

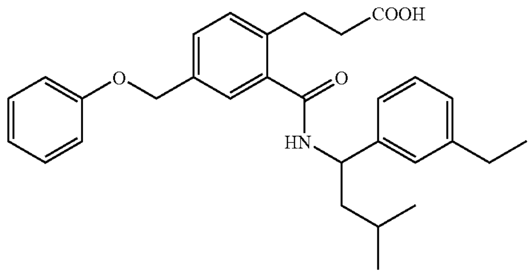

TLC: Rf 0.53 (chloroform:methanol=9:1).

Example 6(94)

3-(2-((3-methyl-1-(3,5-dimethylphenyl)butyl)carbamoyl)-4-phenoxymethylphenyl)propanoic acid

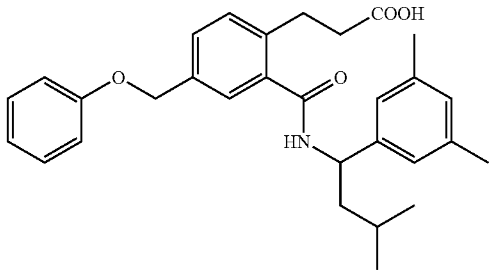

TLC: Rf 0.53 (chloroform:methanol=9:1).

Example 6(95)

3-(2-((3-methyl-1-(3,5-dimethyl-4-methoxyphenyl)butyl)carbamoyl)-4-phenoxymethylphenyl)propanoic acid

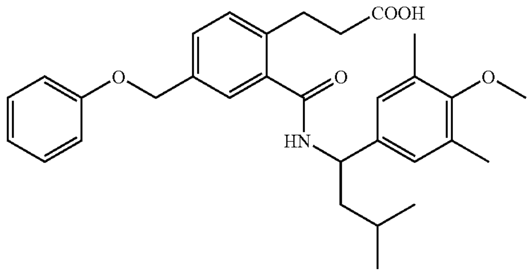

TLC: Rf 0.53 (chloroform:methanol=9:1).

Example 6(96)

3-(2-((3-methyl-1-(5-methyl-2-methoxyphenyl)butyl)carbamoyl)-4-phenoxymethylphenyl)propanoic acid

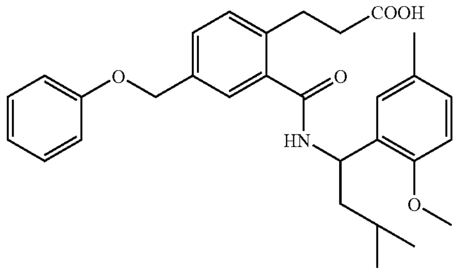

TLC: Rf 0.53 (chloroform:methanol=9:1).

Example 6(97)

3-(2-((3-methyl-1-(4-propylphenyl)butyl)carbamoyl)-4-phenoxymethylphenyl)propanoic acid

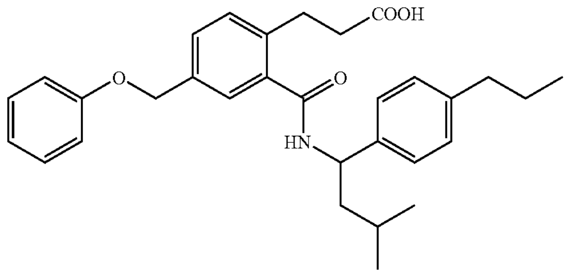

TLC: Rf 0.53 (chloroform:methanol=9:1).

Example 6(98)

3-(2-((3-methyl-1-(3-trifluoromethoxyphenyl)butyl) carbamoyl)-4-phenoxymethylphenyl)propanoic acid

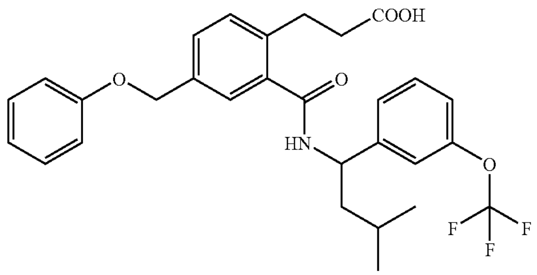

TLC: Rf 0.53 (chloroform:methanol=9:1).

Example 6(99)

3-(2-((3-methyl-1-(3-isopropylphenyl)butyl)carbamoyl)-4-phenoxymethylphenyl)propanoic acid

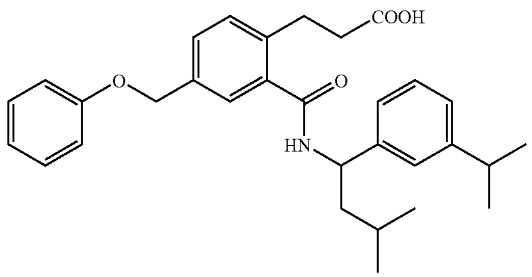

TLC: Rf 0.53 (chloroform:methanol=9:1).

Example 6(100)

3-(2-((3-methyl-1-(3-isopropyloxyphenyl)butyl)carbamoyl)-4-phenoxymethylphenyl)propanoic acid

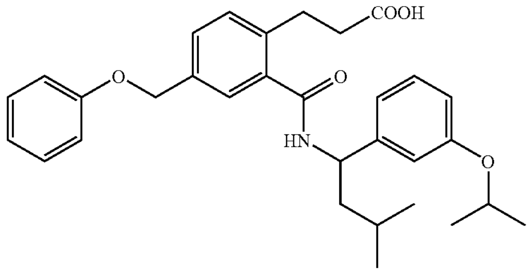

TLC: Rf 0.53 (chloroform:methanol=9:1).

Example 6(101)

3-(2-((3-methyl-1-(1,3-dioxaindan-5-yl)butyl)carbamoyl)-4-phenoxymethylphenyl)propanoic acid

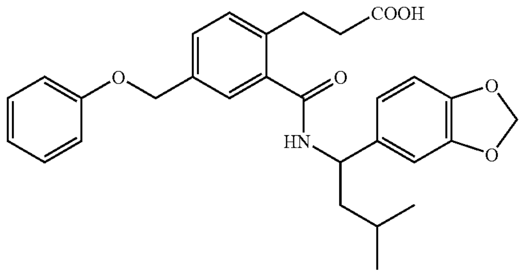

TLC: Rf 0.53 (chloroform:methanol=9:1).

Example 6(102)

3-(2-((3-methyl-1-(4-propoxyphenyl)butyl)carbamoyl)-4-phenoxymethylphenyl)propanoic acid

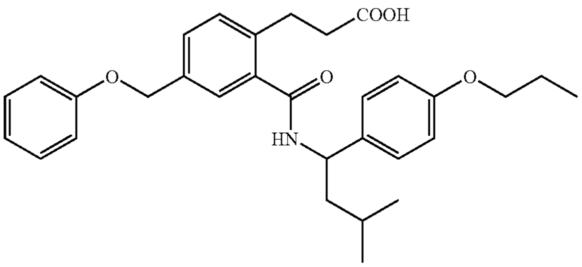

TLC: Rf 0.53 (chloroform:methanol=9:1).

Example 6(103)

3-(2-((3-methyl-1-(2-fluoro-4-trifluoromethylphenyl)butyl)carbamoyl)-4-phenoxymethylphenyl)propanoic acid

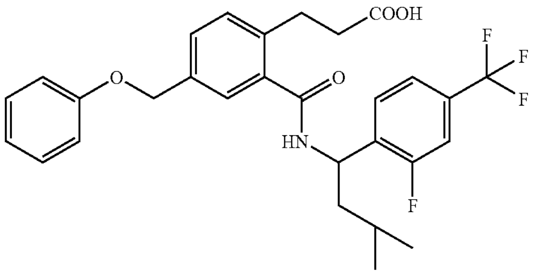

TLC: Rf 0.53 (chloroform:methanol=9:1).

Example 6(104)

3-(2-((3-methyl-1-(4-trifluoromethoxyphenyl)butyl)carbamoyl)-4-phenoxymethylphenyl)propanoic acid

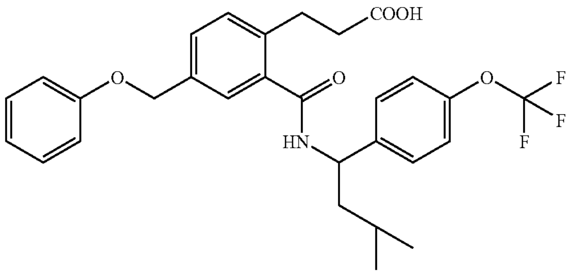

TLC: Rf 0.53 (chloroform:methanol=9:1).

Example 6(105)

3-(2-((3-methyl-1-(2,5-dimethoxyphenyl)butyl)carbamoyl)-4-phenoxymethylphenyl)propanoic acid

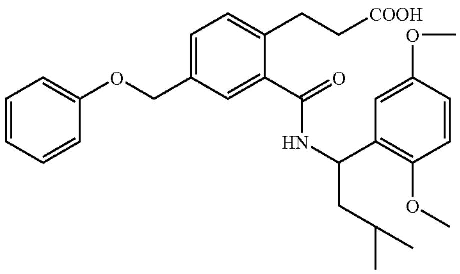

TLC: Rf 0.53 (chloroform:methanol=9:1).

Example 6(106)

3-(2-((3-methyl-1-(1,4-benzodioxan-6-yl)butyl)carbamoyl)-4-phenoxymethylphenyl)propanoic acid

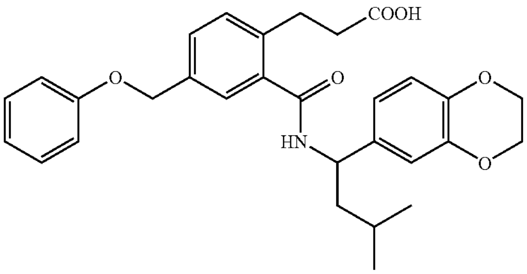

TLC: Rf 0.53 (chloroform:methanol=9:1).

Example 6(107)

3-(2-((3-methyl-1-(4-difluoromethoxyphenyl)butyl)carbamoyl)-4-phenoxymethylphenyl)propanoic acid

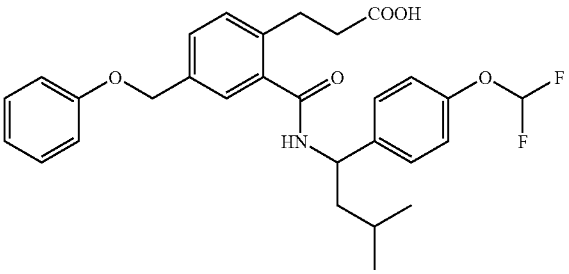

TLC: Rf 0.53 (chloroform:methanol=9:1).

Example 6(108)

3-(2-((3-methyl-1-(3,4,5-trimethoxyphenyl)butyl)carbamoyl)-4-phenoxymethylphenyl)propanoic acid

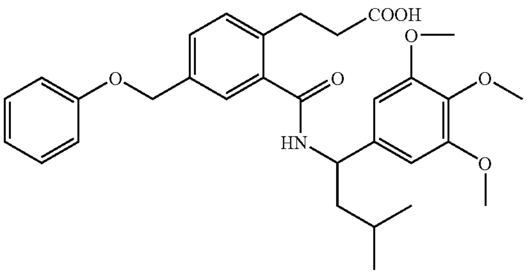

TLC: Rf 0.53 (chloroform:methanol=9:1).

Example 6(109)

3-(2-((3-methyl-1-(2-chloro-3,4-dimethoxyphenyl)butyl)carbamoyl)-4-phenoxymethylphenyl)propanoic acid

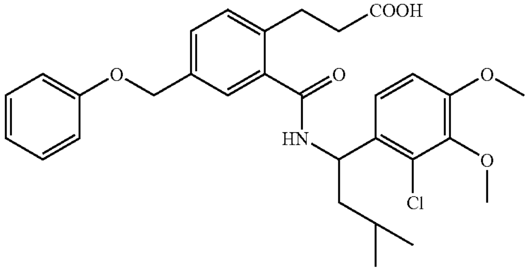

TLC: Rf 0.53 (chloroform:methanol=9:1).

Example 6(110)

3-(2-((3-methyl-1-(4-isobutylphenyl)butyl)carbamoyl)-4-phenoxymethylphenyl)propanoic acid

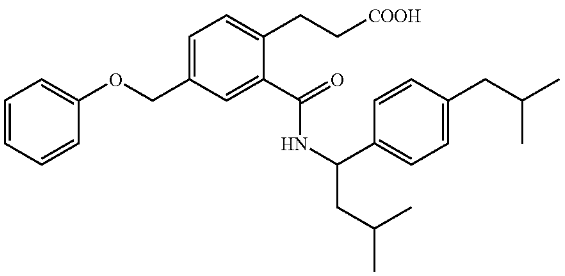

TLC: Rf 0.53 (chloroform:methanol=9:1).

Example 6(111)

3-(2-((3-methyl-1-(2-fluoro-5-trifluoromethylphenyl)butyl)carbamoyl)-4-phenoxymethylphenyl)propanoic acid

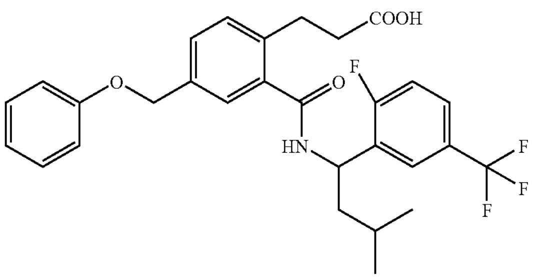

TLC: Rf 0.53 (chloroform:methanol=9:1).

Example 6(112)

3-(2-((3-methyl-1-(2-chloro-6-fluorophenyl)butyl)carbamoyl)-4-phenoxymethylphenyl)propanoic acid

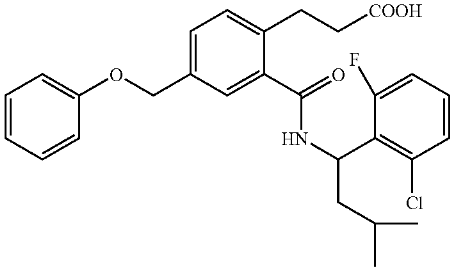

TLC: Rf 0.53 (chloroform:methanol=9:1).

Example 6(113)

3-(2-((3-methyl-1-(2-chloro-5-trifluoromethylphenyl)butyl)carbamoyl)-4-phenoxymethylphenyl)propanoic acid

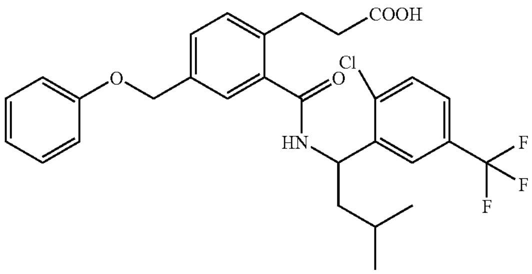

TLC: Rf 0.53 (chloroform:methanol=9:1).

Example 6(114)

3-(2-((3-methyl-1-(2-fluorophenyl)butyl)carbamoyl)-4-phenoxymethylphenyl)propanoic acid

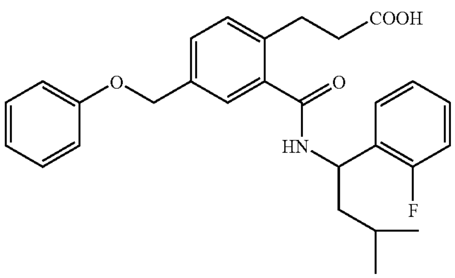

TLC: Rf 0.53 (chloroform:methanol=9:1).

Example 6(115)

2-(2-((3-methyl-1-phenylbutyl)carbamoyl)-4-(2-methylphenoxymethyl)phenoxy)acetic acid

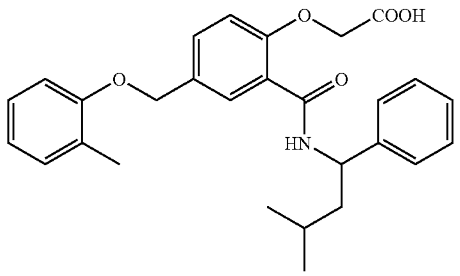

TLC: Rf 0.50 (ethyl acetate:methanol=5:1).

Example 6(116)

2-(2-((3-methyl-1-phenylbutyl)carbamoyl)-4-(2-methoxyphenoxymethyl)phenoxy)acetic acid

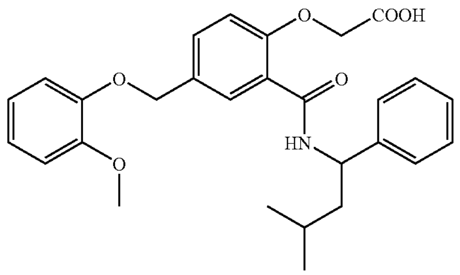

TLC: Rf 0.40 (ethyl acetate:methanol=5:1).

Example 6(117)

3-(2-((3-methyl-1-(4-acetylaminophenyl)butyl)carbamoyl)-4-phenoxymethylphenyl)propanoic acid

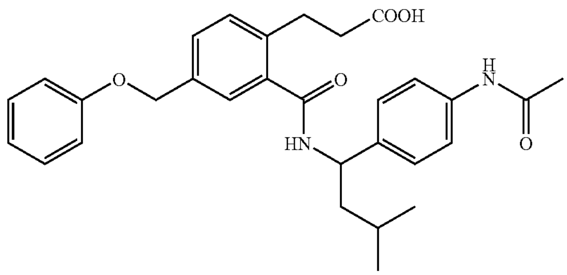

TLC: Rf 0.10 (chloroform:methanol=9:1).

Example 6(118)

3-(2-((3-methyl-1-(3-fluoro-4-trifluoromethylphenyl)butyl)carbamoyl)-4-phenoxymethylphenyl)propanoic acid

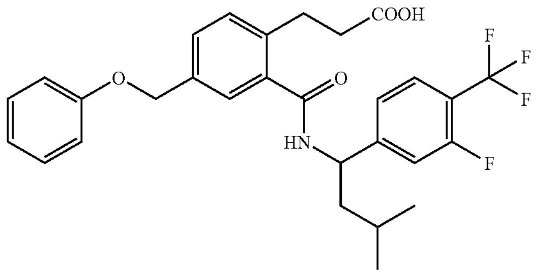

TLC: Rf 0.53 (chloroform:methanol=9:1).

Example 6(119)

3-(2-((3-methyl-1-(4,5-dimethoxy-2-fluorophenyl)butyl)carbamoyl)-4-phenoxymethylphenyl)propanoic acid

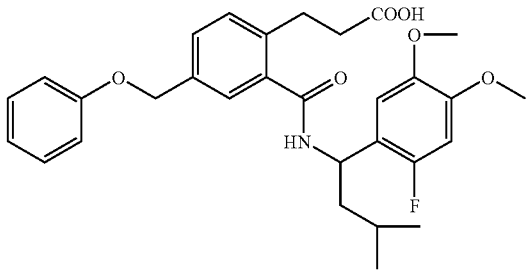

TLC: Rf 0.53 (chloroform:methanol=9:1).

Example 6(120)

3-(2-((3-methyl-1-(2-fluoro-4-methoxyphenyl)butyl)carbamoyl)-4-phenoxymethylphenyl)propanoic acid

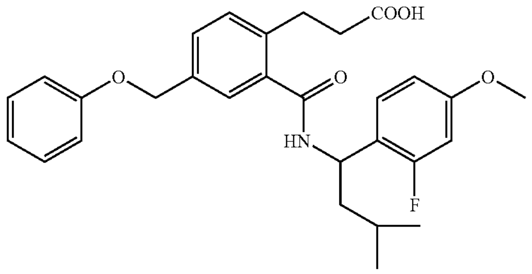

TLC: Rf 0.53 (chloroform:methanol=9:1).

Example 6(121)

3-(2-((3-methyl-1-(3,4-difluorophenyl)butyl)carbamoyl)-4-phenoxymethylphenyl)propanoic acid

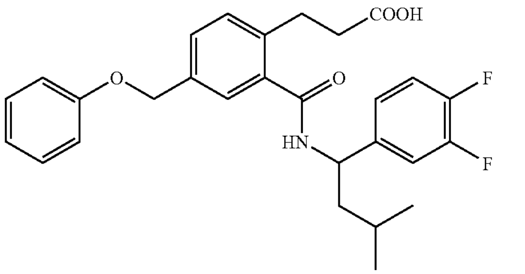

TLC: Rf 0.53 (chloroform:methanol=9:1).

Example 6(122)

3-(2-((3-methyl-1-(4-methoxy-1,3-dioxaindan-6-yl)butyl)carbamoyl)-4-phenoxymethylphenyl)propanoic acid

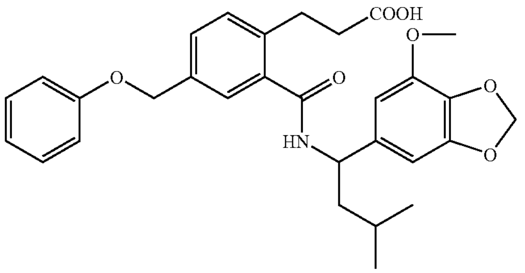

TLC: Rf 0.53 (chloroform:methanol=9:1).

Example 6(123)

3-(2-((3-methyl-1-(3-ethoxyphenyl)butyl)carbamoyl)-4-phenoxymethylphenyl)propanoic acid

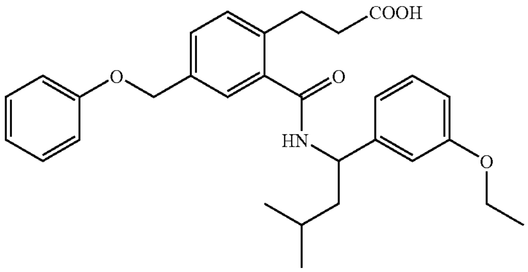

TLC: Rf 0.59 (chloroform:methanol=10:1).

Example 6(124)

3-(2-((3-methyl-1-(4-trifluoromethylthiophenyl)butyl)carbamoyl)-4-phenoxymethylphenyl)propanoic acid

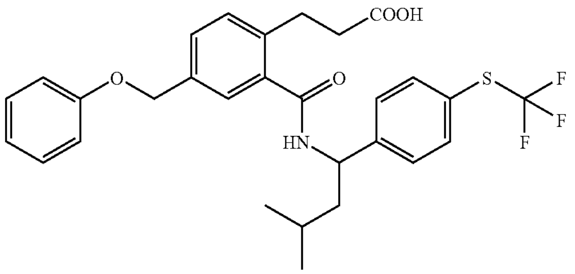

TLC: Rf 0.42 (chloroform:methanol=10:1).

Example 6(125)

3-(2-((3-methyl-1-(2-difluoromethoxyphenyl)butyl)carbamoyl)-4-phenoxymethylphenyl)propanoic acid

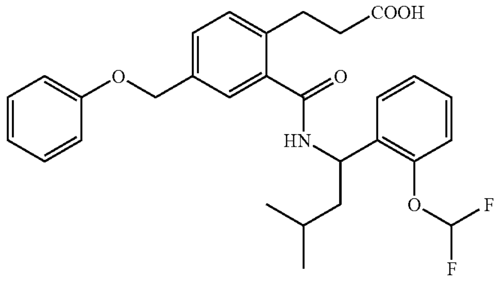

TLC: Rf 0.38 (chloroform:methanol=10:1).

Example 6(126)

3-(2-((3-methyl-1-(2,3,5,6-tetrafluorophenyl)butyl)carbamoyl)-4-phenoxymethylphenyl)propanoic acid

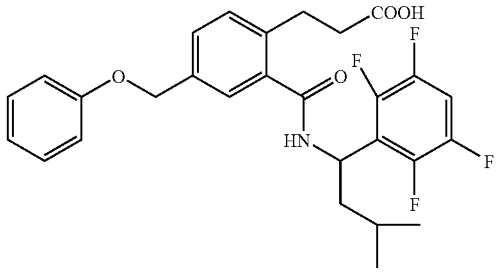

TLC: Rf 0.53 (chloroform:methanol=9:1).

Example 6(127)

3-(2-((3-methyl-1-(2-trifluoromethylphenyl)butyl)carbamoyl)-4-phenoxymethylphenyl)propanoic acid

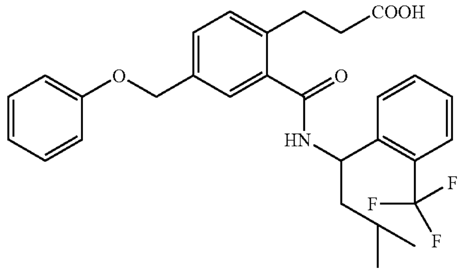

TLC: Rf 0.53 (chloroform:methanol=9:1).

Example 6(128)

3-(2-((3-methyl-1-(2,5-difluorophenyl)butyl)carbamoyl)-4-phenoxymethylphenyl)propanoic acid

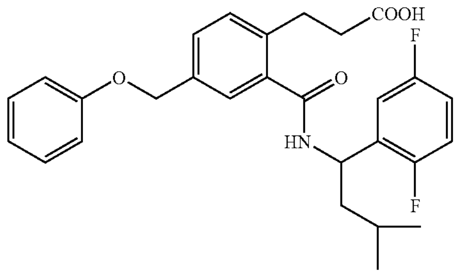

TLC: Rf 0.53 (chloroform:methanol=9:1).

Example 6(129)

3-(2-((3-methyl-1-(2-fluoro-5-methoxyphenyl)butyl)carbamoyl)-4-phenoxymethylphenyl)propanoic acid

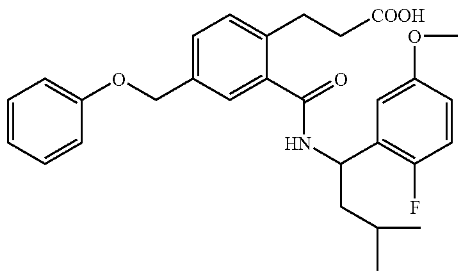

TLC: Rf 0.53 (chloroform:methanol=9:1).

Example 6(130)

3-(2-((3-methyl-1-(3,4-dimethylphenyl)butyl)carbamoyl)-4-phenoxymethylphenyl)propanoic acid

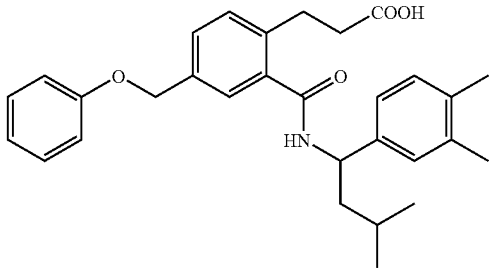

TLC: Rf 0.53 (chloroform:methanol=9:1).

Example 6(131)

3-(2-((3-methyl-1-(2,4-difluorophenyl)butyl)carbamoyl)-4-phenoxymethylphenyl)propanoic acid

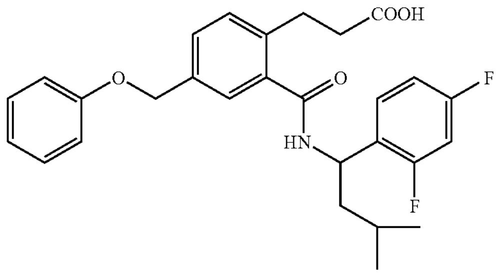

TLC: Rf 0.53 (chloroform:methanol=9:1).

Example 6(132)

3-(2-((3-methyl-1-(2,3,6-trifluorophenyl)butyl)carbamoyl)-4-phenoxymethylphenyl)propanoic acid

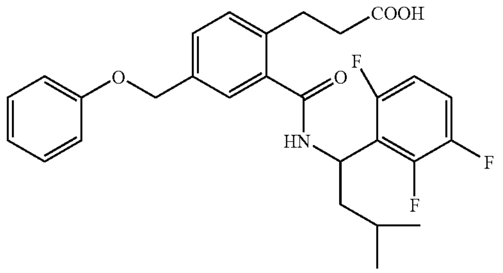

TLC: Rf 0.53 (chloroform:methanol=9:1).

Example 6(133)

3-(2-((3-methyl-1-(4-chloro-2-fluorophenyl)butyl) carbamoyl)-4-phenoxymethylphenyl)propanoic acid

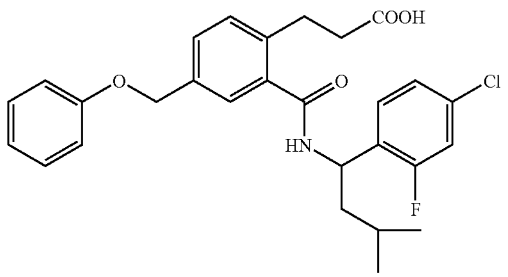

TLC: Rf 0.53 (chloroform:methanol=9:1).

Example 6(134)

3-(2-((3-methyl-1-(2,4,5-trifluorophenyl)butyl)carbamoyl)-4-phenoxymethylphenyl)propanoic acid

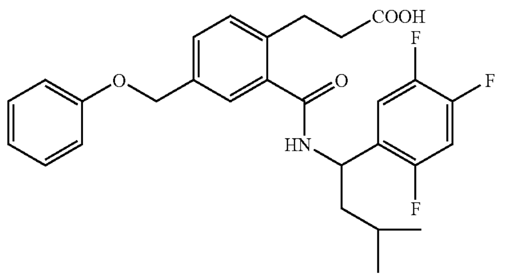

TLC: Rf 0.53 (chloroform:methanol=9:1).

Example 6(135)

3-(2-((3-methyl-1-(2,3-difluorophenyl)butyl)carbamoyl)-4-phenoxymethylphenyl)propanoic acid

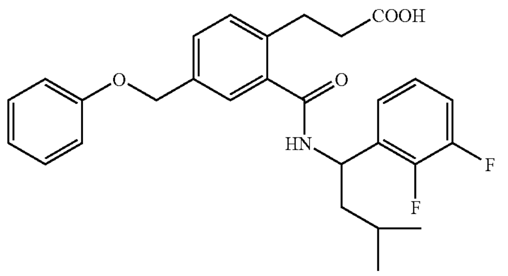

TLC: Rf 0.53 (chloroform:methanol=9:1).

Example 6(136)

3-(2-((3-methyl-1-(2-chloro-4-fluorophenyl)butyl) carbamoyl)-4-phenoxymethylphenyl)propanoic acid

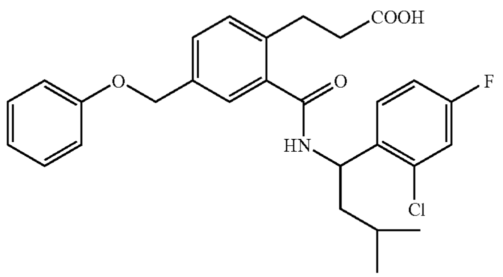

TLC: Rf 0.53 (chloroform:methanol=9:1).

Example 6(137)

3-(2-((3-methyl-1-(2,4,6-trifluorophenyl)butyl)carbamoyl)-4-phenoxymethylphenyl)propanoic acid

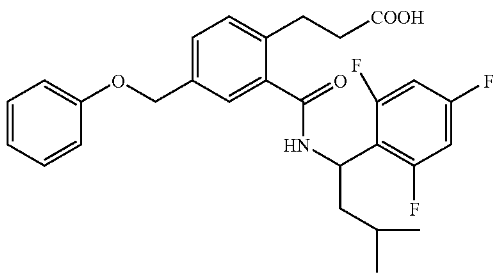

TLC: Rf 0.53 (chloroform:methanol=9:1).

Example 6(138)

3-(2-((3-methyl-1-(2,3-dimethoxyphenyl)butyl)carbamoyl)-4-phenoxymethylphenyl)propanoic acid

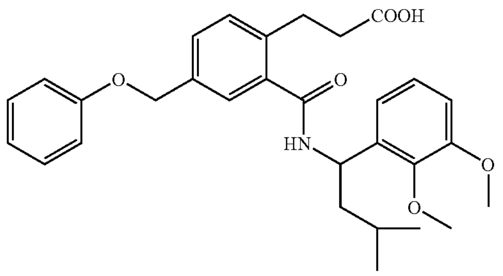

TLC: Rf 0.53 (chloroform:methanol=9:1).

Example 6(139)

3-(2-((3-methyl-1-(4-diethylaminophenyl)butyl)carbamoyl)-4-phenoxymethylphenyl)propanoic acid

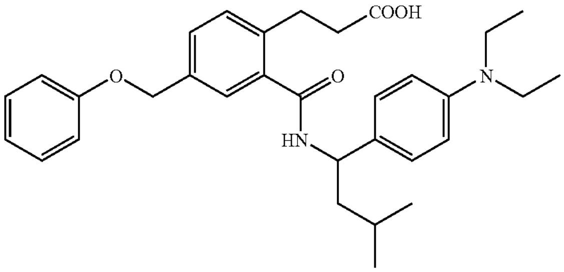

TLC: Rf 0.53 (chloroform:methanol=9:1).

Example 6(140)

3-(2-((3-methyl-1-(2,3,4,5,6-pentafluorophenyl)butyl)carbamoyl)-4-phenoxymethylphenyl)propanoic acid

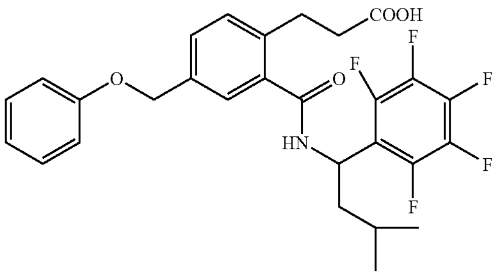

TLC: Rf 0.53 (chloroform:methanol=9:1).

Example 6(141)

(2E)-3-(2-((3-methyl-1-phenylbutyl)carbamoyl)-4-phenoxymethylphenyl)-2-propenoic acid

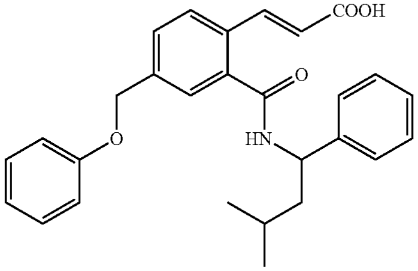

TLC: Rf 0.55 (chloroform:methanol=10:1).

Example 6(142)

3-(2-((3-methyl-1-(4-mesylphenyl)butyl)carbamoyl)-4-phenoxymethylphenyl)propanoic acid

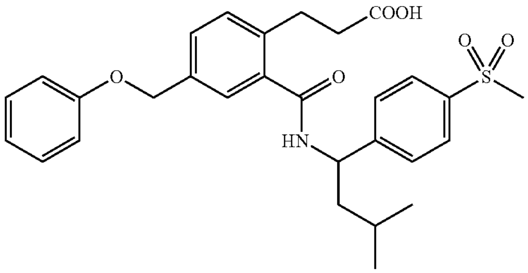

TLC: Rf 0.53 (chloroform:methanol=9:1).

Example 6(143)

3-(2-((3-methyl-1-(3-fluoro-2-methylphenyl)butyl)carbamoyl)-4-phenoxymethylphenyl)propanoic acid

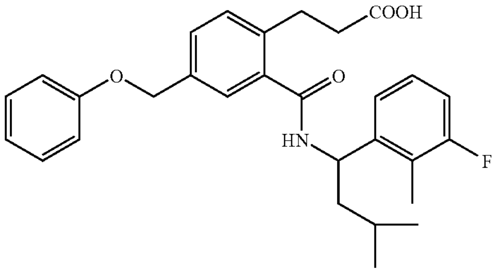

TLC: Rf 0.53 (chloroform:methanol=9:1).

Example 6(144)

3-(2-((3-methyl-1-(2,3,4-trifluorophenyl)butyl)carbamoyl)-4-phenoxymethylphenyl)propanoic acid

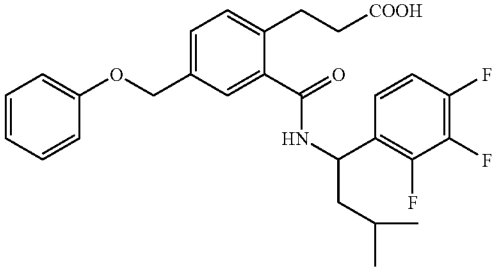

TLC: Rf 0.53 (chloroform:methanol=9:1).

Example 6(145)

3-(2-((3-methyl-1-(4-(pyrrolidin-1-yl)phenyl)butyl)carbamoyl)-4-phenoxymethylphenyl)propanoic acid

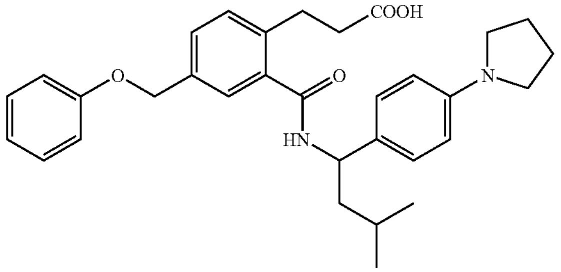

TLC: Rf 0.53 (chloroform:methanol=9:1).

Example 6(146)

3-(2-((3-methyl-1-(4-dimethylaminophenyl)butyl)carbamoyl)-4-phenoxymethylphenyl)propanoic acid

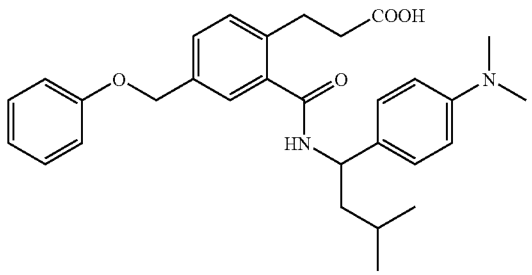

TLC: Rf 0.53 (chloroform:methanol=9:1).

Example 6(147)

3-(2-((3-methyl-1-(4-dimethylamino-2-methoxyphenyl)butyl)carbamoyl)-4-phenoxymethylphenyl)propanoic acid

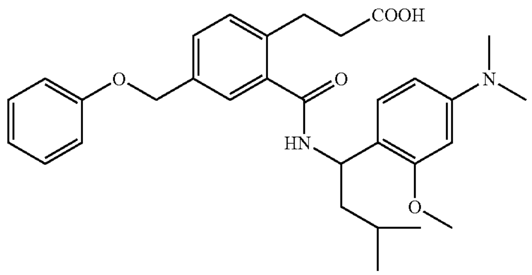

TLC: Rf 0.53 (chloroform:methanol=9:1).

Example 6(148)

3-(2-((3-methyl-1-(2,4-dimethoxyphenyl)butyl)carbamoyl)-4-phenoxymethylphenyl)propanoic acid

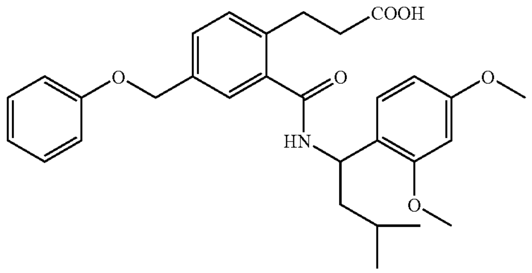

TLC: Rf 0.53 (chloroform:methanol=9:1).

Example 6(149)

3-(2-((3-methyl-1-(4-butoxyphenyl)butyl)carbamoyl)-4-phenoxymethylphenyl)propanoic acid

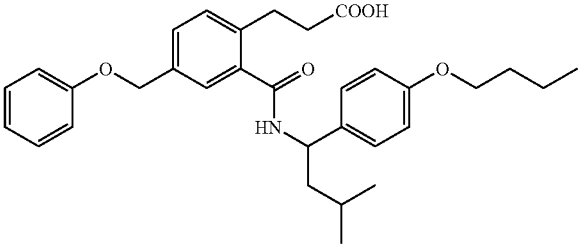

TLC: Rf 0.53 (chloroform:methanol=9:1).

Example 6(150)

3-(2-((3-methyl-1-(4-ethoxy-3-methoxyphenyl)butyl)carbamoyl)-4-phenoxymethylphenyl)propanoic acid

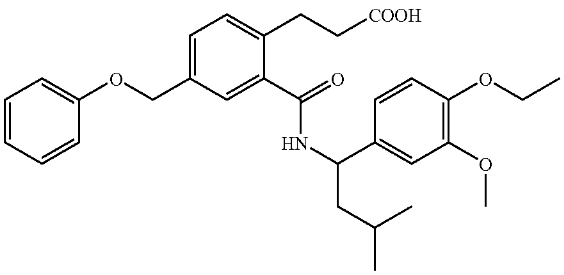

TLC: Rf 0.53 (chloroform:methanol=9:1).

Example 6(151)

3-(2-((3-methyl-1-(4-isopropyloxyphenyl)butyl)carbamoyl)-4-phenoxymethylphenyl)propanoic acid

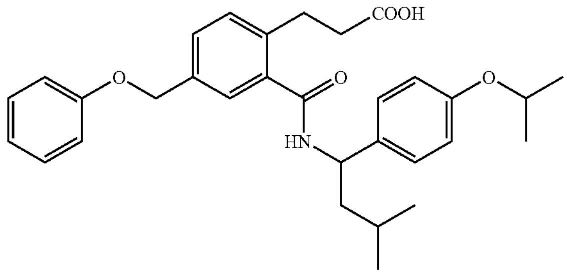

TLC: Rf 0.53 (chloroform:methanol=9:1).

Example 6(152)

3-(2-((3-methyl-1-(3,4-diethoxyphenyl)butyl)carbamoyl)-4-phenoxymethylphenyl)propanoic acid

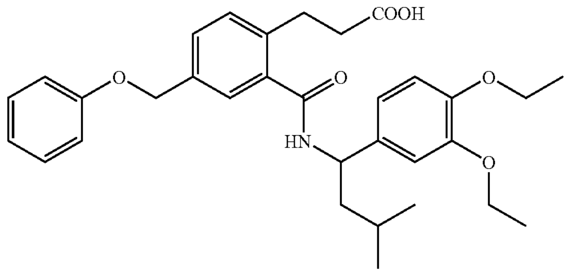

TLC: Rf 0.53 (chloroform:methanol=9:1).

Example 6(153)

3-(2-((3-methyl-1-(2,3,4-trimethoxyphenyl)butyl)carbamoyl)-4-phenoxymethylphenyl)propanoic acid

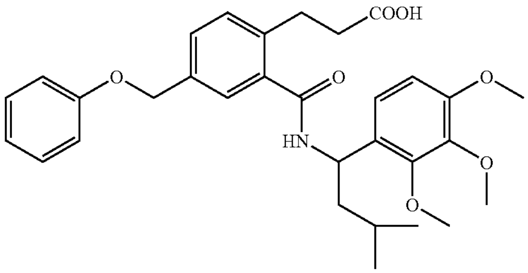

TLC: Rf 0.53 (chloroform:methanol=9:1).

Example 6(154)

3-(2-((3-methyl-1-(2,4-dimethoxy-3-methylphenyl)butyl)carbamoyl)-4-phenoxymethylphenyl)propanoic acid

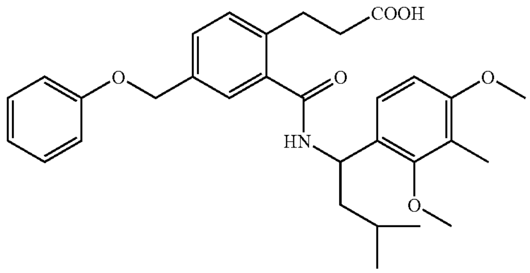

TLC: Rf 0.53 (chloroform:methanol=9:1).

Example 6(155)

3-(2-((3-methyl-1-(thiophen-2-yl)butyl)carbamoyl)-4-phenoxymethylphenyl)propanoic acid

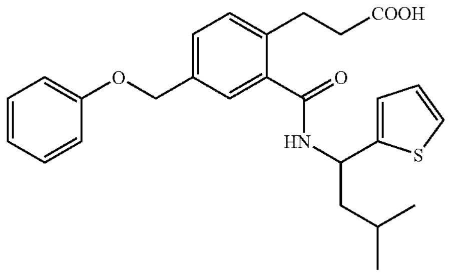

TLC: Rf 0.53 (chloroform:methanol=9:1).

Example 6(156)

3-(2-((3-methyl-1-(2,4,5-trimethoxyphenyl)butyl)carbamoyl)-4-phenoxymethylphenyl)propanoic acid

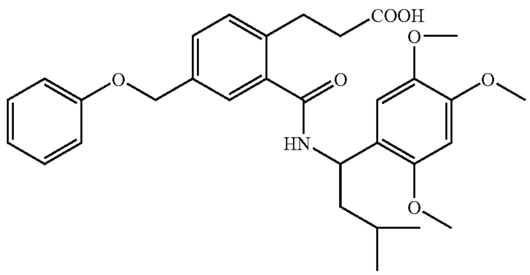

TLC: Rf 0.53 (chloroform:methanol=9:1).

Example 6(157)

3-(2-((3-methyl-1-(3-methylthiophen-2-yl)butyl)carbamoyl)-4-phenoxymethylphenyl)propanoic acid

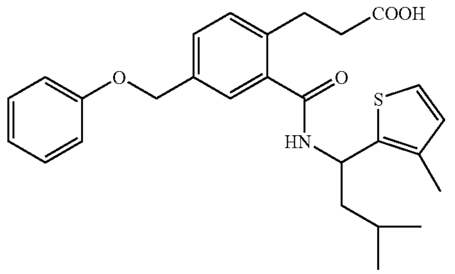

TLC: Rf 0.53 (chloroform:methanol=9:1).

Example 6(158)

3-(2-((3-methyl-1-(2,3-dimethyl-4-methoxyphenyl)butyl)carbamoyl)-4-phenoxymethylphenyl)propanoic acid

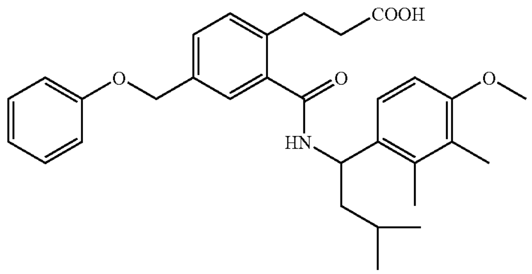

TLC: Rf 0.53 (chloroform:methanol=9:1).

Example 6(159)

3-(2-((3-methyl-1-(2,5-dimethyl-4-methoxyphenyl)butyl)carbamoyl)-4-phenoxymethylphenyl)propanoic acid

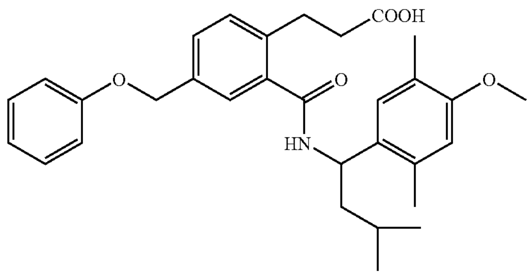

TLC: Rf 0.53 (chloroform:methanol=9:1).

Example 6(160)

3-(2-((3-methyl-1-(4-methoxy-3-methylphenyl)butyl)carbamoyl)-4-phenoxymethylphenyl)propanoic acid

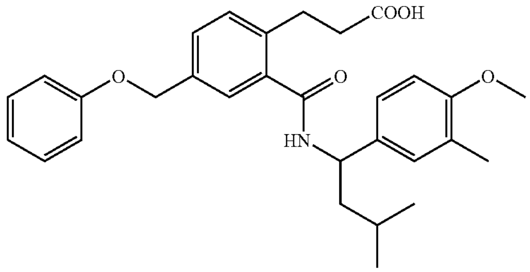

TLC: Rf 0.53 (chloroform:methanol=9:1).

Example 6(161)

3-(2-((3-methyl-1-(5-methylfuran-2-yl)butyl)carbamoyl)-4-phenoxymethylphenyl)propanoic acid

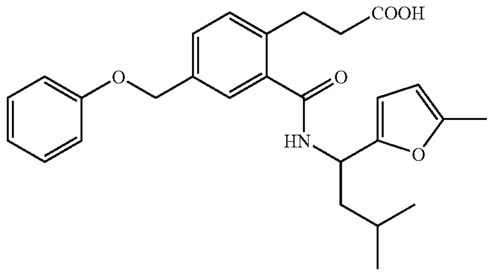

TLC: Rf 0.53 (chloroform:methanol=9:1).

Example 6(162)

3-(2-((3-methyl-1-(2,4-diethoxy-3-methylphenyl)butyl)carbamoyl)-4-phenoxymethylphenyl)propanoic acid

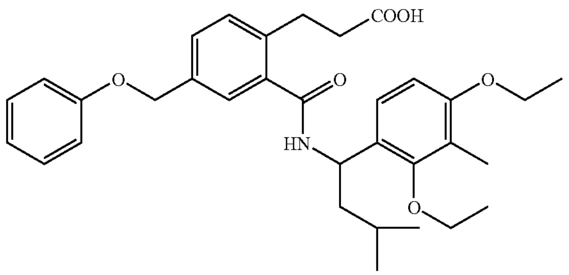

TLC: Rf 0.53 (chloroform:methanol=9:1).

Example 6(163)

3-(2-((3-methyl-1-(1-methylpyrrol-2-yl)butyl)carbamoyl)-4-phenoxymethylphenyl)propanoic acid

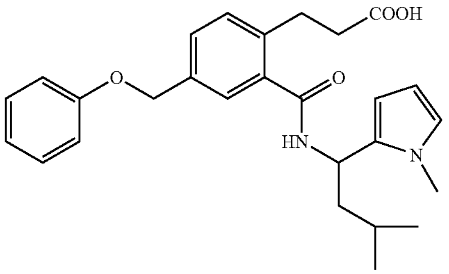

TLC: Rf 0.53 (chloroform:methanol=9:1).

Example 6(164)

3-(2-((3-methyl-1-(4-ethylthiophenyl)butyl)carbamoyl)-4-phenoxymethylphenyl)propanoic acid

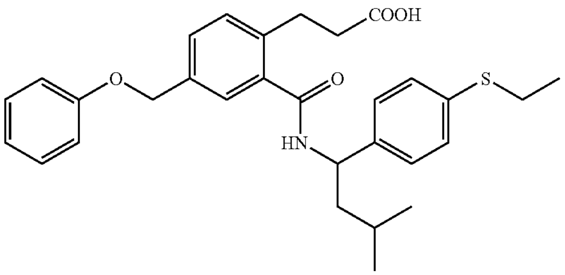

TLC: Rf 0.53 (chloroform:methanol=9:1).

Example 6(165)

3-(2-((3-methyl-1-(3-trifluoromethylthiophenyl)butyl)carbamoyl)-4-phenoxymethylphenyl)propanoic acid

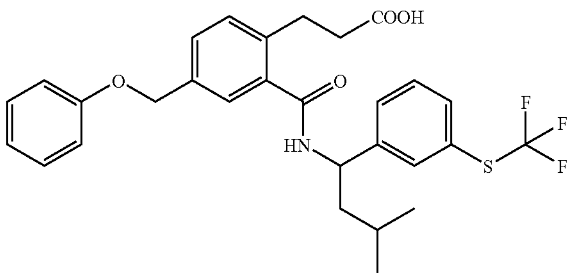

TLC: Rf 0.53 (chloroform:methanol=9:1).

Example 6(166)

3-(2-((3-methyl-1-(4-methylthiophenyl)butyl)carbamoyl)-4-phenoxymethylphenyl)propanoic acid

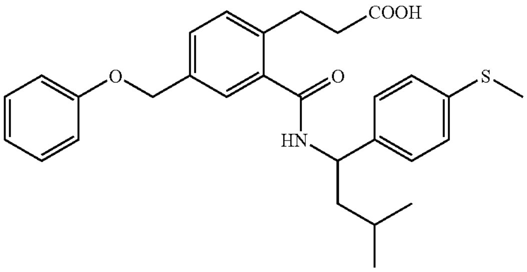

TLC: Rf 0.53 (chloroform:methanol=9:1).

Example 6(167)

3-(2-((3-methyl-1-(4-cyanophenyl)butyl)carbamoyl)-4-phenoxymethylphenyl)propanoic acid

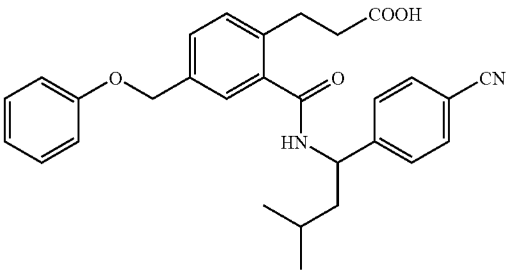

TLC: Rf 0.40 (ｸﾛﾛﾎﾙﾑ:ﾒﾀﾉｰﾙ 10:1)

Example 6(168)

3-(2-((3-methyl-1-(thiophen-3-yl)butyl)carbamoyl)-4-phenoxymethylphenyl)propanoic acid

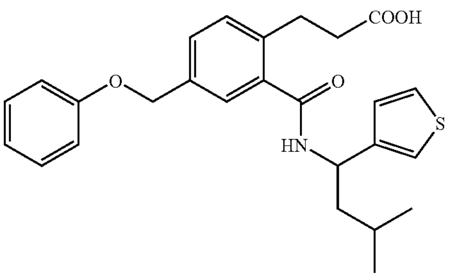

TLC: Rf 0.53 (chloroform:methanol=9:1).

Example 6(169)

3-(2-((3-methyl-1-(2,5-dimethylphenyl)butyl)carbamoyl)-4-phenoxymethylphenyl)propanoic acid

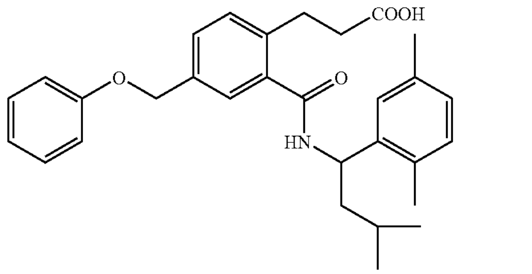

TLC: Rf 0.53 (chloroform:methanol=9:1).

Example 6(170)

3-(2-((3-methyl-1-(3,4-dimethoxyphenyl)butyl)carbamoyl)-4-phenoxymethylphenyl)propanoic acid

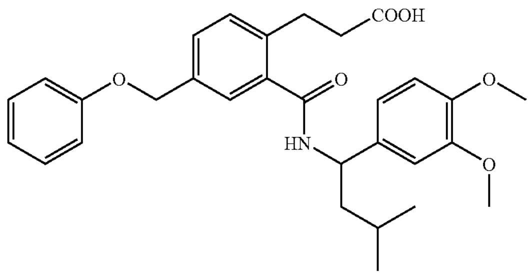

TLC: Rf 0.53 (chloroform:methanol=9:1).

Example 6(171)

3-(2-((3-methyl-1-(1,3-dioxaindan-4-yl)butyl)carbamoyl)-4-phenoxymethylphenyl)propanoic acid

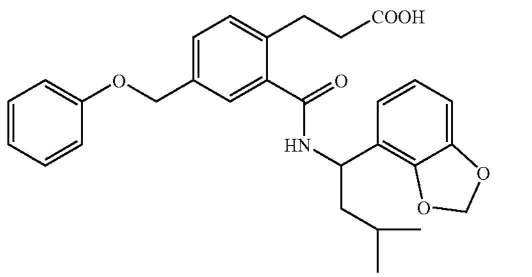

TLC: Rf 0.53 (chloroform:methanol=9:1).

Example 6(172)

3-(2-(N-benzyl-N-methylcarbamoyl)-4-phenoxymethylphenyl)propanoic acid

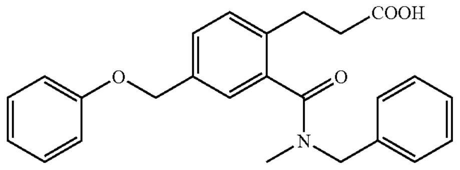

TLC: Rf 0.45 (chloroform:methanol=10:1).

Example 6(173)

3-(2-(N-benzyl-N-propylcarbamoyl)-4-phenoxymethylphenyl)propanoic acid

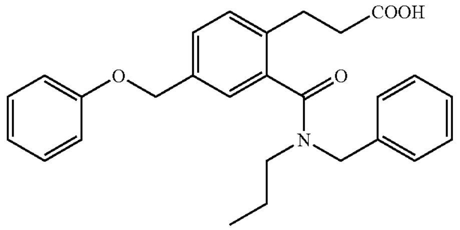

TLC: Rf 0.50 (chloroform:methanol=10:1).

Example 6(174)

3-(2-((3-methyl-1-phenylbutyl)carbamoyl)-4-benzyloxymethylphenyl)propanoic acid

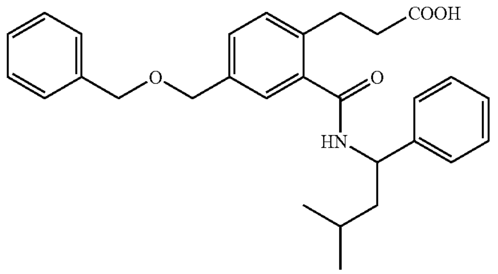

TLC: Rf 0.41 (chloroform:methanol=19:1);

NMR (300 MHz, $CDCl_3$): δ 7.42-7.19 (m, 13H), 6.36 (d, J=8.7 Hz, 1H), 5.24 (m, 1H), 4.57 (s, 2H), 4.52 (s, 2H), 3.04-2.96 (m, 2H), 2.75-2.66 (m, 2H), 1.86-1.52 (m, 3H), 0.99 (d, J=6.5 Hz, 3H), 0.98 (d, J=6.5 Hz, 3H).

Example 6(175)

3-(2-((3-methyl-1-(3-fluoro-5-trifluoromethylphenyl)butyl)carbamoyl)-4-phenoxymethylphenyl)propanoic acid

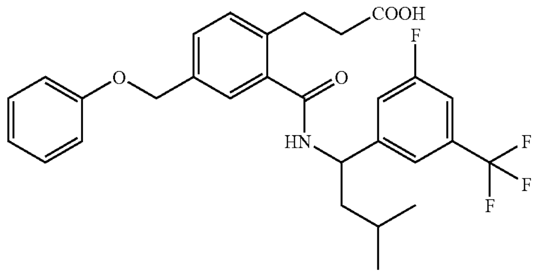

TLC: Rf 0.53 (chloroform:methanol=9:1).

Example 6(176)

3-(2-((3-methyl-1-(4-fluoro-2-trifluoromethylphenyl)butyl)carbamoyl)-4-phenoxymethylphenyl)propanoic acid

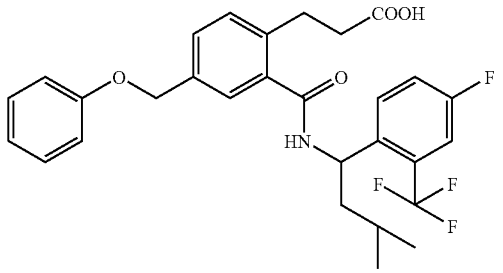

TLC: Rf 0.53 (chloroform:methanol=9:1).

Example 6(177)

3-(2-((3-methyl-1-(2,4-dimethylphenyl)butyl)carbamoyl)-4-phenoxymethylphenyl)propanoic acid

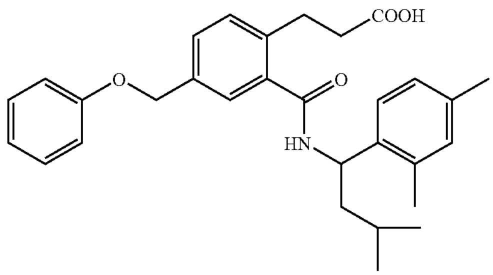

TLC: Rf 0.53 (chloroform:methanol=9:1).

Example 6(178)

3-(2-((3-methyl-1-(2,4-ditrifluoromethylphenyl)butyl)carbamoyl)-4-phenoxymethylphenyl)propanoic acid

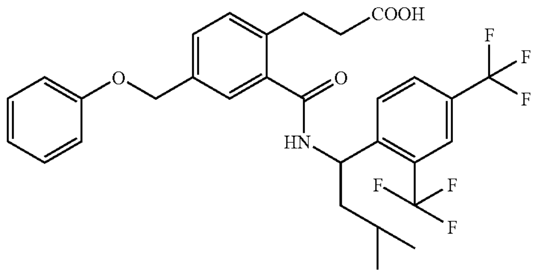

TLC: Rf 0.53 (chloroform:methanol=9:1).

Example 6(179)

3-(2-((3-methyl-1-(2-methylphenyl)butyl)carbamoyl)-4-phenoxymethylphenyl)propanoic acid

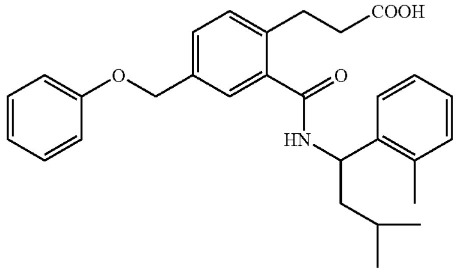

TLC: Rf 0.53 (chloroform:methanol=9:1).

Example 6(180)

3-(2-((3-methyl-1-(2,3-dimethylphenyl)butyl)carbamoyl)-4-phenoxymethylphenyl)propanoic acid

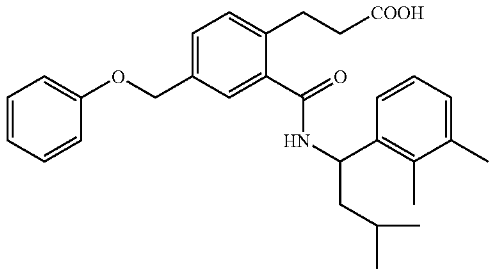

TLC: Rf 0.53 (chloroform:methanol=9:1).

Example 6(181)

3-(2-((3-methyl-1-phenylbutyl)carbamoyl)-4-(furan-2-ylcarbonylaminomethyl)phenyl)propanoic acid

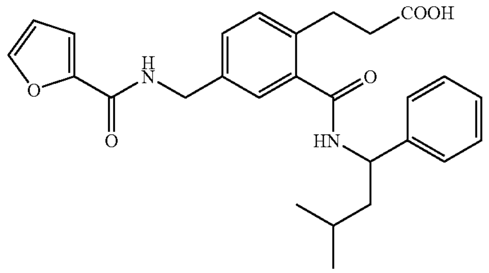

TLC: Rf 0.29 (chloroform:methanol=10:1).

Example 6(182)

3-(2-((3-methyl-1-phenylbutyl)carbamoyl)-4-(pyrazol-1-ylmethyl)phenyl)propanoic acid

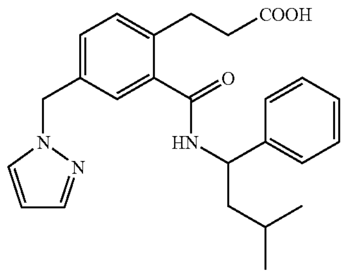

TLC: Rf 0.36 (chloroform:methanol=9:1).

Example 6(183)

3-(2-((3-methyl-1-phenylbutyl)carbamoyl)-4-(2-phenylethyl)phenyl)propanoic acid

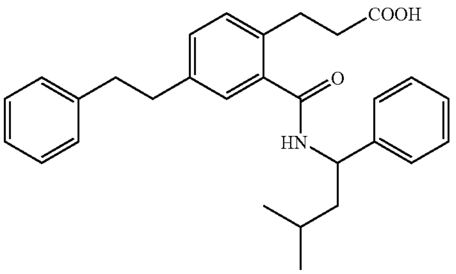

TLC: Rf 0.49 (chloroform:methanol=19:1);

NMR (300 MHz, $CDCl_3$): δ 7.40-7.23 (m, 7H), 7.22-7.15 (m, 3H), 7.13-7.07 (m, 2H), 6.88 (s, 1H), 6.05 (d, J=8.7 Hz, 1H), 5.20 (m, 1H), 3.01-2.92 (m, 2H), 2.88 (s, 4H), 2.74-2.66 (m, 2H), 1.82-1.59 (m, 3H), 0.99 (d, J=6.6 Hz, 3H), 0.98 (d, J=6.6 Hz, 3H).

Example 6(184)

3-(2-((3-methyl-1-phenylbutyl)carbamoyl)-4-cyclopropylmethoxymethylphenyl)propanoic acid

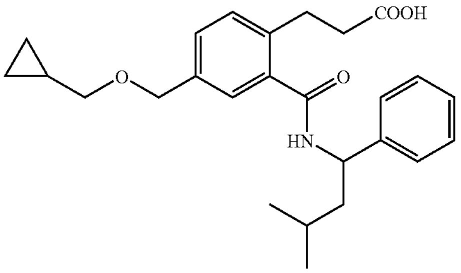

TLC: Rf 0.45 (ethyl acetate);

NMR (300 MHz, DMSO-$d_6$): δ 12.06 (s, 1H), 8.78 (d, J=8.4 Hz, 1H), 7.38-7.18 (m, 8H), 5.09-5.01 (m, 1H), 4.45 (s, 2H), 3.28 (d, J=6.6 Hz, 2H), 2.85-2.79 (m, 2H), 2.46-2.41 (m, 2H), 1.80-1.58 (m, 2H), 1.48-1.39 (m, 1H), 1.80-0.98 (m, 1H), 0.94-0.89 (m, 6H), 0.49-0.43 (m, 2H), 0.19-0.14 (m, 2H).

Example 6(185)

3-(2-((3-methyl-1-(3,5-dimethylphenyl)butyl)carbamoyl)-4-(3-cyanophenoxymethyl)phenyl)propanoic acid

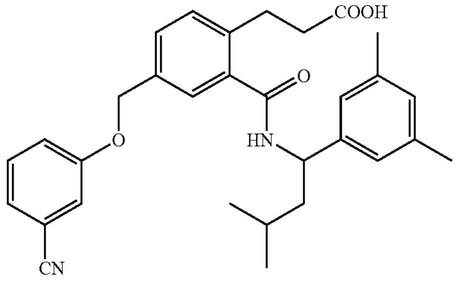

TLC: Rf 0.58 (chloroform:methanol=10:1);

NMR (300 MHz, $CDCl_3$): δ 7.48-7.06 (m, 7H), 6.95 (s, 2H), 6.90 (s, 1H), 6.42 (m, 1H), 5.16 (m, 1H), 5.00 (s, 2H), 3.10-2.92 (m, 2H), 2.78-2.62 (m, 2H), 2.29 (s, 6H), 1.86-1.48 (m, 3H), 0.97 (d, J=6.3 Hz, 6H).

Example 6(186)

3-(2-((3-methyl-1-(3,5-dimethylphenyl)butyl)carbamoyl)-4-(2-methylphenoxymethyl)phenyl)propanoic acid

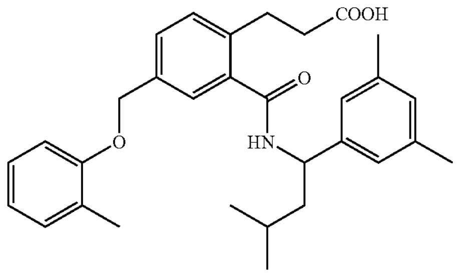

TLC: Rf 0.62 (chloroform:methanol=10:1);

NMR (300 MHz, $CDCl_3$): δ 7.46-7.39 (m, 2H), 7.31-7.22 (m, 1H), 7.20-7.11 (m, 2H), 6.95 (s, 2H), 6.93-6.82 (m, 3H), 6.26 (d, J=8.4 Hz, 1H), 5.17 (m, 1H), 5.04 (s, 2H), 3.14-2.99 (m, 2H), 2.78-2.67 (m, 2H), 2.31 (s, 6H), 2.27 (s, 3H), 1.85-1.52 (m, 3H), 0.99 (d, J=6.6 Hz, 3H), 0.98 (d, J=6.6 Hz, 3H).

Example 6(187)

3-(2-((3-methyl-1-(3,5-dimethylphenyl)butyl)carbamoyl)-4-(2-chloro-5-methylphenoxymethyl)phenyl)propanoic acid

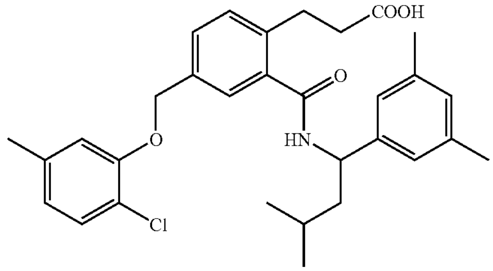

TLC: Rf 0.49 (chloroform:methanol=10:1);

NMR (300 MHz, $CDCl_3$): δ 7.53 (d, J=1.8 Hz, 1H), 7.43 (dd, J=7.5, 1.8 Hz, 1H), 7.33-7.22 (m, 2H), 6.96 (s, 2H), 6.91 (s, 1H), 6.79 (s, 1H), 6.75 (m, 1H), 6.30 (d, J=8.4 Hz, 1H), 5.17 (m, 1H), 5.09 (s, 2H), 3.12-2.98 (m, 2H), 2.78-2.69 (m, 2H), 2.31 (s, 9H), 1.86-1.55 (m, 3H), 0.99 (d, J=6.3 Hz, 3H), 0.98 (d, J=6.3 Hz, 3H).

Example 6(188)

3-(2-((3-methyl-1-(3,5-dimethylphenyl)butyl)carbamoyl)-4-(pyridin-3-yloxymethyl)phenyl)propanoic acid

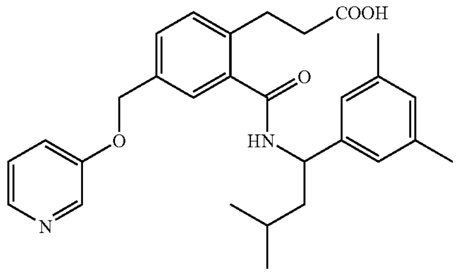

TLC: Rf 0.37 (chloroform:methanol=10:1);

NMR (300 MHz, DMSO-$d_6$): δ 8.79 (d, J=8.7 Hz, 1H), 8.36 (d, J=2.7 Hz, 1H), 8.19 (m, 1H), 7.50-7.41 (m, 2H), 7.39-7.29 (m, 3H), 6.97 (s, 2H), 6.86 (s, 1H), 5.19 (s, 2H), 4.99 (m, 1H), 2.92-2.80 (m, 2H), 2.55-2.42 (m, 2H), 2.26 (s, 6H), 1.82-1.55 (m, 2H), 1.42 (m, 1H), 0.93 (t, J=7.3 Hz, 6H).

Example 6(189)

3-(2-((3-methyl-1-(4-methoxy-1,3-dioxaindan-6-yl)butyl)carbamoyl)-4-(2-chloro-5-methylphenoxymethyl)phenyl)propanoic acid

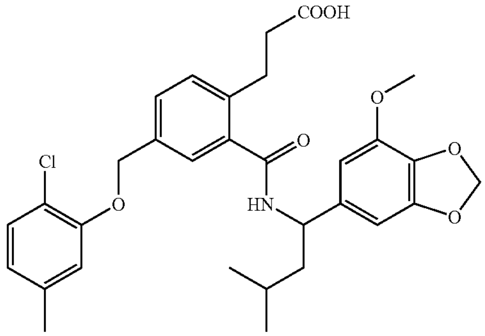

TLC: Rf 0.53 (chloroform:methanol=9:1);

NMR (300 MHz, $CDCl_3$): δ 7.46-7.42 (m, 2H), 7.31-7.11 (m, 2H), 6.94-6.84 (m, 2H), 6.55 (d, J=9.9 Hz, 2H), 6.32 (d, J=8.4 Hz, 1H), 5.95 (s, 2H), 5.15 (m, 1H), 5.05 (s, 2H), 3.91 (s, 3H), 3.03 (t, J=7.2 Hz, 2H), 2.75 (t, J=7.2 Hz, 2H), 2.27 (s, 3H), 1.85-1.50 (m, 3H), 0.98 (d, J=6.0 Hz, 6H).

Example 6(190)

3-(2-((3-methyl-1-(4-methoxy-1,3-dioxaindan-6-yl)butyl)carbamoyl)-4-(3-cyanophenoxymethyl)phenyl)propanoic acid

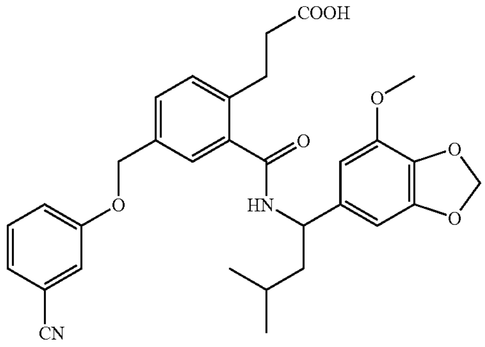

TLC: Rf 0.48 (chloroform:methanol=9:1);

NMR (300 MHz, $CDCl_3$): δ 7.46-7.12 (m, 7H), 6.56 (dd, J=10.5, 1.5 Hz, 2H), 6.46 (d, J=8.4 Hz, 1H), 5.94 (s, 2H), 5.13 (m, 1H), 5.03 (s, 2H), 3.90 (s, 3H), 3.02 (t, J=7.2 Hz, 2H), 2.74 (t, J=7.2 Hz, 2H), 1.85-1.55 (m, 3H), 0.97 (d, J=6.6 Hz, 6H).

Example 6(191)

3-(2-((3-methyl-1-(4-methoxy-1,3-dioxaindan-6-yl)butyl)carbamoyl)-4-(2-methylphenoxymethyl)phenyl)propanoic acid

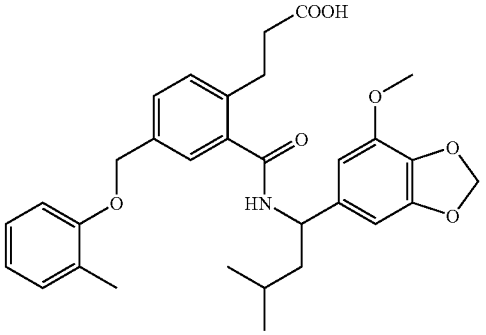

TLC: Rf 0.50 (chloroform:methanol=9:1);

NMR (300 MHz, $CDCl_3$): δ 7.51 (s, 1H), 7.44 (d, J=7.8 Hz, 1H), 7.30-7.23 (m, 3H), 6.79 (s, 1H), 6.75 (d, J=8.4 Hz, 1H) 6.55 (d, J=7.2 Hz, 2H), 6.36 (d, J=8.7 Hz, 1H), 5.95 (s, 2H), 5.13 (m, 1H), 5.09 (s, 2H), 3.91 (s, 3H), 3.04 (t, J=7.2 Hz, 2H), 2.74 (t, J=7.2 Hz, 2H), 2.27 (s, 3H), 1.82-1.50 (m, 3H), 0.98 (d, J=6.3 Hz, 6H).

Example 6(192)

3-(2-((3-methyl-1-(3,5-dichlorophenyl)butyl)carbamoyl)-4-phenoxymethylphenyl)propanoic acid

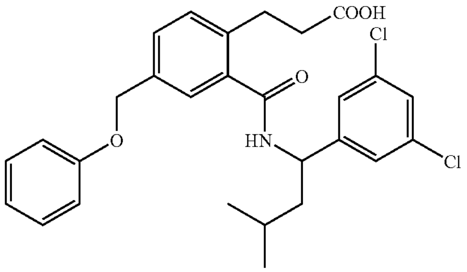

TLC: Rf 0.50 (chloroform:methanol=9:1);

NMR (300 MHz, $CDCl_3$): δ 7.48-7.42 (m, 2H), 7.35-7.24 (m, 6H), 7.02-6.94 (m, 3H), 6.58 (d, J=8.4 Hz, 1H), 5.20-5.10 (m, 1H), 5.05 (s, 2H), 3.05-2.97 (m, 2H), 2.85-2.70 (m, 2H), 1.80-1.40 (m, 3H), 0.99 (d, J=5.7 Hz, 3H), 0.98 (d, J=5.7 Hz, 3H).

Example 6(193)

3-(2-((3-methyl-1-(3-chloro-5-fluorophenyl)butyl)carbamoyl)-4-phenoxymethylphenyl)propanoic acid

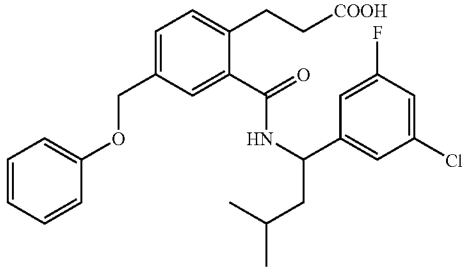

TLC: Rf 0.50 (chloroform:methanol=9:1);

NMR (300 MHz, $CDCl_3$): δ 7.50-7.40 (m, 2H), 7.35-7.15 (m, 6H), 7.05-6.94 (m, 3H), 6.80-6.70 (m, 1H), 6.00-5.85 (m, 1H), 5.04 (s, 2H), 3.10-3.00 (m, 2H), 2.80-2.70 (m, 2H), 2.00-1.40 (m, 3H), 1.02 (d, J=6.0 Hz, 3H), 1.01 (d, J=6.0 Hz, 3H).

Example 6(194)

3-(2-((3-methyl-1-(4-fluoro-3-methylphenyl)butyl)carbamoyl)-4-(2-methylphenoxymethyl)phenyl)propanoic acid

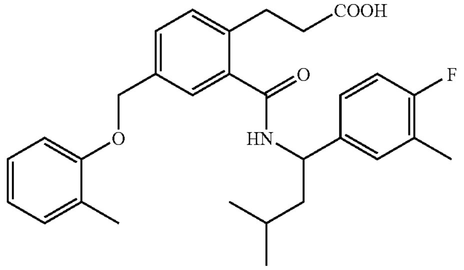

TLC: Rf 0.23 (hexane:ethyl acetate=1:1);

NMR (300 MHz, $CDCl_3$): δ 7.45-7.42 (m, 2H), 7.28 (m, 1H), 7.20-7.10 (m, 4H), 6.97 (m, 1H), 6.92-6.84 (m, 2H), 6.30 (brd, J=8.7 Hz, 1H), 5.17 (m, 1H), 5.05 (s, 2H), 3.08-2.95 (m, 2H), 2.75-2.71 (m, 2H), 2.27 (s, 6H), 1.82-1.55 (m, 3H), 0.99 (d, J=6.3 Hz, 3H), 0.98 (d, J=6.3 Hz, 3H).

Example 6(195)

3-(2-((3-methyl-1-(4-fluoro-3-methylphenyl)butyl)carbamoyl)-4-(2-chloro-5-methylphenoxymethyl)phenyl)propanoic acid

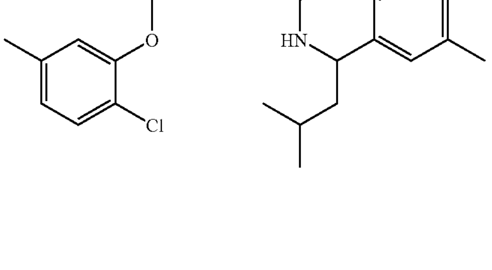

TLC: Rf 0.23 (hexane:ethyl acetate=1:1);

NMR (300 MHz, $CDCl_3$): δ 7.52 (brs, 1H), 7.43 (m, 1H), 7.30-7.24 (m, 2H), 7.18-7.11 (m, 2H), 6.97 (m, 1H), 6.79 (brs, 1H), 6.75 (brd, J=7.8 Hz, 1H), 6.34 (brd, J=8.1 Hz, 1H), 5.16 (m, 1H), 5.09 (s, 2H), 3.11-2.96 (m, 2H), 2.75-2.70 (m, 2H), 2.32 (s, 3H), 2.27 (d, J=1.5 Hz, 3H), 1.87-1.54 (m, 3H), 0.99 (d, J=6.3 Hz, 3H), 0.98 (d, J=6.3 Hz, 3H).

Example 6(196)

3-(2-((3-methyl-1-(3,5-difluorophenyl)butyl)carbamoyl)-4-phenoxymethylphenyl)propanoic acid

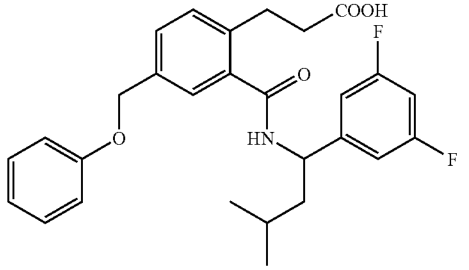

TLC: Rf 0.53 (chloroform:methanol=9:1);

NMR (300 MHz, $CDCl_3$): δ 7.48-7.40 (m, 2H), 7.35-7.24 (m, 3H), 7.02-6.94 (m, 3H), 6.94-6.84 (m, 2H), 6.76-6.66 (m, 1H), 6.54 (brd, J=8.4 Hz, 1H), 5.23-5.13 (m, 1H), 5.04 (s, 2H), 3.02 (t, J=7.2 Hz, 2H), 2.80-2.70 (m, 2H), 1.80-1.40 (m, 3H), 0.99 (d, J=6.0 Hz, 3H), 0.98 (d, J=6.0 Hz, 3H).

Example 6(197)

3-(2-((3-methyl-1-(3,5-dimethoxyphenyl)butyl)carbamoyl)-4-phenoxymethylphenyl)propanoic acid

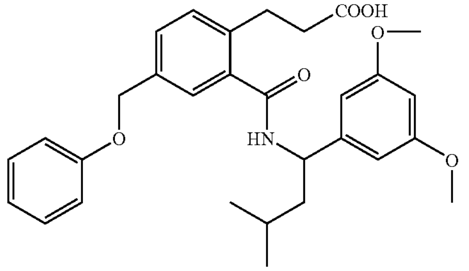

TLC: Rf 0.53 (chloroform:methanol=9:1);

NMR (300 MHz, $CDCl_3$): δ 7.47-7.40 (m, 2H), 7.34-7.20 (m, 3H), 7.02-6.90 (m, 3H), 6.51 (d, J=2.1 Hz, 2H), 6.40-6.35 (m, 2H), 5.20-5.10 (m, 1H), 5.03 (s, 2H), 3.79 (s, 6H), 3.08-3.00 (m, 2H), 2.76 (t, J=7.5 Hz, 2H), 1.80-1.50 (m, 3H), 0.99 (d, J=6.3 Hz, 6H).

Example 6(198)

3-(2-((3-methyl-1-phenylbutyl)carbamoyl)-4-(1-phenoxyethyl)phenyl)propanoic acid

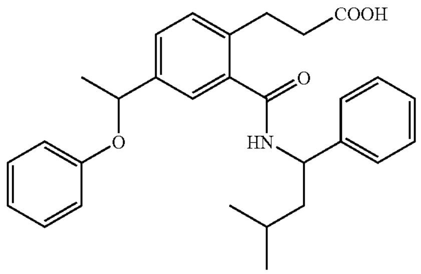

TLC: Rf 0.53 (chloroform:methanol=9:1);

NMR (300 MHz, $CDCl_3$): δ 7.40-7.18 (m, 10H), 6.94-6.82 (m, 3H), 6.25 (d, J=8.4 Hz, 1H), 5.30 (q, J=6.6 Hz, 1H), 5.22 (m, 1H), 2.96 (m, 2H), 2.70 (m, 2H), 1.80-1.45 (m, 3H), 1.62 (m, 3H), 1.00-0.95 (m, 6H).

Example 6(199)

3-(2-((2-methoxy-2-phenylethyl)carbamoyl)-4-phenoxymethylphenyl)propanoic acid

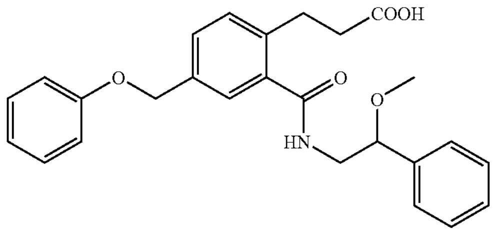

TLC: Rf 0.39 (chloroform:methanol=9:1);

NMR (300 MHz, $CDCl_3$): δ 7.46-7.27 (m, 10H), 7.02-6.95 (m, 3H), 6.51 (m, 1H), 5.03 (s, 2H), 4.41 (dd, J=8.4, 3.9 Hz, 1H), 3.87 (ddd, J=13.5, 6.9, 3.9 Hz, 1H), 3.46 (ddd, J=13.5, 8.4, 4.5 Hz, 1H), 3.28 (s, 3H), 3.07 (t, J=7.5 Hz, 2H), 2.76 (t, J=7.5 Hz, 2H).

Example 6(200)

3-(2-((2-phenylpropyl)carbamoyl)-4-phenoxymethylphenyl)propanoic acid

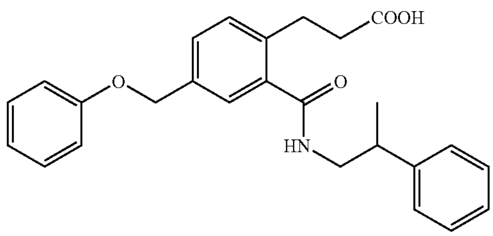

TLC: Rf 0.34 (chloroform:methanol=9:1);

NMR (300 MHz, $CDCl_3$): δ 7.40-7.20 (m, 10H), 7.02-6.91 (m, 3H), 6.03 (dd, J=6.0, 5.7 Hz, 1H), 4.96 (s, 2H), 3.80 (ddd, J=13.5, 6.0, 6.0 Hz, 1H), 3.48 (ddd, J=13.5, 9.3, 5.7 Hz, 1H), 3.10 (m, 1H), 2.95 (t, J=7.5 Hz, 2H), 2.71 (t, J=7.5 Hz, 2H), 1.34 (d, J=6.9 Hz, 3H).

Example 6(201)

3-(2-((3-methyl-1-phenylbutyl)carbamoyl)-4-(2-phenoxyethyl)phenyl)propanoic acid

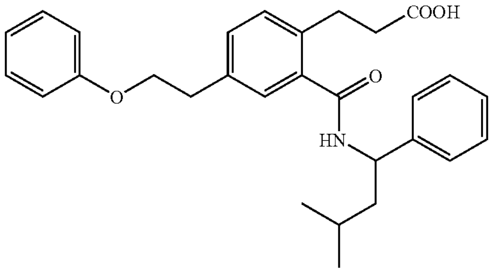

TLC: Rf 0.38 (chloroform:methanol=9:1);

NMR (300 MHz, $CDCl_3$): δ 7.38-7.18 (m, 10H), 6.98-6.84 (m, 3H), 6.30 (d, J=8.1 Hz, 1H), 5.23 (dt, J=8.1, 6.3 Hz, 1H), 4.16 (t, J=6.9 Hz, 2H), 3.07 (t, J=6.9 Hz, 2H), 2.99 (dt, J=3.3, 6.9 Hz, 2H), 2.72 (t, J=6.9 Hz, 2H), 1.82-1.50 (m, 3H), 0.98 (d, J=6.6 Hz, 6H).

Example 6(202)

3-(2-(3-phenylmorpholin-4-ylcarbonyl)-4-phenoxymethylphenyl)propanoic acid

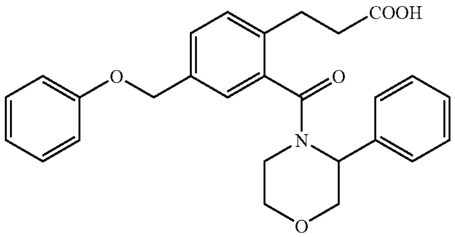

TLC: Rf 0.31 (chloroform:methanol=10:1).

Example 6(203)

3-(2-(4-phenoxypiperidin-1-ylcarbonyl)-4-phenoxymethylphenyl)propanoic acid

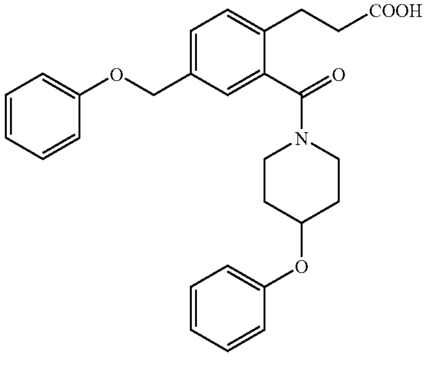

TLC: Rf 0.38 (chloroform:methanol=10:1).

Example 6(204)

3-(2-((2-methoxy-1-(3,5-dimethylphenyl)ethyl)carbamoyl)-4-(2-chloro-5-methylphenoxymethyl)phenyl)propanoic acid

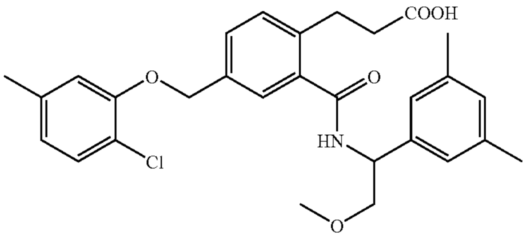

TLC: Rf 0.39 (hexane:ethyl acetate=1:1).

Example 6(205)

3-(2-((4-methyl-2-phenylpentyl)carbamoyl)-4-phenoxymethylphenyl)propanoic acid

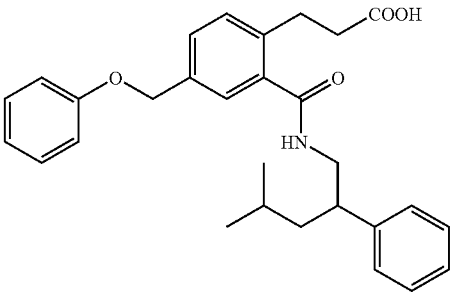

TLC: Rf 0.44 (chloroform:methanol=9:1);

NMR (300 MHz, $CDCl_3$): δ 7.40-7.15 (m, 10H), 7.10-6.90 (m, 3H), 5.92 (t, J=5.4 Hz, 1H), 4.95 (s, 2H), 3.86 (ddd, J=13.5, 5.4, 5.4 Hz, 1H), 3.40 (ddd, J=13.5, 9.9, 5.4 Hz, 1H), 3.01 (m, 1H), 2.94 (t, J=7.2 Hz, 2H), 2.71 (t, J=7.2 Hz, 2H), 1.65-1.40 (m, 3H), 0.89 (d, J=6.6 Hz, 3H), 0.87 (d, J=6.6 Hz, 3H).

Example 6(206)

3-(2-diphenylmethylcarbamoyl-4-phenoxymethylphenyl)propanoic acid

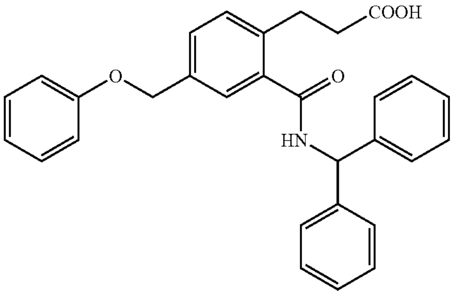

TLC: Rf 0.42 (chloroform:methanol=9:1);

NMR (300 MHz, DMSO-$d_6$): δ 9.39 (d, J=8.7 Hz, 1H), 7.43-7.20 (m, 15H), 7.03-6.90 (m, 3H), 6.36 (d, J=8.7 Hz, 1H), 5.07 (s, 2H), 2.85 (t, J=7.8 Hz, 2H), 2.44 (m, 2H).

Example 6(207)

3-(2-((2-cyclopropyl-1-(3,5-dimethylphenyl)ethyl)carbamoyl)-4-(2-chloro-5-methylphenoxymethyl)phenyl)propanoic acid

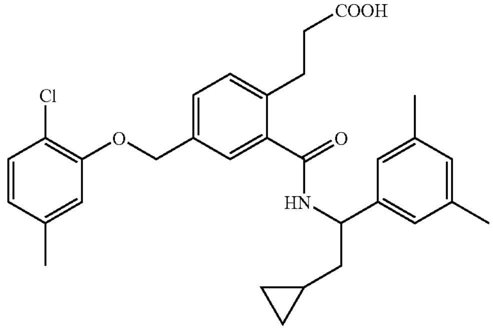

TLC: Rf 0.49 (chloroform:methanol=9:1);

NMR (300 MHz, $CDCl_3$): δ 7.57 (s, 1H), 7.44 (d, J=8.1 Hz, 1H), 7.32-7.24 (m, 2H), 6.96 (s, 2H), 6.91 (s, 1H), 6.79 (s, 1H), 6.74 (d, J=8.1 Hz, 1H), 6.45 (d, J=8.1 Hz, 1H), 5.18 (m, 1H), 5.10 (s, 2H), 3.07 (m, 2H), 2.76 (t, J=7.2 Hz, 2H), 2.31 (s, 9H), 1.76 (m, 2H), 0.69 (m, 1H), 0.55-0.40 (m, 2H), 0.22-0.06 (m, 2H).

Example 6(208)

3-(2-((1-(3,5-dimethylphenyl)ethyl)carbamoyl)-4-(2-chloro-5-methylphenoxymethyl)phenyl)propanoic acid

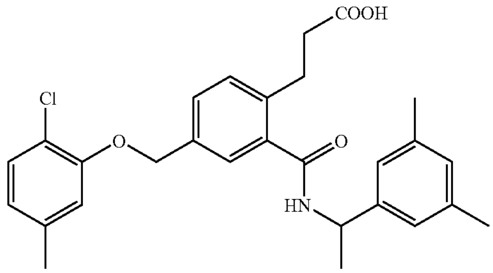

TLC: Rf 0.46 (chloroform:methanol=9:1);

NMR (300 MHz, $CDCl_3$): δ 7.53 (s, 1H), 7.44 (d, J=7.8 Hz, 1H), 7.30-7.23 (m, 2H), 6.99 (s, 2H), 6.92 (s, 1H), 6.78 (s, 1H), 6.74 (d, J=7.8 Hz, 1H), 6.36 (d, J=7.5 Hz, 1H), 5.23 (dq, J=7.5, 6.9 Hz, 1H), 5.08 (s, 2H), 3.08 (t, J=7.5 Hz, 2H), 2.77 (t, J=7.5 Hz, 2H), 2.32 (s, 6H), 2.31 (s, 3H), 1.57 (d, J=6.9 Hz, 3H).

Example 6(209)

3-(2-((3-methyl-1-phenylbutyl)carbamoyl)-4-phenoxymethyl-5-methoxyphenyl)propanoic acid

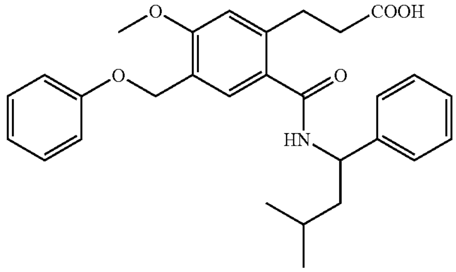

TLC: Rf 0.28 (hexane:ethyl acetate=1:1, 0.5% acetic acid);

NMR (300 MHz, $CDCl_3$): δ 7.46 (s, 1H), 7.38-7.22 (m, 7H), 7.02-6.94 (m, 3H), 6.78 (s, 1H), 6.19 (d, J=8.4 Hz, 1H), 5.19 (m, 1H), 5.06 (s, 2H), 3.87 (s, 3H), 3.06 (m, 2H), 2.76 (t, J=7.5 Hz, 2H), 1.82-1.50 (m, 3H), 0.972 (d, J=6.6 Hz, 3H), 0.969 (d, J=6.6 Hz, 3H).

Example 6(210)

3-(2-((1-methyl-2-phenylethyl)carbamoyl)-4-phenoxymethylphenyl)propanoic acid

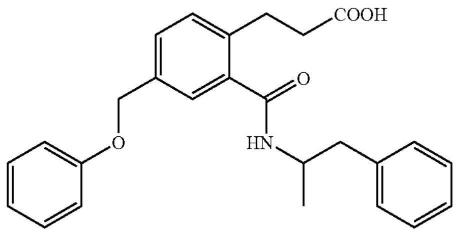

TLC: Rf 0.34 (chloroform:methanol=10:1);

NMR (300 MHz, $CDCl_3$): δ 7.43-7.16 (m, 10H), 7.03-6.92 (m, 3H), 5.99 (d, J=8.1 Hz, 1H), 4.98 (s, 2H), 4.49 (m, 1H), 3.00-2.90 (m, 2H), 2.87 (d, J=6.6 Hz, 2H), 2.80-2.65 (m, 2H), 1.26 (d, J=6.6 Hz, 3H).

Example 6(211)

3-(2-((3-methyl-1-phenylbutyl)carbamoyl)-4-(benzothiazol-2-yl)phenyl)propanoic acid

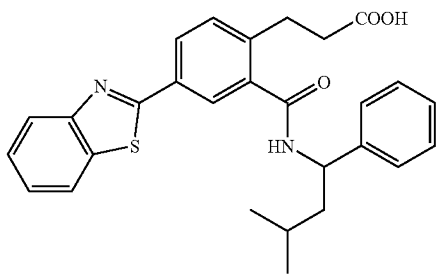

TLC: Rf 0.48 (chloroform:methanol=10:1).

Example 6(212)

3-(2-((3-methyl-1-phenylbutyl)carbamoyl)-4-(1,3-dioxaindan-2-yl)phenyl)propanoic acid

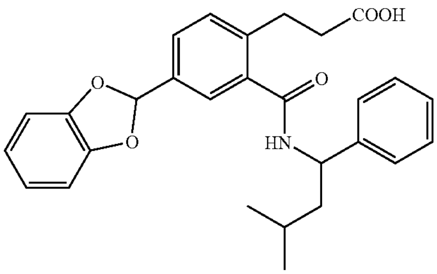

TLC: Rf 0.46 (chloroform:methanol=10:1).

Example 6(213)

3-(2-((3-methyl-1-phenylbutyl)carbamoyl)-4-(indol-1-ylmethyl)phenyl)propanoic acid

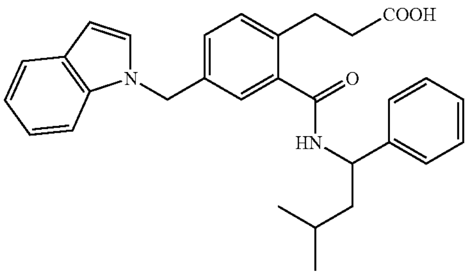

TLC: Rf 0.48 (chloroform:methanol=10:1).

Example 6(214)

3-(2-((4-methyl-1-phenylpentan-2-yl)carbamoyl)-4-phenoxymethylphenyl)propanoic acid

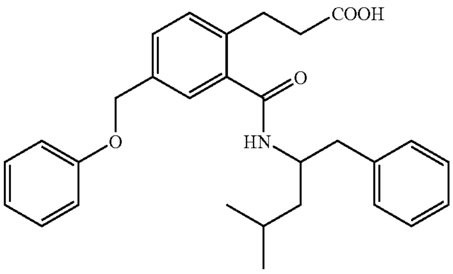

TLC: Rf 0.50 (chloroform:methanol=10:1);

NMR (300 MHz, $CDCl_3$): δ 7.43-7.16 (m, 10H), 7.04-6.93 (m, 3H), 5.76 (d, J=9.0 Hz, 1H), 4.99 (s, 2H), 4.53 (m, 1H), 3.02-2.66 (m, 6H), 1.72 (m, 1H), 1.52-1.35 (m, 2H), 0.97 (d, J=6.0 Hz, 3H), 0.95 (d, J=6.0 Hz, 3H).

Example 6(215)

3-(2-((3-methyl-1-phenylbutyl)carbamoyl)-4-phenoxymethyl-5-methylphenyl)propanoic acid

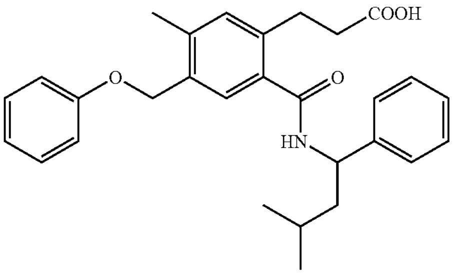

TLC: Rf 0.23 (hexane:ethyl acetate=2:1, 0.5% acetic acid);

NMR (300 MHz, $CDCl_3$): δ 7.40 (s, 1H), 7.36-7.25 (m, 7H), 7.12 (s, 1H), 7.03-6.95 (m, 3H), 6.31 (d, J=8.1 Hz, 1H), 5.21 (m, 1H), 4.99 (s, 2H), 3.01 (m, 2H), 2.74 (t, J=7.5 Hz, 2H), 2.35 (s, 3H), 1.85-1.55 (m, 3H), 0.97 (d, J=6.6 Hz, 6H).

Example 6(216)

3-(2-((naphthalen-2-ylmethyl)carbamoyl)-4-(pyrazol-1-ylmethyl)phenyl)propanoic acid

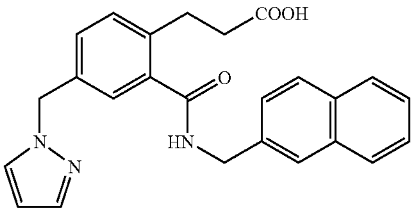

TLC: Rf 0.37 (chloroform:methanol=10:1);

NMR (300 MHz, DMSO-$d_6$): δ 12.14 (brs, 1H), 9.01 (t, J=5.7 Hz, 1H), 7.95-7.77 (m, 5H), 7.57-7.44 (m, 4H), 7.33-7.26 (m, 2H), 7.20 (d, J=8.1 Hz, 1H), 6.28 (m, 1H), 5.34 (s, 2H), 4.60 (d, J=5.7 Hz, 2H), 2.92 (t, J=7.8 Hz, 2H), 2.57-2.48 (m, 2H).

Example 6(217)

3-(2-((3-methyl-1-phenylbutyl)sulfamoyl)-4-phenoxymethylphenyl)propanoic acid

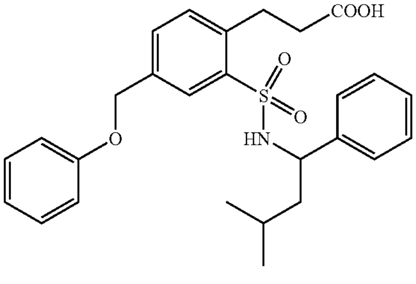

TLC: Rf 0.46 (chloroform:methanol=5:1);

NMR (300 MHz, $CDCl_3$): δ 7.77 (s, 1H), 7.43 (d, J=8.1 Hz, 1H), 7.38-7.25 (m, 2H), 7.20-6.90 (m, 9H), 6.10-5.95 (m, 1H), 4.94 (s, 2H), 4.32 (q, J=7.5 Hz, 1H), 3.25-3.00 (m, 2H), 2.72 (ddd, J=16.2, 10.2, 5.7 Hz, 1H), 2.51 (ddd, J=16.2, 10.5, 5.7 Hz, 1H), 1.80-1.40 (m, 3H), 0.88 (d, J=6.6 Hz, 3H), 0.85 (d, J=6.6 Hz, 3H).

Example 6(218)

3-(2-((3-methyl-1-(3,5-dimethylphenyl)butyl)carbamoyl)-4-(pyrazol-1-ylmethyl)phenyl)propanoic acid

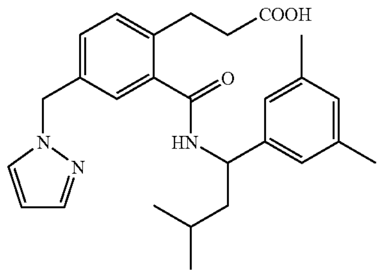

TLC: Rf 0.54 (chloroform:methanol=10:1).

Example 6(219)

3-(2-((3-methyl-1-(3,5-dimethoxyphenyl)butyl)carbamoyl)-4-(pyrazol-1-ylmethyl)phenyl)propanoic acid

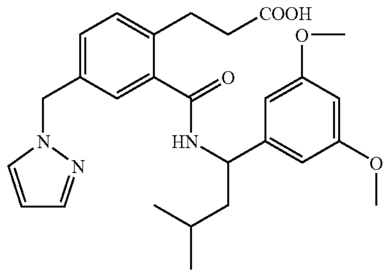

TLC: Rf 0.51 (chloroform:methanol=10:1).

Example 6(220)

3-(2-((3-methyl-1-phenylbutyl)carbamoyl)-3-methyl-4-phenoxymethylphenyl)propanoic acid

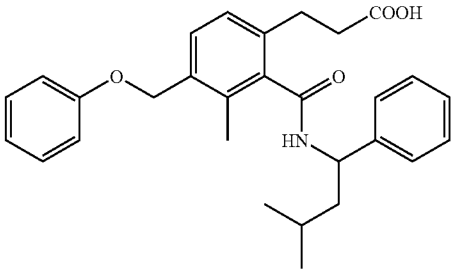

TLC: Rf 0.38 (hexane:ethyl acetate=1:1, 0.5% acetic acid);

NMR (300 MHz, $CDCl_3$): δ 7.40-7.25 (m, 8H), 7.07 (d, J=8.1 Hz, 1H), 7.01-6.93 (m, 3H), 6.18 (d, J=8.7 Hz, 1H), 5.29 (m, 1H), 4.96 (s, 2H), 2.90 (m, 2H), 2.62 (m, 2H), 2.22 (bs, 3H), 1.90-1.55 (m, 3H), 0.99 (d, J=6.3 Hz, 3H), 0.98 (d, J=6.3 Hz, 3H).

Example 6(221)

2-(2-(3-methyl-1-phenylbutyl)carbamoyl-4-phenoxymethylbenzyloxy)acetic acid

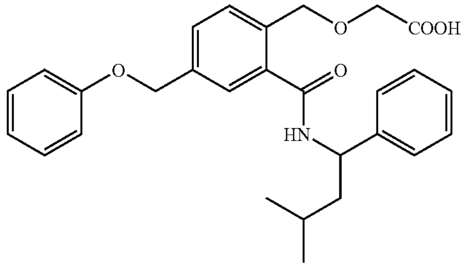

TLC: Rf 0.44 (chloroform:methanol=9:1);

NMR (300 MHz, $CDCl_3$): δ 7.57 (d, J=1.5 Hz, 1H), 7.49 (dd, J=7.8, 1.5 Hz, 1H), 7.39-7.24 (m, 8H), 7.03-6.92 (m, 3H), 6.65 (d, J=8.4 Hz, 1H), 5.24 (m, 1H), 5.08 (s, 2H), 4.67 (d, J=11 Hz, 1H), 4.56 (d, J=11 Hz, 1H), 3.99 (d, J=17 Hz, 1H), 3.94 (d, J=17 Hz, 1H), 1.89-1.52 (m, 3H), 0.99 (d, J=6.5 Hz, 3H), 0.98 (d, J=6.5 Hz, 3H).

Example 6(222)

3-(2-((3-hydroxy-3-methyl-1-phenylbutyl)carbamoyl)-4-phenoxymethylphenyl)propanoic acid

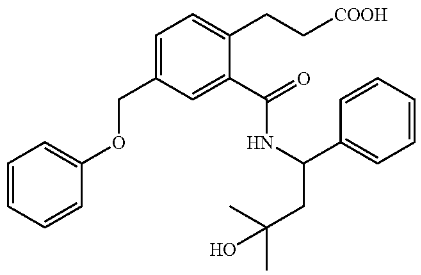

TLC: Rf 0.42 (chloroform:methanol=10:1).

Example 6(223)

4-(3-methyl-1-phenylbutylcarbamoyl)-2-benzofurancarboxylic acid

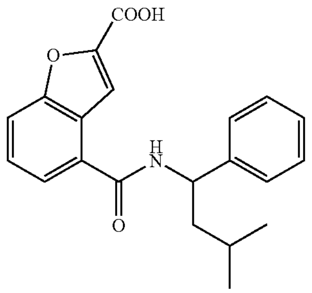

TLC: Rf 0.29 (chloroform:methanol:acetic acid=90:10:1); NMR (300 MHz, DMSO-$d_6$): δ 8.94 (d, J=8.7 Hz, 1H), 7.90-7.82 (m, 2H), 7.79 (d, J=0.6 Hz, 1H), 7.59 (t, J=8.0 Hz, 1H), 7.45-7.39 (m, 2H), 7.36-7.28 (m, 2H), 7.22 (m, 1H), 5.15 (m, 1H), 1.87 (m, 1H), 1.70-1.48 (m, 2H), 0.93 (d, J=6.3 Hz, 6H).

Example 6(224)

7-(3-methyl-1-phenylbutylcarbamoyl)-2-benzofuran-carboxylic acid

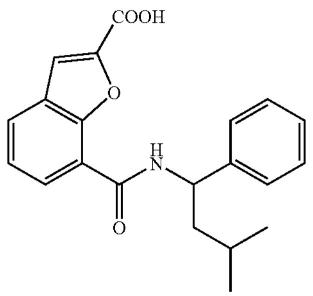

TLC: Rf 0.53 (chloroform:methanol:acetic acid=90:10:1); NMR (300 MHz, DMSO-$d_6$): δ 8.74 (d, J=8.1 Hz, 1H), 7.91 (d, J=8.1 Hz, 1H), 7.76-7.69 (m, 2H), 7.50-7.18 (m, 6H), 5.14 (m, 1H), 1.88-1.71 (m, 2H), 1.52 (m, 1H), 0.95 (d, J=6.2 Hz, 3H), 0.93 (d, J=6.2 Hz, 3H).

Example 6(225)

2-(7-(3-methyl-1-phenylbutylcarbamoyl)indol-1-yl) acetic acid

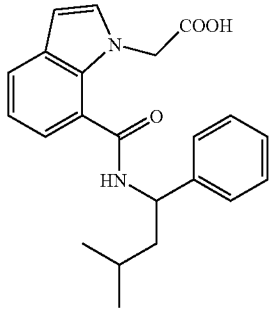

TLC: Rf 0.35 (ethyl acetate);
NMR (300 MHz, DMSO-$d_6$): δ 12.56 (s, 1H), 8.99 (d, J=8.7 Hz, 1H), 7.65 (d, J=7.8 Hz, 1H), 7.41-7.31 (m, 5H), 7.25-7.20 (m, 1H), 7.14 (d, J=6.6 Hz, 1H), 7.05 (t, J=7.8 Hz, 1H), 6.52 (d, J=3.0 Hz, 1H), 5.17 (d, J=18.3 Hz, 1H), 5.12-5.06 (m, 1H), 4.97 (d, J=18.3 Hz, 1H), 1.84-1.74 (m, 1H), 1.68-1.55 (m, 1H), 1.50-1.41 (m, 1H), 0.95 (d, J=6.3 Hz, 3H), 0.91 (d, J=6.3 Hz, 3H).

Example 6(226)

2-(7-(3-methyl-1-phenylbutylcarbamoyl)indol-3-yl) acetic acid

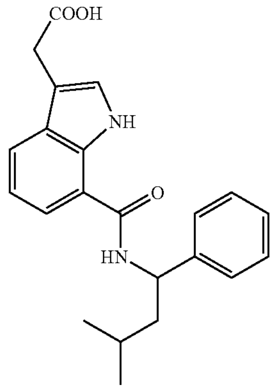

TLC: Rf 0.60 (ethyl acetate);
NMR (300 MHz, $CDCl_3$): δ 10.25 (brs, 1H), 7.76 (d, J=7.8 Hz, 1H), 7.40-7.23 (m, 7H), 7.11 (t, J=7.8 Hz, 1H), 6.98 (d, J=6.9 Hz, 1H), 5.31-5.23 (m, 1H), 3.80 (s, 2H), 1.89-1.58 (m, 3H), 1.01-0.97 (m, 6H).

Example 6(227)

7-(3-methyl-1-phenylbutylcarbamoyl)naphthalen-ecarboxylic acid

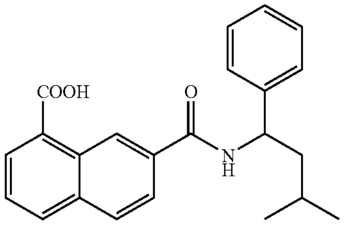

TLC: Rf 0.33 (chloroform:methanol=10:1);
NMR (300 MHz, DMSO-$d_6$): δ 9.31 (s, 1H), 8.96 (d, J=8.4 Hz, 1H), 8.24-8.13 (m, 2H), 8.08 (d, J=8.7 Hz, 1H), 7.97 (d, J=8.7 Hz, 1H), 7.66 (m, 1H), 7.47-7.17 (m, 5H), 5.14 (m, 1H), 1.88 (m, 1H), 1.67 (m, 1H), 1.54 (m, 1H), 0.94 (d, J=6.3 Hz, 6H).

Example 6(228)

2-(1-benzyl-3-(3-methyl-1-phenylbutylcarbamoyl) indol-4-yl)acetic acid

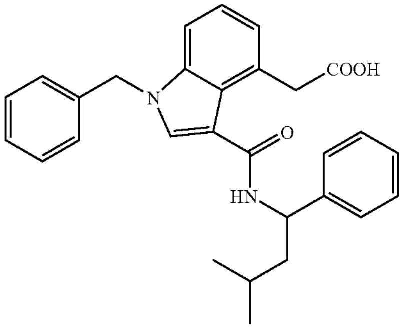

TLC: Rf 0.38 (n-hexane:ethyl acetate=1:1);

NMR (300 MHz, DMSO-$d_6$): δ 12.24 (brs, 1H), 8.56 (brd, J=8.7 Hz, 1H), 8.01 (s, 1H), 7.50-7.20 (m, 11H), 7.09 (t, J=7.5 Hz, 1H), 6.92 (d, J=7.5 Hz, 1H), 5.47 (s, 2H), 5.20-5.05 (m, 1H), 4.24 (d, J=15.3 Hz, 1H), 4.01 (d, J=15.3 Hz, 1H), 1.90-1.45 (m, 3H), 0.95 (t, J=6.0 Hz, 6H).

Example 6(229)

3-(1-benzyl-3-(3-methyl-1-phenylbutylcarbamoyl) indol-4-yl)propanoic acid

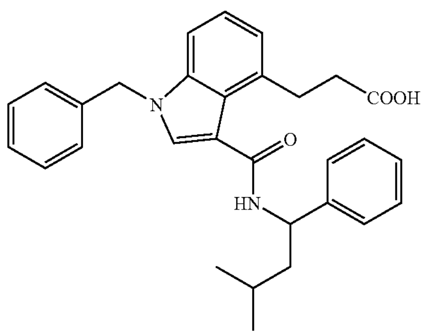

TLC: Rf 0.33 (n-hexane:ethyl acetate=1:1);

NMR (300 MHz, DMSO-$d_6$): δ 11.84 (brs, 1H), 8.48 (brd, J=8.4 Hz, 1H), 7.87 (s, 1H), 7.50-7.20 (m, 11H), 7.04 (t, J=7.2 Hz, 1H), 6.89 (d, J=7.2 Hz, 1H), 5.45 (s, 2H), 5.20-5.05 (m, 1H), 3.40-3.10 (m, 2H), 2.38 (dt, J=2.4, 7.8 Hz, 2H), 1.90-1.45 (m, 3H), 0.95 (t, J=6.3 Hz, 6H).

Example 6(230)

3-(2-((3-methyl-1-phenylbutyl)carbamoyl)-4-methoxymethylphenyl)propanoic acid

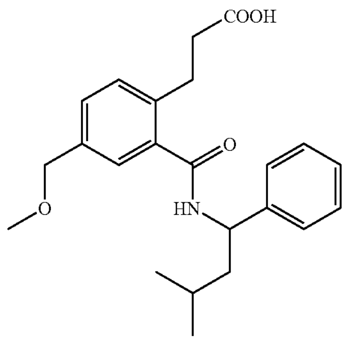

TLC: Rf 0.27 (n-hexane:ethyl acetate=1:1);

NMR (300 MHz, DMSO-$d_6$): δ 8.82 (d, J=8.7 Hz, 1H), 7.41-7.16 (m, 8H), 5.07 (m, 1H), 4.40 (s, 2H), 3.30 (s, 3H), 2.92-2.75 (m, 2H), 2.55-2.40 (m, 2H), 1.85-1.40 (m, 3H), 0.98-0.89 (m, 6H).

Example 6(231)

2-(7-(3-methyl-1-phenylbutylcarbamoyl)indolin-1-yl)acetic acid

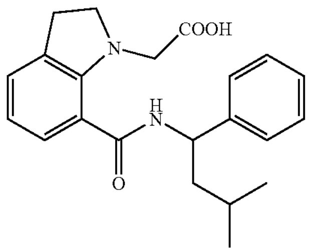

TLC: Rf 0.40 (ethyl acetate);

NMR (300 MHz, DMSO-$d_6$): δ 12.26 (s, 1H), 8.73 (d, J=7.8 Hz, 1H), 7.36-7.28 (m, 4H), 7.22-7.16 (m, 1H), 7.06 (d, J=7.2 Hz, 1H), 6.93 (d, J=7.2 Hz, 1H), 6.57 (t, J=7.5 Hz, 1H), 5.04-4.96 (m, 1H), 4.11 (d, J=18.3 Hz, 1H), 3.85 (d, J=18.3 Hz, 1H), 3.47 (t, J=8.4 Hz, 2H), 2.96-2.90 (m, 2H), 1.80-1.34 (m, 3H), 0.92-0.88 (m, 6H).

Example 6(232)

3-(7-(3-methyl-1-phenylbutylcarbamoyl)indolin-1-yl)propanoic acid

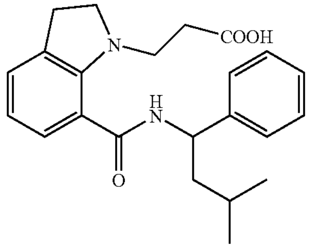

TLC: Rf 0.70 (ethyl acetate);

NMR (300 MHz, DMSO-$d_6$): δ 12.09 (brs, 1H), 8.73 (d, J=9.0 Hz, 1H), 7.38-7.18 (m, 5H), 7.05 (d, J=7.5 Hz, 1H), 6.90 (d, J=7.5 Hz, 1H), 6.57 (t, J=7.5 Hz, 1H), 5.04-4.95 (m, 1H), 3.41-3.35 (m, 2H), 3.23 (t, J=7.5 Hz, 2H), 2.90-2.84 (m, 2H), 2.30-2.24 (m, 2H), 1.80-1.41 (m, 3H), 0.90 (d, J=6.3 Hz, 6H).

Example 6(233)

3-(2-((3-methyl-1-phenylbutyl)carbamoyl)-4-cyanophenyl)propanoic acid

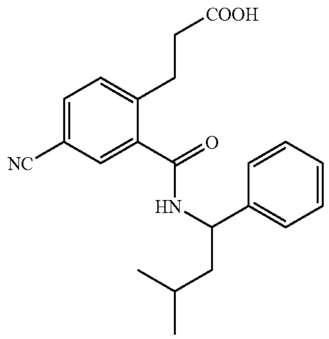

TLC: Rf 0.42 (chloroform:methanol=9:1);

NMR (300 MHz, $CDCl_3$): δ 7.65-7.58 (m, 2H), 7.41-7.25 (m, 6H), 6.50 (d, J=8.1 Hz, 1H), 5.22 (m, 1H), 3.09-2.97 (m, 2H), 2.77-2.65 (m, 2H), 1.87-1.52 (m, 3H), 0.99 (d, J=6.6 Hz, 6H).

Example 6(234)

1-benzyl-3-(3-methyl-1-phenylbutylcarbamoyl)-5-indolecarboxylic acid

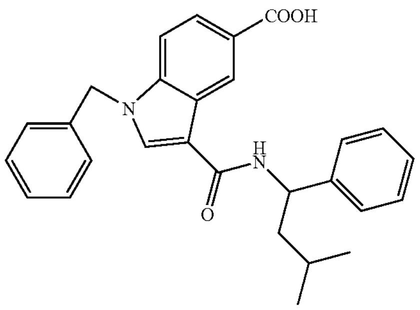

TLC: Rf 0.47 (chloroform:methanol=9:1);

NMR (300 MHz, DMSO-$d_6$): δ 8.81 (s, 1H), 8.39-8.31 (m, 2H), 7.75 (dd, J=8.9, 1.5 Hz, 1H), 7.59 (d, J=8.9 Hz, 1H), 7.43-7.16 (m, 10H), 5.51 (s, 2H), 5.13 (m, 1H), 1.79 (m, 1H), 1.69-1.48 (m, 2H), 0.93 (d, J=6.6 Hz, 6H).

Example 6(235)

3-(8-(3-methyl-1-phenylbutylcarbamoyl)-1,2,3,4-tetrahydroquinolin-1-yl)propanoic acid

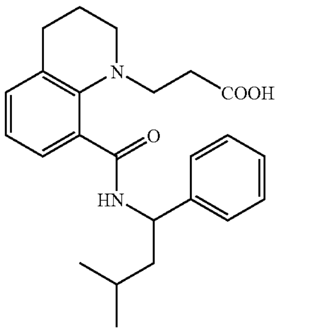

TLC: Rf 0.56 (methylene chloride:methanol=10:1);

NMR (300 MHz, DMSO-$d_6$): δ 8.75 (d, J=8.1 Hz, 1H), 7.40-7.27 (m, 4H), 7.23 (m, 1H), 7.03-6.94 (m, 2H), 6.69 (t, J=7.5 Hz, 1H), 4.98 (m, 1H), 3.22-3.02 (m, 4H), 2.67 (t, J=6.0 Hz, 2H), 2.40-2.17 (m, 2H), 1.84-1.67 (m, 3H), 1.62-1.42 (m, 2H), 0.91 (d, J=6.3 Hz, 3H), 0.90 (d, J=6.3 Hz, 3H).

Example 6(236)

3-(2-((3-methyl-1-phenylbutyl)carbamoyl)-4-methylsulfonylaminophenyl)propanoic acid

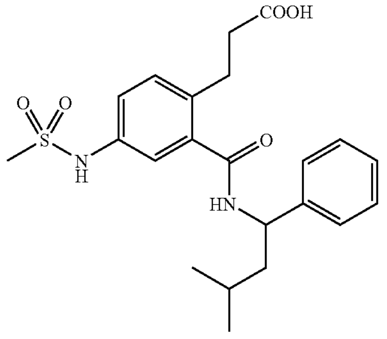

TLC: Rf 0.55 (ethyl acetate).

Example 6(237)

3-(2-((3-methyl-1-phenylbutyl)carbamoyl)-4-(N-methyl-N-methylsulfonylamino)phenyl)propanoic acid

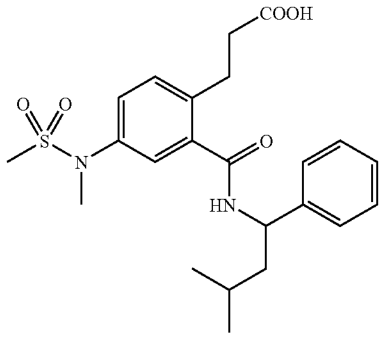

TLC: Rf 0.55 (ethyl acetate).

Example 6(238)

3-(2-((3-methyl-1-phenylbutyl)carbamoyl)-4-methoxycarbonylaminophenyl)propanoic acid

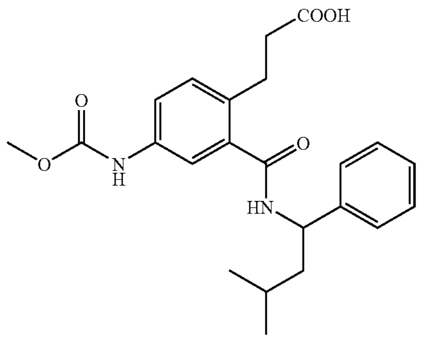

TLC: Rf 0.65 (ethyl acetate).

Example 6(239)

3-(2-((3-methyl-1-(3-methylphenyl)butyl)carbamoyl)-4-(3-cyanophenoxymethyl)phenyl)propanoic acid

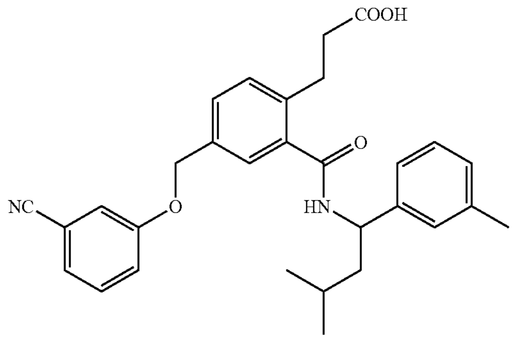

TLC: Rf 0.47 (chloroform:methanol=9:1);

NMR (300 MHz, $CDCl_3$): δ 7.43-7.06 (m, 11H), 6.40 (d, J=8.7 Hz, 1H), 5.21 (dt, J=8.7, 8.7 Hz, 1H), 5.04 (s, 2H), 3.03 (m, 2H), 2.74 (t, J=7.5 Hz, 2H), 2.35 (s, 3H), 1.85-1.58 (m, 3H), 0.99 (d, J=6.3 Hz, 6H).

Example 6(240)

3-(2-((3-methyl-1-(3-methoxyphenyl)butyl)carbamoyl)-4-(3-cyanophenoxymethyl)phenyl)propanoic acid

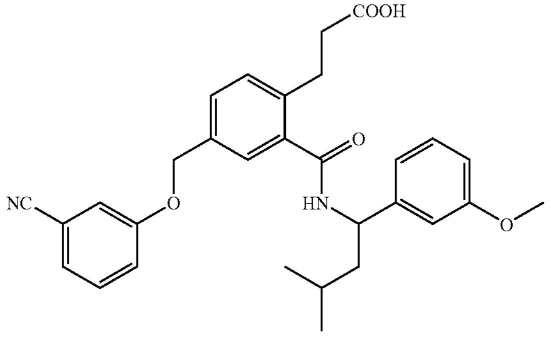

TLC: Rf 0.43 (chloroform:methanol=9:1);

NMR (300 MHz, $CDCl_3$): δ 7.42-7.15 (m, 8H), 6.95 (d, J=7.8 Hz, 1H), 6.91 (m, 1H), 6.81 (dd, J=8.4, 2.7 Hz, 1H), 6.45 (d, J=8.1 Hz, 1H), 5.22 (dt, J=8.1, 8.1 Hz, 1H), 5.03 (s, 2H), 3.81 (s, 3H), 3.02 (t, J=7.2 Hz, 2H), 2.74 (t, J=7.2 Hz, 2H), 1.83-1.58 (m, 3H), 0.98 (d, J=6.3 Hz, 6H).

Example 6(241)

3-(2-((3-methyl-1-phenylbutyl)carbamoyl)-4-dibenzylaminophenyl)propanoic acid

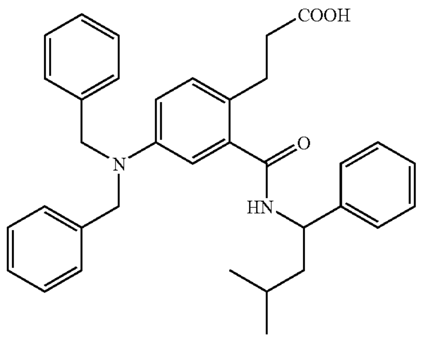

TLC: Rf 0.50 (n-hexane:ethyl acetate=1:1);

NMR (300 MHz, DMSO-$d_6$): δ 11.94 (s, 1H), 8.56 (d, J=8.7 Hz, 1H), 7.35-7.18 (m, 15H), 6.96 (d, J=8.4 Hz, 1H), 6.62 (dd, J=8.4, 2.7 Hz, 1H), 6.56 (d, J=2.7 Hz, 1H), 4.98-4.90 (m, 1H), 4.72 (s, 4H), 2.72-2.58 (m, 2H), 2.34 (t, J=7.8 Hz, 2H), 1.73-1.50 (m, 2H), 1.40-1.31 (m, 1H), 0.86-0.83 (m, 6H).

Example 6(242)

3-(2-((3-methyl-1-phenylbutyl)carbamoyl)-4-phenylsulfonyloxyphenyl)propanoic acid

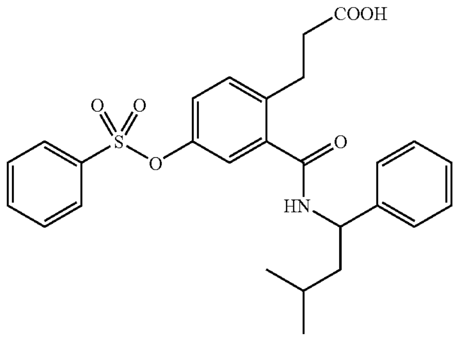

TLC: Rf 0.31 (n-hexane:ethyl acetate=1:1);

NMR (300 MHz, $CDCl_3$): δ 7.84-7.81 (m, 2H), 7.65 (m, 1H), 7.55-7.49 (m, 2H), 7.39-7.26 (m, 5H), 7.18 (d, J=8.4 Hz, 1H), 6.97 (dd, J=8.4, 2.4 Hz, 1H), 6.90 (d, J=2.4 Hz, 1H), 6.39 (d, J=8.1 Hz, 1H), 5.16 (m, 1H), 2.98-2.93 (m, 2H), 2.68-2.62 (m, 2H), 1.81-1.63 (m, 2H), 1.55 (m, 1H), 0.98 (d, J=6.6 Hz, 3H), 0.96 (d, J=6.6 Hz, 3H).

Example 6(243)

3-(2-((3-methyl-1-phenylbutyl)carbamoyl)-4-isopropylsulfonyloxyphenyl)propanoic acid

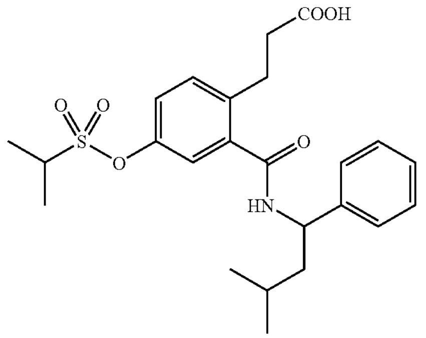

TLC: Rf 0.28 (n-hexane:ethyl acetate=1:1);

NMR (300 MHz, $CDCl_3$): δ 7.36-7.35 (m, 4H), 7.31-7.23 (m, 4H), 6.61 (brd, J=8.4 Hz, 1H), 5.21 (m, 1H), 3.48 (quint, J=6.9 Hz, 1H), 3.01-2.95 (m, 2H), 2.71-2.66 (m, 2H), 1.85-1.66 (m, 2H), 1.58 (m, 1H), 1.55 (d, J=6.9 Hz, 6H), 0.99 (d, J=6.6 Hz, 3H), 0.97 (d, J=6.6 Hz, 3H).

Example 6(244)

3-(1-benzyl-3-(3-methyl-1-(3,5-dimethylphenyl)butylcarbamoyl)indol-4-yl)propanoic acid

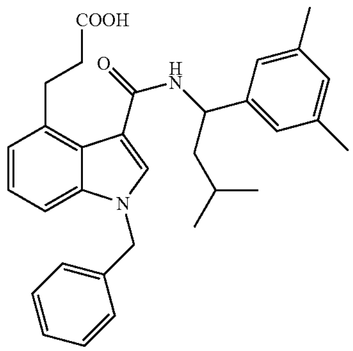

TLC: Rf 0.34 (chloroform:methanol=9:1);

NMR (300 MHz, $CDCl_3$): δ 7.43 (s, 1H), 7.36-7.02 (m, 8H), 6.95 (s, 2H), 6.92 (s, 1H), 6.25 (d, J=8.4 Hz, 1H), 5.31 (s, 2H), 5.17 (dt, J=8.4, 8.4 Hz, 1H), 3.33 (m, 2H), 2.77 (t, J=8.1 Hz, 2H), 2.31 (s, 6H), 1.80-1.50 (m, 3H), 0.99 (d, J=6.3 Hz, 3H), 0.98 (d, J=6.3 Hz, 3H).

Example 6(245)

3-(1-(3-cyanobenzyl)-3-(3-methyl-1-(3,5-dimethylphenyl)butylcarbamoyl)indol-4-yl)propanoic acid

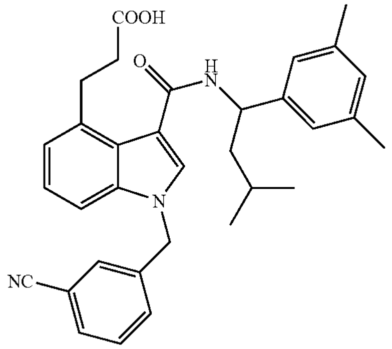

TLC: Rf 0.34 (chloroform:methanol=9:1);

NMR (300 MHz, $CDCl_3$): δ 7.60 (d, J=8.1 Hz, 1H), 7.48-6.90 (m, 10H), 6.28 (d, J=8.4 Hz, 1H), 5.35 (s, 2H), 5.19 (dt, J=8.4, 8.4 Hz, 1H), 3.32 (m, 2H), 2.78 (t, J=8.1 Hz, 2H), 2.32 (s, 6H), 1.93-1.60 (m, 3H), 1.00 (d, J=6.3 Hz, 3H), 0.99 (d, J=6.3 Hz, 3H).

Example 6(246)

2-(8-(3-methyl-1-(3,5-dimethylphenyl)butylcarbamoyl)-1,2,3,4-tetrahydroquinolin-1-yl)acetic acid

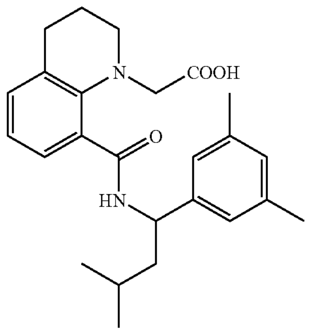

TLC: Rf 0.33 (methylene chloride:methanol=10:1);

NMR (300 MHz, DMSO-$d_6$): δ 8.94 (m, 1H), 7.14 (m, 1H), 7.01 (m, 1H), 6.97 (s, 2H), 6.84 (s, 1H), 6.72 (m, 1H), 4.92 (m, 1H), 3.67 (d, J=17.4 Hz, 1H), 3.57 (d, J=17.4 Hz, 1H), 3.30-3.04 (m, 2H), 2.76-2.66 (m, 2H), 2.25 (s, 6H), 1.96-1.68 (m, 3H), 1.66-1.34 (m, 2H), 0.91 (d, J=6.0 Hz, 3H), 0.90 (d, J=6.0 Hz, 3H).

Example 6(247)

2-(7-((3-methyl-1-(3,5-dimethylphenyl)butyl)carbamoyl)indolin-1-yl)acetic acid

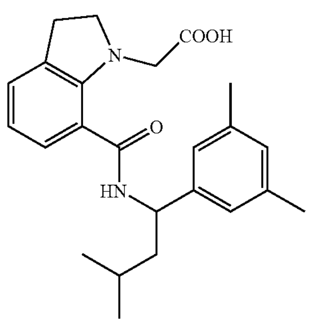

TLC: Rf 0.60 (n-hexane:ethyl acetate=2:1);

NMR (300 MHz, DMSO-$d_6$): δ 12.22 (brs, 1H), 8.63 (d, J=7.8 Hz, 1H), 7.07-6.82 (m, 5H), 6.57 (t, J=7.5 Hz, 1H), 4.97-4.89 (m, 1H), 4.12 (d, J=18.3 Hz, 1H), 3.81 (d, J=18.3 Hz, 1H), 3.47 (t, J=8.7 Hz, 2H), 2.96-2.90 (m, 2H), 2.24 (s, 6H), 1.78-1.68 (m, 1H), 1.62-1.54 (m, 1H), 1.40-1.30 (m, 1H), 0.91-0.87 (m, 6H).

Example 6(248)

3-(2-((3-methyl-1-phenylbutyl)carbamoyl)-4-benzylaminophenyl)propanoic acid

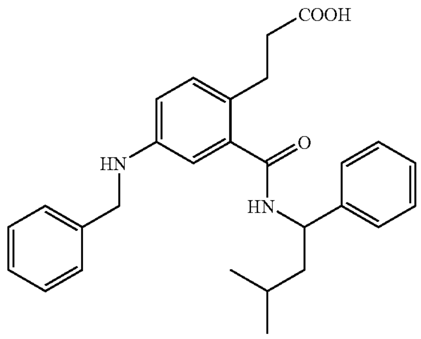

TLC: Rf 0.55 (methylene chloride:methanol=9:1);

NMR (300 MHz, $CDCl_3$): δ 7.40-7.20 (m, 10H), 7.03 (d, J=8.1 Hz, 1H), 6.62 (dd, J=8.1, 2.4 Hz, 1H), 6.54 (d, J=2.4 Hz, 1H), 6.22 (d, J=8.7 Hz, 1H), 5.18 (q, J=8.4 Hz, 1H), 4.30 (s, 2H), 2.86 (t, J=7.2 Hz, 2H), 2.66 (t, J=7.2 Hz, 2H), 1.80-1.50 (m, 3H), 0.96 (d, J=6.3 Hz, 6H).

Example 6(249)

3-(2-((3-methyl-1-(3,4-dimethoxyphenyl)butyl)carbamoyl)-4-(3-cyanophenoxymethyl)phenyl)propanoic acid

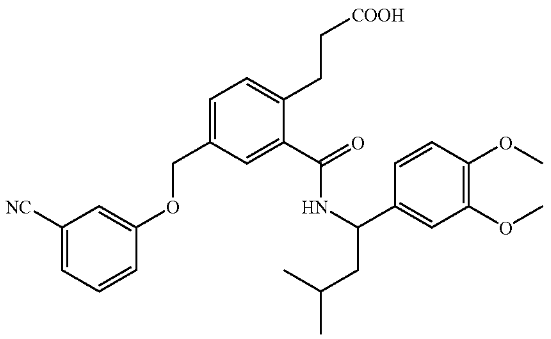

TLC: Rf 0.45 (methylene chloride:methanol=9:1);

NMR (300 MHz, $CDCl_3$): δ 7.44-7.34 (m, 3H), 7.32-7.24 (m, 2H), 7.20-7.14 (m, 2H), 6.94-6.88 (m, 2H), 6.84 (d, J=8.7 Hz, 1H), 6.42 (d, J=8.4 Hz, 1H), 5.20 (q, J=7.2 Hz, 1H), 5.02 (s, 2H), 3.88 (s, 3H), 3.86 (s, 3H), 3.01 (t, J=8.1 Hz, 2H), 2.73 (t, J=8.1 Hz, 2H), 1.90-1.50 (m, 3H), 0.99 (d, J=6.3 Hz, 6H).

Example 6(250)

3-(3-benzyl-1-(3-methyl-1-phenylbutylcarbamoylmethyl)indol-7-yl)propanoic acid

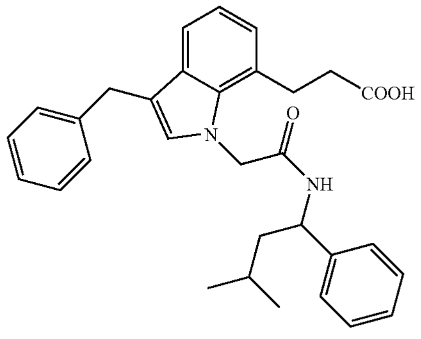

TLC: Rf 0.44 (chloroform:methanol=9:1);

NMR (300 MHz, $CDCl_3$): δ 7.47 (d, J=7.2 Hz, 1H), 7.40-7.15 (m, 9H), 7.09 (t, J=7.2 Hz, 1H), 7.01 (d, J=7.2 Hz, 1H), 6.90-6.80 (m, 2H), 6.67 (s, 1H), 5.17 (brd, J=8.4 Hz, 1H), 5.02-4.83 (m, 3H), 4.09 (s, 2H), 3.11 (dd, J=8.7, 5.7 Hz, 2H), 2.59 (dd, J=8.7, 6.9 Hz, 2H), 1.35-1.15 (m, 2H), 1.15-0.97 (m, 1H), 0.77 (d, J=6.6 Hz, 3H), 0.72 (d, J=6.6 Hz, 3H).

Example 6(251)

3-(2-((3-methyl-1-(3-methyl-4-fluorophenyl)butyl)carbamoyl)-4-(3-cyanophenoxymethyl)phenyl)propanoic acid

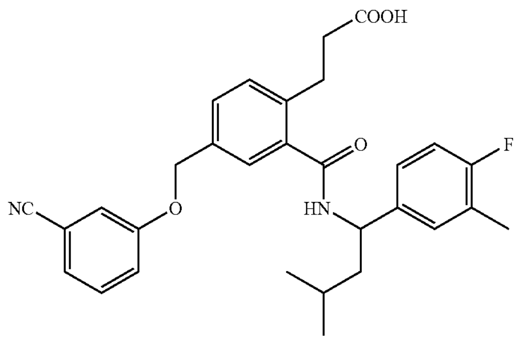

TLC: Rf 0.35 (chloroform:methanol=10:1);

NMR (300 MHz, $CDCl_3$): δ 7.42-7.35 (m, 3H), 7.31-7.25 (m, 2H), 7.21-7.11 (m, 4H), 6.96 (dd, J=8.7, 8.7 Hz, 1H), 6.46 (d, J=8.4 Hz, 1H), 5.17 (m, 1H), 5.03 (s, 2H), 3.06-2.95 (m, 2H), 2.76-2.64 (m, 2H), 2.26 (d, J=1.5 Hz, 3H), 1.81-1.53 (m, 3H), 0.97 (d, J=6.6 Hz, 6H).

Example 6(252)

3-(2-((3-methyl-1-phenylbutyl)carbamoyl)-4-methylsulfonyloxyphenyl)propanoic acid

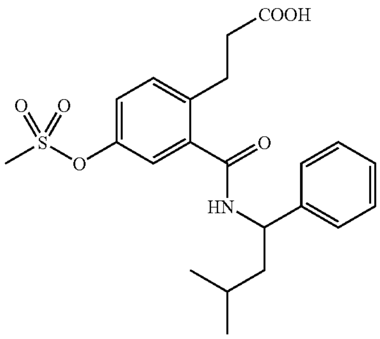

TLC: Rf 0.52 (chloroform:methanol=9:1);

NMR (300 MHz, $CDCl_3$): δ 7.36-7.34 (m, 4H), 7.30-7.24 (m, 4H), 6.67 (brd, J=8.1 Hz, 1H), 5.21 (m, 1H), 3.14 (s, 3H), 3.02-2.91 (m, 2H), 2.70-2.64 (m, 2H), 1.85-1.67 (m, 2H), 1.58 (m, 1H), 0.97 (d, J=6.0 Hz, 6H).

Example 6(253)

3-(2-((3-methyl-1-(3,5-dimethoxyphenyl)butyl)carbamoyl)-4-(3-cyanophenoxymethyl)phenyl)propanoic acid

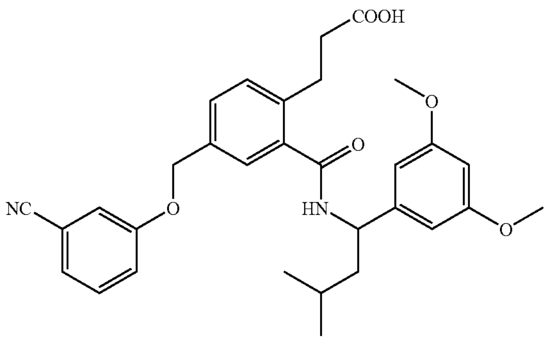

TLC: Rf 0.43 (chloroform:methanol=10:1);

NMR (300 MHz, $CDCl_3$): δ 7.44-7.14 (m, 7H), 6.52 (s, 2H), 6.48 (d, J=8.4 Hz, 1H), 6.37 (s, 1H), 5.17 (m, 1H), 5.03 (s, 2H), 3.79 (s, 6H), 3.03 (t, J=7.2 Hz, 2H), 2.75 (t, J=7.2 Hz, 2H), 1.83-1.56 (m, 3H), 0.98 (d, J=6.3 Hz, 6H).

Example 6(254)

8-(3-methyl-1-(3,5-dimethylphenyl)butylcarbamoyl)-2-naphthalenecarboxylic acid

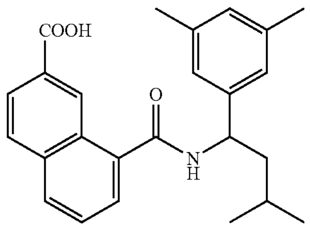

TLC: Rf 0.67 (chloroform:methanol=10:1);

NMR (300 MHz, DMSO-$d_6$): δ 8.97 (d, J=8.4 Hz, 1H), 8.80 (s, 1H), 8.12-7.95 (m, 3H), 7.73-7.58 (m, 2H), 7.02 (s, 2H), 6.87 (s, 1H), 5.12 (m, 1H), 2.27 (s, 6H), 1.84-1.65 (m, 2H), 1.54-1.39 (m, 1H), 1.00 (d, J=6.0 Hz, 3H), 0.93 (d, J=6.0 Hz, 3H).

Example 6(255)

7-(3-methyl-1-(3,5-dimethylphenyl)butylcarbamoyl)-2-benzofurancarboxylic acid

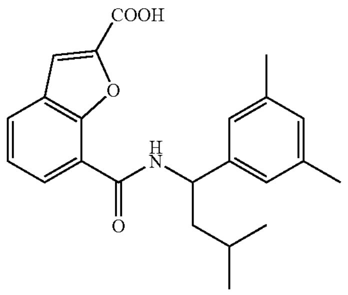

TLC: Rf 0.55 (chloroform:methanol:acetic acid=90:10:1);

NMR (300 MHz, $CDCl_3$): δ 8.29 (dd, J=7.7, 1.3 Hz, 1H), 7.93 (d, J=7.8 Hz, 1H), 7.85 (dd, J=7.7, 1.3 Hz, 1H), 7.74 (s, 1H), 7.45 (t, J=7.7 Hz, 1H), 7.07 (s, 2H), 6.89 (s, 1H), 5.28 (m, 1H), 2.32 (s, 6H), 2.00-1.66 (m, 3H), 1.02 (d, J=8.3 Hz, 3H), 1.00 (d, J=8.3 Hz, 3H).

Example 6(256)

3-(2-((3-methyl-1-(3,5-dimethylphenyl)butyl)carbamoyl)-4-benzyloxycarbonylaminophenyl)propanoic acid

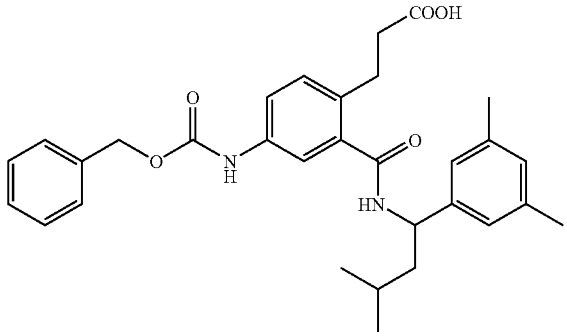

TLC: Rf 0.61 (methylene chloride:methanol=9:1);

NMR (300 MHz, $CDCl_3$): δ 7.46-7.24 (m, 6H), 7.16-7.08 (m, 1H), 6.98-6.80 (m, 4H), 6.56-6.42 (m, 1H), 5.17 (s, 2H), 5.13 (q, J=7.2 Hz, 1H), 3.00-2.85 (m, 2H), 2.70-2.55 (m, 2H), 2.29 (s, 6H), 1.80-1.50 (m, 3H), 0.96 (d, J=5.4 Hz, 6H).

Example 6(257)

3-(2-((3-methyl-1-(3,5-dimethylphenyl)butyl)carbamoyl)-4-benzylaminophenyl)propanoic acid

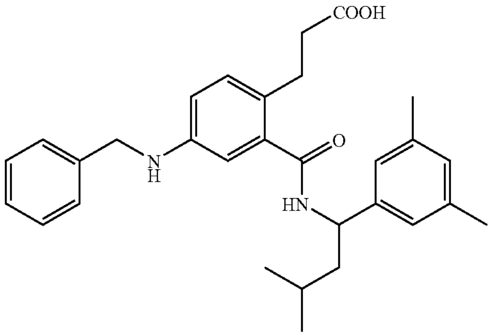

TLC: Rf 0.57 (methylene chloride:methanol=9:1);

NMR (300 MHz, $CDCl_3$): δ 7.38-7.24 (m, 5H), 7.03 (d, J=8.4 Hz, 1H), 6.91 (s, 3H), 6.62 (dd, J=8.4, 2.4 Hz, 1H), 6.55 (d, J=2.4 Hz, 1H), 6.15 (d, J=8.4 Hz, 1H), 5.11 (q, J=8.4 Hz, 1H), 4.30 (s, 2H), 2.88 (t, J=7.5 Hz, 2H), 2.67 (t, J=7.5 Hz, 2H), 2.30 (s, 6H), 1.80-1.50 (m, 3H), 0.96 (d, J=6.3 Hz, 6H).

Example 6(258)

3-(2-((3-methyl-1-(3,5-dimethylphenyl)butyl)carbamoyl)-4-(isoindolin-2-yl)phenyl)propanoic acid

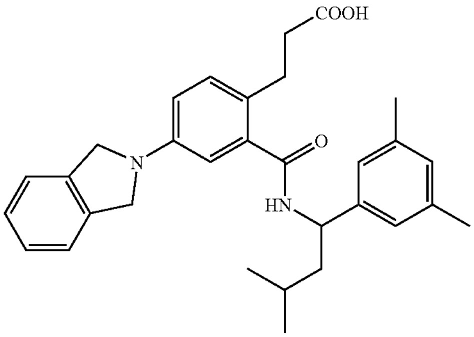

TLC: Rf 0.47 (methylene chloride:methanol=9:1);

NMR (300 MHz, $CDCl_3$): δ 7.40-7.25 (m, 4H), 7.16 (d, J=8.4 Hz, 1H), 6.98 (s, 2H), 6.92 (s, 1H), 6.67 (dd, J=8.4, 2.4 Hz, 1H), 6.60 (d, J=2.4 Hz, 1H), 6.40 (d, J=8.4 Hz, 1H), 5.19 (q, J=8.4 Hz, 1H), 4.62 (s, 4H), 2.92 (t, J=7.2 Hz, 2H), 2.72 (t, J=7.2 Hz, 2H), 2.32 (s, 6H), 1.85-1.55 (m, 3H), 1.00 (d, J=6.3 Hz, 6H).

Example 6(259)

3-(2-((3-methyl-1-(3,5-dimethylphenyl)butyl)carbamoyl)-4-phenoxycarbonylaminophenyl)propanoic acid

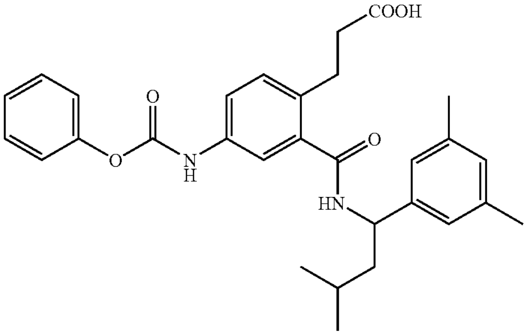

TLC: Rf 0.47 (methylene chloride:methanol=9:1);

NMR (300 MHz, $CDCl_3$): δ 7.52 (s, 1H), 7.42-7.32 (m, 3H), 7.28-7.10 (m, 4H), 6.94 (s, 2H), 6.88 (s, 1H), 6.48 (d, J=8.7 Hz, 1H), 5.13 (q, J=8.7 Hz, 1H), 3.00-2.90 (m, 2H), 2.70-2.60 (m, 2H), 2.28 (s, 6H), 1.80-1.50 (m, 3H), 0.95 (d, J=6.3 Hz, 6H).

Example 6(260)

2-(7-(3-methyl-1-(3,5-dimethylphenyl)butylcarbamoyl)benzofuran-2-yl)acetic acid

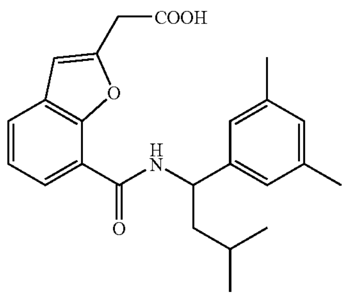

TLC: Rf 0.48 (chloroform:methanol=9:1);

NMR (300 MHz, $CDCl_3$): δ 8.03 (dd, J=7.7, 1.3 Hz, 1H), 7.69 (d, J=7.8 Hz, 1H), 7.64 (dd, J=7.7, 1.3 Hz, 1H), 7.31 (t, J=7.7 Hz, 1H), 6.99 (s, 2H), 6.86 (s, 1H), 6.75 (s, 1H), 5.23 (m, 1H), 3.93 (s, 2H), 2.29 (s, 6H), 1.91-1.59 (m, 3H), 0.97 (d, J=6.2 Hz, 3H), 0.95 (d, J=6.2 Hz, 3H).

Example 6(261)

3-(2-((3-methyl-1-(3,5-difluorophenyl)butyl)carbamoyl)-4-(3-cyanophenoxymethyl)phenyl)propanoic acid

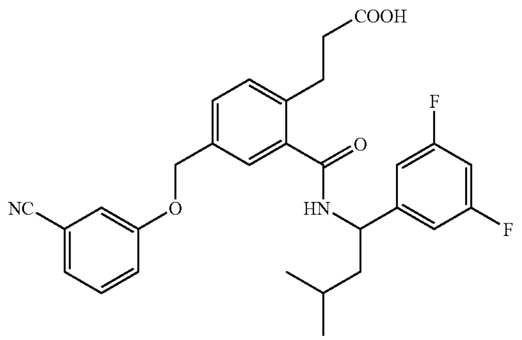

TLC: Rf 0.51 (methylene chloride:methanol=9:1);

NMR (300 MHz, $CDCl_3$): δ 7.45-7.15 (m, 8H), 6.90 (t, J=8.4 Hz, 2H), 6.65 (d, J=8.4 Hz, 1H), 5.72 (q, J=8.4 Hz, 1H), 5.05 (s, 2H), 3.04 (t, J=7.2 Hz, 2H), 2.72 (t, J=7.2 Hz, 2H), 1.95-1.80 (m, 1H), 1.80-1.65 (m, 1H), 1.65-1.50 (m, 1H), 1.00 (d, J=6.0 Hz, 3H), 0.98 (d, J=6.0 Hz, 3H).

Example 6(262)

3-(2-((3-methyl-1-(3,5-dimethylphenyl)butyl)carbamoyl)-4-benzoylaminophenyl)propanoic acid

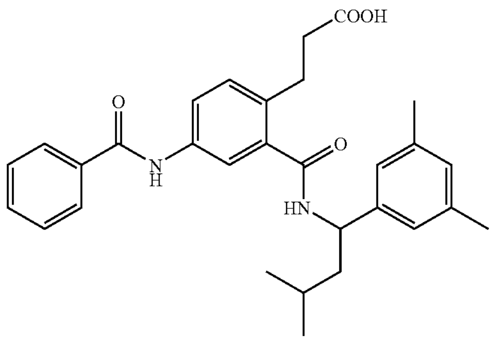

TLC: Rf 0.46 (methylene chloride:methanol=9:1);

NMR (300 MHz, $CDCl_3$): δ 8.10-8.00 (m, 1H), 7.85 (d, J=8.0 Hz, 2H), 7.71 (s, 1H), 7.60-7.42 (m, 4H), 7.24-7.18 (m, 1H), 6.96 (s, 2H), 6.89 (s, 1H), 6.70-6.62 (m, 1H), 5.14 (q, J=7.5 Hz, 1H), 3.05-2.95 (m, 2H), 2.75-2.65 (m, 2H), 2.30 (s, 6H), 1.85-1.55 (m, 3H), 0.97 (d, J=6.6 Hz, 6H).

Example 6(263)

3-(2-((3-methyl-1-(3,5-dimethylphenyl)butyl)carbamoyl)-4-(N-benzyl-N-methylamino)phenyl)propanoic acid

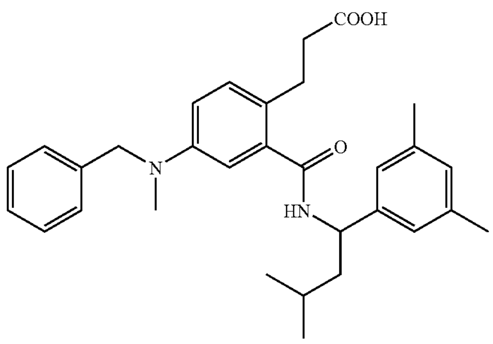

TLC: Rf 0.57 (methylene chloride:methanol=9:1);

NMR (300 MHz, $CDCl_3$): δ 7.36-7.16 (m, 5H), 7.06 (d, J=8.7 Hz, 1H), 6.89 (s, 3H), 6.72 (dd, J=8.7, 3.0 Hz, 1H), 6.64 (d, J=3.0 Hz, 1H), 6.12 (d, J=8.4 Hz, 1H), 5.10 (q, J=8.4 Hz, 1H), 4.50 (s, 2H), 3.04 (s, 3H), 2.88 (t, J=7.5 Hz, 2H), 2.67 (t, J=7.5 Hz, 2H), 2.29 (s, 6H), 1.80-1.45 (m, 3H), 0.96 (d, J=6.6 Hz, 3H), 0.95 (d, J=6.6 Hz, 3H).

Example 6(264)

2-(2-((3-methyl-1-(3,5-dimethylphenyl)butyl)carbamoyl)-4-phenoxymethylphenoxy)acetic acid

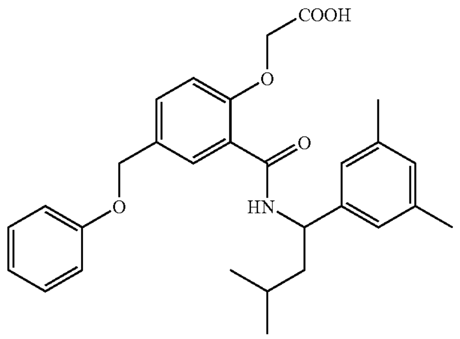

TLC: Rf 0.38 (chloroform:methanol=9:1);

NMR (300 MHz, $CDCl_3$): δ 8.01 (s, 2H), 7.51 (dd, J=7.6, 2.3 Hz, 1H), 7.32-7.22 (m, 2H), 7.13-6.84 (m, 7H), 5.22 (m, 1H), 5.00 (s, 2H), 4.78 (s, 2H), 2.28 (s, 6H), 1.94-1.54 (m, 3H), 0.95 (d, J=6.0 Hz, 6H).

Example 6(265)

2-(2-((3-methyl-1-(3,5-dimethylphenyl)butyl)carbamoyl)-4-(3-cyanophenoxymethyl)phenoxy)acetic acid

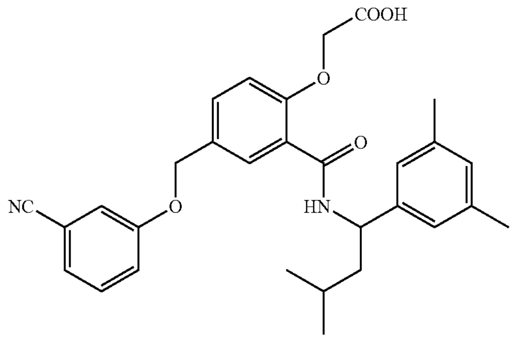

TLC: Rf 0.38 (chloroform:methanol=9:1);

NMR (300 MHz, $CDCl_3$): δ 8.29 (d, J=7.5 Hz, 1H), 8.10 (d, J=1.2 Hz, 1H), 7.48 (dd, J=7.6, 2.3 Hz, 1H), 7.35 (t, J=8.4 Hz, 1H), 7.24 (m, 1H), 7.18-7.10 (m, 2H), 7.01 (s, 2H), 6.93 (d, J=8.4 Hz, 1H), 6.85 (s, 1H), 5.22 (m, 1H), 5.00 (s, 2H), 4.79 (s, 2H), 2.27 (s, 6H), 1.97-1.57 (m, 3H), 0.95 (d, J=6.3 Hz, 6H).

Example 6(266)

3-(2-((3-methyl-1-(3,5-dimethylphenyl)butyl)carbamoyl)-4-phenylcarbamoylphenyl)propanoic acid

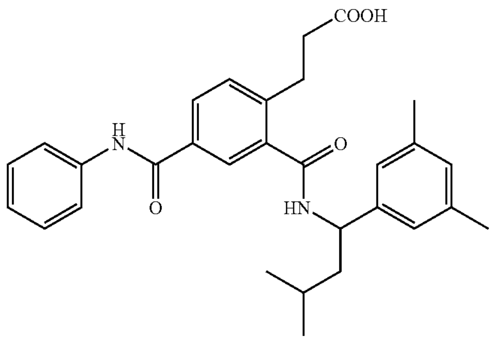

TLC: Rf 0.41 (methylene chloride:methanol=9:1);

NMR (300 MHz, $CD_3OD$): δ 8.92 (d, J=8.7 Hz, 1H), 7.92 (dd, J=8.1, 2.1 Hz, 1H), 7.85 (d, J=2.1 Hz, 1H), 7.66 (d, J=8.4 Hz, 2H), 7.46 (d, J=8.1 Hz, 1H), 7.35 (t, J=8.4 Hz, 2H), 7.14 (t, J=8.4 Hz, 1H), 7.00 (s, 2H), 6.89 (s, 1H), 5.15-5.05 (m, 1H), 3.01 (t, J=7.2 Hz, 2H), 2.55 (t, J=7.2 Hz, 2H), 2.30 (s, 6H), 1.90-1.50 (m, 3H), 1.01 (d, J=6.3 Hz, 3H), 0.99 (d, J=6.3 Hz, 3H).

Example 6(267)

3-(2-((3-methyl-1-(3,5-dimethylphenyl)butyl)carbamoyl)-4-(N-acetyl-N-benzylamino)phenyl)propanoic acid

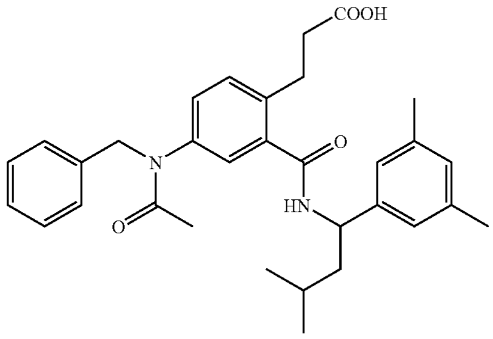

TLC: Rf 0.44 (methylene chloride:methanol=9:1);

NMR (300 MHz, $CDCl_3$): δ 7.30-7.10 (m, 6H), 7.10-7.00 (m, 1H), 7.00-6.85 (m, 3H), 6.68 (s, 1H), 5.86 (d, J=8.1 Hz, 1H), 5.06 (q, J=8.1 Hz, 1H), 4.83 (s, 2H), 3.05-2.95 (m, 2H), 2.70-2.60 (m, 2H), 2.31 (s, 6H), 1.85 (s, 3H), 1.70-1.40 (m, 3H), 0.96 (d, J=6.3 Hz, 3H), 0.95 (d, J=6.3 Hz, 3H).

Example 6(268)

3-(2-((3-methyl-1-(3,5-dimethylphenyl)butyl)carbamoyl)-4-((N-phenylamino)carbonylamino)phenyl) propanoic acid

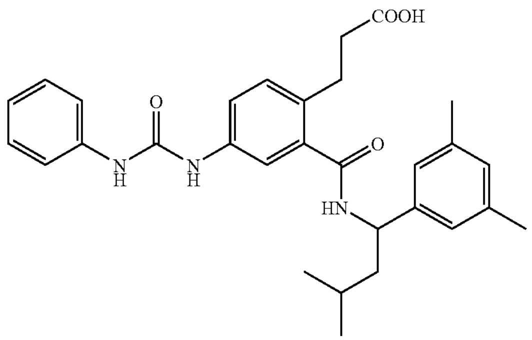

TLC: Rf 0.44 (methylene chloride:methanol=9:1);

NMR (300 MHz, $CD_3OD$): δ 7.46-7.34 (m, 4H), 7.32-7.20 (m, 3H), 7.05-6.98 (m, 3H), 6.88 (s, 1H), 5.08 (dd, J=9.6, 6.0 Hz, 1H), 2.90 (t, J=7.5 Hz, 2H), 2.50 (t, J=7.5 Hz, 2H), 2.30 (s, 6H), 1.85-1.50 (m, 3H), 1.00 (d, J=6.0 Hz, 3H), 0.98 (d, J=6.0 Hz, 3H).

Example 6(269)

3-(2-((3-methyl-1-(3,5-dimethylphenyl)butyl)carbamoyl)-4-phenylsulfonylaminophenyl)propanoic acid

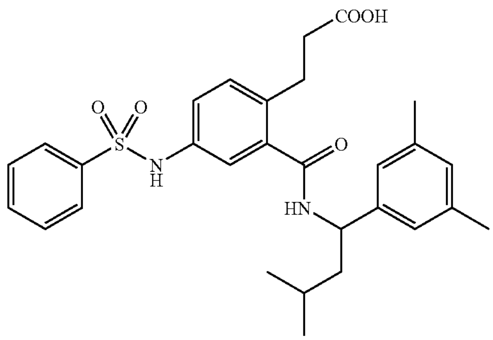

TLC: Rf 0.48 (methylene chloride:methanol=9:1);

NMR (300 MHz, $CDCl_3$): δ 7.71 (d, J=7.5 Hz, 2H), 7.52 (t, J=7.5 Hz, 1H), 7.40 (t, J=7.5 Hz, 2H), 7.20-7.12 (m, 1H), 7.10-7.00 (m, 2H), 6.96-6.88 (m, 4H), 6.42 (d, J=8.7 Hz, 1H), 5.09 (q, J=8.7 Hz, 1H), 2.95-2.85 (m, 2H), 2.65-2.55 (m, 2H), 2.30 (s, 6H), 1.80-1.50 (m, 3H), 0.96 (d, J=6.3 Hz, 6H).

Example 6(270)

3-(2-((3-methyl-1-(3,5-dimethylphenyl)butyl)carbamoyl)-4-(N-benzyl-N-methylsulfonylamino)phenyl)propanoic acid

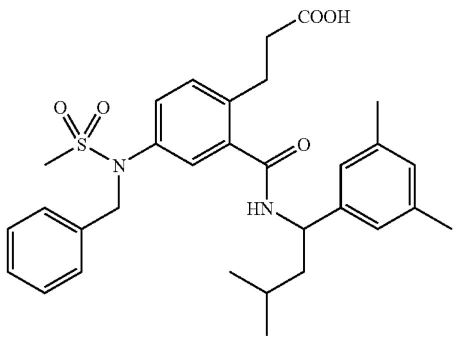

TLC: Rf 0.56 (methylene chloride:methanol=9:1);

NMR (300 MHz, $CDCl_3$): δ 7.30-7.16 (m, 7H), 7.12 (d, J=3.0 Hz, 1H), 6.91 (s, 3H), 6.18 (d, J=8.7 Hz, 1H), 5.09 (q, J=8.7 Hz, 1H), 4.80 (s, 2H), 3.00-2.90 (m, 5H), 2.66 (t, J=7.5 Hz, 2H), 2.31 (s, 6H), 1.80-1.50 (m, 3H), 0.97 (d, J=6.3 Hz, 3H), 0.96 (d, J=6.3 Hz, 3H).

Example 6(271)

3-(3-((3-methyl-1-(3,5-dimethylphenyl)butyl)carbamoyl)-5-(3-cyanophenoxymethyl)phenyl)propanoic acid

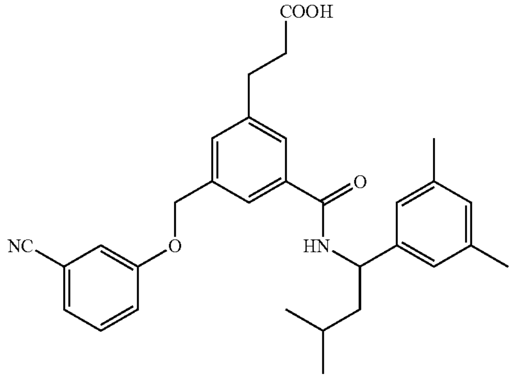

TLC: Rf 0.51 (chloroform:methanol=10:1);

NMR (300 MHz, DMSO-$d_6$): δ 8.65 (d, J=8.4 Hz, 1H), 7.76 (s, 1H), 7.71 (s, 1H), 7.54-7.33 (m, 5H), 6.97 (s, 2H), 6.83 (s, 1H), 5.17 (s, 2H), 5.02 (m, 1H), 2.89 (t, J=7.5 Hz, 2H), 2.58 (t, J=7.5 Hz, 2H), 2.24 (s, 6H), 1.81 (m, 1H), 1.66-1.43 (m, 2H), 0.91 (d, J=6.0 Hz, 3H), 0.89 (d, J=6.0 Hz, 3H).

Example 6(272)

3-(3-((3-methyl-1-(3,5-dimethylphenyl)butyl)carbamoyl)-5-(3-cyanophenoxymethyl)phenyl)propenoic acid

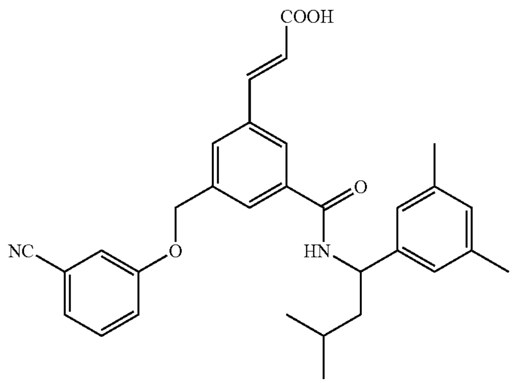

TLC: Rf 0.50 (chloroform:methanol=10:1);

NMR (300 MHz, DMSO-$d_6$): δ 8.76 (d, J=8.4 Hz, 1H), 8.17 (s, 1H), 7.95 (s, 1H), 7.91 (s, 1H), 7.64 (d, J=15.9 Hz, 1H), 7.60-7.34 (m, 4H), 6.97 (s, 2H), 6.84 (s, 1H), 6.84 (d, J=15.9 Hz, 1H), 5.23 (s, 2H), 5.04 (m, 1H), 2.24 (s, 6H), 1.82 (m, 1H), 1.68-1.45 (m, 2H), 0.92 (d, J=6.0 Hz, 3H), 0.90 (d, J=6.0 Hz, 3H).

Example 6(273)

4-(3-((3-methyl-1-(3,5-dimethylphenyl)butyl)carbamoyl)-5-(3-cyanophenoxymethyl)phenyl)butanoic acid

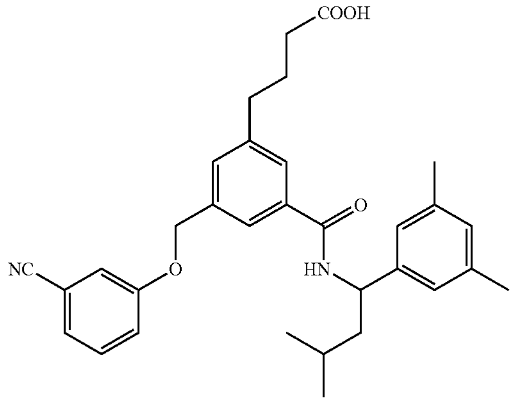

TLC: Rf 0.49 (chloroform:methanol=10:1);

NMR (300 MHz, DMSO-$d_6$): δ 8.67 (d, J=8.4 Hz, 1H), 7.76 (s, 1H), 7.67 (s, 1H), 7.55-7.33 (m, 5H), 6.97 (s, 2H), 6.83 (s, 1H), 5.18 (s, 2H), 5.03 (m, 1H), 2.65 (t, J=7.8 Hz, 2H), 2.28-2.19 (m, 2H), 2.24 (s, 6H), 1.89-1.74 (m, 3H), 1.66-1.43 (m, 2H), 0.91 (d, J=6.0 Hz, 3H), 0.89 (d, J=6.0 Hz, 3H).

Example 6(274)

3-(2-(1-(3,5-dimethylphenyl)butylcarbamoyl)-4-(3-cyanophenoxymethyl)phenyl)propanoic acid

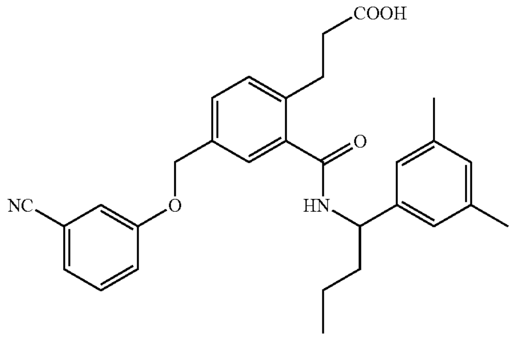

TLC: Rf 0.64 (methylene chloride:methanol=9:1);

NMR (300 MHz, $CDCl_3$): δ 7.44-7.24 (m, 5H), 7.22-7.14 (m, 2H), 6.94 (s, 2H), 6.91 (s, 1H), 6.39 (d, J=8.4 Hz, 1H), 5.07 (q, J=8.4 Hz, 1H), 5.03 (s, 2H), 3.04 (t, J=7.2 Hz, 2H), 2.73 (t, J=7.2 Hz, 2H), 2.30 (s, 6H), 2.00-1.75 (m, 2H), 1.50-1.25 (m, 2H), 0.95 (t, J=7.5 Hz, 3H).

Example 6(275)

3-(2-((3-methyl-1-(3,5-dimethylphenyl)butyl)carbamoyl)-4-(pyrazol-1-ylmethylcarbonyl)phenyl) propanoic acid

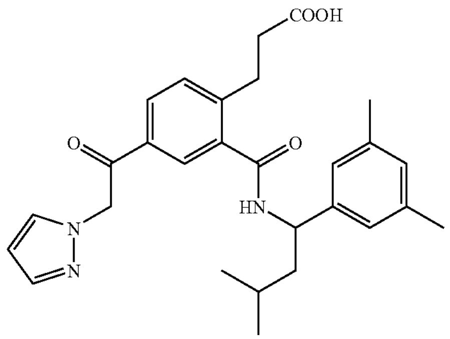

TLC: Rf 0.43 (chloroform:methanol=10:1);

NMR (300 MHz, DMSO-$d_6$): δ 8.88 (d, J=8.7 Hz, 1H), 8.02 (dd, J=7.8, 2.1 Hz, 1H), 7.83 (d, J=2.1 Hz, 1H), 7.72 (d, J=2.1 Hz, 1H), 7.49 (d, J=7.8 Hz, 1H), 7.47 (d, J=2.1 Hz, 1H), 6.96 (s, 2H), 6.85 (s, 1H), 6.30 (t, J=2.1 Hz, 1H), 5.82 (s, 2H), 4.98 (m, 1H), 2.93 (t, J=7.8 Hz, 2H), 2.46 (t, J=7.8 Hz, 2H), 2.25 (s, 6H), 1.80-1.55 (m, 2H), 1.44 (m, 1H), 0.93 (d, J=6.6 Hz, 3H), 0.91 (d, J=6.6 Hz, 3H).

Example 6(276)

3-(2-((1-(3,5-dimethylphenyl)propyl)carbamoyl)-4-(3-cyanophenoxymethyl)phenyl)propanoic acid

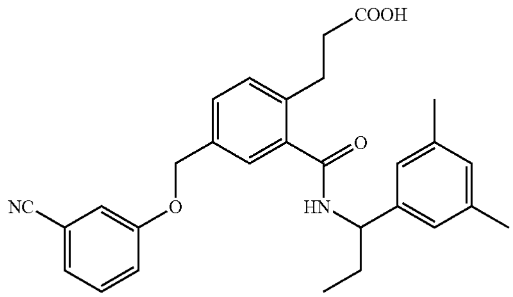

TLC: Rf 0.49 (chloroform:methanol=10:1);

NMR (300 MHz, DMSO-$d_6$): δ 8.74 (d, J=8.4 Hz, 1H), 7.56-7.28 (m, 7H), 6.95 (s, 2H), 6.84 (s, 1H), 5.16 (s, 2H), 4.77 (m, 1H), 2.85 (t, J=7.8 Hz, 2H), 2.46 (t, J=7.8 Hz, 2H), 2.24 (s, 6H), 1.80-1.63 (m, 2H), 0.89 (t, J=7.2 Hz, 3H).

Example 6(277)

3-(2-((3-methyl-1-(3,5-dimethylphenyl)butyl)carbamoyl)-4-(2-phenylvinyl)phenyl)propanoic acid

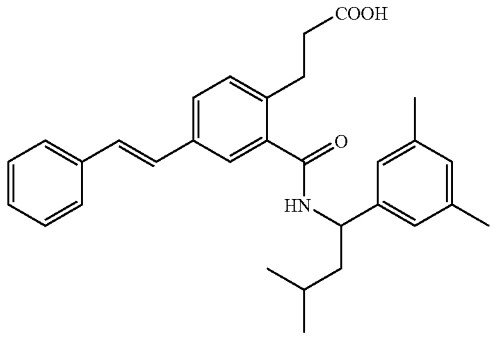

TLC: Rf 0.51 (methylene chloride:methanol=9:1);

NMR (300 MHz, $CDCl_3$): δ 7.54-7.42 (m, 4H), 7.40-7.32 (m, 2H), 7.32-7.22 (m, 2H), 7.09 (d, J=16.5 Hz, 1H), 7.03 (d, J=16.5 Hz, 1H), 6.98 (s, 2H), 6.92 (s, 1H), 6.35 (d, J=8.7 Hz, 1H), 5.19 (q, J=8.7 Hz, 1H), 3.01 (t, J=7.5 Hz, 2H), 2.72 (t, J=7.5 Hz, 2H), 2.32 (s, 6H), 1.85-1.60 (m, 3H), 0.99 (d, J=6.3 Hz, 6H).

Example 6(278)

3-(2-((3-methyl-1-(3,5-dimethylphenyl)butyl)carbamoyl)-4-(2-(pyrazol-1-yl)ethyl)phenyl)propanoic acid

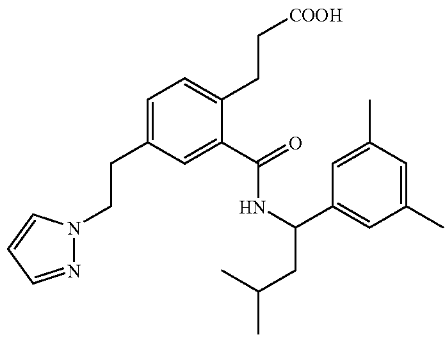

TLC: Rf 0.50 (chloroform:methanol=10:1);

NMR (300 MHz, $CDCl_3$): δ 7.50 (s, 1H), 7.17-6.88 (m, 6H), 6.75 (s, 1H), 6.23 (d, J=8.7 Hz, 1H), 6.12 (t, J=2.1 Hz, 1H), 5.12 (m, 1H), 4.29 (t, J=6.9 Hz, 2H), 3.08 (t, J=6.9 Hz, 2H), 2.98 (t, J=7.2 Hz, 2H), 2.70 (t, J=7.2 Hz, 2H), 2.32 (s, 6H), 1.84-1.52 (m, 3H), 0.99 (d, J=6.6 Hz, 6H).

Example 6(279)

3-(2-((3-methyl-1-(3,5-dimethylphenyl)butyl)carbamoyl)-4-(2-fluorophenoxymethyl)phenyl)propanoic acid

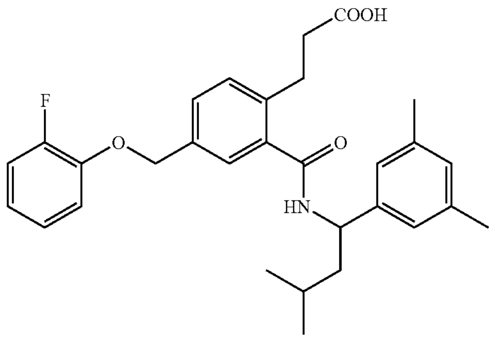

TLC: Rf 0.53 (chloroform:methanol=10:1);

NMR (300 MHz, $CDCl_3$): δ 7.44 (s, 1H), 7.42 (d, J=8.1 Hz, 1H), 7.28 (d, J=8.1 Hz, 1H), 7.15-6.87 (m, 4H), 6.96 (s, 2H), 6.91 (s, 1H), 6.31 (d, J=8.7 Hz, 1H), 5.16 (m, 1H), 5.09 (s, 2H), 3.08-2.97 (m, 2H), 2.72 (t, J=7.2 Hz, 2H), 2.31 (s, 6H), 1.85-1.56 (m, 3H), 0.99 (d, J=6.3 Hz, 6H).

Example 6(280)

3-(2-((3-methyl-1-(3,5-dimethylphenyl)butyl)carbamoyl)-4-(2-chlorophenoxymethyl)phenyl)propanoic acid

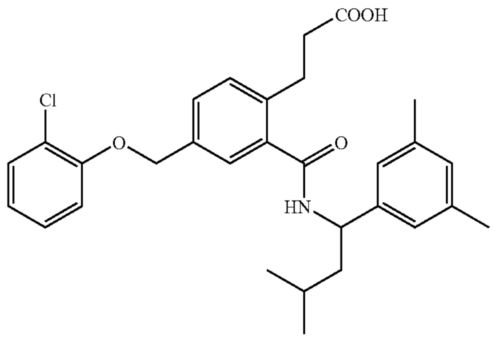

TLC: Rf 0.53 (chloroform:methanol=10:1);

NMR (300 MHz, $CDCl_3$): δ 7.52 (s, 1H), 7.46-7.35 (m, 2H), 7.28 (d, J=8.1 Hz, 1H), 7.21 (m, 1H), 7.00-6.87 (m, 2H), 6.95 (s, 2H), 6.91 (s, 1H), 6.29 (d, J=8.4 Hz, 1H), 5.16 (m, 1H), 5.12 (s, 2H), 3.09-2.97 (m, 2H), 2.73 (t, J=7.2 Hz, 2H), 2.31 (s, 6H), 1.86-1.58 (m, 3H), 0.99 (d, J=6.3 Hz, 6H).

Example 6(281)

3-(2-((3-methyl-1-(3,5-dimethylphenyl)butyl)carbamoyl)-4-(2,4-difluorophenoxymethyl)phenyl)propanoic acid

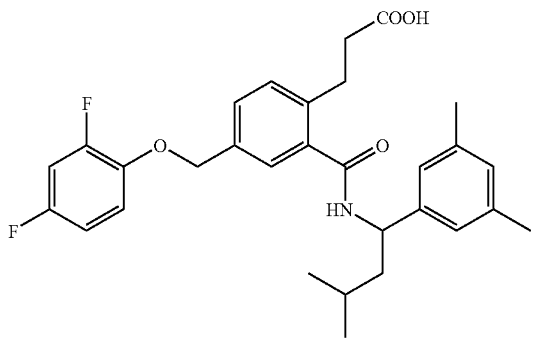

TLC: Rf 0.54 (chloroform:methanol=10:1);

NMR (300 MHz, $CDCl_3$): δ 7.42 (s, 1H), 7.41 (d, J=7.8 Hz, 1H), 7.29 (d, J=7.8 Hz, 1H), 7.00-6.73 (m, 3H), 6.96 (s, 2H), 6.91 (s, 1H), 6.32 (d, J=8.1 Hz, 1H), 5.16 (m, 1H), 5.05 (s, 2H), 3.08-2.98 (m, 2H), 2.73 (t, J=6.6 Hz, 2H), 2.31 (s, 6H), 1.84-1.56 (m, 3H), 0.99 (d, J=6.3 Hz, 6H).

Example 6(282)

3-(2-((3-methyl-1-(3,5-dimethylphenyl)butyl)carbamoyl)-4-(3-fluorophenoxymethyl)phenyl)propanoic acid

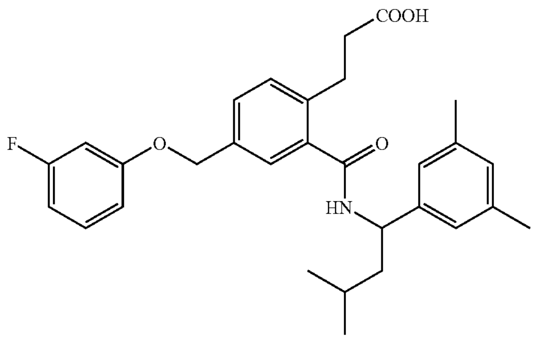

TLC: Rf 0.53 (chloroform:methanol=10:1);

NMR (300 MHz, $CDCl_3$): δ 7.42-7.18 (m, 5H), 6.95 (s, 2H), 6.91 (s, 1H), 6.76-6.63 (m, 2H), 6.30 (d, J=8.7 Hz, 1H), 5.16 (m, 1H), 5.00 (s, 2H), 3.07-2.96 (m, 2H), 2.73 (t, J=6.9 Hz, 2H), 2.31 (s, 6H), 1.84-1.54 (m, 3H), 0.98 (d, J=6.3 Hz, 6H).

Example 6(283)

3-(2-((3-methyl-1-(3,5-dimethylphenyl)butyl)carbamoyl)-4-(2,5-difluorophenoxymethyl)phenyl)propanoic acid

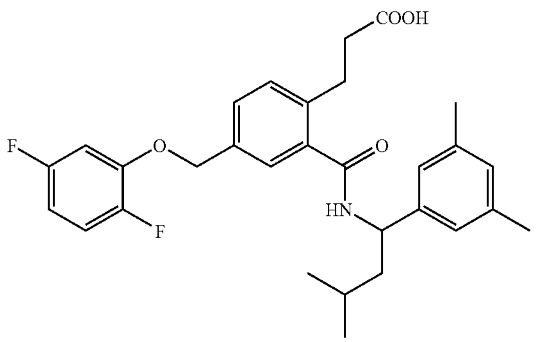

TLC: Rf 0.51 (chloroform:methanol=10:1);

NMR (300 MHz, $CDCl_3$): δ 0.99 (d, J=6.32 Hz, 6H), 1.70 (m, 3H), 2.31 (s, 6H), 2.72 (t, J=7.00 Hz, 2H), 3.03 (m, 2H), 5.06 (s, 2H), 5.16 (m, 1H), 6.31 (d, J=8.24 Hz, 1H), 6.61 (m, 1H), 6.73 (m, 1H), 6.90 (s, 1H), 6.96 (s, 2H), 7.04 (m, 1H), 7.29 (d, J=8.24 Hz, 1H), 7.41 (m, 2H).

Example 6(284)

3-(2-((3-methyl-1-(3,5-dimethylphenyl)butyl)carbamoyl)-4-(2-chloro-5-fluorophenoxymethyl)phenyl)propanoic acid

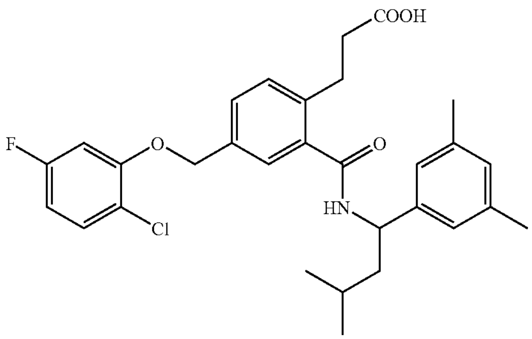

TLC: Rf 0.53 (chloroform:methanol=10:1);

NMR (300 MHz, $CDCl_3$): δ 7.49 (s, 1H), 7.42 (d, J=7.8 Hz, 1H), 7.37-7.23 (m, 2H), 6.96 (s, 2H), 6.91 (s, 1H), 6.74-6.62 (m, 2H), 6.30 (d, J=8.7 Hz, 1H), 5.17 (m, 1H), 5.08 (s, 2H), 3.08-2.98 (m, 2H), 2.73 (t, J=7.5 Hz, 2H), 2.31 (s, 6H), 1.85-1.58 (m, 3H), 0.99 (d, J=6.3 Hz, 3H), 0.98 (d, J=6.3 Hz, 3H).

Example 6(285)

3-(2-((3-methyl-1-(3,5-dimethylphenyl)butyl)carbamoyl)-4-(2-cyanophenoxymethyl)phenyl)propanoic acid

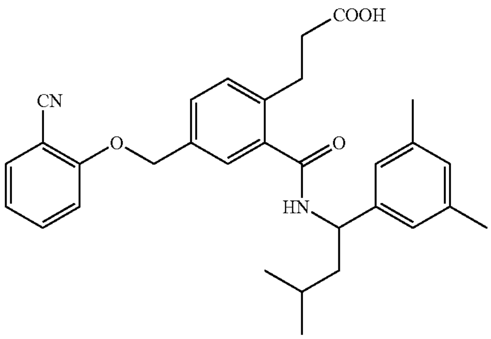

TLC: Rf 0.22 (n-hexane:ethyl acetate=1:1);

NMR (300 MHz, $CDCl_3$): δ 7.60-7.50 (m, 3H), 7.39 (m, 1H), 7.27 (d, J=7.8 Hz, 1H), 7.08-6.96 (m, 4H), 6.90 (brs, 1H), 6.53 (brd, J=8.7 Hz, 1H), 5.18 (m, 1H), 5.16 (s, 2H), 3.07-3.02 (m, 2H), 2.76-2.71 (m, 2H), 2.31 (s, 6H), 1.90-1.57 (m, 3H), 0.98 (d, J=6.3 Hz, 6H).

Example 6(286)

3-(2-((3-methyl-1-(3,5-dimethylphenyl)butyl)carbamoyl)-4-(4-cyanophenoxymethyl)phenyl)propanoic acid

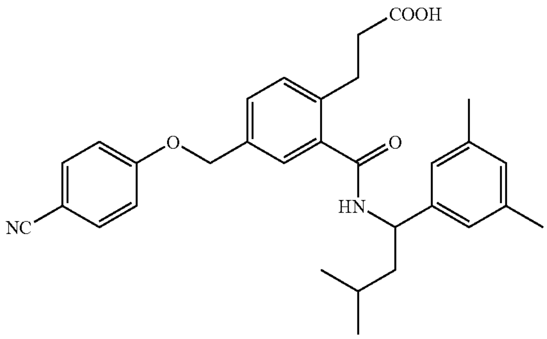

TLC: Rf 0.25 (n-hexane:ethyl acetate=1:1);

NMR (300 MHz, $CDCl_3$): δ 7.62-7.57 (m, 2H), 7.41-7.38 (m, 2H), 7.29 (m, 1H), 7.02-6.98 (m, 2H), 6.95 (brs, 2H), 6.91 (brs, 1H), 6.35 (brd, J=8.4 Hz, 1H), 5.17 (m, 1H), 5.06 (s, 2H), 3.06-3.01 (m, 2H), 2.76-2.71 (m, 2H), 2.31 (s, 6H), 1.83-1.55 (m, 3H), 0.98 (d, J=6.3 Hz, 6H).

Example 6(287)

3-(2-((3-methyl-1-(3,5-dimethylphenyl)butyl)carbamoyl)-4-(4-methoxyphenoxymethyl)phenyl)propanoic acid

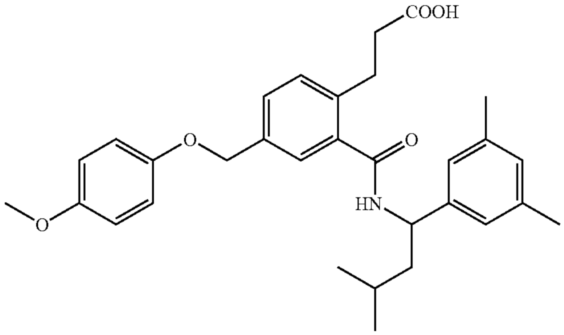

TLC: Rf 0.38 (n-hexane:ethyl acetate=1:1);

NMR (300 MHz, $CDCl_3$): δ 7.41-7.39 (m, 2H), 7.27 (d, J=7.8 Hz, 1H), 6.95 (brs, 2H), 6.91-6.82 (m, 5H), 6.28 (brd, J=8.4 Hz, 1H), 5.16 (m, 1H), 4.97 (s, 2H), 3.77 (s, 3H), 3.06-3.00 (m, 2H), 2.74-2.69 (m, 2H), 2.31 (s, 6H), 1.83-1.56 (m, 3H), 0.98 (d, J=6.3 Hz, 6H).

Example 6(288)

3-(2-((3-methyl-1-(3,5-dimethylphenyl)butyl)carbamoyl)-4-(3-methoxyphenoxymethyl)phenyl)propanoic acid

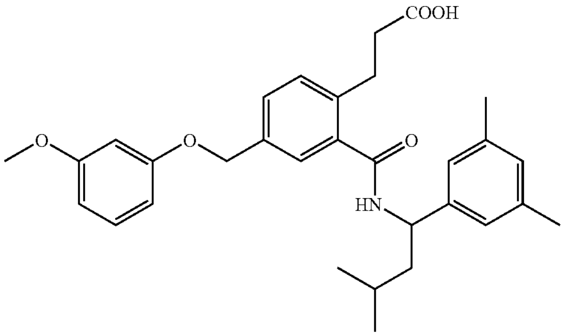

TLC: Rf 0.38 (n-hexane:ethyl acetate=1:1);

NMR (300 MHz, $CDCl_3$): δ 7.45-7.38 (m, 2H), 7.31-7.11 (m, 2H), 6.95 (s, 2H), 6.90 (s, 1H), 6.59-6.50 (m, 3H), 6.28 (d, J=8.4 Hz, 1H), 5.17 (m, 1H), 5.00 (s, 2H), 3.79 (s, 3H), 3.11-2.92 (m, 2H), 2.72 (t, J=7.2 Hz, 2H), 2.31 (s, 6H), 1.85-1.52 (m, 3H), 0.98 (d, J=6.6 Hz, 6H).

Example 6(289)

3-(2-((3-methyl-1-(3,5-dimethylphenyl)butyl)carbamoyl)-4-(3-methylphenoxymethyl)phenyl)propanoic acid

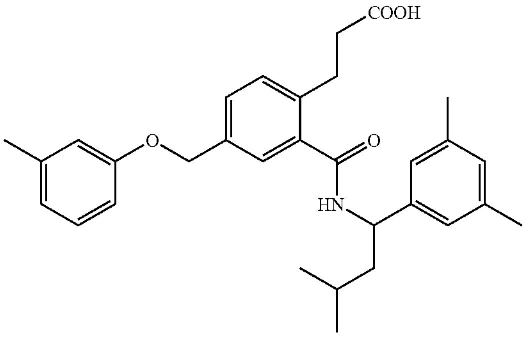

TLC: Rf 0.38 (n-hexane:ethyl acetate=1:1);

NMR (300 MHz, $CDCl_3$): δ 7.47-7.38 (m, 2H), 7.29-7.11 (m, 2H), 6.95 (s, 2H), 6.90 (s, 1H), 6.85-6.72 (m, 3H), 6.29 (d, J=9.0 Hz, 1H), 5.16 (m, 1H), 4.99 (s, 2H), 3.11-2.92 (m, 2H), 2.71 (t, J=7.5 Hz, 2H), 2.33 (s, 3H), 2.30 (s, 6H), 1.86-1.51 (m, 3H), 0.98 (d, J=6.3 Hz, 6H).

Example 6(290)

3-(2-((3-methyl-1-(3,5-dimethylphenyl)butyl)carbamoyl)-4-(2-methoxy-5-cyanophenoxymethyl)phenyl)propanoic acid

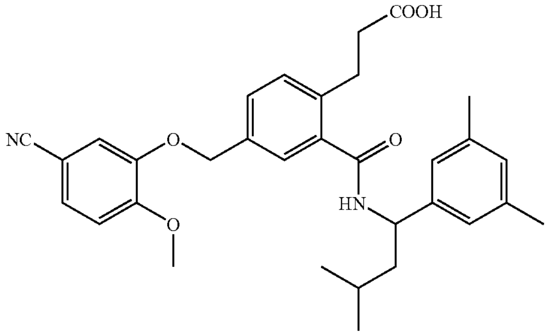

TLC: Rf 0.33 (n-hexane:ethyl acetate=1:1).

Example 6(291)

3-(2-((3-methyl-1-(3,5-dimethylphenyl)butyl)carbamoyl)-4-(2-methoxyphenoxymethyl)phenyl)propanoic acid

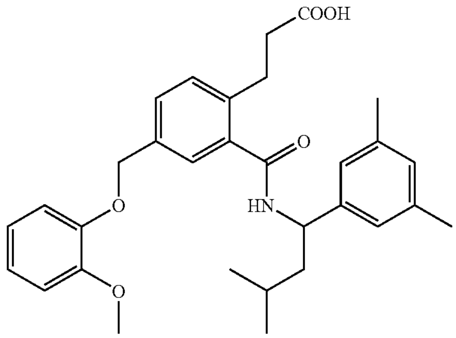

TLC: Rf 0.38 (n-hexane:ethyl acetate=1:1);

NMR (300 MHz, $CDCl_3$): δ 7.47-7.39 (m, 2H), 7.25 (m, 1H), 7.01-6.82 (m, 7H), 6.28 (d, J=8.7 Hz, 1H), 5.17 (m, 1H), 5.09 (s, 2H), 3.86 (s, 3H), 3.10-2.92 (m, 2H), 2.71 (t, J=7.4 Hz, 2H), 2.30 (s, 6H), 1.86-1.53 (m, 3H), 0.98 (d, J=5.7 Hz, 6H).

Example 6(292)

3-(2-((3-methyl-1-(3,5-dimethylphenyl)butyl)carbamoyl)-4-(2-acetylphenoxymethyl)phenyl)propanoic acid

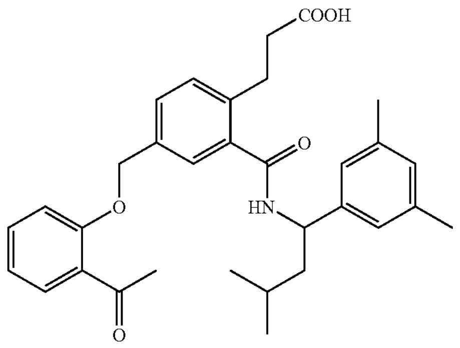

TLC: Rf 0.30 (n-hexane:ethyl acetate=1:1).

Example 6(293)

3-(2-((3-methyl-1-(3,5-dimethylphenyl)butyl)carbamoyl)-4-(2-chloro-4-fluorophenoxymethyl)phenyl)propanoic acid

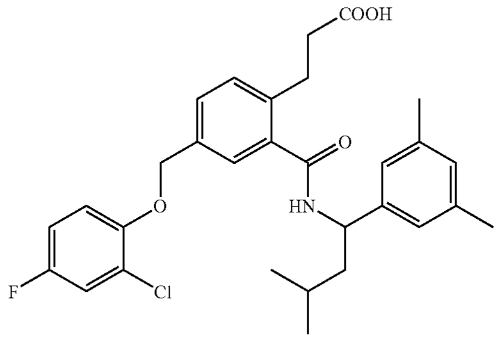

TLC: Rf 0.31 (n-hexane:ethyl acetate=1:1);

NMR (300 MHz, $CDCl_3$): δ 7.32 (brs, 1H), 7.13-7.05 (m, 3H), 6.94-6.91 (m, 3H), 6.81-6.73 (m, 3H), 5.10 (m, 1H), 4.78 (s, 2H), 2.84-2.79 (m, 2H), 2.43-2.39 (m, 2H), 2.21 (s, 6H), 1.78-1.50 (m, 3H), 0.89-0.87 (m, 6H).

Example 6(294)

3-(2-((3-methyl-1-(3,5-dimethylphenyl)butyl)carbamoyl)-4-(2-methyl-4-fluorophenoxymethyl)phenyl)propanoic acid

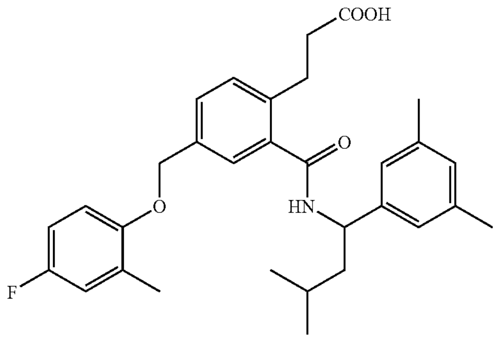

TLC: Rf 0.31 (n-hexane:ethyl acetate=1:1);

NMR (300 MHz, DMSO-$d_6$): δ 7.34-7.17 (m, 3H), 7.04-6.93 (m, 5H), 6.82 (brs, 1H), 5.03 (s, 2H), 4.97 (m, 1H), 2.80-2.76 (m, 2H), 2.43-2.39 (m, 2H), 2.23 (s, 6H), 2.17 (s, 3H), 1.80-1.60 (m, 2H), 1.41 (m, 1H), 0.91 (d, J=6.6 Hz, 3H), 0.89 (d, J=6.6 Hz, 3H).

Example 6(295)

3-(2-((3-methyl-1-(3,5-dimethylphenyl)butyl)carbamoyl)-4-(2,5-dimethylphenoxymethyl)phenyl)propanoic acid

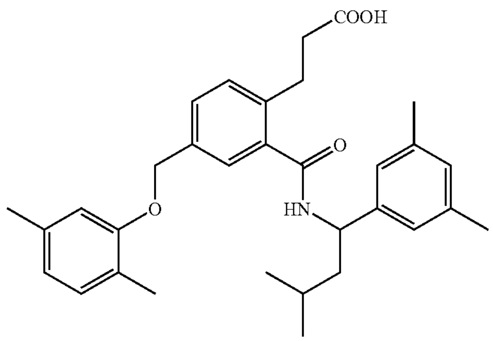

TLC: Rf 0.34 (n-hexane:ethyl acetate=1:1);

NMR (300 MHz, DMSO-$d_6$): δ 9.94 (brs, 1H), 7.38-7.33 (m, 2H), 7.28 (d, J=7.8 Hz, 1H), 7.01-6.99 (m, 3H), 6.83 (d, J=7.5 Hz, 2H), 6.64 (d, J=7.8 Hz, 1H), 5.03 (s, 2H), 4.97 (m, 1H), 2.84-2.77 (m, 2H), 2.44-2.40 (m, 2H), 2.24 (s, 6H), 2.12 (s, 3H), 1.78 (s, 3H), 1.77-1.58 (m, 2H), 1.41 (m, 1H), 0.91 (d, J=6.6 Hz, 3H), 0.89 (d, J=6.6 Hz, 3H).

Example 6(296)

3-(2-((3-methyl-1-(3,5-dimethylphenyl)butyl)carbamoyl)-4-(4-carbamoylmethylphenoxymethyl)phenyl)propanoic acid

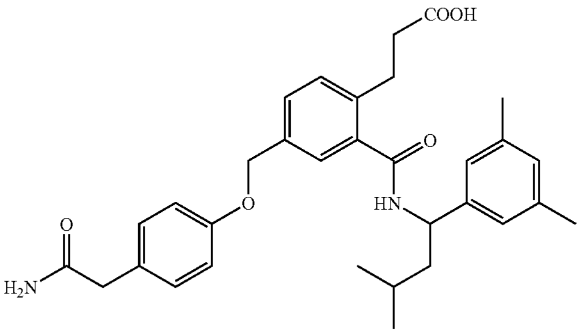

TLC: Rf 0.36 (chloroform:methanol=10:1).

Example 6(297)

3-(2-((3-methyl-1-(3,5-dimethylphenyl)butyl)carbamoyl)-4-(2-methoxy-5-methylphenoxymethyl) phenyl)propanoic acid

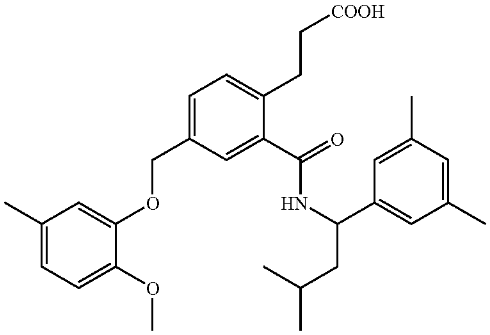

TLC: Rf 0.53 (chloroform:methanol=10:1);

NMR (300 MHz, DMSO-$d_6$): δ 8.76 (d, J=8.4 Hz, 1H), 7.40 (d, J=8.7 Hz, 1H), 7.31 (s, 1H), 7.30 (d, J=8.7 Hz, 1H), 6.95 (s, 2H), 6.89 (s, 1H), 6.84 (d, J=8.7 Hz, 1H), 6.83 (s, 1H), 6.69 (d, J=8.7 Hz, 1H), 5.02 (s, 2H), 4.96 (m, 1H), 3.69 (s, 3H), 2.84 (t, J=8.1 Hz, 2H), 2.45 (t, J=8.1 Hz, 2H), 2.24 (s, 6H), 2.21 (s, 3H), 1.78-1.57 (m, 2H), 1.39 (m, 1H), 0.92 (d, J=6.3 Hz, 3H), 0.89 (d, J=6.3 Hz, 3H).

Example 6(298)

3-(2-((3-methyl-1-(3,5-dimethylphenyl)butyl)carbamoyl)-4-(4-methylphenoxymethyl)phenyl)propanoic acid

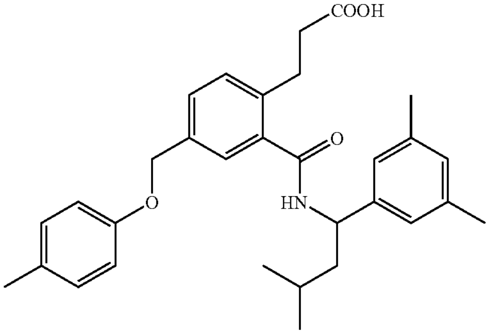

TLC: Rf 0.55 (chloroform:methanol=10:1);

NMR (300 MHz, DMSO-$d_6$): δ 8.74 (d, J=8.7 Hz, 1H), 7.39 (d, J=8.1 Hz, 1H), 7.30 (s, 1H), 7.29 (d, J=8.1 Hz, 1H), 7.08 (d, J=8.4 Hz, 2H), 6.95 (s, 2H), 6.88 (d, J=8.4 Hz, 2H), 6.84 (s, 1H), 5.05 (s, 2H), 4.96 (m, 1H), 2.83 (t, J=8.1 Hz, 2H), 2.44 (t, J=8.1 Hz, 2H), 2.24 (s, 6H), 2.22 (s, 3H), 1.80-1.55 (m, 2H), 1.40 (m, 1H), 0.91 (d, J=6.3 Hz, 3H), 0.89 (d, J=6.3 Hz, 3H).

Example 6(299)

3-(2-((3-methyl-1-(3,5-dimethylphenyl)butyl)carbamoyl)-4-(4-fluorophenoxymethyl)phenyl)propanoic acid

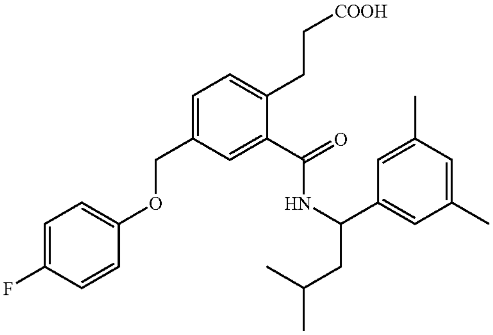

TLC: Rf 0.55 (chloroform:methanol=10:1);

NMR (300 MHz, DMSO-$d_6$): δ 8.74 (d, J=8.7 Hz, 1H), 7.39 (d, J=7.5 Hz, 1H), 7.31 (s, 1H), 7.29 (d, J=7.5 Hz, 1H), 7.16-7.06 (m, 2H), 7.04-6.96 (m, 2H), 6.95 (s, 2H), 6.83 (s, 1H), 5.06 (s, 2H), 4.96 (m, 1H), 2.83 (t, J=8.1 Hz, 2H), 2.44 (t, J=8.1 Hz, 2H), 2.24 (s, 6H), 1.80-1.54 (m, 2H), 1.40 (m, 1H), 0.91 (d, J=6.3 Hz, 3H), 0.89 (d, J=6.3 Hz, 3H).

Example 6(300)

3-(2-((3-methyl-1-(3,5-dimethylphenyl)butyl)carbamoyl)-4-(3-methoxy-5-cyanophenoxymethyl)phenyl)propanoic acid

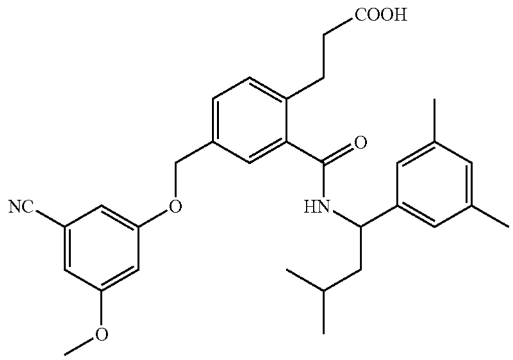

TLC: Rf 0.52 (n-hexane:ethyl acetate=1:1);

NMR (300 MHz, $CDCl_3$): δ 7.41-7.28 (m, 2H), 7.38 (brs, 1H), 6.96 (brs, 2H), 6.91 (brs, 1H), 6.80 (m, 2H), 6.71 (m, 1H), 6.38 (d, J=8.4 Hz, 1H), 5.17 (m, 1H), 5.00 (s, 2H), 3.80 (s, 3H), 3.05-3.00 (m, 2H), 2.76-2.70 (m, 2H), 2.31 (s, 6H), 1.86-1.56 (m, 3H), 0.98 (d, J=6.3 Hz, 6H).

Example 6(301)

3-(2-((3-methyl-1-(3,5-dimethylphenyl)butyl)carbamoyl)-4-(3-chlorophenoxymethyl)phenyl)propanoic acid

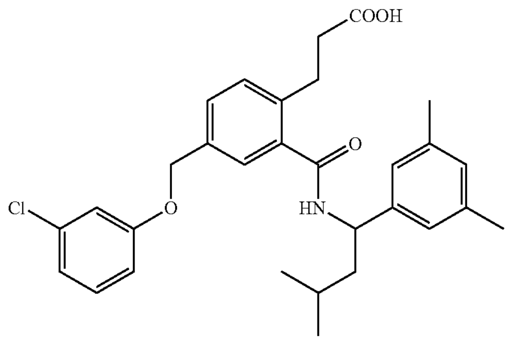

TLC: Rf 0.47 (chloroform:methanol=9:1);

NMR (300 MHz, $CDCl_3$): δ 7.44-7.37 (m, 2H), 7.32-7.17 (m, 2H), 7.00-6.81 (m, 6H), 6.29 (d, J=8.7 Hz, 1H), 5.17 (m, 1H), 5.00 (s, 2H), 3.09-2.97 (m, 2H), 2.73 (t, J=7.1 Hz, 2H), 2.31 (s, 6H), 1.87-1.52 (m, 3H), 0.99 (d, J=6.3 Hz, 6H).

Example 6(302)

3-(2-((3-methyl-1-(3,5-dimethylphenyl)butyl)carbamoyl)-4-(2-fluoro-5-methylphenoxymethyl)phenyl)propanoic acid

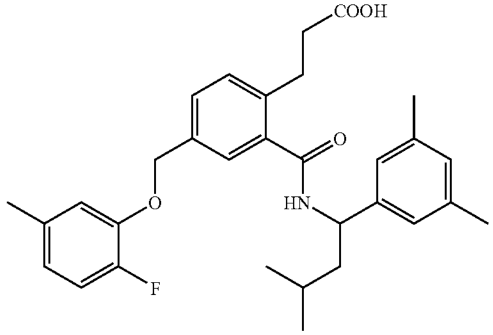

TLC: Rf 0.47 (chloroform:methanol=9:1);

NMR (300 MHz, $CDCl_3$): δ 7.46-7.38 (m, 2H), 7.28 (d, J=7.8 Hz, 1H), 7.02-6.88 (m, 4H), 6.81 (d, J=8.1 Hz, 1H), 6.72 (m, 1H), 6.29 (d, J=8.7 Hz, 1H), 5.17 (m, 1H), 5.07 (s, 2H), 3.12-2.95 (m, 2H), 2.72 (t, J=6.9 Hz, 2H), 2.31 (s, 6H), 2.29 (s, 3H), 1.85-1.53 (m, 3H), 0.99 (d, J=6.3 Hz, 6H).

Example 6(303)

3-(2-((3-methyl-1-(3,5-dimethylphenyl)butyl)carbamoyl)-4-(2,3,4,5,6-pentafluorophenoxymethyl)phenyl)propanoic acid

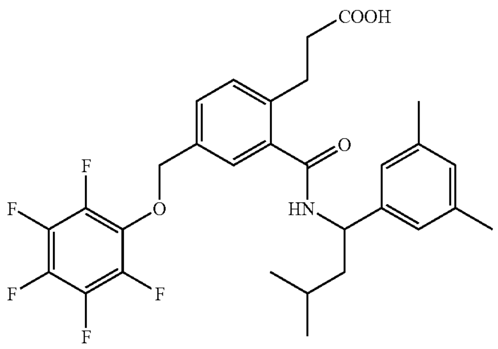

TLC: Rf 0.47 (chloroform:methanol=10:1).

Example 6(304)

3-(2-((3-methyl-1-(3,5-dimethylphenyl)butyl)carbamoyl)-4-(2,6-difluorophenoxymethyl)phenyl)propanoic acid

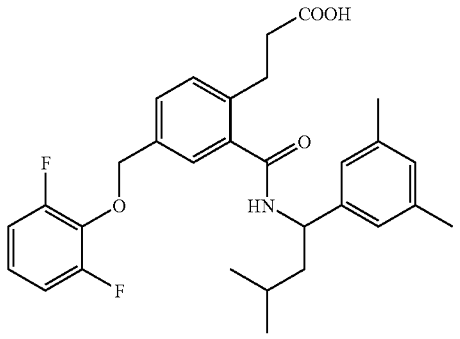

TLC: Rf 0.46 (chloroform:methanol=10:1).

Example 6(305)

3-(2-((3-methyl-1-(3,5-dimethylphenyl)butyl)carbamoyl)-4-(4-chlorophenoxymethyl)phenyl)propanoic acid

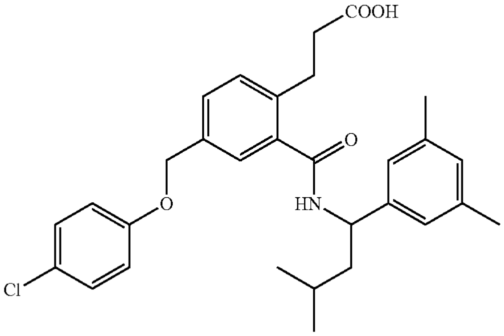

TLC: Rf 0.46 (chloroform:methanol=10:1).

Example 6(306)

3-(2-((3-methyl-1-(3,5-dimethylphenyl)butyl)carbamoyl)-4-(2,3-difluorophenoxymethyl)phenyl)propanoic acid

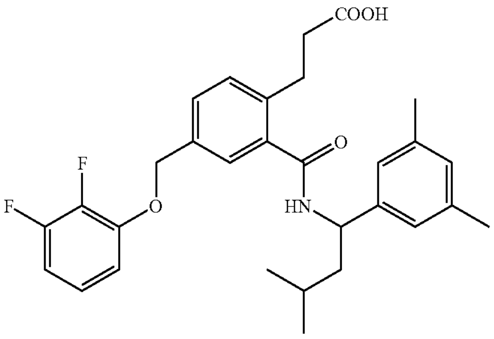

TLC: Rf 0.57 (chloroform:methanol=9:1);

NMR (300 MHz, $CDCl_3$): δ 7.45-7.38 (m, 2H), 7.29 (d, J=7.2 Hz, 1H), 7.02-6.89 (m, 4H), 6.85-6.73 (m, 2H), 6.32 (d, J=8.7 Hz, 1H), 5.17 (m, 1H), 5.10 (s, 2H), 3.07-2.95 (m, 2H), 2.73 (t, J=7.2 Hz, 2H), 2.31 (s, 6H), 1.86-1.53 (m, 3H), 0.99 (d, J=6.3 Hz, 6H).

Example 6(307)

3-(2-((3-methyl-1-(3,5-dimethylphenyl)butyl)carbamoyl)-4-(3,5-difluorophenoxymethyl)phenyl)propanoic acid

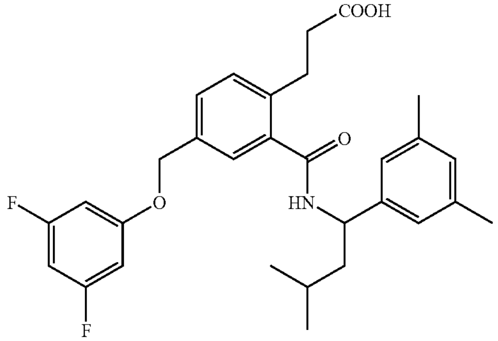

TLC: Rf 0.57 (chloroform:methanol=9:1);

NMR (300 MHz, $CDCl_3$): δ 7.42-7.35 (m, 2H), 7.30 (d, J=7.5 Hz, 1H), 6.95 (s, 2H), 6.91 (s, 1H), 6.54-6.40 (m, 3H), 6.32 (d, J=8.7 Hz, 1H), 5.17 (m, 1H), 4.97 (s, 2H), 3.12-2.94 (m, 2H), 2.73 (t, J=7.3 Hz, 2H), 2.31 (s, 6H), 1.87-1.52 (m, 3H), 0.99 (d, J=6.3 Hz, 6H).

Example 6(308)

3-(2-((3-methyl-1-(naphthalen-1-yl)butyl)carbamoyl)-4-(4-fluorophenoxymethyl)phenyl)propanoic acid

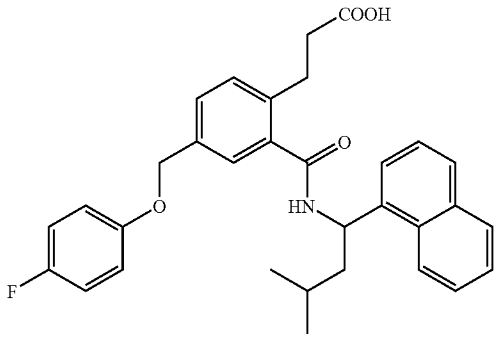

TLC: Rf 0.49 (chloroform:methanol=10:1);

NMR (300 MHz, $CDCl_3$): δ 1.01 (d, J=6.59 Hz, 3H) 1.13 (d, J=6.59 Hz, 3H) 1.82 (m, 1H) 1.97 (m, 2H) 2.74 (t, J=7.20 Hz, 2H) 3.03 (t, J=7.20 Hz, 2H) 4.97 (s, 2H) 6.14 (m, 1H) 6.35 (d, J=8.52 Hz, 1H) 6.66 (m, 3H) 7.42 (m, 8H) 7.80 (d, J=7.69 Hz, 1H) 7.88 (d, J=7.69 Hz, 1H) 8.32 (d, J=8.24 Hz, 1H).

Example 6(309)

3-(2-((3-methyl-1-(naphthalen-1-yl)butyl)carbamoyl)-4-(2,5-difluorophenoxymethyl)phenyl)propanoic acid

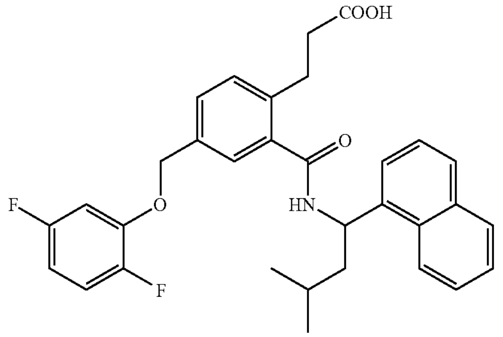

TLC: Rf 0.49 (chloroform:methanol=10:1);

NMR (300 MHz, $CDCl_3$): δ 1.01 (d, J=6.59 Hz, 3H) 1.14 (d, J=6.59 Hz, 3H) 1.82 (m, 1H) 1.97 (t, J=7.14 Hz, 2H) 2.73 (t, J=7.42 Hz, 2H) 3.03 (t, J=7.42 Hz, 2H) 5.02 (s, 2H) 6.14 (m, 1H) 6.38 (d, J=8.52 Hz, 1H) 6.60 (m, 1H) 6.70 (m, 1H) 7.02 (m, 1H) 7.47 (m, 7H) 7.80 (d, J=7.97 Hz, 1H) 7.87 (d, J=7.42 Hz, 1H) 8.32 (d, J=8.79 Hz, 1H).

Example 6(310)

3-(2-((3-methyl-1-(naphthalen-1-yl)butyl)carbamoyl)-4-(3-cyanophenoxymethyl)phenyl)propanoic acid

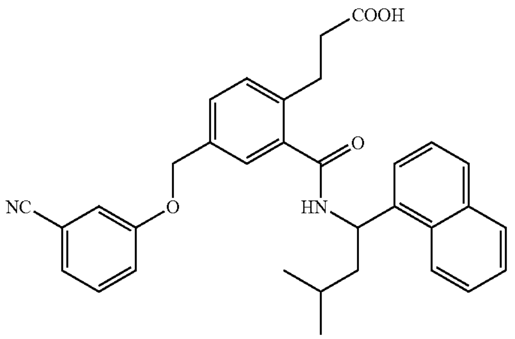

TLC: Rf 0.48 (chloroform:methanol=10:1);

NMR (300 MHz, DMSO-$d_6$): δ 0.91 (d, J=6.32 Hz, 3H) 1.08 (d, J=6.32 Hz, 3H) 1.57 (m, 1H) 1.89 (m, 2H) 2.48 (m, 2H) 2.85 (m, 2H) 5.14 (s, 2H) 5.94 (m, 1H) 7.48 (m, 12H) 7.81 (d, J=8.24 Hz, 1H) 7.94 (d, J=7.97 Hz, 1H) 8.22 (d, J=8.52 Hz, 1H).

Example 6(311)

3-(2-((3-methyl-1-(3,5-dimethylphenyl)butyl)carbamoyl)-4-(3,4-difluorophenoxymethyl)phenyl)propanoic acid

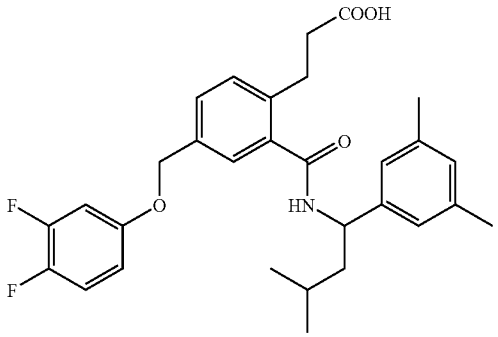

TLC: Rf 0.31 (methylene chloride:methanol=9:1);

NMR (300 MHz, $CDCl_3$): δ 0.98 (d, J=6.32 Hz, 6H) 1.69 (m, 3H) 2.31 (s, 6H) 2.72 (m, 2H) 3.02 (m, 2H) 4.95 (s, 2H) 5.17 (m, 1H) 6.34 (d, J=8.24 Hz, 1H) 6.64 (m, 1H) 6.77 (ddd, J=11.81, 6.59, 3.02 Hz, 1H) 6.91 (s, 1H) 6.95 (s, 2H) 7.07 (m, 1H) 7.32 (m, 3H).

Example 6(312)

3-(2-((3-methyl-1-(3,5-dimethylphenyl)butyl)carbamoyl)-4-(3-methyl-4-fluorophenoxymethyl)phenyl)propanoic acid

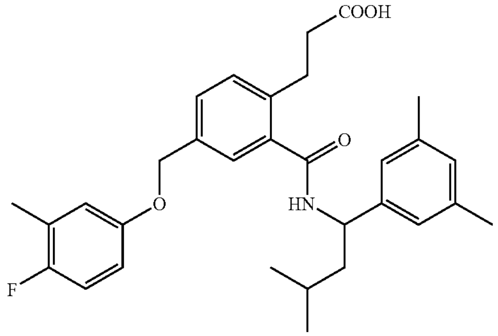

TLC: Rf 0.33 (methylene chloride:methanol=9:1).

Example 6(313)

3-(2-((3-methyl-1-(3,5-dimethylphenyl)butyl)carbamoyl)-4-(2-fluoro-6-methoxyphenoxymethyl)phenyl)propanoic acid

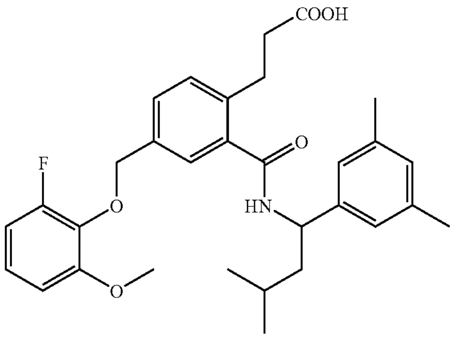

TLC: Rf 0.33 (methylene chloride:methanol=9:1).

Example 6(314)

3-(2-((3-methyl-1-(3,5-dimethylphenyl)butyl)carbamoyl)-4-(2,3,6-trifluorophenoxymethyl)phenyl) propanoic acid

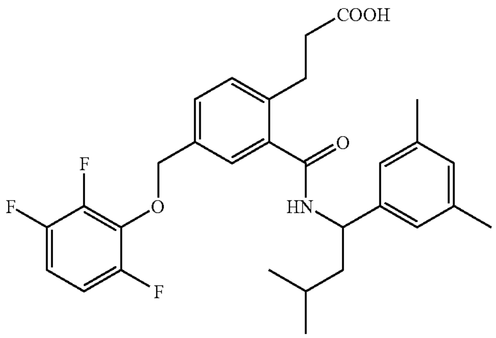

TLC: Rf 0.33 (chloroform:methanol=9:1);

NMR (300 MHz, $CDCl_3$): δ 0.99 (d, J=6.32 Hz, 6H) 1.71 (m, 3H) 2.31 (s, 6H) 2.71 (m, 2H) 3.03 (m, 2H) 5.16 (m, 3H) 6.27 (d, J=8.52 Hz, 1H) 6.83 (m, 2H) 6.91 (s, 1H) 6.96 (s, 2H) 7.26 (m, 1H) 7.40 (m, 1H) 7.47 (m, 1H).

Example 6(315)

3-(2-((3-methyl-1-(3,5-dimethylphenyl)butyl)carbamoyl)-4-(2,3,5,6-tetrafluorophenoxymethyl)phenyl)propanoic acid

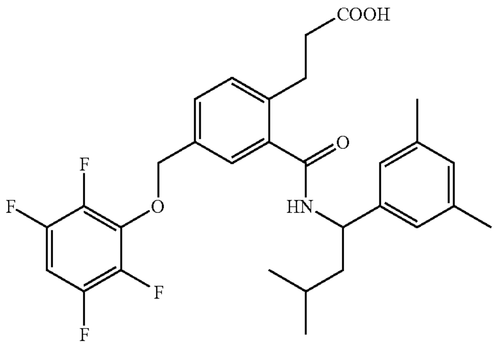

TLC: Rf 0.33 (chloroform:methanol=9:1).

Example 6(316)

3-(2-((3-methyl-1-(3,5-dimethylphenyl)butyl)carbamoyl)-4-(3-fluoro-4-cyanophenoxymethyl)phenyl) propanoic acid

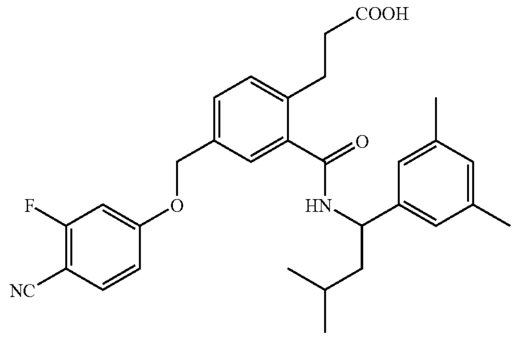

TLC: Rf 0.55 (n-hexane:ethyl acetate=1:1).

Example 6(317)

3-(2-((3-methyl-1-(3,5-dimethylphenyl)butyl)carbamoyl)-4-(3-carbamoylphenoxymethyl)phenyl) propanoic acid

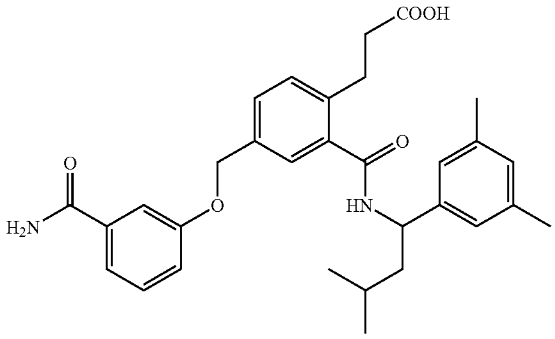

TLC: Rf 0.23 (chloroform:methanol=9:1);

NMR (300 MHz, DMSO-$d_6$): δ 0.91 (m, 6H), 1.39 (m, 1H), 1.68 (m, 2H), 2.24 (s, 6H), 2.44 (m, 2H), 2.84 (t, J=7.97 Hz, 2H), 4.97 (m, 1H), 5.13 (s, 2H), 6.83 (s, 1H), 6.95 (s, 2H), 7.14 (m, 1H), 7.42 (m, 7H), 7.94 (s, 1H) 8.76 (d, J=8.52 Hz, 1H), 12.07 (s, 1H).

Example 6(318)

3-(2-((3-methyl-1-(3,5-dimethylphenyl)butyl)carbamoyl)-4-(3-methylcarbamoylphenoxymethyl)phenyl)propanoic acid

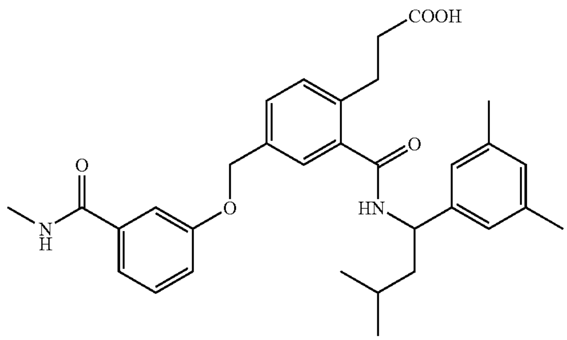

TLC: Rf 0.17 (chloroform:methanol=9:1);

NMR (300 MHz, DMSO-$d_6$): δ 0.90 (m, 6H), 1.40 (m, 1H), 1.67 (m, 2H), 2.24 (s, 6H), 2.43 (m, 2H), 2.76 (d, J=4.40 Hz, 3H), 2.84 (m, 2H), 4.97 (m, 1H), 5.13 (s, 2H), 6.83 (s, 1H), 6.95 (s, 2H), 7.13 (m, 1H), 7.39 (m, 6H) 8.40 (m, 1H), 8.75 (d, J=8.52 Hz, 1H), 12.08 (s, 1H).

Example 6(319)

3-(2-((3-methyl-1-(3,5-dimethylphenyl)butyl)carbamoyl)-4-(3-dimethylcarbamoylphenoxymethyl)phenyl)propanoic acid

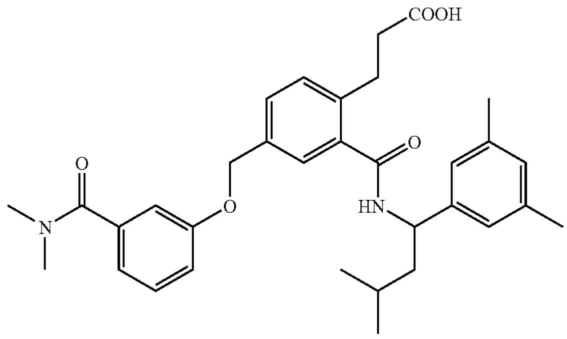

TLC: Rf 0.44 (chloroform:methanol=9:1);

NMR (300 MHz, $CDCl_3$): δ 0.96 (d, J=6.32 Hz, 3H), 0.97 (d, J=6.32 Hz, 3H), 1.69 (m, 3H), 2.29 (s, 6H), 2.68 (m, 2H), 2.98 (m, 5H), 3.08 (s, 3H), 4.98 (s, 2H), 5.16 (m, 1H), 6.85 (m, 2H), 6.97 (m, 5H), 7.28 (m, 4H).

Example 6(320)

3-(2-((3-methyl-1-(3,5-dimethylphenyl)butyl)carbamoyl)-4-(3-hydroxymethylphenoxymethyl)phenyl)propanoic acid

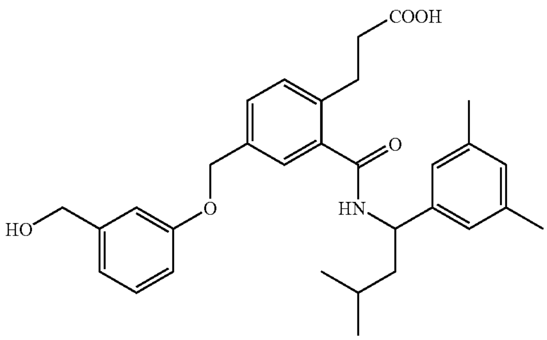

TLC: Rf 0.50 (chloroform:methanol=9:1);

NMR (300 MHz, $CDCl_3$): δ 0.97 (m, 6H), 1.69 (m, 3H), 2.29 (s, 6H), 2.67 (m, 2H), 3.00 (m, 2H), 4.62 (s, 2H), 4.98 (s, 2H), 5.16 (m, 1H), 6.52 (d, J=8.52 Hz, 1H), 6.89 (m, 6H), 7.24 (m, 2H), 7.38 (m, 2H).

Example 6(321)

3-(2-((3-methyl-1-(3,5-dimethylphenyl)butyl)carbamoyl)-4-(3-methoxymethylphenoxymethyl)phenyl)propanoic acid

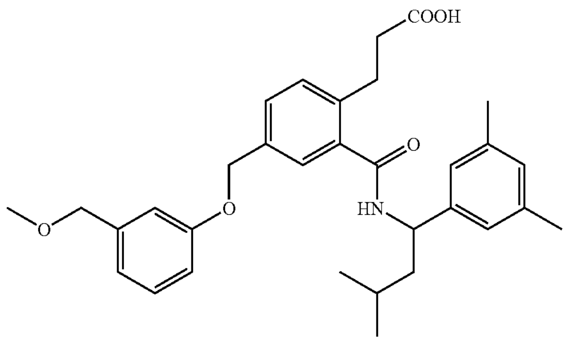

TLC: Rf 0.24 (n-hexane:ethyl acetate=1:1);

NMR (300 MHz, $CDCl_3$): δ 0.98 (d, J=6.32 Hz, 6H), 1.70 (m, 3H), 2.31 (s, 6H), 2.72 (m, 2H), 3.03 (m, 2H), 3.38 (s, 3H), 4.43 (s, 2H), 5.02 (s, 2H), 5.17 (m, 1H), 6.32 (d, J=8.52 Hz, 1H), 6.90 (m, 6H), 7.26 (m, 2H), 7.42 (m, 2H).

Example 6(322)

3-(2-(((1R)-3-methyl-1-(3,5-dimethylphenyl)butyl)carbamoyl)-4-(2,5-difluorophenoxymethyl)phenyl)propanoic acid

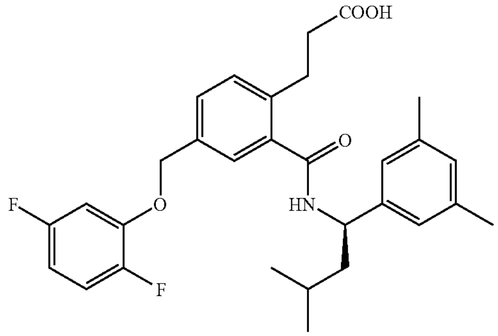

TLC: Rf 0.44 (n-hexane:ethyl acetate=1:2);

NMR (300 MHz, $CDCl_3$): δ 7.45-7.38 (m, 2H), 7.29 (d, J=7.8 Hz, 1H), 7.04 (m, 1H), 6.96 (s, 2H), 6.91 (s, 1H), 6.73 (m, 1H), 6.62 (m, 1H), 6.31 (d, J=8.4 Hz, 1H), 5.17 (m, 1H), 5.06 (s, 2H), 3.11-2.93 (m, 2H), 2.72 (t, J=6.0 Hz, 2H), 2.31 (s, 6H), 1.84-1.52 (m, 3H), 0.99 (d, J=6.3 Hz, 6H).

Example 6(323)

3-(2-(((1S)-3-methyl-1-(3,5-dimethylphenyl)butyl)carbamoyl)-4-(2,5-difluorophenoxymethyl)phenyl)propanoic acid

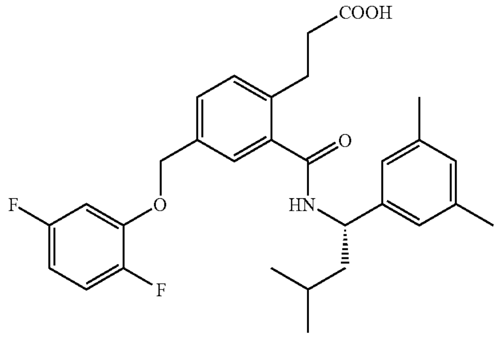

TLC: Rf 0.44 (n-hexane:ethyl acetate=1:2);

NMR (300 MHz, $CDCl_3$): δ 7.45-7.38 (m, 2H), 7.29 (d, J=7.8 Hz, 1H), 7.04 (m, 1H), 6.96 (s, 2H), 6.91 (s, 1H), 6.73 (m, 1H), 6.62 (m, 1H), 6.31 (d, J=8.4 Hz, 1H), 5.17 (m, 1H), 5.06 (s, 2H), 3.11-2.93 (m, 2H), 2.72 (t, J=6.0 Hz, 2H), 2.31 (s, 6H), 1.84-1.52 (m, 3H), 0.99 (d, J=6.3 Hz, 6H).

Example 6(324)

2-(2-(((1R)-3-methyl-1-(3,5-dimethylphenyl)butyl)carbamoyl)-4-(2-phenylethyl)phenoxy)acetic acid

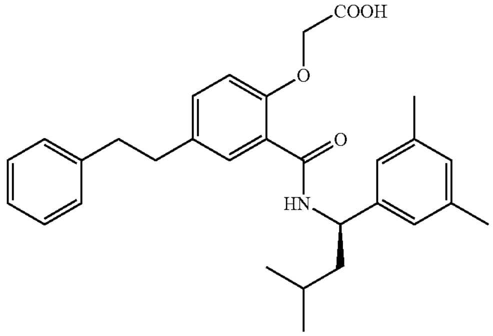

TLC: Rf 0.40 (chloroform:methanol=10:1);

NMR (300 MHz, $CDCl_3$): δ 0.95 (d, J=6.04 Hz, 6H), 1.62 (m, 2H), 1.82 (m, 1H), 2.29 (s, 6H), 2.87 (s, 4H), 4.74 (s, 2H), 5.19 (m, 1H), 6.82 (d, J=8.24 Hz, 1H), 6.88 (brs, 1H), 6.97 (brs, 2H), 7.10 (m, 2H), 7.18 (m, 2H), 7.27 (m, 2H), 7.47 (m, 2H).

Example 6(325)

3-(2-(((1R)-3-methyl-1-(3,5-dimethylphenyl)butyl)carbamoyl)-4-(2-fluorophenoxymethyl)phenyl)propanoic acid

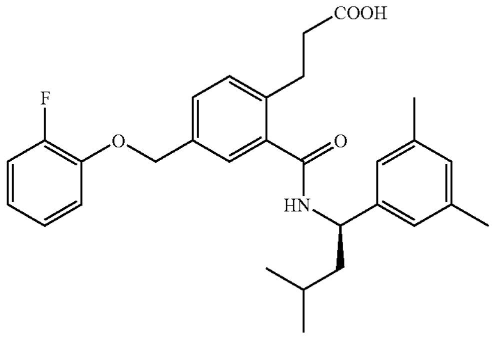

TLC: Rf 0.63 (methylene chloride:methanol=9:1);

NMR (300 MHz, $CDCl_3$): δ 7.46-7.38 (m, 2H), 7.28 (d, J=7.8 Hz, 1H), 7.14-6.88 (m, 7H), 6.31 (d, J=7.8 Hz, 1H), 5.15 (q, J=7.8 Hz, 1H), 5.09 (s, 2H), 3.12-2.95 (m, 2H), 2.72 (t, J=7.2 Hz, 2H), 2.31 (s, 6H), 1.85-1.55 (m, 3H), 0.98 (d, J=5.7 Hz, 6H).

Example 6(326)

3-(2-(((1R)-3-methyl-1-(3,5-dimethylphenyl)butyl) carbamoyl)-4-(4-fluorophenoxymethyl)phenyl)propanoic acid

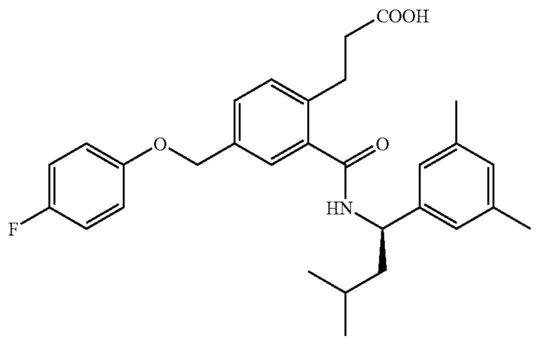

TLC: Rf 0.56 (methylene chloride:methanol=9:1);

NMR (300 MHz, $CDCl_3$): δ 7.42-7.37 (m, 2H), 7.30-7.26 (m, 1H), 7.02-6.85 (m, 7H), 6.30 (d, J=8.1 Hz, 1H), 5.16 (q, J=8.1 Hz, 1H), 4.98 (s, 2H), 3.10-2.95 (m, 2H), 2.73 (t, J=6.9 Hz, 2H), 2.30 (s, 6H), 1.85-1.50 (m, 3H), 0.98 (d, J=6.3 Hz, 6H).

Example 6(327)

3-(2-(((1R)-3-methyl-1-(3,5-dimethylphenyl)butyl) carbamoyl)-4-(2-methoxyphenoxymethyl)phenyl) propanoic acid

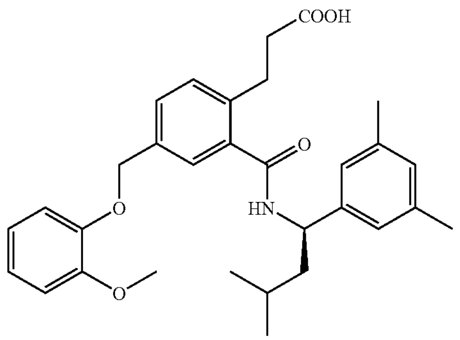

TLC: Rf 0.64 (methylene chloride:methanol=9:1);

NMR (300 MHz, $CDCl_3$): δ 7.44-7.39 (m, 2H), 7.28-7.23 (m, 1H), 7.00-6.80 (m, 7H), 6.32 (d, J=8.7 Hz, 1H), 5.15 (q, J=8.7 Hz, 1H), 5.09 (s, 2H), 3.86 (s, 3H), 3.10-2.95 (m, 2H), 2.71 (t, J=7.5 Hz, 2H), 2.30 (s, 6H), 1.80-1.55 (m, 3H), 0.97 (d, J=6.3 Hz, 6H).

Example 6(328)

3-(2-(((1R)-3-methyl-1-(3,5-dimethylphenyl)butyl) carbamoyl)-4-(2-methylphenoxymethyl)phenyl)propanoic acid

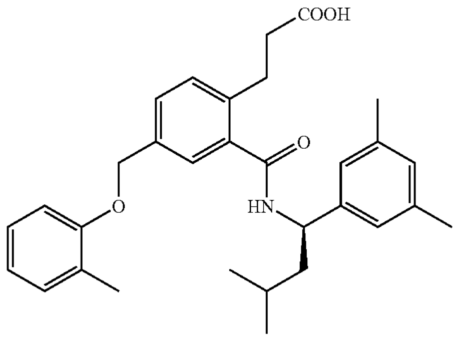

TLC: Rf 0.54 (methylene chloride:methanol=9:1);

NMR (300 MHz, $CDCl_3$): δ 7.44-7.40 (m, 2H), 7.30-7.26 (m, 1H), 7.20-7.12 (m, 2H), 6.96-6.83 (m, 5H), 6.25 (d, J=8.7 Hz, 1H), 5.16 (q, J=8.7 Hz, 1H), 5.04 (s, 2H), 3.13-2.95 (m, 2H), 2.73 (t, J=7.2 Hz, 2H), 2.31 (s, 6H), 2.27 (s, 3H), 1.85-1.55 (m, 3H), 0.99 (d, J=6.3 Hz, 3H), 0.98 (d, J=6.3 Hz, 3H).

Example 6(329)

3-(2-diphenylmethylcarbamoyl-4-(2,5-difluorophenoxymethyl)phenyl)propanoic acid

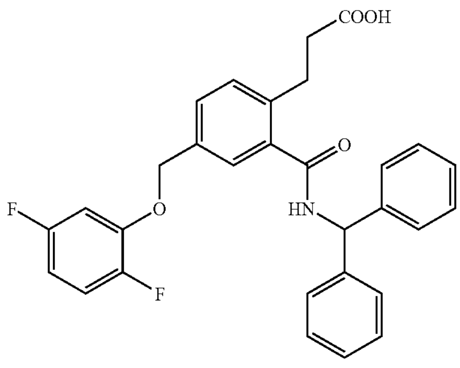

TLC: Rf 0.30 (hexane:ethyl acetate=1:1);

NMR (300 MHz, DMSO-$d_6$): δ 2.42 (m, 2H), 2.72 (m, 2H), 5.11 (s, 2H), 6.43 (d, J=9.07 Hz, 1H), 6.74 (m, 1H), 7.24 (m, 10H), 7.38 (m, J=6.87 Hz, 2H), 7.54-7.52 (m, 4H).

Example 6(330)

3-(2-((1-(3,5-dimethylphenyl)cyclohexyl)carbamoyl)-4-(2,5-difluorophenoxymethyl)phenyl)propanoic acid

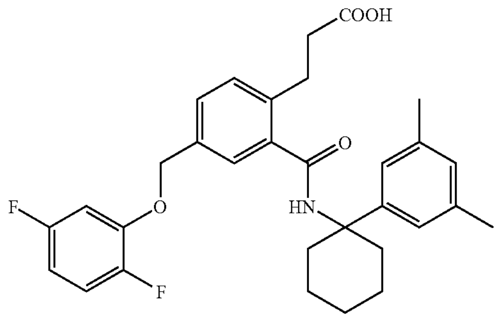

TLC: Rf 0.56 (chloroform:methanol=10:1);

NMR (300 MHz, $CDCl_3$): δ 1.75 (m, 8H), 2.31 (s, 6H), 2.46 (s, 2H), 2.71 (t, J=7.42 Hz, 2H), 3.05 (t, J=7.42 Hz, 2H), 5.12 (s, 2H), 6.18 (s, 1H), 6.63 (m, 1H), 6.76 (m, 1H), 6.88 (s, 1H) 7.04 (m, 1H), 7.08 (s, 2H), 7.31 (d, J=7.97 Hz, 1H), 7.42 (m, 1H), 7.55 (s, 1H).

Example 6(331)

3-(2-((1-(3,5-dimethylphenyl)cyclopentyl)carbamoyl)-4-(2,5-difluorophenoxymethyl)phenyl)propanoic acid

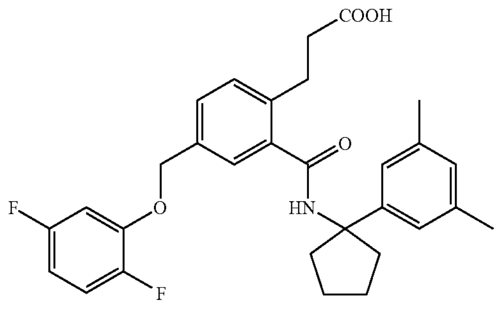

TLC: Rf 0.55 (chloroform:methanol=10:1);

NMR (300 MHz, $CDCl_3$): δ 1.88 (m, 4H), 2.16 (m, 2H), 2.31 (s, 6H), 2.46 (m, 2H), 2.70 (t, J=7.55 Hz, 2H), 3.02 (t, J=7.42 Hz, 2H), 5.08 (s, 2H), 6.63 (m, 1H), 6.75 (m, 1H), 6.88 (s, 1H) 7.02 (d, J=5.22 Hz, 1H), 7.05 (dd, J=5.36, 1.51 Hz, 1H), 7.08 (s, 2H), 7.29 (d, J=7.69 Hz, 1H), 7.40 (m, 1H), 7.45 (s, 1H).

Example 6(332)

3-(2-(((1R)-3-methyl-1-(3,5-dimethylphenyl)butyl)carbamoyl)-4-(3-fluorophenoxymethyl)phenyl)propanoic acid

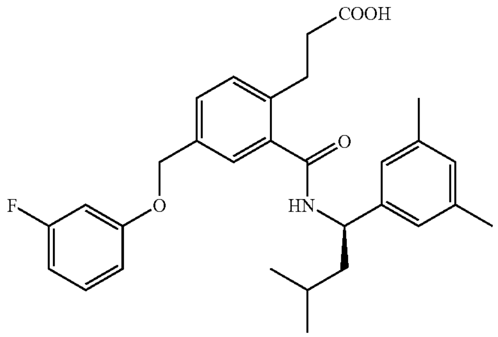

TLC: Rf 0.56 (chloroform:methanol=10:1);

NMR (300 MHz, $CDCl_3$): δ 0.98 (d, J=6.32 Hz, 6H), 1.70 (m, 3H), 2.31 (s, 6H), 2.72 (m, 2H), 3.03 (m, 2H), 5.00 (s, 2H), 5.16 (m, 1H), 6.31 (d, J=8.24 Hz, 1H), 6.70 (m, 3H), 6.91 (s, 1H), 6.95 (s, 2H), 7.25 (m, 2H), 7.40 (m, 2H).

Example 6(333)

3-(2-(((1R)-3-methyl-1-(3,5-dimethylphenyl)butyl)carbamoyl)-4-(2-ethoxyphenoxymethyl)phenyl)propanoic acid

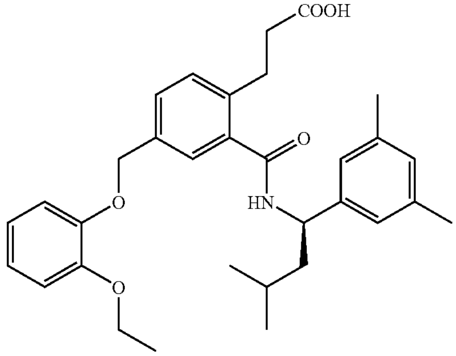

TLC: Rf 0.58 (chloroform:methanol=1:1);

NMR (300 MHz, $CDCl_3$): δ 0.98 (d, J=6.32 Hz, 6H), 1.42 (t, J=6.90 Hz, 3H), 1.55-1.83 (m, 3H), 2.31 (s, 6H), 2.71 (t, J=7.42 Hz, 2H), 3.00-3.06 (m, 2H), 4.09 (q, J=6.90 Hz, 2H), 5.08 (s, 2H), 5.16 (m, 1H), 6.32 (d, J=8.24 Hz, 1H), 6.84-6.95 (m, 7H), 7.26 (t, J=4.26 Hz, 1H), 7.43-7.42 (m, 2H).

Example 6(334)

3-(2-((N-(2-methylpropyl)-N-(3,5-dimethylphenyl)amino)carbamoyl)-4-(2,5-difluorophenoxymethyl)phenyl)propanoic acid

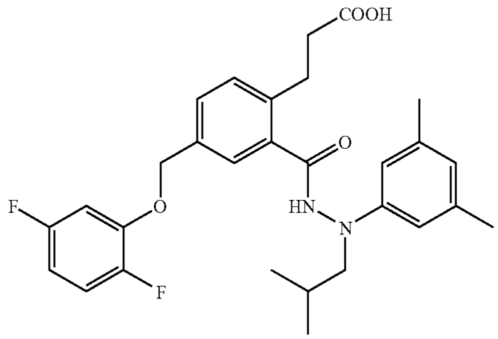

TLC: Rf 0.41 (chloroform:methanol=10:1);

NMR (300 MHz, $CDCl_3$): δ 1.04 (d, J=6.87 Hz, 6H), 2.07 (m, 1H), 2.26 (s, 6H), 2.81 (t, J=7.42 Hz, 2H), 3.15 (t, J=7.42 Hz, 2H), 3.39 (d, J=7.42 Hz, 2H), 5.12 (s, 2H), 6.52 (s, 1H), 6.54 (s, 2H), 6.63 (m, 1H), 6.76 (m, 1H), 7.05 (m, 1H), 7.38 (d, J=7.97 Hz, 1H), 7.48 (dd, J=7.97, 1.10 Hz, 1H), 7.57 (d, J=1.10 Hz, 1H), 7.70 (s, 1H).

Example 6(335)

3-(2-(1-ethyl-1-(3,5-dimethylphenyl)propyl)carbamoyl)-4-(2,5-difluorophenoxymethyl)phenyl)propanoic acid

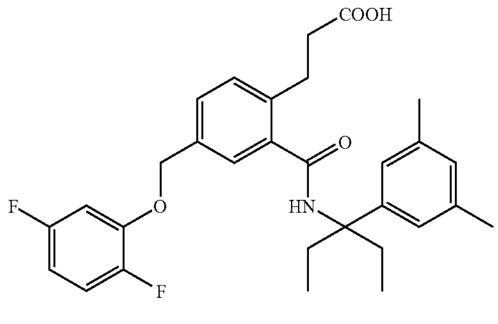

TLC: Rf 0.41 (chloroform:methanol=19:1);

NMR (300 MHz, $CDCl_3$): δ 0.82 (t, J=7.28 Hz, 6H), 2.20 (m, 4H), 2.31 (s, 6H), 2.76 (t, J=7.49 Hz, 2H), 3.09 (t, J=7.49 Hz, 2H), 5.10 (s, 2H), 6.13 (s, 1H), 6.62 (m, 1H), 6.76 (m, 1H), 6.88 (s, 1H), 6.97 (s, 2H), 7.04 (m, 1H), 7.32 (d, J=7.97 Hz, 1H), 7.43 (dd, J=7.97, 1.37 Hz, 1H), 7.54 (d, J=1.37 Hz, 1H).

Example 6(336)

3-(2-(4-(3,5-dimethylphenyl)perhydropyran-4-yl)carbamoyl)-4-(2,5-difluorophenoxymethyl)phenyl)propanoic acid

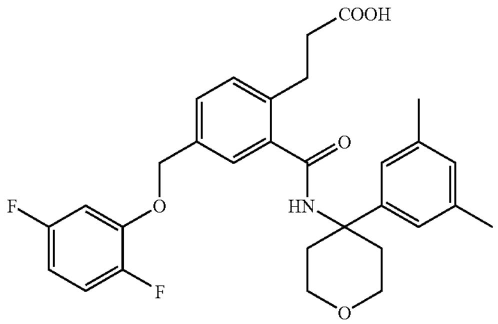

TLC: Rf 0.42 (chloroform:methanol=10:1);

NMR (300 MHz, $CDCl_3$): δ 2.23 (m, 2H), 2.32 (s, 6H), 2.47 (m, 2H), 2.71 (t, J=7.28 Hz, 2H), 3.03 (t, J=7.28 Hz, 2H), 3.84 (m, 4H), 5.09 (s, 2H), 6.50 (s, 1H), 6.63 (m, 1H), 6.75 (m, 1H), 6.91 (s, 1H), 7.05 (m, 1H), 7.09 (s, 2H), 7.30 (d, J=7.80 Hz, 1H), 7.43 (dd, J=7.80, 1.10 Hz, 1H), 7.54 (d, J=1.10 Hz, 1H).

Example 6(337)

3-(2-(((1R)-3-methyl-1-(3,5-dimethylphenyl)butyl)carbamoyl)-4-(3-cyanophenoxymethyl)phenyl)propanoic acid

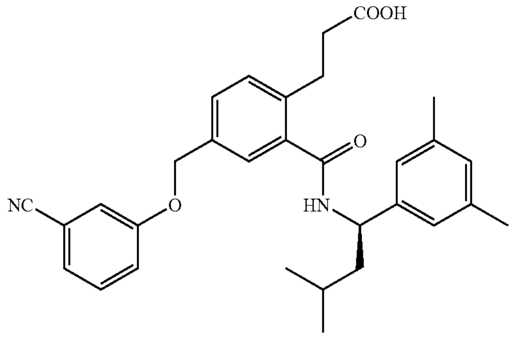

TLC: Rf 0.55 (chloroform:methanol=9:1);

NMR (300 MHz, $CDCl_3$): δ 0.98 (d, J=6.59 Hz, 6H), 1.70 (m, 3H), 2.31 (s, 6H), 2.72 (m, 2H), 3.03 (m, 2H), 5.03 (s, 2H), 5.17 (m, 1H), 6.37 (d, J=8.79 Hz, 1H), 6.91 (s, 1H), 6.96 (s, 2H), 7.17 (m, 2H), 7.28 (m, 2H), 7.39 (m, 3H).

Example 6(338)

3-(2-(((1R)-3-methyl-1-(3,5-dimethylphenyl)butyl) carbamoyl)-4-(2,4-difluorophenoxymethyl)phenyl) propanoic acid

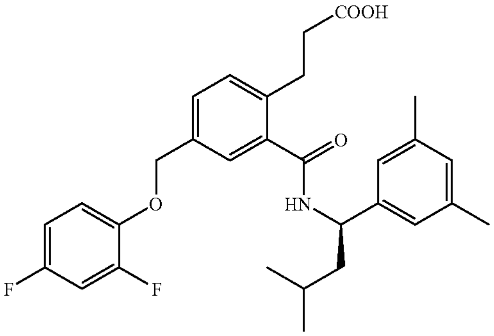

TLC: Rf 0.51 (chloroform:methanol=9:1);

NMR (300 MHz, $CDCl_3$): δ 0.99 (d, J=6.32 Hz, 6H), 1.70 (m, 3H), 2.31 (s, 6H), 2.71 (m, 2H), 3.03 (m, 2H), 5.04 (s, 2H), 5.16 (m, 1H), 6.34 (d, J=8.24 Hz, 1H), 6.77 (m, 1H), 6.90 (m, 5H), 7.27 (m, 1H), 7.39 (m, 2H).

Example 6(339)

3-(2-(((1R)-3-methyl-1-(3,5-dimethylphenyl)butyl) carbamoyl)-4-(2,5-dimethylphenoxymethyl)phenyl) propanoic acid

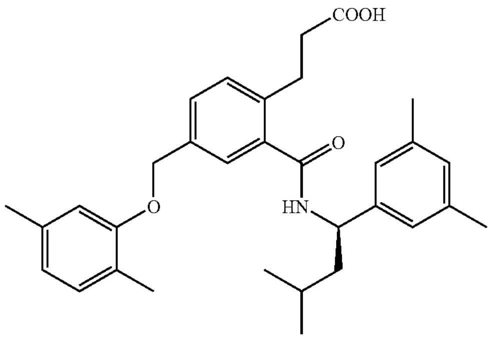

TLC: Rf 0.51 (chloroform:methanol=9:1);

NMR (300 MHz, $CDCl_3$): δ 0.98 (d, J=6.18 Hz, 3H), 0.99 (d, J=6.18 Hz, 3H), 1.71 (m, 3H), 2.22 (s, 3H), 2.30 (s, 6H), 2.31 (s, 3H), 2.72 (t, J=7.55 Hz, 2H), 3.04 (m, 2H), 5.02 (s, 2H), 5.15 (m, 1H), 6.27 (d, J=8.79 Hz, 1H), 6.71 (m, 2H), 6.90 (s, 1H), 6.95 (s, 2H), 7.04 (d, J=7.14 Hz, 1H), 7.28 (d, J=7.69 Hz, 1H), 7.42 (m, 2H).

Example 6(340)

3-(2-(((1R)-3-methyl-1-(3,5-dimethylphenyl)butyl) carbamoyl)-4-(2-chlorophenoxymethyl)phenyl)propanoic acid

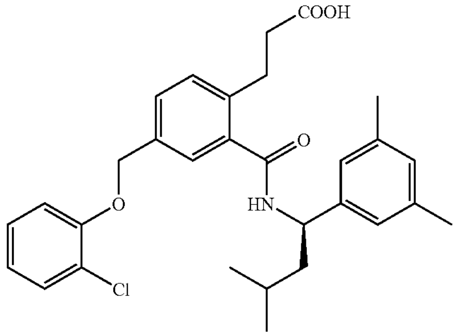

TLC: Rf 0.49 (chloroform:methanol=9:1);

NMR (300 MHz, $CDCl_3$): δ 0.98 (d, J=6.18 Hz, 3H), 0.99 (d, J=6.18 Hz, 3H), 1.71 (m, 3H), 2.31 (s, 6H), 2.72 (t, J=7.14 Hz, 2H), 3.04 (m, 2H), 5.12 (s, 2H), 5.16 (m, 1H), 6.32 (d, J=8.52 Hz, 1H), 6.94 (m, 5H), 7.21 (m, 1H), 7.28 (d, J=7.97 Hz, 1H), 7.41 (m, 2H), 7.52 (d, J=1.65 Hz, 1H).

Example 6(341)

3-(2-(1-methyl-1-(3,5-dimethylphenyl)ethyl)carbamoyl)-4-(2,5-difluorophenoxymethyl)phenyl)propanoic acid

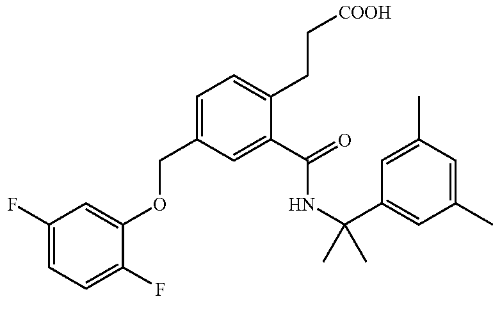

TLC: Rf 0.49 (chloroform:methanol=9:1);

NMR (300 MHz, $CDCl_3$): δ 1.80 (s, 6H), 2.32 (s, 6H), 2.75 (t, J=7.42 Hz, 2H), 3.08 (t, J=7.42 Hz, 2H), 5.08 (s, 2H), 6.33 (s, 1H), 6.62 (m, 1H), 6.75 (m, 1H), 6.90 (s, 1H), 7.03 (m, 1H), 7.07 (s, 2H), 7.30 (d, J=7.98 Hz, 1H), 7.41 (dd, J=7.98, 1.51 Hz, 1H), 7.49 (d, J=1.51 Hz, 1H).

Example 6(342)

3-(2-(((1R)-3-methyl-1-(3,5-dimethylphenyl)butyl)carbamoyl)-4-phenoxymethylphenyl)propanoic acid

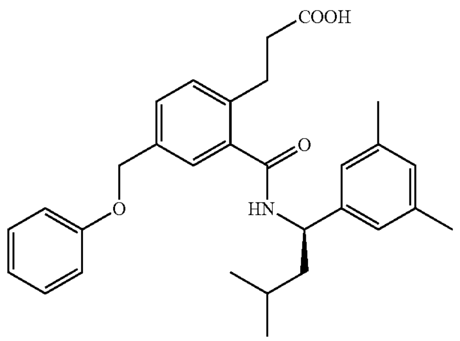

TLC: Rf 0.52 (chloroform:methanol=10:1);

NMR (300 MHz, $CDCl_3$): δ 0.98 (d, J=6.32 Hz, 6H), 1.70 (m, 3H), 2.31 (s, 6H), 2.73 (m, 2H), 3.03 (m, 2H), 5.02 (s, 2H), 5.16 (m, 1H), 6.28 (d, J=8.24 Hz, 1H), 6.91 (s, 1H), 6.97 (m, 5H), 7.29 (m, 3H), 7.42 (m, 2H).

Example 6(343)

3-(2-(((1R)-3-methyl-1-(3,5-dimethylphenyl)butyl)carbamoyl)-4-(2-ethylphenoxymethyl)phenyl)propanoic acid

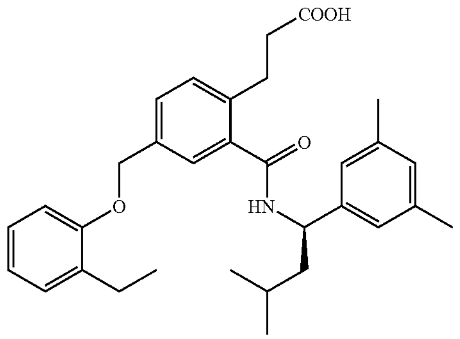

TLC: Rf 0.51 (chloroform:methanol=10:1);

NMR (300 MHz, $CDCl_3$): δ 0.98 (dd, J=6.18, 2.61 Hz, 6H), 1.20 (t, J=7.55 Hz, 3H), 1.70 (m, 3H), 2.30 (s, 6H), 2.71 (m, 4H), 3.03 (m, 2H), 5.05 (s, 2H), 5.17 (m, 1H), 6.23 (d, J=8.52 Hz, 1H), 6.90 (m, 5H), 7.16 (m, 2H), 7.28 (d, J=8.52 Hz, 1H), 7.42 (m, 2H).

Example 6(344)

3-(2-(((1R)-3-methyl-1-(3,5-dimethylphenyl)butyl)carbamoyl)-4-(3-chlorophenoxymethyl)phenyl)propanoic acid

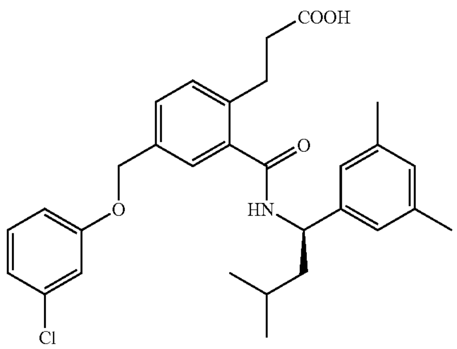

TLC: Rf 0.52 (chloroform:methanol=10:1);

NMR (300 MHz, $CDCl_3$): δ 0.99 (d, J=6.32 Hz, 6H), 1.70 (m, 3H), 2.31 (s, 6H), 2.72 (m, 2H), 3.03 (m, 2H), 5.00 (s, 2H), 5.17 (m, 1H), 6.30 (d, J=8.79 Hz, 1H), 6.84 (m, 1H), 6.91 (s, 1H), 6.96 (m, 4H), 7.24 (m, 2H), 7.40 (m, 2H).

Example 6(345)

3-(2-(4-(3,5-dimethylphenyl)perhydrothiopyran-4-yl)carbamoyl)-4-(2,5-difluorophenoxymethyl)phenyl)propanoic acid

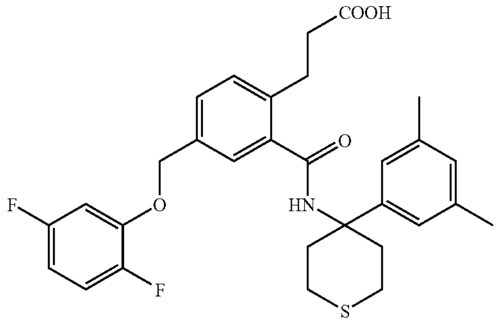

TLC: Rf 0.58 (chloroform:methanol=9:1);

NMR (300 MHz, $CDCl_3$): δ 2.25 (m, 2H), 2.31 (s, 6H), 2.61 (m, 2H), 2.76 (m, 4H), 3.03 (m, 4H), 5.11 (s, 2H), 6.28 (s, 1H), 6.63 (m, 1H), 6.77 (m, 1H), 6.90 (s, 1H), 7.06 (m, 3H), 7.32 (d, J=7.97 Hz, 1H), 7.44 (dd, J=7.97, 1.80 Hz, 1H), 7.57 (d, J=1.80 Hz, 1H).

Example 6(346)

3-(2-(1-benzyl-4-(3,5-dimethylphenyl)piperidin-4-yl)carbamoyl)-4-(2,5-difluorophenoxymethyl)phenyl)propanoic acid

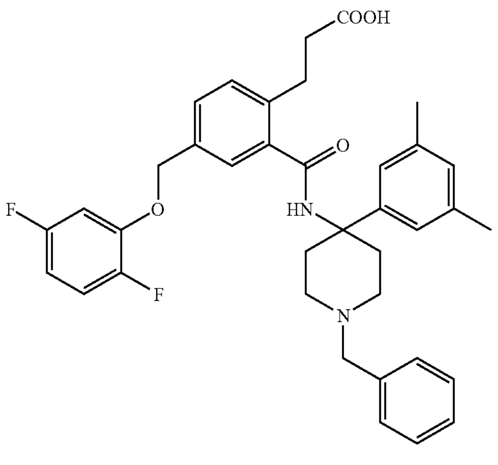

TLC: Rf 0.52 (chloroform:methanol=6:1);

NMR (300 MHz, $CD_3OD$): δ 2.17 (m, 2H), 2.29 (s, 6H), 2.61 (t, J=7.42 Hz, 2H), 2.76 (m, 2H), 2.95 (m, 4H), 3.16 (m, 2H), 4.06 (s, 2H), 5.13 (s, 2H), 6.64 (m, 1H), 6.90 (s, 1H), 6.97 (m, 1H), 7.09 (m, 3H), 7.43 (m, 8H).

Example 6(347)

3-(2-(1,1-dione-4-(3,5-dimethylphenyl)perhydrothiopyran-4-yl)carbamoyl)-4-(2,5-difluorophenoxymethyl)phenyl)propanoic acid

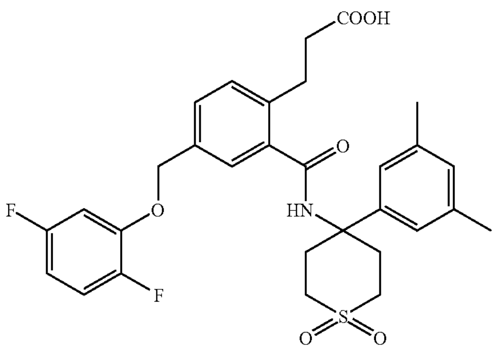

TLC: Rf 0.49 (chloroform:methanol=9:1);

NMR (300 MHz, $CDCl_3$): δ 2.31 (s, 6H), 2.75 (m, 4H), 3.04 (m, 6H), 3.40 (m, 2H), 5.07 (s, 2H), 6.62 (m, 1H), 6.76 (m, 1H), 6.94 (s, 1H), 7.03 (m, 4H), 7.30 (d, J=7.97 Hz, 1H), 7.45 (m, 1H), 7.51 (m, 1H).

Example 6(348)

3-(2-((4-(3,5-dimethylphenyl)perhydropyran-4-yl)carbamoyl)-4-(3-cyanophenoxymethyl)phenyl)propanoic acid

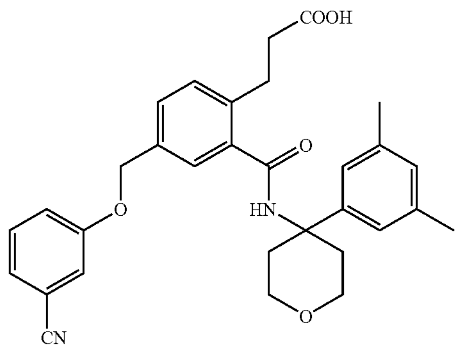

TLC: Rf 0.24 (n-hexane:ethyl acetate:acetic acid=100:100:1);

NMR (300 MHz, DMSO-$d_6$): δ 1.93 (m, 2H), 2.26 (s, 6H), 2.39 (m, 2H), 2.49 (m, 2H), 2.86 (m, 2H), 3.74 (m, 4H), 5.20 (s, 2H), 6.84 (s, 1H), 7.04 (s, 2H), 7.42 (m, 7H), 8.59 (s, 1H), 12.09 (s, 1H).

Example 6(349)

3-(2-((2,6-dimethyl-4-(3,5-dimethylphenyl)-4-heptyl)carbamoyl)-4-(2,5-difluorophenoxymethyl)phenyl)propanoic acid

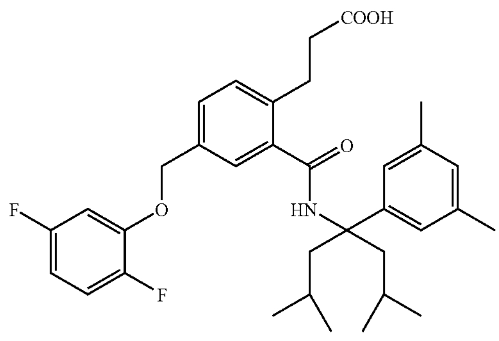

TLC: Rf 0.66 (n-hexane:ethyl acetate=1:1);

NMR (300 MHz, $CDCl_3$): δ 0.75 (d, J=6.59 Hz, 6H), 0.84 (d, J=6.59 Hz, 6H), 1.58 (m, 2H), 2.11 (dd, J=14.28, 5.22 Hz, 2H), 2.22 (dd, J=14.28, 6.06 Hz, 2H), 2.31 (s, 6H), 2.79 (t, J=7.55 Hz, 2H), 3.11 (t, J=7.55 Hz, 2H), 5.12 (s, 2H), 6.25 (s, 1H), 6.62 (m, 1H), 6.76 (m, 1H), 6.86 (s, 1H), 6.94 (s, 2H), 7.04 (m, 1H), 7.34 (d, J=7.91 Hz, 1H), 7.44 (dd, J=7.91, 1.65 Hz, 1H), 7.57 (d, J=1.65 Hz, 1H).

Example 6(350)

3-(2-((4-(3,5-dimethylphenyl)perhydropyran-4-yl) carbamoyl)-4-(2-chloro-5-fluorophenoxymethyl) phenyl)propanoic acid

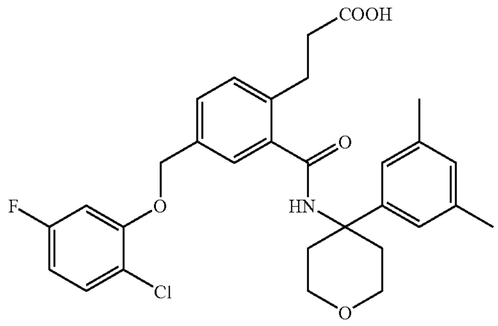

TLC: Rf 0.41 (n-hexane:ethyl acetate:acetic acid=100:100:1);

NMR (300 MHz, $CDCl_3$): δ 2.24 (m, 2H), 2.32 (s, 6H), 2.46 (m, 2H), 2.70 (t, J=7.42 Hz, 2H), 3.03 (t, J=7.42 Hz, 2H), 3.83 (m, 2H), 3.93 (m, 2H), 5.12 (s, 2H), 6.47 (s, 1H), 6.67 (m, 1H), 6.73 (dd, J=10.03, 2.61 Hz, 1H), 6.91 (s, 1H), 7.09 (s, 2H), 7.33 (m, 2H), 7.43 (m, 1H), 7.62 (d, J=1.65 Hz, 1H).

Example 6(351)

3-(2-((4-(3,5-dimethylphenyl)perhydropyran-4-yl) carbamoyl)-4-(2-chloro-5-methylphenoxymethyl) phenyl)propanoic acid

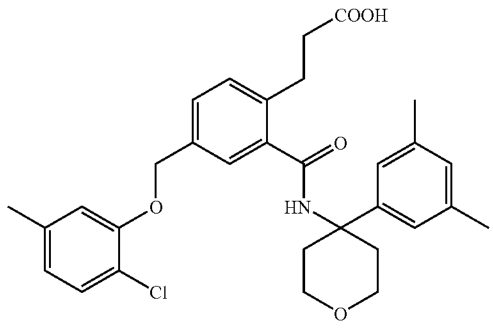

TLC: Rf 0.39 (n-hexane:ethyl acetate:acetic acid=100:100:1);

NMR (300 MHz, $CDCl_3$): δ 2.23 (m, 2H), 2.32 (s, 6H), 2.33 (s, 3H), 2.46 (dd, J=13.32, 1.51 Hz, 2H), 2.69 (t, J=7.28 Hz, 2H), 3.03 (t, J=7.28 Hz, 2H), 3.83 (m, 2H), 3.92 (m, 2H), 5.12 (s, 2H), 6.46 (s, 1H), 6.75 (m, 1H), 6.81 (s, 1H), 6.90 (s, 1H), 7.09 (s, 2H), 7.27 (m, 2H), 7.43 (m, 1H), 7.66 (s, 1H).

Example 6(352)

3-(2-((4-(3,5-dimethylphenyl)perhydropyran-4-yl) carbamoyl)-4-(2,5-dichlorophenoxymethyl)phenyl) propanoic acid

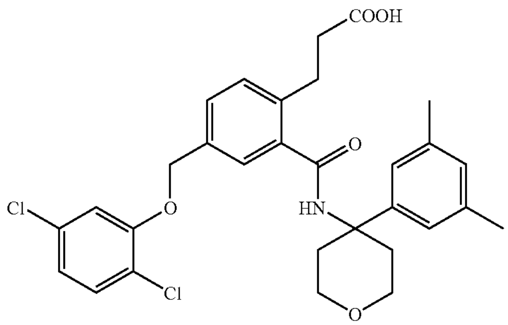

TLC: Rf 0.39 (n-hexane:ethyl acetate:acetic acid=100:100:1);

NMR (300 MHz, $CDCl_3$): δ 2.25 (m, 2H), 2.32 (s, 6H), 2.47 (m, 2H), 2.71 (t, J=7.14 Hz, 2H), 3.04 (t, J=7.14 Hz, 2H), 3.83 (t, J=10.30 Hz, 2H), 3.93 (m, 2H), 5.12 (s, 2H), 6.46 (s, 1H), 6.95 (m, 3H), 7.09 (s, 2H), 7.32 (m, 2H), 7.43 (m, 1H), 7.63 (d, J=1.65 Hz, 1H).

Example 6(353)

3-(2-((4-(3,5-dimethylphenyl)perhydropyran-4-yl) carbamoyl)-4-phenoxymethylphenyl)propanoic acid

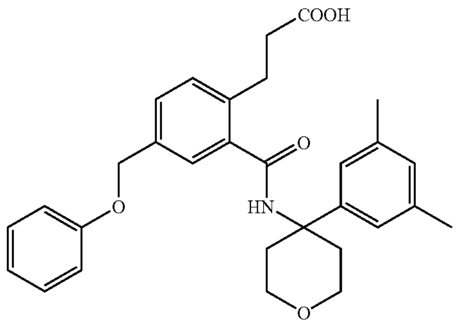

TLC: Rf 0.36 (n-hexane:ethyl acetate:acetic acid=100:100:1);

NMR (300 MHz, $CDCl_3$): δ 2.23 (m, 2H), 2.31 (s, 6H), 2.46 (m, 2H), 2.69 (t, J=7.28 Hz, 2H), 3.02 (t, J=7.28 Hz, 2H), 3.79 (m, 2H), 3.91 (m, 2H), 5.05 (s, 2H), 6.48 (s, 1H), 6.90 (s, 1H), 6.99 (m, 3H), 7.08 (s, 2H), 7.30 (m, 3H), 7.43 (m, 1H), 7.50 (s, 1H).

Example 6(354)

3-(2-((4-(3,5-dimethylphenyl)perhydropyran-4-yl)carbamoyl)-4-(3-chlorophenoxymethyl)phenyl)propanoic acid

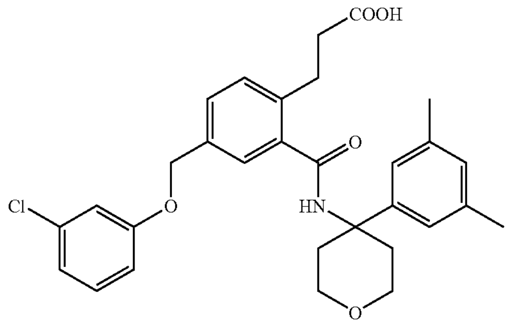

TLC: Rf 0.35 (n-hexane:ethyl acetate:acetic acid=100:100:1);

NMR (300 MHz, $CDCl_3$): δ 2.24 (m, 2H), 2.32 (s, 6H), 2.48 (d, J=15.11 Hz, 2H), 2.71 (t, J=7.14 Hz, 2H), 3.02 (t, J=7.14 Hz, 2H), 3.79 (m, 2H) 3.92 (m, 2H), 5.03 (s, 2H), 6.50 (s, 1H), 6.85 (m, 1H), 6.91 (s, 1H), 6.97 (m, 2H), 7.08 (s, 2H), 7.22 (m, 1H), 7.30 (d, J=7.97 Hz, 1H), 7.41 (m, 1H) 7.47 (s, 1H).

Example 6(355)

3-(2-((4-(3,5-dimethylphenyl)perhydropyran-4-yl)carbamoyl)-4-(3-fluorophenoxymethyl)phenyl)propanoic acid

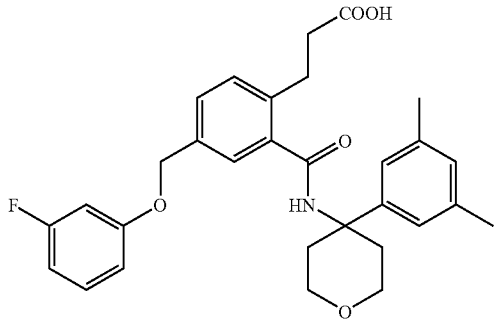

TLC: Rf 0.43 (chloroform:methanol=10:1);

NMR (300 MHz, $CDCl_3$): δ 2.27 (m, 8H), 2.45 (m, 2H), 2.72 (t, J=7.28 Hz, 2H), 3.03 (t, J=7.28 Hz, 2H), 3.87 (m, 4H), 5.04 (s, 2H), 6.48 (s, 1H), 6.72 (m, 3H), 6.91 (s, 1H), 7.09 (s, 2H), 7.22 (m, 1H), 7.30 (d, J=8.24 Hz, TH), 7.43 (d, J=7.97 Hz, 1H), 7.48 (s, 1H).

Example 6(356)

3-(2-((4-(3,5-dimethylphenyl)perhydropyran-4-yl)carbamoyl)-4-(2,5-dimethylphenoxymethyl)phenyl)propanoic acid

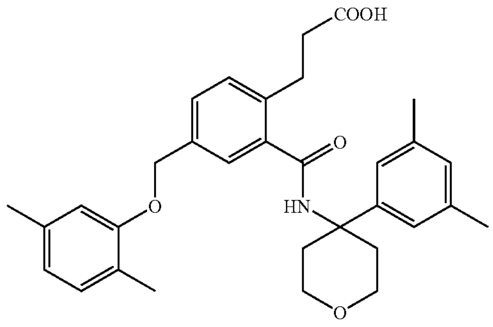

TLC: Rf 0.43 (chloroform:methanol=10:1);

NMR (300 MHz, $CDCl_3$): δ 2.26 (s, 6H), 2.28 (m, 2H), 2.32 (s, 6H), 2.44 (m, 2H), 2.72 (t, J=7.35 Hz, 2H), 3.04 (t, J=7.35 Hz, 2H), 3.82 (m, 2H) 3.93 (m, 2H), 5.06 (s, 2H), 6.40 (s, 1H), 6.73 (m, 2H), 6.91 (s, 1H), 7.06 (d, J=7.69 Hz, 1H), 7.09 (s, 2H), 7.30 (d, J=7.69 Hz, 1H), 7.45 (dd, J=7.69, 1.65 Hz, 1H), 7.56 (d, J=1.65 Hz, 1H).

Example 6(357)

3-(2-((1-methylsulfonyl-4-(3,5-dimethylphenyl)piperidin-4-yl)carbamoyl)-4-(2,5-difluorophenoxymethyl)phenyl)propanoic acid

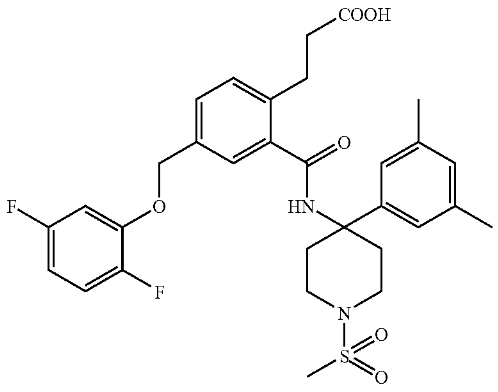

TLC: Rf 0.42 (chloroform:methanol=10:1);

NMR (300 MHz, $CDCl_3$): δ 2.24 (m, 2H), 2.32 (s, 6H), 2.70 (m, 4H), 2.78 (s, 3H), 3.03 (t, J=7.14 Hz, 2H), 3.13 (t, J=11.13 Hz, 2H), 3.68 (m, 2H), 5.07 (s, 2H), 6.52 (s, 1H), 6.63 (m, 1H), 6.75 (m, 1H), 6.92 (s, 1H), 7.03 (m, 1H), 7.08 (s, 2H), 7.29 (d, J=7.97 Hz, 1H), 7.41 (d, J=7.97 Hz, 1H), 7.51 (s, 1H).

Example 6(358)

3-(2-((4-(3,5-dimethylphenyl)perhydropyran-4-yl)carbamoyl)-4-(2-fluorophenoxymethyl)phenyl)propanoic acid

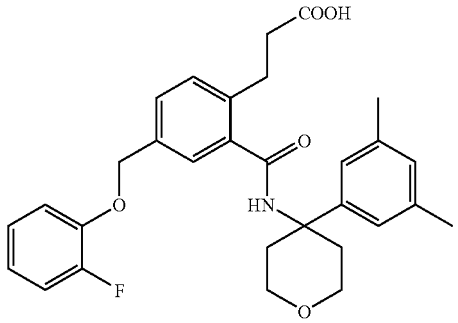

TLC: Rf 0.43 (chloroform:methanol=10:1);

NMR (300 MHz, $CDCl_3$): δ 2.26 (m, 2H), 2.32 (s, 6H), 2.45 (m, 2H), 2.71 (t, J=7.14 Hz, 2H) 3.03 (t, J=7.14 Hz, 2H), 3.82 (m, 4H), 5.13 (s, 2H), 6.48 (s, 1H), 7.02 (m, 7H), 7.30 (d, J=7.69 Hz, 1H), 7.44 (d, J=7.69 Hz, 1H), 7.56 (s, 1H).

Example 6(359)

3-(2-((4-(3,5-dimethylphenyl)perhydropyran-4-yl)carbamoyl)-4-(2-chlorophenoxymethyl)phenyl)propanoic acid

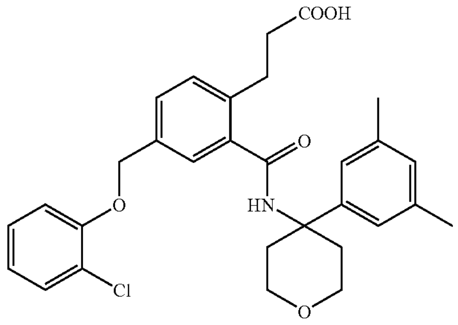

TLC: Rf 0.43 (chloroform:methanol=10:1);

NMR (300 MHz, $CDCl_3$): δ 2.25 (m, 2H), 2.32 (s, 6H), 2.46 (m, 2H), 2.70 (t, J=7.42 Hz, 2H) 3.03 (t, J=7.42 Hz, 2H), 3.85 (m, 2H), 3.93 (m, 2H), 5.15 (s, 2H), 6.45 (s, 1H), 6.91 (s, 1H), 6.97 (m, 2H), 7.09 (s, 2H), 7.22 (m, 1H), 7.30 (d, J=7.97 Hz, TH), 7.42 (m, 2H), 7.65 (s, 1H).

Example 6(360)

3-(2-((4-(3-methylphenyl)perhydropyran-4-yl)carbamoyl)-4-(2,5-difluorophenoxymethyl)phenyl)propanoic acid

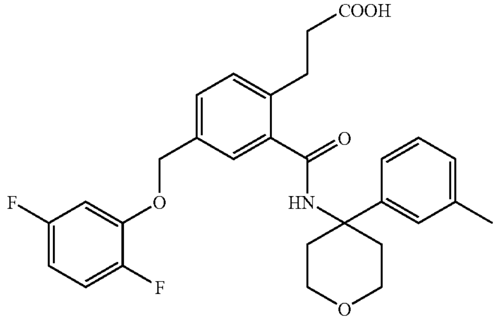

TLC: Rf 0.55 (chloroform:methanol=9:1);

NMR (300 MHz, $CDCl_3$): δ 2.25 (m, 2H), 2.36 (s, 3H), 2.50 (m, 2H), 2.70 (t, J=7.21 Hz, 2H), 3.01 (t, J=7.21 Hz, 2H), 3.88 (m, 4H), 5.08 (s, 2H), 6.57 (s, 1H), 6.63 (m, 1H), 6.76 (m, 1H), 7.05 (m, 2H), 7.27 (m, 4H), 7.42 (dd, J=8.12, 1.71 Hz, 1H), 7.52 (d, J=1.71 Hz, 1H).

Example 6(361)

3-(2-((4-(naphthalen-1-yl)perhydropyran-4-yl)carbamoyl)-4-(2,5-difluorophenoxymethyl)phenyl)propanoic acid

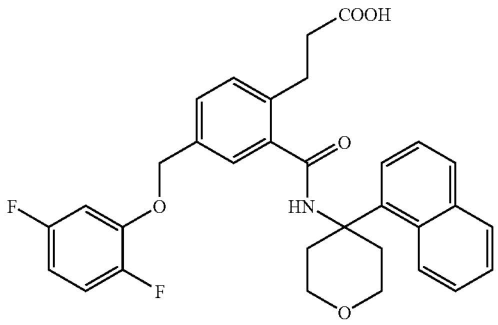

TLC: Rf 0.53 (chloroform:methanol=9:1);

NMR (300 MHz, $CDCl_3$): δ 2.50 (m, 4H), 2.85 (m, 4H), 3.97 (m, 4H), 5.02 (s, 2H), 6.64 (m, 1H), 6.73 (m, 1H), 7.07 (m, 2H), 7.23 (d, J=7.69 Hz, 1H), 7.43 (m, 5H), 7.74 (d, J=7.42 Hz, 1H), 7.80 (d, J=7.97 Hz, 1H), 7.89 (m, 1H), 8.42 (m, 1H).

Example 6(362)

3-(2-((1-methyl-4-(3,5-dimethylphenyl)piperidin-4-yl)carbamoyl)-4-(2,5-difluorophenoxymethyl)phenyl)propanoic acid

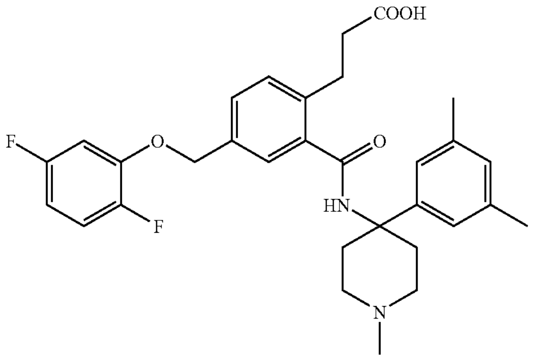

TLC: Rf 0.37 (chloroform:methanol:28% ammonia water=40:10:1);

NMR (300 MHz, DMSO-$d_6$): δ 1.85 (m, 2H), 2.19 (s, 3H), 2.25 (s, 6H), 2.29 (m, 2H), 2.46 (m, 4H), 2.65 (m, 2H), 2.89 (t, J=7.83 Hz, 2H), 5.21 (s, 2H), 6.77 (m, 1H), 6.82 (s, 1H), 7.03 (s, 2H), 7.29 (m, 5H), 8.50 (s, 1H).

Example 6(363)

3-(2-((1-ethyl-4-(3,5-dimethylphenyl)piperidin-4-yl)carbamoyl)-4-(2,5-difluorophenoxymethyl)phenyl)propanoic acid

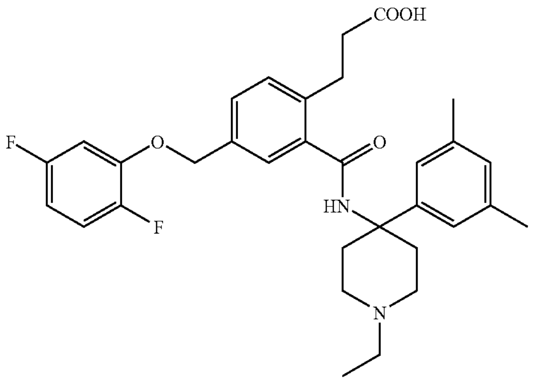

TLC: Rf 0.39 (chloroform:methanol=5:1);

NMR (300 MHz, $CD_3OD$): δ 1.29 (t, J=7.28 Hz, 3H), 2.20 (m, 2H), 2.31 (s, 6H), 2.62 (t, J=7.14 Hz, 2H), 2.85 (m, 2H), 2.98 (t, J=7.14 Hz, 2H), 3.03 (m, 4H), 3.34 (m, 2H), 5.12 (s, 2H), 6.63 (m, 1H), 6.92 (s, 1H), 6.96 (m, 1H), 7.08 (m, 1H), 7.14 (s, 2H), 7.40 (m, 3H).

Example 6(364)

2-(2-((3-methyl-1-(3,5-dimethylphenyl)butyl)carbamoyl)-4-benzyloxyphenoxy)acetic acid

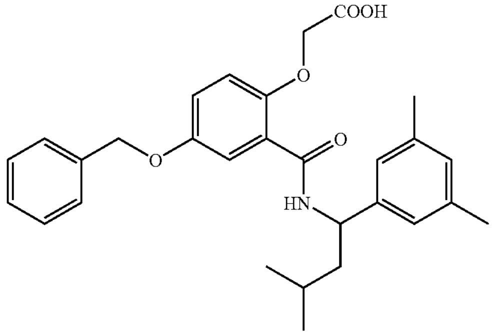

TLC: Rf 0.42 (chloroform:methanol=10:1);

NMR (300 MHz, $CDCl_3$): δ 0.95 (d, J=6.32 Hz, 6H), 1.63 (m, 2H), 1.84 (m, 1H), 2.28 (s, 6H), 4.73 (s, 2H), 5.03 (s, 2H), 5.19 (m, 1H), 6.85 (d, J=8.70 Hz, 1H), 6.87 (s, 1H), 6.98 (s, 2H) 7.02 (dd, J=8.70, 3.02 Hz, 1H), 7.35 (m, 5H), 7.57 (d, J=3.02 Hz, 1H), 7.94 (d, J=8.52 Hz, 1H).

Example 6(365)

2-(2-((3-methyl-1-(3,5-dimethylphenyl)butyl)carbamoyl)-4-(2-chloro-6-fluorobenzyloxy)phenoxy) acetic acid

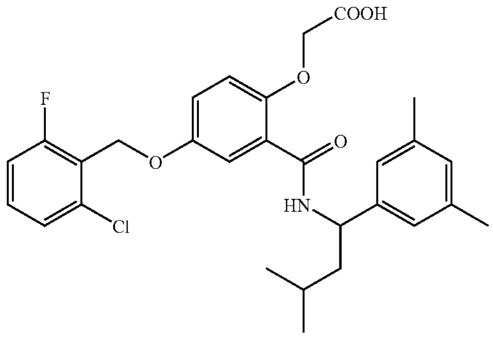

TLC: Rf 0.42 (chloroform:methanol=10:1);

NMR (300 MHz, $CDCl_3$): δ 0.96 (d, J=6.32 Hz, 6H), 1.66 (m, 2H), 1.84 (m, 1H), 2.30 (s, 6H), 4.76 (s, 2H), 5.16 (s, 2H), 5.20 (m, 1H), 7.01 (m, 6H), 7.28 (m, 2H), 7.49 (d, J=3.02 Hz, 1H) 7.54 (d, J=7.97 Hz, 1H).

Reference Example 9

4-(t-butoxycarbonyl)-2-nitrophenyl iodide

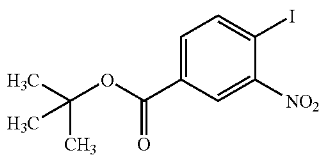

Using 4-carboxy-2-nitroaniline instead of 4-amino-3-hydroxybenzoic acid methyl ester and using t-butanol instead of methanol, the title compound having the following physical data was obtained by the same procedures as a series of reactions of Reference Example 2→Reference Example 1.

TLC: Rf 0.50 (hexane:ethyl acetate=9:1).

Reference Example 10

4-[4-(t-butoxycarbonyl)-2-nitrophenyl]butanoic acid methyl ester

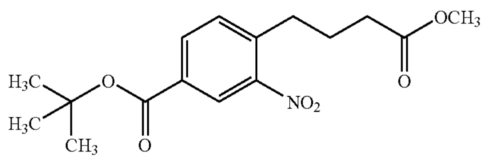

To a suspension of zinc powder (activated, 19.6 g) in tetrahydrofuran (100 ml) was added dibromoethane (0.1 ml) and the mixture was refluxed for 5 minutes. To the mixture was added trimethylsilylchloride (0.1 ml) and the mixture was stirred for 5 minutes. Under refluxing condition, to the mixture was added a solution of methyl 4-iodobutanoate (45.6 g) in tetrahydrofuran (100 ml) slowly. The reaction mixture was refluxed for 3 hours. The mixture was allowed to stand to give a solution of methyl 4-iodobutanoate zincate in tetrahydrofuran. At the same time, to a solution of the compound prepared in Reference Example 9 (34.9 g) in tetrahydrofuran (100 ml) was added (1,1'-bis(diphenylphosphino)ferrocene)palladium (II) dichloride (2.20 g). To the suspension was added dropwise the above-mentioned solution of methyl 4-iodobutanoate zincate in tetrahydrofuran (equivalent to 200 mmol) at room temperature during 15 minutes. The mixture was stirred at room temperature for 30 minutes and then stirred at 60° C. for 30 minutes. After cooling, to the mixture was added a saturated aqueous solution of ammonium chloride. An appeared insoluble material was removed and then the mixture was extracted with ethyl acetate. The organic layer was washed with water and a saturated aqueous solution of sodium chloride subsequently, dried over anhydrous magnesium sulfate and concentrated. The residue was purified by column chromatography on silica gel (hexane:ethyl acetate=9:1→4:1) to give the title compound (24.47 g) having the following physical data.

TLC: Rf 0.24 (hexane:ethyl acetate=9:1).

Reference Example 11

4-(4-carboxy-2-nitrophenyl)butanoic acid methyl ester

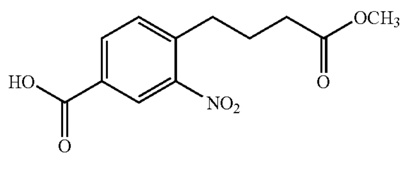

To a solution of the compound prepared in Reference Example 10 (24.4 g) in anisole (38 ml) was added trifluoroacetic acid (29 ml) and the mixture was stirred at 60° C. for 1 hour. The reaction mixture was cooled, added water and hexane and then removed hexane layer (top layer). The remaining layer was extracted with ethyl acetate. The organic layer was washed with water and a saturated aqueous solution of sodium chloride, dried over anhydrous magnesium sulfate and concentrated. The residue was recrystallized from ethyl acetate-hexane to give the title compound (16.72 g) having the following physical data.

TLC: Rf 0.31 (hexane:ethyl acetate=1:1).

Reference Example 12

4-(4-hydroxymethyl-2-nitrophenyl)butanoic acid methyl ester

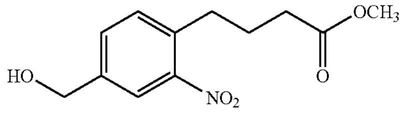

To a solution of the compound prepared in Reference Example 11 (15.58 g), triethylamine (10.6 ml) in tetrahydrofuran (60 ml) was added ethyl chloroformate (6.2 ml) under ice-cooling, and the mixture was stirred for 1 hour. The mixture was filtered and the obtained filtrate was added dropwise to a solution of sodium borohydride (11.1 g) in water (60 ml) under ice-cooling. The mixture was stirred for 30 minutes. To the reaction mixture was added 1N hydrochloric acid slowly and then the mixture was extracted with ethyl acetate. The organic layer was washed with water and a saturated aqueous solution of sodium chloride, dried and concentrated. The residue was purified by column chromatography on silica gel (hexane:ethyl acetate=2:1→1:1) to give the title compound (12.26 g) having the following physical data.

TLC: Rf 0.46 (hexane:ethyl acetate=1:1).

Reference Example 13

4-[4-(t-butyldimethylsilyloxymethyl)-2-nitrophenyl]butanoic acid methyl ester

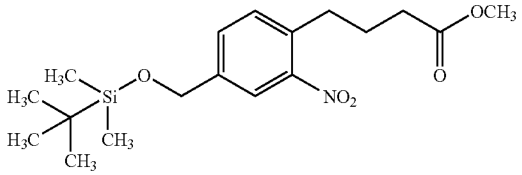

To the compound prepared in Reference Example 12 (4.078 g) and imidazole (1.646 g) in N,N-dimethylformamide (20 ml) was added t-butyldimethylsilyl chloride (2.664 g) under ice-cooling, and the mixture was stirred at room temperature overnight. To the reaction mixture was added water and the mixture was extracted with hexane. The organic layer was washed with water, dried over anhydrous magnesium sulfate and concentrated to give the title compound (6.02 g) having the following physical data.

TLC: Rf 0.69 (hexane:ethyl acetate=3:1).

Reference Example 14

4-[2-amino-4-(t-butyldimethylsilyloxymethyl)phenyl]butanoic acid methyl ester

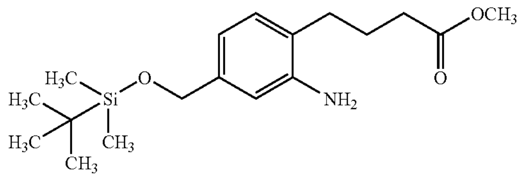

To a solution of the compound prepared in Reference Example 13 (6.02 g) in methanol (30 ml) was added 10% palladium carbon (420 mg) and the mixture was stirred at room temperature for 1 hour under an atmosphere of hydrogen. The reaction mixture was filtered and the filtrate was concentrated to give the title compound (5.43 g) having the following physical data.

TLC: Rf 0.38 (hexane:ethyl acetate=4:1).

Reference Example 15

4-[4-(t-butyldimethylsilyloxymethyl)-2-[1-(1-naphthyl)ethylcarbonylamino]phenyl]butanoic acid methyl ester

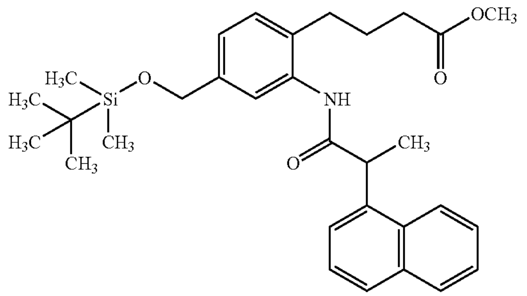

To a solution of the compound prepared in Reference Example 14 (5.43 g) and pyridine (2.60 ml) in methylene chloride (20 ml) was added dropwise a solution of α-methyl-1-naphthylacetyl chloride (3.52 g) in methylene chloride (10 ml) under an atmosphere of argon and the mixture was stirred at room temperature for 30 minutes. To the reaction mixture was added a saturated aqueous solution of sodium bicarbonate and the mixture was extracted with ethyl acetate. The organic layer was washed with water and a saturated aqueous solution of sodium chloride subsequently, dried over anhydrous magnesium sulfate and concentrated to give the title compound having the following physical data.

TLC: Rf 0.39 (hexane:ethyl acetate=4:1).

Example 7

4-(2-((2-(naphthalen-1-yl)propanoyl)amino)-4-hydroxymethylphenyl)butanoic acid methyl ester

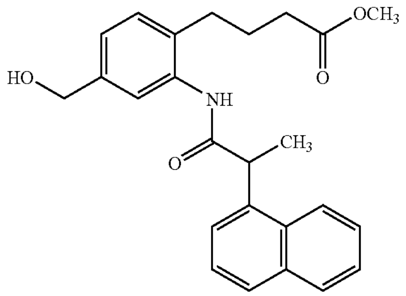

To a solution of the compound prepared in Reference Example 15 in tetrahydrofuran (30 ml) was added tetrabutylammonium fluoride (24 ml) and the mixture was stirred at room temperature overnight. To the reaction mixture was added water and the appeared solid was collected by filtration. The solid was dissolved in ethyl acetate. The solution was dried and then concentrated. The residue was recrystallized from ethyl acetate-hexane to give the title compound (5.02 g).

TLC: Rf 0.27 (hexane:ethyl acetate=1:1).

Example 7(a)

4-(2-(1-(1-naphthyl)ethyl)carbonylamino-4-hydroxymethylphenyl)butanoic acid methyl ester

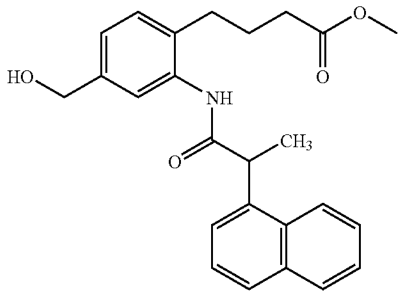

To a solution of the compound prepared in Reference Example 15 in tetrahydrofuran (30 ml) was added tetrabutylammonium fluoride (24 ml) and the mixture was stirred at room temperature overnight. To the reaction mixture was added water and the appeared solid was collected by filtration. The solid was dissolved in ethyl acetate. The solution was dried and then concentrated. The residue was recrystallized from ethyl acetate-hexane to give the title compound (5.02 g).

TLC: Rf 0.27 (hexane:ethyl acetate=1:1).

Example 7(b)

4-(2-((2-(naphthalen-1-yl)propanoyl)amino)-4-(4-ethoxyphenoxymethyl)phenyl)butanoic acid methyl ester

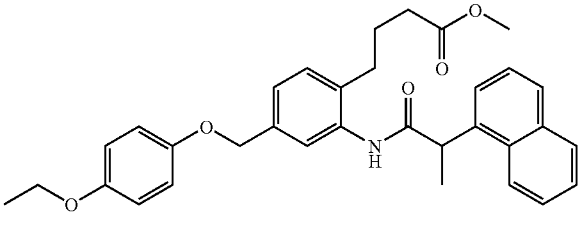

Using the compounds prepared in Example 7(a) or corresponding compounds, the title compounds having the following physical data were obtained by the same procedure of Example 5.

TLC: Rf 0.47 (n-hexane:ethyl acetate=2:1).

Example 7(b-1)~(b-2)

Using corresponding compounds, the following compounds were obtained by the same procedure of Example 7(b).

Example 7(b-1)

2-(2-((4-methyl-2-(naphthalen-1-yl)pentanoyl)amino)-4-phenoxymethylbenzyl)benzoic acid methyl ester

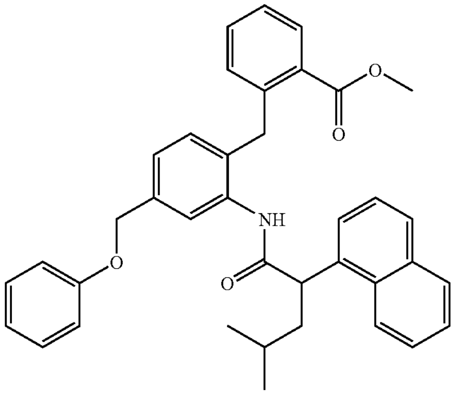

TLC: Rf 0.52 (n-hexane:ethyl acetate=3:1).

Example 7(b-2)

2-(2-((2-(4-fluoronaphthalen-1-yl)propanoyl)amino)-4-phenoxymethylbenzyl)benzoic acid methyl ester

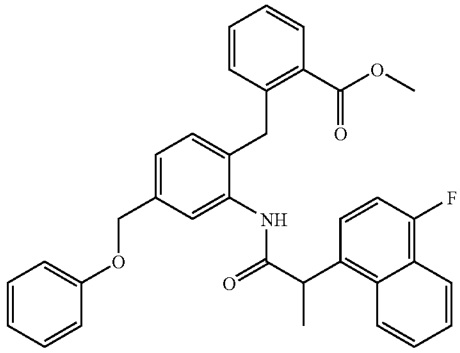

TLC: Rf 0.56 (n-hexane:ethyl acetate=2:1).

Example 8

4-(2-((2-(naphthalen-1-yl)propanoyl)amino)-4-(4-ethoxyphenoxymethyl)phenyl)butanoic acid

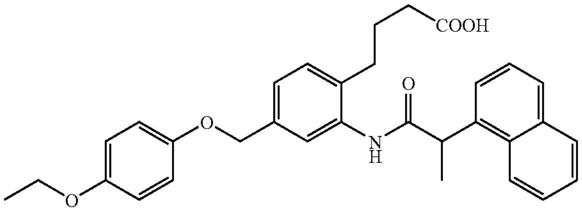

Using the compounds prepared in Example 7(b) or corresponding compounds, the title compounds having the following physical data were obtained by the same procedure of Example 3.

TLC: Rf 0.45 (ethyl acetate);

NMR (300 MHz, DMSO-$d_6$): δ 12.08 (br, 1H), 9.58 (s, 1H), 8.32 (d, J=8.1 Hz, 1H), 7.94 (m, 1H), 7.83 (d, J=8.1 Hz, 1H), 7.62-7.46 (m, 4H), 7.38 (bs, 1H), 7.16 (m, 2H), 6.88 (d, J=9.0 Hz, 2H), 6.81 (d, J=9.0 Hz, 2H), 4.94 (s, 2H), 4.71 (q, J=6.9 Hz, 1H), 3.91 (q, J=6.9 Hz, 2H), 2.43 (m, 2H), 2.02 (t, J=7.5 Hz, 2H), 1.60 (d, J=6.9 Hz, 3H), 1.56 (m, 2H), 1.27 (t, J=6.9 Hz, 3H).

Example 8(1)~Example 8(136)

Using the compounds prepared in Example 7(b-1) or 7(b-2) or corresponding compounds, the title compounds were obtained by the same procedure of Example 8.

Example 8(1)

(2E)-3-(2-((2-(naphthalen-2-yl)acetyl)amino)-4-(pyrazol-1-ylmethyl)phenyl)-2-propenoic acid

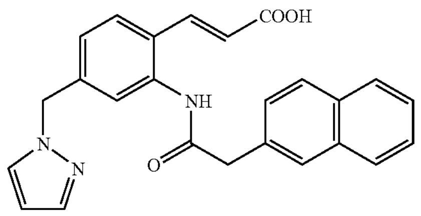

TLC: Rf 0.42 (chloroform:methanol=9:1);

NMR (300 MHz, DMSO-$d_6$): δ 10.12 (bs, 1H), 7.94-7.70 (m, 7H), 7.57-7.41 (m, 4H), 7.24 (s, 1H), 7.02 (d, J=8.1 Hz, 1H), 6.46 (d, J=16 Hz, 1H), 6.25 (t, J=2.0 Hz, 1H), 5.32 (s, 2H), 3.85 (s, 2H).

Example 8(2)

2-(2-((4-methyl-2-(naphthalen-1-yl)pentanoyl)amino)-4-hydroxymethylbenzyl)benzoic acid

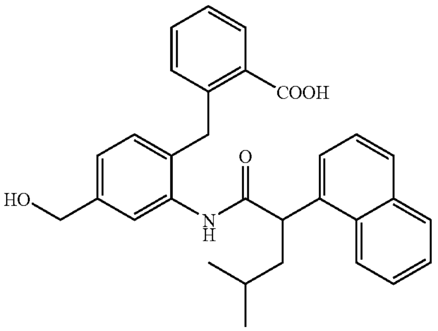

TLC: Rf 0.50 (chloroform:methanol=10:1);

NMR (300 MHz, DMSO-$d_6$): δ 9.62 (s, 1H), 8.32 (d, J=8.4 Hz, 1H), 7.91 (d, J=8.1 Hz, 1H), 7.78 (d, J=8.7 Hz, 1H), 7.75 (m, 1H), 7.65-7.39 (m, 4H), 7.34 (s, 1H), 7.23 (m, 2H), 7.00 (d, J=8.1 Hz, 1H), 6.88 (d, J=7.8 Hz, 1H), 6.79 (m, 1H), 5.12 (t, J=5.7 Hz, 1H), 4.60 (m, 1H), 4.41 (d, J=5.4 Hz, 1H), 4.30 (d, J=16.2 Hz, 1H), 4.18 (d, J=16.2 Hz, 1H), 1.93 (m, 1H), 1.47 (m, 2H), 0.92 (d, J=6.3 Hz, 3H), 0.80 (d, J=6.3 Hz, 3H).

Example 8(3)

2-(2-((4-methyl-2-(naphthalen-1-yl)pentanoyl)amino)-4-mesyloxybenzyl)benzoic acid

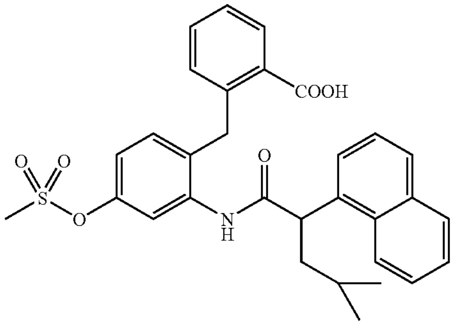

TLC: Rf 0.62 (hexane:ethyl acetate=1:2);

NMR (300 MHz, DMSO-$d_6$): δ 8.15 (s, 1H), 8.10-7.98 (m, 2H), 7.83 (m 1H), 7.67 (m, 1H), 7.60-7.41 (m, 3H), 7.32-7.20 (m, 3H), 7.17-6.96 (m, 3H), 6.81 (d, J=7.2 Hz, 1H), 4.37 (t, J=7.5 Hz, 1H), 4.08 (d, J=16.2 Hz, 1H), 3.80 (d, J=16.2 Hz, 1H), 3.18 (s, 3H), 2.14 (m, 1H), 1.73 (m, 1H), 1.59 (m, 1H), 0.96 (d, J=6.6 Hz, 3H), 0.89 (d, J=6.6 Hz, 3H).

Example 8(4)

2-(2-((4-methyl-2-(naphthalen-1-yl)pentanoyl)amino)-4-acetylaminobenzyl)benzoic acid

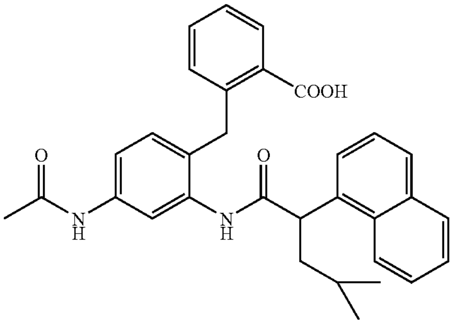

TLC: Rf 0.54 (chloroform:methanol=8:1);

NMR (300 MHz, DMSO-$d_6$): δ 9.85 (s, 1H), 9.67 (bs, 1H), 8.32 (d, J=8.4 Hz, 1H), 7.91 (d, J=7.8 Hz, 1H), 7.78 (d, J=8.1 Hz, 1H), 7.73 (m, 1H), 7.64-7.35 (m, 6H), 7.28-7.15 (m, 2H), 6.86 (d, J=8.4 Hz, 1H), 6.78 (m, 1H), 4.60 (m, 1H), 4.26 (d, J=16.5 Hz, 1H), 4.13 (d, J=16.5 Hz, 1H), 1.97 (s, 3H), 1.92 (m, 1H), 1.52-1.36 (m, 2H), 0.92 (d, J=6.3 Hz, 3H), 0.80 (d, J=6.3 Hz, 3H).

Example 8(5)

2-(2-((4-methyl-2-(naphthalen-1-yl)pentanoyl)amino)-4-mesylaminobenzyl)benzoic acid

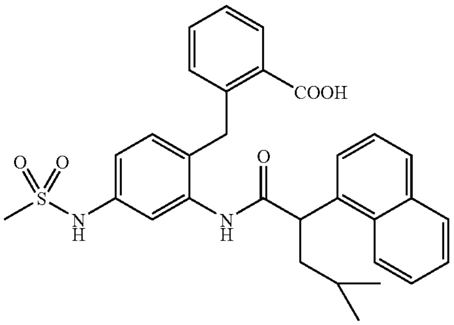

TLC: Rf 0.54 (chloroform:methanol=8:1);

NMR (300 MHz, $CDCl_3$): δ 8.05 (d, J=8.1 Hz, 1H), 7.97 (bs, 2H), 7.82 (d, J=7.5 Hz, 1H), 7.68 (d, J=7.5 Hz, 1H), 7.63 (d, J=7.8 Hz, 1H), 7.55-7.40 (m, 2H), 7.35-7.21 (m, 3H), 7.15 (m, 1H), 7.08-6.96 (m, 2H), 6.83 (d, J=8.1 Hz, 1H), 6.64 (s, 1H), 4.38 (t, J=7.2 Hz, 1H), 4.02 (d, J=16.5 Hz, 1H), 3.78 (d, J=16.5 Hz, 1H), 2.99 (s, 3H), 2.15 (m, 1H), 1.75 (m, 1H), 1.60 (m, 1H), 0.96 (d, J=6.6 Hz, 3H), 0.89 (d, J=6.6 Hz, 3H).

Example 8(6)

2-(2-((4-methyl-2-(naphthalen-1-yl)pentanoyl)amino)-4-(N-mesyl-N-methylamino)benzyl)benzoic acid

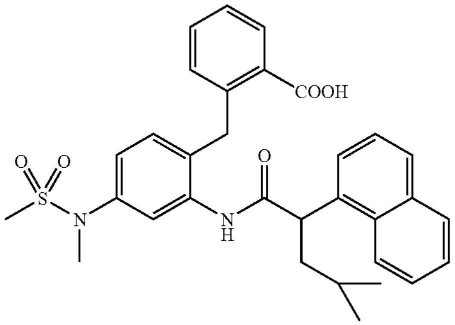

TLC: Rf 0.59 (chloroform:methanol=8:1);

NMR (300 MHz, $CDCl_3$): δ 8.20 (d, J=2.1 Hz, 1H), 8.07 (m, 1H), 8.04 (m, 1H), 7.84 (m, 1H), 7.69 (d, J=6.9 Hz, 1H), 7.59 (d, J=7.5 Hz, 1H), 7.55-7.44 (m, 2H), 7.34-7.23 (m, 3H), 7.18-7.10 (m, 2H), 7.05 (d, J=8.4 Hz, 1H), 6.87 (d, J=7.8 Hz, 1H), 4.38 (t, J=7.2 Hz, 1H), 4.06 (d, J=16.5 Hz, 1H), 3.80 (d, J=16.5 Hz, 1H), 3.32 (m, 3H), 2.89 (s, 3H), 2.15 (m, 1H), 1.76 (m, 1H), 1.61 (m, 1H), 0.97 (d, J=6.6 Hz, 3H), 0.91 (d, J=6.6 Hz, 3H).

Example 8(7)

2-(2-((4-methyl-2-(naphthalen-1-yl)pentanoyl)amino)-4-(pyrazol-1-ylmethyl)benzyl)benzoic acid

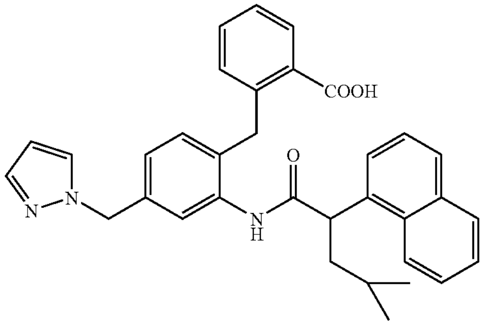

TLC: Rf 0.49 (chloroform:methanol=10:1);

NMR (300 MHz, $CDCl_3$): δ 8.05 (m, 1H), 7.99 (s, 1H), 7.91 (s, 1H), 7.80 (m, 1H), 7.66 (d, J=7.8 Hz, 1H), 7.58 (m, 2H), 7.49-7.38 (m, 3H), 7.34-7.07 (m, 4H), 6.82 (d, J=7.5 Hz, 1H), 6.77 (d, J=7.5 Hz, 1H), 6.63 (d, J=8.1 Hz, 1H), 6.29 (s, 1H), 5.23 (s, 2H), 4.33 (m, 1H), 3.86 (d, J=16.8 Hz, 1H), 3.69 (d, J=16.8 Hz, 1H), 2.12 (m, 1H), 1.69 (m, 1H), 1.56 (m, 1H), 0.93 (d, J=6.3 Hz, 3H), 0.86 (d, J=6.3 Hz, 3H).

Example 8(8)

2-(2-((4-methyl-2-(naphthalen-1-yl)pentanoyl)amino)-4-methoxymethylbenzyl)benzoic acid

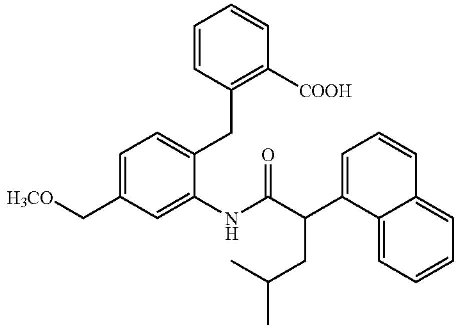

TLC: Rf 0.52 (chloroform:methanol=10:1);

NMR (300 MHz, $CDCl_3$): δ 8.08 (bs, 1H), 8.05 (d, J=7.8 Hz, 1H), 7.81 (m, 1H), 7.72 (m, 1H), 7.74-7.58 (m, 2H), 7.46 (m, 2H), 7.32-7.08 (m, 4H), 7.03 (m, 2H), 6.80 (d, J=7.8 Hz, 1H), 4.43 (s, 2H), 4.34 (t, J=7.5 Hz, 1H), 4.07 (d, J=16.5 Hz, 1H), 3.84 (d, J=16.5 Hz, 1H), 3.39 (s, 3H), 2.16 (m, 1H), 1.72 (m, 1H), 1.61 (m, 1H), 0.96 (d, J=6.3 Hz, 3H), 0.89 (d, J=6.3 Hz, 3H).

Example 8(9)

4-(2-((2-(naphthalen-1-yl)propanoyl)amino)-4-hydroxymethylphenyl)butanoic acid

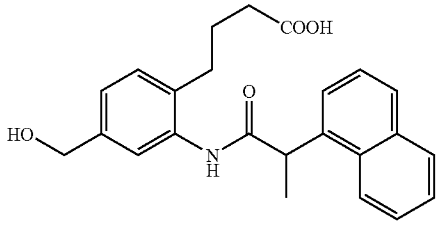

TLC: Rf 0.45 (ethyl acetate);

NMR (300 MHz, $CD_3OD$): δ 8.30-8.25 (m, 1H), 7.92-7.87 (m, 1H), 7.81 (t, J=8.1 Hz, 1H), 7.67-7.44 (m, 4H), 7.33 (s, 1H), 7.13-7.08 (m, 2H), 4.71 (q, J=7.2 Hz, 1H), 4.53 (s, 2H), 2.34-2.27 (m, 2H), 1.96 (t, J=7.2 Hz, 2H), 1.73 (d, J=7.2 Hz, 3H), 1.55-1.44 (m, 2H).

Example 8(10)

4-(2-((2-(naphthalen-1-yl)propanoyl)amino)-4-methoxymethylphenyl)butanoic acid

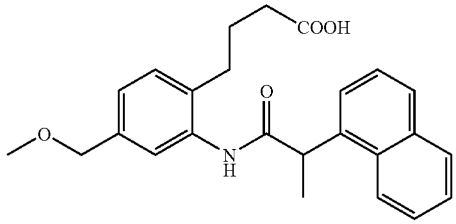

TLC: Rf 0.40 (hexane:ethyl acetate=1:2);

NMR (300 MHz, $CDCl_3$): δ 8.14 (d, J=7.5 Hz, 1H), 7.93-7.84 (m, 3H), 7.63 (d, J=6.6 Hz, 1H), 7.58-7.50 (m, 3H), 7.12 (s, 1H), 7.02-6.95 (m, 2H), 4.57 (q, J=6.9 Hz, 1H), 4.39 (s, 2H), 3.36 (s, 3H), 1.94-1.89 (m, 4H), 1.83 (d, J=6.9 Hz, 3H), 1.30-1.20 (m, 2H).

Example 8(11)

4-(2-((2-(naphthalen-1-yl)propanoyl)amino)-4-phenoxymethylphenyl)butanoic acid

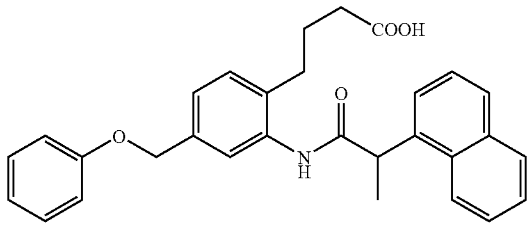

TLC: Rf 0.55 (hexane:ethyl acetate=1:2);

NMR (300 MHz, $CDCl_3$): δ 8.14 (d, J=8.1 Hz, 1H), 7.98 (s, 1H), 7.93-7.84 (m, 2H), 7.63 (d, J=6.6 Hz, 1H), 7.58-7.50 (m, 3H), 7.30-7.24 (m, 2H), 7.13-7.09 (m, 2H), 7.01-6.92 (m, 4H), 4.99 (s, 2H), 4.57 (q, J=7.2 Hz, 1H), 1.95-1.90 (m, 4H), 1.84 (d, J=7.2 Hz, 3H), 1.30-1.20 (m, 2H).

Example 8(12)

2-(2-((4-methyl-2-(naphthalen-1-yl)pentanoyl)amino)-4-mesylmethylbenzyl)benzoic acid

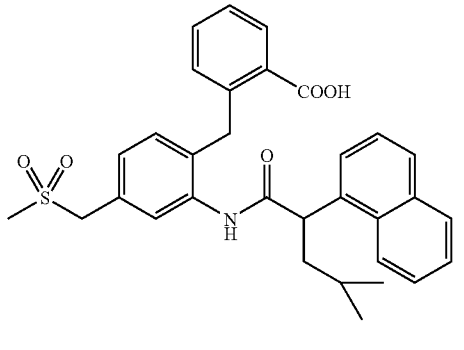

TLC: Rf 0.47 (chloroform:methanol=10:1);

NMR (300 MHz, DMSO-$d_6$): δ 9.72 (bs, 1H), 8.32 (m, 1H), 7.91 (d, J=7.8 Hz, 1H), 7.79-7.74 (m, 2H), 7.63-7.39 (m, 5H), 7.30-7.20 (m, 2H), 7.08 (dd, J=7.8, 1.8 Hz, 1H), 6.91 (d, J=7.8 Hz, 1H), 6.80 (m, 1H), 4.63 (dd, J=8.7, 4.8 Hz, 1H), 4.40 (s, 2H), 4.32 (d, J=16.2 Hz, 1H), 4.19 (d, J=16.2 Hz, 1H), 2.87 (s, 3H), 1.91 (m, 1H), 1.56-1.36 (m, 2H), 0.92 (d, J=6.3 Hz, 1H), 0.80 (d, J=6.3 Hz, 1H).

Example 8(13)

4-(2-((2-(naphthalen-1-yl)propanoyl)amino)-4-methylthiomethylphenyl)butanoic acid

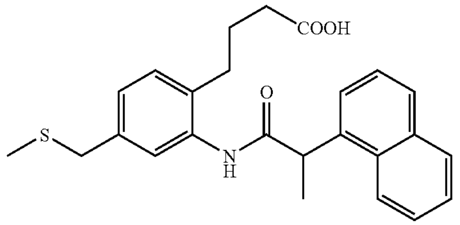

TLC: Rf 0.35 (hexane:ethyl acetate=1:1);

NMR (300 MHz, DMSO-$d_6$): δ 12.03 (s, 1H), 9.45 (s, 1H), 8.31 (d, J=8.1 Hz, 1H), 7.94 (dd, J=8.1, 1.5 Hz, 1H), 7.83 (d, J=8.1 Hz, 1H), 7.62-7.47 (m, 4H), 7.24 (d, J=1.8 Hz, 1H), 7.10 (d, J=7.8 Hz, 1H), 7.04 (dd, J=7.8, 1.8 Hz, 1H), 4.69 (q, J=6.9 Hz, 1H), 3.61 (s, 2H), 2.40 (m, 2H), 2.01 (t, J=7.5 Hz, 2H), 1.92 (s, 3H), 1.60 (d, J=6.9 Hz, 3H), 1.55 (m, 2H).

Example 8(14)

4-(2-((2-(naphthalen-1-yl)propanoyl)amino)-4-methylsulfinylmethylphenyl)butanoic acid

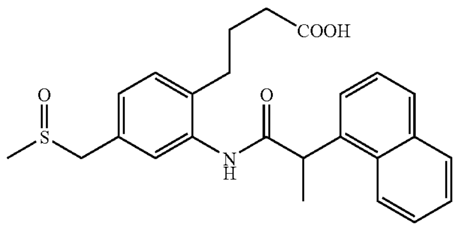

TLC: Rf 0.63 (chloroform:methanol=9:1);

NMR (300 MHz, DMSO-$d_6$): δ 12.03 (s, 1H), 9.52 (s, 1H), 8.31 (d, J=8.1 Hz, 1H), 7.94 (dd, J=8.1, 1.5 Hz, 1H), 7.83 (d, J=8.1 Hz, 1H), 7.63-7.47 (m, 4H), 7.26 (s, 1H), 7.16 (d, J=7.8 Hz, 1H), 7.05 (dd, J=7.8, 1.5 Hz, 1H), 4.70 (q, J=6.9 Hz, 1H), 4.05 (d, J=12.6 Hz, 1H), 3.85 (d, J=12.6 Hz, 1H), 2.45 (s, 3H), 2.42 (m, 2H), 2.02 (t, J=7.2 Hz, 2H), 1.60 (d, J=6.9 Hz, 3H), 1.55 (m, 2H).

Example 8(15)

4-(2-((2-(naphthalen-1-yl)propanoyl)amino)-4-mesylmethylphenyl)butanoic acid

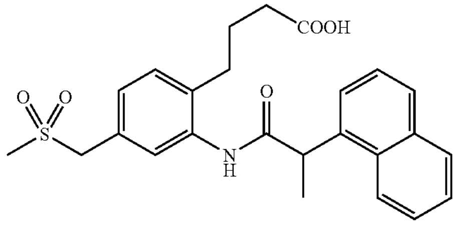

TLC: Rf 0.51 (ethyl acetate);

NMR (300 MHz, DMSO-$d_6$): δ 12.04 (s, 1H), 9.55 (s, 1H), 8.31 (d, J=8.1 Hz, 1H), 7.95 (m, 1H), 7.83 (d, J=8.1 Hz, 1H), 7.63-7.47 (m, 4H), 7.35 (d, J=1.2 Hz, 1H), 7.19 (d, J=7.8 Hz, 1H), 7.14 (dd, J=7.8, 1.2 Hz, 1H), 4.71 (q, J=6.9 Hz, 1H), 4.40 (s, 2H), 2.87 (s, 3H), 2.42 (m, 2H), 2.03 (t, J=7.2 Hz, 2H), 1.60 (d, J=6.9 Hz, 3H), 1.57 (m, 2H).

Example 8(16)

4-(2-((2-(naphthalen-1-yl)propanoyl)amino)-4-aminomethylphenyl)butanoic acid

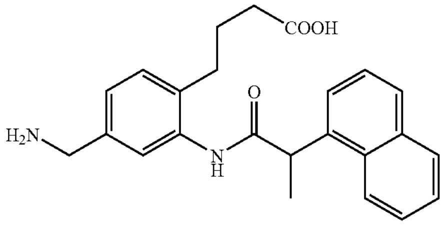

TLC: Rf 0.10 (chloroform:methanol=5:1);

NMR (300 MHz, DMSO-$d_6$): δ 8.39 (d, J=9.1 Hz, 1H), 7.93 (d, J=7.2 Hz, 1H), 7.82 (d, J=7.2 Hz, 1H), 7.63-7.47 (m, 4H), 7.45 (brs, 1H), 7.14 (s, 2H), 4.84 (q, J=6.9 Hz, 1H), 3.80 (s, 2H), 2.59-2.42 (m, 2H), 2.01 (t, J=7.2 Hz, 2H), 1.60 (d, J=6.9 Hz, 3H), 1.62-1.56 (m, 2H).

Example 8(17)

4-(2-((2-(naphthalen-1-yl)propanoyl)amino)-4-acetylaminomethylphenyl)butanoic acid

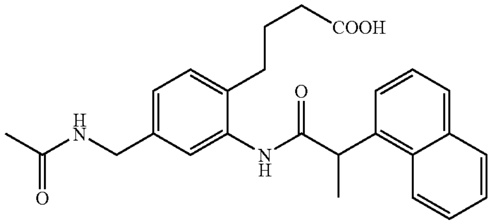

TLC: Rf 0.59 (chloroform:methanol=5:1);

NMR (300 MHz, DMSO-$d_6$): δ 9.46 (brs, 1H), 8.34-8.25 (m, 2H), 7.94 (d, J=8.1 Hz, 1H), 7.83 (d, J=7.8 Hz, 1H), 7.61-7.47 (m, 4H), 7.16 (brs, 1H), 7.09 (d, J=7.8 Hz, 1H), 6.98 (d, J=8.1 Hz, 1H), 4.68 (q, J=7.2 Hz, 1H), 4.15 (d, J=5.7 Hz, 2H), 2.44-2.35 (m, 2H), 2.00 (t, J=7.2 Hz, 2H), 1.82 (s, 3H), 1.59 (d, J=6.6 Hz, 3H), 1.56-1.48 (m, 2H).

Example 8(18)

4-(2-((2-(naphthalen-1-yl)propanoyl)amino)-4-mesylaminomethylphenyl)butanoic acid

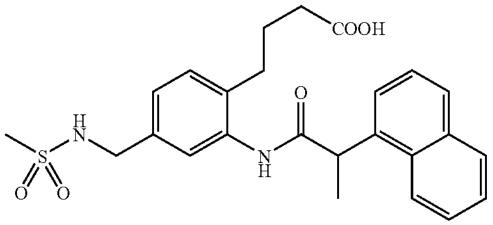

TLC: Rf 0.53 (chloroform:methanol=9:1);

NMR (300 MHz, $CDCl_3$): δ 9.51 (s, 1H), 8.32 (d, J=8.1 Hz, 1H), 7.95 (d, J=7.8 Hz, 1H), 7.83 (d, J=8.1 Hz, 1H), 7.62-7.48 (m, 5H), 7.28 (brs, 1H), 7.14 (d, J=7.5 Hz, 1H), 7.08 (dd, J=7.8, 1.5 Hz, 1H), 4.70 (q, J=7.2 Hz, 1H), 4.06 (d, J=6.3 Hz, 2H), 2.81 (s, 3H), 2.45-2.37 (m, 2H), 2.01 (t, J=7.5 Hz, 2H), 1.60 (d, J=6.9 Hz, 3H), 1.61-1.50 (m, 2H).

Example 8(19)

4-(2-((2-(naphthalen-1-yl)propanoyl)amino)-4-(N-mesyl-N-methylaminomethyl)phenyl)butanoic acid

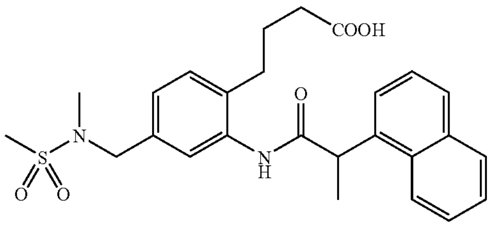

TLC: Rf 0.58 (chloroform:methanol=9:1);

NMR (300 MHz, $CDCl_3$): δ 8.13 (d, J=8.7 Hz, 1H), 7.93-7.85 (m, 3H), 7.63 (d, J=6.3 Hz, 1H), 7.59-7.49 (m, 3H), 7.17 (brs, 1H), 7.05 (dd, J=8.1, 1.5 Hz, 1H), 6.99 (d, J=8.1 Hz, 1H), 4.57 (q, J=7.5 Hz, 1H), 4.25 (s, 2H), 2.83 (s, 3H), 2.76 (s, 3H), 1.94-1.89 (m, 4H), 1.83 (d, J=6.9 Hz, 3H), 1.31-1.22 (m, 2H).

Example 8(20)

4-(2-((2-(naphthalen-1-yl)propanoyl)amino)-4-benzoylaminophenyl)butanoic acid

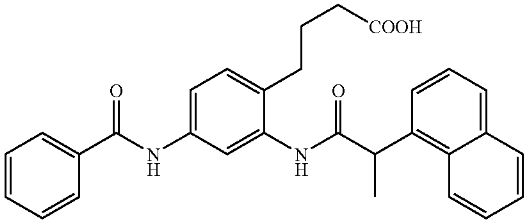

TLC: Rf 0.65 (ethyl acetate);

NMR (300 MHz, DMSO-$d_6$): δ 12.03 (s, 1H), 10.18 (s, 1H), 9.53 (s, 1H), 8.33 (d, J=8.7 Hz, 1H), 7.96-7.91 (m, 3H), 7.84 (d, J=8.1 Hz, 1H), 7.72 (d, J=2.4 Hz, 1H), 7.61-7.47 (m, 8H), 7.13 (d, J=8.4 Hz, 1H), 4.71 (q, J=7.2 Hz, 1H), 2.44-2.38 (m, 2H), 2.03 (t, J=7.5 Hz, 2H), 1.62-1.55 (m, 5H).

Example 8(21)

4-(2-((2-(naphthalen-1-yl)propanoyl)amino)-4-phenylsulfonylaminophenyl)butanoic acid

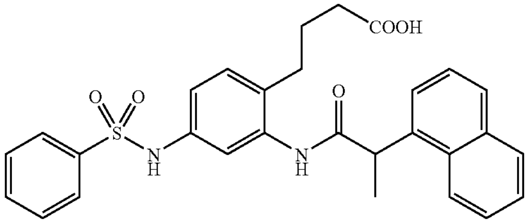

TLC: Rf 0.65 (ethyl acetate);

NMR (300 MHz, $CDCl_3$): δ 8.11-8.07 (m, 1H), 7.92-7.76 (m, 4H), 7.66 (s, 1H), 7.59-7.47 (m, 5H), 7.42-7.37 (m, 2H), 7.16 (s, 1H), 6.99 (s, 1H), 6.92 (dd, J=8.1, 2.1 Hz, 1H), 6.84 (d, J=8.4 Hz, 1H), 4.56 (q, J=7.2 Hz, 1H), 1.91-1.78 (m, 7H), 1.23-1.12 (m, 2H).

Example 8(22)

4-(2-((4-methyl-2-(naphthalen-1-yl)pentanoyl)amino)-4-phenoxymethylphenyl)butanoic acid

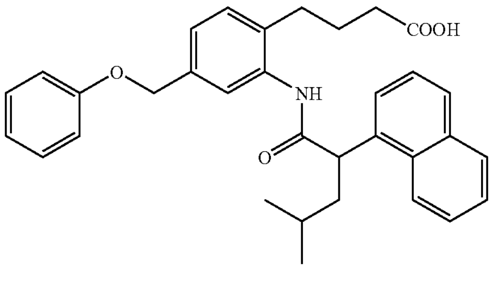

TLC: Rf 0.53 (chloroform:methanol=10:1);

NMR (300 MHz, DMSO-$d_6$): δ 9.57 (s, 1H), 8.39 (d, J=8.1 Hz, 1H), 7.93 (d, J=7.8 Hz, 1H), 7.81 (d, J=8.1 Hz, 1H), 7.66 (d, J=7.2 Hz, 1H), 7.63-7.44 (m, 3H), 7.33-7.13 (m, 5H), 6.98-6.87 (m, 3H), 5.00 (s, 2H), 4.67 (m, 1H), 2.45-2.33 (m, 2H), 2.12 (m, 1H), 1.98-1.89 (m, 2H), 1.66-1.43 (m, 4H), 1.05 (d, J=6.3 Hz, 3H), 0.91 (d, J=6.3 Hz, 3H).

Example 8(23)

4-(2-((2-(naphthalen-1-yl)propanoyl)amino)-4-(2-oxopyridin-1-ylmethyl)phenyl)butanoic acid

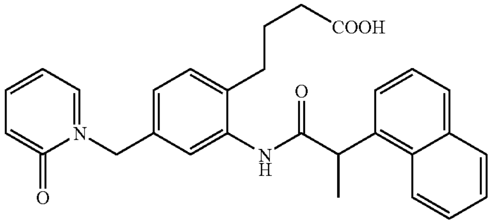

TLC: Rf 0.35 (ethyl acetate);

NMR (300 MHz, DMSO-$d_6$): δ 12.02 (s, 1H), 9.47 (s, 1H), 8.29 (d, J=8.1 Hz, 1H), 7.94 (d, J=7.8 Hz, 1H), 7.83 (d, J=7.8 Hz, 1H), 7.73 (dd, J=6.6, 2.1 Hz, 1H), 7.60-7.46 (m, 4H), 7.42-7.34 (m, 1H), 7.23 (d, J=1.8 Hz, 1H), 7.12 (d, J=8.1 Hz, 1H), 7.02 (dd, J=8.1, 1.8 Hz, 1H), 6.38 (d, J=9.0 Hz, 1H), 6.20 (dt, J=1.5, 6.6 Hz, 1H), 5.01 (s, 2H), 4.69-4.64 (m, 1H), 2.40-2.35 (m, 2H), 1.99 (t, J=7.5 Hz, 2H), 1.59-1.50 (m, 5H).

Example 8(24)

4-(2-((2-(naphthalen-1-yl)propanoyl)amino)-4-(pyridin-3-yloxymethyl)phenyl)butanoic acid

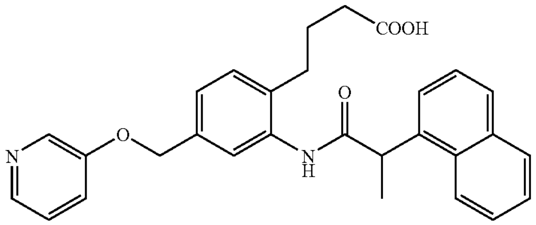

TLC: Rf 0.60 (ethyl acetate);

NMR (300 MHz, DMSO-$d_6$): δ 12.04 (s, 1H), 9.52 (s, 1H), 8.32-8.29 (m, 2H), 8.15 (d, J=4.5 Hz, 1H), 7.95 (dd, J=7.8, 1.5 Hz, 1H), 7.83 (d, J=8.1 Hz, 1H), 7.61-7.40 (m, 6H), 7.31 (dd, J=8.1, 4.5 Hz, 1H), 7.19 (s, 2H), 5.10 (s, 2H), 4.70 (q, J=7.2 Hz, 1H), 2.44-2.41 (m, 2H), 2.02 (t, J=7.2 Hz, 2H), 1.61-1.51 (m, 5H).

Example 8(25)

4-(2-((2-(naphthalen-1-yl)propanoyl)amino)-4-phenylthiomethylphenyl)butanoic acid

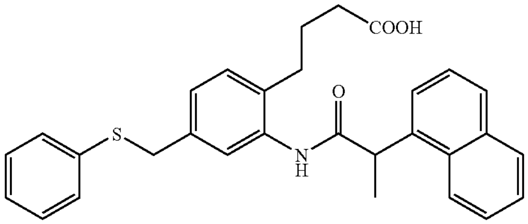

TLC: Rf 0.50 (hexane:ethyl acetate=1:2);

NMR (300 MHz, DMSO-$d_6$): δ 12.00 (br s, 1H), 9.46 (s, 1H), 8.30 (d, J=8.4 Hz, 1H), 7.95 (d, J=7.8 Hz, 1H), 7.83 (d, J=7.8 Hz, 1H), 7.61-7.47 (m, 4H), 7.32-7.23 (m, 5H), 7.17-7.12 (m, 1H), 7.08 (s, 2H), 4.68 (q, J=6.9 Hz, 1H), 4.17 (s, 2H), 2.41-2.36 (m, 2H), 2.00 (t, J=7.5 Hz, 2H), 1.59 (d, J=6.9 Hz, 3H), 1.56-1.51 (m, 2H).

Example 8(26)

4-(2-((2-(naphthalen-1-yl)propanoyl)amino)-4-phenylaminomethylphenyl)butanoic acid

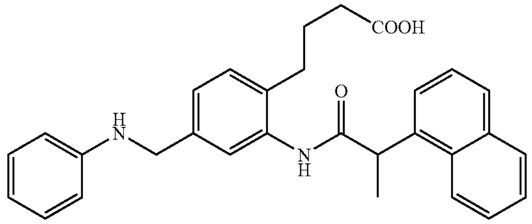

TLC: Rf 0.50 (hexane:ethyl acetate=1:2);

NMR (300 MHz, DMSO-$d_6$): δ 12.02 (s, 1H), 9.44 (s, 1H), 8.29 (d, J=7.8 Hz, 1H), 7.95-7.92 (m, 1H), 7.82 (d, J=7.8 Hz, 1H), 7.58-7.46 (m, 4H), 7.28 (s, 1H), 7.09 (s, 2H), 7.03-6.97 (m, 2H), 6.53-6.45 (m, 3H), 6.17 (t, J=6.0 Hz, 1H), 4.67 (q, J=7.2 Hz, 1H), 4.16 (d, J=6.0 Hz, 2H), 2.40-2.35 (m, 2H), 2.00 (t, J=7.5 Hz, 2H), 1.60-1.50 (m, 5H).

Example 8(27)

4-(2-((2-(naphthalen-1-yl)propanoyl)amino)-4-phenylsulfinylmethylphenyl)butanoic acid

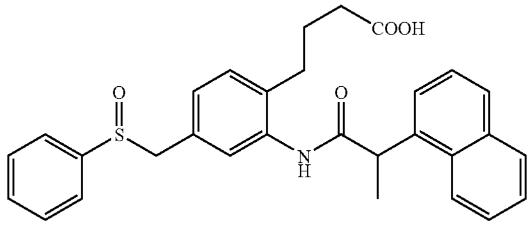

TLC: Rf 0.40 (ethyl acetate);

NMR (300 MHz, DMSO-$d_6$): δ 12.03 (s, 1H), 9.50 (s, 1H), 8.31 (d, J=8.4 Hz, 1H), 7.97-7.94 (m, 1H), 7.84 (d, J=7.8 Hz, 1H), 7.60-7.46 (m, 9H), 7.14-7.13 (m, 1H), 7.06 (d, J=7.8 Hz, 1H), 6.86-6.83 (m, 1H), 4.69 (q, J=6.9 Hz, 1H), 4.20-4.15 (m, 1H), 3.98-3.92 (m, 1H), 2.43-2.39 (m, 2H), 2.03-1.98 (m, 2H), 1.60-1.52 (m, 5H).

Example 8(28)

4-(2-((2-(naphthalen-1-yl)propanoyl)amino)-4-phenylsulfonylmethylphenyl)butanoic acid

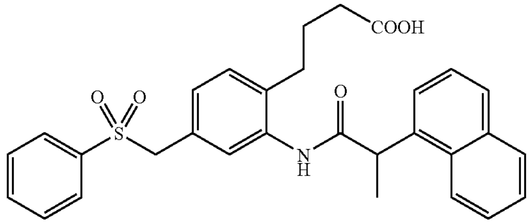

TLC: Rf 0.60 (ethyl acetate);

NMR (300 MHz, DMSO-$d_6$): δ 12.03 (s, 1H), 9.50 (s, 1H), 8.30 (d, J=8.4 Hz, 1H), 7.95 (d, J=7.8 Hz, 1H), 7.84 (d, J=7.5 Hz, 1H), 7.73-7.48 (m, 9H), 7.15 (s, 1H), 7.07 (d, J=8.1 Hz, 1H), 6.88 (dd, J=7.8, 1.5 Hz, 1H), 4.68 (q, J=7.2 Hz, 1H), 4.58 (s, 2H), 2.42-2.38 (m, 2H), 1.99 (t, J=7.5 Hz, 2H), 1.60-1.51 (m, 5H).

Example 8(29)

4-(2-((2-(naphthalen-1-yl)propanoyl)amino)-4-benzyloxyphenyl)butanoic acid

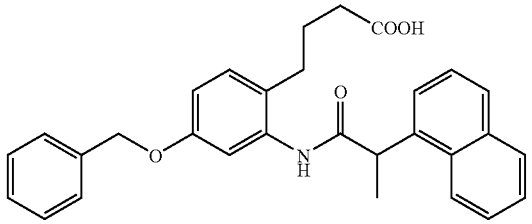

TLC: Rf 0.13 (hexane:ethyl acetate=2:1);

NMR (300 MHz, DMSO-$d_6$): δ 9.39 (brs, 1H), 8.29 (d, J=8.7 Hz, 1H), 7.94 (d, J=7.8 Hz, 1H), 7.83 (d, J=7.5 Hz, 1H), 7.62-7.46 (m, 4H), 7.43-7.28 (m, 5H), 7.06-7.03 (m, 2H), 6.77 (dd, J=8.4, 2.4 Hz, 1H), 5.01 (s, 2H), 4.70 (q, J=7.2 Hz, 1H), 2.36 (m, 2H), 2.01 (t, J=7.2 Hz, 2H), 1.59 (d, J=7.2 Hz, 3H), 1.56-1.45 (m, 2H).

Example 8(30)

4-(2-((2-(naphthalen-1-yl)propanoyl)amino)-4-phenoxyphenyl)butanoic acid

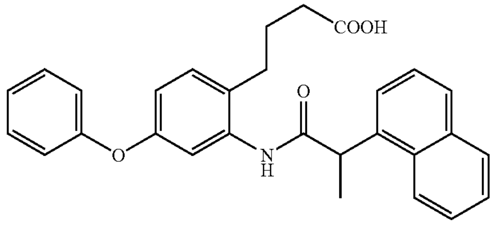

TLC: Rf 0.15 (hexane:ethyl acetate=2:1);

NMR (300 MHz, DMSO-$d_6$): δ 9.44 (brs, 1H), 8.26 (brd, J=8.1 Hz, 1H), 7.93 (m, 1H), 7.82 (brd, J=7.5 Hz, 1H), 7.59-7.45 (m, 4H), 7.40-7.32 (m, 2H), 7.15 (d, J=8.4 Hz, 1H), 7.13-7.08 (m, 2H), 6.98-6.95 (m, 2H), 6.76 (dd, J=8.4, 2.7 Hz, 1H), 4.69 (q, J=6.9 Hz, 1H), 2.45-2.40 (m, 2H), 2.04 (t, J=7.5 Hz, 2H), 1.60-1.52 (m, 2H), 1.57 (d, J=6.9 Hz, 3H).

Example 8(31)

3-(2-((4-methyl-2-(naphthalen-1-yl)pentanoyl)amino)-4-phenoxymethylphenyl)propanoic acid

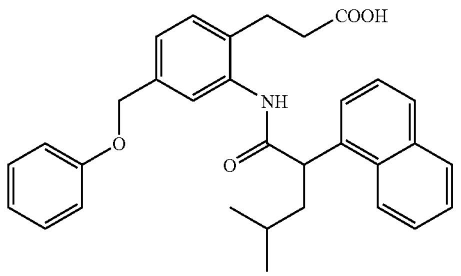

TLC: Rf 0.54 (chloroform:methanol=10:1);

NMR (300 MHz, $CDCl_3$): δ 8.20 (d, J=8.4 Hz, 1H), 7.88-7.70 (m, 4H), 7.63 (d, J=6.9 Hz, 1H), 7.56-7.40 (m, 3H), 7.30-7.20 (m, 2H), 7.13 (m, 1H), 7.03 (d, J=7.5 Hz, 1H), 6.97-6.87 (m, 3H), 4.96 (s, 2H), 4.49 (t, J=7.4 Hz, 1H), 2.41-2.14 (m, 5H), 2.01 (m, 1H), 1.70 (m, 1H), 1.00 (d, J=6.6 Hz, 3H), 0.97 (d, J=6.6 Hz, 3H).

Example 8(32)

4-(2-((4-methyl-2-(naphthalen-1-yl)pentanoyl)amino)-4-(pyrazol-1-ylmethyl)phenyl)butanoic acid

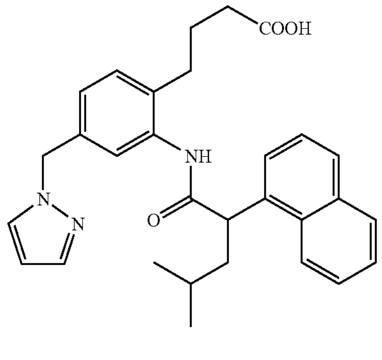

TLC: Rf 0.36 (chloroform:methanol=10:1);

NMR (300 MHz, $CDCl_3$): δ 8.21 (d, J=7.2 Hz, 1H), 7.90 (m, 2H), 7.82 (d, J=7.8 Hz, 1H), 7.64 (d, J=7.2 Hz, 1H), 7.58-7.40 (m, 5H), 6.92 (d, J=8.1 Hz, 1H), 6.78 (d, J=7.8 Hz, 1H), 6.26 (t, J=2.1 Hz, 1H), 5.25 (s, 2H), 4.55 (t, J=7.2 Hz, 1H), 2.30 (m, 2H), 2.05-1.80 (m, 3H), 1.68 (m, 2H), 1.28 (m, 2H), 1.01 (d, J=6.6 Hz, 3H), 0.96 (d, J=6.6 Hz, 3H).

Example 8(33)

4-(2-((2-(naphthalen-1-yl)propanoyl)amino)-4-phenylphenyl)butanoic acid

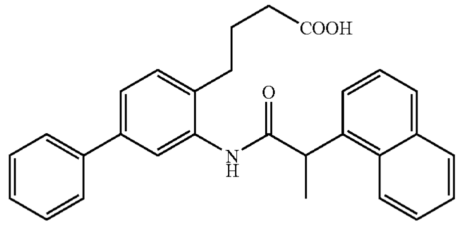

TLC: Rf 0.29 (hexane:ethyl acetate=1:1);

NMR (300 MHz, DMSO-$d_6$): δ 12.05 (s, 1H), 9.54 (s, 1H), 8.33 (d, J=8.1 Hz, 1H), 7.95 (m, 1H), 7.84 (d, J=8.1 Hz, 1H), 7.64-7.37 (m, 10H), 7.33 (m, 1H), 7.25 (d, J=8.1 Hz, 1H), 4.73 (q, J=6.9 Hz, 1H), 2.45 (m, 2H), 2.05 (t, J=7.2 Hz, 2H), 1.62 (d, J=6.9 Hz, 3H), 1.60 (m, 2H).

Example 8(34)

4-(2-((2-(naphthalen-1-yl)propanoyl)amino)-4-benzoylaminomethylphenyl)butanoic acid

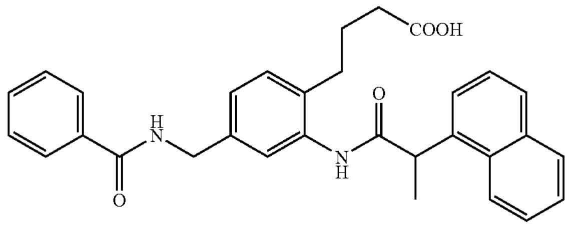

TLC: Rf 0.60 (ethyl acetate);

NMR (300 MHz, DMSO-$d_6$): δ 11.94 (br s, 1H), 9.51 (s, 1H), 9.00 (t, J=6.9 Hz, 1H), 8.29 (d, J=7.2 Hz, 1H), 7.95-7.80 (m, 4H), 7.57-7.44 (m, 7H), 7.24 (s, 1H), 7.12-7.05 (m, 2H), 4.68 (q, J=6.9 Hz, 1H), 4.39 (d, J=6.9 Hz, 2H), 2.42-2.37 (m, 2H), 2.00 (t, J=7.2 Hz, 2H), 1.59-1.50 (m, 5H).

Example 8(35)

4-(2-((2-(naphthalen-1-yl)propanoyl)amino)-4-(pyridin-4-yloxymethyl)phenyl)butanoic acid

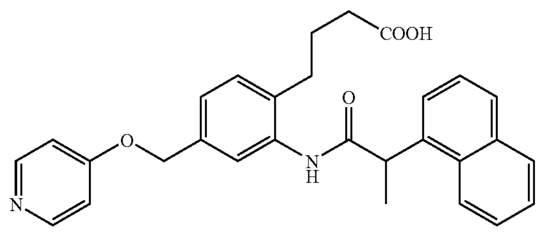

TLC: Rf 0.50 (ethyl acetate:methanol=9:1);

NMR (300 MHz, DMSO-$d_6$): δ 12.03 (br s, 1H), 9.54 (s, 1H), 8.52 (d, J=6.9 Hz, 2H), 8.31 (d, J=7.8 Hz, 1H), 7.94 (dd, J=7.8, 1.5 Hz, 1H), 7.83 (d, J=7.8 Hz, 1H), 7.61-7.47 (m, 4H), 7.43 (s, 1H), 7.25-7.22 (m, 4H), 5.22 (s, 2H), 4.71 (q, J=7.2 Hz, 1H), 2.46-2.44 (m, 2H), 2.03 (t, J=7.2 Hz, 2H), 1.69-1.51 (m, 5H).

Example 8(36)

4-(2-((2-(naphthalen-1-yl)propanoyl)amino)-4-(2-phenoxyethyl)phenyl)butanoic acid

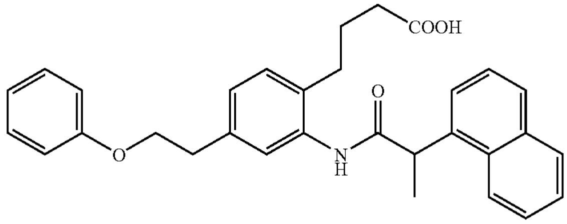

TLC: Rf 0.22 (hexane:ethyl acetate=1:1);

NMR (300 MHz, $CD_3OD$): δ 8.28 (brd, J=8.7 Hz, 1H), 7.91 (brd, J=8.1 Hz, 1H), 7.82 (brd, J=8.4 Hz, 1H), 7.65 (brd, J=6.6 Hz, 1H), 7.60-7.47 (m, 4H), 7.29 (brs, 1H), 7.22 (brt, J=8.7 Hz, 2H), 7.09 (brs, 2H), 6.90-6.85 (m, 3H), 4.72 (q, J=7.2 Hz, 1H), 4.13 (t, J=6.9 Hz, 2H), 3.02-2.97 (m, 2H), 2.33-2.28 (m, 2H), 1.96-1.94 (m, 2H), 1.73 (d, J=7.2 Hz, 3H), 1.53-1.48 (m, 2H).

Example 8(37)

4-(2-((2-(naphthalen-1-yl)propanoyl)amino)-4-(pyridin-2-yloxymethyl)phenyl)butanoic acid

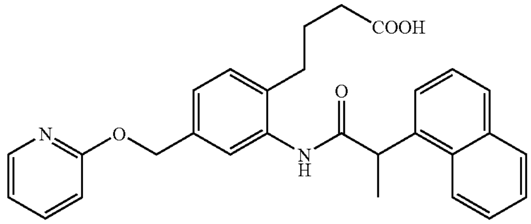

TLC: Rf 0.35 (hexane:ethyl acetate=1:2);

NMR (300 MHz, DMSO-$d_6$): δ 12.04 (s, 1H), 9.50 (s, 1H), 8.30 (d, J=8.7 Hz, 1H), 8.15 (dd, J=5.4, 1.5 Hz, 1H), 7.95 (d, J=7.8 Hz, 1H), 7.83 (d, J=7.8 Hz, 1H), 7.7-7.67 (m, 1H), 7.61-7.47 (m, 4H), 7.36 (s, 1H), 7.21-7.14 (m, 2H), 6.99-6.95 (m, 1H), 6.83 (d, J=8.4 Hz, 1H), 5.26 (s, 2H), 4.69 (q, J=7.2 Hz, 1H), 2.44-2.39 (m, 2H), 2.02 (t, J=7.8 Hz, 2H), 1.61-1.53 (m, 5H).

Example 8(38)

4-(2-((2-(naphthalen-1-yl)propanoyl)amino)-4-(N-methyl-N-phenylaminomethyl)phenyl)butanoic acid

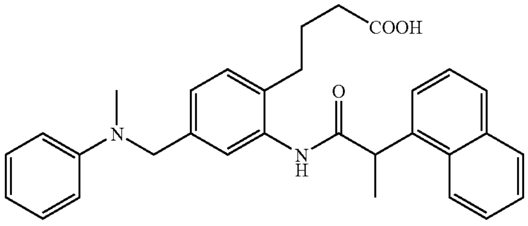

TLC: Rf 0.50 (hexane:ethyl acetate=1:2);

NMR (300 MHz, DMSO-$d_6$): δ 12.02 (s, 1H), 9.43 (s, 1H), 8.28 (d, J=7.5 Hz, 1H), 7.95-7.92 (m, 1H), 7.82 (d, J=8.1 Hz, 1H), 7.56-7.45 (m, 4H), 7.18-7.07 (m, 4H), 6.93 (dd, J=7.8, 1.5 Hz, 1H), 6.67 (d, J=8.1 Hz, 2H), 6.59 (t, J=7.2 Hz, 1H), 4.66 (q, J=7.2 Hz, 1H), 4.47 (s, 2H), 2.95 (s, 3H), 2.40-2.34 (m, 2H), 2.00 (t, J=7.5 Hz, 2H), 1.58-1.51 (m, 5H).

Example 8(39)

4-(2-((2-(naphthalen-1-yl)propanoyl)amino)-4-(N-benzoyl-N-methylamino)phenyl)butanoic acid

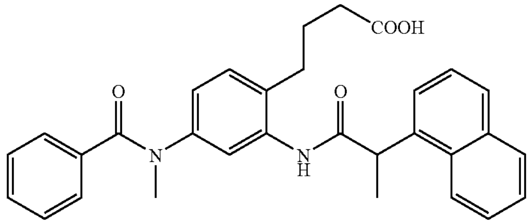

TLC: Rf 0.35 (hexane:ethyl acetate=1:2);

NMR (300 MHz, $CDCl_3$): δ 8.12 (m, 1H), 7.95-7.82 (m, 3H), 7.63-7.48 (m, 4H), 7.33-7.10 (m, 6H), 6.73 (d, J=7.8 Hz, 1H), 6.52 (m, 1H), 4.57 (q, J=7.2 Hz, 1H), 3.45 (s, 3H), 1.95-1.75 (m, 4H), 1.81 (d, J=7.2 Hz, 3H), 1.20 (m, 2H).

Example 8(40)

3-(2-((4-methyl-2-phenylpentanoyl)amino)-4-phenoxyphenyl)propanoic acid

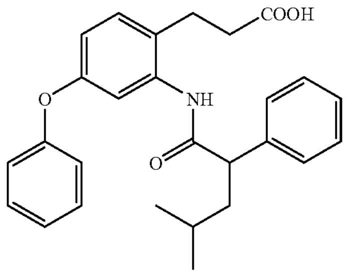

TLC: Rf 0.71 (chloroform:methanol=10:1);

NMR (300 MHz, $CDCl_3$): δ 8.16 (s, 1H), 7.51 (d, J=2.1 Hz, 1H), 7.44-7.20 (m, 7H), 7.12-6.93 (m, 4H), 6.70 (dd, J=8.4, 2.7 Hz, 1H), 3.67 (t, J=7.8 Hz, 1H), 2.65-2.45 (m, 4H), 2.09 (m, 1H), 1.79 (m, 1H), 1.52 (m, 1H), 0.93 (d, J=6.6 Hz, 3H), 0.92 (d, J=6.6 Hz, 3H).

Example 8(41)

4-(2-((2-(4-fluoronaphthalen-1-yl)propanoyl)amino)-4-phenoxymethylphenyl)butanoic acid

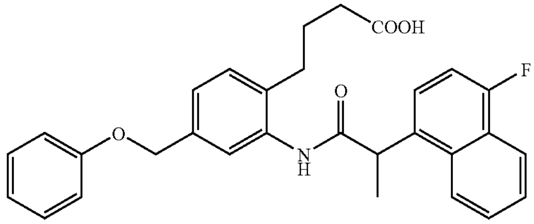

TLC: Rf 0.55 (chloroform:methanol=9:1);

NMR (300 MHz, DMSO-$d_6$): δ 9.57 (brs, 1H), 8.36 (d, J=7.2 Hz, 1H), 8.09 (m, 1H), 7.72-7.62 (m, 2H), 7.55 (dd, J=7.8, 5.4 Hz, 1H), 7.38-7.23 (m, 4H), 7.18 (brs, 2H), 7.09-6.89 (m, 3H), 5.01 (s, 2H), 4.66 (q, J=6.6 Hz, 1H), 2.48-2.40 (m, 2H), 2.04-1.99 (m, 2H), 1.59 (d, J=6.6 Hz, 3H), 1.58-1.53 (m, 2H).

Example 8(42)

4-(2-((2-phenylpropanoyl)amino)-4-phenoxymethylphenyl)butanoic acid

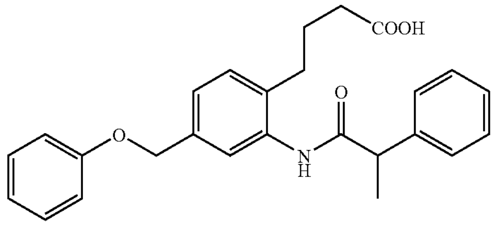

TLC: Rf 0.56 (chloroform:methanol=9:1);

NMR (300 MHz, DMSO-$d_6$): δ 9.41 (brs, 1H), 7.41-7.39 (m, 3H), 7.34-7.23 (m, 5H), 7.20-7.15 (m, 2H), 6.99-6.96 (m, 2H), 6.92 (m, 1H), 5.01 (s, 2H), 3.90 (q, J=7.2 Hz, 1H), 2.43-2.38 (m, 2H), 2.04 (t, J=7.2 Hz, 2H), 1.56-1.48 (m, 2H), 1.41 (d, J=7.2 Hz, 3H).

Example 8(43)

3-(2-((4-methyl-2-phenylpentanoyl)amino)-4-phenoxymethylphenyl)propanoic acid

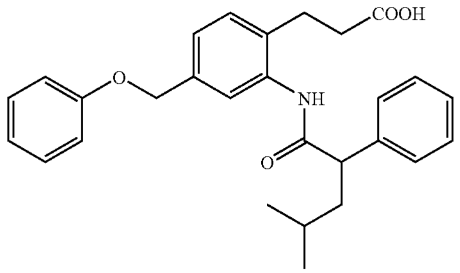

TLC: Rf 0.42 (hexane:ethyl acetate=1:1);

NMR (300 MHz, $CDCl_3$): δ 8.20 (s, 1H), 7.81 (s, 1H), 7.45-7.09 (m, 9H), 6.98-6.90 (m, 3H), 4.98 (s, 2H), 3.69 (t, J=7.7 Hz, 1H), 2.67-2.53 (m, 4H), 2.14 (m, 1H), 1.80 (m, 1H), 1.55 (m, 1H), 0.95 (d, J=6.6 Hz, 3H), 0.94 (d, J=6.6 Hz, 3H).

Example 8(44)

3-(2-((2-phenylpentanoyl)amino)-4-phenoxymethylphenyl)propanoic acid

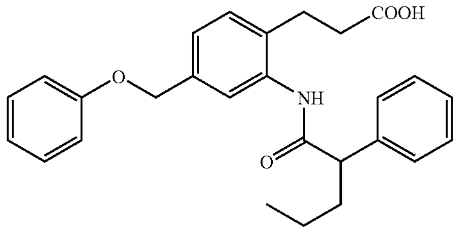

TLC: Rf 0.46 (chloroform:methanol=10:1);

NMR (300 MHz, $CDCl_3$): δ 8.23 (s, 1H), 7.83 (s, 1H), 7.45-7.10 (m, 9H), 6.99-6.90 (m, 3H), 4.99 (s, 2H), 3.60 (t, J=7.5 Hz, 1H), 2.70-2.54 (m, 4H), 2.25 (m, 1H), 1.87 (m, 1H), 1.58-1.24 (m, 2H), 0.95 (t, J=7.5 Hz, 3H).

Example 8(45)

3-(2-((2-phenylpropanoyl)amino)-4-phenoxymethylphenyl)propanoic acid

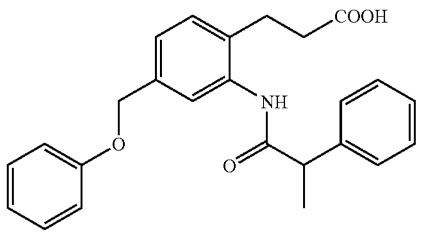

TLC: Rf 0.41 (chloroform:methanol=9:1);

NMR (300 MHz, $CDCl_3$): δ 8.11 (brs, 1H), 7.85 (s, 1H), 7.46-7.24 (m, 7H), 7.22-7.10 (m, 2H), 6.98-6.90 (m, 3H), 5.00 (s, 2H), 3.81 (q, J=6.9 Hz, 1H), 2.65-2.50 (m, 4H), 1.64 (d, J=6.9 Hz, 3H).

Example 8(46)

3-(2-((2-phenylbutanoyl)amino)-4-phenoxymethylphenyl)propanoic acid

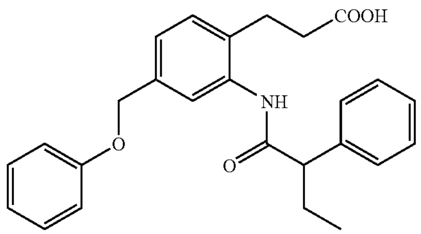

TLC: Rf 0.37 (chloroform:methanol=9:1);

NMR (300 MHz, $CDCl_3$): δ 8.27 (brs, 1H), 7.83 (s, 1H), 7.46-7.23 (m, 7H), 7.23-7.10 (m, 2H), 7.00-6.90 (m, 3H), 4.99 (s, 2H), 3.49 (t, J=7.5 Hz, 1H), 2.70-2.54 (m, 4H), 2.40-2.22 (m, 1H), 2.00-1.82 (m, 1H), 0.97 (t, J=7.5 Hz, 3H).

Example 8(47)

4-(2-((4-methyl-2-(naphthalen-1-yl)pentanoyl) amino)-4-phenoxyphenyl)butanoic acid

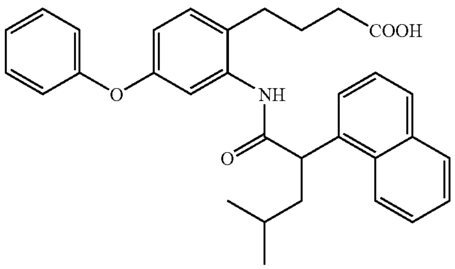

TLC: Rf 0.43 (chloroform:methanol=10:1);

NMR (300 MHz, DMSO-$d_6$): δ 9.50 (s, 1H), 8.37 (d, J=8.4 Hz, 1H), 7.93 (d, J=8.1 Hz, 1H), 7.80 (d, J=8.1 Hz, 1H), 7.64-7.31 (m, 6H), 7.17-6.92 (m, 5H), 6.76 (dd, J=8.1, 2.4 Hz, 1H), 4.68 (m, 1H), 2.46-2.32 (m, 2H), 2.08 (m, 1H), 1.96 (t, J=7.2 Hz, 2H), 1.68-1.41 (m, 4H), 1.02 (d, J=6.3 Hz, 3H), 0.89 (d, J=6.3 Hz, 3H).

Example 8(48)

4-(2-((4-methyl-2-phenylpentanoyl)amino)-4-phenoxyphenyl)butanoic acid

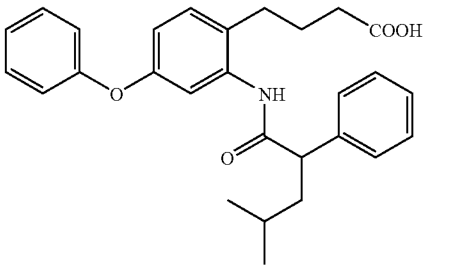

TLC: Rf 0.43 (chloroform:methanol=10:1);

NMR (300 MHz, DMSO-$d_6$): δ 9.40 (s, 1H), 7.40-7.04 (m, 10H), 6.98-6.62 (m, 2H), 6.74 (dd, J=8.4, 2.7 Hz, 1H), 3.88 (m, 1H), 2.42 (t, J=7.8 Hz, 2H), 2.07 (t, J=7.2 Hz, 2H), 1.94 (m, 1H), 1.60-1.35 (m, 4H), 0.91 (d, J=6.3 Hz, 3H), 0.87 (d, J=6.3 Hz, 3H).

Example 8(49)

4-(2-((2-phenylpropanoyl)amino)-4-phenylaminomethylphenyl)butanoic acid

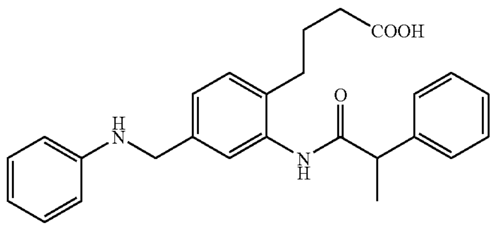

TLC: Rf 0.53 (hexane:ethyl acetate=1:3);

NMR (300 MHz, DMSO-$d_6$): δ 12.02 (brs, 1H), 9.34 (s, 1H), 7.42-7.18 (m, 6H), 7.09 (m, 2H), 7.00 (m, 2H), 6.56-6.44 (m, 3H), 6.17 (t, J=5.7 Hz, 1H), 4.16 (d, J=5.7 Hz, 2H), 3.87 (q, J=6.9 Hz, 1H), 2.35 (m, 2H), 2.01 (t, J=7.2 Hz, 2H), 1.50 (m, 2H), 1.40 (d, J=6.9 Hz, 3H).

Example 8(50)

4-(2-((2-phenylpropanoyl)amino)-4-benzoylaminomethylphenyl)butanoic acid

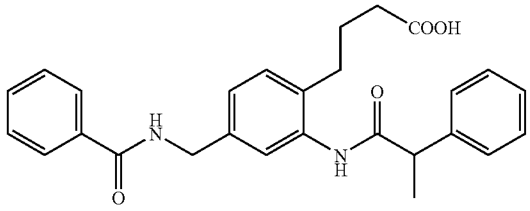

TLC: Rf 0.27 (hexane:ethyl acetate=1:3);

NMR (300 MHz, DMSO-$d_6$): δ 12.02 (brs, 1H), 9.36 (s, 1H), 9.01 (t, J=6.0 Hz, 1H), 7.90-7.84 (m, 2H), 7.56-7.36 (m, 5H), 7.34-7.18 (m, 4H), 7.13-7.03 (m, 2H), 4.40 (d, J=6.0 Hz, 2H), 3.87 (q, J=7.2 Hz, 1H), 2.36 (m, 2H), 2.01 (t, J=7.5 Hz, 2H), 1.50 (m, 2H), 1.40 (d, J=7.2 Hz, 3H).

Example 8(51)

4-(2-((2-(4-fluoronaphthalen-1-yl)propanoyl)amino)-4-benzoylaminomethylphenyl)butanoic acid

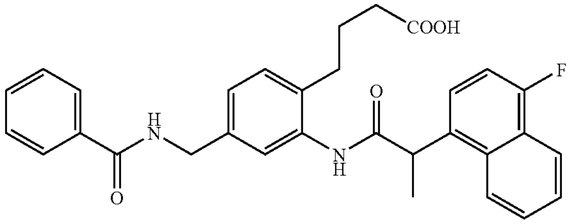

TLC: Rf 0.51 (chloroform:methanol=9:1);

NMR (300 MHz, DMSO-$d_6$): δ 9.52 (brs, 1H), 9.01 (m, 1H), 8.34 (m, 1H), 8.08 (m, 1H), 7.88-7.84 (m, 2H), 7.68-7.61

(m, 2H), 7.56-7.44 (m, 4H), 7.28 (dd, J=10.8, 7.8 Hz, 1H), 7.21 (brs, 1H), 7.13-7.06 (m, 2H), 4.63 (q, J=6.9 Hz, 1H), 4.39 (d, J=5.7 Hz, 2H), 2.43-2.38 (m, 2H), 2.04-1.93 (m, 2H), 1.57 (d, J=6.9 Hz, 3H), 1.53-1.49 (m, 2H).

Example 8(52)

4-(2-((2-(naphthalen-1-yl)propanoyl)amino)-4-phenylsulfonylaminomethylphenyl)butanoic acid

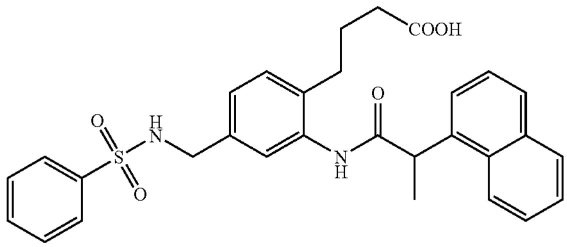

TLC: Rf 0.31 (hexane:ethyl acetate=1:3);

NMR (300 MHz, DMSO-$d_6$): δ 12.03 (s, 1H), 9.45 (s, 1H), 8.31 (d, J=8.1 Hz, 1H), 8.11 (t, J=6.3 Hz, 1H), 7.95 (m, 1H), 7.84 (d, J=8.1 Hz, 1H), 7.80-7.74 (m, 2H), 7.63-7.47 (m, 7H), 7.20 (d, J=1.5 Hz, 1H), 7.05 (d, J=7.8 Hz, 1H), 6.95 (dd, J=7.8, 1.5 Hz, 1H), 4.69 (q, J=6.9 Hz, 1H), 3.89 (d, J=6.3 Hz, 2H), 2.37 (m, 2H), 1.99 (t, J=7.5 Hz, 2H), 1.60 (d, J=6.9 Hz, 3H), 1.52 (m, 2H).

Example 8(53)

4-(2-((2-(naphthalen-1-yl)propanoyl)amino)-4-benzylcarbamoylphenyl)butanoic acid

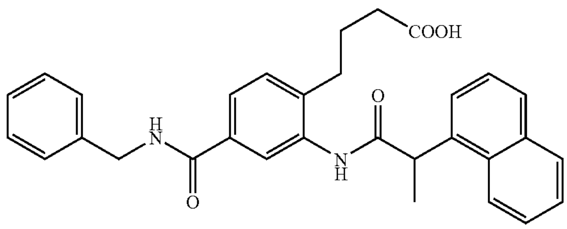

TLC: Rf 0.21 (ethyl acetate);

NMR (300 MHz, DMSO-$d_6$): δ 12.06 (s, 1H), 9.62 (s, 1H), 8.99 (t, J=6.0 Hz, 1H), 8.32 (d, J=8.1 Hz, 1H), 7.95 (m, 1H), 7.84 (d, J=8.1 Hz, 1H), 7.79 (d, J=1.8 Hz, 1H), 7.67 (dd, J=7.8, 1.8 Hz, 1H), 7.63-7.47 (m, 4H), 7.35-7.18 (m, 6H), 4.71 (q, J=6.9 Hz, 1H), 4.44 (d, J=6.0 Hz, 2H), 2.46 (m, 2H), 2.02 (t, J=7.5 Hz, 2H), 1.61 (d, J=6.9 Hz, 3H), 1.57 (m, 2H).

Example 8(54)

4-(2-((2-(naphthalen-1-yl)propanoyl)amino)-4-phenylcarbamoylphenyl)butanoic acid

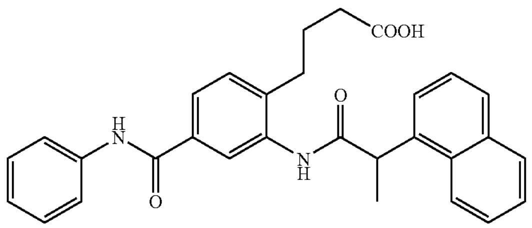

TLC: Rf 0.32 (ethyl acetate);

NMR (300 MHz, DMSO-$d_6$): δ 12.07 (s, 1H), 10.19 (s, 1H), 9.66 (s, 1H), 8.33 (d, J=8.1 Hz, 1H), 7.96 (d, J=8.1 Hz, 1H), 7.88-7.82 (m, 2H), 7.77-7.70 (m, 3H), 7.64-7.48 (m, 4H), 7.37-7.28 (m, 3H), 7.08 (m, 1H), 4.73 (q, J=6.9 Hz, 1H), 2.50 (m, 2H), 2.04 (t, J=7.5 Hz, 2H), 1.62 (d, J=6.9 Hz, 3H), 1.59 (m, 2H).

Example 8(55)

4-(2-((2-(naphthalen-1-yl)propanoyl)amino)-4-benzyloxymethylphenyl)butanoic acid

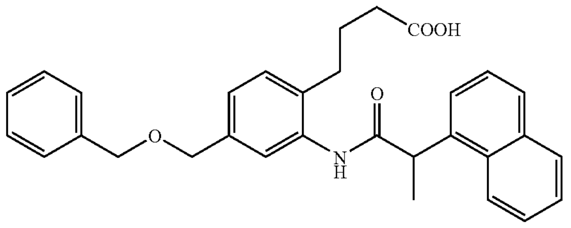

TLC: Rf 0.29 (hexane:ethyl acetate=1:2);

NMR (300 MHz, DMSO-$d_6$): δ 12.04 (s, 1H), 9.49 (s, 1H), 8.31 (d, J=8.1 Hz, 1H), 7.95 (m, 1H), 7.83 (d, J=8.1 Hz, 1H), 7.62-7.46 (m, 4H), 7.38-7.24 (m, 6H), 7.17-7.06 (m, 2H), 4.69 (q, J=6.9 Hz, 1H), 4.49 (s, 2H), 4.45 (s, 2H), 2.43 (m, 2H), 2.02 (t, J=7.5 Hz, 2H), 1.60 (d, J=6.9 Hz, 3H), 1.56 (m, 2H).

Example 8(56)

4-(2-((2-(naphthalen-1-yl)propanoyl)amino)-4-benzylaminomethylphenyl)butanoic acid

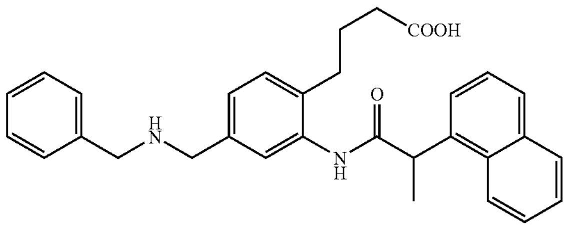

TLC: Rf 0.67 (chloroform:methanol=4:1);

NMR (300 MHz, DMSO-$d_6$): δ 9.54 (s, 1H), 8.32 (d, J=8.1 Hz, 1H), 7.95 (m, 1H), 7.84 (d, J=8.1 Hz, 1H), 7.62-7.46 (m, 4H), 7.42-7.28 (m, 6H), 7.16 (m, 2H), 4.72 (q, J=6.9 Hz, 1H), 3.87 (bs, 2H), 3.82 (bs, 2H), 2.43 (m, 2H), 2.03 (t, J=7.5 Hz, 2H), 1.60 (d, J=6.9 Hz, 3H), 1.56 (m, 2H).

Example 8(57)

4-(2-((2-(4-fluoronaphthalen-1-yl)propanoyl)amino)-4-phenylaminomethylphenyl)butanoic acid

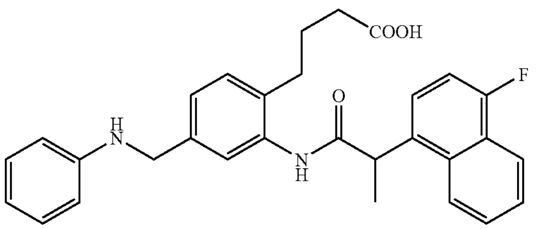

TLC: Rf 0.26 (chloroform:methanol=9:1);

NMR (300 MHz, DMSO-$d_6$): δ 9.51 (brs, 1H), 8.35 (m, 1H), 8.09 (m, 1H), 7.69-7.61 (m, 2H), 7.54 (dd, J=7.8, 6.0 Hz, 1H), 7.34-7.27 (m, 2H), 7.10 (s, 2H), 7.00 (dd, J=8.4, 7.5 Hz, 2H), 6.52-6.44 (m, 3H), 6.17 (t, J=7.2 Hz, 1H), 4.64 (q, J=7.2 Hz, 1H), 4.16 (d, J=6.0 Hz, 2H), 2.43-2.35 (m, 2H), 2.01-1.96 (m, 2H), 1.58 (d, J=7.2 Hz, 3H), 1.55-1.50 (m, 2H).

Example 8(58)

4-(2-((2-(naphthalen-1-yl)propanoyl)amino)-4-(4-cyanophenoxymethyl)phenyl)butanoic acid

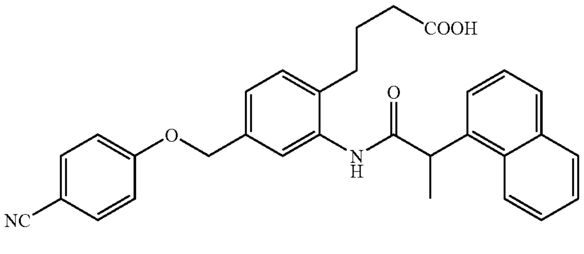

TLC: Rf 0.17 (chloroform:methanol=9:1);

NMR (300 MHz, $CDCl_3$): δ 8.14 (d, J=7.5 Hz, 1H), 8.05 (brs, 1H), 7.92 (m, 1H), 7.86 (d, J=7.8 Hz, 1H), 7.66-7.50 (m, 6H), 7.25 (brs, 1H), 7.06-6.97 (m, 4H), 5.04 (s, 2H), 4.59 (q, J=6.9 Hz, 1H), 1.97-1.89 (m, 4H), 1.83 (d, J=6.9 Hz, 3H), 1.30-1.21 (m, 2H).

Example 8(59)

4-(2-((2-(benzothiophen-3-yl)propanoyl)amino)-4-phenylaminomethylphenyl)butanoic acid

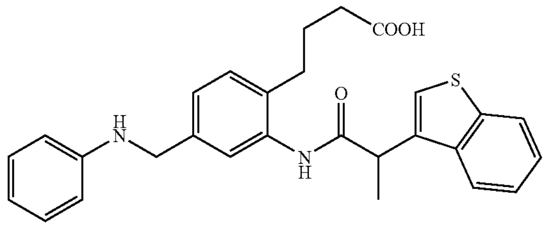

TLC: Rf 0.51 (chloroform:methanol=9:1);

NMR (300 MHz, DMSO-$d_6$): δ 9.51 (s, 1H), 8.01-7.96 (m, 2H), 7.58 (s, 1H), 7.43-7.34 (m, 2H), 7.30 (s, 1H), 7.11 (s, 2H), 7.02 (t, J=7.8 Hz, 2H), 6.57-6.49 (m, 3H), 4.29 (q, J=6.9 Hz, 1H), 4.17 (s, 2H), 2.40 (dd, J=9.3, 6.6 Hz, 2H), 2.04-1.99 (m, 2H), 1.58 (d, J=6.9 Hz, 3H), 1.57-1.50 (m, 2H).

Example 8(60)

2-(2-((2-phenylpropanoyl)amino)-4-phenoxymethylbenzyl)benzoic acid

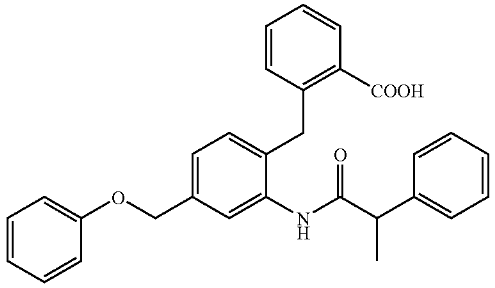

TLC: Rf 0.33 (hexane:ethyl acetate=1:2);

NMR (300 MHz, DMSO-$d_6$): δ 12.97 (s, 1H), 9.49 (s, 1H), 7.81 (dd, J=7.8, 1.5 Hz, 1H), 7.53 (d, J=1.5 Hz, 1H), 7.39-7.10 (m, 10H), 7.00-6.88 (m, 5H), 5.00 (s, 2H), 4.24 (s, 2H), 3.84 (q, J=6.9 Hz, 1H), 1.33 (d, J=6.9 Hz, 3H).

Example 8(61)

2-(2-((2-(naphthalen-1-yl)propanoyl)amino)-4-phenoxymethylbenzyl)benzoic acid

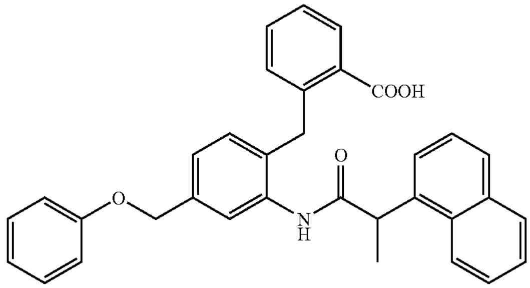

TLC: Rf 0.33 (hexane:ethyl acetate=1:2);

NMR (300 MHz, DMSO-$d_6$): δ 12.95 (s, 1H), 9.62 (s, 1H), 8.20 (m, 1H), 7.91 (m, 1H), 7.82-7.76 (m, 2H), 7.55-7.23 (m, 9H), 7.13 (dd, J=8.1, 1.5 Hz, 1H), 7.00-6.87 (m, 5H), 5.01 (s, 2H), 4.64 (q, J=6.9 Hz, 1H), 4.28 (d, J=16.5 Hz, 1H), 4.22 (d, J=16.5 Hz, 1H), 1.47 (d, J=6.9 Hz, 3H).

Example 8(62)

4-(2-((2-(naphthalen-1-yl)propanoyl)amino)-4-ethoxycarbonylaminomethylphenyl)butanoic acid

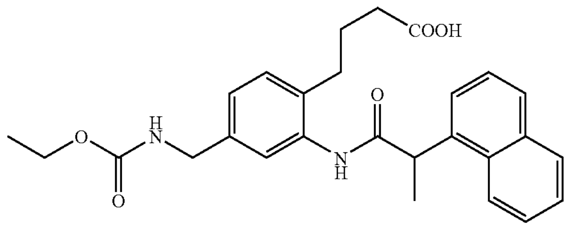

TLC: Rf 0.56 (chloroform:methanol=9:1);

NMR (300 MHz, DMSO-$d_6$): δ 9.59 (brs, 1H), 8.32 (d, J=8.4 Hz, 1H), 7.94 (d, J=8.4 Hz, 1H), 7.83 (d, J=7.5 Hz, 1H), 7.62-7.47 (m, 5H), 7.18 (brs, 1H), 7.09 (d, J=7.5 Hz, 1H), 6.98 (d, J=7.5 Hz, 1H), 4.71 (q, J=6.9 Hz, 1H), 4.07 (d, J=6.0 Hz, 2H), 3.96 (q, J=7.2 Hz, 2H), 2.42-2.37 (m, 2H), 2.02-1.97 (m, 2H), 1.59 (d, J=7.2 Hz, 3H), 1.61-1.51 (m, 2H), 1.13 (t, J=7.2 Hz, 3H).

Example 8(63)

4-(2-((2-(naphthalen-1-yl)propanoyl)amino)-4-(furan-2-ylcarbonylaminomethyl)phenyl)butanoic acid

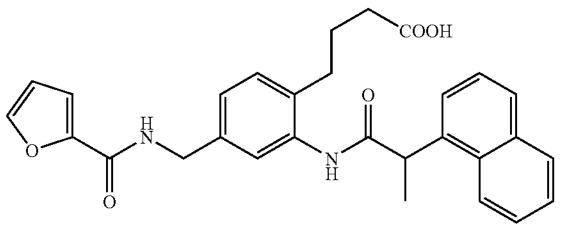

TLC: Rf 0.39 (chloroform:methanol=9:1);

NMR (300 MHz, DMSO-$d_6$): δ 9.50 (s, 1H), 8.88 (t, J=6.0 Hz, 1H), 8.29 (d, J=8.1 Hz, 1H), 7.92 (m, 1H), 7.85-7.81 (m, 2H), 7.57-7.45 (m, 4H), 7.20 (brs, 1H), 7.11-7.09 (m, 2H), 7.03 (dd, J=7.8, 1.5 Hz, 1H), 6.61 (dd, J=3.3, 1.5 Hz, 1H), 4.67 (q, J=7.2 Hz, 1H), 4.32 (d, J=6.0 Hz, 2H), 2.38 (dd, J=8.7, 7.2 Hz, 2H), 1.99 (t, J=7.5 Hz, 2H), 1.58 (d, J=7.2 Hz, 3H), 1.58-1.50 (m, 2H).

Example 8(64)

4-(2-((2-(naphthalen-1-yl)propanoyl)amino)-4-(3-fluorobenzoylaminomethyl)phenyl)butanoic acid

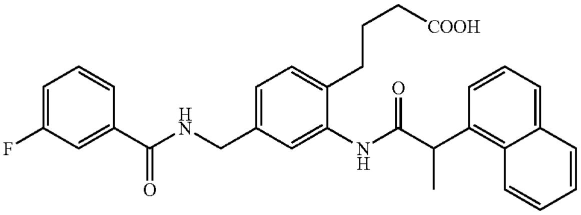

TLC: Rf 0.43 (chloroform:methanol=9:1);

NMR (300 MHz, DMSO-$d_6$): δ 9.49 (s, 1H), 9.11 (t, J=6.0 Hz, 1H), 8.29 (d, J=7.8 Hz, 1H), 7.93 (m, 1H), 7.81 (d, J=8.1 Hz, 1H), 7.72 (d, J=7.5 Hz, 1H), 7.66 (dd, J=9.9, 1.5 Hz, 1H), 7.57-7.42 (m, 5H), 7.39 (m, 1H), 7.23 (brs, 1H), 7.11 (d, J=7.8 Hz, 1H), 7.07 (d, J=7.8 Hz, 1H), 4.67 (q, J=7.2 Hz, 1H), 4.40 (d, J=5.7 Hz, 2H), 2.40 (dd, J=8.7, 7.2 Hz, 2H), 2.01 (t, J=7.2 Hz, 2H), 1.58 (d, J=7.2 Hz, 3H), 1.57-1.49 (m, 2H).

Example 8(65)

3-(2-phenylsulfonylamino-4-phenoxymethylphenyl)propanoic acid

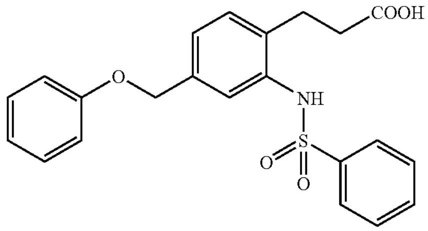

TLC: Rf 0.42 (chloroform:methanol=10:1);

NMR (300 MHz, $CD_3OD$): δ 7.66-7.63 (m, 2H), 7.56-7.53 (m, 2H), 7.46-7.40 (m, 2H), 7.27-7.19 (m, 4H), 7.11 (s, 1H), 6.94-6.87 (m, 3H), 4.94 (s, 2H), 2.70 (t, J=7.8 Hz, 2H), 2.41 (t, J=7.8 Hz, 2H).

Example 8(66)

3-(2-(N-benzylsulfonyl-N-methylamino)-4-phenoxymethylphenyl)propanoic acid

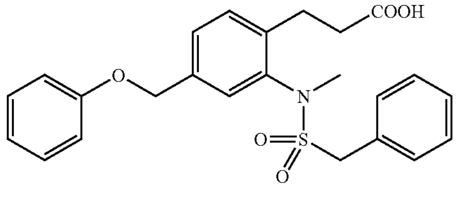

TLC: Rf 0.49 (chloroform:methanol=10:1);

NMR (300 MHz, DMSO-$d_6$): δ 7.40-7.18 (m, 10H), 7.02-6.90 (m, 3H), 5.02 (s, 2H), 4.80-4.40 (m, 2H), 3.15 (s, 3H), 3.00-2.60 (m, 2H), 2.52 (t, J=8.7 Hz, 2H).

Example 8(67)

(2E)-3-(2-(N-benzylsulfonyl-N-methylamino)-4-phenoxymethylphenyl)-2-propenoic acid

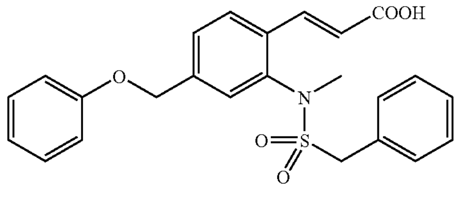

TLC: Rf 0.49 (chloroform:methanol=10:1);

NMR (300 MHz, DMSO-$d_6$): δ 7.91 (d, J=8.1 Hz, 1H), 7.83 (d, J=16.0 Hz, 1H), 7.50-7.20 (m, 9H), 7.01 (d, J=8.1 Hz, 2H), 6.94 (t, J=7.4 Hz, 1H), 6.53 (d, J=16.0 Hz, 1H), 5.09 (s, 2H), 4.59 (brs, 2H), 3.16 (s, 3H).

Example 8(68)

4-(2-((2-(naphthalen-1-yl)propanoyl)amino)-4-(3-methoxybenzoylaminomethyl)phenyl)butanoic acid

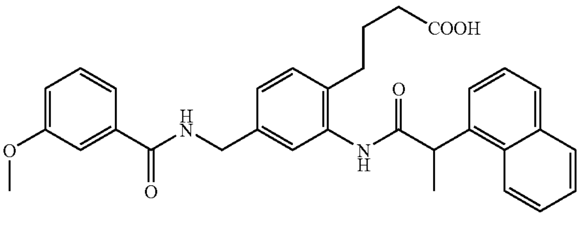

TLC: Rf 0.44 (chloroform:methanol=9:1);

NMR (300 MHz, DMSO-$d_6$): δ 9.50 (brs, 1H), 9.00 (t, J=6.0 Hz, 1H), 8.29 (d, J=8.1 Hz, 1H), 7.93 (m, 1H), 7.81 (d, J=8.1 Hz, 1H), 7.58-7.34 (m, 7H), 7.23 (brs, 1H), 7.12-7.05 (m, 3H), 4.67 (q, J=7.2 Hz, 1H), 4.39 (d, J=6.3 Hz, 2H), 3.79 (s, 3H), 2.39 (dd, J=9.6, 6.0 Hz, 2H), 2.01 (t, J=7.5 Hz, 2H), 1.58 (d, J=7.2 Hz, 3H), 1.57-1.50 (m, 2H).

Example 8(69)

4-(2-((2-(naphthalen-1-yl)propanoyl)amino)-4-cyclopropylcarbonylaminomethylphenyl)butanoic acid

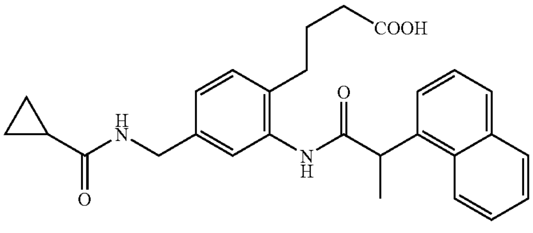

TLC: Rf 0.40 (chloroform:methanol=9:1);

NMR (300 MHz, DMSO-$d_6$): δ 9.51 (s, 1H), 8.53 (t, J=6.0 Hz, 1H), 8.31 (d, J=8.1 Hz, 1H), 7.94 (d, J=7.5 Hz, 1H), 7.83 (d, J=8.1 Hz, 1H), 7.61-7.47 (m, 4H), 7.16 (m, 1H), 7.10 (d, J=7.5 Hz, 1H), 6.99 (d, J=7.5 Hz, 1H), 4.69 (q, J=6.9 Hz, 1H), 4.19 (d, J=5.7 Hz, 2H), 2.39 (dd, J=9.3, 6.0 Hz, 2H), 2.00 (t, J=7.5 Hz, 2H), 1.59 (d, J=6.9 Hz, 3H), 1.60-1.51 (m, 3H), 0.70-0.60 (m, 4H).

Example 8(70)

4-(2-((2-(naphthalen-1-yl)propanoyl)amino)-4-(thiophen-2-ylcarbonylaminomethyl)phenyl)butanoic acid

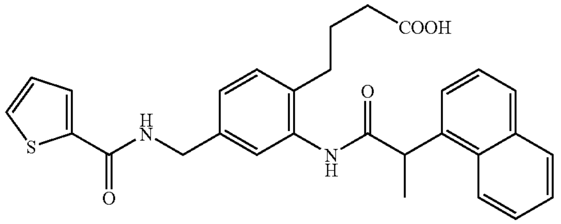

TLC: Rf 0.42 (chloroform:methanol=9:1);

NMR (300 MHz, DMSO-$d_6$): δ 9.50 (brs, 1H), 9.01 (t, J=6.0 Hz, 1H), 8.29 (d, J=6.0 Hz, 1H), 7.94 (m, 1H), 7.82 (d, J=7.8 Hz, 1H), 7.78-7.75 (m, 2H), 7.57-7.44 (m, 4H), 7.22 (brs, 1H), 7.16-7.07 (m, 2H), 7.05 (dd, J=7.8, 1.5 Hz, 1H), 4.67 (q, J=6.9 Hz, 1H), 4.36 (d, J=6.0 Hz, 2H), 2.39 (dd, J=8.7, 6.6 Hz, 2H), 2.00 (t, J=7.5 Hz, 2H), 1.58 (d, J=7.2 Hz, 3H), 1.56-1.49 (m, 2H).

Example 8(71)

4-(2-((2-(naphthalen-1-yl)propanoyl)amino)-4-(3-methylbenzoylaminomethyl)phenyl)butanoic acid

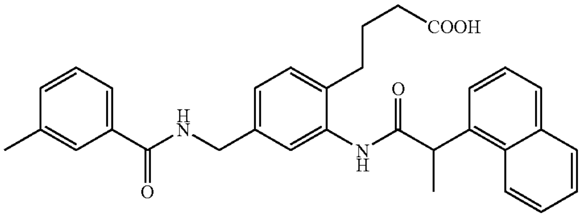

TLC: Rf 0.22 (ethyl acetate);

NMR (300 MHz, DMSO-$d_6$): δ 12.06 (br, 1H), 9.47 (s, 1H), 8.95 (t, J=6.0 Hz, 1H), 8.29 (m, 1H), 7.93 (m, 1H), 7.82 (d, J=7.8 Hz, 1H), 7.70-7.63 (m, 2H), 7.59-7.43 (m, 4H), 7.36-7.32 (m, 2H), 7.22 (bs, 1H), 7.11 (d, J=8.1 Hz, 1H), 7.06 (dd, J=8.1, 1.5 Hz, 1H), 4.67 (q, J=6.9 Hz, 1H), 4.38 (d, J=6.0 Hz, 2H), 2.39 (m, 2H), 2.35 (s, 3H), 2.01 (t, J=7.2 Hz, 2H), 1.58 (d, J=6.9 Hz, 3H), 1.54 (m, 2H).

Example 8(72)

4-(2-((2-(naphthalen-1-yl)propanoyl)amino)-4-(3-chlorobenzoylaminomethyl)phenyl)butanoic acid

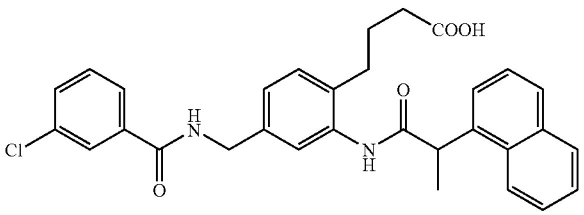

TLC: Rf 0.29 (ethyl acetate);

NMR (300 MHz, DMSO-$d_6$): δ 12.03 (br, 1H), 9.47 (s, 1H), 9.14 (t, J=6.0 Hz, 1H), 8.29 (m, 1H), 7.96-7.79 (m, 4H), 7.64-7.43 (m, 6H), 7.22 (bs, 1H), 7.12 (d, J=8.1 Hz, 1H), 7.06 (dd, J=8.1, 1.5 Hz, 1H), 4.67 (q, J=6.9 Hz, 1H), 4.39 (d, J=6.0 Hz, 2H), 2.39 (m, 2H), 2.01 (t, J=7.2 Hz, 2H), 1.58 (d, J=6.9 Hz, 3H), 1.54 (m, 2H).

Example 8(73)

4-(2-((2-(naphthalen-1-yl)propanoyl)amino)-4-(3-cyanobenzoylaminomethyl)phenyl)butanoic acid

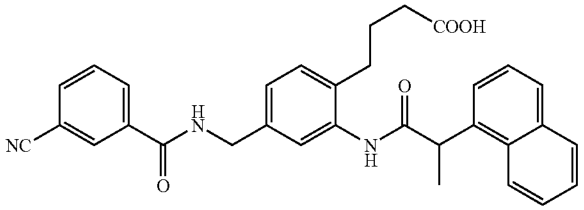

TLC: Rf 0.46 (chloroform:methanol=9:1);

NMR (300 MHz, DMSO-$d_6$): δ 9.49 (s, 1H), 9.22 (m, 1H), 8.30-8.28 (m, 2H), 8.17 (d, J=7.8 Hz, 1H), 7.99 (d, J=7.5 Hz, 1H), 7.93 (d, J=8.1 Hz, 1H), 7.82 (d, J=8.1 Hz, 1H), 7.70 (t, J=7.5 Hz, 1H), 7.58-7.44 (m, 4H), 7.24 (s, 1H), 7.12 (d, J=7.8 Hz, 1H), 7.08 (d, J=7.8 Hz, 1H), 4.67 (q, J=6.9 Hz, 1H), 4.41 (d, J=5.7 Hz, 2H), 2.43-2.37 (m, 2H), 2.01 (t, J=7.2 Hz, 2H), 1.58 (d, J=6.9 Hz, 3H), 1.58-1.49 (m, 2H).

Example 8(74)

4-(2-((2-(naphthalen-1-yl)propanoyl)amino)-4-(4-fluorobenzoylaminomethyl)phenyl)butanoic acid

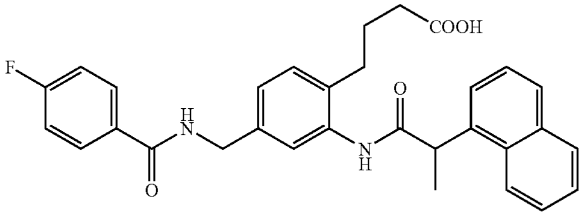

TLC: Rf 0.51 (chloroform:methanol=9:1);

NMR (300 MHz, DMSO-$d_6$): δ 9.49 (s, 1H), 9.03 (t, J=6.0 Hz, 1H), 8.29 (d, J=7.8 Hz, 1H), 7.98-7.90 (m, 3H), 7.82 (d, J=8.1 Hz, 1H), 7.57-7.44 (m, 4H), 7.30 (dd, J=9.3, 7.8 Hz, 2H), 7.22 (s, 1H), 7.11 (d, J=8.1 Hz, 1H), 7.06 (d, J=8.1 Hz, 1H), 4.71 (q, J=6.9 Hz, 1H), 4.39 (d, J=6.3 Hz, 2H), 2.42-2.37 (m, 2H), 2.01 (t, J=7.5 Hz, 2H), 1.58 (d, J=6.9 Hz, 3H), 1.57-1.50 (m, 2H).

Example 8(75)

4-(2-((2-(naphthalen-1-yl)propanoyl)amino)-4-(2-fluorobenzoylaminomethyl)phenyl)butanoic acid

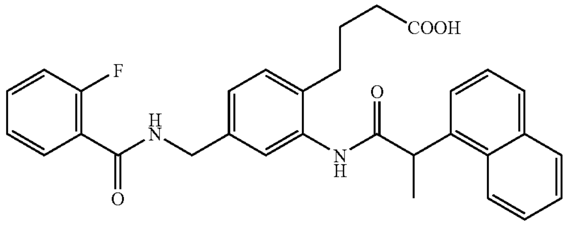

TLC: Rf 0.53 (chloroform:methanol=9:1);

NMR (300 MHz, DMSO-$d_6$): δ 9.51 (s, 1H), 8.83 (m, 1H), 8.31 (d, J=8.1 Hz, 1H), 7.94 (dd, J=7.8, 1.5 Hz, 1H), 7.83 (d, J=7.8 Hz, 1H), 7.64-7.45 (m, 6H), 7.31-7.24 (m, 3H), 7.13 (d, J=7.8 Hz, 1H), 7.08 (dd, J=7.8, 1.2 Hz, 1H), 4.69 (q, J=6.9 Hz, 1H), 4.38 (d, J=6.0 Hz, 2H), 2.43-2.38 (m, 2H), 2.02 (t, J=7.5 Hz, 2H), 1.59 (d, J=6.9 Hz, 3H), 1.57-1.51 (m, 2H).

Example 8(76)

4-(2-((2-(naphthalen-1-yl)propanoyl)amino)-4-(3-chloro-4-fluorobenzoylaminomethyl)phenyl)butanoic acid

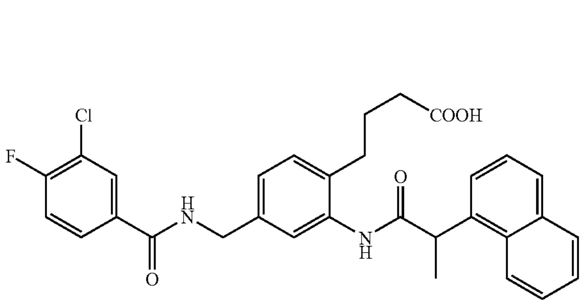

TLC: Rf 0.60 (chloroform:methanol=9:1);

NMR (300 MHz, DMSO-$d_6$): δ 9.49 (s, 1H), 9.14 (t, J=6.0 Hz, 1H), 8.29 (d, J=8.4 Hz, 1H), 8.08 (dd, J=7.2, 2.1 Hz, 1H), 7.93 (d, J=9.0 Hz, 1H), 7.90 (m, 1H), 7.82 (d, J=7.8 Hz, 1H), 7.58-7.45 (m, 5H), 7.23 (brs, 1H), 7.11 (d, J=7.8 Hz, 1H), 7.06 (d, J=8.4 Hz, 1H), 4.67 (q, J=6.9 Hz, 1H), 4.39 (d, J=8.7 Hz, 2H), 2.40 (dd, J=9.0, 6.0 Hz, 2H), 2.01 (t, J=7.5 Hz, 2H), 1.58 (d, J=6.9 Hz, 3H), 1.57-1.52 (m, 2H).

Example 8(77)

4-(2-((2-(2-chlorophenyl)propanoyl)amino)-4-phenoxymethylphenyl)butanoic acid

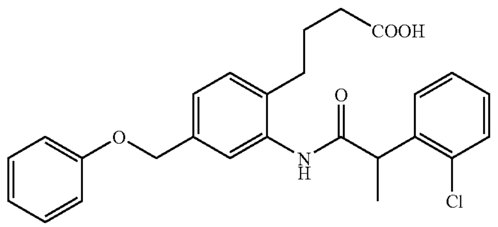

TLC: Rf 0.40 (hexane:ethyl acetate:acetic acid=1:1:0.01); NMR (300 MHz, DMSO-$d_6$): δ 12.50 (bs, 1H), 9.50 (s, 1H), 7.50 (dd, J=7.8, 2.1 Hz, 1H), 7.44 (dd, J=7.8, 2.1 Hz, 1H), 7.40-7.23 (m, 5H), 7.21 (m, 2H), 7.01-6.89 (m, 3H), 5.02 (s, 2H), 4.26 (q, J=7.2 Hz, 1H), 2.50 (m, 2H), 2.14 (t, J=7.2 Hz, 2H), 1.64 (m, 2H), 1.48 (d, J=7.2 Hz, 3H).

Example 8(78)

4-(2-((2-(3-chlorophenyl)propanoyl)amino)-4-phenoxymethylphenyl)butanoic acid

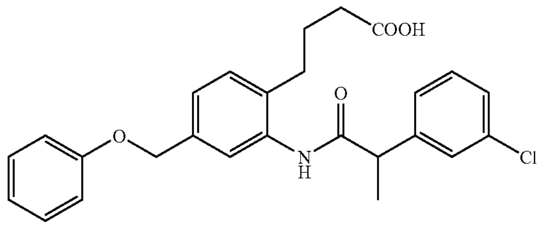

TLC: Rf 0.44 (hexane:ethyl acetate:acetic acid=1:1:0.01); NMR (300 MHz, DMSO-$d_6$): δ 12.05 (bs, 1H), 9.48 (s, 1H), 7.45 (s, 1H), 7.38-7.16 (m, 8H), 7.00-6.88 (m, 3H), 5.02 (s, 2H), 3.92 (q, J=7.2 Hz, 1H), 2.42 (m, 2H), 2.07 (t, J=7.2 Hz, 2H), 1.54 (m, 2H), 1.42 (d, J=7.2 Hz, 3H).

Example 8(79)

4-(2-((2-(4-chlorophenyl)propanoyl)amino)-4-phenoxymethylphenyl)butanoic acid

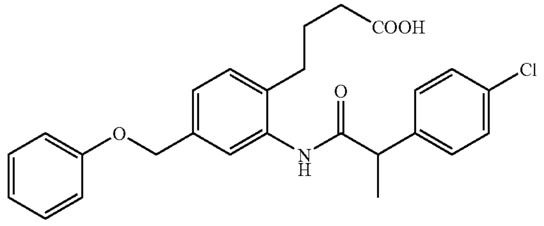

TLC: Rf 0.46 (hexane:ethyl acetate:acetic acid=1:1:0.01); NMR (300 MHz, DMSO-$d_6$): δ 12.06 (bs, 1H), 9.46 (s, 1H), 7.44-7.35 (m, 5H), 7.31-7.15 (m, 4H), 7.00-6.88 (m, 3H), 5.01 (s, 2H), 3.91 (q, J=6.9 Hz, 1H), 2.42 (m, 2H), 2.07 (t, J=6.9 Hz, 2H), 1.55 (m, 2H), 1.41 (d, J=6.9 Hz, 3H).

Example 8(80)

4-(2-((2-(4-fluorophenyl)propanoyl)amino)-4-phenoxymethylphenyl)butanoic acid

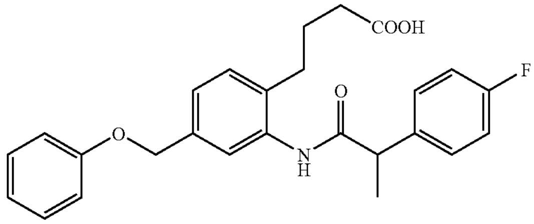

TLC: Rf 0.44 (hexane:ethyl acetate:acetic acid=1:1:0.01); NMR (300 MHz, DMSO-$d_6$): δ 12.05 (bs, 1H), 9.43 (s, 1H), 7.46-7.36 (m, 3H), 7.31-7.23 (m, 2H), 7.22-7.10 (m, 4H), 7.00-6.88 (m, 3H), 5.01 (s, 2H), 3.91 (q, J=6.9 Hz, 1H), 2.42 (m, 2H), 2.06 (t, J=7.5 Hz, 2H), 1.53 (m, 2H), 1.40 (d, J=6.9 Hz, 3H).

Example 8(81)

4-(2-((2-(4-methoxyphenyl)propanoyl)amino)-4-phenoxymethylphenyl)butanoic acid

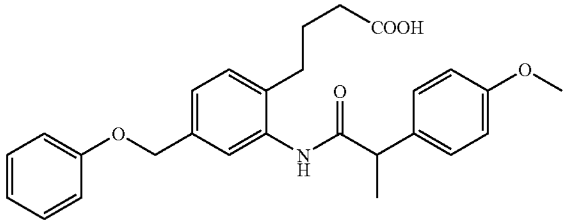

TLC: Rf 0.40 (hexane:ethyl acetate:acetic acid=1:1:0.01); NMR (300 MHz, DMSO-$d_6$): δ 12.05 (bs, 1H), 9.33 (s, 1H), 7.38 (s, 1H), 7.34-7.23 (m, 4H), 7.17 (m, 2H), 7.00-6.85 (m, 5H), 5.01 (s, 2H), 3.83 (q, J=6.9 Hz, 1H), 3.72 (s, 3H), 2.41 (m, 2H), 2.05 (t, J=7.5 Hz, 2H), 1.53 (m, 2H), 1.38 (d, J=6.9 Hz, 3H).

Example 8(82)

4-(2-((2-(naphthalen-1-yl)propanoyl)amino)-4-(3-ethoxybenzoylaminomethyl)phenyl)butanoic acid

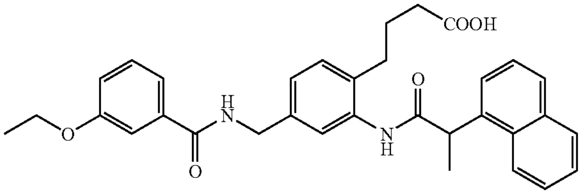

TLC: Rf 0.44 (chloroform:methanol=9:1);

NMR (300 MHz, DMSO-$d_6$): δ 9.50 (s, 1H), 8.98 (t, J=5.7 Hz, 1H), 8.29 (d, J=7.8 Hz, 1H), 7.93 (d, J=7.2 Hz, 1H), 7.81 (d, J=7.8 Hz, 1H), 7.57-7.36 (m, 7H), 7.23 (s, 1H), 7.12-7.04 (m, 3H), 4.67 (q, J=6.0 Hz, 1H), 4.38 (d, J=5.7 Hz, 2H), 4.05 (q, J=6.9 Hz, 2H), 2.40 (dd, J=8.7, 7.2 Hz, 2H), 2.01 (t, J=7.5 Hz, 2H), 1.58 (d, J=6.9 Hz, 3H), 1.57-1.50 (m, 2H), 1.33 (t, J=6.9 Hz, 3H).

Example 8(83)

4-(2-((2-(naphthalen-1-yl)propanoyl)amino)-4-(3,5-difluorobenzoylaminomethyl)phenyl)butanoic acid

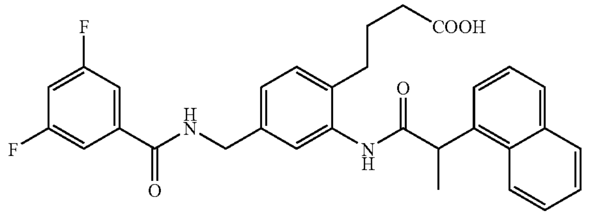

TLC: Rf 0.56 (chloroform:methanol=9:1);

NMR (300 MHz, DMSO-$d_6$): δ 9.50 (s, 1H), 9.18 (t, J=6.0 Hz, 1H), 8.29 (d, J=8.1 Hz, 1H), 7.93 (d, J=7.2 Hz, 1H), 7.82 (d, J=7.8 Hz, 1H), 7.60-7.44 (m, 7H), 7.23 (brs, 1H), 7.11 (d, J=8.1 Hz, 1H), 7.07 (d, J=8.1 Hz, 1H), 4.67 (q, J=6.9 Hz, 1H), 4.39 (d, J=5.7 Hz, 2H), 2.40 (dd, J=9.0, 6.3 Hz, 2H), 2.01 (t, J=7.2 Hz, 2H), 1.58 (d, J=6.9 Hz, 3H), 1.57-1.50 (m, 2H).

Example 8(84)

4-(2-((2-(naphthalen-1-yl)propanoyl)amino)-4-(3-fluorophenoxymethyl)phenyl)butanoic acid

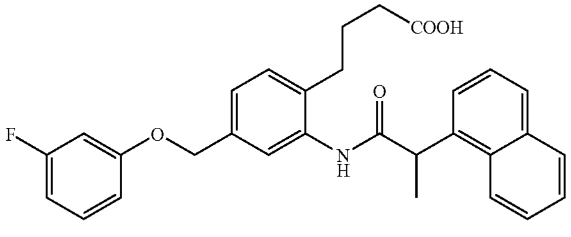

TLC: Rf 0.62 (chloroform:methanol=9:1);

NMR (300 MHz, DMSO-$d_6$): δ 9.54 (s, 1H), 8.33 (d, J=8.7 Hz, 1H), 7.94 (d, J=6.9 Hz, 1H), 7.83 (d, J=7.8 Hz, 1H), 7.61-7.47 (m, 4H), 7.38 (s, 1H), 7.29 (m, 1H), 7.19 (s, 2H), 6.90-6.80 (m, 2H), 6.75 (m, 1H), 5.03 (s, 2H), 4.70 (q, J=6.9 Hz, 1H), 2.44 (dd, J=9.0, 5.1 Hz, 2H), 2.03 (t, J=7.5 Hz, 2H), 1.60 (d, J=6.9 Hz, 3H), 1.59-1.52 (m, 2H).

Example 8(85)

4-(2-((2-(4-methylphenyl)propanoyl)amino)-4-phenoxymethylphenyl)butanoic acid

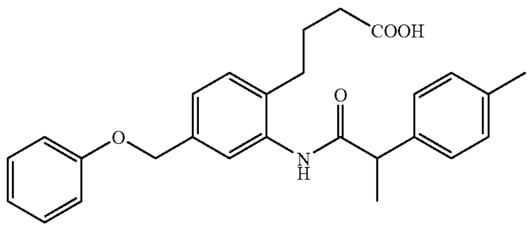

TLC: Rf 0.24 (hexane:ethyl acetate=1:2);

NMR (300 MHz, DMSO-$d_6$): δ 12.04 (s, 1H), 9.34 (s, 1H), 7.37 (bs, 1H), 7.32-7.08 (m, 8H), 7.00-6.88 (m, 3H), 5.01 (s, 2H), 3.84 (q, J=6.9 Hz, 1H), 2.39 (m, 2H), 2.26 (s, 3H), 2.02 (t, J=7.5 Hz, 2H), 1.51 (m, 2H), 1.38 (d, J=6.9 Hz, 3H).

Example 8(86)

4-(2-((2-(naphthalen-1-yl)propanoyl)amino)-4-(4-cyano-2-methoxyphenoxymethyl)phenyl)butanoic acid

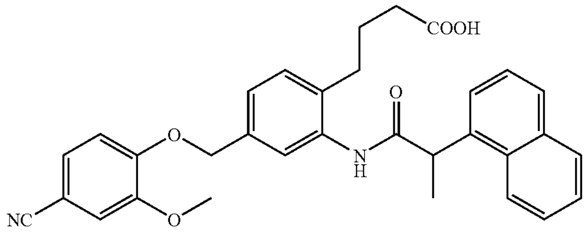

TLC: Rf 0.34 (ethyl acetate);

NMR (300 MHz, DMSO-$d_6$): δ 12.04 (br, 1H), 9.55 (s, 1H), 8.31 (d, J=8.1 Hz, 1H), 7.94 (m, 1H), 7.83 (d, J=8.1 Hz, 1H), 7.62-7.46 (m, 4H), 7.41-7.35 (m, 3H), 7.22-7.14 (m, 3H), 5.10 (s, 2H), 4.70 (q, J=6.9 Hz, 1H), 3.78 (s, 3H), 2.44 (m, 2H), 2.03 (t, J=7.5 Hz, 2H), 1.60 (d, J=6.9 Hz, 3H), 1.57 (m, 2H).

Example 8(87)

4-(2-((2-(naphthalen-1-yl)propanoyl)amino)-4-(3-acetylphenoxymethyl)phenyl)butanoic acid

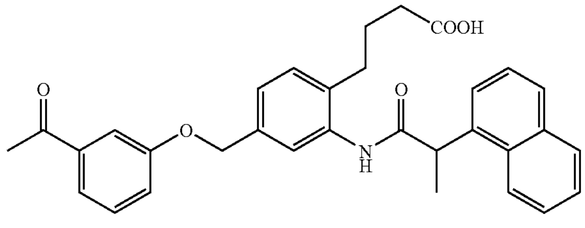

TLC: Rf 0.40 (ethyl acetate);

NMR (300 MHz, DMSO-$d_6$): δ 12.04 (s, 1H), 9.52 (s, 1H), 8.31 (d, J=8.1 Hz, 1H), 7.94 (m, 1H), 7.83 (d, J=8.1 Hz, 1H), 7.62-7.39 (m, 8H), 7.28-7.16 (m, 3H), 5.10 (s, 2H), 4.70 (q, J=6.9 Hz, 1H), 2.55 (s, 3H), 2.44 (m, 2H), 2.03 (t, J=7.2 Hz, 2H), 1.60 (d, J=6.9 Hz, 3H), 1.56 (m, 2H).

Example 8(88)

4-(2-((2-(naphthalen-1-yl)propanoyl)amino)-4-(3-isopropyl-5-methylphenoxymethyl)phenyl)butanoic acid

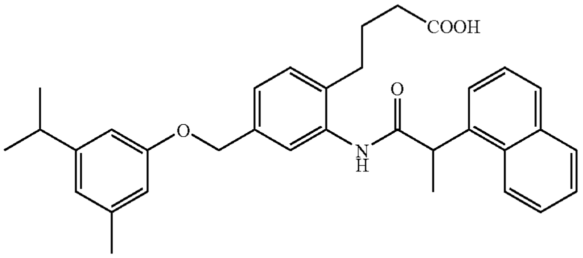

TLC: Rf 0.26 (hexane:ethyl acetate=1:2);

NMR (300 MHz, DMSO-$d_6$): δ 12.04 (s, 1H), 9.51 (s, 1H), 8.31 (d, J=8.1 Hz, 1H), 7.95 (m, 1H), 7.83 (d, J=8.1 Hz, 1H), 7.62-7.47 (m, 4H), 7.37 (s, 1H), 7.18 (m, 2H), 6.65-6.59 (m, 3H), 4.96 (s, 2H), 4.69 (q, J=6.9 Hz, 1H), 2.77 (m, 1H), 2.43 (m, 2H), 2.22 (s, 3H), 2.03 (t, J=7.2 Hz, 2H), 1.60 (d, J=6.9 Hz, 3H), 1.56 (m, 2H), 1.14 (d, J=6.9 Hz, 6H).

Example 8(89)

4-(2-((2-(naphthalen-1-yl)propanoyl)amino)-4-(2,4,6-trifluorophenoxymethyl)phenyl)butanoic acid

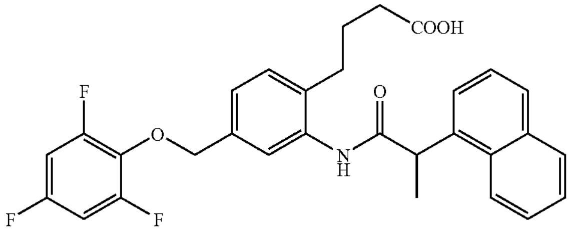

TLC: Rf 0.28 (hexane:ethyl acetate=1:2);

NMR (300 MHz, DMSO-$d_6$): δ 12.12 (br, 1H), 9.70 (bs, 1H), 8.33 (d, J=8.1 Hz, 1H), 7.94 (m, 1H), 7.83 (d, J=8.1 Hz, 1H), 7.62-7.40 (m, 5H), 7.28-7.10 (m, 4H), 5.01 (s, 2H), 4.74 (q, J=6.9 Hz, 1H), 2.45 (m, 2H), 2.01 (t, J=7.5 Hz, 2H), 1.60 (d, J=6.9 Hz, 3H), 1.56 (m, 2H).

Example 8(90)

4-(2-((2-(naphthalen-1-yl)propanoyl)amino)-4-(4-trifluoromethylthiophenoxymethyl)phenyl)butanoic acid

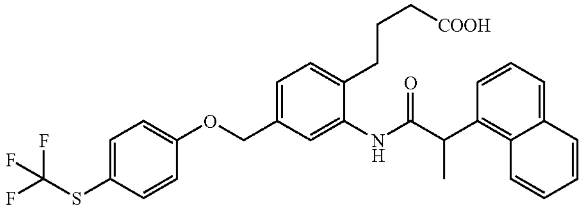

TLC: Rf 0.24 (hexane:ethyl acetate=1:2);

NMR (300 MHz, DMSO-$d_6$): δ 12.05 (bs, 1H), 9.52 (s, 1H), 8.31 (d, J=8.1 Hz, 1H), 7.94 (m, 1H), 7.83 (d, J=8.1 Hz, 1H), 7.62 (d, J=8.4 Hz, 2H), 7.60-7.46 (m, 4H), 7.39 (s, 1H), 7.20 (m, 2H), 7.12 (d, J=8.4 Hz, 2H), 5.09 (s, 2H), 4.70 (q, J=6.9 Hz, 1H), 2.44 (m, 2H), 2.03 (t, J=7.2 Hz, 2H), 1.60 (d, J=6.9 Hz, 3H), 1.56 (m, 2H).

Example 8(91)

4-(2-((2-(naphthalen-1-yl)propanoyl)amino)-4-(4-bromophenoxymethyl)phenyl)butanoic acid

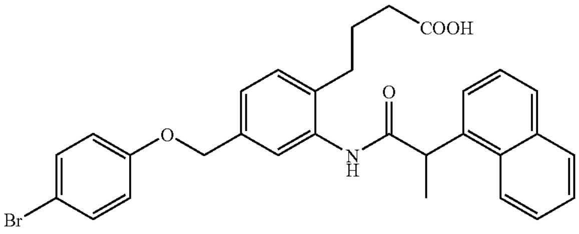

TLC: Rf 0.54 (chloroform:methanol=9:1);

NMR (300 MHz, DMSO-$d_6$): δ 9.54 (s, 1H), 8.31 (d, J=8.1 Hz, 1H), 7.94 (dd, J=7.8, 1.5 Hz, 1H), 7.83 (d, J=8.1 Hz, 1H), 7.61-7.47 (m, 4H), 7.45-7.40 (m, 2H), 7.37 (s, 1H), 7.17 (d, J=0.9 Hz, 2H), 6.96-6.93 (m, 2H), 5.01 (s, 2H), 4.70 (q, J=6.9 Hz, 1H), 2.44 (dd, J=8.7, 6.0 Hz, 2H), 2.02 (t, J=7.5 Hz, 2H), 1.59 (d, J=6.9 Hz, 3H), 1.58-1.52 (m, 2H).

Example 8(92)

4-(2-((2-(naphthalen-1-yl)propanoyl)amino)-4-(3-methoxyphenoxymethyl)phenyl)butanoic acid

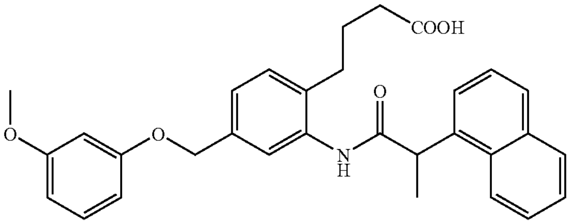

TLC: Rf 0.60 (chloroform:methanol=9:1);

NMR (300 MHz, DMSO-$d_6$): δ 9.54 (s, 1H), 8.31 (d, J=8.4 Hz, 1H), 7.94 (d, J=7.2 Hz, 1H), 7.83 (d, J=7.8 Hz, 1H), 7.60-7.47 (m, 4H), 7.37 (s, 1H), 7.18-7.13 (m, 3H), 6.56-6.48 (m, 3H), 4.99 (s, 2H), 4.70 (q, J=6.9 Hz, 1H), 3.70 (s, 3H), 2.43 (dd, J=8.7, 5.7 Hz, 2H), 2.02 (t, J=7.5 Hz, 2H), 1.60 (d, J=6.9 Hz, 3H), 1.59-1.51 (m, 2H).

Example 8(93)

4-(2-((2-(naphthalen-1-yl)propanoyl)amino)-4-(2-methoxyphenoxymethyl)phenyl)butanoic acid

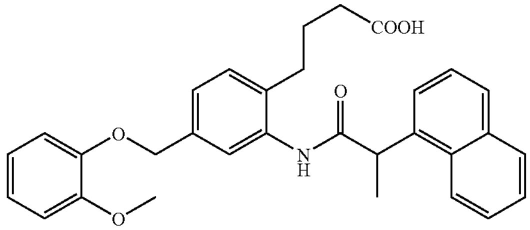

TLC: Rf 0.59 (chloroform:methanol=9:1);

NMR (300 MHz, DMSO-$d_6$): δ 9.55 (s, 1H), 8.33 (d, J=8.4 Hz, 1H), 7.94 (dd, J=7.8, 1.8 Hz, 1H), 7.83 (d, J=8.1 Hz, 1H), 7.61-7.47 (m, 4H), 7.37 (s, 1H), 7.18 (s, 2H), 6.98 (dd, J=7.5, 1.8 Hz, 1H), 6.95 (dd, J=7.5, 2.4 Hz, 1H), 6.91-6.80 (m, 2H), 4.98 (s, 2H), 4.70 (q, J=7.2 Hz, 1H), 3.74 (s, 3H), 2.46-2.41 (m, 2H), 2.03 (t, J=7.5 Hz, 2H), 1.60 (d, J=7.2 Hz, 3H), 1.59-1.52 (m, 2H).

Example 8(94)

4-(2-((2-(naphthalen-1-yl)propanoyl)amino)-4-(2-methylbenzothiazol-5-yloxymethyl)phenyl)butanoic acid

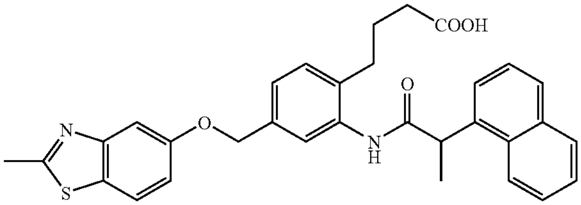

TLC: Rf 0.18 (ethyl acetate);

NMR (300 MHz, DMSO-$d_6$): δ 12.05 (bs, 1H), 9.53 (s, 1H), 8.31 (d, J=8.1 Hz, 1H), 7.94 (m, 1H), 7.86 (d, J=8.7 Hz, 1H), 7.83 (d, J=8.1 Hz, 1H), 7.62-7.46 (m, 5H), 7.41 (d, J=1.5 Hz, 1H), 7.23 (dd, J=7.8, 1.5 Hz, 1H), 7.18 (d, J=7.8 Hz, 1H), 7.06 (dd, J=8.7, 2.4 Hz, 1H), 5.11 (s, 2H), 4.70 (q, J=6.9 Hz, 1H), 2.75 (s, 3H), 2.43 (m, 2H), 2.02 (t, J=7.5 Hz, 2H), 1.60 (d, J=6.9 Hz, 3H), 1.56 (m, 2H).

Example 8(95)

4-(2-((2-(naphthalen-1-yl)propanoyl)amino)-4-(4-(1,2,4-triazol-1-yl)phenoxymethyl)phenyl)butanoic acid

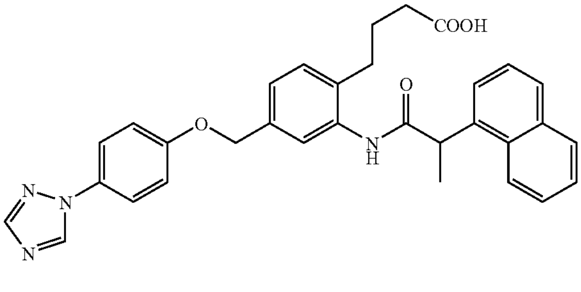

TLC: Rf 0.11 (ethyl acetate);

NMR (300 MHz, DMSO-$d_6$): δ 12.05 (s, 1H), 9.52 (s, 1H), 9.15 (s, 1H), 8.31 (d, J=8.1 Hz, 1H), 8.17 (s, 1H), 7.94 (m, 1H), 7.83 (d, J=8.1 Hz, 1H), 7.74 (d, J=9.0 Hz, 2H), 7.62-7.46 (m, 4H), 7.41 (bs, 1H), 7.25-7.16 (m, 2H), 7.15 (d, J=9.0 Hz, 2H), 5.09 (s, 2H), 4.70 (q, J=6.9 Hz, 1H), 2.43 (m, 2H), 2.03 (t, J=7.5 Hz, 2H), 1.60 (d, J=6.9 Hz, 3H), 1.57 (m, 2H).

Example 8(96)

4-(2-((2-(naphthalen-1-yl)propanoyl)amino)-4-(2-ethoxyphenoxymethyl)phenyl)butanoic acid

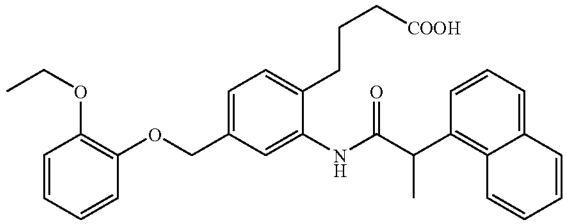

TLC: Rf 0.45 (ethyl acetate);

NMR (300 MHz, DMSO-$d_6$): δ 12.04 (s, 1H), 9.51 (s, 1H), 8.31 (d, J=8.1 Hz, 1H), 7.94 (m, 1H), 7.83 (d, J=8.1 Hz, 1H), 7.62-7.46 (m, 4H), 7.38 (bs, 1H), 7.18 (m, 2H), 7.01-6.92 (m, 2H), 6.90-6.78 (m, 2H), 5.00 (s, 2H), 4.70 (q, J=6.9 Hz, 1H), 3.98 (q, J=6.9 Hz, 2H), 2.43 (m, 2H), 2.03 (t, J=7.5 Hz, 2H), 1.60 (d, J=6.9 Hz, 3H), 1.57 (m, 2H), 1.26 (t, J=6.9 Hz, 3H).

Example 8(97)

4-(2-((2-(naphthalen-1-yl)propanoyl)amino)-4-(2-methoxy-5-methylphenoxymethyl)phenyl)butanoic acid

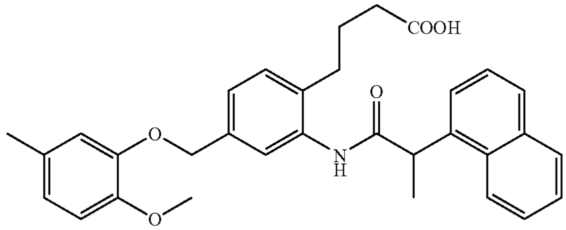

TLC: Rf 0.41 (ethyl acetate);

NMR (300 MHz, DMSO-$d_6$): δ 12.05 (bs, 1H), 9.53 (s, 1H), 8.32 (d, J=8.1 Hz, 1H), 7.94 (m, 1H), 7.83 (d, J=8.1 Hz, 1H), 7.62-7.46 (m, 4H), 7.36 (bs, 1H), 7.18 (m, 2H), 6.85 (d, J=2.1 Hz, 1H), 6.82 (d, J=8.1 Hz, 1H), 6.68 (m, 1H), 4.95 (s, 2H), 4.70 (q, J=6.9 Hz, 1H), 3.68 (s, 3H), 2.44 (m, 2H), 2.19 (s, 3H), 2.03 (t, J=7.5 Hz, 2H), 1.60 (d, J=6.9 Hz, 3H), 1.57 (m, 2H).

Example 8(98)

4-(2-((2-(naphthalen-1-yl)propanoyl)amino)-4-(3,5-dimethoxyphenoxymethyl)phenyl)butanoic acid

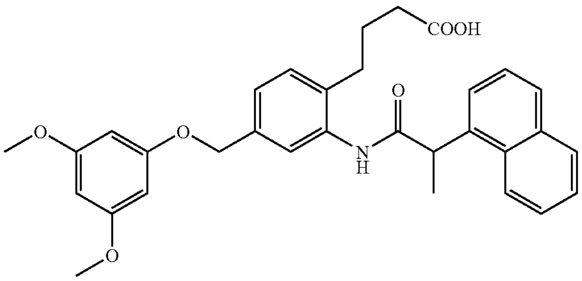

TLC: Rf 0.40 (ethyl acetate);

NMR (300 MHz, DMSO-$d_6$): δ 12.04 (s, 1H), 9.51 (s, 1H), 8.30 (d, J=8.1 Hz, 1H), 7.94 (m, 1H), 7.83 (d, J=8.1 Hz, 1H), 7.62-7.46 (m, 4H), 7.35 (bs, 1H), 7.17 (m, 2H), 6.14 (d, J=2.1 Hz, 2H), 6.07 (t, J=2.1 Hz, 1H), 4.96 (s, 2H), 4.69 (q, J=6.9 Hz, 1H), 3.67 (s, 6H), 2.42 (m, 2H), 2.02 (t, J=7.2 Hz, 2H), 1.59 (d, J=6.9 Hz, 3H), 1.55 (m, 2H).

Example 8(99)

4-(2-((2-(naphthalen-1-yl)propanoyl)amino)-4-(2-fluoro-6-methoxyphenoxymethyl)phenyl)butanoic acid

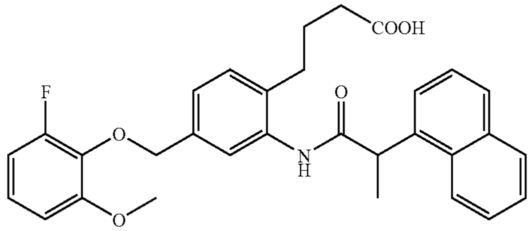

TLC: Rf 0.40 (ethyl acetate);

NMR (300 MHz, DMSO-$d_6$): δ 12.04 (s, 1H), 9.51 (s, 1H), 8.31 (d, J=8.1 Hz, 1H), 7.95 (m, 1H), 7.84 (d, J=8.1 Hz, 1H), 7.62-7.47 (m, 4H), 7.38 (bs, 1H), 7.16 (m, 2H), 7.03 (m, 1H), 6.90-6.76 (m, 2H), 4.92 (s, 2H), 4.70 (q, J=6.9 Hz, 1H), 3.78 (s, 3H), 2.43 (m, 2H), 2.02 (t, J=7.5 Hz, 2H), 1.60 (d, J=6.9 Hz, 3H), 1.56 (m, 2H).

Example 8(100)

4-(2-((2-(naphthalen-1-yl)propanoyl)amino)-4-(2-isopropyloxyphenoxymethyl)phenyl)butanoic acid

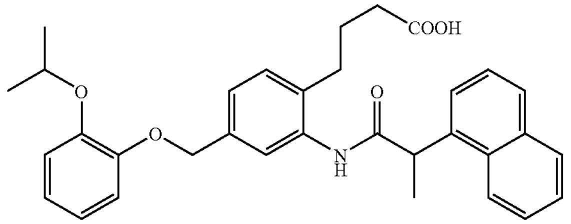

TLC: Rf 0.53 (ethyl acetate);

NMR (300 MHz, DMSO-$d_6$): δ 12.05 (s, 1H), 9.51 (s, 1H), 8.31 (d, J=8.1 Hz, 1H), 7.94 (m, 1H), 7.83 (d, J=8.1 Hz, 1H), 7.62-7.46 (m, 4H), 7.39 (bs, 1H), 7.18 (m, 2H), 7.02-6.92 (m, 2H), 6.89-6.81 (m, 2H), 5.00 (s, 2 H), 4.70 (q, J=6.9 Hz, 1H), 4.47 (m, 1H), 2.43 (m, 2H), 2.03 (t, J=7.5 Hz, 2H), 1.60 (d, J=6.9 Hz, 3H), 1.57 (m, 2H), 1.18 (d, J=6.0 Hz, 6H).

Example 8(101)

4-(2-((2-(naphthalen-1-yl)propanoyl)amino)-4-(2-acetyl-5-methoxyphenoxymethyl)phenyl)butanoic acid

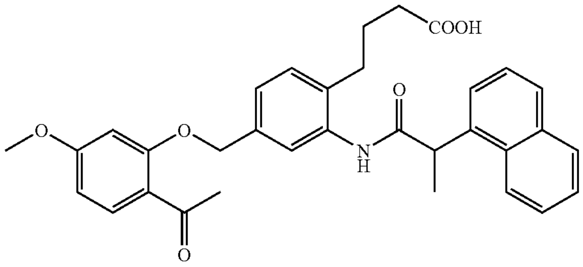

TLC: Rf 0.35 (ethyl acetate);

NMR (300 MHz, DMSO-$d_6$): δ 12.05 (s, 1H), 9.51 (s, 1H), 8.30 (d, J=8.1 Hz, 1H), 7.94 (m, 1H), 7.83 (d, J=8.1 Hz, 1H), 7.65 (d, J=8.7 Hz, 1H), 7.62-7.45 (m, 5H), 7.26 (dd, J=7.8, 1.8 Hz, 1H), 7.20 (d, J=7.8 Hz, 1 H), 6.73 (d, J=2.4 Hz, 1H), 6.59 (dd, J=8.7, 2.4 Hz, 1H), 5.19 (s, 2H), 4.70 (q, J=6.9 Hz, 1H), 3.80 (s, 3H), 2.44 (m, 2H), 2.42 (s, 3H), 2.05 (t, J=7.2 Hz, 2H), 1.60 (d, J=6.9 Hz, 3H), 1.58 (m, 2H).

Example 8(102)

2-(2-((4-methyl-2-(naphthalen-1-yl)pentanoyl)amino)-4-phenoxymethylbenzyl)benzoic acid

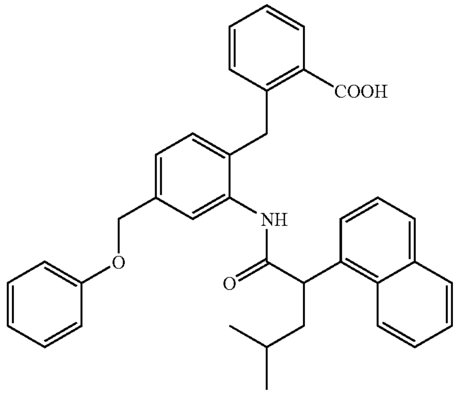

TLC: Rf 0.70 (chloroform:methanol=10:1).

Example 8(103)

4-(2-((2-(naphthalen-1-yl)propanoyl)amino)-4-(2-chloro-4,5-dimethylphenoxymethyl)phenyl)butanoic acid

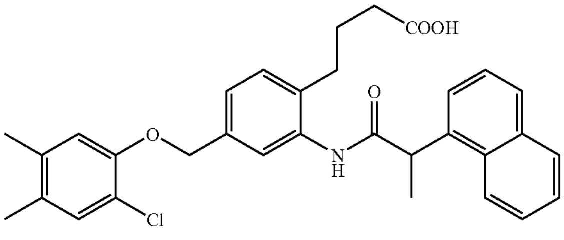

TLC: Rf 0.72 (chloroform:methanol=9:1);

NMR (300 MHz, DMSO-$d_6$): δ 9.55 (s, 1H), 8.31 (d, J=8.4 Hz, 1H), 7.94 (d, J=8.7 Hz, 1H), 7.83 (d, J=8.1 Hz, 1H), 7.60-7.47 (m, 4H), 7.39 (s, 1H), 7.19-7.17 (m, 3H), 7.02 (s, 1H), 5.06 (s, 2H), 4.70 (q, J=6.9 Hz, 1H), 2.44-2.42 (m, 2H), 2.16 (s, 3H), 2.11 (s, 3H), 2.04 (t, J=7.5 Hz, 2H), 1.59 (d, J=6.9 Hz, 3H), 1.59-1.52 (m, 2H).

Example 8(104)

4-(2-((2-(naphthalen-1-yl)propanoyl)amino)-4-(1-oxo-1,2,3,4-tetrahydronaphthalen-6-yloxymethyl)phenyl)butanoic acid

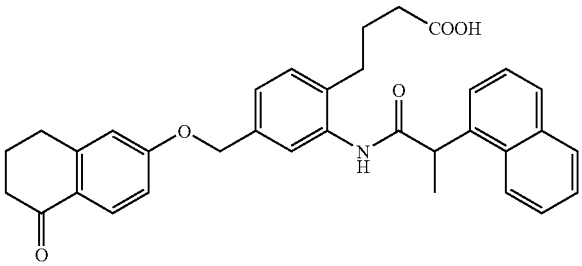

TLC: Rf 0.62 (chloroform:methanol=9:1);

NMR (300 MHz, DMSO-$d_6$): δ 9.56 (s, 1H), 8.31 (d, J=8.1 Hz, 1H), 7.94 (d, J=6.9 Hz, 1H), 7.84-7.78 (m, 2H), 7.59-7.47 (m, 4H), 7.40 (s, 1H), 7.19 (brs, 2H), 6.93-6.91 (m, 2H), 5.10 (s, 2H), 4.70 (q, J=6.9 Hz, 1H), 2.88 (t, J=6.0 Hz, 2H), 2.53-2.50 (m, 2H), 2.44 (dd, J=8.7, 5.4 Hz, 2H), 2.05-1.97 (m, 4H), 1.60 (d, J=6.9 Hz, 3H), 1.59-1.52 (m, 2H).

Example 8(105)

4-(2-((2-(naphthalen-1-yl)propanoyl)amino)-4-(3-cyanophenoxymethyl)phenyl)butanoic acid

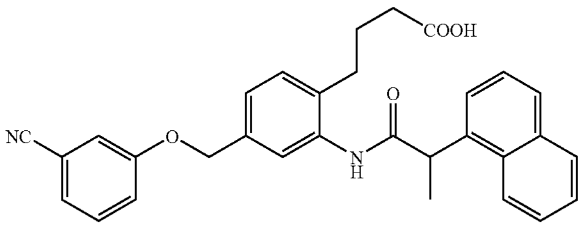

TLC: Rf 0.62 (chloroform:methanol=9:1);

NMR (300 MHz, DMSO-$d_6$): δ 9.53 (s, 1H), 8.30 (d, J=8.1 Hz, 1H), 7.94 (d, J=7.5 Hz, 1H), 7.83 (d, J=7.8 Hz, 1H), 7.62-7.45 (m, 6H), 7.43-7.36 (m, 2H), 7.32 (m, 1H), 7.20 (s, 2H), 5.09 (s, 2H), 4.70 (q, J=6.9 Hz, 1H), 2.48-2.41 (m, 2H), 2.03 (t, J=7.5 Hz, 2H), 1.60 (d, J=6.6 Hz, 3H), 1.58-1.54 (m, 2H).

Example 8(106)

4-(2-((2-(naphthalen-1-yl)propanoyl)amino)-4-(3-chloro-5-methoxyphenoxymethyl)phenyl)butanoic acid

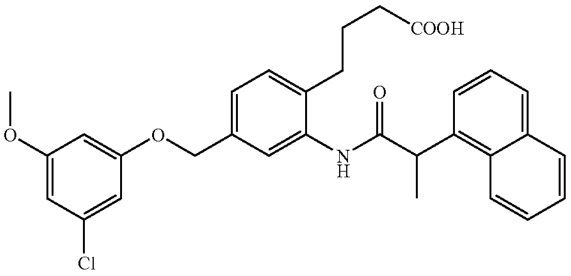

TLC: Rf 0.59 (chloroform:methanol=9:1);

NMR (300 MHz, DMSO-$d_6$): δ 9.55 (s, 1H), 8.31 (d, J=8.4 Hz, 1H), 7.94 (d, J=7.2 Hz, 1H), 7.83 (d, J=7.8 Hz, 1H), 7.61-7.47 (m, 4H), 7.37 (s, 1H), 7.18 (s, 2H), 6.63 (m, 1H), 6.59 (m, 1H), 6.52 (m, 1H), 5.02 (s, 2H), 4.70 (q, J=6.6 Hz, 1H), 3.72 (s, 3H), 2.49-2.41 (m, 2H), 2.02 (t, J=7.2 Hz, 2H), 1.60 (d, J=6.6 Hz, 3H), 1.59-1.51 (m, 2H).

Example 8(107)

4-(2-((2-(naphthalen-1-yl)propanoyl)amino)-4-(4-ethyl-2-methoxyphenoxymethyl)phenyl)butanoic acid

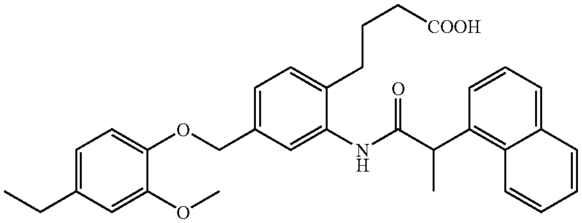

TLC: Rf 0.60 (chloroform:methanol=9:1);

NMR (300 MHz, DMSO-$d_6$): δ 9.54 (s, 1H), 8.31 (d, J=8.1 Hz, 1H), 7.95 (d, J=7.8 Hz, 1H), 7.83 (d, J=8.1 Hz, 1H), 7.61-7.47 (m, 4H), 7.36 (s, 1H), 7.17 (s, 2H), 6.88 (d, J=8.4 Hz, 1H), 6.80 (d, J=1.5 Hz, 1H), 6.65 (dd, J=8.4, 1.5 Hz, 1H), 4.94 (s, 2H), 4.69 (q, J=6.9 Hz, 1H), 3.72 (s, 3H), 2.52 (q, J=7.5 Hz, 2H), 2.43 (dd, J=8.7, 5.4 Hz, 2H), 2.03 (t, J=7.5 Hz, 2H), 1.60 (d, J=6.9 Hz, 3H), 1.59-1.52 (m, 2H), 1.14 (t, J=7.5 Hz, 3H).

Example 8(108)

4-(2-((2-(naphthalen-1-yl)propanoyl)amino)-4-(4-acetylamino-2-chlorophenoxymethyl)phenyl)butanoic acid

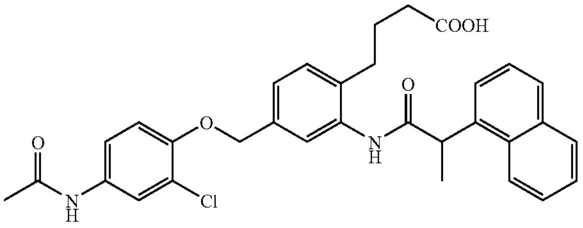

TLC: Rf 0.49 (chloroform:methanol=9:1);

NMR (300 MHz, DMSO-$d_6$): δ 9.95 (s, 1H), 9.56 (s, 1H), 8.31 (d, J=8.4 Hz, 1H), 7.94 (d, J=8.4 Hz, 1H), 7.83 (d, J=7.8 Hz, 1H), 7.76 (d, J=2.4 Hz, 1H), 7.61-7.47 (m, 4H), 7.39 (brs, 1H), 7.34 (dd, J=8.7, 2.4 Hz, 1H), 7.19 (s, 2H), 7.13 (d, J=8.7 Hz, 1H), 5.07 (s, 2H), 4.70 (q, J=6.9 Hz, 1H), 2.47-2.41 (m, 2H), 2.03 (t, J=7.5 Hz, 2H), 2.00 (s, 3H), 1.59 (d, J=6.9 Hz, 3H), 1.59-1.53 (m, 2H).

Example 8(109)

4-(2-((2-(naphthalen-1-yl)propanoyl)amino)-4-(2-methylthiophenoxymethyl)phenyl)butanoic acid

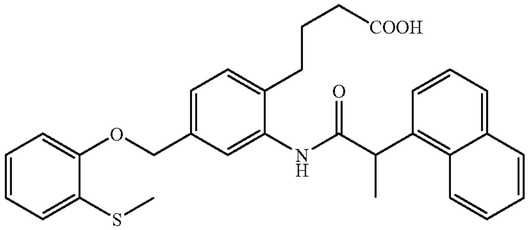

TLC: Rf 0.62 (chloroform:methanol=9:1);

NMR (300 MHz, DMSO-$d_6$): δ 9.56 (s, 1H), 8.31 (d, J=8.1 Hz, 1H), 7.94 (d, J=7.2 Hz, 1H), 7.83 (d, J=8.1 Hz, 1H), 7.62-7.47 (m, 4H), 7.39 (s, 1H), 7.24-6.93 (m, 6H), 5.08 (s, 2H), 4.70 (q, J=6.9 Hz, 1H), 2.47-2.40 (m, 2H), 2.35 (s, 3H), 2.04 (t, J=7.5 Hz, 2H), 1.59 (d, J=6.9 Hz, 3H), 1.59-1.53 (m, 2H).

Example 8(110)

4-(2-((2-(naphthalen-1-yl)propanoyl)amino)-4-(4-butanoylphenoxymethyl)phenyl)butanoic acid

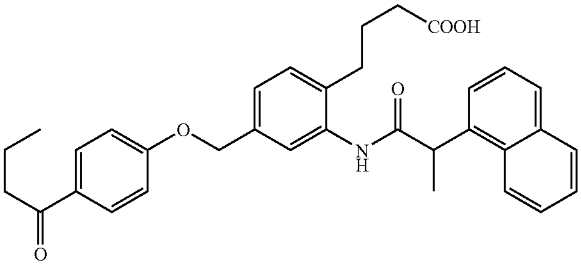

TLC: Rf 0.62 (chloroform:methanol=9:1);

NMR (300 MHz, DMSO-$d_6$): δ 9.55 (s, 1H), 8.31 (d, J=8.1 Hz, 1H), 7.96-7.90 (m, 3H), 7.83 (d, J=7.8 Hz, 1H), 7.61-7.47 (m, 4H), 7.40 (brs, 1H), 7.19 (s, 2H), 7.07 (d, J=9.0 Hz, 2H), 5.12 (s, 2H), 4.70 (q, J=6.9 Hz, 1H), 2.91 (t, J=7.2 Hz, 2H), 2.44 (dd, J=8.7, 5.7 Hz, 2H), 2.03 (t, J=7.2 Hz, 2H), 1.68-1.52 (m, 4H), 1.60 (d, J=6.9 Hz, 3H), 0.90 (t, J=7.5 Hz, 3H).

Example 8(111)

(2E)-3-(2-((4-methyl-2-phenylpentanoyl)amino)-4-phenoxymethylphenyl)-2-propenoic acid

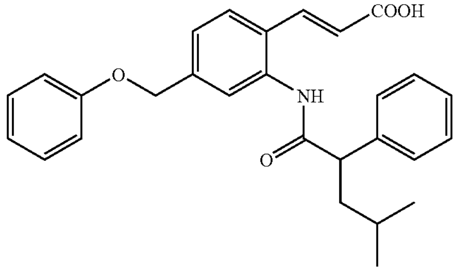

TLC: Rf 0.39 (chloroform:methanol=9:1).

Example 8(112)

4-(2-((2-(4-fluoronaphthalen-1-yl)propanoyl)amino)-4-(pyrazol-1-ylmethyl)phenyl)butanoic acid

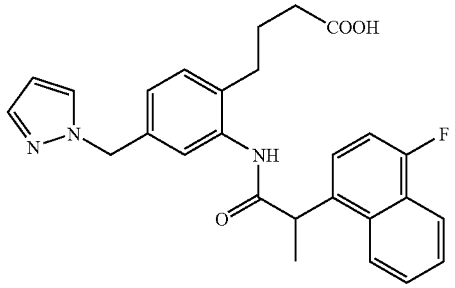

TLC: Rf 0.30 (ethyl acetate);

NMR (300 MHz, DMSO-$d_6$): δ 12.03 (s, 1H), 9.51 (s, 1H), 8.34 (d, J=8.1 Hz, 1H), 8.11-8.08 (m, 1H), 7.77 (d, J=2.1 Hz, 1H), 7.72-7.62 (m, 2H), 7.54 (dd, J=8.1, 5.7 Hz, 1H), 7.42 (d, J=2.1 Hz, 1H), 7.32 (dd, J=10.5, 8.1 Hz, 1H), 7.15-7.10 (m, 2H), 6.95 (dd, J=8.1, 1.5 Hz, 1H), 6.23 (t, J=2.1 Hz, 1H), 5.24 (s, 2H), 4.63 (q, J=6.9 Hz, 1H), 2.38 (t, J=7.8 Hz, 2H), 1.98 (t, J=7.8 Hz, 2H), 1.58 (d, J=6.9 Hz, 3H), 1.54-1.49 (m, 2H).

Example 8(113)

3-(2-((2-(4-fluoronaphthalen-1-yl)propanoyl)amino)-4-phenoxymethylphenyl)propanoic acid

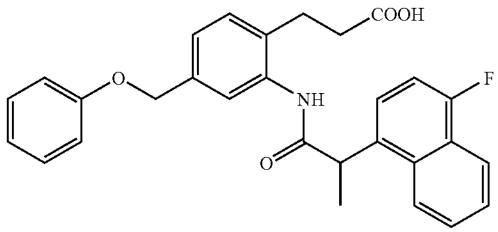

TLC: Rf 0.39 (hexane:ethyl acetate=1:1, 0.5% acetic acid);

NMR (300 MHz, DMSO-$d_6$): δ 12.13 (s, 1H), 9.64 (s, 1H), 8.34 (m, 1H), 8.10 (m, 1H), 7.74-7.61 (m, 2H), 7.54 (dd, J=8.1, 5.7 Hz, 1H), 7.36-7.17 (m, 6H), 6.99-6.88 (m, 3H), 5.01 (s, 2H), 4.66 (q, J=6.9 Hz, 1H), 2.72 (t, J=7.5 Hz, 2H), 2.36 (t, J=7.5 Hz, 2H), 1.59 (d, J=6.9 Hz, 3H).

Example 8(114)

3-(2-((2-(4-fluoronaphthalen-1-yl)propanoyl)amino)-4-phenylaminomethylphenyl)propanoic acid

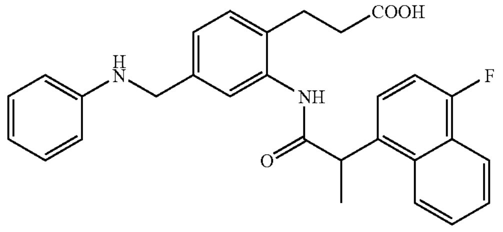

TLC: Rf 0.33 (hexane:ethyl acetate=1:1, 0.5% acetic acid);

NMR (300 MHz, DMSO-$d_6$): δ 12.12 (br, 1H), 9.67 (bs, 1H), 8.33 (m, 1H), 8.09 (m, 1H), 7.71-7.60 (m, 2H), 7.53 (dd, J=7.2, 6.6 Hz, 1H), 7.34-7.22 (m, 2H), 7.17-7.07 (m, 2H), 7.04-6.95 (m, 2H), 6.55-6.44 (m, 3H), 6.17 (t, J=5.7 Hz, 1H), 4.63 (q, J=6.9 Hz, 1H), 4.16 (d, J=5.7 Hz, 2H), 2.67 (t, J=7.5 Hz, 2H), 2.33 (t, J=7.5 Hz, 2H), 1.58 (d, J=6.9 Hz, 3H).

Example 8(115)

3-(2-((2-(4-fluoronaphthalen-1-yl)propanoyl)amino)-4-(pyrazol-1-ylmethyl)phenyl)propanoic acid

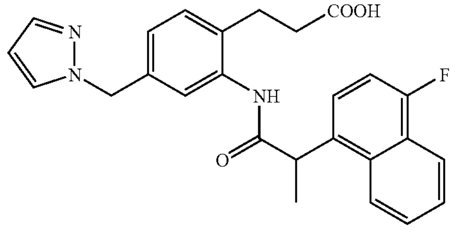

TLC: Rf 0.19 (hexane:ethyl acetate=1:2, 0.5% acetic acid);

NMR (300 MHz, DMSO-$d_6$): δ 12.12 (br, 1H), 9.64 (bs, 1H), 8.32 (m, 1H), 8.09 (m, 1H), 7.76 (d, J=2.1 Hz, 1H), 7.73-7.61 (m, 2H), 7.53 (dd, J=7.8, 5.7 Hz, 1H), 7.42 (d, J=2.1 Hz, 1H), 7.30 (dd, J=10.5, 7.8 Hz, 1H), 7.16 (d, J=7.8 Hz, 1H), 7.13 (d, J=1.5 Hz, 1H), 6.95 (dd, J=7.8, 1.5 Hz, 1H), 6.23 (t, J=2.1 Hz, 1H), 5.24 (s, 2H), 4.63 (q, J=6.9 Hz, 1H), 2.67 (t, J=7.8 Hz, 2H), 2.34 (t, J=7.8 Hz, 2H), 1.57 (d, J=6.9 Hz, 3H).

Example 8(116)

2-(2-((2-(4-fluoronaphthalen-1-yl)acetyl)amino)-4-phenoxymethylbenzyl)benzoic acid

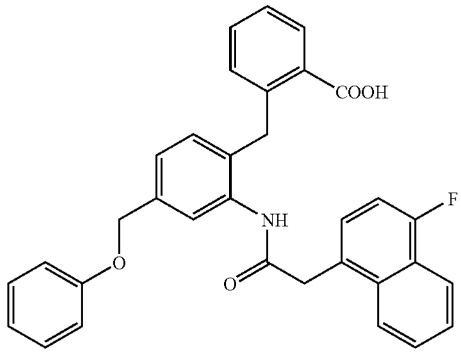

TLC: Rf 0.56 (chloroform:methanol=10:1);

NMR (300 MHz, DMSO-$d_6$): δ 9.79 (s, 1H), 8.12-8.02 (m, 2H), 7.87 (m, 1H), 7.67-7.52 (m, 3H), 7.47-7.11 (m, 7H), 7.06-6.87 (m, 5H), 5.02 (s, 2H), 4.35 (s, 2H), 4.11 (s, 2H).

Example 8(117)

2-(2-((2-(4-fluoronaphthalen-1-yl)propanoyl)amino)-4-phenoxymethylbenzyl)benzoic acid

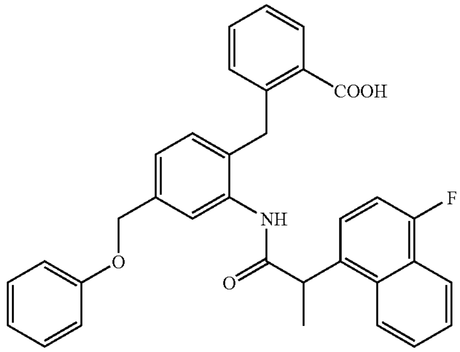

TLC: Rf 0.60 (chloroform:methanol=10:1);

NMR (300 MHz, DMSO-$d_6$): δ 9.70 (s, 1H), 8.26 (m, 1H), 8.07 (m, 1H), 7.79 (m, 1H), 7.68-7.53 (m, 3H), 7.45 (m, 1H), 7.41-7.21 (m, 5H), 7.16 (m, 1H), 7.04-6.86 (m, 5H), 5.03 (s, 2H), 4.62 (q, J=6.9 Hz, 1H), 4.27 (s, 2H), 1.48 (d, J=6.9 Hz, 3H).

Example 8(118)

2-(2-((4-methyl-2-phenylpentanoyl)amino)-4-phenoxymethylbenzyl)benzoic acid

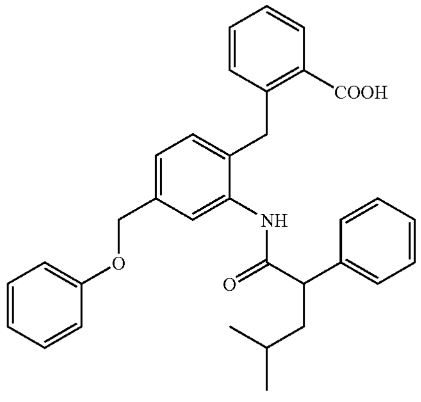

TLC: Rf 0.50 (chloroform:methanol=9:1);

NMR (300 MHz, $CDCl_3$): δ 8.15 (brs, 1H), 8.00-7.94 (m, 1H), 7.94-7.88 (m, 1H), 7.44-7.34 (m, 1H), 7.32-7.02 (m, 11H), 7.00-6.90 (m, 3H), 5.02 (s, 2H), 4.20 (s, 2H), 3.55 (t, J=7.5 Hz, 1H), 2.00-1.30 (m, 3H), 0.85 (d, J=6.0 Hz, 6H).

Example 8(119)

2-(2-((4-methyl-2-(3,5-dimethylphenyl)pentanoyl)amino)-4-phenoxymethylbenzyl)benzoic acid

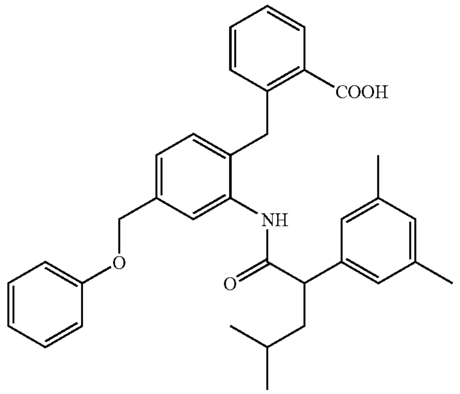

TLC: Rf 0.50 (chloroform:methanol=9:1);

NMR (300 MHz, $CDCl_3$): δ 8.16 (brs, 1H), 7.95 (d, J=7.5 Hz, 1H), 7.84 (brs, 1H), 7.42-7.34 (m, 1H), 7.32-6.90 (m, 9H), 6.81 (s, 3H), 5.02 (s, 2H), 4.25 (d, J=16.2 Hz, 1H), 4.15 (d, J=16.2 Hz, 1H), 3.47 (t, J=7.8 Hz, 1H), 2.22 (s, 6H), 2.04-1.90 (m, 1H), 1.66-1.55 (m, 1H), 1.50-1.30 (m, 1H), 0.85 (d, J=6.6 Hz, 6H).

Example 8(120)

2-(2-((2-(naphthalen-1-yl)acetyl)amino)-4-phenoxymethylbenzyl)benzoic acid

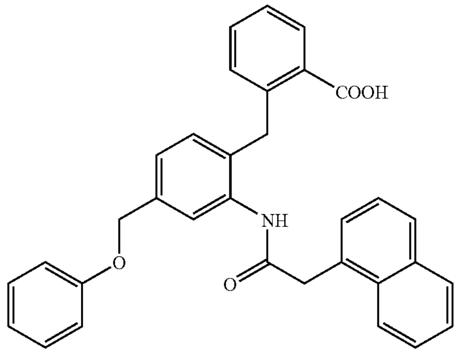

TLC: Rf 0.50 (chloroform:methanol=9:1);

NMR (300 MHz, $CDCl_3$): δ 8.08 (s, 1H), 8.00-7.89 (m, 2H), 7.82-7.73 (m, 1H), 7.72-7.66 (m, 1H), 7.52 (brs, 1H), 7.49-7.38 (m, 2H), 7.34-7.18 (m, 5H), 7.16-7.10 (m, 1H), 7.02-6.90 (m, 4H), 6.84-6.76 (m, 1H), 5.01 (s, 2H), 4.09 (s, 2H), 3.88 (s, 2H).

Example 8(121)

3-(2-((4-methyl-2-(4-fluoro-3-methylphenyl)pentanoyl)amino)-4-phenoxymethylphenyl)propanoic acid

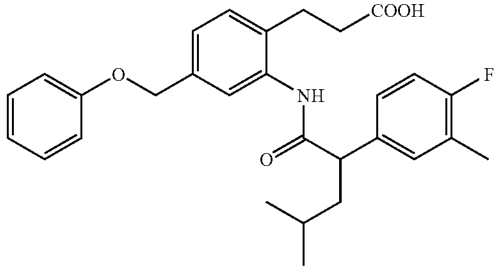

TLC: Rf 0.41 (chloroform:methanol=19:1);

NMR (300 MHz, $CDCl_3$): δ 8.23 (s, 1H), 7.80 (s, 1H), 7.33-7.09 (m, 6H), 7.00-6.90 (m, 4H), 4.98 (s, 2H), 3.62 (t, J=7.7 Hz, 1H), 2.70-2.55 (m, 4H), 2.25 (s, 3H), 2.10 (m, 1H), 1.74 (m, 1H), 1.54 (m, 1H), 0.95 (d, J=6.6 Hz, 3H), 0.93 (d, J=6.6 Hz, 3H).

Example 8(122)

3-(2-((4-methyl-2-(3,5-dimethylphenyl)pentanoyl)amino)-4-phenoxymethylphenyl)propanoic acid

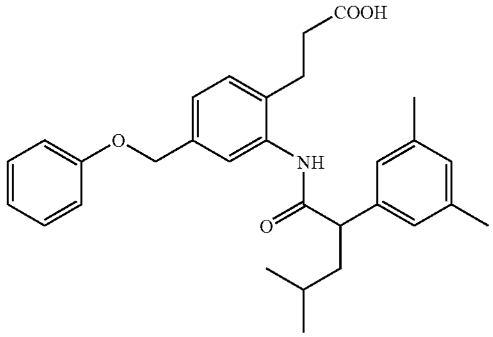

TLC: Rf 0.30 (hexane:ethyl acetate=1:2);

NMR (300 MHz, DMSO-$d_6$): δ 12.09 (s, 1H), 9.51 (s, 1H), 7.30-7.15 (m, 5H), 6.99-6.84 (m, 6H), 5.00 (s, 2H), 3.79-3.74 (m, 1H), 2.70 (t, J=7.5 Hz, 2H), 2.32 (t, J=7.5 Hz, 2H), 2.24 (s, 6H), 2.02-1.94 (m, 1H), 1.54-1.39 (m, 2H), 0.93 (d, J=6.0 Hz, 3H), 0.89 (d, J=6.0 Hz, 3H).

Example 8(123)

3-(2-((4-methyl-2-(4-methoxy-1,3-dioxaindan-6-yl)pentanoyl)amino)-4-phenoxymethylphenyl)propanoic acid

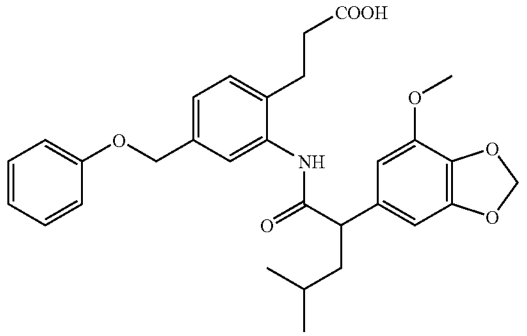

[Salt-free]

TLC: Rf 0.50 (ethyl acetate);

NMR (300 MHz, $CDCl_3$): δ 8.29 (s, 1H), 7.82 (s, 1H), 7.30-7.12 (m, 4H), 6.97-6.93 (m, 3H), 6.61 (d, J=6.0 Hz, 2H), 5.93 (s, 2H), 4.99 (s, 2H), 3.89 (s, 3H), 3.58 (t, J=7.5 Hz, 1H), 2.70-2.64 (m, 4H), 2.12-2.02 (m, 1H), 1.79-1.69 (m, 1H), 1.61-1.52 (m, 1H), 0.96-0.93 (m, 6H).

Sodium Salt:

TLC: Rf 0.35 (n-hexane:ethyl acetate=1:2).

Example 8(124)

2-(2-((2-(naphthalen-1-yl)propanoyl)amino)-4-(2-methylphenoxymethyl)benzyl)benzoic acid

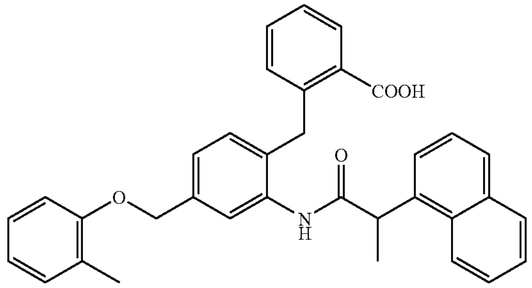

TLC: Rf 0.26 (hexane:ethyl acetate=2:1, 0.5% acetic acid);

NMR (300 MHz, DMSO-$d_6$): δ 12.94 (bs, 1H), 9.62 (bs, 1H), 8.21 (m, 1H), 7.92 (m, 1H), 7.83-7.77 (m, 2H), 7.57-7.25 (m, 7H), 7.17-7.07 (m, 3H), 7.00-6.79 (m, 4H), 5.03 (s, 2H), 4.64 (q, J=6.9 Hz, 1H), 4.28 (d, J=16.5 Hz, 1H), 4.23 (d, J=16.5 Hz, 1H), 2.15 (s, 3H), 1.48 (d, J=6.9 Hz, 3H).

Example 8(125)

2-(2-((2-(naphthalen-1-yl)propanoyl)amino)-4-(2-chloro-5-methylphenoxymethyl)benzyl)benzoic acid

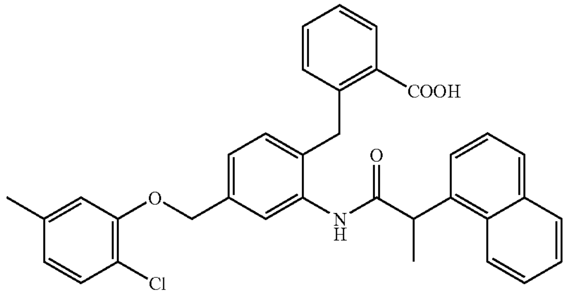

TLC: Rf 0.23 (hexane:ethyl acetate=2:1, 0.5% acetic acid);

NMR (300 MHz, DMSO-$d_6$): δ 12.94 (bs, 1H), 9.64 (bs, 1H), 8.22 (m, 1H), 7.92 (m, 1H), 7.83-7.77 (m, 2H), 7.58-7.25 (m, 8H), 7.15 (dd, J=8.1, 1.5 Hz, 1H), 7.06 (d, J=1.5 Hz, 1H), 6.97-6.88 (m, 2H), 6.76 (dd, J=8.1, 1.5 Hz, 1H), 5.09 (s, 2H), 4.65 (q, J=7.5 Hz, 1H), 4.29 (d, J=16.5 Hz, 1H), 4.23 (d, J=16.5 Hz, 1H), 2.26 (s, 3H), 1.48 (d, J=7.5 Hz, 3H).

Example 8(126)

2-(2-((2-(naphthalen-1-yl)propanoyl)amino)-4-(3-cyanophenoxymethyl)benzyl)benzoic acid

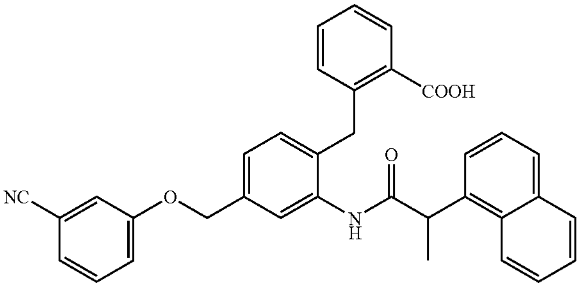

TLC: Rf 0.17 (hexane:ethyl acetate=2:1, 0.5% acetic acid);

NMR (300 MHz, DMSO-$d_6$): δ 12.95 (s, 1H), 9.63 (s, 1H), 8.20 (m, 1H), 7.91 (m, 1H), 7.83-7.76 (m, 2H), 7.57-7.25 (m, 11H), 7.14 (dd, J=8.1, 1.5 Hz, 1H), 6.96-6.87 (m, 2H), 5.09 (s, 2H), 4.64 (q, J=6.9 Hz, 1H), 4.29 (d, J=16.5 Hz, 1H), 4.22 (d, J=16.5 Hz, 1H), 1.47 (d, J=6.9 Hz, 3H).

Example 8(127)

2-(2-((2-(naphthalen-1-yl)propanoyl)amino)-4-(pyridin-3-yloxymethyl)benzyl)benzoic acid

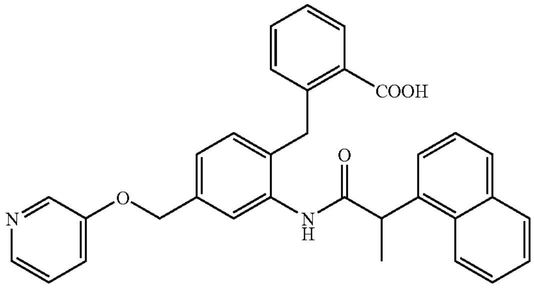

TLC: Rf 0.44 (ethyl acetate, 0.5% acetic acid);

NMR (300 MHz, DMSO-$d_6$): δ 12.95 (bs, 1H), 9.75 (bs, 1H), 8.31 (bs, 1H), 8.23-8.12 (m, 2H), 7.91 (m, 1H), 7.82-7.75 (m, 2H), 7.57 (bs, 1H), 7.54-7.24 (m, 8H), 7.14 (m, 1H), 6.96-6.88 (m, 2H), 5.09 (s, 2H), 4.66 (q, J=6.9 Hz, 1H), 4.29 (d, J=16.5 Hz, 1H), 4.22 (d, J=16.5 Hz, 1H), 1.47 (d, J=6.9 Hz, 3H).

Example 8(128)

4-(2-(naphthalen-1-yl)carbonylamino-4-cyanophenyl)butanoic acid

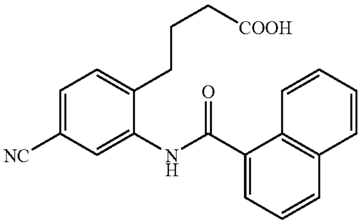

TLC: Rf 0.30 (ethyl acetate);

NMR (300 MHz, DMSO-$d_6$): δ 12.10 (s, 1H), 10.30 (s, 1H), 8.29-8.26 (m, 1H), 8.10-8.00 (m, 3H), 7.83 (dd, J=7.2, 0.9 Hz, 1H), 7.70 (dd, J=7.8, 1.8 Hz, 1H), 7.65-7.58 (m, 3H), 7.52 (d, J=8.1 Hz, 1H), 2.78 (t, J=7.8 Hz, 2H), 2.26 (t, J=7.5 Hz, 2H), 1.88-1.78 (m, 2H).

Example 8(129)

7-((2-(naphthalen-1-yl)acetyl)amino)-2-benzofurancarboxylic acid

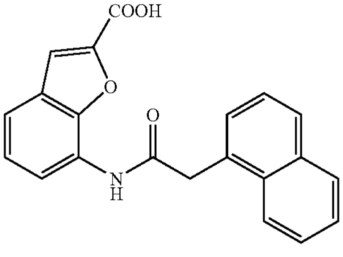

TLC: Rf 0.43 (chloroform:methanol:acetic acid=90:10:1);

NMR (300 MHz, DMSO-$d_6$): δ 10.56 (s, 1H), 8.18 (d, J=8.1 Hz, 1H), 7.97-7.81 (m, 3H), 7.70 (d, J=0.6 Hz, 1H), 7.62-7.43 (m, 5H), 7.26 (t, J=7.8 Hz, 1H), 4.31 (s, 2H).

Example 8(130)

7-((2-(naphthalen-1-yl)propanoyl)amino)-2-benzofurancarboxylic acid

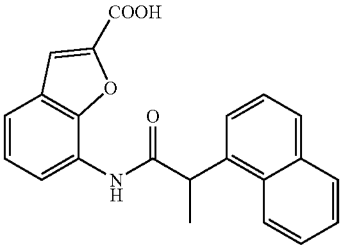

TLC: Rf 0.46 (chloroform:methanol:acetic acid=90:10:1);

NMR (300 MHz, DMSO-$d_6$): δ 10.4 (s, 1H), 8.32 (d, J=8.4 Hz, 1H), 7.94 (d, J=8.4 Hz, 1H), 7.86-7.78 (m, 2H), 7.69-7.45 (m, 6H), 7.27 (m, 1H), 4.91 (q, J=6.9 Hz, 1H), 1.58 (d, J=6.9 Hz, 3H).

Example 8(131)

7-((4-methyl-2-(naphthalen-1-yl)pentanoyl)amino)-2-benzofurancarboxylic acid

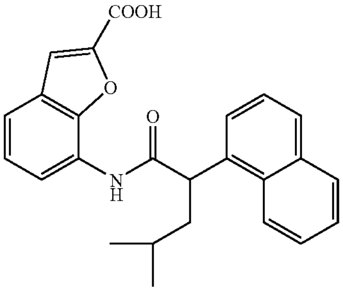

TLC: Rf 0.48 (chloroform:methanol:acetic acid=90:10:1);

NMR (300 MHz, DMSO-$d_6$): δ 10.5 (s, 1H), 8.42 (d, J=8.4 Hz, 1H), 7.94 (d, J=8.1 Hz, 1H), 7.86 (d, J=7.8 Hz, 1H), 7.82 (d, J=7.8 Hz, 1H), 7.74-7.60 (m, 3H), 7.58-7.44 (m, 3H), 7.27 (m, 1H), 4.93 (m, 1H), 2.12 (m, 1H), 1.76-1.53 (m, 2H), 1.07 (d, J=6.3 Hz, 3H), 0.93 (d, J=6.3 Hz, 3H).

Example 8(132)

2-(1-(2-(naphthalen-1-yl)propionyl)indol-3-yl)acetic acid

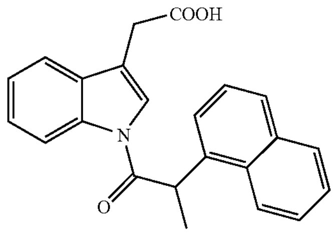

TLC: Rf 0.29 (chloroform:methanol=19:1);

NMR (300 MHz, $CDCl_3$): δ 8.62 (d, J=8.4 Hz, 1H), 8.18 (d, J=8.4 Hz, 1H), 7.90 (d, J=8.4 Hz, 1H), 7.75 (d, J=8.4 Hz, 1H), 7.63 (m, 1H), 7.53 (dd, J=7.8, 7.8 Hz, 1H), 7.46-7.25 (m, 5H), 7.15 (s, 1H), 5.18 (q, J=6.9 Hz, 1H), 3.54 (d, J=17.1 Hz, 1H) 3.46 (d, J=17.1 Hz, 1H), 1.73 (d, J=6.9 Hz, 3H).

Example 8(133)

2-(2-methyl-1-(2-(naphthalen-1-yl)propionyl)indol-3-yl)acetic acid

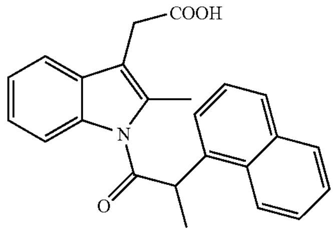

TLC: Rf 0.33 (chloroform:methanol=19:1);

NMR (300 MHz, $CDCl_3$): δ 8.00 (d, J=8.4 Hz, 1H), 7.89 (d, J=8.4 Hz, 1H), 7.79 (d, J=7.8 Hz, 1H), 7.75 (d, J=8.1 Hz, 1H), 7.60-7.35 (m, 5H), 7.18 (dd, J=7.5, 7.5 Hz, 1H), 7.08 (dd, J=7.8, 7.8 Hz, 1H), 5.37 (q, J=6.6 Hz, 1H), 3.63 (s, 2H), 2.48 (s, 3H), 1.78 (d, J=6.6 Hz, 3H).

Example 8(134)

3-(1-(2-(naphthalen-1-yl)propionyl)indol-3-yl)propanoic acid

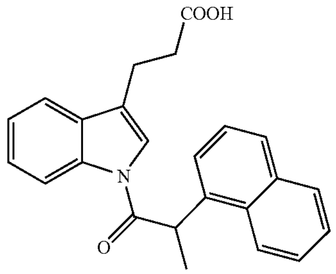

TLC: Rf 0.22 (chloroform:methanol=19:1);

NMR (300 MHz, $CDCl_3$): δ 8.60 (d, J=7.8 Hz, 1H), 8.20 (d, J=8.1 Hz, 1H), 7.92 (d, J=7.8 Hz, 1H), 7.76 (dd, J=7.5, 2.1 Hz, 1H), 7.67 (m, 1H), 7.57 (dd, J=7.5, 7.5 Hz, 1H), 7.46-7.24 (m, 5H), 6.95 (s, 1H), 5.14 (q, J=6.9 Hz, 1H), 2.88-2.73 (m, 2H), 2.45 (t, J=7.5 Hz, 2H), 1.74 (d, J=6.9 Hz, 3H).

Example 8(135)

3-(2-methyl-1-(2-(naphthalen-1-yl)propionyl)indol-3-yl)propanoic acid

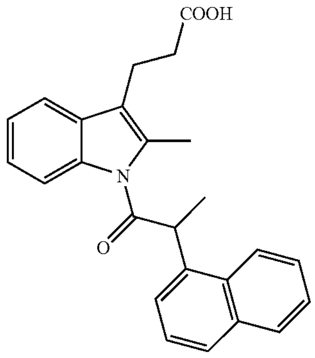

TLC: Rf 0.46 (chloroform:methanol=19:1);

NMR (300 MHz, $CDCl_3$): δ 8.00 (d, J=8.1 Hz, 1H), 7.89 (d, J=8.1 Hz, 1H), 7.84 (d, J=8.1 Hz, 1H), 7.75 (d, J=8.1 Hz, 1H), 7.60-7.34 (m, 5H), 7.18 (dd, J=7.5, 7.5 Hz, 1H), 7.09 (dd, J=7.5, 7.5 Hz, 1H), 5.38 (q, J=6.6 Hz, 1H), 2.94 (t, J=7.5 Hz, 2H), 2.57 (t, J=7.5 Hz, 2H), 2.46 (s, 3H), 1.78 (d, J=6.6 Hz, 3H).

Example 8(136)

3-(6-cyano-1-(2-(naphthalen-1-yl)propionyl)indol-3-yl)propanoic acid

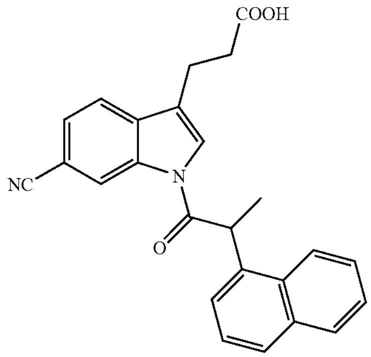

TLC: Rf 0.44 (n-hexane:ethyl acetate:acetic acid=100:100:1);

NMR (300 MHz, DMSO-$d_6$): δ 8.72 (s, 1H), 8.30 (d, J=8.7 Hz, 1H), 7.98 (d, J=8.1 Hz, 1H), 7.85 (d, J=7.5 Hz, 1H), 7.81-7.77 (m, 2H), 7.69-7.55 (m, 3H), 7.47-7.39 (m, 2H), 5.59 (q, J=6.9 Hz, 1H), 2.86-2.67 (m, 2H), 2.53-2.35 (m, 2H), 1.64 (d, J=6.9 Hz, 3H).

Reference Example 16 methyl 4-hydroxymethyl-2-iodobenzoate

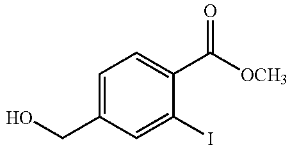

Using methyl 2-amino-4-carboxybenzoate, the title compounds having the following physical data were obtained by the same procedures as a series of reactions of Reference Example 2→Reference Example 12.

NMR (300 MHz, $CDCl_3$): δ 8.02-8.01 (m, 1H), 7.81 (d, J=8.1 Hz, 1H), 7.41-7.37 (m, 1H), 4.71 (s, 2H), 3.93 (s, 3H).

Reference Example 17 methyl 2-iodo-4-phenoxymethylbenzoate

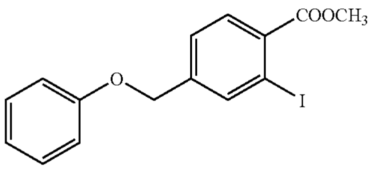

To a solution of the compound prepared in Reference Example 16 (3.66 g) in methylene chloride (20 ml) was added mesyl chloride (1.07 ml) and triethylamine (1.92 ml) at 0° C. under an atmosphere of argon. The mixture was stirred for 10 minutes. To the mixture was added water and the mixture was extracted with ethyl acetate. The organic layer was washed with water and a saturated aqueous solution of sodium chloride, dried over anhydrous magnesium sulfate and concentrated to give the mesylate. To a suspension of sodium hydride (525 mg, 63.1%) in N,N-dimethylformamide (5 ml) was added phenol (1.30 g) and the mixture was stirred at room temperature for 1 hour. To the mixture was added the above-mentioned solution of the mesylate in N,N-dimethylformamide (10 ml) and the mixture was stirred at room temperature for 10 minutes. To the reaction mixture was added 1N hydrochloric acid, the mixture was extracted with ethyl acetate, The organic layer was washed with water and a saturated aqueous solution of sodium chloride subsequently, dried over anhydrous magnesium sulfate and then concentrated. The residue was purified by column chromatography on silica gel to give the title compound (4.44 g) having the following physical data.

NMR (300 MHz, $CDCl_3$): δ 8.08 (s, 1H), 7.82 (d, J=8.1 Hz, 1H), 7.48-7.45 (m, 1H), 7.33-7.28 (m, 2H), 7.02-6.94 (m, 3H), 5.05 (s, 2H), 3.93 (s, 3H).

Reference Example 18

2-(naphthalen-2-ylmethyl)-4-phenoxymethylbenzylalcohol

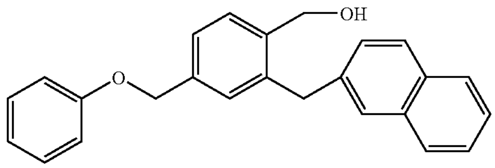

To the suspension of zinc (710 mg) in tetrahydrofuran (2 ml) was added dibromoethane (1 drop) under an atmosphere of argon. The mixture was heated and then added trimethylsilyl chloride (1 drop). The reaction mixture was cooled to 0° C. and added dropwise a solution of 2-bromomethylnaphthalene (1.20 g) in tetrahydrofuran (3 ml). The mixture was stirred at room temperature for 1.5 hour to give the zinc reagent. To a solution of [bis(benzylidene)acetone]palladium (156 mg) and diphenylphosphinoferrocene (151 mg) in tetrahydrofuran (2 ml) was added the compound prepared in Reference Example 17 (1.00 g) in tetrahydrofuran (3 ml) under an atmosphere of argon. To the mixture was added the above-mentioned zinc reagent. The mixture was stirred at room temperature for 30 minutes. To the mixture was added a saturated aqueous solution of ammonium chloride. The mixture was extracted with ethyl acetate. The organic layer was washed with water and a saturated aqueous solution of sodium chloride subsequently, dried over anhydrous magnesium sulfate and concentrated. The residue was purified by column chromatography on silica gel to give methyl 2-(2-naphthylmethyl)-4-phenoxymethylbenzoate. To a suspension of lithium alminium hydride (206 mg) in (2 ml) was added dropwise a solution of the above-mentioned methyl 2-(2-naphthylmethyl)-4-phenoxymethylbenzoate in diethyl ether (3 ml)-tetrahydrofuran (3 ml) under an atmosphere of argon. The mixture was stirred for 30 minutes. To the mixture was added 1N hydrochloric acid. The mixture was extracted with ethyl acetate. The organic layer was washed with water and a saturated aqueous solution of sodium chloride subsequently, dried over anhydrous magnesium sulfate and concentrated. The residue was purified by column chromatography on silica gel to give the title compound (974 mg) having the following physical data.

NMR (300 MHz, $CDCl_3$): δ 7.82-7.71 (m, 3H), 7.53-7.35 (m, 5H), 7.30-7.25 (m, 4H), 6.98-6.93 (m, 3H), 5.04 (s, 2H), 4.69 (d, J=4.8 Hz, 2H), 4.26 (s, 2H), 1.46-1.44 (m, 1H).

Reference Example 19

2-(naphthalen-2-ylmethyl)-4-phenoxymethylbenzaldehyde

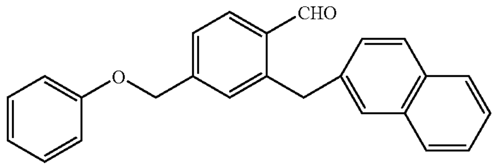

To a solution of the compound prepared in Reference Example 18 (974 mg) in ethyl acetate (5 ml) were added dimethylsulfoxide (1 ml), triethylamine (1.17 ml) and pyridinium sulfate (671 mg) at 0° C. under an atmosphere of argon. The mixture was stirred at room temperature for 1 hour. To the reaction mixture was added water. The mixture was extracted with ethyl acetate. The organic layer was washed with water and a saturated aqueous solution of sodium chloride subsequently, dried over anhydrous magnesium sulfate and concentrated. The residue was purified by column chromatography on silica gel to give the title compound (871 mg) having the following physical data.

NMR (300 MHz, $CDCl_3$): δ 10.27 (s, 1H), 7.90 (d, J=7.5 Hz, 1H), 7.80-7.70 (m, 3H), 7.53-7.25 (m, 8H), 7.00-6.92 (m, 3H), 5.10 (s, 2H), 4.62 (s, 2H).

Example 9

(2E)-3-(2-(naphthalen-2-ylmethyl)-4-phenoxymethylphenyl)-2-propenoic acid

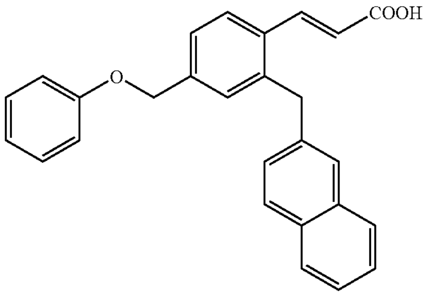

To a solution of the compound prepared in Reference Example 19 (871 mg) in pyridine (5 ml) were added malonic acid (574 mg) and piperidine (0.16 ml). The mixture was stirred at 120° C. overnight. To the reaction mixture was added 1N hydrochloric acid. The mixture was extracted with ethyl acetate. The organic layer was washed with water and a saturated aqueous solution of sodium chloride subsequently, dried over anhydrous magnesium sulfate and concentrated. The residue was washed with n-hexane-ethyl acetate to give the title compound (810 mg) having the following physical data.

TLC: Rf 0.60 (ethyl acetate);

NMR (300 MHz, $CDCl_3$); 8.17 (d, J=15.6 Hz, 1H), 7.80-7.65 (m, 4H), 7.52 (s, 1H), 7.44-7.37 (m, 3H), 7.31-7.25 (m, 4H), 6.99-6.93 (m, 3H), 6.35 (d, J=15.6 Hz, 1H), 5.05 (s, 2H), 4.31 (s, 2H).

Example 9(1)~Example 9(6)

Using corresponding compounds, the following compounds were obtained by the same procedure of Example 9.

Example 9(1)

(2E)-3-(2-(naphthalen-2-ylmethyl)-4-(pyrazol-1-ylmethyl)phenyl)-2-propenoic acid

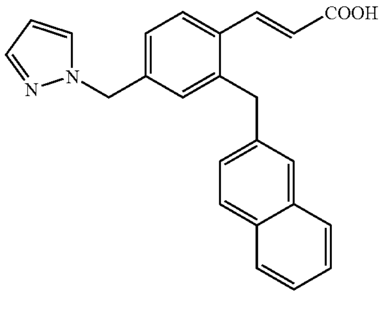

TLC: Rf 0.50 (ethyl acetate).

Example 9(2)

(2E)-3-(2-benzyl-4-phenoxymethylphenyl)-2-propenoic acid

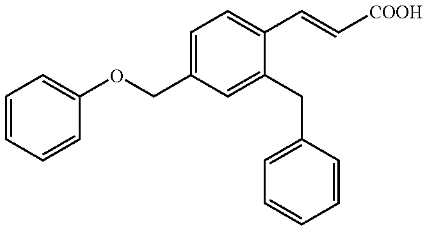

TLC: Rf 0.24 (chloroform:methanol=9:1);

NMR (300 MHz, $CDCl_3$): δ 8.10 (d, J=15.9 Hz, 1H), 7.64 (d, J=8.1 Hz, 1H), 7.40-7.10 (m, 9H), 7.00-6.93 (m, 3H), 6.34 (d, J=15.9 Hz, 1H), 5.06 (s, 2H), 4.15 (s, 2H).

Example 9(3)

3-(2-(naphthalen-2-ylmethyl)-4-phenoxymethylphenyl)propanoic acid

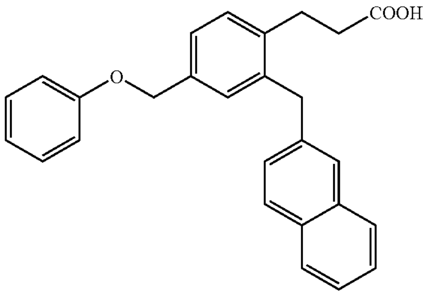

TLC: Rf 0.65 (ethyl acetate);

NMR (300 MHz, DMSO-$d_6$): δ 12.10 (s, 1H), 7.87-7.75 (m, 3H), 7.58 (s, 1H), 7.49-7.41 (m, 2H), 7.31-7.22 (m, 6H), 6.97-6.89 (m, 3H), 5.02 (s, 2H), 4.18 (s, 2H), 2.84 (t, J=8.1 Hz, 2H), 2.39 (t, J=8.1 Hz, 2H).

Example 9(4)

3-(2-(naphthalen-2-ylmethyl)-4-(pyrazol-1-ylmethyl)phenyl)propanoic acid

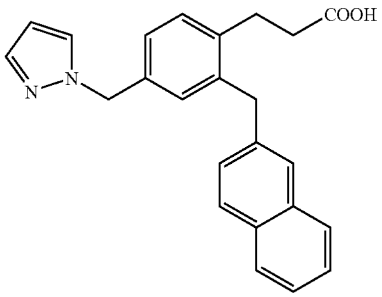

TLC: Rf 0.45 (ethyl acetate);

NMR (300 MHz, DMSO-$d_6$): δ 12.08 (s, 1H), 7.87-7.76 (m, 4H), 7.56 (s, 1H), 7.48-7.41 (m, 3H), 7.27 (dd, J=8.1, 1.5 Hz, 1H), 7.17 (d, J=8.1 Hz, 1H), 7.08 (s, 1H), 6.99 (dd, J=8.1, 1.5 Hz, 1H), 6.22 (t, J=2.1 Hz, 1H), 5.25 (s, 2H), 4.14 (s, 2H), 2.80 (t, J=7.8 Hz, 2H), 2.36 (t, J=7.8 Hz, 2H).

Example 9(5)

(2E)-3-(2-(3-phenylpropyl)-4-(pyrazol-1-ylmethyl)phenyl)-2-propenoic acid

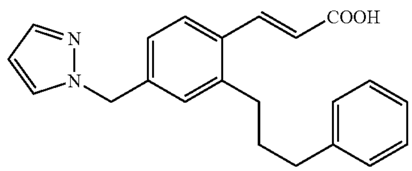

TLC: Rf 0.35 (hexane:ethyl acetate=1:1, 0.5% acetic acid);

NMR (300 MHz, $CDCl_3$): δ 8.01 (d, J=15.9 Hz, 1H), 7.59-7.53 (m, 2H), 7.40 (d, J=2.1 Hz, 1H), 7.32-7.25 (m, 2H), 7.22-7.14 (m, 3H), 7.08-7.02 (m, 2H), 6.35 (d, J=15.9 Hz, 1H), 6.30 (t, J=2.1 Hz, 1H), 5.32 (s, 2H), 2.75 (t, J=7.5 Hz, 2H), 2.66 (t, J=7.5 Hz, 2H), 1.89 (m, 2H).

Example 9(6)

2-(2-(3-(naphthalen-2-yl)propyl)-4-(pyrazol-1-ylmethyl)phenoxy)acetic acid

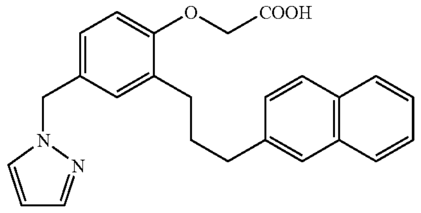

TLC: Rf 0.20 (chloroform:methanol=10:1).

Example 10

(2E)-N-phenylsulfonyl-3-(2-(naphthalen-2-ylmethyl)-4-phenoxymethylphenyl)-2-propenamide

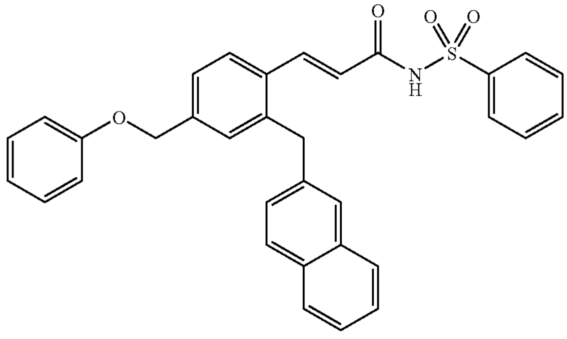

To a solution of the compound prepared in Example 9 (200 mg) in N,N-dimethylformamide (1 ml) were added benzenesulfonamide (120 mg), 1-ethyl-3-[3-(dimethylamino)propyl]carbodiimide hydrochloride (146 mg) and dimethylaminopyridine (19 mg). The mixture was stirred at room temperature overnight. To the reaction mixture was added water. The mixture was extracted with ethyl acetate. The organic layer was washed with water and a saturated aqueous solution of sodium chloride subsequently, dried over anhydrous magnesium sulfate and concentrated. The residue was purified by column chromatography on silica gel to give the title compound (151 mg) having the following physical data.

TLC: Rf 0.55 (n-hexane:ethyl acetate=1:1);

NMR (300 MHz, DMSO-$d_6$): δ 12.27 (s, 1H), 7.94-7.22 (m, 18H), 6.97-6.89 (m, 3H), 6.46 (d, J=15.6 Hz, 1H), 5.10 (s, 2H), 4.26 (s, 2H).

Example 10(1)~Example 10(225)

Using corresponding compounds, the following compounds were obtained by the same procedure of Example 10 or continued conversion to known salts.

Example 10(1)

N-mesyl-3-(2-(2-(naphthalen-2-yl)ethoxy)-4-(pyrazol-1-ylmethyl)phenyl)propanamide

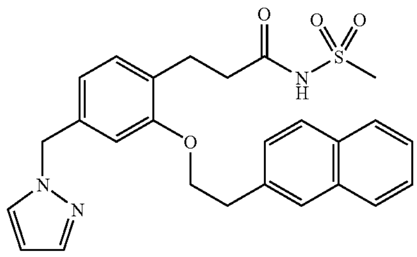

TLC: Rf 0.39 (hexane:ethyl acetate=1:1);

NMR (300 MHz, $CDCl_3$): δ 7.89-7.78 (m, 3H), 7.70 (s, 1H), 7.55-7.35 (m, 5H), 7.04 (d, J=7.8 Hz, 1H), 6.72 (m, 2H), 6.28 (t, J=1.5 Hz, 1H), 5.26 (s, 2H), 4.29 (t, J=6.3 Hz, 2H), 3.26 (t, J=6.3 Hz, 2H), 3.04 (s, 3H), 2.78 (t, J=7.2 Hz, 2H), 2.10 (t, J=7.2 Hz, 2H).

Example 10(2)

N-phenylsulfonyl-3-(2-(2-(naphthalen-2-yl)ethoxy)-4-(pyrazol-1-ylmethyl)phenyl)propanamide

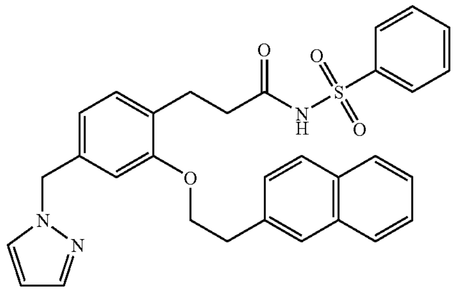

TLC: Rf 0.44 (hexane:ethyl acetate=1:1);

NMR (300 MHz, $CDCl_3$): δ 7.95-7.75 (m, 5H), 7.68 (s, 1H), 7.64-7.35 (m, 8H), 6.90 (d, J=7.5 Hz, 1H), 6.67 (s, 1H), 6.62 (d, J=7.5 Hz, 1H), 6.28 (t, J=2.1 Hz, 1H), 5.24 (s, 2H), 4.25 (t, J=6.3 Hz, 2H), 3.23 (t, J=6.3 Hz, 2H), 2.69 (t, J=7.5 Hz, 2H), 2.05 (t, J=7.5 Hz, 2H).

Example 10(3)

N-phenylsulfonyl-3-(2-((3-methylbutyl)carbamoyl)-4-phenoxymethylphenyl)propanamide

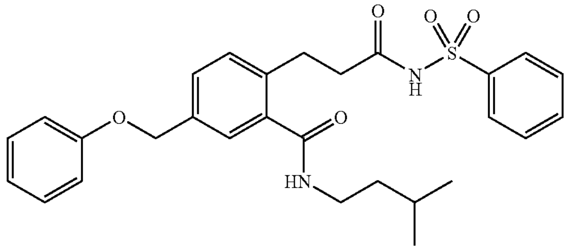

TLC: Rf 0.37 (hexane:ethyl acetate=1:1);

NMR (300 MHz, $CDCl_3$): δ 7.94-7.88 (m, 2H), 7.56 (m, 1H), 7.48-7.40 (m, 3H), 7.38-7.28 (m, 3H), 7.16 (d, J=7.2 Hz, 1H), 7.04-6.95 (m, 3H), 6.03 (m, 1H), 5.03 (s, 2H), 3.56-3.46 (m, 2H), 2.97 (t, J=7.6 Hz, 2H), 2.66 (t, J=7.6 Hz, 2H), 1.70 (m, 1H), 1.58-1.49 (m, 2H), 0.98 (d, J=6.6 Hz, 6H).

Example 10(4)

N-phenylsulfonyl-3-(2-((3-methyl-1-(4-fluorophenyl)butyl)carbamoyl)-4-phenoxymethylphenyl)propanamide

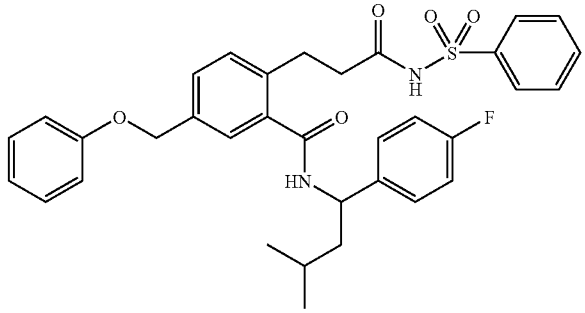

TLC: Rf 0.40 (hexane:ethyl acetate=1:1);

NMR (300 MHz, $CDCl_3$): δ 10.15 (s, 1H), 7.91-7.88 (m, 2H), 7.59-7.53 (m, 1H), 7.47-7.30 (m, 8H), 7.15-6.95 (m, 6H), 6.27 (d, J=8.1 Hz, 1H), 5.25 (q, J=8.1 Hz, 1H), 5.02 (s, 2H), 2.95-2.78 (m, 2H), 2.57-2.51 (m, 2H), 1.86-1.52 (m, 3H), 1.02-0.99 (m, 6H).

Example 10(5)

N-methyl-3-(2-((3-methyl-1-(4-fluorophenyl)butyl)carbamoyl)-4-phenoxymethylphenyl)propanamide

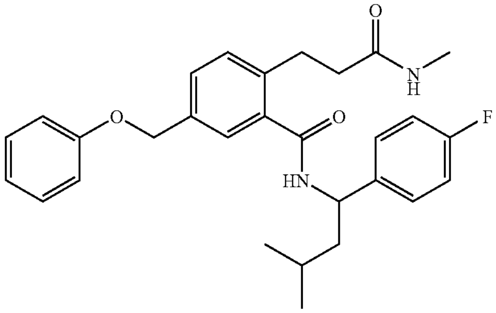

TLC: Rf 0.52 (chloroform:methanol=19:1);

NMR (300 MHz, $CDCl_3$): δ 7.45-7.22 (m, 7H), 7.09-6.93 (m, 6H), 5.86 (m, 1H), 5.19 (m, 1H), 5.02 (s, 2H), 3.05-2.85 (m, 2H), 2.68 (d, J=4.5 Hz, 3H), 2.52 (t, J=7.5 Hz, 2H), 1.81 (m, 1H), 1.73-1.53 (m, 2H), 0.98 (t, J=6.6 Hz, 6H).

Example 10(6)

N-(pyridin-2-yl)-3-(2-((3-methyl-1-(4-fluorophenyl)butyl)carbamoyl)-4-phenoxymethylphenyl)propanamide

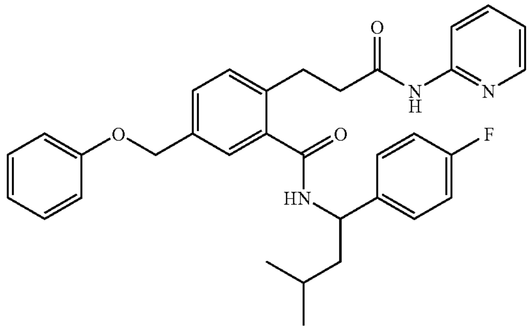

TLC: Rf 0.40 (hexane:ethyl acetate=1:1);

NMR (300 MHz, $CDCl_3$): δ 8.28-8.25 (m, 1H), 8.16-8.10 (m, 2H), 7.71-7.64 (m, 1H), 7.45-7.27 (m, 7H), 7.04-6.94 (m, 6H), 6.87 (d, J=8.1 Hz, 1H), 5.24 (q, J=8.1 Hz, 1H), 5.02 (s, 2H), 3.15-2.98 (m, 2H), 2.75 (t, J=7.5 Hz, 2H), 1.88-1.78 (m, 1H), 1.74-1.57 (m, 2H), 1.00-0.97 (m, 6H).

Example 10(7)

N-(4-trifluoromethylphenylsulfonyl)-3-(2-((3-methyl-1-(4-fluorophenyl)butyl)carbamoyl)-4-phenoxymethylphenyl)propanamide

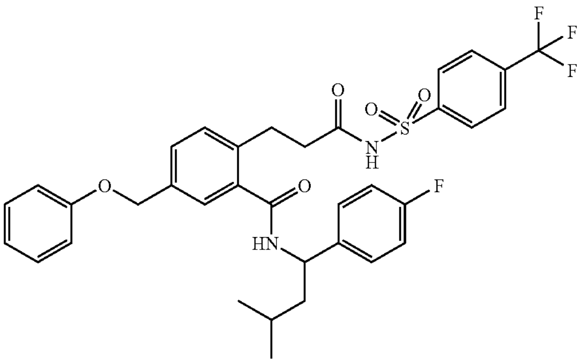

TLC: Rf 0.60 (chloroform:methanol=10:1).

Example 10(8)

N-(naphthalen-2-ylsulfonyl)-3-(2-((3-methyl-1-(4-fluorophenyl)butyl)carbamoyl)-4-phenoxymethylphenyl)propanamide

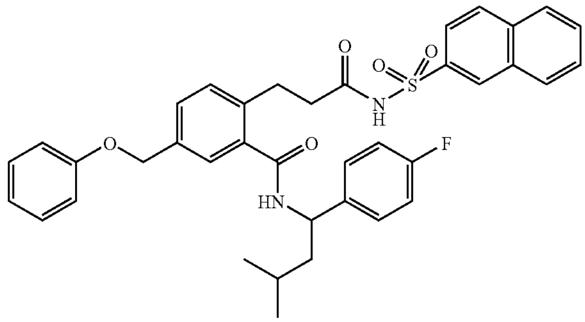

TLC: Rf 0.62 (chloroform:methanol=10:1).

Example 10(9)

N-(3-chloro-4-methylphenylsulfonyl)-3-(2-((3-methyl-1-(4-fluorophenyl)butyl)carbamoyl)-4-phenoxymethylphenyl)propanamide

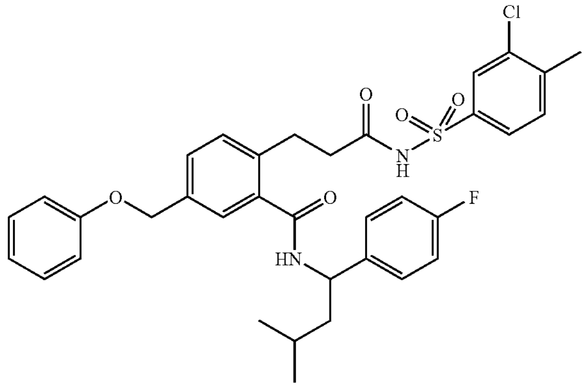

TLC: Rf 0.62 (chloroform:methanol=10:1).

Example 10(10)

N-(4-ethylphenylsulfonyl)-3-(2-((3-methyl-1-(4-fluorophenyl)butyl)carbamoyl)-4-phenoxymethylphenyl)propanamide

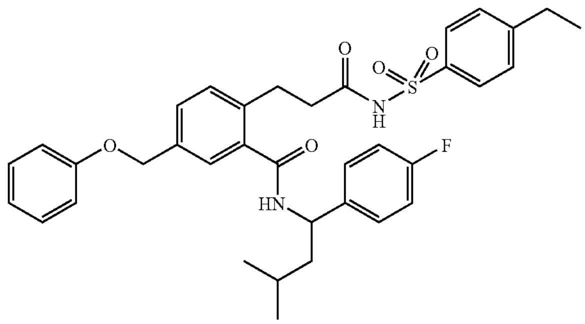

TLC: Rf 0.64 (chloroform:methanol=10:1).

Example 10(11)

N-hydroxy-3-(2-((3-methyl-1-(4-fluorophenyl)butyl)carbamoyl)-4-phenoxymethylphenyl)propanamide

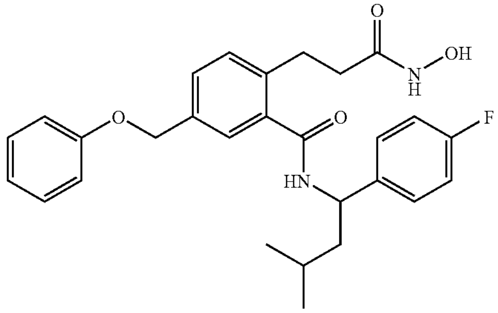

TLC: Rf 0.60 (ethyl acetate).

Example 10(12)

N-isopropylsulfonyl-3-(2-((3-methyl-1-(4-fluorophenyl)butyl)carbamoyl)-4-phenoxymethylphenyl)propanamide

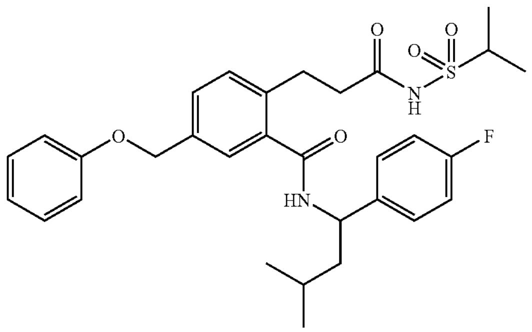

TLC: Rf 0.80 (chloroform:methanol=10:1).

Example 10(13)

N-(4-mesylphenylsulfonyl)-3-(2-((3-methyl-1-(4-fluorophenyl)butyl)carbamoyl)-4-phenoxymethylphenyl)propanamide

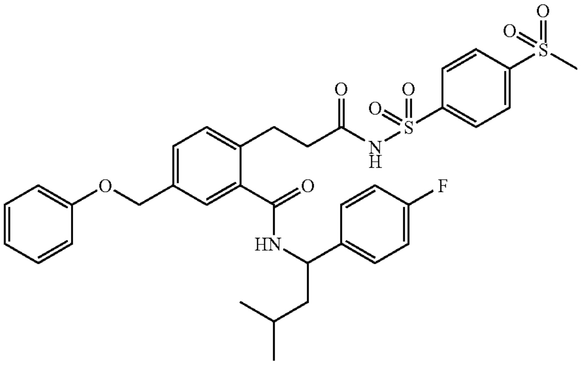

TLC: Rf 0.61 (chloroform:methanol=10:1).

Example 10(14)

N-((1,1'-biphenyl-4-yl)sulfonyl)-3-(2-((3-methyl-1-(4-fluorophenyl)butyl)carbamoyl)-4-phenoxymethylphenyl)propanamide

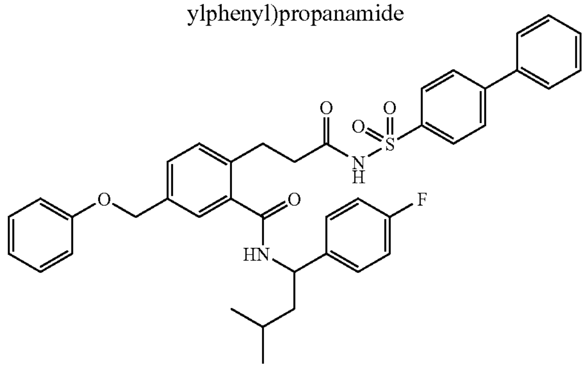

TLC: Rf 0.80 (chloroform:methanol=10:1).

Example 10(15)

N-((1,1'-biphenyl-2-yl)sulfonyl)-3-(2-((3-methyl-1-(4-fluorophenyl)butyl)carbamoyl)-4-phenoxymethylphenyl)propanamide

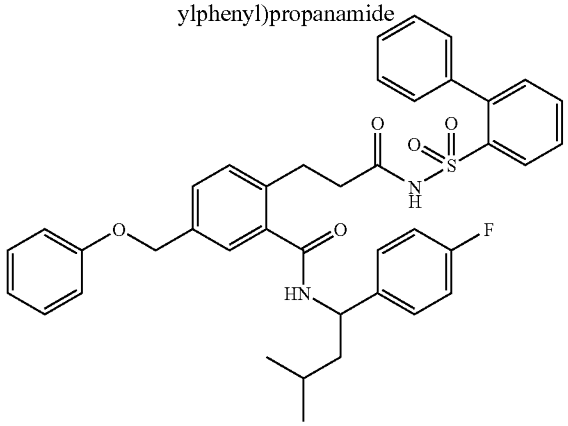

TLC: Rf 0.57 (chloroform:methanol=10:1).

Example 10(16)

N-(3,4-difluorophenylsulfonyl)-3-(2-((3-methyl-1-(4-fluorophenyl)butyl)carbamoyl)-4-phenoxymethylphenyl)propanamide

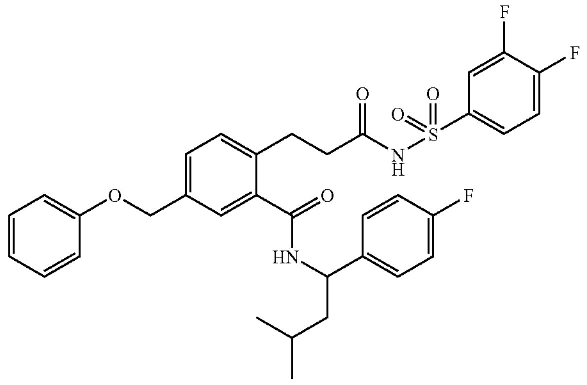

TLC: Rf 0.57 (chloroform:methanol=10:1).

Example 10(17)

N-(2,6-difluorophenylsulfonyl)-3-(2-((3-methyl-1-(4-fluorophenyl)butyl)carbamoyl)-4-phenoxymethylphenyl)propanamide

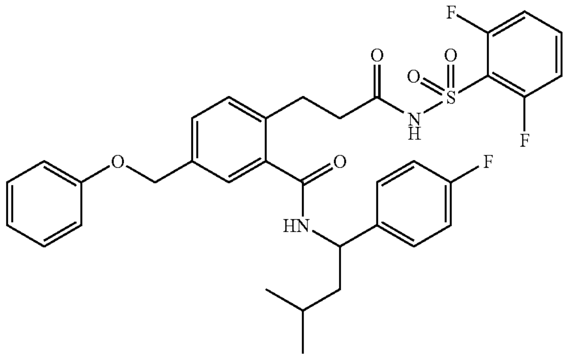

TLC: Rf 0.55 (chloroform:methanol=10:1).

Example 10(18)

N-(2,5-difluorophenylsulfonyl)-3-(2-((3-methyl-1-(4-fluorophenyl)butyl)carbamoyl)-4-phenoxymethylphenyl)propanamide

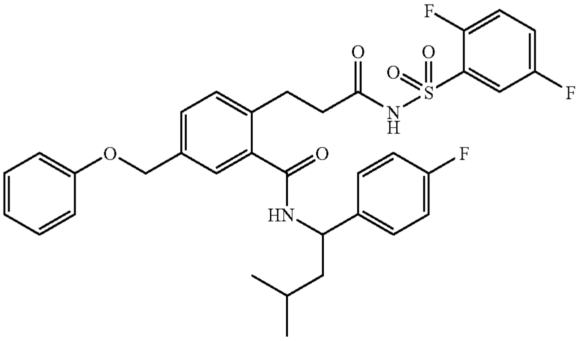

TLC: Rf 0.59 (chloroform:methanol=10:1).

Example 10(19)

N-(2,5-dimethoxyphenylsulfonyl)-3-(2-((3-methyl-1-(4-fluorophenyl)butyl)carbamoyl)-4-phenoxymethylphenyl)propanamide

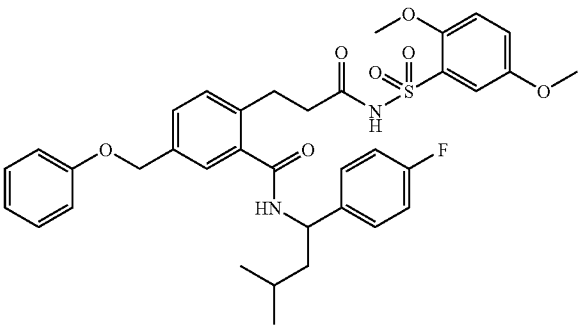

TLC: Rf 0.52 (chloroform:methanol=10:1).

Example 10(20)

N-((E)-2-phenylethenylsulfonyl)-3-(2-((3-methyl-1-(4-fluorophenyl)butyl)carbamoyl)-4-phenoxymethylphenyl)propanamide

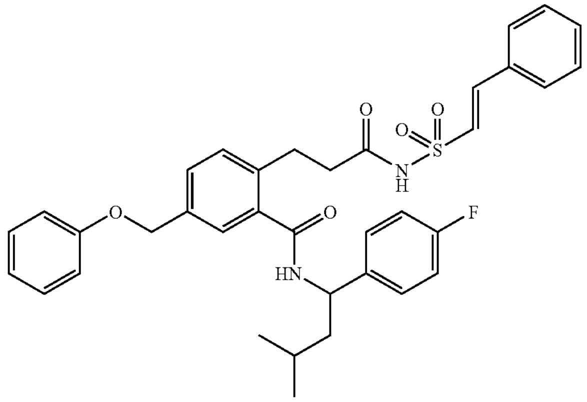

TLC: Rf 0.78 (chloroform:methanol=10:1).

Example 10(21)

N-(furan-2-ylsulfonyl)-3-(2-((3-methyl-1-(4-fluorophenyl)butyl)carbamoyl)-4-phenoxymethylphenyl) propanamide

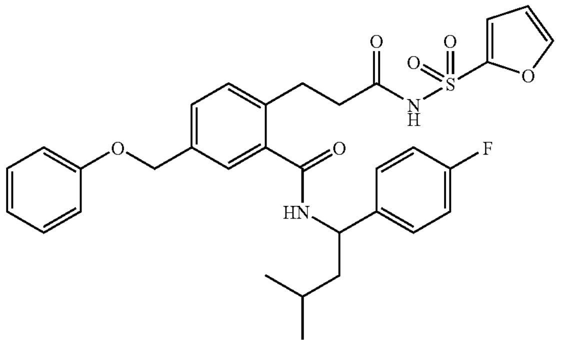

TLC: Rf 0.61 (chloroform:methanol=10:1).

Example 10(22)

N-(thiophen-2-ylsulfonyl)-3-(2-((3-methyl-1-(4-fluorophenyl)butyl)carbamoyl)-4-phenoxymethylphenyl)propanamide

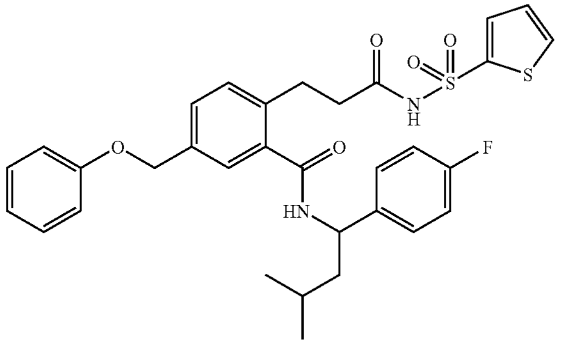

TLC: Rf 0.62 (chloroform:methanol=10:1).

Example 10(23)

N-(7-chlorobenzofurazan-4-ylsulfonyl)-3-(2-((3-methyl-1-(4-fluorophenyl)butyl)carbamoyl)-4-phenoxymethylphenyl)propanamide

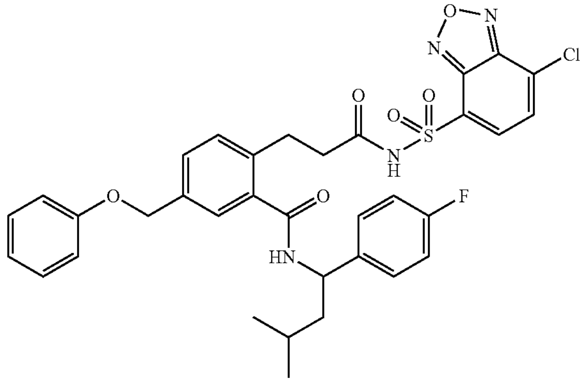

TLC: Rf 0.56 (chloroform:methanol=10:1).

Example 10(24)

N-(3,4-dichlorophenylsulfonyl)-3-(2-((3-methyl-1-(4-fluorophenyl)butyl)carbamoyl)-4-phenoxymethylphenyl)propanamide

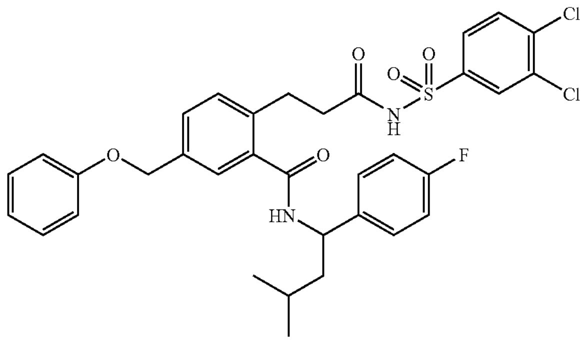

TLC: Rf 0.70 (chloroform:methanol=10:1).

Example 10(25)

N-(4-methoxyphenylsulfonyl)-3-(2-((3-methyl-1-(4-fluorophenyl)butyl)carbamoyl)-4-phenoxymethylphenyl)propanamide

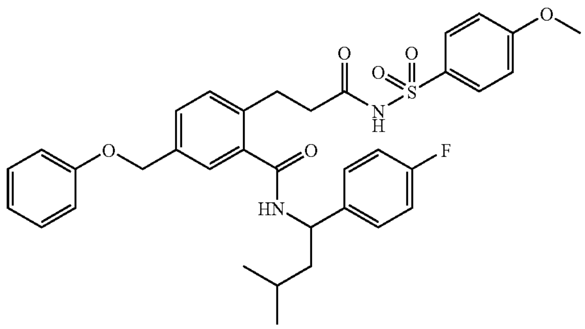

TLC: Rf 0.61 (chloroform:methanol=10:1).

Example 10(26)

N-(3-methylphenylsulfonyl)-3-(2-((3-methyl-1-(4-fluorophenyl)butyl)carbamoyl)-4-phenoxymethylphenyl)propanamide

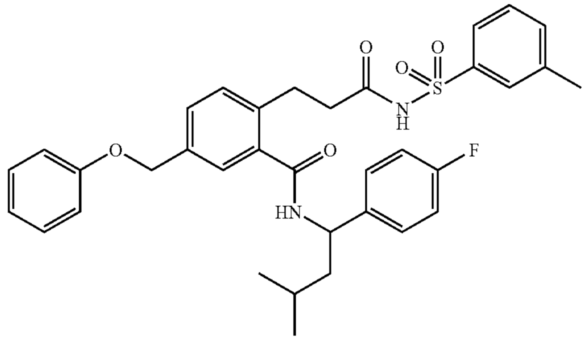

TLC: Rf 0.65 (chloroform:methanol=10:1).

Example 10(27)

N-(2-fluorophenylsulfonyl)-3-(2-((3-methyl-1-(4-fluorophenyl)butyl)carbamoyl)-4-phenoxymethylphenyl)propanamide

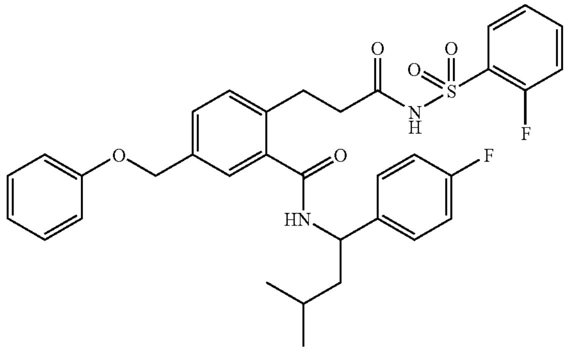

TLC: Rf 0.62 (chloroform:methanol=10:1).

Example 10(28)

N-(4-cyanophenylsulfonyl)-3-(2-((3-methyl-1-(4-fluorophenyl)butyl)carbamoyl)-4-phenoxymethylphenyl)propanamide

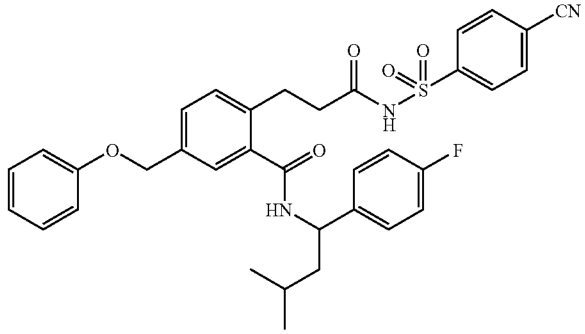

TLC: Rf 0.59 (chloroform:methanol=10:1).

Example 10(29)

N-(3-cyanophenylsulfonyl)-3-(2-((3-methyl-1-(4-fluorophenyl)butyl)carbamoyl)-4-phenoxymethylphenyl)propanamide

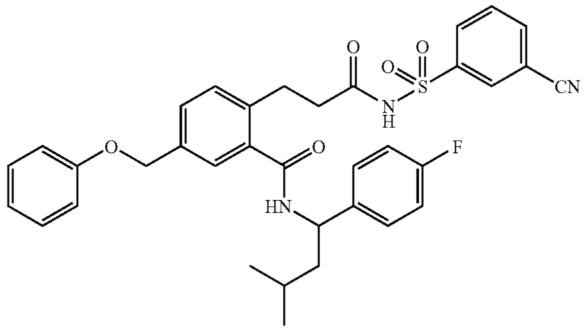

TLC: Rf 0.59 (chloroform:methanol=10:1).

Example 10(30)

N-(2-chloro-4-cyanophenylsulfonyl)-3-(2-((3-methyl-1-(4-fluorophenyl)butyl)carbamoyl)-4-phenoxymethylphenyl)propanamide

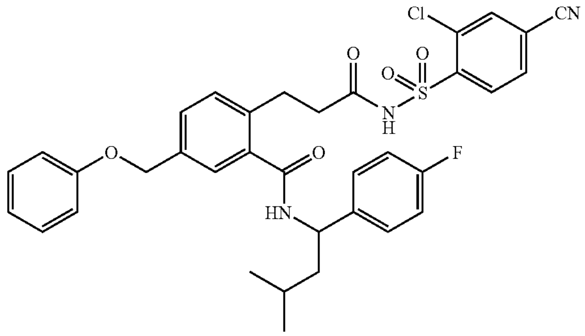

TLC: Rf 0.61 (chloroform:methanol=10:1).

Example 10(31)

N-(3-methoxyphenylsulfonyl)-3-(2-((3-methyl-1-(4-fluorophenyl)butyl)carbamoyl)-4-phenoxymethylphenyl)propanamide

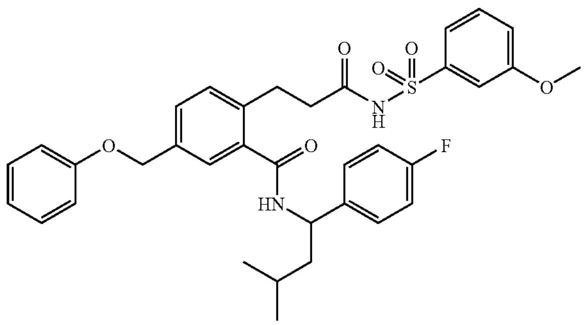

TLC: Rf 0.58 (chloroform:methanol=10:1).

Example 10(32)

N-(4-butoxyphenylsulfonyl)-3-(2-((3-methyl-1-(4-fluorophenyl)butyl)carbamoyl)-4-phenoxymethylphenyl)propanamide

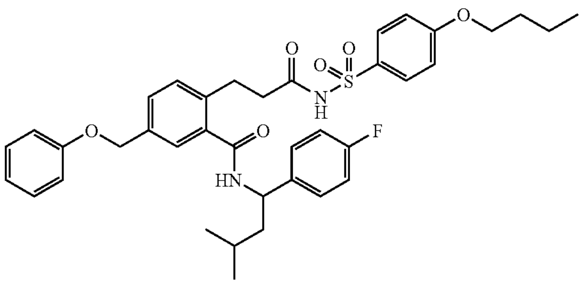

TLC: Rf 0.65 (chloroform:methanol=10:1).

Example 10(33)

N-(4-fluorophenylsulfonyl)-3-(2-((3-methyl-1-(4-fluorophenyl)butyl)carbamoyl)-4-phenoxymethylphenyl)propanamide

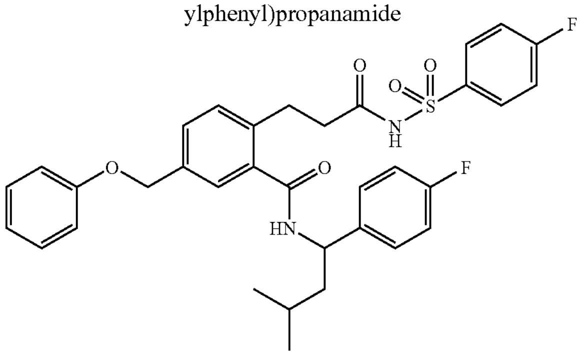

TLC: Rf 0.68 (chloroform:methanol=10:1).

Example 10(34)

N-(2-chloro-6-methylphenylsulfonyl)-3-(2-((3-methyl-1-(4-fluorophenyl)butyl)carbamoyl)-4-phenoxymethylphenyl)propanamide

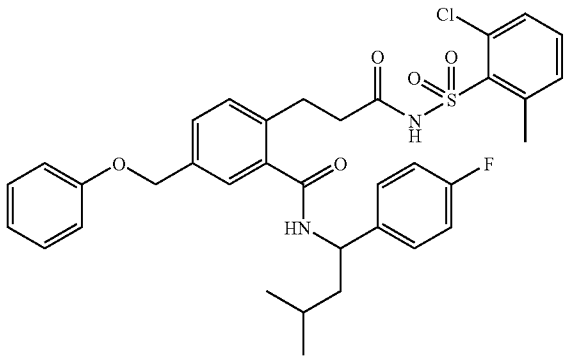

TLC: Rf 0.67 (chloroform:methanol=10:1).

Example 10(35)

N-(2-trifluoromethylphenylsulfonyl)-3-(2-((3-methyl-1-(4-fluorophenyl)butyl)carbamoyl)-4-phenoxymethylphenyl)propanamide

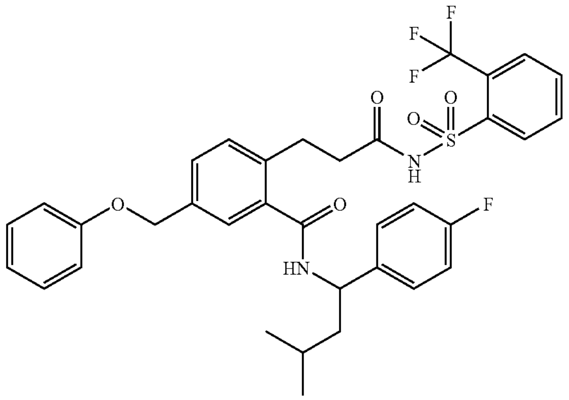

TLC: Rf 0.62 (chloroform:methanol=10:1).

Example 10(36)

N-(3-trifluoromethylphenylsulfonyl)-3-(2-((3-methyl-1-(4-fluorophenyl)butyl)carbamoyl)-4-phenoxymethylphenyl)propanamide

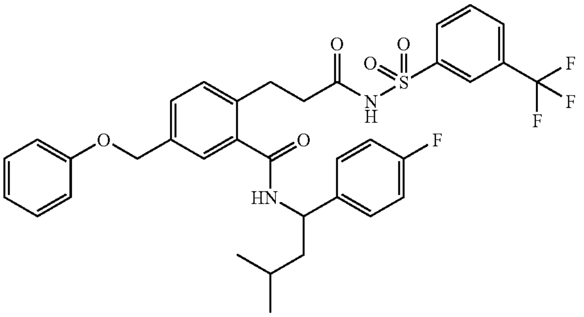

TLC: Rf 0.67 (chloroform:methanol=10:1).

Example 10(37)

N-(4-propylphenylsulfonyl)-3-(2-((3-methyl-1-(4-fluorophenyl)butyl)carbamoyl)-4-phenoxymethylphenyl)propanamide

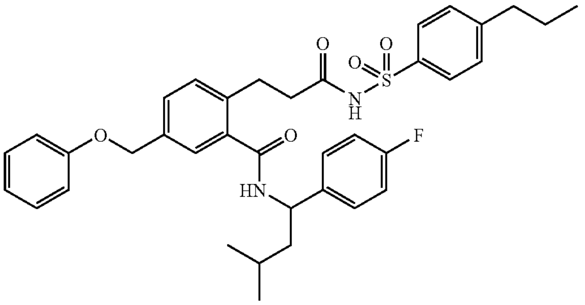

TLC: Rf 0.71 (chloroform:methanol=10:1).

Example 10(38)

N-(4-isopropylphenylsulfonyl)-3-(2-((3-methyl-1-(4-fluorophenyl)butyl)carbamoyl)-4-phenoxymethylphenyl)propanamide

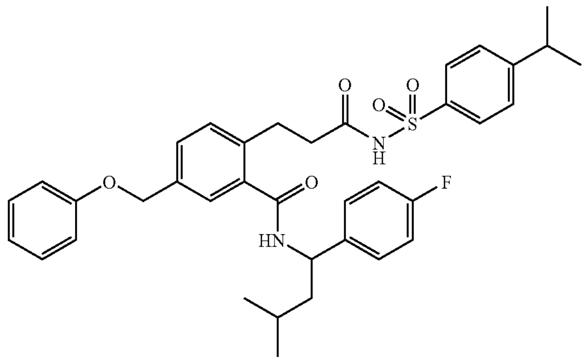

TLC: Rf 0.69 (chloroform:methanol=10:1).

Example 10(39)

N-(naphthalen-1-ylsulfonyl)-3-(2-((3-methyl-1-(4-fluorophenyl)butyl)carbamoyl)-4-phenoxymethylphenyl)propanamide

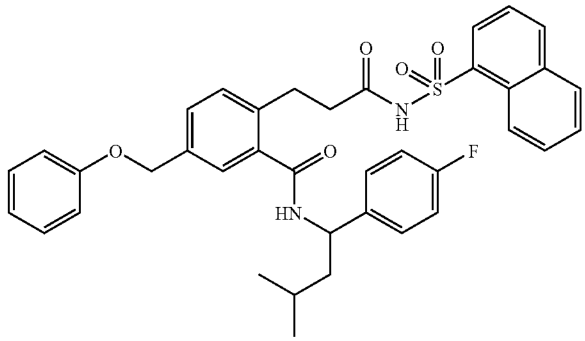

TLC: Rf 0.76 (chloroform:methanol=10:1).

Example 10(40)

N-(4-butylphenylsulfonyl)-3-(2-((3-methyl-1-(4-fluorophenyl)butyl)carbamoyl)-4-phenoxymethylphenyl)propanamide

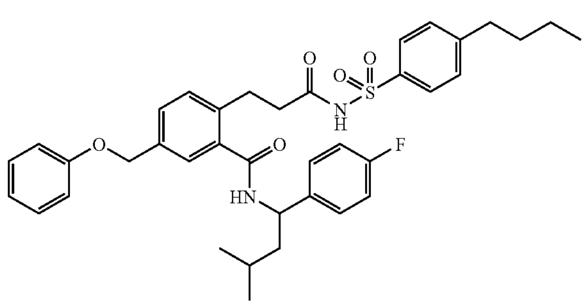

TLC: Rf 0.71 (chloroform:methanol=10:1).

Example 10(41)

N-(5-benzoylaminomethylthiophen-2-ylsulfonyl)-3-(2-((3-methyl-1-(4-fluorophenyl)butyl)carbamoyl)-4-phenoxymethylphenyl)propanamide

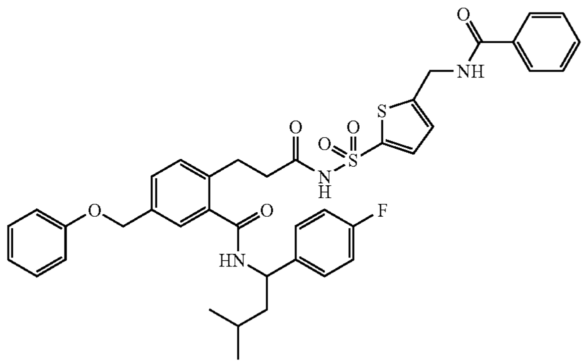

TLC: Rf 0.58 (chloroform:methanol=10:1).

Example 10(42)

N-phenylsulfonyl-2-(2-((3-methyl-1-phenylbutyl)carbamoyl)-4-phenoxymethylphenoxy)acetamide

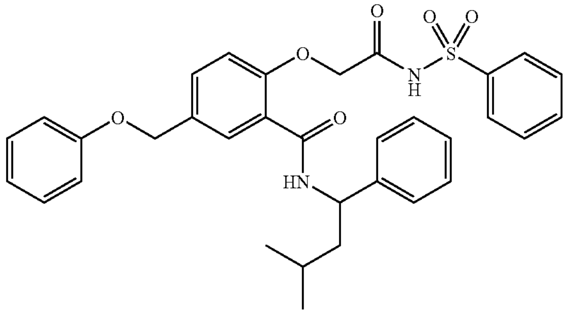

TLC: Rf 0.65 (ethyl acetate:methanol=5:1).

Example 10(43)

N-phenylsulfonyl-2-(2-((3-methyl-1-phenylbutyl)carbamoyl)-4-(2-methylphenoxymethyl)phenoxy)acetamide

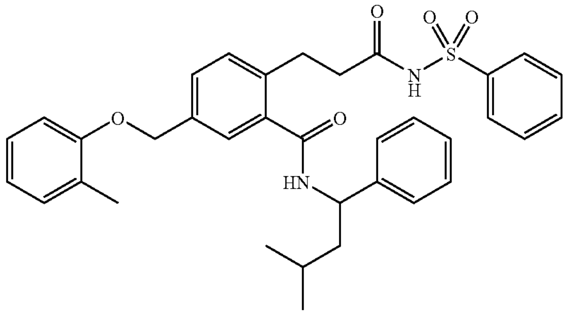

TLC: Rf 0.65 (ethyl acetate:methanol=5:1).

Example 10(44)

N-phenylsulfonyl-2-(2-((3-methyl-1-phenylbutyl)carbamoyl)-4-(2-methoxyphenoxymethyl)phenoxy)acetamide

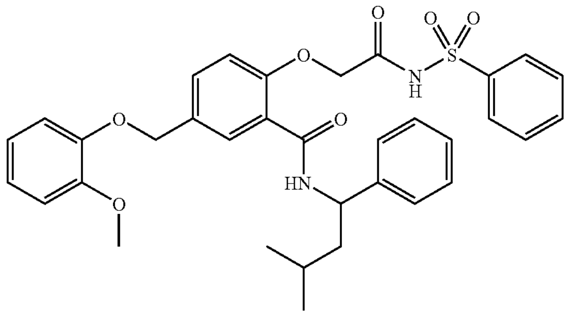

TLC: Rf 0.60 (ethyl acetate:methanol=5:1).

Example 10(45)

N-(5-methylfuran-2-ylsulfonyl)-3-(2-((3-methyl-1-(4-fluorophenyl)butyl)carbamoyl)-4-phenoxymethylphenyl)propanamide

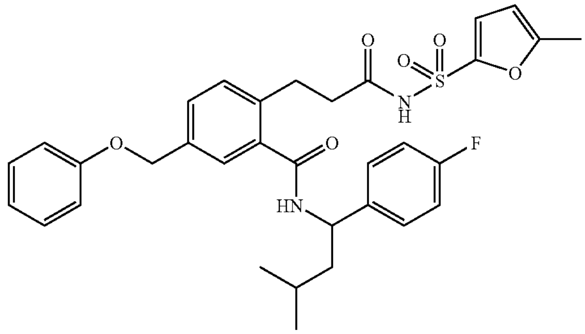

TLC: Rf 0.80 (chloroform:methanol=10:1).

Example 10(46)

N-(thiophen-3-ylsulfonyl)-3-(2-((3-methyl-1-(4-fluorophenyl)butyl)carbamoyl)-4-phenoxymethylphenyl)propanamide

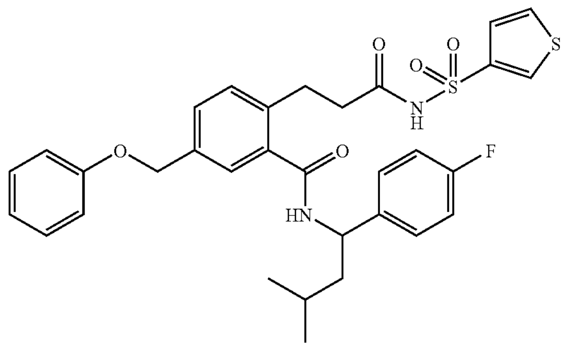

TLC: Rf 0.80 (chloroform:methanol=10:1).

Example 10(47)

N-(furan-3-ylsulfonyl)-3-(2-((3-methyl-1-(4-fluorophenyl)butyl)carbamoyl)-4-phenoxymethylphenyl)propanamide

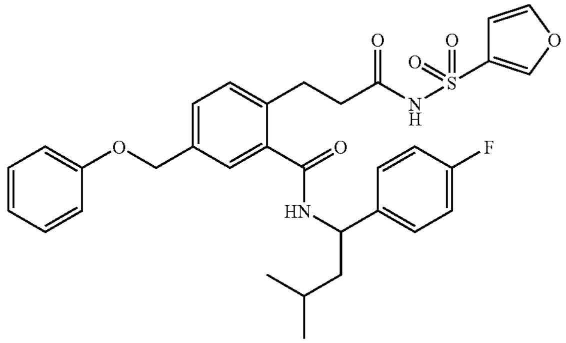

TLC: Rf 0.78 (chloroform:methanol=10:1).

Example 10(48)

N-(1-methylpyrrol-2-ylsulfonyl)-3-(2-((3-methyl-1-(4-fluorophenyl)butyl)carbamoyl)-4-phenoxymethylphenyl)propanamide

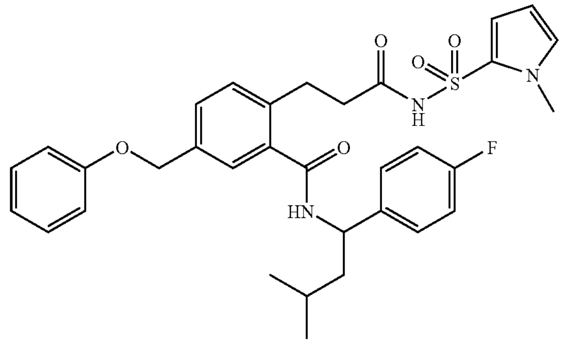

TLC: Rf 0.60 (chloroform:methanol=10:1).

Example 10(49)

N-(3,5-dimethylisoxazol-4-ylsulfonyl)-3-(2-((3-methyl-1-(4-fluorophenyl)butyl)carbamoyl)-4-phenoxymethylphenyl)propanamide

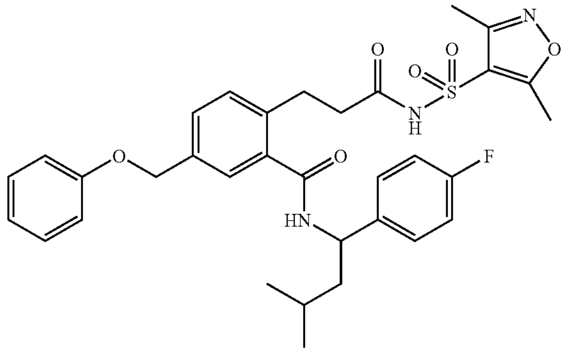

TLC: Rf 0.80 (chloroform:methanol=10:1).

Example 10(50)

N-benzylsulfonyl-3-(2-((3-methyl-1-(4-fluorophenyl)butyl)carbamoyl)-4-phenoxymethylphenyl)propanamide

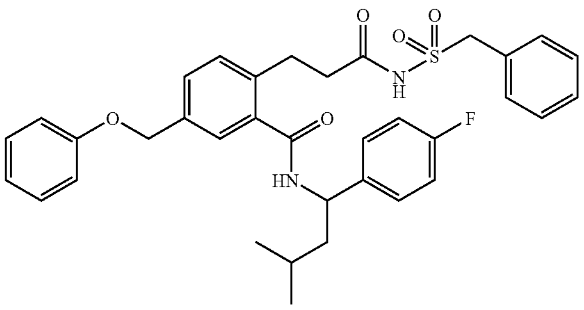

TLC: Rf 0.81 (chloroform:methanol=10:1).

Example 10(51)

N-(5-dimethylaminonaphthalen-1-ylsulfonyl)-3-(2-((3-methyl-1-(4-fluorophenyl)butyl)carbamoyl)-4-phenoxymethylphenyl)propanamide

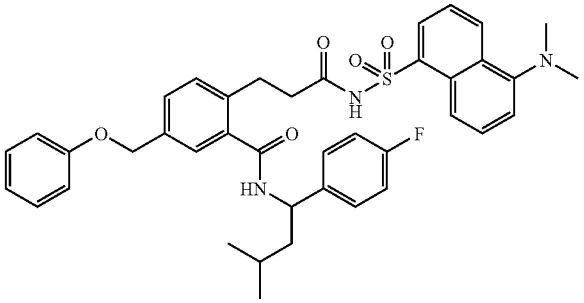

TLC: Rf 0.66 (chloroform:methanol=10:1).

Example 10(52)

N-(4-acetylaminophenylsulfonyl)-3-(2-((3-methyl-1-(4-fluorophenyl)butyl)carbamoyl)-4-phenoxymethylphenyl)propanamide

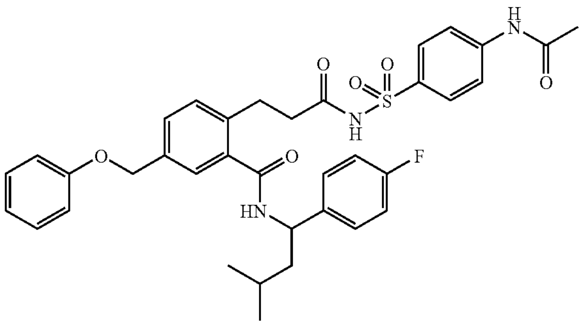

TLC: Rf 0.80 (chloroform:methanol=10:1).

Example 10(53)

N-(4-chlorophenylsulfonyl)-3-(2-((3-methyl-1-(4-fluorophenyl)butyl)carbamoyl)-4-phenoxymethylphenyl)propanamide

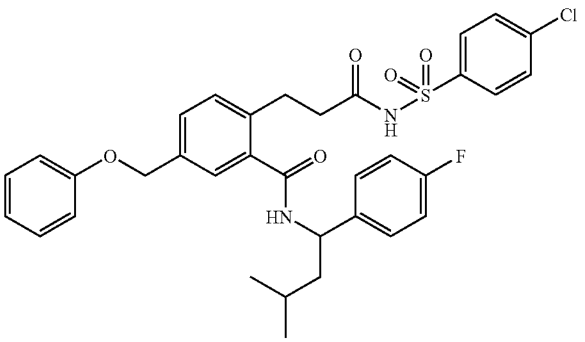

TLC: Rf 0.80 (chloroform:methanol=10:1).

Example 10(54)

N-(2-methoxycarbonylphenylsulfonyl)-3-(2-((3-methyl-1-(4-fluorophenyl)butyl)carbamoyl)-4-phenoxymethylphenyl)propanamide

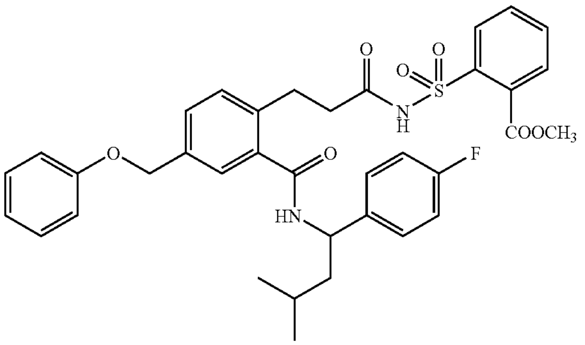

TLC: Rf 0.79 (chloroform:methanol=10:1).

Example 10(55)

N-(3-(3-methyl-5-oxopyrazol-1-yl)phenylsulfonyl)-3-(2-((3-methyl-1-(4-fluorophenyl)butyl)carbamoyl)-4-phenoxymethylphenyl)propanamide

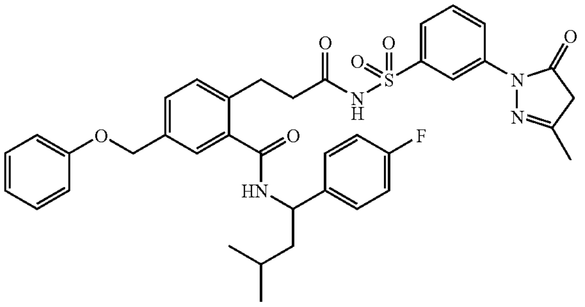

TLC: Rf 0.79 (chloroform:methanol=10:1).

Example 10(56)

N-(tetrazol-5-yl)-3-(2-((3-methyl-1-(4-fluorophenyl)butyl)carbamoyl)-4-phenoxymethylphenyl)propanamide

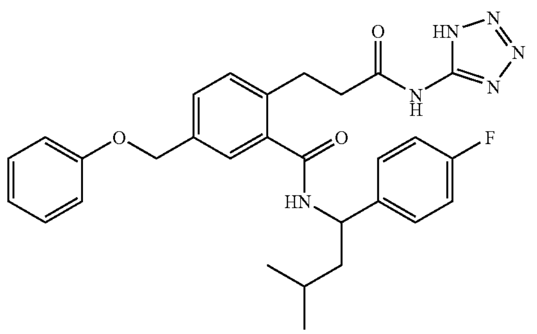

TLC: Rf 0.65 (ethyl acetate:methanol=3:1).

Example 10(57)

(2E)-N-phenylsulfonyl-3-(2-((3-methyl-1-phenylbutyl)carbamoyl)-4-phenoxymethylphenyl)-2-propenamide

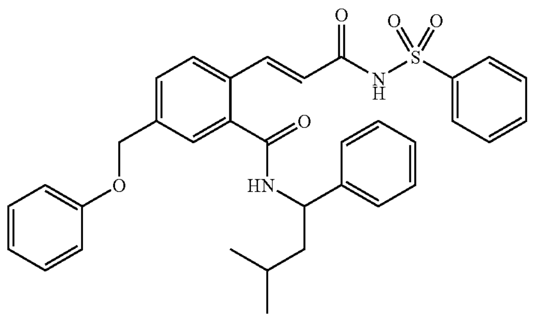

TLC: Rf 0.57 (chloroform:methanol=10:1).

Example 10(58)

N-(pyridin-2-yl)-3-(2-(4-methyl-2-phenylpentyloxy)-4-phenoxymethylphenyl)propanamide

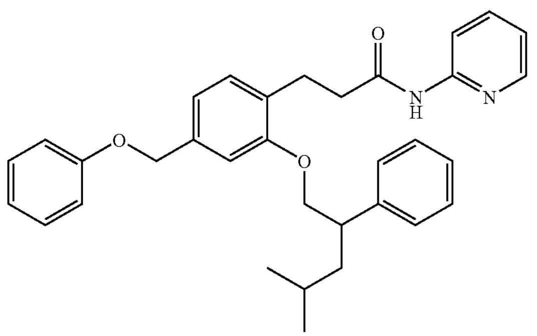

TLC: Rf 0.35 (hexane:ethyl acetate=3:1).

Example 10(59)

N-(tetrazol-5-yl)-3-(2-(4-methyl-2-phenylpentyloxy)-4-phenoxymethylphenyl)propanamide

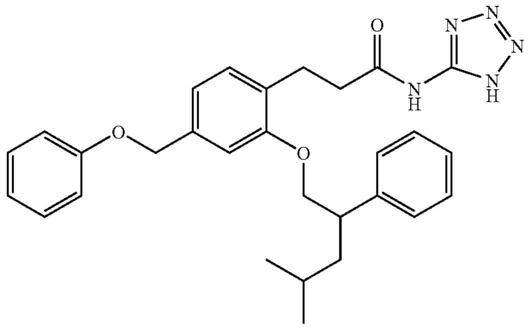

TLC: Rf 0.25 (ethyl acetate).

Example 10(60)

N-phenylsulfonyl-3-(2-(2-(naphthalen-2-yl)ethoxy)-4-phenoxymethylphenyl)propanamide

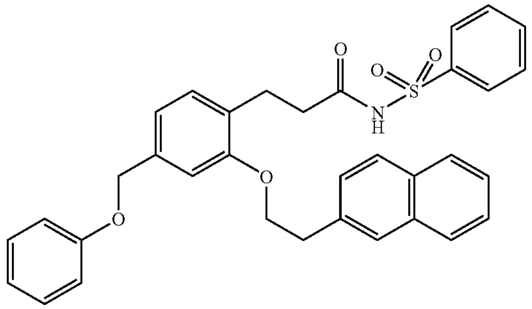

TLC: Rf 0.41 (hexane:ethyl acetate=2:1);

NMR (300 MHz, $CDCl_3$): δ 7.95-7.77 (m, 5H), 7.70 (brs, 1H), 7.63-7.40 (m, 7H), 7.33-7.27 (m, 2H), 7.00-6.93 (m, 5H), 6.81 (m, 1H), 4.99 (s, 2H), 4.34 (t, J=6.3 Hz, 2H), 3.27 (t, J=6.3 Hz, 2H), 2.73 (m, 2H), 2.10 (m, 2H).

Example 10(61)

(2E)-N-(5-bromo-2-methoxyphenylsulfonyl)-3-(2-(naphthalen-2-ylmethyl)-4-phenoxymethylphenyl)-2-propenamide

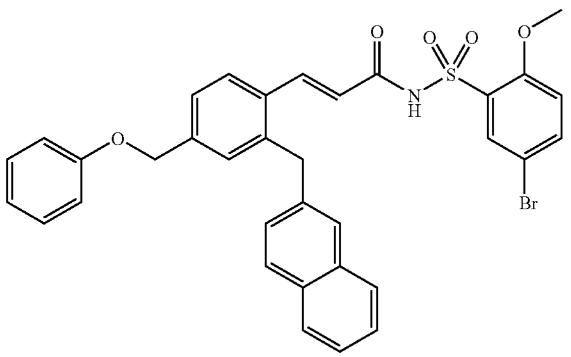

TLC: Rf 0.40 (hexane:ethyl acetate=1:1).

Example 10(62)

(2E)-N-phenylsulfonyl-3-(2-(naphthalen-2-ylmethyl)-4-(pyrazol-1-ylmethyl)phenyl)-2-propenamide

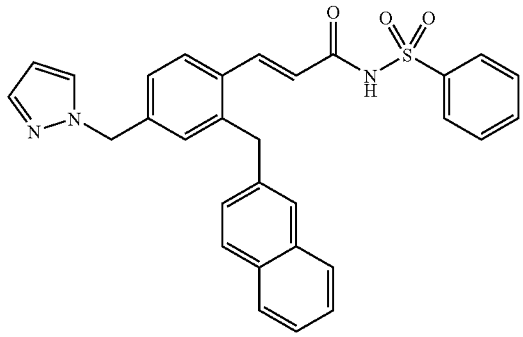

TLC: Rf 0.75 (ethyl acetate).

Example 10(63)

(2E)-N-(5-bromo-2-methoxyphenylsulfonyl)-3-(2-(naphthalen-2-ylmethyl)-4-(pyrazol-1-ylmethyl)phenyl)-2-propenamide

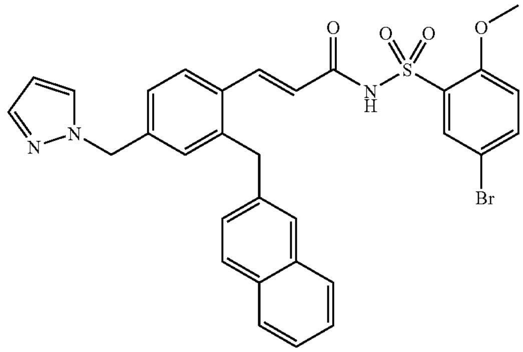

TLC: Rf 0.60 (ethyl acetate).

Example 10(64)

N-phenylsulfonyl-3-(2-((3-methyl-1-phenylbutyl) carbamoyl)-4-(pyrazol 1-ylmethyl)phenyl)propanamide

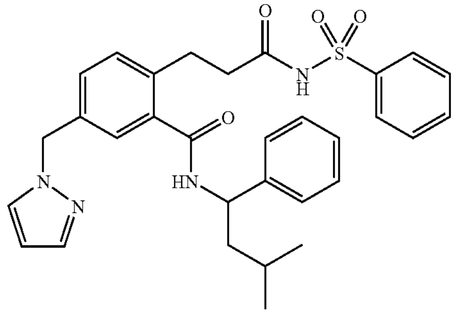

TLC: Rf 0.57 (chloroform:methanol=9:1).

Example 10(65)

N-(tetrazol-5-yl)-3-(2-(2-(naphthalen-2-yl)ethoxy)-4-(pyrazol 1-ylmethyl)phenyl)propanamide

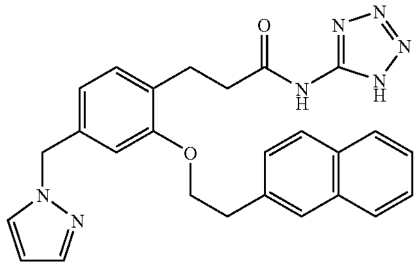

TLC: Rf 0.55 (chloroform:methanol:acetic acid=90:10:1);

NMR (300 MHz, DMSO-$d_6$): δ 7.86-7.74 (m, 6H), 7.52-7.33 (m, 4H), 7.06 (d, J=7.4 Hz, 1H), 6.87 (s, 1H), 6.65 (d, J=7.4 Hz, 1H), 6.23 (t, J=2.0 Hz, 1H), 5.24 (s, 2H), 4.19 (t, J=6.2 Hz, 2H), 3.18 (t, J=6.2 Hz, 2H), 2.84-2.73 (m, 2H), 2.61-2.52 (m, 2H).

Example 10(66)

N-(tetrazol-5-yl)-3-(2-(2-(naphthalen-2-yl)ethoxy)-4-phenoxymethylphenyl)propanamide

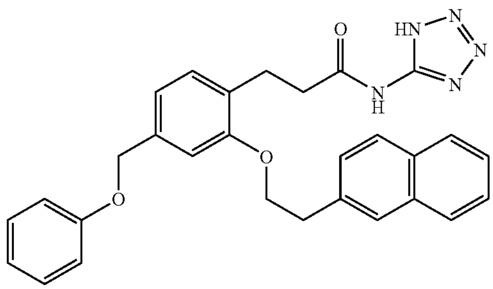

TLC: Rf 0.65 (chloroform:methanol=9:1);

NMR (300 MHz, DMSO-$d_6$): δ 7.84-7.68 (m, 4H), 7.51-7.20 (m, 5H), 7.13-6.87 (m, 6H), 5.01 (s, 2H), 4.98 (m, 1H), 4.27 (t, J=6.3 Hz, 2H), 3.20 (t, J=6.3 Hz, 2H), 2.85-3.18 (m, 2H), 2.61-2.55 (m, 2H).

Example 10(67)

N-phenylsulfonyl-3-(2-(2-phenylethoxy)-4-(pyrazol-1-ylmethyl)phenyl)propanamide

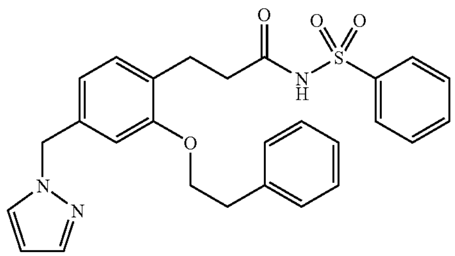

TLC: Rf 0.61 (chloroform:methanol=9:1);

NMR (300 MHz, $CDCl_3$): δ 7.98 (d, J=7.5 Hz, 2H), 7.73 (s, 1H), 7.66-7.48 (m, 4H), 7.37 (d, J=1.5 Hz, 1H), 7.34-7.20 (m, 4H), 6.89 (d, J=7.2 Hz, 1H), 6.66 (s, 1H), 6.62 (d, J=7.5 Hz, 1H), 6.29 (t, J=1.5 Hz, 1H), 5.24 (s, 2H), 4.17 (t, J=6.3 Hz, 2H), 3.07 (t, J=6.3 Hz, 2H), 2.71 (t, J=7.5 Hz, 2H), 2.14 (t, J=7.5 Hz, 2H).

Example 10(68)

N-(tetrazol-5-yl)-3-(2-(2-phenylethoxy)-4-(pyrazol-1-ylmethyl)phenyl)propanamide

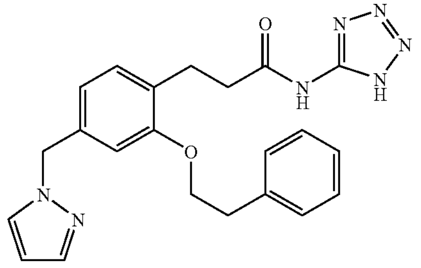

TLC: Rf 0.40 (chloroform:methanol=4:1);

NMR (300 MHz, DMSO-$d_6$): δ 7.77 (d, J=2.1 Hz, 1H), 7.43 (d, J=1.5 Hz, 1H), 7.34-7.23 (m, 5H), 7.18 (d, J=6.3 Hz, 1H), 7.07 (d, J=7.8 Hz, 1H), 6.85 (s, 1H), 6.65 (d, J=7.8 Hz, 1H), 6.23 (t, J=1.8 Hz, 1H), 5.24 (s, 2H), 4.09 (t, J=6.3 Hz, 2H), 3.00 (t, J=6.3 Hz, 2H), 2.75 (t, J=7.5 Hz, 2H), 2.51 (t, J=7.5 Hz, 2H).

Example 10(69)

N-(5-bromo-2-methoxyphenylsulfonyl)-3-(2-(2-phenylethoxy)-4-(pyrazol 1-ylmethyl)phenyl)propanamide

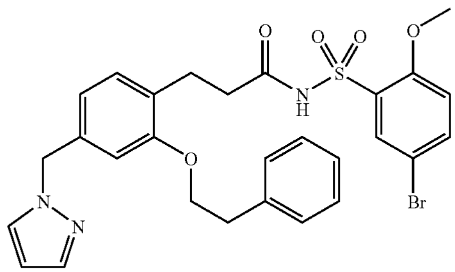

TLC: Rf 0.60 (chloroform:methanol=9:1);

NMR (300 MHz, $CDCl_3$): δ 8.13 (d, J=2.7 Hz, 1H), 7.97 (s, 1H), 7.62 (dd, J=8.7, 2.4 Hz, 1H), 7.56 (d, J=1.8 Hz, 1H), 7.40 (d, J=1.8 Hz, 1H), 7.39-7.25 (m, 5H), 6.95 (d, J=8.4 Hz, 1H), 6.78 (d, J=9.0 Hz, 1H), 6.66-6.62 (m, 2H), 6.30 (t, J=2.1 Hz, 1H), 5.24 (s, 2H), 4.17 (t, J=6.3 Hz, 2H), 3.75 (s, 3H), 3.08 (t, J=6.3 Hz, 2H), 2.73 (t, J=7.5 Hz, 2H), 2.29 (t, J=7.5 Hz, 2H).

Example 10(70)

N-(3,4-difluorophenylsulfonyl)-3-(2-(2-(naphthalen-2-yl)ethoxy)-4-(pyrazol-1-ylmethyl)phenyl)propanamide

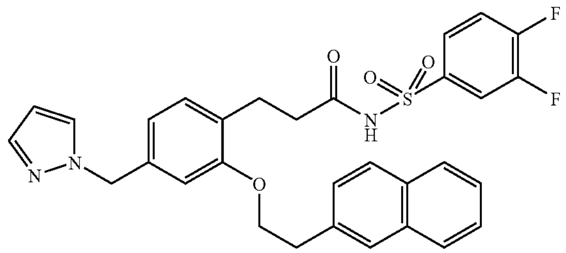

TLC: Rf 0.80 (chloroform:methanol=10:1).

Example 10(71)

N-(7-chlorobenzofurazan-4-ylsulfonyl)-3-(2-(2-(naphthalen-2-yl)ethoxy)-4-(pyrazol-1-ylmethyl)phenyl)propanamide

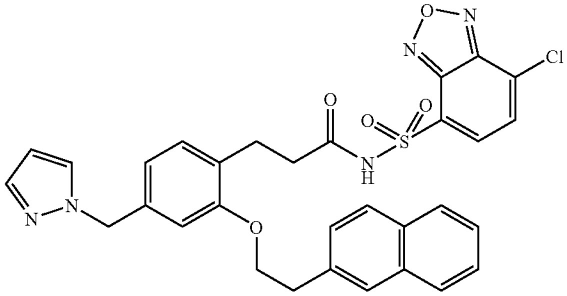

TLC: Rf 0.56 (chloroform:methanol=10:1).

Example 10(72)

N-(3,4-dichlorophenylsulfonyl)-3-(2-(2-(naphthalen-2-yl)ethoxy)-4-(pyrazol 1-ylmethyl)phenyl)propanamide

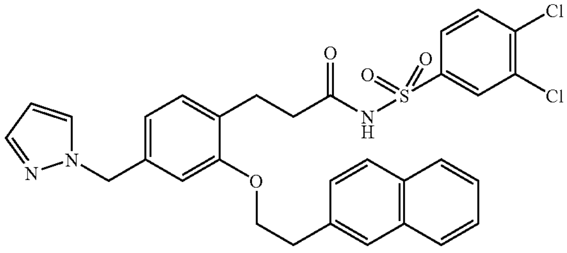

TLC: Rf 0.63 (chloroform:methanol=10:1).

Example 10(73)

N-(3-cyanophenylsulfonyl)-3-(2-(2-(naphthalen-2-yl)ethoxy)-4-(pyrazol 1-ylmethyl)phenyl)propanamide

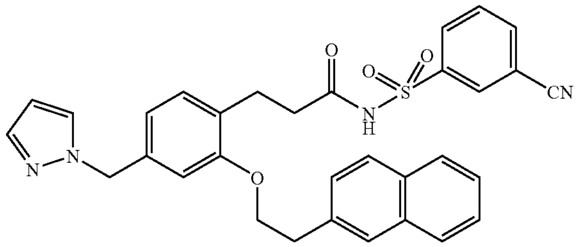

TLC: Rf 0.55 (chloroform:methanol=10:1).

Example 10(74)

N-(3-chloro-4-methylphenylsulfonyl)-3-(2-(2-(naphthalen-2-yl)ethoxy)-4-(pyrazol-1-ylmethyl)phenyl) propanamide

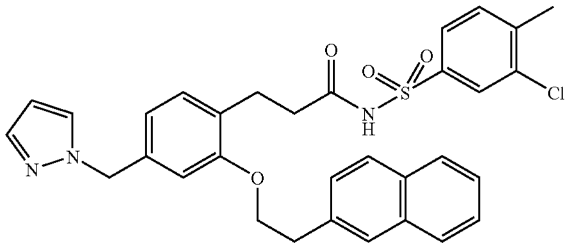

TLC: Rf 0.59 (chloroform:methanol=10:1).

Example 10(75)

N-(3-chloro-4-fluorophenylsulfonyl)-3-(2-(2-(naphthalen-2-yl)ethoxy)-4-(pyrazol-1-ylmethyl)phenyl) propanamide

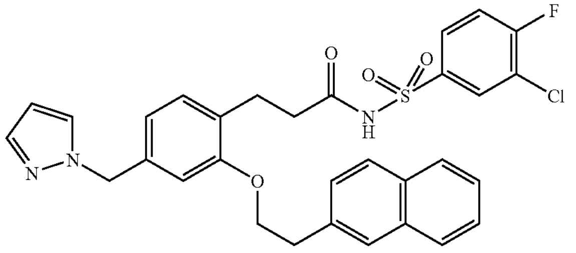

TLC: Rf 0.58 (chloroform:methanol=10:1).

Example 10(76)

N-(5-bromo-2-methoxyphenylsulfonyl)-3-(2-(2-(naphthalen-2-yl)ethoxy)-4-(pyrazol-1-ylmethyl) phenyl)propanamide

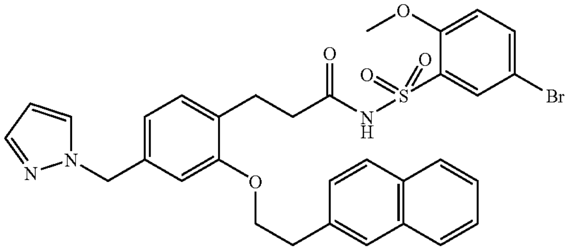

TLC: Rf 0.58 (chloroform:methanol=10:1).

Example 10(77)

N-(5-bromo-2-methoxyphenylsulfonyl)-3-(2-((3-methyl-1-phenylbutyl)carbamoyl)-4-phenoxymethylphenyl)propanamide

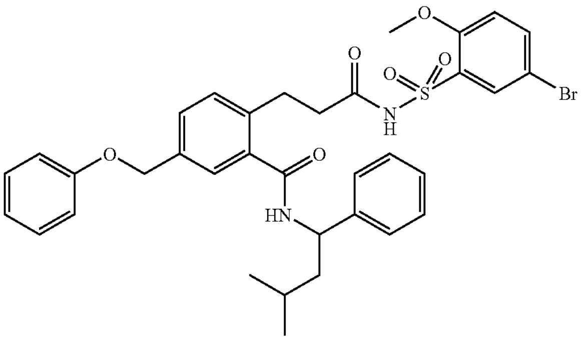

TLC: Rf 0.61 (chloroform:methanol=10:1).

Example 10(78)

N-phenylsulfonyl-3-(2-(2-phenylethoxy)-4-phenoxymethylphenyl)propanamide

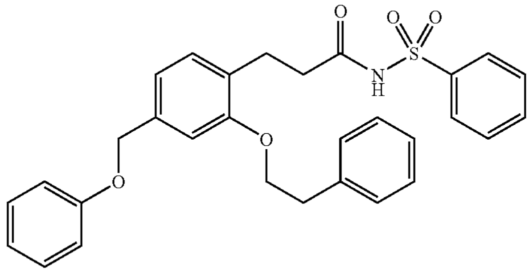

TLC: Rf 0.43 (hexane:ethyl acetate=2:1);

NMR (300 MHz, $CDCl_3$): δ 8.00-7.92 (m, 2H), 7.73 (brs, 1H), 7.62 (m, 1H), 7.56-7.48 (m, 2H), 7.35-7.24 (m, 7H), 7.00-6.90 (m, 5H), 6.82 (d, J=7.2 Hz, 1H), 4.99 (s, 2H), 4.26 (t, J=6.3 Hz, 2H), 3.11 (t, J=6.3 Hz, 2H), 2.77-2.72 (m, 2H), 2.21-2.16 (m, 2H).

Example 10(79)

(2E)-N-(5-bromo-2-methoxyphenylsulfonyl)-3-(2-benzyl-4-(pyrazol-1-ylmethyl)phenyl)-2-propenamide

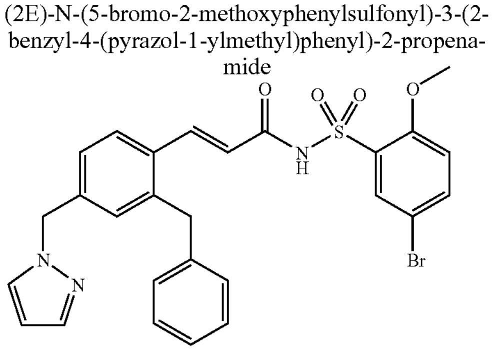

TLC: Rf 0.41 (chloroform:methanol=9:1);

NMR (300 MHz, $CDCl_3$): δ 8.18 (d, J=2.7 Hz, 1H), 7.92 (d, J=15.6 Hz, 1H), 7.65 (dd, J=8.7, 2.7 Hz, 1H), 7.55 (d, J=1.2 Hz, 1H), 7.45 (d, J=8.7 Hz, 1H), 7.40 (d, J=2.4 Hz, 1H), 7.30-7.14 (m, 4H), 7.05-7.00 (m, 3H), 6.87 (d, J=9.3 Hz, 1H), 6.39 (d, J=15.6 Hz, 1H), 6.29 (t, J=2.4 Hz, 1H), 5.30 (s, 2H), 4.02 (s, 2H), 3.86 (s, 3H).

Example 10(80)

(2E)-N-(5-bromo-2-methoxyphenylsulfonyl)-3-(2-benzyl-4-phenoxymethylphenyl)-2-propenamide

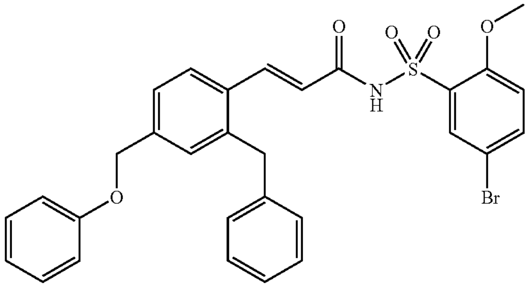

TLC: Rf 0.43 (hexane:ethyl acetate=1:3);

NMR (300 MHz, $CD_3OD$): δ 8.04 (d, J=2.4 Hz, 1H), 7.88 (d, J=15.6 Hz, 1H), 7.65-7.58 (m, 2H), 7.34-6.87 (m, 13H), 6.44 (d, J=15.6 Hz, 1H), 5.05 (s, 2H), 4.09 (s, 2H), 3.81 (s, 3H).

Example 10(81)

N-(5-bromo-2-methoxyphenylsulfonyl)-3-(2-(naphthalen-2-ylmethyl)-4-phenoxymethylphenyl)propanamide

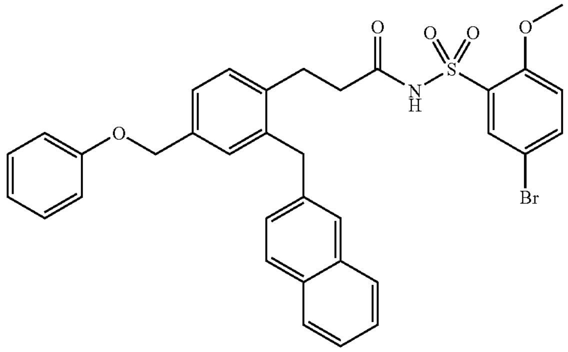

TLC: Rf 0.60 (hexane:ethyl acetate=1:2);

NMR (300 MHz, DMSO-$d_6$): δ 12.22 (s, 1H), 7.86-7.73 (m, 5H), 7.52 (s, 1H), 7.49-7.41 (m, 2H), 7.28-7.06 (m, 7H), 6.96-6.89 (m, 3H), 5.00 (s, 2H), 4.10 (s, 2H), 3.76 (s, 3H), 2.74 (t, J=7.8 Hz, 2H), 2.45-2.43 (m, 2H).

Example 10(82)

N-(5-bromo-2-methoxyphenylsulfonyl)-3-(2-(naphthalen-2-ylmethyl)-4-(pyrazol 1-ylmethyl)phenyl)propanamide

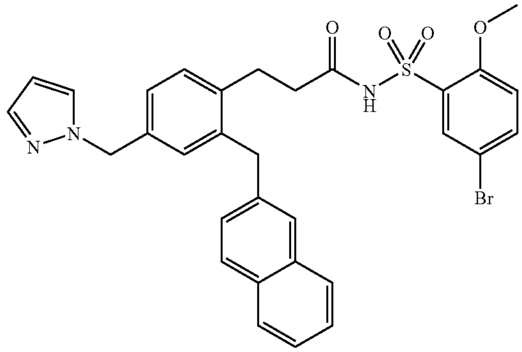

TLC: Rf 0.30 (hexane:ethyl acetate=1:2);

NMR (300 MHz, DMSO-$d_6$): δ 12.21 (br s, 1H), 7.86-7.73 (m, 6H), 7.51-7.43 (m, 4H), 7.22 (dd, J=8.7, 1.8 Hz, 1H), 7.10-7.00 (m, 3H), 6.91 (dd, 8.1, 1.8 Hz, 1H), 6.23 (t, J=2.1 Hz, 1H), 5.23 (s, 2H), 4.05 (s, 2H), 3.68 (s, 3H), 2.73-2.68 (m, 2H), 2.41 (t, J=7.2 Hz, 2H).

Example 10(83)

N-(3-chloro-4-fluorophenylsulfonyl)-3-(2-(2-(naphthalen-2-yl)ethoxy)-4-(3-cyanophenoxymethyl)phenyl)propanamide

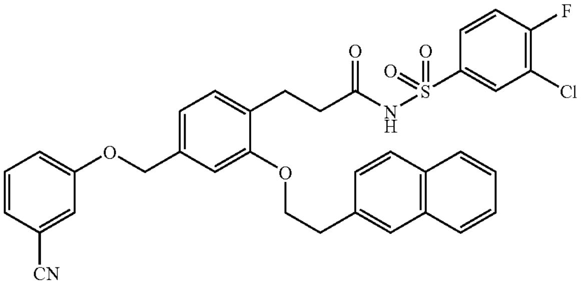

TLC: Rf 0.65 (chloroform:methanol=10:1).

Example 10(84)

N-(3-cyanophenylsulfonyl)-3-(2-(2-(naphthalen-2-yl)ethoxy)-4-(3-cyanophenoxymethyl)phenyl)propanamide

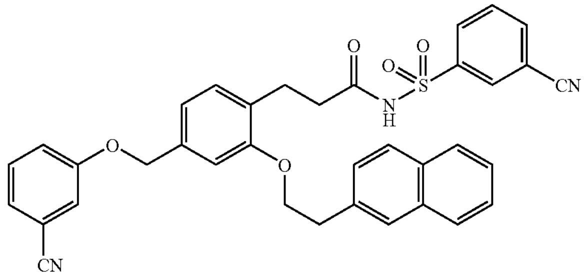

TLC: Rf 0.63 (chloroform:methanol=10:1).

Example 10(85)

N-(3,4-dichlorophenylsulfonyl)-3-(2-(2-(naphthalen-2-yl)ethoxy)-4-(3-cyanophenoxymethyl)phenyl)propanamide

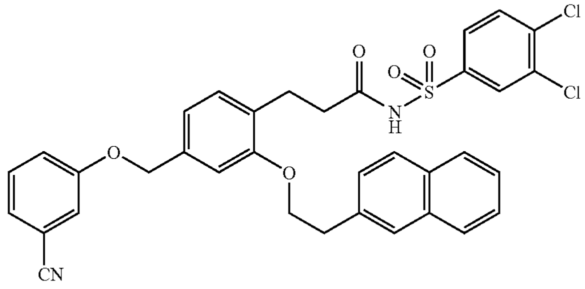

TLC: Rf 0.62 (chloroform:methanol=10:1).

Example 10(86)

N-(3-chloro-4-methylphenylsulfonyl)-3-(2-(2-(naphthalen-2-yl)ethoxy)-4-(3-cyanophenoxymethyl)phenyl)propanamide

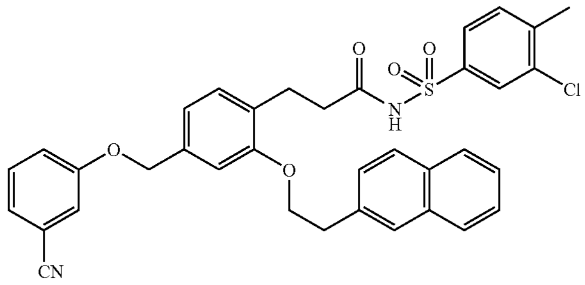

TLC: Rf 0.64 (chloroform:methanol=10:1).

Example 10(87)

N-(7-chlorobenzofurazan-4-ylsulfonyl)-3-(2-(2-(naphthalen-2-yl)ethoxy)-4-(3-cyanophenoxymethyl)phenyl)propanamide

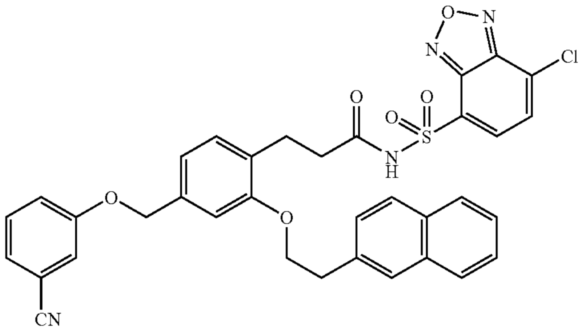

TLC: Rf 0.66 (chloroform:methanol=10:1).

Example 10(88)

N-(3,4-difluorophenylsulfonyl)-3-(2-(2-(naphthalen-2-yl)ethoxy)-4-(3-cyanophenoxymethyl)phenyl)propanamide

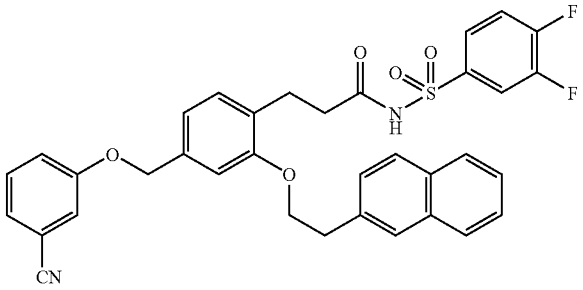

TLC: Rf 0.64 (chloroform:methanol=10:1).

Example 10(89)

N-(5-bromo-2-methoxyphenylsulfonyl)-3-(2-(2-(naphthalen-2-yl)ethoxy)-4-(3-cyanophenoxymethyl)phenyl)propanamide

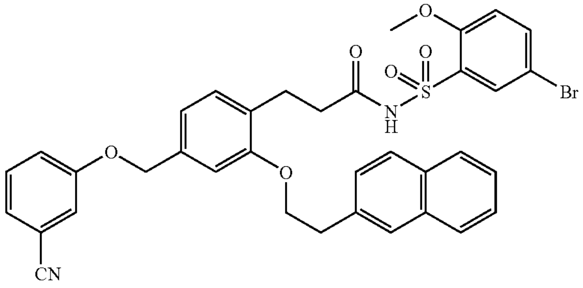

TLC: Rf 0.65 (chloroform:methanol=10:1).

Example 10(90)

N-(3,4-difluorophenylsulfonyl)-3-(2-(2-phenylethoxy)-4-(pyrazol-1-ylmethyl)phenyl)propanamide

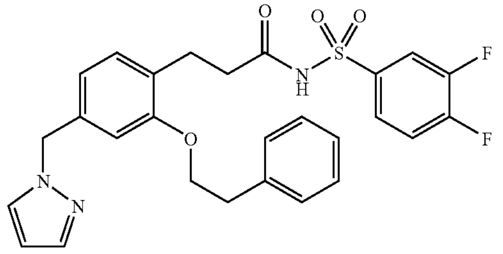

TLC: Rf 0.41 (chloroform:methanol=10:1);

NMR (300 MHz, $CDCl_3$): δ 7.84 (m, 1H), 7.83-7.73 (m, 2H), 7.55 (d, J=1.8 Hz, 1H), 7.40 (d, J=2.7 Hz, 1H), 7.37-7.23 (m, 6H), 6.89 (d, J=7.5 Hz, 1H), 6.67 (s, 1H), 6.63 (d, J=7.5 Hz, 1H), 6.29 (m, 1H), 5.25 (s, 2H), 4.20 (t, J=6.3 Hz, 2H), 3.08 (t, J=6.3 Hz, 2H), 2.70 (t, J=7.5 Hz, 2H), 2.14 (t, J=7.5 Hz, 2H).

Example 10(91)

N-(3,4-difluorophenylsulfonyl)-3-(2-(2-(benzimidazol-1-yl)ethoxy)-4-(pyrazol 1-ylmethyl)phenyl)propanamide

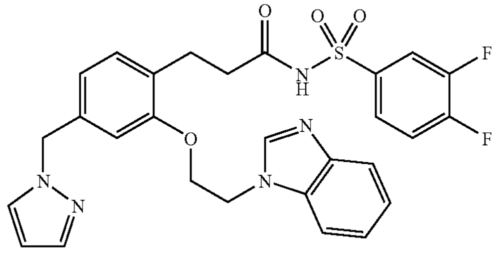

TLC: Rf 0.38 (chloroform:methanol=10:1);

NMR (300 MHz, $CDCl_3$): δ 8.06 (s, 1H), 8.04-7.94 (m, 2H), 7.84 (m, 1H), 7.52 (d, J=2.1 Hz, 1H), 7.45-7.28 (m, 5H), 7.02 (d, J=7.5 Hz, 1H), 6.69 (d, J=7.5 Hz, 1H), 6.54 (s, 1H), 6.26 (m, 1H), 5.20 (s, 2H), 4.64 (t, J=4.8 Hz, 2H), 4.15 (t, J=4.8 Hz, 2H), 2.71 (t, J=8.1 Hz, 2H), 1.81 (t, J=8.1 Hz, 2H).

Example 10(92)

N-(3,4-difluorophenylsulfonyl)-3-(2-(2-(benzoylamino)ethoxy)-4-(pyrazol 1-ylmethyl)phenyl)propanamide

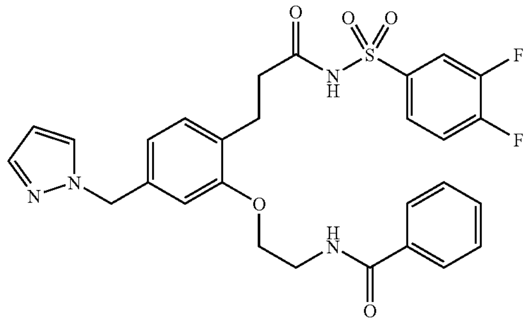

TLC: Rf 0.50 (ethyl acetate);

NMR (300 MHz, $CDCl_3$): δ 7.85-7.80 (m, 4H), 7.56-7.39 (m, 5H), 6.99 (d, J=7.5 Hz, 1H), 6.70-6.61 (m, 3H), 6.28 (t, J=2.1 Hz, 1H), 5.25 (s, 2H), 4.05-3.96 (m, 4H), 2.75-2.69 (m, 2H), 2.43-2.37 (m, 2H).

Example 10(93)

N-(3,4-difluorophenylsulfonyl)-3-(2-(2-(2H-benzotriazol-2-yl)ethoxy)-4-(pyrazol-1-ylmethyl)phenyl)propanamide

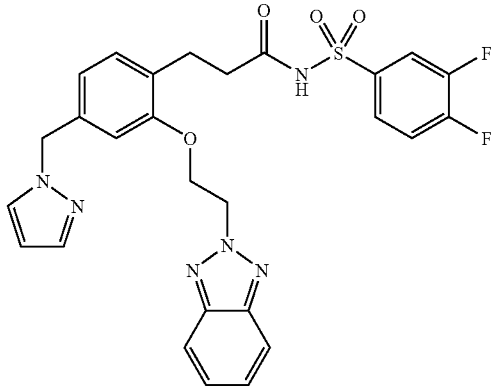

TLC: Rf 0.60 (ethyl acetate:methanol=20:1).

Example 10(94)

N-(3,4-difluorophenylsulfonyl)-3-(2-(2-(1H-benzotriazol-1-yl)ethoxy)-4-(pyrazol-1-ylmethyl)phenyl)propanamide

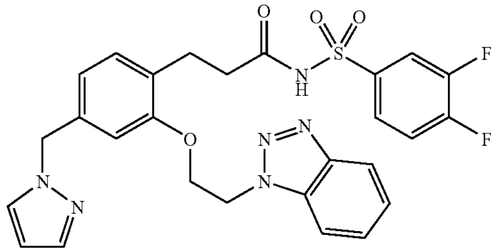

TLC: Rf 0.44 (ethyl acetate:methanol=20:1).

Example 10(95)

N-(3,4-difluorophenylsulfonyl)-3-(2-(2-(2-methylbenzimidazol-1-yl)ethoxy)-4-(pyrazol 1-ylmethyl)phenyl)propanamide

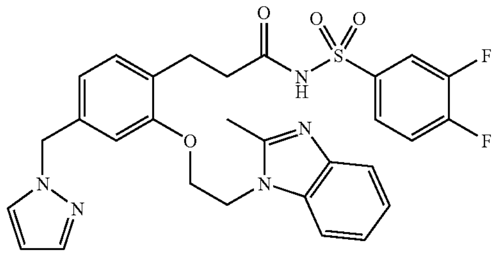

TLC: Rf 0.50 (chloroform:methanol=9:1);

NMR (300 MHz, $CD_3OD$): δ 7.87-7.48 (m, 6H), 7.43-7.18 (m, 3H), 6.93 (d, J=7.2 Hz, 1H), 6.70 (s, 1H), 6.61 (d, J=7.2

Hz, 1H), 6.32 (t, J=2.1 Hz, 1H), 5.21 (s, 2H), 4.69 (t, J=4.8 Hz, 2H), 4.33 (t, J=4.8 Hz, 2H), 2.77-2.54 (m, 5H), 2.34-2.13 (m, 2H).

Example 10(96)

N-(3,4-difluorophenylsulfonyl)-3-(2-(2-(1H-indazol-1-yl)ethoxy)-4-(pyrazol 1-ylmethyl)phenyl)propanamide

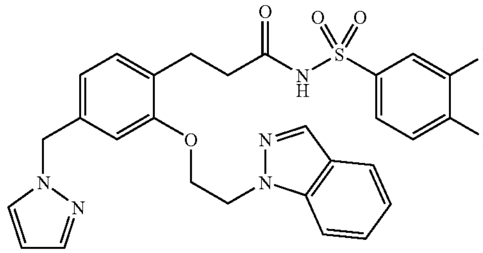

TLC: Rf 0.63 (chloroform:methanol=9:1);

NMR (300 MHz, $CDCl_3$): δ 8.12 (s, 1H), 7.97-7.83 (m, 2H), 7.79 (d, J=7.8 Hz, 1H), 7.55-7.41 (m, 3H), 7.37-7.18 (m, 3H), 6.95 (d, J=7.8 Hz, 1H), 6.66 (d, J=7.2 Hz, 1H), 6.56 (s, 1H), 6.26 (t, J=2.1 Hz, 1H), 5.20 (s, 2H), 4.86 (t, J=4.5 Hz, 2H), 4.32 (t, J=4.5 Hz, 2H), 2.82-2.69 (m, 2H), 2.42-2.29 (m, 2H).

Example 10(97)

(2E)-N-(3,4-difluorophenylsulfonyl)-3-(2-(2-(naphthalen-2-yl)ethoxy)-4-(pyrazol-1-ylmethyl)phenyl)-2-propenamide

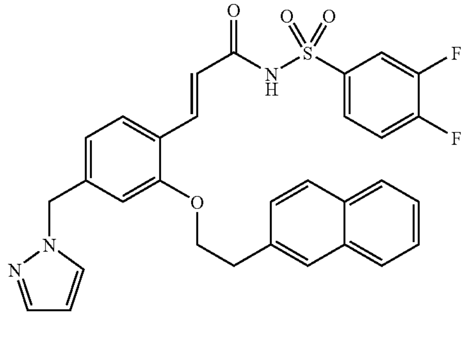

TLC: Rf 0.55 (chloroform:methanol=9:1);

NMR (300 MHz, DMSO-$d_6$): δ 12.46 (brs, 1H), 8.07-7.95 (m, 1H), 7.95-7.65 (m, 8H), 7.55-7.35 (m, 5H), 6.98 (s, 1H), 6.72 (d, J=7.2 Hz, 1H), 6.68 (d, J=15.9 Hz, 1H), 6.25 (t, J=2.1 Hz, 1H), 5.32 (s, 2H), 4.28 (t, J=7.2 Hz, 2H), 3.28 (t, J=7.2 Hz, 2H).

Example 10(98)

N-(3,4-difluorophenylsulfonyl)-3-(2-(2-(naphthalen-2-yl)ethoxy)-4-(4-methylpiperazin-1-ylmethyl)phenyl)propanamide

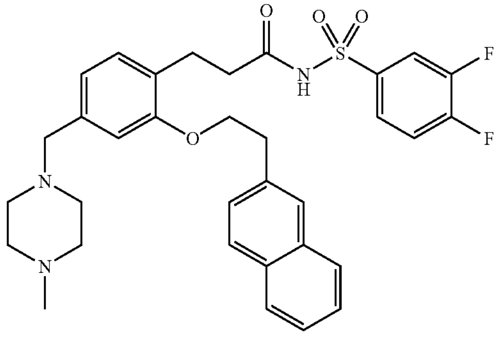

TLC: Rf 0.47 (chloroform:methanol=3:1).

Example 10(99)

N-(3,4-difluorophenylsulfonyl)-3-(2-(2-(naphthalen-2-yl)ethoxy)-4-(4-acetylpiperazin-1-ylmethyl)phenyl)propanamide

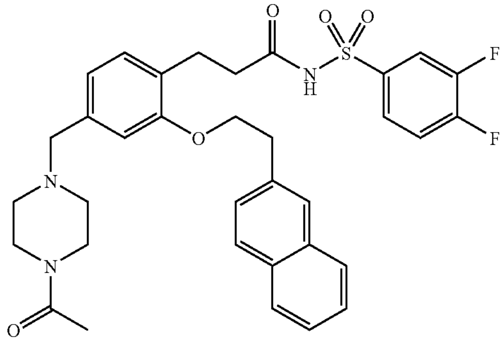

TLC: Rf 0.33 (chloroform:methanol=10:1).

Example 10(100)

N-(3,4-difluorophenylsulfonyl)-3-(2-(2-(naphthalen-2-yl)ethoxy)-4-(morpholin-4-ylmethyl)phenyl)propanamide

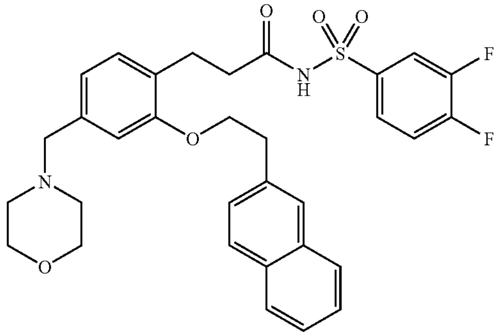

TLC: Rf 0.57 (ethyl acetate:methanol=10:1).

Example 10(101)

N-(3,4-difluorophenylsulfonyl)-3-(2-(2-(naphthalen-2-yl)ethoxy)-4-(pyridin-3-yloxymethyl)phenyl)propanamide

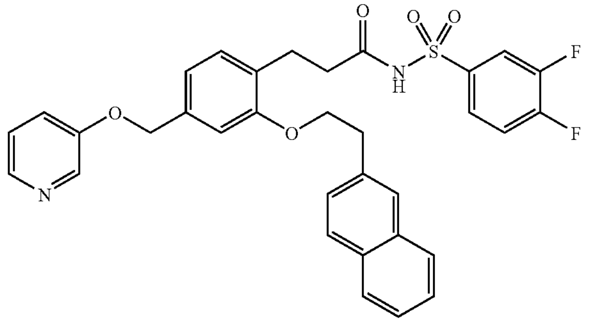

TLC: Rf 0.50 (ethyl acetate).

Example 10(102)

N-phenylsulfonyl-2-(2-(2-(naphthalen-2-yl)ethoxy)-4-(pyrazol-1-ylmethyl)phenyl)acetamide

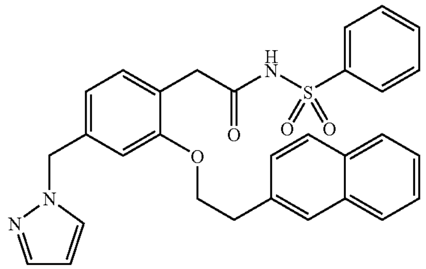

TLC: Rf 0.50 (hexane:ethyl acetate=1:3).

Example 10(103)

N-phenylsulfonyl-4-(2-(2-(naphthalen-2-yl)ethoxy)-4-(pyrazol-1-ylmethyl)phenyl)butanamide

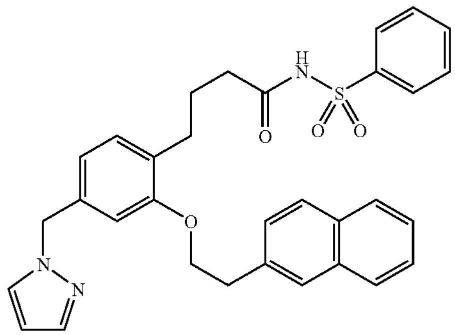

TLC: Rf 0.49 (chloroform:methanol=9:1);

NMR (300 MHz, $CDCl_3$): δ 8.00 (d, J=6.9 Hz, 2H), 7.86-7.76 (m, 3H), 7.70 (s, 2H), 7.64-7.36 (m, 7H), 6.91 (d, J=7.8 Hz, 1H), 6.71-6.65 (m, 2H), 6.28 (dd, J=1.8, 1.8 Hz, 1H), 5.25 (s, 2H), 4.23 (t, J=6.6 Hz, 2H), 3.21 (t, J=6.6 Hz, 2H), 2.42 (t, J=7.2 Hz, 2H), 1.80 (t, J=7.2 Hz, 2H), 1.59 (m, 2H).

Example 10(104)

N-(3,4-difluorophenylsulfonyl)-4-(2-(2-(naphthalen-2-yl)ethoxy)-4-(pyrazol 1-ylmethyl)phenyl)butanamide

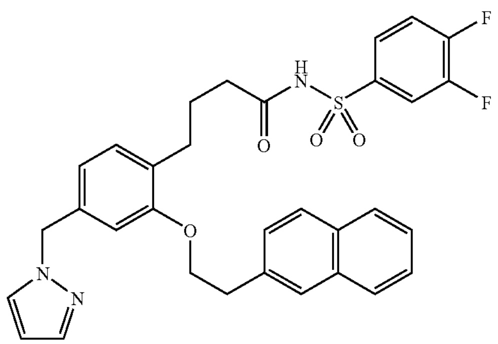

TLC: Rf 0.56 (chloroform:methanol=9:1);

NMR (300 MHz, DMSO-$d_6$): δ 7.98-7.65 (m, 8H), 7.50-7.40 (m, 4H), 6.90 (d, J=7.8 Hz, 1H), 6.84 (s, 1H), 6.63 (d, J=7.8 Hz, 1H), 6.23 (dd, J=2.1, 2.1 Hz, 1H), 5.23 (s, 2H), 4.16 (t, J=6.3 Hz, 2H), 3.15 (t, J=6.3 Hz, 2H), 2.34 (t, J=7.5 Hz, 2H), 2.14 (t, J=7.5 Hz, 2H), 1.55 (m, 2H).

Example 10(105)

N-(pyridin-3-ylsulfonyl)-3-(2-(2-(naphthalen-2-yl)ethoxy)-4-(pyrazol 1-ylmethyl)phenyl)propanamide

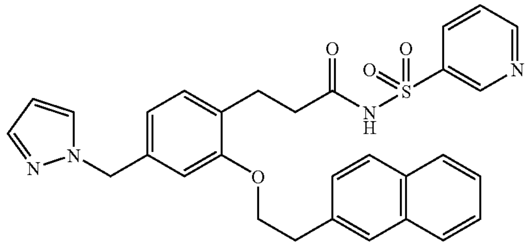

TLC: Rf 0.49 (chloroform:methanol=10:1).

Example 10(106)

N-(1-methylpyrrol-2-ylsulfonyl)-3-(2-(2-(naphthalen-2-yl)ethoxy)-4-(pyrazol-1-ylmethyl)phenyl)propanamide

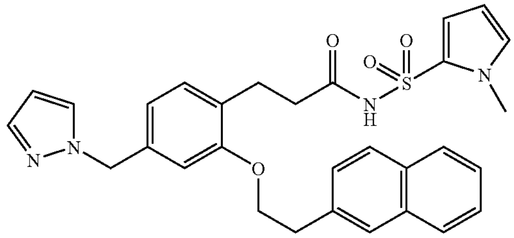

TLC: Rf 0.70 (chloroform:methanol=10:1).

Example 10(107)

N-(4-methylthiazol-2-ylsulfonyl)-3-(2-(2-(naphthalen-2-yl)ethoxy)-4-(pyrazol-1-ylmethyl)phenyl)propanamide

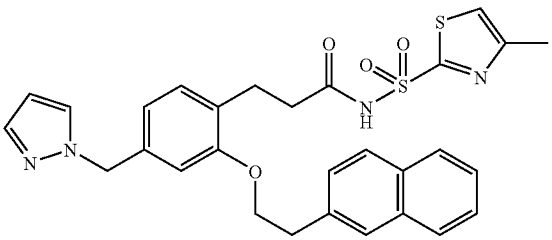

TLC: Rf 0.52 (chloroform:methanol=10:1).

Example 10(108)

N-(3,5-dimethylisoxazol-4-ylsulfonyl)-3-(2-(2-(naphthalen-2-yl)ethoxy)-4-(pyrazol 1-ylmethyl)phenyl)propanamide

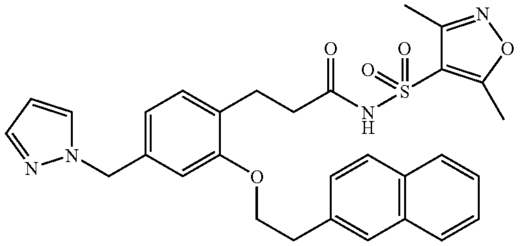

TLC: Rf 0.71 (chloroform:methanol=10:1).

Example 10(109)

N-(pyridin-2-ylsulfonyl)-3-(2-(2-(naphthalen-2-yl)ethoxy)-4-(pyrazol-1-ylmethyl)phenyl)propanamide

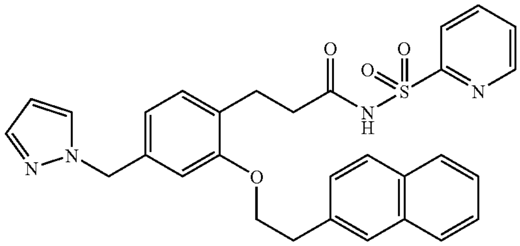

TLC: Rf 0.51 (chloroform:methanol=10:1).

Example 10(110)

N-(1-methylimidazol-2-ylsulfonyl)-3-(2-(2-(naphthalen-2-yl)ethoxy)-4-(pyrazol-1-ylmethyl)phenyl)propanamide

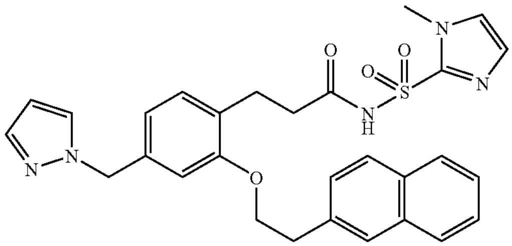

TLC: Rf 0.48 (chloroform:methanol=10:1).

Example 10(111)

N-phenylsulfonyl-2-(2-(naphthalen-2-yl)ethoxy)-4-(pyrazol-1-ylmethyl)benzamide

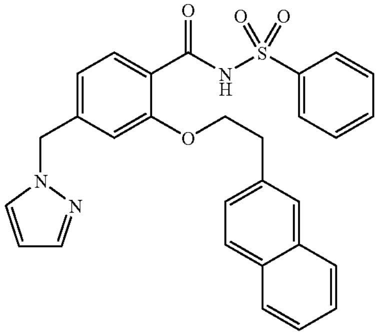

TLC: Rf 0.66 (chloroform:methanol=19:1);

NMR (300 MHz, $CDCl_3$): δ 10.35 (bs, 1H), 7.99 (d, J=8.4 Hz, 1H), 7.93-7.78 (m, 6H), 7.61-7.28 (m, 8H), 6.84 (d, J=8.1 Hz, 1H), 6.78 (s, 1H), 6.31 (t, J=2.1 Hz, 1H), 5.31 (s, 2H), 4.47 (t, J=6.3 Hz, 2H), 3.42 (t, J=6.3 Hz, 2H).

Example 10(112)

N-(5-methylfuran-2-ylsulfonyl)-3-(2-(2-(naphthalen-2-yl)ethoxy)-4-(pyrazol 1-ylmethyl)phenyl)propanamide

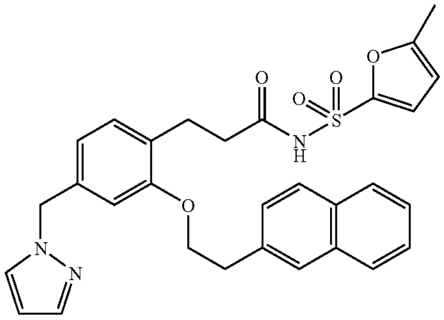

TLC: Rf 0.40 (hexane:ethyl acetate=1:1);

NMR (300 MHz, $CDCl_3$): δ 7.88-7.77 (m, 4H), 7.68 (brs, 1H), 7.54 (d, J=1.5 Hz, 1H), 7.53-7.45 (m, 2H), 7.42-7.36 (m, 2H), 7.16 (d, J=3.6 Hz, 1H), 6.97 (d, J=8.1 Hz, 1H), 6.67-6.65 (m, 2H), 6.27 (t, J=2.1 Hz, 1H), 6.11 (d, J=3.3 Hz, 1H), 5.24 (s, 2H), 4.24 (t, J=6.3 Hz, 2H), 3.23 (t, J=6.3 Hz, 2H), 2.74 (t, J=7.5 Hz, 2H), 2.34 (s, 3H), 2.17 (t, J=7.5 Hz, 2H).

Example 10(113)

N-(furan-3-ylsulfonyl)-3-(2-(2-(naphthalen-2-yl)ethoxy)-4-(pyrazol-1-ylmethyl)phenyl)propanamide

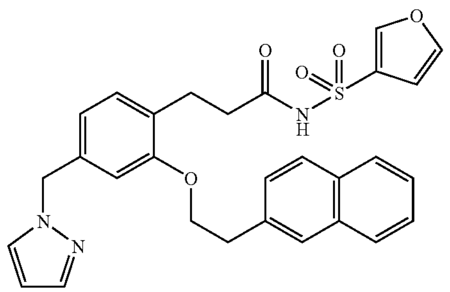

TLC: Rf 0.30 (hexane:ethyl acetate=1:1);

NMR (300 MHz, $CDCl_3$): δ 8.01 (m, 1H), 7.87-7.77 (m, 4H), 7.69 (brs, 1H), 7.54 (m, 1H), 7.53-7.44 (m, 2H), 7.41-7.37 (m, 3H), 6.92 (d, J=7.5 Hz, 1H), 6.67 (d, J=1.5 Hz, 1H), 6.65-6.61 (m, 2H), 6.28 (t, J=2.1 Hz, 1H), 5.24 (s, 2H), 4.25 (t, J=6.3 Hz, 2H), 3.23 (t, J=6.3 Hz, 2H), 2.73 (t, J=7.5 Hz, 2H), 2.09 (t, J=7.5 Hz, 2H).

Example 10(114)

N-(thiophen-3-ylsulfonyl)-3-(2-(2-(naphthalen-2-yl)ethoxy)-4-(pyrazol 1-ylmethyl)phenyl)propanamide

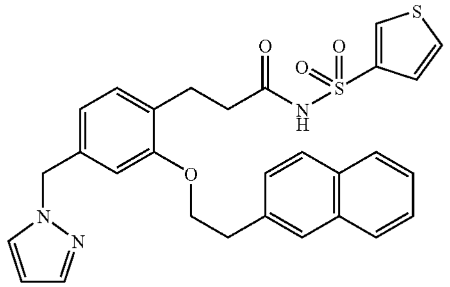

TLC: Rf 0.35 (hexane:ethyl acetate=1:1);

NMR (300 MHz, $CDCl_3$): δ 8.10 (dd, J=3.0, 1.5 Hz, 1H), 7.87-7.77 (m, 4H), 7.68 (brs, 1H), 7.54 (m, 1H), 7.52-7.45 (m, 2H), 7.41-7.30 (m, 4H), 6.89 (d, J=7.8 Hz, 1H), 6.67 (brs, 1H), 6.62 (d, J=7.8 Hz, 1H), 6.28 (t, J=2.1 Hz, 1H), 5.24 (s, 2H), 4.24 (t, J=6.3 Hz, 2H), 3.23 (t, J=6.3 Hz, 2H), 2.71 (t, J=7.5 Hz, 2H), 2.09 (t, J=7.5 Hz, 2H).

Example 10(115)

N-(2,5-dimethoxyphenylsulfonyl)-3-(2-(2-(naphthalen-2-yl)ethoxy)-4-(pyrazol 1-ylmethyl)phenyl)propanamide

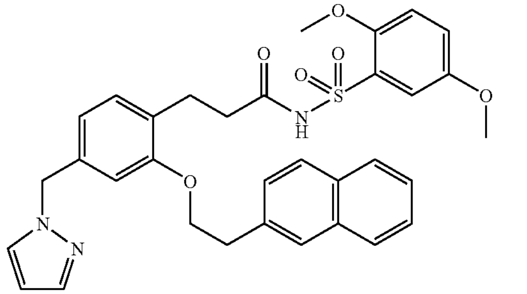

TLC: Rf 0.26 (hexane:ethyl acetate=1:1);

NMR (300 MHz, $CDCl_3$): δ 8.16 (brs, 1H), 7.86-7.76 (m, 3H), 7.67 (brs, 1H), 7.54-7.52 (m, 2H), 7.51-7.43 (m, 2H), 7.39-7.35 (m, 2H), 7.05 (dd, J=9.3, 3.0 Hz, 1H), 6.94 (d, J=7.2 Hz, 1H), 6.80 (d, J=9.1 Hz, 1H), 6.65-6.62 (m, 2H), 6.27 (t, J=2.1 Hz, 1H), 5.23 (s, 2H), 4.18 (t, J=6.6 Hz, 2H), 3.78 (s, 3H), 3.67 (s, 3H), 3.19 (t, J=6.6 Hz, 2H), 2.74 (t, J=7.5 Hz, 2H), 2.33 (t, J=7.5 Hz, 2H).

Example 10(116)

N-(4-methoxyphenylsulfonyl)-3-(2-(2-(naphthalen-2-yl)ethoxy)-4-(pyrazol-1-ylmethyl)phenyl)propanamide

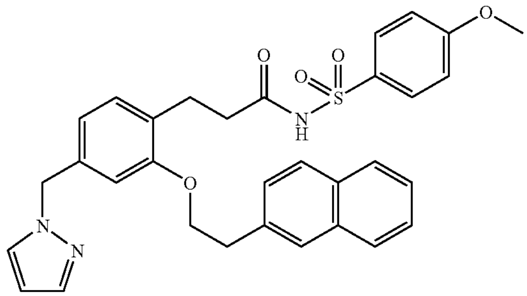

TLC: Rf 0.34 (hexane:ethyl acetate=1:1);

NMR (300 MHz, $CDCl_3$): δ 7.87-7.76 (m, 6H), 7.67 (brs, 1H), 7.53 (m, 1H), 7.52-7.45 (m, 2H), 7.40-7.37 (m, 2H), 6.95-6.88 (m, 3H), 6.66 (brs, 1H), 6.62 (d, J=7.2 Hz, 1H), 6.28 (t, J=2.1 Hz, 1H), 5.24 (s, 2H), 4.23 (t, J=6.3 Hz, 2H), 3.84 (s, 3H), 3.21 (t, J=6.3 Hz, 2H), 2.70 (t, J=7.5 Hz, 2H), 2.07 (t, J=7.5 Hz, 2H).

Example 10(117)

N-(3,4-difluorophenylsulfonyl)-3-(2-(2-cyclohexyloxyethoxy)-4-(pyrazol-1-ylmethyl)phenyl)propanamide

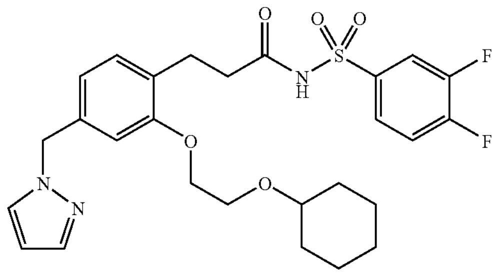

TLC: Rf 0.63 (chloroform:methanol=9:1);

NMR (300 MHz, $CDCl_3$): δ 7.64-7.56 (m, 2H), 7.54 (d, J=1.2 Hz, 1H), 7.40 (d, J=1.8 Hz, 1H), 7.20 (m, 1H), 6.88 (d, J=7.8 Hz, 1H), 6.62 (d, J=7.8 Hz, 1H), 6.57 (s, 1H), 6.28 (dd, J=1.8, 1.2 Hz, 1H), 5.25 (s, 2H), 4.10 (m, 2H), 3.91 (m, 2H), 3.45 (m, 1H), 2.86 (t, J=6.9 Hz, 2H), 2.71 (t, J=6.9 Hz, 2H), 2.05 (m, 2H), 1.80 (m, 2H), 1.42-1.15 (m, 6H).

Example 10(118)

N-(3,4-difluorophenylsulfonyl)-3-(2-(2-(piperidin-1-yl)ethoxy)-4-(pyrazol 1-ylmethyl)phenyl)propanamide

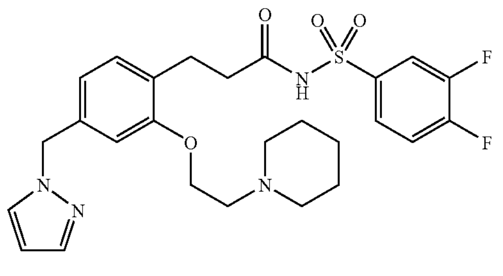

TLC: Rf 0.38 (chloroform:methanol=9:1);

NMR (300 MHz, $CDCl_3$): δ 7.63-7.56 (m, 2H), 7.53 (d, J=2.1 Hz, 1H), 7.40 (d, J=2.1 Hz, 1H), 7.15 (m, 1H), 7.10 (d, J=7.8 Hz, 1H), 6.80 (d, J=7.8 Hz, 1H), 6.62 (s, 1H), 6.28 (dd, J=2.1, 2.1 Hz, 1H), 5.27 (s, 2H), 4.18 (t, J=5.1 Hz, 2H), 3.50 (t, J=5.1 Hz, 2H), 3.24 (brs, 4H), 2.91 (m, 2H), 2.46 (m, 2H), 2.15-2.00 (m, 4H), 1.65 (m, 2H).

Example 10(119)

N-phenylsulfonyl-3-(2-(2-(3-methoxybenzoylamino)ethoxy)-4-(pyrazol 1-ylmethyl)phenyl)propanamide

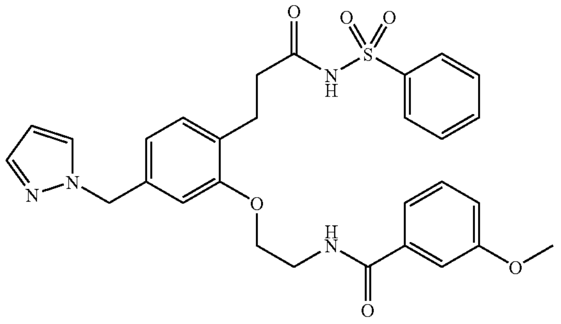

TLC: Rf 0.50 (ethyl acetate);

NMR (300 MHz, $CDCl_3$): δ 11.00 (s, 1H), 8.01-7.98 (m, 2H), 7.61-7.32 (m, 8H), 7.09-7.05 (m, 1H), 6.97 (d, J=7.5 Hz, 1H), 6.76-6.59 (m, 3H), 6.28 (t, J=2.1 Hz, 1H), 5.24 (s, 2H), 4.03-4.00 (m, 2H), 3.95-3.90 (m, 2H), 3.87 (s, 3H), 2.75-2.70 (m, 2H), 2.42-2.36 (m, 2H).

Example 10(120)

N-(3,4-difluorophenylsulfonyl)-3-(2-(2-(3-methoxybenzoylamino)ethoxy)-4-(pyrazol-1-ylmethyl)phenyl)propanamide

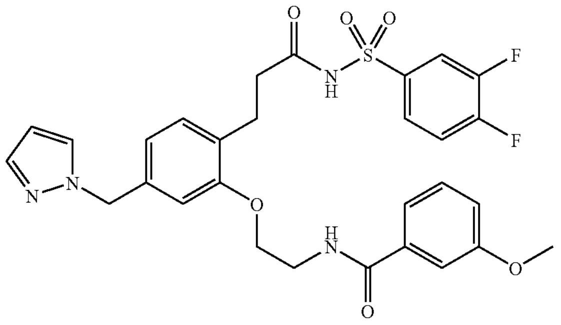

TLC: Rf 0.50 (ethyl acetate);

NMR (300 MHz, $CDCl_3$): δ 11.45 (s, 1H), 7.86-7.81 (m, 2H), 7.55-7.22 (m, 6H), 7.11-7.07 (m, 1H), 6.99 (d, J=7.5 Hz, 1H), 6.70-6.58 (m, 3H), 6.28 (t, J=2.1 Hz, 1H), 5.25 (s, 2H), 4.06-3.94 (m, 4H), 3.88 (s, 3H), 2.74-2.69 (m, 2H), 2.42-2.36 (m, 2H).

Example 10(121)

N-(3,4-difluorophenylsulfonyl)-3-(3-(3-phenylpropoxy)-4-(pyrazol-1-ylmethyl)phenyl)propanamide

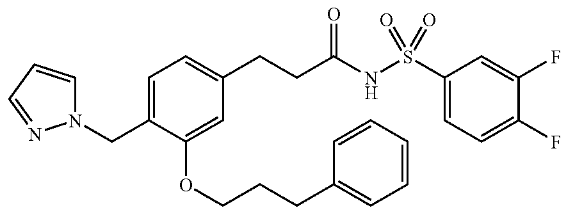

TLC: Rf 0.50 (chloroform:methanol=10:1).

Example 10(122)

N-(3,4-difluorophenylsulfonyl)-3-(3-(3-(naphthalen-1-yl)propoxy)-4-(pyrazol 1-ylmethyl)phenyl)propanamide

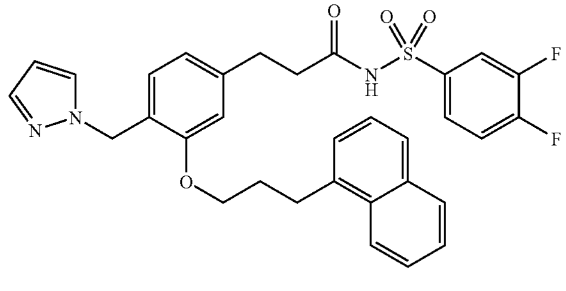

TLC: Rf 0.53 (chloroform:methanol=10:1).

Example 10(123)

N-phenylsulfonyl-3-(2-((naphthalen-1-ylmethyl)carbamoyl)-4-(pyrazol-1-ylmethyl)phenyl)propanamide

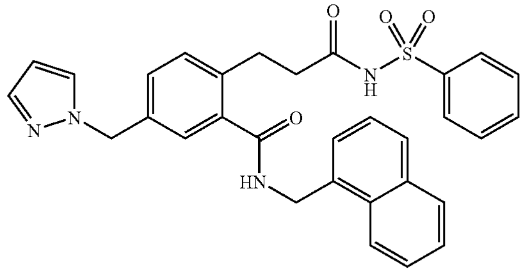

TLC: Rf 0.51 (chloroform:methanol=10:1).

Example 10(124)

N-(3,4-difluorophenylsulfonyl)-3-(2-((naphthalen-1-ylmethyl)carbamoyl)-4-(pyrazol-1-ylmethyl)phenyl)propanamide

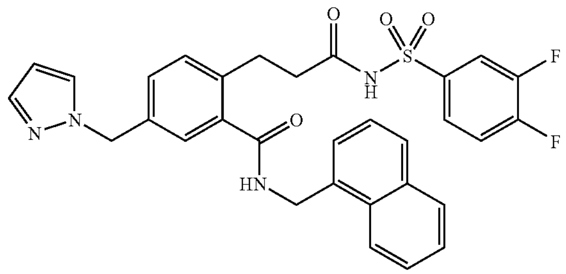

TLC: Rf 0.51 (chloroform:methanol=10:1).

Example 10(125)

N-phenylsulfonyl-3-(2-((naphthalen-2-ylmethyl)carbamoyl)-4-(pyrazol-1-ylmethyl)phenyl)propanamide

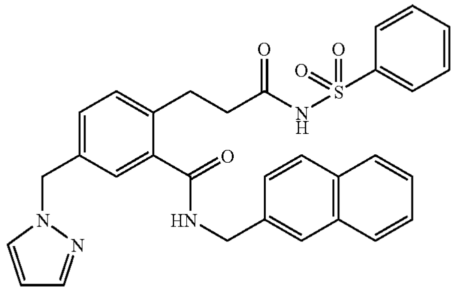

TLC: Rf 0.30 (chloroform:methanol=10:1);

NMR (300 MHz, DMSO-$d_6$): δ 8.96 (t, J=5.7 Hz, 1H), 7.94-7.41 (m, 14H), 7.21 (s, 1H), 7.11 (s, 2H), 6.29 (t, J=1.8 Hz, 1H), 5.32 (s, 2H), 4.57 (d, J=5.7 Hz, 2H), 2.81 (t, J=7.4 Hz, 2H), 2.54 (t, J=7.4 Hz, 2H).

Example 10(126)

N-(3,4-difluorophenylsulfonyl)-3-(2-((naphthalen-2-ylmethyl)carbamoyl)-4-(pyrazol-1-ylmethyl)phenyl)propanamide

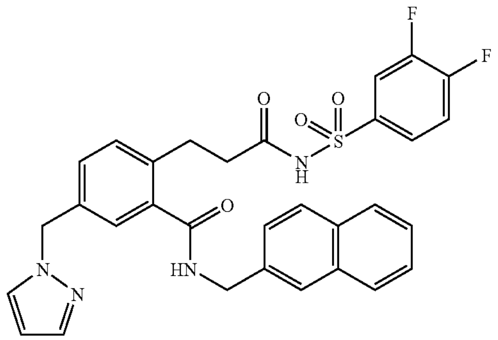

TLC: Rf 0.28 (chloroform:methanol=10:1);

NMR (300 MHz, DMSO-$d_6$): δ 8.98 (t, J=5.7 Hz, 1H), 8.00-7.64 (m, 8H), 7.57-7.42 (m, 4H), 7.28 (s, 1H), 7.20-7.10 (m, 2H), 6.28 (t, J=2.1 Hz, 1H), 5.33 (s, 2H), 4.57 (d, J=5.7 Hz, 1H), 2.83 (t, J=7.1 Hz, 2H), 2.57 (t, J=7.1 Hz, 2H).

Example 10(127)

N-phenylsulfonyl-3-(2-(benzylcarbamoyl)-4-(pyrazol-1-ylmethyl)phenyl)propanamide

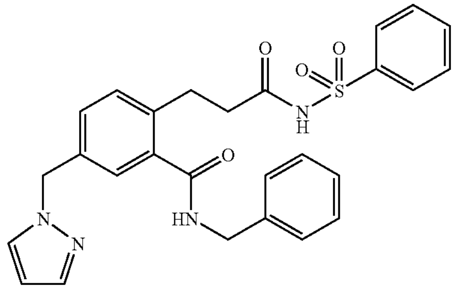

TLC: Rf 0.67 (chloroform:methanol=9:1);

NMR (300 MHz, DMSO-$d_6$): δ 12.10 (brs, 1H), 8.84 (t, J=6.0 Hz, 1H), 7.90-7.88 (m, 2H), 7.81 (m, 1H), 7.71 (m, 1H), 7.63-7.57 (m, 2H), 7.45 (brs, 1H), 7.27-7.21 (m, 6H), 7.08 (brs, 2H), 6.27 (t, J=2.1 Hz, 1H), 5.29 (s, 2H), 4.37 (d, J=6.0 Hz, 2H), 2.77-2.72 (m, 2H), 2.50-2.45 (m, 2H).

Example 10(128)

N-(3,4-difluorophenylsulfonyl)-3-(2-(benzylcarbamoyl)-4-(pyrazol 1-ylmethyl)phenyl)propanamide

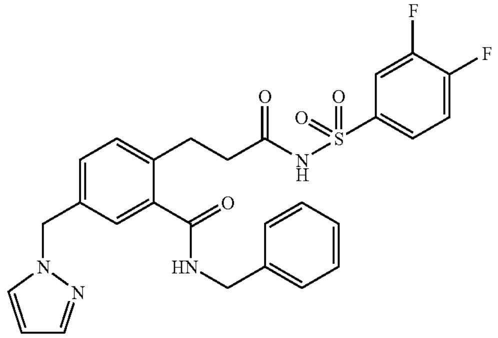

TLC: Rf 0.64 (chloroform:methanol=9:1);

NMR (300 MHz, DMSO-$d_6$): δ 12.30 (brs, 1H), 8.86 (t, J=6.3 Hz, 1H), 7.93 (m, 1H), 7.82-7.66 (m, 3H), 7.45 (brs, 1H), 7.31-7.20 (m, 6H), 7.15-7.08 (m, 2H), 6.26 (m, 1H), 5.29 (s, 2H), 4.38 (d, J=6.0 Hz, 2H), 2.79-2.74 (m, 2H), 2.54-2.49 (m, 2H).

Example 10(129)

N-(3,4-difluorophenylsulfonyl)-3-(3-(3-(naphthalen-2-yl)propoxy)-4-(pyrazol 1-ylmethyl)phenyl)propanamide

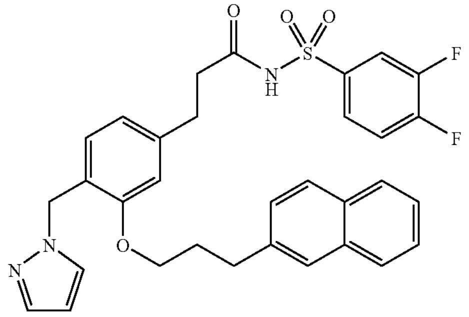

TLC: Rf 0.51 (chloroform:methanol=9:1);

NMR (300 MHz, $CDCl_3$): δ 9.22 (brs, 1H), 7.90-7.70 (m, 5H), 7.60 (s, 1H), 7.51 (d, J=1.5 Hz, 1H), 7.50-7.40 (m, 3H), 7.40-7.20 (m, 2H), 6.82 (d, J=7.8 Hz, 1H), 6.48 (s, 1H), 6.47 (d, J=7.8 Hz, 1H), 6.26 (t, J=1.8 Hz, 1H), 5.29 (s, 2H), 3.90 (t, J=7.5 Hz, 2H), 2.91 (t, J=7.5 Hz, 2H), 2.76 (t, J=7.5 Hz, 2H), 2.37 (t, J=7.5 Hz, 2H), 2.30-2.10 (m, 2H).

Example 10(130)

N-phenylsulfonyl-3-(2-((3-methyl-1-(3,5-dimethylphenyl)butyl)carbamoyl)-4-(pyrazol 1-ylmethyl)phenyl)propanamide

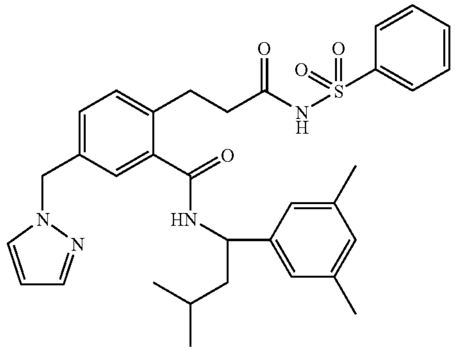

TLC: Rf 0.65 (chloroform:methanol=10:1).

Example 10(131)

N-(3,4-difluorophenylsulfonyl)-3-(2-((3-methyl-1-(3,5-dimethylphenyl)butyl)carbamoyl)-4-(pyrazol-1-ylmethyl)phenyl)propanamide

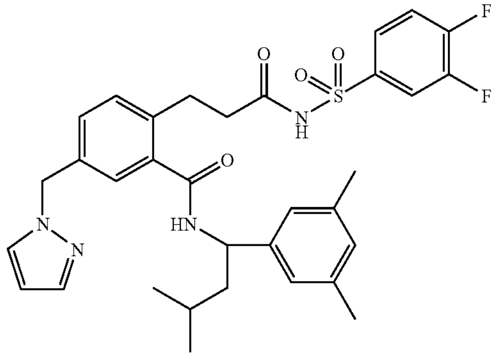

TLC: Rf 0.62 (chloroform:methanol=10:1).

Example 10(132)

N-phenylsulfonyl-3-(2-((3-methyl-1-(3,5-dimethoxyphenyl)butyl)carbamoyl)-4-(pyrazol-1-ylmethyl)phenyl)propanamide

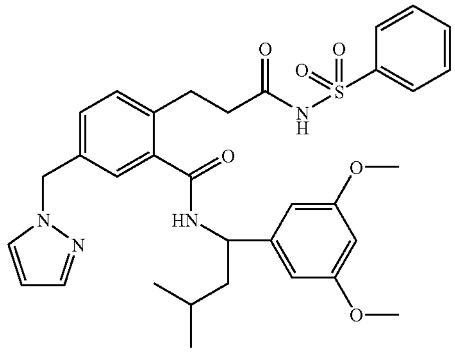

TLC: Rf 0.64 (chloroform:methanol=10:1).

Example 10(133)

N-(3,4-difluorophenylsulfonyl)-3-(2-((3-methyl-1-(3,5-dimethoxyphenyl)butyl)carbamoyl)-4-(pyrazol-1-ylmethyl)phenyl)propanamide

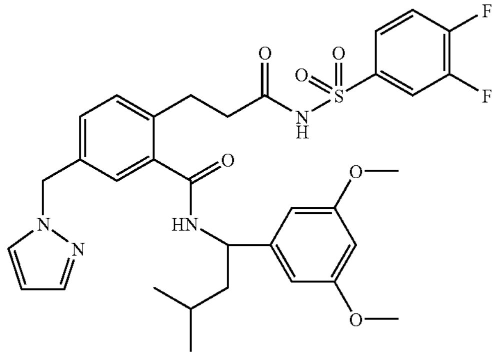

TLC: Rf 0.62 (chloroform:methanol=10:1).

Example 10(134)

(2E)-N-(3,4-difluorophenylsulfonyl)-3-(2-(2-(naphthalen-2-yl)ethoxy)-4-(4-acetylpiperazin-1-ylmethyl)phenyl)-2-propenamide

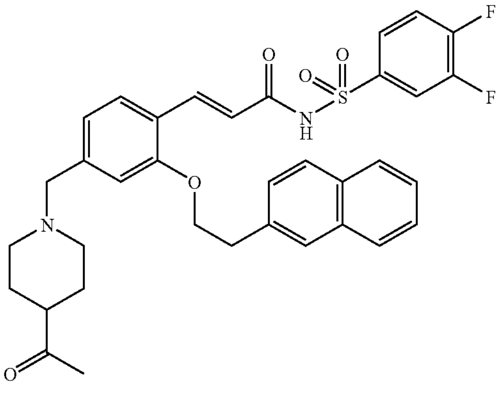

TLC: Rf 0.58 (chloroform:methanol=10:1).

Example 10(135)

(2E)-N-phenylsulfonyl-3-(2-(N-benzylsulfonyl-N-methylamino)-4-(pyrazol-1-ylmethyl)phenyl)-2-propenamide

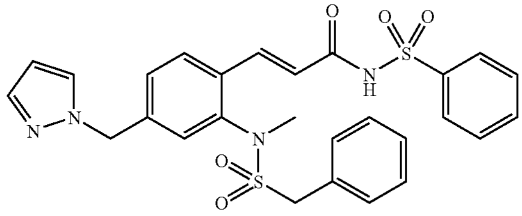

TLC: Rf 0.45 (chloroform:methanol=10:1).

Example 10(136)

(2E)-N-(3,4-difluorophenylsulfonyl)-3-(2-(N-benzylsulfonyl-N-methylamino)-4-(pyrazol-1-ylmethyl)phenyl)-2-propenamide

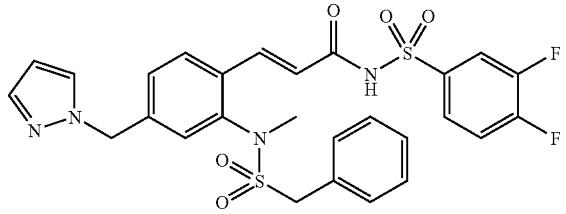

TLC: Rf 0.49 (chloroform:methanol=10:1).

Example 10(137)

N-(3,4-difluorophenylsulfonyl)-3-(2-((2-(naphthalen-1-yl)acetyl)amino)-4-(pyrazol-1-ylmethyl)phenyl)propanamide

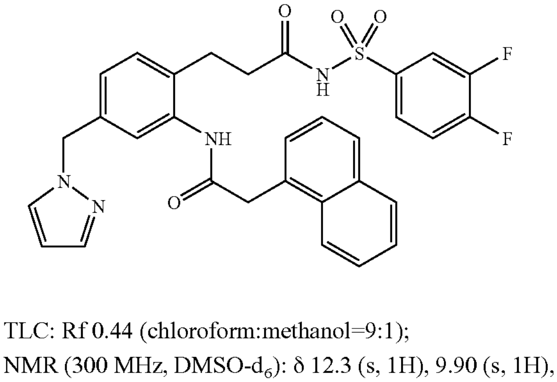

TLC: Rf 0.44 (chloroform:methanol=9:1);

NMR (300 MHz, DMSO-$d_6$): δ 12.3 (s, 1H), 9.90 (s, 1H), 8.12 (m, 1H), 7.96-7.40 (m, 11H) 7.27 (s, 1H), 7.06 (d, J=8.1 Hz, 1H), 6.87 (d, J=8.1 Hz, 1H), 6.22 (dd, J=2.1, 1.8 Hz, 1H), 5.21 (s, 2H), 4.13 (s, 2H), 2.68 (m, 2H), 2.40 (m, 2H).

Example 10(138)

N-(3,4-difluorophenylsulfonyl)-3-(2-(2-(thiophen-2-yl)ethoxy)-4-(pyrazol 1-ylmethyl)phenyl)propanamide

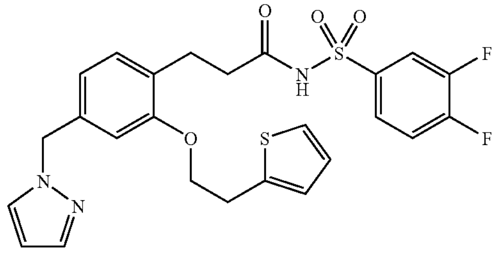

TLC: Rf 0.27 (hexane:ethyl acetate=1:1).

Example 10(139)

N-(3,4-difluorophenylsulfonyl)-3-(2-(2-(thiophen-3-yl)ethoxy)-4-(pyrazol 1-ylmethyl)phenyl)propanamide

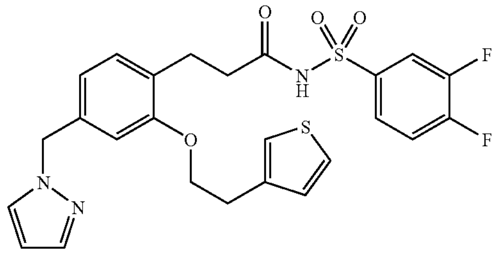

TLC: Rf 0.28 (hexane:ethyl acetate=1:1).

Example 10(140)

N-(tetrazol-5-yl)-3-(2-((3-methyl-1-(3,5-dimethylphenyl)butyl)carbamoyl)-4-(2-chloro-5-methylphenoxymethyl)phenyl)propanamide

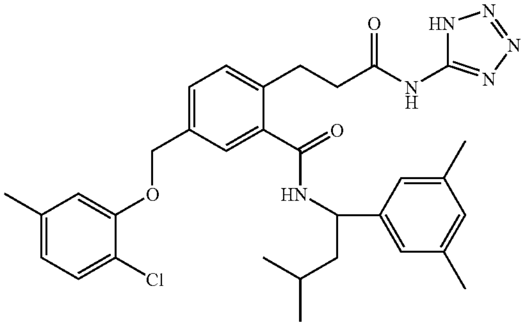

TLC: Rf 0.33 (chloroform:methanol=10:1);

NMR (300 MHz, $CDCl_3$): δ 7.62 (s, 1H), 7.44 (m, 1H), 7.34-7.22 (m, 2H), 6.98 (s, 2H), 6.88 (s, 1H), 6.79 (s, 1H), 6.76 (d, J=8.1 Hz, 1H), 6.34 (d, J=8.4 Hz, 1H), 5.24 (m, 1H), 5.09 (s, 2H), 3.24-2.98 (m, 2H), 2.94-2.72 (m, 2H), 2.32 (s, 3H), 2.28 (s, 6H), 1.90-1.50 (m, 3H), 1.06-0.97 (m, 6H).

Example 10(141)

N-(3,4-difluorophenylsulfonyl)-3-(2-((3-methyl-1-(3,5-dimethylphenyl)butyl)carbamoyl)-4-(2-chloro-5-methylphenoxymethyl)phenyl)propanamide

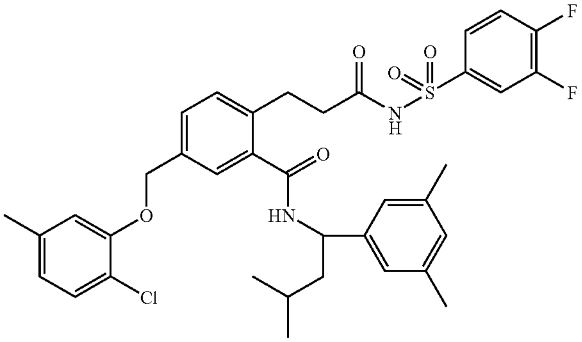

TLC: Rf 0.57 (chloroform:methanol=10:1);

NMR (300 MHz, $CDCl_3$): δ 7.70-7.55 (m, 3H), 7.35 (d, J=8.1 Hz, 1H), 7.31-7.24 (m, 1H), 7.21-7.10 (m, 2H), 6.99 (s, 2H), 7.00-6.92 (m, 1H), 6.82 (s, 1H), 6.77 (d, J=8.1 Hz, 1H), 6.28 (d, J=8.4 Hz, 1H), 5.21 (m, 1H), 5.09 (s, 2H), 3.02-2.81 (m, 2H), 2.67-2.52 (m, 2H), 2.34 (s, 9H), 1.90-1.45 (m, 3H), 1.02 (d, J=6.0 Hz, 6H).

Example 10(142)

N-(3,4-difluorophenylsulfonyl)-2-(2-(2-(naphthalen-2-yl)ethoxy)-4-(pyrazol 1-ylmethyl)benzyloxy)acetamide

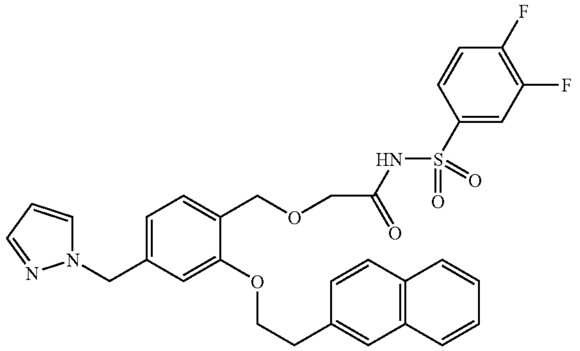

TLC: Rf 0.34 (chloroform:methanol=10:1);

NMR (300 MHz, $CDCl_3$): δ 7.86-7.66 (m, 6H), 7.57 (d, J=1.8 Hz, 1H), 7.49-7.38 (m, 4H), 7.30-7.13 (m, 2H), 6.82-6.75 (m, 2H), 6.30 (t, J=2.1 Hz, 1H), 5.31 (s, 2H), 4.44 (s, 2H), 4.36 (t, J=6.6 Hz, 2H), 3.85 (s, 2H), 3.27 (t, J=6.6 Hz, 2H).

Example 10(143)

N-(3,4-difluorophenylsulfonyl)-3-(2-(2-(naphthalen-2-yl)ethoxy)-4-dimethylaminomethylphenyl)propanamide

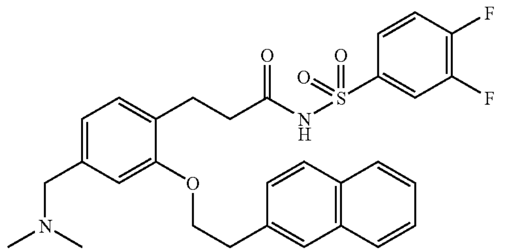

TLC: Rf 0.52 (chloroform:methanol=9:1);

NMR (300 MHz, DMSO-$d_6$): δ 8.31 (s, 1H), 7.86-7.73 (m, 5H), 7.62 (m, 1H), 7.51-7.42 (m, 4H), 7.04 (d, J=8.1 Hz, 1H), 6.99 (brs, 1H), 6.80 (d, J=8.1 Hz, 1H), 4.22-4.18 (m, 2H), 3.97 (brs, 2H), 3.23-3.19 (m, 2H), 2.69-2.64 (m, 2H), 2.55 (s, 6H), 2.26-2.20 (m, 2H).

Example 10(144)

N-(3,4-difluorophenylsulfonyl)-3-(2-(3-cyclohexylpropoxy)-4-(pyrazol 1-ylmethyl)phenyl)propanamide

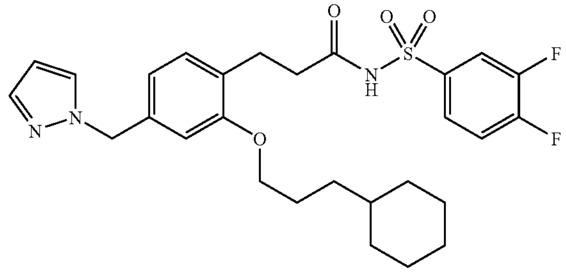

TLC: Rf 0.60 (chloroform:methanol=9:1);

NMR (300 MHz, $CDCl_3$): δ 8.86 (br s, 1H), 7.83-7.72 (m, 2H), 7.54 (d, J=2.1 Hz, 1H), 7.42 (d, J=2.1 Hz, 1H), 7.32-7.23 (m, 1H), 6.88 (d, J=7.8 Hz, 1H), 6.66 (s, 1H), 6.61 (d, J=7.8 Hz, 1H), 6.30 (t, J=2.1 Hz, 1H), 5.27 (s, 2H), 3.88 (t, J=6.6 Hz, 2H), 2.82 (t, J=7.2 Hz, 2H), 2.50 (t, J=7.2 Hz, 2H), 1.78-1.69 (m, 7H), 1.30-1.19 (m, 6H), 0.94-0.84 (m, 2H).

Example 10(145)

N-(3,4-difluorophenylsulfonyl)-3-(2-(2-phenoxyethoxy)-4-(pyrazol-1-ylmethyl)phenyl)propanamide

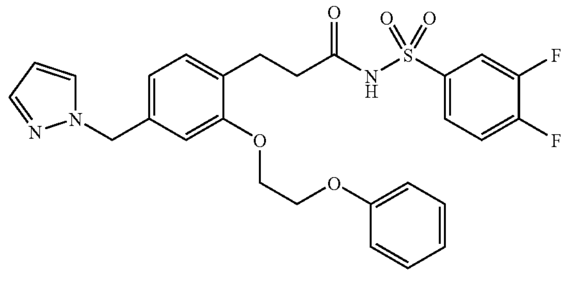

TLC: Rf 0.60 (chloroform:methanol=9:1);

NMR (300 MHz, $CDCl_3$): δ 8.95 (br s, 1H), 7.64-7.54 (m, 3H), 7.42 (d, J=2.1 Hz, 1H), 7.36-7.30 (m, 2H), 7.24-7.15 (m, 1H), 7.06-6.93 (m, 4H), 6.70-6.66 (m, 2H), 6.29 (t, J=2.1 Hz, 1H), 5.28 (s, 2H), 4.38-4.35 (m, 2H), 4.30-4.28 (m, 2H), 2.84 (t, J=7.2 Hz, 2H), 2.52 (t, J=7.2 Hz, 2H).

Example 10(146)

N-(3,4-difluorophenylsulfonyl)-3-(2-(2-(naphthalen-2-yl)ethoxy)-4-(3-methyl-2-oxoimidazolidin-1-ylmethyl)phenyl)propanamide

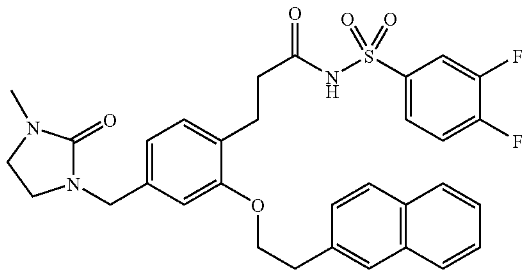

TLC: Rf 0.42 (hexane:ethyl acetate:methanol=2:6:1).

Example 10(147)

N-(3,4-difluorophenylsulfonyl)-3-(2-(2-(naphthalen-2-yl)ethoxy)-4-benzoylaminophenyl)propanamide

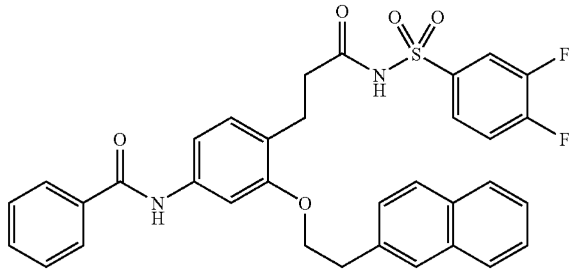

TLC: Rf 0.50 (chloroform:methanol=19:1).

Example 10(148)

N-(3,4-difluorophenylsulfonyl)-3-(2-(2-(naphthalen-2-yl)ethoxy)-4-phenylsulfonylaminophenyl)propanamide

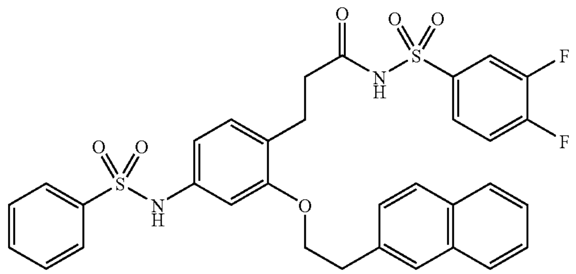

TLC: Rf 0.38 (chloroform:methanol=9:1).

Example 10(149)

N-(3,4-difluorophenylsulfonyl)-3-(2-(2-(naphthalen-2-yl)ethoxy)-4-mesylaminophenyl)propanamide

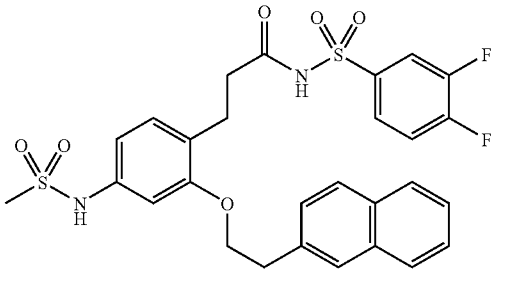

TLC: Rf 0.29 (chloroform:methanol=9:1).

Example 10(150)

N-(3,4-difluorophenylsulfonyl)-3-(2-(naphthalen-1-ylcarbamoylmethoxy)-4-(pyrazol-1-ylmethyl)phenyl)propanamide

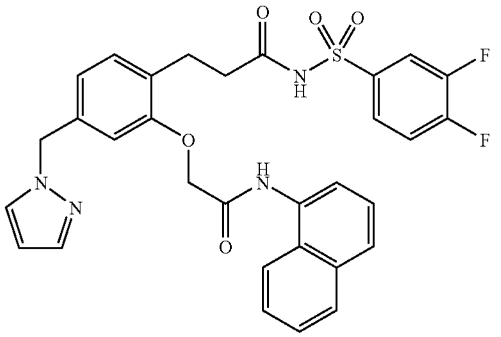

TLC: Rf 0.44 (hexane:ethyl acetate:methanol=2:6:1).

Example 10(151)

N-(3,4-difluorophenylsulfonyl)-3-(2-(benzylcarbamoylmethoxy)-4-(pyrazol 1-ylmethyl)phenyl)propanamide

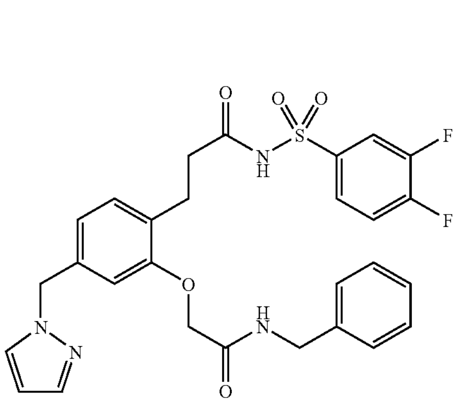

TLC: Rf 0.37 (hexane:ethyl acetate:methanol=2:6:1).

Example 10(152)

N-(3,4-difluorophenylsulfonyl)-3-(2-(2-(3-methylbenzoylamino)ethoxy)-4-(pyrazol-1-ylmethyl)phenyl)propanamide

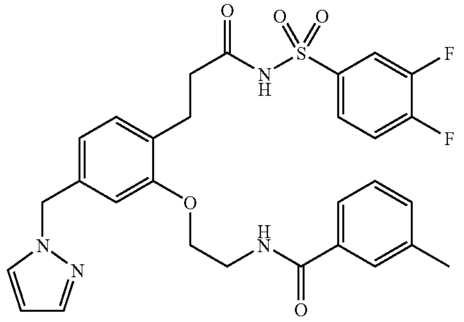

TLC: Rf 0.40 (hexane:ethyl acetate:methanol=2:6:1).

Example 10(153)

N-(3,4-difluorophenylsulfonyl)-3-(2-(2-(3-chlorobenzoylamino)ethoxy)-4-(pyrazol-1-ylmethyl)phenyl)propanamide

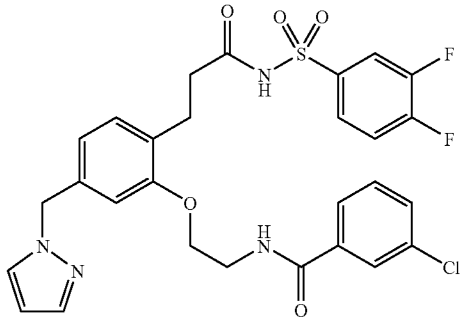

TLC: Rf 0.44 (hexane:ethyl acetate:methanol=2:6:1).

Example 10(154)

N-(3,4-difluorophenylsulfonyl)-3-(2-(3-phenylpropoxy)-4-(pyrazol-1-ylmethyl)phenyl)propanamide

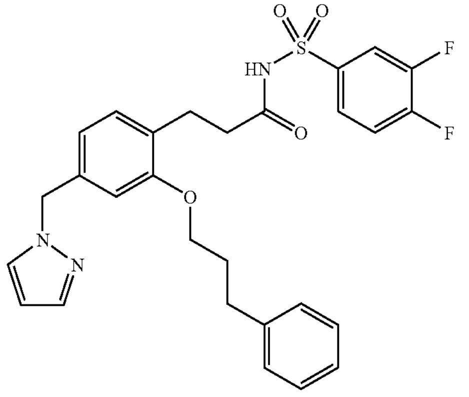

TLC: Rf 0.77 (chloroform:methanol=10:1).

Example 10(155)

N-(3,4-difluorophenylsulfonyl)-3-(2-(4-phenylbutoxy)-4-(pyrazol-1-ylmethyl)phenyl)propanamide

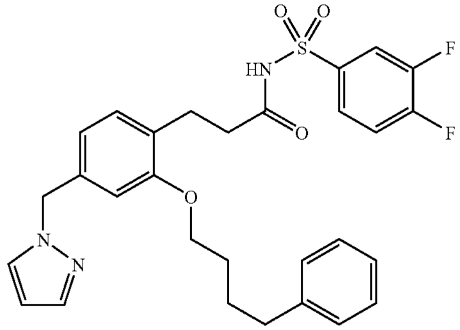

TLC: Rf 0.76 (chloroform:methanol=10:1).

Example 10(156)

(2E)-N-(3,4-difluorophenylsulfonyl)-3-(2-(2-(naphthalen-2-yl)ethoxy)-4-(2-oxopyrrolidin-1-ylmethyl)phenyl)-2-propenamide

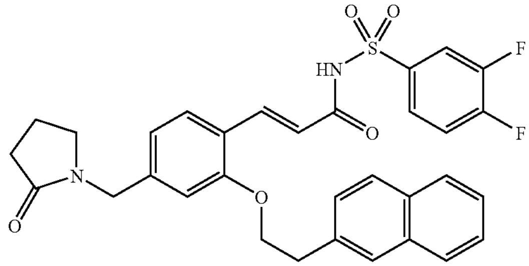

TLC: Rf 0.70 (chloroform:methanol=10:1).

Example 10(157)

N-(3,4-difluorophenylsulfonyl)-3-(2-(2-(3-(piperidin-1-yl)phenyl)ethoxy)-4-(pyrazol 1-ylmethyl)phenyl)propanoic acid

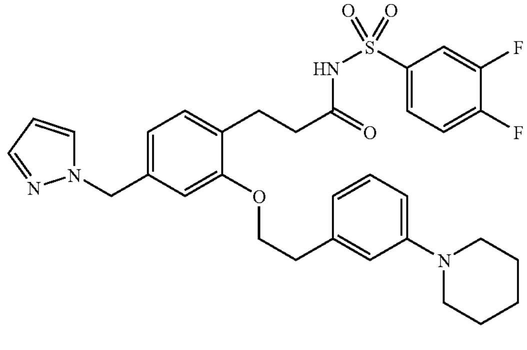

[Salt-free]

TLC: Rf 0.45 (hexane:ethyl acetate=1:1);

NMR (300 MHz, $CDCl_3$): δ 7.74-7.68 (m, 2H), 7.55 (s, 1H), 7.40 (d, J=2.1 Hz, 1H), 7.27-7.19 (m, 2H), 6.95-6.93 (m, 2H), 6.85 (s, 1H), 6.77 (d, J=7.5 Hz, 1H), 6.66-6.61 (m, 2H), 6.29 (t, J=2.1 Hz, 1H), 5.26 (s, 2H), 4.21 (t, J=6.0 Hz, 2H), 3.25-3.22 (m, 4H), 3.03 (t, J=6.0 Hz, 2H), 2.66 (t, J=7.5 Hz, 2H), 2.15 (t, J=7.5 Hz, 2H), 1.76-1.70 (m, 4H), 1.64-1.58 (m, 2H).

Sodium Salt:

TLC: Rf 0.50 (n-hexane:ethyl acetate=1:2).

Example 10(158)

(2E)-N-(3,4-difluorophenylsulfonyl)-3-(2-(2-(naphthalen-2-yl)ethoxy)-4-cyanomethylphenyl)-2-propenamide

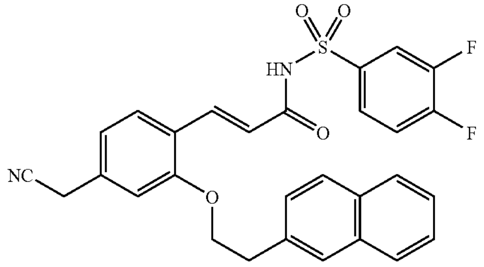

TLC: Rf 0.71 (chloroform:methanol=10:1).

Example 10(159)

N-(3,4-difluorophenylsulfonyl)-3-(2-((3-methyl-1-(3,5-dimethylphenyl)butyl)carbamoyl)-4-(morpholin-4-ylmethyl)phenyl)propanamide

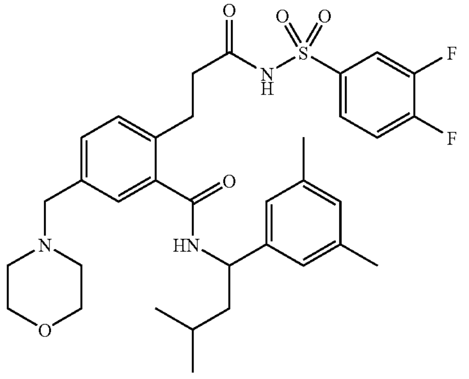

TLC: Rf 0.48 (ethyl acetate:methanol=10:1).

Example 10(160)

N-(3,4-difluorophenylsulfonyl)-3-(2-((3-methyl-1-(3,5-dimethylphenyl)butyl)carbamoyl)-4-(3-cyanophenoxymethyl)phenyl)propanamide

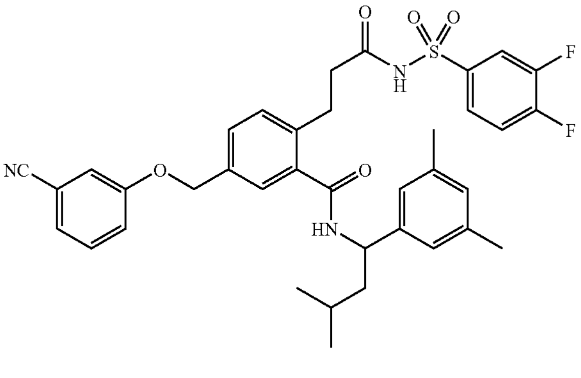

TLC: Rf 0.29 (hexane:ethyl acetate=1:1).

Example 10(161)

N-(3,4-difluorophenylsulfonyl)-2-(2-(3-(naphthalen-2-yl)propyl)-4-(pyrazol 1-ylmethyl)phenoxy)acetamide

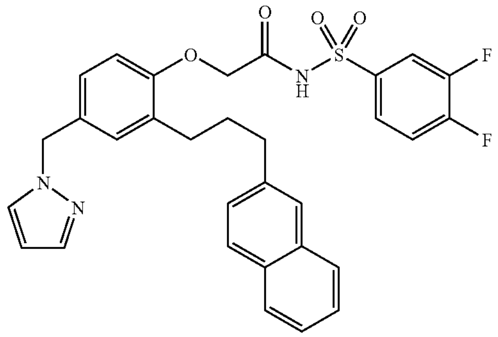

TLC: Rf 0.34 (ethyl acetate).

Example 10(162)

(2E)-N-(3,4-difluorophenylsulfonyl)-3-(2-(2-(naphthalen-2-yl)ethoxy)-4-(thiophen-3-ylmethyl)phenyl)-2-propenamide

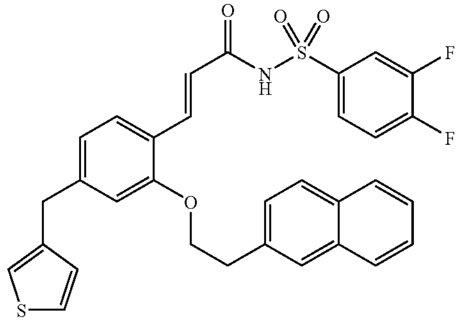

TLC: Rf 0.65 (hexane:ethyl acetate=1:1).

Example 10(163)

(2E)-N-(3,4-difluorophenylsulfonyl)-3-(2-(2-(naphthalen-2-yl)ethoxy)-4-benzylphenyl)-2-propenamide

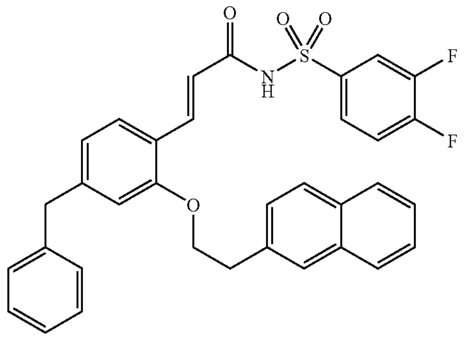

TLC: Rf 0.64 (hexane:ethyl acetate=1:1).

Example 10(164)

(2E)-N-(3,4-difluorophenylsulfonyl)-3-(2-(2-(naphthalen-2-yl)ethoxy)-4-(N-benzoyl-N-methylaminomethyl)phenyl)-2-propenamide

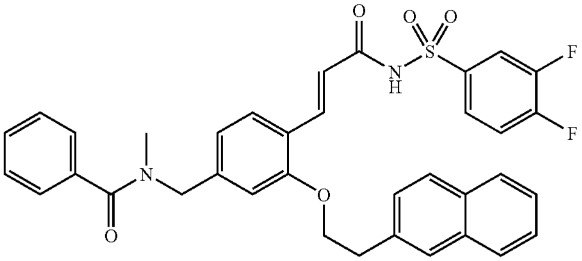

TLC: Rf 0.49 (hexane:ethyl acetate=1:3).

Example 10(165)

N-(3,4-difluorophenylsulfonyl)-3-(2-(2-phenylethoxy)-4-(2-chloro-5-methylphenoxymethyl)phenyl)propanamide

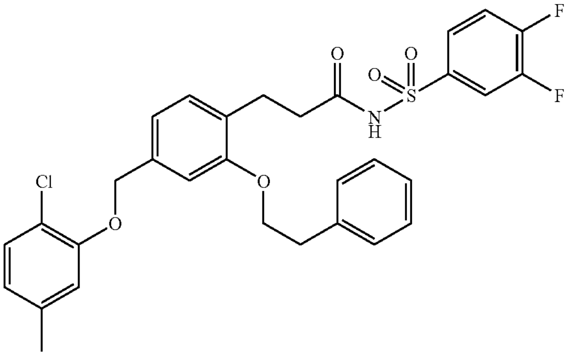

TLC: Rf 0.74 (hexane:ethyl acetate=1:1);

NMR (300 MHz, $CDCl_3$): δ 7.83-7.70 (m, 3H), 7.40-7.24 (m, 7H), 7.05 (s, 1H), 6.93 (d, J=7.8 Hz, 1H), 6.84-6.80 (m, 2H), 6.73 (d, J=7.8 Hz, 1H), 5.06 (s, 2H), 4.31 (t, J=6.3 Hz, 2H), 3.13 (t, J=6.3 Hz, 2H), 2.76-2.71 (m, 2H), 2.31 (s, 3H), 2.20-2.15 (m, 2H).

Example 10(166)

N-(3,4-difluorophenylsulfonyl)-2-(N'-methyl-N'-(2-(2-(naphthalen-2-yl)ethoxy)-4-(pyrazol-1-ylmethyl)phenyl)amino)acetamide

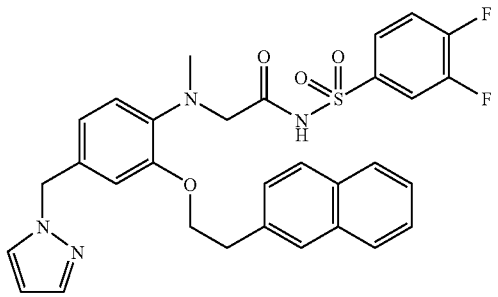

TLC: Rf 0.73 (chloroform:methanol=10:1);

NMR (300 MHz, $CDCl_3$): δ 7.94 (m, 1H), 7.89-7.74 (m, 4H), 7.64 (s, 1H), 7.54 (d, J=1.8 Hz, 1H), 7.52-7.41 (m, 2H), 7.37 (d, J=2.4 Hz, 1H), 7.35-7.16 (m, 2H), 6.93 (d, J=1.3 Hz, 1H), 6.81-6.71 (m, 2H), 6.27 (t, J=1.8 Hz, 1H), 5.23 (s, 2H), 4.24 (t, J=7.5 Hz, 2H), 3.47 (s, 2H), 3.18 (t, J=7.5 Hz, 2H), 2.64 (s, 3H).

Example 10(167)

N-(3,4-difluorophenylsulfonyl)-3-(2-(2-(naphthalen-2-yl)ethoxy)-4-(N'-acetyl-N'-methylaminomethyl)phenyl)propanamide

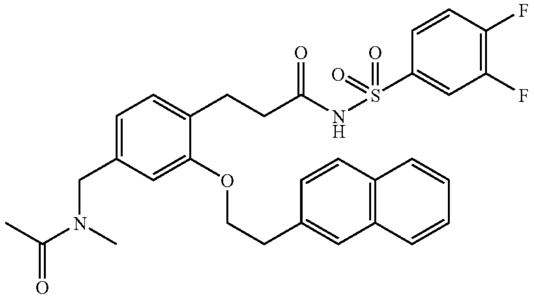

TLC: Rf 0.46 (chloroform:methanol=9:1);

NMR (300 MHz, $CDCl_3$): δ 7.88-7.69 (m, 6H), 7.51-7.38 (m, 3H), 7.26 (m, 1H), 6.96 (d, J=7.5 Hz, 0.4H), 6.87 (d, J=7.2 Hz, 0.6H), 6.70 (s, 0.6H), 6.60-6.56 (m, 1.4H), 4.44 (s, 2H), 4.28 (t, J=6.0 Hz, 0.8H), 4.20 (t, J=6.3 Hz, 1.2H), 3.27 (t, J=6.0 Hz, 0.8H), 3.22 (t, J=6.3 Hz, 1.2H), 2.88 (s, 1.2H), 2.87 (s, 1.8H), 2.75 (t, J=7.5 Hz, 2H), 2.25 (t, J=7.5 Hz, 1.2H), 2.17-2.12 (m, 3.8H).

Example 10(168)

N-(3,4-difluorophenylsulfonyl)-3-(2-(2-(naphthalen-2-yl)ethoxy)-4-(N'-ethoxycarbonyl-N'-methylaminomethyl)phenyl)propanamide

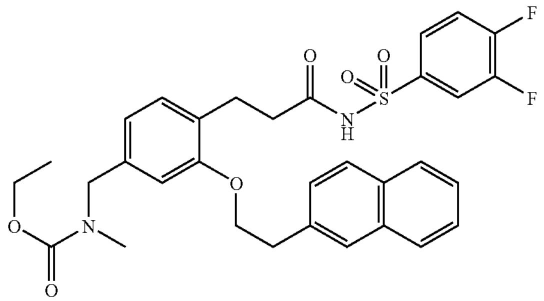

TLC: Rf 0.48 (hexane:ethyl acetate=1:1);

NMR (300 MHz, $CDCl_3$): δ 7.86-7.68 (m, 6H), 7.53-7.41 (m, 3H), 7.25 (m, 1H), 6.90 (d, J=7.2 Hz, 1H), 6.77-6.63 (m, 2H), 4.39 (s, 2H), 4.34-4.30 (m, 2H), 4.18 (q, J=7.2 Hz, 2H), 3.30-3.26 (m, 2H), 2.82 (brs, 3H), 2.73-2.68 (m, 2H), 2.11-2.07 (m, 2H), 1.27 (t, J=7.2 Hz, 3H).

Example 10(169)

N-(3,4-difluorophenylsulfonyl)-3-(2-((2E)-3-phenyl-2-propenyloxy)-4-(pyrazol 1-ylmethyl)phenyl)propanamide

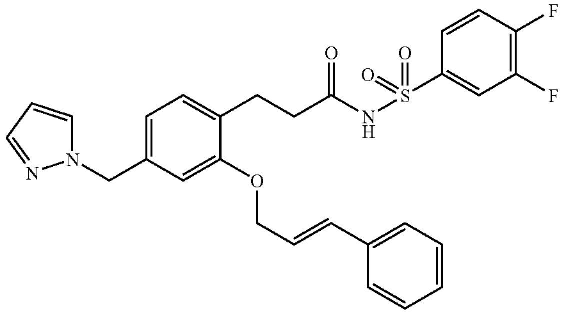

TLC: Rf 0.40 (hexane:ethyl acetate=1:1, 0.5% acetic acid);

NMR (300 MHz, $CDCl_3$): δ 9.01 (br, 1H), 7.82-7.69 (m, 2H), 7.53 (d, J=2.1 Hz, 1H), 7.42-7.17 (m, 7H), 6.92 (d, J=7.5 Hz, 1H), 6.73-6.62 (m, 3H), 6.34 (dt, J=15.9, 5.7 Hz, 1H), 6.27 (t, J=2.1 Hz, 1H), 5.28 (s, 2H), 4.63 (dd, J=5.7, 1.2 Hz, 2H), 2.86 (t, J=7.5 Hz, 2H), 2.51 (t, J=7.5 Hz, 2H).

Example 10(170)

N-(3,4-difluorophenylsulfonyl)-3-(2-(2-(N'-methyl-N'-phenylamino)ethoxy)-4-(pyrazol 1-ylmethyl)phenyl)propanamide

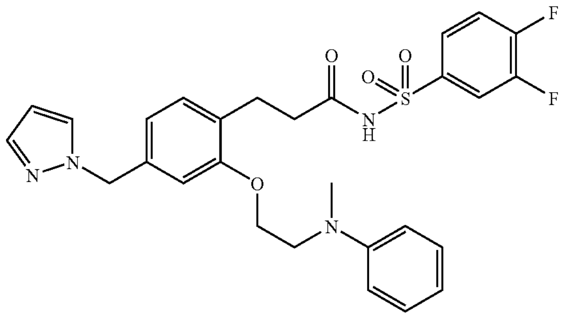

TLC: Rf 0.33 (hexane:ethyl acetate=1:1, 0.5% acetic acid);

NMR (300 MHz, $CDCl_3$): δ 7.81-7.70 (m, 2H), 7.53 (d, J=2.1 Hz, 1H), 7.39 (d, J=2.1 Hz, 1H), 7.31-7.20 (m, 3H), 6.89 (d, J=7.5 Hz, 1H), 6.80-6.70 (m, 3H), 6.68-6.60 (m, 2H), 6.29 (t, J=2.1 Hz, 1H), 5.24 (s, 2H), 4.10 (t, J=5.4 Hz, 2H), 3.75 (t, J=5.4 Hz, 2H), 2.98 (s, 3H), 2.72 (t, J=7.5 Hz, 2H), 2.30 (t, J=7.5 Hz, 2H).

Example 10(171)

(2E)-N-(3,4-difluorophenylsulfonyl)-3-(2-(3-phenylpropyl)-4-(pyrazol-1-ylmethyl)phenyl)-2-propenamide

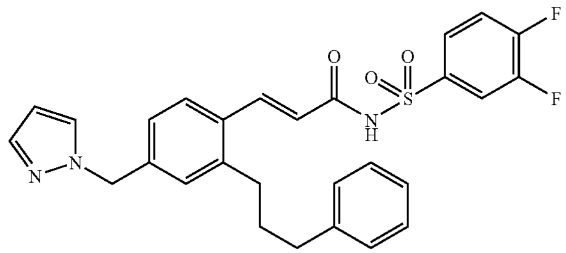

TLC: Rf 0.33 (hexane:ethyl acetate=1:1, 0.5% acetic acid);

NMR (300 MHz, $CDCl_3$): δ 10.6 (br, 1H), 8.01-7.89 (m, 2H), 7.73 (d, J=15.6 Hz, 1H), 7.58 (d, J=2.1 Hz, 1H), 7.55 (d, J=2.1 Hz, 1H), 7.37-7.25 (m, 3H), 7.23-7.13 (m, 3H), 7.10-7.00 (m, 2H), 6.71 (m, 1H), 6.36 (t, J=2.1 Hz, 1H), 5.69 (d, J=15.6 Hz, 1H), 5.34 (s, 2H), 2.65-2.55 (m, 4H), 1.76 (m, 2H).

Example 10(172)

N-(3,4-difluorophenylsulfonyl)-3-(2-(2-phenylethoxy)-4-(3-cyanophenoxymethyl)phenyl)propanamide

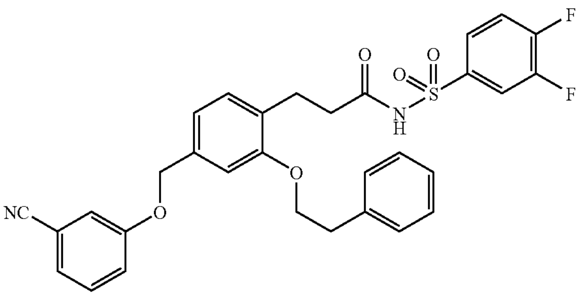

TLC: Rf 0.52 (hexane:ethyl acetate=1:1);

NMR (300 MHz, $CDCl_3$): δ 7.83-7.76 (m, 2H), 7.41-7.25 (m, 8H), 7.20-7.18 (m, 2H), 6.97 (d, J=7.5 Hz, 1H), 6.89 (brs, 1H), 6.82 (d, J=7.5 Hz, 1H), 5.01 (s, 2H), 4.28 (t, J=6.3 Hz, 2H), 3.13 (t, J=6.3 Hz, 2H), 2.76 (t, J=7.5 Hz, 2H), 2.20 (t, J=7.5 Hz, 2H).

Example 10(173)

N-benzyl-N-hydroxy-3-(2-(2-(naphthalen-2-yl)ethoxy)-4-(pyrazol-1-ylmethyl)phenyl)propanamide

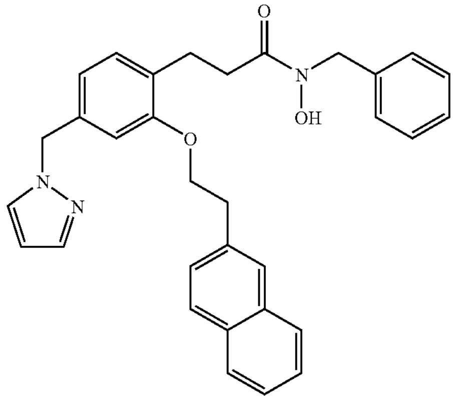

TLC: Rf 0.45 (chloroform:methanol=9:1);

NMR (300 MHz, $CDCl_3$): δ 7.80-7.65 (m, 4H), 7.55 (s, 1H), 7.50-7.20 (m, 8H), 7.08 (d, J=7.5 Hz, 1H), 6.91 (m, 1H), 6.71 (d, J=6.6 Hz, 1H), 6.66 (s, 1H), 6.27 (dd, J=2.1, 2.1 Hz, 1H), 5.25 (s, 2H), 4.14 (m, 4H), 3.17 (m, 2H), 2.93 (s, 2H), 2.39 (m, 2H).

Example 10(174)

N-(3,4-difluorophenylsulfonyl)-3-(2-(2-(naphthalen-2-yl)ethoxy)-4-(thiazol-2-ylaminomethyl)phenyl)propanamide

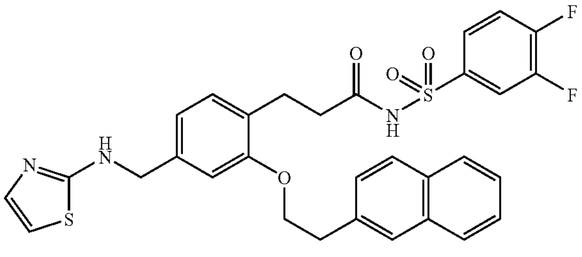

TLC: Rf 0.50 (hexane:ethyl acetate=1:2, 0.5% acetic acid);

NMR (300 MHz, $CDCl_3$): δ 7.89-7.65 (m, 6H), 7.53-7.46 (m, 2H), 7.40 (dd, J=8.4, 1.5 Hz, 1H), 7.28-7.18 (m, 1H), 7.11 (d, J=3.6 Hz, 1H), 6.91 (d, J=7.5 Hz, 1H), 6.86 (bs, 1H), 6.76 (d, J=7.5 Hz, 1H), 6.50 (d, J=3.6 Hz, 1H), 4.41 (s, 2H), 4.31 (t, J=6.6 Hz, 2H), 3.25 (t, J=6.6 Hz, 2H), 2.70 (t, J=7.2 Hz, 2H), 2.08 (t, J=7.2 Hz, 2H).

Example 10(175)

N-(3,4-difluorophenylsulfonyl)-3-(2-(2-(naphthalen-2-yl)ethoxy)-4-phenoxyphenyl)propanamide

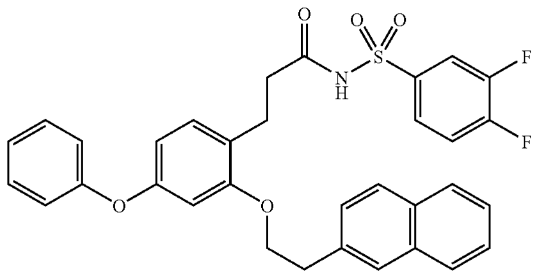

TLC: Rf 0.75 (hexane:ethyl acetate=1:1).

Example 10(176)

N-(3,4-difluorophenylsulfonyl)-3-(2-(2-(naphthalen-2-yl)ethoxy)-4-(pyridin-2-yloxy)phenyl)propanamide

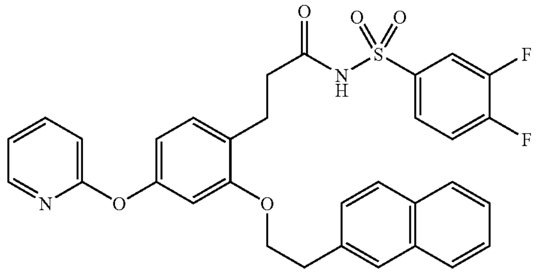

TLC: Rf 0.50 (hexane:ethyl acetate=1:1).

Example 10(177)

N-(3,4-difluorophenylsulfonyl)-5-(2-(2-(naphthalen-2-yl)ethoxy)-4-(pyrazol 1-ylmethyl)phenyl)pentanamide

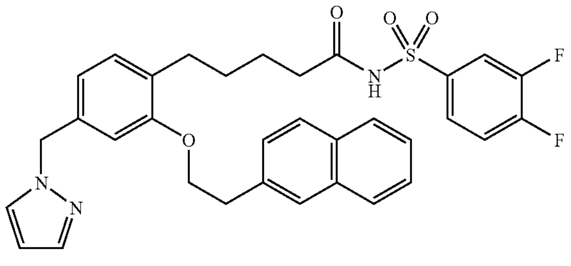

[Salt-free]

TLC: Rf 0.50 (chloroform:methanol=9:1);

NMR (300 MHz, $CDCl_3$): δ 7.90-7.74 (m, 3H), 7.72-7.63 (m, 3H), 7.58-7.38 (m, 6H), 6.95 (d, J=7.8 Hz, 1H), 6.72-6.66 (m, 2H), 6.28 (dd, J=2.1, 1.8 Hz, 1H), 5.29 (s, 2H), 4.25 (t, J=6.6 Hz, 2H), 3.22 (t, J=6.6 Hz, 2H), 2.40 (t, J=7.2 Hz, 2H), 1.63 (t, J=7.2 Hz, 2H), 1.35-1.18 (m, 4H).

Sodium Salt:

TLC: Rf 0.64 (chloroform:methanol=10:1).

Example 10(178)

(2E)-N-(3,4-difluorophenylsulfonyl)-3-(2-(pyrazol-1-ylmethyl)-3-(2-(naphthalen-2-yl)ethoxy)thiophen-4-yl)-2-propenamide

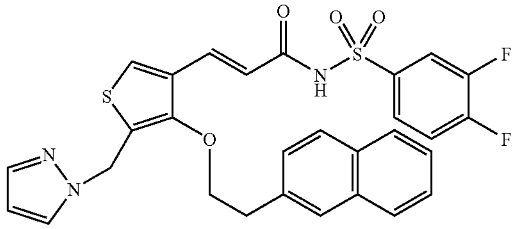

[Salt-free]

TLC: Rf 0.52 (chloroform:methanol=10:1);

NMR (300 MHz, DMSO-$d_6$): δ 8.01 (m, 1H), 7.95-7.65 (m, 7H), 7.54-7.37 (m, 6H), 6.62 (d, J=15.6 Hz, 1H), 6.16 (t, J=2.1 Hz, 1H), 5.23 (s, 2H), 4.22 (t, J=6.6 Hz, 2H), 3.28 (t, J=6.6 Hz, 2H).

Sodium Salt:

TLC: Rf 0.57 (chloroform:methanol=10:1).

Example 10(179)

(2E)-N-(3,4-difluorophenylsulfonyl)-3-(4-(pyrazol-1-ylmethyl)-3-(2-(naphthalen-2-yl)ethoxy)thiophen-2-yl)-2-propenamide

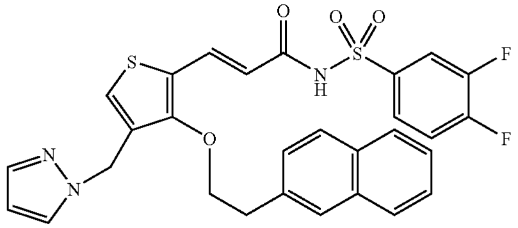

TLC: Rf 0.52 (chloroform:methanol=10:1);

NMR (300 MHz, $CDCl_3$): δ 7.94-7.66 (m, 7H), 7.54-7.23 (m, 5H), 7.11 (m, 1H), 7.05 (s, 1H), 6.17 (t, J=2.1 Hz, 1H), 5.86 (d, J=15.3 Hz, 1H), 4.96 (s, 2H), 4.16 (t, J=6.6 Hz, 2H), 3.18 (t, J=6.6 Hz, 2H).

Example 10(180)

N-(3,4-difluorophenylsulfonyl)-3-(2-(2-(4-phenylpiperazin-1-yl)ethoxy)-4-(pyrazol-1-ylmethyl)phenyl)propanamide

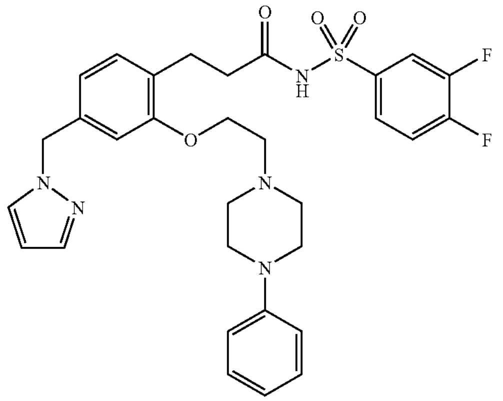

[Salt-free]

TLC: Rf 0.58 (ethyl acetate:methanol=5:1).

Sodium Salt:

TLC: Rf 0.40 (chloroform:methanol=10:1).

Example 10(181)

N-(3,4-difluorophenylsulfonyl)-3-(2-(2-(4-phenyl-1,2,3,6-tetrahydropyridin-1-yl)ethoxy)-4-(pyrazol-1-ylmethyl)phenyl)propanamide

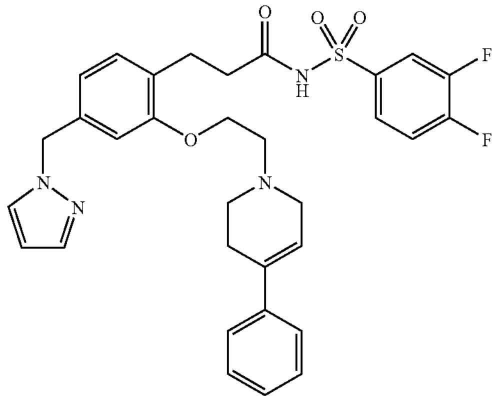

[Salt-free]

TLC: Rf 0.66 (ethyl acetate:methanol=5:1).

Sodium Salt:

TLC: Rf 0.37 (chloroform:methanol=10:1).

Example 10(182)

N-(3,4-difluorophenylsulfonyl)-3-(2-(2-(4-phenylpiperidin-1-yl)ethoxy)-4-(pyrazol-1-ylmethyl)phenyl)propanamide

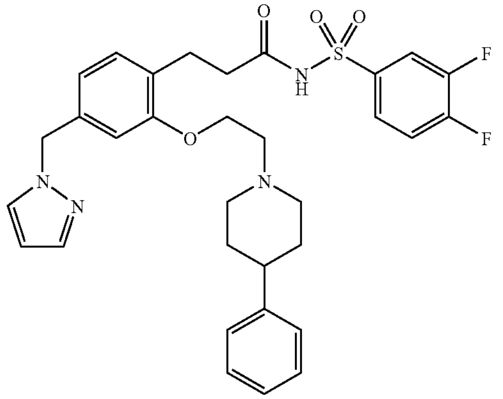

TLC: Rf 0.67 (ethyl acetate:methanol=5:1).

Example 10(183)

N-(3,4-difluorophenylsulfonyl)-4-(2-(2-phenylethoxy)-4-(3-cyanophenoxymethyl)phenyl)butanamide

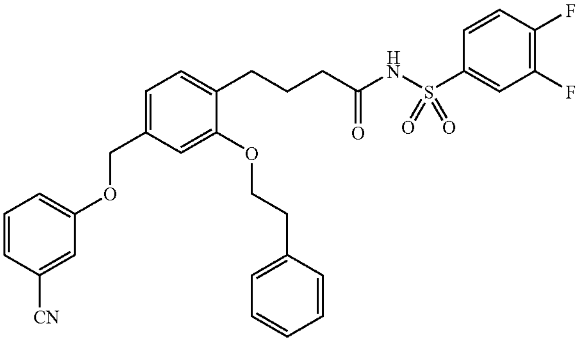

TLC: Rf 0.70 (chloroform:methanol=10:1);

NMR (300 MHz, $CDCl_3$): δ 7.96-7.80 (m, 2H), 7.42-7.14 (m, 10H), 7.03 (d, J=7.2 Hz, 1H), 6.94-6.85 (m, 2H), 5.01 (s, 2H), 4.23 (t, J=6.5 Hz, 2H), 3.10 (t, J=6.5 Hz, 2H), 2.55 (t, J=7.0 Hz, 2H), 1.97 (t, J=7.0 Hz, 2H), 1.80-1.64 (m, 2H).

Example 10(184)

N-(3,4-difluorophenylsulfonyl)-4-(2-(2-(naphthalen-2-yl)ethoxy)-4-(3-cyanophenoxymethyl)phenyl)butanamide

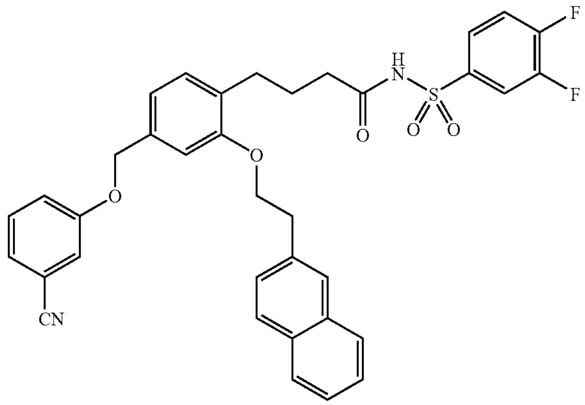

[Salt-free]

TLC: Rf 0.84 (chloroform:methanol=10:1);

NMR (300 MHz, $CDCl_3$): δ 7.92-7.70 (m, 4H), 7.55-7.14 (m, 10H), 7.01 (d, J=7.5 Hz, 1H), 6.94-6.84 (m, 2H), 5.00 (s, 2H), 4.31 (t, J=6.3 Hz, 2H), 3.26 (t, J=6.3 Hz, 2H), 2.49 (t, J=7.2 Hz, 2H), 1.81 (t, J=7.2 Hz, 2H), 1.74-1.50 (m, 2H).

Sodium Salt:

TLC: Rf 0.74 (chloroform:methanol=10:1);

NMR (300 MHz, DMSO-$d_6$): δ 7.90-7.78 (m, 5H), 7.68 (m, 1H), 7.62-7.30 (m, 8H), 7.05 (s, 1H), 7.02 (d, J=7.5 Hz, 1H), 6.91 (d, J=7.5 Hz, 1H), 5.09 (s, 2H), 4.25 (m, 2H), 3.20 (m, 2H), 2.40 (m, 2H), 2.02 (m, 2H), 1.59 (m, 2H).

Example 10(185)

N-(3,4-difluorophenylsulfonyl)-3-(2-(5-phenylpentyloxy)-4-(pyrazol-1-ylmethyl)phenyl)propanamide

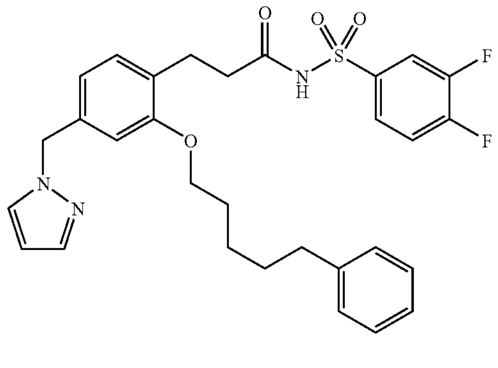

TLC: Rf 0.63 (chloroform:methanol=10:1).

Example 10(186)

N-(3,4-difluorophenylsulfonyl)-3-(2-(6-phenylhexyloxy)-4-(pyrazol-1-ylmethyl)phenyl)propanamide

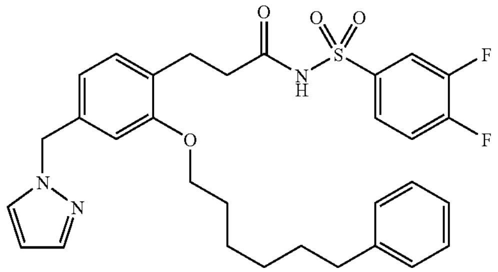

TLC: Rf 0.61 (chloroform:methanol=10:1).

Example 10(187)

N-(3,4-difluorophenylsulfonyl)-3-(2-(2-(naphthalen-2-yl)ethoxy)-4-hydroxymethylphenyl)propanamide

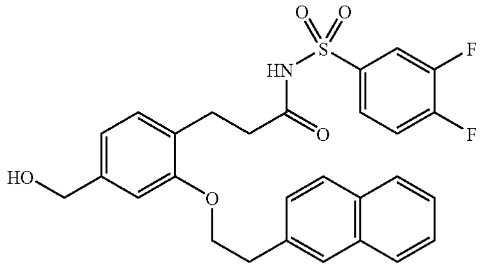

TLC: Rf 0.52 (chloroform:methanol=10:1).

Example 10(188)

N-(3,4-difluorophenylsulfonyl)-2-(2-(2-(naphthalen-2-yl)ethoxy)-4-(pyrazol-1-ylmethyl)phenoxy)acetamide

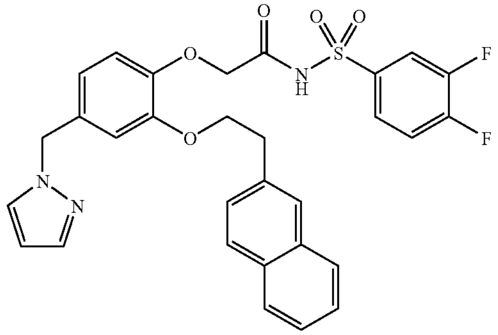

[Salt-free]

TLC: Rf 0.40 (chloroform:methanol=19:1);

NMR (300 MHz, $CDCl_3$): δ 7.93-7.71 (m, 6H), 7.57-7.36 (m, 5H), 7.25 (m, 1H), 6.89-6.74 (m, 3H), 6.29 (t, J=2.3 Hz, 1H), 5.24 (s, 2H), 4.46 (s, 2H), 4.35 (t, J=7.2 Hz, 2H), 3.35 (t, J=7.2 Hz, 2H).

Sodium Salt:

TLC: Rf 0.45 (chloroform:methanol=10:1).

Example 10(189)

N-(3,4-difluorophenylsulfonyl)-3-(2-(2-(pyrazol-1-yl)ethoxy)-4-(pyrazol 1-ylmethyl)phenyl)propanamide

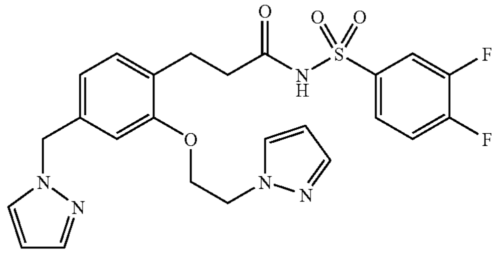

TLC: Rf 0.40 (chloroform:methanol=9:1);

NMR (300 MHz, $CDCl_3$): δ 7.90-7.80 (m, 2H), 7.56 (d, J=2.1 Hz, 1H), 7.53 (d, J=2.1 Hz, 1H), 7.48 (d, J=2.1 Hz, 1H), 7.38 (d, J=2.1 Hz, 1H), 7.33-7.24 (m, 1H), 6.99 (d, J=7.5 Hz, 1H), 6.69 (d, J=7.5 Hz, 1H), 6.56 (s, 1H), 6.35 (t, J=2.1 Hz, 1H), 6.27 (t, J=2.1 Hz, 1H), 5.24 (s, 2H), 4.59 (t, J=4.2 Hz, 2H), 4.23 (t, J=4.2 Hz, 2H), 2.83-2.77 (m, 2H), 2.43-2.38 (m, 2H).

Example 10(190)

N-(3,4-difluorophenylsulfonyl)-3-(2-(2-(2-methylimidazol-1-yl)ethoxy)-4-(pyrazol-1-ylmethyl)phenyl)propanamide

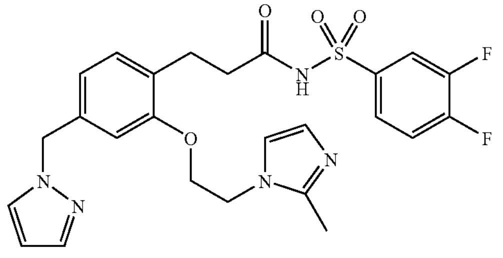

TLC: Rf 0.30 (chloroform:methanol=4:1);

NMR (300 MHz, $CDCl_3$): δ 7.97-7.84 (m, 2H), 7.53 (d, J=2.1 Hz, 1H), 7.38 (d, J=2.1 Hz, 1H), 7.28-7.19 (m, 1H), 7.06-6.97 (m, 3H), 6.73 (d, J=7.8 Hz, 1H), 6.58 (s, 1H), 6.28 (t, J=2.1 Hz, 1H), 5.23 (s, 2H), 4.32 (t, J=5.1 Hz, 2H), 4.14 (t, J=5.1 Hz, 2H), 2.64 (t, J=8.4 Hz, 2H), 2.52 (s, 3H), 1.86 (t, J=8.4 Hz, 2H).

Example 10(191)

N-(3,4-difluorophenylsulfonyl)-2-(2-(2-(naphthalen-2-yl)ethoxy)-4-(pyrazol 1-ylmethyl)benzoylamino) acetamide

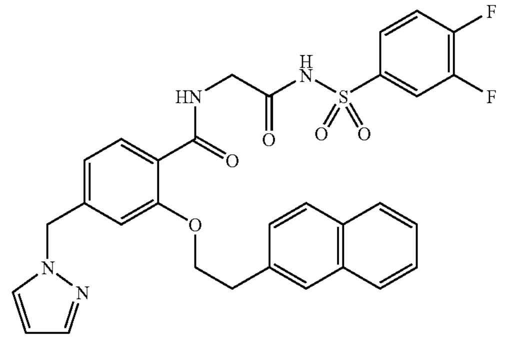

TLC: Rf 0.30 (chloroform:methanol=4:1);

NMR (300 MHz, DMSO-$d_6$): δ 8.38-8.35 (m, 1H), 7.92-7.71 (m, 8H), 7.52-7.43 (m, 5H), 7.05 (s, 1H), 6.74 (d, J=8.1 Hz, 1H), 6.26 (t, J=2.1 Hz, 1H), 5.33 (s, 2H), 4.37 (t, J=6.6 Hz, 2H), 3.76 (d, J=4.5 Hz, 2H), 3.33-3.29 (m, 2H).

Example 10(192)

N-(3,4-difluorophenylsulfonyl)-3-(2-(2-(N-ethyl-N-phenylamino)ethoxy)-4-(pyrazol-1-ylmethyl)phenyl) propanamide

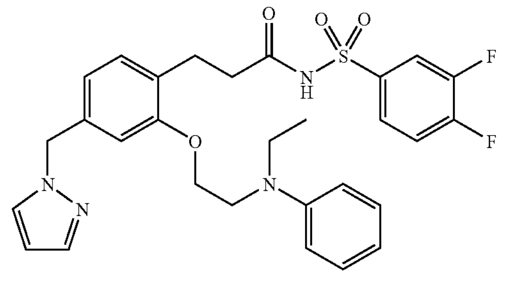

TLC: Rf 0.32 (chloroform:methanol=19:1);

NMR (300 MHz, $CDCl_3$): δ 7.82-7.70 (m, 2H), 7.54 (d, J=1.8 Hz, 1H), 7.38 (d, J=2.1 Hz, 1H), 7.32-7.20 (m, 3H), 6.92 (d, J=7.5 Hz, 1H), 6.78-6.63 (m, 5H), 6.28 (dd, J=2.1, 1.8 Hz, 1H), 5.24 (s, 2H), 4.10 (t, J=5.7 Hz, 2H), 3.71 (t, J=5.7 Hz, 2H), 3.42 (q, J=6.9 Hz, 2H), 2.77 (t, J=7.5 Hz, 2H), 2.35 (t, J=7.5 Hz, 2H), 1.16 (t, J=6.9 Hz, 3H).

Example 10(193)

N-(3,4-difluorophenylsulfonyl)-3-(2-(2-(N-(2-hydroxyethyl)-N-phenylamino)ethoxy)-4-(pyrazol-1-ylmethyl)phenyl)propanamide

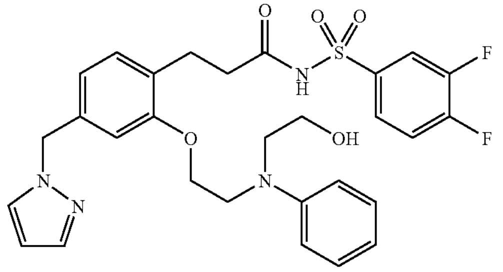

TLC: Rf 0.41 (chloroform:methanol=9:1);

NMR (300 MHz, $CDCl_3$): δ 7.86-7.74 (m, 2H), 7.53 (d, J=2.1 Hz, 1H), 7.37 (d, J=2.4 Hz, 1H), 7.32-7.24 (m, 3H), 6.96 (d, J=7.8 Hz, 1H), 6.87-6.80 (m, 3H), 6.71-6.64 (m, 2H), 6.27 (dd, J=2.4, 2.1 Hz, 1H), 5.22 (s, 2H), 4.18 (t, J=4.5 Hz, 2H), 3.95 (t, J=4.8 Hz, 2H), 3.80 (t, J=4.5 Hz, 2H), 3.64 (t, J=4.8 Hz, 2H), 2.83 (t, J=7.5 Hz, 2H), 2.36 (t, J=7.5 Hz, 2H).

Example 10(194)

N-(3,4-difluorophenylsulfonyl)-3-(2-(3-(N-methyl-N-phenylamino)propoxy)-4-(pyrazol-1-ylmethyl)phenyl)propanamide

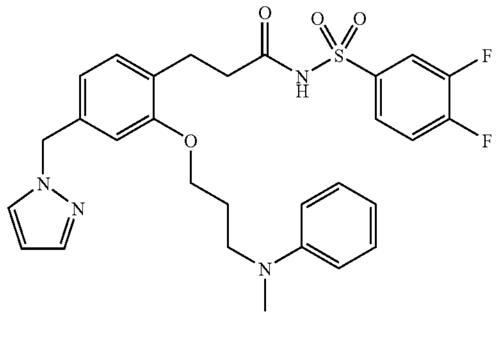

TLC: Rf 0.30 (chloroform:methanol=19:1);

NMR (300 MHz, $CDCl_3$): δ 7.82-7.68 (m, 2H), 7.54 (d, J=1.8 Hz, 1H), 7.40 (d, J=1.8 Hz, 1H), 7.30-7.16 (m, 3H), 6.93 (d, J=8.1 Hz, 1H), 6.74-6.60 (m, 5H), 6.29 (dd, J=1.8, 1.8 Hz, 1H), 5.25 (s, 2H), 3.97 (t, J=6.0 Hz, 2H), 3.48 (t, J=6.9 Hz, 2H), 2.92 (s, 3H), 2.87 (t, J=7.2 Hz, 2H), 2.51 (t, J=7.2 Hz, 2H), 2.05 (m, 2H).

Example 10(195)

N-(3,4-difluorophenylsulfonyl)-3-(2-(2-(naphthalen-2-yl)ethoxy)-4-(1-hydroxy-1-methylethyl)phenyl)propanamide

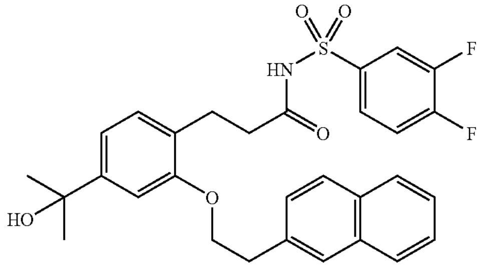

TLC: Rf 0.58 (chloroform:methanol=10:1).

Example 10(196)

N-(3,4-difluorophenylsulfonyl)-3-(2-(2-(naphthalen-2-yl)ethoxy)-4-(pyrazol-1-ylmethyl)phenyl)propynamide

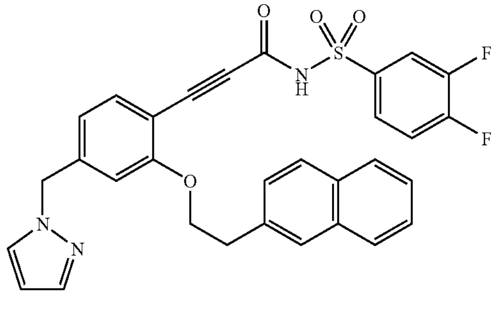

[Salt-free]

TLC: Rf 0.78 (chloroform:methanol:acetic acid=18:1:1).

Sodium Salt:

TLC: Rf 0.17 (chloroform:methanol=10:1);

NMR (300 MHz, DMSO-$d_6$): δ 7.94-7.76 (m, 5H), 7.69 (m, 1H), 7.63-7.38 (m, 6H), 7.31 (d, J=8.1 Hz, 1H), 6.91 (s, 1H), 6.66 (d, J=7.5 Hz, 1H), 6.27 (t, J=2.1 Hz, 1H), 5.31 (s, 2H), 4.21 (m, 2H), 3.19 (m, 2H).

Example 10(197)

N-phenylsulfonyl-3-(2-((3-methyl-1-phenylbutyl)carbamoyl)-4-phenoxymethylphenyl)propanamide

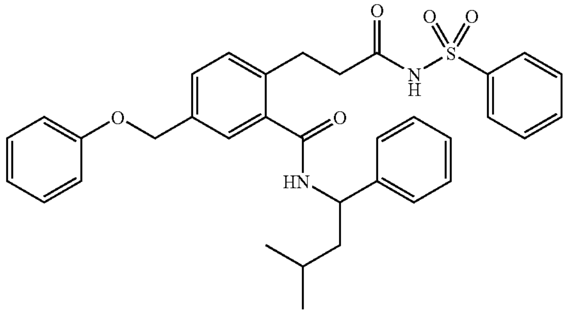

TLC: Rf 0.55 (chloroform:methanol=10:1);

NMR (300 MHz, $CDCl_3$): δ 7.88 (dd, J=7.8, 1.8 Hz, 2H), 7.55 (m, 1H), 7.45-7.30 (m, 11H), 7.13 (d, J=7.8 Hz, 1H), 7.03-6.96 (m, 3H), 6.26 (d, J=8.4 Hz, 1H), 5.27 (dt, J=8.4, 8.4 Hz, 1H), 5.02 (s, 2H), 2.96-2.75 (m, 2H), 2.50 (dt, J=1.8, 8.1 Hz, 2H), 1.90-1.55 (m, 3H), 1.02 (d, J=6.6 Hz, 3H), 1.01 (d, J=6.6 Hz, 3H).

Example 10(198)

N-(3,4-difluorophenylsulfonyl)-3-(2-(2-hydroxy-2-(naphthalen-2-yl)ethoxy)-4-(3-cyanophenoxymethyl)phenyl)propanamide

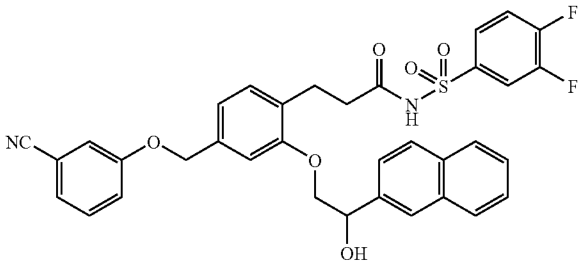

TLC: Rf 0.41 (hexane:ethyl acetate=1:1, 0.5% acetic acid);

NMR (300 MHz, $CDCl_3$): δ 7.98-7.86 (m, 4H), 7.82-7.72 (m, 2H), 7.60-7.52 (m, 3H), 7.36 (m, 1H), 7.30-7.14 (m, 4H), 7.06 (d, J=8.1 Hz, 1H), 6.90-6.84 (m, 2H), 5.46 (dd, J=8.7, 3.0 Hz, 1H), 4.98 (s, 2H), 4.30 (dd, J=9.9, 3.0 Hz, 1H), 4.19 (dd, J=9.9, 8.7 Hz, 1H), 3.05-2.80 (m, 2H), 2.70-2.45 (m, 2H).

Example 10(199)

N-(3,4-difluorophenylsulfonyl)-3-(2-(2-(3-(morpholin-4-yl)phenyl)ethoxy)-4-(pyrazol 1-ylmethyl)phenyl)propanamide

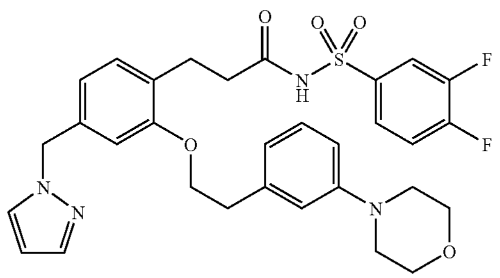

TLC: Rf 0.40 (chloroform:methanol=9:1);

NMR (300 MHz, $CDCl_3$): δ 7.75-7.69 (m, 2H), 7.55 (d, J=2.1 Hz, 1H), 7.40 (d, J=2.1 Hz, 1H), 7.30-7.23 (m, 2H), 6.94-6.80 (m, 4H), 6.67-6.62 (m, 2H), 6.29 (t, J=2.1 Hz, 1H), 5.26 (s, 2H), 4.21 (t, J=6.0 Hz, 2H), 3.89-3.86 (m, 4H), 3.21-3.18 (m, 4H), 3.05 (t, J=6.0 Hz, 2H), 2.69 (t, J=7.5 Hz, 2H), 2.20 (t, J=7.5 Hz, 2H).

Example 10(200)

N-(3,4-difluorophenylsulfonyl)-3-(2-(5-phenylpentyl)-4-(pyrazol-1-ylmethyl)phenyl)propanamide

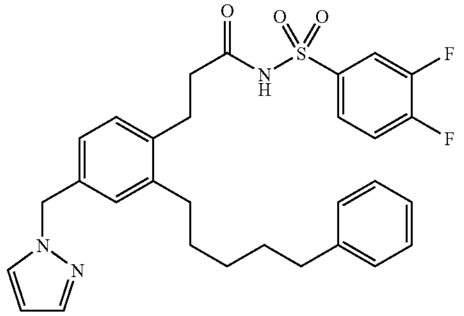

TLC: Rf 0.60 (n-hexane:ethyl acetate=1:2);

NMR (300 MHz, $CDCl_3$): δ 9.12 (brs, 1H), 7.88-7.78 (m, 2H), 7.53 (d, J=2.1 Hz, 1H), 7.43 (d, J=2.1 Hz, 1H), 7.33-7.25 (m, 3H), 7.20-7.15 (m, 3H), 6.96 (s, 1H), 6.82 (s, 2H), 6.30 (t, J=2.1 Hz, 1H), 5.26 (s, 2H), 2.80 (t, J=7.8 Hz, 2H), 2.59 (t, J=7.8 Hz, 2H), 2.43 (t, J=7.8 Hz, 2H), 2.33 (t, J=7.8 Hz, 2H), 1.65-1.56 (m, 2H), 1.54-1.44 (m, 2H), 1.39-1.31 (m, 2H).

Example 10(201)

N-(3,4-difluorophenylsulfonyl)-3-(2-(5-phenyl-1-pentenyl)-4-(pyrazol-1-ylmethyl)phenyl)propanamide

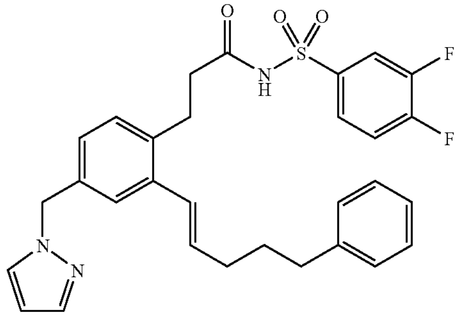

TLC: Rf 0.60 (n-hexane:ethyl acetate=1:2);

NMR (300 MHz, $CDCl_3$): δ 8.82 (brs, 1H), 7.85-7.75 (m, 2H), 7.54 (d, J=2.1 Hz, 1H), 7.43 (d, J=2.1 Hz, 1H), 7.32-7.18 (m, 7H), 6.85 (s, 2H), 6.42 (d, J=15.6 Hz, 1H), 6.30 (t, J=2.1 Hz, 1H), 6.05 (dt, J=15.6, 6.9 Hz, 1H), 5.27 (s, 2H), 2.86 (t, J=7.8 Hz, 2H), 2.65 (t, J=7.8 Hz, 2H), 2.36 (t, J=7.8 Hz, 2H), 2.25-2.18 (m, 2H), 1.83-1.72 (m, 2H).

Example 10(202)

N-(3,4-difluorophenylsulfonyl)-3-(2-(5-phenyl-1-pentynyl)-4-(pyrazol-1-ylmethyl)phenyl)propanamide

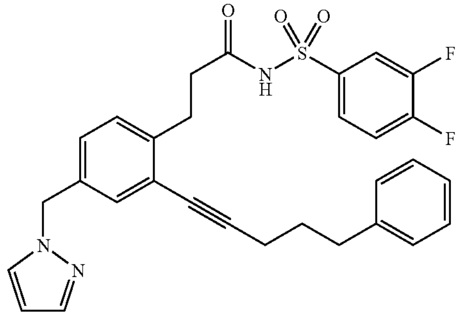

TLC: Rf 0.60 (n-hexane:ethyl acetate=1:2);

NMR (300 MHz, $CDCl_3$): δ 8.41 (brs, 1H), 7.84-7.71 (m, 2H), 7.55 (d, J=2.1 Hz, 1H), 7.41 (d, J=2.1 Hz, 1H), 7.33-7.18 (m, 7H), 6.96-6.95 (m, 2H), 6.30 (t, J=2.1 Hz, 1H), 5.24 (s, 2H), 3.01 (t, J=7.2 Hz, 2H), 2.74 (t, J=7.2 Hz, 2H), 2.56 (t, J=7.2 Hz, 2H), 2.42 (t, J=7.2 Hz, 2H), 1.95-1.85 (m, 2H).

Example 10(203)

N-(3,4-difluorophenylsulfonyl)-3-(2-(N-benzoylpiperazin-1-yl)-4-(pyrazol 1-ylmethyl)phenyl)propanamide

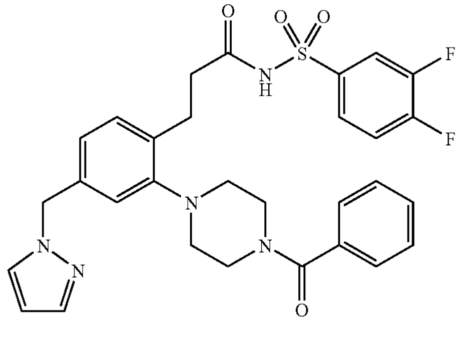

TLC: Rf 0.60 (ethyl acetate);

NMR (300 MHz, $CDCl_3$): δ 7.69-7.61 (m, 2H), 7.54 (d, J=2.1 Hz, 1H), 7.42 (s, 6H), 7.25-7.16 (m, 1H), 7.02 (d, J=8.1 Hz, 1H), 6.91 (s, 1H), 6.83 (d, J=8.1 Hz, 1H), 6.30 (t, J=2.1 Hz, 1H), 5.27 (s, 2H), 3.87 (m, 2H), 3.56 (m, 2H), 2.92-2.84 (m, 6H), 2.59 (t, J=7.2 Hz, 2H).

Example 10(204)

N-(3,4-difluorophenylsulfonyl)-2-(1-(1-(naphthalen-1-yl)ethylcarbonyl)indol-3-yl)acetamide

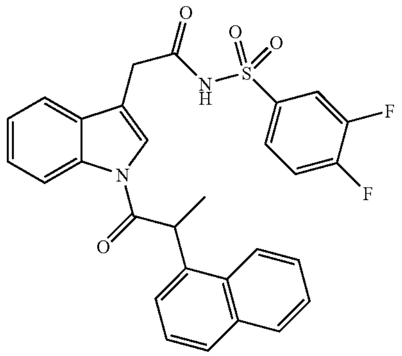

TLC: Rf 0.71 (ethyl acetate:methanol=9:1);

NMR (300 MHz, $CDCl_3$): δ 8.62 (d, J=8.1 Hz, 1H), 8.19 (d, J=8.7 Hz, 1H), 7.95 (d, J=8.1 Hz, 1H), 7.80 (m, 1H), 7.72-7.58 (m, 4H), 7.46-7.35 (m, 3H), 7.21 (d, J=7.5 Hz, 1H), 7.19 (d, J=7.2 Hz, 1H), 7.11 (d, J=7.5 Hz, 1H), 7.05 (s, 1H), 5.16 (q, J=6.6 Hz, 1H), 3.40 (s, 2H), 1.75 (d, J=6.6 Hz, 3H).

Example 10(205)

N-(3,4-difluorophenylsulfonyl)-2-(2-methyl-1-(1-(naphthalen-1-yl)ethylcarbonyl)indol-3-yl)acetamide

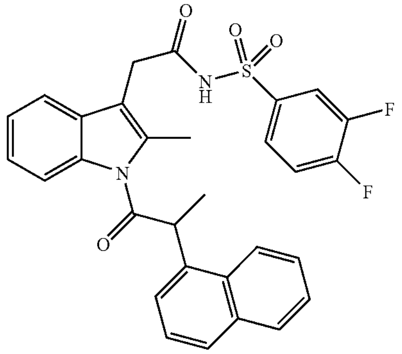

TLC: Rf 0.77 (ethyl acetate:methanol=9:1);

NMR (300 MHz, $CDCl_3$): δ 8.01 (d, J=7.5 Hz, 1H), 7.92 (d, J=8.1 Hz, 1H), 7.82-7.77 (m, 2H), 7.74-7.52 (m, 4H), 7.47 (d, J=6.0 Hz, 1H), 7.40 (dd, J=7.8, 7.8 Hz, 1H), 7.24-7.06 (m, 4H), 5.38 (q, J=6.9 Hz, 1H), 3.57 (s, 2H), 2.41 (s, 3H), 1.81 (d, J=6.9 Hz, 3H).

Example 10(206)

N-(3,4-difluorophenylsulfonyl)-3-(1-(1-(naphthalen-1-yl)ethylcarbonyl)indol-3-yl)propanamide

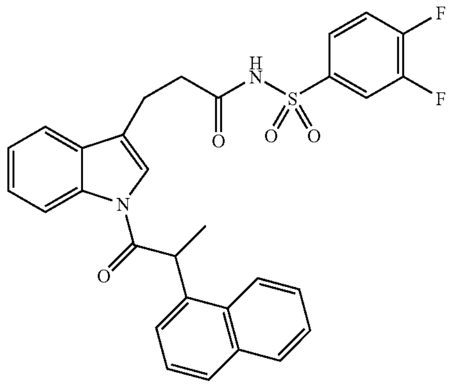

TLC: Rf 0.87 (ethyl acetate:methanol=8:1);

NMR (300 MHz, $CDCl_3$): δ 8.58 (d, J=8.4 Hz, 1H), 8.21 (d, J=7.8 Hz, 1H), 7.94 (d, J=9.0 Hz, 1H), 7.84-7.64 (m, 4H), 7.59 (dd, J=7.5, 7.5 Hz, 1H), 7.42-7.17 (m, 6H), 6.89 (s, 1H), 5.11 (q, J=6.6 Hz, 1H), 2.72 (m, 2H), 2.30 (m, 2H), 1.73 (d, J=6.6 Hz, 3H).

Example 10(207)

N-(3,4-difluorophenylsulfonyl)-3-(2-((3-methyl-1-phenylbutyl)carbamoyl)-4-methoxymethylphenyl)propanamide

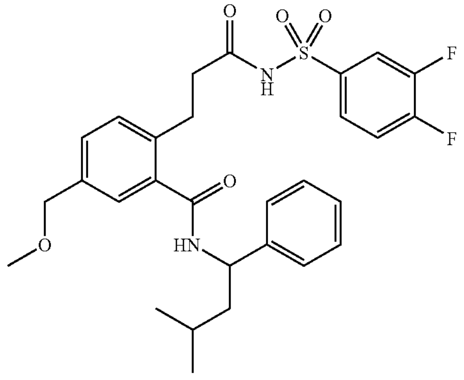

TLC: Rf 0.45 (n-hexane:ethyl acetate=1:2);

NMR (300 MHz, $CDCl_3$): δ 7.68-7.60 (m, 2H), 7.44-7.08 (m, 9H), 6.30 (d, J=9.3 Hz, 1H), 5.27 (m, 1H), 4.42 (s, 2H), 3.44 (s, 3H), 3.00-2.76 (m, 2H), 2.64-2.48 (m, 2H), 1.92-1.70 (m, 3H), 1.02 (d, J=6.6 Hz, 3H), 1.01 (d, J=6.6 Hz, 3H).

Example 10(208)

N-(3,4-difluorophenylsulfonyl)-3-(2-((3-methyl-1-phenylbutyl)carbamoyl)-4-methylsulfonylaminophenyl)propanamide

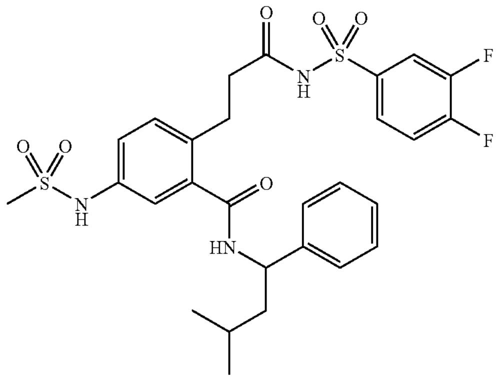

TLC: Rf 0.30 (n-hexane:ethyl acetate=1:2).

Example 10(209)

N-(3,4-difluorophenylsulfonyl)-3-(2-((3-methyl-1-phenylbutyl)carbamoyl)-4-(N-methyl-N-methylsulfonylamino)phenyl)propanamide

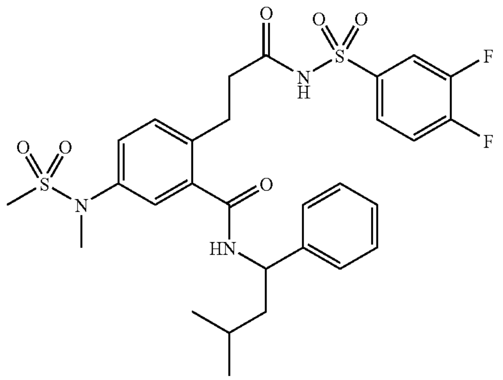

TLC: Rf 0.30 (n-hexane:ethyl acetate=1:2).

Example 10(210)

N-(3,4-difluorophenylsulfonyl)-3-(2-((3-methyl-1-phenylbutyl)carbamoyl)-4-methoxycarbonylaminophenyl)propanamide

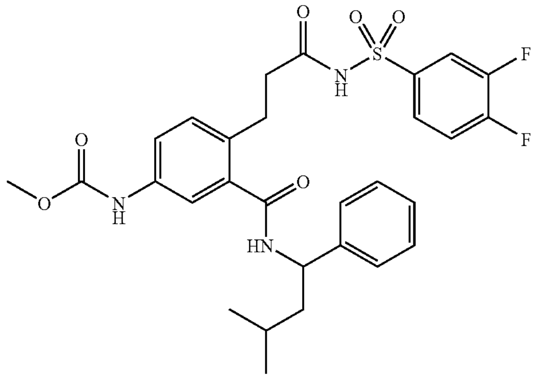

TLC: Rf 0.60 (n-hexane:ethyl acetate=1:2).

Example 10(211)

N-(3,4-difluorophenylsulfonyl)-3-(4-cyano-2-((3-methyl-1-phenylbutyl)carbamoyl)phenyl)propanamide

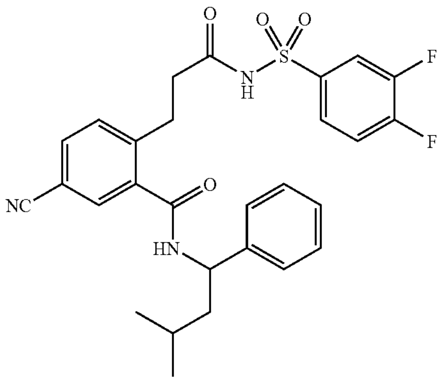

TLC: Rf 0.54 (n-hexane:ethyl acetate=1:2);

NMR (300 MHz, $CDCl_3$): δ 7.84-7.70 (m, 2H), 7.64 (d, J=1.8 Hz, 1H), 7.59 (dd, J=7.8, 1.8 Hz, 1H), 7.46-7.20 (m, 7H), 6.34 (d, J=7.8 Hz, 1H), 5.23 (m, 1H), 3.02-2.80 (m, 2H), 2.51 (t, J=7.4 Hz, 2H), 1.92-1.46 (m, 3H), 1.03 (d, J=5.9 Hz, 3H), 1.01 (d, J=5.9 Hz, 3H).

Example 10(212)

N-(3,4-difluorophenylsulfonyl)-3-(2-((3-methyl-1-phenylbutyl)carbamoyl)-4-isopropylsulfonyloxyphenyl)propanamide

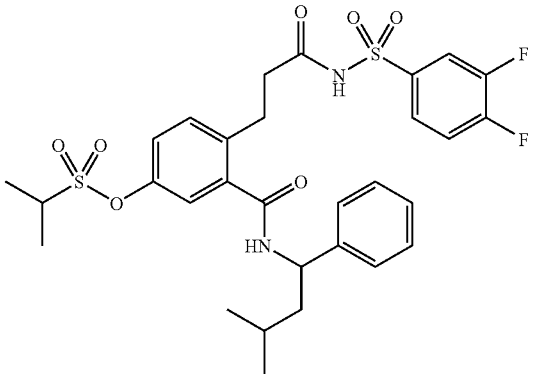

TLC: Rf 0.49 (chloroform:methanol=10:1);

NMR (300 MHz, DMSO-$d_6$): δ 12.30 (brs, 1H), 8.88 (d, J=8.4 Hz, 1H), 7.94 (m, 1H), 7.80-7.68 (m, 2H), 7.33-7.19 (m, 7H), 7.08 (d, J=2.1 Hz, 1H), 4.98 (m, 1H), 3.75 (quint, J=6.9 Hz, 1H), 2.76-2.71 (m, 2H), 2.54-2.49 (m, 2H), 1.75-1.38 (m, 3H), 1.41 (d, J=6.9 Hz, 6H), 0.87-0.83 (m, 6H).

Example 10(213)

N-(3-fluorophenylsulfonyl)-3-(2-(2-(3-methoxyphenylcarbonylamino)ethoxy)-4-(pyrazol-1-ylmethyl)phenyl)propanamide

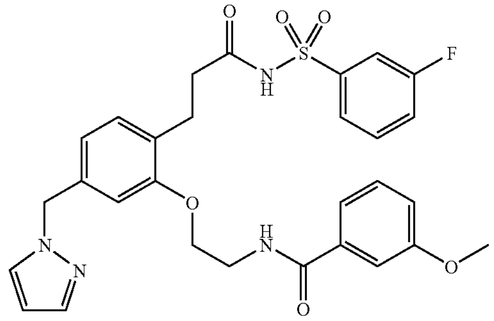

TLC: Rf 0.43 (chloroform:methanol=10:1);

NMR (300 MHz, DMSO-$d_6$): δ 8.62 (t, J=5.4 Hz, 1H), 7.77 (d, J=2.1 Hz, 1H), 7.72-7.53 (m, 4H), 7.45-7.30 (m, 4H), 7.07 (m, 1H), 6.86 (d, J=8.1 Hz, 1H), 6.85 (s, 1H), 6.56 (d, J=8.1 Hz, 1H), 6.24 (t, J=2.1 Hz, 1H), 5.22 (s, 2H), 4.06-3.97 (m, 2H), 3.78 (s, 3H), 3.65-3.56 (m, 2H), 2.66 (t, J=7.2 Hz, 2H), 2.46 (t, J=7.2 Hz, 2H).

Example 10(214)

N-(4-fluorophenylsulfonyl)-3-(2-(2-(3-methoxyphenylcarbonylamino)ethoxy)-4-(pyrazol-1-ylmethyl)phenyl)propanamide

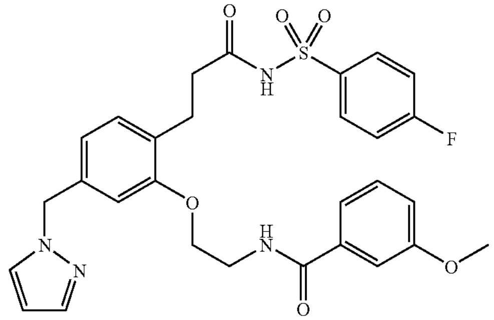

TLC: Rf 0.44 (chloroform:methanol=10:1);

NMR (300 MHz, DMSO-$d_6$): δ 8.62 (t, J=5.4 Hz, 1H), 7.96-7.87 (m, 2H), 7.77 (d, J=2.1 Hz, 1H), 7.47-7.30 (m, 6H), 7.07 (m, 1H), 6.86 (d, J=7.8 Hz, 1H), 6.84 (s, 1H), 6.56 (d, J=7.8 Hz, 1H), 6.24 (t, J=2.1 Hz, 1H), 5.23 (s, 2H), 4.02 (t, J=5.7 Hz, 2H), 3.78 (s, 3H), 3.65-3.56 (m, 2H), 2.65 (t, J=7.2 Hz, 2H), 2.44 (t, J=7.2 Hz, 2H).

Example 10(215)

N-(4-methylphenylsulfonyl)-3-(2-(2-(3-methoxyphenylcarbonylamino)ethoxy)-4-(pyrazol-1-ylmethyl)phenyl)propanamide

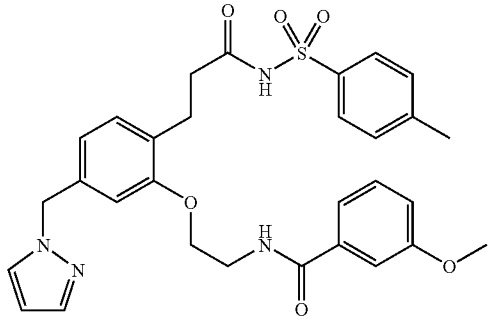

TLC: Rf 0.44 (chloroform:methanol=10:1);

NMR (300 MHz, DMSO-$d_6$): δ 8.62 (t, J=5.7 Hz, 1H), 7.77 (d, J=2.1 Hz, 1H), 7.72 (d, J=8.1 Hz, 2H), 7.47-7.31 (m, 6H), 7.07 (m, 1H), 6.86 (s, 1H), 6.84 (d, J=7.2 Hz, 1H), 6.55 (d, J=7.2 Hz, 1H), 6.24 (t, J=2.1 Hz, 1H), 5.23 (s, 2H), 4.01 (t, J=5.4 Hz, 2H), 3.78 (s, 3H), 3.64-3.55 (m, 2H), 2.64 (t, J=7.5 Hz, 2H), 2.44 (t, J=7.5 Hz, 2H), 2.38 (s, 3H).

Example 10(216)

N-(3-nitrophenylsulfonyl)-3-(2-(2-(3-methoxyphenylcarbonylamino)ethoxy)-4-(pyrazol 1-ylmethyl)phenyl)propanamide

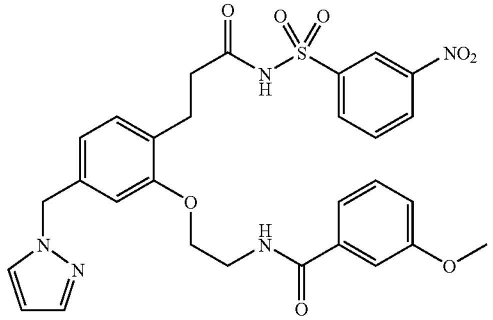

TLC: Rf 0.43 (chloroform:methanol=10:1);

NMR (300 MHz, DMSO-$d_6$): δ 8.61 (t, J=5.4 Hz, 1H), 8.57 (s, 1H), 8.52 (d, J=7.8 Hz, 1H), 8.25 (d, J=7.8 Hz, 1H), 7.89 (t, J=7.8 Hz, 1H), 7.76 (d, J=2.1 Hz, 1H), 7.45-7.28 (m, 4H), 7.07 (m, 1H), 6.85 (d, J=8.4 Hz, 1H), 6.84 (s, 1H), 6.53 (d, J=8.4 Hz, 1H), 6.23 (t, J=2.1 Hz, 1H), 5.21 (s, 2H), 4.01 (t, J=5.7 Hz, 2H), 3.77 (s, 3H), 3.64-3.54 (m, 2H), 2.65 (t, J=7.2 Hz, 2H), 2.46 (t, J=7.2 Hz, 2H).

Example 10(217)

N-(3-cyanophenylsulfonyl)-3-(2-(2-(3-methoxyphenylcarbonylamino)ethoxy)-4-(pyrazol-1-ylmethyl)phenyl)propanamide

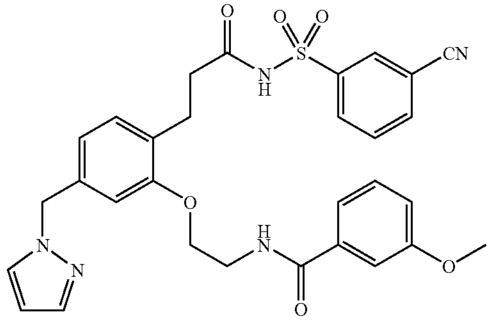

TLC: Rf 0.43 (chloroform:methanol=10:1);

NMR (300 MHz, DMSO-$d_6$): δ 8.62 (t, J=5.4 Hz, 1H), 8.25 (s, 1H), 8.17 (d, J=8.1 Hz, 1H), 8.13 (d, J=8.1 Hz, 1H), 7.80 (t, J=8.1 Hz, 1H), 7.76 (d, J=2.1 Hz, 1H), 7.77 (d, J=2.1 Hz, 1H), 7.46-7.30 (m, 4H), 7.07 (m, 1H), 6.85 (d, J=7.8 Hz, 1H), 6.84 (s, 1H), 6.56 (d, J=7.8 Hz, 1H), 6.24 (t, J=2.1 Hz, 1H), 5.23 (s, 2H), 4.02 (t, J=5.4 Hz, 2H), 3.78 (s, 3H), 3.66-3.56 (m, 2H), 2.65 (t, J=6.9 Hz, 2H), 2.45 (t, J=7.2 Hz, 2H).

Example 10(218)

N-(3-methylphenylsulfonyl)-3-(2-(2-(3-methoxyphenylcarbonylamino)ethoxy)-4-(pyrazol-1-ylmethyl)phenyl)propanamide

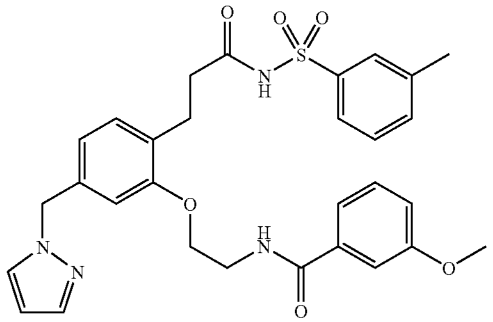

TLC: Rf 0.43 (chloroform:methanol=10:1);

NMR (300 MHz, DMSO-$d_6$): δ 8.62 (t, J=5.4 Hz, 1H), 7.77 (d, J=2.1 Hz, 1H), 7.69-7.60 (m, 2H), 7.52-7.30 (m, 6H), 7.07 (m, 1H), 6.86 (d, J=7.8 Hz, 1H), 6.85 (s, 1H), 6.56 (d, J=7.8 Hz, 1H), 6.24 (t, J=2.1 Hz, 1H), 5.22 (s, 2H), 4.02 (t, J=5.7 Hz, 2H), 3.78 (s, 3H), 3.65-3.55 (m, 2H), 2.65 (t, J=7.2 Hz, 2H), 2.43 (t, J=7.2 Hz, 2H), 2.37 (s, 3H).

Example 10(219)

N-(3-methoxyphenylsulfonyl)-3-(2-(2-(3-methoxyphenylcarbonylamino)ethoxy)-4-(pyrazol-1-ylmethyl)phenyl)propanamide

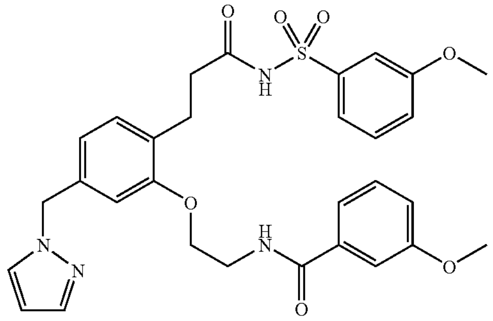

TLC: Rf 0.44 (chloroform:methanol=10:1);

NMR (300 MHz, DMSO-$d_6$): δ 8.63 (t, J=5.4 Hz, 1H), 7.77 (d, J=2.1 Hz, 1H), 7.53-7.23 (m, 9H), 7.07 (m, 1H), 6.86 (d, J=7.8 Hz, 1H), 6.85 (s, 1H), 6.56 (d, J=7.8 Hz, 1H), 6.24 (t, J=2.1 Hz, 1H), 5.23 (s, 2H), 4.02 (t, J=5.7 Hz, 2H), 3.80 (s, 3H), 3.78 (s, 3H), 3.65-3.56 (m, 2H), 2.66 (t, J=7.2 Hz, 2H), 2.44 (t, J=7.2 Hz, 2H).

Example 10(220)

N-(3-trifluoromethylphenylsulfonyl)-3-(2-(2-(3-methoxyphenylcarbonylamino)ethoxy)-4-(pyrazol-1-ylmethyl)phenyl)propanamide

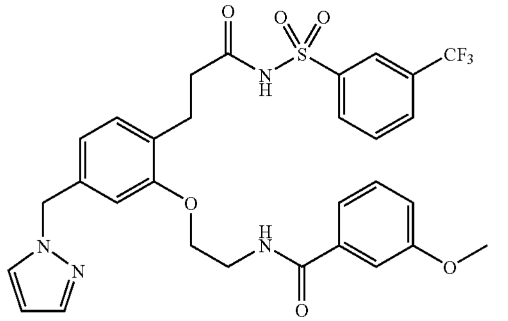

TLC: Rf 0.43 (chloroform:methanol=10:1);

NMR (300 MHz, DMSO-$d_6$): δ 8.62 (t, J=5.4 Hz, 1H), 8.16-8.07 (m, 3H), 7.85 (t, J=8.1 Hz, 1H), 7.76 (d, J=2.1 Hz, 1H), 7.46-7.28 (m, 4H), 7.08 (m, 1H), 6.85 (s, 1H), 6.83 (d, J=7.8 Hz, 1H), 6.53 (d, J=7.8 Hz, 1H), 6.24 (t, J=2.1 Hz, 1H), 5.23 (s, 2H), 4.01 (t, J=5.7 Hz, 2H), 3.77 (s, 3H), 3.65-3.55 (m, 2H), 2.65 (t, J=6.9 Hz, 2H), 2.46 (t, J=6.9 Hz, 2H).

Example 10(221)

N-(3-methoxycarbonylphenylsulfonyl)-3-(2-(2-(3-methoxyphenylcarbonylamino)ethoxy)-4-(pyrazol-1-ylmethyl)phenyl)propanamide

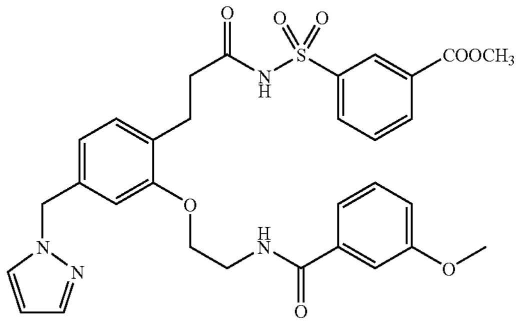

TLC: Rf 0.44 (chloroform:methanol=10:1);

NMR (300 MHz, DMSO-$d_6$): δ 8.61 (t, J=5.4 Hz, 1H), 8.40 (s, 1H), 8.23 (d, J=7.8 Hz, 1H), 8.09 (d, J=7.8 Hz, 1H), 7.78-7.69 (m, 2H), 7.44-7.29 (m, 4H), 7.06 (m, 1H), 6.84 (s, 1H), 6.83 (d, J=7.5 Hz, 1H), 6.53 (d, J=7.5 Hz, 1H), 6.24 (t, J=2.1 Hz, 1H), 5.21 (s, 2H), 4.01 (t, J=5.7 Hz, 2H), 3.90 (s, 3H), 3.77 (s, 3H), 3.64-3.55 (m, 2H), 2.64 (t, J=7.2 Hz, 2H), 2.44 (t, J=7.2 Hz, 2H).

Example 10(222)

N-(3-carboxyphenylsulfonyl)-3-(2-(2-(3-methoxyphenylcarbonylamino)ethoxy)-4-(pyrazol-1-ylmethyl)phenyl)propanamide

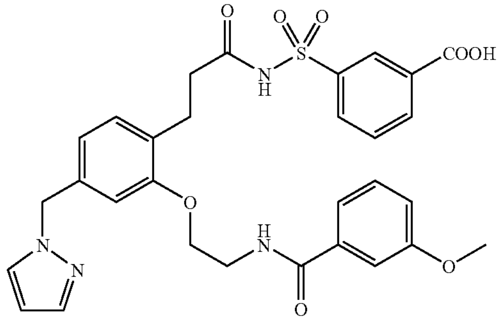

TLC: Rf 0.21 (chloroform:methanol=10:1);

NMR (300 MHz, DMSO-$d_6$): δ 8.62 (t, J=5.4 Hz, 1H), 8.40 (s, 1H), 8.22 (d, J=7.8 Hz, 1H), 8.06 (d, J=7.8 Hz, 1H), 7.79-7.69 (m, 2H), 7.46-7.30 (m, 4H), 7.06 (m, 1H), 6.84 (s, 1H), 6.83 (d, J=7.5 Hz, 1H), 6.53 (d, J=7.5 Hz, 1H), 6.24 (t, J=2.1 Hz, 1H), 5.21 (s, 2H), 4.01 (t, J=5.7 Hz, 2H), 3.77 (s, 3H), 3.64-3.55 (m, 2H), 2.64 (t, J=7.2 Hz, 2H), 2.44 (t, J=7.2 Hz, 2H).

Example 10(223)

N-(3,4-difluorophenylsulfonyl)-3-(6-cyano-1-(1-(naphthalen-1-yl)ethylcarbonyl)indol-3-yl)propanamide

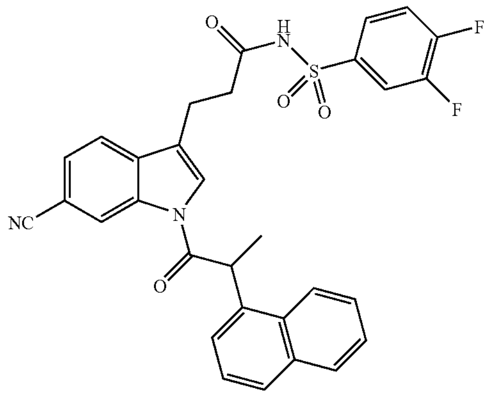

TLC: Rf 0.46 (n-hexane:ethyl acetate:acetic acid=100:100:1);

NMR (300 MHz, DMSO-$d_6$): δ 12.25 (brs, 1H), 8.70 (s, 1H), 8.24 (d, J=8.7 Hz, 1H), 7.98 (m, 1H), 7.89-7.82 (m, 2H), 7.84-7.72 (m, 3H), 7.68-7.55 (m, 4H), 7.44 (t, J=7.5 Hz, 1H), 7.38 (m, 1H), 5.50 (q, J=6.9 Hz, 1H), 2.80-2.60 (m, 2H), 2.57-2.43 (m, 2H), 1.63 (d, J=6.9 Hz, 3H).

Example 10(224)

N-(3,4-difluorophenylsulfonyl)-2-(5-(pyrazol-1-ylmethyl)-2-(naphthalen-1-ylmethyl)isoindolin-3-one-1-yl)acetamide

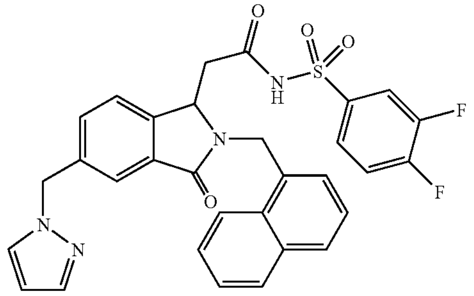

TLC: Rf 0.40 (ethyl acetate:methanol=8:1);

NMR (300 MHz, $CDCl_3$): δ 7.91 (d, J=9.0 Hz, 1H), 7.75 (d, J=7.5 Hz, 1H), 7.67 (m, 2H), 7.50-7.00 (m, 10H), 6.87 (brs, 1H), 6.15 (s, 1H), 5.68 (d, J=15.1 Hz, 1H), 5.15 (s, 2H), 4.52 (d, J=15.1 Hz, 1H), 4.31 (s, 1H), 2.80-2.60 (m, 2H).

Example 10(225)

N-(3,4-difluorophenylsulfonyl)-2-(5-phenoxymethyl-2-(3-methyl-1-phenylbutyl)isoindolin-3-one-1-yl)acetamide

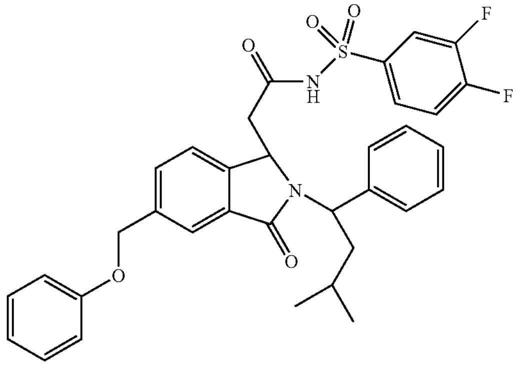

TLC: Rf 0.64 (ethyl acetate:methanol=50:1);

NMR (300 MHz, $CDCl_3$): δ 7.90-6.92 (m, 16H), 5.70-4.70 (m, 2H), 5.08 (m, 2H), 3.00-2.00 (m, 2H), 1.95-1.45 (m, 3H), 0.94 (m, 6H).

Reference Example 20 methyl 3-(2-formyl-4-methoxymethoxymethylphenyl)propanoate

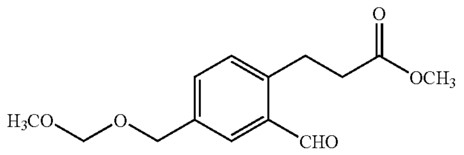

Using methyl 3-(2-carboxy-4-methoxymethoxymethylphenyl)propanoate, the title compounds having the following physical data were obtained by the same procedures as a series of reactions of Reference Example 12→Reference Example 19.

TLC: Rf 0.58 (hexane:ethyl acetate=1:1).

Reference Example 21 methyl 3-(2-(5-methyl-3-phenylhexanoyl)-4-methoxymethoxymethylphenyl)propanoate

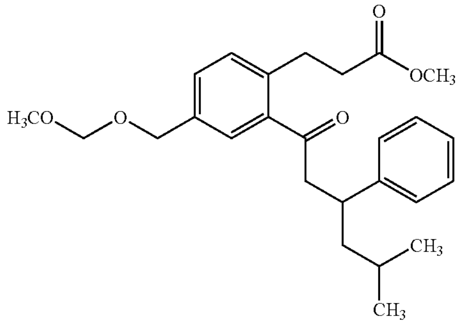

To a solution of the compound prepared in Reference Example 20 in tetrahydrofuran (5 ml) was added dropwise a Grignard reagent prepared by known method (4-methyl-2-phenylpentylmagnesium bromide; 2.33 ml, 0.55M solution in tetrahydrofuran) under an atmosphere of argon. The mixture was stirred at the same temperature for 1 hour. To the mixture was added 0.5 ml of Grignard reagent and then the mixture was stirred for 1 hour. To the reaction mixture was added a saturated aqueous solution of ammonium chloride and the mixture was extracted with ethyl acetate. The organic layer was washed with water and a saturated aqueous solution of sodium chloride subsequently, dried over anhydrous magnesium sulfate and concentrated to give alcohol. The alcohol was mixed with triethylamine (0.71 ml) and dimethylsulfoxide (5 ml). To the mixture was added sulfur trioxide pyridine complex (407 mg) and the mixture was stirred at room temperature for 3 hours. The reaction mixture was poured into crash-ice, and then extracted with ethyl acetate. The organic layer was washed with 1N hydrochloric acid, water and a saturated aqueous solution of sodium chloride subsequently, dried over anhydrous magnesium sulfate and concentrated to give the title compound (225 mg) having the following physical data.

TLC: Rf 0.56 (hexane:ethyl acetate=2:1).

Example 11

3-(2-(5-methyl-3-phenylhexanoyl)-4-hydroxymethylphenyl)propanoic acid methyl ester

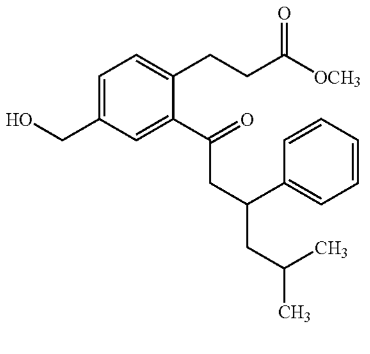

To a solution of the compound prepared in Reference Example 21 (220 mg) in methanol (3 ml) was added 10% hydrogen chloride in methanol (0.5 ml) and the mixture was stirred at room temperature overnight. To the mixture was added 10% hydrogen chloride in methanol (0.5 ml) and the mixture was stirred at 45° C. for 1 hour and then concentrated. The residue was purified by column chromatography on silica gel to give the title compound (200 mg) having the following physical data.

TLC: Rf 0.32 (hexane:ethyl acetate=2:1);

NMR (300 MHz, $CDCl_3$): δ 7.42 (d, J=1.5 Hz, 1H), 7.35-7.13 (m, 7H), 4.66 (d, J=4.5 Hz, 2H), 3.64 (s, 3H), 3.38 (m, 1H), 3.20 (dd, J=16.2, 7.8 Hz, 1H), 3.11 (dd, J=16.2, 6.6 Hz, 1H), 2.88 (m, 2H), 2.49 (m, 2H), 1.70-1.30 (m, 4H), 0.90 (d, J=6.6 Hz, 3H), 0.84 (d, J=6.6 Hz, 3H).

Example 12

3-(2-(5-methyl-3-phenylhexanoyl)-4-phenoxymethylphenyl)propanoic acid

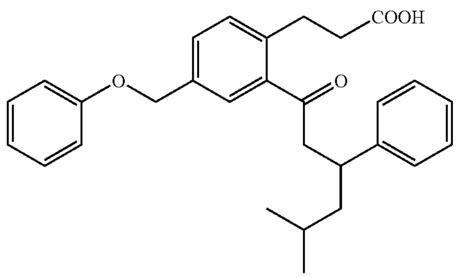

Using the compound prepared in Example 11 or corresponding compounds, the title compounds having the following physical data were obtained by the same procedures as a series of reactions of Reference Example 2→Example 3.

TLC: Rf 0.28 (hexane:ethyl acetate=3:1, 0.5% acetic acid);

NMR (300 MHz, $CDCl_3$): δ 7.52 (d, J=1.5 Hz, 1H), 7.43 (dd, J=7.8, 1.5 Hz, 1H), 7.36-7.21 (m, 5H), 7.19-7.12 (m, 3H), 7.03-6.94 (m, 3H), 5.03 (s, 2H), 3.38 (m, 1H), 3.20 (dd, J=16.2, 7.8 Hz, 1H), 3.11 (dd, J=16.2, 6.6 Hz, 1H), 2.88 (m, 2H), 2.54 (m, 2H), 1.64 (ddd, J=13.2, 9.9, 4.5 Hz, 1H), 1.52-1.30 (m, 2H), 0.89 (d, J=6.6 Hz, 3H), 0.83 (d, J=6.6 Hz, 3H).

Example 13

3-(2-((3-methyl-1-(4-fluorophenyl)butyl)carbamoyl)-4-phenoxymethylphenyl)propanol

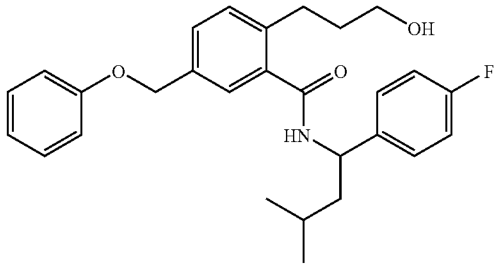

To a solution of the compound prepared in Example 6(40) (2.00 g) in tetrahydrofuran (5 ml) was added dropwise diborane (1M solution in tetrahydrofuran, 8.6 ml) at 0° C. under an atmosphere of argon. The mixture was stirred at room temperature for 30 minutes. To the reaction mixture was added water and the mixture was extracted with ethyl acetate. The organic layer was washed with water and a saturated aqueous solution of sodium chloride subsequently, dried over anhydrous magnesium sulfate and concentrated. The residue was washed with hexane-ethyl acetate to give the title compound (1.67 g) having the following physical data.

TLC: Rf 0.40 (hexane:ethyl acetate=1:1);

NMR (300 MHz, $CDCl_3$): δ 7.43 (dd, J=8.1, 2.1 Hz, 1H), 7.34-7.27 (m, 6H), 7.07-6.95 (m, 5H), 6.13 (d, J=8.1 Hz, 1H), 5.21 (q, J=8.1 Hz, 1H), 5.02 (s, 2H), 3.44 (t, J=5.4 Hz, 2H), 2.87-2.71 (m, 2H), 1.91-1.52 (m, 5H), 0.98 (d, J=6.6 Hz, 6H).

Example 13(1)

3-(2-((3-methyl-1-phenylbutyl)carbamoyl)-4-phenoxymethylphenyl)propanol

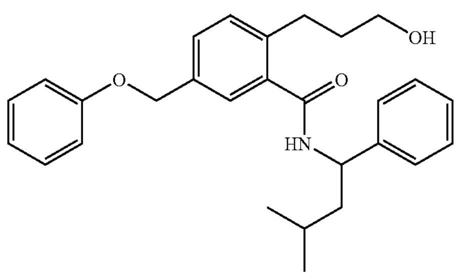

Using the compound prepared in Example 6(33), the title compound having the following physical data was obtained by the same procedure of Example 13.

TLC: Rf 0.61 (chloroform:methanol=10:1);

NMR (300 MHz, $CDCl_3$): δ 7.46-7.25 (m, 10H), 7.02-6.94 (m, 3H), 6.13 (d, J=9.0 Hz, 1H), 5.24 (dt, J=9.0, 9.0 Hz, 1H), 5.02 (s, 2H), 3.50 (brs, 1H), 3.43 (brs, 2H), 2.86-2.72 (m, 2H), 1.85-1.50 (m, 5H), 0.98 (d, J=6.3 Hz, 6H).

Reference Example 22

3-[4-phenoxymethyl-2-[1-(4-fluorophenyl)-3-methylbutylaminocarbonyl]phenyl]propylazide

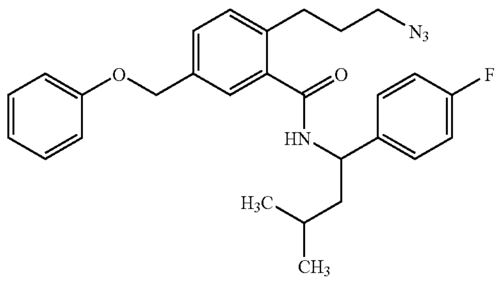

The compound prepared in Example 13(1) (1.46 g) was dissolved in methylene chloride (5 ml). To the solution were added mesyl chloride (0.30 ml) and pyridine (1 ml) and the mixture was stirred at 50° C. for 2 days. To the mixture was added water and the mixture was extracted with ethyl acetate. The organic layer was washed with water and a saturated aqueous solution of sodium chloride subsequently, dried over anhydrous magnesium sulfate and concentrated. The residue was dissolved in N,N-dimethylformamide. The mixture was added sodium azide (354 mg) and then stirred at 80° C. overnight. To the reaction mixture was added water and the mixture was extracted with ethyl acetate. The residue was purified by column chromatography on silica gel to give the title compound (1.16 g) having the following physical data. Mass (APCI, pos. 20V); 475 $(M+H)^+$.

Reference Example 23

3-[4-phenoxymethyl-2-[1-(4-fluorophenyl)-3-methylbutylaminocarbonyl]phenyl]propanamine

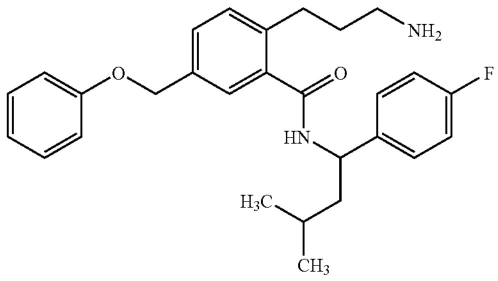

To a solution of the compound prepared in Reference Example 22 (600 mg) in tetrahydrofuran (3 ml) were added triphenylphosphine (500 mg) and water (0.3 ml). The mixture was stirred at room temperature for 2 days. The reaction mixture was concentrated. The residue was purified by column chromatography on silica gel to give the title compound (290 mg) having the following physical data.

NMR (300 MHz, $CDCl_3$): δ 7.42-7.23 (m, 7H), 7.07-6.87 (m, 6H), 5.22 (q, J=8.1 Hz, 1H), 5.02 (s, 2H), 2.80-2.74 (m, 2H), 2.62 (t, J=6.6 Hz, 2H), 1.83-1.55 (m, 5H), 1.00-0.97 (m, 6H).

Example 14

N-(3-methyl-1-(4-fluorophenyl)butyl)-2-(3-mesylaminopropyl)-5-phenoxymethylbenzamide

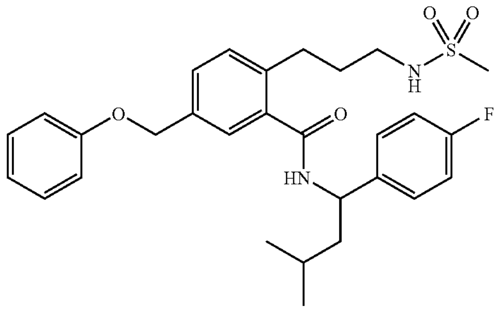

To a solution of the compound prepared in Reference Example 23 (154 mg) in methylene chloride (1 ml) were added mesyl chloride (0.030 ml) and pyridine (0.2 ml). The mixture was stirred at room temperature overnight. To the mixture was added water and the mixture was extracted with ethyl acetate. The organic layer was washed with water and a saturated aqueous solution of sodium chloride subsequently, dried over anhydrous magnesium sulfate and concentrated. The residue was washed with hexane-ethyl acetate to give the title compound (126 mg) having the following physical data.

TLC: Rf 0.20 (hexane:ethyl acetate=1:1);

NMR (300 MHz, $CDCl_3$): δ 7.44 (dd, J=7.8, 1.8 Hz, 1H), 7.36-7.29 (m, 6H), 7.08-6.95 (m, 5H), 6.03 (d, J=8.1 Hz, 1H), 5.70 (t, J=6.3 Hz, 1H), 5.20 (q, J=8.1 Hz, 1H), 5.03 (s, 2H), 3.03-2.96 (m, 2H), 2.84 (s, 3H), 2.81-2.64 (m, 2H), 1.95-1.65 (m, 5H), 0.99 (d, J=6.3 Hz, 6H).

Example 14(1)~Example 14(5)

Using corresponding compounds, the following compounds were obtained by the same procedure of Example 14.

Example 14(1)

N-(3-methyl-1-(4-fluorophenyl)butyl)-2-(3-phenylsulfonylaminopropyl)-5-phenoxymethylbenzamide

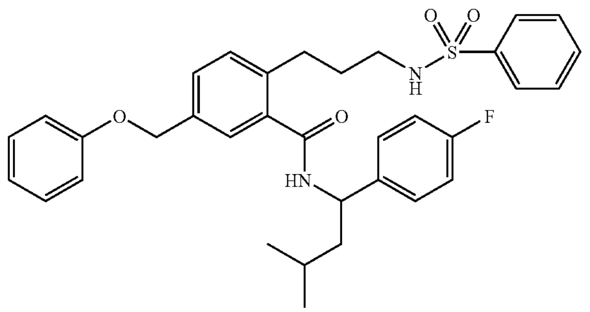

TLC: Rf 0.50 (hexane:ethyl acetate=1:1);

NMR (300 MHz, $CDCl_3$): δ 7.80-7.77 (m, 2H), 7.49-7.29 (m, 9H), 7.18 (d, J=8.1 Hz, 1H), 7.09-6.94 (m, 5H), 6.10 (t, J=6.0 Hz, 1H), 6.02 (d, J=8.1 Hz, 1H), 5.23 (q, J=8.1 Hz, 1H), 5.01 (s, 2H), 2.86-2.58 (m, 4H), 1.83-1.61 (m, 5H), 1.00 (d, J=6.3 Hz, 6H).

Example 14(2)

N-(3-methyl-1-(4-fluorophenyl)butyl)-2-(3-benzoylaminopropyl)-5-phenoxymethylbenzamide

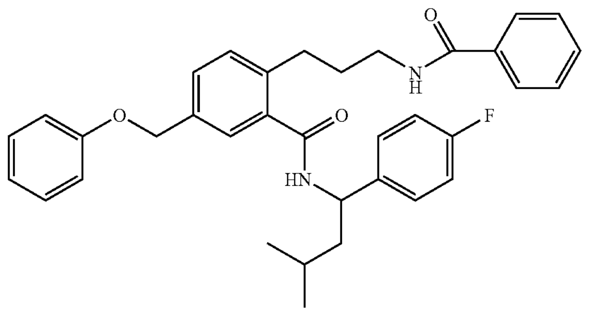

TLC: Rf 0.50 (hexane:ethyl acetate=1:1);

NMR (300 MHz, $CDCl_3$): δ 7.91-7.88 (m, 2H), 7.72-7.68 (m, 1H), 7.48-7.38 (m, 4H), 7.34-7.23 (m, 6H), 7.02-6.95 (m, 5H), 6.10 (d, J=8.1 Hz, 1H), 5.16 (q, J=8.1 Hz, 1H), 5.00 (s, 2H), 3.38-3.31 (m, 2H), 2.88-2.67 (m, 2H), 1.99-1.90 (m, 2H), 1.82-1.61 (m, 3H), 0.97-0.93 (m, 6H).

Example 14(3)

N-(3-methyl-1-(4-fluorophenyl)butyl)-2-(3-formylaminopropyl)-5-phenoxymethylbenzamide

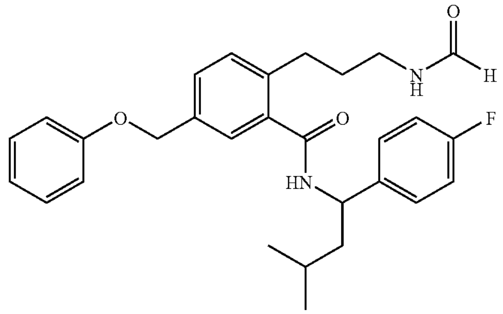

TLC: Rf 0.65 (ethyl acetate);

NMR (300 MHz, $CDCl_3$): δ 8.06 (d, J=1.5 Hz, 1H), 7.45-7.42 (m, 1H), 7.35-7.29 (m, 6H), 7.08-6.95 (m, 5H), 6.75 (br s, 1H), 6.08 (d, J=8.1 Hz, 1H), 5.18 (q, J=8.1 Hz, 1H), 5.03 (s, 2H), 3.20-3.09 (m, 2H), 2.81-2.60 (m, 2H), 1.86-1.61 (m, 5H), 0.99 (d, J=6.3 Hz, 6H).

Example 14(4)

N-phenylsulfonyl-(2-(2-(naphthalen-2-yl)ethoxy)-4-(pyrazol 1-ylmethyl)benzyl)aminocarboxamide

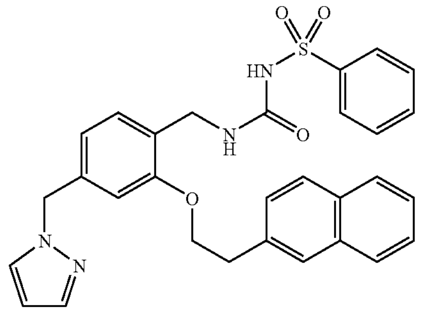

TLC: Rf 0.50 (chloroform:methanol=10:1).

Example 14(5)

N-(3,4-difluorophenylsulfonyl)-N'-(2-(2-(naphthalen-2-yl)ethoxy)-4-(pyrazol 1-ylmethyl)benzyl)urea

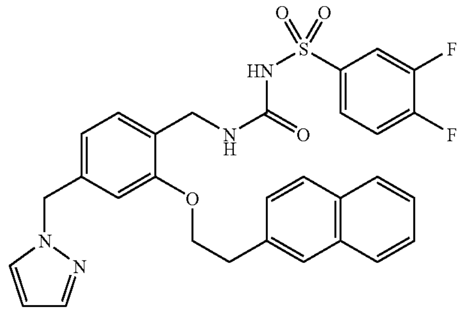

TLC: Rf 0.49 (chloroform:methanol=10:1).

Example 15

3-[4-phenoxymethyl-2-[1-(4-fluorophenyl)-3-methylbutylcarbamoyl]phenyl]propanamide

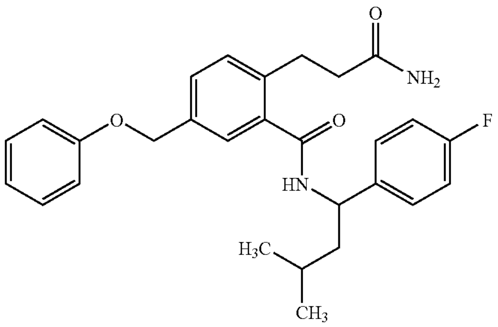

To a solution of the compound prepared in Example 6(40) (150 mg) in tetrahydrofuran (2 ml) were added triethylamine (0.068 ml) and ethyl chloroformate (0.037 ml). The mixture was stirred at room temperature for 30 minutes under an atmosphere of argon. To the reaction mixture was added ammonia water and the mixture was stirred for 10 minutes. To the reaction mixture was added water and then the mixture was extracted with ethyl acetate. The organic layer was washed with 1N hydrochloric acid, water and a saturated aqueous solution of sodium chloride subsequently, dried over anhydrous magnesium sulfate and concentrated. The residue was washed with n-hexane-ethyl acetate to give the title compound (119 mg) having the following physical data.

NMR (300 MHz, $CDCl_3$): 7.44-7.28 (m, 7H), 7.07-6.95 (m, 5H), 6.88 (d, J=8.4 Hz, 1H), 6.04 (br s, 1H), 5.23-5.16 (m, 2H), 5.03 (s, 2H), 3.06-2.89 (m, 2H), 2.61 (t, J=7.2 Hz, 2H), 1.84-1.62 (m, 3H), 0.98 (d, J=6.3 Hz, 6H).

Reference Example 24

N-(3-methyl-1-(4-fluorophenyl)butyl)-2-(2-cyanoethyl)-5-phenoxymethylbenzamide

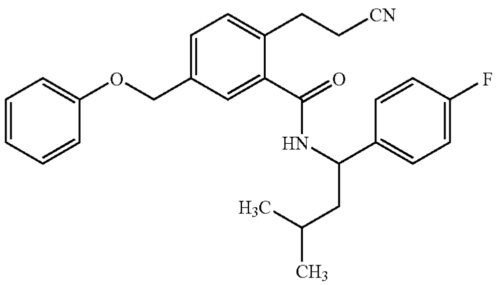

To a suspension of the compound prepared in Example 15 (119 mg) in dioxane (2 ml) were added pyridine (0.1 ml) and trifluoromethanesulfonic acid anhydride (54 μl) at 0° C. under an atmosphere of argon. The mixture was stirred at room temperature for 10 minutes. To the reaction mixture was added water and the mixture was extracted with ethyl acetate. The organic layer was washed with water and a saturated aqueous solution of sodium chloride subsequently, dried over anhydrous magnesium sulfate and concentrated. The residue was washed with n-hexane:ethyl acetate to give the title compound (94 mg) having the following physical data.

NMR (300 MHz, $CDCl_3$): δ 7.50-7.29 (m, 7H), 7.08-6.96 (m, 5H), 6.07 (d, J=8.4 Hz, 1H), 5.17 (q, J=8.4 Hz, 1H), 5.06 (s, 2H), 3.08-2.91 (m, 2H), 2.76-2.62 (m, 2H), 1.82-1.68 (m, 3H), 1.00-0.97 (m, 6H).

Example 16

N-(3-methyl-1-(4-fluorophenyl)butyl)-2-(2-(tetrazol-5-yl)ethyl)-5-phenoxymethylbenzamide

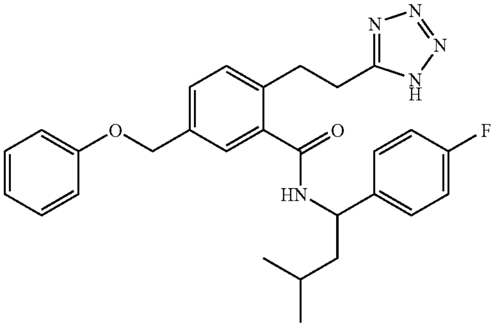

To a solution of the compound prepared in Reference Example 24 (94 mg) in toluene (2 ml) was added trimethyltin azide (65 mg). The mixture was stirred at 120° C. for 3 days. The reaction mixture was concentrated. To the residue were added methanol (3 ml) and 1N hydrochloric acid (2 ml). The mixture was stirred at room temperature for 1 hour. To the reaction mixture was added water and the mixture was extracted with ethyl acetate. The organic layer was washed with water and a saturated aqueous solution of sodium chloride subsequently, dried over anhydrous magnesium sulfate and concentrated. The residue was washed with n-hexane-ethyl acetate to give the title compound (94 mg) having the following physical data.

TLC: Rf 0.30 (ethyl acetate);

NMR (300 MHz, $CDCl_3$): δ 8.90 (d, J=8.4 Hz, 1H), 7.43-7.36 (m, 4H), 7.32-7.24 (m, 3H), 7.11-6.91 (m, 5H), 5.08 (s, 2H), 5.05-5.00 (m, 1H), 3.15-3.04 (m, 4H), 1.62-1.53 (m, 1H), 1.48-1.39 (m, 1H), 0.87 (d, J=6.3 Hz, 6H).

Example 16(1)

1-(2-(tetrazol-5-yl)ethyl)-2-(4-methyl-2-phenylpentyloxy)-4-phenoxymethylbenzene

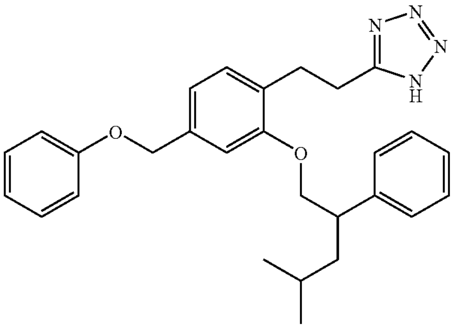

Using corresponding compounds, the compound having the following physical data was obtained by the same procedure of Example 16.

TLC: Rf 0.40 (hexane:ethyl acetate=1:1).

Reference Example 25

N-t-butylmethanesulfonamide

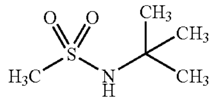

To a solution of tert-butylamine (6.8 ml) and pyridine (7.8 ml) in methylene chloride (50 ml) was added dropwise mesyl chloride (5.0 ml) at 0° C. The mixture was stirred for 30 minutes. The reaction mixture was poured into water and then extracted with methylene chloride. The organic layer was concentrated. The residue was purified by column chromatography to give the title compound (5.2 g) having the following physical data.

TLC: Rf 0.26 (n-hexane:ethyl acetate=2:1);

NMR (300 MHz, $CDCl_3$): δ 4.22 (brs, 1H), 3.02 (s, 3H), 1.39 (s, 9H).

Reference Example 26

4-(1-pyrazolylmethyl)-2-[2-(naphthalen-2-yl)ethyloxy]benzamide

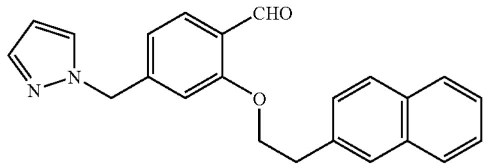

Using methyl 2-hydroxy-4-hydroxymethylbenzoate, the title compounds having the following physical data were obtained by the same procedures as a series of reactions of Reference Reference Example 13→Reference Example 3→Example 7→Example 2→Example 3→Example 13→Reference Example 19.

TLC: Rf 0.49 (n-hexane:ethyl acetate=1:1);

NMR (300 MHz, $CDCl_3$): δ 10.41 (s, 1H), 7.86-7.69 (m, 5H), 7.57 (m, 1H), 7.52-7.35 (m, 4H), 6.79 (d, J=7.8 Hz, 1H), 6.73 (brs, 1H), 6.31 (t, J=2.1 Hz, 1H), 5.32 (s, 2H), 4.30 (t, J=6.6 Hz, 2H), 3.28 (t, J=6.6 Hz, 2H).

Reference Example 27

N-(t-butyl)-2-hydroxy-2-[2-[2-(naphthalen-2-yl)ethyloxy]-4-(1-pyrazolylmethyl)phenyl]ethylsulfonamide

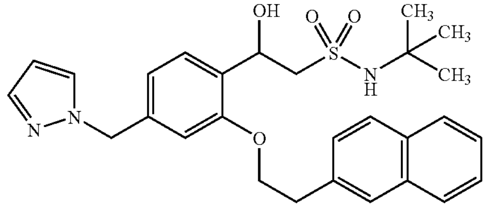

To a solution of the compound prepared in Reference Example 26 (64 mg) in tetrahydrofuran (1.5 ml) was added n-butyl lithium (1.59M solution in hexane, 0.55 ml) at −78° C. The mixture was stirred at 0° C. for 1 hour. The solution was cooled to −78° C. again. To the solution was added a solution of the compound prepared in Reference Example 25 (100 mg) in tetrahydrofuran (1.0 ml), and then the mixture was stirred for 20 minutes. To the reaction mixture was added an aqueous solution of ammonium chloride. The mixture was poured into water and the mixture was extracted with ethyl acetate. The organic layer was washed with water and a saturated aqueous solution of sodium chloride, dried over anhydrous magnesium sulfate and concentrated. The residue was purified by column chromatography on silica gel (n-hexane: ethyl acetate=1:1) to give the title compound (141 mg) having the following physical data.

TLC: Rf 0.28 (n-hexane:ethyl acetate=1:1);

NMR (300 MHz, $CDCl_3$): δ 7.87-7.78 (m, 3H), 7.74 (s, 1H), 7.54 (d, J=2.1 Hz, 1H), 7.42-7.35 (m, 5H), 6.84 (d, J=7.5 Hz, 1H), 6.73 (d, J=1.2 Hz, 1H), 6.28 (t, J=2.1 Hz, 1H), 5.44 (m, 1H), 5.28 (s, 2H), 4.36-4.18 (m, 2H), 3.95 (s, 1H), 3.59 (d, J=3.9 Hz, 1H), 3.37-3.14 (m, 4H), 1.19 (s, 9H).

Example 17

(E)-N-(t-butyl)-2-[2-[2-(naphthalen-2-yl)ethyloxy]-4-(1-pyrazolylmethyl)phenyl]ethenylsulfonamide

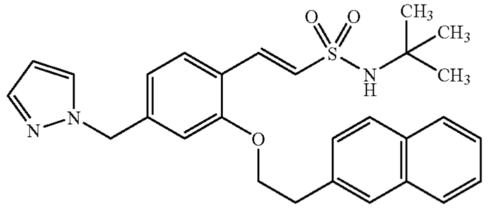

To a solution of the compound prepared in Reference Example 27 (90 mg) in 1,2-dichloroethane (1.8 ml) were added triethylamine (0.12 ml) and mesyl chloride (0.02 ml) at 0° C. The mixture was stirred at 60° C. for 40 minutes. To the reaction mixture was added ice-water and then the mixture was extracted with methylene chloride. The organic layer was washed with a saturated aqueous solution of sodium chloride, dried over anhydrous magnesium sulfate and concentrated. The residue was purified by column chromatography on silica gel (chloroform:acetone=50:1) to give the title compound (77 mg) having the following physical data.

TLC: Rf 0.48 (chloroform:acetone=10:1);

NMR (300 MHz, $CDCl_3$): δ 7.91-7.76 (m, 4H), 7.58-7.38 (m, 5H), 7.30 (d, J=7.8 Hz, 1H), 7.26 (s, 1H), 6.88 (d, J=15.9 Hz, 1H), 6.80-6.71 (m, 2H), 6.30 (t, J=1.8 Hz, 1H), 5.29 (s, 2H), 4.30 (t, J=6.6 Hz, 2H), 3.96 (s, 1H), 3.28 (t, J=6.6 Hz, 2H), 1.14 (s, 9H).

Example 18

N-(t-butyl)-2-[2-[2-(naphthalen-2-yl)ethyloxy]-4-(1-pyrazolylmethyl)phenyl]ethylsulfonamide

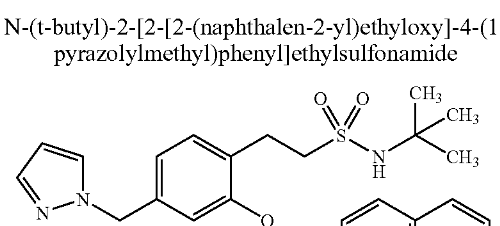

To a solution of the compound prepared in Example 17 (77 mg) in ethanol (2.0 ml) was added platinum dioxide (15 mg) at room temperature. The mixture was stirred at 70° C. for 2 hours under an atmosphere of hydrogen. The atmosphere was substituted with argon. The mixture was filtered. The filtrate was concentrated to give the title compound having the following physical data. The compound was used to the next step without further purification.

TLC: Rf 0.52 (n-hexane:ethyl acetate=1:1);

NMR (300 MHz, $CDCl_3$): δ 7.87-7.68 (m, 4H), 7.58-7.32 (m, 5H), 7.11 (d, J=7.8 Hz, 1H), 6.78-6.65 (m, 2H), 6.26 (t, J=2.1 Hz, 1H), 5.23 (s, 2H), 4.23 (t, J=6.6 Hz, 2H), 3.75 (s, 1H), 3.23 (t, J=6.6 Hz, 2H), 3.18-2.95 (m, 4H), 1.14 (s, 9H).

Example 19

2-[2-[2-(naphthalen-2-yl)ethyloxy]-4-(1-pyrazolylmethyl)phenyl]ethylsulfonamide

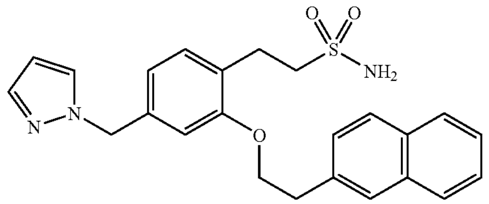

To the compound prepared in Example 18 were added anisole (0.05 ml) and trifluoroacetic acid (0.5 ml). The mixture was stirred at room temperature for 5 hours. The reaction mixture was azeotroped with toluene, added a saturated aqueous solution of sodium bicarbonate and the mixture was extracted with ethyl acetate. The organic layer was dried over anhydrous magnesium sulfate and concentrated. The residue was purified by column chromatography on silica gel (n-hexane:ethyl acetate=1:1) to give the title compound (30 mg) having the following physical data.

TLC: Rf 0.22 (n-hexane:ethyl acetate=1:1);

NMR (300 MHz, $CDCl_3$): δ 7.87-7.78 (m, 3H), 7.74 (s, 1H), 7.58-7.36 (m, 5H), 7.08 (d, J=7.5 Hz, 1H), 6.76-6.68 (m, 2H), 6.28 (brs, 1H), 5.27 (s, 2H), 4.28 (t, J=6.0 Hz, 2H), 3.93 (s, 2H), 3.25 (t, J=6.6 Hz, 2H), 2.99 (s, 4H).

Example 20

N-(2-(2-(2-(naphthalen-2-yl)ethoxy)-4-(pyrazol 1-ylmethyl)phenyl)ethylsulfonyl)benzamide

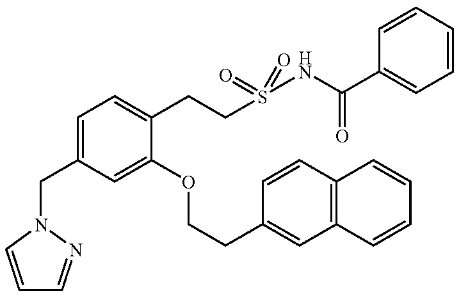

To a solution of the compound prepared in Example 19 (35 mg) and benzoic acid (15 mg) in N,N-dimethylformamide (1.0 ml) were added 1-ethyl-3-[3-(dimethylamino)propyl] carbodiimide hydrochloride (31 mg) and dimethylaminopyridine (30 mg) at 0° C. The mixture was stirred at room temperature overnight. To the reaction mixture was added water and the mixture was extracted with ethyl acetate. The organic layer was dried over anhydrous magnesium sulfate and concentrated. The residue was purified by column chromatography on silica gel (n-hexane:ethyl acetate=2:3 chloroform:methanol=10:1) to give the title compound (25 mg) having the following physical data.

TLC: Rf 0.31 (n-hexane:ethyl acetate=1:2);

NMR (300 MHz, DMSO-$d_6$): δ 7.98-7.91 (m, 2H), 7.89-7.77 (m, 4H), 7.76 (d, J=2.4 Hz, 1H), 7.62 (m, 1H), 7.56-7.40 (m, 6H), 7.13 (d, J=8.1 Hz, 1H), 6.87 (s, 1H), 6.65 (d, J=8.1 Hz, 1H), 6.24 (t, J=2.1 Hz, 1H), 5.23 (s, 2H), 4.17 (t, J=6.6 Hz, 2H), 3.74-3.61 (m, 2H), 3.15 (t, J=6.6 Hz, 2H), 3.01-2.91 (m, 2H).

Example 21

3-[2-[2-(naphthalen-2-yl)ethyloxy]-4-(1-pyrazolylmethyl)phenyl]propanamide

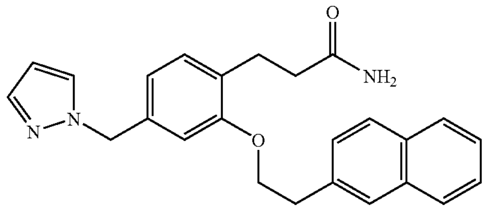

To a solution of the compound prepared in Example 3(12) (700 mg) in methylene chloride (15 ml) were added oxalyl chloride (305 μl) and N,N-dimethylformamide (catalytic amount) at room temperature under an atmosphere of argon. The mixture was stirred for 30 minutes. To the reaction mixture was added 28% ammonia water (5 ml) with vigorously stirring, the mixture was stirred at room temperature for 30 minutes. To the reaction mixture was added 1N hydrochloric acid, and the mixture was extracted with ethyl acetate-tetrahydrofuran. The organic layer was washed with water and a saturated aqueous solution of sodium chloride subsequently, dried over anhydrous sodium sulfate and concentrated to give the title compound (708 mg) having the following physical data.

TLC: Rf 0.35 (chloroform:methanol=10:1);

NMR (300 MHz, $CDCl_3$): δ 7.84-7.76 (m, 3H), 7.72 (s, 1H), 7.54 (d, J=1.5 Hz, 1H), 7.49-7.36 (m, 4H), 7.08 (d, J=7.5 Hz, 1H), 6.71 (d, J=7.5 Hz, 1H), 6.69 (s, 1H), 6.27 (dd, J=2.4, 1.5 Hz, 1H), 5.25 (s, 2H), 4.93 (brs, 1H), 4.72 (brs, 1H), 4.26 (t, J=6.6 Hz, 2H), 3.25 (t, J=6.6 Hz, 2H), 2.80 (t, J=7.5 Hz, 2H), 2.14 (t, J=7.5 Hz, 2H).

Reference Example 28

3-[4-(1-pyrazolylmethyl)-2-[2-(naphthalen-2-yl) ethyloxy]phenyl]propanenitrile

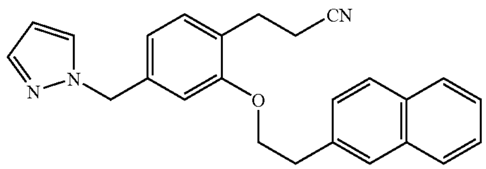

Using the compounds prepared in Example 21, the title compound (1.56 g) having the following physical data was obtained by the same procedure of Reference Example 24.

TLC: Rf 0.50 (n-hexane:ethyl acetate=1:1);

NMR (300 MHz, $CDCl_3$): δ 7.85-7.78 (m, 3H), 7.70 (s, 1H), 7.54 (d, J=1.8 Hz, 1H), 7.51-7.36 (m, 4H), 7.08 (d, J=7.5 Hz, 1H), 6.73 (dd, J=7.5, 1.2 Hz, 1H), 6.69 (d, J=1.2 Hz, 1H), 6.27 (dd, J=2.1, 1.8 Hz, 1H), 5.26 (s, 2H), 4.23 (t, J=6.6 Hz, 2H), 3.23 (t, J=6.6 Hz, 2H), 2.82 (t, J=7.5 Hz, 2H), 2.31 (t, J=7.5 Hz, 2H).

Reference Example 29

3-[4-(1-pyrazolylmethyl)-2-[2-(naphthalen-2-yl)ethyloxy]phenyl]-1-hydroxyiminopropylamine

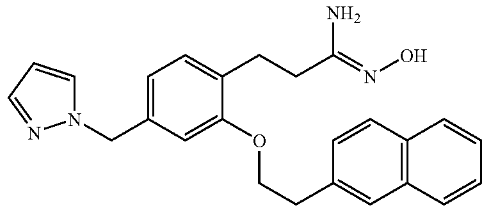

To a solution of the compound prepared in Reference Example 28 in ethanol (30 ml) were added triethylamine (1.06 ml) and hydroxylamine hydrochloride (530 mg). The mixture was refluxed for 2 days. The reaction mixture was standing to cool, and then the mixture was extracted with ethyl acetate. The organic layer was washed with water and a saturated aqueous solution of sodium chloride subsequently, dried over anhydrous sodium sulfate and concentrated. The residue was purified by column chromatography on silica gel (n-hexane:ethyl acetate=1:1→chloroform:methanol=10:1) to give the title compound (920 mg) having the following physical data.

TLC: Rf 0.33 (chloroform:methanol=10:1);

NMR (300 MHz, $CDCl_3$): δ 7.82-7.76 (m, 3H), 7.71 (s, 1H), 7.54 (m, 1H), 7.48-7.35 (m, 4H), 7.06 (d, J=7.5 Hz, 1H), 6.70 (dd, J=7.5, 0.9 Hz, 1H), 6.69 (d, J=0.9 Hz, 1H), 6.26 (dd, J=2.4, 2.1 Hz, 1H), 5.25 (s, 2H), 4.24 (t, J=6.6 Hz, 2H), 4.20 (brs, 2H), 3.24 (t, J=6.6 Hz, 2H), 2.77-2.72 (m, 2H), 2.24-2.18 (m, 2H).

Example 22

3-(2-(2-(2-(naphthalen-2-yl)ethoxy)-4-(pyrazol-1-ylmethyl)phenyl)ethyl-1,2,4-oxadiazole-5-thione

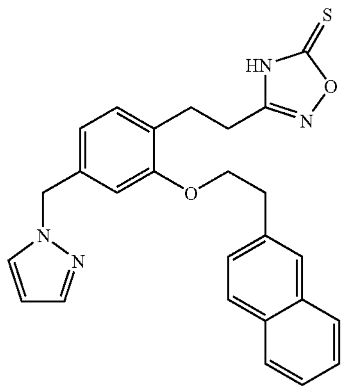

To a solution of the compound prepared in Reference Example 29 (180 mg) in acetonitorile (4.0 ml) were added 1,8-diazabicyclo[5.4.0]undec-7-ene (260 μl) and N,N'-thiocarbonyldiimidazole (116 mg) at room temperature. The mixture was stirred for 1 hour. To the reaction mixture was added 1N hydrochloric acid and the mixture was extracted with ethyl acetate. The organic layer was washed with water and a saturated aqueous solution of sodium chloride subsequently, dried over anhydrous sodium sulfate and concentrated. The residue was purified by column chromatography on silica gel (n-hexane:ethyl acetate=1:1→1:3) to give the title compound (150 mg) having the following physical data.

TLC: Rf 0.41 (chloroform:methanol=10:1);

NMR (300 MHz, $CDCl_3$): δ 7.82-7.73 (m, 3H), 7.69 (s, 1H), 7.58 (d, J=1.8 Hz, 1H), 7.50-7.35 (m, 4H), 6.64 (d, J=7.5 Hz, 1H), 6.58 (d, J=0.9 Hz, 1H), 6.40 (dd, J=7.5, 0.9 Hz, 1H), 6.32 (dd, J=2.1, 1.8 Hz, 1H), 5.19 (s, 2H), 4.19 (t, J=6.6 Hz, 2H), 3.20 (t, J=6.6 Hz, 2H), 2.67 (t, J=7.5 Hz, 2H), 2.32 (t, J=7.5 Hz, 2H).

Example 22(1)~Example 22(5)

The compounds having the following physical data were obtained by the same procedure of Example 22.

Example 22(1)

3-(2-(2-(2-(naphthalen-2-yl)ethoxy)-4-(pyrazol-1-ylmethyl)phenyl)ethyl-1,2,4-oxadiazole-5-one

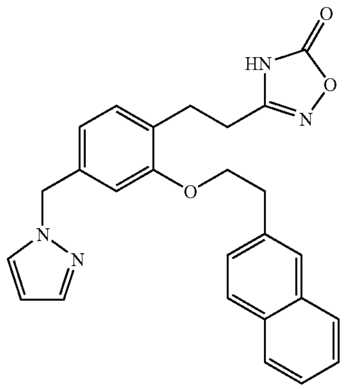

TLC: Rf 0.46 (hexane:ethyl acetate=1:3);

NMR (300 MHz, $CDCl_3$): δ 7.82-7.74 (m, 3H), 7.70 (s, 1H), 7.54 (dd, J=2.4, 0.9 Hz, 1H), 7.51-7.36 (m, 4H), 6.92 (d, J=7.8 Hz, 1H), 6.66 (s, 1H), 6.62 (d, J=7.8 Hz, 1H), 6.29 (dd, J=2.4, 2.1 Hz, 1H), 5.23 (s, 2H), 4.25 (t, J=6.6 Hz, 2H), 3.23 (t, J=6.6 Hz, 2H), 2.75 (t, J=7.5 Hz, 2H), 2.36 (t, J=7.5 Hz, 2H).

Example 22(2)

3-(2-(2-(2-(naphthalen-2-yl)ethoxy)-4-(pyrazol-1-ylmethyl)phenyl)ethyl-1,2,4-thiadiazole-5-one

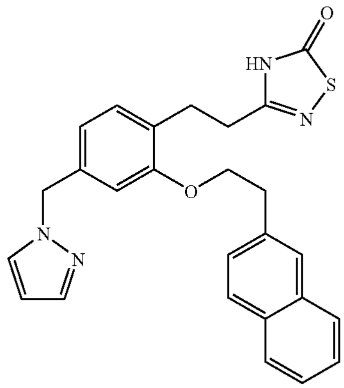

TLC: Rf 0.38 (hexane:ethyl acetate=2:3);

NMR (300 MHz, $CDCl_3$): δ 9.08 (brs, 1H), 7.83-7.73 (m, 3H), 7.70 (s, 1H), 7.54 (d, J=1.8 Hz, 1H), 7.50-7.37 (m, 4H), 7.01 (d, J=8.1 Hz, 1H), 6.70 (s, 1H), 6.69 (d, J=8.1 Hz, 1H), 6.28 (dd, J=2.1, 1.8 Hz, 1H), 5.25 (s, 2H), 4.27 (t, J=6.6 Hz, 2H), 3.25 (t, J=6.6 Hz, 2H), 2.84 (t, J=7.5 Hz, 2H), 2.40 (t, J=7.5 Hz, 2H).

Example 22(3)

4-(2-(2-(2-(naphthalen-2-yl)ethoxy)-4-(pyrazol-1-ylmethyl)phenyl)ethyl-1,2,3,5-oxathiadiazole-2-one

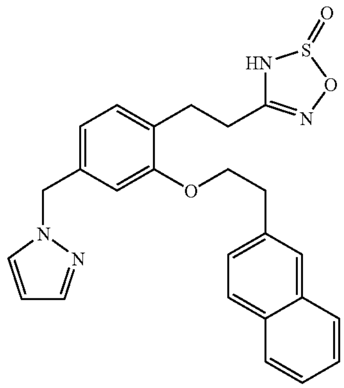

TLC: Rf 0.44 (hexane:ethyl acetate=1:2);

NMR (300 MHz, $CDCl_3$): δ 7.84-7.78 (m, 3H), 7.72 (s, 1H), 7.55 (d, J=1.5 Hz, 1H), 7.52-7.39 (m, 4H), 6.89 (d, J=7.8 Hz, 1H), 6.67 (s, 1H), 6.62 (d, J=7.8 Hz, 1H), 6.30 (dd, J=2.1, 1.5 Hz, 1H), 5.25 (s, 2H), 4.25 (t, J=6.6 Hz, 2H), 3.22 (t, J=6.6 Hz, 2H), 2.72 (t, J=7.5 Hz, 2H), 2.34 (t, J=7.5 Hz, 2H).

Example 22(4)

3-(2-(2-(3-methyl-1-phenylbutylcarbamoyl)-4-phenoxymethyl)phenyl)ethyl-1,2,4-oxadiazole-5-one

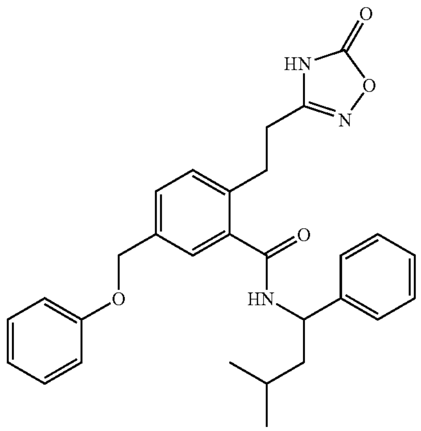

TLC: Rf 0.66 (n-hexane:ethyl acetate=1:2);

NMR (300 MHz, DMSO-$d_6$): δ 8.88 (d, J=8.4 Hz, 1H), 7.47-7.16 (m, 11H), 7.05-6.90 (m, 3H), 5.09 (s, 2H), 5.04 (m, 1H), 2.98-2.87 (m, 2H), 2.79-2.67 (m, 2H), 1.75 (m, 1H), 1.61 (m, 1H), 1.45 (m, 1H), 0.91 (d, J=6.3 Hz, 3H), 0.90 (d, J=6.3 Hz, 3H).

Example 22(5)

3-(2-(2-(3-methyl-1-phenylbutylcarbamoyl)-4-phenoxymethyl)phenyl)ethyl-1,2,4-oxadiazole-5-thione

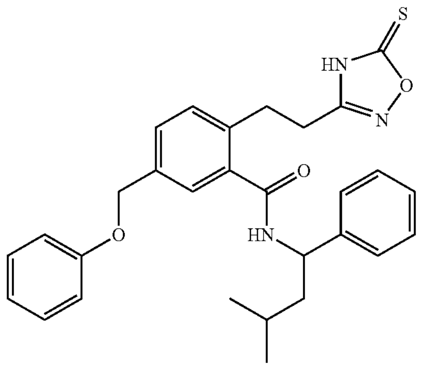

TLC: Rf 0.48 (chloroform:methanol=10:1);

NMR (300 MHz, DMSO-$d_6$): δ 7.52-7.22 (m, 10H), 7.04-6.93 (m, 3H), 6.31 (d, J=8.4 Hz, 1H), 5.24 (m, 1H), 5.05 (s, 2H), 3.17-2.88 (m, 4H), 1.89-1.51 (m, 3H), 1.01 (d, J=6.6 Hz, 3H), 1.00 (d, J=6.6 Hz, 3H).

Reference Example 30

4-phenoxymethyl-2-(2-nitrophenylsulfonylamino) phenyl iodide

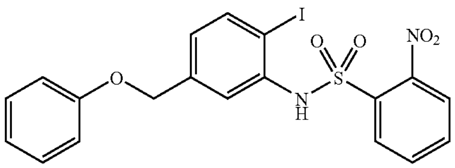

To a solution of 2-iodo-4-phenoxymethylaniline (600 mg) in methylene chloride (4.0 ml) were added pyridine (0.45 ml) and 2-nitrophenylsulfonylchloride (429 mg) at 0° C. The mixture was stirred overnight. The reaction mixture was poured into water and then extracted with ethyl acetate. The organic layer was washed with a saturated aqueous solution of sodium chloride, dried over anhydrous magnesium sulfate and concentrated. The residue was purified by column chromatography on silica gel (n-hexane:ethyl acetate=2:1) to give the title compound having the following physical data.

TLC: Rf 0.38 (n-hexane:ethyl acetate=2:1);

NMR (300 MHz, $CDCl_3$): δ 7.90 (m, 1H), 7.80 (m, 1H), 7.77-7.65 (m, 3H), 7.56 (m, 1H), 7.36-7.23 (m, 3H), 7.05-6.91 (m, 4H), 5.06 (s, 2H).

Reference Example 31

4-phenoxymethyl-2-[N-[2-(naphthalen-2-yl)ethyl]-N-2-nitrophenylsulfonylamino]phenyl iodide

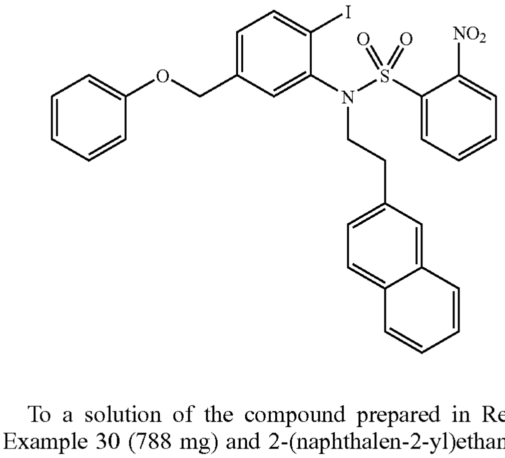

To a solution of the compound prepared in Reference Example 30 (788 mg) and 2-(naphthalen-2-yl)ethanol (385 mg) in tetrahydrofuran (5.0 ml) were added diethylazodicarboxylate (0.97 ml) and triphenylphosphine (585 mg) at room temperature. The mixture was stirred overnight. The reaction mixture was concentrated and the residue was purified by column chromatography on silica gel (n-hexane:ethyl acetate=3:1) to give the title compound having the following physical data.

TLC: Rf 0.47 (n-hexane:ethyl acetate=2:1);

NMR (300 MHz, $CDCl_3$): δ 7.88-7.11 (m, 16H), 7.04-6.85 (m, 3H), 6.87 (d, J=12.3 Hz, 1H), 4.80 (d, J=12.3 Hz, 1H), 4.40 (m, 1H), 3.89 (m, 1H), 3.18-3.00 (m, 2H).

Reference Example 32

4-phenoxymethyl-2-[2-(naphthalen-2-yl)ethylamino] phenyl iodide

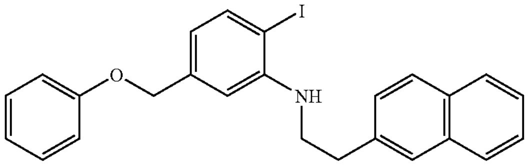

To a solution of the compound prepared in Reference Example 31 (750 mg) in acetonitorile (3.8 ml) were added potassium carbonate (160 mg) and thiophenol (0.14 ml). The mixture was stirred overnight. To the reaction mixture was added water, and the mixture was extracted with ethyl acetate. The organic layer was washed with 2N aqueous solution of sodium hydroxide and a saturated aqueous solution of sodium chloride subsequently, dried over anhydrous magnesium sulfate and concentrated. The residue was purified by column chromatography on silica gel (n-hexane:ethyl acetate=20:1) to give the title compound having the following physical data.

TLC: Rf 0.84 (n-hexane:ethyl acetate=2:1);

NMR (300 MHz, $CDCl_3$): δ 7.86-7.76 (m, 3H), 7.68 (s, 1H), 7.62 (d, J=7.8 Hz, 1H), 7.52-7.41 (m, 2H), 7.39-7.24 (m, 3H), 7.01-6.92 (m, 3H), 6.69 (m, 1H), 6.52 (m, 1H), 4.98 (s, 2H), 4.32 (m, 1H), 3.57-3.45 (m, 2H), 3.10 (t, J=6.9 Hz, 2H).

Reference Example 33

4-phenoxymethyl-2-[N-[2-(naphthalen-2-yl)ethyl]-N-methylamino]phenyl iodide

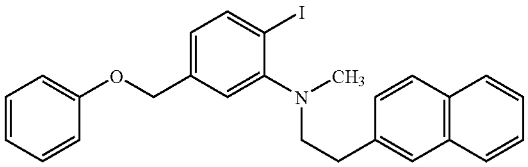

To a solution of the compound prepared in Reference Example 32 (170 mg) in N,N-dimethylformamide (1.2 ml) were added cesium carbonate (570 mg) and methyl iodide (0.07 ml) at room temperature. The mixture was stirred at 60° C. for 1.5 hours. The reaction mixture was cooled to room temperature, poured into water and then extracted with ethyl acetate. The organic layer was washed with a saturated aqueous solution of sodium chloride, dried over anhydrous magnesium sulfate and concentrated to give the title compound having the following physical data.

TLC: Rf 0.47 (n-hexane:ethyl acetate=10:1);

NMR (300 MHz, $CDCl_3$): δ 7.86 (d, J=8.1 Hz, 1H), 7.83-7.71 (m, 3H), 7.63 (s, 1H), 7.48-7.24 (m, 5H), 7.18 (d, J=1.8

Hz, 1H), 7.71-6.92 (m, 3H), 6.86 (dd, J=7.8, 1.8 Hz, 1H), 4.98 (s, 2H), 3.32-3.24 (m, 2H), 3.06-2.97 (m, 2H), 2.84 (s, 3H).

Example 23

4-phenoxymethyl-2-[N-[2-(naphthalen-2-yl)ethyl]-N-methylamino]cinnamic acid ethyl ester

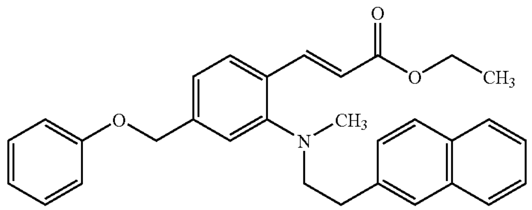

Using the compounds prepared in Reference Example 33, the title compounds having the following physical data were obtained by the same procedure of Example 1.

TLC: Rf 0.26 (n-hexane:ethyl acetate=10:1);

NMR (300 MHz, $CDCl_3$): δ 8.07 (d, J=16.2 Hz, 1H), 7.82-7.69 (m, 3H), 7.60-7.50 (m, 2H), 7.48-7.36 (m, 2H), 7.35-7.22 (m, 3H), 7.15 (s, 1H), 7.08 (m, 1H), 7.03-6.90 (m, 3H), 6.40 (d, J=16.2 Hz, 1H), 5.02 (s, 2H), 4.27 (q, J=7.2 Hz, 2H), 3.32-3.22 (m, 2H), 3.19-2.99 (m, 2H), 2.87 (s, 3H), 1.33 (t, J=7.2 Hz, 3H).

Example 24

3-[4-phenoxymethyl-2-[N-[2-(naphthalen-2-yl)ethyl]-N-methylamino]phenyl]propanoic acid ethyl ester

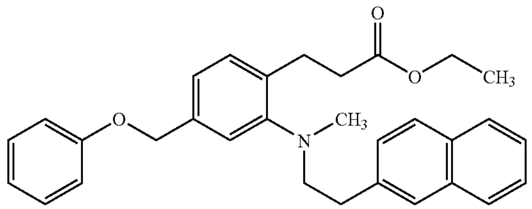

To a solution of the compound prepared in Example 23 (135 mg) in tetrahydrofuran (1.2 ml)-ethanol (0.3 ml) were added portionwise nickel chloride hexahydrate (70 mg) and sodium borohydride (45 mg) at 0° C. The mixture was stirred for 15 minutes. The reaction mixture was extracted with diethyl ether. The organic layer was filtered. The filtrate was extracted with diethyl ether. The organic layer was washed with a saturated aqueous solution of sodium chloride, dried over anhydrous magnesium sulfate and concentrated to give the title compound having the following physical data.

TLC: Rf 0.59 (toluene:ethyl acetate=10:1);

NMR (300 MHz, $CDCl_3$): δ 7.82-7.70 (m, 3H), 7.59 (m, 1H), 7.48-7.06 (m, 8H), 7.02-6.91 (m, 3H), 5.00 (s, 2H), 4.09 (q, J=7.2 Hz, 2H), 3.26-3.16 (m, 2H), 3.01-2.88 (m, 4H), 2.76 (s, 3H), 2.60-2.50 (m, 2H), 1.22 (t, J=7.2 Hz, 3H).

Example 25

3-(2-(N-methyl-N-(2-(naphthalen-2-yl)ethyl)amino)-4-phenoxymethylphenyl)propanoic acid

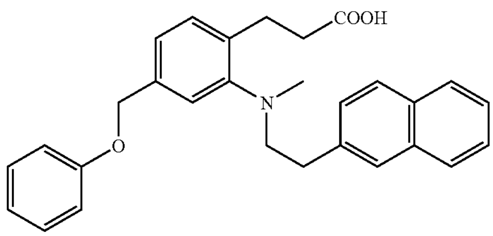

Using the compound prepared in Example 24, the title compound having the following physical data was obtained by the same procedure of Example 3.

TLC: Rf 0.58 (chloroform:methanol=10:1);

NMR (300 MHz, $CDCl_3$): δ 7.82-7.71 (m, 3H), 7.60 (s, 1H), 7.48-7.36 (m, 2H), 7.35-7.12 (m, 6H), 7.02-6.92 (m, 3H), 5.02 (s, 2H), 3.28-3.18 (m, 2H), 3.03-2.88 (m, 4H), 2.80 (s, 3H), 2.62 (t, J=7.2 Hz, 2H).

Reference Example 34

4-phenoxymethyl-2-[N-[2-(naphthalen-2-yl)ethyl]-N-acetylamino]phenyl iodide

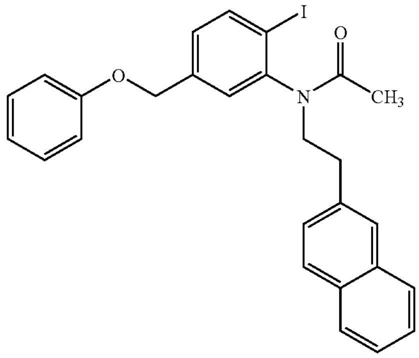

To a solution of the compound prepared in Reference Example 32 (125 mg) in methylene chloride (1.3 ml) were added dimethylaminopyridine (65 mg) and acetylchloride (0.03 ml), and the mixture was stirred for 1 hour. To the reaction mixture was added 1N hydrochloric acid (0.5 ml) and the mixture was extracted with ethyl acetate. The organic layer was washed with a saturated aqueous solution of sodium chloride, dried over anhydrous magnesium sulfate and concentrated to give the title compound having the following physical data.

TLC: Rf 0.30 (n-hexane:ethyl acetate=2:1);

NMR (300 MHz, $CDCl_3$): δ7.89 (d, J=8.4 Hz, 1H), 7.79-7.70 (m, 3H), 7.62 (s, 1H), 7.48-7.36 (m, 2H), 7.34-7.22 (m, 3H), 7.09 (m, 1H), 6.98 (m, 1H), 6.87-6.79 (m, 2H), 6.64 (m, 1H), 4.65 (s, 2H), 4.53 (m, 1H), 3.28 (m, 1H), 3.20-3.01 (m, 2H), 1.76 (s, 3H).

Example 26

3-(2-(N-acetyl-N-(2-(naphthalen-2-yl)ethyl)amino)-4-phenoxymethylphenyl)propanoic acid

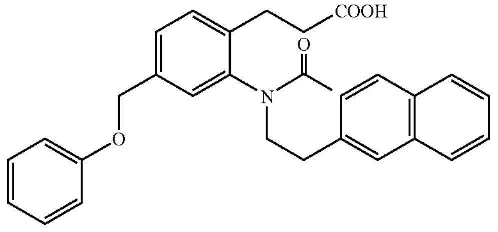

Using the compound prepared in Reference Example 34, the title compound having the following physical data was obtained by the same procedures as a series of reactions of Reference Example 1→Example 24→Example 3.

TLC: Rf 0.49 (chloroform:methanol=10:1);

NMR (300 MHz, $CDCl_3$): δ 7.80-7.68 (m, 3H), 7.61 (s, 1H), 7.48-7.22 (m, 7H), 6.97 (t, J=7.4 Hz, 1H), 6.93-6.83 (m, 2H), 6.70 (s, 1H), 4.77 (s, 2H), 4.55 (m, 1H), 3.25 (m, 1H), 3.10 (t, J=7.7 Hz, 2H), 2.93-2.81 (m, 2H), 2.72-2.61 (m, 2H), 1.76 (s, 3H).

Reference Example 35

2-(naphthalen-2-yl)ethanethiol

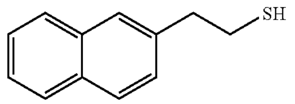

To a solution of 2-vinylnaphthalene (3.0 g) in benzene (20 ml) were added triphenylsilylthiol (6.5 g) and 2,2'-azobis(2-methylpropionitorile (950 mg) at room temperature. The mixture was refluxed for 30 minutes. The reaction mixture was cooled to room temperature, added trifluoroacetic acid (7.5 ml) and stirred for additional 30 minutes. The reaction mixture was concentrated. The residue was purified by column chromatography on silica gel to give the title compound (2.5 g) having the following physical data.

TLC: Rf 0.63 (n-hexane:ethyl acetate=10:1);

NMR (300 MHz, $CDCl_3$): δ 7.86-7.75 (m, 2H), 7.68-7.60 (m, 1H), 7.53-7.10 (m, 4H), 3.09 (t, J=7.4 Hz, 2H), 2.88 (dt, J=7.8, 7.4 Hz, 2H), 1.41 (t, J=7.8 Hz, 1H).

Reference Example 36

4-bromo-2-[2-(naphthalen-2-yl)ethylthio]benzaldehyde

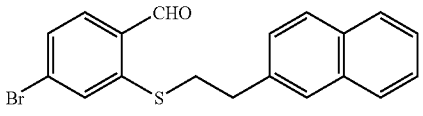

To a solution of the compound prepared in Reference Example 35 (2.8 g) in N,N-dimethylformamide (20 ml) was added sodium hydride (450 mg, 62.7% in oil). The reaction mixture was stirred for 1 hour. To a solution of 4-bromo-2-fluorobenzaldehyde (2.0 g) in N,N-dimethylformamide (10 ml) was added above-mentioned reaction mixture at 0° C. The mixture was stirred for 30 minutes. To the mixture was added ice and an aqueous solution of ammonium chloride and the mixture was extracted with diethyl ether. The organic layer was washed with water and a saturated aqueous solution of sodium chloride subsequently, dried and concentrated. The residue was purified by column chromatography on silica gel (n-hexane:ethyl acetate=20:1) to give the title compound (2.6 g) having the following physical data.

TLC: Rf 0.44 (n-hexane:ethyl acetate=10:1);

NMR (300 MHz, $CDCl_3$): δ 10.28 (s, 1H), 7.89-7.76 (m, 3H), 7.70-7.63 (m, 2H), 7.57-7.32 (m, 5H), 3.36-3.26 (m, 2H), 3.22-3.12 (m, 2H).

Reference Example 37

4-bromo-2-[2-(naphthalen-2-yl)ethylthio]benzylalcohol

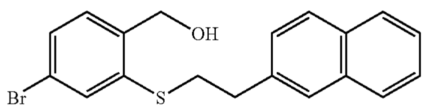

To a solution of the compound prepared in Reference Example 36 (2.5 g) in tetrahydrofuran (15 ml)-ethanol (20 ml) was added sodium borohydride (226 mg). The mixture was stirred at 0° C. for 10 minutes. To the reaction solution were added acetone and ethyl acetate. The mixture was concentrated. The residue was extracted with ethyl acetate. The organic layer was washed, dried over anhydrous magnesium sulfate and then concentrated to give the title crude compound having the following physical data. The compound was used to the next step without further purification.

TLC: Rf 0.13 (n-hexane:ethyl acetate=10:1);

NMR (300 MHz, $CDCl_3$): δ 7.86-7.76 (m, 3H), 7.66-7.61 (m, 1H), 7.52-7.40 (m, 3H), 7.36-7.24 (m, 3H), 4.68 (s, 2H), 3.33-3.24 (m, 2H), 3.16-3.07 (m, 2H).

Reference Example 38

[4-bromo-2-[2-(naphthalen-2-yl)ethylthio]benzyl]-(t-butyldimethylsilyl)ether

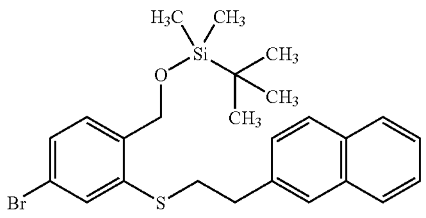

Using the compounds prepared in Reference Example 37, the title compound (2.7 g) having the following physical data was obtained by the same procedure of Reference Example 13.

TLC: Rf 0.89 (n-hexane:ethyl acetate=5:1);

NMR (300 MHz, $CDCl_3$): δ 7.86-7.76 (m, 3H), 7.64 (brs, 1H), 7.52-7.30 (m, 6H), 4.69 (s, 2H), 3.29-3.20 (m, 2H), 3.14-3.05 (m, 2H), 0.94 (s, 9H), 0.10 (s, 6H).

Reference Example 39 ethyl 4-(t-butyldimethylsilyloxymethyl)-3-[2-(naphthalen-2-yl)ethylthio]benzoate

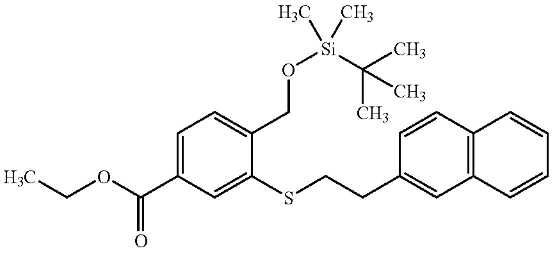

To a solution of the compound prepared in Reference Example 38 (1.5 g), ethanol (12 ml), triethylamine (9 ml) in N,N-dimethylformamide (9 ml) was added palladium bis (triphenylphosphine)dichloride (110 mg). The mixture was stirred at 80° C. for 3 days under an atmosphere of carbon monoxide. To the reaction mixture was added diethyl ether and the mixture was filtered. The filtrate was extracted with diethyl ether. The organic layer was washed, dried and purified by column chromatography on silica gel (n-hexane:ethyl acetate=30:1) to give the title compound (1.6 g) having the following physical data.

TLC: Rf 0.34 (n-hexane:ethyl acetate=20:1);

NMR (300 MHz, $CDCl_3$): δ 8.04 (d, J=1.8 Hz, 1H), 7.90 (dd, J=7.8, 1.8 Hz, 1H), 7.85-7.74 (m, 3H), 7.68-7.60 (m, 2H), 7.51-7.40 (m, 2H), 7.34 (dd, J=8.4, 1.8 Hz, 1H), 4.79 (s, 2H), 4.39 (q, J=7.1 Hz, 2H), 3.35-3.26 (m, 2H), 3.16-3.06 (m, 2H), 1.41 (t, J=7.1 Hz, 3H), 0.95 (s, 9H), 0.11 (s, 6H).

Reference Example 40

4-(pyrazol-1-ylmethyl)-2-[2-(naphthalen-2-yl)ethylthio]benzaldehyde

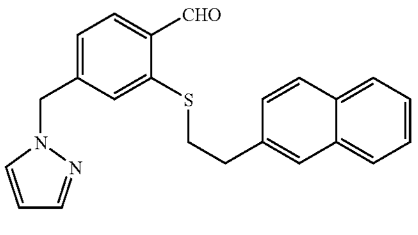

Using the compound prepared in Reference Example 39, the title compound having the following physical data was obtained by the same procedures as a series of reactions of Reference Example 4→Example 2→Example 7→Reference Example 1.

TLC: Rf 0.33 (n-hexane:ethyl acetate=2:1);

NMR (300 MHz, $CDCl_3$): δ 10.33 (s, 1H), 8.65-8.58 (m, 1H), 7.86-7.25 (m, 11H), 6.32 (t, J=2.1 Hz, 1H), 5.33 (s, 2H), 3.27-3.05 (m, 4H).

Example 27

3-(2-(2-(naphthalen-2-yl)ethylthio)-4-(pyrazol-1-ylmethyl)phenyl)propanoic acid ethyl ester

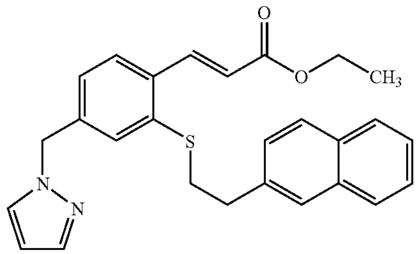

To a solution of diethyl ethoxycarbonylmethylphosphonate (0.56 ml, 2.82 mmol) in tetrahydrofuran (6 ml) was added sodium hydride (98 mg, 63.1% in oil) at 0° C. and the mixture was stirred for 10 minutes. To the solution was added a solution of the compound prepared in Reference Example 40 (2.35 mmol) in tetrahydrofuran (6 ml) and the mixture was stirred for 15 minutes. To the reaction mixture was added a saturated aqueous solution of ammonium chloride. The mixture was extracted with ethyl acetate. The organic layer was washed, dried over anhydrous magnesium sulfate and concentrated to give the title compound having the following physical data. The compound was used to the next step without further purification.

TLC: Rf 0.45 (n-hexane:ethyl acetate=2:1);

NMR (300 MHz, $CDCl_3$): δ 8.20 (d, J=15.9 Hz, 1H), 7.84-7.73 (m, 3H), 7.62-7.36 (m, 6H), 7.30-7.24 (m, 1H), 7.22-7.17 (m, 1H), 7.05-6.69 (m, 1H), 6.35 (d, J=15.9 Hz, 1H), 6.30 (t, J=2.3 Hz, 1H), 5.27 (s, 2H), 4.26 (q, J=6.9 Hz, 2H), 3.21-3.13 (m, 2H), 3.07-3.00 (m, 2H), 1.35 (t, J=6.9 Hz, 3H).

Example 28

3-(2-(2-(naphthalen-2-yl)ethylthio)-4-(pyrazol-1-ylmethyl)phenyl)propanoic acid

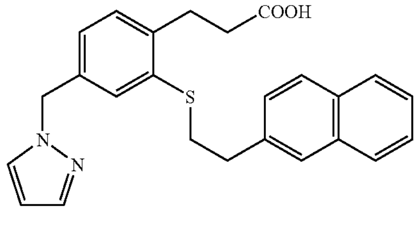

Using the compound prepared in Example 27, the title compound having the following physical data was obtained by the same procedures as a series of reactions of Reference Example 24→Example 3.

TLC: Rf 0.53 (chloroform:methanol=10:1);

NMR (300 MHz, $CDCl_3$): δ 7.84-7.74 (m, 3H), 7.61 (brs, 1H), 7.58-7.54 (m, 1H), 7.50-7.39 (m, 2H), 7.38-7.35 (m, 1H), 7.32-7.26 (m, 1H), 7.21-7.11 (m, 2H), 6.98-6.92 (m, 1H), 6.27 (t, J=1.9 Hz, 1H), 5.26 (s, 2H), 3.23-3.14 (m, 2H), 3.09-2.99 (m, 4H), 2.70-2.60 (m, 2H).

Example 29

3-(2-(2-(naphthalen-2-yl)ethylthio)-4-(pyrazol-1-ylmethyl)phenyl)propanoic acid ethyl ester

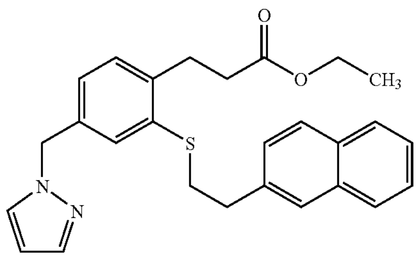

Using the compound prepared in Example 27, the title compound having the following physical data was obtained by the same procedure of Example 24.

TLC: Rf 0.47 (hexane:ethyl acetate=2:1).

Example 30

3-[4-(pyrazol-1-ylmethyl)-2-[2-(naphthalen-2-yl)ethylsulfonyl]phenyl]propanoic acid ethyl ester

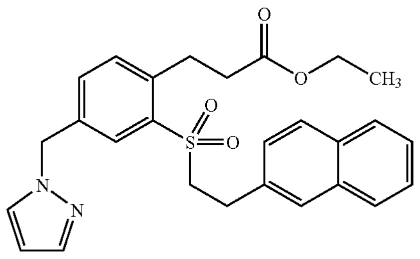

To a solution of the compound prepared in Example 29 (100 mg) in methylene chloride (2.5 ml) were added disodium hydrogenphosphate (97 mg) and 3-chloroperbenzoic acid (105 mg) at −30° C. The mixture was stirred for 1 hour. To the mixture was added 3-chloroperbenzoic acid (30 ml) and the mixture was stirred at room temperature for additional 1 hour. To the reaction solution was added a saturated aqueous solution of sodium bicarbonate and the mixture was extracted with methylene chloride. The organic layer was washed, dried and purified by column chromatography on silica gel (n-hexane:ethyl acetate=3:2) to give the title compound (90 mg) having the following physical data.

TLC: Rf 0.41 (n-hexane:ethyl acetate=1:1);

NMR (300 MHz, $CDCl_3$): δ 7.86-7.69 (m, 5H), 7.60-7.53 (m, 2H), 7.50-7.38 (m, 3H), 7.36-7.19 (m, 2H), 6.31 (t, J=2.1 Hz, 1H), 5.21 (s, 2H), 4.12 (q, J=7.2 Hz, 2H), 3.59-3.50 (m, 2H), 3.36-3.16 (m, 4H), 2.78-2.69 (m, 2H), 1.22 (t, J=7.2 Hz, 3H).

Example 31

3-(2-(2-(naphthalen-2-yl)ethylsulfonyl)-4-(pyrazol-1-ylmethyl)phenyl)propanoic acid

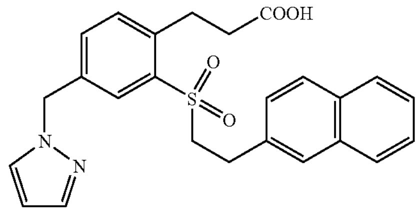

Using the compound prepared in Example 30, the title compound having the following physical data was obtained by the same procedure of Example 3.

TLC: Rf 0.39 (chloroform:methanol=10:1);

NMR (300 MHz, $CDCl_3$): δ 7.84-7.68 (m, 4H), 7.58-7.54 (m, 2H), 7.48-7.39 (m, 3H), 7.35-7.25 (m, 2H), 7.20 (dd, J=8.7, 1.8 Hz, 1H), 6.31 (t, J=2.1 Hz, 1H), 5.26 (s, 2H), 3.58-3.49 (m, 2H), 3.35-3.16 (m, 4H), 2.82-2.72 (m, 2H).

Reference Example 41

7-methoxymethoxycoumarin

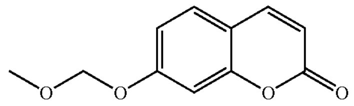

To a solution of 7-hydroxycoumarin (100 g) and isopropylethylamine (161 ml) in anhydrous dimethylformamide (DMF; 500 ml) was added dropwise methoxymethylchloride (70.3 ml) at 0° C. under an atmosphere of argon. The mixture was stirred at room temperature for 4 hours. To the reaction mixture were added hexane/ethyl acetate (2/1, 1000 ml) and a saturated aqueous solution of sodium bicarbonate (1000 ml) and the mixture was extracted twice with ethyl acetate. The organic layer was washed with water (twice) and a saturated aqueous solution of sodium chloride, dried over anhydrous magnesium sulfate and concentrated to give the title compound (74.1 g) having the following physical data. The obtained crude product was used to the next step without further purification.

TLC: Rf 0.50 (hexane:ethyl acetate=3:2);

NMR (300 MHz, $CDCl_3$): δ 7.64 (d, J=9.6 Hz, 1H), 7.39 (d, J=8.7 Hz, 1H), 7.01 (d, J=2.4 Hz, 1H), 6.96 (dd, J=8.7, 2.4 Hz, 1H), 6.28 (d, J=9.6 Hz, 1H), 5.24 (s, 2H), 3.49 (s, 3H).

Reference Example 42

3-(4-methoxymethoxy-2-hydroxyphenyl)propenoic acid methyl ester

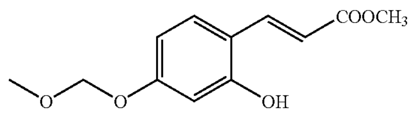

To a suspension of sodium hydride (46.9 g; 63.1%, in oil) in anhydrous tetrahydrofuran (THF; 300 ml) was added anhydrous methanol (60 ml) under ice-cooling under an atmosphere of argon. The mixture was stirred at room temperature for 20 minutes. To the reaction solution was added dropwise a solution of the compound prepared in Reference Example 41 in anhydrous THF (1000 ml)/anhydrous methanol (100 ml) and the mixture was stirred at 60° C. for 40 minutes. To the reaction mixture were added a saturated aqueous solution of ammonium chloride and water and then the organic layer was separated. The aqueous layer was neutralized with 2N hydrochloric acid and then extracted with ethyl acetate. The combined organic layer was washed with water and a saturated aqueous solution of sodium chloride, dried over anhydrous magnesium sulfate and concentrated. To the residue were added ethyl acetate and hexane. The obtained solid was filtered to give the title compound (100.2 g) having the following physical data.

TLC: Rf 0.38 (hexane:ethyl acetate=2:1);

NMR (300 MHz, $CDCl_3$): δ 7.92 (d, J=16 Hz, 1H), 7.39 (d, J=8.5 Hz, 1H), 6.62 (dd, J=8.5, 2.2 Hz, 1H), 6.54 (d, J=2.2 Hz, 1H), 6.51 (d, J=16 Hz, 1H), 6.01 (s, 1H), 5.17 (s, 2H), 3.81 (s, 3H), 3.47 (s, 3H).

Reference Example 43

3-(4-methoxymethoxy-2-hydroxyphenyl)propanoic acid methyl ester

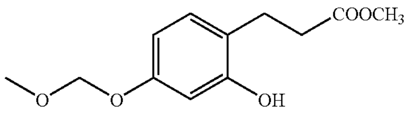

A solution of the compound prepared in Reference Example 42 (45.0 g) and 10% palladium carbon (4.2 g, wet) in methanol (500 ml) was stirred at room temperature for 7 hours under an atmosphere of hydrogen. The reaction was carried out twice and the two reaction mixture were combined and then filtered. The filtrate was concentrated to give the title compound (92.1 g) having the following physical data.

TLC: Rf 0.47 (hexane:ethyl acetate=3:2);

NMR (300 MHz, $CDCl_3$): δ 7.24 (s, 1H), 6.97 (d, J=8.2 Hz, 1H), 6.61 (d, J=2.5 Hz, 1H), 6.57 (dd, J=8.2, 2.5 Hz, 1H), 5.13 (s, 2H), 3.69 (s, 3H), 3.46 (s, 3H), 2.84 (t, J=6.1 Hz, 2H), 2.69 (t, J=6.1 Hz, 2H).

Reference Example 44

3-(4-methoxymethoxy-2-trifluoromethanesulfoxyphenyl)propanoic acid methyl ester

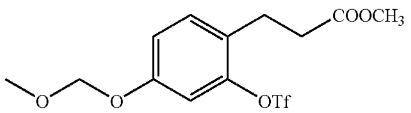

To a solution of the compound prepared in Reference Example 43 (82.8 g) and pyridine (33.5 ml) in methylene chloride (300 ml) was added dropwise trifluoromethanesulfonic acid (63.8 ml) under ice-cooling under an atmosphere of argon and the mixture was stirred for 10 minutes. To the reaction mixture were added ethyl acetate and water, and the organic layer was separated. The organic layer was washed with water and a saturated aqueous solution of sodium chloride, dried over anhydrous magnesium sulfate and concentrated to give the title compound (121.8 g) having the following physical data. The obtained crude product was used to the next step without further purification.

TLC: Rf 0.65 (hexane:ethyl acetate=2:1);

NMR (300 MHz, $CDCl_3$): δ 7.24 (d, J=8.4 Hz, 1H), 7.04-6.96 (m, 2H), 5.16 (s, 2H), 3.68 (s, 3H), 3.47 (s, 3H), 2.98 (t, J=7.5 Hz, 2H), 2.63 (t, J=7.5 Hz, 2H).

Reference Example 45

3-(4-methoxymethoxy-2-carboxyphenyl)propanoic acid methyl ester

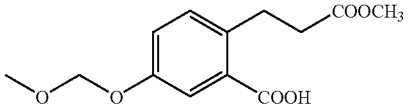

A solution of the compound prepared in Reference Example 44, 1,1'-bis(diphenylphosphino)ferrocene (7.65 g), potassium acetate (169.0 g) and palladium(II) acetate (21.55 g) in anhydrous DMF (400 ml) was stirred at 90° C. for 2 days under an atmosphere of carbon monoxide. The reaction mixture was filtered through celite (trade mark) and the residue was washed with a mixture of t-butylmethyl ether/ethyl acetate (1/1). To the filtrate was added water and the mixture was extracted with ethyl acetate (4 times). The organic layer was washed with water and a saturated aqueous solution of sodium chloride, dried over anhydrous magnesium sulfate and concentrated. The residue was purified by column chromatography (hexane:ethyl acetate=1:1) and then recrystallized from ethyl acetate/hexane to give the title compound (51.4 g) having the following physical data.

TLC: Rf 0.34 (hexane:ethyl acetate=1:1);

NMR (300 MHz, $CDCl_3$): δ 7.71 (d, J=2.7 Hz, 1H), 7.24 (d, J=8.7 Hz, 1H), 7.17 (dd, J=8.7, 2.7 Hz, 1H), 5.20 (s, 2H), 3.67 (s, 3H), 3.49 (s, 3H), 3.27 (t, J=7.6 Hz, 2H), 2.68 (t, J=7.6 Hz, 2H).

Reference Example 46

1-aza-1-benzyloxy-4-methylpent-1-ene

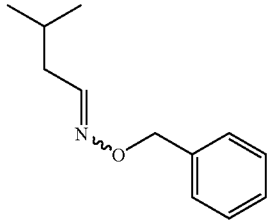

A solution of 3-methylbutanal (60.8 g) and benzyloxyamine hydrochloride (112.7 g) in pyridine (500 ml) was stirred at 80° C. for 2 hours. The reaction solution was concentrated and azeotroped with toluene. The residue was dissolved in ethyl acetate, washed with 1N hydrochloric acid, water and a saturated aqueous solution of sodium chloride, dried over anhydrous sodium sulfate, and concentrated to give the title compound (134 g) having the following physical data.

TLC: Rf 0.85 (n-hexane:ethyl acetate=9:1).

Reference Example 47

N-benzyloxy-N-(3-methyl-1-(3,5-dimethylphenyl)butyl)amine

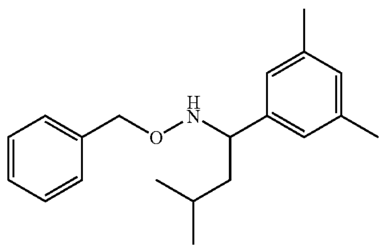

To a solution of 5-bromo-m-xylene (75 g) in THF (575 ml) was added n-butyllithium (235 ml) at −78° C. under an atmosphere of argon. The mixture was stirred for 1 hour. To the mixture were added a solution of the compound prepared in Reference Example 46 (29.8 g) in toluene (338 ml) and boron trifluoride diethyl ether complex (51 ml) subsequently, and the mixture was stirred for 3 hours. To the reaction solution was added water and the mixture was extracted with ethyl acetate. The organic layer was washed with a saturated aqueous solution of sodium chloride, dried over anhydrous sodium sulfate and then concentrated. To the residue was added 4N hydrogen chloride in ethyl acetate (50 ml). The obtained hydrochloride was washed with ethyl acetate/hexane and then dissolved in ethyl acetate. The solution was neutralized with a saturated aqueous solution of sodium bicarbonate, and washed with water and a saturated aqueous solution of sodium chloride to give the title compound (23 g) having the following physical data.

TLC: Rf 0.72 (n-hexane:ethyl acetate=9:1);

NMR (300 MHz, $CDCl_3$): δ 7.20-7.00 (m, 5H), 6.96 (s, 2H), 6.91 (s, 1H), 4.67 (m, 1H), 4.61 (d, J=15.3 Hz, 1H), 4.53 (d, J=15.3 Hz, 1H), 2.32 (s, 6H), 1.80-1.57 (m, 3H), 0.95 (d, J=6.6 Hz, 6H).

Reference Example 48

3-methyl-1-(3,5-dimethylphenyl)butylamine hydrochloride

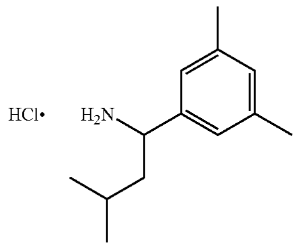

To a solution of the compound prepared in Reference Example 47 (12 g) in methanol (120 ml) was added 10% palladium carbon (1.2 g) and the mixture was stirred overnight under an atmosphere of hydrogen. The reaction mixture was filtered through celite (trade mark) and the filtrate was concentrated. To the residue was added 4N hydrogen chloride in ethyl acetate. The obtained hydrochloride was washed with ethyl acetate/hexane to give the title compound (7.5 g) having the following physical data.

TLC: Rf 0.50 (chloroform:methanol=9:1);

NMR (300 MHz, DMSO-$d_6$): δ 8.32 (br, 3H), 7.11 (s, 2H), 6.98 (s, 1H), 4.07 (m, 1H), 2.23 (s, 6H), 1.74-1.66 (m, 2H), 1.31 (m, 1H), 0.88 (d, J=6.6 Hz, 3H), 0.86 (d, J=6.6 Hz, 3H).

Reference Example 49

(2R)-3-aza-2-phenyl-4-(3,5-dimethylphenyl)but-3-en-1-ol

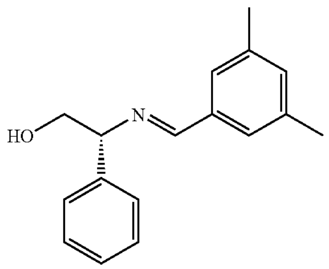

A solution of 3,5-dimethylbenzaldehyde (30.0 g) and (R)-phenylglycinol (30.7 g) in toluene (200 ml) was refluxed for 3 hours with removing water. The reaction solution was concentrated to give the title compound (59.7 g) having the following physical data.

TLC: Rf 0.69 (n-hexane:ethyl acetate=4:1).

Reference Example 50

(2R,4R)-3-aza-2-phenyl-6-methyl-4-(3,5-dimethylphenyl)hept-6-en-1-ol hydrochloride

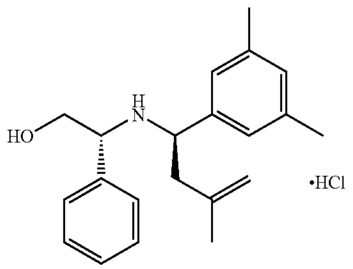

To a solution of magnesium (40.8 g) in anhydrous THF (800 ml) was added dropwise a solution of 3-chloro-2-methyl-1-propene (60.8 g) in anhydrous THF (450 ml) under sodium chloride-ice cooling under an atmosphere of argon. The mixture was stirred for 1.5 hour under ice-cooling. The mixture was stirred for additional 1 hour at room temperature to give Grignard reagent.

To a mixture of the compound prepared in Reference Example 49 in anhydrous toluene (300 ml) was added dropwise Grignard reagent (0.5M; 1120 ml) during 3 hours under an atmosphere of argon and the mixture was stirred for 30 minutes. To the reaction mixture were added a saturated aqueous solution of ammonium chloride and water and the organic layer was separated. The aqueous layer was extracted with ethyl acetate. These organic layer were combined, washed with a saturated aqueous solution of sodium chloride, dried over anhydrous magnesium sulfate and concentrated. To a solution of the residue in ethyl acetate (500 ml) was added 4N hydrochloric acid in dioxane (100 ml) under ice-cooling. The solution was concentrated and recrystallized from iso propanol-hexane to give the title compound (60.9 g) having the following physical data.

TLC: Rf 0.80 (n-hexane:ethyl acetate=1:2);

NMR (300 MHz, $CDCl_3$): δ 9.52 (brs, 2H), 7.39-7.20 (m, 5H), 6.94 (s, 2H), 6.81 (s, 1H), 5.44 (brs, 1H), 4.70 (s, 1H), 4.63 (s, 1H), 4.40-4.20 (m, 2H), 4.14 (m, 1H), 3.83 (m, 1H), 3.11 (dd, J=14, 4.4 Hz, 1H), 2.94 (dd, J=14, 11 Hz, 1H), 2.17 (s, 6H), 1.49 (s, 3H).

Reference Example 51

(1R)-3-methyl-1-(3,5-dimethylphenyl)butylamine hydrochloride

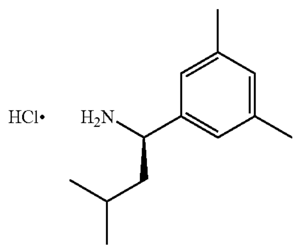

A solution of the compound prepared in Reference Example 50 (33.0 g) and platinum (IV) dioxide (4.60 g) in ethanol (330 ml) was stirred at 60° C. for 40 hours under an atmosphere of hydrogen. The reaction mixture was filtered through celite (trade mark) and the filtrate was concentrated. The residue was recrystallized from ethanol-ethyl acetate to give the title compound (7.30 g) having the following physical data.

TLC: Rf 0.30 (chloroform:methanol=9:1);

NMR (300 MHz, DMSO-$d_6$): δ 8.41 (brs, 3H), 7.11 (s, 2H), 7.01 (s, 1H), 4.10 (m, 1H), 2.27 (s, 6H), 1.82-1.66 (m, 2H), 1.31 (m, 1H), 0.86 (d, J=6.6 Hz, 3H), 0.82 (d, J=6.6 Hz, 3H).

Reference Example 52

4-hydroxy-4-(3,5-dimethylphenyl)tetrahydropyran

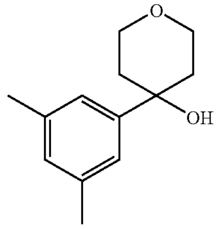

To a solution of 5-bromo-m-xylene (5.55 g) in THF (60 ml) was added n-butyl lithium (17.8 ml) at −78° C. under an atmosphere of argon. The mixture was stirred for 1 hour. To the reaction solution was added tetrahydropyran-4-one (2.0 g) and the mixture was stirred for additional 3 hours. To the reaction solution was added water and the mixture was extracted with ethyl acetate. The organic layer was washed with water and a saturated aqueous solution of sodium chloride, dried over anhydrous sodium sulfate and concentrated. The residue was purified by column chromatography on silica gel (ethyl acetate:n-hexane=1:3) to give the title compound (2.6 g) having the following physical data.

TLC: Rf 0.51 (ethyl acetate:n-hexane=1:1);

NMR (300 MHz, $CDCl_3$): δ 7.10 (s, 2H), 6.93 (s, 1H), 3.99-3.82 (m, 5H), 2.34 (s, 6H), 2.23-2.11 (m, 2H), 1.72-1.63 (m, 2H).

Reference Example 53

N-(4-(3,5-dimethylphenyl)perhydropyran-4-yl)-chloroacetamide

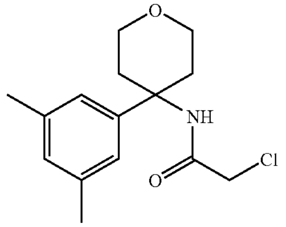

To a solution of the compound prepared in Reference Example 52 (1.51 g) in chloroacetonitorile (5 ml) and acetic acid (10 ml) was added dropwise sulfuric acid (3 drops) slowly under ice-cooling. The mixture was stirred overnight. The reaction solution was poured into ice-water, alkalized with 5N aqueous solution of sodium hydroxide and extracted with t-butylmethyl ether. The organic layer was washed with water and a saturated aqueous solution of sodium chloride, dried over anhydrous sodium sulfate and concentrated. The residue was purified by column chromatography on silica gel (ethyl acetate:n-hexane=1:3) to give the title compound (288 mg) having the following physical data.

TLC: Rf 0.54 (ethyl acetate:n-hexane=1:1);

NMR (300 MHz, $CDCl_3$): δ 6.98 (s, 2H), 6.90 (s, 1H), 6.76 (bs, 1H), 4.02 (s, 2H), 3.89 (dt, J=12.0, 3.3 Hz, 2H), 3.72 (dt, J=12.0, 2.1 Hz, 2H), 2.42-2.34 (m, 2H), 2.32 (s, 6H), 2.29-2.13 (m, 2H).

Reference Example 54

N-(4-(3,5-dimethylphenyl)perhydropyran-4-yl)amine

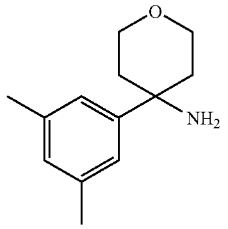

To a solution of the compound prepared in Reference Example 53 (250 mg) in ethanol (2 ml)-acetic acid (0.4 ml) was added thiourea (81.2 mg) and the mixture was stirred at 70° C. overnight. The reaction solution was diluted with t-butylmethyl ether, alkalized with 2N aqueous solution of sodium hydroxide, and then the organic layer was separated. The organic layer was washed with water and a saturated aqueous solution of sodium chloride, dried over anhydrous sodium sulfate and concentrated to give the title compound (160 mg) having the following physical data.

TLC: Rf 0.54 (methanol:chloroform=1:5);

NMR (300 MHz, $CDCl_3$): δ 7.07 (s, 2H), 6.90 (s, 1H), 3.92 (dt, J=11.4, 2.4 Hz, 2H), 3.79 (dt, J=11.4, 4.2 Hz, 2H), 2.34 (s, 6H), 2.24-2.13 (m, 2H), 1.68-1.60 (m, 2H).

Example 32

3-(2-((3-methyl-1-(3,5-dimethylphenyl)butyl)carbamoyl)-4-methoxymethoxyphenyl)propanoic acid methyl ester

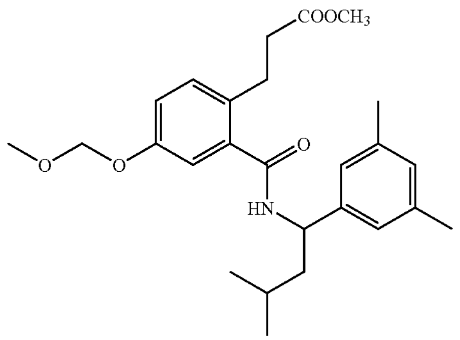

A solution of the compound prepared in Reference Example 45 (1.00 g), the compound prepared in Reference Example 48 (930 mg), 1-ethyl-3-[3-(dimethylamino)propyl] carbodiimide (1.36 g), 1-hydroxybenzotriazole (958 mg) and N-methylmorpholine (1.6 ml) in DMF (14 ml) was stirred at room temperature for 3 hours. To the reaction mixture were added water and ethyl acetate, and the organic layer was separated. The organic layer was washed with water and a saturated aqueous solution of sodium chloride, dried over anhydrous sodium sulfate and concentrated. The obtained crude crystal was recrystallized from ethyl acetate/hexane to give the title compound (1.29 g) having the following physical data.

TLC: Rf 0.84 (hexane:ethyl acetate=1:1);

NMR (300 MHz, $CDCl_3$): δ 7.16-7.12 (m, 1H), 7.04-6.98 (m, 2H), 6.96 (s, 2H), 6.89 (s, 1H), 6.40 (d, J=9.0 Hz, 1H), 5.20-5.10 (m, 3H), 3.62 (s, 3H), 3.46 (s, 3H), 3.00-2.90 (m, 2H), 2.65-2.55 (m, 2H), 2.31 (s, 6H), 1.80-1.60 (m, 3H), 0.98 (d, J=6.3 Hz, 3H), 0.97 (d, J=6.3 Hz, 3H).

Example 33

3-(2-((3-methyl-1-(3,5-dimethylphenyl)butyl)carbamoyl)-4-(4-methylbenzyloxy)phenyl)propanoic acid methyl ester

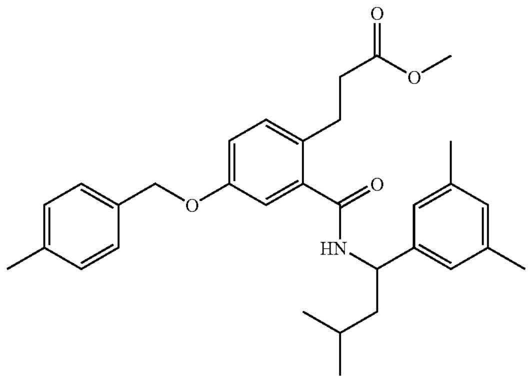

Using the compound prepared in Example 32, the title compounds having the following physical data were obtained by the same procedures as a series of reactions of Example 11→Example 5.

TLC: Rf 0.61 (n-hexane:acetone=2:1).

Example 33(1)~33(21)

Using corresponding compounds, the following compounds were obtained by the same procedure of Example 33.

Example 33(1)

3-(2-((3-methyl-1-(3,5-dimethylphenyl)butyl)carbamoyl)-4-benzyloxyphenyl)propanoic acid ethyl ester

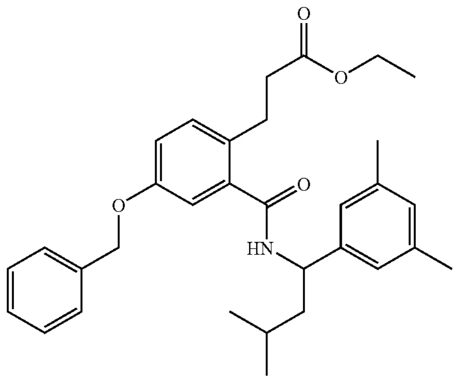

TLC: Rf 0.26 (n-hexane:ethyl acetate=4:1).

Example 33(2)

3-(2-((3-methyl-1-(3,5-dimethylphenyl)butyl)carbamoyl)-4-(3-cyanobenzyloxy)phenyl)propanoic acid ethyl ester

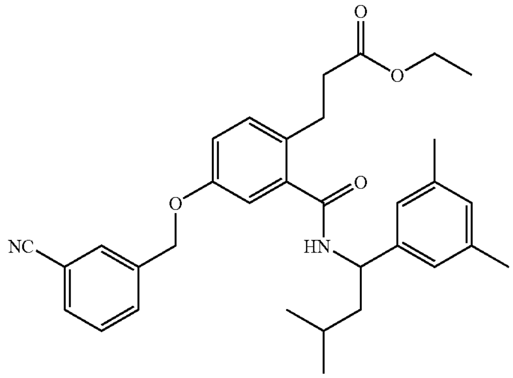

TLC: Rf 0.41 (n-hexane:ethyl acetate=3:1).

Example 33(3)

4-(2-((1R)-1-(naphthalen-1-yl)ethylcarbamoyl)-4-phenoxyphenyl)butanoic acid methyl ester

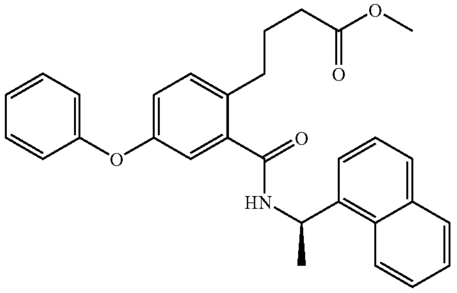

TLC: Rf 0.69 (n-hexane:ethyl acetate=1:1).

Example 33(4)

3-(2-((3-methyl-1-(3,5-dimethylphenyl)butyl)carbamoyl)-4-(2-methoxybenzyloxy)phenyl)propanoic acid methyl ester

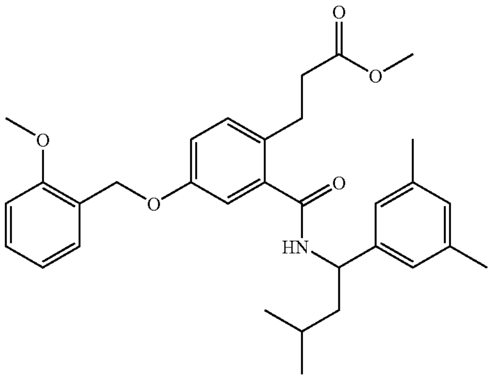

TLC: Rf 0.53 (n-hexane:ethyl acetate=2:1).

Example 33(5)

3-(2-((3-methyl-1-(3,5-dimethylphenyl)butyl)carbamoyl)-4-(2-chlorobenzyloxy)phenyl)propanoic acid methyl ester

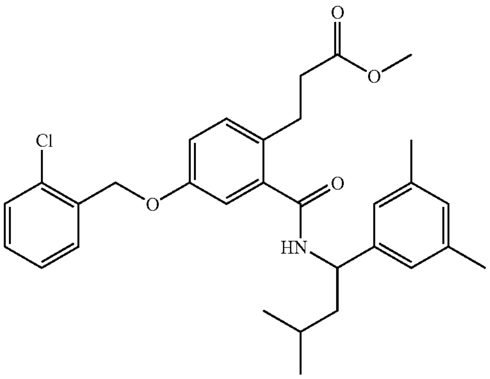

TLC: Rf 0.53 (n-hexane:ethyl acetate=2:1).

Example 33(6)

4-(2-((1R)-1-(naphthalen-1-yl)ethylcarbamoyl)-4-(2-cyanophenoxy)phenyl)butanoic acid methyl ester

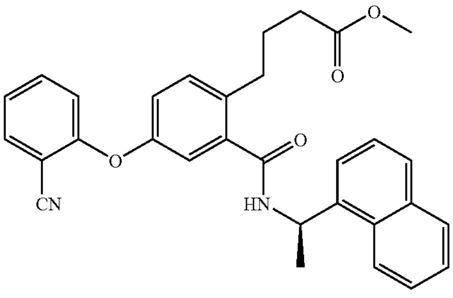

TLC: Rf 0.47 (n-hexane:ethyl acetate=1:1).

Example 33(7)

4-(2-((1R)-1-(naphthalen-1-yl)ethylcarbamoyl)-4-(2-aminophenoxy)phenyl)butanoic acid methyl ester

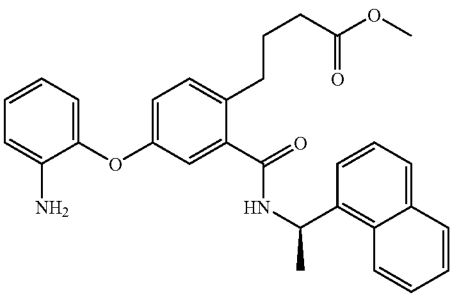

TLC: Rf 0.43 (n-hexane:ethyl acetate=1:1).

Example 33(8)

4-(2-((1R)-1-(naphthalen-1-yl)ethylcarbamoyl)-4-(3-fluorophenoxy)phenyl)butanoic acid methyl ester

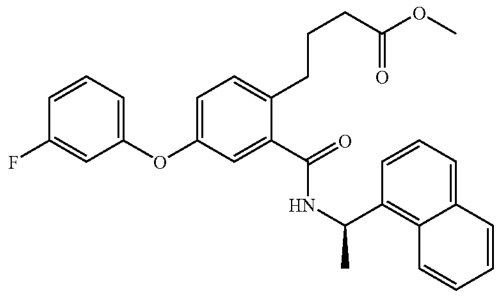

TLC: Rf 0.85 (n-hexane:ethyl acetate=1:1).

Example 33(9)

4-(2-((1R)-1-(naphthalen-1-yl)ethylcarbamoyl)-4-(3-methoxyphenoxy)phenyl)butanoic acid methyl ester

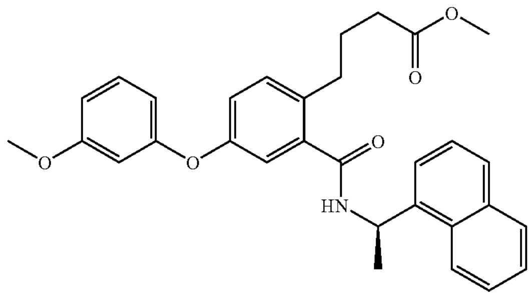

TLC: Rf 0.64 (n-hexane:ethyl acetate=1:1).

Example 33(10)

4-(2-((1R)-1-(naphthalen-1-yl)ethylcarbamoyl)-4-(2-fluorophenoxy)phenyl)butanoic acid methyl ester

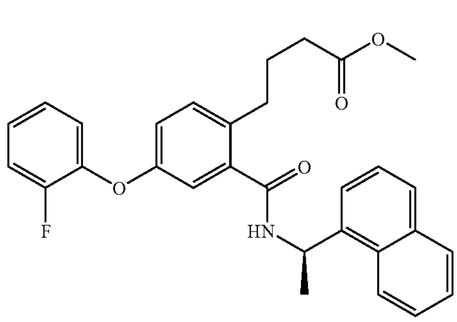

TLC: Rf 0.67 (n-hexane:ethyl acetate=2:1).

Example 33(11)

4-(2-((1R)-1-(naphthalen-1-yl)ethylcarbamoyl)-4-(pyridin-2-yl)oxyphenyl)butanoic acid methyl ester

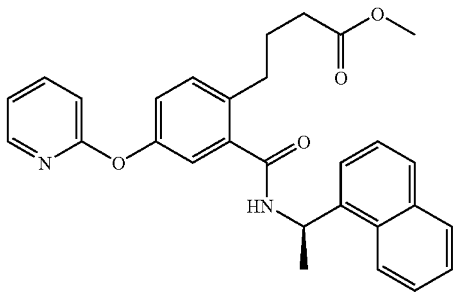

TLC: Rf 0.34 (n-hexane:ethyl acetate=1:1).

Example 33(12)

3-(2-((1R)-3-methyl-1-(3,5-dimethylphenyl)butyl)carbamoyl)-4-phenoxyphenyl)propanoic acid methyl ester

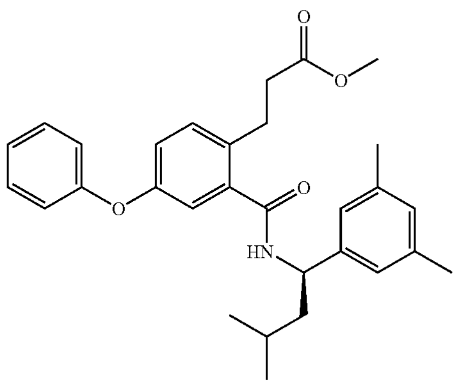

TLC: Rf 0.86 (n-hexane:ethyl acetate=1:1).

Example 33(13)

3-(2-((4-(3,5-dimethylphenyl)perhydropyran-4-yl)carbamoyl)-4-phenoxyphenyl)propanoic acid methyl ester

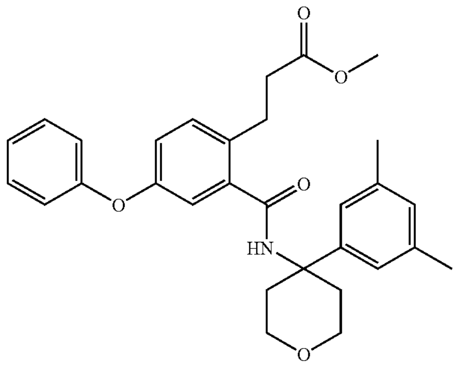

TLC: Rf 0.36 (n-hexane:ethyl acetate=2:1).

Example 33(14)

3-(2-((4-(3,5-dimethylphenyl)perhydropyran-4-yl)carbamoyl)-4-(2-chloro-6-fluorobenzyloxy)phenyl)propanoic acid methyl ester

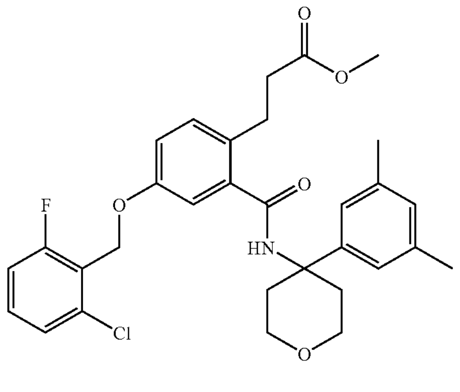

TLC: Rf 0.68 (n-hexane:ethyl acetate=1:1).

Example 33(15)

3-(2-((4-(3,5-dimethylphenyl)perhydropyran-4-yl)carbamoyl)-4-(2,3,6-trifluorobenzyloxy)phenyl)propanoic acid methyl ester

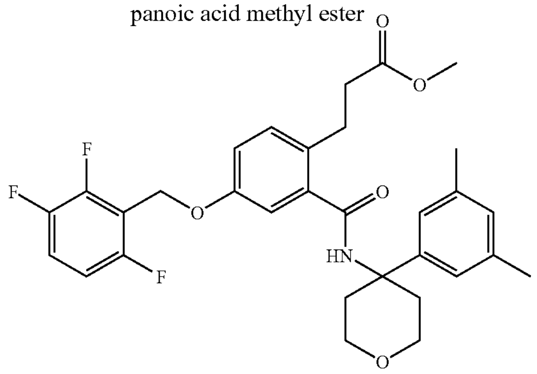

TLC: Rf 0.61 (n-hexane:ethyl acetate=1:1).

Example 33(16)

3-(2-(((1R)-3-methyl-1-(3,5-dimethylphenyl)butyl)carbamoyl)-4-benzyloxyphenyl)propanoic acid methyl ester

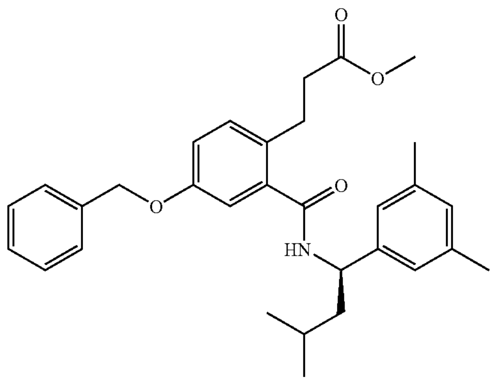

TLC: Rf 0.38 (n-hexane:ethyl acetate=2:1).

Example 33(17)

3-(2-(((1R)-3-methyl-1-(3,5-dimethylphenyl)butyl)carbamoyl)-4-(2-chloro-6-fluorobenzyloxy)phenyl)propanoic acid methyl ester

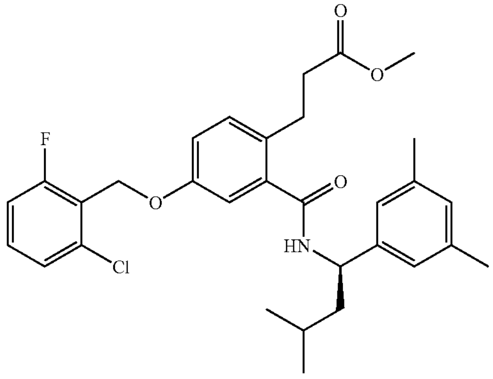

TLC: Rf 0.41 (n-hexane:ethyl acetate=2:1).

Example 33(18)

3-(2-((4-(naphthalen-1-yl)perhydropyran-4-yl)carbamoyl)-4-phenoxyphenyl)propanoic acid methyl ester

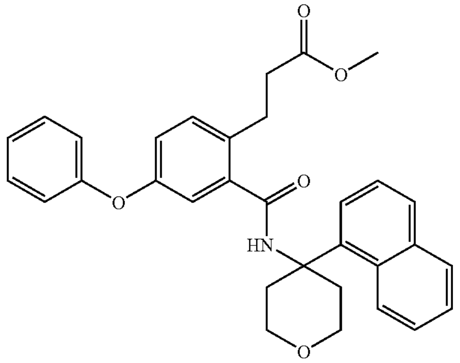

TLC: Rf 0.51 (n-hexane:ethyl acetate=1:1).

Example 33(19)

4-(2-((4-(naphthalen-1-yl)perhydropyran-4-yl)carbamoyl)-4-phenoxyphenyl)butanoic acid methyl ester

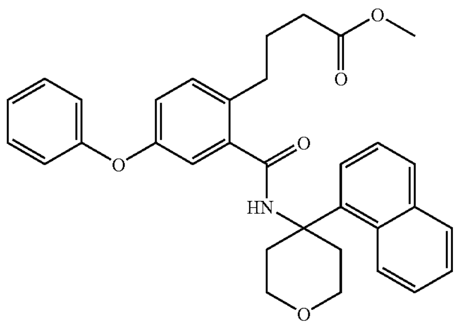

TLC: Rf 0.63 (n-hexane:ethyl acetate=1:1).

Example 33(20)

4-(2-((4-(3,5-dimethylphenyl)perhydropyran-4-yl)carbamoyl)-4-phenoxyphenyl)butanoic acid methyl ester

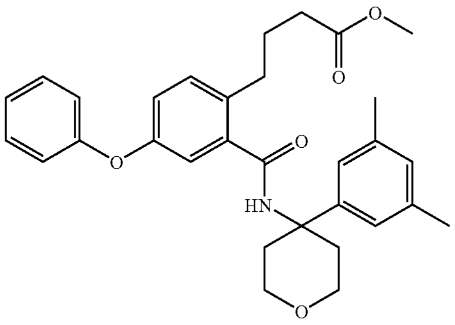

TLC: Rf 0.71 (n-hexane:ethyl acetate=1:1).

Example 33(21)

3-(2-(((1R)-3-methyl-1-(3,5-dimethylphenyl)butyl)carbamoyl)-4-(2,3,6-trifluorobenzyloxy)phenyl)propanoic acid methyl ester

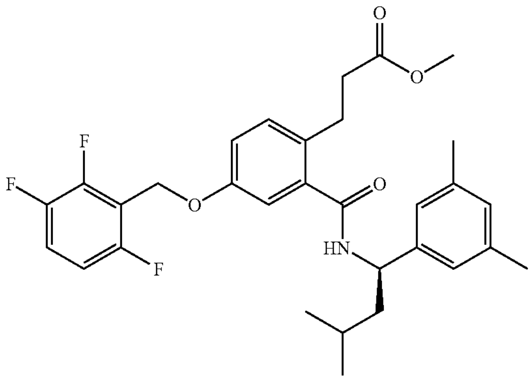

TLC: Rf 0.53 (n-hexane:ethyl acetate=2:1).

Example 34

3-(2-((3-methyl-1-(3,5-dimethylphenyl)butyl)carbamoyl)-4-(4-methylbenzyloxy)phenyl)propanoic acid

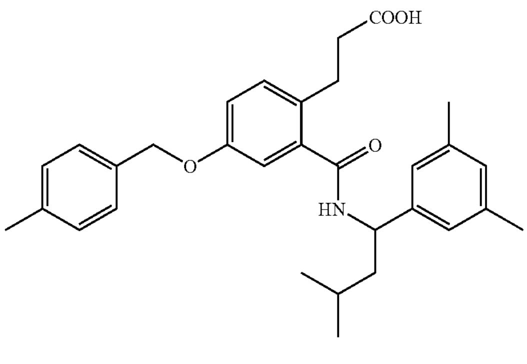

Using the compounds prepared in Example 33, the title compound having the following physical data was obtained by the same procedure of Example 3.

TLC: Rf 0.69 (methylene chloride:methanol=9:1);

NMR (300 MHz, $CDCl_3$): δ 7.29 (d, J=7.8 Hz, 2H), 7.22-7.18 (m, 3H), 6.98-6.88 (m, 5H), 6.21 (d, J=8.4 Hz, 1H), 5.13 (q, J=8.4 Hz, 1H), 4.99 (s, 2H), 3.00-2.90 (m, 2H), 2.69 (t, J=7.5 Hz, 2H), 2.36 (s, 3H), 2.30 (s, 6H), 1.80-1.50 (m, 3H), 0.97 (d, J=6.3 Hz, 3H), 0.97 (d, J=6.3 Hz, 3H).

Example 34(1)~34(191)

Using the compounds prepared in Example 33(1)~33(21), the compounds were obtained by the same procedure of Example 34, or using corresponding compounds and Reference Example 48, Reference Example 51, Reference Example 54 or the compounds corresponding to them, the compounds were obtained by the same procedures as a series of reactions of Reference Example 32→Example 33→Example 34.

Example 34(1)

3-(2-((3-methyl-1-phenylbutyl)carbamoyl)-4-(3-cyanobenzyloxy)phenyl)propanoic acid

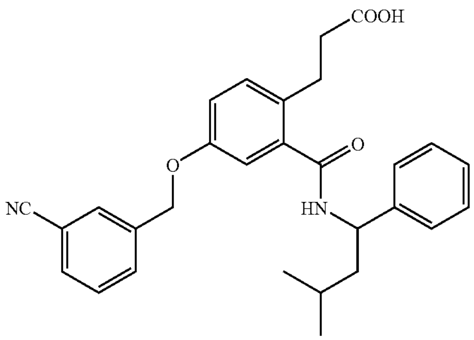

TLC: Rf 0.51 (chloroform:methanol=9:1);

NMR (300 MHz, $CDCl_3$): δ 7.72 (s, 1H), 7.66-7.60 (m, 2H), 7.49 (t, J=7.8 Hz, 1H), 7.39-7.23 (m, 5H), 7.17 (d, J=8.1 Hz, 1H), 6.97-6.89 (m, 2H), 6.47 (d, J=8.4 Hz, 1H), 5.22 (m, 1H), 5.05 (s, 2H), 2.94 (t, J=6.8 Hz, 2H), 2.69 (t, J=6.8 Hz, 2H), 1.88-1.50 (m, 3H), 0.98 (d, J=6.6 Hz, 6H).

Example 34(2)

3-(2-((3-methyl-1-(3,5-dimethylphenyl)butyl)carbamoyl)-4-benzyloxyphenyl)propanoic acid

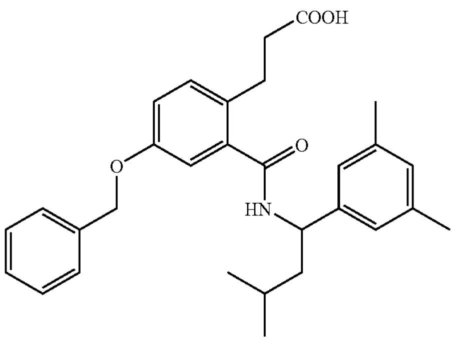

TLC: Rf 0.35 (chloroform:methanol=10:1);

NMR (300 MHz, $CDCl_3$): δ 7.43-7.33 (m, 5H), 7.17 (m, 1H), 6.98-6.90 (m, 5H), 6.24 (d, J=8.4 Hz, 1H), 5.14 (m, 1H), 5.04 (s, 2H), 2.99-2.92 (m, 2H), 2.70 (t, J=7.5 Hz, 2H), 2.31 (s, 6H), 1.80-1.53 (m, 3H), 0.97 (d, J=6.6 Hz, 6H).

Example 34(3)

3-(2-((3-methyl-1-(3,5-dimethylphenyl)butyl)carbamoyl)-4-(3-cyanobenzyloxy)phenyl)propanoic acid

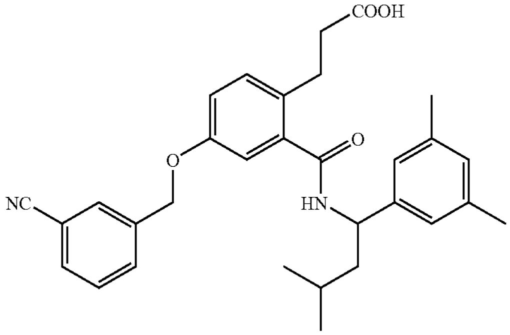

TLC: Rf 0.38 (chloroform:methanol=10:1);

NMR (300 MHz, $CDCl_3$): δ 7.71 (s, 1H), 7.62 (d, J=7.8 Hz, 1H), 7.61 (s, 1H), 7.49 (dd, J=7.8, 7.8 Hz, 1H), 7.17 (d, J=7.8 Hz, 1H), 6.97-6.87 (m, 5H), 6.40 (d, J=8.4 Hz, 1H), 5.15 (m, 1H), 5.04 (s, 2H), 2.98-2.91 (m, 2H), 2.71-2.64 (m, 2H), 2.30 (s, 6H), 1.82-1.53 (m, 3H), 0.97 (d, J=6.6 Hz, 6H).

Example 34(4)

3-(2-(naphthalen-1-ylmethylcarbamoyl)-4-phenoxyphenyl)propanoic acid

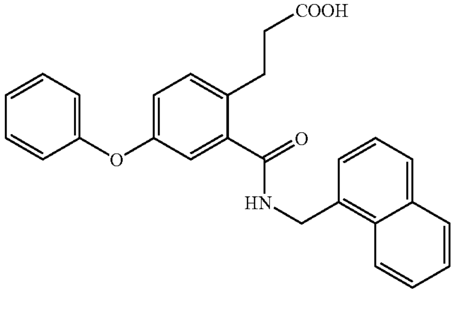

TLC: Rf 0.47 (chloroform:methanol=10:1);

NMR (300 MHz, $CDCl_3$): δ 8.08 (d, J=7.8 Hz, 1H), 7.91-7.79 (m, 2H), 7.58-7.39 (m, 4H), 7.36-7.06 (m, 5H), 7.02-6.90 (m, 3H), 6.27 (m, 1H), 5.06 (d, J=5.4 Hz, 2H), 3.06 (t, J=7.5 Hz, 2H), 2.77 (t, J=7.5 Hz, 2H).

Example 34(5)

3-(2-(1-(naphthalen-2-yl)ethylcarbamoyl)-4-phenoxyphenyl)propanoic acid

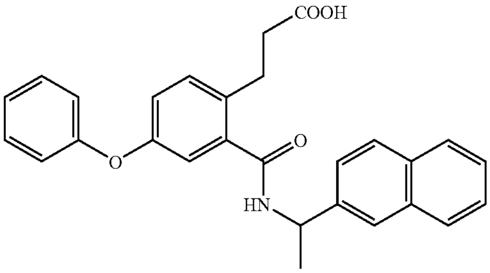

TLC: Rf 0.47 (chloroform:methanol=10:1);

NMR (300 MHz, $CDCl_3$): δ 7.88-7.72 (m, 4H), 7.52-6.92 (m, 11H), 6.46 (d, J=7.5 Hz, 1H), 5.46 (m, 1H), 3.03 (t, J=7.5 Hz, 2H), 2.75 (t, J=7.5 Hz, 2H), 1.67 (d, J=6.6 Hz, 3H).

Example 34(6)

3-(2-((3-methyl-1-(naphthalen-1-yl)butyl)carbamoyl)-4-phenoxyphenyl)propanoic acid

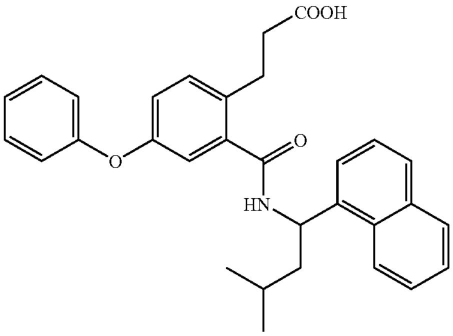

TLC: Rf 0.48 (chloroform:methanol=10:1);

NMR (300 MHz, $CDCl_3$): δ 8.29 (d, J=8.4 Hz, 1H), 7.86 (d, J=7.5 Hz, 1H), 7.78 (d, J=7.5 Hz, 1H), 7.62-7.28 (m, 6H), 7.22-7.07 (m, 2H), 7.02-6.90 (m, 4H), 6.27 (d, J=8.7 Hz, 1H), 6.10 (m, 1H), 2.99 (t, J=7.5 Hz, 2H), 2.71 (t, J=7.5 Hz, 2H), 1.97-1.90 (m, 2H), 1.78 (m, 1H), 1.11 (d, J=6.6 Hz, 3H), 0.99 (d, J=6.6 Hz, 3H).

Example 34(7)

3-(2-(4-methyl-2-phenylpentyl)carbamoyl)-4-phenoxyphenyl)propanoic acid

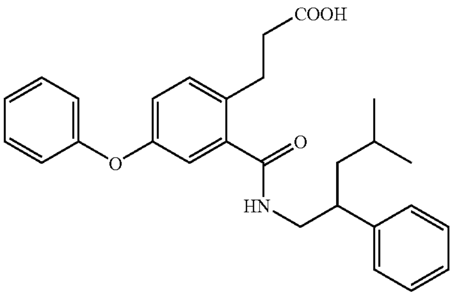

TLC: Rf 0.47 (methylene chloride:methanol=9:1);

NMR (300 MHz, $CDCl_3$): δ 7.35 (t, J=7.5 Hz, 2H), 7.30-7.10 (m, 7H), 7.00-6.90 (m, 3H), 6.73 (d, J=2.7 Hz, 1H), 5.85-5.80 (m, 1H), 3.86-3.76 (m, 1H), 3.40-3.28 (m, 1H), 3.02-2.84 (m, 3H), 2.67 (t, J=7.8 Hz, 2H), 1.65-1.35 (m, 3H), 0.86 (d, J=6.3 Hz, 3H), 0.84 (d, J=6.3 Hz, 3H).

Example 34(8)

3-(2-((1R)-1-(naphthalen-1-yl)ethylcarbamoyl)-4-(2-cyanophenoxy)phenyl)propanoic acid

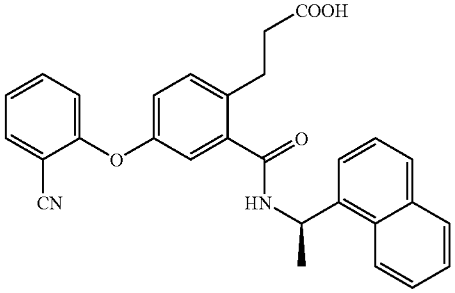

TLC: Rf 0.52 (chloroform:methanol=10:1);

NMR (300 MHz, $CDCl_3$): δ 8.19 (d, J=8.1 Hz, 1H), 7.87 (d, J=8.1 Hz, 1H), 7.81 (d, J=8.1 Hz, 1H), 7.68-7.42 (m, 6H), 7.28 (m, 1H), 7.18-6.98 (m, 3H), 6.84 (d, J=8.4 Hz, 1H), 6.40 (d, J=7.8 Hz, 1H), 6.12 (m, 1H), 3.08 (t, J=7.5 Hz, 2H), 2.77 (t, J=7.5 Hz, 2H), 1.79 (d, J=6.6 Hz, 3H).

Example 34(9)

3-(2-((1R)-1-(naphthalen-1-yl)ethylcarbamoyl)-4-(4-cyanophenoxy)phenyl)propanoic acid

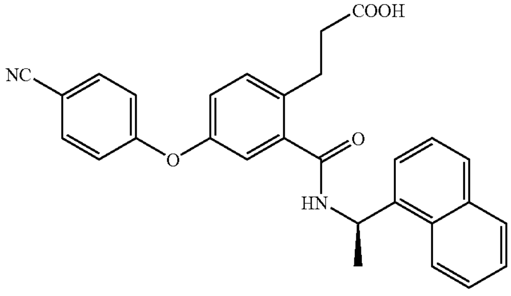

TLC: Rf 0.52 (chloroform:methanol=10:1);

NMR (300 MHz, $CDCl_3$): δ 8.17 (d, J=8.1 Hz, 1H), 7.87 (m, 1H), 7.81 (d, J=8.1 Hz, 1H), 7.60-7.41 (m, 6H), 7.28 (m, 1H), 7.04-6.90 (m, 4H), 6.35 (d, J=8.4 Hz, 1H), 6.11 (m, 1H), 3.13-3.02 (t, J=7.5 Hz, 2H), 2.75 (t, J=7.5 Hz, 2H), 1.79 (d, J=6.6 Hz, 3H).

Example 34(10)

3-(2-((1R)-1-phenylethylcarbamoyl)-4-phenoxyphenyl)propanoic acid

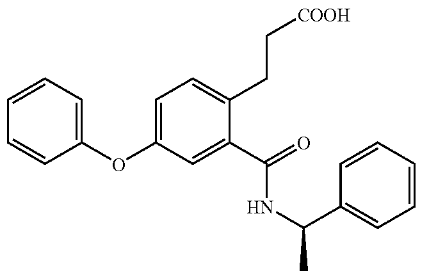

TLC: Rf 0.47 (methylene chloride:methanol=9:1);

NMR (300 MHz, $CDCl_3$): δ 7.40-7.23 (m, 7H), 7.20 (d, J=8.4 Hz, 1H), 7.12 (t, J=7.2 Hz, 1H), 7.05 (d, J=2.4 Hz, 1H), 7.02-6.92 (m, 3H), 6.39 (d, J=7.5 Hz, 1H), 5.28 (q, J=7.5 Hz, 1H), 3.01 (t, J=7.5 Hz, 2H), 2.73 (t, J=7.5 Hz, 2H), 1.57 (d, J=6.9 Hz, 3H).

Example 34(11)

4-(2-((1R)-1-(naphthalen-1-yl)ethylcarbamoyl)-4-phenoxyphenyl)butanoic acid

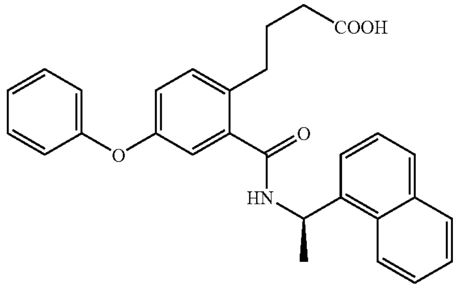

TLC: Rf 0.64 (methylene chloride:methanol=9:1);

NMR (300 MHz, $CDCl_3$): δ 8.19 (d, J=7.8 Hz, 1H), 7.86 (d, J=7.5 Hz, 1H), 7.80 (d, J=8.1 Hz, 1H), 7.58-7.40 (m, 4H), 7.31 (t, J=7.5 Hz, 2H), 7.20-7.06 (m, 2H), 6.98-6.88 (m, 4H), 6.15-6.05 (m, 1H), 6.01 (d, J=8.1 Hz, 1H), 2.85-2.70 (m, 2H), 2.40-2.20 (m, 2H), 2.00-1.80 (m, 2H), 1.76 (d, J=6.3 Hz, 3H).

Example 34(12)

3-(2-((1R)-1-(4-methylphenyl)ethylcarbamoyl)-4-phenoxyphenyl)propanoic acid

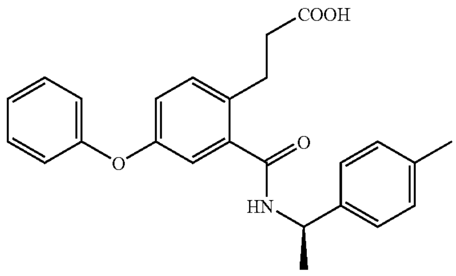

TLC: Rf 0.24 (n-hexane:ethyl acetate=1:1);

NMR (300 MHz, $CDCl_3$): δ 7.37-7.31 (m, 2H), 7.26-7.10 (m, 6H), 7.04 (d, J=2.1 Hz, 1H), 7.00-6.93 (m, 3H), 6.29 (brd, J=5.4 Hz, 1H), 5.25 (m, 1H), 3.05-3.00 (m, 2H), 2.77-2.72 (m, 2H), 2.33 (s, 3H), 1.56 (d, J=6.6 Hz, 3H).

Example 34(13)

3-(2-(1-(4-fluorophenyl)ethylcarbamoyl)-4-phenoxyphenyl)propanoic acid

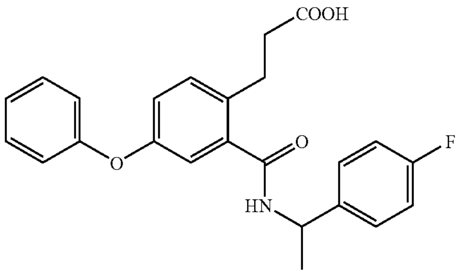

TLC: Rf 0.62 (methylene chloride:methanol=9:1);

NMR (300 MHz, $CDCl_3$): δ 7.38-7.30 (m, 4H), 7.20 (d, J=8.4 Hz, 1H), 7.12 (t, J=7.5 Hz, 1H), 7.05-6.93 (m, 6H), 6.40 (d, J=7.5 Hz, 1H), 5.30-5.20 (m, 1H), 3.00 (t, J=7.5 Hz, 2H), 2.72 (t, J=7.5 Hz, 2H), 1.55 (d, J=6.9 Hz, 3H).

Example 34(14)

3-(2-((1R)-1-indan-1-yl)carbamoyl-4-phenoxyphenyl)propanoic acid

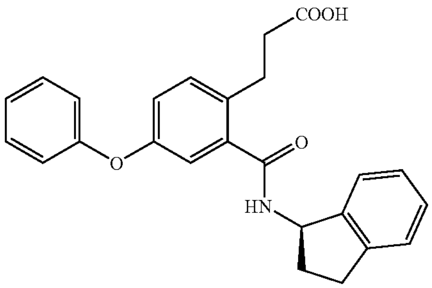

TLC: Rf 0.59 (methylene chloride:methanol=9:1);

NMR (300 MHz, $CDCl_3$): δ 7.40-7.30 (m, 3H), 7.30-7.20 (m, 4H), 7.15-7.05 (m, 2H), 7.03-6.94 (m, 3H), 6.27 (d, J=8.7 Hz, 1H), 5.64 (q, J=7.5 Hz, 1H), 3.10 (t, J=7.5 Hz, 2H), 3.06-2.84 (m, 2H), 2.80 (t, J=7.5 Hz, 2H), 2.76-2.62 (m, 1H), 2.00-1.80 (m, 1H).

Example 34(15)

3-(2-(1-methyl-3-phenylpropyl)carbamoyl-4-phenoxyphenyl)propanoic acid

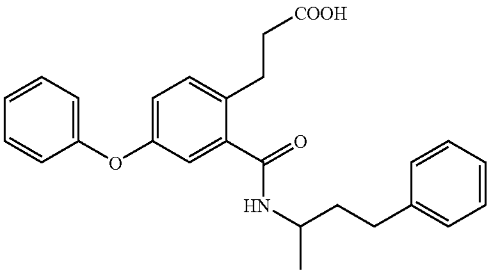

TLC: Rf 0.54 (chloroform:methanol=10:1);

NMR (300 MHz, $CDCl_3$): δ 7.40-6.94 (m, 13H), 5.92 (d, J=8.4 Hz, 1H), 4.22 (m, 1H), 3.05 (t, J=7.5 Hz, 2H), 2.81 (t, J=7.5 Hz, 2H), 2.70 (t, J=7.8 Hz, 2H), 1.93-1.78 (m, 2H), 1.27 (d, J=6.6 Hz, 3H).

Example 34(16)

3-(2-((1R)-1-(4-nitrophenyl)ethylcarbamoyl)-4-phenoxyphenyl)propanoic acid

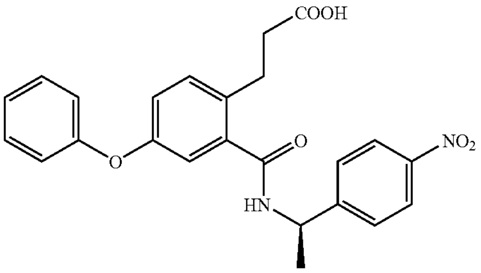

TLC: Rf 0.56 (chloroform:methanol=10:1);

NMR (300 MHz, $CDCl_3$): δ 8.19 (d, J=7.8 Hz, 2H), 7.53 (d, J=7.8 Hz, 2H), 7.40-6.94 (m, 8H), 6.66 (d, J=7.2 Hz, 1H), 5.33 (m, 1H), 2.99 (t, J=7.2 Hz, 2H), 2.73 (t, J=7.2 Hz, 2H), 1.59 (d, J=7.2 Hz, 3H).

Example 34(17)

3-(2-diphenylmethylcarbamoyl-4-phenoxyphenyl)propanoic acid

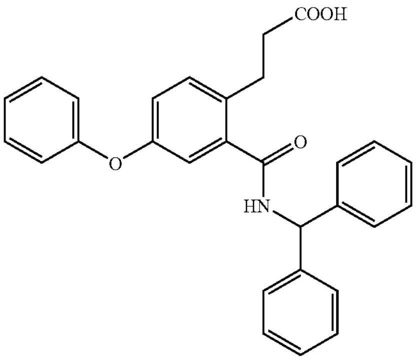

TLC: Rf 0.55 (chloroform:methanol=10:1);

NMR (300 MHz, $CDCl_3$): δ 7.44-6.93 (m, 18H), 6.71 (d, J=8.1 Hz, 1H), 6.42 (d, J=8.1 Hz, 1H), 3.02 (t, J=7.2 Hz, 2H), 2.72 (t, J=7.2 Hz, 2H).

Example 34(18)

3-(2-((3-methyl-1-(3,5-dimethylphenyl)butyl)carbamoyl)-4-phenoxyphenyl)propanoic acid

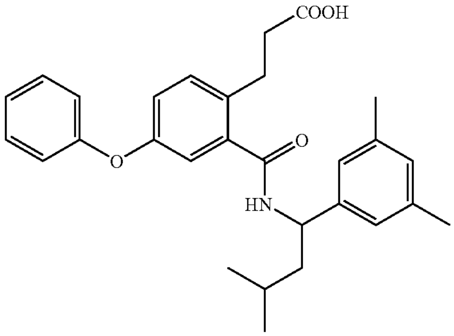

TLC: Rf 0.57 (chloroform:methanol=10:1);

NMR (300 MHz, $CDCl_3$): δ 7.39-7.09 (m, 5H), 7.05-6.87 (m, 6H), 6.21 (d, J=8.4 Hz, 1H), 5.13 (m, 1H), 3.06-2.92 (m, 2H), 2.72 (t, J=7.8 Hz, 2H), 2.29 (s, 6H), 1.81-1.50 (m, 3H), 0.97 (d, J=6.3 Hz, 3H), 0.96 (d, J=6.3 Hz, 3H).

Example 34(19)

3-(2-((1R)-1,2,3,4-tetrahydronaphthalen-1-yl)carbamoyl-4-phenoxyphenyl)propanoic acid

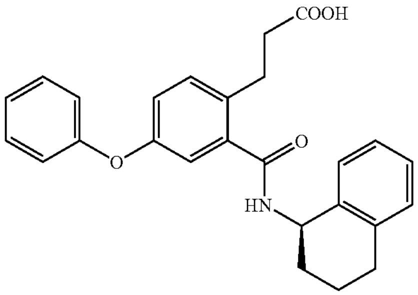

TLC: Rf 0.52 (chloroform:methanol=10:1);

NMR (300 MHz, $CDCl_3$): δ 7.38-6.92 (m, 12H), 6.25 (d, J=8.4 Hz, 1H), 5.35 (m, 1H), 3.10 (t, J=7.2 Hz, 2H), 2.90-2.71 (m, 4H), 2.14 (m, 1H), 2.01-1.78 (m, 3H).

Example 34(20)

3-(2-((1R)-1-(1,1'-biphenyl-4-yl)ethylcarbamoyl)-4-phenoxyphenyl)propanoic acid

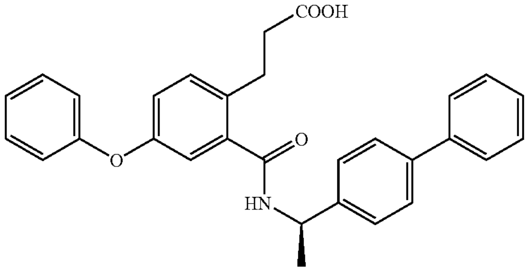

TLC: Rf 0.52 (chloroform:methanol=10:1);

NMR (300 MHz, $CDCl_3$): δ 7.65-6.92 (m, 17H), 6.40 (d, J=8.1 Hz, 1H), 5.33 (m, 1H), 3.03 (t, J=7.2 Hz, 2H), 2.80-2.70 (m, 2H), 1.61 (d, J=6.9 Hz, 3H).

Example 34(21)

3-(2-((1R)-1-(naphthalen-1-yl)ethylcarbamoyl)-4-(4-methylphenoxy)phenyl)propanoic acid

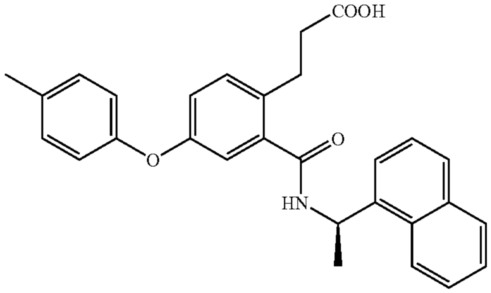

TLC: Rf 0.50 (chloroform:methanol=9:1);

NMR (300 MHz, $CDCl_3$): δ 8.17 (d, J=7.8 Hz, 1H), 7.90-7.77 (m, 2H), 7.59-7.41 (m, 4H), 7.21-7.07 (m, 3H), 6.98-6.80 (m, 4H), 6.29 (d, J=8.1 Hz, 1H), 6.10 (m, 1H), 3.04 (t, J=7.2 Hz, 2H), 2.75 (t, J=7.2 Hz, 2H), 2.33 (s, 3H), 1.78 (d, J=6.9 Hz, 3H).

Example 34(22)

3-(2-(cyano-phenylcarbamoyl)-4-phenoxyphenyl) propanoic acid

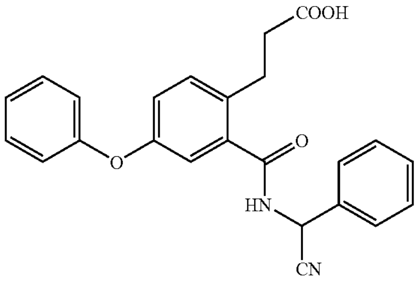

TLC: Rf 0.62 (methylene chloride:methanol=9:1);

NMR (300 MHz, $CD_3OD$): δ7.58-7.54 (m, 2H), 7.48-7.28 (m, 6H), 7.13 (t, J=7.5 Hz, 1H), 7.03-6.97 (m, 4H), 6.29 (s, 1H), 2.97 (t, J=7.2 Hz, 2H), 2.57 (t, J=7.2 Hz, 2H).

Example 34(23)

3-(2-((3-methyl-1-(3,5-dimethylphenyl)butyl)carbamoyl)-4-(4-fluorobenzyloxy)phenyl)propanoic acid

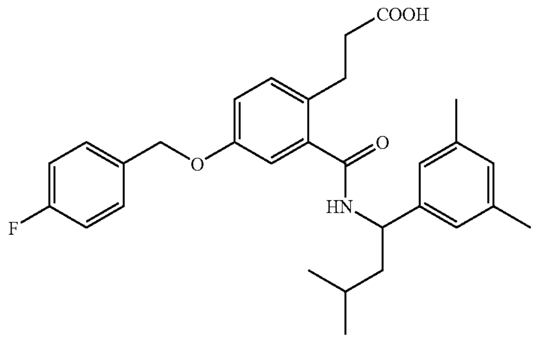

TLC: Rf 0.61 (methylene chloride:methanol=9:1);

NMR (300 MHz, $CDCl_3$): δ 7.40-7.32 (m, 2H), 7.18-7.12 (m, 1H), 7.10-7.02 (m, 2H), 6.96-6.88 (m, 5H), 6.27 (d, J=8.4 Hz, 1H), 5.14 (q, J=8.4 Hz, 1H), 4.98 (s, 2H), 3.00-2.90 (m, 2H), 2.75-2.65 (m, 2H), 2.30 (s, 6H), 1.80-1.50 (m, 3H), 0.97 (d, J=6.3 Hz, 3H), 0.97 (d, J=6.3 Hz, 3H).

Example 34(24)

3-(2-((3-methyl-1-(3,5-dimethylphenyl)butyl)carbamoyl)-4-(2-cyanobenzyloxy)phenyl)propanoic acid

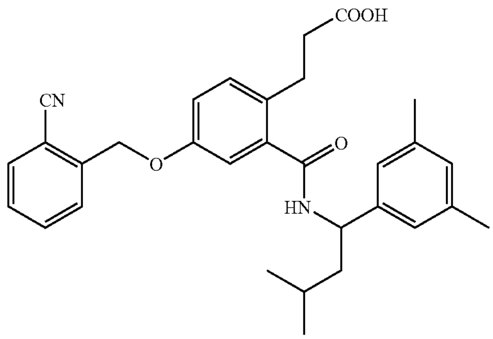

TLC: Rf 0.63 (methylene chloride:methanol=9:1);

NMR (300 MHz, $CDCl_3$): δ 7.70 (d, J=7.5 Hz, 1H), 7.63 (dd, J=4.8, 1.2 Hz, 2H), 7.50-7.40 (m, 1H), 7.18 (d, J=8.7 Hz, 1H), 7.02-6.94 (m, 4H), 6.90 (s, 1H), 6.36 (d, J=8.4 Hz, 1H), 5.23 (s, 2H), 5.15 (q, J=8.4 Hz, 1H), 3.00-2.90 (m, 2H), 2.75-2.65 (m, 2H), 2.30 (s, 6H), 1.85-1.50 (m, 3H), 0.98 (d, J=6.6 Hz, 6H).

Example 34(25)

3-(2-((3-methyl-1-(3,5-dimethylphenyl)butyl)carbamoyl)-4-(2-methoxybenzyloxy)phenyl)propanoic acid

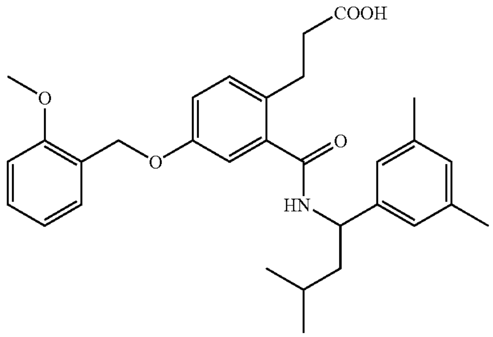

TLC: Rf 0.51 (chloroform:methanol=10:1);

NMR (300 MHz, $CDCl_3$): δ 7.40 (d, J=7.2 Hz, 1H), 7.31 (m, 1H), 7.17 (m, 1H), 7.04-6.87 (m, 7H), 6.22 (d, J=8.4 Hz, 1H), 5.14 (m, 1H), 5.08 (s, 2H), 3.84 (s, 3H), 3.02-2.90 (m, 2H), 2.71 (t, J=7.5 Hz, 2H), 2.31 (s, 6H), 1.83-1.52 (m, 3H), 0.97 (d, J=6.0 Hz, 6H).

Example 34(26)

3-(2-((3-methyl-1-(3,5-dimethylphenyl)butyl)carbamoyl)-4-(2-chlorobenzyloxy)phenyl)propanoic acid

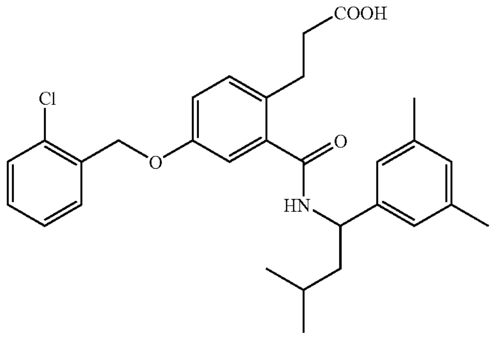

TLC: Rf 0.56 (chloroform:methanol=10:1);

NMR (300 MHz, $CDCl_3$): δ 7.51 (m, 1H), 7.40 (m, 1H), 7.33-7.23 (m, 2H), 7.18 (m, 1H), 7.00-6.87 (m, 5H), 6.23 (d, J=8.7 Hz, 1H), 5.20-5.10 (m, 1H), 5.15 (s, 2H), 3.02-2.89 (m, 2H), 2.70 (t, J=7.5 Hz, 2H), 2.31 (s, 6H), 1.83-1.52 (m, 3H), 0.98 (d, J=6.3 Hz, 6H).

Example 34(27)

3-(2-((3-methyl-1-(3,5-dimethylphenyl)butyl)carbamoyl)-4-(2-phenylbenzyloxy)phenyl)propanoic acid

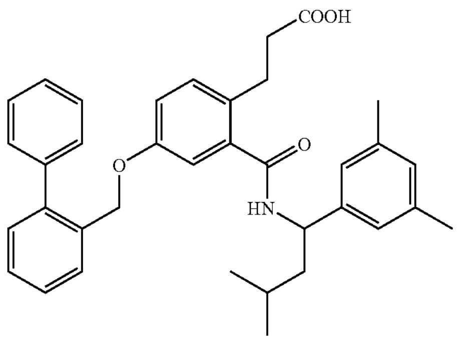

TLC: Rf 0.55 (chloroform:methanol=10:1);

NMR (300 MHz, $CDCl_3$): δ 7.56 (m, 1H), 7.44-7.30 (m, 8H), 7.11 (d, J=8.1 Hz, 1H), 6.95-6.77 (m, 5H), 6.17 (d, J=8.4 Hz, 1H), 5.13 (m, 1H), 4.91 (s, 2H), 2.99-2.87 (m, 2H), 2.68 (t, J=7.5 Hz, 2H), 2.30 (s, 6H), 1.83-1.50 (m, 3H), 0.97 (d, J=6.3 Hz, 6H).

Example 34(28)

3-(2-((3-methyl-1-(3,5-dimethylphenyl)butyl)carbamoyl)-4-(2-methylbenzyloxy)phenyl)propanoic acid

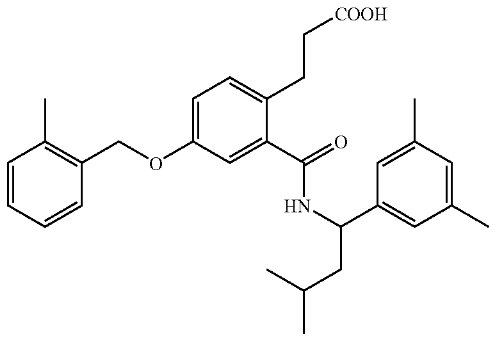

TLC: Rf 0.57 (chloroform:methanol=10:1);

NMR (300 MHz, $CDCl_3$): δ 7.36 (d, J=7.2 Hz, 1H), 7.30-7.14 (m, 4H), 7.01-6.88 (m, 5H), 6.24 (d, J=8.4 Hz, 1H), 5.15 (m, 1H), 5.01 (s, 2H), 3.02-2.90 (m, 2H), 2.68 (t, J=7.5 Hz, 2H), 2.36 (s, 3H), 2.30 (s, 6H), 1.83-1.53 (m, 3H), 0.98 (d, J=6.3 Hz, 6H).

Example 34(29)

3-(2-((3-methyl-1-(3,5-dimethylphenyl)butyl)carbamoyl)-4-(2-fluorobenzyloxy)phenyl)propanoic acid

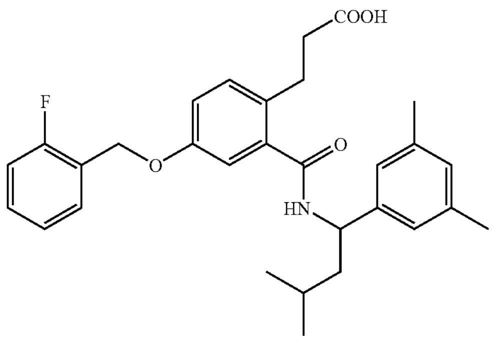

TLC: Rf 0.50 (chloroform:methanol=9:1);

NMR (300 MHz, $CDCl_3$): δ 7.50-7.42 (m, 1H), 7.38-7.28 (m, 1H), 7.23-7.04 (m, 3H), 7.02-6.88 (m, 5H), 6.24 (d, J=8.7 Hz, 1H), 5.20-5.08 (m, 1H), 5.11 (s, 2H), 3.02-2.90 (m, 2H), 2.72 (t, J=7.2 Hz, 2H), 2.31 (s, 6H), 1.84-1.50 (m, 3H), 0.98 (d, J=6.3 Hz, 6H).

Example 34(30)

3-(2-((3-methyl-1-(3,5-dimethylphenyl)butyl)carbamoyl)-4-(4-ethylbenzyloxy)phenyl)propanoic acid

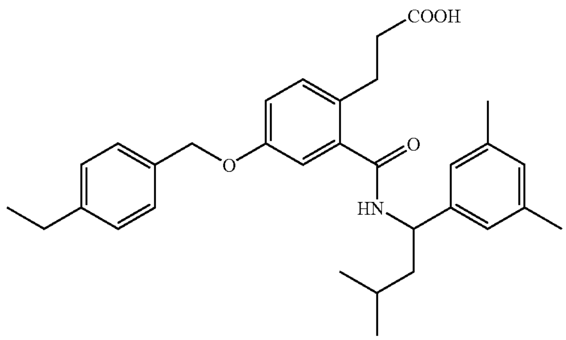

TLC: Rf 0.50 (chloroform:methanol=9:1);

NMR (300 MHz, $CDCl_3$): δ 7.32 (d, J=7.8 Hz, 2H), 7.25-7.14 (m, 3H), 7.00-6.88 (m, 5H), 6.23 (d, J=8.1 Hz, 1H), 5.20-5.10 (m, 1H), 5.00 (s, 2H), 3.02-2.90 (m, 2H), 2.75-2.60 (m, 4H), 2.31 (s, 6H), 1.82-1.50 (m, 3H), 1.24 (t, J=7.5 Hz, 3H), 0.98 (d, J=6.3 Hz, 6H).

Example 34(31)

3-(2-((3-methyl-1-(3,5-dimethylphenyl)butyl)carbamoyl)-4-(2-trifluoromethylbenzyloxy)phenyl)propanoic acid

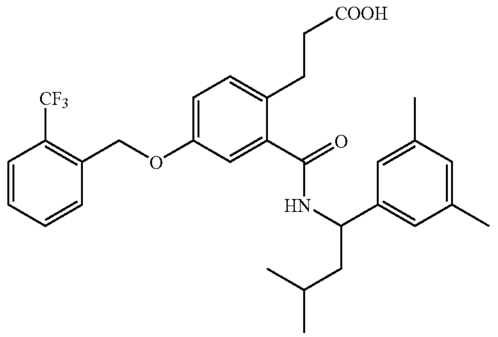

TLC: Rf 0.50 (chloroform:methanol=9:1).

Example 34(32)

3-(2-((3-methyl-1-(3,5-dimethylphenyl)butyl)carbamoyl)-4-(2,3-dimethoxybenzyloxy)phenyl)propanoic acid

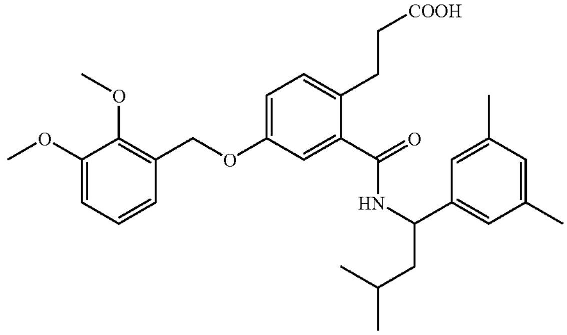

TLC: Rf 0.50 (chloroform:methanol=9:1);

NMR (300 MHz, $CDCl_3$): δ 7.17 (d, J=7.8 Hz, 1H), 7.12-6.88 (m, 8H), 6.27 (d, J=8.7 Hz, 1H), 5.20-5.08 (m, 1H), 5.09 (s, 2H), 3.88 (s, 3H), 3.86 (s, 3H), 3.02-2.90 (m, 2H), 2.71 (t, J=7.2 Hz, 2H), 2.31 (s, 6H), 1.84-1.50 (m, 3H), 0.98 (d, J=6.6 Hz, 6H).

Example 34(33)

3-(2-((3-methyl-1-(3,5-dimethylphenyl)butyl)carbamoyl)-4-(2,6-dimethylbenzyloxy)phenyl)propanoic acid

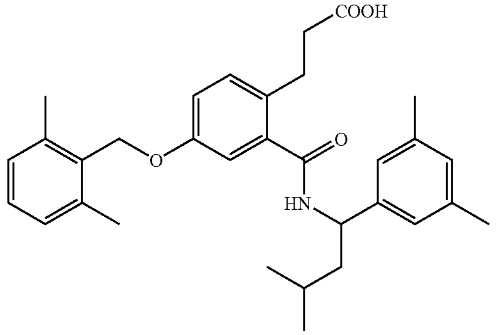

TLC: Rf 0.54 (chloroform:methanol=10:1);

NMR (300 MHz, $CDCl_3$): δ 7.28-7.13 (m, 3H), 7.12-6.95 (m, 3H), 6.94 (s, 2H), 6.90 (s, 1H), 6.29 (d, J=8.7 Hz, 1H), 5.15 (m, 1H), 5.01 (s, 2H), 3.03-2.92 (m, 2H), 2.72 (t, J=6.9 Hz, 2H), 2.38 (s, 6H), 2.30 (s, 6H), 1.82-1.55 (m, 3H), 0.97 (d, J=6.3 Hz, 6H).

Example 34(34)

3-(2-((3-methyl-1-(3,5-dimethylphenyl)butyl)carbamoyl)-4-(3-chlorobenzyloxy)phenyl)propanoic acid

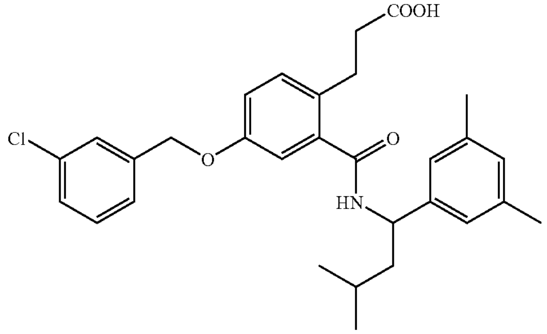

TLC: Rf 0.50 (chloroform:methanol=9:1);

NMR (300 MHz, $CDCl_3$): δ 7.42 (s, 1H), 7.34-7.22 (m, 3H), 7.21-7.14 (m, 1H), 6.97-6.88 (m, 5H), 6.26 (d, J=8.1 Hz, 1H), 5.20-5.10 (m, 1H), 5.01 (s, 2H), 3.00-2.93 (m, 2H), 2.71 (t, J=7.2 Hz, 2H), 2.31 (s, 6H), 1.84-1.50 (m, 3H), 0.98 (d, J=6.3 Hz, 6H).

Example 34(35)

3-(2-((3-methyl-1-(3,5-dimethylphenyl)butyl)carbamoyl)-4-(3-fluorobenzyloxy)phenyl)propanoic acid

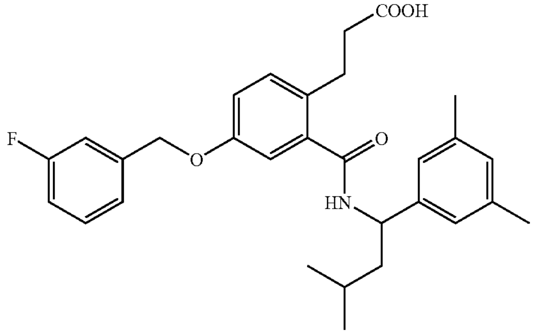

TLC: Rf 0.50 (chloroform:methanol=9:1);

NMR (300 MHz, $CDCl_3$): δ 7.40-7.30 (m, 1H), 7.21-7.10 (m, 3H), 7.07-6.98 (m, 1H), 6.98-6.89 (m, 5H), 6.26 (d, J=8.7 Hz, 1H), 5.20-5.08 (m, 1H), 5.04 (s, 2H), 3.00-2.90 (m, 2H), 2.71 (t, J=7.2 Hz, 2H), 2.31 (s, 6H), 1.84-1.50 (m, 3H), 0.98 (d, J=6.3 Hz, 6H).

Example 34(36)

3-(2-((3-methyl-1-(3,5-dimethylphenyl)butyl)carbamoyl)-4-(3-trifluoromethylbenzyloxy)phenyl)propanoic acid

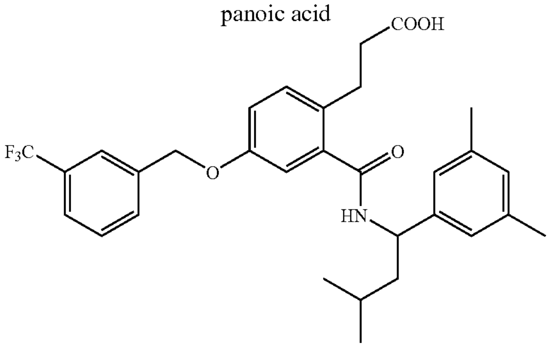

TLC: Rf 0.50 (chloroform:methanol=9:1).

Example 34(37)

3-(2-((3-methyl-1-(3,5-dimethylphenyl)butyl)carbamoyl)-4-(4-trifluoromethyloxybenzyloxy)phenyl)propanoic acid

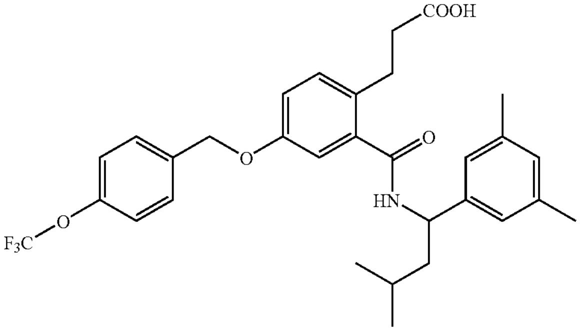

TLC: Rf 0.50 (chloroform:methanol=9:1).

Example 34(38)

3-(2-((3-methyl-1-(3,5-dimethylphenyl)butyl)carbamoyl)-4-(4-isopropylbenzyloxy)phenyl)propanoic acid

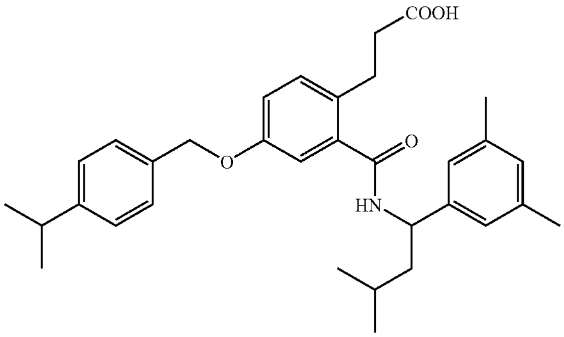

TLC: Rf 0.50 (chloroform:methanol=9:1).

Example 34(39)

3-(2-((3-methyl-1-(3,5-dimethylphenyl)butyl)carbamoyl)-4-(naphthalen-1-yl)methyloxyphenyl)propanoic acid

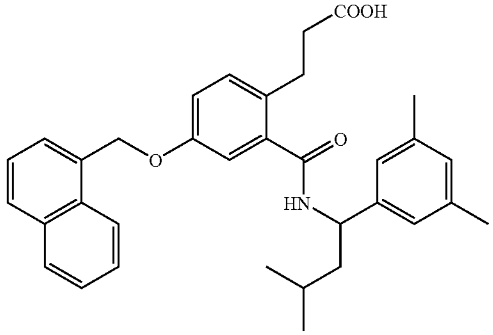

TLC: Rf 0.50 (chloroform:methanol=9:1);

NMR (300 MHz, $CDCl_3$): δ 8.05-7.98 (m, 1H), 7.94-7.84 (m, 2H), 7.60-7.40 (m, 4H), 7.22 (d, J=8.1 Hz, 1H), 7.10-7.00 (m, 2H), 6.96-6.88 (m, 3H), 6.26 (d, J=8.1 Hz, 1H), 5.47 (s, 2H), 5.20-5.10 (m, 1H), 3.05-2.90 (m, 2H), 2.73 (t, J=7.2 Hz, 2H), 2.30 (s, 6H), 1.84-1.50 (m, 3H), 0.97 (d, J=6.3 Hz, 3H), 0.96 (d, J=6.3 Hz, 3H).

Example 34(40)

3-(2-((3-methyl-1-(3,5-dimethylphenyl)butyl)carbamoyl)-4-(4-butylbenzyloxy)phenyl)propanoic acid

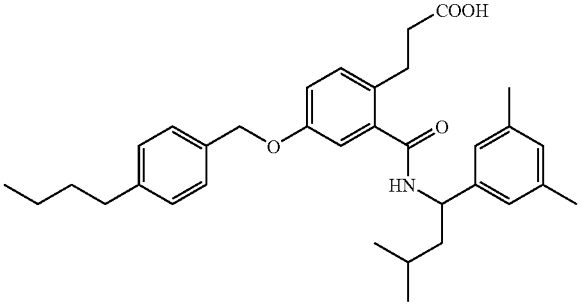

TLC: Rf 0.50 (chloroform:methanol=9:1).

Example 34(41)

3-(2-((3-methyl-1-(3,5-dimethylphenyl)butyl)carbamoyl)-4-(4-t-butylbenzyloxy)phenyl)propanoic acid

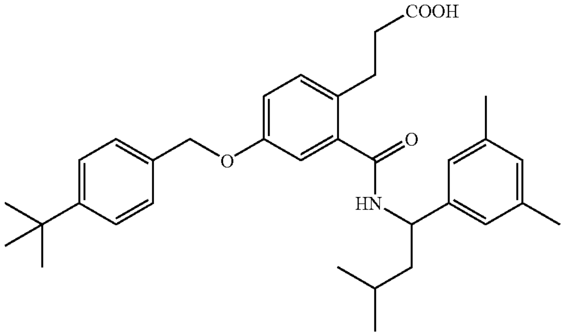

TLC: Rf 0.50 (chloroform:methanol=9:1).

Example 34(42)

3-(2-((3-methyl-1-(3,5-dimethylphenyl)butyl)carbamoyl)-4-(4-phenylbenzyloxy)phenyl)propanoic acid

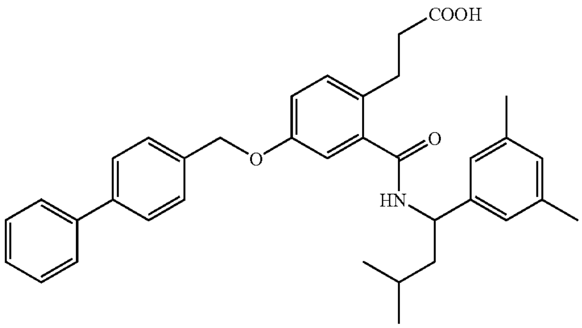

TLC: Rf 0.50 (chloroform:methanol=9:1);

NMR (300 MHz, $CDCl_3$): δ 7.65-7.55 (m, 4H), 7.55-7.32 (m, 5H), 7.23-7.15 (m, 1H), 7.06-6.86 (m, 5H), 6.24 (d, J=8.4 Hz, 1H), 5.20-5.08 (m, 1H), 5.08 (s, 2H), 3.03-2.92 (m, 2H), 2.72 (t, J=6.9 Hz, 2H), 2.30 (s, 6H), 1.84-1.50 (m, 3H), 0.98 (d, J=5.4 Hz, 6H).

Example 34(43)

3-(2-((3-methyl-1-(3,5-dimethylphenyl)butyl)carbamoyl)-4-(2-benzylbenzyloxy)phenyl)propanoic acid

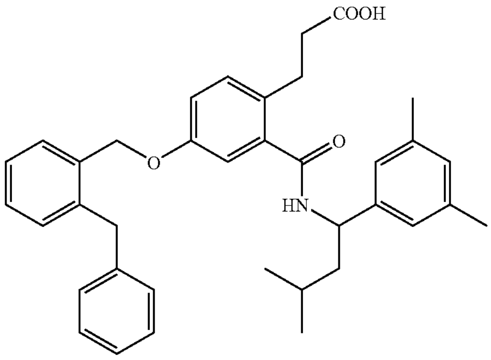

TLC: Rf 0.50 (chloroform:methanol=9:1).

Example 34(44)

3-(2-((3-methyl-1-(3,5-dimethylphenyl)butyl)carbamoyl)-4-(2-chloro-6-fluorobenzyloxy)phenyl) propanoic acid

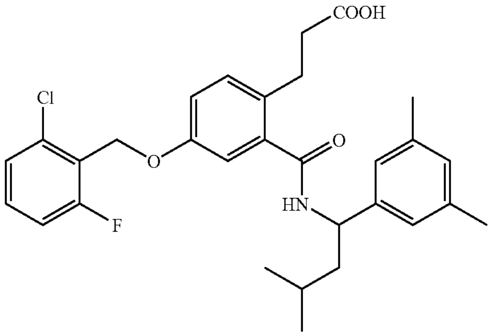

TLC: Rf 0.50 (chloroform:methanol=9:1);

NMR (300 MHz, $CDCl_3$): δ 7.36-7.18 (m, 3H), 7.10-6.88 (m, 6H), 6.27 (d, J=8.7 Hz, 1H), 5.20-5.10 (m, 3H), 3.02-2.94 (m, 2H), 2.73 (t, J=6.9 Hz, 2H), 2.31 (s, 6H), 1.84-1.50 (m, 3H), 0.98 (d, J=6.0 Hz, 6H).

Example 34(45)

3-(2-((3-methyl-1-(3,5-dimethylphenyl)butyl)carbamoyl)-4-(2,5-difluorobenzyloxy)phenyl)propanoic acid

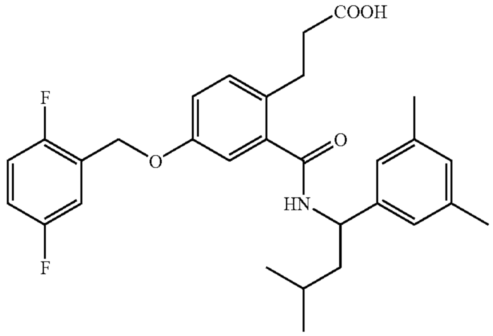

TLC: Rf 0.50 (chloroform:methanol=9:1);

NMR (300 MHz, $CDCl_3$): δ 7.25-7.16 (m, 2H), 7.10-6.90 (m, 7H), 6.28 (d, J=8.1 Hz, 1H), 5.20-5.10 (m, 1H), 5.09 (s, 2H), 3.05-2.90 (m, 2H), 2.72 (t, J=7.5 Hz, 2H), 2.31 (s, 6H), 1.84-1.50 (m, 3H), 0.98 (d, J=6.3 Hz, 6H).

Example 34(46)

3-(2-((3-methyl-1-(3,5-dimethylphenyl)butyl)carbamoyl)-4-(4-chlorobenzyloxy)phenyl)propanoic acid

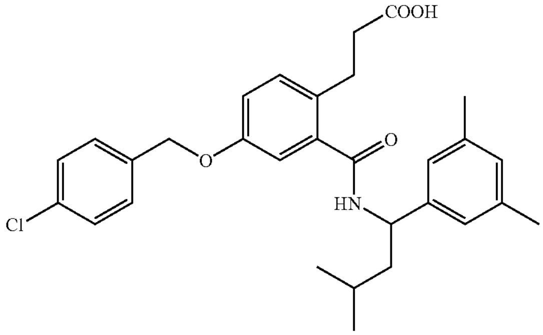

TLC: Rf 0.50 (chloroform:methanol=9:1).

Example 34(47)

3-(2-((3-methyl-1-(3,5-dimethylphenyl)butyl)carbamoyl)-4-(2-fluoro-5-trifluoromethylbenzyloxy)phenyl)propanoic acid

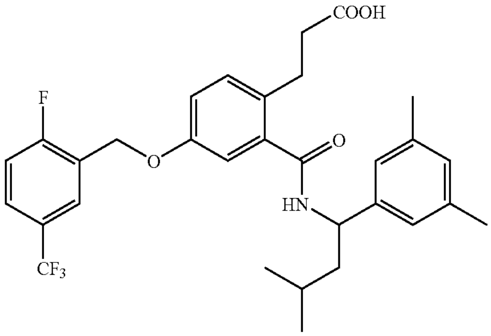

TLC: Rf 0.50 (chloroform:methanol=9:1).

Example 34(48)

3-(2-((3-methyl-1-(3,5-dimethylphenyl)butyl)carbamoyl)-4-(2,4-difluorobenzyloxy)phenyl)propanoic acid

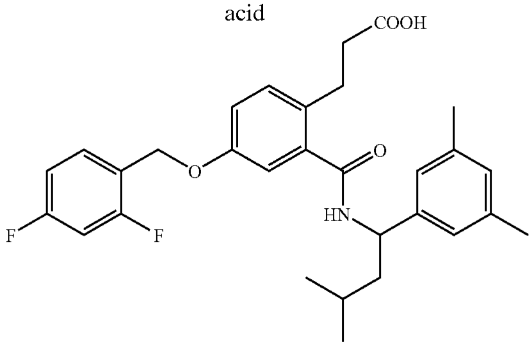

TLC: Rf 0.50 (chloroform:methanol=9:1).

Example 34(49)

3-(2-((3-methyl-1-(3,5-dimethylphenyl)butyl)carbamoyl)-4-(3,5-dimethylbenzyloxy)phenyl)propanoic acid

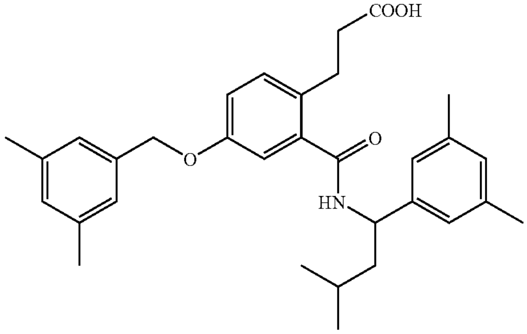

TLC: Rf 0.50 (chloroform:methanol=9:1).

Example 34(50)

3-(2-((3-methyl-1-(3,5-dimethylphenyl)butyl)carbamoyl)-4-(1-ethyl-3-methylpyrazol-5-yl)methoxyphenyl)propanoic acid

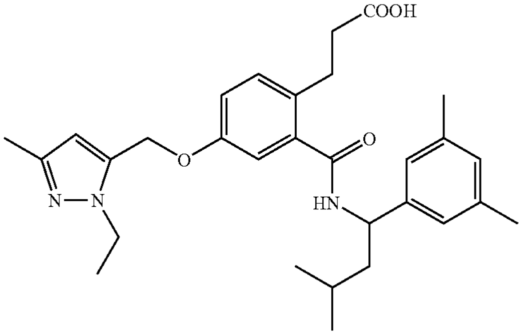

TLC: Rf 0.33 (n-hexane:ethyl acetate=1:1).

Example 34(51)

3-(2-((3-methyl-1-(3,5-dimethylphenyl)butyl)carbamoyl)-4-(2-fluoro-6-trifluoromethylbenzyloxy)phenyl)propanoic acid

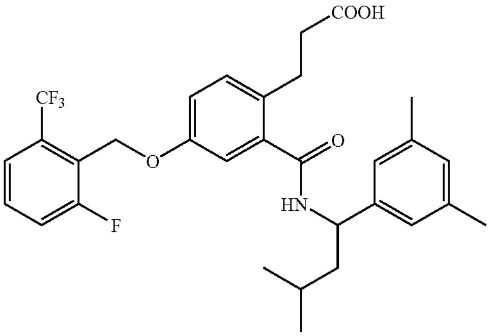

TLC: Rf 0.57 (n-hexane:ethyl acetate=1:1).

Example 34(52)

3-(2-((3-methyl-1-(3,5-dimethylphenyl)butyl)carbamoyl)-4-(2,3-difluorobenzyloxy)phenyl)propanoic acid

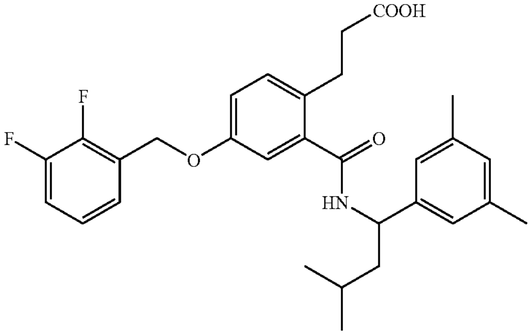

TLC: Rf 0.57 (n-hexane:ethyl acetate=1:1).

Example 34(53)

3-(2-((3-methyl-1-(3,5-dimethylphenyl)butyl)carbamoyl)-4-(2,6-difluorobenzyloxy)phenyl)propanoic acid

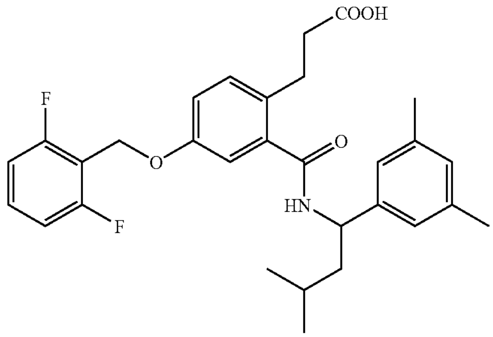

TLC: Rf 0.57 (n-hexane:ethyl acetate=1:1);

NMR (300 MHz, $CDCl_3$+$CD_3OD$): δ 7.34 (m, 1H), 7.19 (d, J=8.4 Hz, 1H), 7.03-6.85 (m, 7H), 6.28 (d, J=8.4 Hz, 1H), 5.15 (m, 1H), 5.11 (s, 2H), 3.11-2.88 (m, 2H), 2.69 (t, J=7.1 Hz, 2H), 2.30 (s, 6H), 1.86-1.52 (m, 3H), 0.98 (d, J=6.3 Hz, 6H).

Example 34(54)

3-(2-((3-methyl-1-(3,5-dimethylphenyl)butyl)carbamoyl)-4-(2-chloro-4-fluorobenzyloxy)phenyl) propanoic acid

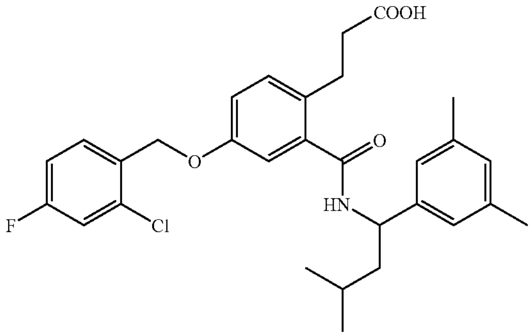

TLC: Rf 0.60 (n-hexane:ethyl acetate=1:1).

Example 34(55)

3-(2-((3-methyl-1-(3,5-dimethylphenyl)butyl)carbamoyl)-4-(3,5-difluorobenzyloxy)phenyl)propanoic acid

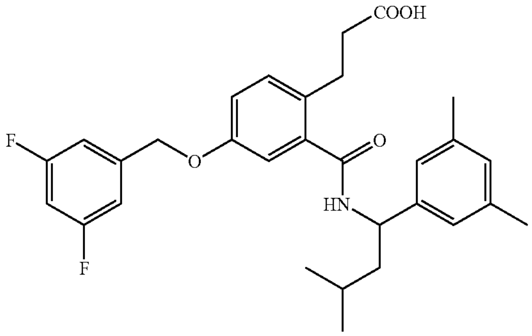

TLC: Rf 0.55 (n-hexane:ethyl acetate=1:1).

Example 34(56)

3-(2-((3-methyl-1-(3,5-dimethylphenyl)butyl)carbamoyl)-4-(3,5-bis(trifluoromethyl)benzyloxy)phenyl)propanoic acid

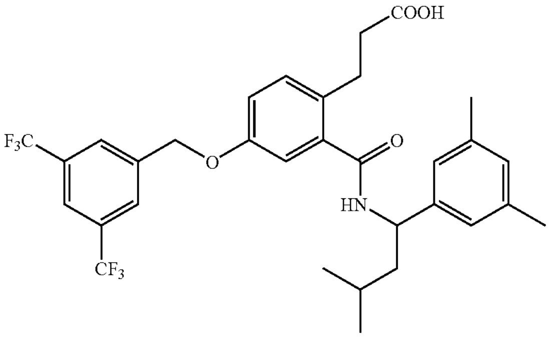

TLC: Rf 0.59 (n-hexane:ethyl acetate=1:1).

Example 34(57)

3-(2-((3-methyl-1-(3,5-dimethylphenyl)butyl)carbamoyl)-4-(3,4-difluorobenzyloxy)phenyl)propanoic acid

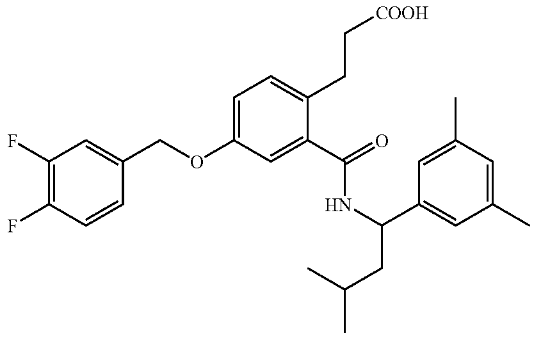

TLC: Rf 0.60 (n-hexane:ethyl acetate=1:1).

Example 34(58)

3-(2-((3-methyl-1-(3,5-dimethylphenyl)butyl)carbamoyl)-4-(3-trifluoromethyloxybenzyloxy)phenyl) propanoic acid

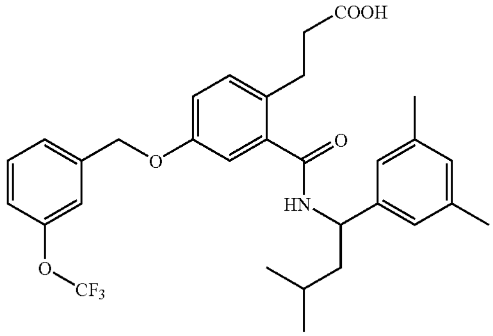

TLC: Rf 0.57 (n-hexane:ethyl acetate=1:1).

Example 34(59)

3-(2-((3-methyl-1-(3,5-dimethylphenyl)butyl)carbamoyl)-4-(3,4-dimethylbenzyloxy)phenyl)propanoic acid

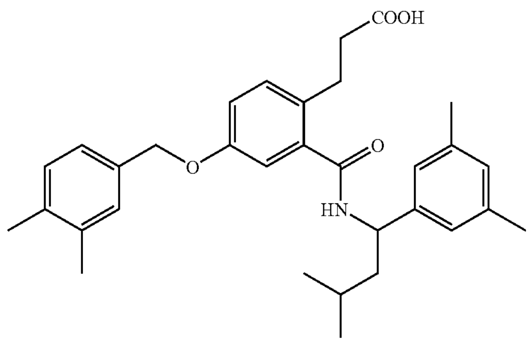

TLC: Rf 0.55 (n-hexane:ethyl acetate=1:1).

Example 34(60)

3-(2-((3-methyl-1-(3,5-dimethylphenyl)butyl)carbamoyl)-4-(2-methoxynaphthalen-1-ylmethyloxy)phenyl)propanoic acid

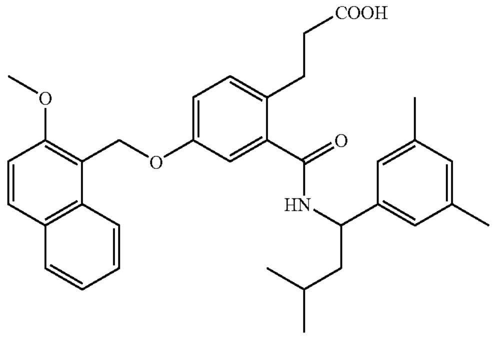

TLC: Rf 0.50 (chloroform:methanol=9:1).

Example 34(61)

3-(2-((3-methyl-1-(3,5-dimethylphenyl)butyl)carbamoyl)-4-(2,3,6-trifluorobenzyloxy)phenyl)propanoic acid

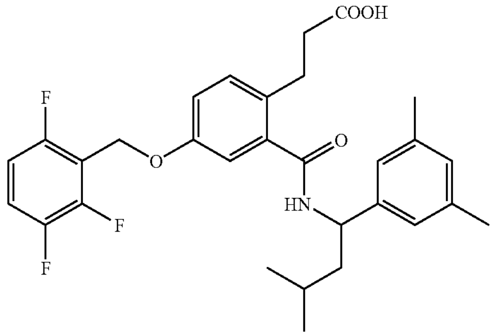

TLC: Rf 0.50 (chloroform:methanol=9:1);

NMR (300 MHz, $CDCl_3$): δ 7.26-7.12 (m, 2H), 7.02-6.84 (m, 6H), 6.29 (d, J=8.7 Hz, 1H), 5.20-5.10 (m, 1H), 5.11 (s, 2H), 3.00-2.92 (m, 2H), 2.70 (t, J=7.2 Hz, 2H), 2.31 (s, 6H), 1.84-1.54 (m, 3H), 0.98 (d, J=6.3 Hz, 6H).

Example 34(62)

4-(2-((3-methyl-1-(3,5-dimethylphenyl)butyl)carbamoyl)-4-benzyloxyphenyl)butanoic acid

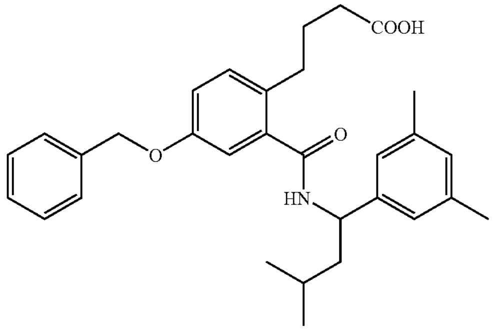

TLC: Rf 0.54 (chloroform:methanol=9:1);

NMR (300 MHz, $CDCl_3$): δ 7.45-7.28 (m, 5H), 7.12 (d, J=8.1 Hz, 1H), 6.99-6.86 (m, 5H), 5.89 (d, J=8.4 Hz, 1H), 5.14 (m, 1H), 5.04 (s, 2H), 2.68 (t, J=7.5 Hz, 2H), 2.31 (s, 6H), 2.26 (t, J=7.2 Hz, 2H), 1.96-1.48 (m, 5H), 0.98 (d, J=4.8 Hz, 6H).

Example 34(63)

4-(2-((1R)-1-(naphthalen-1-yl)ethylcarbamoyl)-4-(4-nitrophenoxy)phenyl)butanoic acid

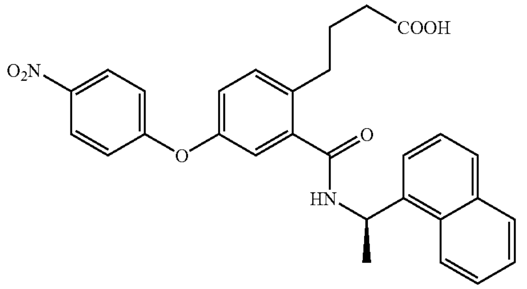

TLC: Rf 0.46 (chloroform:methanol=10:1);

NMR (300 MHz, $CDCl_3$): δ 8.23-8.13 (m, 3H), 7.87 (d, J=8.1 Hz, 1H), 7.82 (d, J=8.1 Hz, 1H), 7.59-7.42 (m, 4H), 7.06-6.92 (m, 4H), 6.12 (m, 1H), 6.01 (d, J=8.7 Hz, 1H), 2.88-2.76 (m, 2H), 2.37-2.29 (m, 2H), 2.00-1.88 (m, 2H), 1.79 (d, J=6.6 Hz, 3H).

Example 34(64)

4-(2-((1R)-1-(naphthalen-1-yl)ethylcarbamoyl)-4-(4-aminophenoxy)phenyl)butanoic acid

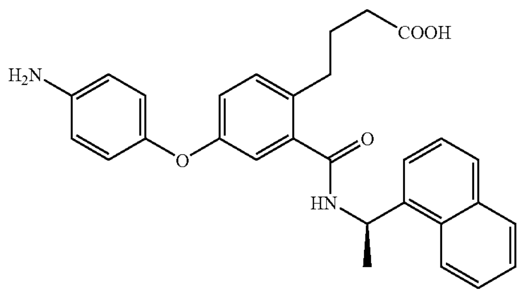

TLC: Rf 0.42 (chloroform:methanol=10:1).

Example 34(65)

4-(2-((1R)-1-(naphthalen-1-yl)ethylcarbamoyl)-4-(4-methylsulfonylphenoxy)phenyl)butanoic acid

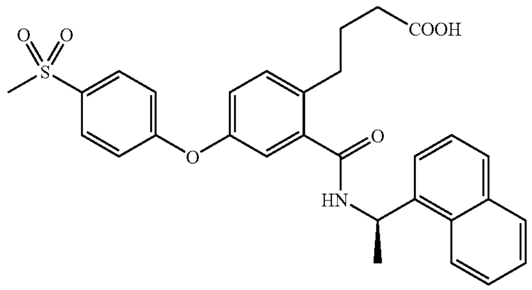

TLC: Rf 0.43 (chloroform:methanol=10:1).

Example 34(66)

3-(2-((3-methyl-1-(3,5-dimethylphenyl)butyl)carbamoyl)-4-(2-thienylmethyloxy)phenyl)propanoic acid

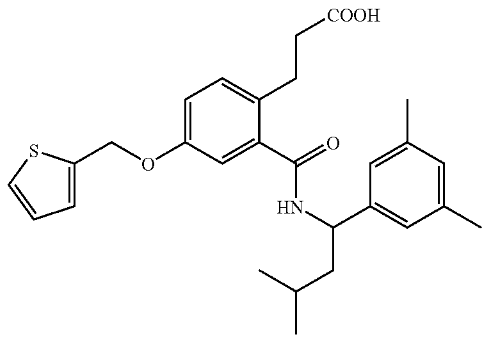

TLC: Rf 0.45 (chloroform:methanol=10:1).

Example 34(67)

3-(2-((3-methyl-1-(3,5-dimethylphenyl)butyl)carbamoyl)-4-(1,3-dioxyindan-4-yl)methyloxyphenyl) propanoic acid

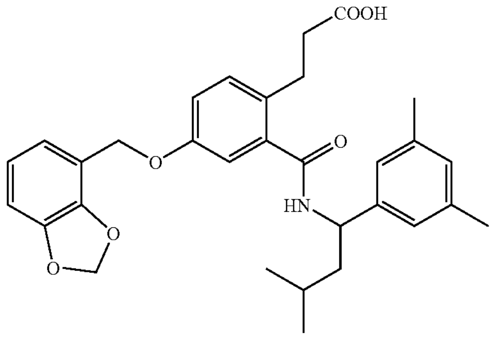

TLC: Rf 0.55 (chloroform:methanol=10:1).

Example 34(68)

3-(2-((3-methyl-1-(3,5-dimethylphenyl)butyl)carbamoyl)-4-(2,4-dimethylbenzyloxy)phenyl)propanoic acid

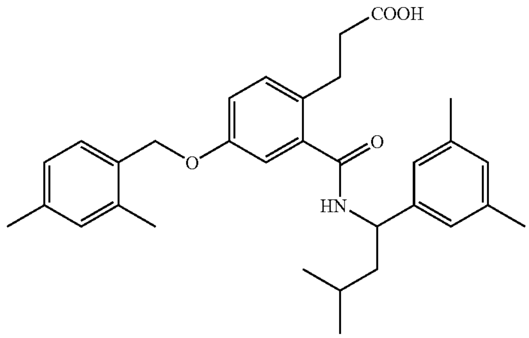

TLC: Rf 0.55 (chloroform:methanol=10:1).

Example 34(69)

3-(2-((3-methyl-1-(3,5-dimethylphenyl)butyl)carbamoyl)-4-(3-methylbenzyloxy)phenyl)propanoic acid

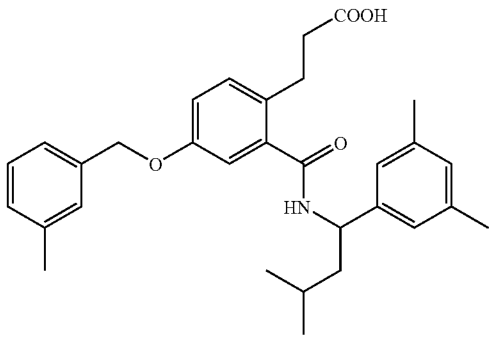

TLC: Rf 0.52 (chloroform:methanol=10:1).

Example 34(70)

3-(2-((3-methyl-1-(3,5-dimethylphenyl)butyl)carbamoyl)-4-(4-methylthiobenzyloxy)phenyl)propanoic acid

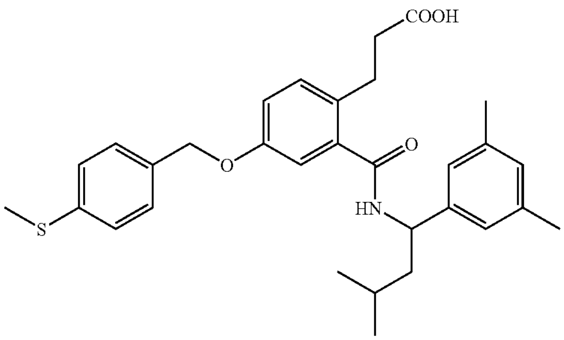

TLC: Rf 0.55 (chloroform:methanol=10:1).

Example 34(71)

3-(2-((3-methyl-1-(3,5-dimethylphenyl)butyl)carbamoyl)-4-(2,5-dimethylbenzyloxy)phenyl)propanoic acid

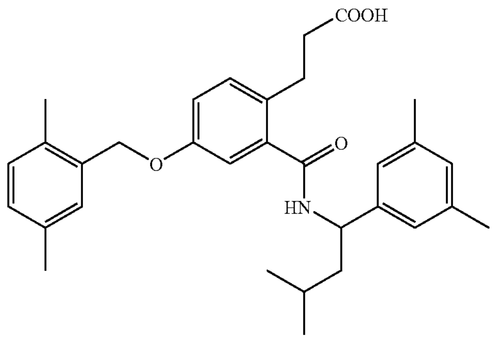

TLC: Rf 0.53 (chloroform:methanol=10:1).

Example 34(72)

3-(2-((3-methyl-1-(3,5-dimethylphenyl)butyl)carbamoyl)-4-(2-fluoro-4-trifluoromethylbenzyloxy)phenyl)propanoic acid

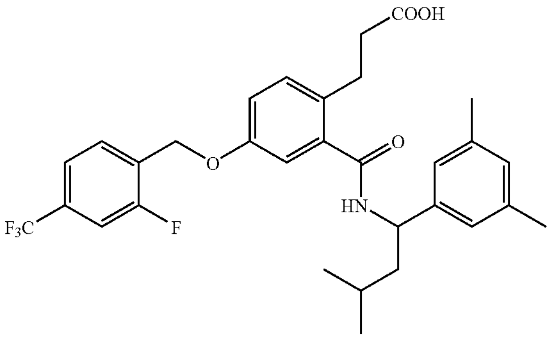

TLC: Rf 0.50 (chloroform:methanol=9:1).

Example 34(73)

3-(2-((3-methyl-1-(3,5-dimethylphenyl)butyl)carbamoyl)-4-(4-fluoro-3-trifluoromethylbenzyloxy)phenyl)propanoic acid

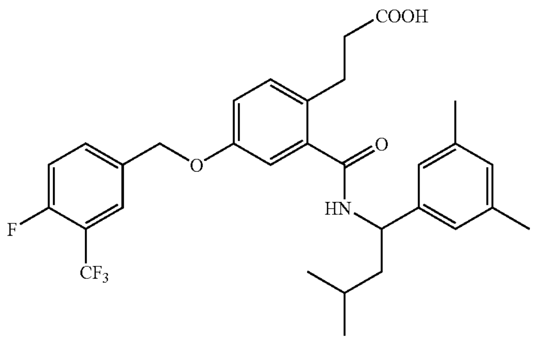

TLC: Rf 0.50 (chloroform:methanol=9:1).

Example 34(74)

3-(2-((3-methyl-1-(3,5-dimethylphenyl)butyl)carbamoyl)-4-(3-fluoro-5-trifluoromethylbenzyloxy)phenyl)propanoic acid

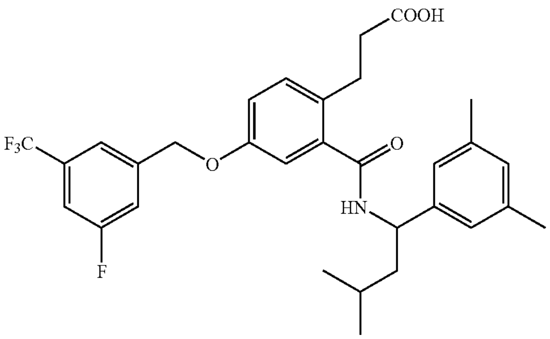

TLC: Rf 0.50 (chloroform:methanol=9:1).

Example 34(75)

3-(2-((3-methyl-1-(3,5-dimethylphenyl)butyl)carbamoyl)-4-(4-fluoro-3-chlorobenzyloxy)phenyl)propanoic acid

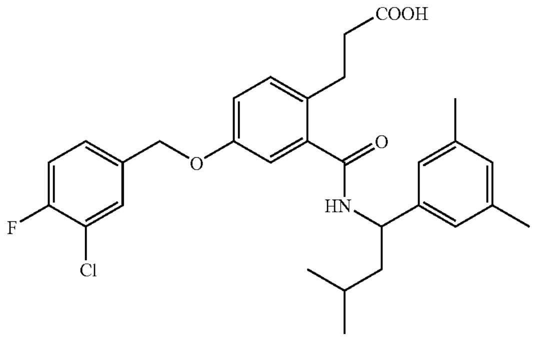

TLC: Rf 0.50 (chloroform:methanol=9:1).

Example 34(76)

3-(2-((3-methyl-1-(3,5-dimethylphenyl)butyl)carbamoyl)-4-(3-fluoro-4-methylbenzyloxy)phenyl) propanoic acid

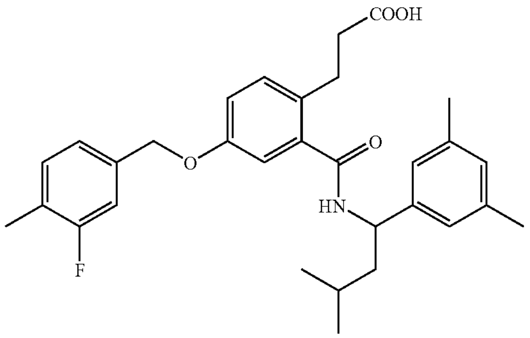

TLC: Rf 0.50 (chloroform:methanol=9:1).

Example 34(77)

3-(2-((3-methyl-1-(3,5-dimethylphenyl)butyl)carbamoyl)-4-(2-fluoro-5-methoxybenzyloxy)phenyl) propanoic acid

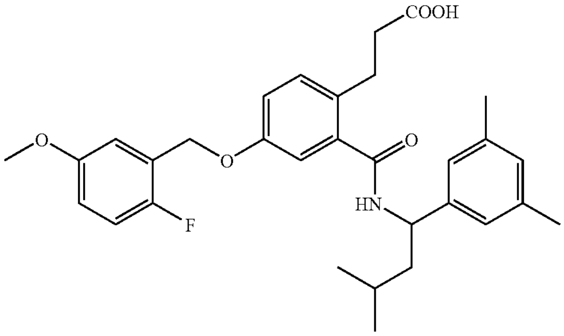

TLC: Rf 0.60 (chloroform:methanol=9:1);

NMR (300 MHz, $CDCl_3$): δ 7.19 (m, 1H), 7.04-6.89 (m, 7H), 6.82 (m, 1H), 6.26 (d, J=8.7 Hz, 1H), 5.15 (m, 1H), 5.07 (s, 2H), 3.78 (s, 3H), 3.00-2.92 (m, 2H), 2.70 (t, J=7.4 Hz, 2H), 2.31 (s, 6H), 1.83-1.50 (m, 3H), 0.98 (d, J=6.0 Hz, 6H).

Example 34(78)

3-(2-((3-methyl-1-(3,5-dimethylphenyl)butyl)carbamoyl)-4-(4-isobutylbenzyloxy)phenyl)propanoic acid

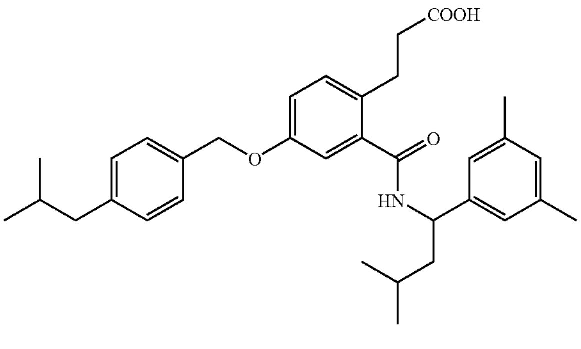

TLC: Rf 0.60 (chloroform:methanol=9:1);

NMR (300 MHz, $CDCl_3$): δ 7.31 (d, J=8.1 Hz, 2H), 7.20-7.13 (m, 3H), 6.99-6.88 (m, 5H), 6.22 (d, J=8.4 Hz, 1H), 5.14 (m, 1H), 5.00 (s, 2H), 3.00-2.91 (m, 2H), 2.70 (t, J=7.5 Hz, 2H), 2.48 (d, J=7.2 Hz, 2H), 2.30 (s, 6H), 1.93-1.52 (m, 4H), 0.98 (d, J=6.3 Hz, 3H), 0.97 (d, J=6.3 Hz, 3H), 0.91 (d, J=6.6 Hz, 6H).

Example 34(79)

3-(2-((3-methyl-1-(3,5-dimethylphenyl)butyl)carbamoyl)-4-(2,4,5-trimethylbenzyloxy)phenyl)propanoic acid

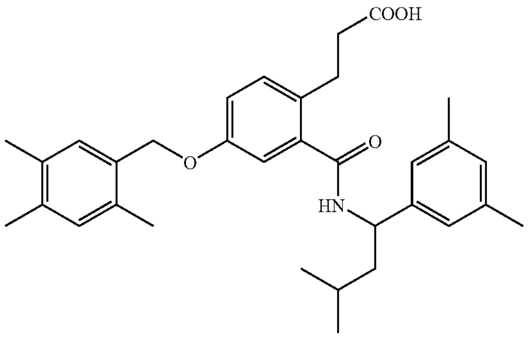

TLC: Rf 0.60 (chloroform:methanol=9:1);

NMR (300 MHz, $CDCl_3$): δ 7.18 (d, J=9.0 Hz, 1H), 7.12 (s, 1H), 7.02-6.88 (m, 6H), 6.25 (d, J=8.4 Hz, 1H), 5.14 (m, 1H), 4.93 (s, 2H), 3.03-2.90 (m, 2H), 2.70 (t, J=7.5 Hz, 2H), 2.30 (s, 6H), 2.29 (s, 3H), 2.23 (s, 6H), 1.83-1.52 (m, 3H), 0.98 (d, J=6.3 Hz, 3H), 0.97 (d, J=6.3 Hz, 3H).

Example 34(80)

3-(2-((3-methyl-1-(3,5-dimethylphenyl)butyl)carbamoyl)-4-(3-(4-methoxyphenoxy)benzyloxy)phenyl)propanoic acid

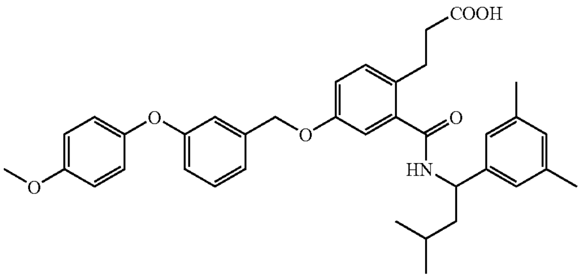

TLC: Rf 0.62 (chloroform:methanol=9:1);

NMR (300 MHz, $CDCl_3$): δ 7.30 (t, J=7.9 Hz, 1H), 7.16 (d, J=8.0 Hz, 1H), 7.07 (d, J=8.0 Hz, 1H), 7.02-6.84 (m, 11H), 6.24 (d, J=8.7 Hz, 1H), 5.14 (m, 1H), 4.99 (s, 2H), 3.80 (s, 3H), 3.00-2.89 (m, 2H), 2.69 (t, J=7.5 Hz, 2H), 2.30 (s, 6H), 1.83-1.50 (m, 3H), 0.98 (d, J=6.3 Hz, 6H).

Example 34(81)

3-(2-((3-methyl-1-(3,5-dimethylphenyl)butyl)carbamoyl)-4-(4-methoxybenzyloxy)phenyl)propanoic acid

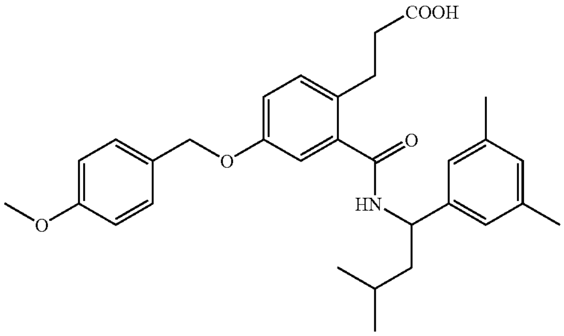

TLC: Rf 0.50 (chloroform:methanol=9:1).

Example 34(82)

3-(2-((3-methyl-1-(3,5-dimethylphenyl)butyl)carbamoyl)-4-(2,3,4-trimethoxybenzyloxy)phenyl)propanoic acid

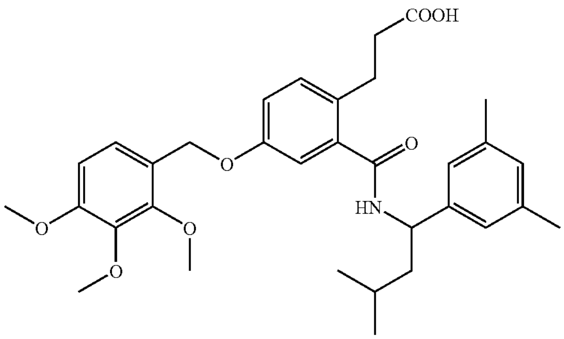

TLC: Rf 0.50 (chloroform:methanol=9:1).

Example 34(83)

4-(2-((1R)-1-(naphthalen-1-yl)ethylcarbamoyl)-4-(4-cyanophenoxy)phenyl)butanoic acid

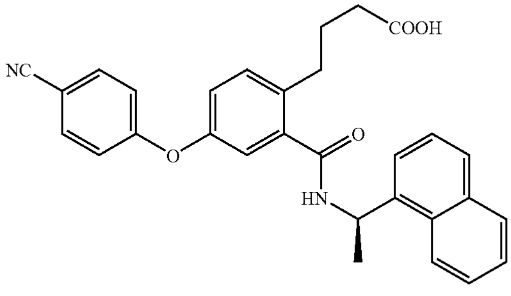

TLC: Rf 0.42 (chloroform:methanol=10:1).

Example 34(84)

4-(2-((1R)-1-(naphthalen-1-yl)ethylcarbamoyl)-4-(4-acetylaminophenoxy)phenyl)butanoic acid

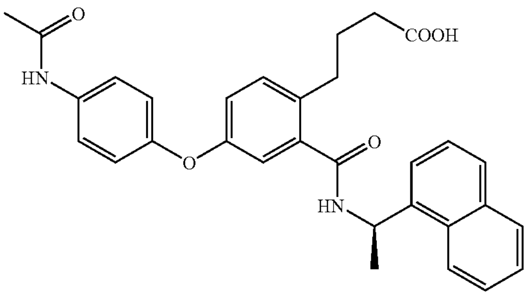

TLC: Rf 0.42 (chloroform:methanol=10:1).

Example 34(85)

4-(2-((1R)-1-(naphthalen-1-yl)ethylcarbamoyl)-4-(4-methylsulfonylaminophenoxy)phenyl)butanoic acid

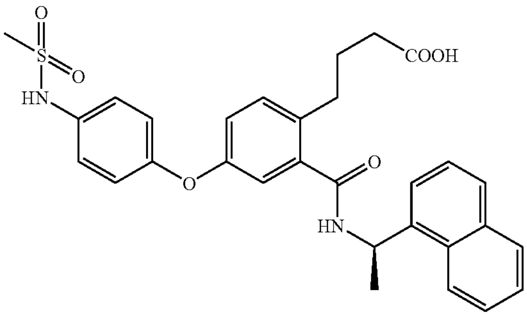

TLC: Rf 0.42 (chloroform:methanol=10:1).

Example 34(86)

3-(2-((3-methyl-1-(3,5-dimethylphenyl)butyl)carbamoyl)-4-(4-fluoro-3-methoxybenzyloxy)phenyl)propanoic acid

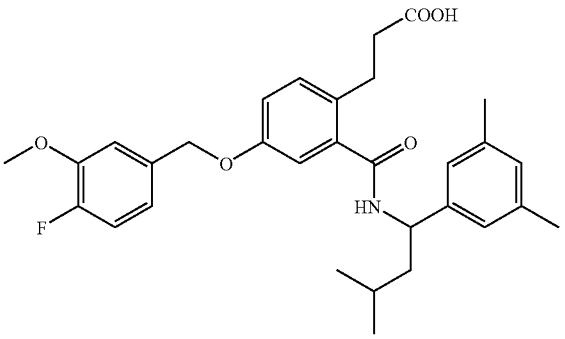

TLC: Rf 0.54 (n-hexane:ethyl acetate=1:1); 7.17 (m, 1H), 7.10-7.00 (m, 2H), 6.95-6.90 (m, 6H), 6.30 (brd, J=8.4 Hz, 1H), 5.14 (m, 1H), 4.96 (s, 2H), 3.89 (s, 3H), 2.98-2.93 (m, 2H), 2.71-2.66 (m, 2H), 2.30 (s, 6H), 1.82-1.50 (m, 3H), 0.97 (d, J=6.3 Hz, 3H), 0.96 (d, J=6.3 Hz, 3H).

Example 34(87)

3-(2-((3-methyl-1-(3,5-dimethylphenyl)butyl)carbamoyl)-4-(4-methoxynaphthalen-1-ylmethyloxy)phenyl)propanoic acid

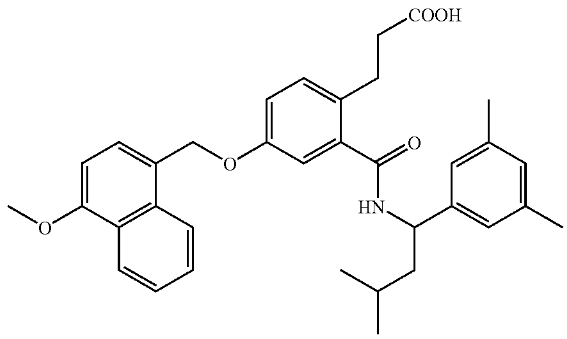

TLC: Rf 0.54 (n-hexane:ethyl acetate=1:1);

NMR (300 MHz, $CDCl_3$): δ 8.33 (m, 1H), 7.96 (m, 1H), 7.58-7.44 (m, 4H), 7.20 (d, J=8.4 Hz, 1H), 7.06-6.89 (m, 4H), 6.77 (d, J=7.8 Hz, 1H), 6.26 (brd, J=8.4 Hz, 1H), 5.36 (s, 2H), 5.14 (m, 1H), 4.01 (s, 3H), 3.00-2.95 (m, 2H), 2.73-2.69 (m, 2H), 2.29 (s, 6H), 1.80-1.52 (m, 3H), 0.96 (d, J=6.3 Hz, 3H), 0.95 (d, J=6.3 Hz, 3H).

Example 34(88)

3-(2-((3-methyl-1-(3,5-dimethylphenyl)butyl)carbamoyl)-4-(2-methoxy-3,5-di(t-butyl)benzyloxy)phenyl)propanoic acid

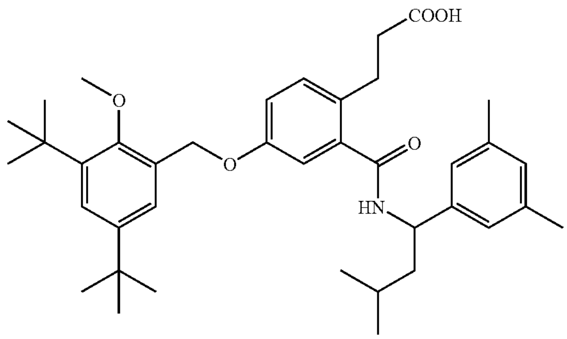

TLC: Rf 0.55 (n-hexane:ethyl acetate=1:1);

NMR (300 MHz, $CDCl_3$): δ 7.36 (d, J=2.4 Hz, 1H), 7.31 (d, J=2.4 Hz, 1H), 7.20 (m, 1H), 7.01-7.00 (m, 2H), 6.95 (brs, 2H), 6.90 (brs, 1H), 6.24 (d, J=8.7 Hz, 1H), 5.15 (m, 1H), 5.03 (s, 2H), 3.79 (s, 3H), 3.00-2.95 (m, 2H), 2.71 (m, 2H), 2.31 (s, 6H), 1.82-1.56 (m, 3H), 1.41 (s, 9H), 1.30 (s, 9H), 0.98 (d, J=6.3 Hz, 3H), 0.97 (d, J=6.3 Hz, 3H).

Example 34(89)

3-(2-((3-methyl-1-(3,5-dimethylphenyl)butyl)carbamoyl)-4-(4-phenoxybenzyloxy)phenyl)propanoic acid

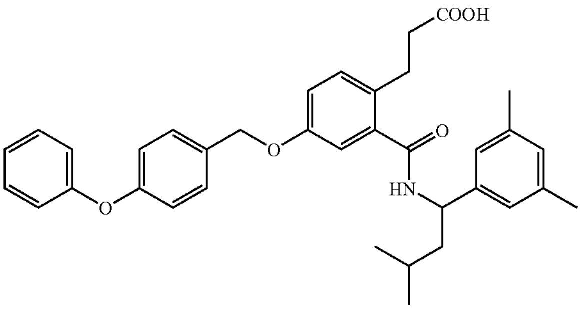

TLC: Rf 0.54 (n-hexane:ethyl acetate=1:1); 7.38-7.32 (m, 4H), 7.19-6.90 (m, 11H), 6.27 (d, J=8.7 Hz, 1H), 5.14 (m, 1H), 4.99 (s, 2H), 2.99-2.93 (m, 2H), 2.71-2.66 (m, 2H), 2.30 (s, 6H), 1.81-1.53 (m, 3H), 0.98 (d, J=6.3 Hz, 3H), 0.97 (d, J=6.3 Hz, 3H).

Example 34(90)

4-(2-((1R)-1-(naphthalen-1-yl)ethylcarbamoyl)-4-(4-acetylphenoxy)phenyl)butanoic acid

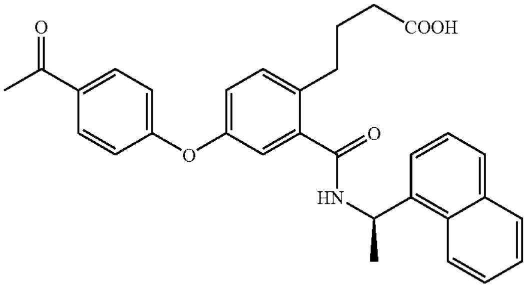

TLC: Rf 0.48 (chloroform:methanol=10:1).

Example 34(91)

3-(2-((3-methyl-1-(3,5-dimethylphenyl)butyl)carbamoyl)-4-(2-furylmethyloxy)phenyl)propanoic acid

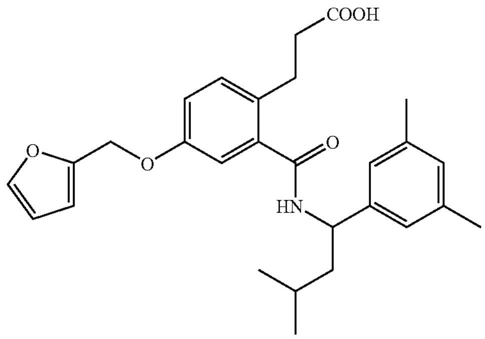

TLC: Rf 0.47 (chloroform:methanol=10:1).

Example 34(92)

3-(2-((3-methyl-1-(3,5-dimethylphenyl)butyl)carbamoyl)-4-(4-chloro-3-fluorobenzyloxy)phenyl) propanoic acid

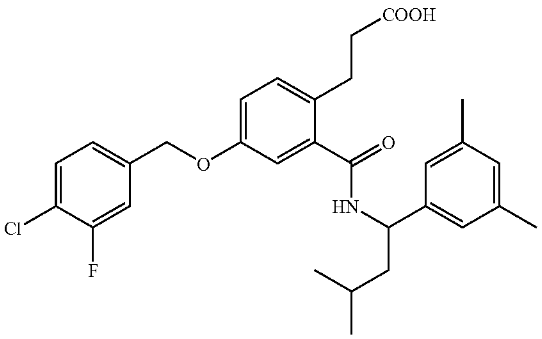

TLC: Rf 0.54 (n-hexane:ethyl acetate=1:1);

NMR (300 MHz, $CDCl_3$): δ 7.40 (m, 1H), 7.24-7.11 (m, 3H), 6.94-6.89 (m, 5H), 6.29 (d, J=9.0 Hz, 1H), 5.15 (m, 1H), 5.00 (s, 2H), 2.98-2.93 (m, 2H), 2.72-2.67 (m, 2H), 2.31 (s, 6H), 1.82-1.55 (m, 3H), 0.98 (d, J=6.3 Hz, 6H).

Example 34(93)

3-(2-((3-methyl-1-(3,5-dimethylphenyl)butyl)carbamoyl)-4-((3,5-dimethyl-4-benzyloxy)benzyloxy) phenyl)propanoic acid

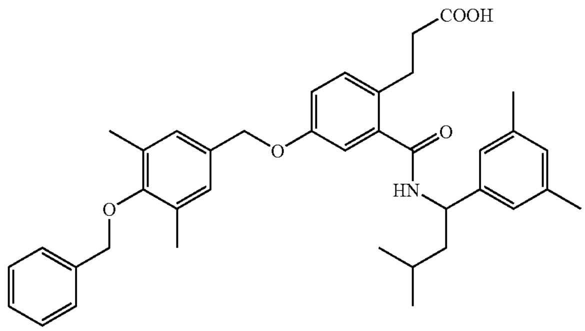

TLC: Rf 0.54 (n-hexane:ethyl acetate=1:1);

NMR (300 MHz, $CDCl_3$): δ 7.51-7.35 (m, 5H), 7.18 (m, 1H), 7.09 (brs, 2H), 6.98-6.90 (m, 5H), 6.25 (d, J=8.4 Hz, 1H), 5.15 (m, 1H), 4.92 (s, 2H), 4.81 (s, 2H), 3.00-2.95 (m, 2H), 2.76-2.70 (m, 2H), 2.32 (s, 6H), 2.31 (s, 6H), 1.82-1.56 (m, 3H), 0.98 (d, J=6.3 Hz, 6H).

Example 34(94)

4-(2-((1R)-1-(naphthalen-1-yl)ethylcarbamoyl)-4-(2,3,4,5,6-pentafluorophenoxy)phenyl)butanoic acid

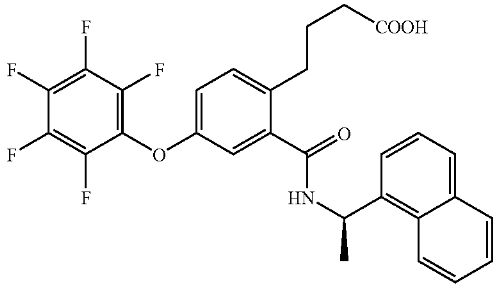

TLC: Rf 0.47 (chloroform:methanol=10:1).

Example 34(95)

3-(2-((3-methyl-1-(3,5-dimethylphenyl)butyl)carbamoyl)-4-(benzo[e]1,4-dioxan-6-yl)methyloxy) phenyl)propanoic acid

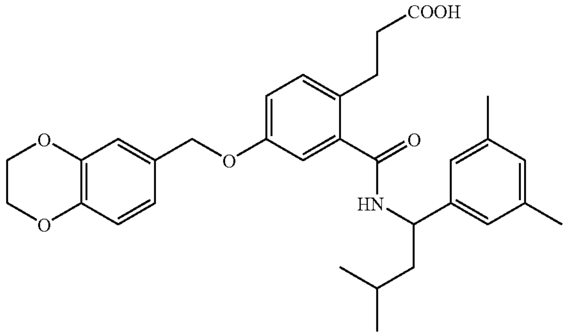

TLC: Rf 0.54 (n-hexane:ethyl acetate=1:1);

NMR (300 MHz, $CDCl_3$): δ 7.15 (m, 1H), 6.94-6.87 (m, 8H), 6.24 (d, J=8.7 Hz, 1H), 5.14 (m, 1H), 4.91 (s, 2H), 4.26 (s, 4H), 2.98-2.91 (m, 2H), 2.71-2.66 (m, 2H), 2.30 (s, 6H), 1.80-1.56 (m, 3H), 0.98 (d, J=6.0 Hz, 6H).

Example 34(96)

3-(2-((3-methyl-1-(3,5-dimethylphenyl)butyl)carbamoyl)-4-(2,4,6-trifluorobenzyloxy)phenyl)propanoic acid

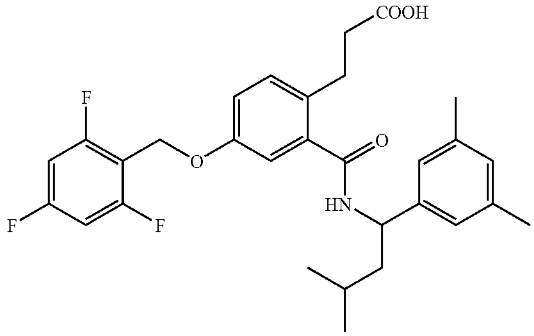

TLC: Rf 0.56 (chloroform:methanol=10:1);

NMR (300 MHz, $CDCl_3$): δ 7.20 (d, J=8.4 Hz, 1H), 7.00-6.95 (m, 4H), 6.91 (brs, 1H), 6.74-6.68 (m, 2H), 6.30 (brd, J=8.7 Hz, 1H), 5.15 (m, 1H), 5.04 (s, 2H), 2.99-2.94 (m, 2H), 2.73-2.68 (m, 2H), 2.31 (s, 6H), 1.83-1.55 (m, 3H), 0.98 (d, J=6.3 Hz, 6H).

Example 34(97)

3-(2-((3-methyl-1-(3,5-dimethylphenyl)butyl)carbamoyl)-4-(2-chloro-4,5-difluorobenzyloxy)phenyl)propanoic acid

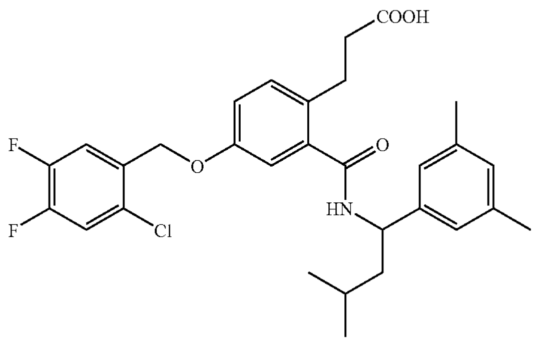

TLC: Rf 0.56 (chloroform:methanol=10:1);

NMR (300 MHz, $CDCl_3$): δ 7.39 (dd, J=10.8, 8.7 Hz, 1H), 7.28-7.18 (m, 2H), 6.95-6.91 (m, 5H), 6.33 (brd, J=8.7 Hz, 1H), 5.15 (m, 1H), 5.06 (s, 2H), 2.99-2.94 (m, 2H), 2.93-2.68 (m, 2H), 2.31 (s, 6H), 1.85-1.54 (m, 3H), 0.98 (d, J=6.3 Hz, 6H).

Example 34(98)

3-(2-((3-methyl-1-(3,5-dimethylphenyl)butyl)carbamoyl)-4-(3-fluoro-4-trifluoromethylbenzyloxy)phenyl)propanoic acid

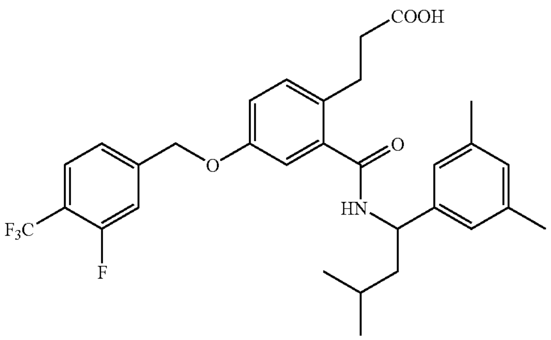

TLC: Rf 0.56 (chloroform:methanol=10:1);

NMR (300 MHz, $CDCl_3$): δ 7.61 (m, 1H), 7.30-7.25 (m, 2H), 7.18 (d, J=8.7 Hz, 1H), 6.95-6.89 (m, 5H), 6.35 (d, J=8.7 Hz, 1H), 5.15 (m, 1H), 5.08 (s, 2H), 2.98-2.93 (m, 2H), 2.72-2.67 (m, 2H), 2.31 (s, 6H), 1.83-1.55 (m, 3H), 0.98 (d, J=6.3 Hz, 6H).

Example 34(99)

3-(2-((3-methyl-1-(3,5-dimethylphenyl)butyl)carbamoyl)-4-(2-chloro-5-trifluoromethylbenzyloxy)phenyl)propanoic acid

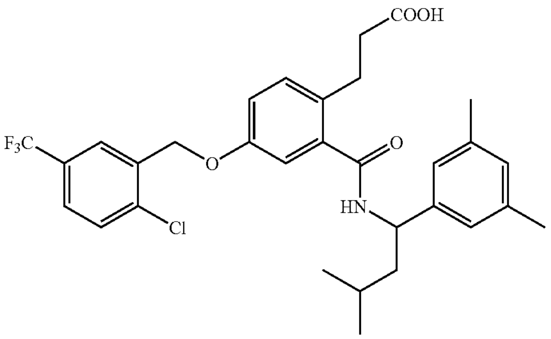

TLC: Rf 0.56 (chloroform:methanol=10:1);

NMR (300 MHz, $CDCl_3$): δ 7.85 (brs, 1H), 7.54-7.53 (m, 2H), 7.21 (m, 1H), 7.00-6.91 (m, 5H), 6.36 (brd, J=7.8 Hz, 1H), 5.16 (m, 1H), 5.15 (s, 2H), 3.00-2.94 (m, 2H), 2.74-2.68 (m, 2H), 2.31 (s, 6H), 1.84-1.56 (m, 3H), 0.98 (d, J=6.3 Hz, 6H).

Example 34(100)

3-(2-((3-methyl-1-(3,5-dimethylphenyl)butyl)carbamoyl)-4-(2,5-diethoxybenzyloxy)phenyl)propanoic acid

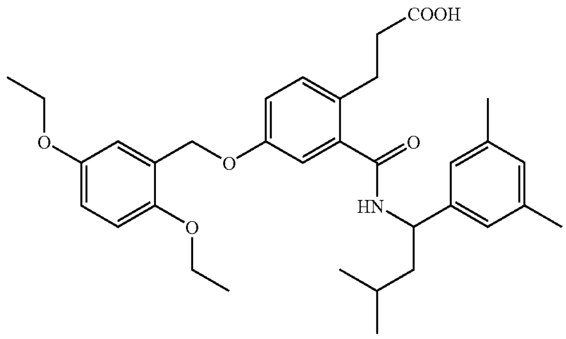

TLC: Rf 0.55 (n-hexane:ethyl acetate=1:2).

Example 34(101)

3-(2-((3-methyl-1-(3,5-dimethylphenyl)butyl)carbamoyl)-4-(3-cyano-4-fluorobenzyloxy)phenyl)propanoic acid

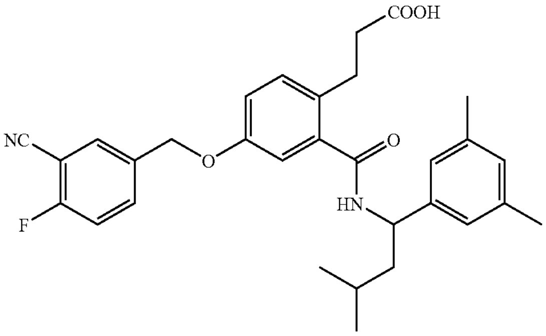

TLC: Rf 0.55 (n-hexane:ethyl acetate=1:2).

Example 34(102)

3-(2-((3-methyl-1-(3,5-dimethylphenyl)butyl)carbamoyl)-4-(3-ethoxybenzyloxy)phenyl)propanoic acid

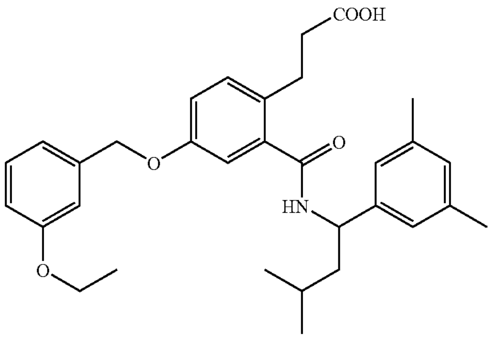

TLC: Rf 0.53 (n-hexane:ethyl acetate=1:2).

Example 34(103)

3-(2-((3-methyl-1-(3,5-dimethylphenyl)butyl)carbamoyl)-4-(4-benzyloxybenzyloxy)phenyl)propanoic acid

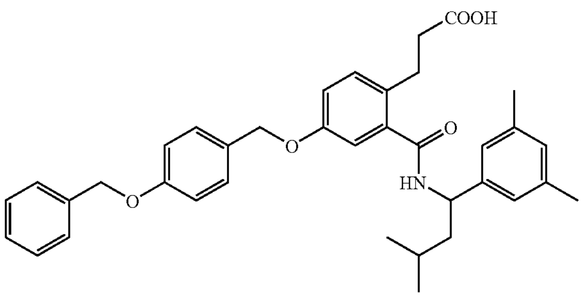

TLC: Rf 0.55 (n-hexane:ethyl acetate=1:2).

Example 34(104)

3-(2-((3-methyl-1-(3,5-dimethylphenyl)butyl)carbamoyl)-4-(2,3,4,5,6-pentafluorobenzyloxy)phenyl) propanoic acid

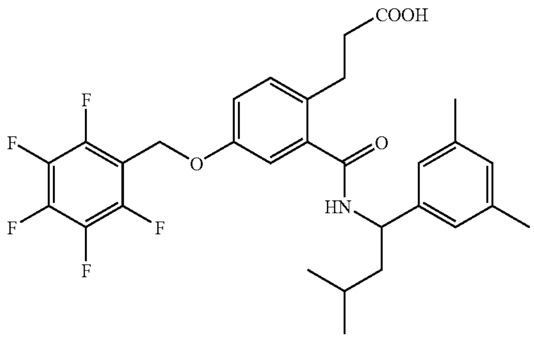

TLC: Rf 0.58 (n-hexane:ethyl acetate=1:2).

Example 34(105)

3-(2-((3-methyl-1-(3,5-dimethylphenyl)butyl)carbamoyl)-4-(2,5-bis(trifluoromethyl)benzyloxy)phenyl)propanoic acid

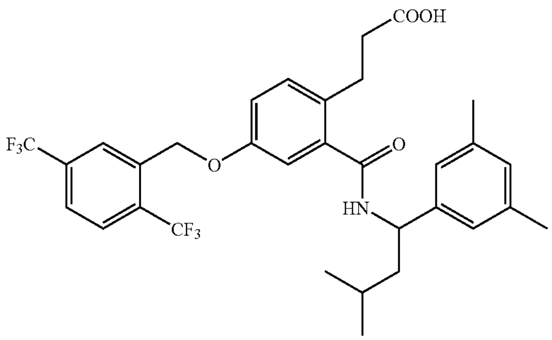

TLC: Rf 0.55 (n-hexane:ethyl acetate=1:2).

Example 34(106)

3-(2-((3-methyl-1-(3,5-dimethylphenyl)butyl)carbamoyl)-4-(2-methyl-5-fluorobenzyloxy)phenyl) propanoic acid

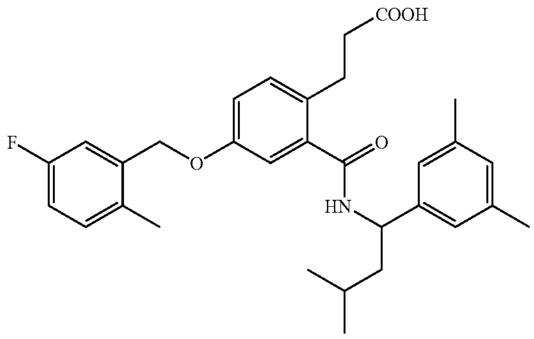

TLC: Rf 0.55 (n-hexane:ethyl acetate=1:2).

Example 34(107)

3-(2-((3-methyl-1-(3,5-dimethylphenyl)butyl)carbamoyl)-4-((4-methylnaphthalen-1-yl)methyloxy)phenyl)propanoic acid

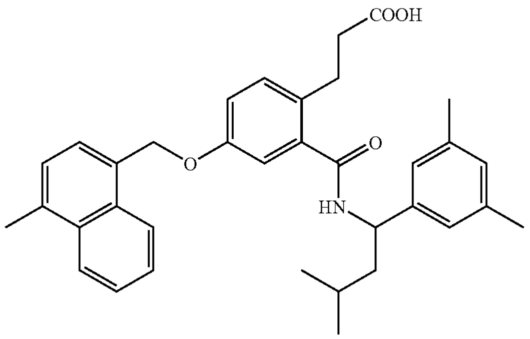

TLC: Rf 0.60 (n-hexane:ethyl acetate=1:2).

Example 34(108)

3-(2-((3-methyl-1-(3,5-dimethylphenyl)butyl)carbamoyl)-4-(4'-trifluoromethyl-1,1'-biphenyl-2-yl)methyloxy)phenyl)propanoic acid

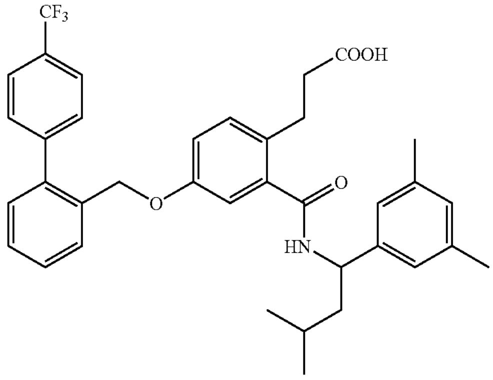

TLC: Rf 0.55 (n-hexane:ethyl acetate=1:2).

Example 34(109)

3-(2-((3-methyl-1-(3,5-dimethylphenyl)butyl)carbamoyl)-4-(2-phenylethoxy)phenyl)propanoic acid

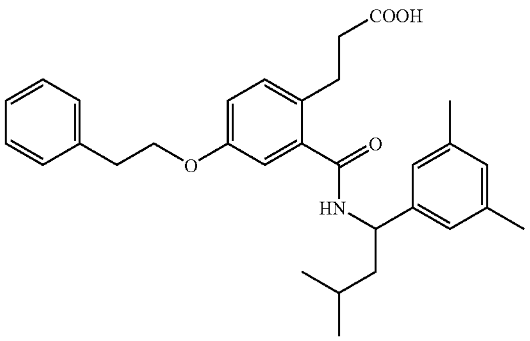

TLC: Rf 0.71 (chloroform:methanol=10:1);

NMR (300 MHz, $CDCl_3$): δ 0.98 (d, J=6.59 Hz, 6H) 1.71 (m, 3H) 2.30 (s, 6H) 2.68 (m, 2H) 2.94 (m, 2H) 3.08 (t, J=7.14 Hz, 2H) 4.16 (t, J=7.14 Hz, 2H) 5.13 (m, 1H) 6.26 (d, J=7.97 Hz, 1H) 6.90 (m, 5H) 7.15 (m, J=8.79 Hz, 1H) 7.29 (m, 5H).

Example 34(110)

3-(2-((3-methyl-1-(3,5-dimethylphenyl)butyl)carbamoyl)-4-(3-phenylpropoxy)phenyl)propanoic acid

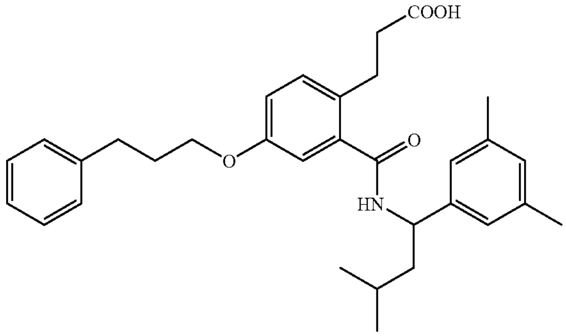

TLC: Rf 0.69 (chloroform:methanol=10:1).

Example 34(111)

3-(2-((3-methyl-1-(3,5-dimethylphenyl)butyl)carbamoyl)-4-(2-(5-methyl-2-phenyloxazol-4-yl)ethoxy)phenyl)propanoic acid

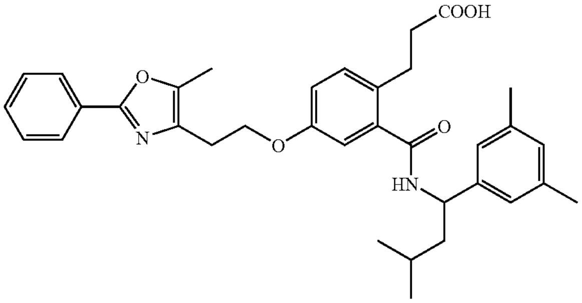

TLC: Rf 0.63 (chloroform:methanol=10:1).

Example 34(112)

3-(2-((3-methyl-1-(3,5-dimethylphenyl)butyl)carbamoyl)-4-(2-methyl-3-chlorobenzyloxy)phenyl)propanoic acid

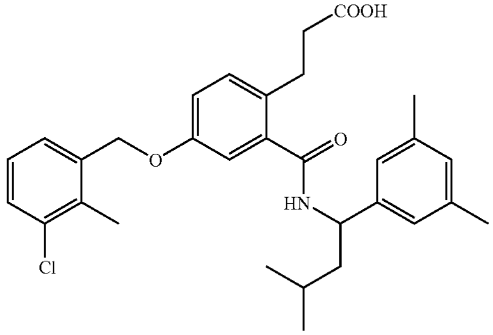

TLC: Rf 0.69 (chloroform:methanol=10:1).

Example 34(113)

3-(2-((3-methyl-1-(3,5-dimethylphenyl)butyl)carbamoyl)-4-(2-trifluoromethyloxybenzyloxy)phenyl) propanoic acid

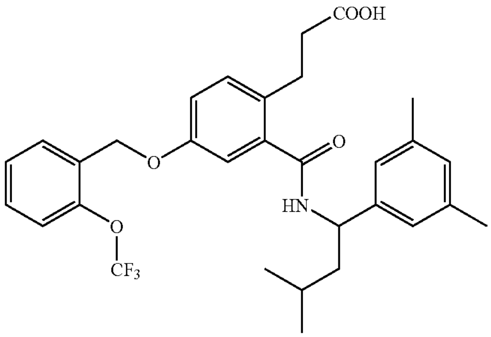

TLC: Rf 0.56 (chloroform:methanol=10:1).

Example 34(114)

3-(2-((3-methyl-1-(3,5-dimethylphenyl)butyl)carbamoyl)-4-(2,4-bis(trifluoromethyl)benzyloxy)phenyl)propanoic acid

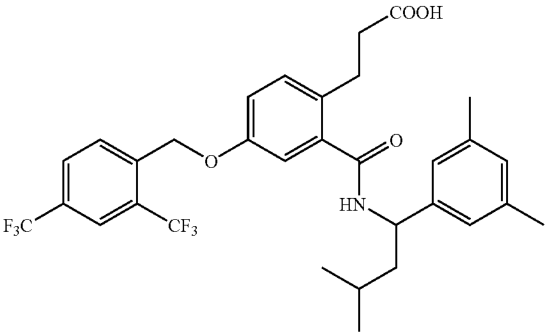

TLC: Rf 0.64 (chloroform:methanol=10:1).

Example 34(115)

3-(2-((3-methyl-1-(3,5-dimethylphenyl)butyl)carbamoyl)-4-(2-ethoxybenzyloxy)phenyl)propanoic acid

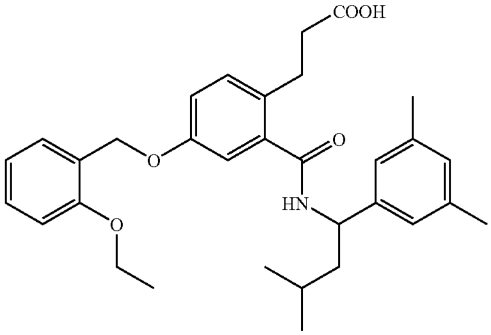

TLC: Rf 0.58 (chloroform:methanol=9:1);

NMR (300 MHz, $CDCl_3$): δ 7.40 (dd, J=7.8, 1.8 Hz, 1H), 7.27 (m, 1H), 7.17 (m, 1H), 7.03-6.84 (m, 7H), 6.22 (d, J=8.1 Hz, 1H), 5.14 (m, 1H), 5.10 (s, 2H), 4.06 (q, J=6.9 Hz, 2H), 3.02-2.89 (m, 2H), 2.70 (t, J=7.5 Hz, 2H), 2.31 (s, 6H), 1.83-1.51 (m, 3H), 1.40 (t, J=6.9 Hz, 3H), 0.98 (d, J=6.3 Hz, 6H).

Example 34(116)

3-(2-((3-methyl-1-(3,5-dimethylphenyl)butyl)carbamoyl)-4-(4-methylsulfonylbenzyloxy)phenyl)propanoic acid

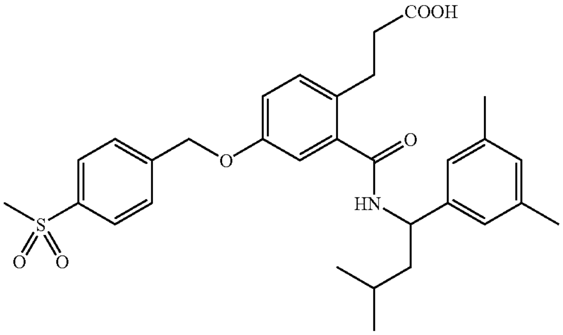

TLC: Rf 0.53 (chloroform:methanol=10:1).

Example 34(117)

3-(2-((3-methyl-1-(3,5-dimethylphenyl)butyl)carbamoyl)-4-(2,3,5,6-tetrafluorobenzyloxy)phenyl) propanoic acid

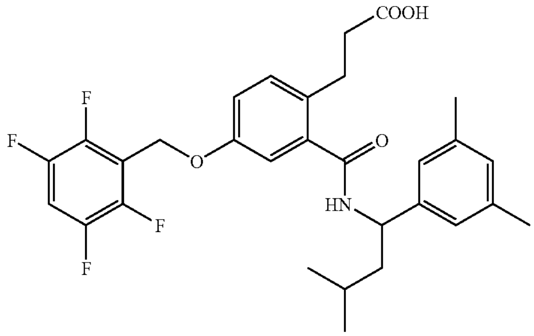

TLC: Rf 0.47 (chloroform:methanol=10:1).

Example 34(118)

3-(2-((3-methyl-1-(3,5-dimethylphenyl)butyl)carbamoyl)-4-(2-chloro-3,6-difluorobenzyloxy)phenyl) propanoic acid

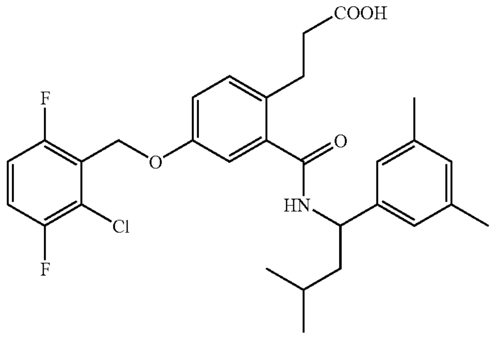

TLC: Rf 0.47 (chloroform:methanol=10:1);

NMR (300 MHz, $CDCl_3$): δ 0.98 (d, J=6.59 Hz, 6H) 1.70 (m, 3H) 2.31 (s, 6H) 2.72 (t, J=7.14 Hz, 2H) 2.97 (m, 2H) 5.16 (m, 1H) 5.16 (s, 2H) 6.27 (d, J=8.52 Hz, 1H) 7.00 (m, 6H) 7.18 (m, 2H).

Example 34(119)

3-(2-((3-methyl-1-(3,5-dimethylphenyl)butyl)carbamoyl)-4-(4-hexylbenzyloxy)phenyl)propanoic acid

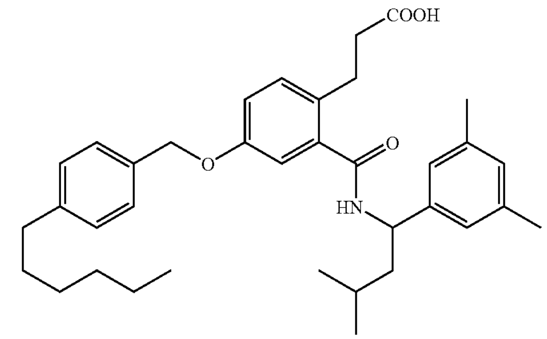

TLC: Rf 0.56 (chloroform:methanol=10:1);

NMR (300 MHz, $CDCl_3$): δ 7.32-7.30 (m, 2H), 7.20-7.15 (m, 3H), 6.97-6.90 (m, 5H), 6.22 (d, J=8.7 Hz, 1H), 5.14 (m, 1H), 4.99 (s, 2H), 2.98-2.93 (m, 2H), 2.71-2.66 (m, 2H), 2.63-2.58 (m, 2H), 2.30 (s, 6H), 1.80-1.56 (m, 5H), 1.37-1.28 (m, 6H), 0.98 (d, J=6.3 Hz, 3H), 0.97 (d, J=6.3 Hz, 3H), 0.90-0.86 (m, 3H).

Example 34(120)

3-(2-((3-methyl-1-(3,5-dimethylphenyl)butyl)carbamoyl)-4-(3,4-diethoxybenzyloxy)phenyl)propanoic acid

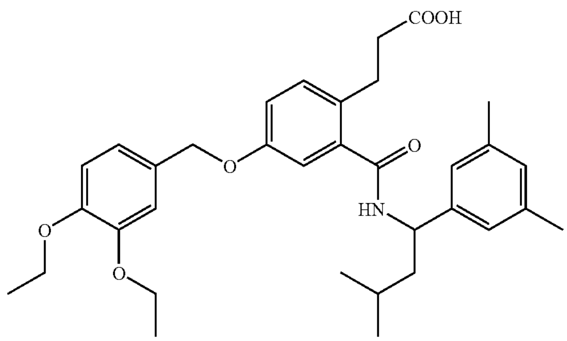

TLC: Rf 0.56 (chloroform:methanol=10:1);

NMR (300 MHz, $CDCl_3$): δ 7.17 (m, 1H), 6.97-6.85 (m, 8H), 6.25 (d, J=9.0 Hz, 1H), 5.14 (m, 1H), 4.94 (s, 2H), 4.09 (q, J=6.9 Hz, 4H), 2.99-2.93 (m, 2H), 2.72-2.68 (m, 2H), 2.31 (s, 6H), 1.82-1.55 (m, 3H), 1.45 (t, J=6.9 Hz, 3H), 1.44 (t, J=6.9 Hz, 3H).

Example 34(121)

3-(2-((3-methyl-1-(3,5-dimethylphenyl)butyl)carbamoyl)-4-(3-trifluoromethylthiobenzyloxy)phenyl)propanoic acid

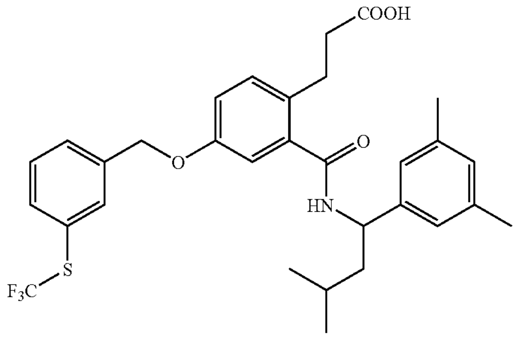

TLC: Rf 0.53 (chloroform:methanol=10:1).

Example 34(122)

3-(2-((3-methyl-1-(3,5-dimethylphenyl)butyl)carbamoyl)-4-(6-chloro-2-fluoro-3-methylbenzyloxy)phenyl)propanoic acid

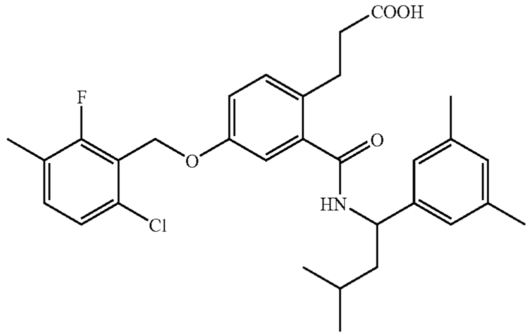

TLC: Rf 0.53 (chloroform:methanol=10:1);

NMR (300 MHz, $CDCl_3$): δ 0.98 (d, J=5.77 Hz, 6H) 1.68 (m, 3H) 2.27 (s, 3H) 2.30 (s, 6H) 2.71 (t, J=7.50 Hz, 2H) 2.98 (m, 2H) 5.15 (s, 2H) 5.16 (m, 1H) 6.25 (d, J=8.24 Hz, 1H) 6.99 (m, 5H) 7.17 (m, 3H).

Example 34(123)

3-(2-((3-methyl-1-(3,5-dimethylphenyl)butyl)carbamoyl)-4-(4-trifluoromethylthiobenzyloxy)phenyl)propanoic acid

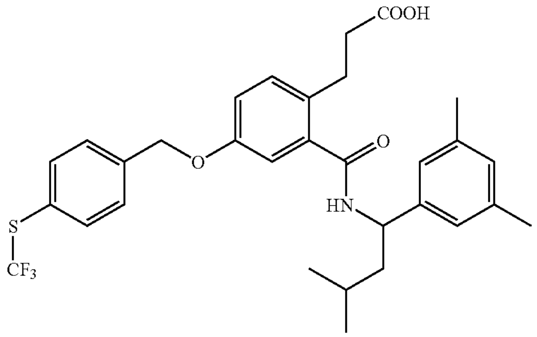

TLC: Rf 0.53 (chloroform:methanol=10:1).

Example 34(124)

3-(2-((3-methyl-1-(3,5-dimethylphenyl)butyl)carbamoyl)-4-(2-chloro-6-fluoro-3-methylbenzyloxy)phenyl)propanoic acid

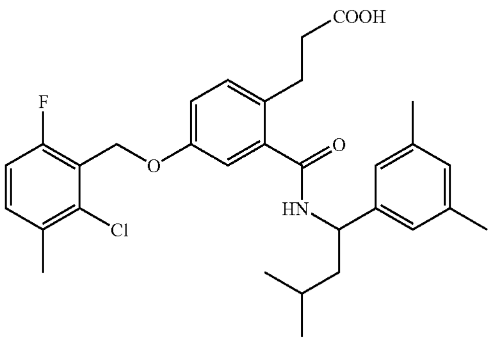

TLC: Rf 0.52 (chloroform:methanol=10:1);

NMR (300 MHz, $CDCl_3$): δ 0.98 (d, J=5.49 Hz, 6H) 1.69 (m, 3H) 2.27 (d, J=2.20 Hz, 3H) 2.31 (s, 6H) 2.72 (t, J=7.42 Hz, 2H) 2.98 (m, 2H) 5.14 (m, 1H) 5.15 (s, 2H) 6.26 (d, J=8.52 Hz, 1H) 7.00 (m, 5H) 7.17 (m, 3H).

Example 34(125)

3-(2-((3-methyl-1-(3,5-dimethylphenyl)butyl)carbamoyl)-4-(2-(4-chlorophenylthio)benzyloxy)phenyl)propanoic acid

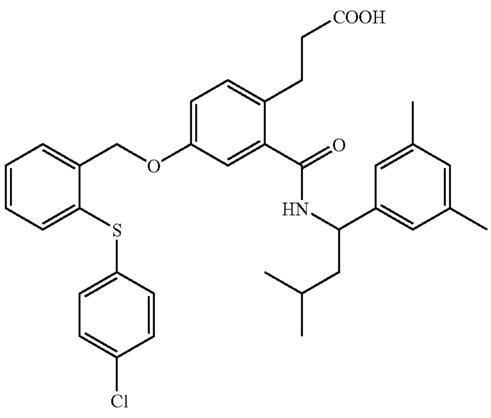

TLC: Rf 0.53 (chloroform:methanol=10:1);

NMR (300 MHz, $CDCl_3$): δ 0.99 (d, J=6.60 Hz, 6H) 1.69 (m, 3H) 2.31 (s, 6H) 2.70 (t, J=7.50 Hz, 2H) 2.95 (m, 2H) 5.13 (m, 2H) 5.14 (s, 1H) 6.23 (d, J=8.52 Hz, 1H) 6.90 (m, 5H) 7.13 (m, 3H) 7.22 (m, 2H) 7.35 (m, 3H) 7.56 (d, J=7.69 Hz, 1H).

Example 34(126)

4-(2-((1R)-1-(naphthalen-1-yl)ethylcarbamoyl)-4-(4-carbamoylphenoxy)phenyl)butanoic acid

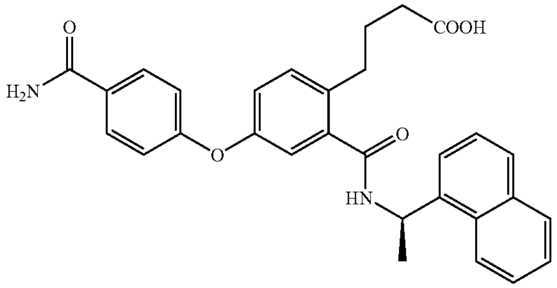

TLC: Rf 0.23 (chloroform:methanol=10:1).

Example 34(127)

4-(2-((1R)-1-(naphthalen-1-yl)ethylcarbamoyl)-4-(4-N-methylcarbamoylphenoxy)phenyl)butanoic acid

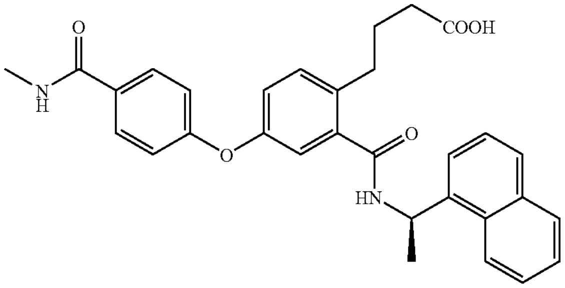

TLC: Rf 0.26 (chloroform:methanol=10:1).

Example 34(128)

4-(2-((1R)-1-(naphthalen-1-yl)ethylcarbamoyl)-4-(4-N,N-dimethylcarbamoylphenoxy)phenyl)butanoic acid

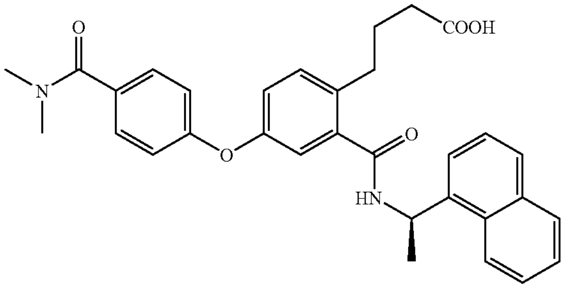

TLC: Rf 0.28 (chloroform:methanol=10:1).

Example 34(129)

3-(2-((3-methyl-1-(3,5-dimethylphenyl)butyl)carbamoyl)-4-(4-pentylbenzyloxy)phenyl)propanoic acid

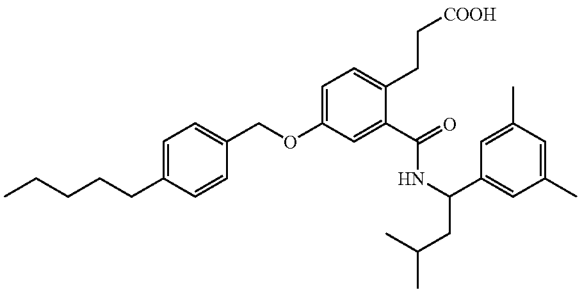

TLC: Rf 0.70 (chloroform:methanol=9:1).

Example 34(130)

3-(2-((3-methyl-1-(3,5-dimethylphenyl)butyl)carbamoyl)-4-(3-(4-methylphenoxy)benzyloxy)phenyl) propanoic acid

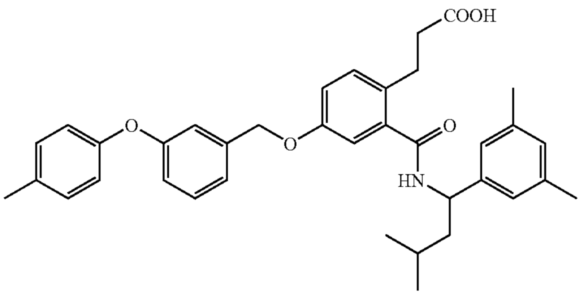

TLC: Rf 0.75 (chloroform:methanol=9:1).

Example 34(131)

3-(2-((3-methyl-1-(3,5-dimethylphenyl)butyl)carbamoyl)-4-(3-chloro-2-fluoro-6-trifluoromethylbenzyloxy)phenyl)propanoic acid

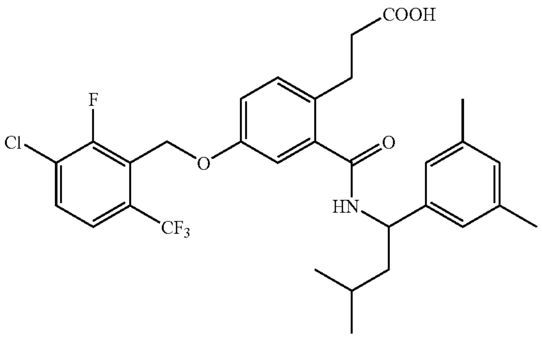

TLC: Rf 0.70 (chloroform:methanol=9:1).

Example 34(132)

3-(2-((3-methyl-1-(3,5-dimethylphenyl)butyl)carbamoyl)-4-(4-difluoromethoxybenzyloxy)phenyl) propanoic acid

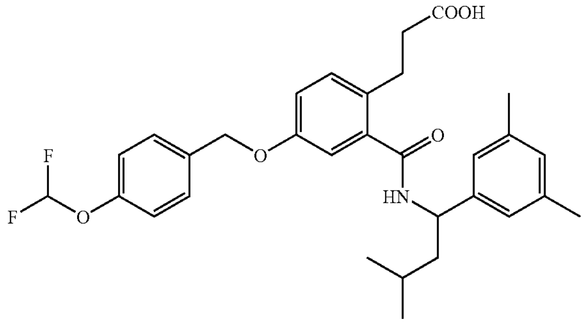

TLC: Rf 0.60 (chloroform:methanol=9:1).

Example 34(133)

3-(2-((3-methyl-1-(3,5-dimethylphenyl)butyl)carbamoyl)-4-(fluoren-2-ylmethyloxy)phenyl)propanoic acid

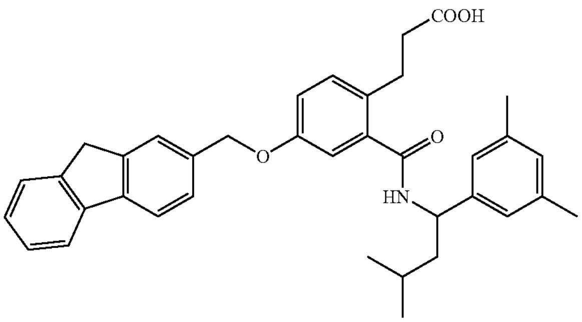

TLC: Rf 0.73 (chloroform:methanol=9:1).

Example 34(134)

3-(2-((3-methyl-1-(3,5-dimethylphenyl)butyl)carbamoyl)-4-(4-chloro-3-trifluoromethylbenzyloxy) phenyl)propanoic acid

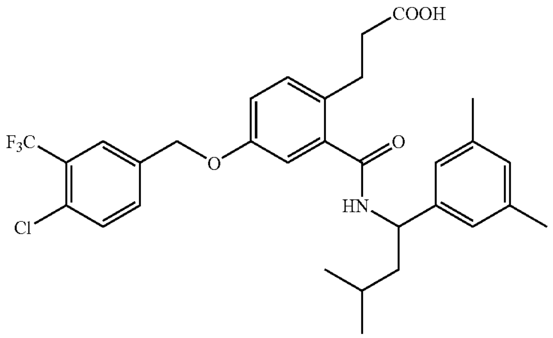

TLC: Rf 0.74 (chloroform:methanol=9:1).

Example 34(135)

3-(2-((3-methyl-1-(3,5-dimethylphenyl)butyl)carbamoyl)-4-(3-fluoro-2-methylbenzyloxy)phenyl) propanoic acid

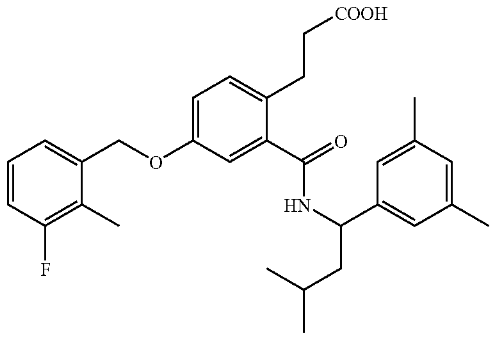

TLC: Rf 0.69 (chloroform:methanol=9:1).

Example 34(136)

3-(2-((3-methyl-1-(3,5-dimethylphenyl)butyl)carbamoyl)-4-(2,3,5-trifluorobenzyloxy)phenyl)propanoic acid

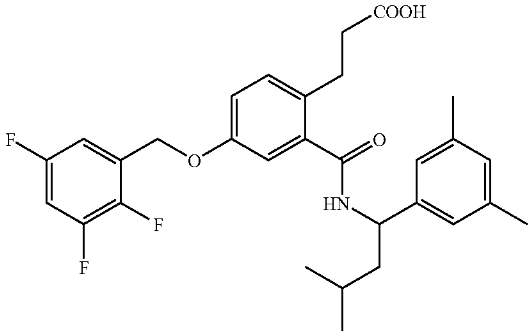

TLC: Rf 0.77 (chloroform:methanol=9:1).

Example 34(137)

3-(2-((3-methyl-1-(3,5-dimethylphenyl)butyl)carbamoyl)-4-(4-(pyridin-2-yl)benzyloxy)phenyl)propanoic acid

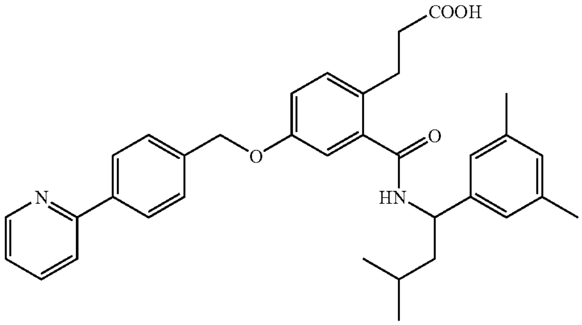

TLC: Rf 0.56 (chloroform:methanol=10:1);

NMR (300 MHz, $CDCl_3$): δ 8.70 (m, 1H), 7.98-7.96 (m, 2H), 7.81-7.70 (m, 2H), 7.49 (d, J=8.4 Hz, 2H), 7.25 (m, 1H), 7.16 (d, J=8.7 Hz, 1H), 6.99-6.89 (m, 5H), 6.41 (d, J=8.4 Hz, 1H), 5.14 (m, 1H), 5.10 (s, 2H), 2.96-2.93 (m, 2H), 2.72-2.67 (m, 2H), 2.29 (s, 6H), 1.80-1.52 (m, 3H), 0.97 (d, J=6.3 Hz, 3H), 0.96 (d, J=6.3 Hz, 3H).

Example 34(138)

3-(2-((3-methyl-1-(3,5-dimethylphenyl)butyl)carbamoyl)-4-(3-(4-t-butylphenoxy)benzyloxy)phenyl) propanoic acid

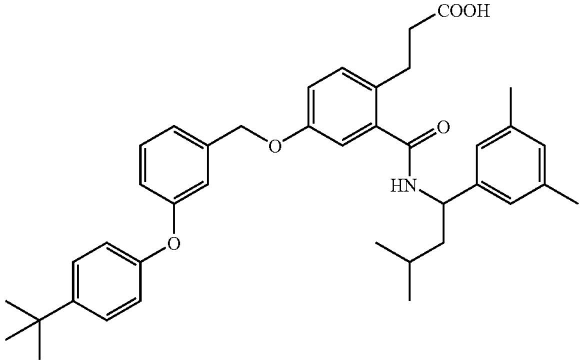

TLC: Rf 0.56 (chloroform:methanol=10:1);

NMR (300 MHz, $CDCl_3$): δ 7.36-7.26 (m, 3H), 7.18-7.07 (m, 3H), 6.95-6.90 (m, 8H), 6.24 (brd, J=8.3 Hz, 1H), 5.14 (m, 1H), 5.00 (s, 2H), 2.99-2.93 (m, 2H), 2.72-2.67 (m, 2H), 2.30 (s, 6H), 1.82-1.55 (m, 3H), 1.32 (s, 9H), 0.98 (d, J=6.3 Hz, 6H).

Example 34(139)

3-(2-((3-methyl-1-(3,5-dimethylphenyl)butyl)carbamoyl)-4-(4-ethylthiobenzyloxy)phenyl)propanoic acid

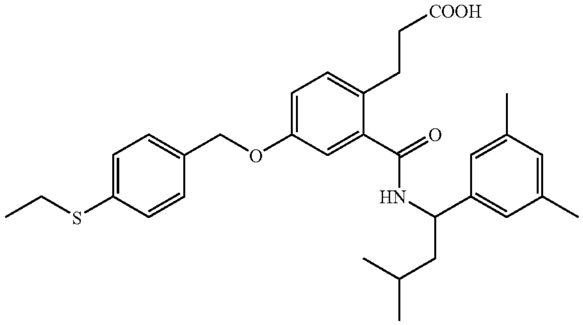

TLC: Rf 0.56 (chloroform:methanol=10:1);

NMR (300 MHz, $CDCl_3$): δ 7.32 (s, 3H), 7.18-7.15 (m, 2H), 6.95-6.90 (m, 5H), 6.25 (brd, J=8.4 Hz, 1H), 5.14 (m, 1H), 4.99 (s, 2H), 2.99-2.92 (m, 4H), 2.72-2.67 (m, 2H), 2.31 (s, 6H), 1.82-1.56 (m, 3H), 1.32 (t, J=7.2 Hz, 3H), 0.98 (t, J=6.3 Hz, 6H).

Example 34(140)

3-(2-((3-methyl-1-(3,5-dimethylphenyl)butyl)carbamoyl)-4-(4-(4-fluorobenzyloxy)benzyloxy)phenyl) propanoic acid

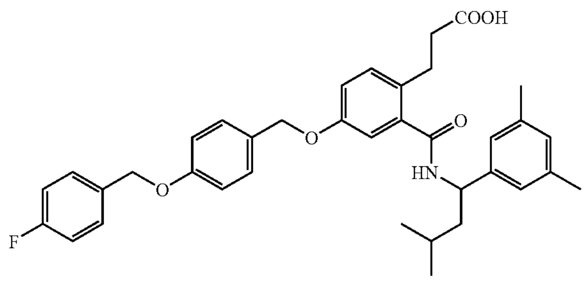

TLC: Rf 0.56 (chloroform:methanol=10:1);

NMR (300 MHz, $CDCl_3$): δ 7.42-7.38 (m, 2H), 7.35-7.32 (m, 2H), 7.16 (m, 1H), 7.10-7.04 (m, 2H), 6.98-6.90 (m, 7H), 6.25 (d, J=8.5 Hz, 1H), 5.14 (m, 1H), 5.03 (s, 2H), 4.96 (s, 2H), 2.98-2.93 (m, 2H), 2.72-2.67 (m, 2H), 2.30 (s, 6H), 1.82-1.55 (m, 3H), 0.98 (d, J=6.3 Hz, 3H), 0.97 (d, J=6.3 Hz, 3H).

Example 34(141)

4-(2-((3-methyl-1-(3,5-dimethylphenyl)butyl)carbamoyl)-4-phenoxyphenyl)butanoic acid

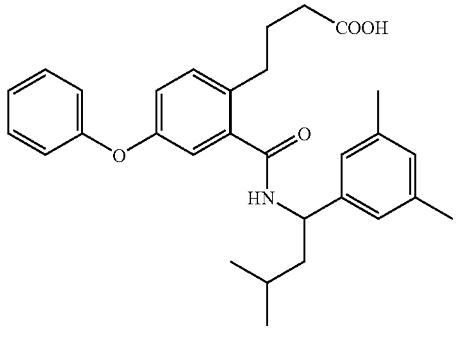

TLC: Rf 0.59 (chloroform:methanol=9:1);

NMR (300 MHz, $CDCl_3$): δ 7.38-7.30 (m, 2H), 7.17 (d, J=8.4 Hz, 1H), 7.12 (t, J=7.4 Hz, 1H), 7.02-6.88 (m, 7H), 5.91 (d, J=8.7 Hz, 1H), 5.12 (m, 1H), 2.73 (t, J=7.7 Hz, 2H), 2.30 (t, J=7.5 Hz, 2H), 2.29 (s, 6H), 1.97-1.49 (m, 5H), 0.97 (d, J=6.6 Hz, 3H), 0.96 (d, J=6.6 Hz, 3H).

Example 34(142)

4-(2-((1R)-1-(naphthalen-1-yl)ethylcarbamoyl)-4-(2-cyanophenoxy)phenyl)butanoic acid

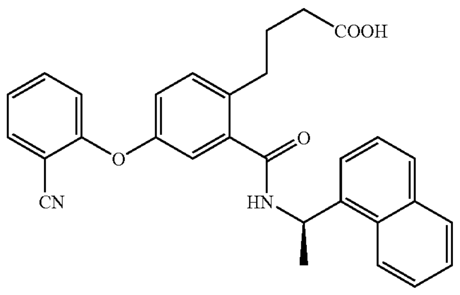

TLC: Rf 0.48 (chloroform:methanol=10:1).

Example 34(143)

3-(2-((3-methyl-1-(3,5-dimethylphenyl)butyl)carbamoyl)-4-(3-(3-trifluoromethylphenoxy)benzyloxy) phenyl)propanoic acid

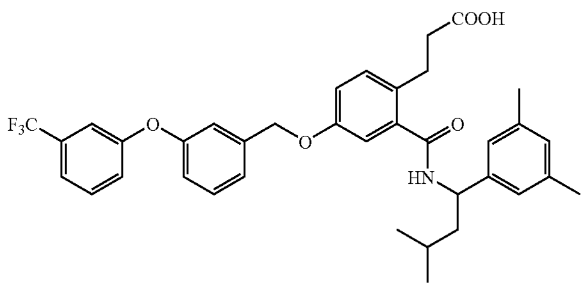

TLC: Rf 0.70 (chloroform:methanol=9:1).

Example 34(144)

3-(2-((3-methyl-1-(3,5-dimethylphenyl)butyl)carbamoyl)-4-(3-chloro-2-fluoro-5-trifluoromethylbenzyloxy)phenyl)propanoic acid

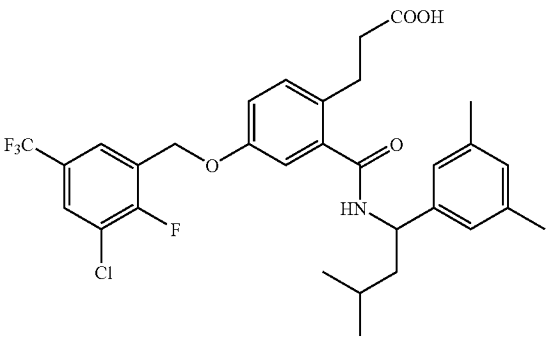

TLC: Rf 0.66 (chloroform:methanol=9:1).

Example 34(145)

3-(2-((3-methyl-1-(3,5-dimethylphenyl)butyl)carbamoyl)-4-(2,3-dimethylbenzyloxy)phenyl)propanoic acid

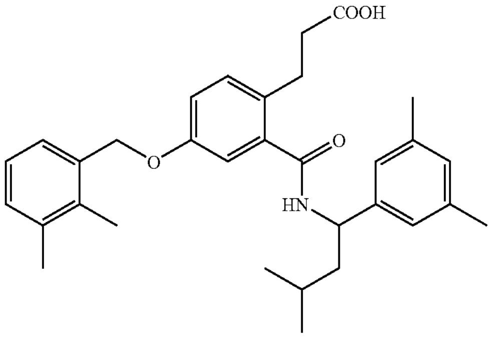

TLC: Rf 0.66 (chloroform:methanol=9:1).

Example 34(146)

3-(2-((3-methyl-1-(3,5-dimethylphenyl)butyl)carbamoyl)-4-(2,3-difluoro-4-methylbenzyloxy)phenyl) propanoic acid

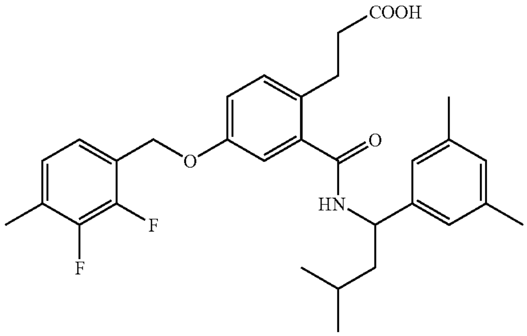

TLC: Rf 0.36 (methylene chloride:methanol=9:1).

Example 34(147)

3-(2-((3-methyl-1-(3,5-dimethylphenyl)butyl)carbamoyl)-4-(3-chloro-2-fluorobenzyloxy)phenyl) propanoic acid

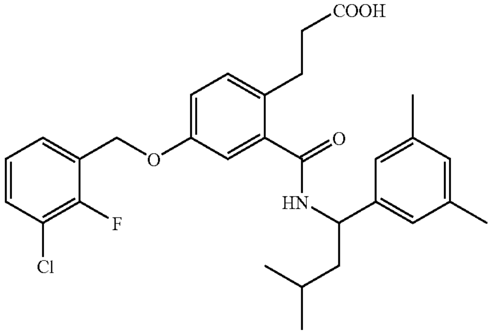

TLC: Rf 0.33 (methylene chloride:methanol=9:1).

Example 34(148)

3-(2-((3-methyl-1-(3,5-dimethylphenyl)butyl)carbamoyl)-4-(3-chloro-2,6-difluorobenzyloxy)phenyl) propanoic acid

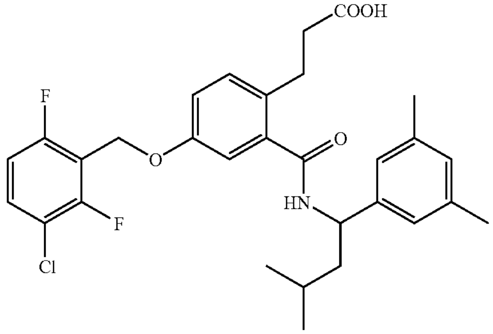

TLC: Rf 0.33 (methylene chloride:methanol=9:1);

NMR (300 MHz, $CDCl_3$): δ 0.98 (d, J=6.04 Hz, 6H) 1.69 (m, 3H) 2.30 (s, 6H) 2.69 (t, J=7.14 Hz, 2H) 2.96 (m, 2H) 5.15 (m, 3H) 6.29 (d, J=8.52 Hz, 1H) 6.94 (m, 6H) 7.20 (d, J=8.79 Hz, 1H) 7.41 (m, 1H).

Example 34(149)

3-(2-((3-methyl-1-(3,5-dimethylphenyl)butyl)carbamoyl)-4-(3,4,5-trifluorobenzyloxy)phenyl)propanoic acid

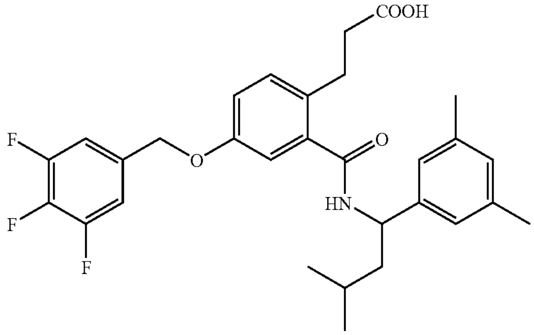

TLC: Rf 0.35 (methylene chloride:methanol=9:1).

Example 34(150)

3-(2-((3-methyl-1-(3,5-dimethylphenyl)butyl)carbamoyl)-4-(4-fluoro-3-methylbenzyloxy)phenyl) propanoic acid

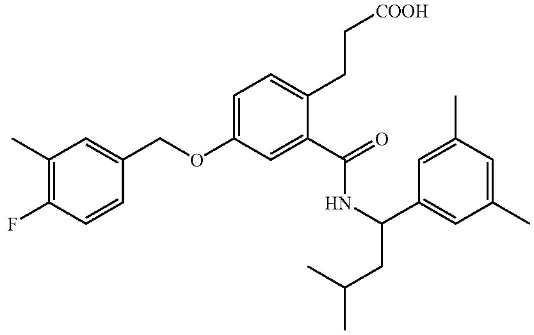

TLC: Rf 0.35 (methylene chloride:methanol=9:1).

Example 34(151)

3-(2-((3-methyl-1-(3,5-dimethylphenyl)butyl)carbamoyl)-4-(3-(4-chlorophenoxy)benzyloxy)phenyl) propanoic acid

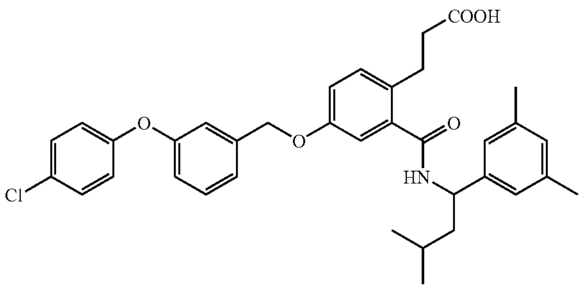

TLC: Rf 0.35 (methylene chloride:methanol=9:1).

Example 34(152)

3-(2-((3-methyl-1-(3,5-dimethylphenyl)butyl)carbamoyl)-4-(4-(4-propylphenyl)benzyloxy)phenyl) propanoic acid

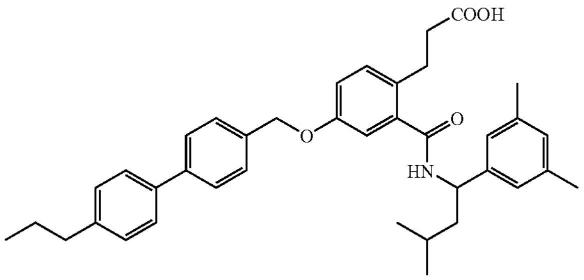

TLC: Rf 0.56 (chloroform:methanol=9:1).

Example 34(153)

3-(2-((3-methyl-1-(3,5-dimethylphenyl)butyl)carbamoyl)-4-(2-phenoxybenzyloxy)phenyl)propanoic acid

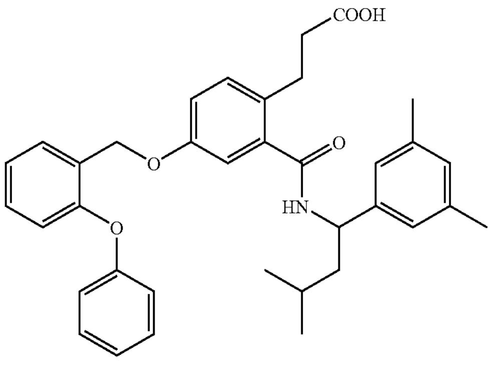

TLC: Rf 0.53 (chloroform:methanol=9:1).

Example 34(154)

3-(2-((3-methyl-1-(3,5-dimethylphenyl)butyl)carbamoyl)-4-(5-chloro-2-methoxybenzyloxy)phenyl) propanoic acid

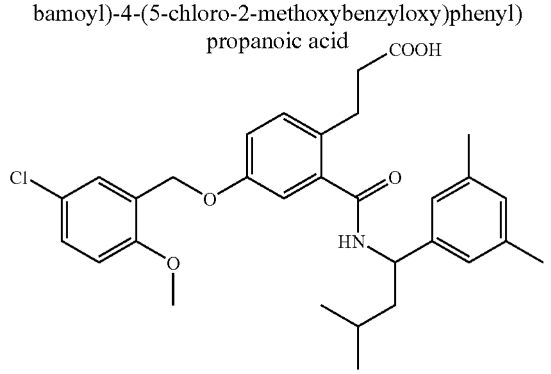

TLC: Rf 0.51 (chloroform:methanol=9:1);

NMR (300 MHz, $CDCl_3$): δ 0.98 (d, J=6.32 Hz, 6H) 1.68 (m, 3H) 2.31 (s, 6H) 2.71 (m, 2H) 2.97 (m, 2H) 3.82 (s, 3H) 5.03 (s, 2H) 5.15 (m, 1H) 6.28 (d, J=8.24 Hz, 1H) 6.82 (d, J=8.79 Hz, 1H) 6.95 (m, 5H) 7.18 (d, J=8.24 Hz, 1H) 7.23 (d, J=2.75 Hz, 1H) 7.42 (d, J=2.47 Hz, 1H).

Example 34(155)

3-(2-((3-methyl-1-(3,5-dimethylphenyl)butyl)carbamoyl)-4-(3-dimethylaminobenzyloxy)phenyl)propanoic acid

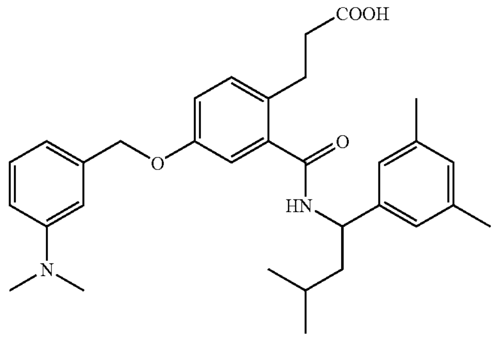

TLC: Rf 0.44 (chloroform:methanol=9:1).

Example 34(156)

3-(2-((3-methyl-1-(3,5-dimethylphenyl)butyl)carbamoyl)-4-(2-chloro-5-methylthiobenzyloxy)phenyl) propanoic acid

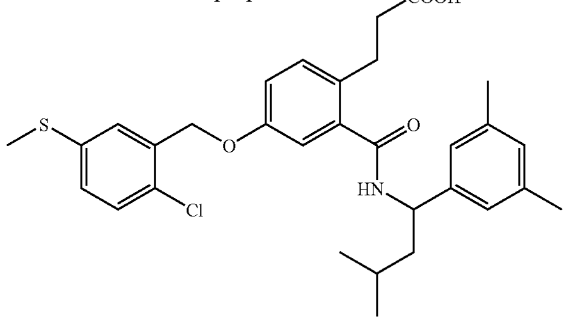

TLC: Rf 0.44 (chloroform:methanol=9:1).

Example 34(157)

4-(2-((1R)-1-(naphthalen-1-yl)ethylcarbamoyl)-4-(2-nitrophenoxy)phenyl)butanoic acid

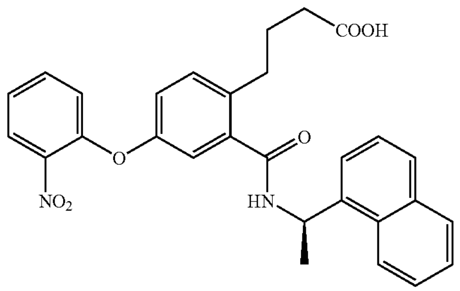

TLC: Rf 0.52 (chloroform:methanol=10:1);

NMR (300 MHz, $CDCl_3$): δ 1.78 (d, J=6.32 Hz, 3H), 1.93 (m, 2H), 2.30 (m, 2H), 2.78 (m, 2H), 6.10 (m, 2H), 6.96 (m, 3H), 7.21 (m, 2H), 7.49 (m, 5H), 7.81 (d, J=7.97 Hz, 1H), 7.87 (dd, J=7.20, 1.80 Hz, 1H), 7.93 (dd, J=8.10, 1.51 Hz, 1H), 8.20 (d, J=7.97 Hz, 1H).

Example 34(158)

4-(2-((1R)-1-(naphthalen-1-yl)ethylcarbamoyl)-4-(2-aminophenoxy)phenyl)butanoic acid

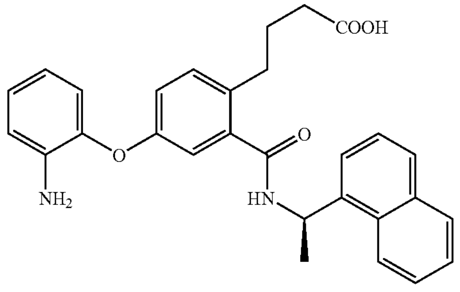

TLC: Rf 0.46 (chloroform:methanol=10:1);

NMR (300 MHz, $CDCl_3$): δ 1.77 (d, J=6.04 Hz, 3H), 1.91 (m, 2H), 2.27 (m, 2H), 2.75 (m, 2H), 6.09 (m, 2H), 6.68 (m, 1H), 6.81 (m, 3H), 6.96 (m, 2H), 7.11 (d, J=8.52 Hz, 1H), 7.50 (m, 4H), 7.81 (d, J=7.97 Hz, 1H), 7.87 (m, 1H), 8.19 (d, J=7.69 Hz, 1H).

Example 34(159)

4-(2-((1R)-1-(naphthalen-1-yl)ethylcarbamoyl)-4-(2-acetylaminophenoxy)phenyl)butanoic acid

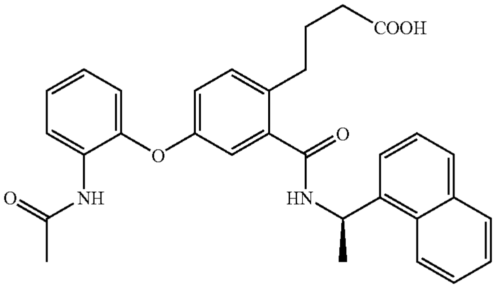

TLC: Rf 0.40 (chloroform:methanol=10:1);

NMR (300 MHz, DMSO-$d_6$): δ 1.55 (d, J=6.87 Hz, 3H), 1.70 (m, 2H), 1.99 (s, 3H), 2.09 (m, 2H), 2.62 (m, 2H), 5.87 (m, 1H), 6.91 (m, 3H), 7.10 (m, 2H), 7.21 (d, J=8.24 Hz, 1H), 7.52 (m, 4H), 7.82 (d, J=7.97 Hz, 1H), 7.93 (m, 2H), 8.20 (d, J=8.24 Hz, 1H), 8.94 (d, J=7.97 Hz, 1H), 9.44 (s, 1H), 12.01 (s, 1H).

Example 34(160)

4-(2-((1R)-1-(naphthalen-1-yl)ethylcarbamoyl)-4-(2-methylsulfonylaminophenoxy)phenyl)butanoic acid

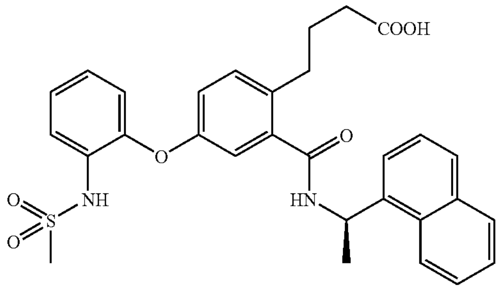

TLC: Rf 0.41 (chloroform:methanol=10:1);

NMR (300 MHz, $CDCl_3$): δ 1.78 (d, J=6.59 Hz, 3H), 1.90 (m, 2H), 2.27 (m, 2H), 2.76 (m, 2H), 2.90 (s, 3H), 6.10 (m, 1H), 6.22 (d, J=8.40 Hz, 1H), 6.77 (s, 1H), 6.88 (m, 3H), 7.13 (m, 3H), 7.51 (m, 5H), 7.81 (d, J=8.24 Hz, 1H), 7.88 (m, 1H), 8.18 (m, 1H).

Example 34(161)

4-(2-((1R)-1-(naphthalen-1-yl)ethylcarbamoyl)-4-(4-methoxyphenoxy)phenyl)butanoic acid

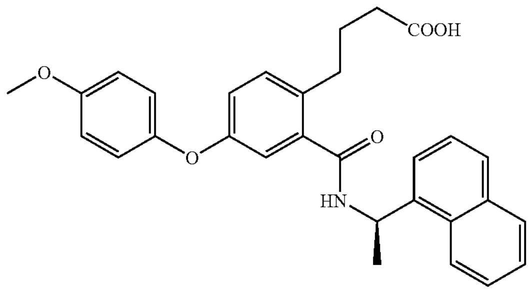

TLC: Rf 0.15 (n-hexane:ethyl acetate=1:1);

NMR (300 MHz, $CDCl_3$): δ 8.18 (m, 1H), 7.87 (m, 1H), 7.80 (d, J=8.4 Hz, 1H), 7.56-7.42 (m, 4H), 7.11 (d, J=8.4 Hz, 1H), 6.92-6.83 (m, 6H), 6.09 (m, 1H), 5.99 (brd, J=8.4 Hz, 1H), 3.80 (s, 3H), 2.83-2.67 (m, 2H), 2.32-2.67 (m, 2H), 1.95-1.86 (m, 2H), 1.76 (d, J=6.6 Hz, 3H).

Example 34(162)

4-(2-((1R)-1-(naphthalen-1-yl)ethylcarbamoyl)-4-(4-fluorophenoxy)phenyl)butanoic acid

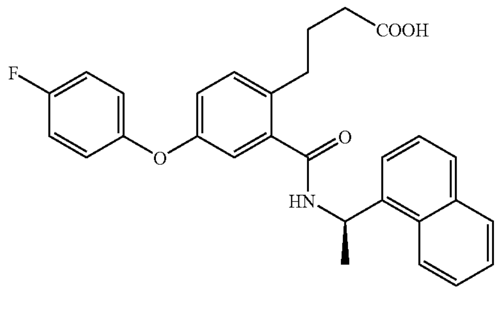

TLC: Rf 0.19 (n-hexane:ethyl acetate=1:1);

NMR (300 MHz, $CDCl_3$): δ 8.18 (m, 1H), 7.88 (m, 1H), 7.81 (d, J=8.1 Hz, 1H), 7.55-7.42 (m, 4H), 7.14 (m, 1H), 7.02-6.92 (m, 2H), 6.90-6.86 (m, 4H), 6.09 (m, 1H), 5.98 (brd, J=7.8 Hz, 1H), 2.85-2.68 (m, 2H), 2.39-2.22 (m, 2H), 1.96-1.87 (m, 2H), 1.77 (d, J=6.6 Hz, 3H).

Example 34(163)

4-(2-((1R)-1-(naphthalen-1-yl)ethylcarbamoyl)-4-(3-fluorophenoxy)phenyl)butanoic acid

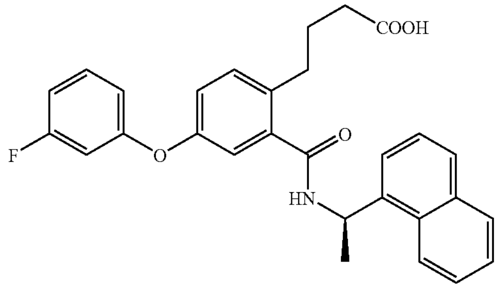

TLC: Rf 0.22 (n-hexane:ethyl acetate=1:1);

NMR (300 MHz, $CDCl_3$): δ 8.19 (d, J=8.1 Hz, 1H), 7.86 (m, 1H), 7.81 (d, J=7.8 Hz, 1H), 7.55-7.42 (m, 4H), 7.27-7.17 (m, 2H), 6.96-6.94 (m, 2H), 6.78 (m, 1H), 6.69 (m, 1H), 6.63 (m, 1H), 6.11 (m, 1H), 6.02 (m, 1H), 2.83-2.73 (m, 2H), 2.35-2.28 (m, 2H), 1.98-1.88 (m, 2H), 1.78 (d, J=6.6 Hz, 3H).

Example 34(164)

4-(2-((1R)-1-(naphthalen-1-yl)ethylcarbamoyl)-4-(3-methoxyphenoxy)phenyl)butanoic acid

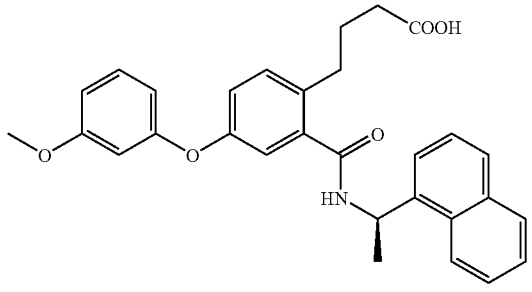

TLC: Rf 0.25 (n-hexane:ethyl acetate=1:1);

NMR (300 MHz, $CDCl_3$): δ 8.19 (d, J=8.1 Hz, 1H), 7.87 (m, 1H), 7.81 (d, J=7.8 Hz, 1H), 7.57-7.42 (m, 4H), 7.22-7.15 (m, 2H), 6.95-6.91 (m, 2H), 6.64 (m, 1H), 6.51-6.49 (m, 2H), 6.10 (m, 1H), 6.01 (brd, J=8.4 Hz, 1H), 3.75 (s, 3H), 2.85-2.70 (m, 2H), 2.34-2.28 (m, 2H), 1.97-1.88 (m, 2H), 1.77 (d, J=6.6 Hz, 3H).

Example 34(165)

3-(2-((3-methyl-1-(3,5-dimethylphenyl)butyl)carbamoyl)-4-(4-chloro-2,6-difluorobenzyloxy)phenyl)propanoic acid

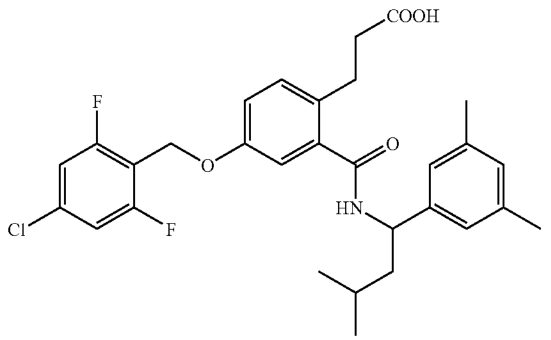

TLC: Rf 0.62 (chloroform:methanol=9:1).

Example 34(166)

3-(2-((3-methyl-1-(3,5-dimethylphenyl)butyl)carbamoyl)-4-(2-ethylbenzyloxy)phenyl)propanoic acid

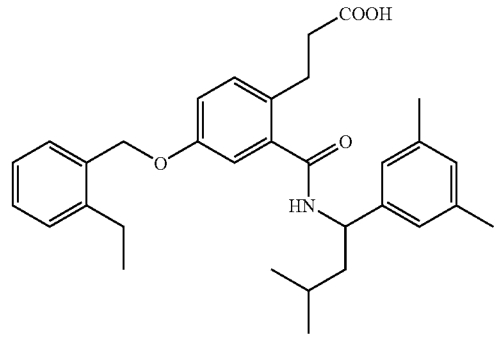

TLC: Rf 0.62 (chloroform:methanol=9:1).

Example 34(167)

3-(2-((3-methyl-1-(3,5-dimethylphenyl)butyl)carbamoyl)-4-(4-chloro-2-methoxybenzyloxy)phenyl)propanoic acid

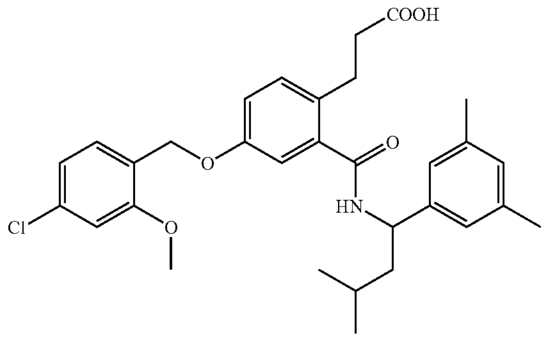

TLC: Rf 0.62 (chloroform:methanol=9:1).

Example 34(168)

3-(2-((3-methyl-1-(3,5-dimethylphenyl)butyl)carbamoyl)-4-(4-methyl-3-methoxybenzyloxy)phenyl) propanoic acid

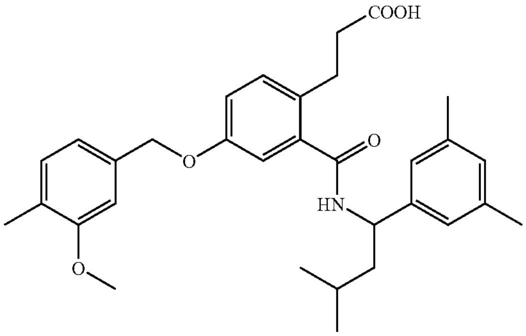

TLC: Rf 0.62 (chloroform:methanol=9:1).

Example 34(169)

3-(2-((3-methyl-1-(3,5-dimethylphenyl)butyl)carbamoyl)-4-(2-methyl-4-methoxybenzyloxy)phenyl) propanoic acid

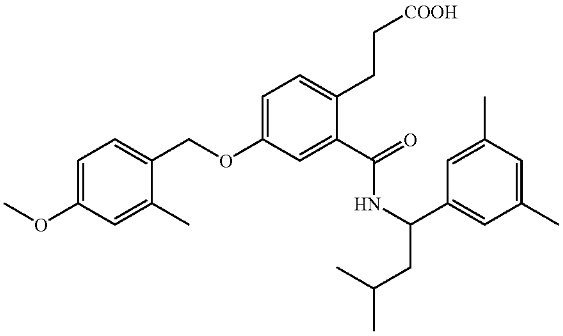

TLC: Rf 0.62 (chloroform:methanol=9:1).

Example 34(170)

4-(2-(3-methyl-1-phenylbutyl)carbamoyl)-4-phenoxyphenyl)butanoic acid

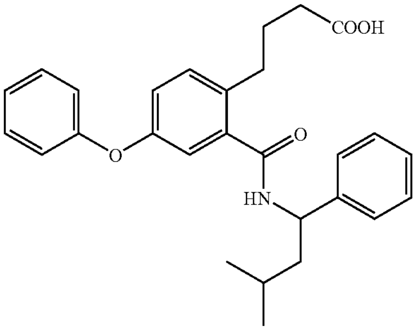

TLC: Rf 0.31 (n-hexane:ethyl acetate=1:1);

NMR (300 MHz, $CDCl_3$): δ 0.97 (d, J=6.32 Hz, 6H), 1.74 (m, 5H), 2.29 (m, 2H), 2.71 (m, 2H), 5.20 (m, 1H), 5.97 (d, J=8.52 Hz, 1H), 6.96 (m, 4H), 7.14 (m, 2H), 7.31 (m, 7H).

Example 34(171)

4-(2-((1R)-1-(naphthalen-1-yl)ethylcarbamoyl)-4-(2-fluorophenoxy)phenyl)butanoic acid

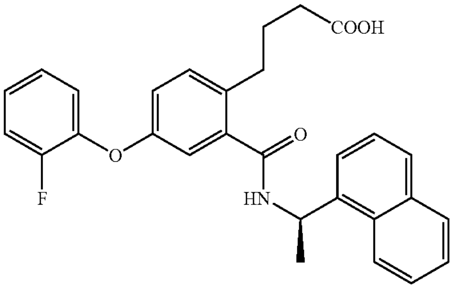

TLC: Rf 0.24 (n-hexane:ethyl acetate=1:1);

NMR (300 MHz, $CDCl_3$): δ 8.18 (m, 1H), 7.86 (m, 1H), 7.80 (d, J=8.0 Hz, 1H), 7.56-7.41 (m, 4H), 7.18-7.03 (m, 4H), 7.01 (m, 1H), 6.92 (d, J=2.8 Hz, 1H), 6.85 (dd, J=8.5, 2.8 Hz, 1H), 6.13-6.04 (m, 2H), 2.83-2.67 (m, 2H), 2.38-2.20 (m, 2H), 1.94-1.86 (m, 2H), 1.76 (d, J=6.3 Hz, 3H).

Example 34(172)

4-(2-((1R)-1-(naphthalen-1-yl)ethylcarbamoyl)-4-cyclohexyloxyphenyl)butanoic acid

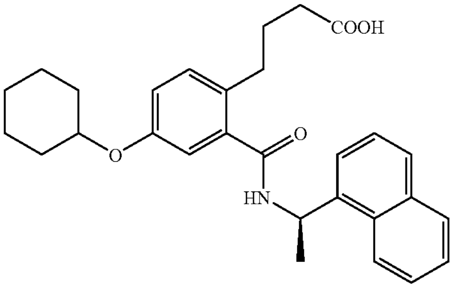

TLC: Rf 0.15 (n-hexane:ethyl acetate=1:1);

NMR (300 MHz, $CDCl_3$): δ 1.36 (m, 6H), 1.84 (m, 9H), 2.28 (m, 2H), 2.72 (m, 2H), 4.12 (m, 1H), 6.07 (m, 2H), 6.81 (m, 2H), 7.09 (d, J=8.24 Hz, 1H), 7.54 (m, 4H), 7.85 (m, 2H), 8.23 (d, J=8.52 Hz, 1H).

Example 34(173)

4-(2-((1R)-1-(naphthalen-1-yl)ethylcarbamoyl)-4-(pyridin-2-yl)oxyphenyl)butanoic acid

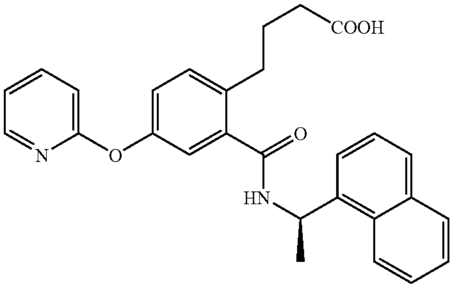

TLC: Rf 0.45 (chloroform:methanol=9:1);

NMR (300 MHz, $CDCl_3$): δ 1.74 (d, J=6.87 Hz, 3H), 1.86 (m, 2H), 2.19 (m, 2H), 2.73 (m, 2H), 6.10 (m, 1H), 6.58 (d, J=8.52 Hz, 1H), 6.91 (d, J=8.24 Hz, 1H), 7.02 (m, 3H), 7.19 (m, 1H), 7.49 (m, 4H), 7.69 (m, 1H), 7.77 (d, J=8.24 Hz, 1H), 7.84 (m, 1H), 8.08 (m, 1H), 8.21 (d, J=8.24 Hz, 1H).

Example 34(174)

4-(2-((1R)-1-(naphthalen-1-yl)ethylcarbamoyl)-4-(2-acetylphenoxy)phenyl)butanoic acid

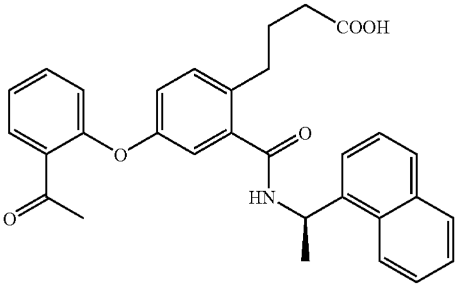

TLC: Rf 0.45 (chloroform:methanol=9:1);

NMR (300 MHz, $CDCl_3$): δ 1.77 (d, J=6.04 Hz, 3H), 1.90 (m, 2H), 2.29 (m, 2H), 2.55 (s, 3H), 2.76 (m, 2H), 6.12 (m, J=6.04 Hz, 2H), 6.83 (m, J=8.24 Hz, 1H), 6.90 (m, 1H), 6.96 (d, J=2.75 Hz, 1H), 7.15 (m, 2H), 7.45 (m, 5H), 7.79 (m, 2H), 7.86 (m, 1H), 8.20 (d, J=7.97 Hz, 1H).

Example 34(175)

4-(2-(1-(naphthalen-1-yl)propylcarbamoyl)-4-phenoxyphenyl)butanoic acid

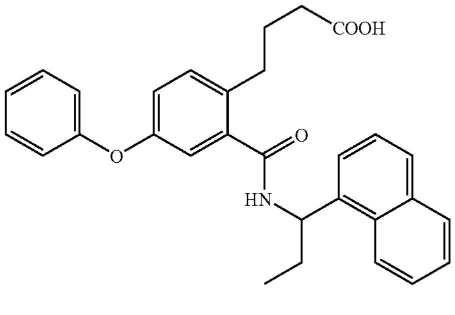

TLC: Rf 0.12 (n-hexane:ethyl acetate=1:1);

NMR (300 MHz, $CDCl_3$): δ 1.08 (t, J=7.42 Hz, 3H), 1.89 (m, 2H), 2.20 (m, 4H), 2.73 (m, 2H), 5.96 (m, 2H), 6.93 (m, 4H), 7.13 (m, 2H), 7.32 (m, 2H), 7.51 (m, 4H), 7.80 (m, 1H), 7.87 (m, 1H), 8.26 (d, J=8.24 Hz, 1H).

Example 34(176)

4-(2-(1-(naphthalen-1-yl)butylcarbamoyl)-4-phenoxyphenyl)butanoic acid

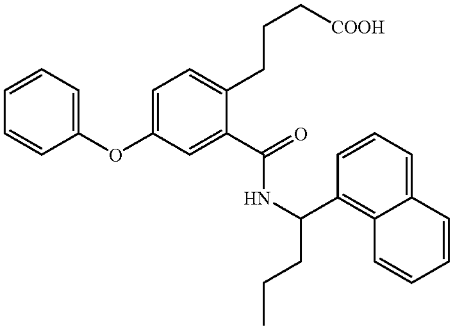

TLC: Rf 0.12 (n-hexane:ethyl acetate=1:1);

NMR (300 MHz, $CDCl_3$): δ 1.01 (m, 3H), 1.52 (m, 2H), 1.87 (m, 2H), 2.05 (m, 2H), 2.25 (m, 2H), 2.72 (t, J=7.69 Hz, 2H), 6.00 (m, 2H), 6.94 (m, 4H), 7.12 (m, 2H), 7.32 (m, 2H), 7.50 (m, 4H), 7.80 (m, 1H), 7.86 (m, 1H), 8.27 (d, J=8.52 Hz, 1H).

Example 34(177)

4-(2-((3-methyl-1-(naphthalen-1-yl)butyl)carbamoyl)-4-phenoxyphenyl)butanoic acid

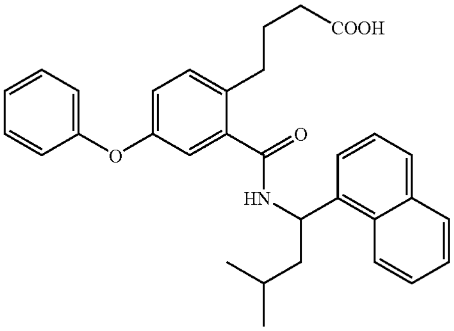

TLC: Rf 0.18 (n-hexane:ethyl acetate=2:1);

NMR (300 MHz, DMSO-$d_6$): δ 8.99 (d, J=8.1 Hz, 1H), 8.18 (d, J=8.7 Hz, 1H), 7.94 (m, 1H), 7.80 (d, J=7.8 Hz, 1H), 7.62-7.38 (m, 6H), 7.24 (d, J=8.7 Hz, 1H), 7.16 (m, 1H), 7.05-7.02 (m, 2H), 6.98 (dd, J=8.1, 2.4 Hz, 1H), 6.88 (d, J=2.4 Hz, 1H), 5.85 (m, 1H), 2.68-2.50 (m, 2H), 2.10-2.05 (m, 2H), 1.90-1.65 (m, 4H), 1.56 (m, 1H), 1.06 (d, J=6.6 Hz, 3H), 0.89 (d, J=6.3 Hz, 1H).

Example 34(178)

4-(2-((3-methyl-1-(4-fluoro-3-methylphenyl)butyl) carbamoyl)-4-phenoxyphenyl)butanoic acid

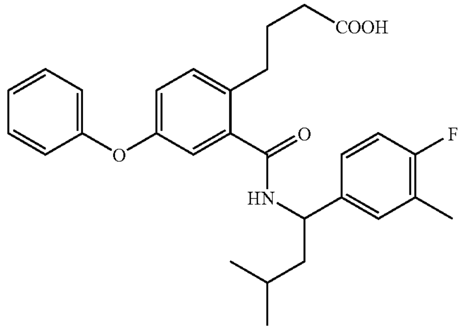

TLC: Rf 0.16 (n-hexane:ethyl acetate=2:1);

NMR (300 MHz, DMSO-$d_6$): δ 8.73 (d, J=8.7 Hz, 1H), 7.43-7.37 (m, 2H), 7.24-7.13 (m, 4H), 7.07-6.95 (m, 4H), 6.83 (d, J=2.4 Hz, 1H), 4.95 (m, 1H), 2.61-2.54 (m, 2H), 2.18 (brs, 3H), 2.08-2.03 (m, 2H), 1.75-1.53 (m, 4H), 1.39 (m, 1H), 0.89 (d, J=6.0 Hz, 3H), 0.87 (d, J=6.3 Hz, 3H).

Example 34(179)

3-(2-(((1R)-3-methyl-1-(3,5-dimethylphenyl)butyl) carbamoyl)-4-(3-methoxyphenoxy)phenyl)butanoic acid

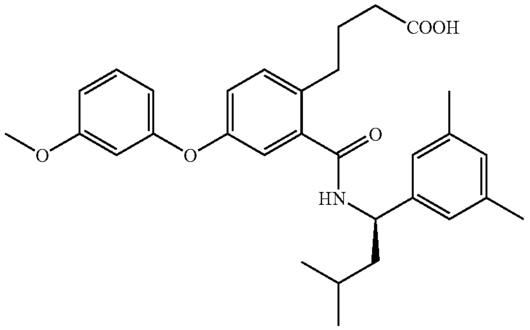

TLC: Rf 0.52 (chloroform:methanol=10:1);

NMR (300 MHz, $CDCl_3$): δ 0.96 (d, J=6.32 Hz, 3H), 0.97 (d, J=6.32 Hz, 3H), 1.75 (m, 5H), 2.30 (m, 2H), 2.29 (s, 6H), 2.73 (t, J=7.69 Hz, 2H), 3.78 (s, 3H), 5.13 (m, 1H), 5.94 (d, J=8.52 Hz, 1H), 6.56 (m, 2H), 6.66 (m, 1H), 6.95 (m, 5H), 7.19 (m, 2H).

Example 34(180)

3-(2-(((1R)-3-methyl-1-(3,5-dimethylphenyl)butyl) carbamoyl)-4-phenoxyphenyl)propanoic acid

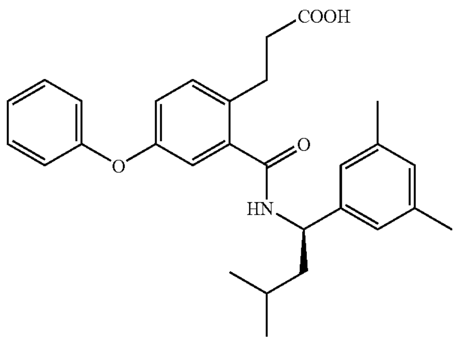

TLC: Rf 0.57 (methylene chloride:methanol=9:1);

NMR (300 MHz, $CDCl_3$): δ 7.40-7.30 (m, 2H), 7.17 (d, J=8.1 Hz, 1H), 7.16-7.09 (m, 1H), 7.04-6.82 (m, 7H), 6.19 (d, J=8.4 Hz, 1H), 5.13 (q, J=8.4 Hz, 1H), 3.08-2.92 (m, 2H), 2.71 (t, J=6.9 Hz, 2H), 2.29 (s, 6H), 1.80-1.50 (m, 3H), 0.96 (dd, J=6.3, 1.8 Hz, 6H).

Example 34(181)

3-(2-(((1R)-3-methyl-1-(3,5-dimethylphenyl)butyl) carbamoyl)-4-(benzothiazol-2-yl)oxyphenyl)propanoic acid

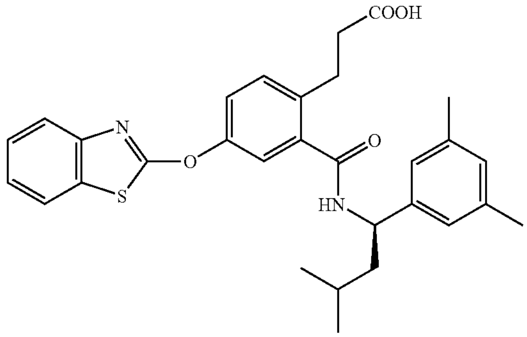

TLC: Rf 0.55 (chloroform:methanol=9:1);

NMR (300 MHz, $CDCl_3$): δ 0.96 (d, J=6.32 Hz, 3H), 0.97 (d, J=6.32 Hz, 3H), 1.68 (m, 3H), 2.28 (s, 6H), 2.68 (m, 2H), 3.01 (m, 2H), 5.14 (m, 1H), 6.64 (d, J=8.24 Hz, 1H), 6.88 (s, 1H), 6.95 (s, 2H), 7.34 (m, 5H), 7.69 (m, 2H).

Example 34(182)

3-(2-((4-(3,5-dimethylphenyl)perhydropyran-4-yl)carbamoyl)-4-phenoxyphenyl)propanoic acid

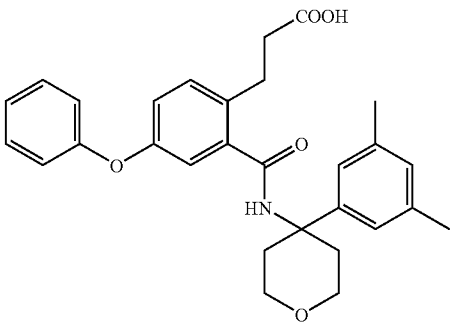

TLC: Rf 0.35 (n-hexane:ethyl acetate:acetic acid=100:100:1);

NMR (300 MHz, DMSO-$d_6$): δ 1.89 (m, 2H), 2.20 (s, 6H), 2.35 (m, 2H), 2.46 (m, J=7.48 Hz, 2H), 2.84 (t, J=7.48 Hz, 2H), 3.68 (m, 4H), 6.81 (s, 1H), 6.91 (d, J=2.75 Hz, 1H), 7.02 (m, 5H), 7.17 (m, 1H), 7.30 (d, J=8.52 Hz, 1H), 7.41 (m, 2H), 8.55 (s, 1H), 12.10 (s, 1H).

Example 34(183)

3-(2-((4-(3,5-dimethylphenyl)perhydropyran-4-yl)carbamoyl)-4-benzyloxyphenyl)propanoic acid

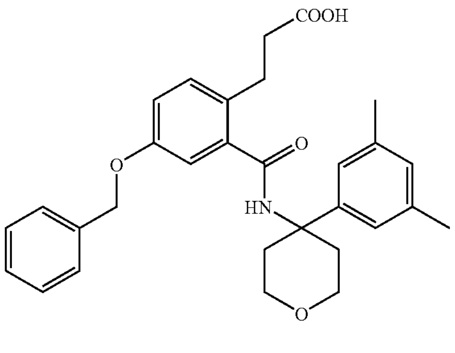

TLC: Rf 0.47 (chloroform:methanol=9:1);

NMR (300 MHz, $CDCl_3$): δ 2.22 (m, 2H), 2.32 (s, 6H), 2.44 (m, 2H), 2.67 (t, J=7.28 Hz, 2H), 2.95 (t, J=7.28 Hz, 2H), 3.77 (m, 2H), 3.92 (m, 2H), 5.07 (s, 2H), 6.35 (s, 1H), 6.90 (s, 1H), 6.98 (dd, J=8.50, 2.75 Hz, 1H), 7.04 (d, J=2.75 Hz, 1H), 7.07 (s, 2H), 7.18 (d, J=8.50 Hz, 1H), 7.39 (m, 5H).

Example 34(184)

3-(2-((4-(3,5-dimethylphenyl)perhydropyran-4-yl)carbamoyl)-4-(2-chloro-6-fluorobenzyloxy)phenyl)propanoic acid

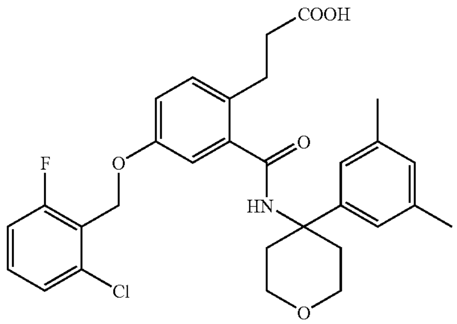

TLC: Rf 0.46 (chloroform:methanol=9:1);

NMR (300 MHz, $CDCl_3$): δ 2.23 (m, 2H), 2.32 (s, 6H), 2.47 (m, 2H), 2.68 (t, J=7.28 Hz, 2H), 2.96 (t, J=7.28 Hz, 2H), 3.87 (m, 4H), 5.19 (d, J=1.92 Hz, 2H), 6.41 (s, 1H), 6.90 (s, 1H), 7.06 (m, 5H), 7.22 (d, J=8.50 Hz, 1H), 7.31 (m, 2H).

Example 34(185)

3-(2-((4-(3,5-dimethylphenyl)perhydropyran-4-yl)carbamoyl)-4-(2,3,6-trifluorobenzyloxy)phenyl)propanoic acid

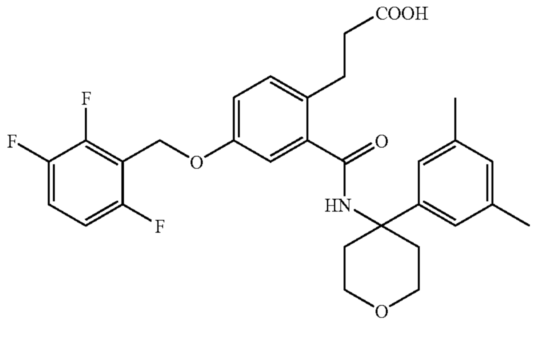

TLC: Rf 0.40 (chloroform:methanol=9:1);

NMR (300 MHz, $CDCl_3$): δ 2.23 (m, 2H), 2.32 (s, 6H), 2.47 (m, 2H), 2.67 (t, J=7.28 Hz, 2H) 2.96 (t, J=7.28 Hz, 2H), 3.85 (m, 4H), 5.13 (s, 2H), 6.49 (s, 1H), 6.90 (m, 2H), 7.00 (dd, J=8.52, 2.75 Hz, 1H), 7.06 (d, J=2.75 Hz, 1H), 7.08 (s, 2H) 7.20 (m, 1H), 7.20 (d, J=8.52 Hz, 1H).

Example 34(186)

3-(2-(((1R)-3-methyl-1-(3,5-dimethylphenyl)butyl)carbamoyl)-4-benzyloxyphenyl)propanoic acid

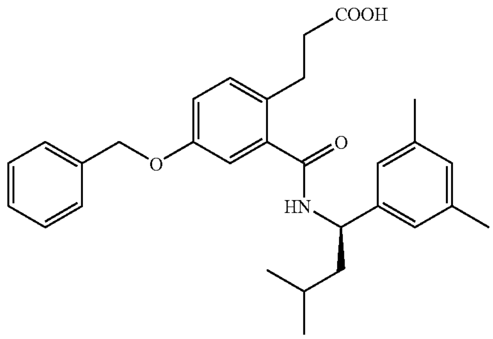

TLC: Rf 0.40 (chloroform:methanol=9:1);

NMR (300 MHz, $CDCl_3$): δ 0.98 (d, J=6.32 Hz, 6H), 1.67 (m, 3H), 2.31 (s, 6H), 2.69 (m, 2H), 2.95 (m, 2H), 5.04 (s, 2H), 5.14 (m, 1H), 6.24 (d, J=8.52 Hz, 1H), 6.90 (s, 1H), 6.96 (m, 4H), 7.17 (m, 1H), 7.37 (m, 5H).

Example 34(187)

3-(2-(((1R)-3-methyl-1-(3,5-dimethylphenyl)butyl)carbamoyl)-4-(2-chloro-6-fluorobenzyloxy)phenyl)propanoic acid

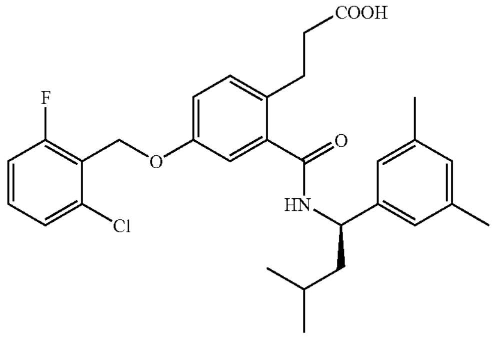

TLC: Rf 0.40 (chloroform:methanol=9:1);

NMR (300 MHz, $CDCl_3$): δ 0.98 (m, 6H), 1.70 (m, 3H), 2.30 (s, 6H), 2.70 (m, 2H), 2.97 (m, 2H), 5.15 (m, 3H), 6.28 (d, J=8.79 Hz, 1H), 6.90 (s, 1H), 6.94 (s, 2H), 7.03 (m, 3H), 7.21 (d, J=8.52 Hz, 1H), 7.29 (m, 2H).

Example 34(188)

3-(2-((4-(naphthalen-1-yl)perhydropyran-4-yl)carbamoyl)-4-phenoxyphenyl)propanoic acid

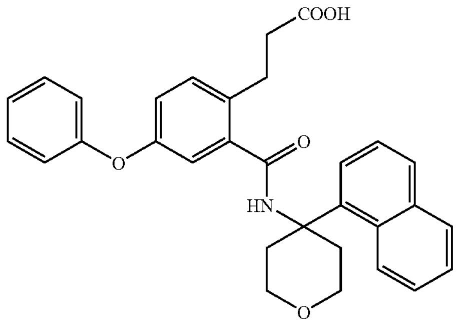

TLC: Rf 0.50 (chloroform:methanol=9:1);

NMR (300 MHz, $CDCl_3$): δ 2.49 (m, 4H), 2.83 (m, 4H), 3.92 (m, 4H), 6.88 (s, 1H), 6.98 (m, 4H), 7.19 (m, 3H), 7.34 (m, 3H), 7.48 (t, J=7.82 Hz, 1H), 7.72 (d, J=6.59 Hz, 1H), 7.78 (d, J=8.24 Hz, 1H), 7.86 (dd, J=8.24, 1.37 Hz, 1H), 8.33 (d, J=8.52 Hz, 1H).

Example 34(189)

4-(2-((4-(naphthalen-1-yl)perhydropyran-4-yl)carbamoyl)-4-phenoxyphenyl)butanoic acid

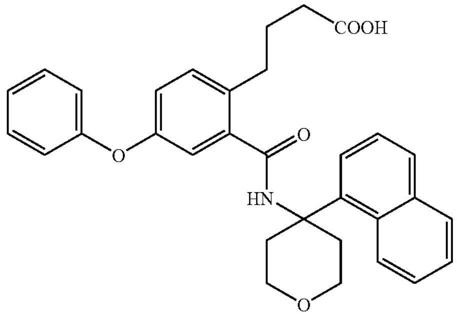

TLC: Rf 0.29 (n-hexane:ethyl acetate:acetic acid=50:50:1);

NMR (300 MHz, DMSO-$d_6$): δ 1.56 (m, 2H), 1.91 (t, J=7.55 Hz, 2H), 2.08 (m, 2H), 2.35 (m, 2H), 2.77 (m, 2H), 3.82 (m, 4H), 6.73 (d, J=2.47 Hz, 1H), 6.99 (m, 3H), 7.16 (m, 3H), 7.39 (m, 3H), 7.47 (d, J=7.69 Hz, 1H), 7.63 (d, J=7.42 Hz, 1H), 7.78 (d, J=8.24 Hz, 1H), 7.89 (d, J=7.14 Hz, 1H), 8.61 (d, J=8.79 Hz, 1H), 9.06 (s, 1H).

Example 34(190)

4-(2-((4-(3,5-dimethylphenyl)perhydropyran-4-yl) carbamoyl)-4-phenoxyphenyl)butanoic acid

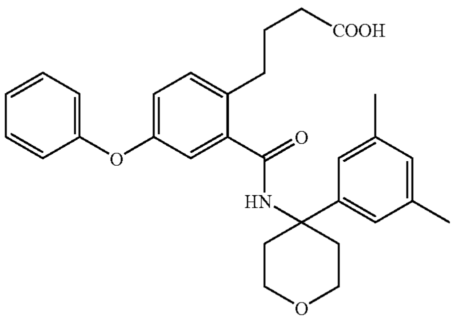

TLC: Rf 0.35 (n-hexane:ethyl acetate:acetic acid=50:50:1);

NMR (300 MHz, DMSO-$d_6$): δ 1.72 (m, 2H), 1.88 (m, 2H), 2.11 (t, J=7.55 Hz, 2H), 2.21 (s, 6H), 2.38 (m, 2H), 2.59 (m, 2H), 3.63 (m, 2H), 3.74 (m, 2H), 6.82 (s, 1H), 6.90 (d, J=2.75 Hz, 1H), 7.01 (m, 3H), 7.07 (m, 2H), 7.17 (m, 1H), 7.25 (d, J=8.52 Hz, 1H), 7.42 (m, 2H), 8.51 (s, 1H).

Example 34(191)

3-(2-(((1R)-3-methyl-1-(3,5-dimethylphenyl)butyl) carbamoyl)-4-(2,3,6-trifluorobenzyloxy)phenyl)propanoic acid

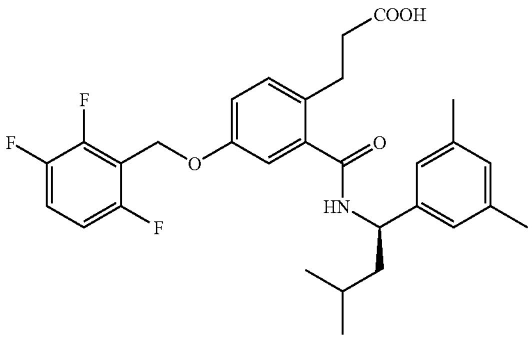

TLC: Rf 0.49 (chloroform:methanol=9:1);

NMR (300 MHz, $CDCl_3$): δ 0.97 (m, 6H), 1.68 (m, 3H), 2.30 (s, 6H), 2.69 (m, 2H), 2.95 (m, 2H), 5.11 (s, 2H), 5.17 (m, 1H), 6.27 (d, J=8.52 Hz, 1H), 6.93 (m, 6H), 7.17 (m, 2H).

Reference Example 55

7-bromomethylcoumarin

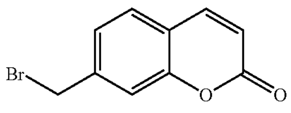

To a solution of 7-methylcoumarin (50 g) in acetonitorile (1.2 L) were added N-bromosuccinimide (56 g) α,α'-azobisisobutyronitrile (510 mg) and the mixture was stirred at 78° C. for 30 minutes. The reaction solution was concentrated and then added water (1 L). The appeared crystal was filtrated to give the title compound (76 g) having the following physical data.

NMR (300 MHz, $CDCl_3$): δ 7.69 (d, 9.6 Hz, 1H), 7.46 (d, J=8.1 Hz, 1H), 7.34 (d, J=1.8 Hz, 1H), 7.30 (dd, J=8.1, 1.8 Hz, 1H), 6.43 (d, 9.6 Hz, 1H), 4.52 (s, 2H).

Reference Example 56

7-(2,5-difluorophenoxymethyl)coumarin

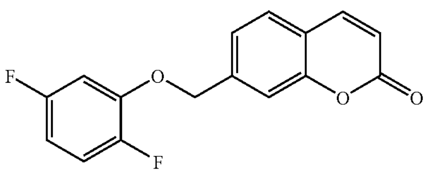

A mixture of the compound prepared in Reference Example 55 (40 g), 2,5-difluorophenol (21.8 g) and potassium carbonate (46.4 g) in DMF (250 ml) was stirred at 60° C. for 50 minutes. The reaction solution was cooled to room temperature and then added water. The appeared solid was filtered and dried to give the title compound (43.9 g) having the following physical data.

NMR (300 MHz, DMSO-$d_6$): δ 8.05 (d, J=9.6 Hz, 1H), 7.74 (d, J=7.8 Hz, 1H), 7.46 (brs, 1H), 7.41 (brd, J=7.8 Hz, 1H), 7.32-7.18 (m, 2H), 6.78 (m, 1H), 6.49 (d, J=9.6 Hz, 1H), 5.30 (s, 2H).

Reference Example 57

3-(2-hydroxy-4-(2,5-difluorophenoxymethyl)phenyl) propenoic acid methyl ester

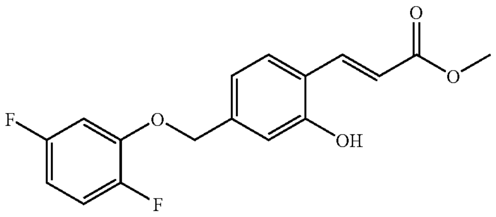

Using the compounds prepared in Reference Example 56 (43.9 g), the title compound (46.5 g) having the following physical data was obtained by the same procedure of Reference Example 42.

NMR (300 MHz, DMSO-$d_6$): δ 10.4 (s, 1H), 7.84 (d, J=16.2 Hz, 1H), 7.64 (d, J=7.8 Hz, 1H), 7.26 (m, 1H), 7.16 (m, 1H), 6.98 (s, 1H), 6.89 (d, J=7.8 Hz, 1H), 6.77 (m, 1H), 6.61 (d, J=16.2 Hz, 1H), 5.15 (s, 2H), 3.70 (s, 3H).

Reference Example 58

3-(2-hydroxy-4-(2,5-difluorophenoxymethyl)phenyl) propanoic acid methyl ester

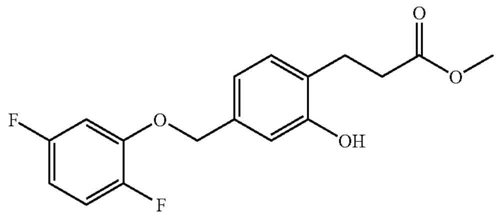

Using the compounds prepared in Reference Example 57 (46.5 g), the title compound (23.6 g) having the following physical data was obtained by the same procedure of Example 24.

NMR (300 MHz, $CDCl_3$): δ 7.20 (s, 1H), 7.10 (d, J=7.8 Hz, 1H), 7.01 (ddd, J=10.5, 9.0, 5.4 Hz, 1H), 6.96-6.91 (m, 2H), 6.71 (m, 1H), 6.58 (m, 1H), 5.03 (s, 2H), 3.70 (s, 3H), 2.92-2.88 (m, 2H), 2.74-2.70 (m, 2H).

Reference Example 59

3-(2-carboxy-4-(2,5-difluorophenoxymethyl)phenyl) propanoic acid methyl ester

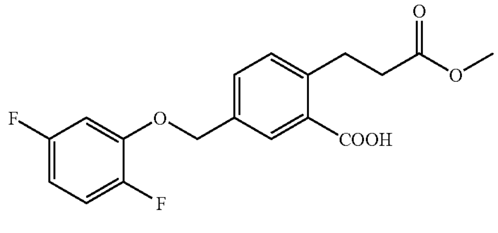

Using the compound prepared in Reference Example 58 (250 mg), the title compound (193 mg) having the following physical data was obtained by the same procedures as a series of reactions of Reference Example 44→Reference Example 45.

NMR (300 MHz, $CDCl_3$): δ 8.11 (d, J=1.8 Hz, 1H), 7.59 (dd, J=8.1, 1.8 Hz, 1H), 7.38 (d, J=8.1 Hz, 1H), 7.04 (ddd, J=10.5, 9.0, 5.1 Hz, 1H), 6.74 (ddd, J=9.6, 6.6, 3.0 Hz, 1H), 6.62 (m, 1H), 5.11 (s, 2H), 3.67 (s, 3H), 3.38-3.33 (m, 2H), 2.74-2.69 (m, 2H).

Example 35

3-(2-((3-methyl-1-(3,5-dimethylphenyl)butyl)carbamoyl)-4-(2,5-difluorophenoxymethyl)phenyl)propanoic acid

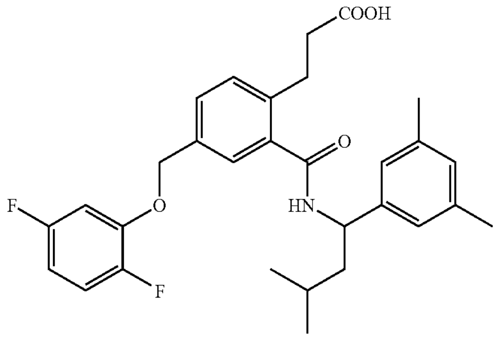

Using the compound prepared in Reference Example 59 and the compound prepared in Reference Example 48, the title compound having the following physical data was obtained by the same procedures as a series of reactions of Reference Example 8→Example 3.

TLC: Rf 0.51 (chloroform:methanol=10:1);

NMR (300 MHz, $CDCl_3$): δ 0.99 (d, J=6.32 Hz, 6H), 1.70 (m, 3H), 2.31 (s, 6H), 2.72 (t, J=7.00 Hz, 2H), 3.03 (m, 2H), 5.06 (s, 2H), 5.16 (m, 1H), 6.31 (d, J=8.24 Hz, 1H), 6.61 (m, 1H), 6.73 (m, 1H), 6.90 (s, 1H), 6.96 (s, 2H), 7.04 (m, 1H), 7.29 (d, J=8.24 Hz, 1H), 7.41 (m, 2H).

Reference Example 60

3-(2-trifluoromethanesulfoxy-4-(pyrazol-1-ylmethyl) phenyl)propanoic acid methyl ester

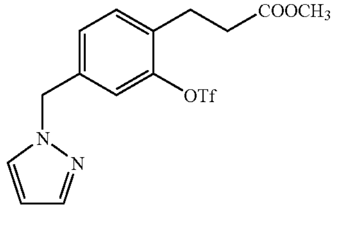

Using 3-(2-hydroxy-4-(pyrazol-1-ylmethyl)phenyl)propanoic acid methyl ester (1.00 g), the title compound (1.48 g) having the following physical data was obtained by the same procedure of Reference Example 44.

NMR (300 MHz, $CDCl_3$): δ 7.57 (m, 1H), 7.42 (d, J=2.1 Hz, 1H), 7.32 (d, J=8.1 Hz, 1H), 7.12 (d, J=8.1 Hz, 1H), 7.04 (s, 1H), 6.32 (t, J=2.1 Hz, 1H), 3.67 (s, 3H), 3.02 (t, J=7.5 Hz, 2H), 2.64 (t, J=7.5 Hz, 2H).

Example 36

3-(2-(5-phenyl-1-pentynyl)-4-(pyrazol-1-ylmethyl)phenyl)propanoic acid methyl ester

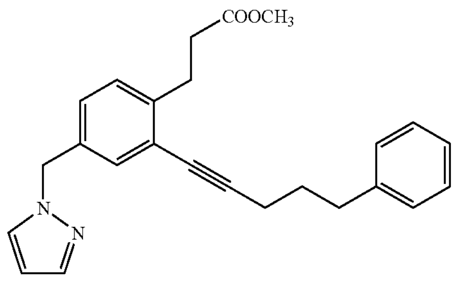

To a solution of the compound prepared in Reference Example 60 (300 mg) in DMF (3 ml) were added 5-phenyl-1-pentyne (165 mg), di(triphenylphosphine)palladium dichloride (54 mg), copper iodide (44 mg), tetrabutylammonium iodide (848 mg) and triethylamine (0.6 ml) under an atmosphere of argon. The mixture was stirred at room temperature overnight. To the reaction mixture was added water, the mixture was extracted with ethyl acetate. The organic layer was washed with water and a saturated aqueous solution of sodium chloride, dried over anhydrous magnesium sulfate and concentrated. The residue was purified by column chromatography on silica gel to give the title compound (128 mg) having the following physical data.

NMR (300 MHz, $CDCl_3$): δ 7.55 (d, J=2.1 Hz, 1H), 7.37 (d, J=2.1 Hz, 1H), 7.32-7.16 (m, 7H), 7.05 (dd, J=7.8, 1.8 Hz, 1H), 6.28 (t, J=2.1 Hz, 1H), 5.26 (s, 2H), 3.62 (s, 3H), 3.08 (t, J=7.5 Hz, 2H), 2.78 (t, J=7.5 Hz, 2H), 2.65 (t, J=7.5 Hz, 2H), 2.44 (t, J=7.5 Hz, 2H), 1.97-1.87 (m, 2H).

Example 37

3-(2-(5-phenylpentyl)-4-(pyrazol-1-ylmethyl)phenyl)propanoic acid

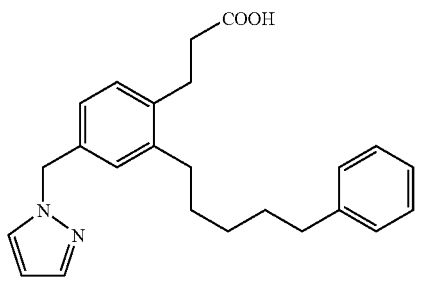

To a solution of the compound prepared in Example 36 (300 mg) in methanol (3 ml) was added 10% palladium carbon (30 mg) and the mixture was stirred at room temperature overnight under an atmosphere of hydrogen. The reaction mixture was filtered through Cellite (trade mark) and then the filtrate was concentrated. To a solution of the residue in THF were added 1N aqueous solution of sodium hydroxide (2 ml) and methanol (2 ml) and the mixture was stirred at room temperature overnight. The reaction solution was neutralized with 1N hydrochloric acid and then extracted with ethyl acetate. The organic layer was washed with water and a saturated aqueous solution of sodium chloride, dried over anhydrous magnesium sulfate and concentrated. The residue was purified by column chromatography on silica gel to give the title compound (220 mg) having the following physical data.

TLC: Rf 0.50 (n-hexane:ethyl acetate=1:2);

NMR (300 MHz, $CDCl_3$): δ 7.54 (d, J=2.1 Hz, 1H), 7.35 (d, J=2.1 Hz, 1H), 7.30-7.25 (m, 2H), 7.19-7.11 (m, 4H), 6.99-6.96 (m, 2H), 6.27 (t, J=2.1 Hz, 1H), 5.26 (s, 2H), 2.94 (t, J=7.8 Hz, 2H), 2.63-2.55 (m, 6H), 1.70-1.52 (m, 4H), 1.45-1.37 (m, 2H).

Example 38

3-(2-(5-phenyl-1-pentenyl)-4-(pyrazol-1-ylmethyl)phenyl)propanoic acid methyl ester

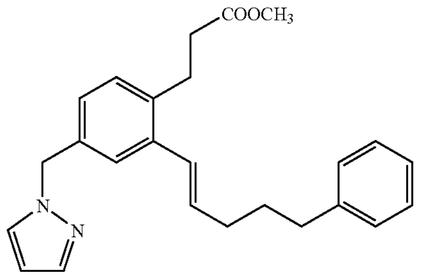

To a solution of the compound prepared in Reference Example 60 (133 mg) in DMF (1 ml) were added boronic acid (129 mg), tetrakis(triphenylphosphine)palladium (39 mg) and potassium phosphate (144 mg) under an atmosphere of argon, the mixture was stirred at 80° C. for 2 hours. To the mixture was added water and the mixture was extracted with ethyl acetate. The organic layer was washed with water and a saturated aqueous solution of sodium chloride, dried over anhydrous magnesium sulfate and concentrated. The residue was purified by column chromatography on silica gel to give the title compound (131 mg) having the following physical data.

NMR (300 MHz, $CDCl_3$): δ 7.54 (m, 1H), 7.38 (d, J=2.1 Hz, 1H), 7.32-7.16 (m, 6H), 7.11 (d, J=7.8 Hz, 1H), 7.01-6.97 (m, 1H), 6.57 (d, J=15.6 Hz, 1H), 6.27 (t, J=2.1 Hz, 1H), 6.13-6.03 (m, 1H), 5.27 (s, 2H), 3.65 (s, 3H), 2.97 (t, J=7.8 Hz, 2H), 2.67 (t, J=7.8 Hz, 2H), 2.54 (t, J=7.8 Hz, 2H), 2.30-2.22 (m, 2H), 1.86-1.75 (m, 2H).

Example 39(1)~39(2)

Using the compounds prepared in Example 36 and Example 38, the following compounds were obtained by the same procedure of Example 3.

Example 39(1)

3-(2-(5-phenyl-1-pentynyl)-4-(pyrazol-1-ylmethyl)phenyl)propanoic acid

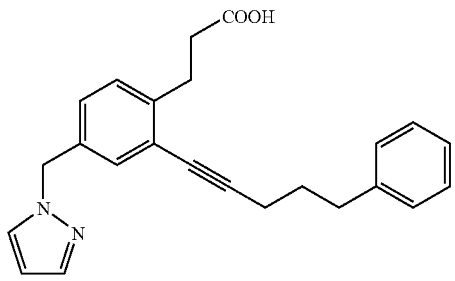

TLC: Rf 0.45 (n-hexane:ethyl acetate=1:2);

NMR (300 MHz, $CDCl_3$): δ 7.54 (d, J=2.1 Hz, 1H), 7.38 (d, J=2.1 Hz, 1H), 7.32-7.27 (m, 3H), 7.22-7.18 (m, 4H), 7.05 (dd, J=8.1, 2.1 Hz, 1H), 6.28 (t, J=2.1 Hz, 1H), 5.25 (s, 2H), 3.09 (t, J=7.8 Hz, 2H), 2.80-2.68 (m, 4H), 2.44 (t, J=6.9 Hz, 2H), 1.97-1.87 (m, 2H).

Example 39(2)

3-(2-(5-phenyl-1-pentenyl)-4-(pyrazol-1-ylmethyl)phenyl)propanoic acid

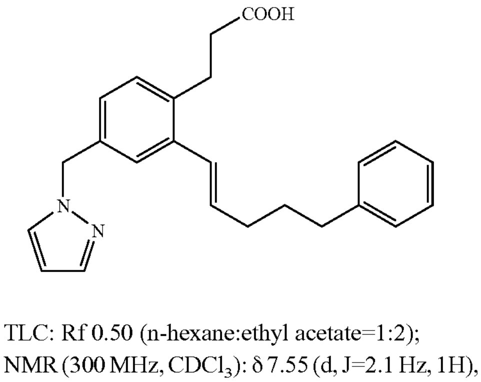

TLC: Rf 0.50 (n-hexane:ethyl acetate=1:2);

NMR (300 MHz, $CDCl_3$): δ 7.55 (d, J=2.1 Hz, 1H), 7.38 (d, J=2.1 Hz, 1H), 7.31-7.27 (m, 3H), 7.21-7.11 (m, 4H), 6.99 (dd, J=8.1, 2.1 Hz, 1H), 6.57 (d, J=15.6 Hz, 1H), 6.27 (t, J=2.1 Hz, 1H), 6.08 (dt, J=15.6, 6.9 Hz, 1H), 5.28 (s, 2H), 2.98 (t, J=8.1 Hz, 2H), 2.70-2.56 (m, 4H), 2.30-2.22 (m, 2H), 1.86-1.76 (m, 2H).

Reference Example 61

3-(4-(pyrazol-1-ylmethyl)-2-hydroxymethylphenyl)propanoic acid methyl ester

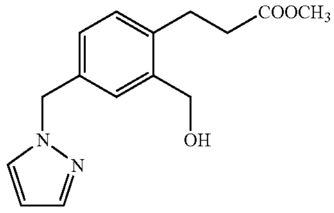

To a solution of 3-(4-(pyrazol-1-ylmethyl)-2-carboxyphenyl)propanoic acid methyl ester (600 mg) in anhydrous THF (8.0 ml) was added dropwise a solution of borane-tetrahydrofuran complex in THF (3.2 ml) at 0° C. and the mixture was stirred at room temperature for 2.5 hours. To the mixture was added a solution of borane-tetrahydrofuran complex in THF (3.5 ml) and the mixture was stirred for 1 hour. To the reaction solution was added ice and the mixture was extracted with ethyl acetate. The organic layer was washed with water and a saturated aqueous solution of sodium chloride, dried over anhydrous magnesium sulfate and concentrated. The residue was purified by column chromatography on silica gel (hexane:ethyl acetate=1:2) to give the title compound (420 mg) having the following physical data.

TLC: Rf 0.59 (chloroform:methanol=10:1);

NMR (300 MHz, $CDCl_3$): δ 7.75 (m, 1H), 7.34-7.06 (m, 4H), 6.32 (t, J=2.4 Hz, 1H), 5.34 (s, 2H), 4.74 (d, J=4.8 Hz, 2H), 3.67 (s, 3H), 3.02 (t, J=7.5 Hz, 2H), 2.70 (t, J=7.5 Hz, 2H), 2.23 (m, 1H).

Reference Example 62

3-(4-(pyrazol-1-ylmethyl)-2-(1,3-dioneisoindolin-2-ylmethyl)phenyl)propanoic acid methyl ester

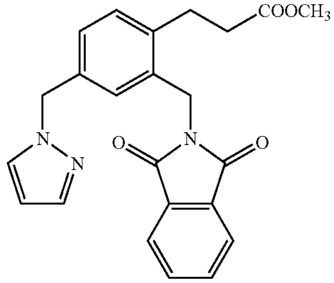

To a solution of the compound prepared in Reference Example 61 (420 mg) in THF (4 ml) were added triethylamine (0.35 ml) and methanesulfonylchloride (0.13 ml) at 0° C., and the mixture was stirred for 30 minutes. To the reaction solution was added ice, and then the mixture was extracted with ethyl acetate. The organic layer was dried over anhydrous magnesium sulfate and concentrated. The residue was dissolved in DMF. To the solution was added potassium phthalimide (370 mg) and the mixture was stirred for 3 hours. To the reaction solution was added a saturated aqueous solution of ammonium chloride and the mixture was extracted with ethyl acetate. The organic layer was washed with a saturated aqueous solution of sodium chloride, dried over anhydrous magnesium sulfate and concentrated. The residue was purified by column chromatography on silica gel (hexane:ethyl acetate=2:1). The obtained solid was washed with hexane/ethyl:acetate (5:1) to give the title compound (320 mg) having the following physical data.

TLC: Rf 0.63 (hexane:ethyl acetate=1:2);

NMR (300 MHz, $CDCl_3$): δ 7.91-7.82 (m, 2H), 7.79-7.70 (m, 2H), 7.44 (m, 1H), 7.32 (m, 1H), 7.15 (d, J=7.8 Hz, 1H), 7.08 (m, 1H), 6.99 (m, 1H), 6.20 (t, J=2.1 Hz, 1H), 5.23 (s, 2H), 4.89 (s, 2H), 3.69 (s, 3H), 3.17 (t, J=7.8 Hz, 2H), 2.67 (t, J=7.8 Hz, 2H).

Reference Example 63

3-(4-(pyrazol-1-ylmethyl)-2-aminomethylphenyl) propanoic acid hydrochloride

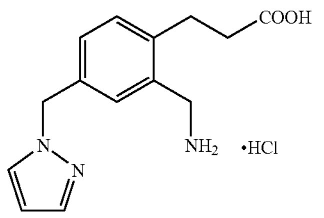

To a solution of the compound prepared in Reference Example 62 (300 mg) in 1,2-dichloroethane (1 ml) and methanol (1 ml) was added hydrazine monohydrate (0.043 ml) and the mixture was stirred at 60° C. overnight. The reaction solution was cooled to room temperature, poured into water and then extracted with ethyl acetate. The organic layer was concentrated to give 3-(4-(1-pyrazol-1-ylmethyl)-2-aminomethylphenyl)propanoic acid. The aqueous layer was concentrated and then added ethyl acetate. The insoluble material was removed by filtration and the filtrate was concentrated to give the title compound. The obtained compounds were combined. To the mixture was added concentrated hydrochloric acid (5 ml) and the mixture was stirred at 100° C. for 1 hour. The reaction solution was concentrated and azeotropted with toluene to give the title compound (190 mg) having the following physical data.

TLC: Rf 0.09 (chloroform:methanol=10:1);

NMR (300 MHz, $CDCl_3$): δ 8.24 (m, 3H), 7.81 (d, J=2.1 Hz, 1H), 7.46 (d, J=2.1 Hz, 1H), 7.38 (m, 1H), 7.27 (d, J=7.8 Hz, 1H), 7.16 (m, 1H), 6.28 (t, J=2.1 Hz, 1H), 5.30 (s, 2H), 4.12-4.00 (m, 2H), 2.87 (t, J=4.5 Hz, 2H), 2.62-2.40 (m, 2H).

Example 40

3-(4-(pyrazol-1-ylmethyl)-2-(naphthalen-2-ylcarbonylaminomethyl)phenyl)propanoic acid

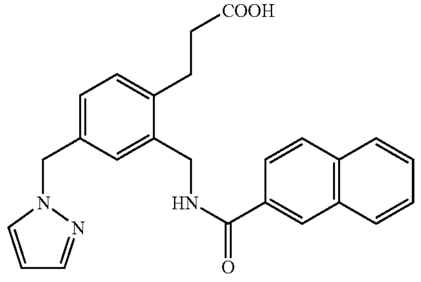

To a solution of the compound prepared in Reference Example (90 mg) in methylene chloride (4 ml) were added triethylamine (0.13 ml) and 2-naphthalenecarboxylic acid chloride (65 mg) at 0° C. and the mixture was stirred at 0° C. for 30 minutes. The reaction mixture was neutralized with 2N hydrochloric acid and then extracted with ethyl acetate. The organic layer was dried over anhydrous magnesium sulfate and concentrated. The residue was purified by column chromatography on silica gel (chloroform:methanol=100:1) to give the title compound (4.5 mg) having the following physical data.

TLC: Rf 0.40 (chloroform:methanol=10:1);

NMR (300 MHz, DMSO-$d_6$): δ 9.10 (t, J=6.3 Hz, 1H), 8.48 (s, 1H), 8.33-7.84 (m, 4H), 7.77 (d, J=2.1 Hz, 1H), 7.68-7.55 (m, 2H), 7.39 (d, J=2.1 Hz, 1H), 7.28-7.12 (m, 2H), 7.04 (d, J=8.4 Hz, 1H), 6.21 (t, J=2.1 Hz, 1H), 5.28 (s, 2H), 4.54 (d, J=6.3 Hz, 2H), 2.93 (t, J=7.6 Hz, 2H), 2.64-2.40 (m, 2H).

Example 41

3-(4-(pyrazol-1-ylmethyl)-2-(4-benzoylpiperazin-1-yl)phenyl)propenoic acid ethyl ester

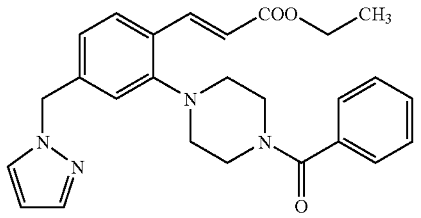

To a solution of tris(dibenzylideneacetone)dipalladium(0) (60 mg) and 2-dicyclohexylphosphino-2'-(N,N-dimethylamino)biphenyl (48 mg) in dioxane (3 ml) and t-butanol (3 ml) were added cesium carbonate (598 mg), 3-(2-iodo-4-(pyrazol-1-ylmethyl)phenyl)propenoic acid (500 mg) and piperazine (226 mg) under an atmosphere of argon and the mixture was stirred at 100° C. for 5 hours. To the reaction mixture was added water and the mixture was extracted with ethyl acetate. The organic layer was extracted with 1N hydrochloric acid. The aqueous layer was neutralized with 1N aqueous solution of sodium hydroxide and then extracted with ethyl acetate. The organic layer was washed with water and a saturated aqueous solution of sodium chloride, dried over anhydrous magnesium sulfate and concentrated. The residue was dissolved in methylene chloride (2 ml) under an atmosphere of argon. To the mixture were added benzoylchloride (0.15 ml) and pyridine (0.4 ml) and the mixture was stirred at room temperature for 2 hours. To the reaction solution was added water and the mixture was extracted with ethyl acetate. The organic layer was washed with water and a saturated aqueous solution of sodium chloride, dried over anhydrous magnesium sulfate and concentrated. The residue was purified by column chromatography on silica gel to give the title compound (306 mg) having the following physical data.

TLC: Rf 0.45 (hexane:ethyl acetate=1:2);

NMR (300 MHz, $CDCl_3$): δ 8.00 (d, J=16.2 Hz, 1H), 7.58-7.42 (m, 8H), 6.90 (d, J=8.4 Hz, 1H), 6.82 (s, 1H), 6.38

(d, J=16.2 Hz, 1H), 6.32-6.30 (m, 1H), 5.32 (s, 2H), 4.25 (q, J=7.2 Hz, 2H), 3.95 (m, 2H), 3.61 (m, 2H), 2.98-2.85 (m, 4H), 1.33 (t, J=7.2 Hz, 3H).

Example 42

3-(2-(N-benzoylpiperazin-1-yl)-4-(pyrazol-1-ylmethyl)phenyl)propanoic acid

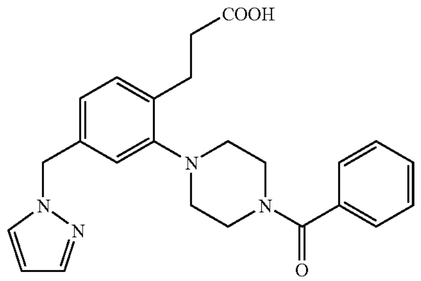

Using the compounds prepared in Example 41 (306 mg), the title compound (210 mg) having the following physical data was obtained by the same procedure of Example 37.

TLC: Rf 0.45 (ethyl acetate);

NMR (300 MHz, $CDCl_3$): δ 7.56 (d, J=2.1 Hz, 1H), 7.43 (s, 5H), 7.39 (d, J=2.1 Hz, 1H), 7.18 (d, J=8.4 Hz, 1H), 6.93-6.91 (m, 2H), 6.29 (t, J=2.1 Hz, 1H), 5.28 (s, 2H), 3.92 (m, 2H), 3.57 (m, 2H), 2.99 (t, J=7.8 Hz, 2H), 2.91-2.84 (m, 4H), 2.69 (t, J=7.8 Hz, 2H).

Example 43

3-(4-methoxymethoxy-2-(naphthalen-2-ylmethylcarbamoyl)phenyl)propenoic acid methyl ester

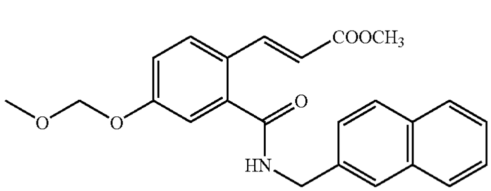

Using 3-(2-hydroxy-4-methoxymethoxymethylphenyl)propenoic acid methyl ester, the title compound having the following physical data was obtained by the same procedures as a series of reactions of Reference Example 44→Reference Example 45→Example 32.

TLC: Rf 0.51 (chloroform:methanol=10:1).

Example 44

2-(5-hydroxymethyl-2-(naphthalen-2-ylmethyl)isoindolin-3-one-1-yl)acetic acid methyl ester

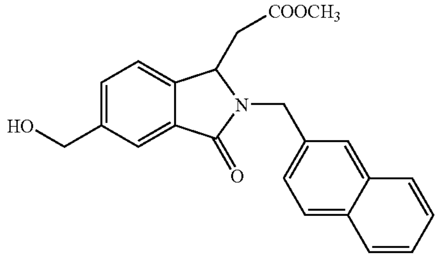

To a solution of the compound prepared in Example 43 (672 mg) in methanol (7 ml) was added potassium carbonate (478 mg) and the mixture was stirred for 3 hours. The reaction mixture was diluted with ethyl acetate, washed with 1N hydrochloric acid, water and a saturated aqueous solution of sodium chloride, dried over anhydrous sodium sulfate and concentrated. The residue was dissolved in methanol. To the solution was added trimethylsilyldiazomethane (3 ml) and the mixture was stirred for 1 hour and then concentrated. To the residue was added methanol (10 ml) and a 4N solution of hydrogen chloride in dioxane (10 ml). The mixture was stirred for 2 hours. The reaction solution was concentrated. The residue was purified by column chromatography on silica gel (ethyl acetate:hexane=1:5→1:3→1:1 ethyl acetate) to give the title compound (300 mg) having the following physical data.

TLC: Rf 0.26 (ethyl acetate:toluene=2:1);

NMR (300 MHz, $CDCl_3$): δ 7.93 (s, 1H), 7.85-7.74 (m, 3H), 7.71 (s, 1H), 7.58-7.34 (m, 5H), 5.35 (d, J=15.3 Hz, 1H), 4.84 (m, 1H), 4.81 (s, 2H), 4.59 (d, J=15.3 Hz, 1H), 3.58 (s, 3H), 2.84 (dd, J=15.9, 5.4 Hz, 1H), 2.62 (dd, J=15.9, 6.9 Hz, 1H).

Example 45

2-(5-phenoxymethyl-2-(naphthalen-2-ylmethyl)isoindolin-3-one-1-yl)acetic acid

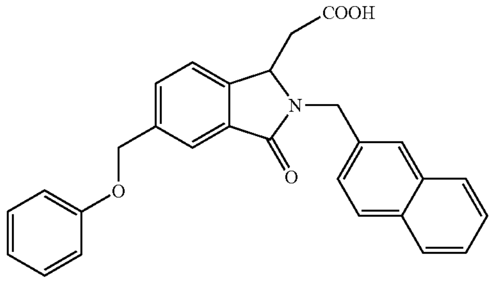

Using the compound prepared in Example 44 (85 mg), the title compound (29 mg) having the following physical data was obtained by the same procedures as a series of reactions of Example 5→Example 6.

TLC: Rf 0.46 (chloroform:methanol=10:1);

NMR (300 MHz, DMSO-$d_6$): δ 7.90-7.78 (m, 5H), 7.68 (d, J=8.4 Hz, 1H), 7.57 (d, J=7.8 Hz, 1H), 7.53-7.44 (m, 2H), 7.40 (d, J=8.4 Hz, 1H), 7.34-7.25 (m, 2H), 7.06-7.00 (m, 2H), 6.94 (m, 1H), 5.22 (s, 2H), 5.21 (d, J=15.3 Hz, 1H), 4.76 (m, 1H), 4.58 (d, J=15.3 Hz, 1H), 3.02 (dd, J=16.5, 4.2 Hz, 1H), 2.69 (dd, J=16.5, 7.2 Hz, 1H).

Example 45(1)

2-(5-(4-cyanophenoxymethyl)-2-(naphthalen-2-ylmethyl)isoindolin-3-one-1-yl)acetic acid

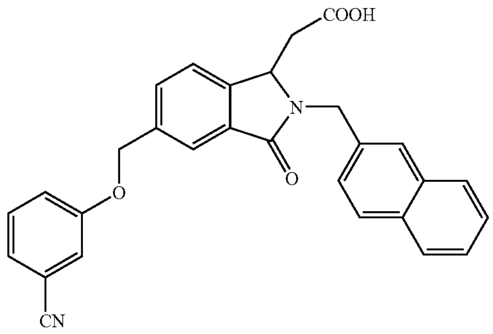

Using the compounds prepared in Example 44, the title compound having the following physical data was obtained by the same procedure of Example 45.

TLC: Rf 0.46 (chloroform:methanol=10:1);

NMR (300 MHz, DMSO-$d_6$): δ 7.91-7.35 (m, 14H), 5.29 (s, 2H), 5.21 (d, J=15.6 Hz, 1H), 4.77 (m, 1H), 4.59 (d, J=15.6 Hz, 1H), 3.02 (dd, J=16.5, 4.2 Hz, 1H), 2.69 (dd, J=16.5, 7.2 Hz, 1H).

Example 45(2)

2-(5-(pyrazol-1-ylmethyl)-2-(naphthalen-2-ylmethyl)isoindolin-3-one-1-yl)acetic acid

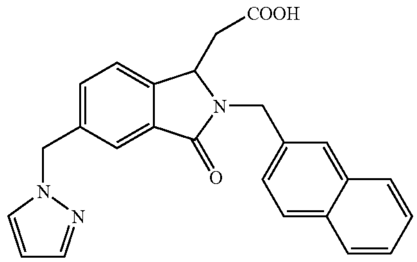

Using the compound prepared in Example 44, the title compound having the following physical data was obtained by the same procedures as a series of reactions of Example 2→Example 3.

TLC: Rf 0.27 (chloroform:methanol=10:1);

NMR (300 MHz, $CDCl_3$): δ 7.84-7.62 (m, 5H), 7.57-7.33 (m, 7H), 6.30 (t, J=2.4 Hz, 1H), 5.41 (d, J=15.0 Hz, 1H), 5.40 (s, 2H), 4.78 (m, 1H), 4.52 (d, J=15.0 Hz, 1H), 3.02 (dd, J=16.2, 4.5 Hz, 1H), 2.51 (dd, J=16.2, 8.7 Hz, 1H).

Example 45(3)

2-(5-(pyrazol-1-ylmethyl)-2-(naphthalen-1-ylmethyl)isoindolin-3-one-1-yl)acetic acid

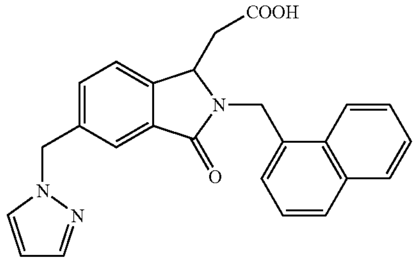

Using the compound prepared in Example 44, the title compound having the following physical data was obtained by the same procedures as a series of reactions of Example 2→Example 3.

TLC: Rf 0.23 (chloroform:methanol=10:1);

NMR (300 MHz, $CDCl_3$): δ 8.16-8.08 (m, 1H), 7.88-7.77 (m, 2H), 7.73 (brs, 1H), 7.58-7.33 (m, 8H), 6.29 (t, J=2.1 Hz, 1H), 5.86 (d, J=15.3 Hz, 1H), 5.39 (s, 2H), 4.66 (d, J=15.3 Hz, 1H), 4.54 (dd, J=9.3, 3.3 Hz, 1H), 3.12 (dd, J=15.9, 3.3 Hz, 1H), 2.48 (dd, J=15.9, 9.3 Hz, 1H).

Example 45(4)

2-(5-phenoxymethyl-2-(3-methyl-1-phenylbutyl)isoindolin-3-one-1-yl)acetic acid

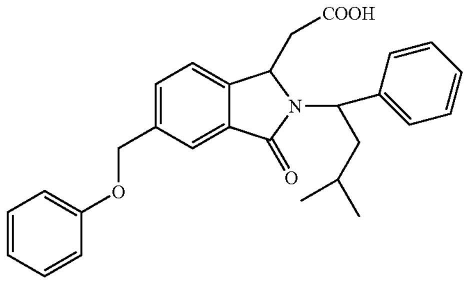

Using the compounds prepared in Example 44, the title compound having the following physical data was obtained by the same procedure of Example 45.

TLC: Rf 0.62 (chloroform:methanol=10:1).

Formulation Example 1

The following components were admixed in conventional method and punched out to obtain 100 tablets each containing 5 mg of active ingredient.

(2E)-3-(2-(2-(naphthalen-2-yl)ethoxy)-4-(pyrazol-1-ylmethyl)phenyl)-2-propenoic acid . . . 500 mg Carboxymethylcellulose calcium (disintegrating agent) . . . 200 mg Magnesium stearate (lubricating agent) . . . 100 mg Microcrystalline cellulose . . . 9.2 g

The invention claimed is:

1. A carboxylic acid derivative of formula (I):

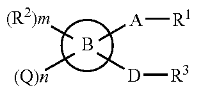

(I)

wherein $R^1$ is —COOH, —$COOR^4$, $R^4$ is C1-6 alkyl or —(C1-4 alkylene)-$R^{11}$, $R^{11}$ is hydroxy, C1-4 alkoxy, —COOH, C1-4 alkoxycarbonyl or —$CONR^7R^8$, $R^7$ and $R^8$ each independently, is (i) hydrogen, (ii) C1-6 alkyl, (iii) hydroxy, (iv) —$COR^{17}$, (v) a C3-15 mono-, bi- or tri-carbocyclic ring or a 3- to 15-membered mono-, bi- or tri-heterocyclic ring which is substituted with 1-5 of $R^{12}$ or unsubstituted, or (vi) C1-4 alkyl substituted with a C3-15 mono-, bi- or tri-carbocyclic ring or a 3- to 15-membered mono-, bi- or tri-heterocyclic ring which is substituted with 1-5 of $R^{12}$ or unsubstituted, $R^{12}$ is (a) C1-6 alkyl, (b) C1-6 alkoxy, (c) C1-6 alkylthio, (d) halogen, (e) $CF_3$, (f) cyano, (g) nitro, (h) hydroxy, (i) —$COOR^{13}$, (j) —$NHCOR^{13}$, (k) —$SO_2R^{14}$, (l) —$NR^{15}R^{16}$, (m) a C3-7 mono-carbocyclic ring which is substituted with C1-4 alkyl or oxo or unsubstituted, (n) a 3- to 7-membered mono-heterocyclic ring which is substituted with enhanced C1-4 alkyl or oxo or unsubstituted, or (o) C1-4 alkyl substituted with hydroxy, —$COOR^{13}$, —$NHCOR^{13}$, —$SO_2R^{14}$ or —$NR^{15}R^{16}$, $R^{13}$ is hydrogen, C1-4 alkyl, phenyl, or phenyl-(C1-4) alkyl, $R^{14}$ is C1-4 alkyl, $R^{15}$ and $R^{16}$ each independently, is hydrogen, C1-4 alkyl, phenyl, or phenyl-(C1-4) alkyl, $R^{17}$ is C1-4 alkyl or phenyl, A is (i) C1-6 alkylene, (ii) C2-6 alkenylene, cr (iii) —(C1-4 alkylene)-Cyc1 the alkylene, alkenylene in A may be substituted with 1-6 of the following substituents of (a)-(i):

(a) C1-6 alky, (b) C1-6 alkoxy, (c) halogen, (d) $CHF_2$, (e) $CF_3$, (f) $OCHF_2$, (g) $OCF_3$, (h) hydroxy, (i) hydroxy-(C1-4) alkyl, Cyc1 is a benzene which is substituted with 1-4 of C1-6 alkyl, C1-6 alkoxy, C1-6 alkylthio, C2-6 alkenyl, C2-6 alkynyl, halogen, $CHF_2$, $CF_3$, nitro or cyano, or unsubstituted, B ring is a benzene $R^2$ is C1-6 alkyl, C1-6 alkoxy, C1-6 alkylthio, C2-6 alkenyl, C2-6 alkynyl, halogen, $CHF_2$, $CF_3$, nitro, cyano, phenyl or oxo, m is 0, 1 or 2, n is 1

Q is (1)(i) —(C1-4 alkylene, C2-4 alkenylene or C2-4 alkynylene)-Cyc2, or (ii) —(C1-4 alkylene)-Z-Cyc3, $R^{22}$ is hydrogen, C1-4 alkyl, —$SO_2$—(C1-4) alkyl or C2-5 acyl, $R^{23}$ is hydrogen, C1-4 alkyl, phenyl or phenyl(C1-4) alkyl, $R^{30}$ is C1-8 alkyl, C1-8 alkoxy, C1-8 alkylthio, halogen, $CF_3$, $OCF_3$, $SCF_3$, $CHF_2$, $SCHF_2$, hydroxy, cyano, nitro, —$NR^{31}R^{32}$, —$CONR^{31}R^{32}$, formyl, C2-5 acyl, hydroxy(C1-4) alkyl, C1-4 alkoxy(C1-4) alkyl, C1-4 alkylthio(C1-4) alkyl, —(C1-4 alkylene)-$CONR^{31}R^{32}$, —$SO_2$(C1-4) alkyl, —$NR^{23}CO$—(C1-4) alkyl, —$NR^{23}SO_2$—(C1-4) alkyl, benzoyl, oxo, a C3-7 mono-carbocyclic ring, a 3- to 7-membered mono-heterocyclic ring, —(C1-4 alkylene)-$NR^{31}R^{32}$, -M-(C3-7 mono-carbocyclic ring), or -M-(3- to 7-membered mono-heterocyclic ring), the C3-7 mono-carbocyclic ring and 3- to 7-membered mono-heterocyclic ring in $R^{30}$ may be substituted with 1-5 of the following substituents (a)-(l):

(a) C1-6 alkyl, (b) C2-6 alkenyl, (c) C2-6 alkyl, (d) c1-6 alkoxy, (e) C1-6 alkylthio, (f) halogen, (g) $CHF_2$, (h) $CF_3$, (I) nitro, (j) cyano, (k) hydroxy, (l) amino;

M is —O—, —S—, C1-4 alkylene, —O—(C1-4 alkylene)-, —S—(C1-4 alkylene)-, —(C1-4 alkylene)-O— or —(C1-4 alkylene)-S—, $R^{31}$ and $R^{32}$ each independently, is hydrogen or C1-4 alkyl, Cyc2 is a C3-15 mono-, bi- tri-carbocyclic ring or a 3- to 15-membered mono-, bi-tri-heterocyclic ring which is substituted with 1-5 of $R^{30}$ or unsubstituted, Z is —O—, —$S(O)_p$—, —$NR^{22}$—, —$NR^{23}CO$—, —$NR^{23}SO_2$—, —$NR^{22}$—(C1-4 alkylene)-, —$S(O)_p$—(C1-4 alkylene)-, —O—(C2-4 alkylene)-, —$NR^{23}CO$—(C1-4 alkylene) or —$NR^{23}SO_2$—(C1-4 alkylene), p is 0, 1 or 2, Cyc3 is a C3-15 mono-, bi- tri-carbocyclic ring or a 3- to 15-membered mono-, bi-tri-heterocyclic ring which is substituted with 1-5 of $R^{30}$ or unsubstituted, D is (1) —NHCO—$CH_2$—, —$NR^{40-1}CO$—$CH_2$—, —NHCO—$CHR^{40}$—, —NHCO—$C(R^{40})_2$—, —NHCO—$(CH_2)_2$—, —NHCO—$CHR^{40}$—$CH_2$—, —NHCO—$CH_2$—$CHR^{40}$—, —NHCO—$CHR^{40}$—$CH^{40}$—, $R^{40}$ is (a) C1-8 alkyl, (b) C2-8 alkenyl, (c) C2-8 alkynyl, (d) oxo, (e) halogen, (f) $CF_3$, (g) hydroxy, (h) C1-6 alkoxy, (i) C2-6 alkenyloxy, (j) C2-6 alkynyloxy, (k) $OCF_3$, (l) —$S(O)_p$—(C1-6) alkyl, (m) —$S(O)_p$—(C2-6) alkenyl, (n) —$S(O)_p$—(C2-6) alkynyl, (o) C2-5 acyl, (p) Cyc9, (q) C1-4 alkoxy(C1-4) alkoxy, or (r) C1-8 alkyl, C2-8 alkenyl or C2-8 alkynyl substituted with 1 or 2 of substituents selected from halogen, $CF_3$, $OCF_3$, hydroxy, cyano, C1-4 alkoxy, —$S(O)_p$—(C1-6) alkyl, Cyc9 and C1-4 alkoxy(C1-4) alkoxy or $R^{40-1}$ is methyl, ethyl, propyl, isopropyl, butyl, isobutyl, methoxymethyl, methoxyethyl, hydroxymethyl, hydroxyethyl, cyanomethyl, cyanoethyl, methylsulfonyl, cyclopropyl, cyclohexyl, benzene, cyclopropylmethyl, cyclohexylmethyl, benzyl, or acetyl Cyc9 is a C3-6 mono-carbocyclic ring or a 3- to 6-membered mono-heterocyclic ring, which is substituted with 1-5 of $R^{41}$ or unsubstituted, $R^{41}$ is C1-4 alkyl, C1-4 alkoxy, C1-4 alkylthio, C1-4 alkoxy(C1-4) alkyl, halogen, $CF_3$, $OCF_3$, $SCF_3$, hydroxy, cyano, formyl, C2-5 acyl, —$SO_2$—(C1-4) alkyl, —$NR^{23}CO$—(C1-4) alkyl, benzoyl or oxo, $R^3$ is (1) a benzene or naphthalene which is substituted with 1-5 of $R^{42}$ or unsubstituted, $R^{42}$ is (a) C1-6 alkyl, (b) C1-6 alkoxy, (c) C1-6 alkylthio, (d) halogen, (e) cyano, (f) $CF_3$, (g) $CHF_2$, (h) $OCF_3$, (i) $OCHF_2$, (j) $SCF_3$, (k) —$NR^{43}R^{44}$, (l) —$SO_2R^{45}$, (m)

—$NR^{46}COR^{47}$, (n) hydroxy, (o) oxo, (p) C1-4 alkoxy (C1-4) alkyl, (q) Cyc10, (r) C1-6 alkylene-Cyc10, (s) —CO-Cyc10, (t) —W-Cyc10, (u) —(C1-6 alkylene)-W-Cyc10, (v) —W—(C1-6 alkylene)-Cyc10 or (w) —(C1-6 alkylene)-W—(C1-6 alkylene)-Cyc10, $R^{43}$ and $R^{44}$ each independently, is hydrogen or C1-4 alkyl, $R^{45}$ is C1-4 alkyl, $R^{46}$ is hydrogen or C1-4 alkyl, $R^{47}$ is hydrogen or C1-4 alkyl, Cyc10 is a C3-12 mono- or bi-carbocyclic ring or a 3- to 12-membered mono- or bi-heterocyclic ring which is substituted with 1-5 of substitutes of the following (a)-(j) or unsubstituted, (a) C1-4 alkyl, (b) C2-5 acyl, (c) 1-4 alkoxy, (d) halogen, (e) hydroxy, (f) nitro, (g) cyano, (h) amine, (i) $CF_3$, (j) $OCF_3$, W is —O—, —$S(O)_p$— or —$NR^{48}$—, $R^{48}$ is hydrogen or C1-4 alkyl;

or a non-toxic salt thereof.

2. The compound according to the claim 1, which is selected from (1) 4-(2-((2-(naphthalen-1-yl)propanoyl)amino)-4-(4-ethoxyphenoxymethyl)phenyl)butanoic acid, (2) (2E)-3-(2-((2-(naphthalen-2-yl)acetyl)amino)-4-(pyrazol-1-ylmethyl)phenyl)-2-propenoic acid, (3) 2-(2-((4-methyl-2-(naphthalen-1-yl)pentanoyl)amino)-4-(pyrazol-1-ylmethyl)benzyl)benzoic acid, (4) 4-(2-((2-(naphthalen-1-yl)propanoyl)amino)-4-phenoxymethylphenyl)butanoic acid, (5) 4-(2-((4-methyl-2-(naphthalen-1-yl)pentanoyl)amino)-4-phenoxymethylphenyl)butanoic acid, (6) 4-(2-((2-(naphthalen-1-yl)propanoyl)amino)-4-(2-oxopyridin-1-ylmethyl)phenyl)butanoic acid, (7) 4-(2-((2-(naphthalen-1-yl)propanoyl)amino)-4-(pyridin-3-yloxymethyl)phenyl)butanoic acid, (8) 4-(2-((2-(naphthalen-1-yl)propanoyl)amino)-4-phenylthiomethylphenyl)butanoic acid, (9) 4-(2-((2-(naphthalen-1-yl)propanoyl)amino)-4-phenylaminomethylphenyl)butanoic acid,

(10) 4-(2-((2-(naphthalen-1-yl)propanoyl)amino)-4-phenylsulfinylmethylphenyl)butanoic acid,

(11) 4-(2-((2-(naphthalen-1-yl)propanoyl)amino)-4-phenylsulfonylmethylphenyl)butanoic acid,

(12) 3-(2-((4-methyl-2-(naphthalen-1-yl)pentanoyl)amino)-4-phenoxymethylphenyl)propanoic acid,

(13) 4-(2-((4-methyl-2-(naphthalen-1-yl)pentanoyl)amino)-4-(pyrazol-1-ylmethyl)phenyl)butanoic acid,

(14) 4-(2-((2-(naphthalen-1-yl)propanoyl)amino)-4-benzoylaminomethylphenyl)butanoic acid,

(15) 4-(2-((2-(naphthalen-1-yl)propanoyl)amino)-4-(pyridin-4-yloxymethyl)phenyl)butanoic acid,

(16) 4-(2-((2-(naphthalen-1-yl)propanoyl)amino)-4-(2-phenoxyethyl)phenyl)butanoic acid,

(17) 4-(2-((2-(naphthalen-1-yl)propanoyl)amino)-4-(pyridin-2-yloxymethyl)phenyl)butanoic acid,

(18) 4-(2-((2-(naphthalen-1-yl)propanoyl)amino)-4-(N-methyl-N-phenylaminomethyl)phenyl)butanoic acid,

(19) 4-(2-((2-(4-fluoronaphthalen-1-yl)propanoyl)amino)-4-phenoxymethylphenyl)butanoic acid,

(20) 4-(2-((2-phenylpropanoyl)amino)-4-phenoxymethylphenyl)butanoic acid,

(21) 3-(2-((4-methyl-2-phenylpentanoyl)amino)-4-phenoxymethylphenyl)propanoic acid,

(22) 3-(2-((2-phenylpentanoyl)amino)-4-phenoxymethylphenyl)propanoic acid,

(23) 3-(2-((2-phenylpropanoyl)amino)-4-phenoxymethylphenyl)propanoic acid,

(24) 3-(2-((2-phenylbutanoyl)amino)-4-phenoxymethylphenyl)propanoic acid,

(25) 4-(2-((2-phenylpropanoyl)amino)-4-phenylaminomethylphenyl)butanoic acid,

(26) 4-(2-((2-phenylpropanoyl)amino)-4-benzoylaminomethylphenyl)butanoic acid,

(27) 4-(2-((2-(4-fluoronaphthalen-1-yl)propanoyl)amino)-4-benzoylaminomethylphenyl)butanoic acid,

(28) 4-(2-((2-(naphthalen-1-yl)propanoyl)amino)-4-phenylsulfonylaminomethylphenyl)butanoic acid,

(29) 4-(2-((2-(naphthalen-1-yl)propanoyl)amino)-4-benzylaminomethylphenyl)butanoic acid,

(30) 4-(2-((2-(4-fluoronaphthalen-1-yl)propanoyl)amino)-4-phenylaminomethylphenyl)butanoic acid,

(31) 4-(2-((2-(naphthalen-1-yl)propanoyl)amino)-4-(4-cyanophenoxymethyl)phenyl)butanoic acid, phenylaminomethylphenyl)butanoic acid,

(32) 2-(2-((2-phenylpropanoyl)amino)-4-phenoxymethylbenzyl)benzoic acid,

(33) 2-(2-((2-(naphthalen-1-yl)propanoyl)amino)-4-phenoxymethylbenzyl)benzoic acid,

(34) 4-(2-((2-(naphthalen-1-yl)propanoyl)amino)-4-(furan-2-ylcarbonylaminomethyl)phenyl)butanoic acid,

(35) 4-(2-((2-(naphthalen-1-yl)propanoyl)amino)-4-(3-fluorobenzoylaminomethyl)phenyl)butanoic acid,

(36) 4-(2-((2-(naphthalen-1-yl)propanoyl)amino)-4-(3-methoxybenzoylaminomethyl)phenyl)butanoic acid,

(37) 4-(2-((2-(naphthalen-1-yl)propanoyl)amino)-4-cyclopropylcarbonylaminomethylphenyl)butanoic acid,

(38) 4-(2-((2-(naphthalen-1-yl)propanoyl)amino)-4-(thiophen-2-ylcarbonylaminomethyl)phenyl)butanoic acid,

(39) 4-(2-((2-(naphthalen-1-yl)propanoyl)amino)-4-(3-methylbenzoylaminomethyl)phenyl)butanoic acid,

(40) 4-(2-((2-(naphthalen-1-yl)propanoyl)amino)-4-(3-chlorobenzoylaminomethyl)phenyl)butanoic acid,

(41) 4-(2-((2-(naphthalen-1-yl)propanoyl)amino)-4-(3-cyanobenzoylaminomethyl)phenyl)butanoic acid,

(42) 4-(2-((2-(naphthalen-1-yl)propanoyl)amino)-4-(4-fluorobenzoylaminomethyl)phenyl)butanoic acid,

(43) 4-(2-((2-(naphthalen-1-yl)propanoyl)amino)-4-(2-fluorobenzoylaminomethyl)phenyl)butanoic acid,

(44) 4-(2-((2-(naphthalen-1-yl)propanoyl)amino)-4-(3-chloro-4-fluorobenzoylaminomethyl)phenyl)butanoic acid,

(45) 4-(2-((2-(2-chlorophenyl)propanoyl)amino)-4-phenoxymethylphenyl)butanoic acid,

(46) 4-(2-((2-(3-chlorophenyl)propanoyl)amino)-4-phenoxymethylphenyl)butanoic acid,

(47) 4-(2-((2-(4-chlorophenyl)propanoyl)amino)-4-phenoxymethylphenyl)butanoic acid,

(48) 4-(2-((2-(4-fluorophenyl)propanoyl)amino)-4-phenoxymethylphenyl)butanoic acid,

(49) 4-(2-((2-(4-methoxyphenyl)propanoyl)amino)-4-phenoxymethylphenyl)butanoic acid,

(50) 4-(2-((2-(naphthalen-1-yl)propanoyl)amino)-4-(3-ethoxybenzoylaminomethyl)phenyl)butanoic acid,

(51) 4-(2-((2-(naphthalen-1-yl)propanoyl)amino)-4-(3,5-difluorobenzoylaminomethyl)phenyl)butanoic acid,

(52) 4-(2-((2-(naphthalen-1-yl)propanoyl)amino)-4-(3-fluorophenoxymethyl)phenyl)butanoic acid,

(53) 4-(2-((2-(4-methylphenyl)propanoyl)amino)-4-phenoxymethylphenyl)butanoic acid,

(54) 4-(2-((2-(naphthalen-1-yl)propanoyl)amino)-4-(4-cyano-2-methoxyphenoxymethyl)phenyl)butanoic acid,

(55) 4-(2-((2-(naphthalen-1-yl)propanoyl)amino)-4-(3-acetylphenoxymethyl)phenyl)butanoic acid,

(56) 4-(2-((2-(naphthalen-1-yl)propanoyl)amino)-4-(3-isopropyl-5-methylphenoxymethyl)phenyl)butanoic acid,

(57) 4-(2-((2-(naphthalen-1-yl)propanoyl)amino)-4-(2,4,6-trifluorophenoxymethyl)phenyl)butanoic acid,

(58) 4-(2-((2-(naphthalen-1-yl)propanoyl)amino)-4-(4-trifluoromethylthiophenoxymethyl)phenyl)butanoic acid,

(59) 4-(2-((2-(naphthalen-1-yl)propanoyl)amino)-4-(4-bromophenoxymethyl)phenyl)butanoic acid,

(60) 4-(2-((2-(naphthalen-1-yl)propanoyl)amino)-4-(3-methoxyphenoxymethyl)phenyl)butanoic acid,

(61) 4-(2-((2-(naphthalen-1-yl)propanoyl)amino)-4-(2-methoxyphenoxymethyl)phenyl)butanoic acid,

(62) 4-(2-((2-(naphthalen-1-yl)propanoyl)amino)-4-(2-methylbenzothiazol-5-yloxymethyl)phenyl)butanoic acid,

(63) 4-(2-((2-(naphthalen-1-yl)propanoyl)amino)-4-(4-(1,2,4-triazol-1-yl)phenoxymethyl)phenyl)butanoic acid,

(64) 4-(2-((2-(naphthalen-1-yl)propanoyl)amino)-4-(2-ethoxyphenoxymethyl)phenyl)butanoic acid,

(65) 4-(2-((2-(naphthalen-1-yl)propanoyl)amino)-4-(2-methoxy-5-methylphenoxymethyl)phenyl)butanoic acid,

(66) 4-(2-((2-(naphthalen-1-yl)propanoyl)amino)-4-(3,5-dimethoxyphenoxymethyl)phenyl)butanoic acid,

(67) 4-(2-((2-(naphthalen-1-yl)propanoyl)amino)-4-(2-fluoro-6-methoxyphenoxymethyl)phenyl)butanoic acid,

(68) 4-(2-((2-(naphthalen-1-yl)propanoyl)amino)-4-(2-isopropyloxyphenoxymethyl)phenyl)butanoic acid,

(69) 4-(2-((2-(naphthalen-1-yl)propanoyl)amino)-4-(2-acetyl-5-methoxyphenoxymethyl)phenyl)butanoic acid,

(70) 2-(2-((4-methyl-2-(naphthalen-1-yl)pentanoyl)amino)-4-phenoxymethylbenzyl)benzoic acid,

(71) 4-(2-((2-(naphthalen-1-yl)propanoyl)amino)-4-(2-chloro-4,5-dimethylphenoxymethyl)phenyl)butanoic acid,

(72) 4-(2-((2-(naphthalen-1-yl)propanoyl)amino)-4-(1-oxo-1,2,3,4-tetrahydronaphthalen-6-yloxymethyl)phenyl)butanoic acid,

(73) 4-(2-((2-(naphthalen-1-yl)propanoyl)amino)-4-(3-cyanophenoxymethyl)phenyl)butanoic acid,

(74) 4-(2-((2-(naphthalen-1-yl)propanoyl)amino)-4-(3-chloro-5-methoxyphenoxymethyl)phenyl)butanoic acid,

(75) 4-(2-((2-(naphthalen-1-yl)propanoyl)amino)-4-(4-ethyl-2-methoxyphenoxymethyl)phenyl)butanoic acid,

(76) 4-(2-((2-(naphthalen-1-yl)propanoyl)amino)-4-(4-acetylamino-2-chlorophenoxymethyl)phenyl)butanoic acid,

(77) 4-(2-((2-(naphthalen-1-yl)propanoyl)amino)-4-(2-methylthiophenoxymethyl)phenyl)butanoic acid,

(78) 4-(2-((2-(naphthalen-1-yl)propanoyl)amino)-4-(4-butanoylphenoxymethyl)phenyl)butanoic acid,

(79) (2E)-3-(2-((4-methyl-2-phenylpentanoyl)amino)-4-phenoxymethylphenyl)-2-propenoic acid,

(80) 4-(2-((2-(4-fluoronaphthalen-1-yl)propanoyl)amino)-4-(pyrazol-1-ylmethyl)phenyl)butanoic acid,

(81) 3-(2-((2-(4-fluoronaphthalen-1-yl)propanoyl)amino)-4-phenoxymethylphenyl)propanoic acid,

(82) 3-(2-((2-(4-fluoronaphthalen-1-yl)propanoyl)amino)-4-phenylaminomethylphenyl)propanoic acid,

(83) 3-(2-((2-(4-fluoronaphthalen-1-yl)propanoyl)amino)-4-(pyrazol-1-ylmethyl)phenyl)propanoic acid,

(84) 2-(2-((2-(4-fluoronaphthalen-1-yl)acetyl)amino)-4-phenoxymethylbenzyl)benzoic acid,

(85) 2-(2-((2-(4-fluoronaphthalen-1-yl)propanoyl)amino)-4-phenoxymethylbenzyl)benzoic acid,

(86) 2-(2-((4-methyl-2-phenylpentanoyl)amino)-4-phenoxymethylbenzyl)benzoic acid,

(87) 2-(2-((4-methyl-2-(3,5-dimethylphenyl)pentanoyl)amino)-4-phenoxymethylbenzyl)benzoic acid,

(88) 2-(2-((2-(naphthalen-1-yl)acetyl)amino)-4-phenoxymethylbenzyl)benzoic acid,

(89) 3-(2-((4-methyl-2-(4-fluoro-3-methylphenyl)pentanoyl)amino)-4-phenoxymethylphenyl)propanoic acid,

(90) 3-(2-((4-methyl-2-(3,5-dimethylphenyl)pentanoyl)amino)-4-phenoxymethylphenyl)propanoic acid,

(91) 2-(2-((2-(naphthalen-1-yl)propanoyl)amino)-4-(2-methylphenoxymethyl)benzyl)benzoic acid,

(92) 2-(2-((2-(naphthalen-1-yl)propanoyl)amino)-4-(2-chloro-5-methylphenoxymethyl)benzyl)benzoic acid,

(93) 2-(2-((2-(naphthalen-1-yl)propanoyl)amino)-4-(3-cyanophenoxymethyl)benzyl)benzoic acid,

(94) 2-(2-((2-(naphthalen-1-yl)propanoyl)amino)-4-(pyridin-3-yloxymethyl)benzyl)benzoic acid, methyl ester thereof, ethyl ester therof or non-toxic salts thereof.

3. A pharmaceutical composition, which comprises the compound of formula (I) according to claim 1, or a non-toxic salt thereof.

4. The compound according to claim 1, which is 2-(2-((4-methyl-2-(naphthalen-1-yl)pentanoyl)amino)-4-(pyrazol-1-ylmethyl) benzyl)benzoic acid.

* * * * *